(12) United States Patent
Kiyoto et al.

(10) Patent No.: US 8,524,738 B2
(45) Date of Patent: Sep. 3, 2013

(54) QUINOLINONES AND QUINOXALINONES AS ANTIBACTERIAL COMPOSITION

(75) Inventors: Taro Kiyoto, Toyama (JP); Tadashi Tanaka, Toyama (JP); Yasuhiro Tsutsui, Toyama (JP); Junichi Ando, Toyama (JP); Mai Motono, Toyama (JP); Yasuko Kawaguchi, Toyama (JP); Toshiya Noguchi, Tokyo (JP); Yasunobu Ushiki, Tokyo (JP); Fumihito Ushiyama, Tokyo (JP); Hiroki Urabe, Tokyo (JP)

(73) Assignees: Toyama Chemical Co., Ltd., Tokyo (JP); Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/463,434

(22) Filed: May 3, 2012

(65) Prior Publication Data

US 2012/0214990 A1    Aug. 23, 2012

Related U.S. Application Data

(62) Division of application No. 11/993,652, filed as application No. PCT/JP2006/312515 on Jun. 22, 2006, now Pat. No. 8,329,694.

(30) Foreign Application Priority Data

Jun. 24, 2005 (JP) .................. 2005-184542
Mar. 20, 2006 (JP) .................. 2006-076850

(51) Int. Cl.
    *A61K 31/47* (2006.01)
(52) U.S. Cl.
    USPC .......................... 514/312; 546/157
(58) Field of Classification Search
    USPC .......................... 514/312; 546/157
    See application file for complete search history.

(56) References Cited

U.S. PATENT DOCUMENTS

| | | |
|---|---|---|
| 7,875,715 B2 | 1/2011 | Breault et al. |
| 8,211,908 B2 | 7/2012 | Kiyoto et al. |
| 2010/0168418 A1 | 7/2010 | Kiyoto et al. |
| 2010/0249417 A1 | 9/2010 | Kiyoto et al. |
| 2011/0092495 A1 | 4/2011 | Breault et al. |

FOREIGN PATENT DOCUMENTS

| | | |
|---|---|---|
| JP | 63-290821 | 11/1988 |
| JP | 2-169569 | 6/1990 |
| JP | 2 264773 | 10/1990 |
| JP | 5 4984 | 1/1993 |
| JP | 5 239037 | 9/1993 |
| JP | 5 320157 | 12/1993 |
| JP | 9 227561 | 9/1997 |
| JP | 2003 148972 | 5/2003 |
| JP | 2004 123849 | 4/2004 |
| WO | 98 07703 | 2/1998 |
| WO | 99 07682 | 2/1999 |
| WO | WO 01/64670 A1 | 9/2001 |
| WO | 03 057672 | 7/2003 |
| WO | 2004 002490 | 1/2004 |
| WO | 2004 002992 | 1/2004 |
| WO | WO 2004/110444 A1 | 12/2004 |
| WO | 2006 035954 | 4/2006 |
| WO | WO 2006/059164 A2 | 6/2006 |
| WO | WO 2006/068904 A1 | 6/2006 |
| WO | WO 2006/134378 A1 | 12/2006 |
| WO | WO 2008/009700 A1 | 1/2008 |
| WO | WO 2008/071961 A1 | 6/2008 |
| WO | WO 2008/071981 A1 | 6/2008 |
| WO | WO 2009/001126 A1 | 12/2008 |

OTHER PUBLICATIONS

Morris Fishman and Philip A. Cruickshank "Studies in Alkylation. I. Synthesis and Reactions of Spiro [oxirane-2,4'-piperidines]" Aug. 1968, pp. 467-468, vol. 5.
Office Action issued May 22, 2012, in Japanese Patent Application No. 2007-522363.
U.S. Appl. No. 13/468,140, filed May 10, 2012, Kiyoto, et al.

*Primary Examiner* — Douglas M Willis
(74) *Attorney, Agent, or Firm* — Oblon, Spivak, McClelland, Maier & Neustadt, L.L.P.

(57) ABSTRACT

A nitrogen-containing heterocyclic compound or pharmaceutically acceptable salt thereof represented by the general formula:

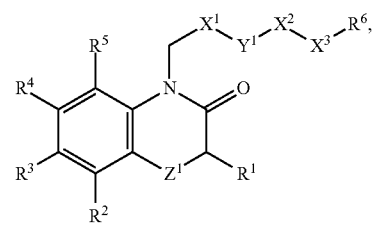

which have a potent antibacterial activity and a high safety. Thus, the compounds are useful as antibacterial agents against gram-positive bacteria, gram-negative bacteria and drug resistant bacteria.

9 Claims, No Drawings

QUINOLINONES AND QUINOXALINONES AS ANTIBACTERIAL COMPOSITION

CROSS-REFERENCE TO RELATED APPLICATIONS

The present application is division of U.S. Ser. No. 11/993,652 (now U.S. Pat. No. 8,329,694), filed Dec. 21, 2007, which is a National Stage (371) of PCT/JP2006/312515, filed on Jun. 22, 2006, and claims priority to JP 2005-184542, filed on Jun. 24, 2005, and JP 2006-076850, filed on Mar. 20, 2006.

BACKGROUND OF THE INVENTION

1. Field of the Invention

The present invention relates to novel compounds or salts thereof having strong antibacterial activities against gram-positive bacteria, gram-negative bacteria and drug resistant bacteria, and antibacterial agents comprising the same.

2. Description of Related Art

Various antibacterial agents and synthetic antibacterial agents have been used in the treatment of infectious diseases by those involved in health care. However, various drug resistant bacteria such as methicillin-resistant *Staphylococcus aureus* (MRSA), vancomycin-resistant *Enterococci* (VRE) and penicillin-resistant *Streptococcus pneumoniae* (PRSP) have been emerging in recent years. It is a critical issue for physicians to treat patients who are infected with such drug resistant bacteria. Moreover, the emergence of multiply resistant bacteria, which have gained resistance to multiple drugs, is of serious concern worldwide as they cause intractable infectious diseases.

The development of antibiotics which are effective against the above mentioned drug resistant bacteria has been long-awaited. For example, the International Publication No. WO99/07682 (Patent Document 1) discloses the quinolone type compounds which are effective against MRSA. Moreover, in International Publication No. WO2004/002490 (Patent Document 2) and International Publication No. WO2004/002992 (Patent Document 3), the compounds which do not work by any known mechanisms of action have been described.

[Patent Document 1] International Publication No. WO99/07682

[Patent Document 2] International Publication No. WO2004/002490

[Patent Document 3] International Publication No. WO2004/002992

It is desired to develop a long-awaited agent which has sufficient safety and strong antibacterial activities against gram-positive bacteria, gram-negative bacteria and drug resistant bacteria.

BRIEF SUMMARY OF THE INVENTION

Under the circumstances, as a result of intensive study, the present inventors discovered that the compounds represented by the general formula

[Formula 1]

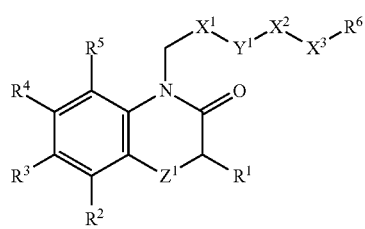

wherein the dashed line represents a single bond or a double bond; $R^1$, $R^2$, $R^3$, $R^4$ and $R^5$ are the same or different and represent a hydrogen atom, a halogen atom, a hydroxyl group, a nitro group, a formyl group, an amino group which may be protected or substituted, a lower alkyl, cycloalkyl, aryl, lower alkoxy, cycloalkyloxy, aralkyloxy, alkanoyl, ureido or monocyclic heterocyclic group which may be substituted or a group represented by the general formula $-Q^1-CONR^7R^8$, $-Q^1-CO_2R^9$ or $-Q^1-CN$ (wherein $R^7$ and $R^8$ are the same or different and represent a hydrogen atom, a lower alkyl, cycloalkyl, aralkyl, aryl, lower alkoxy, alkanesulfonyl or monocyclic heterocyclic group which may be substituted, or $R^7$ and $R^8$, together with the nitrogen atom to which they are attached, represent a cyclic amino group which may be substituted; $R^9$ represents a hydrogen atom or a carboxyl protective group; $Q^1$ represents a lower alkylene or lower alkenylene group which may be substituted, a lower oxyalkylene group which is attached to the ring via a terminal oxygen atom and which may be substituted or a bond); $R^6$ represents a lower alkyl, aryl, monocyclic heterocyclic, bicyclic heterocyclic or tricyclic heterocyclic group which may be substituted; $X^1$ represents a lower alkylene group which may be substituted with one or more groups selected from a hydroxyl and a carboxyl groups which may be protected, a lower alkyl group, a lower alkenyl group, a lower alkynyl group, a lower alkoxy group and an aryl group; $X^2$ represents a lower alkylene, lower alkenylene or lower alkynylene group which may be substituted; $X^3$ represents an oxygen atom, a sulfur atom, a sulfinyl group, a sulfonyl group, a group represented by the general formula $NR^{10}$ (wherein $R^{10}$ represents a hydrogen atom, a lower alkyl or lower alkynyl group which may be substituted or an imino protective group) or a bond; $Y^1$ represents a group represented by the general formula

[Formula 2]

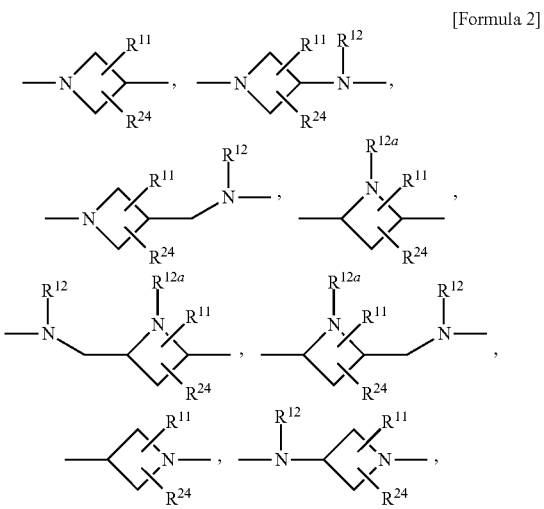

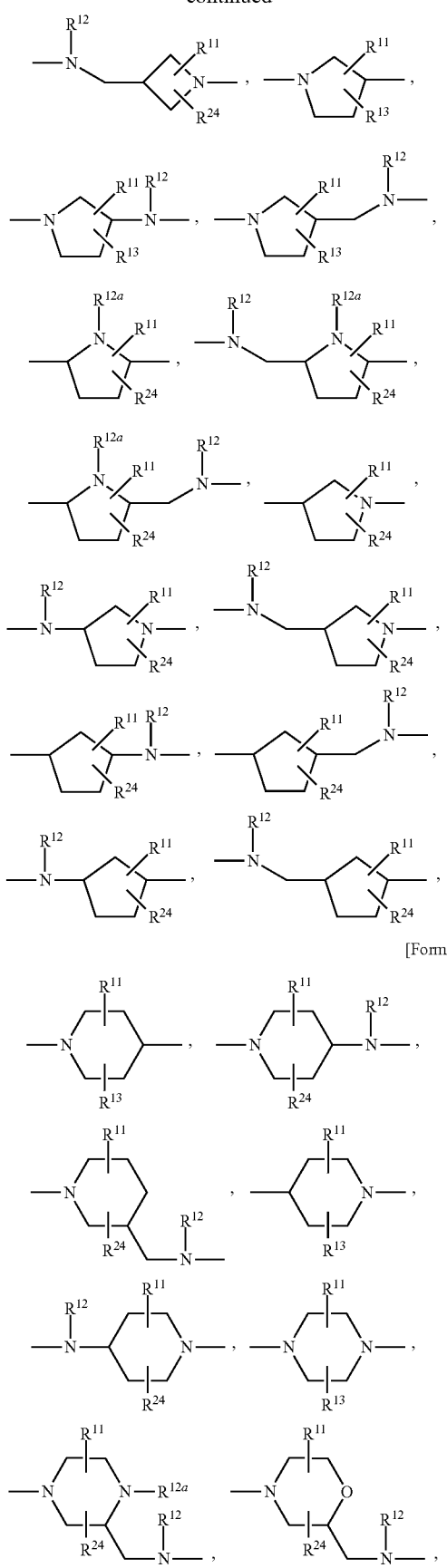

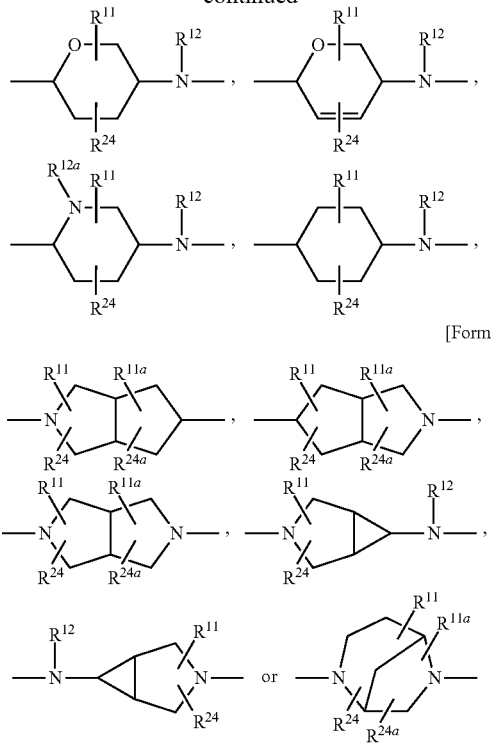

[Formula 4]

(wherein $R^{11}$, $R^{11a}$, $R^{24}$ and $R^{24a}$ are the same or different and represent a hydrogen atom, a halogen atom, a hydroxyl group, an amino, lower alkyl or lower alkoxy group which may be substituted, an oxo group or a group represented by the general formula $-Q^2-CONR^{14}R^{15}$, $-Q^2-CO_2R^{16}$ or $-Q^2-CN$ (wherein $R^{14}$ and $R^{15}$ are the same or different and represent a hydrogen atom, a lower alkyl, cycloalkyl, aralkyl, aryl, lower alkoxy, alkanesulfonyl or monocyclic heterocyclic group which may be substituted, or $R^{14}$ and $R^{15}$, together with the nitrogen atom to which they are attached, represent a cyclic amino group which may be substituted; $R^{16}$ represents a hydrogen atom or a carboxyl protective group; $Q^2$ represents a lower alkylene or lower alkenylene group which may be substituted, a lower oxyalkylene group which is attached to the ring via a terminal oxygen atom and which may be substituted or a bond); $R^{12}$ and $R^{12a}$ are the same or different and represent a hydrogen atom, a lower alkyl or lower alkynyl group which may be substituted or an imino protective group; $R^{13}$ represents a halogen atom, a hydroxyl group, an amino, lower alkyl or lower alkoxy group which may be substituted, an oxo group or a group represented by the general formula $-Q^3-CONR^{17}R^{18}$, $-Q^3CO_2R^{19}$ or $-Q^3-CN$ (wherein $R^{17}$ and $R^{18}$ are the same or different and represent a hydrogen atom, a lower alkyl, cycloalkyl, aralkyl, aryl, lower alkoxy, alkanesulfonyl or monocyclic heterocyclic group which may be substituted, or $R^{17}$ and $R^{18}$, together with the nitrogen atom to which they are attached, represent a cyclic amino group which may be substituted; $R^{19}$ represents a hydrogen atom or a carboxyl protective group; $Q^3$ represents a lower alkylene or lower alkenylene group which may be substituted, a lower oxyalkylene group which is attached to the ring via a terminal oxygen atom and which may be substituted or a bond); or $R^{11}$ and $R^{24}$ together and $R^{12a}$ and $R^{24}$ together represent a lower alkylene group which may be substituted); $Z^1$ represents (1) when the dashed line represents a double bond, a nitrogen atom or a group represented by the general formula $CR^{20}$ (wherein $R^{20}$ represents a hydrogen atom, a halogen atom, a hydroxyl group, a nitro group, a formyl group, an amino group which may be protected or substituted, a lower alkyl, cycloalkyl, aryl, lower alkoxy, cycloalkyloxy, aralkyloxy, alkanoyl, ureido or monocyclic heterocyclic group which may be substituted or a group represented by the general formula $-Q^4-CONR^{21}R^{22}$, $-Q^4-CO_2R^{23}$ or $-Q^4-CN$ (wherein $R^{21}$ and $R^{22}$ are the same or different and represent a hydrogen atom, a lower alkyl, cycloalkyl, aralkyl, aryl, lower alkoxy, alkanesulfonyl or monocyclic heterocyclic group which may be substituted, or $R^{21}$ and $R^{22}$, together with the nitrogen atom to which they are attached, represent a cyclic amino group which may be substituted; $R^{23}$ represents a hydrogen atom or a carboxyl protective group; $Q^4$ represents a lower alkylene or lower alkenylene group which may be substituted, a lower oxyalkylene group which is attached to the ring via a terminal oxygen atom and which may be substituted or a bond)); (2) when the dashed line represents a single bond, a group represented by the general formula $NR^{40}$ (wherein $R^{40}$ represents a hydrogen atom, a hydroxyl group, a lower alkyl, cycloalkyl, lower alkenyl, lower alkynyl, aryl, lower alkoxy, cycloalkyloxy or monocyclic heterocyclic group which may be substituted or an imino protective group) or a group represented by the general formula $CHR^{20}$ (wherein $R^{20}$ is as defined above), or salts thereof have strong antibacterial activities and sufficient safety. Based on this scientific knowledge, the inventors have achieved the present invention.

The compound represented by the general formula [1] or a salt thereof is useful as an antibiotic agent due to its strong antibacterial activities and sufficient safety. Moreover, the compound represented by the general formula [1] or a salt thereof has certain properties which make it a more promising antibiotic agent, including strong antibacterial activities against drug resistant bacteria such as MRSA and significant tissue permeability.

DETAILED DESCRIPTION OF THE INVENTION

The compounds of the present invention will now be described hereinafter.

In this description, unless otherwise specified, a halogen atom refers to a fluorine atom, a chlorine atom, a bromine atom and an iodine atom; an alkyl group refers to, for example, a linear or branched $C_{1-12}$ alkyl group such as methyl, ethyl, propyl, isopropyl, butyl, sec-butyl, isobutyl, tert-butyl, pentyl, hexyl and octyl; a lower alkyl group refers to, for example, a linear or branched $C_{1-6}$ alkyl group such as methyl, ethyl, propyl, isopropyl, butyl, sec-butyl, isobutyl, tert-butyl, pentyl and isopentyl; an alkenyl group refers to, for example, a linear or branched $C_{2-12}$ alkenyl group such as vinyl, allyl, propenyl, isopropenyl, butenyl, isobutenyl, pentenyl, hexenyl, heptenyl and octenyl; a lower alkenyl group refers to, for example, a linear or branched $C_{2-6}$ alkenyl group such as vinyl, allyl, propenyl, isopropenyl, butenyl, isobutenyl, pentenyl and hexenyl; a lower alkynyl group refers to, for example, a linear or branched $C_{2-6}$ alkynyl group such as ethynyl, 2-propynyl and 2-butynyl; a cycloalkyl group refers to, for example, a $C_{3-8}$ cycloalkyl group such as cyclopropyl, cyclobutyl, cyclopentyl and cyclohexyl; an aryl group refers to, for example, phenyl, naphthyl, dihydronaphthyl, anthracenyl and phenanthryl; an aralkyl group refers to, for example, an ar-$C_{1-6}$ alkyl group such as benzyl, diphenylmethyl, trityl, phenethyl and naphthylmethyl;

a lower alkoxy group refers to, for example, a linear or branched $C_{1-6}$ alkyloxy group such as methoxy, ethoxy, propoxy, isopropoxy, butoxy, isobutoxy, sec-butoxy, tert-butoxy, pentyloxy and isopentyloxy; a cycloalkyloxy group refers to, for example, a $C_{3-8}$ cycloalkyloxy group such as cyclopropyloxy, cyclobutyloxy, cyclopentyloxy and cyclohexyloxy; an aralkyloxy group refers to, for example, an ar-$C_{1-6}$ alkyloxy group such as benzyloxy and phenethyloxy; an alkoxyalkyl group refers to, for example, a $C_{1-6}$ alkyloxy $C_{1-6}$ alkyl group such as methoxymethyl and 1-ethoxyethyl; an aralkyloxyalkyl group refers to, for example, an ar-$C_{1-6}$ alkyloxy $C_{1-6}$ alkyl group such as benzyloxymethyl and phenethyloxymethyl; a lower alkylene group refers to, for example, a $C_{1-6}$ alkylene group such as methylene, ethylene, propylene, butylene and hexylene; a lower alkenylene group refers to, for example, a $C_{2-6}$ alkenylene group such as vinylene, propenylene, butenylene and pentenylene; a lower alkynylene group refers to, for example, a $C_{2-6}$ alkynylene group such as ethynylene, propynylene, butynylene and pentynylene; a lower oxyalkylene group refers to, for example, an —O—$C_{1-6}$ alkylene group such as oxymethylene, oxyethylene, oxypropylene, oxybutylene and oxyhexylene;

an alkanoyl group refers to, for example, a linear or branched $C_{2-12}$ alkanoyl group such as acetyl, propionyl, butyryl, isovaleryl and pivaloyl; an acyl group refers to, for example, a formyl group, a linear or branched $C_{2-12}$ alkanoyl group such as acetyl, propionyl, butyryl, isovaleryl and pivaloyl, an ar-$C_{1-6}$ alkylcarbonyl group such as benzylcarbonyl, a cyclic hydrocarbon carbonyl group such as benzoyl and naphthoyl, a heterocyclic carbonyl group such as nicotinoyl, thenoyl, pyrrolidinocarbonyl and furoyl, a succinyl group, a glutaryl group, a maleoyl group, a phthaloyl group, and a linear or branched α-aminoalkanoyl group which is derived from an amino acid (examples of an amino acid includes glycine, alanine, valine, leucine, isoleucine, serine, threonine, cysteine, methionine, asparagine acid, glutamic acid, asparagine, glutamine, arginine, lysine, histidine, hydroxylysine, phenylalanine, tyrosine, tryptophan, proline and hydroxyproline), wherein the N-terminal may be protected;

an acylalkyl group refers to, for example, a group such as acetylmethyl, benzoylmethyl, p-nitrobenzoylmethyl, p-bromobenzoylmethyl, p-methoxybenzoylmethyl and 1-benzoylethyl; an acyloxy group refers to, for example, a linear or branched $C_{2-6}$ alkanoyloxy group such as acetyloxy and propionyloxy, and an aroyloxy group such as benzoyloxy; an acyloxyalkyl group refers to, for example, a group such as acetoxymethyl, propionyloxymethyl and pivaloyloxymethyl;

an alkyloxycarbonyl group refers to, for example, a linear or branched $C_{1-12}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl and tert-pentyloxycarbonyl; an aralkyloxycarbonyl group refers to, for example, an ar-$C_{1-6}$ alkyloxycarbonyl group such as benzyloxycarbonyl and phenethyloxycarbonyl; an aryloxycarbonyl group refers to, for example, a group such as phenyloxycarbonyl;

an alkylthio group refers to, for example, a $C_{1-6}$ alkylthio group such as methylthio, ethylthio and propylthio; an arylthio group refers to, for example, a group such as phenylthio; an alkylthioalkyl group refers to, for example, a $C_{1-6}$ alkylthio $C_{1-6}$ alkyl group such as methylthiomethyl, ethylthiomethyl and propylthiomethyl; an arylthioalkyl group refers to, for example, a group such as (phenylthio)methyl and 2-(p-nitrophenylthio)ethyl; an alkanesulfonyl group refers to, for example, a $C_{1-6}$ alkanesulfonyl group such as methanesulfonyl, ethanesulfonyl and propanesulfonyl; an arylsulfonyl group refers to, for example, a group such as benzenesulfonyl, toluenesulfonyl and naphthalenesulfonyl;

an arylsulfonylalkyl group refers to, for example, a group such as p-toluenesulfonylethyl; an alkanesulfonyloxy group refers to, for example, a $C_{1-6}$ alkanesulfonyloxy group such as methanesulfonyloxy, trifluoromethanesulfonyloxy and ethanesulfonyloxy; an arylsulfonyloxy group refers to, for example, a group such as benzenesulfonyloxy and toluenesulfonyloxy;

a lower alkylamino group refers to, for example, a mono $C_{1-6}$ alkylamino group such as methylamino, ethylamino, propylamino, isopropylamino, butylamino, tert-butylamino and pentylamino, a $C_{3-6}$ cycloalkylamino group such as cyclopropylamino, cyclobutylamino and cyclopentylamino, and a di $C_{1-6}$ alkylamino group such as dimethylamino, diethylamino, dipropylamino and dibutylamino; a cyclic amino group refers to, for example, a group such as piperazinyl, piperidinyl, morpholino and pyrrolidinyl; a nitrogen-containing heterocyclic group refers to, for example, a group such as piperazinyl, piperidinyl, morpholino, pyrrolidinyl, imidazol-1-yl and triazol-1-yl; an oxygen-containing heterocyclic group refers to, for example, a group such as 2-tetrahydropyranyl and 2-tetrahydrofuranyl; a sulfur-containing heterocyclic group refers to, for example, a group such as tetrahydrothiopyranyl;

an oxygen-containing heterocyclic alkyl group refers to, for example, a group such as 5-methyl-2-oxo-2H-1,3-dioxol-4-ylmethyl; a nitrogen-containing heterocyclic alkyl group refers to, for example, a group such as phthalimidomethyl and succinimidomethyl; a heterocyclicoxycarbonyl group refers to, for example, a group such as 2-furfuryloxycarbonyl and 8-quinolyloxycarbonyl;

a cycloalkylidene group refers to, for example, a group such as cyclopentylidene and cyclohexylidene; an aralkylidene group refers to, for example, a group such as benzylidene and naphthylmethylene; a dialkylaminoalkylidene group refers to, for example, a group such as N,N-dimethylaminomethylene and N,N-diethylaminomethylene;

a nitrogen-containing heterocyclic alkylidene group refers to, for example, a group such as 3-hydroxy-4-pyridylmethylene; a diarylphosphoryl group refers to, for example, a group such as diphenylphosphoryl; a diaralkylphosphoryl group refers to, for example, a group such as dibenzylphosphoryl; a substituted silyl group refers to, for example, a group such as trimethylsilyl, triethylsilyl and tributylsilyl; an alkylsilylalkyl group refers to, for example, a group such as 2-(trimethylsilyl)ethyl;

a monocyclic heterocyclic group refers to, for example, a group such as furyl, thienyl, pyrrolyl, imidazolyl, pyrazolyl, thiazolyl, isothiazolyl, oxazolyl, isoxazolyl, thiadiazolyl, furazanyl, pyrrolidinyl, imidazolidinyl, pyridyl, pyrimidinyl, pyridazinyl, pyrazinyl, piperazinyl, piperidyl, morpholinyl and thiomorpholinyl; a bicyclic heterocyclic group refers to, for example, a group such as thieno[2,3-b]thienyl, thieno[3,2-b]thienyl, 1H-thieno[2,3-c]pyrazolyl, benzofuranyl, 2,3-dihydrobenzofuranyl, isobenzofuranyl, benzothienyl, indolinyl, isoindolinyl, indolizinyl, benzimidazolyl, benzoxazolyl, benzisoxazolyl, benzothiazolyl, benzoisothiazolyl, 1H-indazolyl, purinyl, coumarinyl, phthalazinyl, naphthyridinyl, quinoxalinyl, quinazolinyl, cinnolinyl, chromanyl, isochromanyl, chromenyl, thiochromenyl, quinuclidinyl, 1,3-benzodioxolyl, 1H-1,2,3-benzotriazolyl, 2,1,3-benzothiadiazolyl, 2,1,3-benzoxadiazolyl, 1,3-benzodioxanyl, 1,4-benzodioxanyl, 1,4-benzodioxinyl, benzomorpholinyl, quinolyl, isoquinolyl, 1,2,3,4-tetrahydroquinolyl, 2,3-dihydro[1,4]dioxino[2,3-b]pyridyl, 2,3-dihydro[1,4]dioxino[2,3-c]pyridyl, 3,4-dihydro-2H-1,4-benzoxadinyl, 3,4-dihydro-2H-1,4-benzothiadinyl, 2,3-dihydro-1H-pyrido[2,3-b][1,4]oxadinyl, 2,3-dihydro-1H-pyrido[3,4-b][1,4]oxadinyl, 2,3-dihydro-1H-pyrido[2,3-b][1,4]b][1,4]thiadinyl, 3,4-dihydro-2H-pyrido[3,2-b][1,4]oxadinyl, 3,4-dihydro-2H-pyrido[3,2-b][1,4]thiadinyl, 2,3-dihydro-1,4-benzodithiinyl, 3,4-dihydro-2H-benzo[b][1,5]dioxepynyl and 3,4-dihydro-2H-[1,4]dioxepyno[2,3-c]pyridyl; a tricyclic heterocyclic group refers to, for example, a group such as thianthrenyl, xanthenyl, phenoxathiinyl, 4aH-carbazolyl, carbazolyl, phenanthridinyl, acridinyl, perimidinyl, phenanthrolinyl, phenazinyl, phenothiazinyl, phenoxazinyl and 2,3-dihydro-(1H,5H)-benzo[IJ]quinolyl;

a carbonyl group which is protected refers to, for example, a group consisting of an alcohol and a carbonyl group such as dimethoxymethylene, diethoxymethylene, bis(benzyloxy)methylene, 1,3-dioxolan-2-ylidene and 1,3-dioxan-2-ylidene, a group consisting of a thiol and a carbonyl group such as bis(methylthio)methylene, bis(ethylthio)methylene, bis(benzylthio)methylene, 1,3-dithiolan-2-ylidene and 1,3-dithian-2-ylidene, and a group such as oxazolin-2-ylidene, imidazolidin-2-ylidene and thiazolidin-2-ylidene.

An imino protective group includes any group which can be normally used as a protective group of an imino group, for example, the groups described in W. Greene et al. "Protective Groups in Organic Synthesis" Third Edition, pp. 494 to 653, John Wiley & Sons, INC., 1999. More specifically, examples of an imino protective group include an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkanesulfonyl group, an arylsulfonyl group, a diarylphosphoryl group, a diaralkylphosphoryl group, an oxygen-containing heterocyclic alkyl group and a substituted silyl group.

An amino protective group includes any group which can be normally used as a protective group of an amino group, for example, the groups described in W. Greene et al. "Protective Groups in Organic Synthesis" Third Edition, pp. 494 to 653, John Wiley & Sons, INC., 1999. More specifically, examples of an amino protective group include an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkanesulfonyl group, an arylsulfonyl group, a dialkylaminoalkylidene group, an aralkylidene group, a nitrogen-containing heterocyclic alkylidene group, a cycloalkylidene group, a diarylphosphoryl group, a diaralkylphosphoryl group, an oxygen-containing heterocyclic alkyl group and a substituted silyl group.

A hydroxyl protective group includes any group which can be normally used as a protective group of a hydroxyl group, for example, the groups described in W. Greene et al. "Protective Groups in Organic Synthesis" Third Edition, pp. 17 to 245, John Wiley & Sons, INC., 1999. More specifically, examples of a hydroxyl protective group include an acyl group, an alkyloxycarbonyl group, an aralkyloxycarbonyl group, a heterocyclicoxycarbonyl group, an alkyl group, an alkenyl group, an aralkyl group, an oxygen-containing heterocyclic group, a sulfur-containing heterocyclic group, an alkoxyalkyl group, an aralkyloxyalkyl group, an alkanesulfonyl group, an arylsulfonyl group and a substituted silyl group.

A carboxyl protective group includes any group which can be normally used as a protective group of a carboxyl group, for example, the groups described in W. Greene et al. "Protective Groups in Organic Synthesis" Third Edition, pp. 369 to 453, John Wiley & Sons, INC., 1999. More specifically, examples of a carboxyl protective group include an alkyl group, an aryl group, an aralkyl group, an acylalkyl group, an arylthioalkyl group, an arylsulfonylalkyl group, an oxygen-containing heterocyclic group, an alkylsilylalkyl group, an acyloxyalkyl group, a nitrogen-containing heterocyclic alkyl group, a cycloalkyl group, an alkoxyalkyl group, an aralkyloxyalkyl group, an alkylthioalkyl group, an alkenyl group and a substituted silyl group.

Examples of a leaving group include a halogen atom, an alkanesulfonyloxy group, an arylsulfonyloxy group and an acyloxy group.

A salt of a compound of general formula [1] includes commonly known salts formed from a basic group such as an amino group, or from an acidic group such as a phenolic hydroxyl group and a carboxyl group.

Examples of salts formed with a basic group include salts with mineral acid such as hydrochloric acid, hydrobromic acid and sulfuric acid; salts with organic carboxylic acid such as tartaric acid, formic acid, acetic acid, citric acid, trichloroacetic acid and trifluoroacetic acid; and salts with sulfonic acid such as methanesulfonic acid, benzenesulfonic acid, p-toluenesulfonic acid, mesitylenesulfonic acid and naphthalenesulfonic acid.

Examples of salts formed with an acidic group include salts with alkaline metal such as sodium and potassium; salts with alkaline earth metal such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine and N,N'-dibenzylethylenediamine.

Moreover, among the above described salts, a preferable salt of a compound of general formula [1] is a pharmaceutically acceptable salt thereof.

A substituent group for a lower alkyl, cycloalkyl, aryl, lower alkoxy, cycloalkyloxy, aralkyloxy, alkanoyl, ureido and monocyclic heterocyclic group in $R^1$, $R^2$, $R^3$, $R^4$, $R^5$ and $R^{20}$ includes one or more groups selected from a halogen atom, a hydroxyl and carboxyl group which may be protected, a lower alkyl, lower alkenyl, lower alkynyl and lower alkoxy group which may be substituted with a halogen atom, a hydroxyimino group, a lower alkyl, lower alkenyl and lower alkynyl group which may be substituted with an aryl group, an aryl group, a monocyclic heterocyclic group and the like. Preferable substituent groups include one or more groups selected from a halogen atom, a hydroxyl and carboxyl group which may be protected, a lower alkyl group which may be substituted with a halogen atom, and a hydroxyimino group. More preferable substituent groups include one or more groups selected from a halogen atom, a hydroxyl group, a methyl group, an ethyl group and a hydroxyimino group.

A substituent group for a lower alkyl, cycloalkyl, lower alkenyl, lower alkynyl, aryl, lower alkoxy, cycloalkyloxy and monocyclic heterocyclic group in $R^{40}$ includes one or more groups selected from a halogen atom, a hydroxyl and carboxyl group which may be protected, a lower alkyl, lower alkenyl, lower alkynyl and lower alkoxy group which may be substituted with a halogen atom, a hydroxyimino group, a lower alkyl, lower alkenyl and lower alkynyl group which may be substituted with an aryl group, an aryl group, a monocyclic heterocyclic group and the like. Preferable substituent groups include one or more groups selected from a halogen atom, a hydroxyl and carboxyl group which may be protected, a lower alkyl group which may be substituted with a halogen atom and a hydroxyimino group. More preferable substituent groups include one or more groups selected from a halogen atom, a hydroxyl group, a methyl group, an ethyl group and a hydroxyimino group.

A substituent group for an amino group in $R^1$, $R^2$, $R^3$, $R^4$, $R^5$, $R^{11}$, $R^{11a}$, $R^{13}$, $R^{20}$, $R^{24}$ and $R^{24a}$ includes one or more groups selected from a lower alkyl, lower alkenyl, lower alkynyl, acyl, alkyloxycarbonyl, aryl and monocyclic heterocyclic group which may be substituted with a halogen atom. Preferable substituent groups include one or more groups selected from a lower alkyl, lower alkenyl, acyl, alkyloxycarbonyl and aryl group which may be substituted with a halogen atom. More preferable substituent groups include one or more groups selected from a methyl group, an ethyl group, a trifluoromethyl group, a formyl group, an acetyl group, a methoxycarbonyl group and an ethoxycarbonyl group.

A substituent group for a lower alkyl group, an aryl group, a monocyclic heterocyclic group, a bicyclic heterocyclic group and a tricyclic heterocyclic group in $R^6$ includes one or more groups selected from a halogen atom, a hydroxyl and carboxyl group which may be protected, a lower alkyl, lower alkenyl, lower alkynyl and lower alkoxy group which may be substituted with a halogen atom, an alkylthio group, an amino group, a lower alkylamino group, an acyl group, an aryl group, a monocyclic heterocyclic group and an oxo group. Preferable substituent groups include one or more groups selected from a halogen atom, a hydroxyl and carboxyl group which may be protected, a lower alkyl, lower alkenyl and lower alkoxy group which may be substituted with a halogen atom, an alkylthio group, an amino group, a lower alkylamino group, an acyl group, an aryl group, a monocyclic heterocyclic group and an oxo group. More preferable substituent groups include one or more groups selected from a halogen atom, a hydroxyl group, a carboxyl group, a methyl group, an ethyl group, a tert-butyl group, a vinyl group, a trifluoromethyl group, a methoxy group, an ethoxy group, a trifluoromethoxy group, a methylthio group, an amino group, a dimethylamino group, an acetyl group, a phenyl group, a thienyl group, a pyrrolidinyl group, a benzylpiperazinyl group and an oxo group.

A substituent group for a lower alkyl, cycloalkyl, aralkyl, aryl, lower alkoxy, alkanesulfonyl and monocyclic heterocyclic group in $R^7$, $R^8$, $R^{14}$, $R^{15}$, $R^{17}$, $R^{18}$, $R^{21}$ and $R^{22}$ includes one or more groups selected from a halogen atom, a hydroxyl and carboxyl group which may be protected, lower alkyl, lower alkenyl, lower alkynyl and lower alkoxy group which may be substituted with a halogen atom, an aryl group, a monocyclic heterocyclic group and the like. Preferable substituent groups include one or more groups selected from a halogen atom, a hydroxyl and carboxyl group which may be protected, a lower alkyl and lower alkoxy group which may be substituted with a halogen atom, an aryl group and a monocyclic heterocyclic group. More preferable substituent groups include one or more groups selected from a halogen atom, a hydroxyl group, a methyl group, an ethyl group, a methoxy group, a phenyl group and a pyridyl group.

A substituent group for a cyclic amino group which is formed by $R^7$ and $R^8$, $R^{14}$ and $R^{15}$, $R^{17}$ and $R^{18}$ as well as $R^{21}$ and $R^{22}$, together with the nitrogen atom to which they are attached, includes one or more groups selected from a halogen atom, a hydroxyl and carboxyl group which may be protected, a lower alkyl, lower alkenyl, lower alkynyl and lower alkoxy group which may be substituted with a halogen atom, an acyl group, an amino group, a lower alkylamino group, an alkylthio group, an aryl group, a monocyclic heterocyclic group, an oxo group and the like. Preferable substituent groups include one or more groups selected from a halogen atom, a hydroxyl and carboxyl group which may be protected, a lower alkyl, lower alkenyl and lower alkoxy group which may be substituted with a halogen atom, an alkanoyl group, a lower alkylamino group, an aryl group, an oxo group and the like. More preferable substituent groups include one or more groups selected from a halogen atom, a hydroxyl group, a carboxyl group, a methyl group, an ethyl group, a methoxy group, an ethoxy group, a dimethylamino group, a phenyl group, an oxo group and the like.

A substituent group for a lower alkyl group and a lower alkynyl group in $R^{10}$, $R^{12}$ and $R^{12a}$ includes one or more groups selected from a halogen atom, a hydroxyl and carboxyl group which may be protected, a lower alkyl, lower alkenyl, lower alkynyl and lower alkoxy group which may be substituted with a halogen atom, an aryl group, a monocyclic heterocyclic group, an oxo group and the like. Preferable substituent groups include one or more groups selected from a halogen atom, a hydroxyl and carboxyl group which may be protected, a lower alkyl group which may be substituted with a halogen atom, an aryl group, an oxo group and the like. More preferable substituent groups include one or more groups selected from a halogen atom, a methyl group, an ethyl group, a phenyl group and the like.

A substituent group for a lower alkyl group and a lower alkoxy group in $R^{11}$, $R^{11a}$, $R^{13}$, $R^{24}$ and $R^{24a}$ includes one or more groups selected from a halogen atom, a hydroxyl and carboxyl group which may be protected, a lower alkoxy group which may be substituted with a halogen atom, an aryl group, a monocyclic heterocyclic group and the like. Preferable substituent groups include one or more groups selected from a halogen atom and a hydroxyl and carboxyl group which may be protected. More preferable substituent groups include one or more groups selected from a halogen atom and a hydroxyl group.

A substituent group for a lower alkylene group which is formed by $R^{11}$ and $R^{24}$ together and $R^{12a}$ and $R^{24}$ together includes one or more groups selected from a halogen atom, a lower alkyl group which may be substituted with a halogen atom, an oxo group and the like. Preferable substituent groups include one or more groups selected from a halogen atom and an oxo group. More preferable substituent groups include an oxo group.

A substituent group for a lower alkylene group, a lower alkenylene group, and a lower oxyalkylene group which is attached to the ring via a terminal oxygen atom in $Q^1$, $Q^2$, $Q^3$ and $Q^4$ includes one or more groups selected from an oxo group, a hydroxyl and carboxyl group which may be protected, a lower alkyl group, a lower alkenyl group, a lower alkynyl group, a lower alkoxy group, an aryl group and the like. Preferable substituent groups include one or more groups selected from an oxo group, a hydroxyl and carboxyl group which may be protected, a lower alkyl group, a lower alkoxy group and an aryl group. More preferable substituent groups include one or more groups selected from an oxo group, a hydroxyl group, a carboxyl group, a methyl group, a methoxy group and a phenyl group.

A substituent group for a lower alkylene group, a lower alkenylene group and a lower alkynylene group in $X^2$ includes one or more groups selected from a hydroxyl and a carboxyl groups which may be protected, a lower alkyl, lower alkenyl, lower alkynyl and lower alkoxy group which may be substituted with a halogen atom, an aryl group, an oxo group and the like. Preferable substituent groups include one or more groups selected from a lower alkyl group which may be substituted with a halogen atom, an aryl group and an oxo group. More preferable substituent groups include one or more groups selected from a methyl group, an ethyl group and an oxo group.

Preferred compounds represented by the general formula [1] in the present invention are described hereinafter.

In a preferred compound, the dashed line represents a double bond.

In a preferred compound, $R^1$, $R^2$, $R^3$, $R^4$ and $R^5$ are the same or different and represent a hydrogen atom, a halogen atom, a hydroxyl group, a cyano group, an amino, lower alkyl or lower alkoxy group which may be substituted or a group represented by the general formula -$Q^{1a}$-$CONR^{7a}R^{8a}$ or -$Q^{1a}$-$CO_2R^9$ (wherein $R^{7a}$ and $R^{8a}$ are the same or different and represent a hydrogen atom, a lower alkyl, cycloalkyl, aralkyl or aryl group which may be substituted, or $R^{7a}$ and $R^{8a}$, together with the nitrogen atom to which they are attached, represent a cyclic amino group which may be substituted; $R^9$ represents a hydrogen atom or a carboxyl protective group; $Q^{1a}$ represents a lower alkylene or lower alkenylene group which may be substituted or a bond); in a more preferred compound, $R^1$, $R^2$, $R^3$, $R^4$ and $R^5$ are the same or different and represent a hydrogen atom, a halogen atom, a lower alkyl or lower alkoxy group which may be substituted, or a group represented by the general formula -$Q^{1a}$-$CONR^{7a}R^{8a}$ (wherein $R^{7a}$, $R^{8a}$ and $Q^{1a}$ are as defined above); in an even more preferred compound, $R^1$ represents a hydrogen atom or a lower alkyl group, $R^2$, $R^3$, $R^4$ and $R^5$ are the same or different and represent a hydrogen atom, a halogen atom, or a lower alkoxy group which may be substituted.

In a preferred compound, $R^1$ represents a hydrogen atom.

In a preferred compound, $R^2$ represents a hydrogen atom, or a compound represented by the general formula —$CONR^{7b}R^{8b}$ (wherein $R^{7b}$ and $R^{8b}$ are the same or different and represent a hydrogen atom, or a lower alkyl group which may be substituted). In a more preferred compound, $R^2$ represents a hydrogen atom.

In a preferred compound, $R^3$ represents a hydrogen atom.

In a preferred compound, $R^4$ represents a halogen atom or a lower alkoxy group.

In a preferred compound, $R^5$ represents a hydrogen atom, or a lower alkoxy group which may be substituted. In a more preferred compound, $R^5$ represents a hydrogen atom or a lower alkoxy group.

In a preferred compound, $R^6$ represents an aryl, monocyclic heterocyclic or bicyclic heterocyclic group which may be substituted. In a more preferred compound, $R^6$ represents a 3-fluoro-4-methylphenyl, 3-fluoro-4-(trifluoromethyl)phenyl, 4-ethylphenyl, naphthyl, 5-fluoro-6-methylpyridin-3-yl, 5-chloro-6-methylpyridin-3-yl, benzo[b]thiophen-2-yl, 5-(thiophen-2-yl)isoxazol-3-yl, thieno[3,2-b]thiophene, 2,3-dihydro-1,4-benzodithiin-6-yl, 2,3-dihydrobenzo-1,4-dioxin-6-yl, benzo[1,3]dioxol-5-yl, 2,3-dihydro-1,4-dioxino[2,3-c]pyridin-7-yl, 3-oxo-3,4-dihydro-2H-pyrido[3,2-b][1,4]oxazin-6-yl, 3-oxo-3,4-dihydro-2H-pyrido[3,2-b][1,4]thiazin-6-yl, 7-chloro-3-oxo-3,4-dihydro-2H-pyrido[3,2-b][1,4]thiazin-6-yl, or 3-oxo-3,4-dihydro-2H-benzothiazin-6-yl group. In an even more preferred compound, $R^6$ represents a 2,3-dihydrobenzo-1,4-dioxin-6-yl or 2,3-dihydro[1,4]dioxino[2,3-c]pyridin-7-yl group. In a further preferred compound, $R^6$ represents a 2,3-dihydro[1,4]dioxino[2,3-c]pyridin-7-yl group.

In a preferred compound, $X^1$ represents a methylene group, an ethylene group or a propylene group.

In a preferred compound, $X^2$ represents a lower alkylene group which may be substituted. In a more preferred compound, $X^2$ represents a methylene, ethylene or propylene group which may be substituted. In an even more preferred compound, $X^2$ represents a methylene group, an ethylene group or a propylene group.

In a preferred compound, $X^3$ represents an oxygen atom, a sulfur atom, a sulfinyl group, a sulfonyl group, a group represented by the general formula $NR^{10a}$ (wherein $R^{10a}$ represents a hydrogen atom, a lower alkyl group which may be substituted or an imino protective group) or a bond. In a more preferred compound, $X^3$ represents a sulfur atom, an NH group or a bond. In an even more preferred compound, $X^3$ represents a bond.

In a preferred compound, $Y^1$ represents a group represented by the general formula

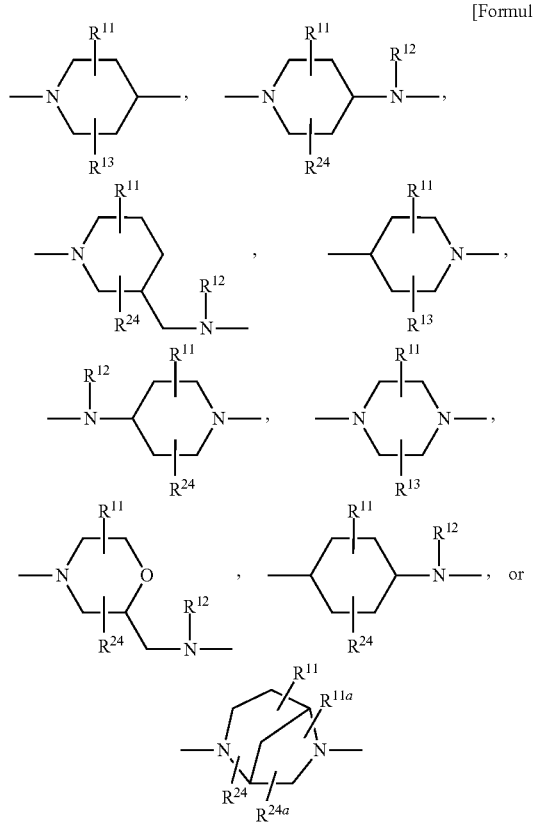

[Formula 5]

wherein $R^{11}$, $R^{11a}$, $R^{12}$, $R^{13}$, $R^{24}$ and $R^{24a}$ are as defined above. In a more preferred compound, $Y^1$ represents a group represented by the general formula

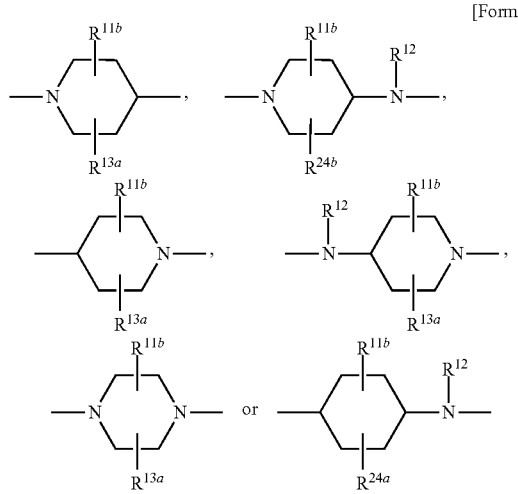

[Formula 6]

wherein $R^{11b}$ and $R^{24b}$ are the same or different and represent a hydrogen atom, a halogen atom, a hydroxyl group, an amino, lower alkyl or lower alkoxy group which may be substituted or a group represented by the general formula $-Q^2-CONR^{14}R^{15}$, $-Q^2-CO_2R^{16}$ or $-Q^2-CN$ (wherein $R^{14}$, $R^{15}$, $R^{16}$ and $Q^2$ are as defined above); $R^{13a}$ represents a group represented by the general formula $-Q^{3a}-CONR^{17a}R^{18a}$ or $-Q^{3a}CO_2R^{19}$ (wherein $R^{17a}$ and $R^{18a}$ are the same or different and represent a hydrogen atom, a lower alkyl, cycloalkyl, aralkyl or aryl group which may be substituted, or $R^{17a}$ and $R^{18a}$, together with the nitrogen atom to which they are attached, represent a cyclic amino group which may be substituted; $Q^{3a}$ represents a lower alkylene or lower alkenylene group which may be substituted or a bond; $R^{19}$ is as defined above); $R^{12}$ is as defined above. In an even more preferred compound, $Y^1$ represents a group represented by the general formula

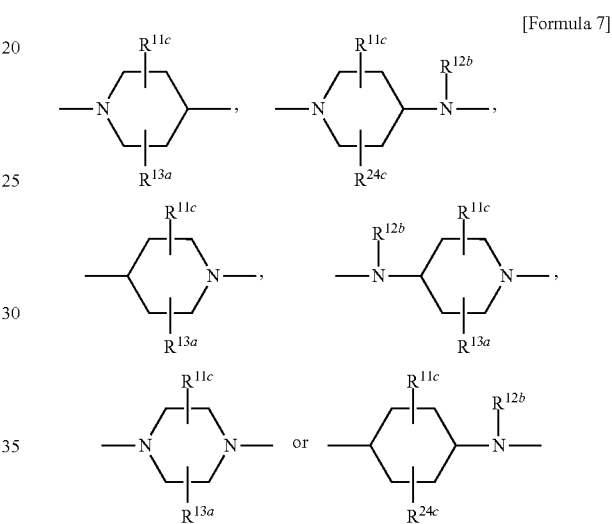

[Formula 7]

wherein $R^{11c}$ and $R^{24c}$ are the same or different and represent a hydrogen atom, a halogen atom, a hydroxyl group, a cyano group, an amino, lower alkyl or lower alkoxy group which may be substituted or a group represented by the general formula $-Q^{2a}-CONR^{14a}R^{15a}$ or $-Q^{2a}-CO_2R^{16}$ (wherein $R^{14a}$ and $R^{15a}$ are the same or different and represent a hydrogen atom, a lower alkyl, cycloalkyl, aralkyl or aryl group which may be substituted, or $R^{14a}$ and $R^{15a}$, together with the nitrogen atom to which they are attached, represent a cyclic amino group which may be substituted; $Q^{2a}$ represents a lower alkylene or lower alkenylene group which may be substituted or a bond; $R^{16}$ is as defined above); $R^{12b}$ represents a hydrogen atom, a lower alkyl group which may be substituted or an imino protective group; $R^{13a}$ is as defined above. In a further preferred compound, $Y^1$ represents a group represented by the general formula

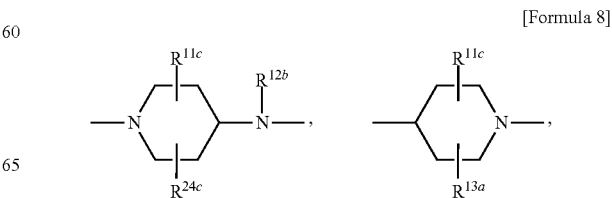

[Formula 8]

-continued

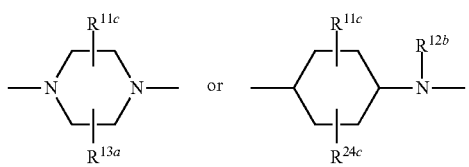

wherein $R^{11c}$, $R^{12b}$, $R^{13a}$ and $R^{24c}$ are as defined above. In an even further preferred compound, $Y^1$ represents a group represented by the general formula

[Formula 9]

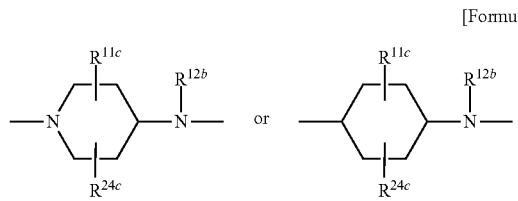

wherein $R^{11c}$, $R^{12b}$ and $R^{24c}$ are as defined above. In a most preferred compound, $Y^1$ represents a group represented by the general formula

[Formula 10]

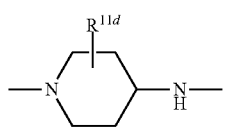

wherein $R^{11d}$ represents a hydrogen atom, a halogen atom or a group represented by the general formula —$CONR^{14b}R^{15b}$ or —$CO_2R^{16}$, wherein $R^{14b}$ and $R^{15b}$ are the same or different and represent a hydrogen atom or a lower alkyl group; $R^{16}$ is as defined above.

In a preferred compound, $Z^1$ represents a nitrogen atom or a group represented by the general formula $CR^{20a}$, wherein $R^{20a}$ represents a hydrogen atom, a hydroxyl group, a cyano group, an amino, lower alkyl or lower alkoxy group which may be substituted or a group represented by the general formula -$Q^{4a}$-$CONR^{21a}R^{22a}$ or -$Q^{4a}$-$CO_2R^{23}$, wherein $R^{21a}$ and $R^{22a}$ are the same or different and represent a hydrogen atom, a lower alkyl, cycloalkyl, aralkyl or aryl group which may be substituted, or $R^{21a}$ and $R^{22a}$, together with the nitrogen atom to which they are attached, represent a cyclic amino group which may be substituted; $Q^{4a}$ represents a lower alkylene or lower alkenylene group which may be substituted or a bond; $R^{23}$ is as defined above. In a more preferred compound, $Z^1$ represents a nitrogen atom.

Tables 1 to 5 show some representative examples of the compounds of the present invention.

TABLE 1

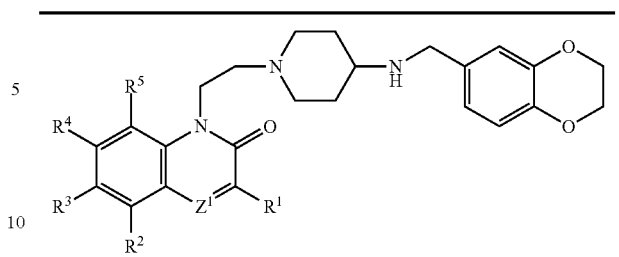

| $Z^1$ | $R^1$ | $R^2$ | $R^3$ | $R^4$ | $R^5$ |
|---|---|---|---|---|---|
| C—Me | H | H | H | OMe | H |
| C—CH=CH—$CO_2H$ | H | H | H | OMe | H |
| CH | H | H | H | OMe | H |
| C—$CO_2$Me | H | H | H | OMe | H |
| C—$CO_2$H | H | H | H | OMe | H |
| CH | H | Br | H | OMe | H |
| CH | H | CH=CH—$CO_2$Et | H | OMe | H |
| CH | H | CH=CH—$CO_2$H | H | OMe | H |
| CH | H | H | H | H | H |
| C—CONHMe | H | H | H | OMe | H |
| CH | $CO_2$Me | H | H | OMe | H |
| CH | $CO_2$H | H | H | OMe | H |
| C—Me | H | H | H | H | H |
| CH | H | H | H | Me | H |

TABLE 2

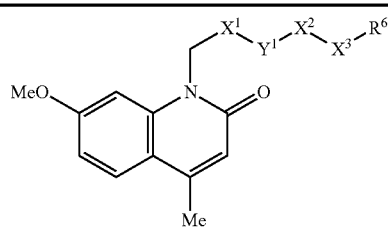

| $X^1$ | —$Y^1$— | $X^2$ | $X^3$ | —$R^6$ |
|---|---|---|---|---|
| $CH_2$ | 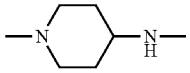 | $SO_2$ | Bond | 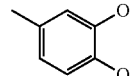 |
| $CH_2$ | 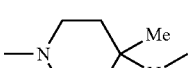 | $CH_2$ | Bond | 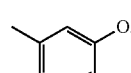 |
| $CH_2CH_2$ | 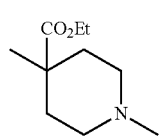 | $CH_2CH_2$ | S | 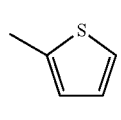 |
| $CH_2CH_2$ | 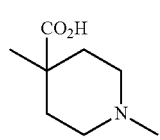 | $CH_2CH_2$ | S | 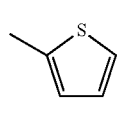 |
| $CH_2$ | 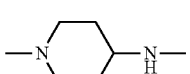 | $CH_2CO$ | N | 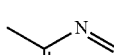 |

TABLE 2-continued

Structure: 7-MeO, 4-Me quinolin-2(1H)-one with N-CH2-X¹-Y¹-X²-X³-R⁶ substituent

| X¹ | —Y¹— | X² | X³ | —R⁶ |
|---|---|---|---|---|
| CH₂ | 1,4-dimethylpiperazine-2-yl with CO₂Et | CH₂CH₂ | Bond | 2,3-dihydro-1,4-benzodioxin-6-yl |
| CH₂ | 1,4-dimethylpiperazine-2-yl with CO₂H | CH₂CH₂ | Bond | 2,3-dihydro-1,4-benzodioxin-6-yl |
| CH₂ | piperazine with EtO₂C at 2-position, N-methyl | CH₂CH₂ | Bond | 2,3-dihydro-1,4-benzodioxin-6-yl |
| CH₂ | piperazine with HO₂C at 2-position, N-methyl | CH₂CH₂ | Bond | 2,3-dihydro-1,4-benzodioxin-6-yl |

TABLE 3

Structure: R⁴-substituted benzo[Z¹]-oxazin-3-one with N-CH2-X¹-Y¹-X²-X³-R⁶ substituent

| R⁴ | Z¹ | X¹ | —Y¹— | X² | X³ | —R⁶ |
|---|---|---|---|---|---|---|
| MeO | CMe | CH₂ | 4-(methylamino)piperidin-1-yl | CH₂CH₂CH₂ | Bond | phenyl |
| MeO | CMe | CH₂ | 4-(methylamino)piperidin-1-yl | CH₂CH₂ | S | thiophen-2-yl |
| MeO | CH | CH₂ | 4-(methylamino)piperidin-1-yl | CH₂ | Bond | 2,3-dihydro-[1,4]dioxino[2,3-c]pyridin-7-yl |
| MeO | CH | CH₂CH₂ | 4-CO₂H, 1-methylpiperidin-4-yl | CH₂CH₂CH₂ | Bond | phenyl |
| MeO | CH | CH₂CH₂ | 4-CO₂H, 1-methylpiperidin-4-yl | CH₂ | Bond | 2,3-dihydro-[1,4]dioxino[2,3-c]pyridin-7-yl |
| MeO | CH | CH₂CH₂ | 4-CO₂H, 1-methylpiperidin-4-yl | CH₂ | Bond | 2,3-dihydro-1,4-benzodioxin-6-yl |

TABLE 3-continued
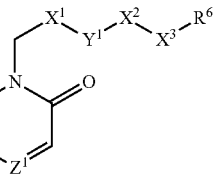
| R⁴ | Z¹ | X¹ | —Y¹— | X² | X³ | —R⁶ |
|---|---|---|---|---|---|---|
| MeO | CMe | CH₂CH₂ | 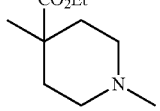 | CH₂CH₂ | S | 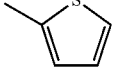 |
| MeO | CMe | CH₂CH₂ | 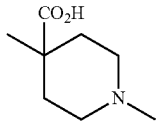 | CH₂CH₂ | S | 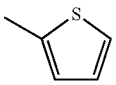 |
| H | N | CH₂ | 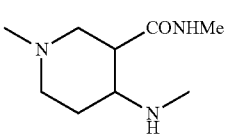 | CH₂ | Bond | 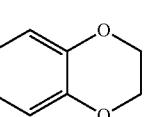 |
| H | N | CH₂ | 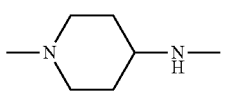 | CH₂CO | NH | 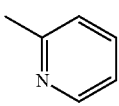 |
| MeO | CH | CH₂CH₂ | 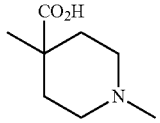 | CH₂CH₂ | S | 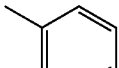 |
| MeO | CH | CH₂CH₂ | 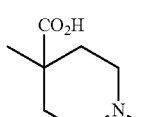 | CH₂CH₂ | S | 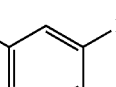 |
TABLE 4 (1)
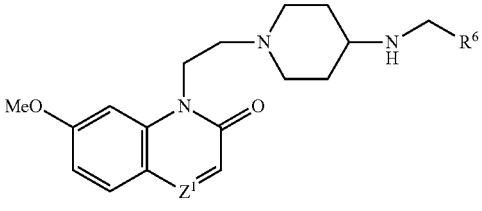
| —Z¹ | —R⁶ |
|---|---|
| C—CONHMe | 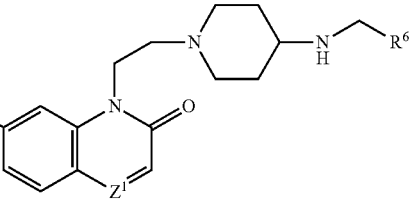 |
| C—CONH | 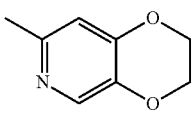 |
TABLE 4 (1)-continued
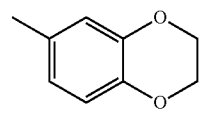
| —Z¹ | —R⁶ |
|---|---|
| C—CONHEt | 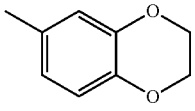 |
| C—CONH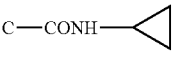 | 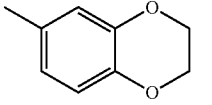 |

TABLE 4 (1)-continued
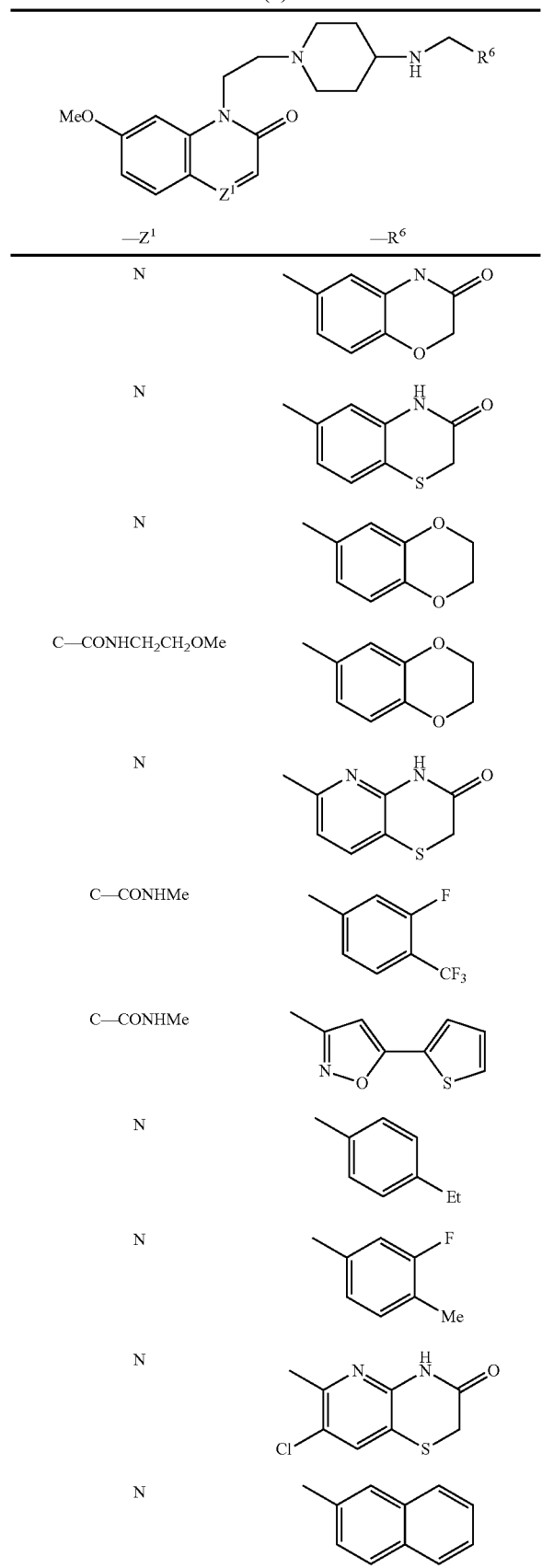
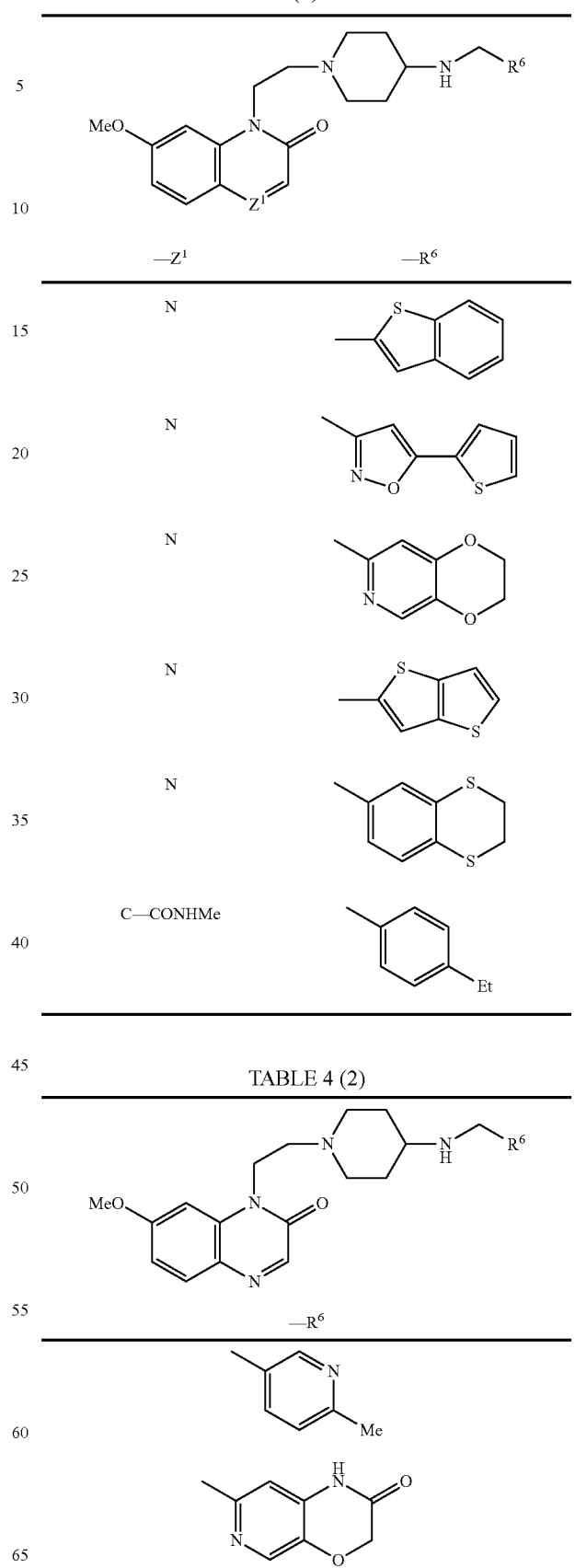
TABLE 4 (2)

TABLE 4 (2)-continued
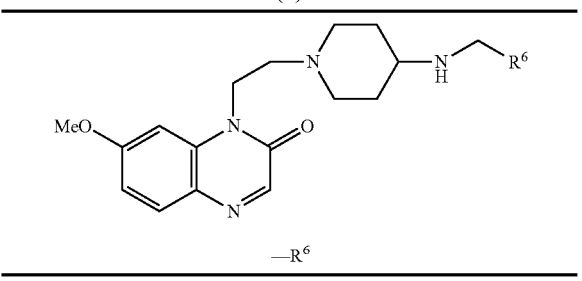
—R⁶
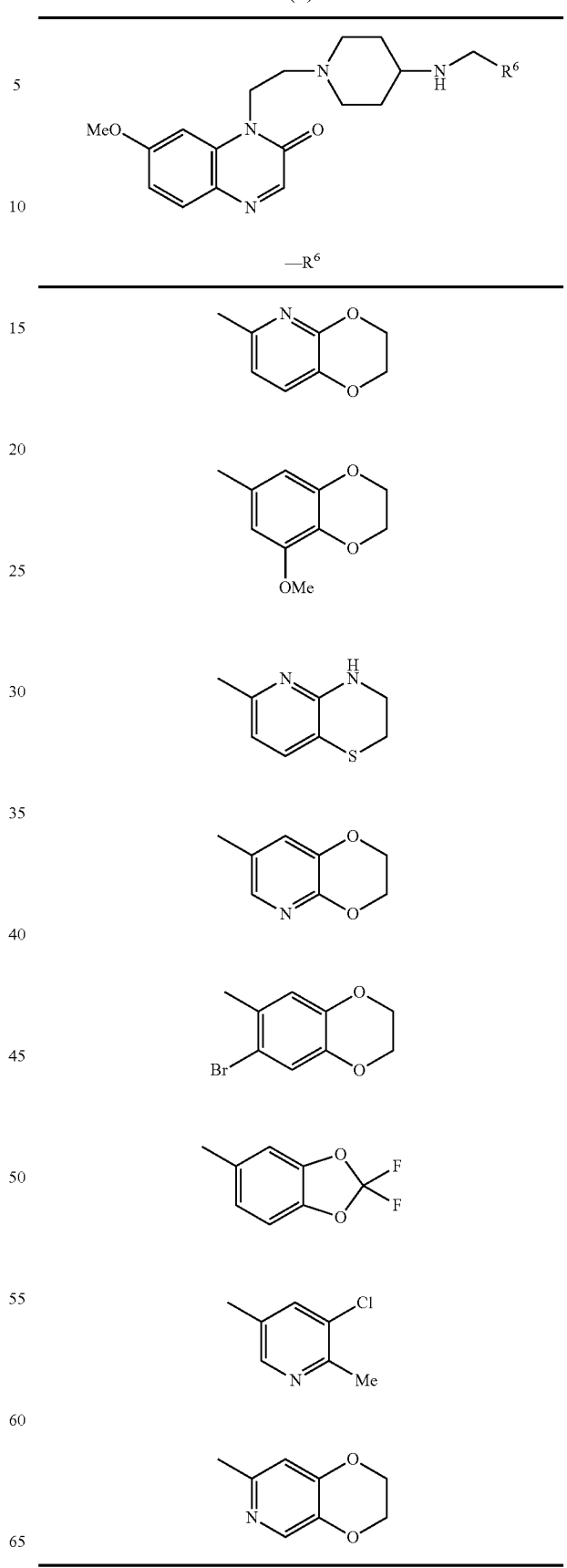

TABLE 4 (3)
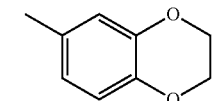
| R² | R⁴ | R⁵ | Z¹ | X² | —R⁶ |
|---|---|---|---|---|---|
| CONHMe | MeO | H | CH | CH₂ | 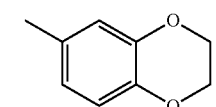 |
| H | H | MeO | CH | CH₂ | 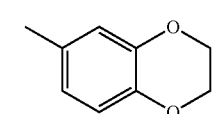 |
| NH₂ | H | H | CH | CH₂ | 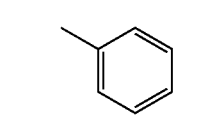 |
| H | MeO | H | C—CONHMe | CH₂C≡C | 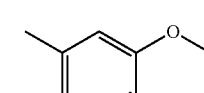 |
| H | F | H | N | CH₂ | 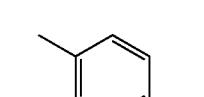 |
| H | F | H | N | CH₂ | 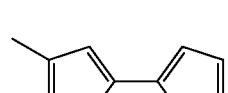 |
| H | F | H | N | CH₂ | 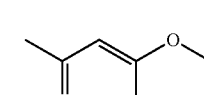 |
| H | F | H | N | CH₂ | 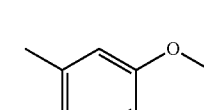 |
| H | Br | H | N | CH₂ |  |

TABLE 4 (3)-continued
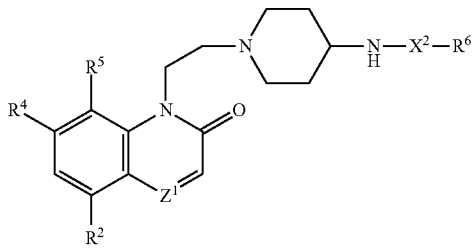
| R² | R⁴ | R⁵ | Z¹ | X² | —R⁶ |
|----|----|----|----|----|-----|
| H | F | H | N | CH₂ | 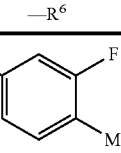 |
| H | F | H | N | CH₂ | 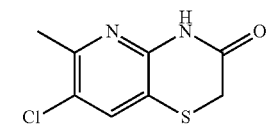 |
| H | F | H | N | CH₂ | 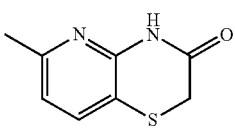 |
TABLE 5 (1)
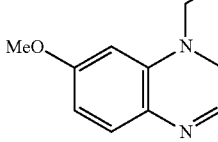
| —Y¹— |
|------|
| 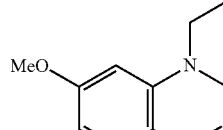 |
| 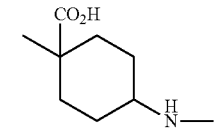 |
| 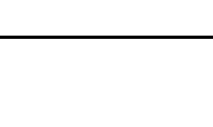 |
| 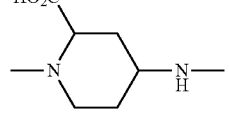 |
|  |
TABLE 5 (1)-continued
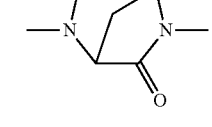
| —Y¹— |
|------|
| 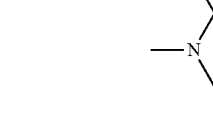 |
|  |
|  |
|  |

TABLE 5 (2)

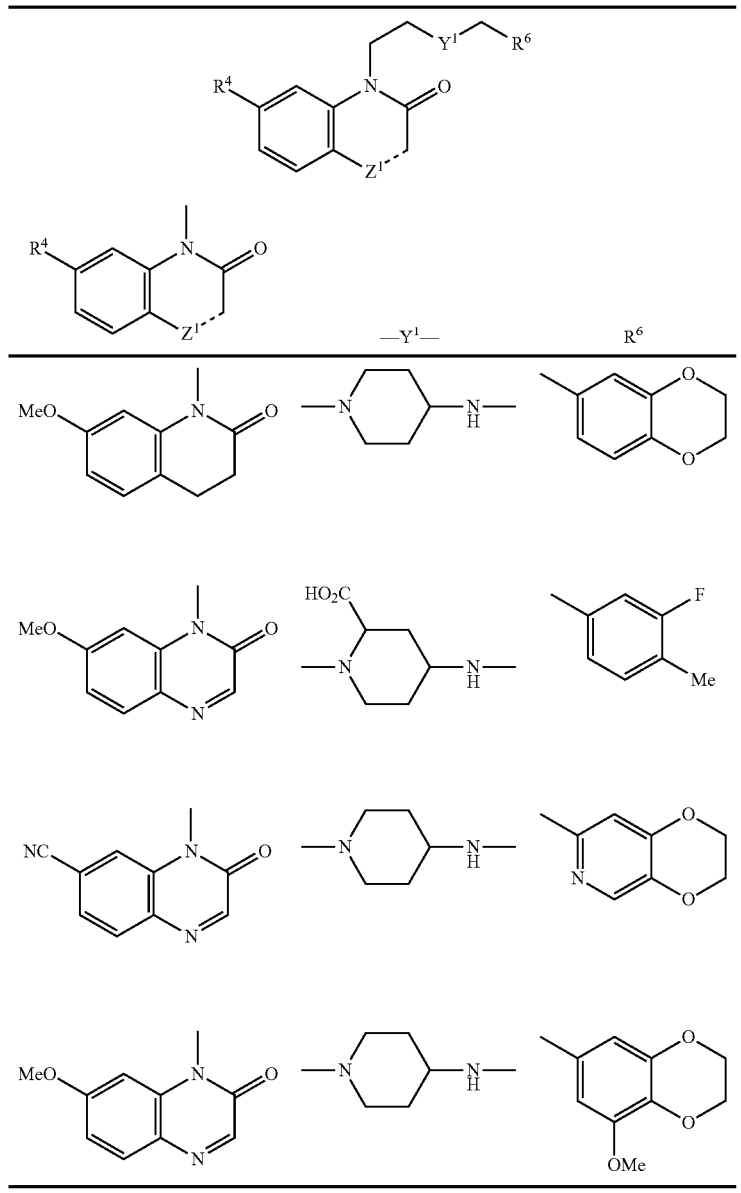

Manufacturing processes of the compounds of the present invention are described hereinafter.

The compounds of the present invention can be manufactured by combining various known methods. Examples of manufacturing process of the same are described below.

[Manufacturing Process 1]

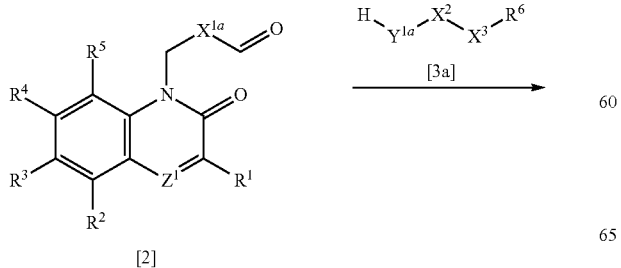

-continued

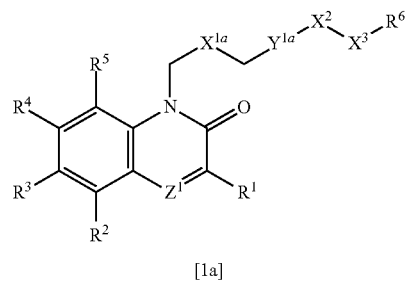

(wherein $X^{1a}$ represents a lower alkylene group which may be substituted or a bond; $Y^{1a}$ represents a group represented by the general formula

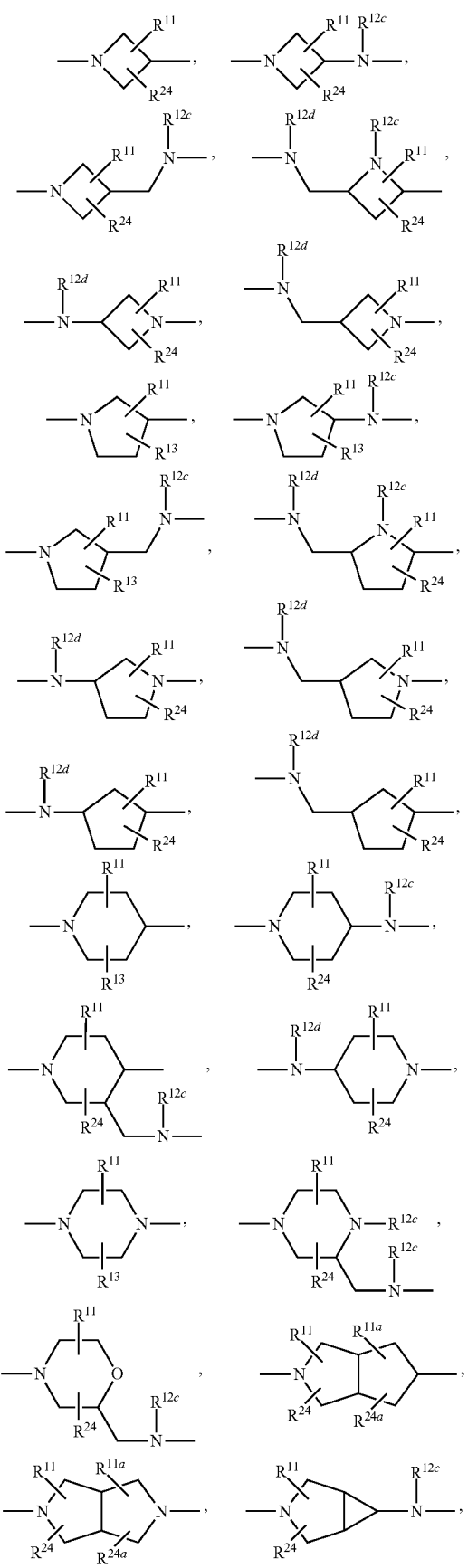

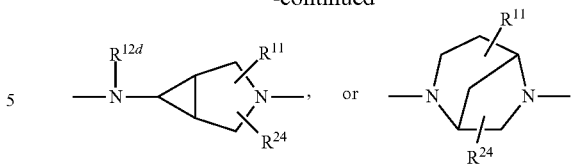

(wherein $R^{12c}$ represents a lower alkyl group which may be substituted or an imino protective group; $R^{12d}$ represents a hydrogen atom or a lower alkyl group which may be substituted; and $R^{11}$, $R^{11a}$, $R^{13}$, $R^{24}$ and $R^{24a}$ are as defined above); and $R^1$, $R^2$, $R^3$, $R^4$, $R^5$, $R^6$, $X^2$, $X^3$ and $Z^1$ are as defined above).

A compound represented by the general formula [1a] can be manufactured by reacting a compound represented by the general formula [2] with a compound represented by the general formula [3a] in the presence of a reducing agent.

The reaction may be performed in accordance with, for example, the methods described in WO02/50061, WO02/56882 and Jerry March "Advanced Organic Chemistry" Fourth Edition, pp. 898 to 900, John Wiley & Sons, INC., 1992 or a method conforming to the methods described above.

The solvent to be used in the reaction may be any solvent which does not adversely affect the reaction. Examples of suitable solvent include alcohols such as methanol, ethanol, 2-propanol and 2-methyl-2-propanol; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethylsulfoxide; esters such as ethyl acetate; amides such as N,N-dimethylformamide, N,N-dimethylacetamide and 1-methyl-2-pyrrolidone, water, and combinations thereof.

Examples of reducing agent to be used in the reaction include hydrogenated complex compounds such as lithium aluminum hydride, sodium triacetoxyborohydride, sodium cyanoborohydride and sodium tetrahydroborate, borane, sodium and sodium amalgam. Electrolysis reduction with a copper or a platinum cathode; catalytic reduction using Raney nickel, platinum oxide or palladium black and the "zinc-acid" reduction can also be used.

The amounts of the compound represented by the general formula [3a] and the reducing agent used in the reaction are in the range of from 1 to 50 moles, preferably 1 to 5 moles per mol of the compound represented by the general formula [2].

The reaction may be performed at −30 to 150° C., preferably at 0 to 100° C., for 30 minutes to 120 hours.

[Manufacturing Process 2]

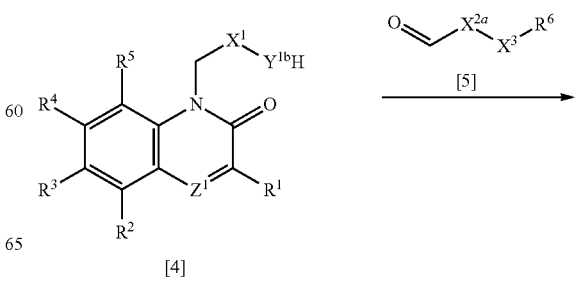

-continued

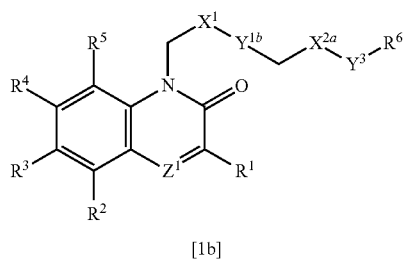

[1b]

(wherein $X^{2a}$ represents a lower alkylene group which may be substituted or a bond; $Y^{1b}$ represents a group represented by the general formula

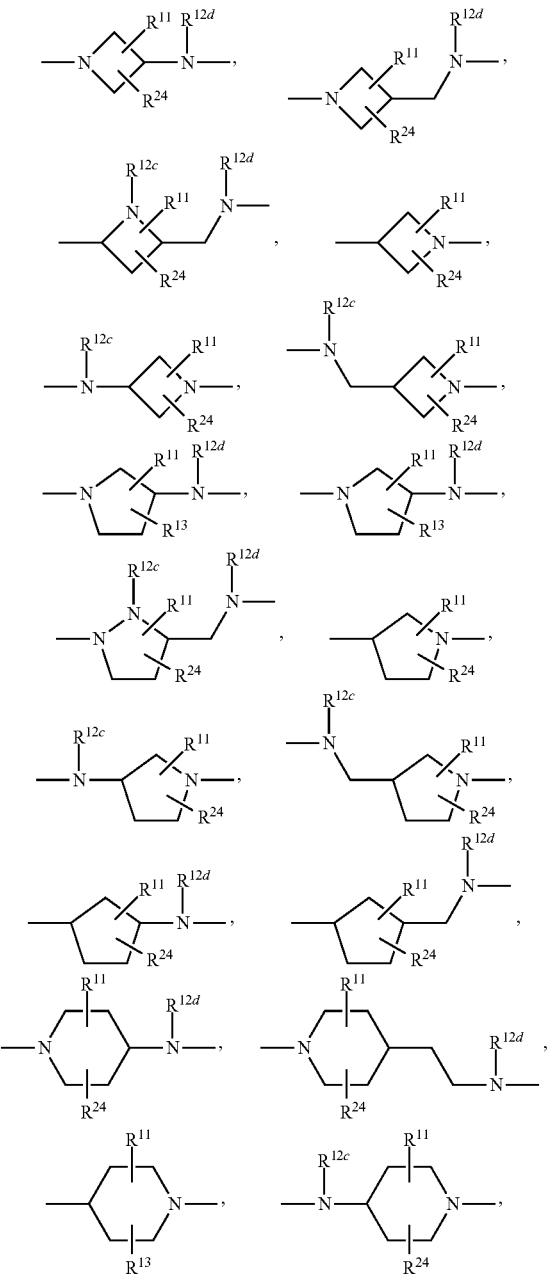

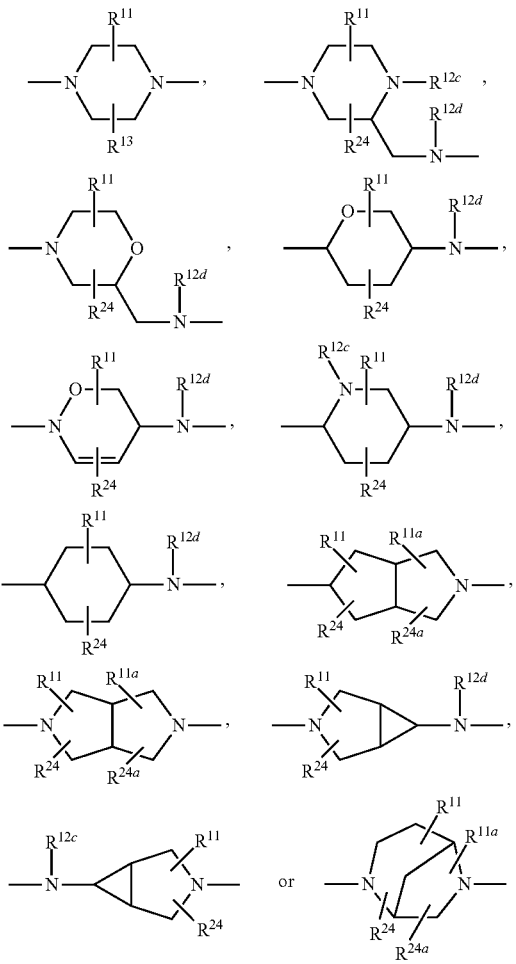

(wherein $R^{11}$, $R^{11a}$, $R^{12c}$, $R^{12d}$, $R^{13}$, $R^{24}$ and $R^{24a}$ are as defined above); $R^1$, $R^2$, $R^3$, $R^4$, $R^5$, $R^6$, $X^1$, $X^3$ and $Z^1$ are as defined above).

Examples of compounds represented by the general formula [5] include 1,4-benzodioxane-6-carbaldehyde and (2,3-dihydro-1,4-benzodioxin-6-yl)acetaldehyde.

A compound represented by the general formula [1b] can be manufactured by reacting a compound represented by the general formula [4] with a compound represented by the general formula [5] in the presence of a reducing agent. The reaction may be performed in accordance with a method conforming to Manufacturing process 1.

[Manufacturing Process 3]

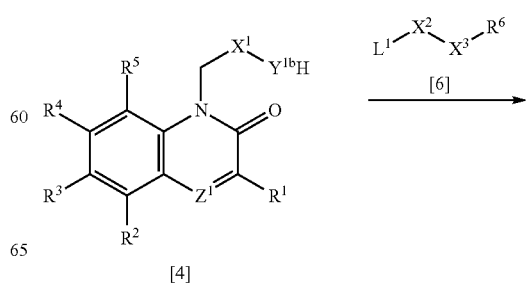

[4]

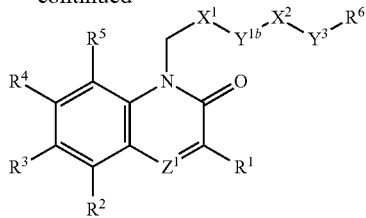

[1c]

(wherein $L^1$ represents a leaving group; $R^1$, $R^2$, $R^3$, $R^4$, $R^5$, $R^6$, $X^1$, $X^2$, $X^3$, $Y^{1b}$ and $Z^1$ are as defined above).

Examples of compounds represented by the general formula [6] include 2-(3-oxo-3,4-dihydro-2H-benzothiazin-6-yl)ethyl methanesulfonate, 2-(benzo[1,3]dioxol-5-yl)ethyl methanesulfonate, 2-((2-bromoethyl)thio)thiophene and 2-bromo-N-(pyridin-2-yl)acetamide.

A compound represented by the general formula [1c] can be manufactured by reacting a compound represented by the general formula [4] with a compound represented by the general formula [6] in the presence or absence of a base.

The reaction may be performed in accordance with, for example, the method described in U.S. Pat. No. 6,603,005 or a method conforming to the method described above.

The solvent to be used in the reaction may be any solvent which does not adversely affect the reaction. Examples of suitable solvent include alcohols such as methanol, ethanol, 2-propanol and 2-methyl-2-propanol; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethylsulfoxide; ketones such as acetone and 2-butanone, esters such as ethyl acetate; amides such as N,N-dimethylformamide, N,N-dimethylacetamide and 1-methyl-2-pyrrolidone, water, and combinations thereof.

A base may be used in the reaction if desired. Examples of suitable base include organic bases such as pyridine, dimethylaminopyridine and triethylamine; inorganic bases such as sodium hydroxide, potassium hydroxide, sodium hydrogen carbonate, potassium carbonate and sodium carbonate.

The amounts of the compound represented by the general formula [6] and the base, if it is desired, used in the reaction are in the range of from 1 to 20 moles per mol of the compound represented by the general formula [4].

The reaction may be performed at 0 to 200° C., preferably at 0 to 150° C., for 30 minutes to 48 hours.

[Manufacturing Process 4]

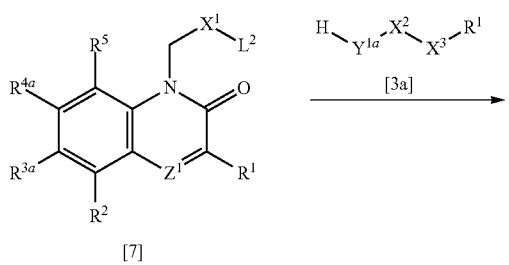

[7]

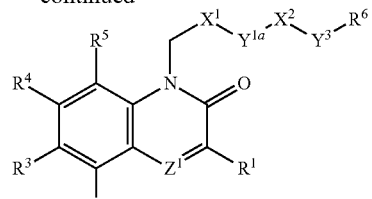

[1d]

(wherein $L^2$ represents a leaving group; $R^1$, $R^2$, $R^3$, $R^4$, $R^5$, $R^6$, $X^1$, $X^2$, $X^3$, $Y^{1a}$ and $Z^1$ are as defined above).

A compound represented by the general formula [1d] can be manufactured by reacting a compound represented by the general formula [7] with a compound represented by the general formula [3a] in the presence or absence of a base. The reaction may be performed in accordance with a method conforming to Manufacturing process 3.

[Manufacturing Process 5]

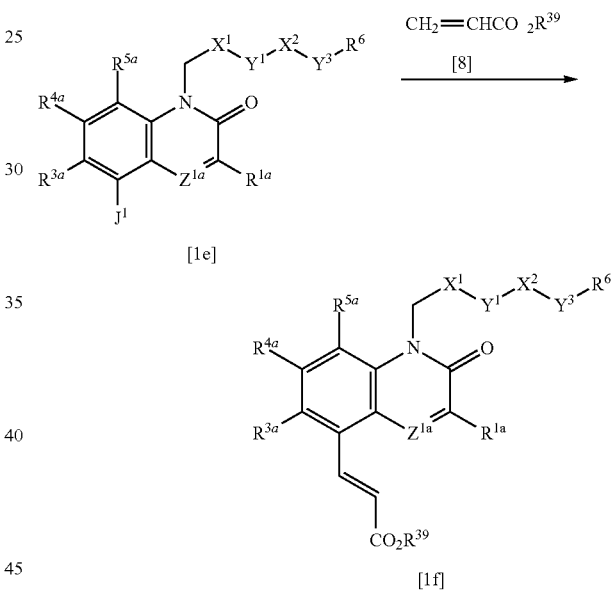

(wherein $R^{1a}$, $R^{3a}$, $R^{4a}$ and $R^{5a}$ are the same or different and represent a hydrogen atom, a cyano group, an amino group which is protected, a lower alkyl or lower alkoxy group which may be substituted or a group represented by the general formula $Q^1CONR^7R^8$ or $Q^1CO_2R^{9a}$ (wherein $R^{9a}$ represents a carboxyl protective group; $R^7$, $R^8$ and $Q^1$ are as defined above); $R^{39}$ represents a carboxyl protective group; $Z^{1a}$ represents a nitrogen atom or a group represented by the general formula $CR^{20c}$ (wherein $R^{20c}$ represents a hydrogen atom, a cyano group, an amino group which is protected, a lower alkyl or lower alkoxy group which may be substituted or a group represented by the general formula $Q^4CONR^{21}R^{22}$ or $Q^4CO_2R^{23a}$ (wherein $R^{23a}$ represents a carboxyl protective group; $R^{21}$, $R^{22}$ and $Q^4$ are as defined above)); $J^1$ represents a chlorine atom, a bromine atom, an iodine atom, or an alkanesulfonyloxy group which may be substituted; $R^6$, $X^1$, $X^2$, $X^3$ and $Y^1$ are as defined above).

Examples of compounds represented by the general formula [8] include methyl acrylate, ethyl acrylate and tert-butyl acrylate.

A compound represented by the general formula [1f] can be manufactured by reacting a compound represented by the general formula [1e] with a compound represented by the general formula [8] in the presence of a catalyst and in the presence or absence of a base. The reaction may be performed in accordance with, for example, the method described in Tsuji et al. "Organic synthesis by means of transition metal" pp. 19 to 22, Maruzen, 1997 or a method conforming to the method described above.

The solvent to be used in the reaction may be any solvent which does not adversely affect the reaction. Examples of suitable solvent include alcohols such as methanol, ethanol, 2-propanol and 2-methyl-2-propanol; amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethylsulfoxide; ketones such as acetone and 2-butanone; esters such as ethyl acetate; nitriles such as acetonitrile, water, and combinations thereof.

Examples of catalyst to be used in the reaction include tetrakis(triphenylphosphine)palladium(0), palladium(II) acetate, palladium(II) chloride, bis(tri-tert-butylphosphine)palladium(0) and tris(dibenzylideneacetone)dipalladium(0).

A base may be used in the reaction if desired. Examples of suitable base include organic bases such as pyridine, dimethylaminopyridine, triethylamine, N,N-dimethylbenzylamine, sodium acetate and potassium acetate; inorganic bases such as sodium hydroxide, potassium hydroxide, sodium hydrogen carbonate, potassium carbonate and sodium carbonate.

The amount of the compound represented by the general formula [8] used in the reaction is in the range of from 1 to 10 moles, preferably 1 to 5 moles per mol of the compound represented by the general formula [1e].

The amount of the catalyst used in the reaction is in the range of from 0.001 to 10 moles, preferably 0.01 to 2 moles per mol of the compound represented by the general formula [1e].

The amount of the base, if it is desired, used in the reaction is in the range of from 1 to 10 moles, preferably 1 to 5 moles per mol of the compound represented by the general formula [1e].

The reaction may be performed at −30 to 200° C., preferably at 0 to 100° C., for 30 minutes to 48 hours.

Reactions may be performed at positions 3, 4, 6, 7 and 8 of the 2-oxoquinoline ring and at positions 3, 6, 7 and 8 of the 2-oxoquinoxaline ring in the same manner as in Manufacturing process 5.

[Manufacturing Process 6]

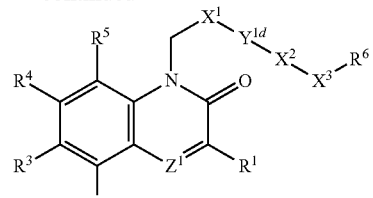

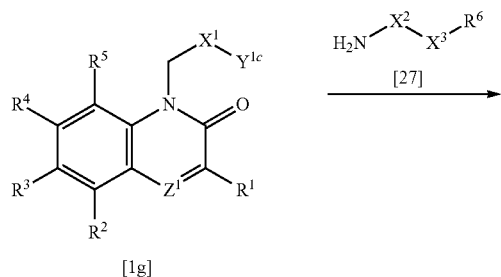

[1g]

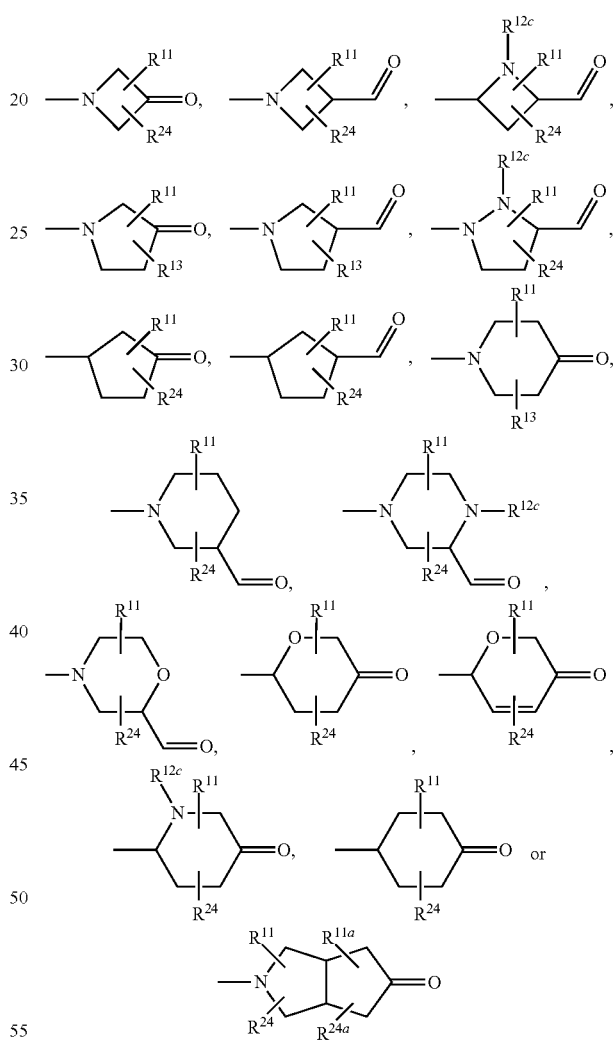

[1h]

(wherein $Y^{1c}$ represents a group represented by the general formula (wherein $R^{11}$, $R^{11a}$, $R^{12c}$, $R^{13}$, $R^{24}$ and $R^{24a}$ are as defined above); $Y^{1d}$ represents a group represented by the general formula

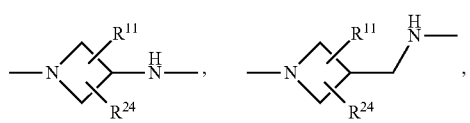

-continued

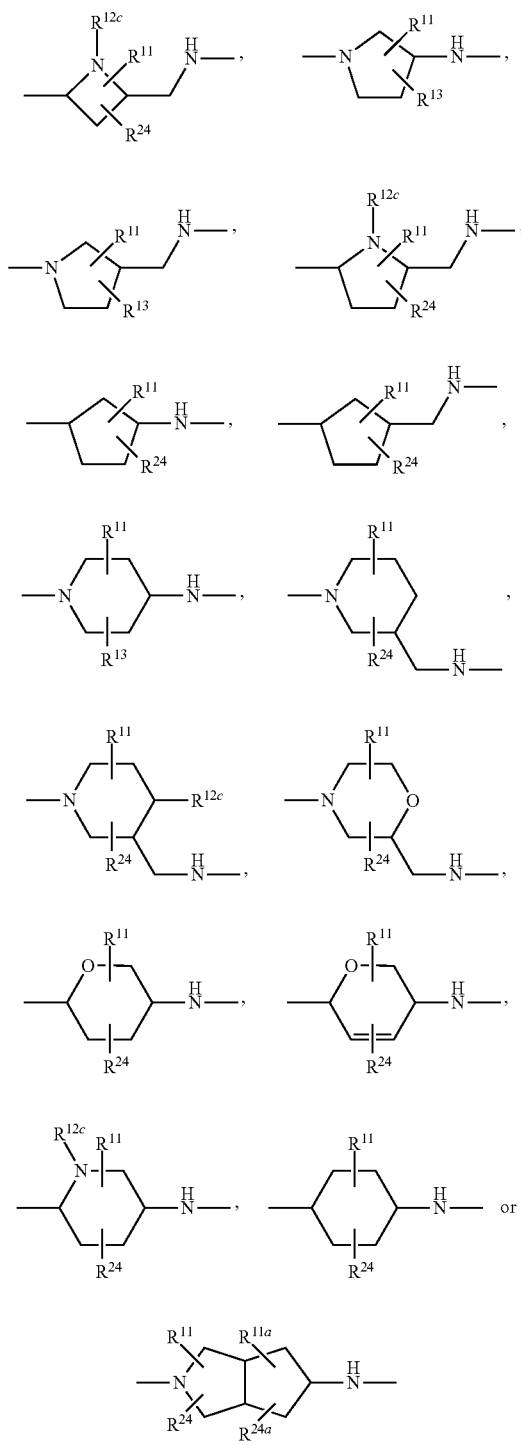

(wherein $R^{11}$, $R^{11a}$, $R^{12c}$, $R^{13}$, $R^{24}$ and $R^{24a}$ are as defined above); $R^1$, $R^2$, $R^3$, $R^4$, $R^5$, $R^6$, $X^1$, $X^2$, $X^3$ and $Z^1$ are as defined above).

A compound represented by the general formula [1h] can be manufactured by reacting a compound represented by the general formula [1g] with a compound represented by the general formula [27] in the presence of a reducing agent. The reaction may be performed in accordance with a method conforming to Manufacturing process 1.

[Manufacturing Process 7]

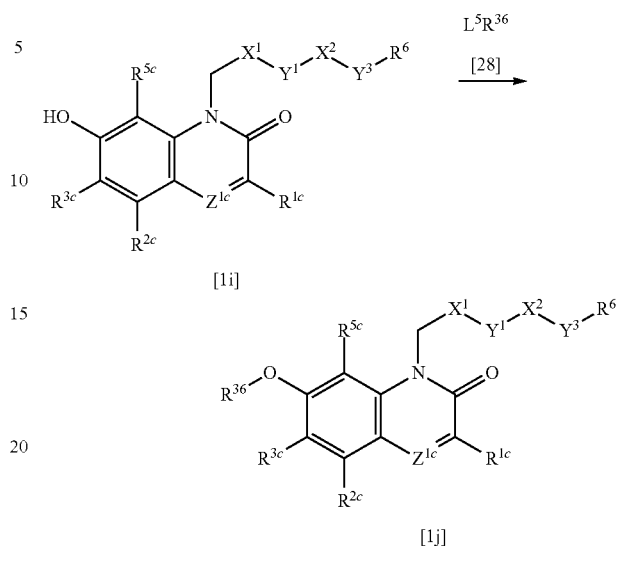

(wherein $L^5$ represents a leaving group; $R^{36}$ represents a lower alkyl or aralkyl group which may be substituted; $R^{1c}$, $R^{2c}$, $R^{3c}$ and $R^{5c}$ are the same or different and represent a hydrogen atom, a halogen atom, a cyano group, an amino group which is protected, a lower alkyl or lower alkoxy group which may be substituted, or a group represented by the general formula -$Q^1$-$CONR^7R^8$ or -$Q^1$-$CO_2R^{9c}$ (wherein $R^{9c}$ represents a carboxyl protective group; $R^7$, $R^8$ and $Q^1$ are as defined above); $Z^{1c}$ represents a nitrogen atom or a group represented by the general formula $CR^{20e}$ (wherein $R^{20e}$ represents a hydrogen atom, a cyano group, an amino group which is protected, a lower alkyl or lower alkoxy group which may be substituted, or a group represented by the general formula -$Q^4$-$CONR^{21}R^{22}$ or -$Q^4$-$CO_2R^{23a}$ (wherein $R^{21}$, $R^{22}$, $R^{23a}$ and $Q^4$ are as defined above)); $R^6$, $X^1$, $X^2$, $X^3$ and $Y^1$ are as defined above).

Examples of compounds represented by the general formula [28] include ethyl iodide, butyl bromide and isopropyl bromide.

A compound represented by the general formula [1j] can be manufactured by reacting a compound represented by the general formula [1i] with a compound represented by the general formula [28] in the presence or absence of a base. The reaction may be performed in accordance with, for example, the method described in Richard C. Larock "Comprehensive Organic Transformation" pp. 445 to 448, VCH Publishers, INC., 1989 or a method conforming to the method described above.

The solvent to be used in the reaction may be any solvent which does not adversely affect the reaction. Examples of suitable solvent include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethylsulfoxide; ketones such as acetone and 2-butanone; esters such as ethyl acetate; nitriles such as acetonitrile, water, and combinations thereof.

A base may be used in the reaction if desired. Examples of suitable base include organic bases such as pyridine, dimethylaminopyridine, triethylamine, N,N-dimethylbenzylamine, sodium acetate and potassium acetate; inorganic bases such as sodium hydride, sodium hydroxide, potassium hydroxide, sodium hydrogen carbonate, potassium carbonate and sodium carbonate.

The amount of the compound represented by the general formula [28] used in the reaction is in the range of from 1 to 10 moles, preferably 1 to 5 moles per mol of the compound represented by the general formula [1i].

The amount of the base, if it is desired, used in the reaction is in the range of from 1 to 10 moles, preferably 1 to 5 moles per mol of the compound represented by the general formula [1i].

The reaction may be performed at −30 to 200° C., preferably at 0 to 100° C., for 30 minutes to 48 hours.

Reactions may be performed at positions 3, 4, 5, 6 and 8 of the 2-oxoquinoline ring and at positions 3, 5, 6 and 8 of the 2-oxoquinoxaline ring in the same manner as in Manufacturing process 7.

[Manufacturing Process 8]

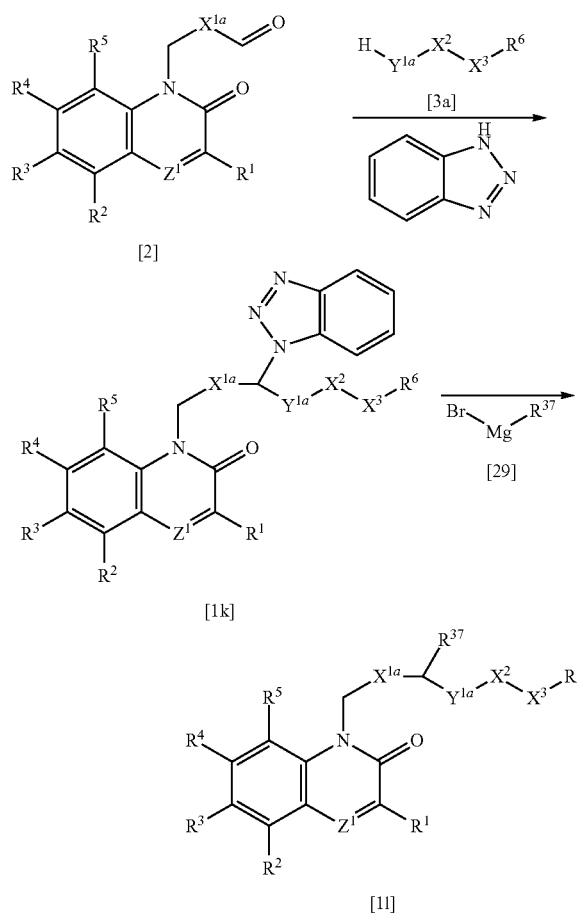

(wherein $R^{37}$ represents a lower alkyl group which may be substituted; $R^1$, $R^2$, $R^3$, $R^4$, $R^5$, $R^6$, $X^{1a}$, $X^2$, $X^3$, $Y^{1a}$ and $Z^1$ are as defined above).

(8-A) A compound represented by the general formula [1k] can be manufactured by reacting a compound represented by the general formula [2] with a compound represented by the general formula [3a] and benzotriazole.

The reaction may be performed in accordance with, for example, the method described in "Synthesis" pp. 1173 to 1176, 1990 or a method conforming to the method described above.

The solvent to be used in the reaction may be any solvent which does not adversely affect the reaction. Examples of suitable solvent include alcohols such as methanol, ethanol, 2-propanol and 2-methyl-2-propanol; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethylsulfoxide; esters such as ethyl acetate, water, and combinations thereof.

The amounts of the compound represented by the general formula [3a] and benzotriazole used in the reaction are in the range of from 1 to 50 moles, preferably 1 to 5 moles per mol of the compound represented by the general formula [2].

The reaction may be performed at −30 to 150° C., preferably at 0 to 100° C., for 30 minutes to 120 hours.

(8-B) A compound represented by the general formula [11] can be manufactured by reacting a compound represented by the general formula [1k] with a compound represented by the general formula [29].

The reaction may be performed in accordance with, for example, the method described in "Synthesis" pp. 1173 to 1176, 1990 or a method conforming to the method described above.

The solvent to be used in the reaction may be any solvent which does not adversely affect the reaction. Examples of suitable solvent include aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether, and combinations thereof.

The amount of the compound represented by the general formula [29] used in the reaction is in the range of from 1 to 50 moles, preferably 1 to 5 moles per mol of the compound represented by the general formula [1k].

The reaction may be performed at −30 to 150° C., preferably at 0 to 100° C., for 30 minutes to 120 hours.

[Manufacturing Process 9]

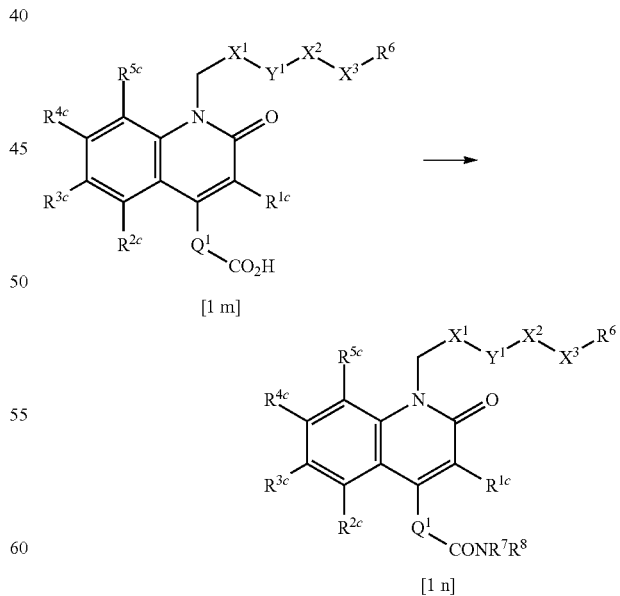

(wherein $R^{4c}$ is the same or different and represents a hydrogen atom, a halogen atom, or an amino group which is protected; $R^{1c}$, $R^{2c}$, $R^{3c}$, $R^{5c}$, $R^6$, $R^7$, $R^8$, $Q^1$, $X^1$, $X^2$, $X^3$ and $Y^1$ are as defined above).

A compound represented by the general formula [1n] can be manufactured by converting a compound represented by the general formula [1m] into a reactive derivative thereof which is then subjected to a reaction with amines or sulfonamides. The reaction may be performed in accordance with, for example, the method described in Izumiya et al. "Basis and Experimentals of Peptide Synthesis" pp. 89 to 142, Maruzen, 1985 or a method conforming to the method described above.

The solvent to be used in the reaction may be any solvent which does not adversely affect the reaction. Examples of suitable solvent include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; sulfoxides such as dimethylsulfoxide; ketones such as acetone and 2-butanone, esters such as ethyl acetate, and combinations thereof.

Examples of base to be used in the reaction if desired include organic bases such as pyridine, dimethylaminopyridine and triethylamine; inorganic bases such as sodium hydroxide, potassium hydroxide, sodium hydrogen carbonate, potassium carbonate and sodium carbonate.

Examples of reactive derivative converted from a compound represented by the general formula [1m] include acid halides such as acid chloride and acid bromide; active esters such as p-nitrophenyl ester, N-hydroxysuccinimide ester and N-hydroxyphthalimide ester; mixed acid anhydrides with monoalkyl carbonate such as ethyl chlorocarbonate and isobutyl chlorocarbonate, and mixed acid anhydrides with organic acid such as pivalic acid. The above described reactive derivatives may be used without being isolated.

A coupling reagent may be used to produce a reactive derivative within the system. Examples of suitable coupling reagent include carbodiimides such as N,N'-dicyclohexylcarbodiimide and N-ethyl-N'-(3-dimethylaminopropyl)carbodiimide; carbonyls such as carbonyldiimidazole; acid azides such as diphenyl phosphoryl azide; acid cyanides such as diethyl phosphoryl cyanide; 2-ethoxy-1-ethoxycarbonyl-1,2-dihydroquinoline; O-benzotriazol-1-yl-1,1,3,3-tetramethyluronium hexafluorophosphate and O-(7-azabenzotriazol-1-yl)-1,1,3,3-tetramethyluronium hexafluorophosphate.

Examples of amine to be used in the reaction include monoalkylamines such as methylamine, ethylamine, propylamine, isopropylamine, butylamine, tert-butylamine, pentylamine, 2-methoxyethylamine, 3-methoxypropylamine, ethanolamine, propanolamine, 2,3-dihydroxypropylamine, butanolamine, 2-chloroethylamine and 3-chloropropylamine; cycloalkylamines such as cyclopropylamine, cyclobutylamine and cyclopentylamine; dialkylamines such as dimethylamine, diethylamine, dipropylamine, diethanolamine and dipropanolamine; aralkylamines such as benzylamine and 2-phenylethylamine; 3-(aminomethyl)pyridine, 4-(aminomethyl)pyridine and 5-(aminomethyl)tetrazole.

Examples of sulfonamide to be used in the reaction include methanesulfonamide, ethanesulfonamide and propanesulfonamide.

The amounts of the coupling reagent, the base, if it is desired, and amine or sulfonamide used in the reaction are in the range of from 1 to 50 moles, preferably 1 to 5 moles per mol of a reactive derivative converted from the compound represented by the general formula [1m].

The reaction may be performed at −30 to 150° C., preferably at 0 to 100° C., for 30 minutes to 48 hours.

Reactions may be performed at positions 3, 5, 6, 7 and 8 of the 2-oxoquinoline ring; at positions 3, 5, 6, 7 and 8 of the 2-oxoquinoxaline ring; and with $Y^1$ in the same manner as in Manufacturing process 9.

[Manufacturing Process 10]

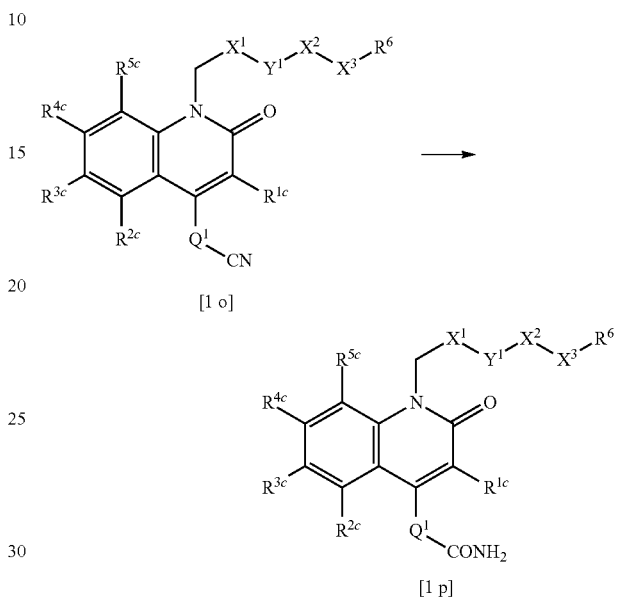

(wherein $R^{1c}, R^{2c}, R^{3c}, R^{4c}, R^{5c}, R^6, Q^1, X^1, X^2, X^3$ and $Y^1$ are as defined above).

A compound represented by the general formula [1p] can be manufactured by hydrating a compound represented by the general formula [1o] in the presence of a catalyst. The reaction may be performed in accordance with, for example, the method described in Richard C. Larock "Comprehensive Organic Transformation" pp. 994, VCH Publishers, INC., 1989 or a method conforming to the method described above.

The solvent to be used in the reaction may be any solvent which does not adversely affect the reaction. Examples of suitable solvent include alcohols such as methanol, ethanol, 2-propanol and 2-methyl-2-propanol; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethylsulfoxide; esters such as ethyl acetate, water, and combinations thereof.

Examples of catalyst to be used for the reaction include acidic catalysts such as sulfuric acid, hydrochloric acid and polyphosphoric acid; basic catalysts such as sodium oxide, potassium hydroxide, ammonia water-hydrogen peroxide and sodium hydroxide-hydrogen peroxide, metallic catalysts such as copper and dihydrotetrakis(triphenylphosphine)ruthenium.

Reactions may be performed at positions 3, 5, 6, 7 and 8 of the 2-oxoquinoline ring; at positions 3, 5, 6, 7 and 8 of the 2-oxoquinoxaline ring; and with $Y^1$ in the same manner as in Manufacturing process 10.

[Manufacturing Process 11]

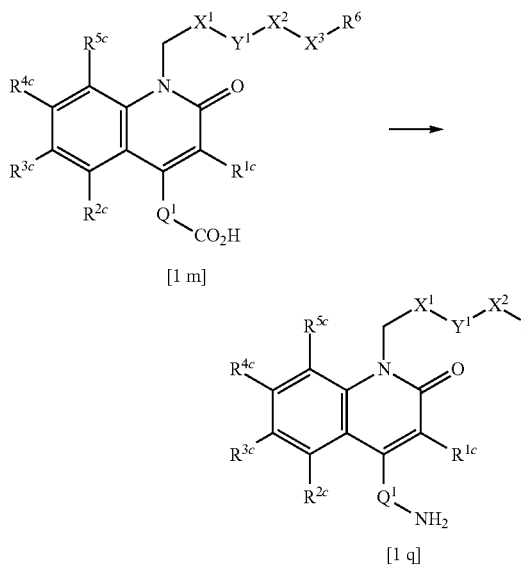

(wherein $R^{1c}, R^{2c}, R^{3c}, R^{4c}, R^{5c}, R^6, Q^1, X^1, X^2, X^3$ and $Y^1$ are as defined above).

A compound represented by the general formula [1q] can be manufactured by the Curtius, Lossen, or Schmidt rearrangement of a compound represented by the general formula [1m]. Alternatively, a compound represented by the general formula [1q] can be manufactured by the Hoffmann rearrangement of a compound represented by the general formula [1p]. The reactions may be performed in accordance with, for example, the method described in Richard C. Larock "Comprehensive Organic Transformation" pp. 431 to 432, VCH Publishers, INC., 1989 or a method conforming to the method described above.

Reactions may be performed at positions 3, 5, 6, 7 and 8 of the 2-oxoquinoline ring; at positions 3, 5, 6, 7 and 8 of the 2-oxoquinoxaline ring; and with $Y^1$ in the same manner as in Manufacturing process 11.

[Manufacturing Process 12]

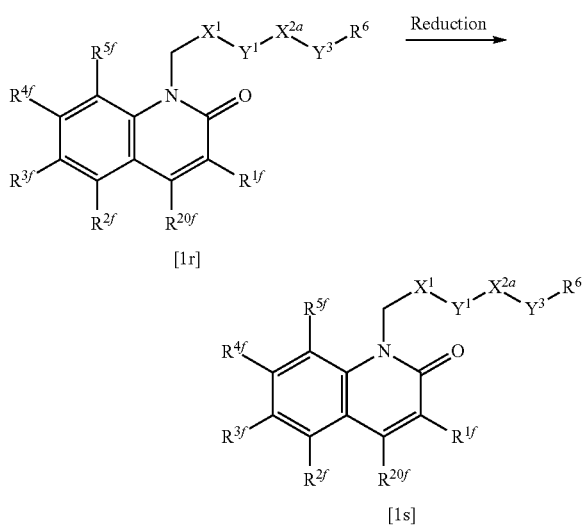

(wherein $R^{1f}, R^{2f}, R^{3f}, R^{4f}, R^{5f}$ and $R^{20f}$ are the same or different and represent a hydrogen atom, a halogen atom, a hydroxyl group, a cyano group, a formyl group, an amino group which may be protected or substituted, a lower alkyl, cycloalkyl, aryl, lower alkoxy, cycloalkyloxy, aralkyloxy, alkanoyl, ureido or monocyclic heterocyclic group which may be substituted, or a group represented by the general formula $-Q^1-CONR^7R^8$, $-Q^1-CO_2R^9$ or $-Q^1-CN$ (wherein $R^7$, $R^8$, $R^9$ and $Q^1$ are as defined above); $R^6, X^1, X^{2a}, X^3$ and $Y^1$ are as defined above).

A compound represented by the general formula [1s] can be manufactured by hydrogenating a compound represented by the general formula [1r] in the presence of a catalyst.

The reaction may be performed in accordance with, for example, the method described in Richard C. Larock "Comprehensive Organic Transformation" pp. 6 to 17, VCH Publishers, INC., 1989 or a method conforming to the method described above.

The solvent to be used in the reaction may be any solvent which does not adversely affect the reaction. Examples of suitable solvent include alcohols such as methanol, ethanol, 2-propanol and 2-methyl-2-propanol; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethylsulfoxide; esters such as ethyl acetate; amides such as N,N-dimethylformamide, N,N-dimethylacetamide and 1-methyl-2-pyrrolidone, water, and combinations thereof.

Examples of catalyst to be used for the reaction include palladium carbon, platinum oxide, rhodium carbon and ruthenium chloride.

The amount of the catalyst used in the reaction is in the range of from 0.0001 to 5 moles, preferably 0.01 to 1 moles per mol of the compound represented by the general formula [1r].

The reaction may be performed at −30 to 150° C., preferably at 0 to 100° C., for 30 minutes to 120 hours.

By known reactions such as, for example, condensation, addition, oxidation, reduction, rearrangement, substitution, halogenation, dehydration and hydrolysis, or arbitrarily combining the reactions, compounds represented by the general formula [1] or salts thereof which are obtained in accordance with Manufacturing processes 1 to 12 can be converted into other compounds represented by the general formula [1] or salts thereof.

The compounds obtained by the manufacturing processes described above, which can exist as isomers (for example, optical isomers, geometric isomers, and tautomers), can also be used. Moreover, solvates, hydrates, and crystals in various shapes thereof can also be used.

Manufacturing process of the compounds represented by the general formulae [2], [3], [4] and [7], which are the raw materials for manufacturing the compounds of the present invention, are described hereinafter. The compounds of the present invention can be manufactured by combining various known methods. Examples of manufacturing process of the same are described below.

[Manufacturing Process A]

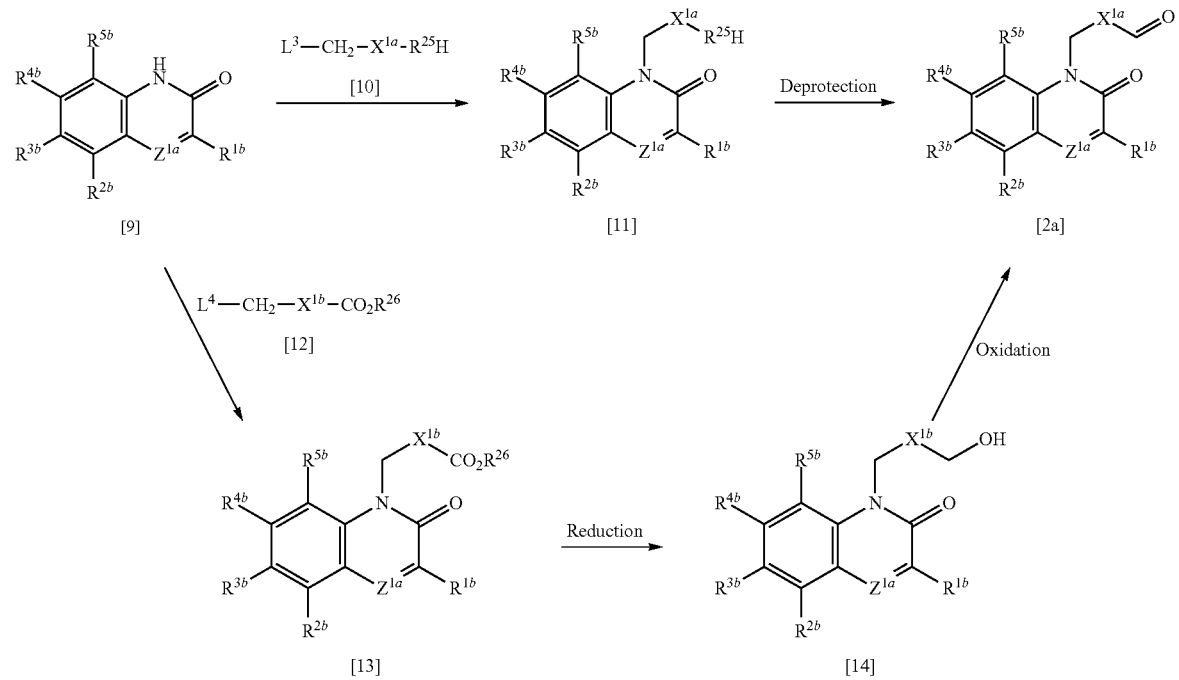

(wherein $R^{1b}$, $R^{2b}$, $R^{3b}$, $R^{4b}$ and $R^{5b}$ are the same or different and represent a hydrogen atom, a halogen atom, a cyano group, an amino group which is protected, a lower alkyl or lower alkoxy group which may be substituted, or a group represented by the general formula -$Q^1$-$CONR^7R^8$ or -$Q^1$-$CO_2R^{9a}$ (wherein $R^7$, $R^8$, $R^{9a}$ and $Q^1$ are as defined above); $R^{25}$ represents a carbonyl group which is protected; $R^{26}$ represents a carboxyl protective group; $X^{1b}$ represents a lower alkylene group which may be substituted or a bond; $L^3$ and $L^4$ represent a leaving group; $X^{1a}$ and $Z^{1a}$ are as defined above).

Examples of known compounds represented by the general formula [10] include 2-(2-bromomethyl)-1,3-dioxolane, 2-(2-bromoethyl)-1,3-dioxolane, and 2-(2-bromoethyl)-1,3-dioxane.

Examples of known compounds represented by the general formula [12] include ethyl bromoacetate, ethyl 3-bromopropionate and ethyl 4-bromobutyrate.

(A-1) A compound represented by the general formula [11] can be manufactured by reacting a compound represented by the general formula [9] with a compound represented by the general formula [10] either in the presence or absence of a base.

The solvent to be used in the reaction may be any solvent which does not adversely affect the reaction. Examples of suitable solvent include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethylsulfoxide; esters such as ethyl acetate, water, and combinations thereof.

Examples of base to be used in the reaction if desired include organic bases such as pyridine, dimethylaminopyridine and triethylamine; inorganic bases such as sodium hydride, sodium hydroxide, potassium hydroxide, sodium hydrogen carbonate, potassium carbonate, sodium carbonate and cesium carbonate.

The amounts of the base, if it is desired, and the compound represented by the general formula [10] used in the reaction are in the range of from 1 to 50 moles, preferably 1 to 5 moles per mol of the compound represented by the general formula [9].

The reaction may be performed at −30 to 150° C., preferably at 0 to 100° C., for 30 minutes to 48 hours.

(A-2) A compound represented by the general formula [2a] can be manufactured by deprotection of a compound represented by the general formula [11]. The reaction may be performed in accordance with, for example, the method described in "Protective Groups in Organic Synthesis" Third Edition, pp. 293 to 368, John Wiley & Sons, INC., 1999 or a method conforming to the method described above.

(A-3) A compound represented by the general formula [13] can be manufactured by reacting a compound represented by the general formula [9] with a compound represented by the general formula [12] either in the presence or absence of a base.

The solvent to be used in the reaction may be any solvent which does not adversely affect the reaction. Examples of suitable solvent include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethylsulfoxide; esters such as ethyl acetate, water, and combinations thereof.

Examples of base to be used in the reaction if desired include organic bases such as pyridine, dimethylaminopyridine and triethylamine; inorganic bases such as sodium hydride, sodium hydroxide, potassium hydroxide, sodium hydrogen carbonate, potassium carbonate and sodium carbonate.

The amounts of the base, if it is desired, and the compound represented by the general formula [12] used in the reaction are in the range of from 1 to 50 moles, preferably 1 to 5 moles per mol of the compound represented by the general formula [9].

The reaction may be performed at −30 to 150° C., preferably at 0 to 100° C., for 30 minutes to 48 hours.

(A-4) A compound represented by the general formula [14] can be manufactured by reduction of a compound represented by the general formula [13].

The reaction may be performed in accordance with, for example, the method described in Jerry March "Advanced Organic Chemistry" Fourth Edition, pp. 1214, John Wiley & Sons, INC., 1992 or a method conforming to the method described above.

The solvent to be used in the reaction may be any solvent which does not adversely affect the reaction. Examples of suitable solvent include aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether, and combinations thereof.

Examples of reducing agent to be used in the reaction include aluminum hydride compounds such as lithium aluminum hydride and alane (aluminum hydride), or borohydride compounds such as sodium borohydride and borane.

The amount of the reducing agent used in the reaction is in the range of from 1 to 50 moles, preferably 1 to 5 moles per mol of the compound represented by the general formula [13].

The reaction may be performed at −30 to 150° C., preferably at 0 to 100° C., for 30 minutes to 120 hours.

(A-5) A compound represented by the general formula [2a] can be manufactured by oxidation of a compound represented by the general formula [14]. The reaction may be performed in accordance with, for example, the methods described in Jerry March "Advanced Organic Chemistry" Fourth Edition, pp. 1167 to 1171, John Wiley & Sons, INC., 1992, and Richard C. Larock "Comprehensive Organic Transformation" pp. 604 to 614, VCH Publishers, INC., 1989 or a method conforming to the methods described above.

The solvent to be used in the reaction may be any solvent which does not adversely affect the reaction. Examples of suitable solvent include halogenated hydrocarbons such as methylene chloride, chloroform and dichloroethane; aromatic hydrocarbons such as benzene, toluene and xylene; sulfoxides such as dimethylsulfoxide; acids such as acetic acid, water, and combinations thereof.

Examples of oxidizing agent to be used in the reaction include dimethylsulfoxide, chromium trioxide, manganese dioxide and chromyl chloride.

The amount of the oxidizing agent used in the reaction is in the range of from 0.5 to 10 moles per mol of the compound represented by the general formula [14].

The reaction may be performed at −78 to 200° C., preferably at −78 to 100° C., for 30 minutes to 48 hours.

[Manufacturing Process B]

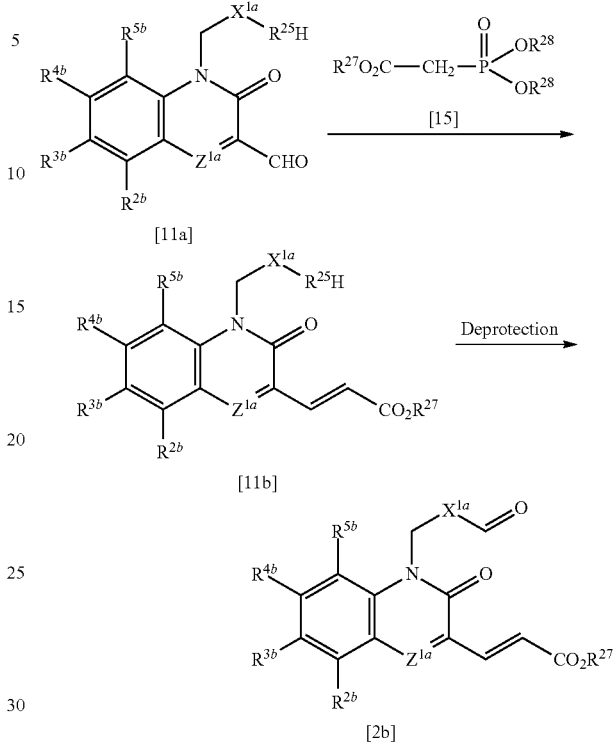

(wherein $R^{27}$ represents a carboxyl protective group; $R^{28}$ represents a lower alkyl group; $R^{2b}$, $R^{3b}$, $R^{4b}$, $R^{5b}$, $R^{25}$, $X^{1a}$ and $Z^{1a}$ are as defined above).

Examples of known compounds represented by the general formula [15] include triethyl phosphonoacetate and trimethyl phosphonoacetate.

(B-1) A compound represented by the general formula [11b] can be manufactured by reacting a compound represented by the general formula [11a] with a compound represented by the general formula [15] in the presence of a base.

The reaction may be performed in accordance with, for example, the methods described in Jerry March "Advanced Organic Chemistry" Fourth Edition, pp. 958 to 959, John Wiley & Sons, INC., 1992, and Richard C. Larock "Comprehensive Organic Transformations" pp. 176, VCH Publishers, INC., 1989 or a method conforming to the methods described above.

The solvent to be used in the reaction may be any solvent which does not adversely affect the reaction. Examples of suitable solvent include halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether, diethylene glycol diethyl ether and ethylene glycol monomethyl ether; sulfoxides such as dimethylsulfoxide, esters such as ethyl acetate, and combinations thereof.

Examples of base to be used in the reaction include organic bases such as 1,8-diazabicyclo[5.4.0]undec-7-en and dimethylaminopyridine; inorganic bases such as sodium hydride, potassium hydride, lithium hydride and potassium carbonate; lithium diisopropylamide and lithium hexamethyldisilazide.

The amounts of the compound represented by the general formula [15] and the base used in the reaction are in the range of from 1 to 50 moles, preferably 1 to 5 moles per mol of the compound represented by the general formula [11a].

The reaction may be performed at −30 to 150° C., preferably at 0 to 100° C., for 30 minutes to 120 hours.

(B-2) A compound represented by the general formula [2b] can be manufactured by deprotection of a compound represented by the general formula [11b]. The reaction may be performed in accordance with a method conforming to Manufacturing process A-2.

Reactions may be performed at positions 4, 5, 6, 7 and 8 of the 2-oxoquinoline ring and at positions 5, 6, 7 and 8 of the 2-oxoquinoxaline ring in the same manner as in Manufacturing process B.

[Manufacturing Process C]

Organic Chemistry" Fourth Edition, pp. 393 to 400, John Wiley & Sons, INC., 1992 or a method conforming to the method described above.

(C-2) A compound represented by the general formula [2c] can be manufactured by deprotection of a compound represented by the general formula [11d]. The reaction may be performed in accordance with a method conforming to Manufacturing process A-2.

(C-3) A compound represented by the general formula [11e] can be manufactured by reacting a reactive derivative of a compound represented by the general formula [11c] with a

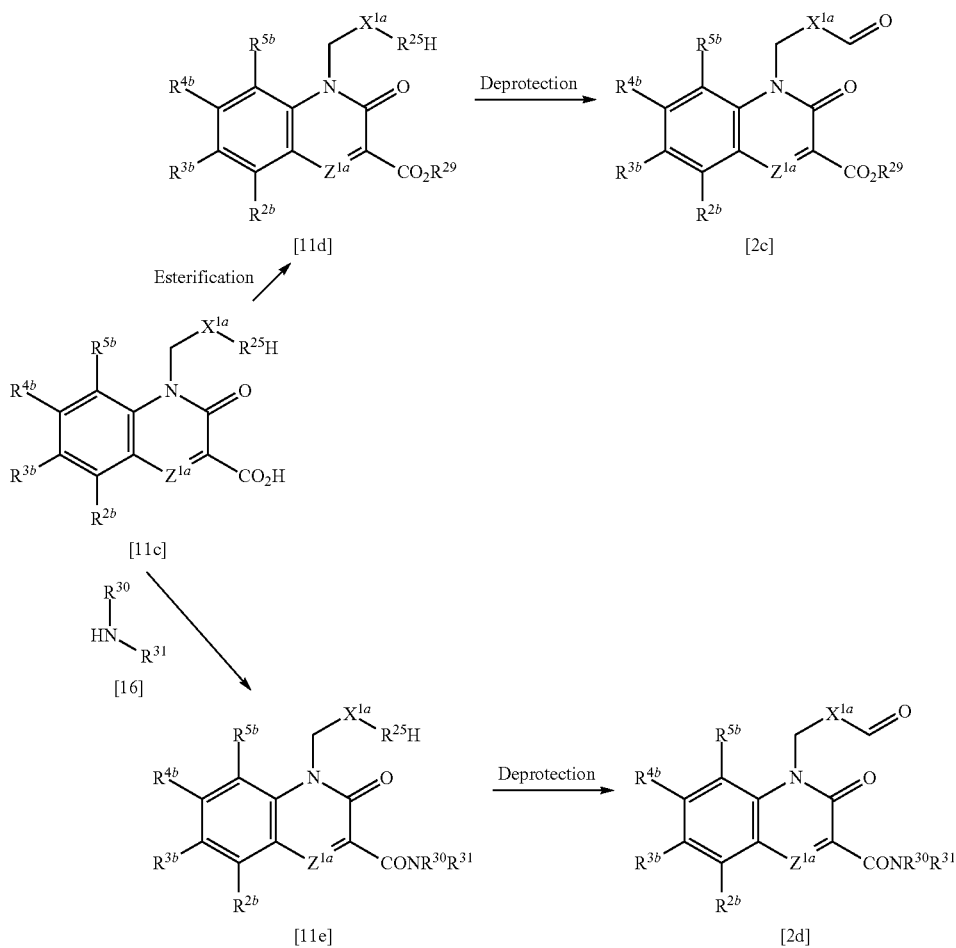

compound represented by the general formula [16] either in the presence or absence of a base.

The reaction may be performed in accordance with, for example, the method described in Izumiya et al. "Basis and Experimentals of Peptide Synthesis" pp. 89 to 142, Maruzen, 1985 or a method conforming to the method described above.

The solvent to be used in the reaction may be any solvent which does not adversely affect the reaction. Examples of suitable solvent include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether;

(wherein $R^{29}$ represents a lower alkyl or aralkyl group which may be substituted; $R^{30}$ and $R^{31}$ are the same or different and represent a hydrogen atom, or a lower alkyl, cycloalkyl, aralkyl or aryl group which may be substituted; $R^{2b}$, $R^{3b}$, $R^{4b}$, $R^{5b}$, $R^{25}$, $X^{1a}$ and $Z^{1a}$ are as defined above).

Examples of compounds represented by the general formula [16] include ammonia, methylamine, dimethylamine, ethylamine, diethylamine, propylamine, cyclopropylamine, benzylamine, 4-chlorobenzylamine, 4-fluorobenzylamine, aniline and 4-chloroaniline.

(C-1) A compound represented by the general formula [11d] can be manufactured by esterification of a compound represented by the general formula [11c].

The reaction may be performed in accordance with, for example, the method described in Jerry March "Advanced sulfoxides such as dimethylsulfoxide; ketones such as acetone and 2-butanone, esters such as ethyl acetate, and combinations thereof.

Examples of base to be used in the reaction if desired include organic bases such as pyridine, dimethylaminopyridine and triethylamine; inorganic bases such as sodium hydroxide, potassium hydroxide, sodium hydrogen carbonate, potassium carbonate and sodium carbonate.

Examples of reactive derivative converted from a compound represented by the general formula [11c] include acid halides such as acid chloride and acid bromide; active esters such as p-nitrophenyl ester, N-hydroxysuccinimide ester and N-hydroxyphthalimide ester; mixed acid anhydrides with carbonate monoalkyl ester such as ethyl chlorocarbonate and isobutyl chlorocarbonate, and mixed acid anhydrides with organic acid such as pivalic acid. The above described reactive derivatives may be used without being isolated.

A coupling reagent may be used to produce a reactive derivative of a compound represented by the general formula [11c] within the system. Examples of suitable coupling reagent include carbodiimides such as N,N'-dicyclohexylcarbodiimide and N-ethyl-N'-(3-dimethylaminopropyl)carbodiimide; carbonyls such as carbonyldiimidazole; acid azides such as diphenylphosphorylazide; acid cyanides such as diethylphosphorylcyanide; 2-ethoxy-1-ethoxycarbonyl-1,2-dihydroquinoline; O-benzotriazol-1-yl-1,1,3,3-tetramethyluronium hexafluorophosphate and O-(7-azabenzotriazol-1-yl)-1,1,3,3-tetramethyluronium hexafluorophosphate.

The amounts of the base, if it is desired, the compound represented by the general formula [16] and the coupling reagent used in the reaction may be in the range of from 1 to 50 moles, preferably 1 to 5 moles per mol of the compound represented by the general formula [11c].

The reaction may be performed at −30 to 150° C., preferably at 0 to 100° C., for 30 minutes to 48 hours.

(C-4) A compound represented by the general formula [2d] can be manufactured by deprotection of a compound represented by the general formula [11e]. The reaction may be performed in accordance with a method conforming to Manufacturing process A-2.

Reactions may be performed at positions 4, 5, 6, 7 and 8 of the 2-oxoquinoline ring and at positions 5, 6, 7 and 8 of the 2-oxoquinoxaline ring in the same manner as in Manufacturing process C.

[Manufacturing Process D]

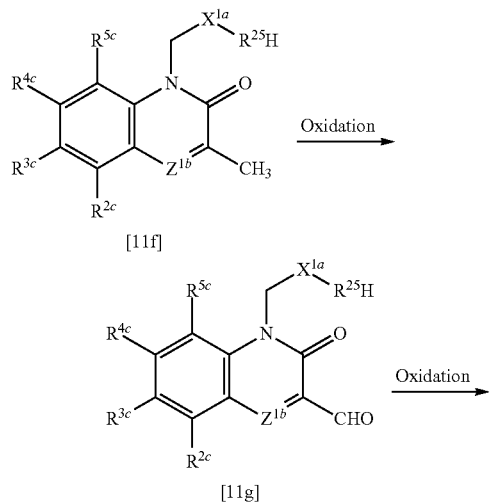

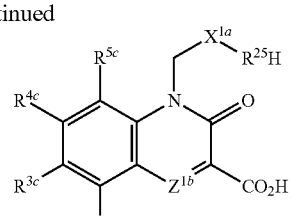

(wherein $Z^{1b}$ represents a nitrogen atom or a group represented by the general formula $CR^{20d}$ (wherein $R^{20d}$ represents a hydrogen atom or an amino group which is protected); $R^{2c}$, $R^{3c}$, $R^{4c}$, $R^{5c}$, $R^{25}$ and $X^{1a}$ are as defined above).

(D-1) A compound represented by the general formula [11g] can be manufactured by oxidation of a compound represented by the general formula [11f].

The reaction may be performed in accordance with, for example, the methods described in Richard C. Larock "Comprehensive Organic Transformations" pp. 591 to 592, VCH Publishers, INC., 1989, and "Chem. Pharm. Bull.", Volume 40, pp. 1322 to 1324, 1992 or a method conforming to the methods described above.

The solvent to be used in the reaction may be any solvent which does not adversely affect the reaction. Examples of suitable solvent include halogenated hydrocarbons such as methylene chloride, chloroform and dichloroethane; aromatic hydrocarbons such as benzene, toluene and xylene; sulfoxides such as dimethylsulfoxide; acids such as acetic acid, water, and combinations thereof.

Examples of oxidizing agent to be used in the reaction include chromium trioxide, manganese dioxide, chromyl chloride and selenium dioxide.

The amount of the oxidizing agent used in the reaction is in the range of from 0.5 to 10 moles per mol of the compound represented by the general formula [11f].

The reaction may be performed at 0 to 200° C., preferably at 0 to 150° C., for 30 minutes to 48 hours.

(D-2) A compound represented by the general formula [11h] can be manufactured by oxidation of a compound represented by the general formula [11g].

The reaction may be performed in accordance with, for example, the methods described in WO03/042150, and Richard C. Larock "Comprehensive Organic Transformations" pp. 838 to 840, VCH Publishers, INC., 1989 or a method conforming to the methods described above.

The solvent to be used in the reaction may be any solvent which does not adversely affect the reaction. Examples of suitable solvent include halogenated hydrocarbons such as methylene chloride, chloroform and dichloroethane; aromatic hydrocarbons such as benzene, toluene and xylene; sulfoxides such as dimethylsulfoxide; nitriles such as acetonitrile; acids such as acetic acid, water, and combinations thereof.

Examples of oxidizing agent to be used in the reaction include sodium chlorite, hydrogen peroxide, potassium permanganate, silver oxide, and mixtures thereof.

The amount of the oxidizing agent used in the reaction is in the range of from 0.5 to 10 moles per mol of the compound represented by the general formula [11g].

The reaction may be performed at 0 to 200° C., preferably at 0 to 150° C., for 30 minutes to 48 hours.

(D-3) A compound represented by the general formula [11h] can be manufactured by oxidation of a compound represented by the general formula [11f] without any need for isolating a compound represented by the general formula [11g]. The reaction may be performed in accordance with a method conforming to Manufacturing processes D-1 and D-2.

Reactions may be performed at positions 4, 5, 6, 7 and 8 of the 2-oxoquinoline ring and at positions 5, 6, 7 and 8 of the 2-oxoquinoxaline ring in the same manner as in Manufacturing process D.

[Manufacturing Process E]

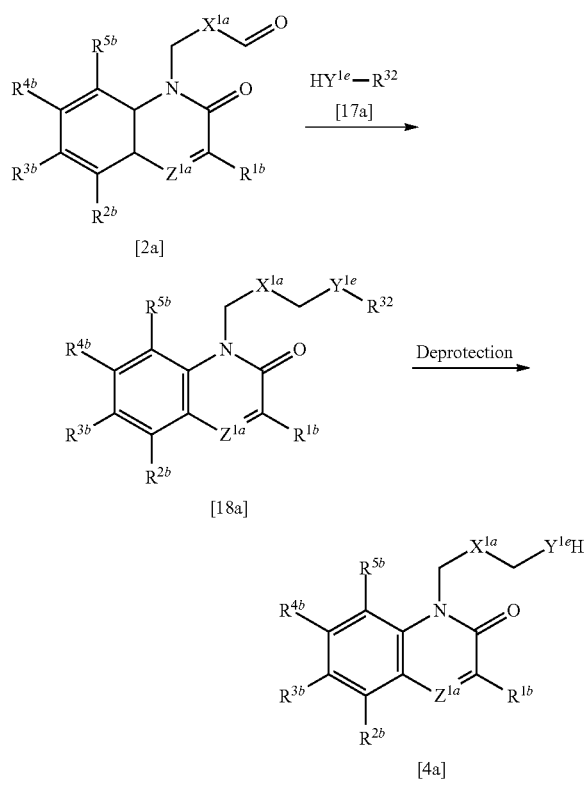

(wherein $R^{32}$ represents an amino protective group or an imino protective group; $Y^{1e}$ represents a group represented by the general formula

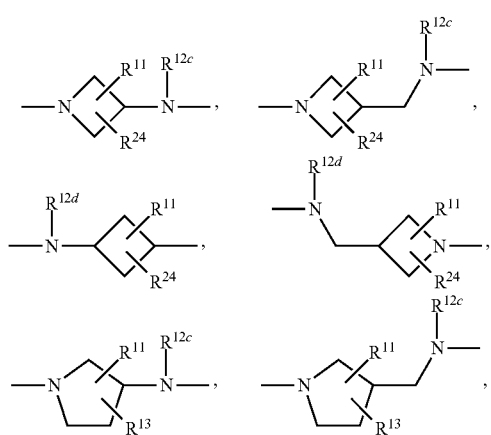

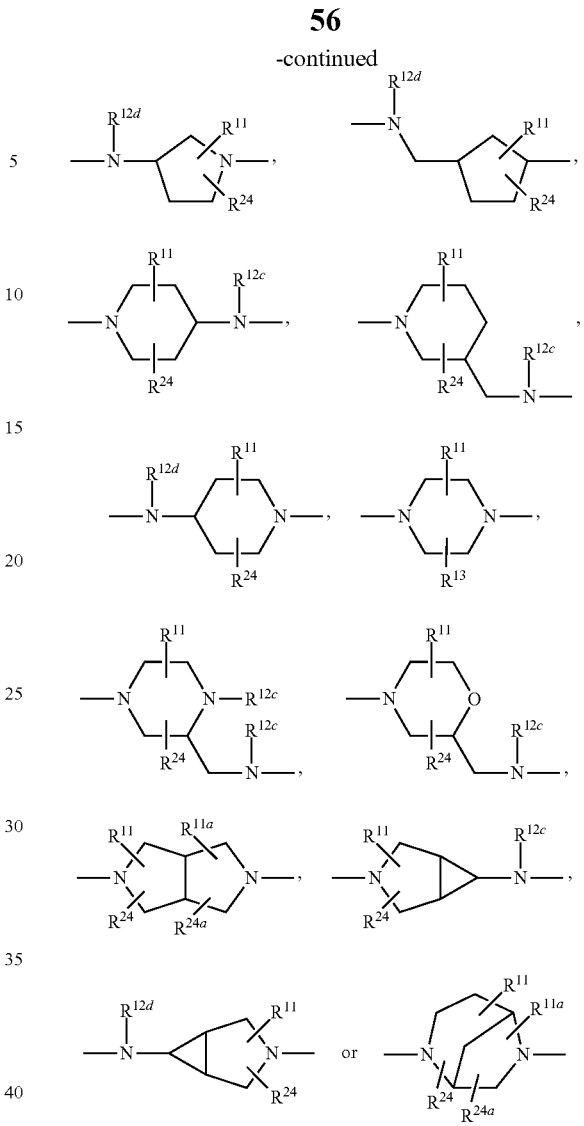

(wherein $R^{11}$, $R^{11a}$, $R^{12c}$, $R^{12d}$, $R^{13}$, $R^{24}$ and $R^{24a}$ are as defined above); $R^{1b}$, $R^{2b}$, $R^{3b}$, $R^{4b}$, $R^{5b}$, $X^{1a}$ and $Z^{1a}$ are as defined above).

Examples of compounds represented by the general formula [17a] include methyl 4-(tert-butoxycarbonyl)piperazine-2-carboxylate and 4-((benzyloxycarbonyl)amino)-4-methylpiperidine.

(E-1) A compound represented by the general formula [18a] can be manufactured by reacting a compound represented by the general formula [2a] with a compound represented by the general formula [17a] in the presence of a reducing agent. The reaction may be performed in accordance with a method conforming to Manufacturing process 1.

(E-2) A compound represented by the general formula [4a] can be manufactured by deprotection of a compound represented by the general formula [18a]. The reaction may be performed in accordance with, for example, the method described in "Protective Groups in Organic Synthesis" Third Edition, pp. 494 to 653, John Wiley & Sons, INC., 1999 or a method conforming to the method described above.

[Manufacturing Process F]

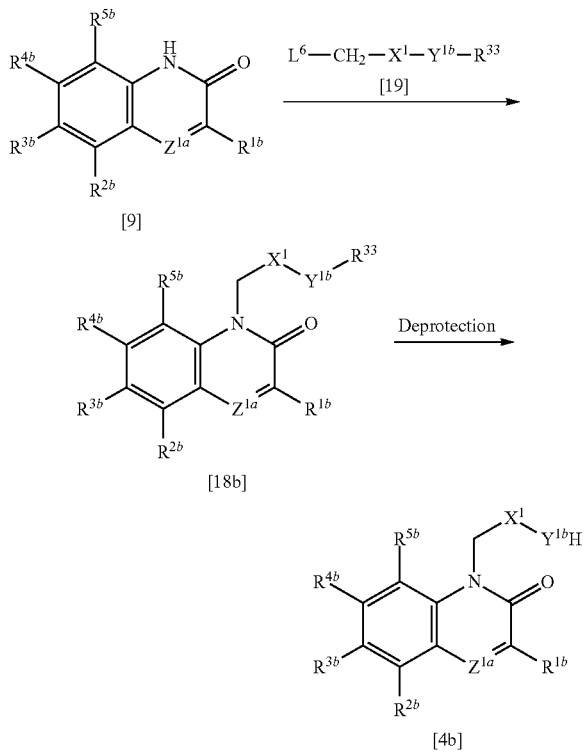

(wherein $R^{33}$ represents an amino protective group or an imino protective group; $L^6$ represents a leaving group; $R^{1b}$, $R^{2b}$, $R^{3b}$, $R^{4b}$, $R^{5b}$, $X^1$, $Y^{1b}$ and $Z^{1a}$ are as defined above).

Examples of known compounds represented by the general formula [19] include 1-tert-butyl 4-ethyl 4-(2-(methanesulfonyloxy)ethyl)-1,4-piperidinedicarboxylate and 1-tert-butyl 4-ethyl 4-(3-bromopropyl)-1,4-piperidinedicarboxylate.

(F-1) A compound represented by the general formula [18b] can be manufactured by reacting a compound represented by the general formula [9] with a compound represented by the general formula [19] either in the presence or absence of a base. The reaction may be performed in accordance with a method conforming to Manufacturing processes A-1 and A-3.

(F-2) A compound represented by the general formula [4b] can be manufactured by deprotection of a compound represented by the general formula [18b]. The reaction may be performed in accordance with a method conforming to Manufacturing process E-2.

[Manufacturing Process G]

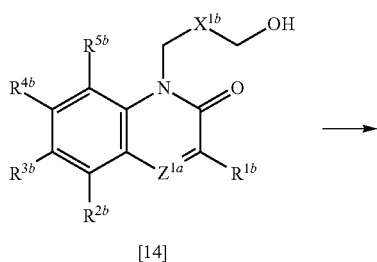

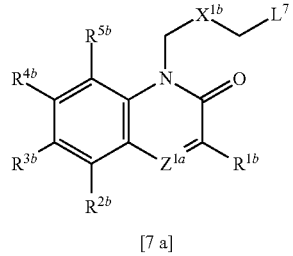

(wherein $L^7$ represents a leaving group; $R^{1b}$, $R^{2b}$, $R^{3b}$, $R^{4b}$, $R^{5b}$, $X^{1b}$ and $Z^{1a}$ are as defined above).

A compound represented by the general formula [7a] can be manufactured by converting the hydroxyl group in a compound represented by the general formula [14] to a leaving group.

When a leaving group represents an alkanesulfonyloxy group or an arylsulfonyloxy group, a compound represented by the general formula [14] can be reacted with, for example, alkanesulfonylchlorides such as methanesulfonylchloride, or arylsulfonylchlorides such as p-toluenesulfonyl chloride either in the presence or absence of a base.

The amounts of alkanesulfonylchloride and arylsulfonylchloride used in the reaction are in the range of from 1 to 10 moles, preferably 1 to 3 moles per mol of the compound represented by the general formula [14].

Examples of base to be used in the reaction if desired include metallic alkoxides such as sodium methoxide, sodium ethoxide, potassium tert-butoxide and sodium tert-butoxide; inorganic bases such as sodium hydroxide, potassium hydroxide, sodium hydrogen carbonate, sodium carbonate, potassium carbonate, sodium hydride and potassium hydride; organic bases such as triethylamine, N,N-diisopropylethylamine and pyridine.

The amount of the base, if it is desired, used in the reaction is in the range of from 1 to 10 moles, preferably 1 to 3 moles per mol of the compound represented by the general formula [14].

The reaction may be performed at 0 to 200° C., preferably at 0 to 50° C., for 30 minutes to 48 hours.

When a leaving group represents a halogen atom, a compound represented by the general formula [14] can be reacted with thionyl chloride, thionyl bromide, boron tribromide, tetrabromomethane-triphenylphosphine and the like. The amount of the compound used in the reaction is in the range of from 1 to 10 moles, preferably 1 to 3 moles per mol of the compound represented by the general formula [14].

The solvent to be used in the reaction may be any solvent which does not adversely affect the reaction without being limited. Examples of suitable solvent include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, diethylene glycol dimethyl ether, diethylene glycol diethyl ether and ethylene glycol monomethyl ether; nitriles such as acetonitrile; sulfoxides such as dimethylsulfoxide, heteroaromatics such as pyridine, and combinations thereof.

The reaction may be performed at 0 to 200° C., preferably at 0 to 50° C., for 30 minutes to 48 hours.

[Manufacturing Process H]

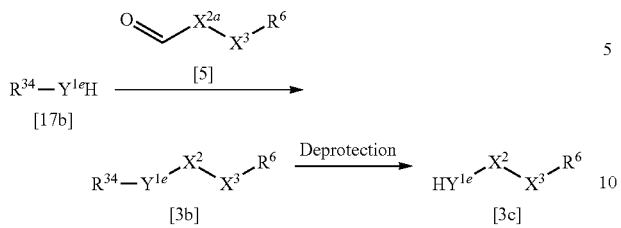

(wherein $R^{34}$ represents an amino protective group or an imino protective group; $R^6$, $X^2$, $X^{2a}$, $X^3$ and $Y^{1e}$ are as defined above).

Examples of known compounds represented by the general formula [17b] include 1-(tert-butoxycarbonyl)-4-aminopiperidine and methyl 4-(tert-butoxycarbonyl)piperazine-2-carboxylate.

(H-1) A compound represented by the general formula [3b] can be manufactured by reacting a compound represented by the general formula [17b] with a compound represented by the general formula [5] in the presence of a reducing agent. The reaction may be performed in accordance with a method conforming to Manufacturing process 2.

(H-2) A compound represented by the general formula [3c] can be manufactured by deprotection of a compound represented by the general formula [3b]. The reaction may be performed in accordance with a method conforming to Manufacturing process E-2.

[Manufacturing Process I]

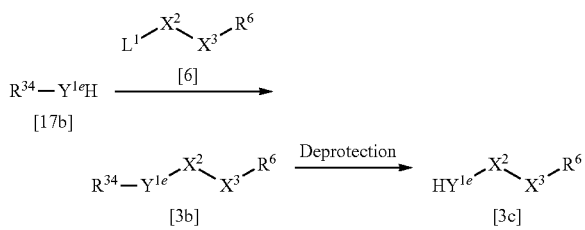

(wherein $R^6$, $R^{34}$, $X^2$, $X^3$, $Y^{1e}$ and $L^1$ are as defined above).

Examples of known compounds represented by the general formula [6] include 2-(3-oxo-3,4-dihydro-2H-benzothiazin-6-yl)ethyl methanesulfonate, 2-(benzo[1,3]dioxol-5-yl)ethyl methanesulfonate, 2-((2-bromoethyl)thio)thiophene and 2-bromo-N-(pyridin-2-yl)acetamide.

(I-1) A compound represented by the general formula [3b] can be manufactured by reacting a compound represented by the general formula [17b] with a compound represented by the general formula [6] either in the presence or absence of a base. The reaction may be performed in accordance with a method conforming to Manufacturing process 3.

(I-2) A compound represented by the general formula [3c] can be manufactured by deprotection of a compound represented by the general formula [3b]. The reaction may be performed in accordance with a method conforming to Manufacturing process E-2.

[Manufacturing Process J]

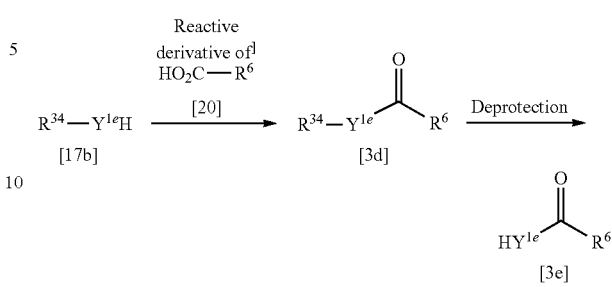

(wherein $R^6$, $R^{34}$ and $Y^{1e}$ are as defined above).

Examples of known compounds represented by the general formula [20] include 2,3-dihydro-1,4-benzodioxin-6-carboxylic acid.

(J-1) A compound represented by the general formula [3d] can be manufactured by reacting a reactive derivative of a compound represented by the general formula [20] with a compound represented by the general formula [17b] either in the presence or absence of a base. The reaction may be performed in accordance with a method conforming to Manufacturing process C-3.

(J-2) A compound represented by the general formula [3e] can be manufactured by deprotection of a compound represented by the general formula [3d]. The reaction may be performed in accordance with a method conforming to Manufacturing process E-2.

[Manufacturing Process K]

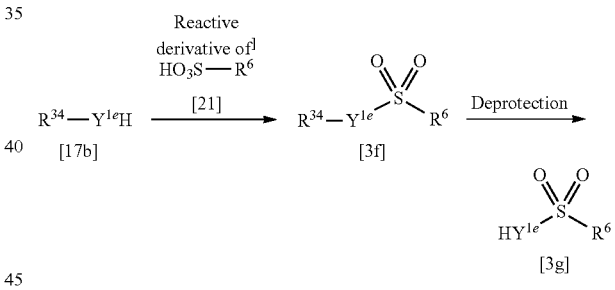

(wherein $R^6$, $R^{34}$ and $Y^{1e}$ are as defined above).

Examples of reactive derivative converted from a compound represented by the general formula [21] include 2,3-dihydro-1,4-benzodioxin-6-sulfonylchloride, 2-naphthalenesulfonylchloride, coumarin-6-sulfonylchloride and 4-methyl-3,4-dihydro-2H-1,4-benzoxazine-7-sulfonylchloride.

(K-1) A compound represented by the general formula [3f] can be manufactured by reacting a reactive derivative of a compound represented by the general formula [21] with a compound represented by the general formula [17b] either in the presence or absence of a base. The reaction may be performed in accordance with the method described in Jerry March "Advanced Organic Chemistry" Fourth Edition, pp. 499, John Wiley & Sons, INC., 1992 or a method conforming to the method described above.

(K-2) A compound represented by the general formula [3g] can be manufactured by deprotection of a compound represented by the general formula [3f]. The reaction may be performed in accordance with a method conforming to Manufacturing process E-2.

[Manufacturing Process L]

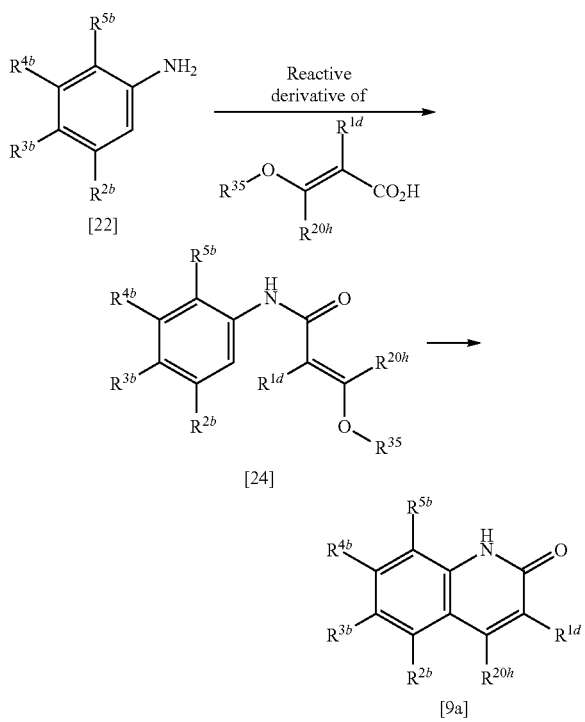

(wherein $R^{1d}$ represents a hydrogen atom, a cyano group, a lower alkyl or lower alkoxy group which may be substituted, or a group represented by the general formula -$Q^1$-CONR$^7$R$^8$ or -$Q^1$-CO$_2$R$^{9a}$ (wherein $R^7$, $R^8$, $R^{9a}$ and $Q^1$ are as defined above); $R^{20h}$ represents a hydrogen atom or a lower alkyl group which may be substituted; $R^{35}$ represents a hydrogen atom or a lower alkyl group which may be substituted; $R^{2b}$, $R^{3b}$, $R^{4b}$ and $R^{5b}$ are as defined above).

Examples of known compounds represented by the general formula [23] include (E)-3-ethoxyacrylic acid, (E)-3-methoxy-2-methylacrylic acid and (E)-3-methoxy-3-methylacrylic acid.

(L-1) A compound represented by the general formula [24] can be manufactured by reacting a reactive derivative of a compound represented by the general formula [23] with a compound represented by the general formula [22] either in the presence or absence of a base. The reaction may be performed in accordance with a method conforming to Manufacturing process C-3.

(L-2) A compound represented by the general formula [9a] can be manufactured by performing ring-closure of a compound represented by the general formula [24] either in the presence or absence of a solvent and in the presence of an acid. The reaction may be performed in accordance with, for example, a method described in JP-A-62-240677 or a method conforming to the method described above.

The solvent to be used in the reaction if desired may be any solvent which does not adversely affect the reaction. Examples of suitable solvent include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; sulfoxides such as dimethylsulfoxide; ketones such as acetone and 2-butanone, esters such as ethyl acetate, and combinations thereof.

Examples of acid to be used in the reaction include inorganic acids such as hydrochloric acid, hydrobromic acid, sulfuric acid and phosphoric acid; Lewis acids such as aluminum chloride, boron trifluoride and titanium tetrachloride, organic acids such as formic acid, acetic acid, methanesulfonic acid and p-toluenesulfonic acid.

The amount of the acid used in the reaction is in the range of from 0.1 to 1000 moles, preferably 0.1 to 100 moles per mol of the compound represented by the general formula [24].

The reaction may be performed at −30 to 200° C., preferably at −20 to 100° C., for 30 minutes to 48 hours.

[Manufacturing Process M]

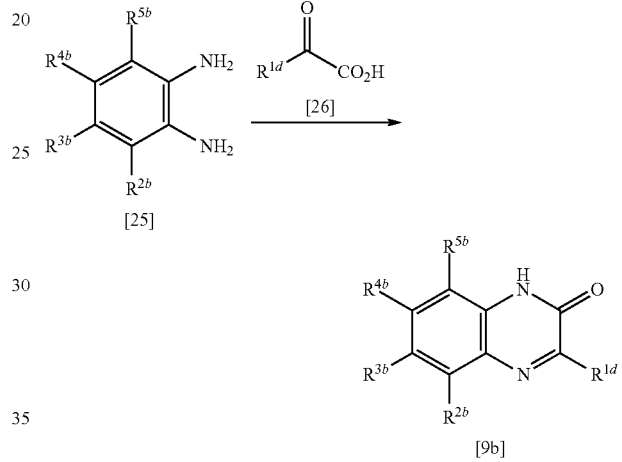

(wherein $R^{1d}$, $R^{2b}$, $R^{3b}$, $R^{4b}$ and $R^{5b}$ are as defined above).

Examples of compounds represented by the general formula [26] include pyruvic acid and glyoxylic acid.

A compound represented by the general formula [9b] can be manufactured by reacting a compound represented by the general formula [25] with a compound represented by the general formula [26]. The reaction may be performed in accordance with, for example, the method described in "J. Med. Chem.". Volume 44, pp. 594 to 601, 2001 or a method conforming to the method described above.

The solvent to be used in the reaction may be any solvent which does not adversely affect the reaction. Examples of suitable solvent include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; sulfoxides such as dimethylsulfoxide; ketones such as acetone and 2-butanone, esters such as ethyl acetate, and combinations thereof.

The amount of the compound represented by the general formula [26] used in the reaction is in the range of from 1 to 10 moles, preferably 1 to 5 moles per mol of the compound represented by the general formula [25].

The reaction may be performed at −30 to 200° C., preferably at 0 to 100° C., for 30 minutes to 48 hours.

[Manufacturing Process N]

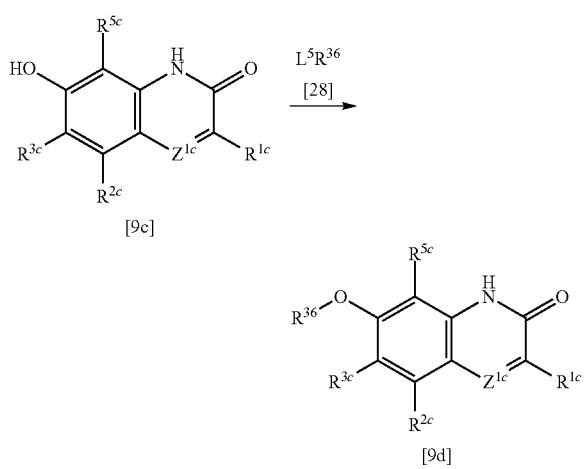

(wherein $R^{1c}$, $R^{2c}$, $R^{3c}$, $R^{5c}$, $R^{36}$, $L^5$ and $Z^{1c}$ are as defined above).

A compound represented by the general formula [9d] can be manufactured by reacting a compound represented by the general formula [9c] with a compound represented by the general formula [28] either in the presence or absence of a base. The reaction may be performed in accordance with a method conforming to Manufacturing process 8.

Reactions may be performed at positions 3, 4, 5, 6 and 8 of the 2-oxoquinoline ring and at positions 3, 5, 6 and 8 of the 2-oxoquinoxaline ring in the same manner as in Manufacturing process N.

[Manufacturing Process O]

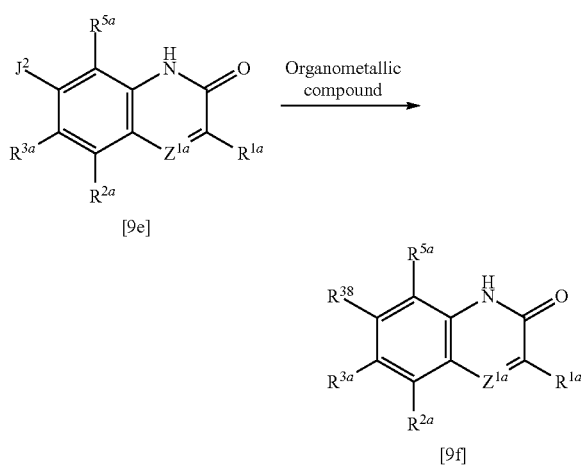

(wherein $R^{2a}$ represents a hydrogen atom, a cyano group, an amino group which is protected, a lower alkyl or lower alkoxy group which may be substituted, or a group represented by the general formula $Q^1CONR^7R^8$ or $Q^1CO_2R^{9a}$ (wherein $R^7$, $R^8$, $R^{9a}$ and $Q^1$ are as defined above); $R^{38}$ represents an alkyl, alkenyl, alkynyl, cycloalkyl or aryl group which may be substituted; $R^{1a}$, $R^{3a}$, $R^{5a}$, $J^1$ and $Z^{1a}$ are as defined above).

A compound represented by the general formula [9f] can be manufactured by reacting a compound represented by the general formula [9e] with an organometallic compound in the presence of a catalyst, either in the presence or absence of a base, and either in the presence or absence of phosphine.

Examples of organometallic compound to be used in the reaction include organoboron compounds such as phenylboronic acid and organotin compounds such as 2-thienyltributyltin.

The reaction may be performed in accordance with, for example, the method described in Tsuji et al. "Organic synthesis by means of transition metal" pp. 25 to 35, Maruzen, 1997 or a method conforming to the method described above.

The solvent to be used in the reaction may be any solvent which does not adversely affect the reaction. Examples of suitable solvent include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; sulfoxides such as dimethylsulfoxide; ketones such as acetone and 2-butanone, esters such as ethyl acetate, water, and combinations thereof.

Examples of base to be used in the reaction if desired include organic bases such as sodium tert-butoxide, pyridine, dimethylaminopyridine and triethylamine; inorganic bases such as sodium hydroxide, potassium hydroxide, sodium hydrogen carbonate, potassium carbonate, sodium carbonate and cesium carbonate.

Examples of catalyst to be used for the reaction include palladium carbon, tetrakis(triphenylphosphine)palladium, palladium(II) acetate, palladium(II) chloride and tris(dibenzylideneacetone)dipalladium(O).

Examples of phosphine to be used in the reaction if desired include triphenylphosphine, tri-tert-butylphosphine, diphenyl(orthotolyl)phosphine, tri(tolyl)phosphine and 2,2'-bis(diphenylphosphino)-1,1'-binaphthyl.

The amounts of the organometallic compound and the base, if it is desired, used in the reaction are in the range of from 1 to 50 moles, preferably 1 to 5 moles per mol of the compound represented by the general formula [9e].

The amount of the catalyst used in the reaction is in the range of from 0.001 to 10 moles, preferably 0.01 to 2 moles per mol of the compound represented by the general formula [9e].

The amount of phosphine, if it is desired, used in the reaction is in the range of from 0.001 to 40 moles, preferably 0.01 to 8 moles per mol of the compound represented by the general formula [9e].

The reaction may be performed at -30 to 150° C., preferably at 0 to 100° C., for 30 minutes to 48 hours.

Reactions may be performed at positions 3, 4, 5, 6 and 8 of the 2-oxoquinoline ring and at positions 3, 5, 6 and 8 of the 2-oxoquinoxaline ring in the same manner as in Manufacturing process P.

[Manufacturing Process P]

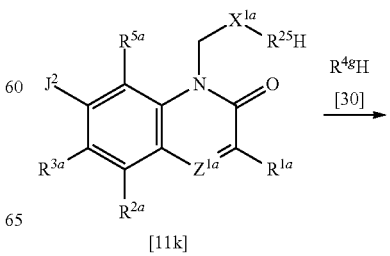

-continued

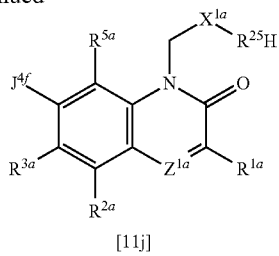

[11j]

(wherein $R^{4g}$ represents a nitrogen-containing heterocyclic group; $J^2$ represents a halogen atom; $R^{1a}$, $R^{2a}$, $R^{3a}$, $R^{5a}$, $R^{25}$, $X^{1a}$ and $Z^{1a}$ are as defined above).

Examples of compounds represented by the general formula [30] include pyrrolidine, piperidine, piperazine, morpholine, imidazole and triazole.

A compound represented by the general formula [11j] can be manufactured by reacting a compound represented by the general formula [11i] with a compound represented by the general formula [30] in the presence of a base and a copper catalyst.

The reaction may be performed in accordance with, for example, the method described in "Bioorganic. Med. Chem. Lett.," Volume 12, pp. 2251 to 2273, 2004 or a method conforming to the method described above.

The solvent to be used in the reaction may be any solvent which does not adversely affect the reaction. Examples of suitable solvent include amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, ethylene glycol dimethyl ether, diethylene glycol dimethyl ether and diethylene glycol diethyl ether; sulfoxides such as dimethylsulfoxide; ketones such as acetone and 2-butanone, esters such as ethyl acetate, water, and combinations thereof.

Examples of base to be used in the reaction include organic bases such as sodium tert-butoxide, pyridine, dimethylaminopyridine and triethylamine; inorganic bases such as sodium hydride, sodium hydrogen carbonate, potassium carbonate, sodium carbonate and cesium carbonate.

Examples of copper catalyst to be used in the reaction include copper oxide, copper bromide and copper acetate.

The amount of the catalyst used in the reaction is in the range of from 0.1 to 10 moles, preferably 0.5 to 2 moles per mol of the compound represented by the general formula [11i].

The amount of the compound represented by the general formula [30] used in the reaction is in the range of from 1 to 40 moles, preferably 1 to 5 moles per mol of the compound represented by the general formula [11i].

The reaction may be performed at −30 to 150° C., preferably at 0 to 100° C., for 30 minutes to 48 hours.

Reactions may be performed at positions 3, 4, 5, 6 and 8 of the 2-oxoquinoline ring and at positions 3, 5, 6 and 8 of the 2-oxoquinoxaline ring in the same manner as in Manufacturing process P.

[Manufacturing Process Q]

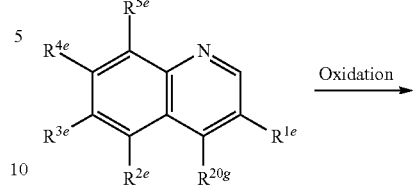

[31]

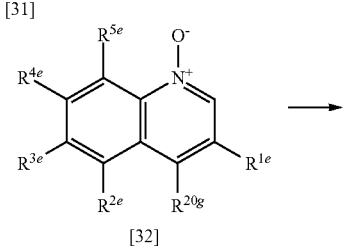

[32]

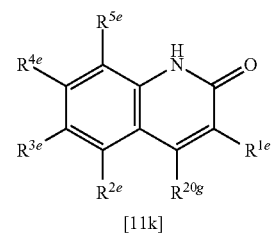

[11k]

(wherein $R^{1e}$, $R^{2e}$, $R^{3e}$, $R^{4e}$, $R^{5e}$ and $R^{20g}$ are the same or different and represent a hydrogen atom, a cyano group, an amino group which is protected, a lower alkyl or lower alkoxy group which may be substituted, or a group represented by the general formula $-Q^1\text{-CONR}^7R^8$ or $-Q^1\text{-CO}_2R^{9a}$ (wherein $R^7$, $R^8$, $R^{9a}$ and $Q^1$ are as defined above)).

(Q-1) A compound represented by the general formula [32] can be manufactured by oxidation of a compound represented by the general formula [31].

The reaction may be performed in accordance with, for example, the methods described in "Heterocycles" Volume 32, pp. 1579 to 1586, 1991, and "Heterocycles" Volume 34, pp. 1055 to 1063, 1992 or a method conforming to the methods described above.

The solvent to be used in the reaction may be any solvent which does not adversely affect the reaction. Examples of suitable solvent include halogenated hydrocarbons such as methylene chloride, chloroform and dichloroethane; aromatic hydrocarbons such as benzene, toluene and xylene; sulfoxides such as dimethylsulfoxide, water, and combinations thereof.

Examples of oxidizing agent to be used in the reaction include m-chloroperbenzoic acid and acetyl hydroperoxide.

The amount of the oxidizing agent used in the reaction is in the range of from 1 to 10 moles per mol of the compound represented by the general formula [31].

The reaction may be performed at 0 to 200° C., preferably at 0 to 50° C., for 30 minutes to 48 hours.

(Q-2) A compound represented by the general formula [11k] can be manufactured by reacting a compound represented by the general formula [32] with sulfonylchlorides which is then subjected to a hydration reaction.

The reaction may be performed in accordance with, for example, the methods described in "Heterocycles" Volume 32, pp. 1579 to 1586, 1991, and "Heterocycles" Volume 34, pp. 1055 to 1063, 1992 or a method conforming to the methods described above.

The solvent to be used together with water in the reaction may be any solvent which does not adversely affect the reaction. Examples of suitable solvent include halogenated hydrocarbons such as methylene chloride, chloroform and dichloroethane; aromatic hydrocarbons such as benzene, toluene and xylene; sulfoxides such as dimethylsulfoxide; nitriles such as acetonitrile, and combinations thereof.

Examples of sulfonylchlorides to be used in the reaction include p-toluenesulfonylchloride and benzenesulfonylchloride.

The amount of sulfonylchloride used in the reaction is in the range of from 1 to 10 moles per mol of the compound represented by the general formula [32].

The reaction may be performed at 0 to 200° C., preferably at 0 to 50° C., for 30 minutes to 48 hours.

By known reactions such as, for example, condensation, addition, oxidation, reduction, rearrangement, substitution, halogenation, dehydration and hydrolysis, or arbitrarily combining the reactions, compounds which are obtained in accordance with Manufacturing processes A to Q can be converted into other compounds.

For use in medicine, the compounds of the present invention may be arbitrarily mixed with formulation additives such as excipients, carriers and dilution agents which are generally used for formulation. By the law of the art, these compositions may be formulated as tablets, capsules, powders, syrups, granules, pills, suspensions, emulsions, liquids, powder formulations, suppositories, eye drops, nose drops, ear drops, adhesive skin patches, ointments, injections and the like, and may be administered either orally or parenterally. Moreover, the mode of administration, dosage and the number of doses of the preparations may be arbitrarily determined in accordance with various conditions such as age and weight of the patient, and the severity of the patient's symptoms. The recommended dose range for adult patients is generally 0.01 to 1000 mg/kg/day for oral or parenteral administration (for example, injection, intravenous drip and rectal administration) either at once or in several installments.

EXAMPLES

The usefulness of the compounds of the present invention will now be described in the test examples hereinafter.

Test Example 1

Sensitivity Test 1

Test compounds were initially dissolved in dimethylsulfoxide. Antibacterial activities (MICs) of the same compounds were determined by the micro-dilution method as recommended by the Japanese Society of Chemotherapy.

*Staphylococcus aureus* (*S. aureus* FDA209P) was used as the test organism. The bacterial cells were grown overnight at 35° C. on Mueller-Hinton agar (MHA) plates. The bacterial cells were then suspended in sterile saline and adjusted to the turbidity of a 0.5 McFarland standard. The inoculum was prepared by 10-fold dilution of this suspension. Approximately 0.005 mL aliquots of the inoculum prepared above were subsequently inoculated into Cation-adjusted Mueller-Hinton broth (CAMHB, 100 μL/well) including the test compounds for overnight incubation at 35° C. The lowest concentration of agent at which bacteria virtually showed no growth was read as the antibacterial activity (MIC). The results are shown in Table 6.

TABLE 6

| Example No. | MIC(μg/mL) |
|---|---|
| 2 | 0.0313 |
| 7 | 0.25 |
| 18 | 0.25 |
| 25 | 0.0625 |
| 28 | 0.0625 |
| 36 | 0.125 |
| 39 | 0.0625 |
| 51 | 0.125 |
| 53 | 1 |
| 57 | 0.0625 |
| 63 | 0.0625 |
| 64 | 0.0156 |
| 66 | 0.25 |
| 70 | 0.25 |
| 77 | 0.125 |
| 79 | 0.0625 |
| 83 | 0.0625 |
| 90 | 0.0313 |
| 91 | 0.0313 |
| 97 | 0.125 |
| 104 | 0.0625 |
| 107 | 0.0313 |
| 109 | 0.125 |
| 117 | 0.0313 |
| 125 | 0.0313 |
| 127 | 0.0625 |
| 129 | 0.0625 |
| 141 | 0.125 |
| 155 | 0.125 |
| 176 | 0.0625 |
| 179 | 0.0156 |
| 182 | 0.0625 |
| 186 | 0.25 |
| 189 | 0.0625 |
| 244 | 0.0625 |
| 263 | 0.125 |
| 339 | 0.0625 |
| 340 | 0.0313 |
| 341 | 0.0313 |
| 342 | 0.0313 |
| 343 | 0.125 |
| 344 | 0.125 |
| 346 | 0.0156 |
| 347 | 0.0156 |
| 349 | 0.0156 |
| 351 | 0.0078 |
| 352 | 0.0156 |
| 353 | 0.0156 |
| 354 | 0.0078 |
| 355 | 0.0156 |
| 356 | 0.0156 |
| 357 | 0.0156 |
| 358 | 0.0078 |
| 359 | 0.0313 |
| 360 | 0.0078 |
| 363 | 0.0313 |
| 367 | 0.0156 |
| 368 | 0.0156 |
| 369 | 0.0313 |
| 370 | 0.0039 |
| 375 | 0.0156 |
| 389(B) | 0.0156 |
| 400 | 0.0156 |

Test Example 2

Sensitivity Test 2

Methicillin-resistant *Staphylococcus aureus* (*S. aureus* F-3095) was used as the test organism. Antibacterial activities (MICs) were determined in the same manner as in Test Example 1. Results are shown in Table 7.

TABLE 7

| Example No. | MIC(µg/mL) |
| --- | --- |
| 2 | 0.0313 |
| 25 | 0.125 |
| 64 | 0.0156 |
| 90 | 0.0625 |
| 91 | 0.0313 |
| 117 | 0.0313 |
| 141 | 0.25 |
| 179 | 0.0313 |
| 263 | 0.25 |
| 340 | 0.0625 |
| 341 | 0.0625 |
| 352 | 0.0313 |
| 359 | 0.0313 |
| 367 | 0.0156 |
| 369 | 0.0313 |
| 389(B) | 0.0625 |

Test Example 3

Cytotoxicity Test

Test compounds were initially dissolved in dimethylsulfoxide. The test compound solutions were then diluted with Eagle's Minimum Essential Medium (E'MEM) supplemented with 10% Fetal Bovine Serum (FBS) to a concentration of 102.4 µg/mL. Cultures were performed at 37° C. for 3 days in 5% $CO_2$ incubator after combining the test compound solution (100 µL/well) and Vero cells suspended in E'MEM containing 10% FBS ($3 \times 10^3$ cells/100 µL/well). 50 µL of E'MEM containing 1 mg/mL of 2,3-bis-(2-methoxy-4-nitro-5-sulfophenyl)-5-[(phenylamino)carbonyl]-2H-tetrazolium inner salt monosodium salt (XTT) and 25 µmol/L of phenazine methosulfate (PMS) was added to each well for further incubation at 37° C. for 2 hours. After incubation, absorbance was read at 450 nm and 655 nm in a spectrophotometric microplate reader. The values were expressed as the ratio between the value for the well treated with 51.2 µg/mL of each test compound and the value for the well untreated with the test compound (T/C). Results are shown in Table 8.

TABLE 8

| Example No. | T/C(%) |
| --- | --- |
| 7 | >50 |
| 25 | >50 |
| 63 | >50 |
| 90 | >50 |
| 141 | >50 |
| 263 | >50 |
| 340 | >50 |
| 341 | >50 |
| 352 | >50 |
| 359 | >50 |
| 367 | >50 |
| 369 | >50 |
| 389(B) | >50 |

Test Example 4

Infection Test

*S. aureus* Smith which was grown overnight at 37° C. on Mueller-Hinton agar (MHA) plates were suspended to give a final concentration of $10^9$ CFU/mL. The inoculum was prepared by diluting this suspension 10-fold in 1/15 mol/L phosphate buffer (pH 7) containing 5.6% mucin. ICR mice (4 to 4.5 weeks of age, male, 5 mice per group) were intraperitoneally administered with the inoculum (approximately $2 \times 10^7$ CFU per mice) to induce infection.

After dissolving the test compounds in 0.1 mol/L hydrochloric acid, 20% 2-hydroxypropyl-β-cyclodextrin (HP-β-CD) or a mixture of 20% HP-β-CD and 0.1 mol/L hydrochloric acid at a proportion of 1:1 was added to give a final concentration of 1 mg/mL. Each of the test compound solutions (10 mg/kg) was subcutaneously administered once to a group of mice at 1 hour after infection. The control group was administered with 10% HP-β-CD. The mice were observed daily and the number of surviving mice in each group was recorded 3 days after infection. Results are shown in Table 9.

TABLE 9

| Example No. | Number of surviving mice |
| --- | --- |
| 2 | 4 |
| 25 | 5 |
| 90 | 5 |
| 91 | 5 |
| 117 | 5 |
| 141 | 5 |
| 179 | 5 |
| 263 | 5 |
| 340 | 5 |
| 341 | 5 |
| 352 | 5 |
| 359 | 5 |
| 367 | 5 |
| 369 | 5 |
| Control | 0 |

The present invention will be then explained with reference to Reference Examples and Examples; however, the present invention is not limited to these Examples.

A mixing ratio for an eluent is indicated as a volume ratio.

Unless otherwise stated, the carrier used in silica gel column chromatography is B. W. silica gel, BW-127ZH, manufactured by Fuji Silysia Chemical Ltd.; the carrier used in basic silica gel column chromatography is silica gel, FL100D, manufactured by Fuji Silysia Chemical Ltd.; and the carrier used in reversed phase silica gel column chromatography is ODS-AM120-S50, manufactured by YMC Co., Ltd.

Flash silica gel column chromatography is performed with a medium pressure liquid chromatograph, YFLC-Wprep2XY. N, manufactured by YAMAZEN CORPORATION. Unless otherwise stated, a silica gel column is a Hi-Flash column, W001, W002, W003 or W004, manufactured by YAMAZEN CORPORATION.

In Examples, abbreviations stand for the following meanings:

Ac: acetyl, Bn: benzyl, Boc: tert-butoxycarbonyl, Bu: butyl, Et: ethyl, Me: methyl, Ms: methanesulfonyl, Ph: phenyl, Tf: trifluoromethanesulfonyl, Ts: p-toluenesulfonyl, and DMSO-$d_6$: deuterated dimethylsulfoxide.

Reference Example 1

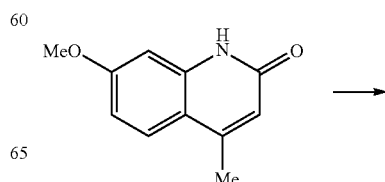

-continued

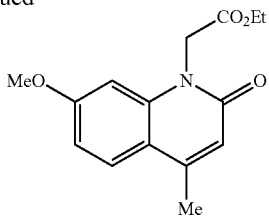

To 10 mL of an N,N-dimethylformamide suspension containing 0.80 g of 7-methoxy-4-methylquinolin-2(1H)-one, 0.19 g of 60% sodium hydride was added under cooling with ice, and the mixture was stirred for 30 minutes. Thereto was added 0.52 mL of ethyl bromoacetate, the temperature of the reaction mixture was increased to room temperature, and the reaction mixture was stirred for 1 hour. Water and ethyl acetate were then added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; hexane:ethyl acetate=1:1] to obtain 0.80 g of a white solid, ethyl (7-methoxy-4-methyl-2-oxoquinolin-1(2H)-yl)acetate.

$^1$H-NMR (CDCl$_3$) δ:
1.26 (3H, t, J=7.1 Hz), 2.44 (3H, d, J=1.0 Hz), 3.88 (3H, s), 4.23 (2H, q, J=7.1 Hz), 5.06 (2H, s), 6.47 (1H, d, J=1.0 Hz), 6.55 (1H, d, J=2.3 Hz), 6.84 (1H, dd, J=8.9, 2.3 Hz), 7.64 (1H, d, J=8.9 Hz)

Reference Example 2

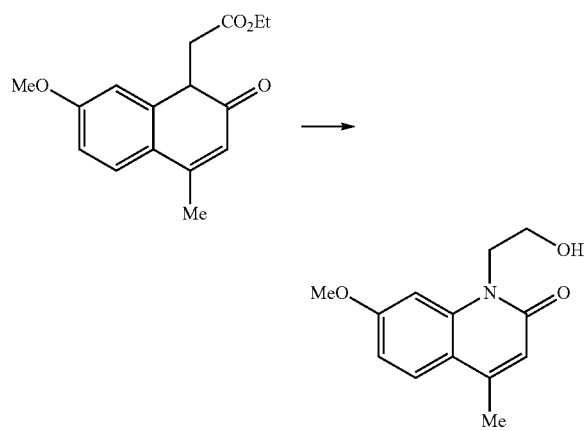

To 10 mL of a tetrahydrofuran suspension containing 0.22 g of lithium aluminum hydride, 5 mL of a tetrahydrofuran solution containing 0.80 g of ethyl (7-methoxy-4-methyl-2-oxoquinolin-1(2H)-yl)acetate was added at 5° C. The reaction mixture was stirred for 1 hour, and thereto were added water and ethyl acetate, and the insoluble material filtered off. The organic layer was separated, and the aqueous layer was extracted twice with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; chloroform:methanol=100:1] to obtain 0.46 g of a white solid, 1-(2-hydroxyethyl)-7-methoxy-4-methylquinolin-2(1H)-one.

$^1$H-NMR (CDCl$_3$) δ:
2.45 (3H, s), 3.91 (3H, s), 4.04 (2H, t, J=5.5 Hz), 4.50 (2H, t, J=5.5 Hz), 6.47 (1H, s), 6.85-6.88 (2H, m), 7.65 (1H, d, J=9.5 Hz)

Reference Example 3

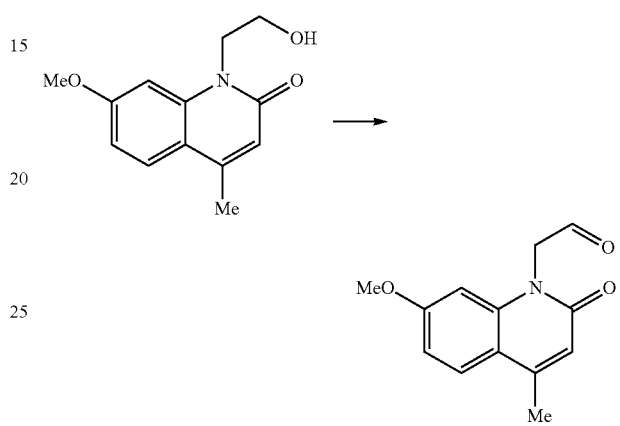

To 5 mL of a dichloromethane solution containing 0.10 mL of oxalyl chloride, 0.15 mL of dimethyl sulfoxide was added dropwise at −60° C., and the mixture was stirred for 10 minutes. Thereto was added dropwise 15 mL of a dichloromethane solution containing 0.20 g of 1-(2-hydroxyethyl)-7-methoxy-4-methylquinolin-2(1H)-one at the same temperature, and the mixture was stirred for 10 minutes. Thereto was added 0.48 mL of triethylamine at the same temperature, and the mixture was stirred for 30 minutes. The temperature of the reaction mixture was increased to room temperature, the reaction mixture was stirred for 1 hour, and water was added thereto. The organic layer was separated, and the aqueous layer was extracted twice with chloroform. The organic layer and the extract were combined, the resultant solution was dried over anhydrous magnesium sulfate, and the solvent was removed under reduced pressure. The residue thus obtained was purified by silica gel column chromatography [eluent; chloroform:methanol=100:1] to obtain 0.17 g of a white solid, (7-methoxy-4-methyl-2-oxoquinolin-1(2H)-yl)acetaldehyde.

$^1$H-NMR (CDCl$_3$) δ:
2.46 (3H, s), 3.87 (3H, s), 5.10 (2H, s), 6.48 (1H, d, J=2.3 Hz), 6.49 (1H, s), 6.86 (1H, dd, J=8.9, 2.3 Hz), 7.66 (1H, d, J=8.9 Hz), 9.63 (1H, s)

Reference Example 4

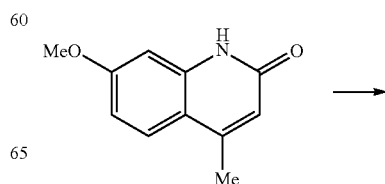

-continued

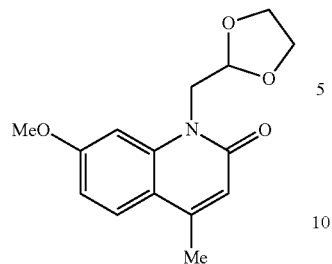

To 5 mL of an N,N-dimethylformamide solution containing 0.50 g of 7-methoxy-4-methylquinolin-2(1H)-one, 0.12 g of 60% sodium hydride was added at 5° C., and the mixture was stirred for 15 minutes. Thereto was added 0.46 mL of 2-bromomethyl-1,3-dioxolane, the temperature of the reaction mixture was increased to 60° C., and the reaction mixture was stirred for 4 hours. Thereto was added 0.12 g of 60% sodium hydride, the temperature of the reaction mixture was increased to 95° C., and the reaction mixture was stirred for 4 hours. Thereto was added 0.23 mL of 2-bromomethyl-1,3-dioxolane, the temperature of the reaction mixture was increased to 95° C., and the reaction mixture was stirred for 3 hours. Water and ethyl acetate were then added thereto. The organic layer was separated, and the aqueous layer was extracted twice with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was added with diethyl ether, and a solid substance was collected by filtration to obtain 0.18 g of a pale yellow solid, 1-(1,3-dioxolan-2-ylmethyl)-7-methoxy-4-methylquinolin-2(1H)-one.

$^1$H-NMR (CDCl$_3$) δ:
2.42 (3H, s), 3.85-3.95 (2H, m), 3.91 (3H, s), 4.03-4.08 (2H, m), 4.51 (2H, d, J=4.4 Hz), 5.24 (1H, t, J=4.4 Hz), 6.45 (1H, s), 6.83 (1H, dd, J=8.8, 2.4 Hz), 7.10 (1H, d, J=2.4 Hz), 7.60 (1H, d, J=8.8 Hz)

Reference Example 5

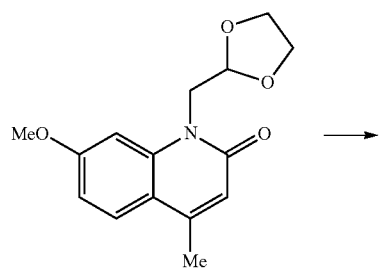

-continued

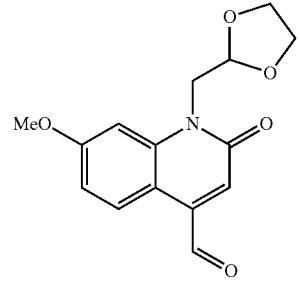

To 3 mL of a xylene solution containing 50 mg of 1-(1,3-dioxolan-2-ylmethyl)-7-methoxy-4-methylquinolin-2(1H)-one, 20 mg of serene dioxide was added, and the mixture was stirred for 6 hours under reflux. The reaction mixture was cooled to 60° C., the insoluble material filtered off, and the filtration residue was washed with chloroform. The filtrate and the washing solution were combined, and the solvent was removed under reduced pressure. The residue thus obtained was added with diethyl ether, and a solid substance was collected by filtration to obtain a yellow solid, 34 mg of 1-(1,3-dioxolan-2-ylmethyl)-7-methoxy-2-oxo-1,2-dihydroquinoline-4-carbaldehyde.

$^1$H-NMR (CDCl$_3$) δ:
3.87-3.95 (2H, m), 3.93 (3H, s), 4.03-4.08 (2H, m), 4.56 (2H, d, J=4.4 Hz), 5.27 (1H, t, J=4.4 Hz), 6.91 (1H, dd, J=9.0, 2.4 Hz), 7.01 (1H, s), 7.14 (1H, d, J=2.4 Hz), 8.75 (1H, d, J=9.0 Hz), 10.09 (1H, s)

Reference Example 6

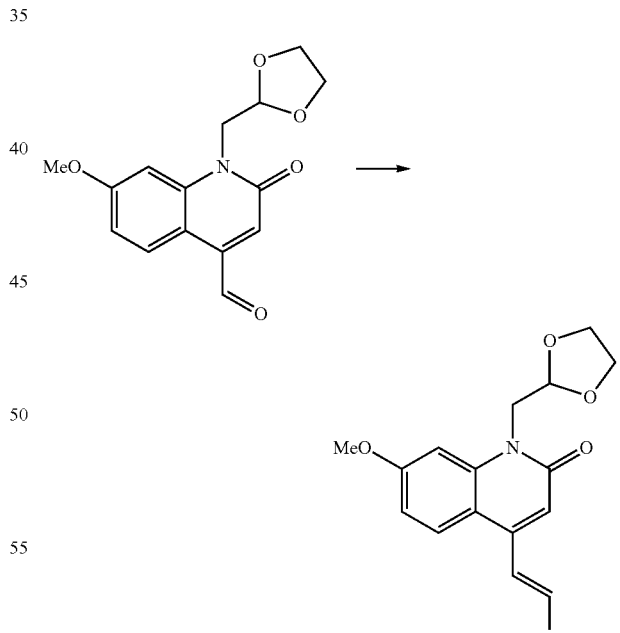

To 4 mL of an N,N-dimethylformamide solution containing 0.16 mL of ethyl diethyl phosphonoacetate, 30 mg of 60% sodium hydride was added, and the mixture was stirred for 10 minutes. Thereto was added 0.20 g of 1-(1,3-dioxolan-2-ylmethyl)-7-methoxy-2-oxo-1,2-dihydroquinoline-4-carbaldehyde, and the mixture was stirred for 1 hour. Water and ethyl acetate were then added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; chloroform] to obtain 0.18 g of a pale yellow solid, ethyl (2E)-3-(1-(1,3-dioxolan-2-ylmethyl)-7-methoxy-2-oxo-1,2-dihydroquinolin-4-yl)acrylate.

$^1$H-NMR (CDCl$_3$) δ:

1.36 (3H, t, J=7.1 Hz), 3.75-3.91 (2H, m), 3.92 (3H, s), 4.04-4.08 (2H, m), 4.31 (2H, q, J=7.1 Hz), 4.53 (2H, d, J=4.4 Hz), 5.25 (1H, t, J=4.4 Hz), 6.47 (1H, d, J=15.7 Hz), 6.70 (1H, s), 6.86 (1H, dd, J=8.9, 2.4 Hz), 7.14 (1H, d, J=2.4 Hz), 7.69 (1H, d, J=8.9 Hz), 8.03 (1H, d, J=15.7 Hz)

Reference Example 7

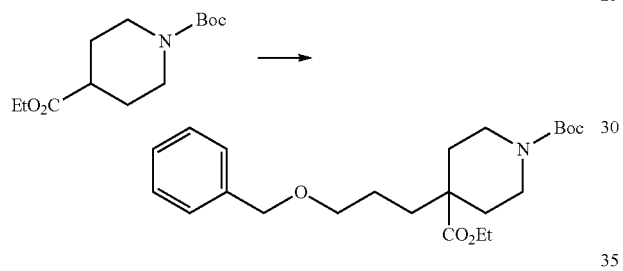

To 20 mL of a tetrahydrofuran solution containing 1.2 mL of diisopropylamine, 5.8 mL of 1.6 mol/L butyllithium/hexane was added dropwise at −78° C., and the mixture was stirred at the same temperature for 1 hour. Thereto was added dropwise 2 mL of a tetrahydrofuran solution containing 2.0 g of 1-tert-butyl 4-ethyl piperidine-1,4-dicarboxylate, and the mixture was stirred for 1 hour. Thereto was added 1.7 mL of benzyl 3-bromopropyl ether, and the temperature of the reaction mixture was increased to room temperature, and the reaction mixture was stirred for 10 hours. Water was added thereto, and the reaction mixture was adjusted to pH 2.0 with 6 mol/L hydrochloric acid. The organic layer was separated, and the aqueous layer was extracted twice with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; hexane:ethyl acetate=10:1 ] to obtain 2.0 g of a colorless oily substance, 1-tert-butyl 4-ethyl 4-(3-(benzyloxy)propyl)piperidine-1,4-dicarboxylate.

$^1$H-NMR (CDCl$_3$) δ:

1.25 (3H, t, J=7.2 Hz), 1.25-1.45 (2H, m), 1.45 (9H, s), 1.50-1.65 (4H, m), 2.05-2.15 (2H, m), 2.75-3.00 (2H, m), 3.42 (2H, t, J=6.1 Hz), 3.75-3.95 (2H, m), 4.16 (2H, q, J=7.2 Hz), 4.47 (2H, s), 7.26-7.37 (5H, m)

Reference Example 8

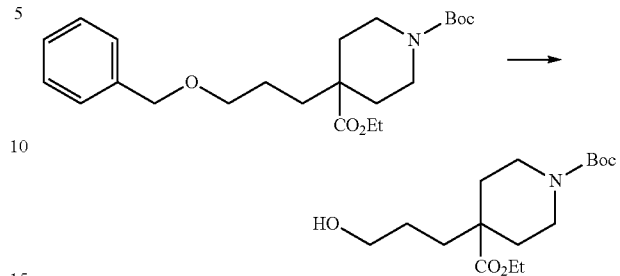

To 20 mL of an ethanol solution containing 2.0 g of 1-tert-butyl 4-ethyl 4-(3-(benzyloxy)propyl)piperidine-1,4-dicarboxylate, 2 mL of an ethanol suspension containing 0.30 g of 10% palladium carbon was added, and the mixture was stirred for 4 hours under a hydrogen atmosphere. The insoluble material filtered off, and the solvent was removed under reducer pressure to obtain 1.7 g of a colorless oily substance, 1-tert-butyl 4-ethyl 4-(3-hydroxypropyl)piperidine-1,4-dicarboxylate.

$^1$H-NMR (CDCl$_3$) δ:

1.27 (3H, t, J=7.2 Hz), 1.23-1.62 (6H, m), 1.45 (9H, s), 2.05-2.15 (2H, m), 2.80-2.95 (2H, m), 3.58-3.63 (2H, m), 3.75-3.95 (2H, m), 4.18 (2H, q, J=7.2 Hz)

Reference Example 9

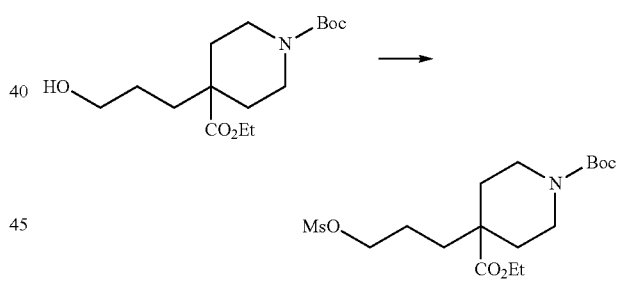

To 20 mL of a tetrahydrofuran solution containing 1.7 g of 1-tert-butyl 4-ethyl 4-(3-hydroxypropyl)piperidine-1,4-dicarboxylate, 0.82 mL of triethylamine and 0.58 mL of methane sulfonylchloride were added at 5° C., and the mixture was stirred at room temperature for 1 hour. Ethyl acetate and water were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure to obtain 1.9 g of a colorless oily substance, 1-tert-butyl 4-ethyl 4-(3-((methanesulfonyl)oxy)propyl)piperidine-1,4-dicarboxylate.

$^1$H-NMR (CDCl$_3$) δ:

1.25-1.75 (6H, m), 1.28 (3H, t, J=7.2 Hz), 1.45 (9H, s), 2.05-2.15 (2H, m), 2.80-2.95 (2H, m), 3.00 (3H, s), 3.80-3.95 (2H, m), 4.19 (2H, q, J=7.2 Hz), 4.15-4.22 (2H, m)

Reference Example 10

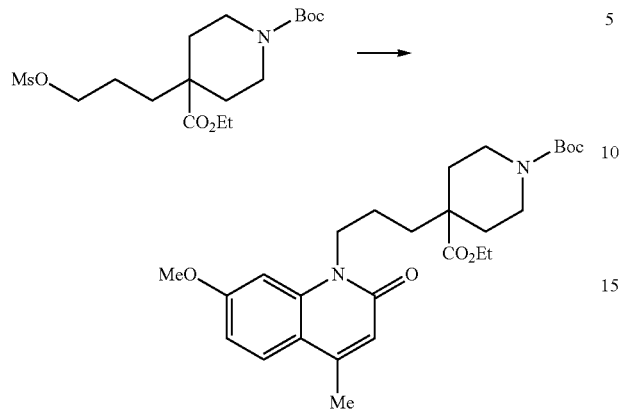

To 5 mL of an N,N-dimethylformamide suspension containing 0.50 g of 7-methoxy-4-methylquinolin-2(1H)-one, 0.11 g of 60% sodium hydride was added, and the mixture was stirred at 60° C. for 20 minutes. Thereto was added 1.09 g of 1-tert-butyl 4-ethyl 4-(3-((methanesulfonyl)oxy)propyl)piperidine-1,4-dicarboxylate, the temperature of the reaction mixture was increased to 70° C., and the reaction mixture was stirred for 4 hours. Thereto was added 0.11 g of 60% sodium hydride, and the resultant solution was stirred for 4 hours. Water and ethyl acetate were then added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; hexane:ethyl acetate=1:1] to obtain 0.45 g of a yellow oily substance, 1-tert-butyl 4-ethyl 4-(3-(7-methoxy-4-methyl-2-oxoquinolin-1(2H)-yl)propyl)piperidine-1,4-dicarboxylate.

$^1$H-NMR (CDCl$_3$) δ:
1.19 (3H, t, J=7.1 Hz), 1.30-1.45 (2H, m), 1.44 (9H, s), 1.60-1.75 (4H, m), 2.02-2.12 (2H, m), 2.41 (3H, d, J=1.0 Hz), 2.80-2.95 (2H, m), 3.75-3.95 (2H, m), 3.91 (3H, s), 4.11 (2H, q, J=7.1 Hz), 4.15-4.25 (2H, m), 6.42 (1H, d, J=1.0 Hz), 6.77 (1H, d, J=2.4), 6.83 (1H, dd, J=8.9, 2.4 Hz), 7.62 (1H, d, J=8.9 Hz)

Reference Example 11

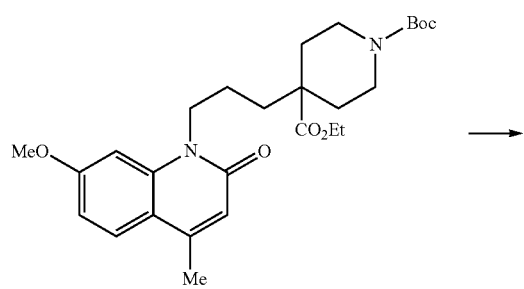

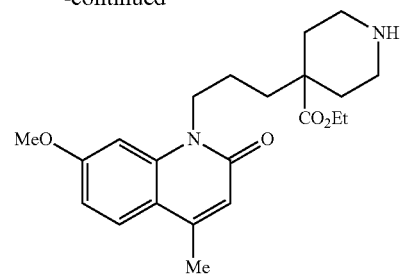

To 2 mL of a chloroform solution containing 0.45 g of 1-tert-butyl 4-ethyl 4-(3-(7-methoxy-4-methyl-2-oxoquinolin-1(2H)-yl)propyl)piperidine-1,4-dicarboxylate, 1 mL of trifluoroacetic acid was added, and the mixture was stirred for 14 hours. The solvent was removed under reduced pressure, and water and diethyl ether were added thereto. The aqueous layer was separated, ethyl acetate was added thereto, and the resultant solution was adjusted to pH 12.5 with a 20% aqueous sodium hydroxide solution. The organic layer was separated, and the aqueous layer was extracted twice with ethyl acetate. The organic layer and the extract were combined, and the resultant solution was washed with an aqueous saturated sodium chloride solution and dried over anhydrous magnesium sulfate, and the solvent was removed under reduced pressure to obtain 0.29 g of a yellow oily substance, ethyl 4-(3-(7-methoxy-4-methyl-2-oxoquinolin-1(2H)-yl)propyl)piperidine-4-carboxylate.

$^1$H-NMR (CDCl$_3$) δ:
1.19 (3H, t, J=7.1 Hz), 1.35-1.45 (2H, m), 1.60-1.75 (4H, m), 2.05-2.20 (2H, m), 2.41 (3H, s), 2.60-2.72 (2H, m), 2.90-3.10 (2H, m), 3.91 (3H, s), 4.11 (2H, q, J=7.1 Hz), 4.10-4.30 (2H, m), 6.41 (1H, s), 6.73 (1H, d, J=2.4), 6.83 (1H, dd, J=8.9, 2.4 Hz), 7.61 (1H, d, J=8.9 Hz)

Reference Example 12

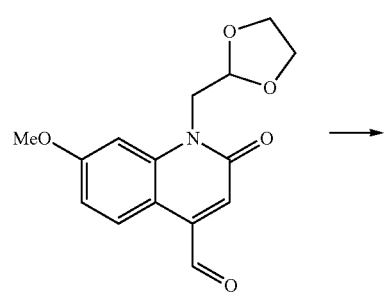

To a mixed solution of 2 mL of acetonitrile containing 0.30 g of 1-(1,3-dioxolan-2-ylmethyl)-7-methoxy-2-oxo-1,2-dihydroquinoline-4-carbaldehyde and 1 mL of water, a solution of 1 mL of water containing 0.88 g of sodium dihydrogen phosphate, 0.18 mL of a 30% hydrogen peroxide solution and 0.19 g of a sodium chlorite were added, and the mixture was stirred at room temperature for 1 hour and 30 minutes. Water and ethyl acetate were added thereto. The organic layer was separated, and the aqueous layer was extracted twice with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was dissolved in chloroform, thereto was added a diethyl ether solution containing 0.09 g of diazomethane, and the resultant solution was left to stand for 10 minutes. After adding 0.5 mL of acetic acid, an aqueous saturated sodium hydrogen carbonate solution was added thereto. The organic layer was separated, and the aqueous layer was extracted with chloroform. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; chloroform:methanol=100:1] to obtain 0.20 g of a pale yellow oily substance, methyl 1-(1,3-dioxolan-2-ylmethyl)-7-methoxy-2-oxo-1,2-dihydroquinoline-4-carboxylate.

$^1$H-NMR (CDCl$_3$) δ:

3.86-3.94 (2H, m), 3.92 (3H, s), 3.97 (3H, s), 4.02-4.06 (2H, m), 4.53 (2H, d, J=4.3 Hz), 5.24 (1H, t, J=4.3 Hz), 6.86 (1H, dd, J=9.2, 2.4 Hz), 7.03 (1H, s), 7.13 (1H, d, J=2.4 Hz), 8.24 (1H, d, J=9.2 Hz)

Reference Example 13

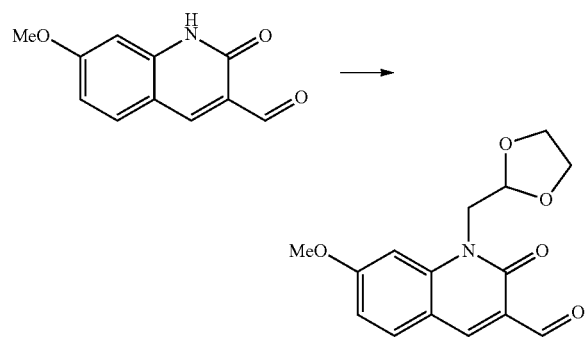

To 30 mL of an N,N-dimethylformamide solution containing 1.5 g of 7-methoxy-2-oxo-1,2-dihydroquinoline-3-carbaldehyde, 0.32 g of 60% sodium hydride was added, and the mixture was stirred at 50° C. for 30 minutes. Thereto was added 1.53 mL of 2-bromomethyl-1,3-dioxolane, and the reaction mixture was stirred at 80 to 90° C. for 2 hours. Thereto was added 1.53 mL of 2-bromomethyl-1,3-dioxolane, and the reaction mixture was stirred for 3 hours and 30 minutes. Water and ethyl acetate were then added thereto, and the reaction mixture was adjusted to pH 1.5 with 6 mol/L hydrochloric acid. The organic layer was separated, and the aqueous layer was extracted twice with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was added with a mixed solution of diethyl ether and ethyl acetate, and a solid substance collected by filtration, and then purified by silica gel column chromatography [eluent; chloroform] to obtain 0.35 g of a yellow solid, 1-(1,3-dioxolan-2-ylmethyl)-7-methoxy-2-oxo-1,2-dihydroquinoline-3-carbaldehyde.

$^1$H-NMR (CDCl$_3$) δ:

3.88-3.93 (2H, m), 3.95 (3H, s), 4.00-4.10 (2H, m), 4.56 (2H, d, J=4.3 Hz), 5.26 (1H, t, J=4.3 Hz), 6.88 (1H, dd, J=8.8, 2.2 Hz), 7.09 (1H, d, J=2.2 Hz), 7.63 (1H, d, J=8.8 Hz), 8.32 (1H, s), 10.42 (1H, s)

Reference Example 14

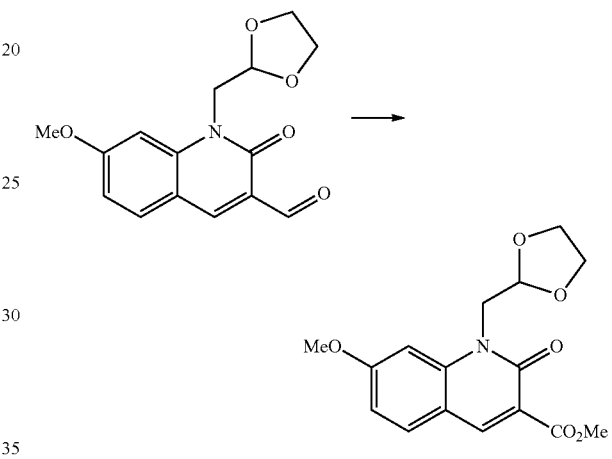

To a mixed solution of 4 mL of acetonitrile containing 0.35 g of 1-(1,3-dioxolan-2-ylmethyl)-7-methoxy-2-oxo-1,2-dihydroquinoline-3-carbaldehyde and 2 mL of water, 0.49 g of sodium dihydrogen phosphate, 0.20 mL of 30% hydrogen peroxide solution and 0.21 g of sodium chlorite were added thereto, and the mixture was stirred at room temperature for 3 hours and 20 minutes. Water and chloroform were added thereto. The organic layer was separated, and the aqueous layer was extracted with chloroform. The organic layer and the extract were combined, and the resultant solution was washed with an aqueous saturated sodium chloride solution and dried over anhydrous magnesium sulfate. Thereto was added a diethyl ether solution containing 0.15 g of diazomethane, and the resultant solution was left to stand for 10 minutes. After adding 0.5 mL of acetic acid, water and aqueous saturated sodium hydrogen carbonate solution were added thereto. The organic layer was separated, and the aqueous layer was extracted with chloroform. The organic layer and the extract were combined, and the resultant solution was washed with an aqueous saturated sodium chloride solution and dried over anhydrous magnesium sulfate, and the solvent was removed under reduced pressure to obtain 0.42 g of a pale yellow solid, methyl 1-(1,3-dioxolan-2-ylmethyl)-7-methoxy-2-oxo-1,2-dihydroquinoline-3-carboxylate.

$^1$H-NMR (CDCl$_3$) δ:

3.85-3.95 (2H, m), 3.93 (3H, s), 3.94 (3H, s), 4.00-4.10 (2H, m), 4.52 (2H, d, J=4.5 Hz), 5.26 (1H, t, J=4.5 Hz), 6.86 (1H, dd, J=8.7, 2.3 Hz), 7.07 (1H, d, J=2.3 Hz), 7.56 (1H, d, J=8.7 Hz), 8.46 (1H, s)

Reference Example 15

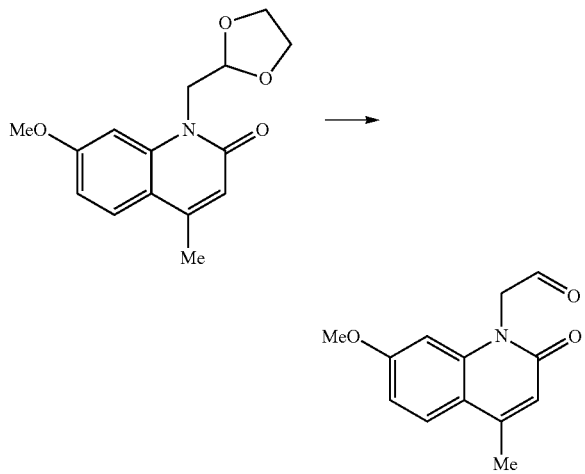

To 4 mL of a 90% aqueous trifluoroacetic acid solution, 0.40 g of 1-(1,3-dioxolan-2-ylmethyl)-7-methoxy-4-methylquinolin-2(1H)-one was added, and the mixture was stirred at room temperature for 15 hours. The solvent was removed under reduced pressure, and ethyl acetate and water were added thereto. The reaction mixture was adjusted to pH 7.0 with an aqueous saturated sodium hydrogen carbonate solution, and stirred at room temperature for 4 hours. The organic layer was separated, and the aqueous layer was extracted with ethyl acetate. The organic layer and the extract were combined, and the resultant solution was washed sequentially with water and an aqueous saturated sodium chloride solution and dried over anhydrous magnesium sulfate, and the solvent was removed under reduced pressure. The residue thus obtained was added with hexane, and a solid substance was collected by filtration to obtain 0.30 g of white solid, (7-methoxy-4-methyl-2-oxoquinolin-1(2H)-yl)acetaldehyde.

$^1$H-NMR in CDCl$_3$ corresponded to values of Reference Example 3.

Reference Example 16

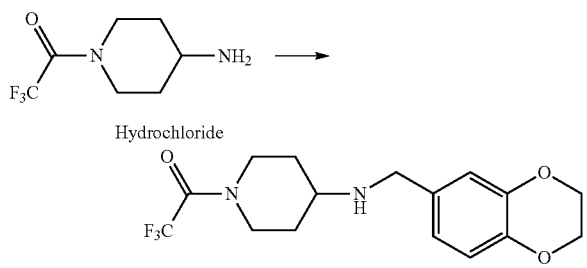

To 20 mL of a dichloromethane suspension containing 1.0 g of 1-(trifluoroacetyl)piperidine-4-amine hydrochloride, 0.71 g of 2,3-dihydro-1,4-benzodioxin-6-carbaldehyde and 0.25 mL of acetic acid were added, the mixture was stirred at room temperature for 2 hours. The reaction mixture was added with 1.37 g of sodium triacetoxyborohydride was added and stirred at the same temperature for 30 minutes. The solvent was removed under reduced pressure, then water and ethyl acetate were added thereto, and the reaction mixture was adjusted to pH 1.5 with 1 mol/L hydrochloric acid. The aqueous layer was separated and washed with ethyl acetate, then ethyl acetate was added thereto, and the resultant solution was adjusted to pH 7.8 with an aqueous saturated sodium hydrogen carbonate solution. The organic layer was separated, and the aqueous layer was extracted with ethyl acetate. The organic layer and the extract were combined, and the resultant solution was washed with an aqueous saturated sodium chloride solution and dried over anhydrous magnesium sulfate, and the solvent was removed under reduced pressure to obtain 1.4 g of a colorless oily substance, N-(2,3-dihydro-1,4-benzodioxin-6-ylmethyl)-1-(trifluoroacetyl)piperidine-4-amine.

$^1$H-NMR (CDCl$_3$) δ:
1.35-1.50 (2H, m), 1.90-2.00 (2H, m), 2.80-2.88 (1H, m), 3.02-3.12 (1H, m), 3.18-3.28 (1H, m), 3.71 (2H, s), 3.90-4.00 (1H, m), 4.25 (4H, s), 4.25-4.32 (1H, m), 6.75-6.83 (3H, m)

Reference Example 17

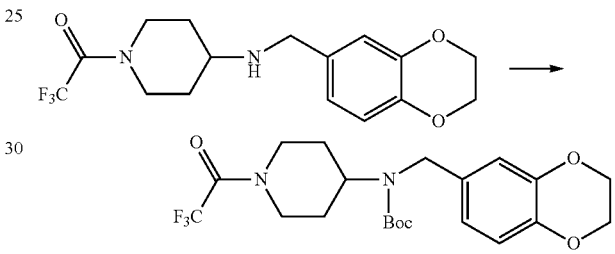

To 20 mL of a dichloromethane solution containing 1.4 g of N-(2,3-dihydro-1,4-benzodioxin-6-ylmethyl)-1-(trifluoroacetyl)piperidine-4-amine, 0.88 g of di-tert-butyl dicarbonate was added, the mixture was stirred at room temperature for 30 minutes. Thereto was added 0.28 mL of triethylamine, and the mixture was stirred at the same temperature for 10 minutes. Then, 0.44 g of di-tert-butyl dicarbonate was further added thereto, and the mixture was stirred for 10 minutes. After the reaction mixture was stirred at 40° C. for 30 minutes, the solvent was removed under reduced pressure, and the residue thus obtained was purified by silica gel column chromatography [eluent; hexane:ethyl acetate=1:1] to obtain 1.4 g of a white foam, tert-butyl (2,3-dihydro-1,4-benzodioxin-6-ylmethyl) (1-(trifluoroacetyl)piperidin-4-yl)carbamate.

$^1$H-NMR (CDCl$_3$) δ:
1.44 (9H, s), 1.60-1.82 (4H, m), 2.60-2.80 (1H, m), 3.00-3.20 (1H, m), 3.95-4.05 (1H, m), 4.15-4.40 (3H, m), 4.25 (4H, s), 4.50-4.65 (1H, m), 6.60-6.75 (2H, m), 6.70-6.73 (1H, m), 6.79 (1H, d, J=8.3 Hz)

Reference Example 18

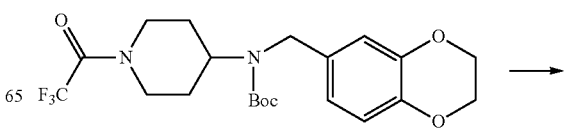

-continued

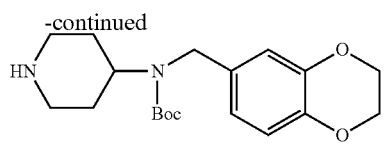

To 20 mL of a methanol solution containing 1.4 g of tert-butyl (2,3-dihydro-1,4-benzodioxin-6-ylmethyl)(1-(trifluoroacetyl)piperidin-4-yl)carbamate, 5 mL of water and 0.53 g of potassium carbonate were added, and the mixture was stirred at room temperature for 1 hour and 15 minutes. The solvent was removed under reduced pressure, and ethyl acetate and water were added thereto. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure to obtain 1.0 g of a pale yellow oily substance, tert-butyl (2,3-dihydro-1,4-benzodioxin-6-ylmethyl) (piperidin-4-yl)carbamate.

$^1$H-NMR (CDCl$_3$) δ:
1.42 (9H, s), 1.35-1.70 (4H, m), 2.55-2.70 (2H, m), 3.05-3.15 (2H, m), 4.15-4.35 (3H, m), 4.24 (4H, s), 6.66-6.71 (1H, m), 6.73-6.75 (1H, m), 6.78 (1H, d, J=8.3 Hz)

Reference Example 19

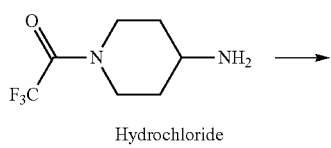

To 10 mL of a dichloromethane suspension containing 0.50 g of 1-(trifluoroacetyl)piperidine-4-amine hydrochloride, 0.50 g of 2,3-dihydro-1,4-benzodioxin-6-sulfonyl chloride was added, and the mixture was added dropwise with 0.59 mL of triethylamine under cooling with ice. The temperature of the reaction mixture was increased to room temperature, and the mixture was stirred for 1 hour. Chloroform and water were added thereto. The organic layer was separated, and the aqueous layer was extracted with chloroform. The organic layer and the extract were combined, the resultant solution was washed sequentially with 1 mol/L hydrochloric acid, water and an aqueous saturated sodium chloride solution, and dried over anhydrous magnesium sulfate, and the solvent was removed under reduced pressure to obtain 0.30 g of a light brown foam, N-(1-(trifluoroacetyl)piperidin-4-yl)-2,3-dihydro-1,4-benzodioxin-6-sulfonamide.

$^1$H-NMR (CDCl$_3$) δ:
1.37-1.53 (2H, m), 1.86-1.98 (2H, m), 2.95-3.02 (1H, m), 3.16-3.24 (1H, m), 3.39-3.46 (1H, m), 3.84-3.92 (1H, m), 4.20-4.40 (5H, m), 4.48 (1H, d, J=7.3 Hz), 6.97 (1H, d, J=8.5 Hz), 7.36 (1H, dd, J=8.5, 2.2 Hz), 7.40 (1H, d, J=2.2 Hz)

Reference Example 20

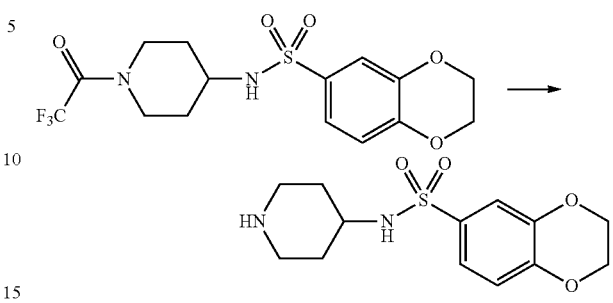

To 2 mL of a methanol solution containing 0.29 g of N-(1-(trifluoroacetyl)piperidin-4-yl)-2,3-dihydro-1,4-benzodioxin-6-sulfonamide, 0.5 mL of water and 0.12 g of potassium carbonate were added, and the mixture was stirred at room temperature for 1 hour. Chloroform and water were added thereto, and the reaction mixture was adjusted to pH 8.0 with 1 mol/L hydrochloric acid. The organic layer was separated, and the aqueous layer was extracted twice with chloroform. The organic layer and the extract were combined and dried over anhydrous magnesium sulfate, and the solvent was removed under reduced pressure. The residue thus obtained was added with hexane, and a solid substance was collected by filtration to obtain 0.11 g of a light brown solid, N-(piperidin-4-yl)-2,3-dihydro-1,4-benzodioxin-6-sulfonamide.

$^1$H-NMR (DMSO-d$_6$) δ:
1.12-1.30 (2H, m), 1.44-1.52 (2H, m), 2.26-2.35 (2H, m), 2.74-2.84 (2H, m), 2.88-2.98 (1H, m), 4.27-4.38 (4H, m), 6.98-7.04 (1H, m), 7.23-7.30 (2H, m)

Reference Example 21

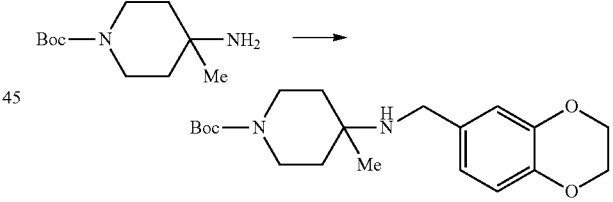

To 5 mL of a dichloromethane solution containing 0.50 g of tert-butyl 4-amino-4-methylpiperidine-1-carboxylate, 0.38 g of 2,3-dihydro-1,4-benzodioxin-6-carbaldehyde and 0.13 mL of acetic acid were added, and the mixture was stirred at room temperature for 3 hours. The reaction mixture was added with 0.74 g of sodium triacetoxyborohydride and stirred at the same temperature for 30 minutes. The reaction mixture was added with 0.74 g of sodium triacetoxyborohydride and stirred at the same temperature for 30 minutes, and then the reaction mixture was stirred for 1 hour under reflux by heating. Thereto were added chloroform and an aqueous saturated sodium hydrogen carbonate solution. The organic layer was separated, and the aqueous layer was extracted with chloroform. The organic layer and the extract were combined, and the resultant solution was washed with an aqueous saturated sodium chloride solution and dried over anhydrous magnesium sulfate, and the solvent was removed under reduced pressure to obtain 0.81 g of a light brown oily substance, tert-butyl 4-((2,3-dihydro-1,4-benzodioxin-6-ylmethyl)amino)-4-methylpiperidine-1-carboxylate.

¹H-NMR (CDCl₃) δ:
1.17 (3H, s), 1.46 (9H, s), 1.36-1.60 (4H, m), 3.35-3.55 (3H, m), 3.58 (2H, s), 4.20-4.30 (6H, m), 6.80-6.90 (3H, m)

Reference Example 22

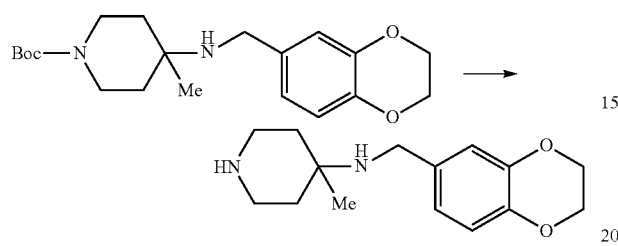

To 5 mL of a dichloromethane solution containing 0.66 g of tert-butyl 4-((2,3-dihydro-1,4-benzodioxin-6-ylmethyl)amino)-4-methylpiperidine-1-carboxylate, 5 mL of trifluoroacetic acid was added, and the mixture was stirred at room temperature for 1 hour. The solvent was removed under reduced pressure, and thereto were added chloroform, water and 6 mol/L hydrochloric acid. The aqueous layer was separated, and the aqueous layer was washed with chloroform. Chloroform was added to the aqueous layer, and the resultant solution was adjusted to pH 13 with a 20% aqueous sodium hydroxide solution. The organic layer was separated, and the aqueous layer was extracted with chloroform. The organic layer and the extract were combined, the resultant solution was dried over anhydrous magnesium sulfate, and the solvent was removed under reduced pressure to obtain 0.26 g of a colorless oily substance, N-(2,3-dihydro-1,4-benzodioxin-6-ylmethyl)-4-methylpiperidine-4-amine.

¹H-NMR (CDCl₃) δ:
1.16 (3H, s), 1.47-1.60 (4H, m), 2.73-2.79 (2H, m), 2.93-3.01 (2H, m), 3.59 (2H, s), 4.24 (4H, s), 6.80-6.82 (2H, m), 6.88-6.90 (1H, m)

Reference Example 23

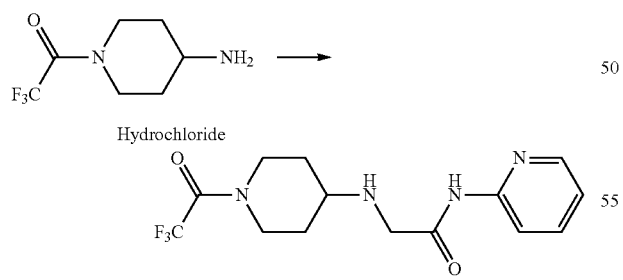

To 15 mL of an N,N-dimethylformamide solution containing 1.5 g of 1-(trifluoroacetyl)piperidine-4-amine hydrochloride, 1.4 g of 2-bromo-N-(pyridin-2-yl)acetamide and 1.8 g of potassium carbonate were added, and the mixture was stirred at room temperature for 4 hours. The reaction mixture was added with ethyl acetate and water. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure. The residue thus obtained was purified by silica gel column chromatography [eluent; chloroform:methanol=10:1] to obtain 1.1 g of a light brown oily substance, N-(pyridin-2-yl)-N²-(1-(trifluoroacetyl)piperidin-4-yl)glycinamide.

¹H-NMR (CDCl₃) δ:
1.35-1.55 (2H, m), 2.00-2.10 (2H, m), 2.77-2.98 (2H, m), 3.15-3.23 (1H, m), 3.48 (2H, s), 3.97-4.05 (1H, m), 4.42-4.50 (1H, m), 7.06 (1H, ddd, J=7.3, 4.9, 1.0 Hz), 7.72 (1H, td, J=7.9, 1.9 Hz), 8.23 (1H, d, J=8.3 Hz), 8.31 (1H, ddd, J=4.9, 1.9, 1.0 Hz), 9.59 (1H, s)

Reference Example 24

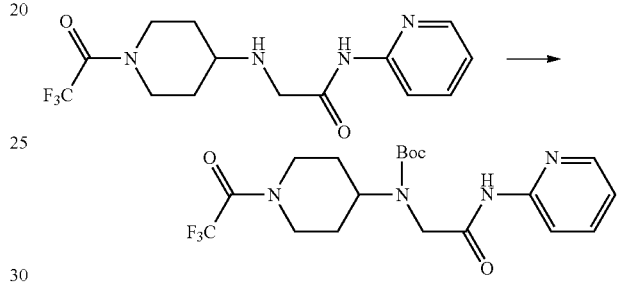

To 10 mL of a dichloromethane solution containing 1.1 g of N-(pyridin-2-yl)-N²-(1-(trifluoroacetyl)piperidin-4-yl)glycinamide, 0.87 g of di-tert-butyl dicarbonate was added, and the mixture was stirred at room temperature for 1 hour. The mixture was added with 0.87 g of di-tert-butyl dicarbonate and stirred for 2 hours under reflux by heating. Thereto was further added 1.75 g of di-tert-butyl dicarbonate and, the mixture was stirred for 1 hour under reflux by heating. The solvent was removed under reduced pressure, and the residue thus obtained was purified by silica gel column chromatography [eluent; hexane:ethyl acetate=1:1] to obtain 0.84 g of a white foam, tert-butyl (2-oxo-2-(pyridin-2-ylamino)ethyl)(1-(trifluoroacetyl)piperidin-4-yl)carbamate.

¹H-NMR (CDCl₃) δ:
1.47 (9H, s), 1.55-1.70 (2H, m), 1.90-2.00 (2H, m), 2.79 (1H, t, J=12.6 Hz), 3.18 (1H, t, J=12.7 Hz), 3.88 (2H, s), 4.05-4.13 (1H, m), 4.15-4.50 (1H, m), 4.62-4.70 (1H, m), 7.06 (1H, ddd, J=7.3, 5.0, 0.9 Hz), 7.69-7.74 (1H, m), 8.17 (1H, d, J=8.3 Hz), 8.28 (1H, ddd, J=5.0, 2.0, 0.9 Hz)

Reference Example 25

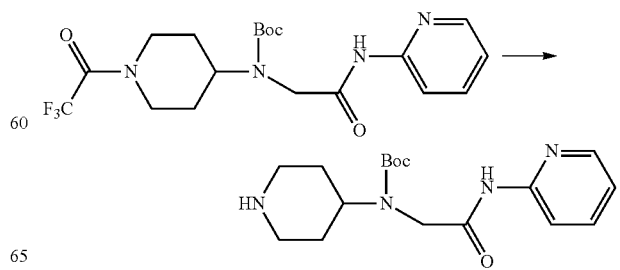

To 8 mL of a methanol solution containing 0.80 g of tert-butyl (2-oxo-2-(pyridin-2-ylamino)ethyl)(1-trifluoroacetyl)piperidin-4-yl)carbamate, 2 mL of water and 0.31 g of potassium carbonate were added, and the mixture was stirred at room temperature for 1 hour. Thereto were added chloroform and water. The organic layer was separated, and the aqueous layer was extracted with chloroform. The organic layer and the extract were combined, and the resultant solution was washed with an aqueous saturated sodium chloride solution and dried over anhydrous magnesium sulfate, and the solvent was removed under reduced pressure to obtain 0.61 g of a light brown foam, tert-butyl (2-oxo-2-(pyridin-2-ylamino)ethyl)(piperidin-4-yl)carbamate.

$^1$H-NMR (CDCl$_3$) δ:

1.46 (9H, s), 1.40-1.60 (2H, m), 1.76-1.83 (2H, m), 2.65-2.71 (2H, m), 3.10-3.18 (2H, m), 3.92 (2H, s), 4.00-4.25 (1H, m), 7.04 (1H, ddd, J=7.3, 4.9, 0.9 Hz), 7.67-7.73 (1H, m), 8.20 (1H, d, J=8.3 Hz), 8.27 (1H, ddd, J=4.9, 2.0, 0.8 Hz)

Reference Example 26

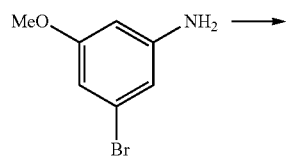

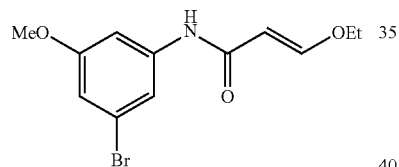

To 14 mL of a pyridine solution containing 1.4 g of 3-bromo-5-methoxyaniline, 1.0 g of (2E)-3-ethoxyacryloyl chloride was added under cooling with ice, and the mixture was stirred at room temperature for 30 minutes. The reaction mixture was fed into ice water, and the precipitate was collected by filtration. Ethyl acetate and water were added thereto, and the resultant solution was adjusted to pH 4.0 with 1 mol/L hydrochloric acid. The organic layer was separated, and the aqueous layer was extracted with ethyl acetate. The organic layer and the extract were combined, and the resultant solution was washed sequentially with water and an aqueous saturated sodium chloride solution and dried over anhydrous magnesium sulfate, and the solvent was removed under reduced pressure to obtain 1.7 g of a light brown solid, (2E)-N-(3-bromo-5-methoxyphenyl)-3-ethoxyacrylamide.

$^1$H-NMR (CDCl$_3$) δ:

1.26 (3H, t, J=7.1 Hz), 3.79 (3H, s), 3.96 (2H, q, J=7.1 Hz), 5.28 (1H, d, J=12.1 Hz), 6.79 (1H, t, J=1.9 Hz), 6.87 (1H, s), 7.20 (1H, t, J=1.9 Hz), 7.24 (1H, t, J=1.9 Hz), 7.63 (1H, d, J=12.1 Hz)

Reference Example 27

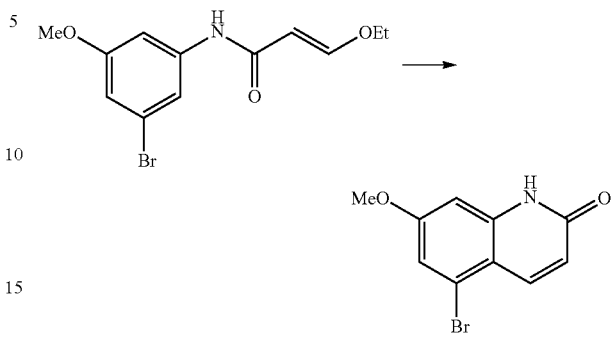

To 5.0 mL of concentrated sulfuric acid, 1.5 g of (2E)-N-(3-bromo-5-methoxyphenyl)-3-ethoxyacrylamide was dividedly added under cooling with ice over 15 minutes. The reaction mixture was fed into ice water, and the precipitate was collected by filtration and washed with water. Chloroform and water were added to the solid thus obtained, and the resultant solution was adjusted to pH 10 with a 20% aqueous sodium hydroxide solution. The solid was collected by filtration and washed sequentially with water and chloroform to obtain 1.0 g of a light brown solid, 5-bromo-7-methoxyquinolin-2(1H)-one.

$^1$H-NMR (DMSO-d$_6$) δ:

3.82 (3H, s), 6.43 (1H, d, J=9.8 Hz), 6.84 (1H, d, J=2.3 Hz), 7.14 (1H, d, J=2.3), 7.91 (1H, d, J=9.8 Hz), 11.70-11.90 (1H, broad)

Reference Example 28

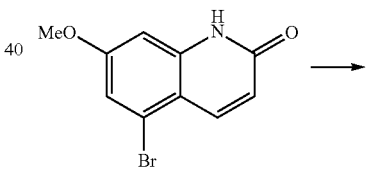

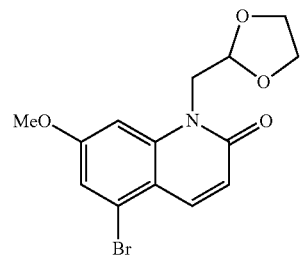

To 15 mL of an N,N-dimethylformamide suspension containing 0.98 g of 5-bromo-7-methoxyquinolin-2(1H)-one, 0.23 g of 60% sodium hydride was added at room temperature, and the mixture was stirred at 60° C. for 30 minutes. Thereto was added 0.60 mL of 2-bromomethyl-1,3-dioxolane, and the mixture was stirred at the same temperature for 30 minutes. Thereto were added 0.23 g of 60% sodium hydride and 0.60 mL of 2-bromomethyl-1,3-dioxolane, and the mixture was stirred at 90 to 95° C. for 4 hours. Thereto were added 0.23 g of 60% sodium hydride and 0.60 mL of 2-bromomethyl-1,3-dioxolane, and the mixture was stirred at 90 to 95° C. for 1 hour. The reaction mixture was cooled to room temperature, then ethyl acetate and water was added thereto, and the resultant solution was adjusted to pH 3.0 with 1 mol/L hydrochloric acid. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure. The residue thus obtained was purified by silica gel column chromatography [eluent; hexane:ethyl acetate 1:2] to obtain 0.27 g of a light brown solid, 5-bromo-1-(1,3-dioxolan-2-ylmethyl)-7-methoxyquinolin-2(1H)-one.

$^1$H-NMR (CDCl$_3$) δ:

3.86-3.93 (2H, m), 3.90 (3H, s), 4.02-4.06 (2H, m), 4.51 (2H, d, J=4.4 Hz), 5.21 (1H, t, J=4.4 Hz), 6.62 (1H, d, J=9.8), 7.09 (1H, d, J=2.2 Hz), 7.11 (1H, d, J=2.2 Hz), 8.04 (1H, dd, J=9.8, 0.6 Hz)

Reference Example 29

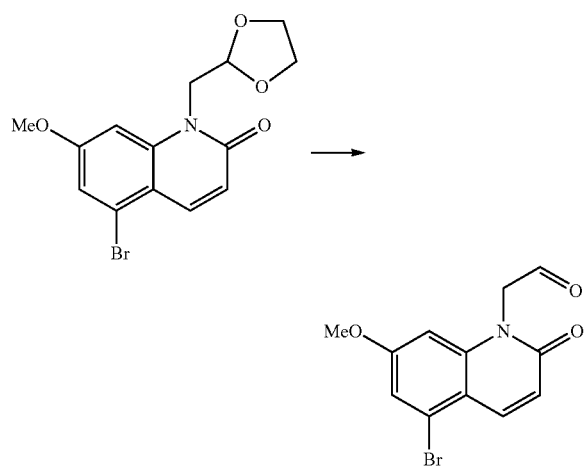

To 0.23 g of 5-bromo-1-(1,3-dioxolan-2-ylmethyl)-7-methoxyquinolin-2(1H)-one, 3 mL of a 90% aqueous trifluoroacetic acid solution was added, the mixture was stirred at room temperature, and then the reaction mixture was stood still for 13 hours at the same temperature. The solvent was removed under reduced pressure, and ethyl acetate and water were added thereto, and the reaction mixture was adjusted to pH 7.0 with a 20% aqueous sodium hydroxide solution. The organic layer was separated, and the aqueous layer was extracted twice with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was added with hexane and ethyl acetate, and a solid was collected by filtration to obtain 0.20 g of a light brown solid, (5-bromo-7-methoxy-2-oxoquinolin-1(2H)-yl)acetaldehyde.

$^1$H-NMR (DMSO-d$_6$) δ:

3.87 (3H, s), 5.29 (2H, s), 6.59 (1H, d, J=9.9 Hz), 6.92 (1H, d, J=2.1 Hz), 7.27 (1H, d, J=2.1 Hz), 8.05 (1H, d, J=9.9 Hz), 9.68 (1H, s)

Reference Example 30

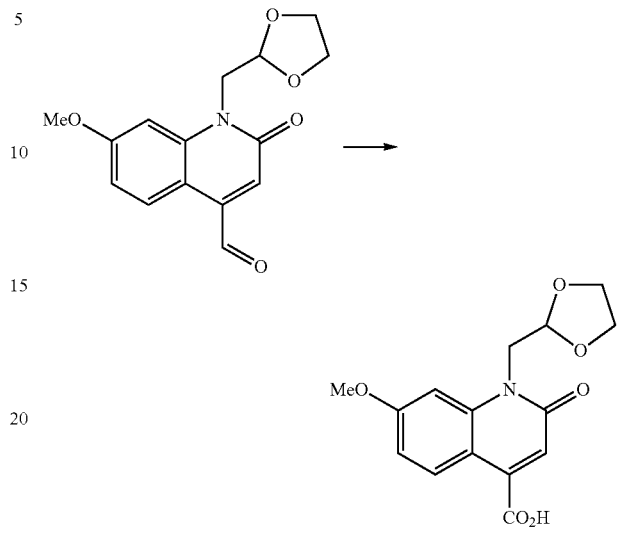

To 4 mL of an acetonitrile suspension containing 0.26 g of 1-(1,3-dioxolan-2-ylmethyl)-7-methoxy-2-oxo-1,2-dihydroquinoline-4-carbaldehyde, a solution of 2 mL of water containing 0.37 g of sodium dihydrogen phosphate, 0.15 mL of a 30% hydrogen peroxide solution, and a solution of 1 mL of water containing 0.16 g of sodium chlorite were added, and the mixture was stirred at room temperature for 2 hours. The reaction mixture was added with chloroform and water, the resultant solution was adjusted to pH 2.0 with 1 mol/L hydrochloric acid, and then methanol was added thereto. The organic layer was separated, and the aqueous layer was extracted with chloroform. The organic layer and the extract were combined, the resultant solution was washed with an aqueous saturated sodium chloride solution and dried over anhydrous magnesium sulfate, and the solvent was removed under reduced pressure. The residue thus obtained was added with hexane and ethyl acetate, and a solid was collected by filtration to obtain 0.22 g of a light brown solid, 1-(1,3-dioxolan-2-ylmethyl)-7-methoxy-2-oxo-1,2-dihydroquinoline-4-carboxylic acid.

$^1$H-NMR (DMSO-d$_6$) δ:

3.79-3.83 (2H, m), 3.90 (3H, s), 3.97-4.02 (2H, m), 4.48 (2H, d, J=4.6 Hz), 5.13 (1H, t, J=4.6 Hz), 6.76 (1H, s), 6.96 (1H, dd, J=9.0, 2.2 Hz), 7.20 (1H, d, J=2.2 Hz), 8.09 (1H, d, J=9.0 Hz)

Reference Example 31

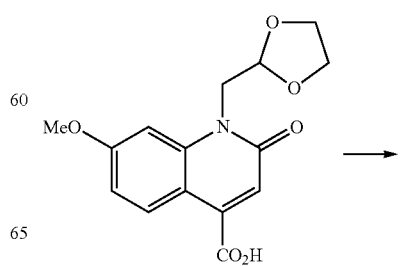

-continued

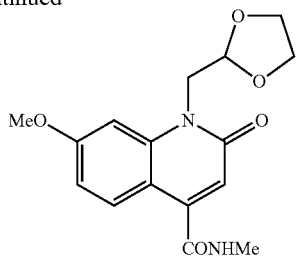

To 3 mL of an N,N-dimethylformamide solution containing 0.20 g of 1-(1,3-dioxolan-2-ylmethyl)-7-methoxy-2-oxo-1,2-dihydroquinoline-4-carboxylic acid, 67 mg of methylamine hydrochloride, 0.25 g of O-(7-azabenzotriazol-1-yl)-1,1,3,3-tetramethyluronium hexafluorophosphate and 0.55 mL of triethylamine were added at room temperature, and the mixture was stirred at the same temperature for 2 hours, then stirred at 40° C. for 1 hour. The mixture was cooled to room temperature, and thereto were added 67 mg of methylamine hydrochloride, 0.25 g of O-(7-azabenzotriazol-1-yl)-1,1,3,3-tetramethyluronium hexafluorophosphate and 0.55 mL of triethylamine, and the mixture was stirred at the same temperature for 1 hour. Ethyl acetate and water were added thereto, and the reaction mixture was adjusted to pH 4.0 with 1 mol/L hydrochloric acid. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure. The residue thus obtained was purified by silica gel column chromatography [eluent; chloroform:methanol=10:1] to obtain 0.11 g of a light brown solid, 1-(1,3-dioxolan-2-ylmethyl)-7-methoxy-N-methyl-2-oxo-1,2-dihydroquinoline-4-carboxamide.

$^1$H-NMR (CDCl$_3$) δ:
3.05 (3H, d, J=4.9 Hz), 3.84-3.88 (2H, m), 3.91 (3H, s), 4.00-4.04 (2H, m), 4.46 (2H, d, J=4.2 Hz), 5.18 (1H, t, J=4.2 Hz), 6.19-6.25 (1H, m), 6.58 (1H, s), 6.84 (1H, dd, J=9.0, 2.4 Hz), 7.07 (1H, d, J=2.4 Hz), 7.86 (1H, d, J=9.0 Hz)

Reference Example 32

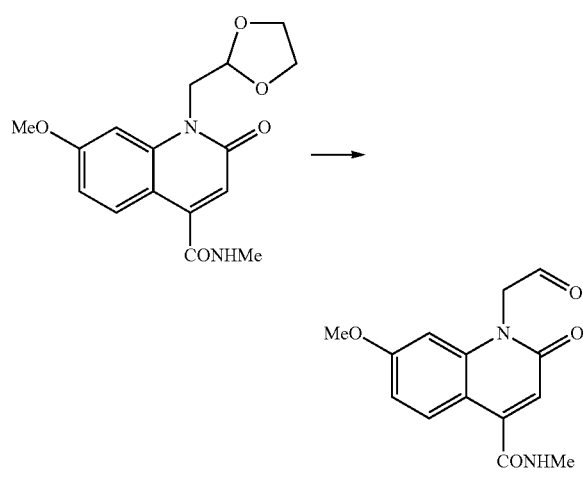

To 0.10 g of 1-(1,3-dioxolan-2-ylmethyl)-7-methoxy-N-methyl-2-oxo-1,2-dihydroquinoline-4-carboxamide, 3 mL of a 90% aqueous trifluoroacetic acid solution was added, the mixture was stirred at room temperature for 1 hour, and then the solvent was removed under reduced pressure. The residue thus obtained was added with chloroform and water, and the reaction mixture was adjusted to pH 6.0 with a 20% aqueous sodium hydroxide solution. The organic layer was separated, and the aqueous layer was extracted 3 times with chloroform. The organic layer and the extract were combined, and the resultant solution was washed with an aqueous saturated sodium chloride solution and dried over anhydrous magnesium sulfate, and the solvent was removed under reduced pressure to obtain 85 mg of a light brown solid, 7-methoxy-N-methyl-2-oxo-1-(2-oxoethyl)-1,2-dihydroquinoline-4-carboxamide.

$^1$H-NMR (CDCl$_3$) δ:
3.06 (3H, d, J=5.1 Hz), 3.87 (3H, s), 5.09 (2H, s), 6.12-6.22 (1H, m), 6.45 (1H, d, J=2.2 Hz), 6.62 (1H, s), 6.86 (1H, dd, J=9.0, 2.2 Hz), 7.92 (1H, d, J=9.0 Hz), 9.65 (1H, s)

Reference Example 33

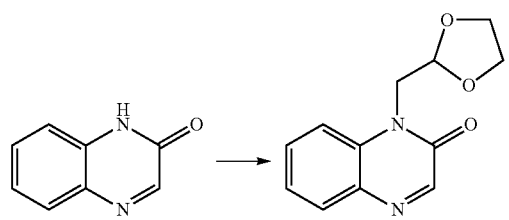 [SMILES: O=c1cnc2ccccc2[nH]1 ; O=c1cnc2ccccc2n1CC1OCCO1]

To 20 mL of an N,N-dimethylformamide suspension containing 2.0 g of quinoxalin-2(1H)-one, 0.82 g of 60% sodium hydride was dividedly added at room temperature, and the mixture was stirred at 40° C. for 15 minutes. Thereto was added 2.1 mL of 2-bromomethyl-1,3-dioxolane, and the mixture was stirred at 60° C. for 30 minutes, and stirred at 110 to 120° C. for 1 hour. Thereto was added 2.1 mL of 2-bromomethyl-1,3-dioxolane, and the mixture was stirred at 110 to 120° C. for 5 hours. The reaction mixture was cooled to room temperature, ethyl acetate and water were added, and the resultant solution was adjusted to pH 2.0 with 6 mol/L hydrochloric acid. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure. The residue thus obtained was purified by silica gel column chromatography [eluent; hexane:ethyl acetate 1:2] to obtain 1.5 g of a light brown oily substance, 1-(1,3-dioxolan-2-ylmethyl)quinoxalin-2(1H)-one.

$^1$H-NMR (CDCl$_3$) δ:
3.86-3.91 (2H, m), 4.00-4.05 (2H, m), 4.50 (2H, d, J=4.4 Hz), 5.28 (1H, t, J=4.4 Hz), 7.36 (1H, ddd, J=8.0, 6.1, 2.1 Hz), 7.54-7.61 (2H, m), 7.85-7.89 (1H, m), 8.32 (1H, s)

Reference Example 34

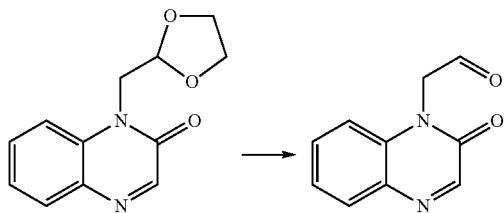 [SMILES: O=c1cnc2ccccc2n1CC1OCCO1 ; O=CCn1c(=O)cnc2ccccc21]

To 1.0 g of 1-(1,3-dioxolan-2-ylmethyl)quinoxalin-2(1H)-one, 10 mL of a 90% aqueous trifluoroacetic acid solution was added, and the mixture was stirred at room temperature for 3 hours and at 40° C. for 2 hours. Thereto was added 5 mL of a 90% aqueous trifluoroacetic acid solution, and the mixture was stirred at 40° C. for 2 hours, and then stood still at room temperature for 37 hours. The solvent was removed under reduced pressure, and chloroform and water was added thereto, and the reaction mixture was adjusted to pH 7.0 with a 1 mol/L aqueous sodium hydroxide solution. The organic layer was separated, and the aqueous layer was extracted twice with chloroform. The organic layer and the extract were combined, the resultant solution was washed with an aqueous saturated sodium chloride solution and dried over anhydrous magnesium sulfate, and the solvent was removed under reduced pressure. The residue thus obtained was added with hexane, ethyl acetate and a diisopropyl ether, and a solid was collected by filtration to obtain 0.11 g of a red brown solid, (2-oxoquinoxalin-1(2H)-yl)acetaldehyde.

$^1$H-NMR (CDCl$_3$) δ:
5.13 (2H, s), 7.02 (1H, d, J=8.5 Hz), 7.40 (1H, t, J=7.7 Hz), 7.54-7.59 (1H, m), 7.92-7.96 (1H, m), 8.38 (1H, s), 9.74 (1H, s)

Reference Example 35

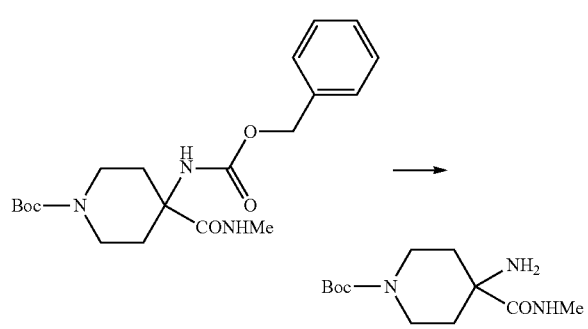

To 10 mL of an ethanol solution containing 0.75 g of tert-butyl 4-(((benzyloxy)carbonyl)amino)-4-((methylamino)carbonyl)piperidine-1-carboxylate, 75 mg of 20% palladium hydroxide-carbon was added at room temperature, and the mixture was stirred at 40° C. for 2 hours under a hydrogen atmosphere. Thereto was added 75 mg of 20% palladium hydroxide-carbon, and the mixture was stirred at 40° C. for 3 hours under a hydrogen atmosphere. The insoluble material filtered off, and the filtration residue was washed 3 times with chloroform. The filtrate and the washing solution were combined, and the solvent was removed under reduced pressure to obtain 0.62 g of a light gray foam, tert-butyl 4-amino-4-((methylamino)carbonyl)piperidine-1-carboxylate.

$^1$H-NMR (CDCl$_3$) δ:
1.45 (9H, s), 1.40-3.80 (8H, m), 2.84 (3H, d, J=4.6 Hz), 7.75-7.85 (1H, broad)

Reference Example 36

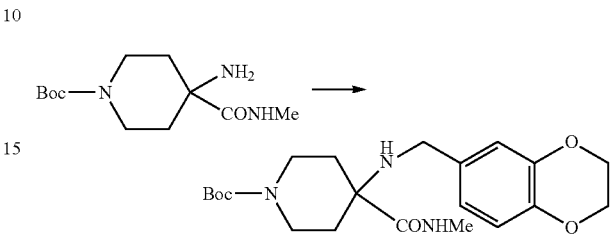

To 5 mL of a dichloromethane solution containing 0.30 g of tert-butyl 4-amino-4-((methylamino)carbonyl)piperidine-1-carboxylate, 0.16 g of 2,3-dihydro-1,4-benzodioxin-6-carbaldehyde and 57 μL of acetic acid were added, the mixture was stirred at room temperature for 2 hours. The reaction mixture was added with 0.32 g of sodium triacetoxyborohydride and stirred at the same temperature for 30 minutes. Thereto were added chloroform and an aqueous saturated sodium hydrogen carbonate solution. The organic layer was separated, and the aqueous layer was extracted with chloroform. The organic layer and the extract were combined, the resultant solution was washed sequentially with water and an aqueous saturated sodium chloride solution and dried over anhydrous magnesium sulfate, and the solvent was removed under reduced pressure. The residue thus obtained was purified by silica gel column chromatography [eluent; chloroform:methanol=10:1] to obtain 0.31 g of a pale yellow oily substance, tert-butyl 4-((2,3-dihydro-1,4-benzodioxin-6-ylmethyl)amino)-4-((methylamino)carbonyl)piperidine-1-carboxylate.

$^1$H-NMR (CDCl$_3$) δ:
1.46 (9H, s), 1.57-1.67 (2H, m), 2.03-2.15 (2H, m), 2.83 (3H, d, J=4.9 Hz), 3.13-3.23 (2H, m) 3.48 (2H, s), 3.77-3.88 (2H, m), 4.26 (4H, s), 6.75 (1H, dd, J=8.3, 2.0 Hz), 6.83-6.90 (2H, m), 7.21-7.29 (1H, m)

Reference Example 37

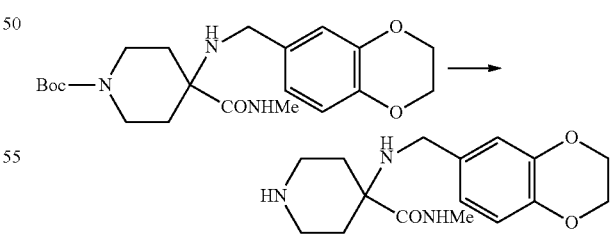

To 3 mL of a dichloromethane solution containing 0.30 g of tert-butyl 4-((2,3-dihydro-1,4-benzodioxin-6-ylmethyl)amino)-4-((methylamino)carbonyl)piperidine-1-carboxylate, 3 mL of trifluoroacetic acid was added, and the mixture was stirred at room temperature for 2 hours. The solvent was removed under reduced pressure, thereto were added chloroform and water, and the reaction mixture was adjusted to pH 13 with a 1.0 mol/L aqueous sodium hydroxide solution. The organic layer was separated, and the aqueous layer was extracted with chloroform. The organic layer and the extract were combined, the resultant solution was dried over anhydrous magnesium sulfate, and the solvent was removed under reduced pressure to obtain 0.22 g of a pale yellow foam, 4-((2,3-dihydro-1,4-benzodioxin-6-ylmethyl)amino)-N-methylpiperidine-4-carboxamide.

$^1$H-NMR (CDCl$_3$) δ:
1.58-1.68 (2H, m), 2.05-2.14 (2H, m), 2.76-2.84 (2H, m), 2.82 (3H, d, J=5.1 Hz), 3.01-3.07 (2H, m), 3.47 (2H, s), 4.00-4.20 (2H, m), 4.27 (4H, s), 6.77 (1H, dd, J=8.0, 1.8 Hz), 6.84-6.87 (2H, m), 7.32-7.38 (1H, m)

Reference Example 38

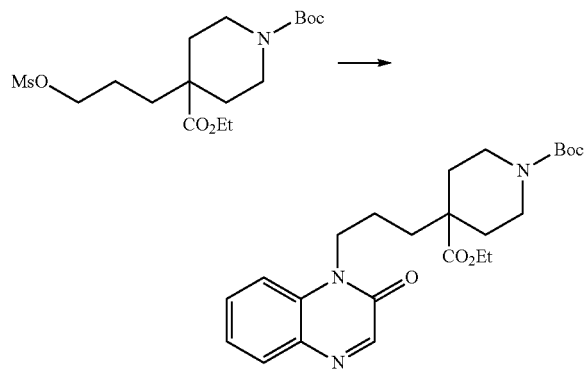

To 5 mL of an N,N-dimethylformamide suspension containing 0.25 g of quinoxalin-2(1H)-one, 0.10 g of 60% sodium hydride was added at room temperature, and the mixture was stirred at 50° C. for 30 minutes. Thereto was dividedly added 0.68 g of 1-tert-butyl 4-ethyl 4-(3-((methanesulfonyl)oxy)propyl)piperidine-1,4-dicarboxylate at the same temperature, and the mixture was stirred at 80 to 90° C. for 2 hours. The reaction mixture was cooled to room temperature, ethyl acetate and water were added thereto, and the resultant solution was adjusted to pH 2.0 with 6 mol/L hydrochloric acid. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure. The residue thus obtained was purified by silica gel column chromatography [eluent; hexane:ethyl acetate=1:1] to obtain 0.18 g of a yellow brown oily substance, 1-tert-butyl 4-ethyl 4-(3-(2-oxoquinoxalin-1(2H)-yl)propyl)piperidine-1,4-dicarboxylate.

$^1$H-NMR (CDCl$_3$) δ:
1.18 (3H, t, J=7.1 Hz), 1.30-1.40 (2H, m), 1.44 (9H, s), 1.50-1.76 (4H, m), 2.04-2.12 (2H, m), 2.76-2.92 (2H, m), 3.76-3.96 (2H, m), 4.11 (2H, q, J=7.1 Hz), 4.16-4.24 (2H, m), 7.26 (1H, d, J=7.8 Hz), 7.33-7.38 (1H, m), 7.55-7.60 (1H, m), 7.90 (1H, dd, J=8.0, 1.5 Hz), 8.30 (1H, s)

Reference Example 39

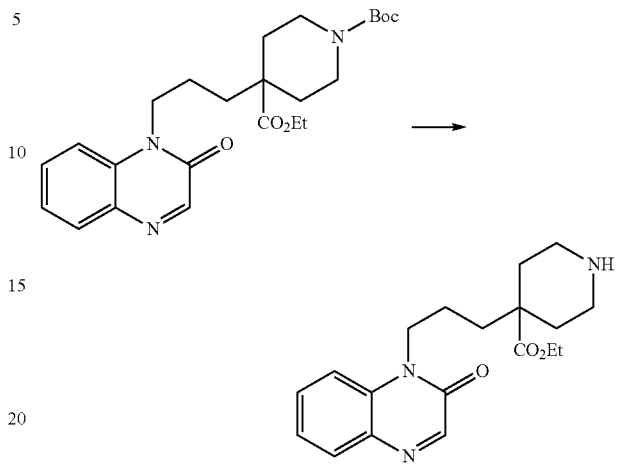

To 3 mL of a dichloromethane solution containing 0.18 g of 1-tert-butyl 4-ethyl 4-(3-(2-oxoquinoxalin-1(2H)-yl)propyl) piperidine-1,4-dicarboxylate, 3 mL of trifluoroacetic acid was added, and the mixture was stirred at room temperature for 1 hour. The solvent was removed under reduced pressure, and ethyl acetate and water were added thereto, and the reaction mixture was adjusted to pH 11 with a 1 mol/L aqueous sodium hydroxide solution. The organic layer was separated, and the aqueous layer was extracted with ethyl acetate. The organic layer and the extract were combined, the resultant solution was washed with a saturated sodium chloride solution, and dried over anhydrous magnesium sulfate, and the solvent was removed under reduced pressure to obtain 0.10 g of a yellow brown oily substance, ethyl 4-(3-(2-oxoquinoxalin-1(2H)-yl)propyl)piperidine-4-dicarboxylate.

$^1$H-NMR (CDCl$_3$) δ:
1.18 (3H, t, J=7.1 Hz), 1.32-1.44 (2H, m), 1.64-1.74 (2H, m), 1.80-2.18 (4H, m), 2.60-2.72 (2H, m), 2.95 (2H, dt, J=12.9, 3.7 Hz), 4.10 (2H, q, J=7.1 Hz), 4.16-4.24 (1H, m), 7.26-7.30 (1H, m), 7.32-7.40 (1H, m), 7.54-7.62 (1H, m), 7.90 (1H, dd, J=8.0, 1.5 Hz), 8.29 (1H, s)

Reference Example 40

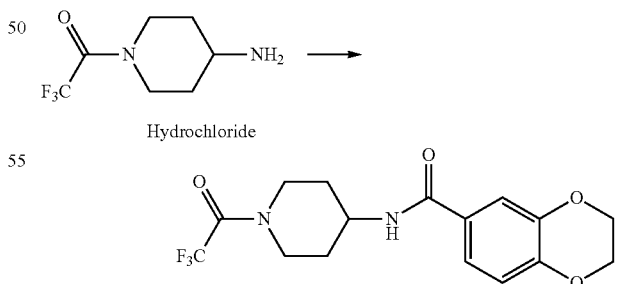

To 5 mL of an N,N-dimethylformamide solution containing 0.50 g of 2,3-dihydro-1,4-benzodioxin-6-carboxylic acid, 0.65 g of 1-(trifluoroacetyl)piperidine-4-amine hydrochloride and 1.1 g of O-(7-azabenzotriazol-1-yl)-1,1,3,3-tetramethyluronium hexafluorophosphate and 0.78 mL of triethylamine were added at room temperature, and the mixture was stirred at the same temperature for 6 hours. The reaction mixture was added with ethyl acetate and water. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure to obtain 0.84 g of a light brown solid, N-(1-(trifluoroacetyl)piperidin-4-yl)-2,3-dihydro-1,4-benzodioxin-6-carboxamide.

¹H-NMR (CDCl₃) δ:
1.42-1.56 (2H, m), 2.12-2.24 (2H, m), 2.92-3.02 (1H, m), 3.24-3.34 (1H, m), 4.00-4.08 (1H, m), 4.20-4.34 (5H, m), 4.50-4.60 (1H, m), 5.85-5.90 (1H, m), 6.89 (1H, d, J=8.5), 7.23 (1H, dd, J=8.5, 2.1 Hz), 7.29 (1H, d, J=2.1 Hz)

Reference Example 41

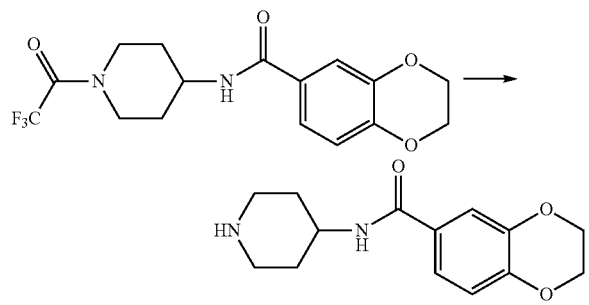

To 10 mL of a methanol solution containing 0.80 g of N-(1-(trifluoroacetyl)piperidin-4-yl)-2,3-dihydro-1,4-benzodioxin-6-carboxamide, 2.5 mL of water and 0.37 g of potassium carbonate were added, and the mixture was stirred at room temperature for 3 hours. The solvent was removed under reduced pressure, chloroform and water were added thereto, and the reaction mixture was adjusted to pH 0.1 with 6 mol/L hydrochloric acid. The aqueous layer was separated, and washed with chloroform. Chloroform was added to the aqueous layer, and the resultant solution was adjusted to pH 13.5 with a 20% aqueous sodium hydroxide solution. The organic layer was separated, and the aqueous layer was extracted with chloroform. The organic layer and the extract were combined, the resultant solution was dried over anhydrous magnesium sulfate, and the solvent was removed under reduced pressure to obtain 0.41 g of a pale yellow white solid, N-(piperidin-4-yl)-2,3-dihydro-1,4-benzodioxin-6-carboxamide.

¹H-NMR (CDCl₃) δ:
1.33-1.44 (2H, m), 1.98-2.06 (2H, m), 2.75 (2H, td, J=12.4, 2.3), 3.10 (2H, td, J=12.4, 3.3), 4.00-4.10 (1H, m), 4.24-4.32 (4H, m), 5.80-5.90 (1H, m), 6.89 (1H, d, J=8.4), 7.25 (1H, dd, J=8.4, 2.0 Hz), 7.30 (1H, d, J=2.0 Hz)

Reference Example 42

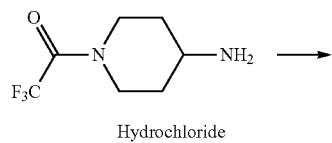
Hydrochloride

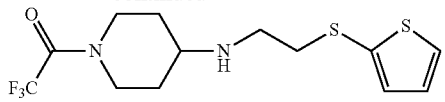

To 2 mL of an N,N-dimethylformamide solution containing 0.14 g of 2-(2-bromoethylthio)thiophene, 95 mg of potassium carbonate and 0.16 g of 1-(trifluoroacetyl)piperidine-4-amine hydrochloride were added under cooling with ice, and the mixture was stirred at room temperature for 40 minutes. Thereto was added 95 mg of potassium carbonate under cooling with ice, and the mixture was stirred for 45 minutes, and stirred at 70° C. for 3 hours. The reaction mixture was cooled to room temperature, and then ethyl acetate and water were added thereto. The organic layer was separated, washed with an aqueous saturated sodium chloride solution, and dried over anhydrous magnesium sulfate, and the solvent was removed under reduced pressure. The residue thus obtained was purified by silica gel column chromatography [eluent; chloroform:methanol=50:1] to obtain 62 mg of a yellow oily substance, N-(2-(2-thienylthio)ethyl)-1-(trifluoroacetyl) piperidine-4-amine.

¹H-NMR (CDCl₃) δ:
1.30-1.50 (2H, m), 1.88-2.00 (2H, m), 2.74-2.95 (5H, m), 3.01-3.12 (1H, m), 3.18-3.28 (1H, m), 3.90-3.98 (1H, m), 4.24-4.34 (1H, m), 6.99 (1H, dd, J=5.4, 3.4 Hz), 7.13 (1H, dd, J=3.4, 1.2 Hz), 7.36 (1H, dd, J=5.4, 1.2 Hz)

Reference Example 43

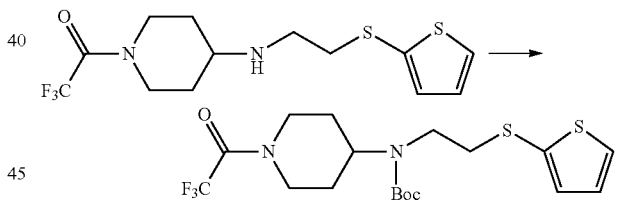

To 0.8 mL of a dichloromethane solution containing 60 mg of N-(2-(2-thienylthio)ethyl)-1-(trifluoroacetyl)piperidine-4-amine, 60 μL of di-tert-butyl dicarbonate was added under cooling with ice, the mixture was stirred at the same temperature for 1 hour and stirred at room temperature for 1 hour. Thereto was added 40 μL of di-tert-butyl dicarbonate, and the mixture was stirred at room temperature for 1 hour. The solvent was removed under reduced pressure, and the residue thus obtained was purified by silica gel column chromatography [eluent; hexane:ethyl acetate=4:1] to obtain 67 mg of a colorless oily substance, tert-butyl (2-(2-thienylthio) ethyl) (1-(trifluoroacetyl)piperidin-4-yl)carbamate.

¹H-NMR (CDCl₃) δ:
1.26-1.50 (2H, m), 1.40 (9H, s), 1.70-1.80 (2H, m), 2.66-2.74 (1H, m), 2.74-2.87 (2H, m), 3.06-3.13 (1H, m), 3.16-3.30 (2H, m), 3.95-4.05 (1H, m), 4.05-4.25 (1H, m), 4.53-4.61 (1H, m), 6.97 (1H, dd, J=5.4, 3.6 Hz), 7.15 (1H, dd, J=3.6, 1.1 Hz), 7.36 (1H, dd, J=5.4, 1.1 Hz)

Reference Example 44

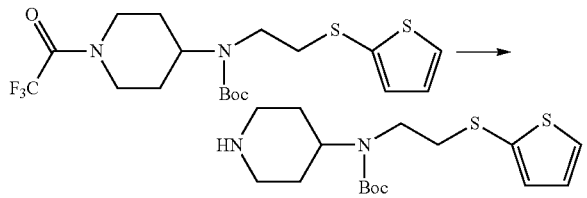

To 1 mL of a methanol solution containing 66 mg of tert-butyl (2-(2-thienylthio)ethyl) (1-(trifluoroacetyl)piperidin-4-yl)carbamate, 0.2 mL of water was added, and 32 mg of potassium carbonate was added under cooling with ice, and the mixture was stirred at a room temperature for 20 minutes. Thereto was added 0.5 mL of methanol, and the mixture was stirred at room temperature for 1 hour and 10 minutes. The reaction mixture was added with 0.6 mL of tetrahydrofuran, and stirred for 10 minutes, and the solvent was removed under reduced pressure. The residue thus obtained was added with ethyl acetate and water. The organic layer was separated, washed with an aqueous saturated sodium chloride solution and dried over anhydrous magnesium sulfate, and the solvent was removed under reduced pressure to obtain 43 mg of a colorless oily substance, tert-butyl (piperidin-4-yl) (2-(2-thienylthio) ethyl) carbamate.

$^1$H-NMR (CDCl$_3$) δ:
1.20-1.74 (6H, m), 1.37 (9H, s), 2.55-2.95 (3H, m), 3.05-3.40 (3H, m), 3.86-4.10 (1H, m), 6.98 (1H, dd, J=5.4, 3.4 Hz), 7.10-7.20 (1H, m), 7.35 (1H, d, J=5.4 Hz)

Reference Example 45

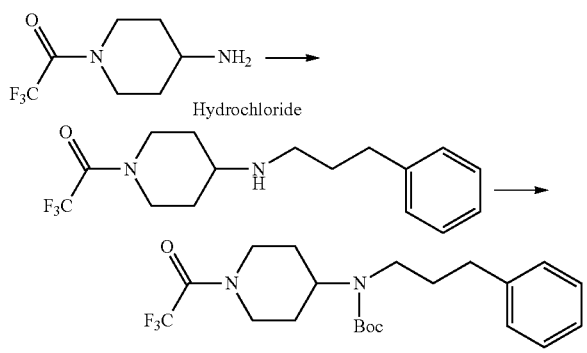

(1) To 2 mL of an N,N-dimethylformamide solution containing 0.38 mL of (3-bromopropyl)benzene, 0.76 g of potassium carbonate and 0.64 g of 1-(trifluoroacetyl)piperidine-4-amine hydrochloride were added, and the mixture was stirred at room temperature for 2 hours and 30 minutes. The reaction mixture was added with ethyl acetate and water. The organic layer was separated, washed sequentially with water and an aqueous saturated sodium chloride solution, and dried over anhydrous magnesium sulfate, and the solvent was removed under reduced pressure. Thereto were further added 2 mL of N,N-dimethylformamide, 0.40 g of 1-(trifluoroacetyl)piperidine-4-amine dihydrochloride and 0.60 g of potassium carbonate, and the mixture was stirred at room temperature for 15 minutes. The reaction mixture was added with ethyl acetate and water. The organic layer was separated, washed sequentially with water and an aqueous saturated sodium chloride solution and dried over anhydrous magnesium sulfate, and the solvent was removed under reduced pressure to obtain 0.99 g of a yellow oily substance, N-(3-phenylpropyl)-1-(trifluoroacetyl)piperidine-4-amine.

(2) To 3 mL of a dichloromethane solution containing 0.99 g of N-(3-phenylpropyl)-1-(trifluoroacetyl)piperidine-4-amine, 0.82 g of di-tert-butyl dicarbonate was added under cooling with ice, and the mixture was stirred at the same temperature for 30 minutes and at room temperature for 1 hour. Thereto was further added 0.20 g of di-tert-butyl dicarbonate, and the mixture was left to stand at room temperature overnight. The solvent was removed under reduced pressure, and the residue thus obtained was purified by silica gel column chromatography [eluent; hexane:ethyl acetate=5:1] to obtain 0.63 g of a colorless oily substance, tert-butyl (3-phenylpropyl) (1-(trifluoroacetyl)piperidin-4-yl)carbamate.

$^1$H-NMR (CDCl$_3$) δ:
1.44 (9H, s), 1.50-1.70 (2H, m), 1.76-1.88 (4H, m), 2.59 (2H, t, J=7.7 Hz), 2.68-2.78 (1H, m), 2.95-3.20 (3H, m), 4.00-4.08 (1H, m), 4.11-4.27 (1H, m), 4.58-4.66 (1H, m), 7.14-7.23 (3H, m), 7.25-7.33 (2H, m)

Reference Example 46

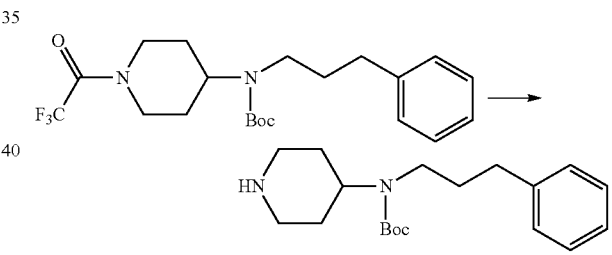

To 2 mL of a methanol solution containing 0.60 g of tert-butyl (3-phenylpropyl) (1-(trifluoroacetyl)piperidin-4-yl) carbamate, 0.4 mL of water was added, and 0.28 g of potassium carbonate was added under cooling with ice, and the mixture was stirred at the same temperature for 2 hours and 10 minutes and at room temperature for 2 hours and 15 minutes. Thereto was added 2 mL of methanol and 0.5 mL of water, and the mixture was left to stand at room temperature overnight. The solvent was removed under reduced pressure, and the residue thus obtained was added with ethyl acetate and water. The organic layer was separated, washed with an aqueous saturated sodium chloride solution and dried over anhydrous magnesium sulfate, and the solvent was removed under reduced pressure to obtain 0.45 g of a colorless oily substance, tert-butyl (3-phenylpropyl)(piperidin-4-yl)carbamate.

$^1$H-NMR (CDCl$_3$) δ:
1.45 (9H, s), 1.50-1.75 (4H, m), 1.78-1.90 (2H, m), 2.08-2.24 (1H, m), 2.58 (2H, t, J=7.8 Hz), 2.62-2.72 (2H, m), 3.06-3.18 (4H, m), 3.96-4.13 (1H, m), 7.14-7.22 (3H, m), 7.24-7.32 (2H, m)

Reference Example 47

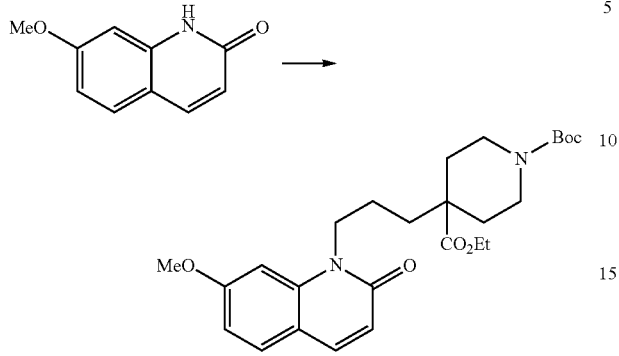

To 7 mL of an N,N-dimethylformamide solution containing 0.64 g of 7-methoxyquinolin-2(1H)-one, 0.15 g of 60% sodium hydride was added at room temperature, and the mixture was stirred at 60° C. for 20 minutes. Thereto was added 1.50 g of 1-tert-butyl 4-ethyl 4-(3-((methanesulfonyl)oxy)propyl)piperidine-1,4-dicarboxylate, the mixture was stirred at 70 to 80° C. for 1 hour and 30 minutes, and thereto was further added 75 mg of 60% sodium hydride, and the mixture was stirred for 2 hours and 30 minutes. The reaction mixture was cooled to room temperature, and then ethyl acetate and water were added thereto. The organic layer was separated, and the aqueous layer was extracted with ethyl acetate. The organic layer and the extract were combined, the resultant solution was washed with a saturated sodium chloride solution and dried over anhydrous magnesium sulfate, and the solvent was removed under reduced pressure. The residue thus obtained was purified by silica gel column chromatography [eluent; hexane:ethyl acetate=1:1] to obtain 0.72 g of a yellow oily substance, 1-tert-butyl 4-ethyl 4-(3-(7-methoxy-2-oxoquinolin-1(2H)-yl)propyl)piperidine-1,4-dicarboxylate.

$^1$H-NMR (CDCl$_3$) δ:

1.20 (3H, t, J=7.1 Hz), 1.30-1.42 (2H, m), 1.44 (9H, s), 1.61-1.72 (4H, m), 2.05-2.12 (2H, m), 2.80-2.92 (2H, m), 3.79-3.90 (2H, m), 3.91 (3H, s), 4.12 (2H, q, J=7.1 Hz), 4.16-4.24 (2H, m), 6.52 (1H, d, J=9.5 Hz), 6.72 (1H, d, J=2.2 Hz), 6.81 (1H, dd, J=8.5, 2.2 Hz), 7.47 (1H, d, J=8.5 Hz), 7.58 (1H, d, J=9.5 Hz)

Reference Example 48

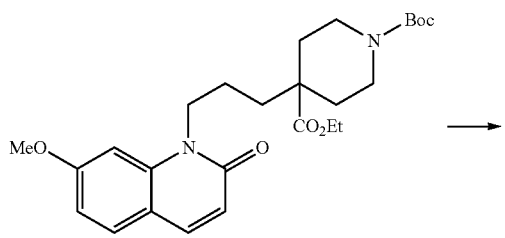

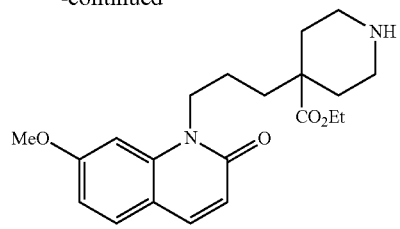

To 3 mL of a chloroform solution containing 0.72 g of 1-tert-butyl 4-ethyl 4-(3-(7-methoxy-2-oxoquinolin-1(2H)-yl)propyl)piperidine-1,4-dicarboxylate, 1.5 mL of trifluoroacetic acid was added under cooling with ice, and the mixture was stirred at room temperature for 1 hour. The solvent was removed under reduced pressure, and diethyl ether and water were added thereto. The aqueous layer was separated, ethyl acetate was added thereto, and the resultant solution was adjusted to pH 12.3 with a 20% aqueous sodium hydroxide solution. The organic layer was separated, and the aqueous layer was extracted twice with ethyl acetate. The organic layer and the extract were combined, the resultant solution was washed with a saturated sodium chloride solution and dried over anhydrous magnesium sulfate, and the solvent was removed under reduced pressure to obtain 0.60 g of a yellow oily substance, ethyl 4-(3-(7-methoxy-2-oxoquinolin-1(2H)-yl)propyl)piperidine-1,4-carboxylate.

$^1$H-NMR (CDCl$_3$) δ:

1.20 (3H, t, J=7.2 Hz), 1.36-1.47 (2H, m), 1.64-1.74 (4H, m), 2.10-2.17 (2H, m), 2.32-2.46 (1H, m), 2.64-2.71 (2H, m), 2.97 (2H, dt, J=12.9, 3.7 Hz), 3.91 (3H, s), 4.12 (2H, q, J=7.2 Hz), 4.16-4.25 (2H, m), 6.52 (1H, d, J=9.3 Hz), 6.72 (1H, d, J=2.3 Hz), 6.81 (1H, dd, J=8.5, 2.3 Hz), 7.46 (1H, d, J=8.5 Hz), 7.58 (1H, d, J=9.3 Hz)

Reference Example 49

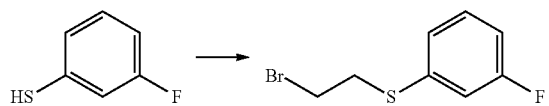 [SMILES: Fc1cccc(S)c1 ; Fc1cccc(SCCBr)c1]

To 2 mL of a methanol solution containing 0.83 g of 28% sodium methoxide/methanol, 1.0 mL of 1,2-dibromoethane and 0.50 g of 3-fluorobenzenethiol were added under cooling with ice, the mixture was stirred at the same temperature for 1 hour, at room temperature for 2 hours, and at 50° C. for 1 hour, and then the reaction mixture was refluxed by heating for 5 hours. The reaction mixture was cooled to room temperature, and then ethyl acetate and water were added thereto. The organic layer was separated, washed with an aqueous saturated sodium chloride solution and dried over anhydrous magnesium sulfate, and the solvent was removed under reduced pressure. The residue thus obtained was purified by silica gel column chromatography [eluent; hexane] to obtain 0.62 g of a pale yellow oily substance, 1-(3-fluorophenyl)thio-2-bromoethane.

$^1$H-NMR (CDCl$_3$) δ:

3.26-3.38 (2H, m), 3.40-3.54 (2H, m), 6.94 (1H, tdd, J=8.7, 2.4, 0.9 Hz), 7.08 (1H, dt, J=8.7, 2.1 Hz), 7.14 (1H, ddd, J=7.9, 1.7, 0.9 Hz), 7.28 (1H, td, J=7.9, 5.9 Hz)

Reference Example 50

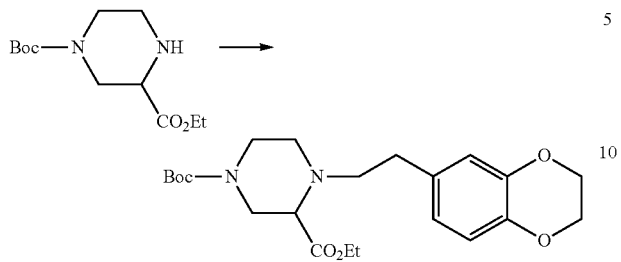

To 20 mL of a dichloromethane solution containing 0.50 g of 1-tert-butyl 3-ethyl piperazine-1,3-dicarboxylate, 0.38 g of (2,3-dihydrobenzo[b][1,4]dioxin-6-yl)acetaldehyde and 0.20 mL of acetic acid were added at room temperature, and the mixture was stirred at the same temperature for 15 minutes. Then, the reaction mixture was added with 0.49 g of sodium triacetoxyborohydride at the same temperature and stirred for 30 minutes. The reaction mixture was added with water and chloroform, and the resultant solution was adjusted to pH 0.5 with 6 mol/L hydrochloric acid. The organic layer was separated, washed with an aqueous saturated sodium chloride solution and dried over anhydrous magnesium sulfate, and the solvent was removed under reduced pressure. The residue thus obtained was purified by silica gel column chromatography [eluent; hexane:ethyl acetate=3:1] to obtain 0.60 g of a white solid, 1-tert-butyl 3-ethyl 4-(2-(2,3-dihydro-1,4-benzodioxin-6-yl)ethyl)piperazine-1,3-dicarboxylate.

$^1$H-NMR (CDCl$_3$) δ:
1.26 (3H, t, 7.1 Hz), 1.45 (9H, s), 2.37-2.48 (1H, m), 2.58-2.72 (3H, m), 2.78-2.88 (1H, m), 3.08-3.16 (1H, m), 3.22-3.30 (1H, m), 3.37-3.47 (1H, m), 3.47-3.64 (1H, m), 4.22-4.27 (4H, m), 4.23 (4H, s), 6.64 (1H, dd, J=8.2, 2.0 Hz), 6.68 (1H, d, J=2.0 Hz), 6.76 (1H, d, J=8.2 Hz)

Reference Example 51

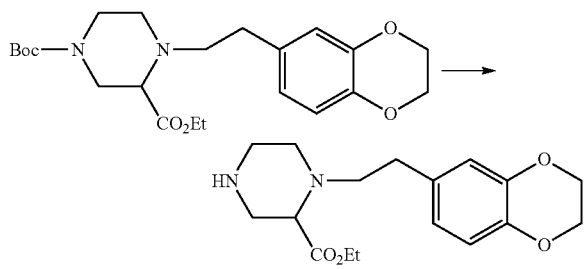

To 0.60 g of 1-tert-butyl 3-ethyl 4-(2-(2,3-dihydro-1,4-benzodioxin-6-yl)ethyl)piperazine-1,3-dicarboxylate, 12 mL of 10 mol/L hydrogen chloride/ethanol was added, and the mixture was stirred for 2 hours, and then the solvent was removed under reduced pressure. The residue thus obtained was added with water and ethyl acetate. The aqueous layer was separated, ethyl acetate was added thereto, and the resultant solution was adjusted to pH 14 with a 5 mol/L aqueous sodium hydroxide solution. The organic layer was separated and dried over potassium carbonate, and the solvent was removed under reduced pressure to obtain 0.34 g of a brown oily substance, ethyl 1-(2-(2,3-dihydro-1,4-benzodioxin-6-yl)ethyl)piperazine-2-carboxylate.

$^1$H-NMR (CDCl$_3$) δ:
1.28 (3H, t, 7.2 Hz), 2.32-2.45 (1H, m), 2.54-2.82 (4H, m), 2.88-3.12 (5H, m), 3.18-3.27 (1H, m), 4.20 (2H, q, J=7.2 Hz), 4.23 (4H, s), 6.64 (1H, dd, J=8.1, 2.0 Hz), 6.69 (1H, d, J=2.0 Hz), 6.77 (1H, d, J=8.1 Hz)

Reference Example 52

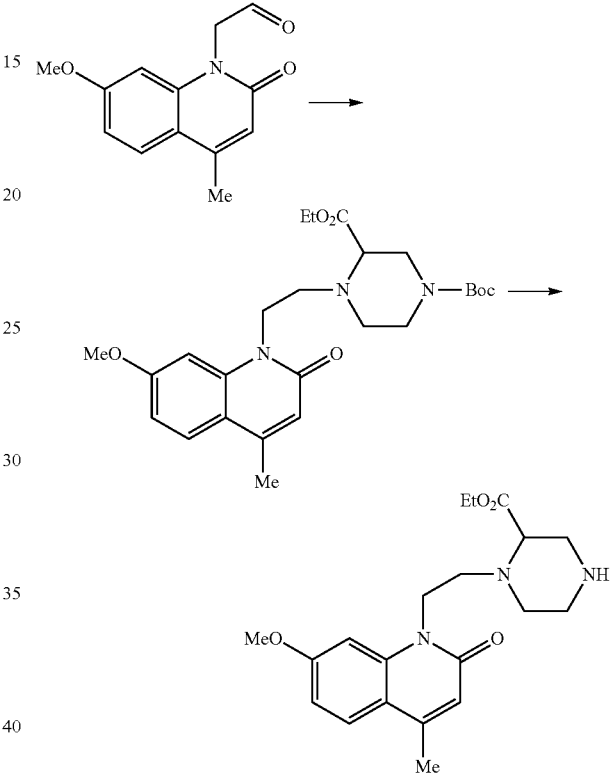

(1) To 3 mL of a dichloromethane solution containing 0.10 g of (7-methoxy-4-methyl-2-oxoquinolin-1(2H)-yl)acetaldehyde, 0.12 g of 1-tert-butyl 3-ethyl piperazine-1,3-dicarboxylate, 30 μl of acetic acid and 0.14 g of sodium triacetoxyborohydride were added at room temperature, and the mixture was stirred at room temperature for 1 hour and 40 minutes. The reaction mixture was added with water and chloroform. The organic layer was separated, and the aqueous layer was extracted twice with chloroform. The organic layer and the extract were combined, the resultant solution was dried over anhydrous magnesium sulfate, and the solvent was removed under reduced pressure. The residue thus obtained was purified by silica gel column chromatography [eluent; chloroform:acetone=100:1] to obtain a colorless foam, 1-tert-butyl 3-ethyl 4-(2-(7-methoxy-4-methyl-2-oxoquinolin-1(2H)-yl)ethyl)piperazine-1,3-dicarboxylate.

(2) To 2.6 mL of a dichloromethane solution containing 1-tert-butyl 3-ethyl 4-(2-(7-methoxy-4-methyl-2-oxoquinolin-1(2H)-yl)ethyl)piperazine-1,3-dicarboxylate, 1.3 mL of trifluoroacetic acid was added, the mixture was stirred at room temperature for 2 hours, and the solvent was removed under reduced pressure. The residue thus obtained was added with ethyl acetate and water, and the resultant solution was adjusted to pH 1.0 with 6 mol/L hydrochloric acid. The aqueous layer was separated, and the organic layer was extracted twice with 20 mL of 0.1 mol/L hydrochloric acid. The aqueous layer and an extract were combined, thereto was added ethyl acetate, and the resultant solution was adjusted to pH 8.5 with a 5 mol/L aqueous sodium hydroxide solution. The organic layer was separated, and the aqueous layer was adjusted to pH 11.5 with a 5 mol/L aqueous sodium hydroxide solution, and extracted with ethyl acetate. The organic layer and the extract were combined, the resultant solution was washed with a saturated sodium chloride solution, and dried over anhydrous magnesium sulfate, and the solvent was removed under reduced pressure to obtain 89 mg of a colorless foam, ethyl 1-(2-(7-methoxy-4-methyl-2-oxoquinolin-1 (2H)-yl)ethyl)piperazine-2-carboxylate.

$^1$H-NMR (CDCl$_3$) δ:

1.25 (3H, t, J=7.1 Hz), 2.42 (3H, s), 2.52-2.60 (1H, m), 2.66-2.76 (1H, m), 2.82-3.22 (6H, m), 3.26-3.34 (1H, m), 3.95 (3H, s), 4.17 (2H, q, J=7.1 Hz), 4.20-4.31 (1H, m), 4.52-4.65 (1H, m), 6.42 (1H, s), 6.83 (1H, dd, J=8.8, 2.3 Hz), 6.98 (1H, d, J=2.3 Hz), 7.60 (1H, dd, J=8.8, 1.5 Hz)

Reference Example 53

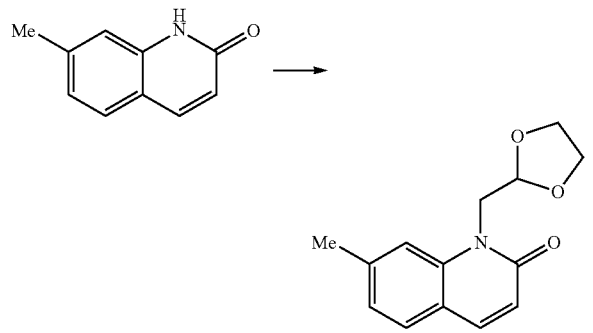

To 6.3 mL of a dimethyl sulfoxide solution containing 1.1 g of 2-bromomethyl-1,3-dioxolane, 1.0 g of 7-methylquinolin-2(1H)-one and 3.1 g of cesium carbonate were added, and the mixture was stirred at 60 to 70° C. for 1 hour. The reaction mixture was added with ethyl acetate, water and an aqueous saturated sodium hydrogen carbonate solution. The organic layer was separated, and the aqueous layer was extracted with ethyl acetate. The organic layer and the extract were combined, the resultant solution was washed with water and dried over anhydrous magnesium sulfate, and the solvent was removed under reduced pressure. The residue thus obtained was purified by silica gel column chromatography [eluent; hexane:ethyl acetate=2:3] to obtain 0.60 g of a brown oily substance, 1-(1,3-dioxolan-2-ylmethyl)-7-methylquinolin-2 (1H)-one.

$^1$H-NMR (CDCl$_3$) δ:

2.50 (3H, s), 3.84-3.92 (2H, m), 4.02-4.10 (2H, m), 4.53 (2H, d, J=4.6 Hz), 5.28 (1H, t, J=4.6 Hz), 6.64 (1H, d, J=9.4 Hz), 7.04 (1H, d, J=8.2 Hz), 7.36 (1H, s), 7.42 (1H, d, J=8.2 Hz), 7.64 (1H, d, J=9.4 Hz)

Reference Example 54

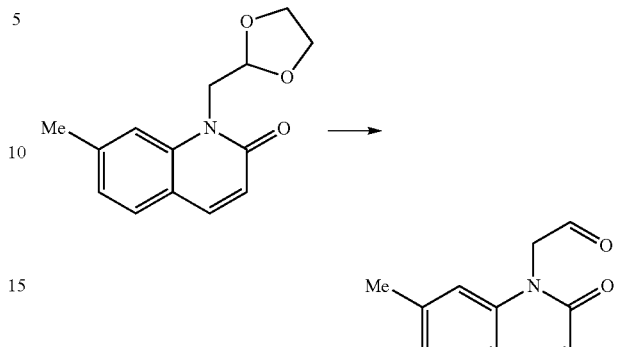

To 0.37 g of 1-(1,3-dioxolan-2-ylmethyl)-7-methylquinolin-2(1H)-one, 3.7 mL of a 90% aqueous trifluoroacetic acid solution was added, the mixture was stirred at room temperature for 1 hour, and the solvent was removed under reduced pressure. The residue thus obtained was added with ethyl acetate and an aqueous saturated sodium hydrogen carbonate solution. The organic layer was separated, and the aqueous layer was extracted twice with ethyl acetate. The organic layer and an extract were combined, the resultant solution was washed with an aqueous saturated sodium chloride solution and dried over anhydrous magnesium sulfate, and the solvent was removed under reduced pressure to obtain 0.32 g of a brown oily substance, (7-methyl-2-oxoquinolin-1(2H)-yl)acetaldehyde.

$^1$H-NMR (CDCl$_3$) δ:

2.46 (3H, s), 5.13 (2H, s), 6.69 (1H, d, J=9.5 Hz), 6.83 (1H, s), 7.08 (1H, d, J=7.8 Hz), 7.49 (1H, d, J=7.8 Hz), 7.73 (1H, d, J=9.5 Hz), 9.69 (1H, s)

Reference Example 55

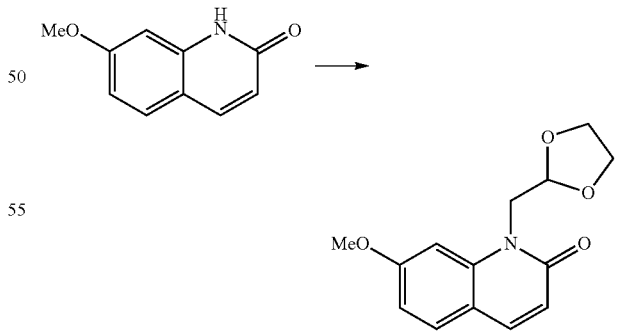

To 6.5 mL of an N,N-dimethylformamide solution containing 0.65 g of 7-methoxyquinolin-2(1H)-one, 0.16 g of 60% sodium hydride was added, and the mixture was stirred at 55 to 63° C. for 30 minutes. Thereto was added 0.42 mL of 2-bromomethyl-1,3-dioxolane, and the reaction mixture was stirred at 60 to 65° C. for 1 hour and 30 minutes and at 85 to 90° C. for 1 hour. The reaction mixture was further added with 0.16 g of 60% sodium hydride and 0.39 mL of 2-bromomethyl-1,3-dioxolane, and stirred at the same temperature for 3 hours. The mixture was cooled to room temperature, and then water and ethyl acetate were added thereto. The organic layer was separated, and the aqueous layer was extracted with ethyl acetate. The organic layer and the extract were combined, the resultant solution was dried over anhydrous magnesium sulfate, and the solvent was removed under reduced pressure. The residue thus obtained was purified by silica gel column chromatography [eluent; hexane:ethyl acetate=1:1] to obtain 0.60 g of a pale yellow solid, 1-(1,3-dioxolan-2-ylmethyl)-7-methoxyquinolin-2(1H)-one.

$^1$H-NMR (CDCl$_3$) δ:

3.86-3.90 (2H, m), 3.91 (3H, s), 4.04-4.08 (2H, m), 4.51 (2H, d, J=4.4 Hz), 5.25 (1H, t, J=4.4 Hz), 6.55 (1H, d, J=9.5 Hz), 6.82 (1H, dd, J=8.7, 2.2 Hz), 7.09 (1H, d, J=2.2 Hz), 7.44 (1H, d, J=8.7 Hz), 7.61 (1H, d, J=9.5 Hz)

Reference Example 56

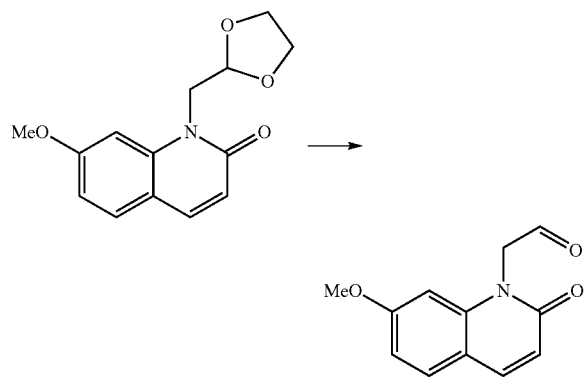

To 0.56 g of 1-(1,3-dioxolan-2-ylmethyl)-7-methoxyquinolin-2(1H)-one, 5.6 mL of a 90% aqueous trifluoroacetic acid solution was added, the mixture was stirred at room temperature for 2 hours. The solvent was removed under reduced pressure, water and chloroform was added thereto, and the reaction mixture was adjusted to pH 7.0 with an aqueous saturated sodium hydrogen carbonate solution and stirred for 2 hours. The organic layer was separated, and the aqueous layer was extracted with chloroform. The organic layer and the extract were combined, the resultant solution was washed sequentially with water and an aqueous saturated sodium chloride solution and dried over anhydrous magnesium sulfate, and the solvent was removed under reduced pressure to obtain 0.36 g of a yellow oily substance, (7-methoxy-2-oxoquinolin-1(2H)-yl)acetaldehyde.

$^1$H-NMR (CDCl$_3$) δ:

3.86 (3H, s), 5.10 (2H, s), 6.48 (1H, d, J=2.2 Hz), 6.59 (1H, d, J=9.5 Hz), 6.84 (1H, dd, J=8.8, 2.2 Hz), 7.51 (1H, d, J=8.8 Hz), 7.68 (1H, d, J=9.5 Hz), 9.67 (1H, s)

Reference Example 57

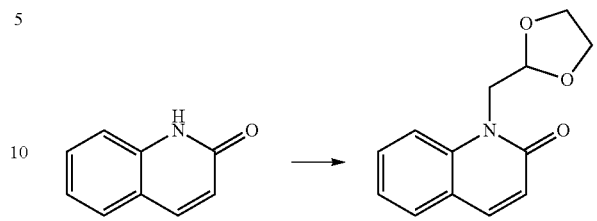

To 11.5 mL of an N,N-dimethylformamide solution containing 1.15 g of quinolin-2(1H)-one, 0.35 g of 60% sodium hydride was added, and the mixture was stirred at 50 to 55° C. for 20 minutes. Thereto was added 0.90 mL of 2-bromomethyl-1,3-dioxolane, and the reaction mixture was stirred at 85 to 95° C. for 30 minutes. The reaction mixture was further added with 0.35 g of 60% sodium hydride and 0.90 mL of 2-bromomethyl-1,3-dioxolane, and stirred for 1 hour. The mixture was further added with 0.35 g of 60% sodium hydride and 0.90 mL of 2-bromomethyl-1,3-dioxolane, and stirred for 1 hour and 30 minutes. The reaction mixture was cooled to room temperature, and then water and ethyl acetate were added thereto. The organic layer was separated, and the aqueous layer was extracted twice with ethyl acetate. The organic layer and the extract were combined, the resultant solution was washed with a saturated sodium chloride solution and dried over anhydrous magnesium sulfate, the solvent was removed under reduced pressure, and the residue thus obtained was purified by silica gel column chromatography [eluent; hexane:ethyl acetate 2:1] to obtain 0.89 g of a yellow oily substance, 1-(1,3-dioxolan-2-ylmethyl)quinolin-2(1H)-one.

$^1$H-NMR (CDCl$_3$) δ:

3.86-3.90 (2H, m), 4.03-4.07 (2H, m), 4.55 (2H, d, J=4.5 Hz), 5.27 (1H, t, J=4.5 Hz), 6.71 (1H, d, J=9.5 Hz), 7.20-7.25 (1H, m), 7.52-7.61 (3H, m), 7.69 (1H, d, J=9.5 Hz),

Reference Example 58

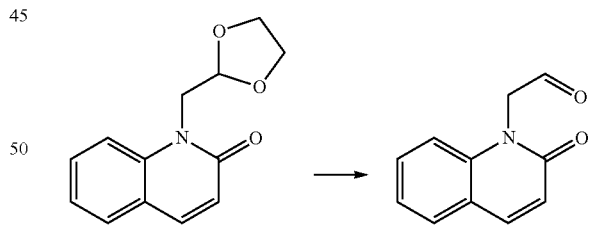

To 0.88 g of 1-(1,3-dioxolan-2-ylmethyl)quinolin-2(1H)-one, 8.8 mL of a 90% aqueous trifluoroacetic acid solution was added, and the mixture was stirred at room temperature for 2 hours. The solvent was removed under reduced pressure, thereto were added an aqueous saturated sodium hydrogen carbonate solution and ethyl acetate, and the mixture was stirred at room temperature for 30 minutes. The organic layer was separated, and the aqueous layer was extracted 5 times with ethyl acetate. The organic layer and an extract were combined, the resultant solution was dried over anhydrous magnesium sulfate, and the solvent was removed under reduced pressure to obtain 0.55 g of (2-oxoquinolin-1(2H)-yl)acetaldehyde.

¹H-NMR (CDCl₃) δ:
5.20 (2H, s), 6.82 (1H, d, J=9.5 Hz), 7.25-7.32 (1H.m), 7.52-7.65 (3H, m), 7.80 (1H, d, J=9.5 Hz), 9.71 (1H, s)

Reference Example 59

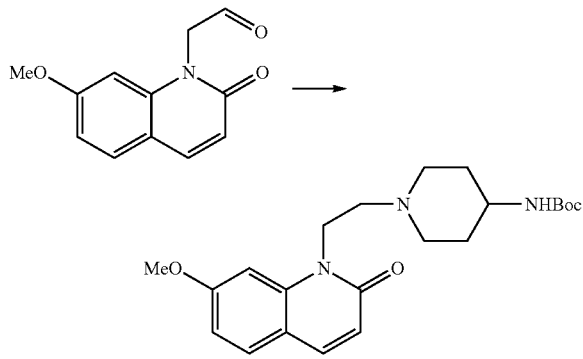

To 10 mL of a dichloromethane solution containing 0.23 g of (7-methoxy-2-oxoquinolin-1(2H)-yl)acetaldehyde, 0.21 g of tert-butyl (piperidin-4-yl)carbamate and 60 μL of acetic acid were added, and the mixture was stirred for 10 minutes. Thereto was added 0.34 g of sodium triacetoxyborohydride, and the mixture was stirred at room temperature for 4 hours and 30 minutes. The reaction mixture was added with water and ethyl acetate, and the reaction solution was neutralized with an aqueous saturated sodium hydrogen carbonate solution. The organic layer was separated, washed with an aqueous saturated sodium chloride solution and dried over anhydrous magnesium sulfate, and the solvent was removed under reduced pressure to obtain 0.43 g of a colorless oily substance, tert-butyl (1-(2-(7-methoxy-2-oxoquinolin-1(2H)-yl)ethyl)piperidin-4-yl)carbamate.

¹H-NMR (CDCl₃) δ:
1.41-1.51 (2H, m), 1.45 (9H, m), 1.92-1.99 (2H, m), 2.23-2.31 (2H, m), 2.62-2.70 (2H, m), 2.94-3.02 (2H, m), 3.45-3.60 (1H, m), 3.91 (3H, s), 4.36-4.42 (2H, m), 4.55-4.60 (1H, m), 6.52 (1H, d, J=9.5 Hz), 6.82 (1H, dd, J=8.6, 2.1 Hz), 6.89 (1H, d, J=2.1 Hz), 7.46 (1H, d, J=8.6 Hz), 7.59 (1H, d, J=9.5 Hz)

Reference Example 60

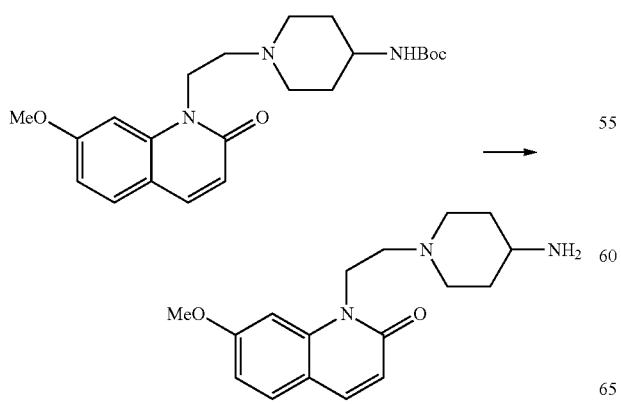

To 5 mL of a chloroform solution containing 0.43 g of tert-butyl (1-(2-(7-methoxy-2-oxoquinolin-1(2H)-yl)ethyl)piperidin-4-yl)carbamate, 2 mL of trifluoroacetic acid was added, and the mixture was stirred at room temperature for 3 hours. The solvent was removed under reduced pressure, and water and diethyl ether were added thereto. The aqueous layer was separated and adjusted to pH 12 with a 20% aqueous sodium hydroxide solution, and then ethyl acetate was added thereto. The organic layer was separated, the aqueous layer was extracted with ethyl acetate, and then the aqueous layer was added with sodium chloride and extracted 5 times with ethyl acetate. The organic layer and an extract were combined, the resultant solution was dried over anhydrous magnesium sulfate, and the solvent was removed under reduced pressure to obtain 0.30 g of a colorless foam, (1-(2-(4-aminopiperidin-1-yl)ethyl)-7-methoxyquinolin-2(1H)-one.

¹H-NMR (CDCl₃) δ:
1.46-1.58 (2H, m), 1.87-1.95 (2H, m), 2.18-2.27 (2H, m), 2.64-2.70 (2H, m), 2.75-2.95 (1H, m), 2.98-3.07 (2H, m) 3.58-3.81 (2H, m), 3.91 (3H, s), 4.36-4.45 (2H, m), 6.51 (1H, d, J=9.4 Hz), 6.82 (1H, d, J=8.7 Hz), 6.90 (1H, s), 7.46 (1H, d, J=8.7 Hz), 7.59 (1H, d, J=9.4 Hz)

Reference Example 61

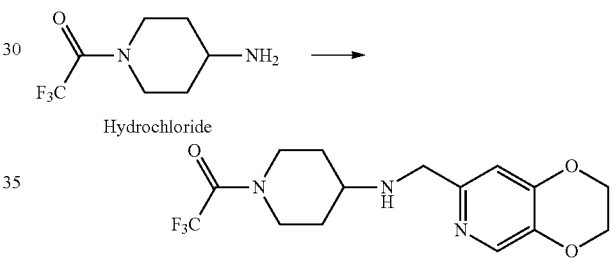

In the same method as in Reference Example 16, N-(2,3-dihydro-1,4-dioxino[2,3-c]pyridin-7-ylmethyl)-1-trifluoroacetyl)piperidine-4-amine was obtained from 1-(trifluoroacetyl)piperidine-4-amine hydrochloride and 2,3-dihydro-1,4-dioxino[2,3-c]pyridine-7-carbaldehyde.

¹H-NMR (CDCl₃) δ:
1.39-1.51 (2H, m), 1.93-2.01 (2H, m), 2.79-2.88 (1H, m), 3.02-3.10 (1H, m), 3.19-3.27 (1H, m), 3.80 (2H, s), 3.90-3.99 (1H, m), 4.25-4.35 (5H, m), 6.80 (1H, s), 8.11 (1H, s)

Reference Example 62

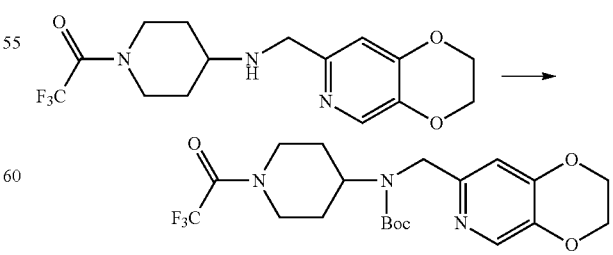

In the same method as in Reference Example 17, tert-butyl (2,3-dihydro-1,4-dioxino[2,3-c]pyridin-7-ylmethyl)(1-(trifluoroacetyl)piperidin-4-yl)carbamate was obtained from N-(2,3-dihydro-1,4-dioxino[2,3-c]pyridin-7-ylmethyl)-1-(trifluoroacetyl)piperidine-4-amine.

$^{1}$H-NMR (CDCl$_{3}$) δ:
1.43 (9H, s), 1.37-1.84 (4H, m), 2.60-2.80 (1H, m), 3.00-3.20 (1H, m), 3.98-4.06 (1H, m), 4.25-4.41 (7H, m), 4.54-4.62 (1H, m), 6.74 (1H, s), 8.05 (1H, s)

Reference Example 63

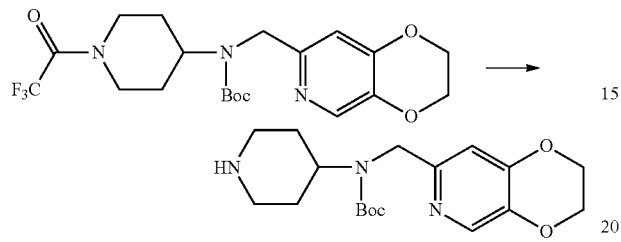

In the same method as in Reference Example 18, tert-butyl (2,3-dihydro-1,4-dioxino[2,3-c]pyridin-7-ylmethyl)(piperidin-4-yl)carbamate was obtained from tert-butyl (2,3-dihydro-1,4-dioxino[2,3-c]pyridin-7-ylmethyl)(1-(trifluoroacetyl)piperidin-4-yl)carbamate.

$^{1}$H-NMR (CDCl$_{3}$) δ:
1.39 (9H, s), 1.34-1.71 (4H, m), 2.52-2.70 (2H, m), 3.04-3.11 (2H, m), 4.11-4.48 (7H, m), 6.75 (1H, s), 8.05 (1H, s)

Reference Example 64

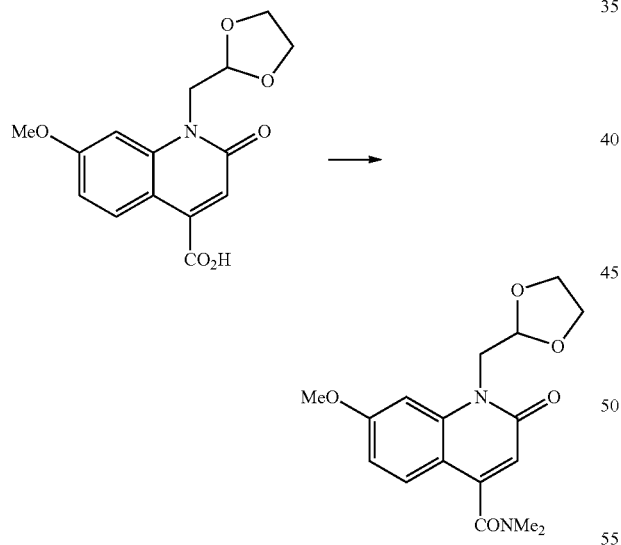

In the same method as in Reference Example 31, 1-(1,3-dioxolan-2-ylmethyl)-7-methoxy-N,N-dimethyl-2-oxo-1,2-dihydroquinoline-4-carboxamide was obtained from 1-(1,3-dioxolan-2-ylmethyl)-7-methoxy-2-oxo-1,2-dihydroquinoline-4-carboxylic acid and dimethylamine hydrochloride.

$^{1}$H-NMR (CDCl$_{3}$) δ:
2.93 (3H, s), 3.19 (3H, s), 3.85-3.94 (2H, m), 3.91 (3H, s), 4.01-4.10 (2H, m), 4.48-4.55 (2H, m), 5.23 (1H, t, J=4.4 Hz), 6.47 (1H, s), 6.82 (1H, dd, J=8.8, 2.2 Hz), 7.13 (1H, d, J=2.2 Hz), 7.37 (1H, d, J=8.8 Hz)

Reference Example 65

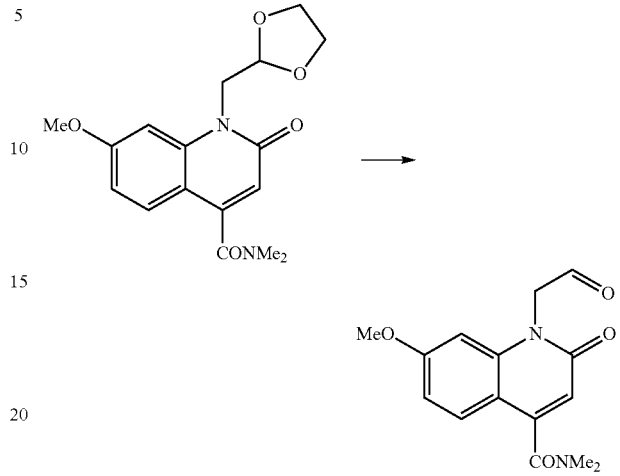

In the same method as in Reference Example 32, 7-methoxy-N,N-dimethyl-2-oxo-1-(2-oxoethyl)-1,2-dihydroquinoline-4-carboxamide was obtained from 1-(1,3-dioxolan-2-ylmethyl)-7-methoxy-N,N-dimethyl-2-oxo-1,2-dihydroquinoline-4-carboxamide.

$^{1}$H-NMR (CDCl$_{3}$) δ:
2.96 (3H, s), 3.21 (3H, s), 3.87 (3H, s), 5.07-5.16 (2H, m), 6.49 (1H, d, J=2.3 Hz), 6.51 (1H, s), 6.85 (1H, dd, J=8.9, 2.3 Hz), 7.44 (1H, d, J=8.9 Hz), 9.68 (1H, s)

Reference Example 66

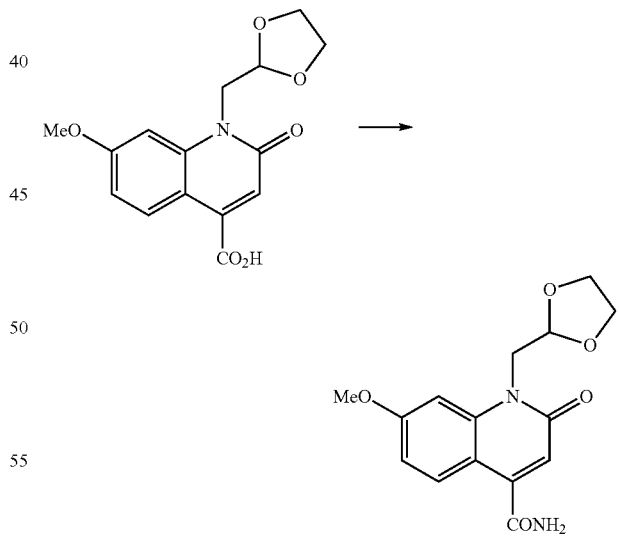

To 5.0 mL of a tetrahydrofuran suspension containing 0.22 g of 1-(1,3-dioxolan-2-ylmethyl)-7-methoxy-2-oxo-1,2-dihydroquinoline-4-carboxylic acid, 0.11 mL of triethylamine was added at room temperature, and the mixture was cooled to −60° C., and thereto was added dropwise 73 μL of ethyl chlorocarbonate. The temperature of the reaction mixture was increased to 5° C., and the mixture was stirred for 3 hours and 20 minutes under cooling with ice. The mixture was again cooled to −60° C., thereto were added 0.10 mL of triethylamine and 70 μL of ethyl chlorocarbonate, and the mixture was stirred for 30 minutes under cooling with ice. Thereto were further added 0.10 mL of triethylamine and 70 μL of ethyl chlorocarbonate, and the mixture was stirred for 1 hour. Thereto were added 5.0 mL of a 3.7 mol/L ammonia/ethanol solution, the mixture was stirred for 4 hours and 30 minutes, and then the temperature of the mixture was increased to room temperature. Thereto was further added 5.0 mL of a 3.7 mol/L ammonia/ethanol solution, and the mixture was stirred at 60° C. for 40 minutes and for 3 hours under reflux. The reaction mixture was cooled to room temperature, then the solvent was removed under reduced pressure, and the residue was added with ethyl acetate and water. The organic layer was separated, and the aqueous layer was extracted with ethyl acetate. The organic layer and an extraction layer were combined, a resultant solution was washed with an aqueous saturated sodium chloride solution and dried over anhydrous magnesium sulfate, and the solvent was removed under reduced pressure. The residue thus obtained was added with diethyl ether, and a solid substance was collected by filtration to obtain 96 mg of a yellow solid, 1-(1,3-dioxolan-2-ylmethyl)-7-methoxy-2-oxo-1,2-dihydroquinoline-4-carboxamide.

$^1$H-NMR (CDCl$_3$) δ:

3.82-3.90 (2H, m), 3.91 (3H, s), 3.98-4.07 (2H, m), 4.48 (2H, d, J=4.1 Hz), 5.20 (1H, t, J=4.1 Hz), 5.84 (1H, s), 6.21 (1H, s), 6.69 (1H, s), 6.87 (1H, dd, J=8.9, 2.4 Hz), 7.09 (1H, d, J=2.4 Hz), 7.93 (1H, d, J=8.9 Hz)

Reference Example 67

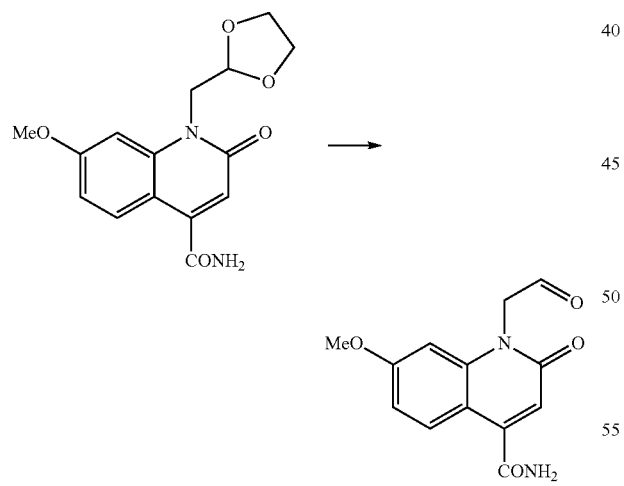

In the same method as in Reference Example 32, 7-methoxy-2-oxo-1-(2-oxoethyl)-1,2-dihydroquinoline-4-carboxamide was obtained from 1-(1,3-dioxolan-2-ylmethyl)-7-methoxy-2-oxo-1,2-dihydroquinoline-4-carboxamide.

$^1$H-NMR (CDCl$_3$) δ:

3.88 (3H, s), 5.13 (2H, s), 5.84 (1H, s), 6.07 (1H, s), 6.47 (1H, d, J=2.3 Hz), 6.73 (1H, s), 6.89 (1H, dd, J=8.9, 2.3 Hz), 7.99 (1H, d, J=8.9 Hz), 9.69 (1H, s)

Reference Example 68

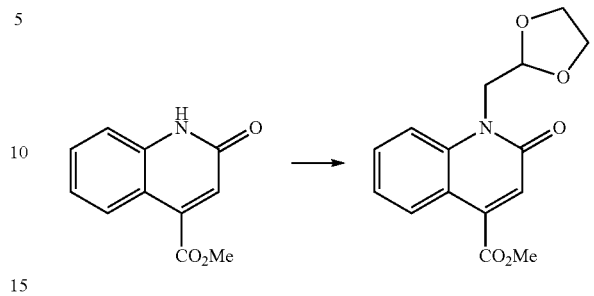

To 45 mL of an N,N-dimethylformamide suspension containing 3.0 g of methyl 2-oxo-1,2-dihydroquinoline-4-carboxylate, 2.2 g of potassium carbonate was dividedly added at room temperature. Thereto was added 1.8 mL of 2-bromomethyl-1,3-dioxolane at the same temperature, and the mixture was stirred at 60° C. for 1 hour and 30 minutes and at 100° C. for 3 hours and 30 minutes. Thereto were added 0.76 mL of 2-bromomethyl-1,3-dioxolane and 1.0 g of potassium carbonate at the same temperature, and the mixture was stirred for 4 hours. The mixture was cooled to room temperature, ethyl acetate and water were added thereto, and the resultant solution was adjusted to pH 3.0 with 1 mol/L hydrochloric acid. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure. The residue thus obtained was purified by flash silica gel column chromatography [chloroform: gradient elution of methanol=100:0 to 90:10], diethyl ether was added to the obtained solid, and the solid substance was collected by filtration to obtain 0.89 g of a yellow solid, methyl 1-(1,3-dioxolan-2-ylmethyl)-2-oxo-1,2-dihydroquinoline-4-carboxylate.

$^1$H-NMR (CDCl$_3$) δ:

3.84-3.93 (2H, m), 3.99 (3H, s), 4.00-4.08 (2H, m), 4.58 (2H, d, J=4.4 Hz), 5.27 (1H, t, J=4.4 Hz), 7.19 (1H, s), 7.26-7.31 (1H, m), 7.56-7.66 (2H, m), 8.30 (1H, dd, J=8.4, 1.5 Hz)

Reference Example 69

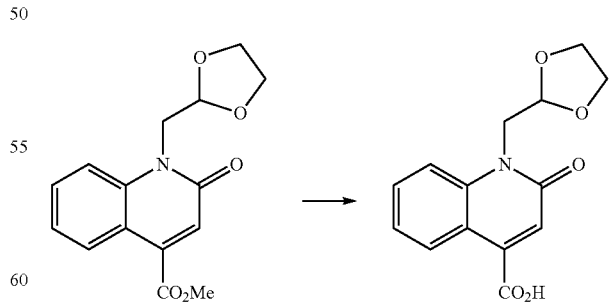

To a mixed solution of 5 mL of tetrahydrofuran containing 0.89 g of methyl 1-(1,3-dioxolan-2-ylmethyl)-2-oxo-1,2-dihydroquinoline-4-carboxylate and 5 mL of methanol, 1.8 mL of a 20% aqueous sodium hydroxide solution was added at room temperature, and the mixture was stirred for 1 hour and 30 minutes. The organic solvent was removed under reduced pressure, and 10 mL of water was added thereto. Then, the resultant solution was adjusted to pH 1.8 with 1 mol/L hydrochloric acid, and a solid substance was collected by filtration to obtain 0.80 g of a white solid, 1-(1,3-dioxolan-2-ylmethyl)-2-oxo-1,2-dihydroquinoline-4-carboxylic acid.

$^1$H-NMR (DMSO-d$_6$) δ:

3.75-3.85 (2H, m), 3.93-4.02 (2H, m), 4.48 (2H, d, J=4.7 Hz), 5.15 (1H, t, J=4.7 Hz), 6.92 (1H, s), 7.29-7.34 (1H, m), 7.63-7.68 (1H, m), 7.76 (1H, d, J=8.2 Hz), 8.14 (1H, dd, J=8.2, 1.5 Hz)

Reference Example 70

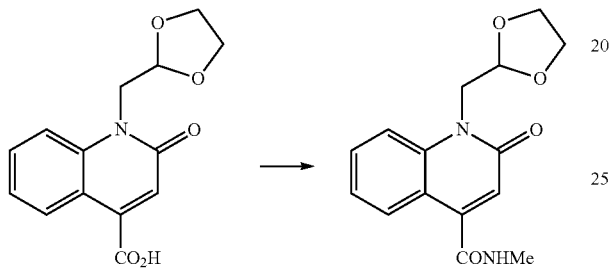

In the same method as in Reference Example 31, 1-(1,3-dioxolan-2-ylmethyl)-N-methyl-2-oxo-1,2-dihydroquinoline-4-carboxamide was obtained from 1-(1,3-dioxolan-2-ylmethyl)-2-oxo-1,2-dihydroquinoline-4-carboxylic acid and methylamine hydrochloride.

$^1$H-NMR (CDCl$_3$) δ:

3.06 (3H, d, J=4.9 Hz), 3.79-3.88 (2H, m), 3.95-4.04 (2H, m), 4.45 (2H, d, J=4.3 Hz), 5.17 (1H, t, J=4.3 Hz), 6.31-6.39 (1H, m), 6.73 (1H, s), 7.23-7.28 (1H, m), 7.56-7.59 (2H, m), 7.90-7.93 (1H, m)

Reference Example 71

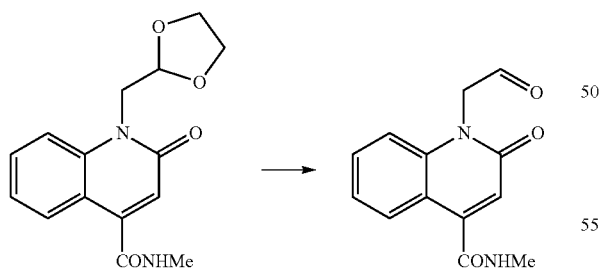

In the same method as in Reference Example 32, N-methyl-2-oxo-1-(2-oxoethyl)-1,2-dihydroquinoline-4-carboxamide was obtained from 1-(1,3-dioxolan-2-ylmethyl)-N-methyl-2-oxo-1,2-dihydroquinoline-4-carboxamide.

$^1$H-NMR (CDCl$_3$) δ:

3.08 (3H, d, J=4.9 Hz), 5.15 (2H, s), 6.15-6.28 (1H, m), 6.79 (1H, s), 7.02-7.05 (1H, m), 7.25-7.32 (1H, m), 7.54-7.60 (1H, m), 7.95-8.00 (1H, m), 9.69 (1H, s)

Reference Example 72

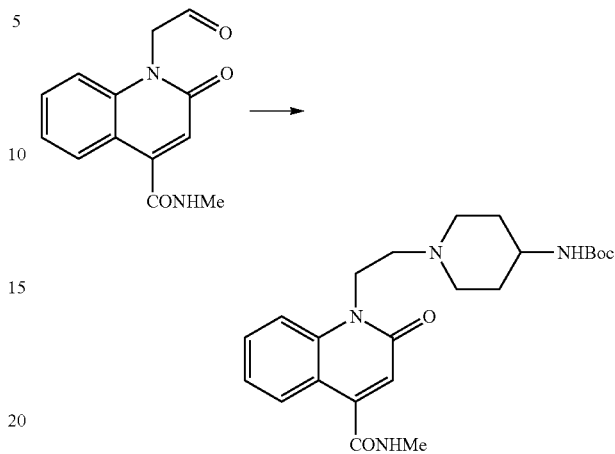

In the same method as in Reference Example 59, tert-butyl (1-(2-(4-(methylamino)carbonyl)-2-oxo-1,2-dihydroquinolin-1-yl)ethyl)piperidin-4-yl)carbamate was obtained from N-methyl-2-oxo-1-(2-oxoethyl)-1,2-dihydroquinoline-4-carboxamide and tert-butyl (piperidin-4-yl)carbamate.

$^1$H-NMR (CDCl$_3$) δ:

1.37-1.49 (2H, m), 1.45 (9H, s), 1.90-1.98 (2H, m), 2.20-2.28 (2H, m), 2.58-2.64 (2H, m), 2.89-2.96 (2H, m), 3.07 (3H, d, J=4.9 Hz), 3.42-3.53 (1H, m), 4.35-4.48 (3H, m), 6.15-6.22 (1H, m), 6.73 (1H, s), 7.22-7.29 (1H, m), 7.42 (1H, d, J=8.2 Hz), 7.57-7.62 (1H, m), 7.94 (1H, dd, J=8.2, 1.4 Hz)

Reference Example 73

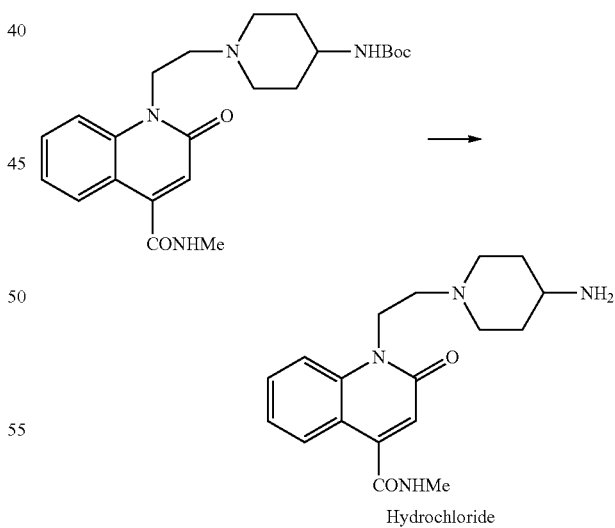

To 5.0 mL of an ethanol solution containing 0.42 g of tert-butyl (1-(2-(4-((methylamino)carbonyl)-2-oxo-1,2-dihydroquinolin-1-yl)ethyl)piperidin-4-yl)carbamate, 10 mL of 6.2 mol/L hydrogen chloride/ethanol was added, and the mixture was stirred for 2 hours and 30 minutes. Thereto was further added 10 mL of 6.2 mol/L hydrogen chloride/ethanol, and the mixture was stirred for 2 hours and 20 minutes. The solvent was removed under reduced pressure, then diethyl ether was added to the residue thus obtained, and a solid substance was collected by filtration to obtain 0.37 g of a slight yellow solid, 1-(2-(4-aminopiperidin-1-yl)ethyl)-N-methyl-2-oxo-1,2-dihydroquinoline-4-carboxamide hydrochloride.

$^1$H-NMR (D$_2$O) δ:

1.90-2.05 (2H, m), 2.32-2.42 (2H, m), 3.00 (3H, s), 3.16-3.28 (2H, m), 3.53-3.65 (3H, m), 3.85-3.95 (2H, m), 4.73-4.84 (2H, m), 6.85 (1H, s), 7.47 (1H, t, J=7.3 Hz), 7.64 (1H, d, J=8.6 Hz), 7.78-7.84 (1H, m), 7.85 (1H, dd, J=8.0, 1, 4 Hz)

Reference Example 74

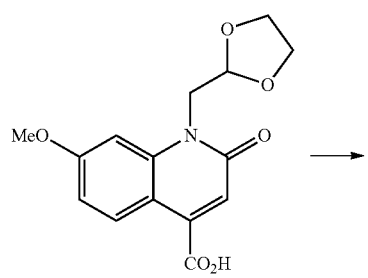

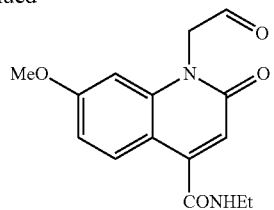

In the same method as in Reference Example 32, N-ethyl-7-methoxy-2-oxo-1-(2-oxoethyl)-1,2-dihydroquinoline-4-carboxamide was obtained from 1-(1,3-dioxolan-2-ylmethyl)-N-ethyl-7-methoxy-2-oxo-1,2-dihydroquinoline-4-carboxamide.

$^1$H-NMR (CDCl$_3$) δ:

1.29 (3H, t, J=7.3 Hz), 3.48-3.58 (2H, m), 3.87 (3H, s), 5.09 (2H, s), 6.09-6.16 (1H, m), 6.45 (1H, d, J=2.3 Hz), 6.63 (1H, s), 6.87 (1H, dd, J=8.9, 2.3 Hz), 7.92 (1H, d, J=8.9 Hz), 9.65 (1H, s)

Reference Example 76

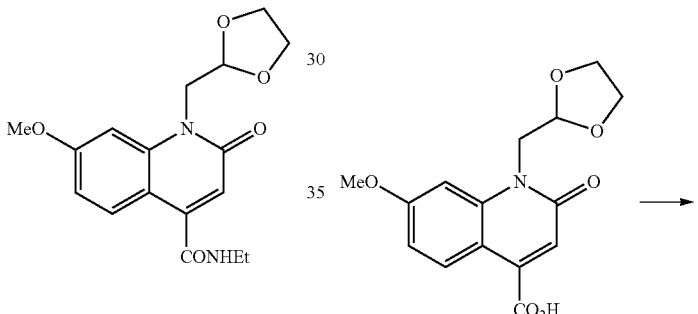

In the same method as in Reference Example 31, 1-(1,3-dioxolan-2-ylmethyl)-N-ethyl-7-methoxy-2-oxo-1,2-dihydroquinoline-4-carboxamide was obtained from 1-(1,3-dioxolan-2-ylmethyl)-7-methoxy-2-oxo-1,2-dihydroquinoline-4-carboxylic acid and ethylamine hydrochloride.

$^1$H-NMR (CDCl$_3$) δ:

1.28 (3H, t, J=7.2 Hz), 3.49-3.57 (2H, m), 3.82-3.89 (2H, m), 3.91 (3H, s), 3.98-4.06 (2H, m), 4.48 (2H, d, J=4.2 Hz), 5.19 (1H, t, J=4.2 Hz), 6.09-6.16 (1H, m), 6.59 (1H, s), 6.85 (1H, dd, J=9.0, 2.3 Hz), 7.07 (1H, d, J=2.3 Hz), 7.86 (1H, d, J=9.0 Hz)

Reference Example 75

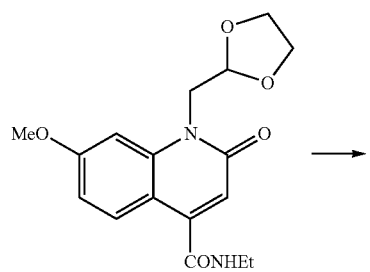

In the same method as in Reference Example 31, N-cyclopropyl-1-(1,3-dioxolan-2-ylmethyl)-7-methoxy-2-oxo-1,2-dihydroquinoline-4-carboxamide was obtained from 1-(1,3-dioxolan-2-ylmethyl)-7-methoxy-2-oxo-1,2-dihydroquinoline-4-carboxylic acid and cyclopropylamine.

$^1$H-NMR (CDCl$_3$) δ:

0.64-0.70 (2H, m), 0.89-0.95 (2H, m), 2.93-3.00 (1H, m), 3.79-3.86 (2H, m), 3.90 (3H, s), 3.97-4.04 (2H, m), 4.42 (2H, d, J=4.2 Hz), 5.13 (1H, t, J=4.2 Hz), 6.47-6.51 (1H, m), 6.54 (1H, s), 6.84 (1H, dd, J=8.9, 2.2 Hz), 7.04 (1H, d, J=2.2 Hz), 7.86 (1H, d, J=8.9 Hz)

Reference Example 77

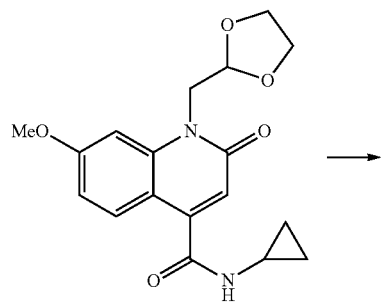

In the same method as in Reference Example 32, N-cyclopropyl-7-methoxy-2-oxo-1-(2-oxoethyl)-1,2-dihydroquinoline-4-carboxamide was obtained from N-cyclopropyl-1-(1,3-dioxolan-2-ylmethyl)-7-methoxy-2-oxo-1,2-dihydroquinoline-4-carboxamide.

$^1$H-NMR (DMSO-d$_6$) δ:
0.54-0.60 (2H, m), 0.69-0.75 (2H, m), 2.84-2.92 (1H, m), 3.85 (3H, s), 5.30 (2H, s), 6.43 (1H, s), 6.88 (1H, d, J=2.4 Hz), 6.93 (1H, dd, J=9.0, 2.4 Hz), 7.71 (1H, d, J=9.0 Hz), 8.79-8.83 (1H, m), 9.69 (1H, s)

Reference Example 78

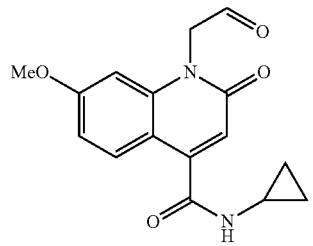

In the same method as in Reference Example 31, N-cyclopentyl-1-(1,3-dioxolan-2-ylmethyl)-7-methoxy-2-oxo-1,2-dihydroquinoline-4-carboxamide was obtained from 1-(1,3-dioxolan-2-ylmethyl)-7-methoxy-2-oxo-1,2-dihydroquinoline-4-carboxylic acid and cyclopentylamine.

$^1$H-NMR (CDCl$_3$) δ:
1.45-1.58 (2H, m), 1.64-1.76 (4H, m), 2.05-2.16 (2H, m), 3.83-3.89 (2H, m), 3.91 (3H, s), 4.00-4.05 (2H, m), 4.39-4.47 (1H, m), 4.49 (2H, d, J=4.3 Hz), 5.21 (1H, t, J=4.3 Hz), 5.96-6.02 (1H, m), 6.58 (1H, s), 6.85 (1H, dd, J=9.0, 2.4 Hz), 7.08 (1H, d, J=2.4 Hz), 7.87 (1H, d, J=9.0 Hz)

Reference Example 79

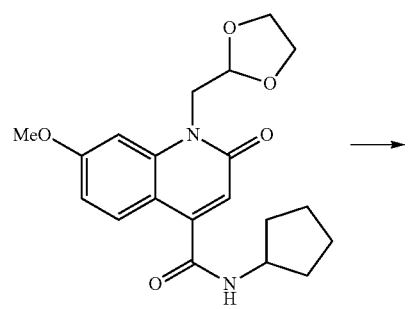

In the same method as in Reference Example 32, N-cyclopentyl-7-methoxy-2-oxo-1-(2-oxoethyl)-1,2-dihydroquinoline-4-carboxamide was obtained from N-cyclopentyl-1-(1,3-dioxolan-2-ylmethyl)-7-methoxy-2-oxo-1,2-dihydroquinoline-4-carboxamide.

$^1$H-NMR (CDCl$_3$) δ:
1.47-1.61 (2H, m), 1.65-1.79 (4H, m), 2.07-2.18 (2H, m), 3.87 (3H, s), 4.40-4.50 (1H, m), 5.10 (2H, s), 6.04-6.11 (1H, m), 6.45 (1H, d, J=2.3 Hz), 6.61 (1H, s), 6.87 (1H, dd, J=8.9, 2.3 Hz), 7.91 (1H, d, J=8.9 Hz), 9.65 (1H, s)

Reference Example 80

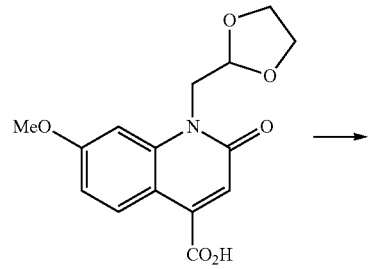

-continued

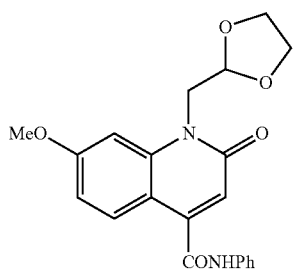

In the same method as in Reference Example 31, 1-(1,3-dioxolan-2-ylmethyl)-7-methoxy-2-oxo-N-phenyl-1,2-dihydroquinoline-4-carboxamide was obtained from 1-(1,3-dioxolan-2-ylmethyl)-7-methoxy-2-oxo-1,2-dihydroquinoline-4-carboxylic acid and aniline.

$^1$H-NMR (CDCl$_3$) δ:
3.78-3.84 (2H, m), 3.91 (3H, s), 3.95-4.01 (2H, m), 4.39 (2H, d, J=4.3 Hz), 5.08 (1H, t, J=4.3 Hz), 6.75 (1H, s), 6.87 (1H, dd, J=9.0, 2.2 Hz), 7.05 (1H, d, J=2.2 Hz), 7.21 (1H, t, J=7.4 Hz), 7.41 (2H, t, J=7.9 Hz), 7.74 (2H, d, J=8.3 Hz), 7.94 (1H, d, J=9.0 Hz), 8.48 (1H, s)

Reference Example 81

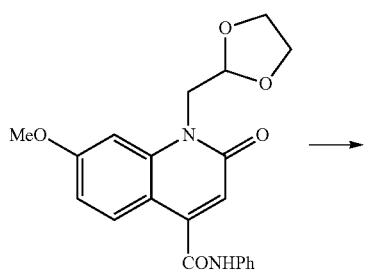

In the same method as in Reference Example 32, 7-methoxy-2-oxo-1-(2-oxoethyl)-N-phenyl-1,2-dihydroquinoline-4-carboxamide was obtained from 1-(1,3-dioxolan-2-ylmethyl)-7-methoxy-2-oxo-N-phenyl-1,2-dihydroquinoline-4-carboxamide.

$^1$H-NMR (CDCl$_3$) δ:
3.87 (3H, s), 5.02 (2H, s), 6.43 (1H, d, J=2.3 Hz), 6.76 (1H, s), 6.88 (1H, dd, J=8.9, 2.3 Hz), 7.22 (1H, t, J=7.7 Hz), 7.41 (2H, t, J=7.7 Hz), 7.72 (2H, d, J=7.7 Hz), 7.98 (1H, d, J=8.9 Hz), 8.41 (1H, s), 9.56 (1H, s)

Reference Example 82

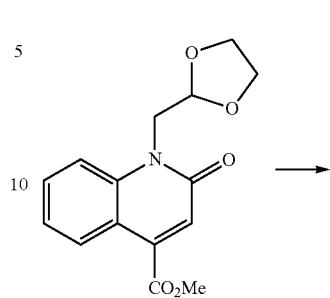

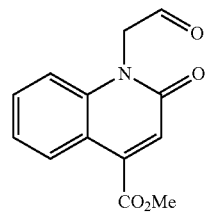

An 80% aqueous trifluoroacetic acid solution in an amount of 5 mL containing 1.0 g of methyl 1-(1,3-dioxolan-2-ylmethyl)-2-oxo-1,2-dihydroquinoline-4-carboxylate was stirred at room temperature for 2 hours, and stood still at 5° C. for 12.5 hours. Thereto were added 30 mL of ethyl acetate and 5 mL of an aqueous saturated sodium hydrogen carbonate solution, the mixture was subsequently added with 9 mL of a 20% aqueous sodium hydroxide solution under cooling with ice, and the reaction mixture was adjusted to pH 7.5 with an aqueous saturated sodium hydrogen carbonate solution. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure to obtain 0.84 g of a yellow solid, methyl 2-oxo-1-(2-oxoethyl)-1,2-dihydroquinoline-4-carboxylate.

$^1$H-NMR (CDCl$_3$) δ:
4.01 (3H, s), 5.19 (2H, s), 7.05-7.08 (1H, m), 7.24 (1H, s), 7.28-7.36 (1H, m), 7.54-7.62 (1H, m), 8.38 (1H, dd, J=8.3, 1.2 Hz), 9.71 (1H, s)

Reference Example 83

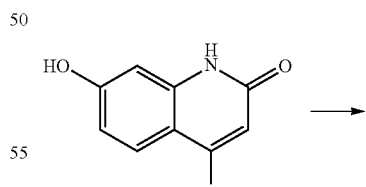

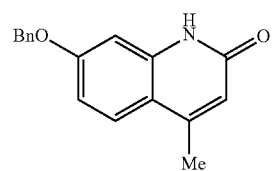

To 40 mL of a tetrahydrofuran suspension containing 0.50 g of 7-hydroxy-4-methylquinolin-2(1H)-one, 0.35 mL of a benzyl alcohol and 0.90 g of triphenyl phosphine were added at room temperature, and thereto was dropwise 0.67 mL of diisopropyl azodicarboxylate at 25 to 40° C., and then the mixture was stirred at room temperature for 1 hour. Thereto were added 0.35 mL of a benzyl alcohol and 0.90 g of triphenyl phosphine at room temperature, and the mixture was added dropwise with 0.67 mL of diisopropyl azodicarboxylate at 25 to 40° C. and then stirred at room temperature for 2 hours. A solid substance was collected by filtration to obtain 0.47 g of a light brown solid, 7-(benzyloxy)-4-methylquinolin-2(1H)-one.

¹H-NMR (DMSO-$d_6$) δ:
2.37 (3H, s), 5.15 (2H, s), 6.21 (1H, s), 6.86-6.94 (2H, m), 7.30-7.54 (5H, m), 7.60-7.64 (1H, m), 11.45 (1H, s)

Reference Example 84

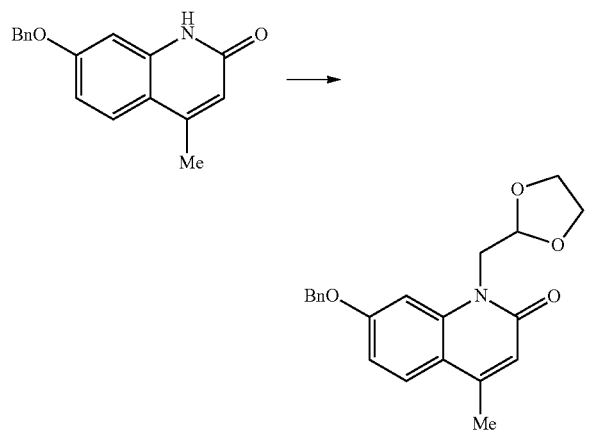

To 10 mL of an N,N-dimethylformamide suspension containing 0.50 g of 7-(benzyloxy)-4-methylquinolin-2(1H)-one, 0.15 g of 60% sodium hydride was added at room temperature, and the mixture was stirred at 50° C. for 30 minutes, at 60° C. for 30 minutes and at 80° C. for 15 minutes. Thereto was added 0.39 mL of 2-bromomethyl-1,3-dioxolane, and the mixture was stirred at 80° C. for 50 minutes, 100 to 105° C. for 3 hours, and 120° C. for 1 hour. The reaction mixture was cooled to room temperature, then ethyl acetate and water were added thereto, and the resultant solution was adjusted to pH 4.0 with 6 mol/L hydrochloric acid. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure. The residue thus obtained was added with diisopropyl ether to collect a solid substance by filtration. The solid substance thus obtained was added with ethyl acetate, after stirring at room temperature for 15 minutes, the mixture was filtered, and the filtrate was concentrated under reduced pressure. The residue thus obtained was added with diisopropyl ether, and a solid substance was collected by filtration to obtain 0.35 g of a pale yellow solid, 7-(benzyloxy)-1-(1,3-dioxolan-2-ylmethyl)-4-methylquinolin-2(1H)-one.

¹H-NMR (CDCl₃) δ:
2.41 (3H, s), 3.82-3.92 (2H, m), 3.96-4.06 (2H, m), 4.46 (2H, d, J=4.6 Hz), 5.16-5.22 (3H, m), 6.45 (1H, s), 6.90 (1H, dd, J=8.9, 2.4 Hz), 7.15 (1H, d, J=2.4 Hz), 7.32-7.50 (5H, m), 7.59 (1H, d, J=8.9 Hz)

Reference Example 85

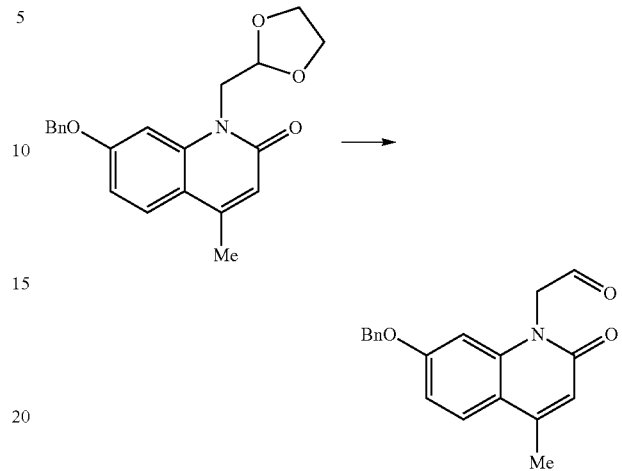

To 3.0 g of 7-(benzyloxy)-1-(1,3-dioxolan-2-ylmethyl)-4-methylquinolin-2(1H)-one, 15 mL of an 80% aqueous trifluoroacetic acid solution was added at room temperature, and the mixture was stirred at room temperature for 10 hours, and then stood still at room temperature overnight. Thereto were added ethyl acetate and water, the reaction mixture was adjusted to pH 6.0 with a 20% aqueous sodium hydroxide solution, and then adjusted pH 7.5 with an aqueous saturated sodium hydrogen carbonate solution. The organic layer was separated, and the aqueous layer was extracted twice with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was added with ethyl acetate and diisopropyl ether, and a solid substance was collected by filtration to obtain 2.4 g of a pale yellow solid, (7-(benzyloxy)-4-methyl-2-oxo-1,2-dihydroquinolin-1-yl)acetaldehyde.

¹H-NMR (CDCl₃) δ:
2.46 (3H, s), 5.06 (2H, s), 5.13 (2H, s), 6.49 (1H, s), 6.54 (1H, d, J=2.3 Hz), 6.92 (1H, dd, J=8.8, 2.3 Hz), 7.32-7.46 (5H, m), 7.65 (1H, d, J=8.8 Hz), 9.62 (1H, s)

Reference Example 86

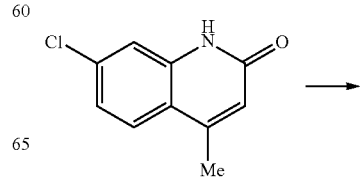

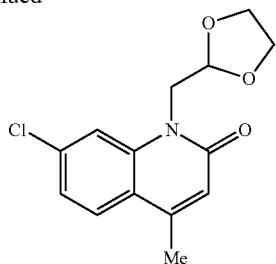

A temperature of 20 mL of an N,N-dimethylformamide solution containing 1.0 g of 7-chloro-4-methylquinolin-2(1H)-one was increased to 90° C., the solution was added with 0.31 g of 60% sodium hydride, and the mixture was stirred for 30 minutes. Thereto was added 5.36 mL of 2-bromomethyl-1,3-dioxolane, and the reaction mixture was stirred at 90 to 100° C. for 3 hours. Water and ethyl acetate were added thereto. The organic layer was separated, washed with an aqueous diluted hydrochloric acid solution and an aqueous saturated sodium chloride solution and dried over anhydrous magnesium sulfate, and the solvent was removed under reduced pressure. The residue thus obtained was purified by silica gel column chromatography [eluent; hexane:ethyl acetate=1:1] to obtain 0.61 g of a white solid, 7-chloro-1-(1,3-dioxolan-2-ylmethyl)-4-methylquinolin-2(1H)-one.

$^1$H-NMR (CDCl$_3$) δ:
2.44 (3H, d, J=1.1 Hz), 3.86-3.91 (2H, m), 4.03-4.08 (2H, m), 4.48 (2H, d, J=4.5 Hz), 5.24 (1H, t, J=4.5 Hz), 6.58 (1H, d, J=1.1 Hz), 7.21 (1H, dd, J=8.5, 1.9 Hz), 7.60 (1H, d, J=8.5 Hz), 7.61 (1H, d, J=1.9 Hz)

Reference Example 87

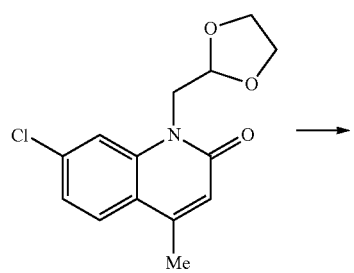

To 18 mL of an 80% aqueous trifluoroacetic acid solution, 0.56 g of 7-chloro-1-(1,3-dioxolan-2-ylmethyl)-4-methylquinolin-2(1H)-one was added, and the mixture was stirred at room temperature for 2 hours and stood still for 14 hours. The solvent was removed under reduced pressure, ethyl acetate and water were added thereto, and the reaction mixture was adjusted to pH 7.0 with an aqueous saturated sodium hydrogen carbonate solution, and the insoluble material filtered off. The organic layer was separated, washed sequentially with water and an aqueous saturated sodium chloride solution and dried over anhydrous magnesium sulfate, and the solvent was removed under reduced pressure. The residue thus obtained was added with hexane, and an solid substance was collected by filtration to obtain 0.27 g of a white solid, (7-chloro-4-methyl-2-oxo-1,2-dihydroquinolin-1-yl)acetaldehyde.

$^1$H-NMR (CDCl$_3$) δ:
2.49 (3H, d, J=1.0 Hz), 5.13 (2H, s), 6.62 (1H, d, J=1.0 Hz), 7.01 (1H, d, J=2.0 Hz), 7.21-7.28 (1H, m), 7.66 (1H, d, J=8.5 Hz), 9.72 (1H, s)

Reference Example 88

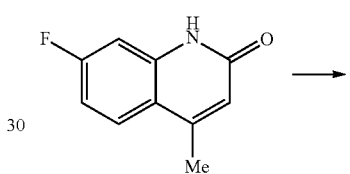

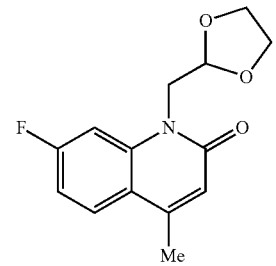

To 50 mL of an N,N-dimethylformamide suspension containing 5.0 g of 7-fluoro-4-methylquinolin-2(1H)-one, 1.70 g of 60% sodium hydride was added at 70 to 75° C., and the mixture was stirred at 90 to 100° C. for 10 minutes. Thereto was added 4.39 mL of 2-bromomethyl-1,3-dioxolan, and the mixture was stirred at the same temperature for 12 hours. Ethyl acetate and water were added thereto, and the reaction mixture was adjusted to pH 6.0 with 6 mol/L hydrochloric acid. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure. The residue thus obtained was purified by silica gel column chromatography [eluent; hexane:ethyl acetate=1:1] to obtain 3.6 g of a white solid, 1-(1,3-dioxolan-2-ylmethyl)-7-fluoro-4-methylquinolin-2(1H)-one.

$^1$H-NMR (CDCl$_3$) δ:
2.44 (3H, d, J=1.1 Hz), 3.86-3.93 (2H, m), 4.00-4.08 (2H, m), 4.47 (2H, d, J=4.5 Hz), 5.23 (1H, t, J=4.5 Hz), 6.54 (1H, d, J=1.1 Hz), 6.94-7.00 (1H, m), 7.33 (1H, dd, J=11.5, 2.4 Hz), 7.66 (1H, dd, J=9.0, 6.2 Hz)

Reference Example 89

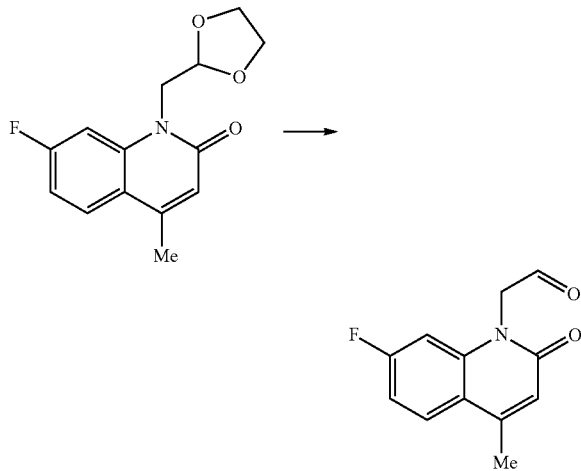

To 0.20 g of 1-(1,3-dioxolan-2-ylmethyl)-7-fluoro-4-methylquinolin-2(1H)-one, 7 mL of an 80% aqueous trifluoroacetic acid solution was added, and the mixture was stirred at room temperature for 2 hours, and then stood still at the same temperature for 14 hours. Thereto were added ethyl acetate and water, the organic layer was separated, the aqueous layer was adjusted to pH 8.0 with an aqueous saturated sodium hydrogen carbonate solution and extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure to obtain 0.15 g of a white solid, (7-fluoro-4-methyl-2-oxo-1,2-dihydroquinolin-1-yl)acetaldehyde.

$^1$H-NMR (DMSO-$d_6$) δ:
2.49 (3H, d, J=1.0 Hz), 5.11 (2H, s), 6.59 (1H, s), 6.72 (1H, dd, J=10.8, 2.4 Hz), 6.98-7.04 (1H, m), 7.73 (1H, dd, J=9.0, 6.1 Hz), 9.71 (1H, s)

Reference Example 90

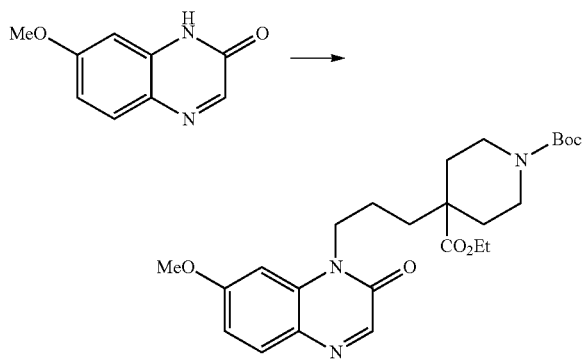

10 mL of an N,N-dimethylformamide solution containing 1.0 g of 7-methoxyquinoxalin-2(1H)-one was subjected to azeotropic dehydration with toluene, then 0.24 g of 60% sodium hydride was added thereto at room temperature, and the mixture was stirred at 60° C. for 30 minutes. Thereto was added 2 mL of an N,N-dimethylformamide solution containing 2.3 g of 1-tert-butyl 4-ethyl 4-(3-((methanesulfonyl)oxy)propyl)piperidine-1,4-dicarboxylate, and the mixture was stirred at the same temperature for 6 hours and then left to stand for 13 hours. Thereto was further added 0.12 g of 60% sodium hydride, and the mixture was stirred for 1 hour. The reaction mixture was cooled to room temperature, and ethyl acetate and water were added thereto. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure. The residue thus obtained was purified by silica gel column chromatography [eluent; hexane:ethyl acetate 2:1] to obtain 0.60 g of a yellow oily substance, 1-tert-butyl 4-ethyl 4-(3-(7-methoxy-2-oxo-1,2-dihydroquinoxalin-1-yl)propyl)piperidine-1,4-dicarboxylate.

$^1$H-NMR (DMSO-$d_6$) δ:
1.06 (3H, t, J=7.1 Hz), 1.20-1.36 (2H, m), 1.37 (9H, s), 1.48-1.65 (4H, m), 1.86-1.95 (2H, m), 2.71-2.87 (2H, m), 3.64-3.74 (2H, m), 3.91 (3H, s), 4.01 (2H, q, J=7.1 Hz), 4.13-4.21 (2H, m), 6.97 (1H, d, J=2.4 Hz), 7.01 (1H, dd, J=8.8, 2.4 Hz), 7.76 (1H, d, J=8.8 Hz), 8.03 (1H, s)

Reference Example 91

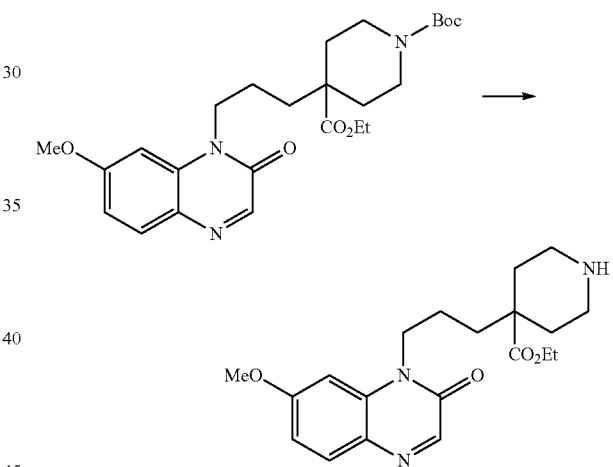

To 3.0 mL of a chloroform solution containing 0.60 g of 1-tert-butyl 4-ethyl 4-(3-(7-methoxy-2-oxo-1,2-dihydroquinoxalin-1-yl)propyl)piperidine-1,4-dicarboxylate, 1.5 mL of trifluoroacetic acid was added under cooling with ice, and the mixture was stirred at room temperature for 1 hour and 30 minutes. Thereto were added ethyl acetate and water. The aqueous layer was separated, ethyl acetate was added thereto, and the resultant solution was adjusted to pH 11.0 with a 20% aqueous saturated sodium hydroxide solution. The organic layer was separated, and washed with an aqueous saturated sodium chloride solution and dried over anhydrous magnesium sulfate, and the solvent was removed under reduced pressure to obtain 0.21 g of a pale yellow oily substance, ethyl 4-(3-(7-methoxy-2-oxo-1,2-dihydroquinoxalin-1-yl)propyl)piperidine-4-carboxylate.

$^1$H-NMR (CDCl$_3$) δ:
1.20 (3H, t, J=7.1 Hz), 1.35-1.45 (2H, m), 1.61-1.81 (4H, m), 2.08-2.16 (2H, m), 2.62-2.72 (2H, m), 2.93-3.01 (2H, m), 3.93 (3H, s), 4.12 (2H, q, J=7.1 Hz), 4.08-4.21 (2H, m), 6.69 (1H, d, J=2.4 Hz), 6.92 (1H, dd, J=9.0, 2.4 Hz), 7.79 (1H, d, J=9.0 Hz), 8.12 (1H, s)

Reference Example 92

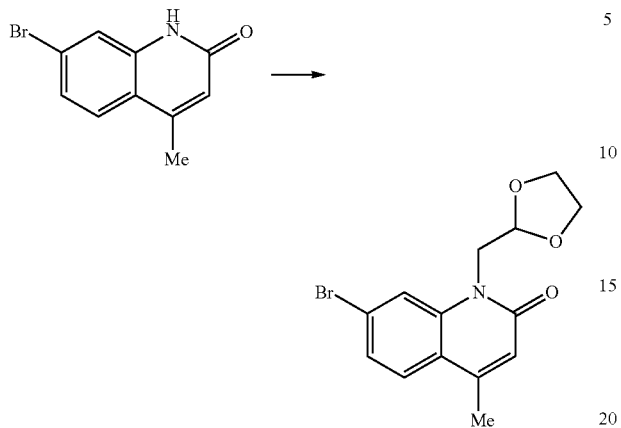

In the same method as in Reference Example 4, 7-bromo-1-(1,3-dioxolan-2-ylmethyl)-4-methylquinolin-2(1H)-one was obtained from 7-bromo-4-methylquinolin-2(1H)-one and 2-bromomethyl-1,3-dioxolane.

$^1$H-NMR (CDCl$_3$) δ:
2.44 (3H, d, J=1.0 Hz), 3.81-3.92 (2H, m), 4.00-4.09 (2H, m), 4.48 (2H, d, J=4.6 Hz), 5.25 (1H, t, J=4.6 Hz), 6.59 (1H, d, J=1.0 Hz), 7.35 (1H, dd, J=8.5, 1.7 Hz), 7.53 (1H, d, J=8.5 Hz), 7.77 (1H, d, d=1.7 Hz)

Reference Example 93

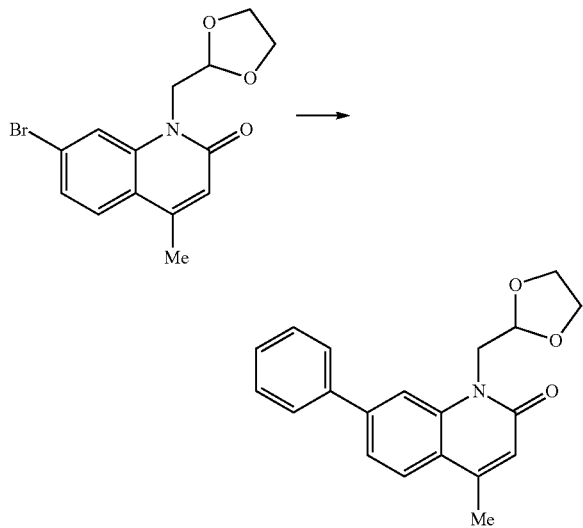

To a suspension of 2.9 mL of 1-methyl-2-pyrrolidinone containing 0.20 g of 7-bromo-1-(1,3-dioxolan-2-ylmethyl)-4-methylquinolin-2(1H)-one and 1.1 mL of water, 0.078 g of sodium carbonate and 0.095 g of phenylboric acid were added at room temperature, thereto was added 0.013 g of palladium-carbon at 100 to 110° C., and the mixture was stirred at 100 to 120° C. for 3 hours. Thereto was added 0.078 g of phenylboric acid, and the mixture was stirred at room temperature for 2 hours and stood still at the same temperature for 16 hours. Ethyl acetate and water were added thereto, the organic layer was separated, and washed with an aqueous saturated sodium hydrogen carbonate solution and dried over anhydrous magnesium sulfate, and the solvent was removed under reduced pressure. The residue thus obtained was added with diisopropyl ether, and a solid substance was collected by filtration to obtain 0.12 g of a pale yellow solid, 1-(1,3-dioxolan-2-ylmethyl)-4-methyl-7-phenylquinolin-2(1H)-one.

$^1$H-NMR (CDCl$_3$) δ:
2.49 (3H, d, J=1.0 Hz), 3.85-3.94 (2H, m), 4.01-4.11 (2H, m), 4.62 (2H, d, J=4.4 Hz), 5.31 (1H, t, J=4.4 Hz), 6.61 (1H, d, J=1.0 Hz), 7.40-7.44 (1H, m), 7.46-7.53 (3H, m), 7.64-7.70 (2H, m), 7.75 (1H, d, J=8.3 Hz), 7.82 (1H, d, J=1.4 Hz)

Reference Example 94

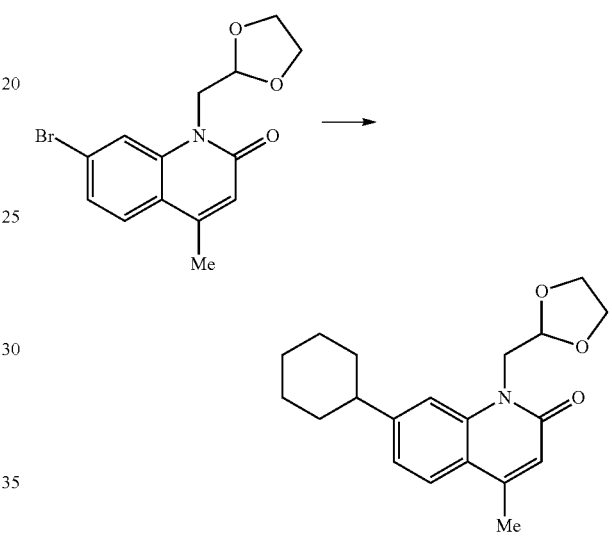

To 5 mL of a dimethyl acetamide solution containing 0.50 g of 7-bromo-1-(1,3-dioxolan-2-ylmethyl)-4-methylquinolin-2(1H)-one and 1.5 mL of cyclohexene, 17 mg of palladium acetate, 0.73 mL of tributylamine and 47 mg of tri(o-tolyl)phosphine were added at room temperature under a nitrogen atmosphere, and the mixture was refluxed by heating for 6 hours under a nitrogen atmosphere. Thereto were added ethyl acetate and water, the insoluble material filtered off, and the reaction mixture was adjusted to pH 4.5 with 6 mol/L hydrochloric acid. The organic layer was separated, washed with an aqueous saturated sodium chloride solution and then dried over anhydrous magnesium sulfate, and the solvent was removed under reduced pressure. The residue thus obtained was purified by silica gel column chromatography [eluent; hexane:ethyl acetate=1:1] to obtain 0.39 g of a pale yellow oily substance, a mixture of 7-(2-cyclohexen-1-yl)-1-(1,3-dioxolan-2-ylmethyl)-4-methylquinolin-2(1H)-one and 7-(1-cyclohexen-1-yl)-1-(1,3-dioxolan-2-ylmethyl)-4-methylquinolin-2(1H)-one.

To 5 mL of an ethanol solution containing 0.39 g of the mixture of 7-(2-cyclohexen-1-yl)-1-(1,3-dioxolan-2-ylmethyl)-4-methylquinolin-2(1H)-one and 7-(1-cyclohexen-1-yl)-1-(1,3-dioxolan-2-ylmethyl)-4-methylquinolin-2(1H)-one, 0.12 g of 5% palladium carbon was added, the mixture was stirred at room temperature for 1 hour and 30 minutes under a hydrogen atmosphere. The insoluble material filtered off, and the solvent was removed under reduced pressure to obtain 0.31 g of a colorless oily substance, 7-cyclohexyl-1-(1,3-dioxolan-2-ylmethyl)-4-methylquinolin-2(1H)-one.

¹H-NMR (CDCl₃) δ:
1.19-1.37 (1H, m), 1.38-1.54 (4H, m), 1.76-1.83 (1H, m), 1.86-1.97 (4H, m), 2.43 (3H, s), 2.58-2.68 (1H, m), 3.86-3.94 (2H, m), 4.02-4.08 (2H, m), 4.55 (2H, d, J=4.6 Hz), 5.29 (1H, t, J=4.6 Hz), 6.54 (1H, s), 7.11 (1H, d, J=8.3 Hz), 7.41 (1H, s), 7.60 (1H, d, J=8.3 Hz)

Reference Example 95

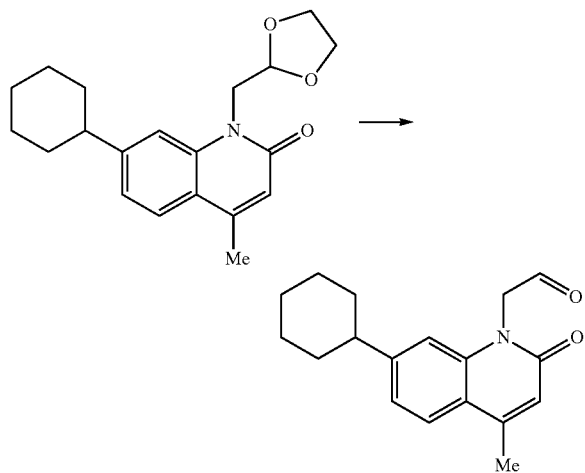

To 0.31 g of 7-cyclohexyl-1-(1,3-dioxolan-2-ylmethyl)-4-methylquinolin-2(1H)-one, 10 mL of a 80% aqueous trifluoroacetic acid solution was added, the mixture was stirred at room temperature for 2 hours and then stood still at room temperature for 15 hours. Thereto were added ethyl acetate and water, and the reaction mixture was adjusted to pH 7.5 with an aqueous saturated sodium hydrogen carbonate solution. The organic layer was separated, and the aqueous layer was extracted with ethyl acetate. The organic layer and the extract were combined, the resultant solution was washed sequentially with water and an aqueous saturated sodium chloride solution and dried over anhydrous magnesium sulfate, and the solvent was removed under reduced pressure to obtain 0.11 g of a colorless oily substance, (7-cyclohexyl-4-methyl-2-oxo-1,2-dihydroquinolin-1-yl)acetaldehyde.

¹H-NMR (CDCl₃) δ:
1.20-1.48 (5H, m), 1.74-1.92 (5H, m), 2.48 (3H, d, J=1.0 Hz), 2.52-2.63 (1H, m), 5.14 (2H, s), 6.59 (1H, d, J=1.0 Hz), 6.84 (1H, d, J=1.5 Hz), 7.15 (1H, dd, J=8.3, 1.5 Hz), 7.67 (1H, d, J=8.3 Hz), 9.66 (1H, s)

Reference Example 96

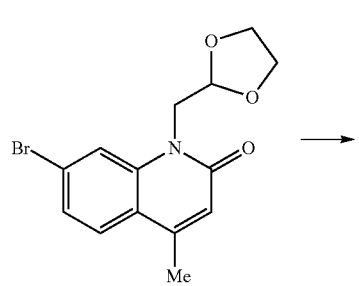

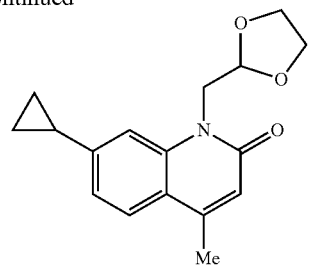

To a suspension of 10 mL of toluene containing 0.50 g of 7-bromo-1-(1,3-dioxolan-2-ylmethyl)-4-methylquinolin-2(1H)-one and 170 mg of cyclopropylboric acid and 0.5 mL of water, 1.2 g of potassium phosphate, 0.90 mL of tricyclohexyl phosphine and 17 mg of palladium acetate were added at room temperature, and the mixture was refluxed by heating for 4 hours under nitrogen atmosphere. Thereto were added 50 mg of cyclopropylboric acid, 0.1 mL of tricyclohexyl phosphine and 6 mg of palladium acetate, and the mixture was refluxed by heating for 1 hour and 30 minutes. Ethyl acetate and water were added thereto, the organic layer was separated, and the aqueous layer was extracted with ethyl acetate. The organic layer and the extract were combined, the resultant solution was dried over anhydrous magnesium sulfate, and the solvent was removed under reduced pressure. The residue thus obtained was purified by silica gel column chromatography [eluent; hexane:ethyl acetate 2:1]. The pale yellow oily substance thus obtained was purified by flash silica gel column chromatography [eluent; chloroform:ethyl acetate=99:1] to obtain 0.11 g of a white solid, 7-cyclopropyl-1-(1,3-dioxolan-2-ylmethyl)-4-methylquinolin-2(1H)-one.

¹H-NMR (CDCl₃) δ:
0.78-0.83 (2H, m), 1.05-1.11 (2H, m), 1.98-2.05 (1H, m), 2.42 (3H, d, J=1.0), 3.86-3.94 (2H, m), 4.02-4.08 (2H, m), 4.53 (2H, d, J=4.5 Hz), 5.25 (1H, t, J=4.5 Hz), 6.51 (1H, d, J=1.0 Hz), 6.93 (1H, dd, J=8.4, 1.5 Hz), 7.29 (1H, d, J=1.5 Hz), 7.56 (1H, d, J=8.4 Hz)

Reference Example 97

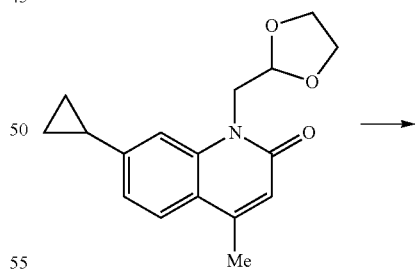

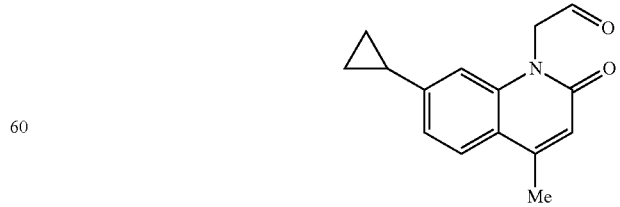

To 0.10 g of 7-cyclopropyl-1-(1,3-dioxolan-2-ylmethyl)-4-methylquinolin-2(1H)-one, 3 mL of an 80% aqueous trifluoroacetic acid solution was added, the mixture was stirred at room temperature for 1 hour, and then stood still at room temperature for 13 hours. Thereto were added 3 mL of ethyl acetate and 4 mL of water, and the mixture was neutralized with an aqueous saturated sodium hydrogen carbonate solution. The organic layer was separated, washed with water and dried over anhydrous magnesium sulfate, and the solvent was removed under reduced pressure to obtain 59 mg of a light brown oily substance, (7-cyclopropyl-4-methyl-2-oxo-1,2-dihydroquinolin-1-yl)acetaldehyde.

$^1$H-NMR (CDCl$_3$) δ:
0.73-0.78 (2H, m), 1.04-1.10 (2H, m), 1.93-2.01 (1H, m), 2.47 (3H, d, J=1.1 Hz), 5.13 (2H, d, J=1.0 Hz), 6.56 (1H, d, J=1.3 Hz), 6.75 (1H, d, J=1.5 Hz), 6.91 (1H, dd, J=8.3, 1.5 Hz), 7.62 (1H, d, J=8.3 Hz), 9.66 (1H, s)

Reference Example 98

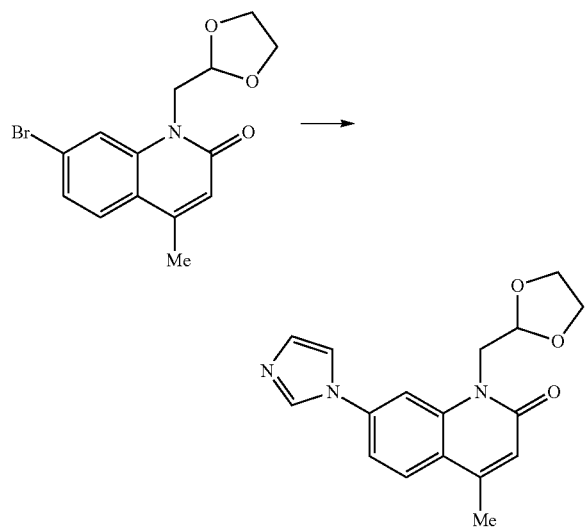

To 0.7 mL of an N,N-dimethylformamide solution containing 74 mg of 60% sodium hydride, 0.14 g of imidazole was added at room temperature, and the mixture was stirred for 10 minutes. Thereto were added 0.20 g of 7-bromo-1-(1,3-dioxolan-2-ylmethyl)-4-methylquinolin-2(1H)-one and 17 mg of copper(II) oxide, and the mixture was heated to 140 to 145° C. and stirred for 40 minutes. Thereto was further added 2 mL of N,N-dimethylformamide, and the mixture was further stirred for 1 hour. The reaction mixture was cooled to room temperature, then chloroform and water were added thereto, and the insoluble material filtered off. The organic layer was separated, and the aqueous layer was extracted with chloroform. The organic layer and the extract were combined, the resultant solution was dried over anhydrous magnesium sulfate, and the solvent was removed under reduced pressure. The residue thus obtained was purified by silica gel column chromatography [eluent; chloroform:methanol=10:1] to obtain 77 mg of a brown oily substance, 1-(1,3-dioxolan-2-ylmethyl)-7-(1H-imidazol-1-yl)-4-methylquinolin-2(1H)-one.

$^1$H-NMR (CDCl$_3$) δ:
2.49 (3H, d, J=1.2 Hz), 3.86-3.92 (2H, m), 3.98-4.07 (2H, m), 4.57 (2H, d, J=4.3 Hz), 5.19 (1H, t, J=4.3 Hz), 6.63 (1H, d, J=1.2 Hz), 7.11-7.40 (3H, m), 7.72 (1H, d, J=2.0 Hz), 7.78 (1H, d, J=8.6 Hz), 7.97 (1H, s)

Reference Example 99

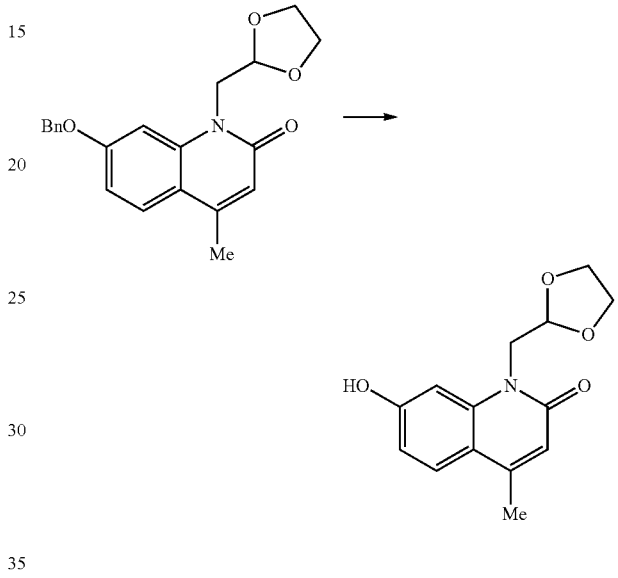

To a mixed solution of 10 mL of tetrahydrofuran containing 0.20 g of 7-(benzyloxy)-1-(1,3-dioxolan-2-ylmethyl)-4-methylquinolin-2(1H)-one and 10 mL of ethanol, 20 mg of 5% palladium carbon was added, and the mixture was stirred at room temperature for 3 hours under a hydrogen atmosphere. Thereto were added 20 mg of 5% palladium carbon and 10 mL of ethanol, and the mixture was stirred at room temperature for 4 hours. Thereto were added 40 mg of 5% palladium carbon and 10 mL of ethanol, and the mixture was stirred at 40 to 45° C. for 1 hour and 30 minutes under hydrogen atmosphere (reaction solution A).

To a mixed solution of 16 mL of tetrahydrofuran containing 2.0 g of 7-(benzyloxy)-1-(1,3-dioxolan-2-ylmethyl)-4-methylquinolin-2(1H)-one and 45 mL of ethanol, 2 mL of an ethanol suspension containing 0.40 g of 5% palladium carbon was added, and the mixture was stirred at 40 to 45° C. for 4 hours under a hydrogen atmosphere (reaction solution B).

The reaction solution A and the reaction solution B were combined, and the insoluble material filtered off. The solvent was removed under reduced pressure to obtain 1.3 g of a white solid, 1-(1,3-dioxan-2-ylmethyl)-7-hydroxy-4-methylquinolin-2(1H)-one.

$^1$H-NMR (DMSO-d$_6$) δ:
2.36 (3H, d, J=1.0 Hz), 3.78-3.86 (2H, m), 3.94-4.04 (2H, m), 4.29 (2H, d, J=4.6 Hz), 5.08 (1H, t, J=4.6 Hz), 6.28 (1H, d, J=1.0 Hz), 6.74 (1H, dd, J=8.8, 2.2 Hz), 6.97 (1H, d, J=2.2 Hz), 7.59 (1H, d, J=8.8 Hz) 10.18 (1H, s)

Reference Example 100

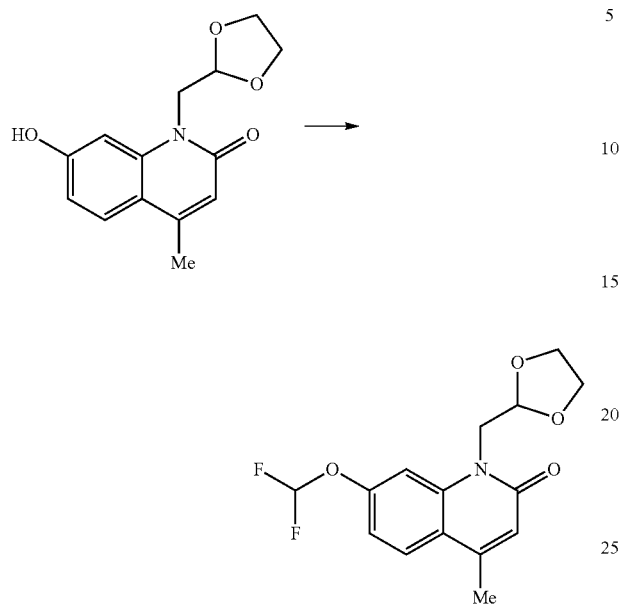

To 1.5 mL of a toluene solution containing 0.15 g of 1-(1,3-dioxolan-2-ylmethyl)-7-hydroxy-4-methylquinolin-2(1H)-one, 1 mL of a 40% aqueous sodium hydroxide solution, 90 mg of tetrabutylammonium bromide, and 0.25 mL of a 10 mol/L chlorodifluoromethane/N,N-dimethylformamide solution were added, the mixture was stirred at room temperature for 1 hour and 30 minutes. Thereto was further added 0.3 mL of a 10 mol/L chlorodifluoromethane/N,N-dimethylformamide solution, and the mixture was stirred at room temperature for 40 minutes. Thereto was added 1 mL of a 40% aqueous sodium hydroxide solution, and the mixture was stirred at room temperature for 2 hours. Thereto was further added 0.5 mL of a 10 mol/L chlorodifluoromethane/N,N-dimethylformamide solution, and the mixture was stirred at room temperature for 1 hour and 30 minutes, and stood still at room temperature for 13 hours. Water and toluene were added thereto, the organic layer was separated, and the aqueous layer was extracted twice with ethyl acetate. The organic layer and the extract were combined, washed sequentially with water and an aqueous saturated sodium chloride solution and then dried over anhydrous magnesium sulfate, and the solvent was removed under reduced pressure. The residue thus obtained was added with diisopropyl ether, and a solid substance was collected by filtration to obtain 0.10 g of a pale yellow solid, 7-(difluoromethoxy)-1-(1,3-dioxolan-2-ylmethyl)-4-methylquinolin-2(1H)-one.

$^1$H-NMR (CDCl$_3$) δ:
2.45 (3H, s), 3.84-3.94 (2H, m), 3.95-4.08 (2H, m), 4.48 (2H, d, J=4.5 Hz), 5.23 (1H, t, J=4.5 Hz), 6.56 (1H, s), 6.61 (1H, t, J=73.3 Hz), 7.01 (1H, dd, J=8.7, 1.9 Hz), 7.40 (1H, d, J=1.9 Hz), 7.67 (1H, d, J=8.7 Hz)

Reference Example 101

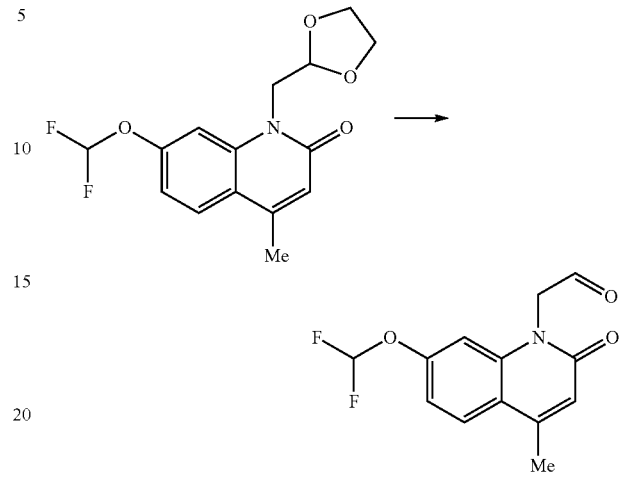

To 0.16 g of 7-(difluoromethoxy)-1-(1,3-dioxolan-2-ylmethyl)-4-methylquinolin-2(1H)-one, 2 mL of an 80% aqueous trifluoroacetic acid solution was added, and the mixture was stirred at room temperature for 6 hours. Thereto were added ethyl acetate and water, and the mixture was neutralized with an aqueous sodium hydroxide solution and an aqueous saturated sodium hydrogen carbonate solution. The organic layer was separated, and the aqueous layer was extracted with ethyl acetate. The organic layer and the extract were combined, the resultant solution was washed sequentially with water and an aqueous saturated sodium chloride solution, and dried over anhydrous magnesium sulfate, and the solvent was removed under reduced pressure to obtain 0.15 g of a white solid, (7-(difluoromethoxy)-4-methyl-2-oxo-1,2-dihydroquinolin-1-yl)acetaldehyde.

$^1$H-NMR (CDCl$_3$) δ:
2.49 (3H, d, J=1.0 Hz), 5.13 (2H, s), 6.57 (1H, t, J=72.9 Hz), 6.61 (1H, s), 6.74-6.76 (1H, m), 7.05 (1H, dd, J=8.8, 2.2 Hz), 7.74 (1H, d, J=8.8 Hz), 9.71 (1H, s)

Reference Example 102

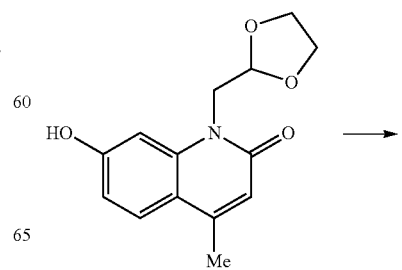

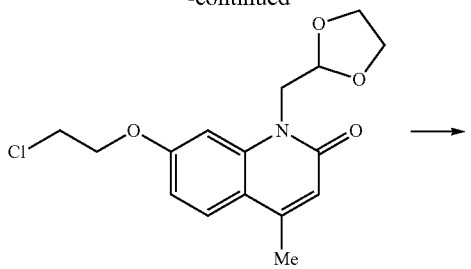

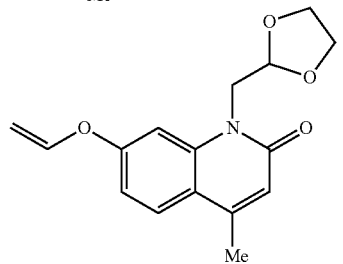

(1) To 5 mL of an N,N-dimethylformamide solution containing 0.50 g of 1-(1,3-dioxolan-2-ylmethyl)-7-hydroxy-4-methylquinolin-2(1H)-one, 0.53 g of potassium carbonate and 0.35 mL of 2-chloroethyl p-toluenesulfonate were added, the mixture was stirred at 50 to 55° C. for 3 hours and 30 minutes. Thereto was further added 0.35 mL of 2-chloroethyl p-toluenesulfonate, and the mixture was stirred at 50 to 55° C. for 8 hours, then water and ethyl acetate were added thereto, and the mixture was neutralized with 6 mol/L hydrochloric acid. The organic layer was separated, washed sequentially with water and an aqueous saturated sodium chloride solution and dried over anhydrous magnesium sulfate, and the solvent was removed under reduced pressure. The residue thus obtained was added with diisopropyl ether and hexane, and a solid substance was collected by filtration to obtain 0.70 g of a white solid, 7-(2-chloroethoxy)-1-(1,3-dioxolan-2-ylmethyl)-4-methylquinolin-2(1H)-one.

$^1$H-NMR (CDCl$_3$) δ:

2.42 (3H, d, J=1.1 Hz), 3.84-3.93 (4H, m), 4.01-4.10 (2H, m), 4.34 (2H, t, J=5.8 Hz), 4.50 (2H, d, J=4.4 Hz), 5.22 (1H, t, J=4.4 Hz), 6.47 (1H, d, J=1.1 Hz), 6.84 (1H, dd, J=8.8, 2.4 Hz), 7.13 (1H, d, J=2.4 Hz), 7.60 (1H, d, J=8.8 Hz)

(2) To 10 mL of an N,N-dimethylformamide solution containing 0.84 g of 7-(2-chloroethoxy)-1-(1,3-dioxolan-2-ylmethyl)-4-methylquinolin-2(1H)-one, 0.58 g of potassium tert-butoxide was added, and the mixture was stirred at 95 to 100° C. for 1 hour and 30 minutes. Thereto was added 0.29 g of tert-butoxy potassium, and the mixture was stirred at 95 to 100° C. for 40 minutes. Ethyl acetate and water were added thereto, the organic layer was separated, and the aqueous layer was extracted with ethyl acetate. The organic layer and the extract were combined, the resultant solution was washed sequentially with water and an aqueous saturated sodium chloride solution and dried over sodium sulfate anhydride, and the solvent was removed under reduced pressure. The residue thus obtained was added with diisopropyl ether and hexane, and a solid substance was collected by filtration to obtain 0.43 g of a white solid, 1-(1,3-dioxolan-2-ylmethyl)-4-methyl-7-(vinyloxy)quinolin-2(1H)-one.

$^1$H-NMR (CDCl$_3$) δ:

2.43 (3H, d, J=1.2 Hz), 3.84-3.93 (2H, m), 4.00-4.10 (2H, m), 4.48 (2H, d, J=4.5 Hz), 4.59 (1H, dd, J=6.1, 1.8 Hz), 4.91 (1H, dd, J=13.7, 1.8 Hz), 5.25 (1H, t, J=4.5 Hz), 6.51 (1H, d, J=1.2 Hz) 6.71 (1H, dd, J=13.7, 6.1 Hz), 6.91 (1H, dd, J=8.8, 2.2 Hz), 7.22 (1H, d, J=2.2 Hz), 7.63 (1H, d, J=8.8 Hz)

Reference Example 103

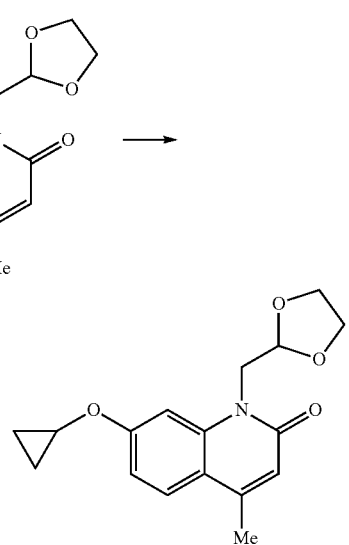

To 8 mL of a dichloroethane solution containing 0.40 g of 1-(1,3-dioxolan-2-ylmethyl)-4-methyl-7-(vinyloxy)quinolin-2(1H)-one, 0.96 mL of chloroiodomethane was added at 0 to 5° C. Thereto was added dropwise 6.6 mL of diethylzinc under a nitrogen atmosphere, and the mixture was stirred at room temperature for 1 hour and 30 minutes. The reaction mixture was added with 12 mL of an aqueous saturated ammonium chloride solution, 2 mL of a 20% aqueous ammonium solution and 12 mL of chloroform, the organic layer was separated, and the aqueous layer was extracted with chloroform. The organic layer and the extract were combined, the resultant solution was washed with an aqueous saturated ammonium chloride solution, dried over sodium sulfate anhydride, and the solvent was removed under reduced pressure. The residue thus obtained was purified by silica gel column chromatography [eluent; chloroform:ethyl acetate=5:1] to obtain 0.14 g of a white solid, 7-(cyclopropoxy)-1-(1,3-dioxolan-2-ylmethyl)-4-methylquinolin-2(1H)-one.

$^1$H-NMR (CDCl$_3$) δ:

0.80-0.89 (4H, m), 2.42 (3H, d, J=1.1), 3.80-3.90 (3H, m), 4.00-4.10 (2H, m), 4.51 (2H, d, J=4.6 Hz), 5.25 (1H, t, J=4.6 Hz), 6.46 (1H, d, J=1.1 Hz), 6.95 (1H, dd, J=8.9, 2.4 Hz), 7.31 (1H, d, J=2.4 Hz), 7.59 (1H, d, J=8.9 Hz)

Reference Example 104

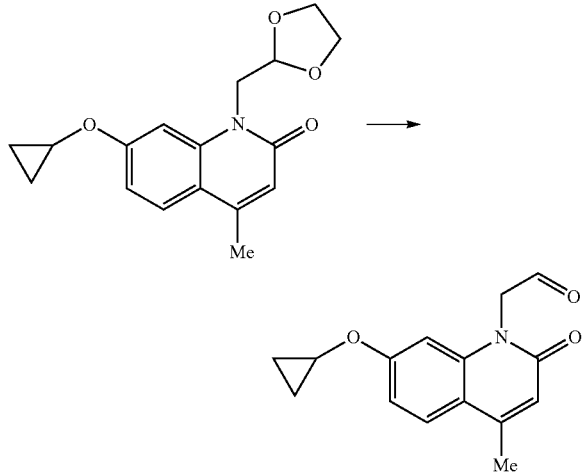

To 95 mg of 7-(cyclopropoxy)-1-(1,3-dioxolan-2-ylm-ethyl)-4-methylquinolin-2(1H)-one, 1.5 mL of an 80% aqueous trifluoroacetic acid solution was added, the mixture was stirred at room temperature for 6 hours, and then stood still at room temperature for 14 hours. Thereto were added ethyl acetate and water, and the mixture was neutralized with an aqueous saturated sodium hydrogen carbonate solution and an aqueous sodium hydroxide solution. The organic layer was separated, washed sequentially with water and an aqueous saturated sodium chloride solution and dried over anhydrous magnesium sulfate, and the solvent was removed under reduced pressure to obtain 84 mg of a yellow oily substance, (7-(cyclopropoxy)-4-methyl-2-oxo-1,2-dihydroquinolin-1-yl)acetaldehyde.

$^1$H-NMR (CDCl$_3$) δ:

0.76-0.88 (4H, m), 2.47 (3H, d, J=1.0 Hz), 3.76-3.81 (1H, m), 5.10 (2H, d, J=1.1 Hz), 6.50 (1H, d, J=1.0 Hz), 6.67 (1H, d, J=2.2 Hz), 7.00 (1H, dd, J=8.8, 2.2 Hz), 7.66 (1H, d, J=8.8 Hz), 9.65 (1H, t, J=1.1 Hz)

Reference Example 105

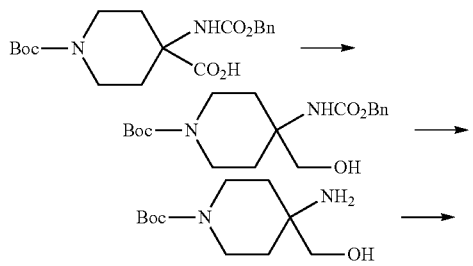

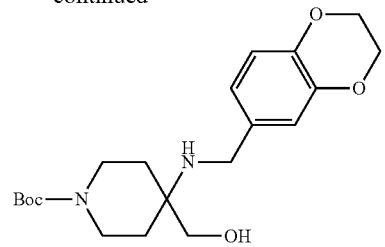

To 20 mL of a tetrahydrofuran suspension containing 1.0 g of 4-(((benzyloxy)carbonyl)amino)-1-(tert-butoxycarbonyl)piperidine-4-carboxylic acid, 0.41 mL of triethylamine was added at room temperature, then the mixture cooled to −15° C., and thereto was added dropwise 0.28 mL of ethyl chlorocarbonate. The reaction mixture was stirred at 5 to 10° C. for 1 hour. Thereto were added 0.11 g of sodium borohydride and 3 mL of water, and the mixture was stirred at room temperature for 1 hour, and stood still overnight. The reaction mixture was added with ethyl acetate and water. The organic layer was separated, and the aqueous layer was extracted with ethyl acetate. The organic layer and the extract were combined, and the resultant solution was washed with water and an aqueous saturated sodium chloride solution and dried over anhydrous magnesium sulfate, and the solvent was removed under reduced pressure to obtain 0.55 g of a colorless oily substance, tert-butyl 4-(((benzyloxy)carbonyl)amino)-4-(hydroxymethyl)piperidine-1-carboxylate.

To 10 mL of an ethanol solution containing 0.55 g of tert-butyl 4-(((benzyloxy)carbonyl)amino)-4-(hydroxymethyl)piperidine-1-carboxylate, 0.10 g of 20% palladium hydroxide-carbon was added at room temperature, and the mixture was stirred at 40° C. for 3 hours under a hydrogen atmosphere. The insoluble material filtered off, and the filtration residue thus obtained was washed 3 times with chloroform. The filtrate and the washing solution were combined, and the solvent was removed under reduced pressure to obtain 0.39 g of a dark brown oily substance, tert-butyl 4-amino-4-(hydroxymethyl)piperidine-1-carboxylate.

To 10 mL of a dichloromethane solution containing 0.39 g of tert-butyl 4-amino-4-(hydroxymethyl)piperidine-1-carboxylate, 0.25 g of 2,3-dihydro-1,4-benzodioxin-6-carbaldehyde and 86 µL of acetic acid were added, and the mixture was stirred at room temperature for 2 hours. The reaction mixture was added with 0.48 g of sodium triacetoxyborohydride, and stirred at the same temperature for 2 hours. Thereto were added chloroform and an aqueous saturated sodium hydrogen carbonate solution. The organic layer was separated, and the aqueous layer was extracted with chloroform. The organic layer and the extract were combined, and the resultant solution was washed sequentially with water and an aqueous saturated sodium chloride solution and dried over anhydrous magnesium sulfate, and the solvent was removed under reduced pressure. The residue thus obtained was purified by flash silica gel column chromatography [chloroform: gradient elution of methanol=100:0 to 80:20] to obtain 91 mg of a colorless oily substance, tert-butyl 4-((2,3-dihydro-1,4-benzodioxin-6-ylmethyl)amino)-4-(hydroxymethyl)piperidine-1-carboxylate.

$^1$H-NMR (CDCl$_3$) δ:

1.46 (9H, s), 1.40-1.70 (4H, m), 3.00-3.62 (8H, m), 4.25 (4H, s), 6.79 (1H, dd, J=8.2, 1.7 Hz), 6.83 (1H, d, J=8.2), 6.86 (1H, d, J=1.7 Hz)

Reference Example 106

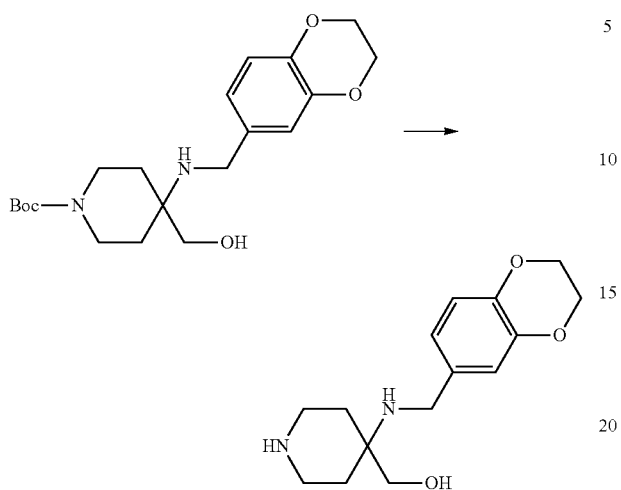

In the same method as in Reference Example 11, (4-((2,3-dihydro-1,4-benzodioxin-6-ylmethyl)amino)piperidin-4-yl)methanol was obtained from tert-butyl 4-((2,3-dihydro-1,4-benzodioxin-6-ylmethyl)amino)-4-(hydroxymethyl)piperidine-1-carboxylate.

$^1$H-NMR (CDCl$_3$) δ:
1.50-1.80 (4H, m), 2.82-2.90 (4H, m), 3.43 (2H, s), 3.54 (2H, s), 4.25 (4H, s), 6.80 (1H, dd, J=8.1, 1.8 Hz), 6.83 (1H, d, J=8.1), 6.87 (1H, d, J=1.8 Hz)

Reference Example 107

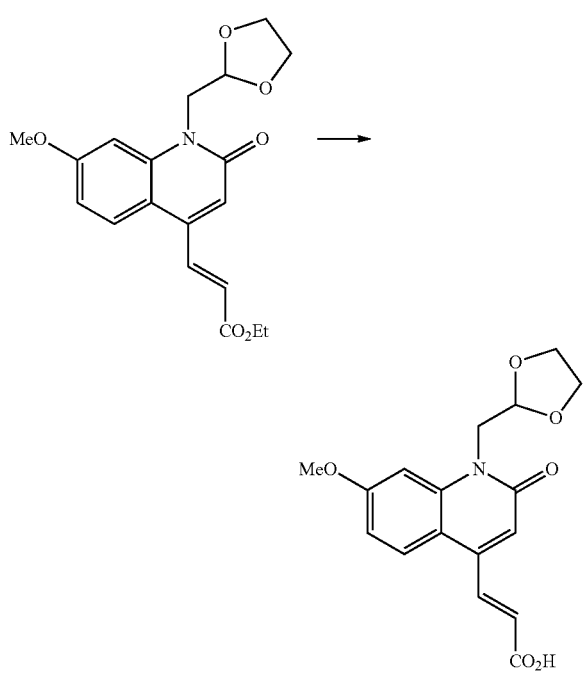

In the same method as in Example 5, (2E)-3-(1-(1,3-dioxolan-2-ylmethyl)-7-methoxy-2-oxo-1,2-dihydroquinolin-4-yl)acrylic acid was obtained from ethyl (2E)-3-(1-(1,3-dioxolan-2-ylmethyl)-7-methoxy-2-oxo-1,2-dihydroquinolin-4-yl)acrylate.

$^1$H-NMR (DMSO-d$_6$) δ:
3.77-3.86 (2H, m), 3.90 (3H, s), 3.95-4.04 (2H, m), 4.46 (2H, d, J=4.6 Hz), 5.12 (1H, d, J=4.6 Hz), 6.58 (1H, d, J=15.9 Hz), 6.71 (1H, s), 6.94 (1H, dd, J=8.9, 2.4 Hz), 7.19 (1H, d, J=2.4 Hz), 7.77 (1H, d, J=8.9 Hz), 7.95 (1H, d, J=15.9 Hz)

Reference Example 108

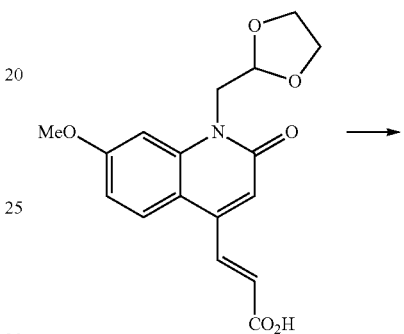

In the same method as in Reference Example 31, (2E)-3-(1-(1,3-dioxolan-2-ylmethyl)-7-methoxy-2-oxo-1,2-dihydroquinolin-4-yl)-N-methylacrylamide was obtained from (2E)-3-(1-(1,3-dioxolan-2-ylmethyl)-7-methoxy-2-oxo-1,2-dihydroquinolin-4-yl)acrylic acid.

$^1$H-NMR (DMSO-d$_6$) δ:
2.74 (3H, d, J=4.4 Hz), 3.76-3.86 (2H, m), 3.90 (3H, s), 3.95-4.04 (2H, m), 4.46 (2H, d, J=4.5 Hz), 5.12 (1H, t, J=4.5 Hz), 6.56 (1H, s), 6.65 (1H, d, J=15.6 Hz), 6.94 (1H, dd, J=8.9, 2.3 Hz), 7.18 (1H, d, J=2.3 Hz), 7.77 (1H, d, J=8.9 Hz), 7.77 (1H, d, J=15.6 Hz), 8.24-8.30 (1H, m)

Reference Example 109

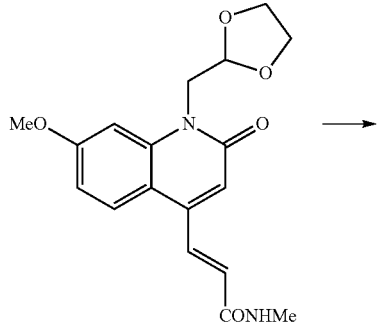

In the same method as in Reference Example 32, (2E)-3-(7-methoxy-2-oxo-1-(2-oxoethyl)-1,2-dihydroquinolin-4-yl)-N-methylacrylamide was obtained from (2E)-3-(1-(1,3-dioxolan-2-ylmethyl)-7-methoxy-2-oxo-1,2-dihydroquinolin-4-yl)-N-methylacrylamide.

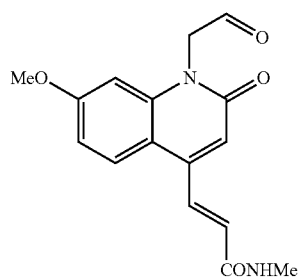

¹H-NMR (CDCl₃) δ:
2.99 (3H, d, J=4.9 Hz), 3.88 (3H, s), 5.12 (2H, s), 5.80-5.90 (1H, m), 6.46 (1H, d, J=15.1 Hz), 6.49 (1H, d, J=2.4 Hz), 6.69 (1H, s), 6.87 (1H, dd, J=9.0, 2.4 Hz), 7.80 (1H, d, J=9.0 Hz), 8.04 (1H, d, J=15.1 Hz), 9.68 (1H, s)

Reference Example 110

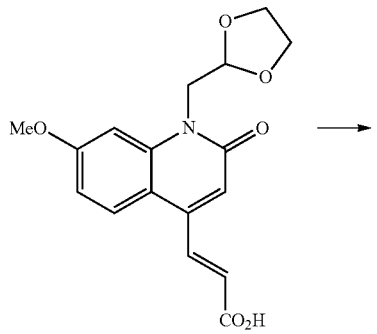

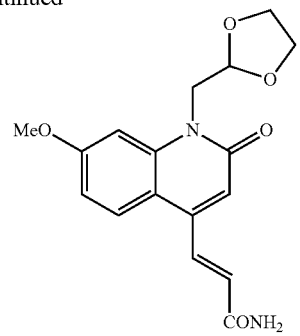

To 5 mL of a tetrahydrofuran suspension containing 0.30 g of (2E)-3-(1-(1,3-dioxolan-2-ylmethyl)-7-methoxy-2-oxo-1,2-dihydroquinolin-4-yl)acrylic acid, 0.14 mL of triethylamine and 5 mL of N,N-dimethylformamide were added at room temperature, then the mixture was cooled to 5 to 7° C., and thereto was added dropwise 0.10 mL of ethyl chlorocarbonate. After stirring at the same temperature for 1 hour, the reaction mixture was added dropwise with 20 mL of a 25% aqueous ammonium solution under cooling with ice. After stirring at 10° C. for 30 minutes, the reaction mixture was adjusted to pH 3.0 with 6 mol/L hydrochloric acid. Thereto was added ethyl acetate, and a solid substance was collected by filtration to obtain 0.21 g of a pale yellow solid, (2E)-3-(1-(1,3-dioxolan-2-ylmethyl)-7-methoxy-2-oxo-1,2-dihydroquinolin-4-yl)acrylamide.

¹H-NMR (DMSO-d₆) δ:
3.76-3.87 (2H, m), 3.90 (3H, s), 3.94-4.06 (2H, m), 4.42-4.50 (2H, m), 5.10-5.16 (1H, m), 6.57 (1H, s), 6.66 (1H, d, J=15.6 Hz), 6.92-6.98 (1H, m), 7.18-7.21 (1H, m), 7.33-7.38 (1H, m), 7.72-7.84 (3H, m)

Reference Example 111

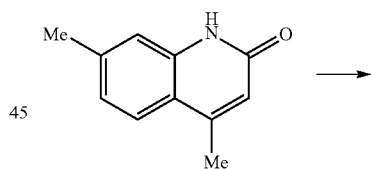

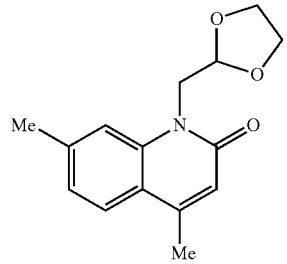

In the same method as in Reference Example 4, 1-(1,3-dioxolan-2-ylmethyl)-4,7-dimethylquinolin-2(1H)-one was obtained from 4,7-dimethylquinolin-2(1H)-one and 2-bromomethyl-1,3-dioxolane.

¹H-NMR (CDCl₃) δ:
2.44 (3H, s), 2.50 (3H, s), 3.84-3.95 (2H, m), 4.02-4.13 (2H, m), 4.53 (2H, d, J=4.6 Hz), 5.28 (1H, t, J=4.6 Hz), 6.54 (1H, s), 7.07 (1H, d, J=8.2 Hz), 7.37 (1H, s), 7.57 (1H, d, J=8.2 Hz)

Reference Example 112

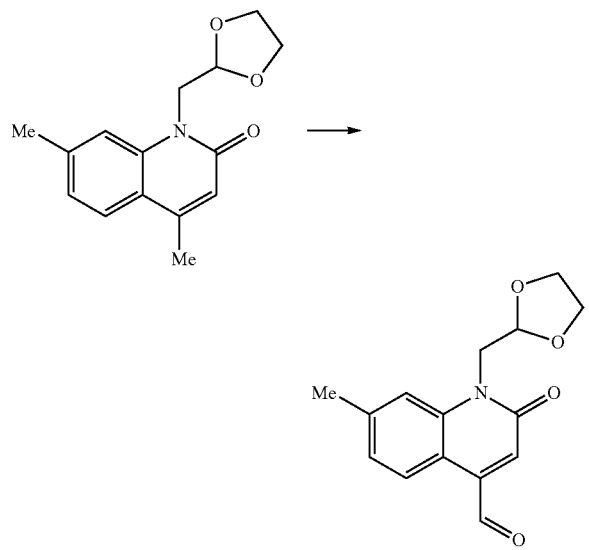

In the same method as in Reference Example 5, 1-(1,3-dioxolan-2-ylmethyl)-7-methyl-2-oxo-1,2-dihydroquinoline-4-carbaldehyde was obtained from 1-(1,3-dioxolan-2-ylmethyl)-4,7-dimethylquinolin-2(1H)-one.

$^1$H-NMR (DMSO-$d_6$) δ:
2.47 (3H, s), 3.76-3.86 (2H, m), 3.94-4.04 (2H, m), 4.49 (2H, d, J=4.8 Hz), 5.19 (1H, t, J=4.8 Hz), 7.18-7.21 (1H, m), 7.21 (1H, s), 7.60 (1H, s), 8.56 (1H, d, J=8.3 Hz), 10.18 (1H, s)

Reference Example 113

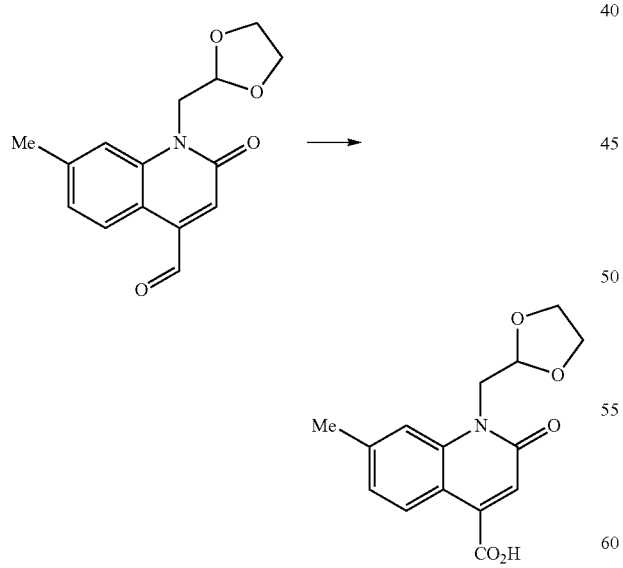

In the same method as in Reference Example 30, 1-(1,3-dioxolan-2-ylmethyl)-7-methyl-2-oxo-1,2-dihydroquinoline-4-carboxylic acid was obtained from 1-(1,3-dioxolan-2-ylmethyl)-7-methyl-2-oxo-1,2-dihydroquinoline-4-carbaldehyde.

$^1$H-NMR (DMSO-$d_6$) δ:
2.46 (3H, s), 3.76-3.86 (2H, m), 3.94-4.04 (2H, m), 4.46 (2H, d, J=4.7 Hz), 5.17 (1H, t, J=4.7 Hz), 6.83 (1H, s), 7.15 (1H, d, J=8.3 Hz), 7.56 (1H, s), 8.03 (1H, d, J=8.3 Hz)

Reference Example 114

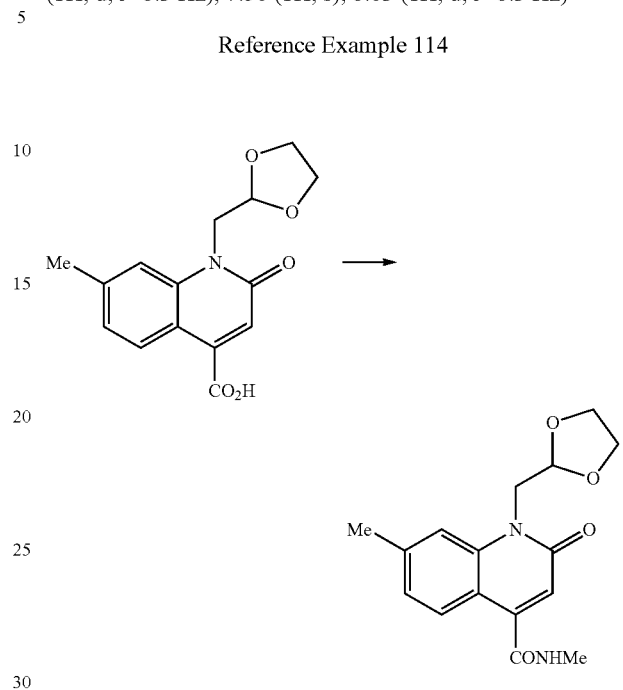

In the same method as in Reference Example 31, 1-(1,3-dioxolan-2-ylmethyl)-N-methyl-7-methyl-2-oxo-1,2-dihydroquinoline-4-carboxamide was obtained from 1-(1,3-dioxolan-2-ylmethyl)-7-methyl-2-oxo-1,2-dihydroquinoline-4-carboxylic acid.

$^1$H-NMR (DMSO-$d_6$) δ:
2.45 (3H, s), 2.80 (3H, d, J=4.6 Hz), 3.76-3.86 (2H, m), 3.94-4.04 (2H, m), 4.45 (2H, d, J=4.7 Hz), 5.16 (1H, t, J=4.7 Hz), 6.53 (1H, s), 7.11 (1H, d, J=8.2 Hz), 7.54 (1H, s), 7.65 (1H, d, J=8.2 Hz), 8.65-8.71 (1H, m)

Reference Example 115

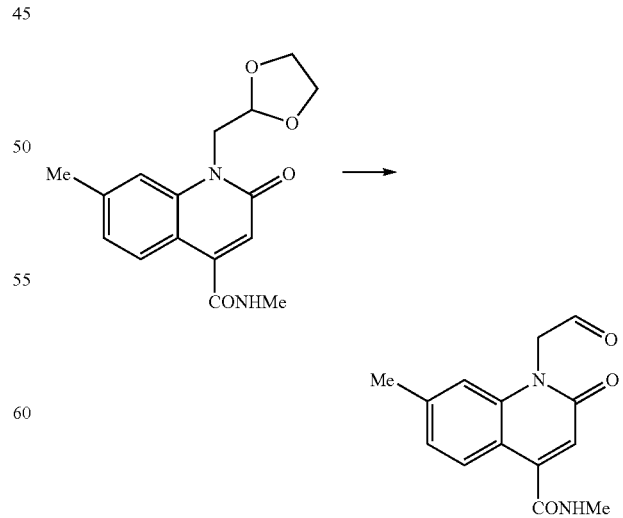

In the same method as in Reference Example 32, N-methyl-7-methyl-2-oxo-1-(2-oxoethyl)-1,2-dihydroquinoline- 4-carboxamide was obtained from 1-(1,3-dioxolan-2-ylmethyl)-N-methyl-7-methyl-2-oxo-1,2-dihydroquinoline-4-carboxamide.

$^1$H-NMR (CDCl$_3$) δ:
2.45 (3H, s), 3.06 (3H, d, J=4.9 Hz), 5.10 (2H, s), 6.35-6.43 (1H, m), 6.70 (1H, s), 6.80 (1H, s), 7.11 (1H, d, J=8.3 Hz), 7.85 (1H, d, J=8.3 Hz), 9.65 (1H, s)

Reference Example 116

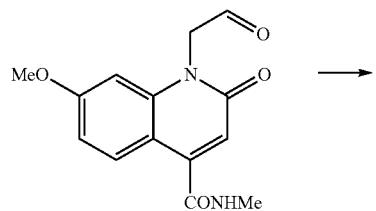

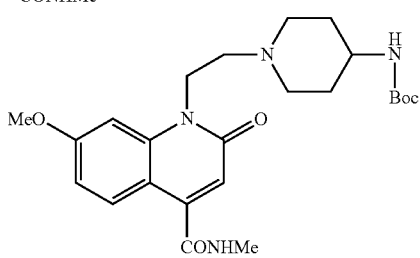

To 20 mL of a dichloromethane solution containing 1.7 g of 7-methoxy-N-methyl-2-oxo-1-(2-oxoethyl)-1,2-dihydroquinoline-4-carboxamide, 1.24 g of tert-butyl (piperidin-4-yl)carbamate and 0.36 mL of acetic acid were added, and the mixture was stirred for 1 hour. Thereto was dividedly added 2.0 g of sodium triacetoxyborohydride, and the mixture was stirred at room temperature for 1 hour. Water and chloroform were added thereto, and the reaction mixture was adjusted to pH 10 with a 1 mol/L aqueous sodium hydroxide solution. The organic layer was separated, and the aqueous layer was extracted with chloroform. The organic layer and the extract were combined, and the resultant solution was washed with an aqueous saturated sodium chloride solution and dried over anhydrous magnesium sulfate, and the solvent was removed under reduced pressure. The residue thus obtained was added with ethyl acetate, and a solid substance was collected by filtration to obtain 1.7 g of a pale yellow solid, tert-butyl (1-(2-(7-methoxy-4-((methylamino)carbonyl)-2-oxo-1,2-dihydroquinolin-1-yl)ethyl)piperidin-4-yl)carbamate.

$^1$H-NMR (CDCl$_3$) δ:
1.37-1.49 (2H, m), 1.45 (9H, s), 1.91-1.99 (2H, m), 2.20-2.30 (2H, m), 2.58-2.65 (2H, m), 2.91-2.98 (2H, m), 3.05 (3H, d, J=4.9 Hz), 3.42-3.55 (1H, m), 3.91 (3H, s), 4.32-4.47 (3H, m), 6.07-6.14 (1H, m), 6.57 (1H, s), 6.85 (1H, dd, J=8.9, 2.3 Hz), 6.88 (1H, d, J=2.3 Hz), 7.88 (1H, d, J=8.9 Hz)

Reference Example 117

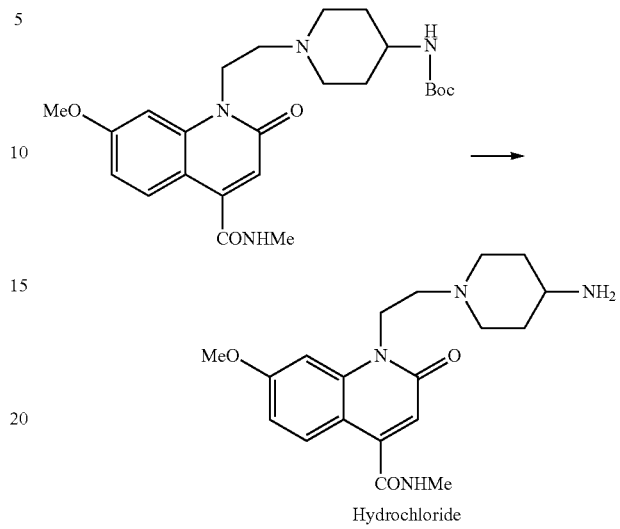

To 20 mL of an ethanol suspension containing 1.7 g of tert-butyl (1-(2-(7-methoxy-4-((methylamino)carbonyl)-2-oxo-1,2-dihydroquinolin-1-yl)ethyl)piperidin-4-yl)carbamate, 40 mL of 6.2 mol/L hydrogen chloride/ethanol was added, and the mixture was stirred at room temperature for 3 hours. The solvent was removed under reduced pressure, the residue thus obtained was added with diethyl ether, and a solid substance was collected by filtration to obtain 1.6 g of a pale yellow solid, 1-(2-(4-aminopiperidin-1-yl)ethyl-7-methoxy-N-methyl-2-oxo-1,2-dihydroquinoline-4-carboxamide hydrochloride.

$^1$H-NMR (DMSO-d$_6$) δ:
1.90-2.08 (2H, m), 2.10-2.22 (2H, m), 2.80 (3H, d, J=4.1 Hz), 3.08-3.82 (7H, m), 3.98 (3H, s), 4.67-4.77 (2H, m), 6.47 (1H, s), 6.94-6.99 (1H, m), 7.19-7.24 (1H, m), 7.75 (1H, d, J=9.0 Hz), 8.34-8.54 (3H, m), 8.66-8.72 (1H, m), 11.22-11.34 (1H, broad)

Reference Example 118

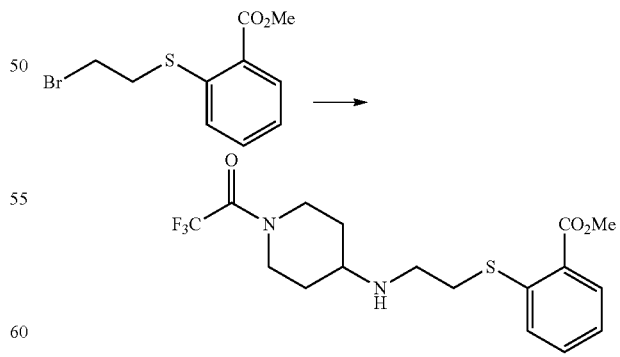

To 5 mL of an N,N-dimethylformamide suspension containing 0.30 g of methyl 2-((2-bromoethyl)thio)benzoate, 0.32 g of potassium carbonate and 0.28 g of 1-(trifluoroacetyl)piperidine-4-amine hydrochloride were added, and the mixture was stirred at 70° C. for 2 hours. Thereto was further added 2 mL of dimethyl sulfoxide, and the mixture was stirred for 4 hours. The reaction mixture was cooled to room temperature, and then ethyl acetate and water were added thereto. The organic layer was separated, washed with an aqueous saturated sodium chloride solution and dried over anhydrous magnesium sulfate, and the solvent was removed under reduced pressure. The residue thus obtained was purified by silica gel column chromatography [eluent; chloroform:methanol=20:1] to obtain 0.11 g of a yellow oily substance, methyl 2-((2-(1-(trifluoroacetyl)piperidin-4-yl)amino)ethyl)thio)benzoate.

$^1$H-NMR (CDCl$_3$) δ:

1.32-1.46 (2H, m), 1.90-1.99 (2H, m), 2.78-3.14 (6H, m), 3.19-3.27 (1H, m), 3.90-3.98 (1H, m), 3.92 (3H, s), 4.24-4.33 (1H, m), 7.16-7.22 (1H, m), 7.34-7.38 (1H, m), 7.43-7.48 (1H, m), 7.93-7.97 (1H, m)

Reference Example 119

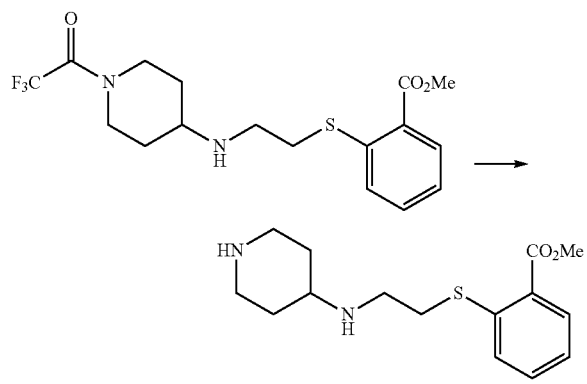

To a mixed solution of 2 mL of methanol containing 0.10 g of methyl 2-((2-(1-(trifluoroacetyl)piperidin-4-yl)amino)ethyl)thio)benzoate and 0.5 mL of water, 45 mg of potassium carbonate was added under cooling with ice, and the mixture was stirred at room temperature for 3 hours. In the reaction mixture, the solvent was removed under reduced pressure. The residue thus obtained was added with chloroform and water. The organic layer was separated, and the aqueous layer was extracted with chloroform. The organic layer and the extract were combined, the resultant solution was washed with an aqueous saturated sodium chloride solution and dried over anhydrous magnesium sulfate, and the solvent was removed under reduced pressure to obtain 62 mg of a pale yellow oily substance, methyl 2-((2-(piperidin-4-ylamino)ethyl)thio)benzoate.

$^1$H-NMR (CDCl$_3$) δ:

1.17-1.28 (2H, m), 1.83-1.90 (2H, m), 2.52-2.75 (3H, m), 2.99 (2H, t, J=6.6 Hz), 3.05-3.12 (2H, m), 3.11 (2H, t, J=6.6 Hz), 3.92 (3H, s), 7.14-7.20 (1H, m), 7.34-7.38 (1H, m), 7.41-7.48 (1H, m), 7.93-7.96 (1H, m)

Reference Example 120

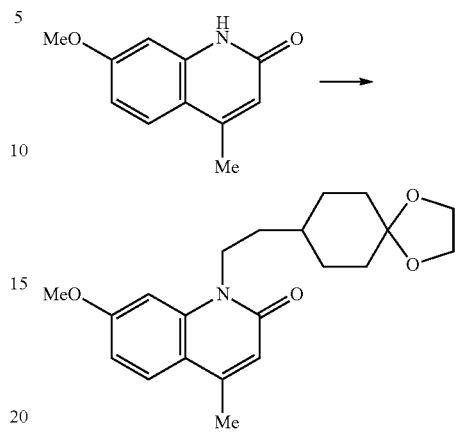

To 3 mL of an N,N-dimethylformamide solution containing 0.12 g of 7-methoxy-4-methylquinolin-2(1H)-one, 28 mg of a 60% aqueous sodium hydride solution was added at 50° C., and the mixture was stirred at 60 to 65° C. for 30 minutes. Thereto was added 2 mL of an N,N-dimethylformamide solution containing 0.18 g of 2-(1,4-dioxaspiro[4.5]decan-8-yl)ethyl methanesulfonate at 50° C., and the mixture was stirred at 60 to 65° C. for 1 hour and 20 minutes. Thereto was added 14 mg of a 60% aqueous sodium hydride solution at the same temperature, and the mixture was stirred for 1 hour and 45 minutes. The reaction mixture was cooled to room temperature, and then water and ethyl acetate were then added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by flash silica gel column chromatography [hexane:gradient elution of ethyl acetate=40:60 to 30:70] to obtain 65 mg of a colorless oily substance, 1-(2-(1,4-dioxaspiro[4.5]decan-8-yl)ethyl)-7-methoxy-4-methylquinolin-2(1H)-one.

$^1$H-NMR (CDCl$_3$) δ:

1.20-1.82 (7H, m), 1.84-1.92 (2H, m), 2.41 (3H, d, J=1.0 Hz), 3.66-3.72 (2H, s), 3.91 (3H, s), 3.93-3.96 (4H, m), 4.22-4.30 (2H, m), 6.43 (1H, s), 6.79 (1H, d, J=2.4 Hz), 6.83 (1H, dd, J=8.9, 2.4 Hz), 7.62 (1H, d, J=8.9 Hz)

Reference Example 121

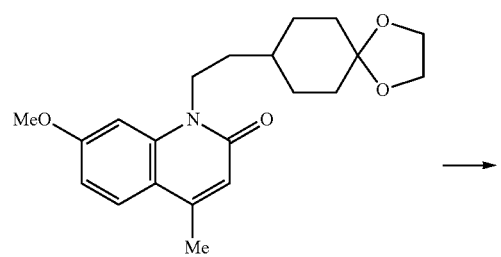

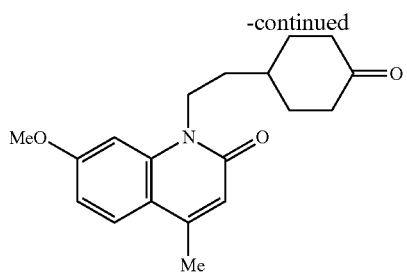

To 1.5 mL of an ethanol solution containing 65 mg of 1-(2-(1,4-dioxaspiro[4.5]decan-8-yl)ethyl)-7-methoxy-4-methylquinolin-2(1H)-one, 0.5 mL of an 80% aqueous trifluoroacetic acid solution was added under cooling with ice, and the mixture was stirred at room temperature for 3 hours. The solvent was removed under reduced pressure, and water and ethyl acetate were added thereto. The reaction mixture was adjusted to pH 7.7 with an aqueous saturated sodium hydrogen carbonate solution. The organic layer was separated, washed with an aqueous saturated sodium chloride solution and then dried over anhydrous magnesium sulfate, and the solvent was removed under reduced pressure to obtain 48 mg of a colorless oily substance, 7-methoxy-4-methyl-1-(2-(4-oxocyclohexyl)ethyl)quinolin-2(1H)-one.

$^{1}$H-NMR (CDCl$_3$) δ:
1.40-2.28 (7H, m), 2.33-2.42 (4H, m), 2.43 (3H, d, J=1.1 Hz), 3.92 (3H, s), 4.30-4.36 (1H, m), 6.45 (1H, d, J=1.1 Hz), 6.79 (1H, d, J=2.3 Hz), 6.86 (1H, dd, J=8.8, 2.3 Hz), 7.65 (1H, d, J=8.8 Hz)

Reference Example 122

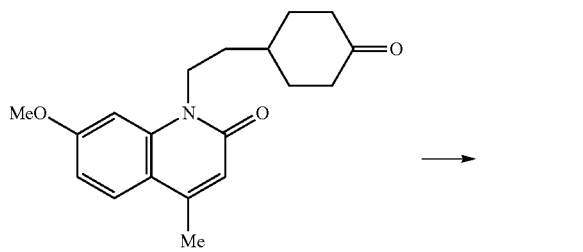

To 1.5 mL of an ethanol solution containing 10 mg of 7-methoxy-4-methyl-1-(2-(4-oxocyclohexyl)ethyl)quinolin-2(1H)-one, 3.7 mg of ammonium acetate and 15 mg of molecular sieves 3A were added at room temperature, the mixture was stirred for 1 hour, then thereto was added 5.0 mg of sodium cyanoborohydride, and the mixture was stirred at the same temperature for 4 hours and 30 minutes. Thereto was further added 3.0 mg of sodium cyanoborohydride, and the mixture was stirred for 30 minute, and then left to stand overnight. The solvent was removed under reduced pressure, water and ethyl acetate were added thereto, the reaction mixture was adjusted to pH 3 to 4 (pH test paper) with 2.0 mol/L hydrochloric acid, and the aqueous layer was separated. The aqueous layer was added with ethyl acetate, and the resultant solution was adjusted to pH 8 to 9 (pH test paper) with a 2.0 mol/L aqueous sodium hydroxide solution. The organic layer was separated, washed with an aqueous saturated sodium chloride solution and dried over anhydrous magnesium sulfate, and the solvent was removed under reduced pressure to obtain 6.0 mg of a colorless oily substance, 1-(2-(4-aminocyclohexyl)ethyl)-7-methoxy-4-methylquinolin-2(1H)-one.

$^{1}$H-NMR (CDCl$_3$) δ:
1.00-1.80 (5H, m), 1.88-2.00 (2H, m), 2.10-2.24 (4H, m), 2.41 (3H, s), 2.65-3.10 (1H, m), 3.91 (3H, s), 4.20-4.30 (2H, m), 6.43 (1H, s), 6.78-6.85 (2H, m), 7.62 (1H, d, J=8.8 Hz)

Reference Example 123

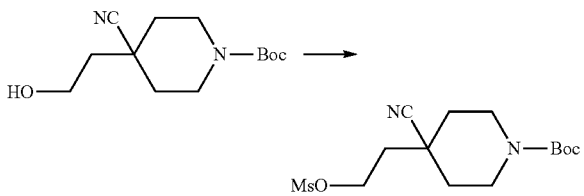

To 10 mL of a tetrahydrofuran solution containing 1.0 g of tert-butyl 4-cyano-4-(2-hydroxyethyl)piperidine-1-carboxylate, 0.77 mL of triethylamine was added at room temperature, thereto was added 0.37 mL of methane sulfonyl chloride under cooling with ice, and the mixture was stirred at the same temperature for 2 hours and 30 minutes. The reaction mixture was added with an aqueous saturated sodium hydrogen carbonate solution and ethyl acetate. The organic layer was separated, washed with an aqueous saturated sodium chloride solution and dried over anhydrous magnesium sulfate, and the solvent was removed under reduced pressure to obtain 1.3 g of a brown oily substance, tert-butyl 4-cyano-4-(2-((methylsulfonyl)oxy)ethyl)piperidine-1-carboxylate.

$^{1}$H-NMR (CDCl$_3$) δ:
1.46 (9H, s), 1.44-1.55 (2H, m), 1.94-2.02 (2H, m), 2.06 (2H, t, J=6.5 Hz), 2.97-3.11 (2H, m), 3.07 (3H, s), 4.06-4.24 (2H, m), 4.47 (2H, t, J=6.5 Hz)

Reference Example 124

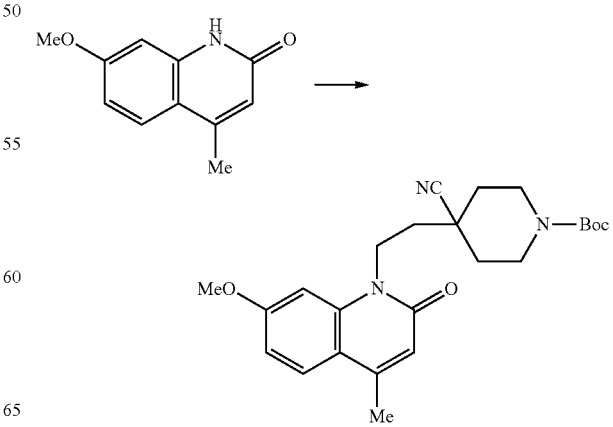

To 5 mL of an N,N-dimethylformamide solution containing 0.19 g of 7-methoxy-4-methylquinolin-2(1H)-one, 47 mg of a 60% aqueous sodium hydride solution was added at 50° C., and the mixture was stirred at the same temperature for 40 minutes. Thereto was added dropwise 4 mL of an N,N-dimethylformamide solution containing 0.36 g of tert-butyl 4-cyano-4-(2-((methylsulfonyl)oxy)ethyl)piperidine-1-carboxylate at 50° C., and the mixture was stirred at 50 to 55° C. for 3 hours. Thereto was added 0.27 g of potassium carbonate at the same temperature, and the mixture was further stirred for 3 hours and 10 minutes. The reaction mixture was cooled to room temperature, and then water and ethyl acetate were added thereto. The organic layer was separated, washed with an aqueous saturated sodium chloride solution and dried over anhydrous magnesium sulfate, and the solvent was removed under reduced pressure. The residue thus obtained was purified by flash silica gel column chromatography [hexane:gradient elution of ethyl acetate=75:25 to 50:50] to obtain 70 mg of a colorless oily substance, tert-butyl 4-cyano-4-(2-(7-methoxy-4-methyl-2-oxo-1,2-dihydroquinolin-1-yl)ethyl)piperidine-1-carboxylate.

$^1$H-NMR (CDCl$_3$) δ:
1.47 (9H, s), 1.50-1.66 (2H, m), 1.94-2.08 (4H, m), 2.43 (3H, s), 3.00-3.16 (2H, m), 3.94 (3H, s), 4.02-4.24 (2H, m), 4.36-4.58 (2H, m), 6.42 (1H, s), 6.87 (1H, dd, J=8.9, 2.3 Hz), 6.91 (1H, d, J=2.3 Hz), 7.63 (1H, d, J=8.9 Hz)

Reference Example 125

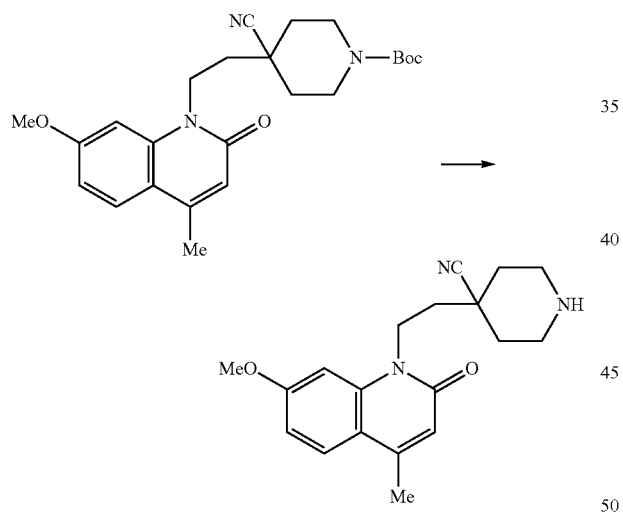

To 5 mL of a dichloromethane solution containing 70 mg of tert-butyl 4-cyano-4-(2-(7-methoxy-4-methyl-2-oxo-1,2-dihydroquinolin-1-yl)ethyl)piperidine-1-carboxylate, 0.5 mL of trifluoroacetic acid was added under cooling with ice, and the mixture was stirred at room temperature for 1 hour and 10 minutes. The reaction mixture solution was added with water, and the resultant mixture solution was adjusted to pH 10 with a 20% aqueous sodium hydroxide solution, and thereto was added chloroform. The organic layer was separated, and the aqueous layer was extracted with chloroform. The organic layer and the extract were combined, and the resultant solution was washed with an aqueous saturated sodium chloride solution and then dried over anhydrous magnesium sulfate, and the solvent was removed under reduced pressure to obtain 43 mg of a white solid, 4-(2-(7-methoxy-4-methyl-2-oxo-1,2-dihydroquinolin-1-yl)ethyl)piperidine-4-carbonitrile.

$^1$H-NMR (CDCl$_3$) δ:
1.55-1.68 (2H, m), 1.96-2.08 (4H, m), 2.43 (3H, s), 2.93-3.01 (2H, m), 3.06-3.14 (2H, m), 3.94 (3H, s), 4.45-4.53 (2H, m), 6.43 (1H, s), 6.86 (1H, dd, J=8.9, 2.3 Hz), 6.94 (1H, d, J=2.3 Hz), 7.63 (1H, d, J=8.9 Hz)

Reference Example 126

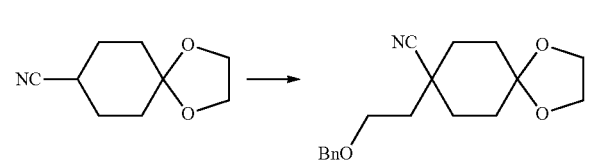 [SMILES: N#CC1CCC2(CC1)OCCO2 ; N#CC1(CCOCc2ccccc2)CCC2(CC1)OCCO2]

To 8 mL of a tetrahydrofuran solution containing 0.94 mL of diisopropylamine, 4.5 mL of 1.6 mol/L butyllithium/hexane was added dropwise at −78° C., the mixture was stirred at the same temperature for 1 hour, and then thereto was added dropwise 7 mL of a tetrahydrofuran solution containing 0.60 g of 1,4-dioxaspiro[4.5]decane-8-carbonitrile. After stirring at −78° C. for 1 hour, the mixture was added dropwise with 0.85 mL of benzyl 2-bromoethyl ether, and further stirred for 1 hour. The temperature of the reaction mixture was increased to room temperature, and then a 10% aqueous citric acid solution and ethyl acetate were added thereto. The organic layer was separated, and the aqueous layer was extracted with ethyl acetate. The organic layer and the extract were combined, the resultant solution was washed with an aqueous saturated sodium chloride solution and then dried over anhydrous magnesium sulfate, and the solvent was removed under reduced pressure. The residue thus obtained was purified by silica gel column chromatography [eluent; hexane:ethyl acetate=6:1] to obtain 1.1 g of a colorless oily substance, 8-(2-(benzyloxy)ethyl)-1,4-dioxaspiro[4.5]decane-8-carbonitrile.

$^1$H-NMR (CDCl$_3$) δ:
1.62-1.78 (4H, m), 1.84-1.96 (4H, m), 1.98-2.08 (2H, m), 3.71 (2H, t, J=6.5 Hz), 3.88-4.00 (4H, m), 4.52 (2H, s), 7.25-7.39 (5H, m)

Reference Example 127

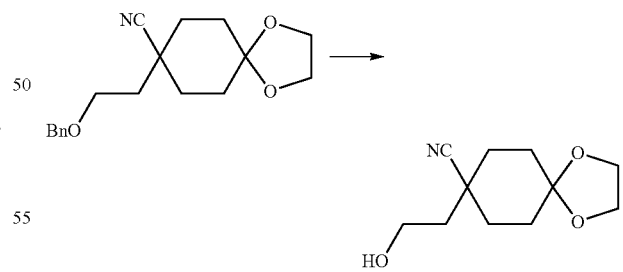

To 10 mL of an ethanol solution containing 1.0 g of 8-(2-(benzyloxy)ethyl)-1,4-dioxaspiro[4.5]decane-8-carbonitrile, 0.50 g of 10% palladium-carbon was added at room temperature, and the mixture was stirred at 40 to 45° C. for 1 hour and 30 minutes under a hydrogen atmosphere. The insoluble material filtered off, and the solvent was removed under reduced pressure to obtained 0.80 g of a colorless oily substance, 8-(2-hydroxyethyl)-1,4-dioxaspiro[4.5]decane-8-carbonitrile.

¹H-NMR (CDCl₃) δ:
1.56-1.79 (4H, m), 1.82-1.97 (4H, m), 2.00-2.09 (2H, m), 3.86-4.02 (6H, m)

Reference Example 128

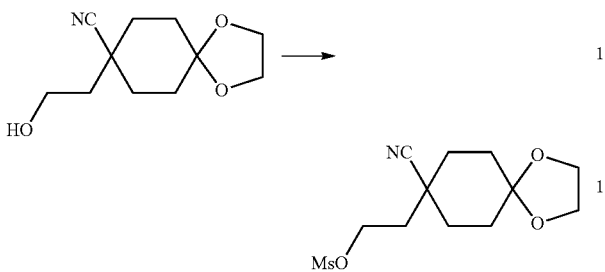

To 10 mL of a dichloromethane solution containing 0.71 g of 8-(2-hydroxyethyl)-1,4-dioxaspiro[4.5]decane-8-carbonitrile, 0.65 mL of triethylamine was added, thereto was added 0.30 mL of methanesulfonyl chloride under cooling with ice, and the mixture was stirred at the same temperature for 2 hours. The reaction mixture was added with an aqueous saturated sodium hydrogen carbonate solution and chloroform. The organic layer was separated, washed with an aqueous saturated sodium chloride solution and then dried over anhydrous magnesium sulfate, and the solvent was removed under reduced pressure to obtain 0.99 g of a white solid, 2-(8-cyano-1,4-dioxaspiro[4.5]decan-8-yl)ethyl methanesulfonate.
¹H-NMR (CDCl₃) δ:
1.66-1.80 (4H, m), 1.88-1.96 (2H, m), 2.00-2.10 (2H, m), 2.06 (2H, t, J=6.5 Hz), 3.06 (3H, s), 3.89-4.01 (4H, m), 4.45 (2H, t, J=6.5 Hz)

Reference Example 129

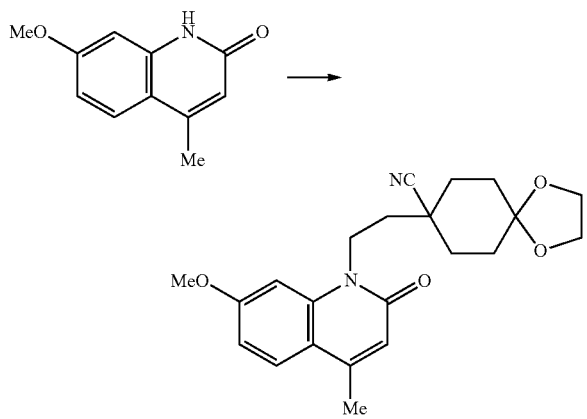

To 10 mL of an N,N-dimethylformamide suspension containing 0.63 g of 7-methoxy-4-methylquinolin-2(1H)-one, 0.17 g of 60% sodium hydride at 55° C., and the mixture was stirred at the same temperature for 35 minutes. Thereto was added dropwise 8 mL of an N,N-dimethylformamide solution containing 0.99 g of 2-(8-cyano-1,4-dioxaspiro[4.5]decan-8-yl)ethyl methanesulfonate at 50° C., and the mixture was stirred at 50 to 55° C. for 2 hours and 50 minutes. Thereto was added 53 mg of 60% sodium hydride at the same temperature, and after further stirring for 3 hours, the mixture was added with 0.46 g of potassium carbonate at the same temperature, and further stirred for 3 hours. The reaction mixture was cooled to room temperature, and then water and ethyl acetate were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by flash silica gel column chromatography [hexane: gradient elution of ethyl acetate 30:70] to obtain 200 mg g of a white solid, 8-(2-(7-methoxy-4-methyl-2-oxo-1,2-dihydroquinolin-1-yl)ethyl)-1,4-dioxaspiro[4.5]decane-8-carbonitrile.
¹H-NMR (CDCl₃) δ:
1.75-2.15 (10H, m), 2.42 (3H, d, J=1.2 Hz), 3.88-4.01 (4H, m), 3.94 (3H, s), 4.42-4.52 (2H, m), 6.42 (1H, s), 6.86 (1H, dd, J=8.9, 2.4 Hz), 6.93 (1H, d, J=2.4 Hz), 7.62 (1H, d, J=8.9 Hz)

Reference Example 130

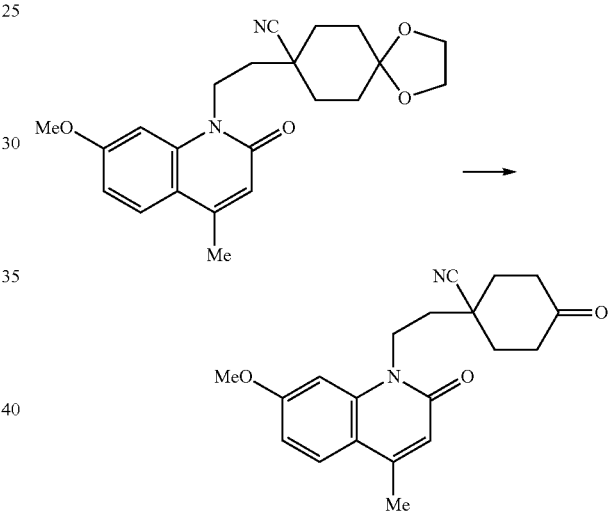

To 1.5 mL of an ethanol solution containing 0.20 g of 8-(2-(7-methoxy-4-methyl-2-oxo-1,2-dihydroquinolin-1-yl)ethyl)-1,4-dioxaspiro[4.5]decane-8-carbonitrile, 7.5 mL of an 80% aqueous trifluoroacetic acid solution was dividedly added at room temperature over 4 hours and 30 minutes, and the mixture was left to stand at room temperature overnight. The solvent was removed under reduced pressure, ethyl acetate was added thereto, and the reaction mixture was adjusted to pH 7.2 with a 20% aqueous sodium hydroxide solution. The organic layer was separated, and the aqueous layer was extracted with ethyl acetate. The organic layer and the extract were combined, the resultant solution was washed with an aqueous saturated sodium chloride solution and then dried over anhydrous magnesium sulfate, and the solvent was removed under reduced pressure to obtain 0.19 g of a white solid, 1-(2-(7-methoxy-4-methyl-2-oxo-1,2-dihydroquinolin-1-yl)ethyl)-4-oxocyclohexanecarbonitrile.
¹H-NMR (CDCl₃) δ:
1.86-1.98 (2H, m), 2.06-2.13 (2H, m), 2.40-2.58 (4H, m), 2.44 (3H, d, J=1.2 Hz), 2.68-2.78 (2H, m), 3.96 (3H, s), 4.48-4.58 (2H, m), 6.44 (1H, s), 6.88 (1H, dd, J=8.9, 2.2 Hz), 6.94 (1H, d, J=2.2 Hz), 7.65 (1H, d, J=8.9 Hz)

Reference Example 131

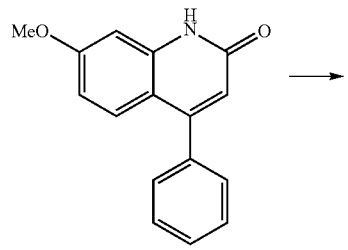

In the same method as in Reference Example 4, 1-(1,3-dioxolan-2-ylmethyl)-7-methoxy-4-phenylquinolin-2(1H)-one was obtained from 7-methoxy-4-phenylquinolin-2(1H)-one and 2-bromomethyl-1,3-dioxolane.

¹H-NMR (CDCl₃) δ:
3.88-3.92 (2H, m), 3.91 (3H, s), 4.05-4.15 (2H, m), 4.58 (2H, d, J=4.4 Hz), 5.31 (1H, t, J=4.4 Hz), 6.52 (1H, s), 6.75 (1H, dd, J=9.0, 2.4 Hz), 7.17 (1H, d, J=2.4 Hz), 7.38-7.50 (6H, m)

Reference Example 132

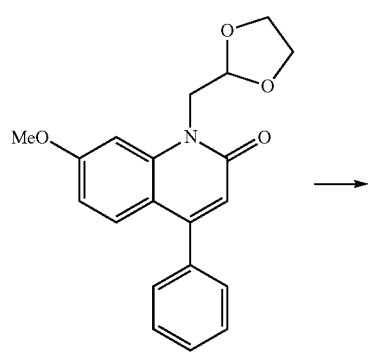

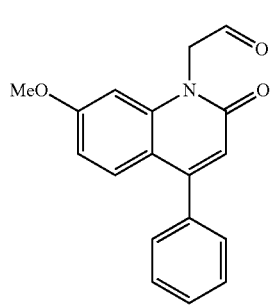

In the same method as in Reference Example 15, (7-methoxy-2-oxo-4-phenyl-1,2-dihydroquinolin-1-yl)acetaldehyde was obtained from 1-(1,3-dioxolan-2-ylmethyl)-7-methoxy-4-phenylquinolin-2(1H)-one.

¹H-NMR (CDCl₃) δ:
3.87 (3H, s), 5.18 (2H, s), 6.50-6.58 (2H, m), 6.74-6.83 (1H, m), 7.38-7.55 (6H, m), 9.73 (1H, m)

Reference Example 133

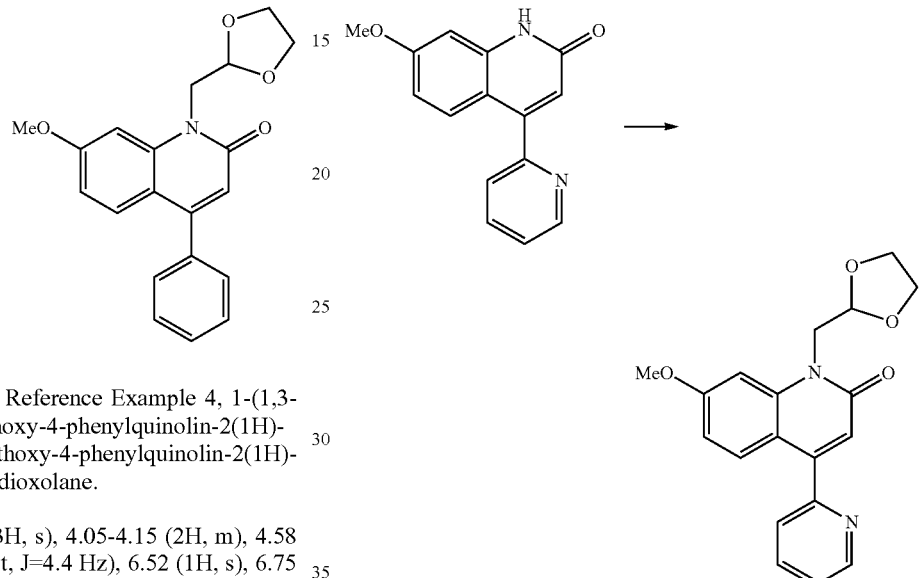

In the same method as in Reference Example 4, 1-(1,3-dioxolan-2-ylmethyl)-7-methoxy-4-(pyridin-2-yl)quinolin-2(1H)-one was obtained from 7-methoxy-4-(pyridin-2-yl)quinolin-2(1H)-one and 2-bromomethyl-1,3-dioxolane.

¹H-NMR (CDCl₃) δ:
3.85-3.95 (2H, m), 3.91 (3H, s), 4.05-4.11 (2H, m), 4.59 (2H, d, J=4.2 Hz), 5.29 (1H, t, J=4.2 Hz), 6.64 (1H, s), 6.78 (1H, dd, J=8.9, 2.4 Hz), 7.17 (1H, d, J=2.4 Hz), 7.37-7.41 (1H, m), 7.51 (1H, d, J=7.8 Hz), 7.65 (1H, d, J=8.9 Hz), 7.82-7.88 (1H, m), 8.74-8.78 (1H, m)

Reference Example 134

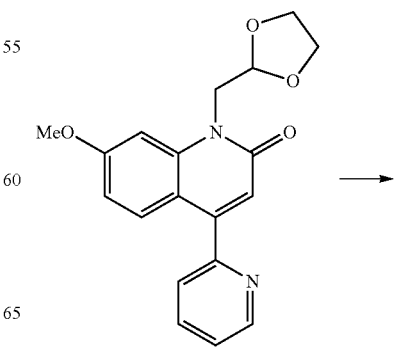

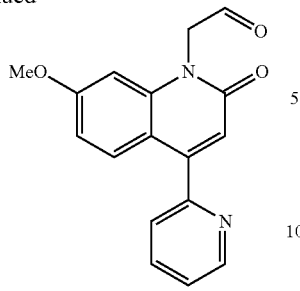

In the same method as in Reference Example 15, (7-methoxy-2-oxo-4-(pyridin-2-yl)-1,2-dihydroquinolin-1-yl)acetaldehyde was obtained from 1-(1,3-dioxolan-2-ylmethyl)-7-methoxy-4-(pyridin-2-yl)quinolin-2(1H)-one.

$^1$H-NMR (CDCl$_3$) δ:

3.86 (3H, s), 5.17 (2H, d, J=1.0 Hz), 6.53 (1H, d, J=2.2 Hz), 6.68 (1H, s), 6.81 (1H, dd, J=9.0, 2.2 Hz), 7.40-7.44 (1H, m), 7.54-7.57 (1H, m), 7.72 (1H, d, J=9.0 Hz), 7.85-7.90 (1H, m), 8.76-8.80 (1H, m), 9.70 (1H, d, J=1.0 Hz)

Reference Example 135

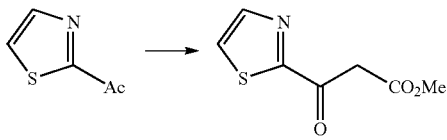 [SMILES: CC(=O)c1nccs1 ; COC(=O)CC(=O)c1nccs1]

To 50 mL of a tetrahydrofuran solution containing 5.0 g of 1-(1,3-thiazol-2-yl)ethanone, 6.3 mL of dimethyl carbonate and 3.0 g of 60% sodium hydride were added at 10° C. The temperature of the reaction mixture was increased to room temperature, and the mixture was stirred for 16 hours. Thereto was further added 0.75 g of 60% sodium hydride, and the mixture was stirred for 4 hours. Water and ethyl acetate were then added thereto, and the reaction mixture was adjusted to pH 3.0 with 6 mol/L hydrochloric acid. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; hexane:ethyl acetate=5:1] to obtain 2.3 g of a yellow oily substance, methyl 3-oxo-3-(1,3-thiazol-2-yl)propionate.

$^1$H-NMR (CDCl$_3$) δ:

3.76 (3H, s), 4.18 (2H, s), 7.74 (1H, d, J=2.9 Hz), 8.03 (1H, d, J=2.9 Hz)

Reference Example 136

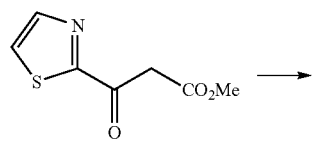

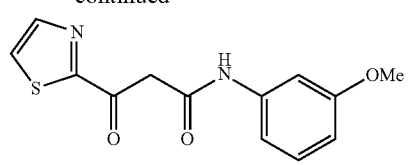

To 30 mL of a xylene solution containing 2.3 g of methyl 3-oxo-3-(1,3-thiazol-2-yl)propionate, 1.4 mL of m-anisidine was added. The reaction mixture was stirred for 6 hours under reflux by heating. The solvent was removed under reduced pressure, and water and ethyl acetate were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure to obtain 3.3 g of a brown oily substance, N-(3-methoxyphenyl)-3-oxo-3-(1,3-thiazol-2-yl)propaneamide.

$^1$H-NMR (CDCl$_3$) δ:

3.80 (3H, s), 4.33 (2H, s), 6.65-6.69 (1H, m), 7.00-7.04 (1H, m), 7.21 (1H, t, J=8.2 Hz), 7.30-7.33 (1H, m), 7.80 (1H, d, J=3.1 Hz), 8.10 (1H, d, J=3.1 Hz)

Reference Example 137

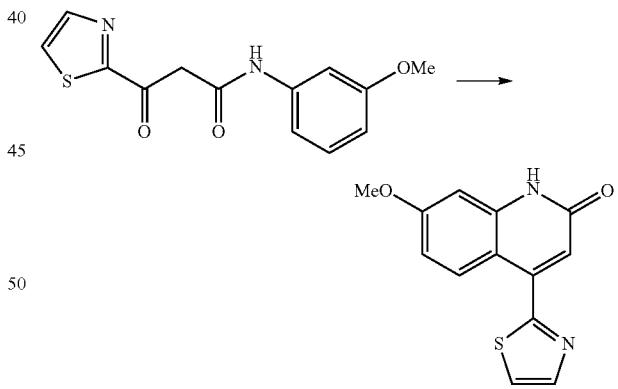

In the same method as in Reference Example 27, 7-methoxy-4-(1,3-thiazol-2-yl)quinolin-2(1H)-one was obtained from N-(3-methoxyphenyl)-3-oxo-3-(1,3-thiazol-2-yl)propaneamide.

$^1$H-NMR (DMSO-d$_6$) δ:

3.84 (3H, s), 6.68 (1H, s), 6.87 (1H, dd, J=9.0, 2.5 Hz), 6.92 (1H, d, J=2.5 Hz), 8.03 (1H, d, J=3.3 Hz), 8.15 (1H, d, J=3.3 Hz), 8.37 (1H, d, J=9.0 Hz)

Reference Example 138

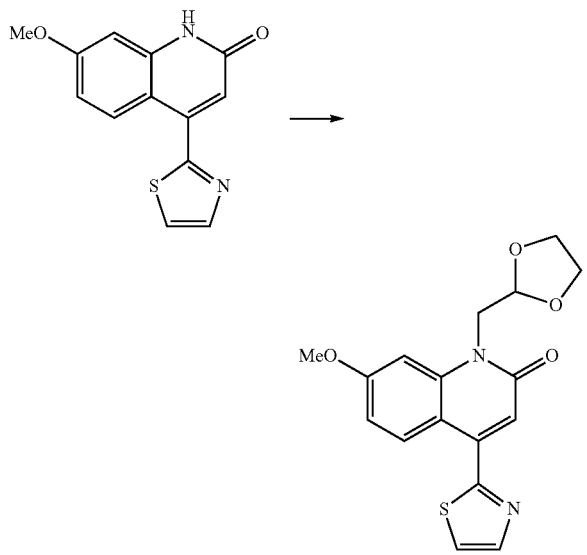

In the same method as in Reference Example 4, 1-(1,3-dioxolan-2-ylmethyl)-7-methoxy-4-(1,3-thiazol-2-yl)quinolin-2(1H)-one was obtained from 7-methoxy-4-(1,3-thiazol-2-yl)quinolin-2(1H)-one and 2-bromomethyl-1,3-dioxolane.

$^1$H-NMR (CDCl$_3$) δ:
3.86-3.95 (2H, m), 3.93 (3H, s), 4.02-4.10 (2H, m), 4.58 (2H, d, J=4.3 Hz), 5.29 (1H, t, J=4.3 Hz), 6.87 (1H, dd, J=9.0, 2.4 Hz), 6.90 (1H, s), 7.16 (1H, d, J=2.4 Hz), 7.51 (1H, d, J=3.3 Hz), 8.05 (1H, d, J=3.3 Hz), 8.48 (1H, d, J=9.0 Hz)

Reference Example 139

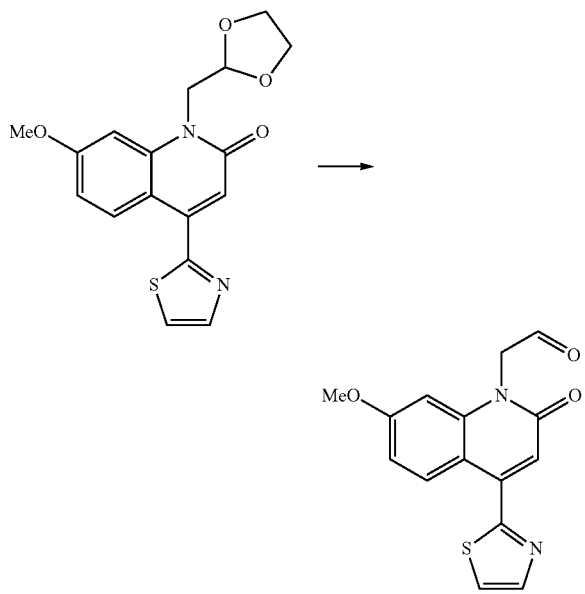

In the same method as in Reference Example 15, (7-methoxy-2-oxo-4-(1,3-thiazol-2-yl)-1,2-dihydroquinolin-1-yl)acetaldehyde was obtained from 1-(1,3-dioxolan-2-ylmethyl)-7-methoxy-4-(1,3-thiazol-2-yl) quinolin-2(1H)-one.

$^1$H-NMR (CDCl$_3$) δ:
3.88 (3H, s), 5.17 (2H, s), 6.52 (1H, d, J=2.4 Hz), 6.89 (1H, dd, J=9.1, 2.4 Hz), 6.93 (1H, s), 7.54 (1H, d, J=3.2 Hz), 8.08 (1H, d, J=3.2 Hz), 8.56 (1H, d, J=9.1 Hz), 9.71 (1H, s)

Reference Example 140

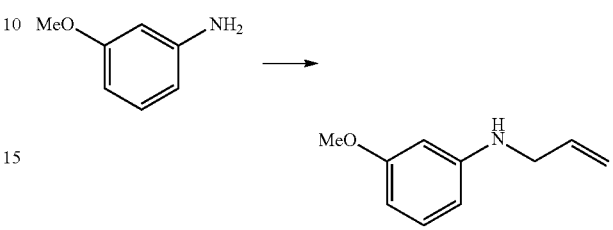

To 10 mL of a tetrahydrofuran solution containing 1.0 g of m-anisidine, 1.2 mL of triethylamine and 0.70 mL of allyl bromide were added under cooling with ice. The reaction mixture was stirred for 30 minutes. Water and ethyl acetate were added thereto. The organic layer was separated, and the aqueous layer was separated with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; hexane:ethyl acetate=5:1] to obtain 0.36 g of a yellow oily substance, N-allyl-3-methoxyaniline.

$^1$H-NMR (CDCl$_3$) δ:
3.40 (2H, t, J=5.1 Hz), 3.47 (3H, s), 4.67 (1H, t, J=5.1 Hz), 5.60-5.80 (2H, m), 7.24-7.30 (1H, m), 7.35 (1H, dd, J=8.2, 1.1 Hz), 7.45 (1H, dd, J=8.2, 1.1 Hz), 7.52-7.57 (1H, m)

Reference Example 141

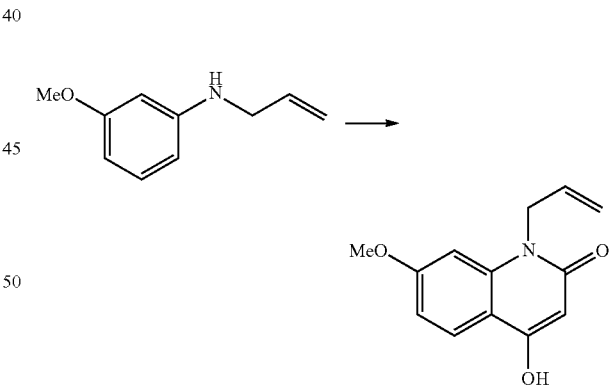

To 6 mL of a phosphorus oxychloride solution containing 0.35 g of N-allyl-3-methoxyaniline, 0.45 g of malonic acid was added. The reaction mixture was heated to 90° C., and stirred for 1 hour and 30 minutes. The reaction mixture was fed into ice. Thereto was added chloroform, the organic layer was separated, and the aqueous layer was extracted with chloroform. The organic layer and the extract were combined, and the resultant solution was adjusted to pH 5.5 with a 20% aqueous sodium hydroxide solution. The organic layer was separated and dried over anhydrous magnesium sulfate, and the solvent was removed under reduced pressure. The residue thus obtained was purified by silica gel column chromatography [eluent; chloroform:methanol=50:1] to obtain 0.15 g of a light brown solid, 1-allyl-4-hydroxy-7-methoxyquinolin-2 (1H)-one.

¹H-NMR (CDCl₃) δ:

3.84 (3H, s), 4.56-4.63 (2H, m), 5.04 (1H, d, J=17.3 Hz), 5.18 (1H, d, J=10.5 Hz), 5.79-5.90 (1H, m), 5.98 (1H, s), 6.39-6.44 (1H, m), 6.72 (1H, dd, J=8.9, 2.1 Hz), 7.83 (1H, d, J=8.9 Hz)

Reference Example 142

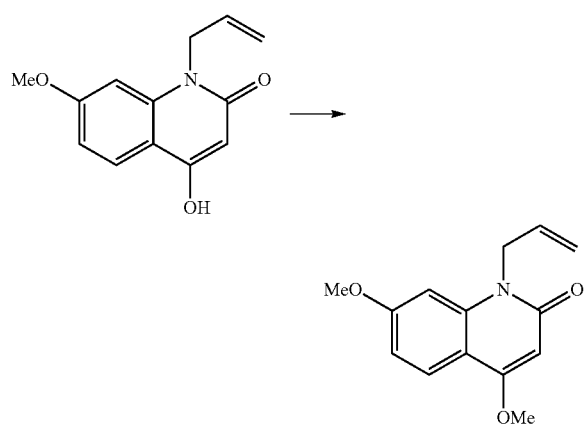

To 2 mL of a tetrahydrofuran solution containing 0.15 g of 1-allyl-4-hydroxy-7-methoxyquinolin-2(1H)-one, 94 mg of potassium carbonate and 64 μL of dimethylsulfuric acid were added. The reaction mixture was stirred at room temperature for 1 hour and 30 minutes. Water and ethyl acetate were added thereto, the organic layer was separated, and the aqueous layer was extracted with ethyl acetate. The organic layer and the extract were combined, and the resultant solution was washed with an aqueous saturated sodium chloride solution and dried over anhydrous magnesium sulfate, and the solvent was removed under reduced pressure. The residue thus obtained was purified by silica gel column chromatography [eluent; hexane:ethyl acetate 2:1] to obtain 0.10 g of a white solid, 1-allyl-4,7-dimethoxyquinolin-2(1H)-one.

¹H-NMR (CDCl₃) δ:

3.88 (3H, s), 3.93 (3H, s), 4.85-4.90 (2H, m), 5.11 (1H, d, J=17.1 Hz), 5.21 (1H, d, J=10.5 Hz), 5.88-5.99 (2H, m), 6.75 (1H, d, J=2.3 Hz), 6.79 (1H, dd, J=8.9, 2.3 Hz), 7.87 (1H, d, J=8.9 Hz)

Reference Example 143

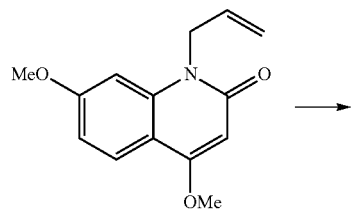

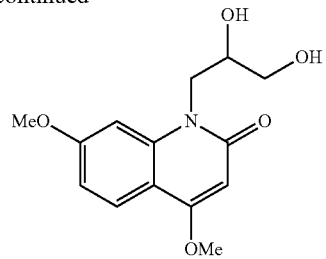

To a mixed solution of 2 mL of dioxane containing 0.10 g of 1-allyl-4,7-dimethoxyquinolin-2(1H)-one and 2 mL of water, 10 mg of osmium tetroxide and 0.11 g of sodium metaperiodate were added. The reaction mixture was stirred at room temperature for 3 hours. Thereto were added a 10% aqueous sodium thiosulfate solution and ethyl acetate. The organic layer was separated, and the aqueous layer was extracted with ethyl acetate. The organic layer and the extract were combined, and the resultant solution was washed with an aqueous saturated sodium chloride solution and dried over anhydrous magnesium sulfate, and the solvent was removed under reduced pressure. The residue thus obtained was purified by silica gel column chromatography [eluent; chloroform:methanol=50:1] to obtain 80 mg of a white solid, 1-(2, 3-dihydroxypropyl)-4,7-dimethoxyquinolin-2(1H)-one.

¹H-NMR (CDCl₃) δ:

3.50-3.55 (1H, m), 3.60-3.73 (2H, m), 3.91 (3H, s), 3.94 (3H, s), 3.95-4.07 (2H, m), 4.17 (1H, dd, J=14.6, 5.6 Hz), 4.58 (1H, dd, J=14.6, 7.8 Hz), 5.93 (1H, s), 6.85 (1H, dd, J=8.9, 2.2 Hz), 6.98 (1H, dd, J=2.2 Hz), 7.90 (1H, d, 8.9 Hz)

Reference Example 144

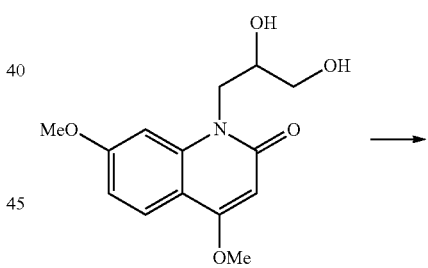

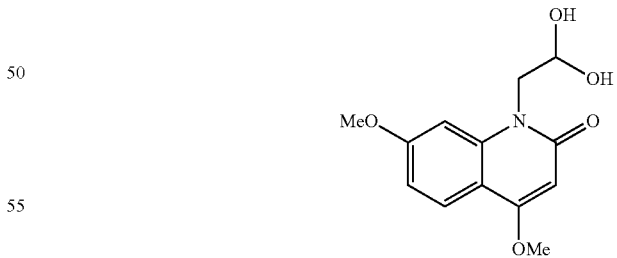

To a mixed solution of 1 mL of dioxane containing 80 mg of 1-(2,3-dihydroxypropyl)-4,7-dimethoxyquinolin-2(1H)-one and 1 mL of water, 80 mg of sodium metaperiodate was added. The reaction mixture was stirred at room temperature for 5 hours. Water and ethyl acetate were added thereto. The organic layer was separated, and the aqueous layer was extracted with ethyl acetate. The organic layer and the extract were combined, and the resultant solution was washed with an aqueous saturated sodium chloride solution and dried over anhydrous magnesium sulfate, and the solvent was removed under reduced pressure to obtain 36 mg of a white solid, 1-(2,2-dihydroxyethyl)-4,7-dimethoxyquinolin-2(1H)-one.

$^1$H-NMR (DMSO-d$_6$) δ:
3.86 (3H, s), 3.91 (3H, s), 4.13 (2H, d, J=5.4 Hz), 5.05-5.12 (1H, m), 5.89 (1H, s), 6.02-6.04 (2H, m), 6.85 (1H, d, J=8.9 Hz), 7.14 (1H, d, J=1.2 Hz), 7.77 (1H, dd, J=8.9, 1.2 Hz)

Reference Example 145

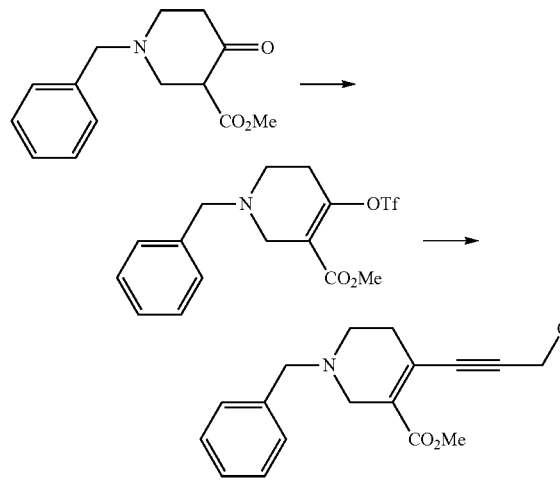

To 20 mL of a tetrahydrofuran solution containing 1.0 g of 60% sodium hydride, 2.8 g of methyl 1-benzyl-4-oxopiperidine-3-carboxylate and 6.4 g of N-phenyl-bis(trifluoromethanesulfonimide) was added under cooling with ice. The temperature of the reaction mixture was increased to 40° C., and the mixture was stirred for 2 hours. Water and ethyl acetate were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; chloroform] to obtain 5.5 g of a brown oily substance, methyl 1-benzyl-4-(((trifluoromethyl)sulfonyl)oxy)-1,2,5,6-tetrahydropyridine-3-carboxylate.

To 13 mL of an N,N-dimethylformamide solution containing 3.6 g of methyl 1-benzyl-4-(((trifluoromethyl)sulfonyl)oxy)-1,2,5,6-tetrahydropyridine-3-carboxylate, 0.75 mL of 2-propine-1-al and 2.2 mL of N,N-diisopropylethylamine, 61 mg of copper(I) iodide, and 0.14 g of bis(triphenylphosphine)palladium(II) dichloride were added under a nitrogen atmosphere. The reaction mixture was stirred at room temperature for 30 minutes. Water and ethyl acetate were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; chloroform] to obtain 2.7 g of a brown oily substance, methyl 1-benzyl-4-(3-hydroxy-1-propin-1-yl)-1,2,5,6-tetrahydropyridine-3-carboxylate containing N,N-dimethylformamide.

$^1$H-NMR (CDCl$_3$) δ:
2.40-2.50 (2H, m), 2.52-2.58 (2H, m), 3.29-3.35 (2H, m), 3.63 (2H, s), 3.73 (3H, s), 4.48 (2H, s), 7.22-7.40 (5H, m)

Reference Example 146

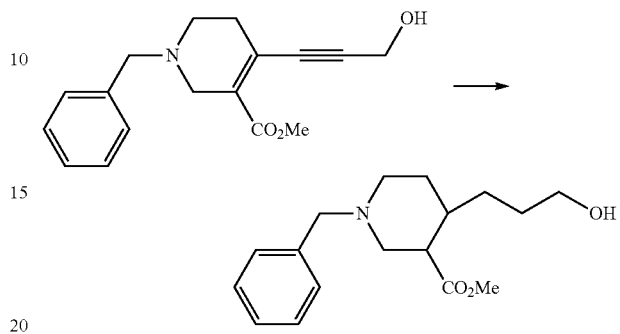

To 40 mL of an ethanol solution containing 2.6 g of methyl 1-benzyl-4-(3-hydroxy-1-propin-1-yl)-1,2,5,6-tetrahydropyridine-3-carboxylate, 1.0 g of palladium carbon was added, and the mixture was stirred for 2 hours under a hydrogen atmosphere. Thereto was added 0.7 g of palladium carbon, and the mixture was stirred for 2 hours under a hydrogen atmosphere. The insoluble material filtered off, and the solvent was removed under reduced pressure. The residue thus obtained was purified by silica gel column chromatography [eluent; hexane:ethyl acetate 1:2] to obtain 0.50 g of a brown oily substance, methyl 1-benzyl-4-(3-hydroxypropyl)piperidine-3-carboxylate.

$^1$H-NMR (CDCl$_3$) δ:
1.50-1.60 (1H, m), 1.72-1.80 (2H, m), 2.25-2.33 (2H, m), 2.50-2.54 (2H, m), 2.58-2.62 (2H, m), 2.75-2.85 (1H, m), 3.23 (2H, s), 3.55-3.70 (4H, m), 3.70 (3H, s), 7.25-7.35 (5H, m)

Reference Example 147

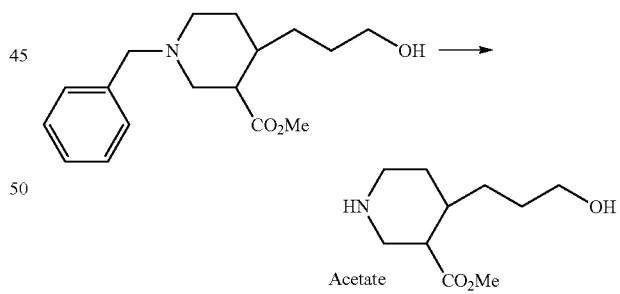

To 3 mL of a methanol solution containing 0.15 g of methyl 1-benzyl-4-(3-hydroxypropyl)piperidine-3-carboxylate, 0.12 mL of acetic acid and 0.15 g of palladium hydroxide were added, and the reaction mixture was stirred for 1 hour and 30 minutes under a hydrogen atmosphere. The insoluble material filtered off, and the solvent was removed under reduced pressure to obtain 0.12 g of a colorless oily substance, methyl 4-(3-hydroxypropyl)piperidine-3-carboxylate acetate. 1.34-1.41 (2H, m), 1.58-1.75 (4H, m), 1.87-1.95 (1H, m), 2.06 (3H, s), 2.80-2.90 (2H, m), 3.01 (1H, dd, J=3.7, 13.7 Hz), 3.20-3.28 (1H, m), 3.29-3.35 (1H, m), 3.65 (2H, t, J=6.3 Hz), 3.73 (3H, s)

Reference Example 148

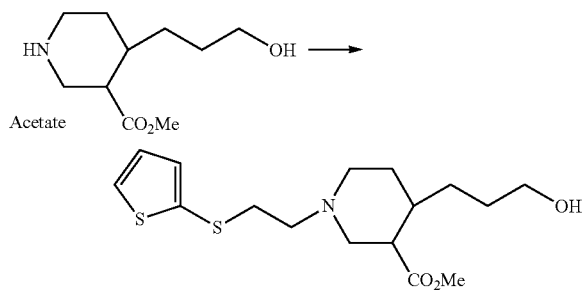

To 3.1 mL of an N,N-dimethylformamide solution containing 0.12 g of methyl 4-(3-hydroxypropyl)piperidine-3-carboxylate acetate, 0.19 mL of triethylamine and 0.14 g of 2-((2-bromoethyl)thio)thiophene were added, and the mixture was stirred at 70 to 80° C. for 2.5 hours. Water and ethyl acetate were added thereto, and the organic layer was separated. The organic layer was washed sequentially with water and an aqueous saturated sodium chloride solution and dried over anhydrous magnesium sulfate, and the solvent was removed under reduced pressure. The residue thus obtained was purified by silica gel column chromatography [eluent; chloroform:methanol=50:1] to obtain 0.10 g of a brown oily substance, methyl 4-(3-hydroxypropyl)-1-(2-(2-thienylthio)ethyl)piperidine-3-carboxylate.

$^1$H-NMR (CDCl$_3$) δ:
1.28-1.70 (5H, m), 1.77-1.86 (2H, m), 2.30-2.40 (1H, m), 2.44-2.74 (6H, m), 2.87-2.92 (2H, m), 3.60-3.65 (2H, m), 3.67 (3H, s), 6.96 (1H, dd, J=5.4, 3.5 Hz), 7.11 (1H, dd, J=3.5, 1.2 Hz), 7.33 (1H, dd, J=5.4, 1.2 Hz)

Reference Example 149

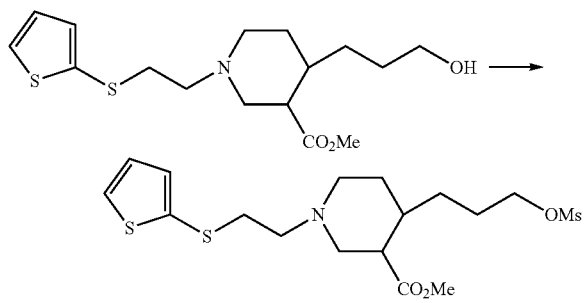

In the same method as in Reference Example 9, methyl 4-(3-((methylsulfonyl)oxy)propyl)-1-(2-(2-thienylthio)ethyl)piperidine-3-carboxylate was obtained from methyl 4-(3-hydroxypropyl)-1-(2-(2-thienylthio)ethyl)piperidine-3-carboxylate and methanesulfonyl chloride.

$^1$H-NMR (CDCl$_3$) δ:
1.35-1.88 (7H, m), 2.24-2.38 (1H, m), 2.45-2.82 (6H, m), 2.85-2.92 (2H, m), 3.00 (3H, s), 3.68 (3H, s), 4.18-4.22 (2H, m), 6.96 (1H, dd, J=5.2, 3.5 Hz), 7.11 (1H, dd, J=3.5, 1.2 Hz), 7.33 (1H, dd, J=5.2, 1.2 Hz)

Reference Example 150

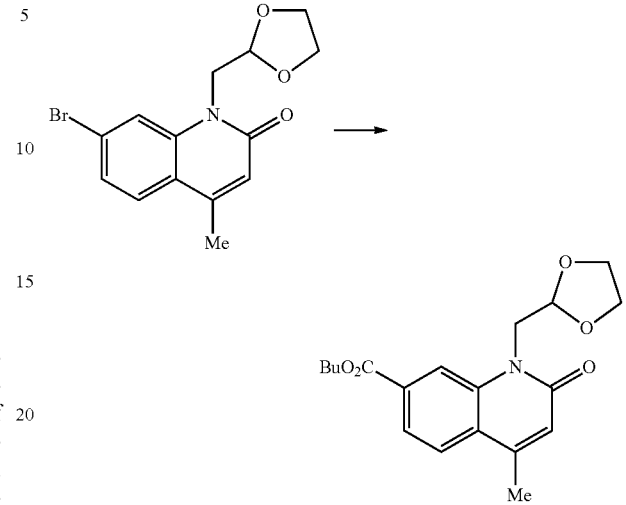

To a mixed solution of 36 mL of butanol containing 3.0 g of 7-bromo-1-(1,3-dioxolan-2-ylmethyl)-4-methylquinolin-2(1H)-one and 24 mL of triethylamine, 0.65 g of bis(triphenylphosphine)palladium dichloride was added, and the mixture was stirred with reflux for 2 hours under carbon monoxide atmosphere. The solvent was removed under reduced pressure. The residue thus obtained was purified by silica gel column chromatography [eluent; chloroform] to obtain 1.0 g of a brown solid, butyl 1-(1,3-dioxolan-2-ylmethyl)-4-methyl-2-oxo-1,2-dihydroquinoline-7-carboxylate.

$^1$H-NMR (CDCl$_3$) δ:
1.01 (3H, t, J=7.4 Hz), 1.46-1.58 (2H, m), 1.74-1.84 (2H, m), 2.49 (3H, d, J=1.2 Hz), 3.84-3.94 (2H, m), 4.02-4.14 (2H, m), 4.39 (2H, t, J=6.6 Hz), 4.57 (2H, d, J=4.6 Hz), 5.31 (1H, t, J=4.6 Hz), 6.67-6.69 (1H, m), 7.73 (1H, d, J=8.3 Hz), 7.88 (1H, dd, J=8.3, 1.5 Hz), 8.32 (1H, d, J=1.5 Hz)

Reference Example 151

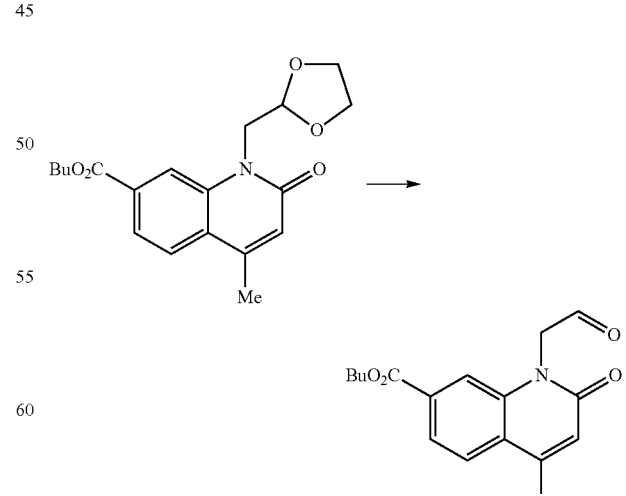

In the same method as in Reference Example 15, butyl 4-methyl-2-oxo-1-(2-oxoethyl)-1,2-dihydroquinoline-7-carboxylate was obtained from butyl 1-(1,3-dioxolan-2-ylmethyl)-4-methyl-2-oxo-1,2-dihydroquinoline-7-carboxylate.

$^1$H-NMR (CDCl$_3$) δ:
1.00 (3H, t, J=7.3 Hz), 1.42-1.54 (2H, m), 1.74-1.83 (2H, m), 2.58 (3H, s), 4.38 (2H, t, J=6.7 Hz), 5.31 (2H, s), 6.86 (1H, s), 7.78 (1H, d, J=1.3 Hz), 7.85 (1H, d, J=8.3 Hz), 7.97 (1H, dd, J=8.3, 1.3 Hz), 9.78 (1H, s)

Reference Example 152

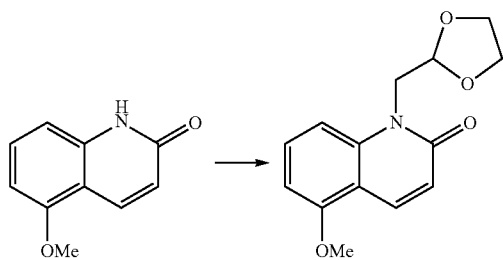 [SMILES: COc1cccc2[nH]c(=O)ccc12 ; COc1cccc2c1ccc(=O)n2CC1OCCO1]

In the same method as in Reference Example 4, 1-(1,3-dioxolan-2-ylmethyl)-5-methoxyquinolin-2(1H)-one was obtained from 5-methoxyquinolin-2(1H)-one and 2-bromomethyl-1,3-dioxolane.

$^1$H-NMR (CDCl$_3$) δ:
3.85-3.90 (2H, m), 3.94 (3H, s), 4.03-4.08 (2H, m), 4.53 (2H, d, J=4.6 Hz), 5.27 (1H, t, J=4.6 Hz), 6.65 (1H, d, J=9.8 Hz), 6.67 (1H, d, J=8.5 Hz), 7.16 (1H, d, J=8.5 Hz), 7.46 (1H, t, J=8.5 Hz), 8.16 (1H, d, J=9.8 Hz)

Reference Example 153

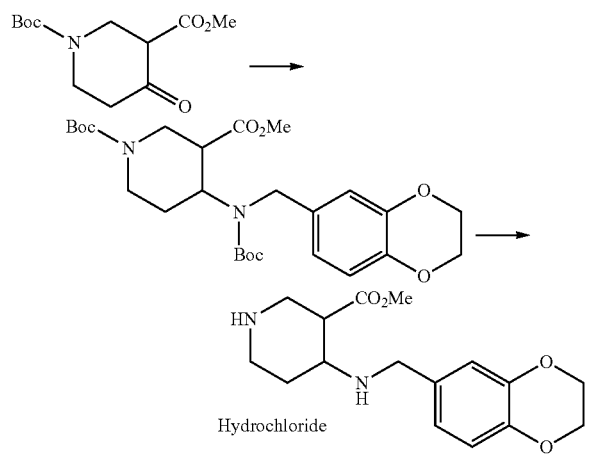

To 6.0 mL of a dichloromethane solution containing 0.77 g of 1-tert-butyl 3-methyl 4-oxopiperidine-1,3-dicarboxylate, 0.50 g of 6-aminomethyl-2,3-dihydro-1,4-benzodioxin and 60 μL of acetic acid were added. The mixture was stirred at room temperature for 1.0 hour, and the solvent was removed under reduced pressure. The residue thus obtained was added with 6.0 mL of methanol and 0.31 g of platinum oxide, and the mixture was stirred for 7 hours and 30 minutes under a hydrogen atmosphere. After the insoluble material filtered off, the solvent was removed under reduced pressure, and a colorless oily substance was obtained. To 12 mL of a methanol solution containing this colorless oily substance, 2.1 g of potassium carbonate and 0.66 g of di-tert-butyl dicarbonate were added. The mixture was stirred at room temperature for 1 hour, and the solvent was removed under reduced pressure. The residue thus obtained was purified by silica gel column chromatography [eluent; hexane:ethyl acetate 1:3] to obtain 1.1 g of a brown oily substance, 1-tert-butyl 3-methyl 4-((tert-butoxycarbonyl)(2,3-dihydro-1,4-benzodioxin-6-ylmethyl)amino)piperidine-1,3-dicarboxylate.

To 2.0 mL of a methanol solution containing 0.53 g of 1-tert-butyl 3-methyl 4-((tert-butoxycarbonyl)(2,3-dihydro-1,4-benzodioxin-6-ylmethyl)amino)piperidine-1,3-dicarboxylate, 2.0 mL of 3.2 mol/L hydrogen chloride/dioxane was added. The mixture was stirred at room temperature, and then the solvent was removed under reduced pressure to obtain 0.40 g of a white solid, methyl 4-((2,3-dihydro-1,4-benzodioxin-6-ylmethyl)amino) piperidine-3-carboxylate hydrochloride.

$^1$H-NMR (DMSO-d$_6$) δ:
1.86-2.40 (2H, m), 2.94-4.24 (11H, m), 4.26 (4H, s), 6.95 (1H, d, J=8.3 Hz), 6.99 (1H, dd, J=8.3, 1.9 Hz), 7.06 (1H, d, J=1.9 Hz), 8.18 (1H, s)

Reference Example 154

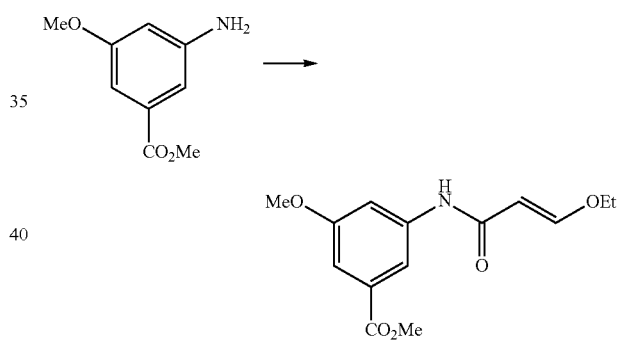

To 80 mL of a chloroform solution containing 1.51 g of methyl 3-amino-5-methoxybenzoate, 5 mL of pyridine and 1.39 g of 3-ethoxyacryloyl chloride were added, and the mixture was stirred at room temperature overnight. The solvent was removed under reduced pressure, and the resultant solution was acidified with 1 mol/L hydrochloric acid, and then, extracted with ethyl acetate. The organic layer was washed sequentially with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform:methanol=20:1] and further recrystallized in acetone-hexane to obtain 0.47 g of a pale yellow solid, methyl 3-((3-ethoxyacryloyl)amino)-5-methoxybenzoate.

$^1$H-NMR (CDCl$_3$) δ:
1.36 (3H, t, J=7.0 Hz), 3.84 (3H, s), 3.90 (3H, s), 3.95 (2H, q, J=7.0 Hz), 5.31 (1H, d, J=11.9 Hz), 7.29 (1H, dd, J=2.6, 1.3 Hz), 7.52-7.55 (1H, m), 7.61-7.70 (2H, m)

Reference Example 155

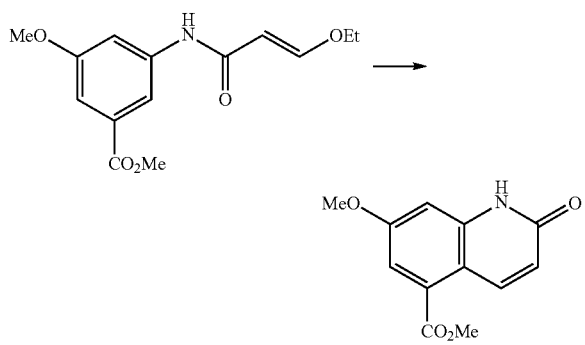

To 5 mL of concentrated sulfuric acid cooled with ice, 1.86 g of methyl 3-((3-ethoxyacryloyl)amino)-5-methoxybenzoate was added little by little, and the mixture was stirred for 1 hour under cooling with ice. The reaction mixture was fed into water cooled with ice, the insoluble material was collected by filtration, and the insoluble material thus obtained was purified by silica gel column chromatography [silica gel; Silica gel 60 manufactured by Kanto Chemical Co., Inc., eluent; chloroform:methanol=50:1] to obtain 346 mg of methyl 7-methoxy-2-oxo-1,2-dihydroquinoline-5-carboxylate.

$^1$H-NMR (DMSO-$d_6$) δ:
3.85 (3H, s), 3.90 (3H, s), 6.45 (1H, d, J=9.7 Hz), 7.05 (1H, d, J=2.6 Hz), 7.27 (1H, d, J=2.6 Hz), 8.48 (1H, d, J=9.7 Hz), 11.81 (1H, s)

Reference Example 156

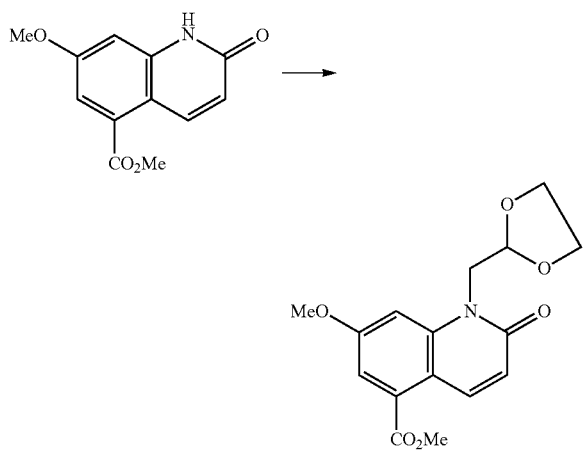

Into 50 mL of N,N-dimethylformamide, 1.67 g of methyl 7-methoxy-2-oxo-1,2-dihydroquinoline-5-carboxylate was dissolved, thereto was added 860 mg of 60% sodium hydride, and the mixture was stirred at room temperature for 1 hour. Thereto was added 3.7 mL of 2-bromomethyl-1,3-dioxolane, and the mixture was stirred at 90° C. for 1 hour. The reaction mixture was cooled to room temperature, and then ethyl acetate and 1 mol/L hydrochloric acid were added thereto. The organic layer was separated, the resultant solution was washed sequentially with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform:methanol=50:1] to obtain 370 mg of a white solid, methyl 1-(1,3-dioxolan-2-ylmethyl)-7-methoxy-2-oxo-1,2-dihydroquinoline-5-carboxylate.

$^1$H-NMR (CDCl$_3$) δ:
3.87-3.92 (2H, m), 3.93 (3H, s), 3.97 (3H, s), 4.00-4.06 (2H, m), 4.55 (2H, d, J=4.4 Hz), 5.22 (1H, t, J=4.4 Hz), 6.65 (1H, d, J=10.1 Hz), 7.32 (1H, d, J=2.6 Hz), 7.40 (1H, d, J=2.6 Hz), 8.64 (1H, d, J=10.1 Hz)

Reference Example 157

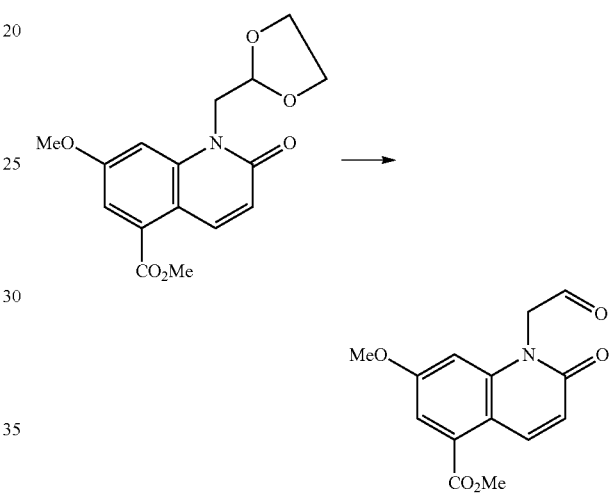

Into 5 mL of a 90% aqueous trifluoroacetic acid solution, 350 mg of methyl 1-(1,3-dioxolan-2-ylmethyl)-7-methoxy-2-oxo-1,2-dihydroquinoline-5-carboxylate was dissolved, and the mixture was stirred at room temperature overnight. The solvent was removed under reduced pressure, and the resultant solution was alkalified with an aqueous saturated sodium hydrogen carbonate solution, and then extracted with ethyl acetate. The organic layer was washed sequentially with water and an aqueous saturated sodium chloride solution and dried over anhydrous magnesium sulfate, and the solvent was removed under reduced pressure to obtain 476 mg of a pale yellow oily substance, methyl 7-methoxy-2-oxo-1-(2-oxoethyl)-1,2-dihydroquinoline-5-carboxylate.

$^1$H-NMR (CDCl$_3$) δ:
3.90 (3H, s), 3.99 (3H, s), 5.16 (2H, s), 6.64 (1H, d, J=2.2 Hz), 6.70 (1H, d, J=10.1 Hz), 7.43 (1H, d, J=2.2 Hz), 8.74 (1H, d, J=10.1 Hz), 9.68 (1H, s)

Reference Example 158

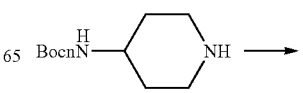

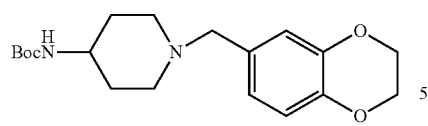

To 20 mL of a chloroform solution containing 2.17 g of 1,4-benzodioxane-6-carbaldehyde and 2.67 g of tert-butyl (piperidin-4-yl)carbamate, 0.76 mL of acetic acid was added, and the mixture was stirred at room temperature for 1 hour. The reaction mixture was added with 4.27 g of sodium triacetoxyborohydride, and stirred overnight. Thereto was added an aqueous saturated sodium hydrogen carbonate solution, and the organic layer was separated. The organic layer was washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane=5:1] to obtain 2.96 g of tert-butyl (1-(2,3-dihydro-1,4-benzodioxin-6-ylmethyl)-piperidin-4-yl)carbamate.

$^1$H-NMR (CDCl$_3$) δ:

1.38-1.42 (2H, m), 1.44 (9H, s), 1.71-1.75 (1H, m), 1.86-1.92 (2H, m), 2.02-2.08 (2H, m), 2.75-2.80 (2H, m), 3.37 (2H, s), 4.24 (4H, s), 6.74-6.77 (1H, m), 6.78-6.80 (1H, m), 6.82 (1H, d, J=1.8 Hz)

Reference Example 159

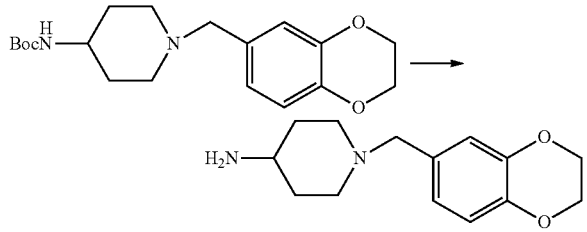

To 100 mL of an ethyl acetate solution containing 3.62 g of tert-butyl (1-(2,3-dihydro-1,4-benzodioxin-6-ylmethyl)piperidin-4-yl)carbamate, 30 mL of 4 mol/L hydrogen chloride/ethyl acetate was added, and the mixture was stirred at room temperature for 6 hours. The solvent was removed under reduced pressure, the residue thus obtained was added with ethyl acetate, and a solid substance was collected by filtration. The solid substance thus obtained was purified by silica gel column chromatography [silica gel; Chromatorex-NH, manufactured by Fuji Silysia Chemical Ltd., eluent; chloroform:methanol=5:1] to obtain 1.35 g of a pale yellow oily substance, 1-(2,3-dihydro-1,4-benzodioxin-6-ylmethyl)piperidin-4-ylamine.

$^1$H-NMR (CDCl$_3$) δ:

1.67-1.87 (3H, m), 1.90-2.11 (2H, m), 2.51-2.73 (2H, m), 2.72-2.92 (2H, m), 3.48 (2H, s), 4.24 (4H, s), 6.71-6.87 (3H, m)

Reference Example 160

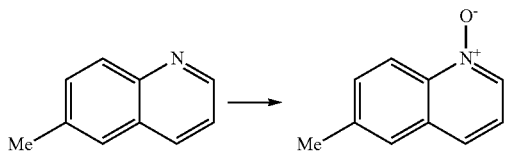 [SMILES: Cc1ccc2ncccc2c1 ; Cc1ccc2c(ccc[n+]2[O-])c1]

To 40 mL of a chloroform solution containing 2.0 g of 6-methylquinoline, 3.6 g of m-chloroperbenzoic acid was added, and the mixture was stirred at room temperature for 20 hours. Thereto was added an aqueous saturated sodium hydrogen carbonate solution, the organic layer was separated, and the aqueous layer was extracted with chloroform. The organic layer and the extract were combined, and the resultant solution was washed with an aqueous saturated sodium chloride solution and dried over anhydrous magnesium sulfate, and the solvent was removed under reduced pressure to obtain 2.0 g of a brown solid, 6-methylquinoline N-oxide.

$^1$H-NMR (CDCl$_3$) δ:

2.54 (3H, s), 7.22-7.30 (1H, m), 7.55-7.71 (3H, m), 8.46-8.51 (1H, m), 8.61-8.67 (1H, m)

Reference Example 161

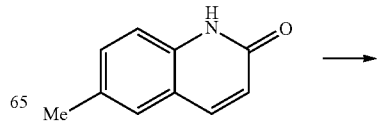

To 15 mL of a chloroform solution containing 0.50 g of 6-methylquinoline N-oxide, 0.72 g of p-toluenesulfonyl chloride and 15 mL of a 10% aqueous potassium carbonate solution were added, and the mixture was stirred at room temperature for 2 hours. The solid substance was collected by filtration, and washed with water and chloroform to obtained 210 mg of a yellow solid, 6-methylquinolin-2(1H)-one.

$^1$H-NMR (DMSO-d$_6$) δ:

2.33 (3H, s), 6.46 (1H, d, J=9.6 Hz), 7.20 (1H, d, J=8.3 Hz), 7.32 (1H, d, J=8.3 Hz), 7.44 (1H, s), 7.82 (1H, d, J=9.6 Hz), 11.64 (1H, s)

Reference Example 162

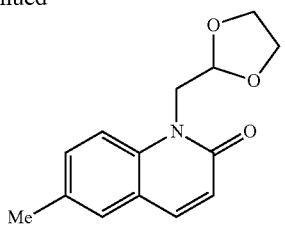

Into 5 mL of N,N-dimethylformamide, 297 mg of 6-methylquinolin-2(1H)-one was dissolved, thereto was added 282 mg of 60% sodium hydride, and the mixture was stirred at room temperature for 1 hour. Thereto was added 1.0 mL of 2-bromomethyl-1,3-dioxolane, and the mixture was stirred at 90° C. for 8 hours. The reaction mixture was cooled to room temperature, and then ethyl acetate and 1 mol/L hydrochloric acid were added thereto. The organic layer was separated, washed sequentially with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane=3:1] to obtain 253 mg of a white solid, 1-(1,3-dioxolan-2-ylmethyl)-6-methylquinolin-2(1H)-one.

$^{1}$H-NMR (CDCl$_3$) δ:
2.41 (3H, s), 3.85-3.91 (2H, m), 3.99-4.08 (2H, m), 4.53 (2H, d, J=4.8 Hz), 5.26 (1H, t, J=4.8 Hz), 6.69 (1H, d, J=9.7 Hz), 7.30-7.40 (2H, m), 7.42-7.53 (1H, m), 7.62 (1H, d, J=9.7 Hz)

Reference Example 163

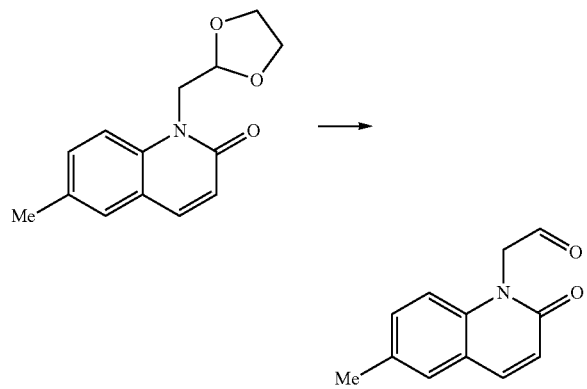

Into 3 mL of a 90% aqueous trifluoroacetic acid solution, 243 mg of 1-(1,3-dioxolan-2-ylmethyl)-6-methyl-2-oxo-1,2-dihydroquinoline was dissolved, and the mixture was stirred at room temperature overnight. The solvent was removed under reduced pressure, the resultant solution was alkalified with an aqueous saturated sodium hydrogen carbonate solution, and then extracted with ethyl acetate. The organic layer was washed sequentially with water and an aqueous saturated sodium chloride solution, and dried over anhydrous magnesium sulfate, and the solvent was removed under reduced pressure to obtain 236 mg of a pale yellow oily substance, (6-methyl-2-oxoquinolin-1(2H)-yl)acetaldehyde.

$^{1}$H-NMR (CDCl$_3$) δ:
2.42 (3H, s), 5.13 (2H, d, J=0.9 Hz), 6.74 (1H, d, J=9.7 Hz), 6.94 (1H, d, J=8.4 Hz), 7.30-7.44 (2H, m), 7.71 (1H, d, J=9.7 Hz), 9.68 (1H, t, J=0.9 Hz)

Reference Example 164

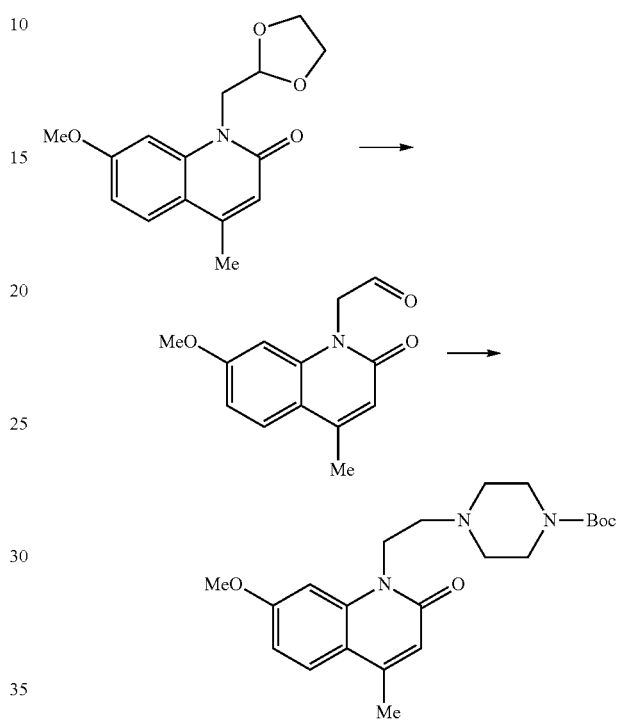

Into 2 mL of an 80% aqueous trifluoroacetic acid solution, 200 mg of 1-(1,3-dioxolan-2-ylmethyl)-7-methoxy-4-methyl-2-oxo-1,2-dihydroquinoline was dissolved, and the mixture was stirred at room temperature for 11 hours. The reaction mixture was added with an aqueous saturated sodium hydrogen carbonate solution to be alkalified, and then extracted with ethyl acetate. The organic layer was washed with an aqueous saturated sodium chloride solution and dried over anhydrous magnesium sulfate, and the solvent was removed under reduced pressure to obtain a yellow oily substance, (7-methoxy-4-methyl-2-oxoquinolin-1(2H)-yl)acetaldehyde.

Into 5 mL of chloroform, (7-methoxy-4-methyl-2-oxoquinolin-1(2H)-yl)acetaldehyde was dissolved, thereto were added 135 mg of tert-butyl piperazine-1-carboxylate and 43.6 mg of acetic acid, and the mixture was stirred at room temperature for 1 hour. The reaction mixture was added with 231 mg of sodium triacetoxyborohydride, and stirred for 1 hour. Thereto was added an aqueous saturated sodium hydrogen carbonate solution, and the organic layer was separated. The organic layer was washed with an aqueous saturated sodium chloride solution and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; ethyl acetate] to obtain 173 mg of a yellow oily substance, tert-butyl 4-(2-(7-methoxy-4-methyl-2-oxoquinolin-1(2H)-yl)ethyl)piperazine-1-carboxylate.

¹H-NMR (CDCl₃) δ:
1.47 (9H, s), 2.45 (3H, d, J=0.9 Hz), 2.87-3.00 (2H, m), 3.24-3.42 (6H, m), 3.76-3.89 (2H, m), 3.97 (3H, s), 4.69-4.82 (2H, m), 6.44 (1H, d, J=0.9 Hz), 6.86-6.94 (1H, m), 7.05 (1H, d, J=2.2 Hz), 7.64 (1H, d, J=8.8 Hz)

Reference Example 165

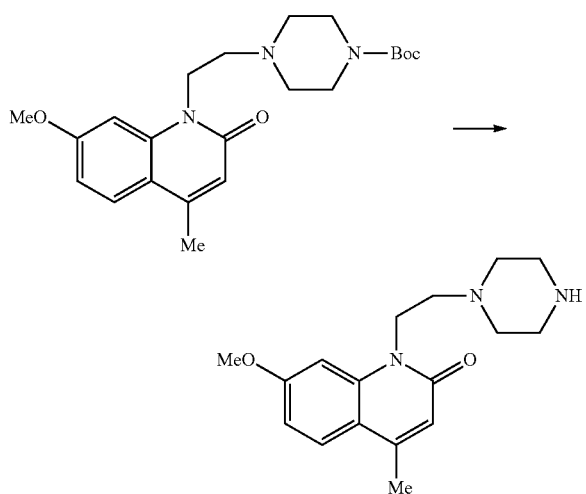

To 170 mg of tert-butyl 4-(2-(7-methoxy-4-methyl-2-oxoquinolin-1(2H)-yl)ethyl)piperazine-1-carboxylate, 10 mL of 4 mol/L hydrogen chloride/ethyl acetate was added, and the mixture was stirred at room temperature for 2.5 hours. The reaction mixture was added with an aqueous saturated sodium hydrogen carbonate solution and chloroform. The organic layer was separated, washed with an aqueous saturated sodium chloride solution and dried over anhydrous magnesium sulfate, and the solvent was removed under reduced pressure to obtain 78 mg of a light brown solid, 1-(2-(piperazin-1-yl)ethyl)-7-methoxy-4-methylquinolin-2(1H)-one.
¹H-NMR (CDCl₃) δ:
2.43 (3H, d, J=0.9 Hz), 2.74-2.77 (2H, m), 2.82-2.85 (4H, m), 3.12-3.15 (4H, m), 3.92 (3H, s), 4.38-4.42 (2H, m), 6.42 (1H, d, J=0.9 Hz), 6.81-6.83 (1H, m), 6.83-6.86 (1H, m), 7.63-7.65 (1H, m)

Reference Example 166

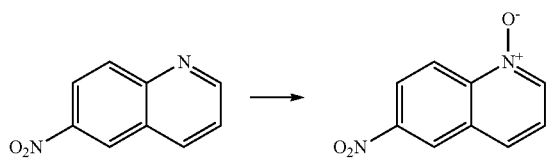 [SMILES: O=[N+]([O-])c1ccc2ncccc2c1 ; O=[N+]([O-])c1ccc2c(ccc[n+]2[O-])c1]

To 40 mL of a chloroform solution containing 2.0 g of 6-nitroquinoline, 3.0 g of m-chloroperbenzoic acid was added, and the mixture was stirred at room temperature overnight. Thereto was added an aqueous saturated sodium hydrogen carbonate solution, and the organic layer was separated, and the aqueous layer was extracted with chloroform. The organic layer and the extract were combined, and the resultant solution was washed with an aqueous saturated sodium chloride solution and dried over anhydrous magnesium sulfate, and the solvent was removed under reduced pressure to obtain 2.1 g of a yellow solid, 6-nitroquinoline N-oxide.
¹H-NMR (CDCl₃) δ:
7.49 (1H, dd, J=8.7, 6.0 Hz), 7.92 (1H, d, J=8.7 Hz), 8.51 (1H, dd, J=9.6, 2.3 Hz), 8.66 (1H, d, J=6.0 Hz), 8.84 (1H, d, J=2.3 Hz), 8.93 (1H, d, J=9.6 Hz)

Reference Example 167

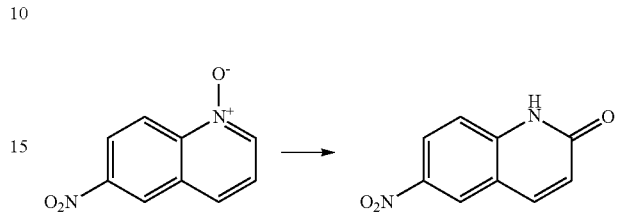

To 30 mL of a chloroform solution containing 2.1 g of 6-nitroquinoline N-oxide, 2.5 g of p-toluenesulfonyl chloride and 30 mL of a 10% aqueous potassium carbonate solution were added, and the mixture was stirred at room temperature overnight. The solid substance was collected by filtration to obtain 1.7 g of a yellow solid, 6-nitroquinolin-2(1H)-one.
¹H-NMR (DMSO-d₆) δ:
6.68 (1H, d, J=9.6 Hz), 7.44 (1H, d, J=9.2 Hz), 8.13 (1H, d, J=9.6 Hz), 8.33 (1H, dd, J=9.2, 2.1 Hz), 8.71 (1H, d, J=2.1 Hz), 12.30 (1H, s)

Reference Example 168

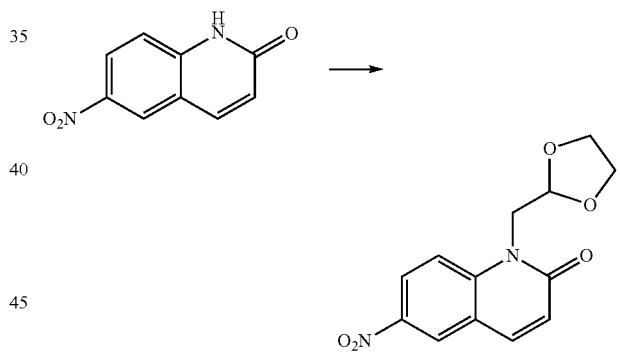

To 5 mL of an N,N-dimethylformamide solution containing 0.50 g of 6-nitroquinolin-2(1H)-one, 0.32 g of 60% sodium hydride was added under a nitrogen atmosphere, and the mixture was stirred at room temperature for 30 minutes. Thereto was added 2.2 g of 2-bromomethyl-1,3-dioxolane, and the mixture was stirred at 90° C. for 36 hours. The reaction mixture was cooled to room temperature, and then ethyl acetate and 1 mol/L hydrochloric acid were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate=4:1] to obtain 0.24 g of a pale yellow solid, 1-(1,3-dioxolan-2-ylmethyl)-6-nitroquinolin-2(1H)-one.

¹H-NMR (CDCl₃) δ:
3.87-3.90 (2H, m), 4.00-4.04 (2H, m), 4.58 (2H, d, J=4.1 Hz), 5.23 (1H, t, J=4.1 Hz), 6.84 (1H, d, J=9.2 Hz), 7.73 (1H, d, J=9.2 Hz), 7.78 (1H, d, J=9.6 Hz), 8.37 (1H, dd, J=9.6, 2.8 Hz), 8.46 (1H, d, J=2.8 Hz)

Reference Example 169

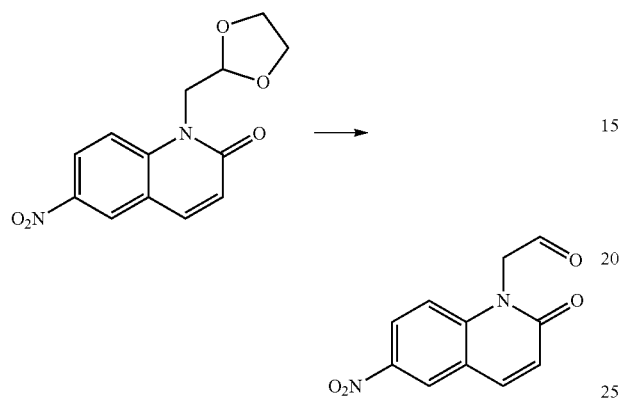

To 0.23 g of 1-(1,3-dioxolan-2-ylmethyl)-6-nitroquinolin-2(1H)-one, 2 mL of a 90% aqueous trifluoroacetic acid solution was added, and the mixture was stirred at room temperature overnight. The solvent was removed under reduced pressure, and ethyl acetate and an aqueous saturated sodium hydrogen carbonate solution were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure to obtain 0.21 g of a pale yellow solid, (6-nitro-2-oxoquinolin-1(2H)-yl)acetaldehyde.

¹H-NMR (CDCl₃) δ:
5.26 (2H, s), 6.90 (1H, d, J=9.6 Hz), 7.11 (1H, d, J=9.2 Hz), 7.87 (1H, d, J=9.6 Hz), 8.37 (1H, dd, J=9.2, 2.5 Hz), 8.53 (1H, d, J=2.5 Hz), 9.79 (1H, s)

Reference Example 170

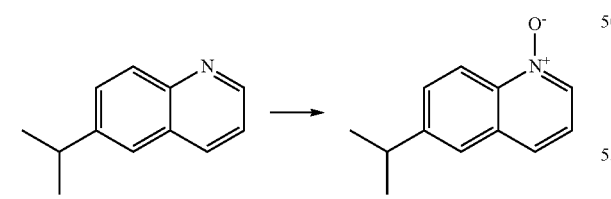

To 40 mL of a chloroform solution containing 2.0 g of 6-isopropylquinoline, 2.9 g of m-chloroperbenzoic acid was added, and the mixture was stirred at room temperature overnight. Thereto was added an aqueous saturated sodium hydrogen carbonate solution, the organic layer was separated, and the aqueous layer was extracted with chloroform. The organic layer and the extract were combined, and the resultant solution was washed with an aqueous saturated sodium chloride solution and dried over anhydrous magnesium sulfate, and the solvent was removed under reduced pressure to obtain 2.1 g of a brown oily substance, 6-isopropylquinoline N-oxide.

¹H-NMR (CDCl₃) δ:
1.35 (6H, d, J=6.9 Hz), 3.06-3.15 (1H, m), 7.25-7.29 (1H, m), 7.64-7.73 (3H, m), 8.49 (1H, d, J=6.9 Hz), 8.67 (1H, d, J=9.2 Hz)

Reference Example 171

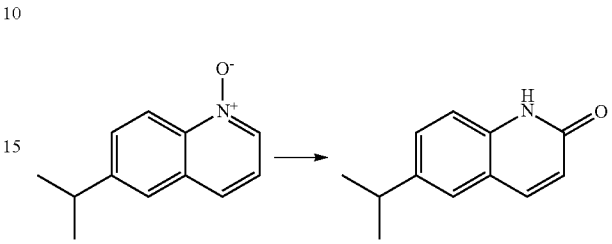

To 30 mL of a chloroform solution containing 2.0 g of 6-isopropylquinoline N-oxide, 2.4 g of p-toluenesulfonyl chloride and 30 mL of a 10% aqueous potassium carbonate solution were added, and the mixture was stirred at room temperature overnight. The organic layer was separated, and the aqueous layer was extracted with chloroform. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate=1:1] to obtain 1.3 g of a white solid, 6-isopropylquinolin-2(1H)-one.

¹H-NMR (DMSO-d₆) δ:
1.22 (6H, d, J=6.9 Hz), 2.88-2.97 (1H, m), 6.46 (1H, d, J=9.6 Hz), 7.24 (1H, d, J=8.7 Hz), 7.41 (1H, dd, J=8.7, 1.8 Hz), 7.50 (1H, d, J=1.8 Hz), 7.86 (1H, d, J=9.6 Hz), 11.64 (1H, s)

Reference Example 172

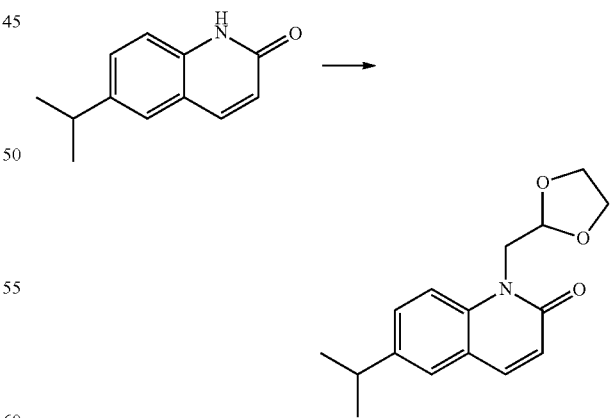

To 5 mL of an N,N-dimethylformamide solution containing 0.50 g of 6-isopropylquinolin-2(1H)-one, 0.32 g of 60% sodium hydride was added under a nitrogen atmosphere, and the mixture was stirred at room temperature for 30 minutes. Thereto was added 2.2 g of 2-bromomethyl-1,3-dioxolane, and the reaction mixture was stirred at 90° C. for 6 hours. The reaction mixture was cooled to room temperature, and then ethyl acetate and 1 mol/L hydrochloric acid were added thereto. The organic layer was separated, and the aqueous layer was extracted with ethyl acetate. The organic layer and the extract were combined, and the resultant solution was washed with an aqueous saturated sodium chloride solution and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate=3:1] to obtain 0.43 g of a white solid, 1-(1,3-dioxolan-2-ylmethyl)-6-isopropylquinolin-2(1H)-one.

$^1$H-NMR (CDCl$_3$) δ:

1.29 (6H, d, J=7.3 Hz), 2.95-3.01 (1H, m), 3.86-3.90 (2H, m), 4.04-4.08 (2H, m), 4.53 (2H, d, J=4.6 Hz), 5.27 (1H, t, J=4.6 Hz), 6.69 (1H, d, J=9.6 Hz), 7.36 (1H, d, J=1.8 Hz), 7.42-7.45 (1H, m), 7.52 (1H, d, J=8.7 Hz), 7.65 (1H, d, J=9.6 Hz)

Reference Example 173

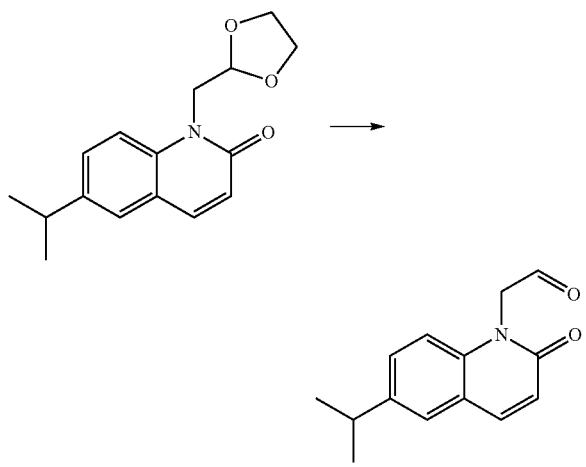

To 0.42 g of 1-(1,3-dioxolan-2-ylmethyl)-6-isopropylquinolin-2(1H)-one, 4 mL of a 90% aqueous trifluoroacetic acid solution was added, and the mixture was stirred at room temperature overnight. The solvent was removed under reduced pressure, and ethyl acetate and an aqueous saturated sodium hydrogen carbonate solution were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure to obtain 0.41 g of a pale yellow oily substance, (6-isopropyl-2-oxoquinolin-1(2H)-yl)acetaldehyde.

$^1$H-NMR (CDCl$_3$) δ:

1.29 (6H, d, J=7.3 Hz), 2.96-3.03 (1H, m), 5.16 (2H, s), 6.79 (1H, d, J=9.6 Hz), 7.01 (1H, d, J=8.7 Hz), 7.42-7.46 (2H, m), 7.78 (1H, d, J=9.6 Hz), 9.69 (1H, s)

Reference Example 174

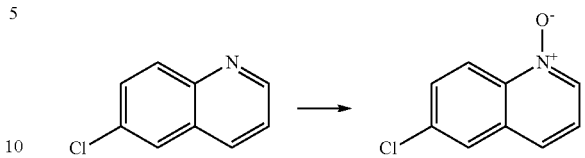

To 40 mL of a chloroform solution containing 2.0 g of 6-chloroquinoline, 3.0 g of m-chloroperbenzoic acid was added, and the mixture was stirred at room temperature overnight. Thereto was added an aqueous saturated sodium hydrogen carbonate solution, the organic layer was separated, and the aqueous layer was extracted with chloroform. The organic layer and the extract were combined, the resultant solution was washed with an aqueous saturated sodium chloride solution and dried over anhydrous magnesium sulfate, and the solvent was removed under reduced pressure to obtain 2.0 g of a light brown solid, 6-chloroquinoline N-oxide.

$^1$H-NMR (CDCl$_3$) δ:

7.33 (1H, dd, J=8.7, 6.0 Hz), 7.65 (1H, d, J=8.7 Hz), 7.70 (1H, dd, J=9.2, 2.3 Hz), 7.87 (1H, d, J=2.3 Hz), 8.51 (1H, d, J=6.0 Hz), 8.71 (1H, d, J=9.2 Hz)

Reference Example 175

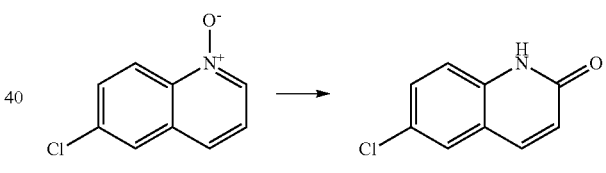

To 30 mL of a chloroform solution containing 2.0 g of 6-chloroquinoline N-oxide, 2.5 g of p-toluenesulfonyl chloride and 30 mL of a 10% aqueous potassium carbonate solution were added, and the mixture was stirred at room temperature overnight. A solid substance was collected by filtration to obtain 1.6 g of a white solid, 6-chloroquinolin-2 (1H)-one.

$^1$H-NMR (DMSO-d$_6$) δ:

6.56 (1H, d, J=9.6 Hz), 7.31 (1H, d, J=8.7 Hz), 7.53 (1H, dd, J=8.7, 2.3 Hz), 7.79 (1H, d, J=2.3 Hz), 7.88 (1H, d, J=9.6 Hz), 11.86 (1H, s)

Reference Example 176

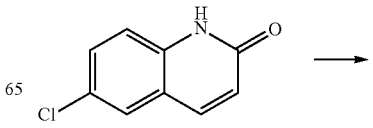

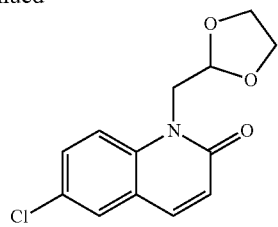

To 5 mL of an N,N-dimethylformamide solution containing 0.50 g of 6-chloroquinolin-2(1H)-one, 0.33 g of 60% sodium hydride was added under a nitrogen atmosphere, and the mixture was stirred at room temperature for 30 minutes. Thereto was added 2.3 g of 2-bromomethyl-1,3-dioxolane, and the mixture was stirred at 90° C. for 6 hours. The reaction mixture was cooled to room temperature, and then ethyl acetate and 1 mol/L hydrochloric acid were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate=4:1] to obtain 0.45 g of a white solid, 1-(1,3-dioxolan-2-ylmethyl)-6-chloroquinolin-2(1H)-one.

$^1$H-NMR (CDCl$_3$) δ:
3.86-3.89 (2H, m), 4.01-4.04 (2H, m), 4.52 (2H, d, J=4.6 Hz), 5.23 (1H, t, J=4.6 Hz), 6.74 (1H, d, J=9.6 Hz), 7.47-7.50 (1H, m), 7.52 (1H, d, J=2.3 Hz), 7.54-7.56 (1H, m), 7.60 (1H, d, J=9.6 Hz)

Reference Example 177

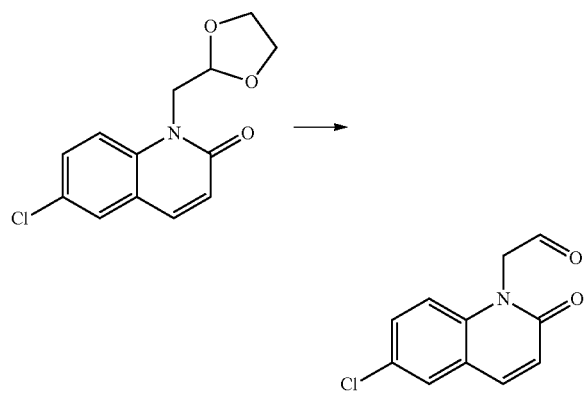

To 0.44 g of 1-(1,3-dioxolan-2-ylmethyl)-6-chloroquinolin-2(1H)-one, 4 mL of a 90% aqueous trifluoroacetic acid solution was added, and the mixture was stirred at room temperature overnight. The solvent was removed under reduced pressure, and ethyl acetate and an aqueous saturated sodium hydrogen carbonate solution were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure to obtain 0.44 g of a pale yellow foam, (6-chloro-2-oxoquinolin-1(2H)-yl)acetaldehyde.

$^1$H-NMR (CDCl$_3$) δ:
5.15 (2H, s), 6.80 (1H, d, J=9.2 Hz), 6.98 (1H, d, J=9.2 Hz), 7.48 (1H, dd, J=9.2, 2.3 Hz), 7.60 (1H, d, J=2.3 Hz), 7.69 (1H, d, J=9.2 Hz), 9.72 (1H, s)

Reference Example 178

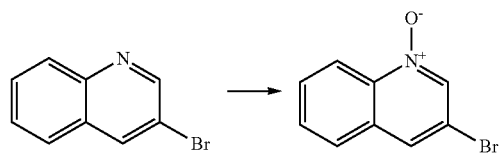 [SMILES: Brc1cnc2ccccc2c1 ; [O-][n+]1cc(Br)cc2ccccc21]

To 40 mL of a chloroform solution containing 2.0 g of 3-bromoquinoline, 2.4 g of m-chloroperbenzoic acid was added, and the mixture was stirred at room temperature overnight. Thereto was added an aqueous saturated sodium hydrogen carbonate solution, the organic layer was separated, and the aqueous layer was extracted with chloroform. The organic layer and the extract were combined, the resultant solution was washed with an aqueous saturated sodium chloride solution and dried over anhydrous magnesium sulfate, and the solvent was removed under reduced pressure to obtain 2.1 g of a light brown solid, 3-bromoquinoline N-oxide.

$^1$H-NMR (CDCl$_3$) δ:
7.68 (1H, t, J=7.6 Hz), 7.76-7.82 (2H, m), 7.94 (1H, s), 8.66-8.71 (2H, m)

Reference Example 179

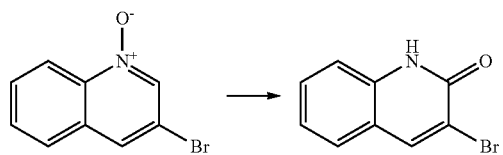 [SMILES: [O-][n+]1cc(Br)cc2ccccc21 ; O=c1[nH]c2ccccc2cc1Br]

To 30 mL of a chloroform solution containing 2.1 g of 3-bromoquinoline N-oxide, 2.1 g of p-toluenesulfonyl chloride and 30 mL of a 10% aqueous potassium carbonate solution were added, and the mixture was stirred at room temperature overnight. A solid substance was collected by filtration to obtain 0.87 g of a white solid, 3-bromoquinolin-2(1H)-one.

$^1$H-NMR (DMSO-d$_6$) δ:
7.22 (1H, t, J=7.6 Hz), 7.33 (1H, d, J=7.6 Hz), 7.55 (1H, t, J=7.6 Hz), 7.68 (1H, d, J=7.6 Hz), 8.51 (1H, s), 12.26 (1H, s)

Reference Example 180

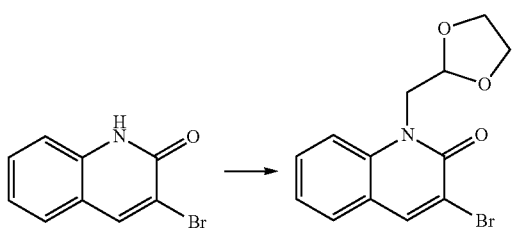 [SMILES: O=c1[nH]c2ccccc2cc1Br ; O=c1c(Br)cc2ccccc2n1CC1OCCO1]

To 5 mL of an N,N-dimethylformamide solution containing 0.50 g of 3-bromoquinolin-2(1H)-one, 0.27 g of 60% sodium hydride was added under a nitrogen atmosphere, and the mixture was stirred at room temperature for 30 minutes. Thereto was added 1.9 g of 2-bromomethyl-1,3-dioxolane, and the mixture was stirred at 90° C. for 12 hours. The reaction mixture was cooled to room temperature, and then ethyl acetate and 1 mol/L hydrochloric acid were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate=4:1] to obtain 0.39 g of a white solid, 1-(1,3-dioxolan-2-ylmethyl)-3-bromoquinolin-2(1H)-one.

$^1$H-NMR (CDCl$_3$) δ:
3.87-3.91 (2H, m), 4.04-4.08 (2H, m), 4.59 (2H, d, J=4.6 Hz), 5.31 (1H, t, J=4.6 Hz), 7.23-7.28 (1H, m), 7.51 (1H, d, J=7.3 Hz), 7.58 (2H, m), 8.14 (1H, s)

Reference Example 181

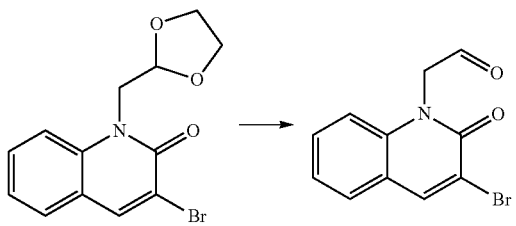 [SMILES: O=c1c(Br)cc2ccccc2n1CC1OCCO1 ; O=CCn1c(=O)c(Br)cc2ccccc21]

To 0.38 g of 1-(1,3-dioxolan-2-ylmethyl)-3-bromoquinolin-2(1H)-one, 4 mL of a 90% aqueous trifluoroacetic acid solution was added, and the mixture was stirred at room temperature overnight. The solvent was removed under reduced pressure, and ethyl acetate and an aqueous saturated sodium hydrogen carbonate solution were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure to obtain 0.36 g of a pale yellow solid, (3-bromo-2-oxoquinolin-1(2H)-yl)acetaldehyde.

$^1$H-NMR (CDCl$_3$) δ:
5.23 (2H, s), 7.04 (1H, d, J=8.7 Hz), 7.28-7.31 (1H, m), 7.58 (2H, m), 8.22 (1H, s), 9.73 (1H, s)

Reference Example 182

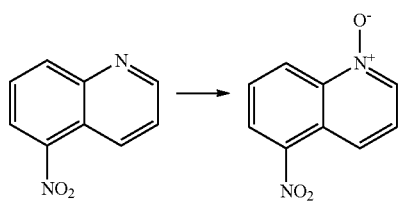 [SMILES: O=[N+]([O-])c1cccc2ncccc12 ; O=[N+]([O-])c1cccc2c1ccc[n+]2[O-]]

To 40 mL of a chloroform solution containing 2.0 g of 5-nitroquinoline, 2.9 g of m-chloroperbenzoic acid was added, and the mixture was stirred at room temperature overnight. Thereto was added an aqueous saturated sodium hydrogen carbonate solution, the organic layer was separated, and the aqueous layer was extracted with chloroform. The organic layer and the extract were combined, the resultant solution was washed with an aqueous saturated sodium chloride solution and dried over anhydrous magnesium sulfate, and the solvent was removed under reduced pressure to obtain 2.0 g of a yellow solid, 5-nitroquinoline N-oxide.

$^1$H-NMR (CDCl$_3$) δ:
7.50-7.56 (1H, m), 7.86 (1H, t, J=8.3 Hz), 8.43-8.53 (2H, m), 8.61 (1H, d, J=6.0 Hz), 9.15 (1H, d, J=8.3 Hz)

Reference Example 183

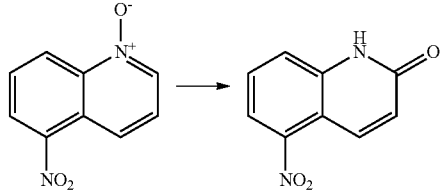 [SMILES: O=[N+]([O-])c1cccc2c1ccc[n+]2[O-] ; O=c1ccc2c([N+](=O)[O-])cccc2[nH]1]

To 30 mL of a chloroform solution containing 1.9 g of 5-nitroquinoline N-oxide, 2.3 g of p-toluenesulfonyl chloride and 30 mL of a 10% aqueous potassium carbonate solution were added, and the mixture was stirred at room temperature overnight. A solid substance was collected by filtration to obtain 1.5 g of a yellow solid, 5-nitroquinolin-2(1H)-one.

$^1$H-NMR (DMSO-d$_6$) δ:
6.75 (1H, d, J=10.0 Hz), 7.64-7.67 (1H, d, J=8.0 Hz), 7.71 (1H, t, J=8.0 Hz), 7.88 (1H, d, J=8.0 Hz), 8.25 (1H, d, J=10.0 Hz), 12.26 (1H, s)

Reference Example 184

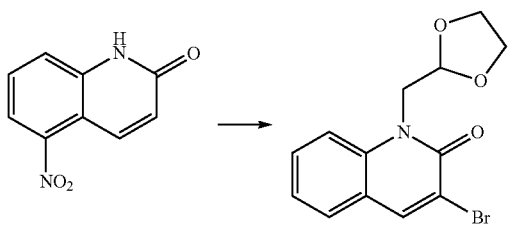 [SMILES: O=c1ccc2c([N+](=O)[O-])cccc2[nH]1 ; O=c1c(Br)cc2ccccc2n1CC1OCCO1]

To 5 mL of an N,N-dimethylformamide solution containing 0.50 g of 5-nitroquinolin-2(1H)-one, 0.32 g of 60% sodium hydride was added under a nitrogen atmosphere, and the mixture was stirred at room temperature for 30 minutes. Thereto was added 2.2 g of 2-bromomethyl-1,3-dioxolane, and the mixture was stirred at 90° C. for 36 hours. The reaction mixture was cooled to room temperature, and then ethyl acetate and 1 mol/L hydrochloric acid were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate=4:1] to obtain 0.17 g of a yellow solid, 1-(1,3-dioxolan-2-ylmethyl)-5-nitroquinolin-2(1H)-one.

$^1$H-NMR (CDCl$_3$) δ:
3.86-3.90 (2H, m), 4.00-4.04 (2H, m), 4.60 (2H, d, J=4.4 Hz), 5.23 (1H, t, J=4.4 Hz), 6.90 (1H, d, J=10.0 Hz), 7.60-7.66 (1H, m), 7.80 (1H, d, J=7.8 Hz), 7.93 (1H, d, J=8.7 Hz), 8.28 (1H, d, J=10.0 Hz)

Reference Example 185

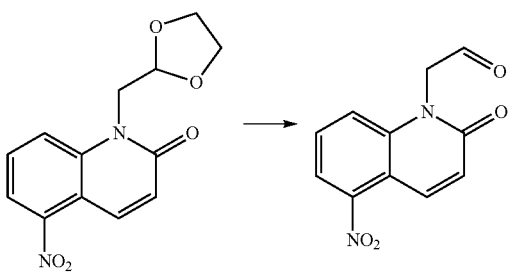 [SMILES: O=c1ccc2c([N+](=O)[O-])cccc2n1CC1OCCO1 ; O=CCn1c(=O)ccc2c([N+](=O)[O-])cccc21]

To 0.15 g of 1-(1,3-dioxolan-2-ylmethyl)-5-nitroquinolin-2(1H)-one, 2 mL of a 90% aqueous trifluoroacetic acid solution was added, and the mixture was stirred at room temperature overnight. The solvent was removed under reduced pressure, and ethyl acetate and an aqueous saturated sodium hydrogen carbonate solution were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure to obtain 0.14 g of a yellow solid, (5-nitro-2-oxoquinolin-1(2H)-yl)acetaldehyde.

$^1$H-NMR (CDCl$_3$) δ:
5.26 (2H, s), 6.95 (1H, d, J=10.1 Hz), 7.26-7.29 (1H, m), 7.64 (1H, t, J=8.3 Hz), 7.85 (1H, d, J=8.3 Hz), 8.37 (1H, d, J=10.1 Hz), 9.77 (1H, s)

Reference Example 186

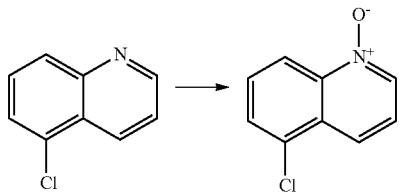 [SMILES: Clc1cccc2ncccc12 ; [O-][n+]1cccc2c(Cl)cccc21]

To 20 mL of a chloroform solution containing 1.0 g of 5-chloroquinoline, 1.9 g of m-chloroperbenzoic acid was added, and the mixture was stirred at room temperature overnight. Thereto was added an aqueous saturated sodium hydrogen carbonate solution, the organic layer was separated, and the aqueous layer was extracted with chloroform. The organic layer and the extract were combined, and the resultant solution was washed with an aqueous saturated sodium chloride solution and dried over anhydrous magnesium sulfate, and the solvent was removed under reduced pressure to obtain 1.0 g of a yellow solid, 5-chloroquinoline N-oxide.

$^1$H-NMR (CDCl$_3$) δ:
7.42 (1H, dd, J=8.7, 6.0 Hz), 7.67-7.76 (2H, m), 8.17 (1H, d, J=8.7 Hz), 8.64 (1H, d, J=6.0 Hz), 8.72 (1H, d, J=8.7 Hz)

Reference Example 187

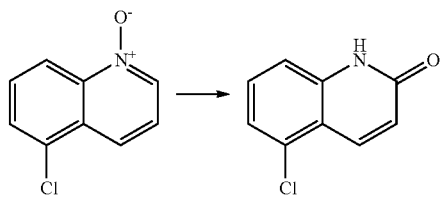 [SMILES: [O-][n+]1cccc2c(Cl)cccc21 ; O=c1ccc2c(Cl)cccc2[nH]1]

To 30 mL of a chloroform solution containing 1.0 g of 5-chloroquinoline N-oxide, 1.3 g of p-toluenesulfonyl chloride and 30 mL of a 10% aqueous potassium carbonate solution were added, and the mixture was stirred at room temperature for 6 hours. A solid substance was collected by filtration to obtain 0.68 g of a light brown solid, 5-chloroquinolin-2(1H)-one.

$^1$H-NMR (DMSO-d$_6$) δ:
6.64 (1H, d, J=10.1 Hz), 7.24-7.34 (2H, m), 7.50 (1H, t, J=8.0 Hz), 8.08 (1H, d, J=10.1 Hz), 12.01 (1H, s)

Reference Example 188

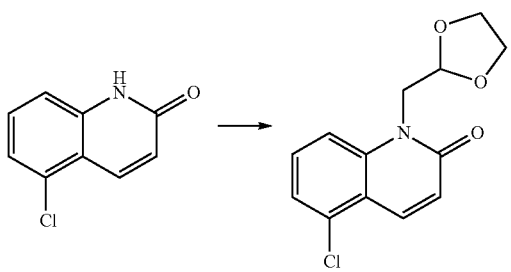 [SMILES: O=c1ccc2c(Cl)cccc2[nH]1 ; O=c1ccc2c(Cl)cccc2n1CC1OCCO1]

To 5 mL of an N,N-dimethylformamide solution containing 0.50 g of 5-chloroquinolin-2(1H)-one, 0.34 g of 60% sodium hydride was added under a nitrogen atmosphere, and the mixture was stirred at room temperature for 30 minutes. Thereto was added 2.3 g of 2-bromomethyl-1,3-dioxolane, and the mixture was stirred at 90° C. for 24 hours. The reaction mixture was cooled to room temperature, and then ethyl acetate and 1 mol/L hydrochloric acid were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate=3:1] to obtain 0.38 g of a white solid, 1-(1,3-dioxolan-2-ylmethyl)-5-chloroquinolin-2(1H)-one.

$^1$H-NMR (CDCl$_3$) δ:
3.86-3.90 (2H, m), 4.02-4.05 (2H, m), 4.55 (2H, d, J=4.6 Hz), 5.24 (1H, t, J=4.6 Hz), 6.80 (1H, d, J=9.6 Hz), 7.29 (1H, d, J=7.8 Hz), 7.46 (1H, t, J=7.8 Hz), 7.53 (1H, d, J=7.8 Hz), 8.18 (1H, d, J=9.6 Hz)

Reference Example 189

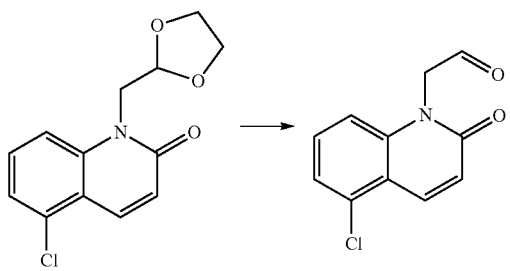 [SMILES: O=c1ccc2c(Cl)cccc2n1CC1OCCO1 ; O=CCn1c(=O)ccc2c(Cl)cccc21]

To 0.36 g of 1-(1,3-dioxolan-2-ylmethyl)-5-chloroquinolin-2(1H)-one, 4 mL of a 90% aqueous trifluoroacetic acid solution was added, and the mixture was stirred at room temperature overnight. The solvent was removed under reduced pressure, and ethyl acetate and an aqueous saturated sodium hydrogen carbonate solution were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure to obtain 0.36 g of a white solid, (5-chloro-2-oxoquinolin-1(2H)-yl)acetaldehyde.

$^1$H-NMR (CDCl$_3$) δ:
5.18 (2H, s), 6.85 (1H, d, J=10.1 Hz), 6.95 (1H, d, J=8.3 Hz), 7.33 (1H, d, J=8.3 Hz), 7.40-7.46 (1H, m), 8.25 (1H, d, J=10.1 Hz), 9.71 (1H, s)

Reference Example 190

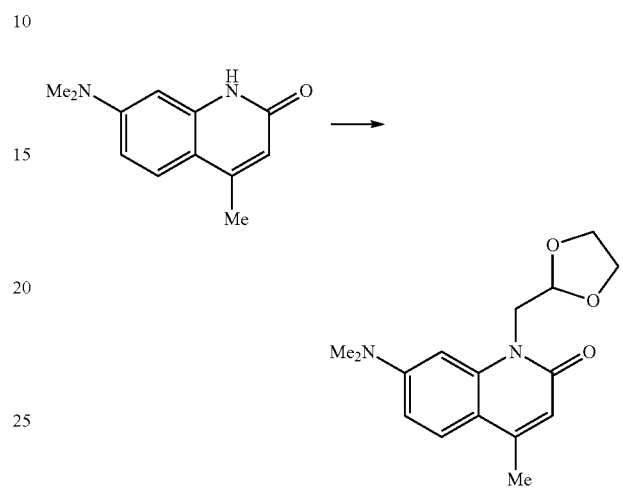

To 5 mL of an N,N-dimethylformamide solution containing 0.45 g of 7-dimethylamino-4-methylquinolin-2(1H)-one, 0.27 g of 60% sodium hydride was added under a nitrogen atmosphere, and the mixture was stirred at room temperature for 30 minutes. Thereto was added 1.9 g of 2-bromomethyl-1,3-dioxolane, and the mixture was stirred at 90° C. for 48 hours. The reaction mixture was cooled to room temperature, and then ethyl acetate and 1 mol/L hydrochloric acid were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate 2:1] to obtain 0.33 g of a pale yellow solid, 1-(1,3-dioxolan-2-ylmethyl)-7-dimethylamino-4-methylquinolin-2(1H)-one.

$^1$H-NMR (CDCl$_3$) δ:
2.38 (3H, s), 3.08 (6H, s), 3.86-3.91 (2H, m), 4.04-4.10 (2H, m), 4.53 (2H, d, J=4.1 Hz), 5.25 (1H, t, J=4.1 Hz), 6.33 (1H, s), 6.67 (1H, d, J=8.7 Hz), 6.76 (1H, s), 7.52 (1H, d, J=8.7 Hz)

Reference Example 191

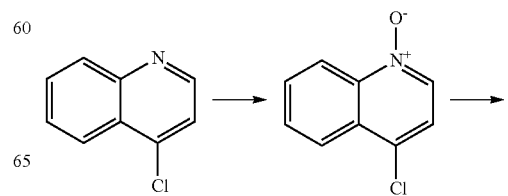

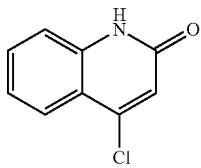

To 20 mL of a chloroform solution containing 816 mg of 4-chloroquinoline, 1.33 g of m-chloroperbenzoic acid was added, and the mixture was left to stand at room temperature for 2 hours. The reaction mixture was added with an aqueous saturated sodium hydrogen carbonate solution to be alkalified. The organic layer was separated, the resultant solution was washed sequentially with water and an aqueous saturated sodium chloride solution, and dried over anhydrous magnesium sulfate, and the solvent was removed under reduced pressure to obtain 920 mg of a pale yellow solid, 4-chloroquinoline N-oxide.

To 30 mL of a chloroform solution containing 910 mg of 4-chloroquinoline N-oxide, 1.21 g of p-toluenesulfonyl chloride and 10 mL of an aqueous solution containing 2.47 g of potassium carbonate were added, and the mixture was stirred at room temperature for 5 hours. The reaction mixture was added with water, the organic layer was separated, the resultant solution was washed sequentially with water and an aqueous saturated sodium chloride solution, and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform:methanol=4:1] to obtain 560 mg of a pale yellow solid, 4-chloroquinolin-2(1H)-one.

$^1$H-NMR (CDCl$_3$) δ:
6.88 (1H, s), 7.27-7.37 (1H, m), 7.38-7.45 (1H, m), 7.54-7.65 (1H, m), 7.97 (1H, dd, J=8.4, 1.3 Hz)

Reference Example 192

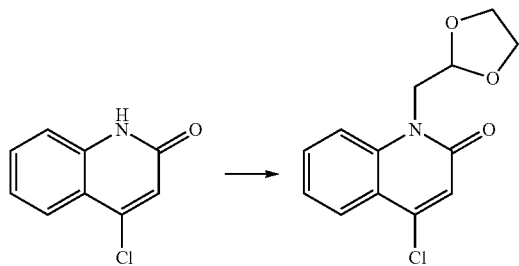 [SMILES: O=c1cc(Cl)c2ccccc2[nH]1 ; O=c1cc(Cl)c2ccccc2n1CC1OCCO1]

To 20 mL of an N,N-dimethylformamide solution containing 540 mg of 4-chloroquinolin-2(1H)-one, 376 mg of 60% sodium hydride was added, and the mixture was stirred at room temperature for 1 hour. Thereto was added 3.2 mL of 2-bromomethyl-1,3-dioxolane, and the mixture was stirred at 90° C. for 16 hours. The reaction mixture was cooled to room temperature, and then ethyl acetate and 1 mol/L hydrochloric acid were added thereto. The organic layer was separated, the resultant solution was washed sequentially with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane=1:1] to obtain 165 mg of a white solid, 1-(1,3-dioxolan-2-ylmethyl)-4-chloroquinolin-2(1H)-one.

$^1$H-NMR (CDCl$_3$) δ:
3.84-3.92 (2H, m), 3.99-4.05 (2H, m), 4.54 (2H, d, J=4.4 Hz), 5.25 (1H, t, J=4.4 Hz), 6.91 (1H, s), 7.24-7.37 (1H, m), 7.60-7.68 (2H, m), 8.02 (1H, d, J=7.9 Hz)

Reference Example 193

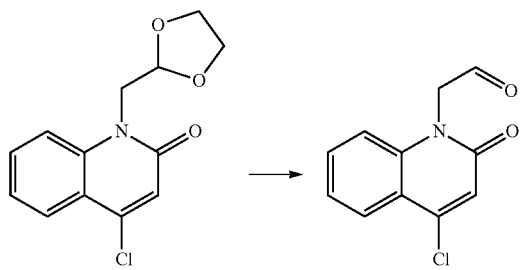 [SMILES: O=c1cc(Cl)c2ccccc2n1CC1OCCO1 ; O=CCn1c(=O)cc(Cl)c2ccccc21]

Into 3 mL of a 90% aqueous trifluoroacetic acid solution, 156 mg of 1-(1,3-dioxolan-2-ylmethyl)-4-chloroquinolin-2 (1H)-one was dissolved, and the mixture was stirred at room temperature overnight. The solvent was removed under reduced pressure, and the reaction mixture was alkalified with an aqueous saturated sodium hydrogen carbonate solution, and then extracted with ethyl acetate. The organic layer was washed sequentially with water and an aqueous saturated sodium chloride solution, and dried over anhydrous magnesium sulfate, and the solvent was removed under reduced pressure to obtain 192 mg of a pale yellow oily substance, (4-chloro-2-oxoquinolin-1(2H)-yl)acetaldehyde.

$^1$H-NMR (CDCl$_3$) δ:
5.17 (2H, s), 6.95 (1H, s), 7.30-7.42 (1H, m), 7.56-7.67 (2H, m), 8.00-8.13 (1H, m), 9.71 (1H, s)

Reference Example 194

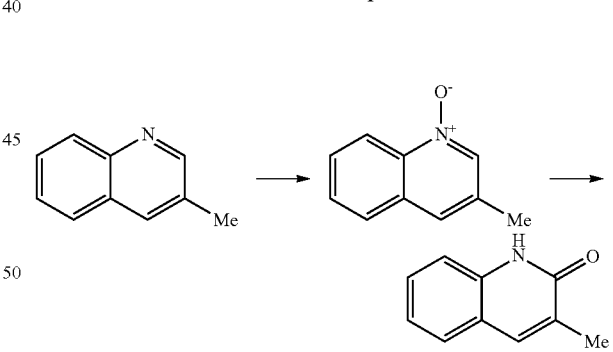

To 20 mL of a chloroform solution containing 1.02 g of 3-methylquinoline, 1.92 g of m-chloroperbenzoic acid was added, and the mixture was left to stand at room temperature for 2.5 hours. The reaction mixture was added with an aqueous saturated sodium hydrogen carbonate solution to be alkalified. The organic layer was separated, the resultant solution was washed sequentially with water and an aqueous saturated sodium chloride solution and dried over anhydrous magnesium sulfate, and the solvent was removed under reduced pressure to obtain 1.62 g of a pale yellow solid, 3-methylquinoline N-oxide.

To 30 mL of a chloroform solution containing 1.59 g of 3-methylquinoline N-oxide, 2.35 g of p-toluenesulfonyl chloride and 15 mL of an aqueous solution containing 4.84 g of potassium carbonate were added, and the mixture was stirred at room temperature for 5 hours. The reaction mixture was added with water, the organic layer was separated, washed sequentially with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform:methanol=3:1] to obtain 770 mg of a pale yellow solid, 3-methylquinolin-2(1H)-one.

$^1$H-NMR (CDCl$_3$) δ:
2.30 (3H, s), 7.10-7.36 (2H, m), 7.44-7.46 (2H, m), 7.65 (1H, s)

Reference Example 195

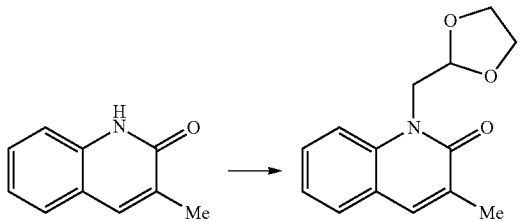 [SMILES: Cc1cc2ccccc2[nH]c1=O ; Cc1cc2ccccc2n(CC2OCCO2)c1=O]

To 20 mL of an N,N-dimethylformamide solution containing 760 mg of 3-methylquinolin-2(1H)-one, 613 mg of 60% sodium hydride was added, and the mixture was stirred at room temperature for 1 hour. Thereto was added 5.0 mL of 2-bromomethyl-1,3-dioxolane, and the mixture was stirred at 90° C. for 13 hours. The reaction mixture was cooled to room temperature, and then ethyl acetate and 1 mol/L hydrochloric acid were added thereto. The organic layer was separated, washed sequentially with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane=1:1] to obtain 375 mg of a white solid, 1-(1,3-dioxolan-2-ylmethyl)-3-methylquinolin-2(1H)-one.

$^1$H-NMR (CDCl$_3$) δ:
2.26 (3H, s), 3.83-3.93 (2H, m), 4.01-4.12 (2H, m), 4.57 (2H, d, J=4.4 Hz), 5.28 (1H, t, J=4.4 Hz), 7.14-7.25 (2H, m), 7.42-7.54 (2H, m), 7.57 (1H, s)

Reference Example 196

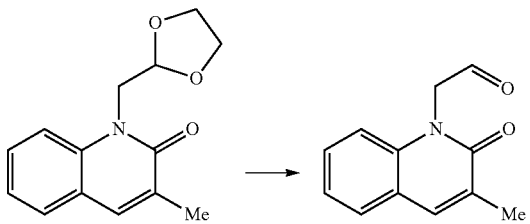 [SMILES: Cc1cc2ccccc2n(CC2OCCO2)c1=O ; Cc1cc2ccccc2n(CC=O)c1=O]

Into 3 mL of a 90% aqueous trifluoroacetic acid solution, 361 mg of 1-(1,3-dioxolan-2-ylmethyl)-3-methylquinolin-2 (1H)-one was dissolved, and the mixture was stirred at room temperature overnight. The solvent was removed under reduced pressure, and the reaction mixture was alkalified with an aqueous saturated sodium hydrogen carbonate solution, and then extracted with ethyl acetate. The organic layer was washed sequentially with water and an aqueous saturated sodium chloride solution and dried over anhydrous magnesium sulfate, and the solvent was removed under reduced pressure to obtain 354 mg of a pale yellow oily substance, (3-methyl-2-oxoquinolin-1(2H)-yl)acetaldehyde.

$^1$H-NMR (CDCl$_3$) δ:
2.05 (3H, s), 5.14-5.19 (2H, m), 7.02 (1H, d, J=8.4 Hz), 7.18-7.29 (1H, m), 7.40-7.59 (2H, m), 7.64 (1H, s), 9.70 (1H, s)

Reference Example 197

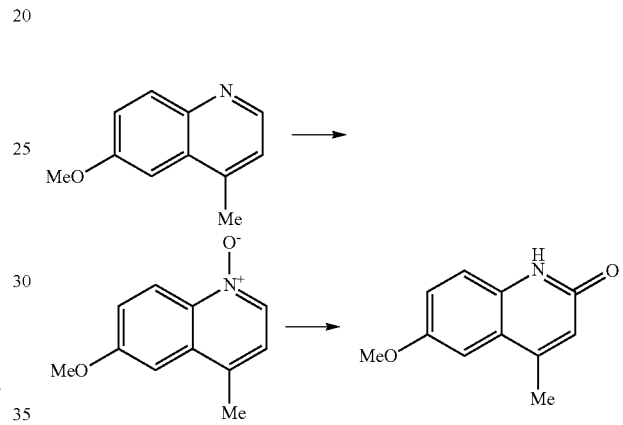

To 20 mL of a chloroform solution containing 1.01 g of 4-methyl-6-methoxyquinoline, 1.62 g of m-chloroperbenzoic acid was added, and the mixture was left to stand at room temperature for 2 hours. The reaction mixture was added with an aqueous saturated sodium hydrogen carbonate solution to be alkalified. The organic layer was separated, washed sequentially with water and an aqueous saturated sodium chloride solution and dried over anhydrous magnesium sulfate, and the solvent was removed under reduced pressure to obtain 1.12 g of a light brown solid, 4-methyl-6-methoxyquinoline N-oxide.

To 20 mL of a chloroform solution containing 1.11 g of 4-methyl-6-methoxyquinoline N-oxide, 1.36 g of p-toluenesulfonyl chloride and 5 mL of an aqueous solution containing 2.89 g of potassium carbonate were added, and the mixture was stirred at room temperature overnight. The reaction mixture was added with water, the organic layer was separated, washed sequentially with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform:methanol=20:1] to obtain 250 mg of a pale yellow solid, 4-methyl-6-methoxyquinolin-2(1H)-one.

$^1$H-NMR (DMSO-d$_6$) δ:
2.41 (3H, s), 3.81 (3H, s), 6.39 (1H, s), 7.13 (1H, d, J=2.8 Hz), 7.15-7.18 (1H, m), 7.25 (1H, d, J=8.7 Hz), 11.47 (1H, s)

Reference Example 198

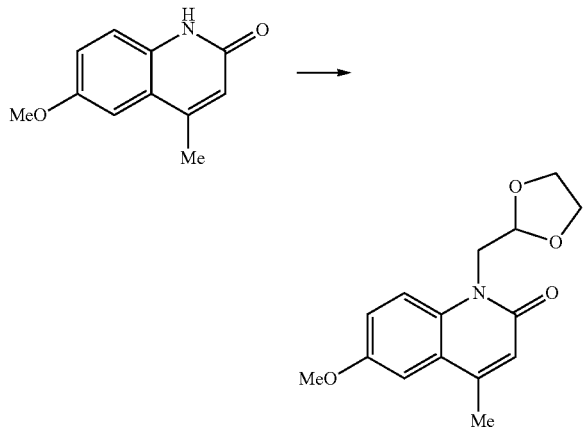

Into 15 mL of N,N-dimethylformamide, 240 mg of 4-methyl-6-methoxyquinolin-2(1H)-one was suspended, 160 mg of 60% sodium hydride was added to the suspension, and the mixture was stirred at room temperature for 1 hour. Thereto was added 0.66 mL of 2-bromomethyl-1,3-dioxolane, and the mixture was stirred at 90° C. for 6 hours. The reaction mixture was cooled to room temperature, and then ethyl acetate and 1 mol/L hydrochloric acid were added thereto. The organic layer was separated, washed sequentially with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane 3:2] to obtain 114 mg of a white solid, 1-(1,3-dioxolan-2-ylmeythyl)-4-methyl-6-methoxyquinolin-2(1H)-one.

$^1$H-NMR (CDCl$_3$) δ:
2.44 (3H, d, J=0.9 Hz), 3.85-3.89 (2H, m), 3.88 (3H, s), 4.03-4.06 (2H, m), 4.52 (2H, d, J=4.6 Hz), 5.24 (1H, t, J=4.6 Hz), 6.62 (1H, d, J=0.9 Hz), 7.11 (1H, d, J=2.8 Hz), 7.16-7.17 (1H, m), 7.54 (1H, d, J=9.2 Hz)

Reference Example 199

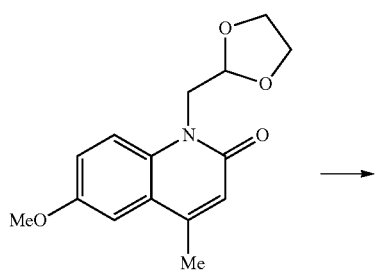

-continued

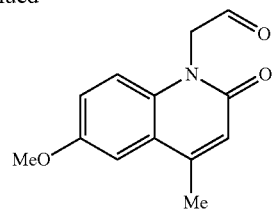

Into 3 mL of a 90% aqueous trifluoroacetic acid solution, 102 mg of 1-(1,3-dioxolan-2-ylmeythyl)-4-methyl-6-methoxyquinolin-2(1H)-one was dissolved, and the mixture was stirred at room temperature overnight. The solvent was removed under reduced pressure, and the resultant solution was alkalified with an aqueous saturated sodium hydrogen carbonate solution, and then extracted with ethyl acetate. The organic layer was washed sequentially with water and an aqueous saturated sodium chloride solution, and dried over anhydrous magnesium sulfate, and the solvent was removed under reduced pressure to obtain 72 mg of a pale yellow solid, (4-methyl-6-methoxy-2-oxoquinolin-1(2H)-yl)acetaldehyde.

$^1$H-NMR (CDCl$_3$) δ:
2.49 (3H, d, J=0.9 Hz), 3.88 (3H, s), 5.13-5.14 (2H, m), 6.67 (1H, d, J=0.9 Hz), 6.98 (1H, d, J=8.7 Hz), 7.13-7.16 (1H, m), 7.1 (1H, d, J=2.8 Hz), 9.67-9.68 (1H, m)

Reference Example 200

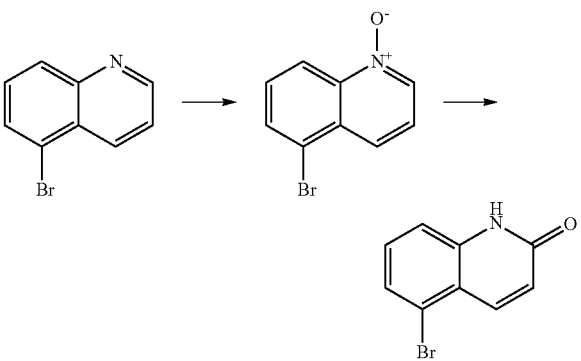

To 20 mL of a chloroform solution containing 2.15 g of 5-bromoquinoline, 2.74 g of m-chloroperbenzoic acid was added, and the mixture was left to stand at room temperature for 3.5 hours. The reaction mixture was added with an aqueous saturated sodium hydrogen carbonate solution to be alkalified. The organic layer was separated, and the resultant solution was washed sequentially with water and an aqueous saturated sodium chloride solution, and dried over anhydrous magnesium sulfate, and the solvent was removed under reduced pressure to obtain 2.57 g of a light brown solid, 5-bromoquinoline N-oxide.

To 20 mL of a chloroform solution containing 2.56 g of 5-bromoquinoline N-oxide, 2.68 g of p-toluenesulfonyl chloride and 10 mL of an aqueous solution containing 5.54 g of potassium carbonate were added, and the mixture was stirred at room temperature for 1 hour. The insoluble material was collected by filtration, and the residue thus obtained was purified by silica gel column chromatography [silica gel; Silica gel 60 manufactured by Kanto Chemical Co., Inc., eluent; chloroform:methanol=10:1] to obtain 930 mg of a pale yellow solid, 5-bromoquinolin-2(1H)-one.

¹H-NMR (DMSO-d₆) δ:
6.63 (1H, d, J=9.6 Hz), 7.33 (1H, d, J=8.3 Hz), 7.42 (1H, t, J=8.3 Hz), 7.47-7.49 (1H, m), 8.03 (1H, d, J=9.6 Hz), 11.99 (1H, s)

Reference Example 201

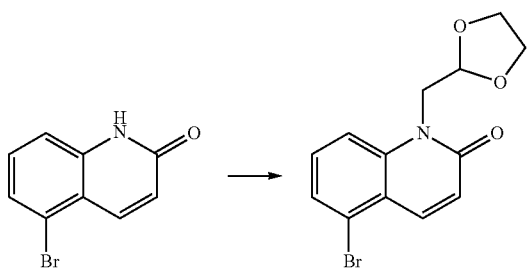 [SMILES: O=c1ccc2c(Br)cccc2[nH]1 ; O=c1ccc2c(Br)cccc2n1CC1OCCO1]

To 15 mL of an N,N-dimethylformamide solution containing 920 mg of 5-bromoquinolin-2(1H)-one, 530 mg of 60% sodium hydride was added, and the mixture was stirred at room temperature for 1 hour. Thereto was added 2.13 mL of 2-bromomethyl-1,3-dioxolane, and the mixture was stirred at 90° C. for 11 hours. The reaction mixture was cooled to room temperature, and then ethyl acetate and 1 mol/L hydrochloric acid were added thereto. The organic layer was separated, the resultant solution was washed sequentially with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane 1:4] to obtain 484 mg of a pale yellow solid, 1-(1,3-dioxolan-2-ylmethyl)-5-bromoquinolin-2(1H)-one.

¹H-NMR (CDCl₃) δ:
3.86-3.90 (2H, m), 4.01-4.05 (2H, m), 4.55 (2H, d, J=4.1 Hz), 5.22-5.26 (1H, m), 6.79 (1H, d, J=9.6 Hz), 7.37 (1H, dd, J=8.7, 7.8 Hz), 7.48 (1H, dd, J=7.8, 0.9 Hz), 7.55-7.60 (1H, m), 8.13-8.18 (1H, m)

Reference Example 202

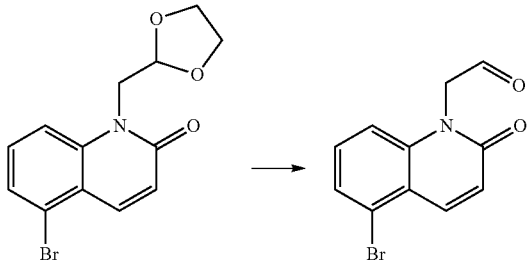 [SMILES: O=c1ccc2c(Br)cccc2n1CC1OCCO1 ; O=CCn1c(=O)ccc2c(Br)cccc21]

Into 3 mL of a 90% aqueous trifluoroacetic acid solution, 460 mg of 1-(1,3-dioxolan-2-ylmethyl)-5-bromoquinolin-2(1H)-one was dissolved, and the mixture was stirred at room temperature overnight. The solvent was removed under reduced pressure, and the resultant solution was alkalified with an aqueous saturated sodium hydrogen carbonate solution, and then extracted with ethyl acetate. The organic layer was washed sequentially with water and an aqueous saturated sodium chloride solution, and dried over anhydrous magnesium sulfate, and the solvent was removed under reduced pressure to obtain 550 mg of a pale yellow solid, (5-bromo-2-oxoquinolin-1(2H)-yl)acetaldehyde.

¹H-NMR (CDCl₃) δ:
5.18 (2H, s), 6.85 (1H, d, J=9.7 Hz), 6.99 (1H, d, J=8.4 Hz), 7.38 (1H, d, J=8.4 Hz), 7.49-7.56 (1H, m), 8.24 (1H, d, J=9.7 Hz), 9.71 (1H, s)

Reference Example 203

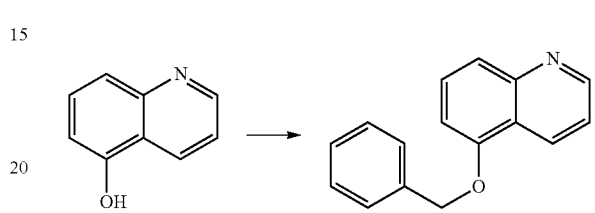

To 25 mL of an N,N-dimethylformamide solution containing 1.71 g of 5-quinolinol, 2.49 g of potassium carbonate and 1.7 mL of benzyl bromide were added, and the mixture was stirred at room temperature for 1.5 hours. The reaction mixture was added with water, and extracted with a mixed solution of ethyl acetate:toluene of=5:1. The organic layer was washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane 1:3] to obtain 1.70 g of a light brown solid, 5-(benzyloxy)quinoline.

¹H-NMR (CDCl₃) δ:
5.26 (2H, s), 6.95 (1H, d, J=7.5 Hz), 7.34-7.57 (6H, m), 7.63 (1H, d, J=7.5 Hz), 7.68-7.76 (1H, m), 8.66 (1H, dd, J=7.9, 1.8 Hz), 8.92 (1H, dd, J=4.4, 1.8 Hz)

Reference Example 204

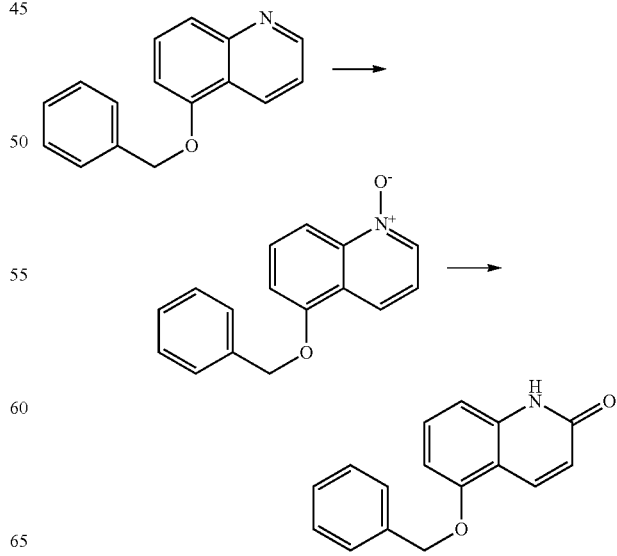

To 20 mL of a chloroform solution containing 1.67 g of 5-(benzyloxy)quinoline, 1.89 g of m-chloroperbenzoic acid was added, and the mixture was left to stand at room temperature overnight. The reaction mixture was added with an aqueous saturated sodium hydrogen carbonate solution to be alkalified. The organic layer was separated, and the resultant solution was washed sequentially with water and an aqueous saturated sodium chloride solution, and dried over anhydrous magnesium sulfate, and the solvent was removed under reduced pressure to obtain 1.91 g of a pale yellow solid, 5-(benzyloxy)quinoline N-oxide.

To 25 mL of a chloroform solution containing 1.89 g of 5-(benzyloxy)quinoline N-oxide, 1.85 g of p-toluenesulfonyl chloride and 10 mL of an aqueous solution containing 3.65 g of potassium carbonate were added, and the mixture was stirred at room temperature for 2 hours. The insoluble material was collected by filtration, and the residue thus obtained was purified by silica gel column chromatography [silica gel; Silica gel 60 manufactured by Kanto Chemical Co., Inc., eluent; chloroform:methanol=10:1] to obtain 1.19 g of a pale yellow solid, 5-(benzyloxy)quinolin-2(1H)-one.

$^1$H-NMR (CDCl$_3$) δ:
5.26 (2H, s), 7.02-7.09 (1H, m), 7.23-7.32 (1H, m), 7.39-7.54 (4H, m), 7.67 (1H, dd, J=8.8, 7.9 Hz), 8.20-8.27 (1H, m), 8.33 (1H, d, J=9.2 Hz), 8.60 (1H, dd, J=6.2, 0.9 Hz)

Reference Example 205

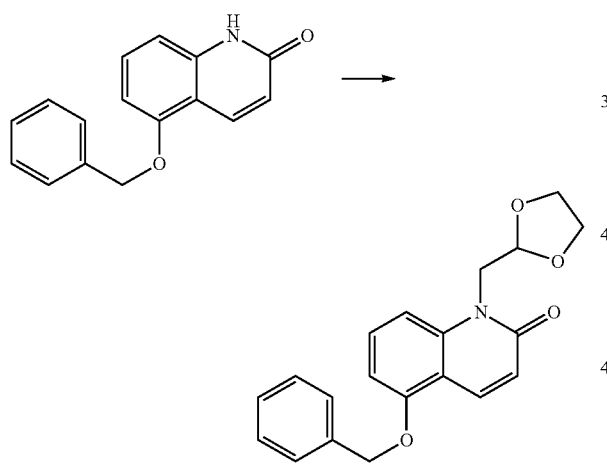

To 15 mL of an N,N-dimethylformamide solution containing 1.15 g of 5-(benzyloxy)quinolin-2(1H)-one, 599 mg of 60% sodium hydride was added, and the mixture was stirred at room temperature for 1 hour. Thereto was added 2.4 mL of 2-bromomethyl-1,3-dioxolane, and the mixture was stirred at 90° C. for 9 hours. The reaction mixture was cooled to room temperature, and then ethyl acetate and 1 mol/L hydrochloric acid were added thereto. The organic layer was separated, the resultant solution was washed sequentially with water and an aqueous saturated sodium chloride solution, and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane=1:1] to obtain 800 mg of a pale yellow solid, 1-(1,3-dioxolan-2-ylmethyl)-5-(benzyloxy)quinolin-2(1H)-one.

$^1$H-NMR (CDCl$_3$) δ:
3.99-4.09 (2H, m), 4.17-4.25 (2H, m), 4.53 (2H, d, J=4.4 Hz), 5.19 (2H, s), 5.27 (1H, t, J=4.4 Hz), 6.65 (1H, d, J=9.7 Hz), 6.74 (1H, d, J=7.9 Hz), 7.17 (1H, d, J=7.9 Hz), 7.36-7.53 (5H, m), 7.98-8.04 (1H, m), 8.23 (1H, d, J=9.7 Hz)

Reference Example 206

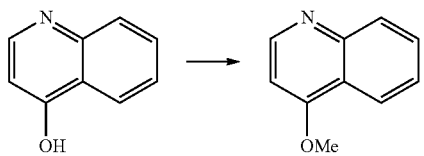 [SMILES: Oc1ccnc2ccccc12 ; COc1ccnc2ccccc12]

To 15 mL of methanol containing 4.02 g of 4-hydroxyquinoline and 130 mL of an acetonitrile solution, 5.01 g of diisopropylethylamine and 19.4 mL of a 2.0 mol/L trimethylsilyldiazomethane/hexane solution were added at room temperature, and the mixture was stirred for 13 hours, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate 2:1] to obtain 1.79 g of a yellow oily substance, 4-methoxyquinoline.

$^1$H-NMR (CDCl$_3$) δ:
4.05 (3H, s), 6.74 (1H, d, J=5.3 Hz), 7.45-7.56 (1H, m), 7.64-7.76 (1H, m), 8.04 (1H, dd, J=8.1, 1.1), 8.20 (1H, dd, J=8.1, 1.1), 8.75 (1H, d, J=5.3 Hz)

Reference Example 207

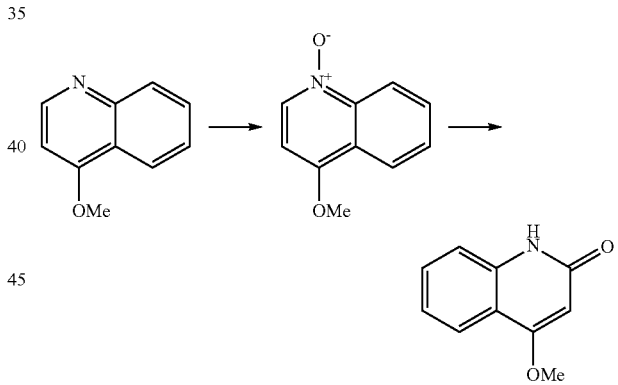

To 25 mL of a chloroform solution containing 1.72 g of 4-methoxyquinoline, 3.16 g of m-chloroperbenzoic acid was added, and the mixture was stirred at room temperature for 12 hours. The reaction mixture was added with 20 mL of an aqueous saturated sodium hydrogen carbonate solution. The organic layer was separated, and the aqueous layer was extracted with chloroform. The organic layer and the extract were combined, the resultant solution was washed with an aqueous saturated sodium chloride solution, and dried over anhydrous magnesium sulfate, and the solvent was removed under reduced pressure to obtain a light brown oily substance, 4-methoxyquinoline N-oxide.

To 60 mL of a chloroform solution containing 4-methoxyquinoline N-oxide, 2.58 g of p-toluenesulfonyl chloride, 5.23 g of potassium carbonate and 20 mL of water were added, and the mixture was stirred at room temperature for 3 hours. The reaction mixture was added with water, the organic layer was separated, and the aqueous layer was extracted with chloroform. The organic layer and the extract were combined, the resultant solution was washed with an aqueous saturated sodium chloride solution, and dried over anhydrous magnesium sulfate, and the solvent was removed under reduced pressure. The residue thus obtained was added with ethyl acetate, and a solid substance was collected by filtration to obtain 0.98 g of a white solid, 4-methoxyquinolin-2(1H)-one.

$^1$H-NMR (CDCl$_3$) δ:
3.99 (3H, s), 6.00 (1H, s), 7.21 (1H, ddd, J=8.4, 7.0, 1.3), 7.27-7.33 (1H, m), 7.52 (1H, ddd, J=8.4, 7.0, 1.3), 7.91 (1H, dd, J=8.4, 1.3 Hz)

Reference Example 208

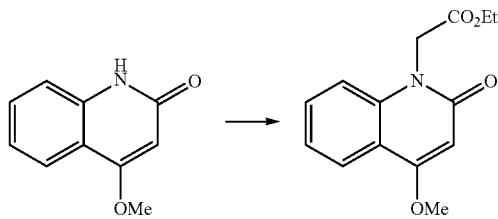 [SMILES: COc1cc(=O)[nH]c2ccccc12 ; CCOC(=O)Cn1c(=O)cc(OC)c2ccccc21]

To 30 mL of N,N-dimethylformamide containing 0.51 g of 4-methoxyquinolin-2(1H)-one and 5 mL of a tetrahydrofuran solution, 0.17 g of 60% sodium hydride was added at room temperature, and the mixture was stirred for 30 minutes, and then 0.64 g of ethyl bromoacetate was added thereto, and the mixture was stirred for 30 minutes. The reaction mixture was added with water and ethyl acetate. The organic layer was separated, and the aqueous layer was extracted with ethyl acetate. The organic layer and the extract were combined, the resultant solution was washed with an aqueous saturated sodium chloride solution, and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; hexane:ethyl acetate=1:1] to obtain 0.60 g of a white solid, ethyl (4-methoxy-2-oxoquinolin-1(2H)-yl)acetate.

$^1$H-NMR (CDCl$_3$) δ:
1.26 (3H, t, J=7.2 Hz), 3.97 (3H, s), 4.23 (2H, q, J=7.2 Hz), 5.07 (2H, s), 6.06 (1H, s), 7.08 (1H, d, J=8.4 Hz), 7.15-7.31 (1H, m), 7.54 (1H, ddd, J=8.4, 7.9, 1.3 Hz), 8.00 (1H, dd, J=7.9, 1.3 Hz)

Reference Example 209

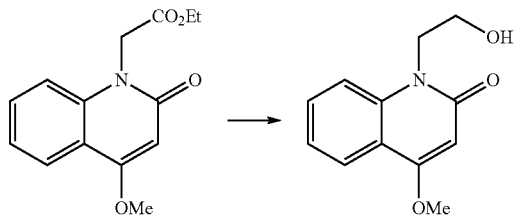 [SMILES: CCOC(=O)Cn1c(=O)cc(OC)c2ccccc21 ; COc1cc(=O)n(CCO)c2ccccc12]

To 10 mL of a tetrahydrofuran suspension containing 0.17 g of lithium aluminum hydride, 20 mL of a tetrahydrofuran solution containing 0.57 g of ethyl (4-methoxy-2-oxoquinolin-1(2H)-yl)acetate was added at 0° C. The reaction mixture was stirred for 1 hour, water and ethyl acetate were added thereto, and the insoluble material filtered off. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform:methanol=10:1] to obtain 0.24 g of a yellow solid, 1-(2-hydroxyethyl)-4-methoxyquinolin-2(1H)-one.

$^1$H-NMR (CDCl$_3$) δ:
3.97 (3H, s), 4.02 (2H, t, J=5.3 Hz), 4.51 (2H, t, J=5.3 Hz), 6.06 (1H, s), 7.18-7.30 (1H, m), 7.34-7.42 (1H, m), 7.52-7.65 (1H, m), 8.01 (1H, dd, J=8.1, 1.5 Hz)

Reference Example 210

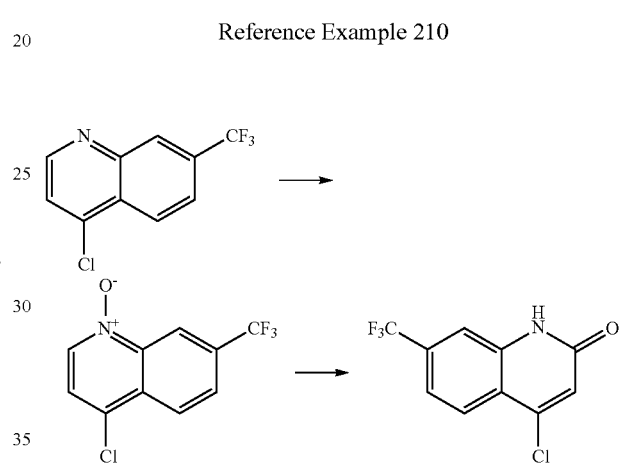

To 14 mL of a chloroform solution containing 0.90 g of 4-chloro-7-trifluoromethylquinoline, 1.04 g of m-chloroperbenzoic acid was added, and the mixture was stirred at room temperature for 3.5 hours. The reaction mixture was added with 15 mL of an aqueous saturated sodium hydrogen carbonate solution. The organic layer was separated, and the aqueous layer was extracted with chloroform. The organic layer and the extract were combined, the resultant solution was washed with an aqueous saturated sodium chloride solution, and dried over anhydrous magnesium sulfate, and the solvent was removed under reduced pressure to obtain a yellow solid, 4-chloro-7-trifluoromethylquinoline N-oxide.

To 27 mL of a chloroform solution containing 4-chloro-7-trifluoromethylquinoline N-oxide, 0.93 g of p-toluenesulfonyl chloride, 1.88 g of potassium carbonate and 9 mL of water were added, and the mixture was stirred at room temperature for 13 hours. The reaction mixture was added with water, the organic layer was separated, and the aqueous layer was extracted with chloroform. The organic layer and the extract were combined, the resultant solution was washed with an aqueous saturated sodium chloride solution, and dried over anhydrous magnesium sulfate, and the solvent was removed under reduced pressure. The residue thus obtained was added with ethyl acetate, and a solid substance was collected by filtration to obtain 0.46 g of a white solid, 4-chloro-7-trifluoromethylquinolin-2(1H)-one.

$^1$H-NMR (DMSO-d$_6$) δ:
7.02 (1H, d, J=1.8 Hz), 7.62 (1H, dd, J=8.3, 1.8 Hz), 7.69 (1H, s), 8.08 (1H, d, J=8.3 Hz), 12.28 (1H, s)

Reference Example 211

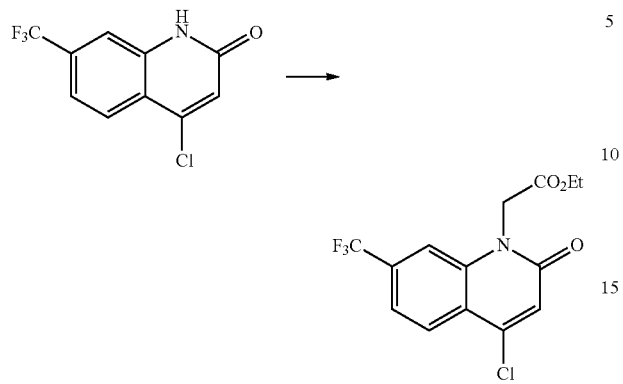

To 15 mL of an N,N-dimethylformamide solution containing 0.30 g of 4-chloro-7-trifluoromethylquinolin-2(1H)-one, 56 mg of 60% sodium hydride was added at room temperature, the mixture was stirred for 1 hour. Then, 0.15 mL of ethyl bromoacetate was added thereto, and the mixture was stirred for 1 hour. The reaction mixture was fed into a mixed solution of 5 mL of 1 mol/L hydrochloric acid and 60 mL of water, and thereto was added 100 mL of ethyl acetate. The organic layer was separated, washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; hexane:ethyl acetate=5:1] to obtain 0.21 g of a white solid, ethyl (4-chloro-2-oxo-7-trifluoromethylquinolin-1(2H)-yl)acetate.

$^1$H-NMR (CDCl$_3$) δ:
1.29 (3H, t, J=7.3 Hz), 4.27 (2H, q, J=7.3 Hz), 5.09 (2H, s), 7.03 (1H, s), 7.34 (1H, s), 7.56 (1H, d, J=8.3 Hz), 8.18 (1H, d, J=8.3 Hz)

Reference Example 212

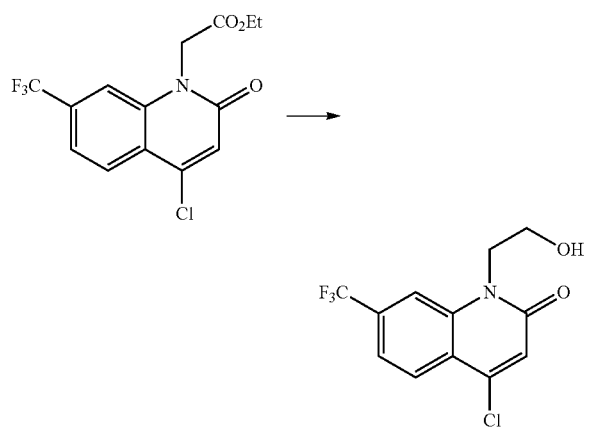

To 5 mL of a tetrahydrofuran suspension containing 17 mg of lithium aluminum hydride, 5 mL of a tetrahydrofuran solution containing 0.20 g of ethyl (4-chloro-2-oxo-7-trifluoromethylquinolin-1(2H)-yl)acetate was added at 0° C. The reaction mixture was stirred for 1 hour, thereto were added 5 mL of water and 30 mL of ethyl acetate, and the insoluble material filtered off. The organic layer was separated, washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; hexane:ethyl acetate=3:1] to obtain 34 mg of a pale yellow solid, 1-(2-hydroxyethyl)-4-chloro-7-trifluoromethylquinolin-2(1H)-one.

$^1$H-NMR (CDCl$_3$) δ:
4.07 (2H, m), 4.55 (2H, t, J=5.5 Hz), 7.02 (1H, s), 7.56 (1H, d, J=8.3 Hz), 7.78 (1H, s), 8.17 (1H, d, J=8.3 Hz)

Reference Example 213

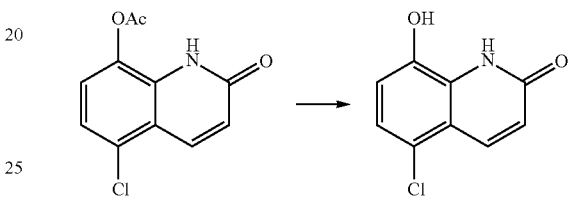

To 50 mL of a methanol solution containing 1.02 g of 8-acetoxy-5-chloroquinolin-2(1H)-one, 2.13 g of potassium carbonate was added, and the mixture was stirred at 50° C. for 3 hours. The reaction mixture was cooled to room temperature, then water was added thereto, and the resultant solution was adjusted to pH 6 with acetic acid. Then, chloroform was added to the reaction mixture, and a solid substance was collected by filtration to obtain 0.86 g of a light brown solid, 5-chloro-8-hydroxyquinolin-2(1H)-one.

$^1$H-NMR (DMSO-d$_6$) δ:
6.62 (1H, d, J=10.1 Hz), 6.90 (1H, d, J=8.8 Hz), 7.10 (1H, d, J=8.8 Hz), 8.00 (1H, d, J=10.1 Hz)

Reference Example 214

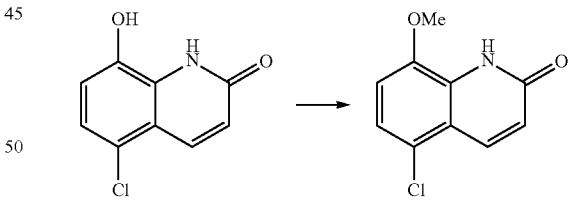

To 50 mL of acetone containing 1.22 g of 5-chloro-8-hydroxyquinolin-2(1H)-one and 50 mL of an N,N-dimethylformamide solution, 3.46 g of potassium carbonate and 7.10 g of methyl iodide were added, and the mixture was stirred at 40° C. for 4 hours. The reaction mixture was cooled to room temperature, then the insoluble material filtered off, and the solvent was removed under reduced pressure. The residue thus obtained was added with chloroform and water, the organic layer was separated, washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; hexane:

ethyl acetate 1:2] to obtain 1.04 g of a yellow solid, 5-chloro-8-methoxyquinolin-2(1H)-one.

¹H-NMR (CDCl₃) δ:
3.97 (3H, s), 6.74 (1H, d, J=10.1 Hz), 6.88 (1H, d, J=8.8 Hz), 7.17 (1H, d, J=8.8 Hz), 8.10 (1H, d, J=10.1 Hz)

Reference Example 215

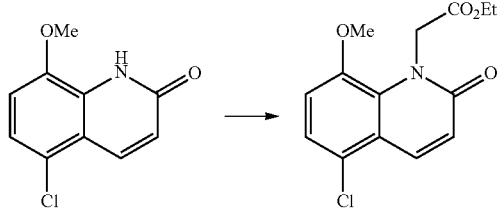 [SMILES: COc1ccc(Cl)c2ccc(=O)[nH]c12 ; CCOC(=O)Cn1c(=O)ccc2c(Cl)ccc(OC)c21]

To 28 mL of an N,N-dimethylformamide solution containing 0.69 g of 5-chloro-8-methoxyquinolin-2(1H)-one, 0.19 g of 60% sodium hydride was added at room temperature, the mixture was stirred for 30 minutes, and then 0.71 g of ethyl bromoacetate was added thereto, and the mixture was stirred at room temperature for 30 minutes and at 40° C. for 2 hours. The reaction mixture was cooled to room temperature, and then thereto were added 40 mL of water and 40 mL of ethyl acetate. The organic layer was separated, and the aqueous layer was extracted with ethyl acetate. The organic layer and the extract were combined, and the resultant solution was washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; hexane:ethyl acetate=1:1] to obtain 0.15 g of a yellow solid, ethyl (5-chloro-8-methoxy-2-oxoquinolin-1(2H)-yl)acetate.

¹H-NMR (CDCl₃) δ:
1.28 (3H, t, J=7.3 Hz), 3.82 (3H, s), 4.24 (2H, q, J=7.3 Hz), 5.34 (2H, s), 6.81 (1H, d, J=10.1 Hz), 6.94 (1H, d, J=8.8 Hz), 7.23 (1H, d, J=8.8 Hz), 8.16 (1H, d, J=10.1 Hz)

Reference Example 216

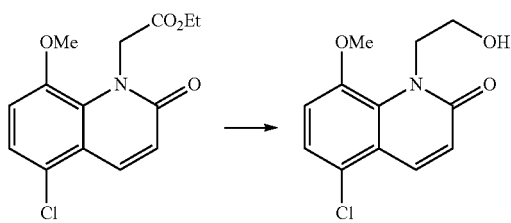 [SMILES: CCOC(=O)Cn1c(=O)ccc2c(Cl)ccc(OC)c21 ; COc1ccc(Cl)c2ccc(=O)n(CCO)c12]

To 20 mL of a tetrahydrofuran solution containing 146 mg of ethyl (5-chloro-8-methoxy-2-oxoquinolin-1(2H)-yl)acetate, 21 mg of lithium aluminum hydride was added at 0° C. The reaction mixture was stirred for 1 hour, and 5 mL of water was added thereto. The insoluble material filtered off, and the solvent was removed under reduced pressure. The residue thus obtained was purified by silica gel column chromatography [silica gel; Silica gel 60 manufactured by Kanto Chemical Co., Inc., eluent; hexane:ethyl acetate 2:1] to obtain 31 mg of a white solid, 5-chloro-1-(2-hydroxyethyl)-8-methoxyquinolin-2(1H)-one.

¹H-NMR (CDCl₃) δ:
3.92 (3H, s), 4.09-4.14 (2H, m), 4.64-4.68 (2H, m), 6.83 (1H, d, J=9.6 Hz), 7.00 (1H, d, J=8.7 Hz), 7.27 (1H, d, J=8.7 Hz), 8.20 (1H, d, J=9.6 Hz)

Reference Example 217

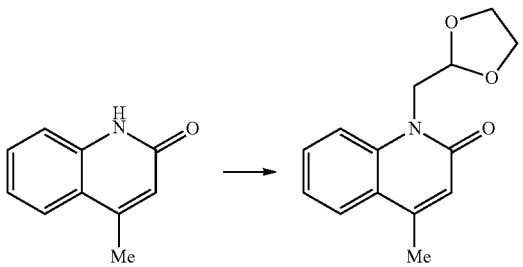 [SMILES: Cc1cc(=O)[nH]c2ccccc12 ; Cc1cc(=O)n(CC2OCCO2)c2ccccc12]

To 70 mL of an N,N-dimethylformamide solution containing 1.40 g of 4-methylquinolin-2(1H)-one, 1.06 g of 60% sodium hydride was added, and the mixture was stirred at room temperature for 1 hour. Thereto was added 7.34 g of 2-bromomethyl-1,3-dioxolane, and the mixture was stirred at 90° C. for 5 hours. The reaction mixture was cooled to room temperature, and then ethyl acetate, toluene and 1 mol/L hydrochloric acid were added thereto. The organic layer was separated, washed with an aqueous saturated sodium chloride solution and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; ethyl acetate] to obtain 0.75 g of a white solid, 1-(1,3-dioxolan-2-ylmethyl)-4-methylquinolin-2(1H)-one.

¹H-NMR (CDCl₃) δ:
2.47 (3H, s) 3.86-3.89 (2H, m) 4.03-4.07 (2H, m) 4.55 (2H, d, J=4.6 Hz) 5.27 (1H, t, J=4.6 Hz) 6.61 (1H, s) 7.23-7.25 (1H, m) 7.53-7.57 (1H, m) 7.59-7.61 (1H, m) 7.68-7.71 (1H, m)

Reference Example 218

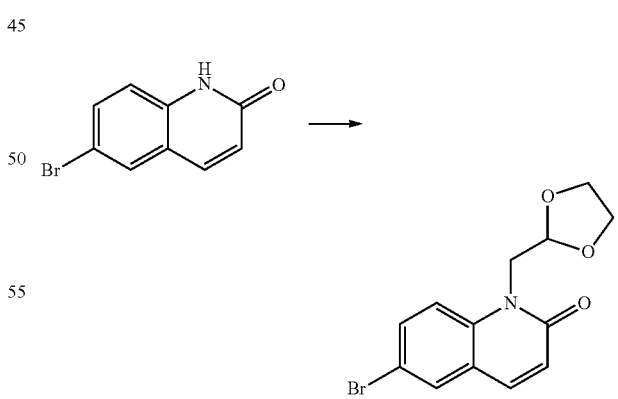

To 70 mL of an N,N-dimethylformamide solution containing 1.00 g of 6-bromoquinolin-2(1H)-one, 0.54 g of 60% sodium hydride was added, and the mixture was stirred at room temperature for 1 hour. Thereto was added 3.73 g of 2-bromomethyl-1,3-dioxolane, and the mixture was stirred at 90° C. for 5 hours. The reaction mixture was cooled to room temperature, and then ethyl acetate, toluene and 1 mol/L hydrochloric acid were added thereto. The organic layer was separated, washed sequentially with water, an aqueous saturated sodium hydrogen carbonate solution and an aqueous saturated sodium chloride solution, and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; ethyl acetate] to obtain 0.56 g of a white solid, 1-(1,3-dioxolan-2-ylmethyl)-6-bromoquinolin-2(1H)-one.

$^1$H-NMR (CDCl$_3$) δ:
3.86-3.91 (2H, m), 4.00-4.05 (2H, m), 4.49-4.53 (2H, m), 5.21-5.24 (1H, m), 6.72-6.75 (1H, m), 7.47-7.51 (1H, m), 7.57-7.60 (1H, m), 7.60-7.63 (1H, m), 7.66-7.68 (1H, m)

Reference Example 219

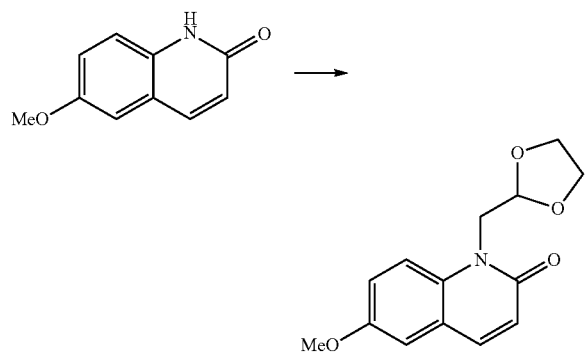

To 6 mL of an N,N-dimethylformamide solution containing 200 mg of 6-methoxyquinolin-2(1H)-one, 137 mg of 60% sodium hydride was added, and the mixture was stirred at room temperature for 1 hour. Thereto was added 953 mg of 2-bromomethyl-1,3-dioxolane, and the mixture was stirred at 90° C. for 4.5 hours. The reaction mixture was cooled to room temperature, and then ethyl acetate, toluene and 1 mol/L hydrochloric acid were added thereto. The organic layer was separated, washed sequentially with water, an aqueous saturated sodium hydrogen carbonate solution and an aqueous saturated sodium chloride solution, and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; ethyl acetate:hexane=4:1] to obtain 96 mg of a white solid, 1-(1,3-dioxolan-2-ylmethyl)-6-methoxyquinolin-2(1H)-one.

$^1$H-NMR (CDCl$_3$) δ:
3.86 (3H, s), 3.86-3.89 (2H, m), 4.03-4.06 (2H, m), 4.53 (2H, d, J=4.6 Hz), 5.25 (1H, t, J=4.6 Hz), 6.71-6.73 (1H, m), 6.97-6.99 (1H, m), 7.15-7.18 (1H, m), 7.51-7.54 (1H, m), 7.61-7.64 (1H, m)

Reference Example 220

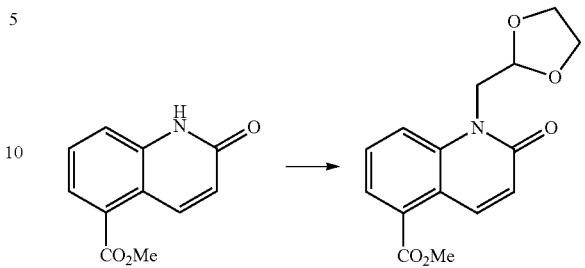

To 90 mL of an N,N-dimethylformamide solution containing 500 mg of methyl 1,2-dihydro-2-oxoquinoline-5-carboxylate, 295 mg of 60% sodium hydride was added, and the mixture was stirred at room temperature for 2 hours. Thereto was added 2.05 g of 2-bromomethyl-1,3-dioxolane, and the mixture was stirred at 90° C. for 2 hours. The reaction mixture was added to 1 mol/L hydrochloric acid cooled with ice, and then ethyl acetate and toluene were added thereto. The organic layer was separated, washed sequentially with water, an aqueous saturated sodium hydrogen carbonate solution and an aqueous saturated sodium chloride solution, and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; ethyl acetate] to obtain 22.6 mg of a white solid, methyl 1-(1,3-dioxolan-2-ylmethyl)-1,2-dihydro-2-oxoquinoline-5-carboxylate.

$^1$H-NMR (CDCl$_3$) δ:
3.86-3.90 (2H, m), 3.97-3.98 (3H, s), 4.02-4.05 (2H, m), 4.58-4.61 (2H, m), 5.25 (1H, t, J=4.4 Hz), 6.81 (1H, d, J=10.1 Hz), 7.56-7.59 (1H, m), 7.81-7.84 (2H, m), 8.78 (1H, d, J=10.1 Hz)

Reference Example 221

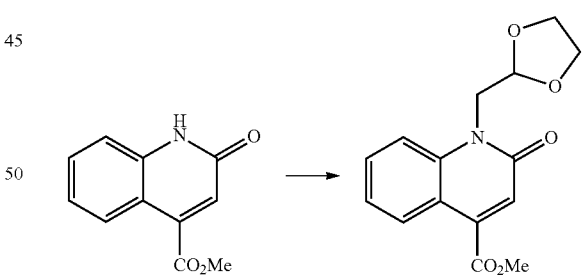

To 40 mL of N,N-dimethylformamide containing 645 mg of methyl 1,2-dihydro-2-oxoquinoline-4-carboxylate, 381 mg of 60% sodium hydride was added, and the mixture was stirred at room temperature for 1 hour. Thereto was added 2.05 g of 2-bromomethyl-1,3-dioxolane, and the mixture was stirred at 90° C. for 2 hours. The reaction mixture was added to 1 mol/L hydrochloric acid cooled with ice, and then ethyl acetate and toluene were added thereto. The organic layer was separated, washed sequentially with water, an aqueous saturated sodium hydrogen carbonate solution and an aqueous saturated sodium chloride solution, and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; ethyl acetate:hexane=1:1] to obtain 100 mg of a white solid, methyl 1-(1,3-dioxolan-2-ylmethyl)-1,2-dihydro-2-oxoquinoline-4-carboxylate.

$^1$H-NMR (CDCl$_3$) δ:
3.87-3.90 (2H, m), 3.99 (3H, s), 4.03-4.05 (2H, m), 4.57-4.58 (2H, m), 5.26-5.28 (1H, m), 7.19 (1H, s), 7.27-7.30 (1H, m), 7.57-7.61 (1H, m), 7.63-7.65 (1H, m), 8.29-8.31 (1H, m)

Reference Example 222

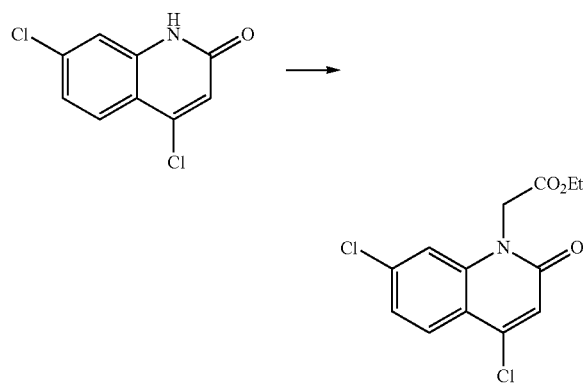

To 40 mL of N,N-dimethylformamide containing 580 mg of 4,7-dichloroquinolin-2(1H)-one and 5 mL of a tetrahydrofuran solution, 141 mg of 60% sodium hydride was added, and the mixture was stirred at room temperature for 30 minutes. Thereto was added 588 mg of ethyl bromoacetate, and the mixture was stirred at room temperature for 1 hour. The reaction mixture was added with an aqueous saturated ammonium chloride solution, water and ethyl acetate. The organic layer was separated, and washed sequentially with water, an aqueous saturated sodium hydrogen carbonate solution and an aqueous saturated sodium chloride solution, and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; ethyl acetate:hexane 1:3] to obtain 0.25 g of a white solid, ethyl (4,7-dichloro-2-oxoquinolin-1(2H)-yl)acetate.

$^1$H-NMR (CDCl$_3$) δ:
1.30 (3H, t, J=7.3 Hz), 4.27 (2H, q, J=7.3 Hz), 5.02 (2H, s), 6.90 (1H, s), 7.12 (1H, d, J=1.8 Hz), 7.30 (1H, dd, J=8.7, 1.8 Hz), 7.97 (1H, d, J=8.7 Hz)

Reference Example 223

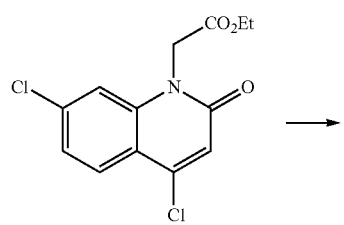

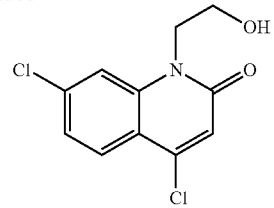

To a tetrahydrofuran solution containing 0.24 g of ethyl (4,7-dichloro-2-oxoquinolin-1(2H)-yl)acetate, 0.04 g of lithium aluminum hydride was added at 0° C., and the mixture was stirred for 3 hours. The reaction mixture was added with an aqueous saturated ammonium chloride solution and chloroform. The organic layer was separated, washed sequentially with water, an aqueous saturated sodium hydrogen carbonate solution and an aqueous saturated sodium chloride solution, and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; chloroform:methanol=10:1] to obtain 86 mg of a pale yellow solid, 1-(2-hydroxyethyl)-4,7-dichloroquinolin-2(1H)-one.

$^1$H-NMR (CDCl$_3$) δ:
2.40 (1H, s), 4.04 (2H, t, J=5.5 Hz), 4.48 (2H, t, J=5.5 Hz), 6.89 (1H, s), 7.30 (1H, dd, J=8.7, 1.8 Hz), 7.52 (1H, d, J=1.8 Hz), 7.97 (1H, d, J=8.7 Hz)

Reference Example 224

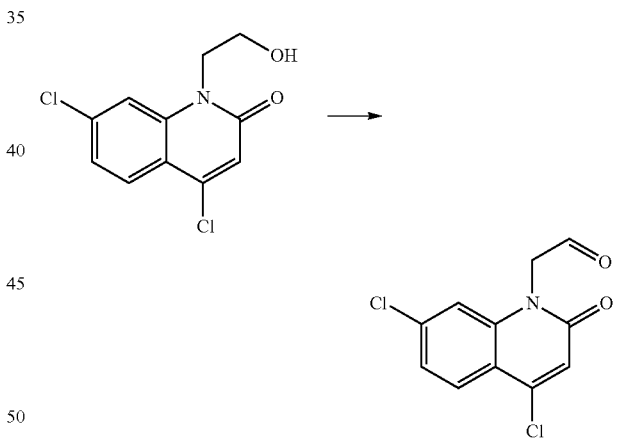

To 2 mL of a chloroform solution containing 54 mg of oxalyl chloride, 64 mg of dimethyl sulfoxide was added dropwise at −60° C., and the mixture was stirred for 15 minutes. Thereto was added dropwise 2 mL of a chloroform solution containing 85 mg of 1-(2-hydroxyethyl)-4,7-dichloroquinolin-2(1H)-one at the same temperature, and the reaction mixture was stirred for 15 minutes. Thereto was added 133 mg of triethylamine at the same temperature, then the mixture was stirred at room temperature for 45 minutes, and water was added thereto. The organic layer was separated, washed with an aqueous saturated sodium chloride solution and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent;

chloroform:methanol=10:1] to obtain 69 mg of a brown oily substance, (4,7-dichloro-2-oxoquinolin-1(2H)-yl)acetaldehyde.

¹H-NMR (CDCl₃) δ:
5.14 (2H, s), 6.92 (1H, s), 7.04 (1H, d, J=1.8 Hz), 7.31 (1H, dd, J=8.7, 1.8 Hz), 7.99 (1H, d, J=8.7 Hz), 9.75 (1H, s)

Reference Example 225

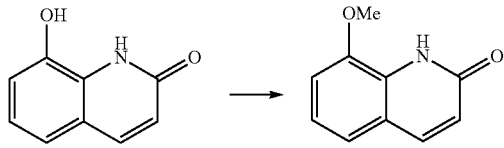 [SMILES: O=c1ccc2cccc(O)c2[nH]1 ; COc1cccc2ccc(=O)[nH]c12]

To 300 mL of an N,N-dimethylformamide solution of containing 4.16 g of 8-hydroxyquinolin-2(1H)-one, 14.27 g of potassium carbonate and 13 mL of methyl iodide were added, and the mixture was stirred at 40° C. for 2 hours. The reaction mixture was cooled to room temperature, then the insoluble material filtered off, and the filtrate was concentrated under reduced pressure. The residue thus obtained was added with chloroform and water, and the organic layer was separated. The organic layer was washed with an aqueous saturated sodium chloride solution and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate=1:1] to obtain 3.02 g of a yellow solid, 8-methoxyquinolin-2(1H)-one.

¹H-NMR (CDCl₃) δ:
3.98 (3H, s), 6.67 (1H, d, J=9.7 Hz), 6.98 (1H, dd, J=6.2, 3.1 Hz), 7.11-7.19 (2H, m), 7.73 (1H, d, J=9.7 Hz), 9.15 (1H, s)

Reference Example 226

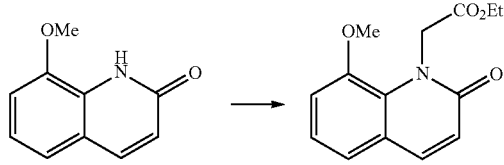 [SMILES: COc1cccc2ccc(=O)[nH]c12 ; CCOC(=O)Cn1c(=O)ccc2cccc(OC)c21]

To 90 mL of an N,N-dimethylformamide solution containing 3.01 g of 8-methoxyquinolin-2(1H)-one, 0.97 g of 60% sodium hydride was added at room temperature, the mixture was stirred for 70 minutes, then 3.73 g of ethyl bromoacetate was added, and the mixture was stirred at the same temperature for 30 minutes and at 40° C. for 70 minutes. The reaction mixture was cooled to room temperature, and then water and ethyl acetate were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; hexane:ethyl acetate=1:1] to obtain 0.72 g of a yellow solid, ethyl (8-methoxy-2-oxo-quinolin-1(2H)-yl)acetate.

¹H-NMR (CDCl₃) δ:
1.28 (3H, t, J=7.3 Hz), 3.83 (3H, s), 4.24 (2H, q, J=7.3 Hz), 5.36 (2H, s), 6.72 (1H, d, J=9.2 Hz), 6.99-7.08 (1H, m), 7.11-7.20 (2H, m), 7.65 (1H, d, J=9.2 Hz)

Reference Example 227

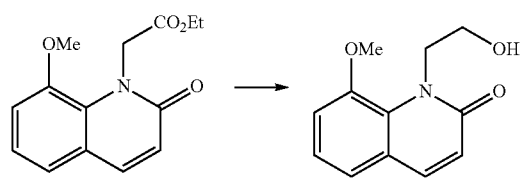 [SMILES: CCOC(=O)Cn1c(=O)ccc2cccc(OC)c21 ; COc1cccc2ccc(=O)n(CCO)c12]

To 30 mL of a tetrahydrofuran solution containing 0.68 g of ethyl (8-methoxy-2-oxoquinolin-1(2H)-yl)acetate, 0.16 g of lithium aluminum hydride was added at 0° C., and the mixture was stirred for 2 hours. The reaction mixture was added with water and ethyl acetate, and the insoluble material filtered off. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform:methanol=10:1] to obtain 0.16 g of a yellow solid, 1-(2-hydroxyethyl)-8-methoxyquinolin-2(1H)-one.

¹H-NMR (CDCl₃) δ:
3.93 (3H, s), 4.06-4.24 (2H, m), 4.63-4.75 (2H, m), 6.74 (1H, d, J=9.2 Hz), 7.09 (1H, dd, J=6.2, 3.1 Hz), 7.15-7.23 (2H, m), 7.68 (1H, d, J=9.2 Hz)

Reference Example 228

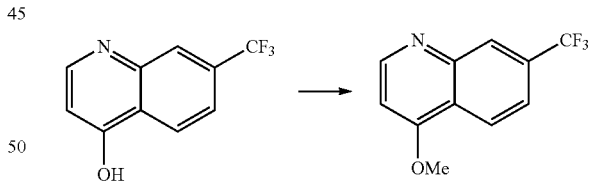

To 50 mL of methanol containing 4.02 g of 7-trifluoromethyl-4-quinolinol and 90 mL of an acetonitrile solution, 3.41 g of diisopropylethylamine and 13.2 mL of a 2.0 mol/L trimethylsilyldiazomethane/hexane solution were added dropwise, then the mixture was stirred for 15 minutes. and the reaction mixture was concentrated under reduced pressure. The residue thus obtained was purified by silica gel column chromatography [silica gel; Chromatorex-NH, manufactured by Fuji Silysia Chemical Ltd., eluent; hexane:ethyl acetate 2:1] to obtain 1.10 g of a yellow solid, 4-methoxy-7-trifluoromethylquinoline.

¹H-NMR (CDCl₃) δ:
4.09 (3H, s), 6.84 (1H, d, J=5.3 Hz), 7.68 (1H, dd, J=8.8, 1.8 Hz), 8.25-8.42 (2H, m), 8.85 (1H, d, J=5.3 Hz)

Reference Example 229

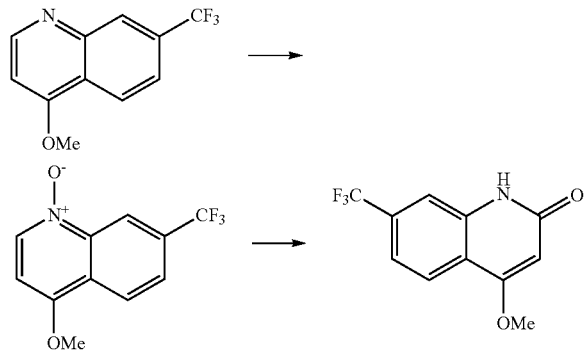

To 15 mL of a chloroform solution containing 1.06 g of 4-methoxy-7-trifluoromethylquinoline, 1.36 g of m-chloroperbenzoic acid was added, and the mixture was stirred at room temperature for 16 hours. The reaction mixture was added with 20 mL of an aqueous saturated sodium hydrogen carbonate solution. The organic layer was separated, and the aqueous layer was extracted with chloroform. The organic layer and the extract were combined, the resultant solution was washed with an aqueous saturated sodium chloride solution, and dried over anhydrous magnesium sulfate, and the solvent was removed under reduced pressure to obtain a yellow solid, 4-methoxy-7-trifluoromethylquinoline N-oxide.

To 35 mL of a chloroform solution containing 4-methoxy-7-trifluoromethylquinoline N-oxide, 1.11 g of p-toluenesulfonyl chloride, 2.26 g of potassium carbonate and 11 mL of water were added, and the mixture was stirred at room temperature for 2 hours. The reaction mixture was added with water, the organic layer was separated, and the aqueous layer was extracted with chloroform. The organic layer and the extract were combined, the resultant solution was washed with an aqueous saturated sodium chloride solution, and dried over anhydrous magnesium sulfate, and the solvent was removed under reduced pressure. The residue thus obtained was added with ethyl acetate, and a solid substance was collected by filtration to obtain 0.44 g of a white solid, 4-methoxy-7-trifluoromethylquinolin-2(1H)-one.

$^1$H-NMR (CDCl$_3$) δ:
4.02 (3H, s), 6.09 (1H, s), 7.43 (1H, dd, J=8.4, 1.8 Hz), 7.52-7.57 (1H, m), 8.03 (1H, d, J=8.4 Hz)

Reference Example 230

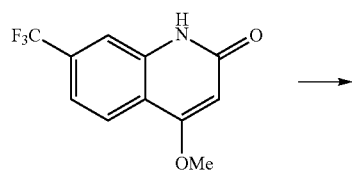

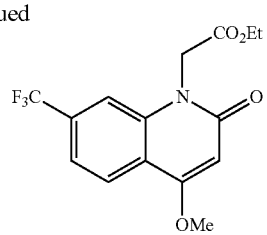

To 20 mL of an N,N-dimethylformamide solution containing 0.43 g of 4-methoxy-7-trifluoromethylquinolin-2(1H)-one, 0.10 g of 60% sodium hydride was added at room temperature, the mixture was stirred for 35 minutes, then 0.38 g of ethyl bromoacetate was added thereto, and the mixture was stirred for 45 minutes. The reaction mixture was added with water and ethyl acetate. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; hexane:ethyl acetate=1:1] to obtain 0.45 g of a white solid, ethyl (4-methoxy-2-oxo-7-trifluoromethylquinolin-1(2H)-yl)acetate.

$^1$H-NMR (CDCl$_3$) δ:
1.28 (3H, t, J=7.2 Hz), 3.99 (3H, s), 4.25 (2H, q, J=7.2 Hz), 5.07 (2H, s), 6.12 (1H, s), 7.28 (1H, m), 7.42-7.49 (1H, m), 8.11 (1H, d, J=8.4 Hz)

Reference Example 231

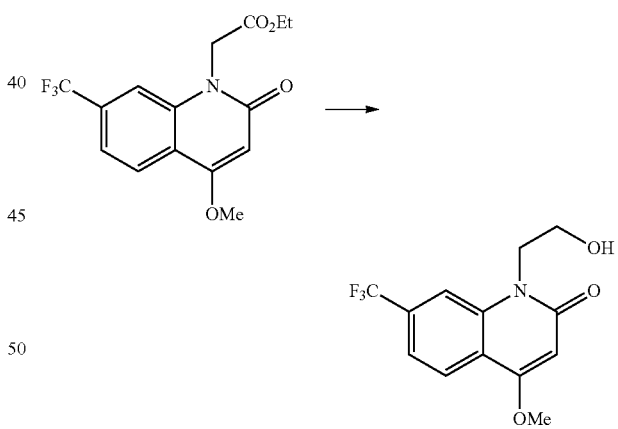

To 20 mL of a tetrahydrofuran solution containing 0.44 g of ethyl (4-methoxy-2-oxo-7-trifluoromethylquinolin-1(2H)-yl)acetate, 3.4 mL of a 1.01 mol/L diisobutylaluminum hydride/toluene solution was added at 0° C., and the mixture was stirred for 2 hours. The reaction mixture was added with 20 mL of water and 20 mL of ethyl acetate, the organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; hexane:ethyl acetate=1:1] to obtain 0.09 g of a yellow solid, 1-(2-hydroxyethyl)-4-methoxy-7-trifluoromethylquinolin-2(1H)-one.

¹H-NMR (CDCl₃) δ:
3.99 (3H, s), 4.04 (2H, t, J=5.5 Hz), 4.52 (2H, t, J=5.5 Hz), 6.13 (1H, s), 7.43-7.51 (1H, m), 7.65 (1H, s), 8.12 (1H, d, J=8.8 Hz)

Reference Example 232

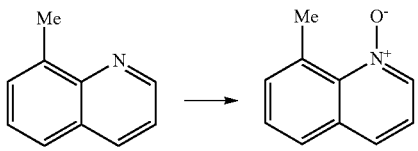 [SMILES: Cc1cccc2cccnc12 ; Cc1cccc2ccc[n+]([O-])c12]

To 40 mL of a chloroform solution containing 2.0 g of 8-methylquinoline, 3.6 g of m-chloroperbenzoic acid was added, and the mixture was stirred at room temperature overnight. Thereto was added 1.0 g of m-chloroperbenzoic acid, and the mixture was stirred at room temperature overnight. An aqueous saturated sodium hydrogen carbonate solution was added to the reaction mixture, the organic layer was separated, and the aqueous layer was extracted with chloroform. The organic layer and the extract were combined, the resultant solution was washed with an aqueous saturated sodium chloride solution, and dried over anhydrous magnesium sulfate, and the solvent was removed under reduced pressure to obtain 2.2 g of a brown oily substance, 8-methylquinoline N-oxide.

¹H-NMR (CDCl₃) δ:
3.19 (3H, s), 7.18 (1H, dd, J=8.3, 6.0 Hz), 7.39-7.46 (2H, m), 7.63-7.66 (2H, m), 8.41 (1H, dd, J=6.0, 0.9 Hz)

Reference Example 233

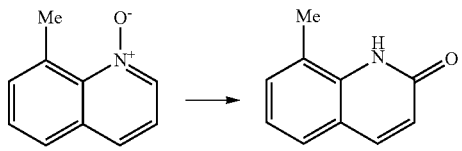 [SMILES: Cc1cccc2ccc[n+]([O-])c12 ; Cc1cccc2ccc(=O)[nH]c12]

To 30 mL of a chloroform solution containing 2.1 g of 8-methylquinoline N-oxide, 3.0 g of p-toluenesulfonyl chloride and 30 mL of a 10% aqueous potassium carbonate solution were added, and the mixture was stirred at room temperature overnight. The organic layer was separated, and the aqueous layer was extracted with chloroform. The organic layer and the extract were combined, the resultant solution was washed with an aqueous saturated sodium chloride solution, and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; hexane:ethyl acetate 2:1] to obtain 0.18 g of a white solid, 8-methylquinolin-2(1H)-one.

¹H-NMR (DMSO-d₆) δ:
3.33 (3H, s), 6.51 (1H, d, J=9.6 Hz), 7.09 (1H, t, J=7.6 Hz), 7.35 (1H, d, J=7.6 Hz), 7.50 (1H, d, J=7.6 Hz), 7.90 (1H, d, J=9.6 Hz), 10.89 (1H, s)

Reference Example 234

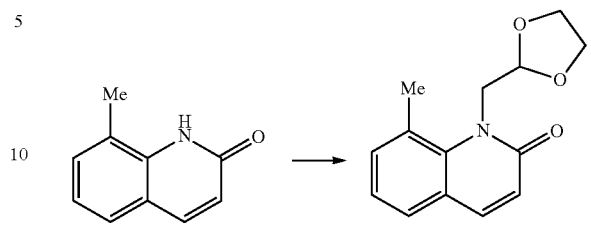

To 3 mL of an N,N-dimethylformamide solution containing 0.17 g of 8-methylquinolin-2(1H)-one, 0.13 g of 60% sodium hydride was added under a nitrogen atmosphere, and the mixture was stirred at room temperature for 30 minutes. Thereto was added 0.89 g of 2-bromomethyl-1,3-dioxolane, and the mixture was stirred at 90° C. for 48 hours. The reaction mixture was cooled to room temperature, then ethyl acetate and 1 mol/L hydrochloric acid were added thereto. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [silica gel; Chromatorex-NH, manufactured by Fuji Silysia Chemical Ltd., eluent; hexane:ethyl acetate=8:1] to obtain 0.18 g of a pale yellow oily substance, 1-(1,3-dioxolan-2-ylmethyl)-8-methylquinolin-2(1H)-one.

¹H-NMR (CDCl₃) δ:
2.69 (3H, s), 3.98-4.01 (2H, m), 4.08-4.12 (2H, m), 4.59 (2H, d, J=4.6 Hz), 5.42 (1H, t, J=4.6 Hz), 6.97 (1H, d, J=8.7 Hz), 7.28 (1H, t, J=7.3 Hz), 7.48 (1H, d, J=7.3 Hz), 7.56 (1H, d, J=7.3 Hz), 7.98 (1H, d, J=8.7 Hz)

Reference Example 235

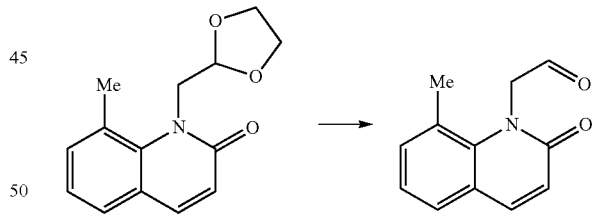

To 0.17 g of 1-(1,3-dioxolan-2-ylmethyl)-8-methylquinolin-2(1H)-one, 2 mL of a 90% aqueous trifluoroacetic acid solution was added, and the mixture was stirred at room temperature for 4 days, at 40° C. for 3 days, and at room temperature for 5 days. The solvent was removed under reduced pressure, and the reaction mixture was added with ethyl acetate and an aqueous saturated sodium hydrogen carbonate solution. The organic layer was separated, and the aqueous layer was extracted with ethyl acetate. The organic layer and the extract were combined, the resultant solution was washed with an aqueous saturated sodium chloride solution, and dried over anhydrous magnesium sulfate, and the solvent was removed under reduced pressure to obtain 0.14 g of a brown oily substance, (8-methyl-2-oxoquinolin-1(2H)-yl)acetaldehyde.

¹H-NMR (CDCl₃) δ:
2.59 (3H, s), 4.91 (2H, s), 7.05 (1H, d, J=8.7 Hz), 7.32 (1H, t, J=7.8 Hz), 7.50 (1H, d, J=7.8 Hz), 7.60 (1H, d, J=7.8 Hz), 8.07 (1H, d, J=8.7 Hz), 9.82 (1H, s)

Reference Example 236

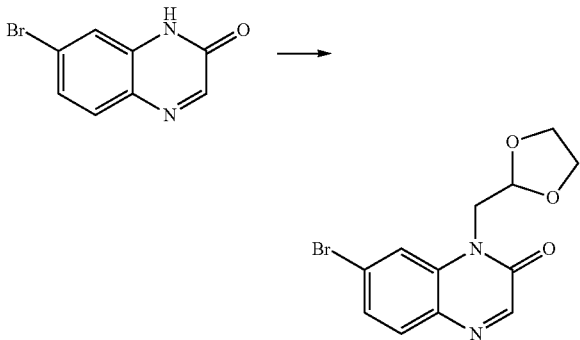

To 250 mL of an N,N-dimethylformamide solution containing 2.50 g of 7-bromoquinoxalin-2(1H)-one, 0.80 g of 60% sodium hydride was added, and the mixture was stirred at room temperature for 1 hour. Thereto was added 9.28 g of 2-bromomethyl-1,3-dioxolane was added, and the mixture was stirred at 90° C. for 3 hours. The reaction mixture was cooled with water, and then ethyl acetate, toluene and 1 mol/L hydrochloric acid were added thereto. The organic layer was separated, washed sequentially with water, an aqueous saturated sodium hydroxide solution and an aqueous saturated sodium chloride solution, and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; ethyl acetate: hexane=2:3] to obtain 0.70 g of a white solid, 1-(1,3-dioxolan-2-ylmethyl)-7-bromoquinoxalin-2(1H)-one.

¹H-NMR (CDCl₃) δ:
3.77-3.84 (2H, m), 3.91-3.98 (2H, m), 4.43 (2H, d, J=4.1 Hz), 5.13-5.16 (1H, m), 7.54-7.56 (1H, m), 7.75 (1H, d, J=8.7 Hz), 7.95 (1H, d, J=1.8 Hz), 8.28 (1H, s)

Reference Example 237

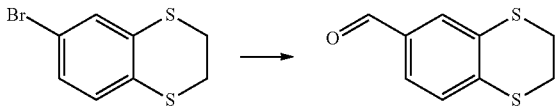 [SMILES: Brc1ccc2c(c1)SCCS2 ; O=Cc1ccc2c(c1)SCCS2]

To 5 mL of a tetrahydrofuran solution containing 500 mg of 6-bromo-2,3-dihydro-1,4-benzodithiin, 0.67 mL of a 2.67 mol/L butyllithium/hexane was added at −78° C., the mixture was stirred for 0.5 hour, then 300 mg of ethyl formate was added thereto, and the mixture was further stirred for 2 hours. Thereto was added 1 mol/L hydrochloric acid, and ethyl acetate was then added to the mixture. The organic layer was separated, washed with an aqueous saturated sodium hydrogen carbonate solution and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; ethyl acetate:hexane 1:4] to obtain 121 mg of a brown oily substance, 2,3-dihydro-1,4-benzodithiin-6-carbaldehyde.

¹H-NMR (CDCl₃) δ:
3.27-3.31 (2H, m), 3.35-3.38 (2H, m), 7.26 (1H, d, J=8.3 Hz), 7.44-7.49 (1H, m), 7.62 (1H, d, J=1.8 Hz), 9.84 (1H, s)

Reference Example 238

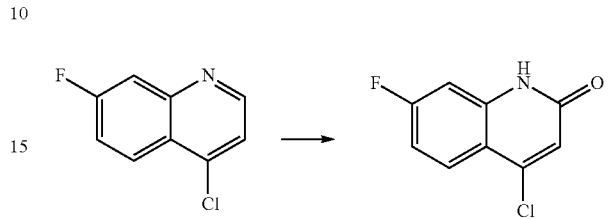

To 30 mL of a chloroform solution containing 2.0 g of 4-chloro-7-fluoroquinoline, 2.95 g of m-chloroperbenzoic acid was added, and the mixture was stirred at room temperature for 12 hours. The reaction mixture was added with an aqueous saturated sodium hydrogen carbonate solution to be alkalified. The organic layer was separated, washed with an aqueous saturated sodium chloride solution, and dried over anhydrous magnesium sulfate, and the solvent was removed under reduced pressure. The residue thus obtained was dissolved in chloroform, thereto were added 2.62 g of p-toluenesulfonyl chloride and 20 mL of an aqueous solution containing 5.33 g of potassium carbonate, and the mixture was stirred at room temperature for 24 hours. The reaction mixture was added with water, and a solid substance was collected by filtration to obtain 1.94 g of a white solid, 4-chloro-7-fluoroquinolin-2(1H)-one.

¹H-NMR (DMSO-d₆) δ:
6.76 (1H, s), 7.09-7.16 (2H, m), 7.89 (1H, dd, J=8.7, 6.0 Hz)

Reference Example 239

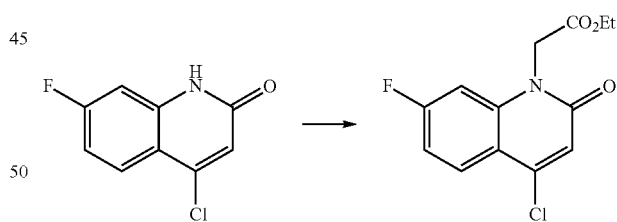

To 55 mL of an N,N-dimethylformamide solution containing 1.00 g of 4-chloro-7-fluoroquinolin-2(1H)-one, 0.61 g of 60% sodium hydride was added, and the mixture was stirred at room temperature for 30 minutes. Thereto was added 1.10 g of ethyl bromoacetate, and the mixture was stirred at room temperature for 15 minutes. The reaction mixture was added with an aqueous saturated ammonium chloride solution, water, ethyl acetate and toluene at 0° C. The organic layer was separated, washed with an aqueous saturated sodium chloride solution and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; ethyl acetate:hexane=1:1] to obtain 0.80 g of a white solid, ethyl (4-chloro-7-fluoro-2-oxoquinolin-1(2H)-yl)acetate.

¹H-NMR (CDCl₃) δ:
1.29 (3H, t, J=7.1 Hz), 4.26 (2H, q, J=7.1 Hz), 5.01 (2H, s), 6.83 (1H, dd, J=10.5, 2.3 Hz), 6.87 (1H, s), 7.03-7.08 (1H, m), 8.04 (1H, dd, J=8.9, 6.2 Hz)

Reference Example 240

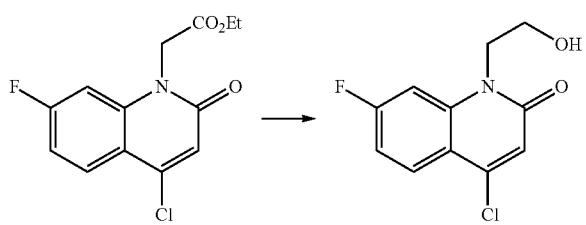 [SMILES: CCOC(=O)Cn1c(=O)cc(Cl)c2ccc(F)cc21 ; O=c1cc(Cl)c2ccc(F)cc2n1CCO]

To 30 mL of a tetrahydrofuran solution containing 0.80 g of ethyl (4-chloro-7-fluoro-2-oxoquinolin-1(2H)-yl)acetate, 0.13 g of lithium aluminum hydride was added at 0° C., and the mixture was stirred for 30 minutes. The reaction mixture was added with an aqueous saturated ammonium chloride solution, water and chloroform. The organic layer was separated, washed with an aqueous saturated sodium chloride solution and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; chloroform:methanol=10:1] to obtain 94 mg of a brown solid, 1-(2-hydroxyethyl)-4-chloro-7-fluoroquinolin-2(1H)-one.

¹H-NMR (CDCl₃) δ:
4.02 (2H, t, J=5.7 Hz), 4.45 (2H, t, J=5.7 Hz), 6.85 (1H, s), 7.04-7.08 (1H, m), 7.23 (1H, dd, J=11.0, 2.3 Hz), 8.03 (1H, dd, J=8.9, 6.2 Hz)

Reference Example 241

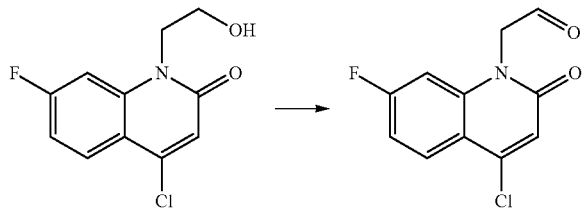 [SMILES: O=c1cc(Cl)c2ccc(F)cc2n1CCO ; O=CCn1c(=O)cc(Cl)c2ccc(F)cc21]

To 200 mL of a chloroform solution containing 0.76 g of 1-(2-hydroxyethyl)-4-chloro-7-fluoroquinolin-2(1H)-one, 1.33 g of Dess-Martin periodinane was added, and the mixture was stirred at room temperature for 1 hour. The reaction mixture was added with an aqueous saturated sodium hydrogen carbonate solution. The organic layer was separated, washed with an aqueous saturated sodium chloride solution and dried over anhydrous magnesium sulfate, and the solvent was removed under reduced pressure. The residue thus obtained was purified by TLC plate [TLC plate; manufactured by Merck Ltd., silica gel column chromatography [silica gel; Silica gel 60N manufactured by Kanto Chemical Co., Inc., eluent; chloroform:methanol=10:1] to obtain 0.71 g of a brown solid, (4-chloro-7-fluoro-2-oxoquinolin-1(2H)-yl)acetaldehyde.

¹H-NMR (CDCl₃) δ:
5.13 (2H, s), 6.75 (1H, dd, J=10.1, 2.3 Hz), 6.89 (1H, s), 7.05-7.10 (1H, m), 8.06 (1H, dd, J=9.2, 6.0 Hz), 9.74 (1H, s)

Reference Example 242

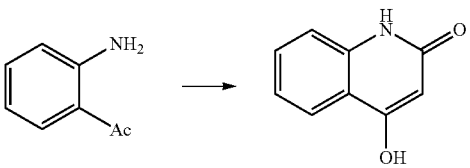 [SMILES: CC(=O)c1ccccc1N ; O=c1cc(O)c2ccccc2[nH]1]

To 150 mL of a toluene suspension containing 12.51 g of 55% sodium hydride, 50 mL of a toluene solution containing 15.50 g of 2'-aminoacetophenone and 20.32 g of diethyl carbonate was added, and the mixture was stirred for 5 hours while gradually increasing the temperature from 60° C. to 100° C., and then cooled to room temperature. The solvent was removed under reduced pressure, water was added thereto and the mixture was stirred, and then the reaction mixture was adjusted to pH 7 with concentrated hydrochloric acid. A solid substance was collected by filtration to obtain 9.12 g of a yellow solid, 4-hydroxyquinolin-2-(1H)-one.

¹H-NMR (DMSO-d₆) δ:
5.73 (1H, s), 7.08-7.18 (1H, m), 7.21-7.28 (1H, m), 7.43-7.53 (1H, m), 7.77 (1H, dd, J=7.9, 1.3 Hz), 11.17 (1H, s)

Reference Example 243

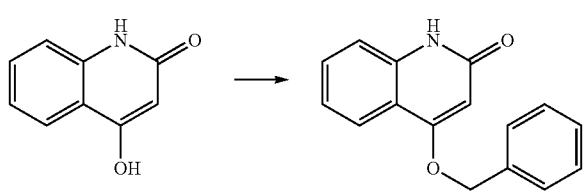 [SMILES: O=c1cc(O)c2ccccc2[nH]1 ; O=c1cc(OCc2ccccc2)c2ccccc2[nH]1]

To 200 mL of an N,N-dimethylformamide solution containing 8.28 g of 4-hydroxyquinolin-2(1H)-one, 6.7 mL of benzyl bromide and 18.31 g of potassium carbonate were added at room temperature, the mixture was stirred at 105° C. for 3 hours, and then cooled to room temperature. The insoluble material filtered off, and the filtrate was concentrated under reduced pressure. The residue thus obtained was added with ethyl acetate and water, and the resultant solution was stirred under cooling with ice. A solid substance was collected by filtration to obtain 1.77 g of a white solid, 4-benzyloxyquinolin-2(1H)-one.

¹H-NMR (CDCl₃) δ:
5.21 (2H, s), 6.10 (1H, s), 7.15-7.25 (1H, m), 7.31-7.57 (7H, m), 7.97 (1H, dd, J=8.1, 1.1 Hz), 11.41 (1H, s)

Reference Example 244

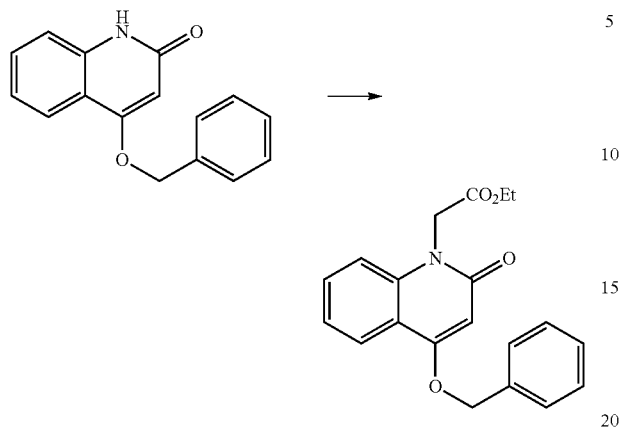

To 60 mL of an N,N-dimethylformamide solution containing 1.77 g of 4-(benzyloxy)quinolin-2(1H)-one, 0.40 g of 60% sodium hydride was added at room temperature, the mixture was stirred for 30 minutes, and then 1.53 g of ethyl bromoacetate was added thereto, and the mixture was stirred for 2 hours. The reaction mixture was added with water and ethyl acetate. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. The residue thus obtained was purified by silica gel column chromatography [eluent; hexane:ethyl acetate 1:2] to obtain 1.75 g of a white solid, ethyl (4-(benzyloxy)-2-oxoquinolin-1(2H)-yl)acetate.

$^1$H-NMR (CDCl$_3$) δ:
1.26 (3H, t, J=7.2 Hz), 4.23 (2H, q, J=7.2 Hz), 5.07 (2H, s), 5.19 (2H, s), 6.14 (1H, s), 7.08 (1H, d, J=8.8 Hz), 7.17-7.23 (1H, m), 7.36-7.50 (5H, m), 7.50-7.60 (1H, m), 8.06 (1H, dd, J=8.1, 1.5 Hz)

Reference Example 245

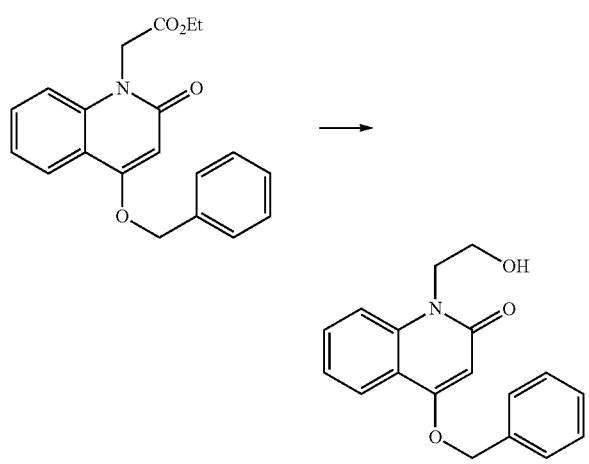

To 50 mL of a tetrahydrofuran suspension containing 0.46 g of lithium aluminum hydride, 100 mL of a tetrahydrofuran solution containing 2.71 g of ethyl (4-(benzyloxy)-2-oxoquinolin-1(2H)-yl)acetate was added at 0° C. The reaction mixture was stirred for 1 hour, water and ethyl acetate were added thereto, and the insoluble material filtered off. The organic layer was separated, and the aqueous layer was extracted with ethyl acetate. The organic layer and the extract were combined, the resultant solution was washed with an aqueous saturated sodium chloride solution and dried over anhydrous magnesium sulfate, and the solvent was removed under reduced pressure. At the time of distilling off the solvent to be about 30 mL, the resultant solid substance was collected by filtration to obtain 1.69 g of a light brown solid, 4-(benzyloxyl)-1-(2-hydroxyethyl)quinolin-2(1H)-one.

$^1$H-NMR (CDCl$_3$) δ:
3.11 (1H, t, J=5.1 Hz), 3.97-4.07 (2H, m), 4.52 (2H, t, J=5.3 Hz), 5.19 (2H, s), 6.15 (1H, s), 7.19-7.29 (1H, m), 7.35-7.51 (6H, m), 7.54-7.64 (1H, m), 8.08 (1H, dd, J=7.9, 1.8 Hz)

Reference Example 246

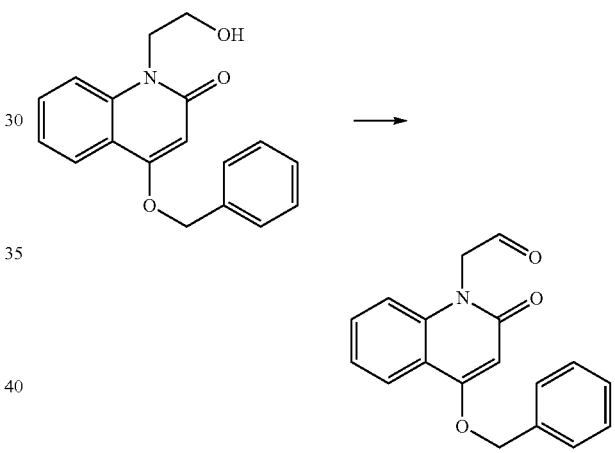

To 50 mL of a dichloromethane solution containing 0.64 mL of oxalyl chloride, 1.02 mL of dimethyl sulfoxide was added dropwise at −60° C. under a nitrogen atmosphere, and the mixture was stirred for 18 minutes. Thereto was added dropwise 120 mL of a dichloromethane solution containing 1.69 g of 4-(benzyloxyl)-1-(2-hydroxyethyl)quinolin-2(1H)-one at the same temperature, and the reaction mixture was stirred for 20 minutes. Thereto was added 3.20 mL of triethylamine at the same temperature, then the mixture was stirred at room temperature for 1 hour, and water was added thereto. The organic layer was separated, and the aqueous layer was extracted with chloroform. The organic layer and the extract were combined, the resultant solution was dried over anhydrous magnesium sulfate, and the solvent was removed under reduced pressure. The residue thus obtained was purified by silica gel column chromatography [eluent; chloroform:methanol=50:1] to obtain 1.28 g of a yellow foam, (4-(benzyloxyl)-2-oxoquinolin-1(1H)-yl)acetaldehyde.

$^1$H-NMR (CDCl$_3$) δ:
5.11 (2H, d, J=0.9 Hz), 5.20 (2H, s), 6.16 (1H, s), 7.02 (1H, d, J=8.4 Hz), 7.19-7.29 (1H, m), 7.36-7.60 (6H, m), 8.08 (1H, dd, J=7.9, 1.3 Hz), 9.68 (1H, s)

Reference Example 247

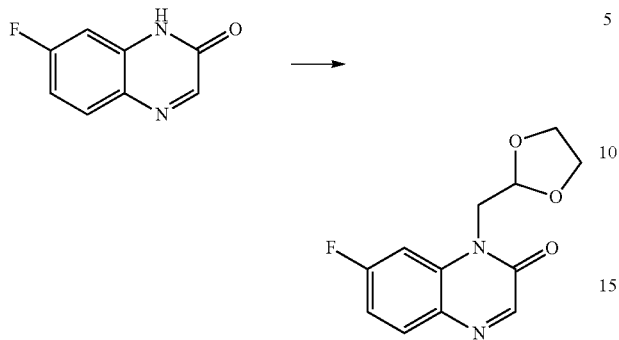

To 100 mL of an N,N-dimethylformamide solution containing 6.58 g of 7-fluoroquinoxalin-2(1H)-one, 3.32 g of 60% sodium hydride was added, and the mixture was stirred at room temperature for 1 hour. Thereto was added 12.5 mL of 2-bromomethyl-1,3-dioxolane, and the mixture was stirred at 90° C. for 15 hours. The reaction mixture was cooled to room temperature, and then ethyl acetate and 1 mol/L hydrochloric acid were added thereto. The organic layer was separated, and washed sequentially with water and an aqueous saturated sodium chloride solution, and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate: hexane 1:2] to obtain 2.92 g of a pale yellow solid, 1-(1,3-dioxolan-2-ylmethyl)-7-fluoroquinoxalin-2(1H)-one.

$^1$H-NMR (CDCl$_3$) δ:
3.88-3.91 (2H, m), 4.00-4.04 (2H, m), 4.42 (2H, d, J=4.6 Hz), 5.24 (1H, t, J=4.6 Hz), 7.05-7.09 (1H, m), 7.26-7.30 (1H, m), 7.85 (1H, dd, J=8.9, 6.2 Hz), 8.25 (1H, s)

Reference Example 248

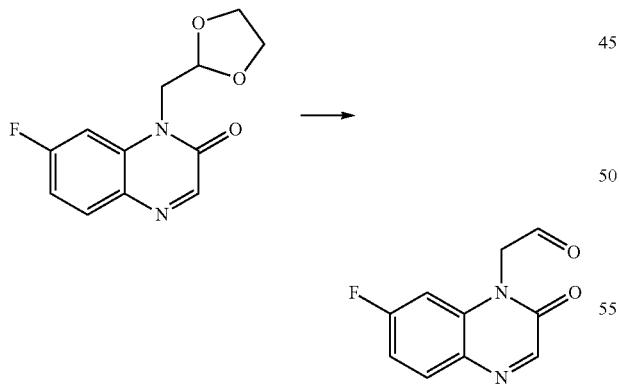

Into 20 mL of a 90% aqueous trifluoroacetic acid solution, 2.91 g of 1-(1,3-dioxolan-2-ylmethyl)-7-fluoroquinoxalin-2(1H)-one was dissolved, and the mixture was stirred at 60° C. for 5 hours. The reaction mixture was cooled to room temperature, then the solvent was removed under reduced pressure, the reaction mixture was alkalified with an aqueous saturated sodium hydrogen carbonate solution, and then extracted with ethyl acetate. The organic layer was washed sequentially with water and an aqueous saturated sodium chloride solution, and dried over anhydrous magnesium sulfate, and the solvent was removed under reduced pressure to obtain 2.63 g of a brown solid, (7-fluoro-2-oxoquinoxalin-1(2H)-yl)acetaldehyde.

$^1$H-NMR (CDCl$_3$) δ:
5.09 (2H, s), 6.70 (1H, dd, J=9.6, 2.8 Hz), 7.08-7.12 (1H, m), 7.92 (1H, dd, J=8.7, 6.0 Hz), 8.30 (1H, s), 9.76 (1H, s)

Reference Example 249

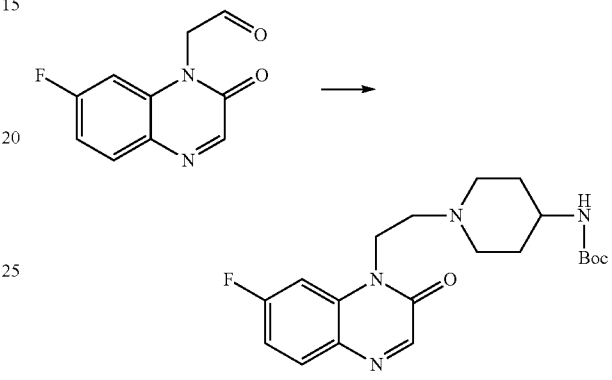

To 20 mL of a chloroform solution containing 2.63 g of (7-fluoro-2-oxoquinoxalin-1(2H)-yl)acetaldehyde and 2.32 g of tert-butyl (piperidin-4-yl)carbamate, 0.73 mL of acetic acid was added, and the mixture was stirred at room temperature for 1 hour. The reaction mixture was added with 4.07 g of sodium triacetoxyborohydride, and stirred for 4 hours. Thereto was added an aqueous saturated sodium hydrogen carbonate solution, and the organic layer was separated. The organic layer was washed with an aqueous saturated sodium chloride solution, and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate: hexane=4:1] to obtain 1.84 g of a brown solid, tert-butyl (1-(2-(7-fluoro-2-oxoquinoxalin-1(2H)-yl)ethyl)piperidin-4-yl)carbamate.

$^1$H-NMR (CDCl$_3$) δ:
1.56 (9H, s), 1.91-1.97 (2H, m), 2.20-2.27 (2H, m), 2.62-2.68 (2H, m), 2.88-2.94 (2H, m), 3.45-3.50 (1H, m), 4.27-4.31 (2H, m), 4.39-4.45 (2H, m), 7.05-7.09 (1H, m), 7.09-7.13 (1H, m), 7.86 (1H, dd, J=8.7, 6.0 Hz), 8.22 (1H, s)

Reference Example 250

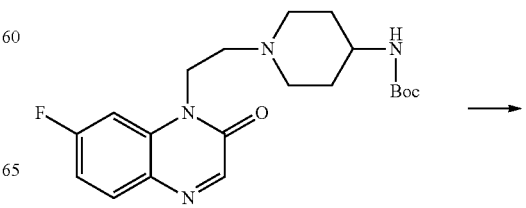

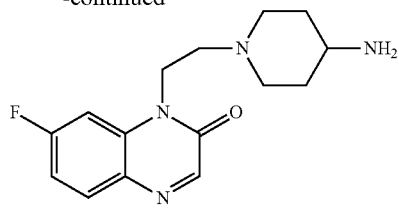

To 20 mL of a chloroform solution containing 1.84 g of tert-butyl (1-(2-(7-fluoro-2-oxoquinoxalin-1(2H)-yl)ethyl)piperidin-4-yl)carbamate, 20 mL of trifluoroacetic acid was added, and the mixture was left to stand at room temperature for 5 hours. The solvent was removed under reduced pressure, the reaction mixture was alkalified with an aqueous saturated sodium hydrogen carbonate solution, and then the solvent was removed under reduced pressure. The residue thus obtained was purified by silica gel column chromatography [silica gel; Silica gel 60 manufactured by Kanto Chemical Co., Inc., eluent; ethyl acetate:hexane=4:1] to obtain 1.50 g of a brown solid, 1-(2-(4-aminopiperidin-1-yl)ethyl)-7-fluoro-quinoxalin-2(1H)-one.

$^1$H-NMR (CDCl$_3$) δ:
1.35-1.41 (2H, m), 1.80-1.85 (2H, m), 2.16-2.22 (2H, m), 2.65-2.68 (3H, m), 2.92-2.97 (2H, m), 4.29-4.32 (2H, m), 7.05-7.09 (1H, m), 7.13 (1H, dd, J=10.1, 2.8 Hz), 7.86 (1H, dd, J=8.9, 6.2 Hz), 8.22 (1H, s)

Reference Example 251

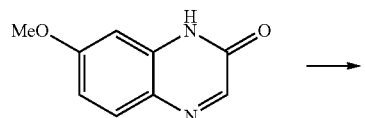

To an N,N-dimethylformamide solution containing 8.77 g of 7-methoxyquinoxalin-2(1H)-one, 3.58 g of 60% sodium hydride was added, and the mixture was stirred at room temperature for 30 minutes. Thereto was added 24.9 g of 2-bromomethyl-1,3-dioxolane, and the mixture was stirred at 90° C. for 15 hours. The reaction mixture was cooled with water, and then ethyl acetate, toluene and water were added thereto. The organic layer was separated, and washed with an aqueous saturated sodium chloride solution, and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; ethyl acetate:hexane=1:1] to obtain 2.26 g of a pale yellow solid, 1-(1,3-dioxolan-2-ylmethyl)-7-methoxyquinoxalin-2(1H)-one.

$^1$H-NMR (CDCl$_3$) δ:
3.88-3.91 (2H, m), 3.92 (3H, s), 4.01-4.04 (2H, m), 4.45-4.46 (2H, m), 5.25-5.27 (1H, m), 6.91-6.94 (1H, m), 7.01-7.02 (1H, m), 7.75-7.78 (1H, m), 8.15 (1H, s)

Reference Example 252

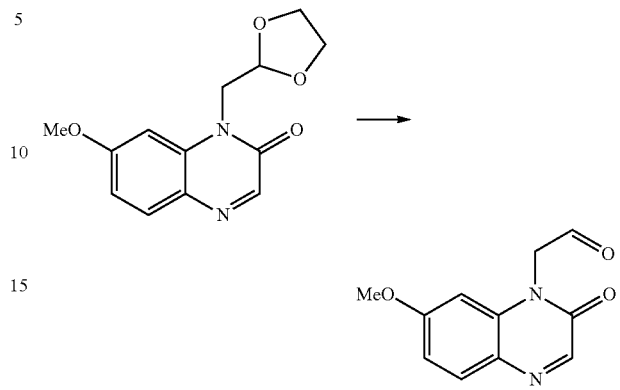

Into 40 mL of an 80% aqueous trifluoroacetic acid solution, 1.00 g of 1-(1,3-dioxolan-2-ylmethyl)-7-methoxyquinoxalin-2(1H)-one was dissolved, and the mixture was stirred at room temperature for 8 hours. The solvent was removed under reduced pressure, the reaction mixture was alkalified with an aqueous saturated sodium hydrogen carbonate solution, and then extracted with ethyl acetate. The organic layer was washed with an aqueous saturated sodium chloride solution, and dried over anhydrous magnesium sulfate, and the solvent was removed under reduced pressure to obtain 236 mg of a pale yellow oily substance, (7-methoxy-2-oxoquinoxalin-1(2H)-yl)acetaldehyde.

$^1$H-NMR (CDCl$_3$) δ:
3.89 (3H, s), 5.07 (2H, s), 6.42 (1H, d, J=2.8 Hz), 6.94-6.96 (1H, m), 7.84 (1H, d, J=9.2 Hz), 8.20 (1H, s), 9.71 (1H, s)

Reference Example 253

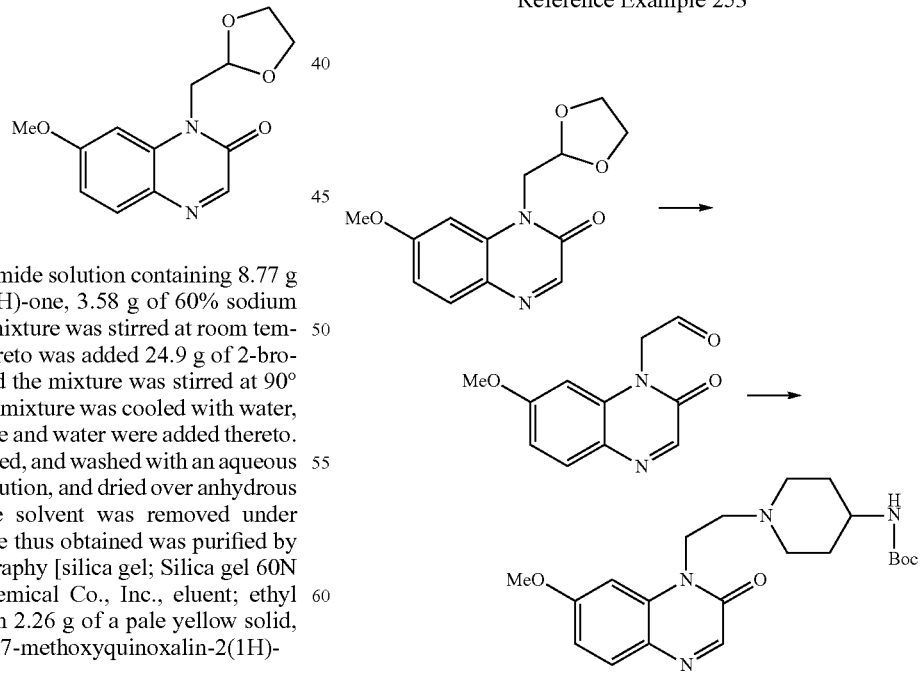

Into 200 mL of an 80% aqueous trifluoroacetic acid solution, 13g of 1-(1,3-dioxolan-2-ylmethyl)-7-methoxyquinoxalin-2(1H)-one was dissolved, and the mixture was stirred at room temperature for 16 hours. The solvent was removed under reduced pressure, the reaction mixture was alkalified with an aqueous saturated sodium hydrogen carbonate solution, and then extracted with ethyl acetate. The organic layer was washed with an aqueous saturated sodium chloride solution, and dried over anhydrous magnesium sulfate, and the solvent was removed under reduced pressure to obtain (7-methoxy-2-oxoquinoxalin-1(2H)-yl)acetaldehyde.

To 300 mL of a chloroform solution containing (7-methoxy-2-oxoquinoxalin-1(2H)-yl)acetaldehyde thus obtained, 9.93 g of tert-butyl (piperidin-4-yl)carbamate and 2.98 g of acetic acid were added, and the mixture was stirred at room temperature for 30 minutes. The reaction mixture was added with 15.8 g of sodium triacetoxyborohydride, and stirred for 2 hours. Thereto was added an aqueous saturated sodium hydrogen carbonate solution, and the organic layer was separated. The organic layer was washed with an aqueous saturated sodium chloride solution, and dried over anhydrous magnesium sulfate, and the solvent was removed under reduced pressure. The residue thus obtained was purified by silica gel column chromatography [silica gel; Silica gel 60N manufactured by Kanto Chemical Co., Inc., eluent; chloroform:methanol=20:1] to obtain 4.88 g of a brown solid, tert-butyl (1-(2-(7-methoxy-2-oxoquinoxalin-1(2H)-yl)ethyl)piperidin-4-yl)carbamate.

$^1$H-NMR (CDCl$_3$) δ:

1.45 (9H, s), 1.75-1.81 (2H, m), 1.92-1.97 (2H, m), 2.23-2.29 (2H, m), 2.65-2.69 (3H, m), 2.92-2.97 (2H, m), 3.93 (3H, s), 4.31-4.35 (2H, m), 6.83 (1H, d, J=2.3 Hz), 6.93 (1H, dd, J=9.2, 2.3 Hz), 7.79 (1H, d, J=9.2 Hz), 8.12 (1H, s)

Reference Example 254

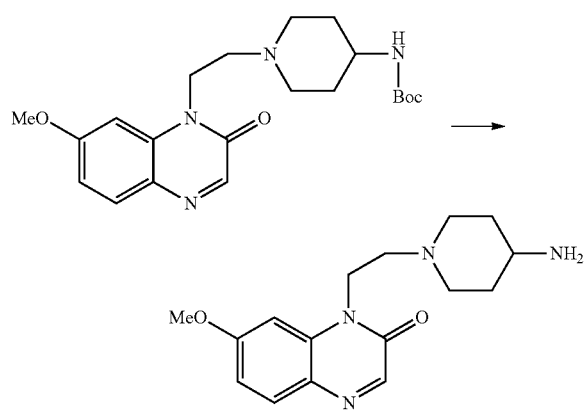

To 70 mL of a chloroform solution containing 9.53 g of tert-butyl (1-(2-(7-methoxy-2-oxoquinoxalin-1(2H)-yl) ethyl)piperidin-4-yl)carbamate, 20 mL of trifluoroacetic acid was added, and the mixture was stirred at room temperature for 10 hours. The solvent was removed under reduced pressure, the reaction mixture was alkalified with an aqueous saturated sodium hydrogen carbonate solution, and then the solvent was removed under reduced pressure. The residue thus obtained was purified by silica gel column chromatography [silica gel; Chromatorex-NH, manufactured by Fuji Silysia Chemical Ltd., eluent; chloroform:methanol=50:1] to obtain 5.97 g of a brown oily substance, 1-(2-(4-aminopiperidin-1-yl)ethyl)-7-methoxyquinoxalin-2(1H)-one.

$^1$H-NMR (CDCl$_3$) δ:

1.33-1.44 (4H, m), 1.80-1.86 (2H, m), 2.16-2.23 (2H, m), 2.65-2.73 (3H, m), 2.95-3.00 (2H, m), 3.93 (3H, s), 4.32-4.37 (2H, m), 6.84-6.88 (1H, m), 6.91-6.94 (1H, m), 7.77-7.80 (1H, m), 8.12 (1H, s)

Reference Example 255

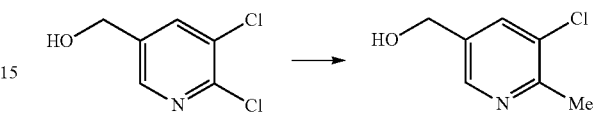

To 15 mL of a 1,4-dioxane solution containing 0.50 g of (5,6-dichloropyridin-3-yl)methanol, 1.2 g of potassium carbonate, 0.39 mL of trimethylboroxin and 0.32 g of tetrakis (triphenylphosphine) palladium(0) were added, and the mixture was stirred for 9 hours under reflux by heating. Thereto was added 0.32 g of tetrakis(triphenylphosphine) palladium (0), and the reaction mixture was stirred for 11 hours under reflux by heating under a nitrogen atmosphere. The insoluble material filtered off, and the solvent was removed under reduced pressure. The residue thus obtained was purified by silica gel column chromatography eluent; chloroform:methanol=50:1] to obtain 0.29 g of a white solid, (5-chloro-6-methylpyridin-3-yl)methanol.

$^1$H-NMR (CDCl$_3$) δ:

2.13-2.27 (1H, m), 2.62 (3H, s), 4.70 (2H, d, J=5.1 Hz), 7.69 (1H, d, J=1.7 Hz), 8.33 (1H, d, J=1.7 Hz)

Reference Example 256

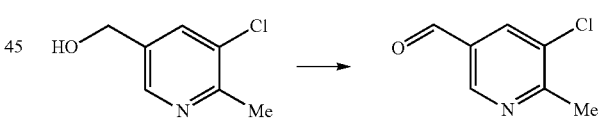

To 8 mL of a dichloromethane solution containing 0.22 g of (5-chloro-6-methylpyridin-3-yl)methanol, 0.55 g of molecular sieves 3A and 0.25 g of 4-methylmorpholine N-oxide were added, and the mixture was stirred at room temperature for 10 minutes. Thereto was added 34 mg of tetrapropylammonium perruthenate, and the mixture was stirred at room temperature for 1 hour and 30 minutes. Thereto was added 17 mg of tetrapropylammonium perruthenate, and the mixture was stirred at room temperature for 1 hour. The insoluble material filtered off, and the solvent was removed under reduced pressure. The residue thus obtained was purified by silica gel column chromatography [eluent; chloroform:methanol=100: 1] to obtain 0.11 g of a white solid, 5-chloro-6-methylnicotinealdehyde.

$^1$H-NMR (CDCl$_3$) δ:

2.74 (3H, s), 8.10 (1H, d, J=1.8 Hz), 8.84 (1H, d, J=1.8 Hz), 10.06 (1H, s)

Reference Example 257

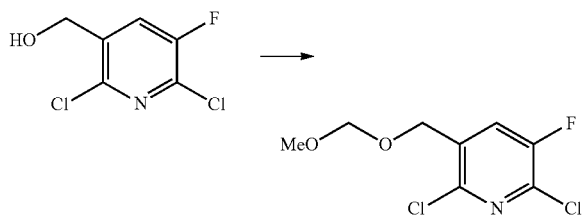

To 100 mL of a tetrahydrofuran solution containing 5.8 g of (2,6-dichloro-5-fluoropyridin-3-yl)methanol, 1.8 g of 60% sodium hydride and 2 mL of a tetrahydrofuran solution containing 2.4 mL of chloromethyl methyl ether were added under cooling with ice, and the mixture was stirred at room temperature for 1 hour. Water and ethyl acetate were added thereto, the organic layer was separated, washed sequentially with water and an aqueous saturated sodium chloride solution, and dried over anhydrous magnesium sulfate, and the solvent was removed under reduced pressure. The residue thus obtained was purified by silica gel column chromatography [eluent; hexane:ethyl acetate=8:1] to obtain 5.6 g of a colorless oily substance, 2,6-dichloro-3-fluoro-5-((methoxy)methyl)pyridine.

$^1$H-NMR (CDCl$_3$) δ:
3.42 (3H, s), 4.62 (2H, s), 4.79 (2H, s), 7.72 (1H, d, J=8.1 Hz)

Reference Example 258

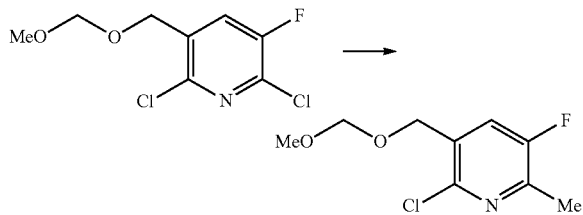

In the same method as in Reference Example 255, 2-chloro-5-fluoro-3-((methoxymethoxy)methyl)-6-methylpyridine was obtained from 2,6-dichloro-3-fluoro-5-((methoxymethoxy)methyl)pyridine.

$^1$H-NMR (CDCl$_3$) δ:
2.49 (3H, d, J=2.9 Hz), 3.42 (3H, s), 4.62 (2H, s), 4.77 (2H, s), 7.54 (1H, d, J=8.9 Hz)

Reference Example 259

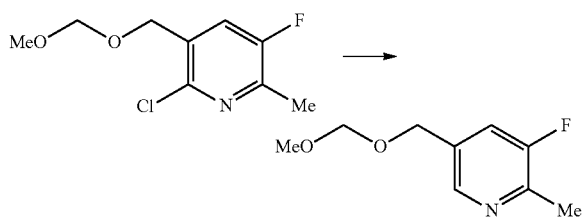

To 30 mL of a 1,4-dioxane solution containing 2.4 g of 2-chloro-5-fluoro-3-((methoxymethoxy)methyl)-6-methylpyridine, 2.3 mL of triethylamine, 0.61 mL of formic acid and 0.63 g of tetrakis(triphenylphosphine)palladium(0) were added, and the mixture was stirred for 2 hours with reflux by heating under a nitrogen atmosphere. Thereto was added 30 mL of N,N-dimethylformamide, and the mixture was stirred at 90 to 100° C. for 1 hour. Thereto were added 2.3 mL of triethylamine, 0.61 mL of formic acid and 0.63 g of tetrakis(triphenylphosphine)palladium(0), and the mixture was stirred at 90 to 100° C. for 1 hour. Water and ethyl acetate were added thereto, the organic layer was separated, and the aqueous layer was extracted with ethyl acetate. The organic layer and the extract were combined, and the resultant solution was washed sequentially with water and an aqueous saturated sodium chloride solution, and dried over anhydrous magnesium sulfate, and the solvent was removed under reduced pressure. The residue thus obtained was purified by flash silica gel column chromatography [hexane:gradient elution of ethyl acetate=95:5 to 80:20] to obtain 1.8 g of a yellow oily substance, 3-fluoro-5-((methoxymethoxy)methyl)-2-methylpyridine.

$^1$H-NMR (CDCl$_3$) δ:
2.52 (3H, d, J=2.9 Hz), 3.41 (3H, s), 4.59 (2H, s), 4.71 (2H, s), 7.35 (1H, dd, J=9.9, 1.3 Hz), 8.28 (1H, s)

Reference Example 260

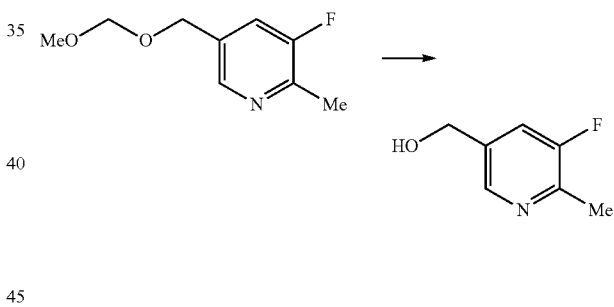

To 5 mL of a 1,4-dioxane solution containing 1.8 g of 3-fluoro-5-((methoxymethoxy)methyl)-2-methylpyridine, 2.5 mL of 6.0 mol/L hydrochloric acid was added, and the mixture was stirred at 30 to 40° C. for 1 hour. Thereto was added 2.5 mL of 6.0 mol/L hydrochloric acid, and the mixture was stirred at 30 to 40° C. for 30 minutes. Water and ethyl acetate were added thereto, and the reaction mixture was adjusted to pH 7.2 with a 20% aqueous sodium hydroxide solution and an aqueous saturated sodium hydrogen carbonate solution. The organic layer was separated, and the aqueous layer was extracted with ethyl acetate. The organic layer and the extract were combined, and the resultant solution was washed with an aqueous saturated sodium chloride solution and dried over anhydrous magnesium sulfate, and the solvent was removed under reduced pressure to obtain 1.3 g of a white solid, (5-fluoro-6-methylpyridin-3-yl)methanol.

$^1$H-NMR (CDCl$_3$) δ:
2.50-2.57 (1H, m), 2.51 (3H, d, J=2.7 Hz), 4.72 (2H, d, J=4.4 Hz), 7.39 (1H, d, J=9.8 Hz), 8.24 (1H, s)

Reference Example 261

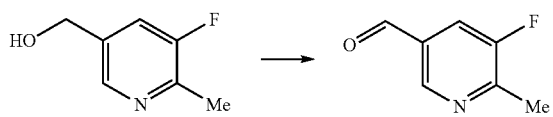 [SMILES: Cc1ncc(CO)cc1F ; Cc1ncc(C=O)cc1F]

In the same method as in Reference Example 256, 5-fluoro-6-methylnicotinealdehyde was obtained from (5-fluoro-6-methylpyridin-3-yl)methanol.

$^1$H-NMR (CDCl$_3$) δ:

2.64 (3H, d, J=3.2 Hz), 7.77 (1H, dd, J=8.8, 1.6 Hz), 8.78 (1H, s), 10.08 (1H, d, J=2.4 Hz)

Reference Example 262

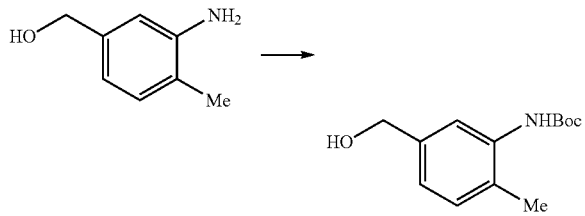

To 20 mL of a 1,4-dioxane solution containing 1.0 g of (3-amino-4-methylphenyl)methanol, 1.6 g of di-tert-butyl dicarbonate was added, and the mixture was stirred at 90 to 95° C. for 1 hour and 50 minutes. The reaction mixture was cooled to room temperature, then water and ethyl acetate were added thereto, the organic layer was separated, and the aqueous layer was extracted with ethyl acetate. The organic layer and the extract were combined, and the resultant solution was washed with an aqueous saturated sodium chloride solution and dried over anhydrous magnesium sulfate, and the solvent was removed under reduced pressure to obtain 1.8 g of a white solid, tert-butyl (5-(hydroxymethyl)-2-methylphenyl)carbamate.

$^1$H-NMR (CDCl$_3$) δ:

1.52 (9H, s), 2.23 (3H, s), 4.59-4.67 (2H, m), 6.25-6.35 (1H, m), 7.00 (1H, dd, J=7.8, 1.5 Hz), 7.13 (1H, d, J=7.8 Hz), 7.83 (1H, s)

Reference Example 263

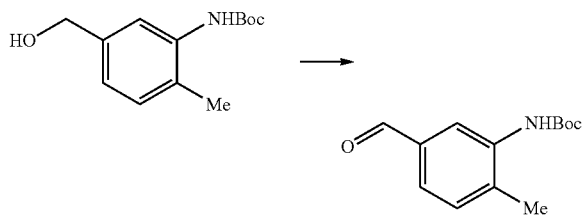

To 35 mL of a chloroform solution containing 1.8 g of tert-butyl (5-(hydroxymethyl)-2-methylphenyl)carbamate, 3.2 g of manganese dioxide was added at room temperature, and the mixture was stirred at the same temperature for 50 minutes, and at 50 to 60° C. for 2 hours and 45 minutes. The reaction mixture was cooled to room temperature, then the insoluble material filtered off, and the solvent was removed under reduced pressure. The residue thus obtained was added with 2-propanol and hexane, and a solid substance was collected by filtration to obtain 1.4 g of a pale yellow solid, tert-butyl (5-formyl-2-methylphenyl)carbamate.

$^1$H-NMR (CDCl$_3$) δ:

1.54 (9H, s), 2.33 (3H, s), 6.40 (1H, s), 7.30 (1H, d, J=7.7 Hz), 7.53 (1H, dd, J=7.7, 1.6 Hz), 8.38-8.42 (1H, m), 9.96 (1H, s)

Reference Example 264

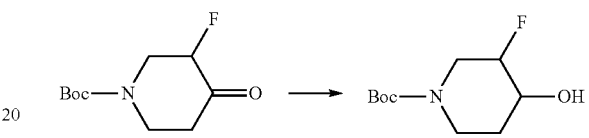

To 6.5 mL of an ethanol solution containing 0.49 g of tert-butyl 3-fluoro-4-oxopiperidine-1-carboxylate, 94 mg of sodium borohydride was added under cooling with ice, and the mixture was stirred for 1 hour. The reaction mixture was added with water and ethyl acetate. The organic layer was separated, washed with an aqueous saturated sodium chloride solution, and dried over anhydrous magnesium sulfate, and the solvent was removed under reduced pressure to obtain 0.42 g of a colorless oily substance, tert-butyl 3-fluoro-4-hydroxypiperidine-1-carboxylate.

$^1$H-NMR (CDCl$_3$) δ:

1.46 (9H, s), 1.70-2.25 (2H, m), 3.00-4.80 (6H, m)

Reference Example 265

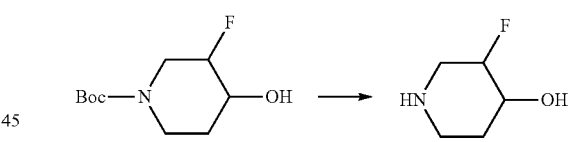

To 2 mL of a chloroform solution containing 0.42 g of tert-butyl 3-fluoro-4-hydroxypiperidine-1-carboxylate, 2.0 mL of trifluoroacetic acid was added, and the mixture was stirred for 2 hours. The solvent was removed under reduced pressure, and the residue thus obtained was added with water, an aqueous saturated sodium hydrogen carbonate solution and ethyl acetate. The aqueous layer was separated, washed with ethyl acetate, and the solvent was removed under reduced pressure. The residue thus obtained was added with chloroform and methanol, the insoluble material filtered off, and the solvent was removed under reduced pressure. The residue thus obtained was purified by reversed silica gel column chromatography [eluent; acetonitrile:water 1:4] to obtain 0.2 g of a colorless oily substance, 3-fluoropiperidin-4-ol.

$^1$H-NMR (DMSO-d$_6$, D$_2$O) δ:

1.20-1.82 (2H, m), 2.31-2.46 (1H, m), 2.50-2.70 (1H, m), 2.72-2.84 (1H, m), 2.93-3.10 (1H, m), 3.40-3.70 (1H, m), 4.00-4.50 (1H, m)

Reference Example 266

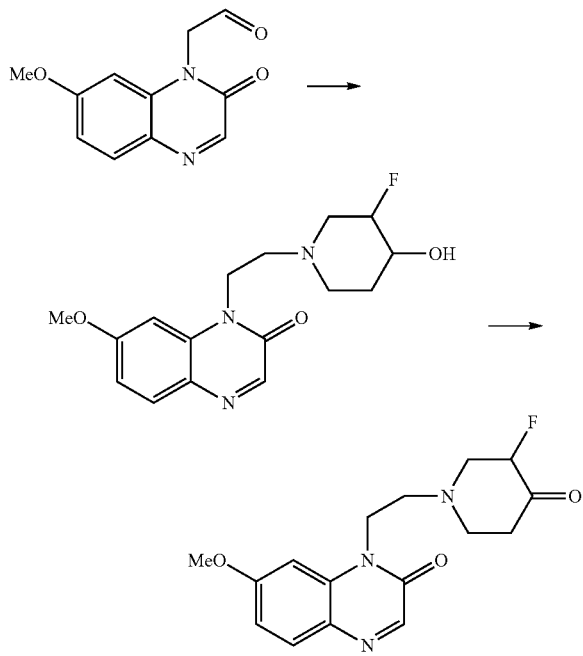

(1) To 2 mL of an N,N-dimethylformamide solution containing 0.18 g of (7-methoxy-2-oxoquinoxalin-1(2H)-yl)acetaldehyde and 0.1 g of 3-fluoropiperidin-4-ol, 0.14 mL of acetic acid was added, the mixture was stirred at room temperature for 1 hour, thereto was added 0.18 g of sodium triacetoxyborohydride was added, and the mixture was stirred for 30 minutes. The reaction mixture was added with an aqueous saturated sodium hydrogen carbonate solution and ethyl acetate. The organic layer was separated, and the aqueous layer was extracted with ethyl acetate. The organic layer and the extract were combined, the resultant solution was washed with an aqueous saturated sodium chloride solution, and dried over anhydrous magnesium sulfate, and the solvent was removed under reduced pressure to obtain 0.22 g of a brown oily substance, 1-(2-(3-fluoro-4-hydroxypiperidin-1-yl)ethyl)-7-methoxyquinoxalin-2(1H)-one.

(2) To 4 mL of a dichloromethane solution containing 0.22 g of 1-(2-(3-fluoro-4-hydroxypiperidin-1-yl)ethyl)-7-methoxyquinoxalin-2(1H)-one, 0.29 g of Dess-Martin periodinane was added at room temperature, the mixture was stirred for 4 hours, and thereto was added 0.15 g of Dess-Martin periodinane was added, and the mixture was stirred for 1 hour. The reaction mixture was added with an aqueous saturated sodium hydrogen carbonate solution and chloroform. The organic layer was separated, and the aqueous layer was extracted with chloroform. The organic layer and the extract were combined, the resultant solution was dried over anhydrous magnesium sulfate, and the solvent was removed under reduced pressure. The residue thus obtained was purified by flash silica gel column chromatography [chloroform:gradient elution of methanol=99:1 to 98:2] to obtain 48 mg of a brown foam, 1-(2-(3-fluoro-4-oxopiperidin-1-yl)ethyl)-7-methoxyquinoxalin-2(1H)-one.

$^1$H-NMR (CDCl$_3$) δ:
2.46-2.68 (4H, m), 2.88-2.96 (2H, m), 3.18-3.27 (1H, m), 3.52-3.60 (1H, m), 3.94 (3H, s), 4.39 (2H, t, J=6.7 Hz), 4.91 (1H, ddd, J=48.1, 10.2, 6.6 Hz), 6.79 (1H, d, J=2.4 Hz), 6.95 (1H, dd, J=8.8, 2.4 Hz), 7.83 (1H, d, J=8.8 Hz), 8.14 (1H, s)

Reference Example 267

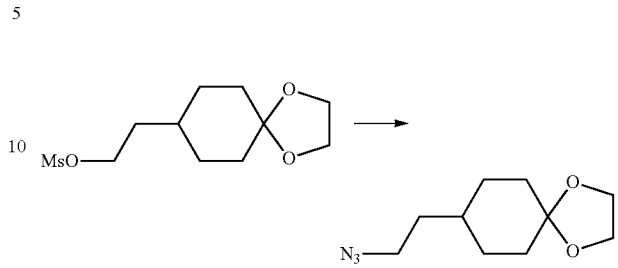

To 10 mL of an N,N-dimethylformamide solution containing 1.4 g of 2-(1,4-dioxaspiro(4.5)decan-8-yl)ethyl methanesulfonate, 0.45 g of sodium azide was added at room temperature, and the mixture was stirred at 45 to 50° C. for 1 hour and 30 minutes. Thereto was further added 70 mg of sodium azide, and the mixture was stirred at the same temperature for 2 hours. The reaction mixture was cooled to room temperature, and then water and ethyl acetate were added thereto. The organic layer was separated, washed with an aqueous saturated sodium chloride solution and then dried over anhydrous magnesium sulfate, and the solvent was removed under reduced pressure. The residue thus obtained was purified by silica gel column chromatography [eluent; hexane:ethyl acetate=4:1] to obtain 1.0 g of a colorless oily substance, 2-(1,4-dioxaspiro(4.5)decan-8-yl)ethyl azide.

$^1$H-NMR (CDCl$_3$) δ:
1.20-1.34 (2H, m), 1.38-1.48 (1H, m), 1.48-1.58 (4H, m), 1.68-1.78 (4H, m), 3.31 (2H, t, J=7.1 Hz), 3.90-3.98 (4H, m)

Reference Example 268

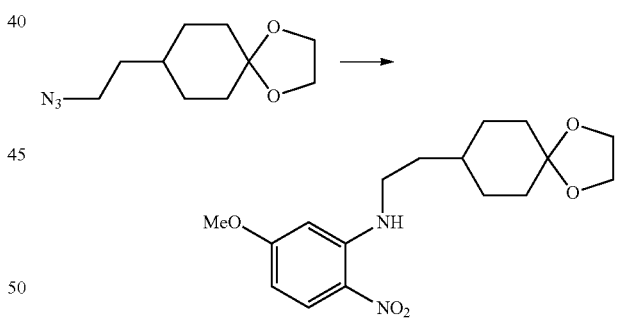

To 5 mL of a tetrahydrofuran solution containing 0.7 g of 2-(1,4-dioxaspiro(4.5)decan-8-yl)ethyl azide, 90 μL of water and 1.3 g of triphenylphosphine were added at room temperature, and the mixture was stirred at the same temperature for 2 hours and 50 minutes. Thereto were added 0.92 g of potassium carbonate, 5 mL of N,N-dimethylformamide and 0.57 g of 2-fluoro-4-methoxy-1-nitrobenzene, and the mixture was stirred at room temperature for 2 hours and 30 minutes. The reaction mixture was added with water and ethyl acetate, the organic layer was separated, washed with an aqueous saturated sodium chloride solution and then dried over anhydrous magnesium sulfate, and the solvent was removed under reduced pressure. The residue thus obtained was purified by basic silica gel column chromatography [eluent; hexane:ethyl acetate=15:1] to obtain 0.96 g of a yellow solid, N-(2-(1,4-dioxaspiro(4.5)decan-8-yl)ethyl)-5-methoxy-2-nitroaniline.

$^1$H-NMR (CDCl$_3$) δ:

1.28-1.41 (2H, m), 1.44-1.62 (3H, m), 1.66-1.83 (6H, m), 3.25-3.34 (2H, m), 3.87 (3H, s), 3.95 (4H, s), 6.13 (1H, d, J=2.7 Hz), 6.23 (1H, dd, J=9.5, 2.7 Hz), 8.14 (1H, d, J=9.5 Hz), 8.23-8.30 (1H, broad)

Reference Example 269

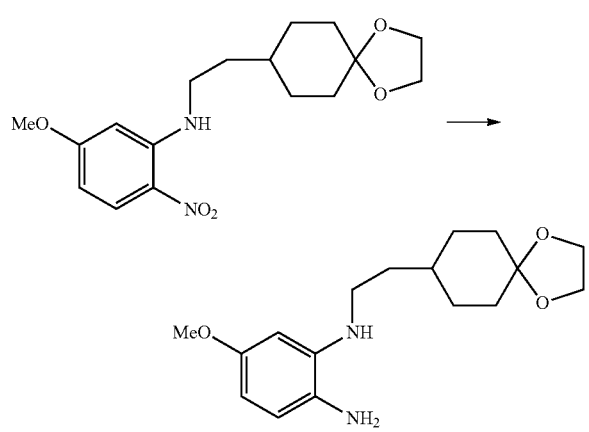

To 45 mL of an ethanol solution containing 0.8 g of N-(2-(1,4-dioxaspiro(4.5)decan-8-yl)ethyl)-5-methoxy-2-nitroaniline, 0.25 g of 10% palladium-carbon was added at room temperature, and the mixture was stirred at 40° C. for 3 hours and 30 minutes under a hydrogen atmosphere. The insoluble material filtered off, and the solvent was removed under reduced pressure to obtain 0.81 g of a violet oily substance, 2-(2-(1,4-dioxaspiro(4.5)decan-8-yl)ethyl)amino-4-methoxyaniline.

$^1$H-NMR (CDCl$_3$) δ:

1.22-1.40 (2H, m), 1.44-1.68 (5H, m), 1.68-1.84 (4H, m), 3.12 (2H, t, J=7.2 Hz), 3.75 (3H, s), 3.94 (4H, s), 6.17 (1H, dd, J=8.1, 2.6 Hz), 6.24 (1H, d, J=2.6 Hz), 6.64 (1H, d, J=8.1 Hz)

Reference Example 270

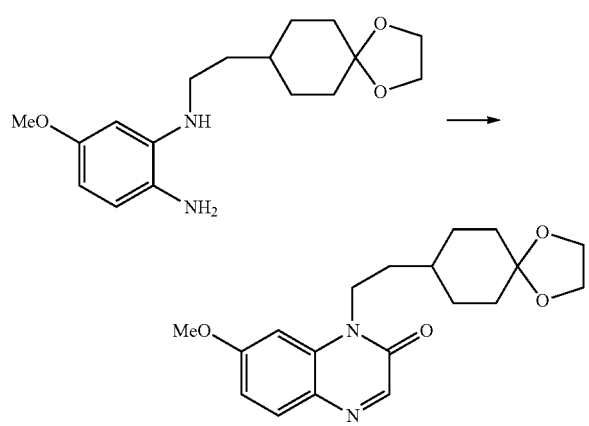

To 4 mL of a dioxane solution containing 50 mg of 2-(2-(1,4-dioxaspiro(4.5)decan-8-yl)ethyl)amino-4-methoxyaniline, 44 mg of a 45 to 50% toluene solution containing ethyl oxoacetate was added at room temperature, and the mixture was stirred for 45 minutes, and then thereto was added 40 mg of sodium triacetoxyborohydride, and the mixture was stirred for 1 hour and 50 minutes. The solvent was removed under reduced pressure, the residue thus obtained was added with 3 mL of dichloromethane and 40 mg of sodium triacetoxyborohydride, the reaction mixture was stirred for 6 hours and 50 minutes, and left to stand overnight. The reaction mixture was added with an aqueous saturated sodium hydrogen carbonate solution and chloroform, the organic layer was separated, and the aqueous layer was extracted with chloroform. The organic layer and the extract were combined, the resultant solution was washed with an aqueous saturated sodium chloride solution and dried over anhydrous magnesium sulfate, and the solvent was removed under reduced pressure. The residue thus obtained was added with 2 mL of chloroform and 2.5 g of silica gel, left to stand at room temperature for 2 hours, and then purified by silica gel column chromatography [eluent; chloroform:methanol=100:1] to obtain 22 mg of a pale yellow solid, 1-(2-(1,4-dioxaspiro(4.5)decan-8-yl)ethyl)-7-methoxyquinoxalin-2(1H)-one.

$^1$H-NMR (CDCl$_3$, D$_2$O) δ:

1.33-1.45 (2H, m), 1.45-1.63 (3H, m), 1.65-1.92 (6H, m), 3.92 (3H, s), 3.94-3.97 (4H, m), 4.18-4.26 (2H, m), 6.73 (1H, d, J=2.4 Hz), 6.93 (1H, dd, J=8.9, 2.4 Hz), 7.79 (1H, d, J=8.9 Hz), 8.12 (1H, s)

Reference Example 271

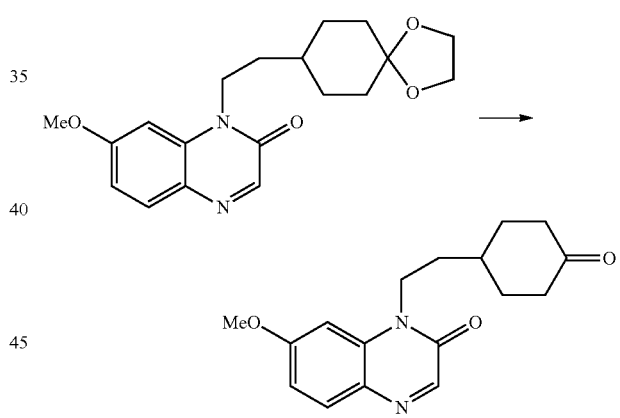

To 0.16 g of 1-(2-(1,4-dioxaspiro(4.5)decan-8-yl)ethyl)-7-methoxyquinoxalin-2(1H)-one, 1.5 mL of an 80% aqueous trifluoroacetic acid solution was added at room temperature, and the mixture was stirred at the same temperature for 15 minutes. Thereto was added ethyl acetate under cooling with ice, and the reaction mixture was adjusted to pH 8.0 with an aqueous saturated sodium hydrogen carbonate solution. The organic layer was separated, washed with an aqueous saturated sodium chloride solution and dried over anhydrous magnesium sulfate, and the solvent was removed under reduced pressure to obtain 0.18 g of a brown oily substance, 7-methoxy-1-(2-(4-oxocyclohexyl)ethyl)quinoxalin-2(1H)-one.

$^1$H-NMR (CDCl$_3$) δ:

1.47-1.60 (2H, m), 1.78 (2H, q, J=7.4 Hz), 1.85-1.96 (1H, m), 2.17-2.27 (2H, m), 2.32-2.48 (4H, m), 3.93 (3H, s), 4.25-4.32 (2H, m), 6.73 (1H, d, J=2.5 Hz), 6.95 (1H, dd, J=8.8, 2.5 Hz), 7.82 (1H, d, J=8.8 Hz), 8.14 (1H, s)

Reference Example 272

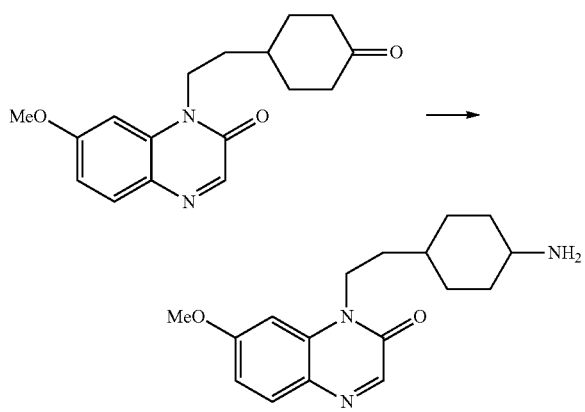

To 9 mL of an ethanol solution containing 0.16 g of 7-methoxy-1-(2-(4-oxocyclohexyl)ethyl)quinoxalin-2(1H)-one, 54 mg of ammonium acetate and 0.32 g of molecular sieves 3A were added at room temperature, and the mixture was stirred in an external bath at 30 to 35° C. for 1 hour and 30 minutes. The reaction mixture was cooled to room temperature, 35 mg of sodium cyanoborohydride was added thereto, and the mixture was stirred for 15 minutes. The reaction mixture was added with water and ethyl acetate, and the resultant solution was adjusted to pH 5.2 with 2.0 mol/L hydrochloric acid, and the aqueous layer was separated. The aqueous layer was added with ethyl acetate, and the resultant solution was adjusted to pH 9.5 with an aqueous sodium hydrogen carbonate solution. The organic layer was separated, and the aqueous layer was extracted sequentially with ethyl acetate and chloroform. The organic layer and the extract were combined, the resultant solution was dried over anhydrous magnesium sulfate, and the solvent was removed under reduced pressure to obtain 60 mg of a yellow oily substance, 1-(2-(4-aminocyclohexyl)ethyl)-7-methoxyquinoxalin-2(1H)-one.

$^{1}$H-NMR (CDCl$_{3}$) δ:
1.00-2.00 (12H, m), 3.93 (3H, s), 4.17-4.25 (2H, m), 6.71-6.76 (1H, m), 6.93 (1H, dd, J=8.8, 2.6 Hz), 7.79 (1H, d, J=8.8 Hz), 8.12 (1H, s)

Reference Example 273

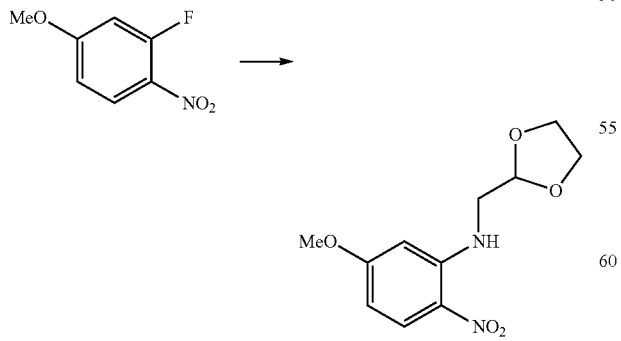

To 10 mL of an N,N-dimethylformamide solution containing 5.5 g of 2-fluoro-4-methoxy-1-nitrobenzene, 8.8 g of potassium carbonate and 2 mL of an N,N-dimethylformamide solution containing 4.3 g of 1-(1,3-dioxolan-2-yl)methaneamine were added at room temperature, and the mixture was stirred for 1 hour and 50 minutes, and left to stand overnight. The reaction mixture was added with water and ethyl acetate, the organic layer was separated, washed with an aqueous saturated sodium chloride solution, and dried over anhydrous magnesium sulfate, and the solvent was removed under reduced pressure to obtain 9.1 g of a yellow solid, N-(1,3-dioxolan-2-ylmethyl)-5-methoxy-2-nitroaniline.

$^{1}$H-NMR (CDCl$_{3}$) δ:
3.55 (2H, dd, J=5.5, 3.3 Hz), 3.86 (3H, s), 3.92-4.10 (4H, m), 5.19 (1H, t, J=3.3 Hz), 6.22-6.28 (2H, m), 8.14 (1H, d, J=10.0 Hz), 8.42-8.52 (1H, broad)

Reference Example 274

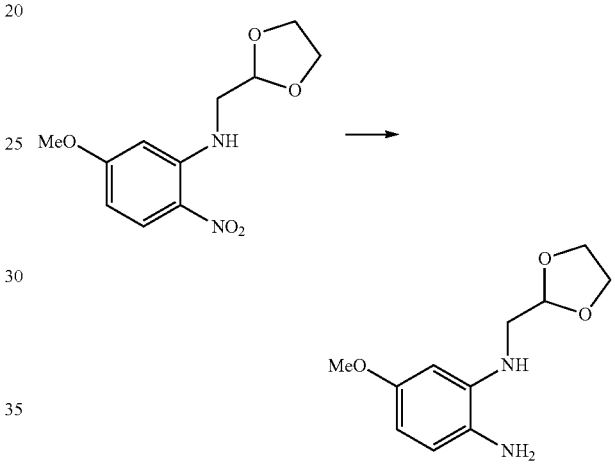

To 100 mL of an ethanol suspension containing 4.5 g of N-(1,3-dioxolan-2-ylmethyl)-5-methoxy-2-nitroaniline, 1.3 g of 10% palladium-carbon was added at room temperature, and the mixture was stirred at 40° C. for 3 hours and 40 minutes under a hydrogen atmosphere. The insoluble material filtered off, and the solvent was removed under reduced pressure to obtain 3.5 g of a violet oily substance, 2-(1,3-dioxolan-2-ylmethyl)amino-4-methoxyaniline.

$^{1}$H-NMR (CDCl$_{3}$) δ:
2.98-3.08 (2H, broad), 3.31 (2H, dd, J=6.2, 4.3 Hz), 3.75 (3H, s), 3.88-4.06 (4H, m), 5.16 (1H, t, J=4.3 Hz), 6.20 (1H, dd, J=8.3, 2.6 Hz), 6.30 (1H, d, J=2.6 Hz), 6.65 (1H, d, J=8.3 Hz)

Reference Example 275

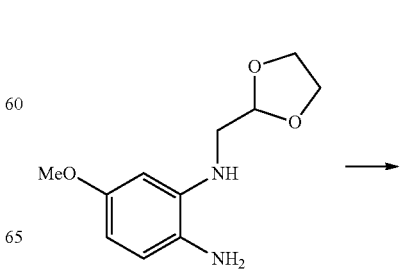

-continued

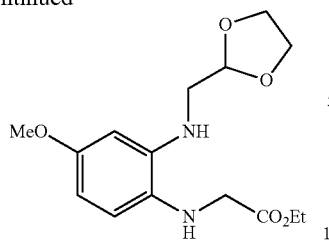

To 8 mL of an ethanol solution containing 0.25 g of 2-(1,3-dioxolan-2-ylmethyl)amino-4-methoxyaniline, 0.46 g of a 45 to 50% toluene solution containing ethyl oxoacetate was added at room temperature, the mixture was stirred for 15 minutes, and then thereto was added 46 mg of sodium triacetoxyborohydride, and the mixture was stirred for 1 hour and 15 minutes. The reaction mixture was added with water and ethyl acetate, the organic layer was separated, washed with an aqueous saturated sodium chloride solution and dried over anhydrous magnesium sulfate, and the solvent was removed under reduced pressure. The residue thus obtained was purified by basic silica gel column chromatography [eluent; hexane:ethyl acetate=5:1] to obtain 0.24 g of a yellow solid, ethyl N-(2-((1,3-dioxolan-2-ylmethyl)amino)-4-methoxyphenyl)glycinate.

$^1$H-NMR (CDCl$_3$) δ:
1.29 (3H, t, J=7.1 Hz), 3.26-3.34 (2H, m), 3.40-3.50 (1H, broad), 3.75 (3H, s), 3.79 (2H, s), 3.90-4.07 (4H, m), 4.23 (2H, q, J=7.1 Hz), 5.16 (1H, t, J=4.1 Hz), 6.25 (1H, dd, J=8.5, 2.8 Hz), 6.32 (1H, d, J=2.8 Hz), 6.60 (1H, d, J=8.5 Hz)

Reference Example 276

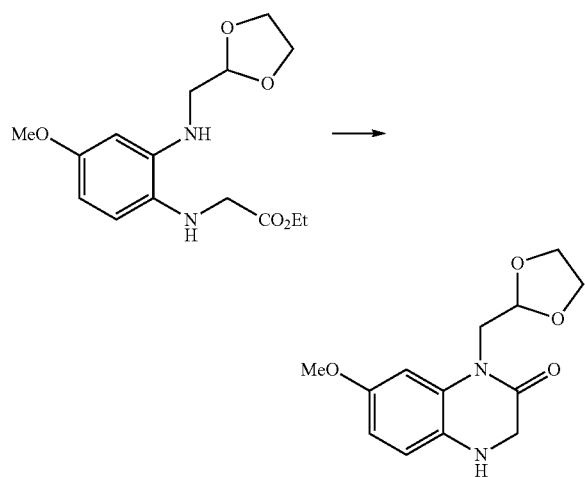

To 30 mL of a dioxane solution containing 3.3 g of ethyl N-(2-(1,3-dioxolan-2-ylmethyl)amino-4-methoxyphenyl)glycinate, 0.47 g of 60% sodium hydride was added under cooling with ice, and the mixture was stirred at 40 to 50° C. for 30 minutes. The reaction mixture was cooled to room temperature, then water and ethyl acetate were added thereto, the organic layer was separated, and the aqueous layer was extracted with chloroform. The organic layer and the extract were combined, the resultant solution was washed with an aqueous saturated sodium chloride solution and dried over anhydrous magnesium sulfate, and the solvent was removed under reduced pressure to obtain 3.1 g of a brown solid, 1-(1,3-dioxolan-2-ylmethyl)-7-methoxy-3,4-dihydroquinoxalin-2(1H)-one.

$^1$H-NMR (CDCl$_3$) δ:
3.59-3.66 (1H, broad), 3.78 (3H, s), 3.86-3.95 (4H, m), 4.00-4.08 (2H, m), 4.12 (2H, d, J=4.5 Hz), 5.18 (1H, t, J=4.5 Hz), 6.50 (1H, dd, J=8.6, 2.7 Hz), 6.65 (1H, d, J=8.6 Hz), 6.90 (1H, d, J=2.7 Hz)

Reference Example 277

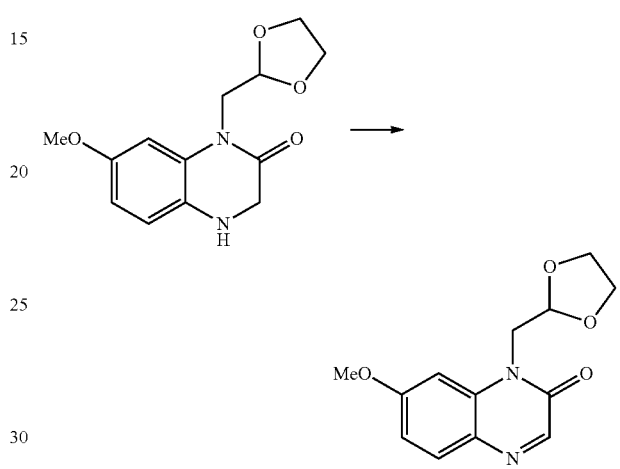

To 20 mL of a dioxane solution containing 3.0 g of 1-(1,3-dioxolan-2-ylmethyl)-7-methoxy-3,4-dihydroquinoxalin-2(1H)-one, a solution of 4 mL of water containing 1.1 g of sodium chlorite was added at room temperature, and the mixture was stirred for 1 hour and 20 minutes. Thereto was further added 0.45 g of sodium chlorite, the mixture was stirred for 3 hours and 30 minutes, left to stand overnight, and then further stirred at room temperature for 6 hours. The reaction mixture was added with water and ethyl acetate, the organic layer was separated, and the aqueous layer was extracted with ethyl acetate. The organic layer and the extract were combined, and the resultant solution was washed with an aqueous saturated sodium chloride solution and dried over anhydrous magnesium sulfate, and the solvent was removed under reduced pressure. The residue thus obtained was added with diethyl ether, and a solid substance was collected by filtration to obtain 2.0 g of a brown solid, 1-(1,3-dioxolan-2-ylmethyl)-7-methoxyquinoxalin-2(1H)-one.

$^1$H-NMR (CDCl$_3$) δ:
3.86-3.95 (2H, m), 3.92 (3H, s), 3.98-4.06 (2H, m), 4.46 (2H, d, J=4.1 Hz), 5.26 (1H, t, J=4.1 Hz), 6.92 (1H, dd, J=9.0, 2.5 Hz), 7.02 (1H, d, J=2.5 Hz), 7.77 (1H, d, J=9.0 Hz), 8.15 (1H, s)

Reference Example 278

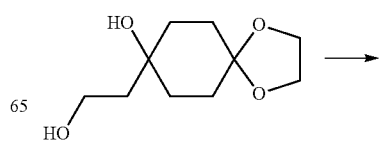

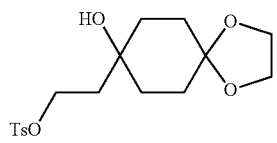

To 30 mL of a chloroform solution containing 4.2 g of 8-(2-hydroxyethyl)-1,4-dioxaspiro(4.5)decan-8-ol, 2.18 mL of pyridine was added at room temperature, and 4.0 g of p-toluenesulfonyl chloride was dividedly added thereto under cooling with ice, the mixture was stirred at room temperature for 1 hour and 35 minutes, left to stand overnight, and then further stirred at 30 to 40° C. for 1 hour. The reaction mixture was added with water and chloroform under cooling with ice. The organic layer was separated, washed with an aqueous saturated sodium chloride solution, and then dried over anhydrous magnesium sulfate, and the solvent was removed under reduced pressure. The residue thus obtained was purified by silica gel column chromatography [eluent; chloroform:methanol=50:1] to obtain 4.2 g of a yellow oily substance, 2-(8-hydroxy-1,4-dioxaspiro(4.5)decan-8-yl)ethyl 4-methylbenzenesulfonate.

$^1$H-NMR (CDCl$_3$) δ:

1.51-1.66 (6H, m), 1.78-1.90 (2H, m), 1.86 (2H, t, J=6.8 Hz), 2.45 (3H, s), 3.88-3.98 (4H, m), 4.23 (2H, t, J=6.8 Hz), 7.35 (2H, d, J=8.2 Hz), 7.79 (2H, d, J=8.2 Hz)

Reference Example 279

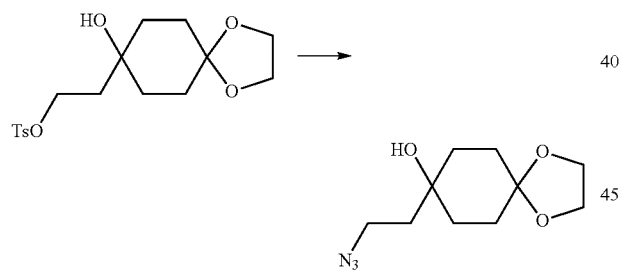

To 24 mL of an N,N-dimethylformamide solution containing 4.0 g of 2-(8-hydroxy-1,4-dioxaspiro(4.5)decan-8-yl) ethyl 4-methylbenzenesulfonate, 0.91 g of sodium azide was added at room temperature, and the mixture was stirred at 40° C. for 2 hours. The reaction mixture was added with water, ethyl acetate and sodium chloride under cooling with water, the organic layer was separated, and dried over anhydrous magnesium sulfate, and the solvent was removed under reduced pressure to obtain 2.7 g of a yellow oily substance, 8-(2-azidethyl)-1,4-dioxaspiro(4.5)decan-8-ol.

$^1$H-NMR (CDCl$_3$) δ:

1.55-1.74 (6H, m), 1.78 (2H, t, J=7.2 Hz), 1.85-1.95 (2H, m), 3.49 (2H, t, J=7.2 Hz), 3.90-4.00 (4H, m)

Reference Example 280

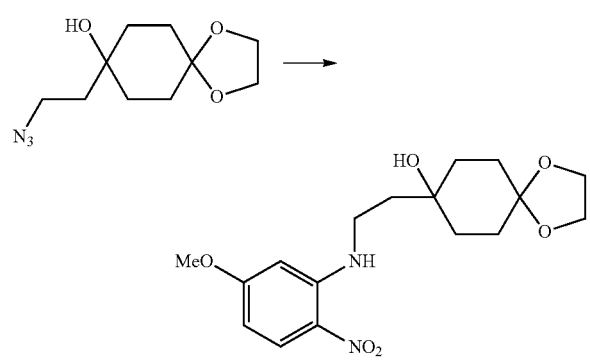

To 20 mL of a tetrahydrofuran suspension containing 2.6 g of 8-(2-azidethyl)-1,4-dioxaspiro(4.5)decan-8-ol, 0.6 mL of water and 2.8 g of triphenylphosphine were added under cooling with water, and the mixture was stirred at 30 to 40° C. for 3 hours. The reaction mixture was added with 3.2 g of potassium carbonate, 10 mL of N,N-dimethylformamide and 2.0 g of 2-fluoro-4-methoxy-1-nitrobenzene under cooling with water, and the mixture was stirred at room temperature for 1 hour and 10 minutes and at 30 to 40° C. for 3 hours. The reaction mixture was cooled to room temperature, then water and ethyl acetate were added thereto, the organic layer was separated, and the aqueous layer was extracted with ethyl acetate. The organic layer and the extract were combined, and the resultant solution was washed with an aqueous saturated sodium chloride solution and dried over anhydrous magnesium sulfate, and the solvent was removed under reduced pressure. The residue thus obtained was purified by silica gel column chromatography [eluent; chloroform:methanol=100:1] to obtain 3.2 g of an orange oily substance, 8-(2-((5-methoxy-2-nitrophenyl)amino)ethyl)-1,4-dioxaspiro(4.5) decan-8-ol.

$^1$H-NMR (CDCl$_3$) δ:

1.60-1.68 (2H, m), 1.73-1.79 (4H, m), 1.83-1.96 (2H, m), 1.93 (2H, t, J=7.2 Hz), 3.40-3.48 (2H, m), 3.87 (3H, s), 3.91-4.00 (4H, m), 6.18 (1H, d, J=2.7 Hz), 6.23 (1H, dd, J=9.5, 2.7 Hz), 8.14 (1H, d, J=9.5 Hz), 8.45-8.52 (1H, broad)

Reference Example 281

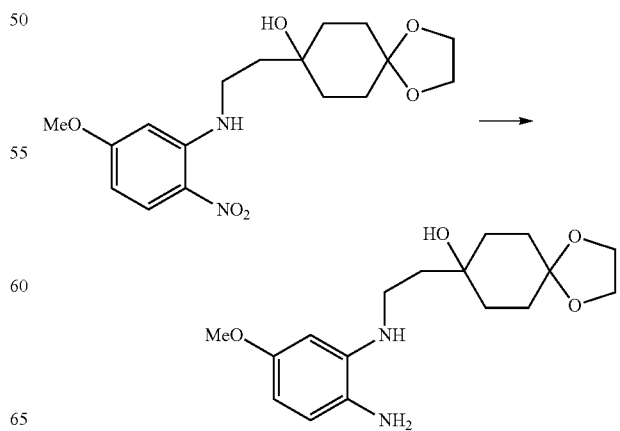

To 35 mL of an ethanol suspension containing 0.62 g of iron powder, 20 mL of water and 0.64 g of sodium chloride were added at room temperature, and the mixture was refluxed by heating for 30 minutes. The reaction mixture was cooled to 50 to 60° C., then added with 5 mL of an ethanol solution containing 0.65 g of 8-(2-((5-methoxy-2-nitrophenyl)amino)ethyl)-1,4-dioxaspiro(4.5)decan-8-ol, and the mixture was stirred at 80° C. for 2 hours and 10 minutes. The reaction mixture was cooled to room temperature, then the insoluble material filtered off, and the solvent was removed under reduced pressure. The residue thus obtained was added with water, chloroform, and sodium chloride. The organic layer was separated and dried over anhydrous magnesium sulfate, and the solvent was removed under reduced pressure. The residue thus obtained was purified by basic silica gel column chromatography [eluent; chloroform:methanol=100:1] to obtain 0.60 g of a gray solid, 8-(2-((2-amino-5-methoxyphenyl)amino)ethyl)-1,4-dioxaspiro(4.5)decan-8-ol.

$^1$H-NMR (CDCl$_3$) δ:
1.52-1.82 (6H, m), 1.84-1.96 (2H, m), 1.87 (2H, t, J=6.6 Hz), 3.29 (2H, t, J=6.6 Hz), 3.76 (3H, s), 3.91-4.00 (4H, m), 6.22 (1H, dd, J=8.3, 2.7 Hz), 6.31 (1H, d, J=2.7 Hz), 6.65 (1H, d, J=8.3 Hz)

Reference Example 282

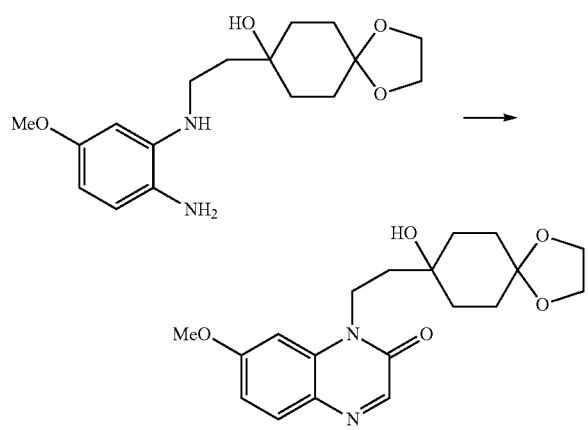

To 15 mL of a dichloromethane solution containing 0.6 g of 8-(2-((2-amino-5-methoxyphenyl)amino)ethyl)-1,4-dioxaspiro(4.5)decan-8-ol, 0.60 g of a 45 to 50% toluene solution containing ethyl oxoacetate was added under cooling with ice, the mixture was stirred for 25 minutes, and then thereto was added 0.39 g of sodium triacetoxyborohydride, and the mixture was stirred at room temperature for 1 hour and 40 minutes, and left to stand overnight. An aqueous saturated sodium hydrogen carbonate solution and chloroform were added with the reaction mixture, the organic layer was separated, washed with an aqueous saturated sodium chloride solution and dried over anhydrous magnesium sulfate, and the solvent was removed under reduced pressure. The residue thus obtained was purified by silica gel column chromatography [eluent; hexane:ethyl acetate=2:3] to obtain 0.26 g of a yellow solid, 1-(2-(8-hydroxy-1,4-dioxaspiro(4.5)decan-8-yl)ethyl)-7-methoxyquinoxalin-2(1H)-one.

$^1$H-NMR (CDCl$_3$) δ:
1.53-1.68 (2H, m), 1.72-1.80 (4H, m), 1.86-1.99 (4H, m), 3.90-4.00 (4H, m), 3.93 (3H, s), 4.35-4.41 (2H, m), 6.91 (1H, d, J=2.4 Hz), 6.94 (1H, dd, J=8.8, 2.4 Hz), 7.80 (1H, d, J=8.8 Hz), 8.13 (1H, s)

Reference Example 283

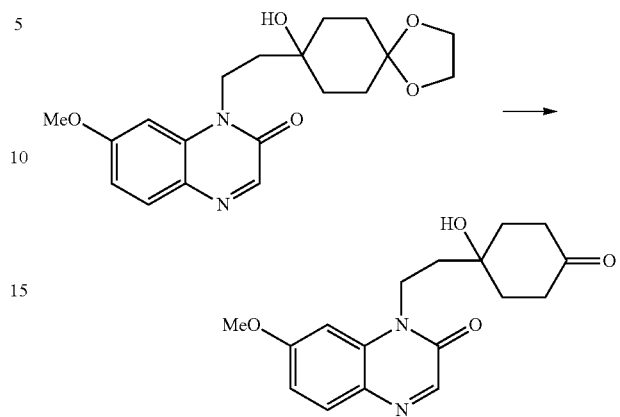

To 8 mL of a dioxane suspension containing 0.25 g of 1-(2-(8-hydroxy-1,4-dioxaspiro(4.5)decan-8-yl)ethyl)-7-methoxyquinoxalin-2(1H)-one, 3 mL of an 80% aqueous trifluoroacetic acid solution was dividedly added at room temperature, and the mixture was stirred for 5 hours and 15 minutes. An aqueous saturated sodium hydrogen carbonate solution was added with the reaction mixture, and then added with ethyl acetate and sodium chloride. The organic layer was separated, and dried over anhydrous magnesium sulfate, and the solvent was removed under reduced pressure. The residue thus obtained was purified by silica gel column chromatography [eluent; hexane:ethyl acetate 1:3] to obtain 0.10 g of a colorless oily substance, 1-(2-(1-hydroxy-4-oxocyclohexyl)ethyl)-7-methoxyquinoxalin-2(1H)-one.

$^1$H-NMR (CDCl$_3$) δ:
1.75-1.88 (2H, m), 2.00-2.15 (4H, m), 2.23-2.32 (2H, m), 2.72-2.82 (2H, m), 3.94 (3H, s), 4.42 (2H, t, J=6.8 Hz), 6.83 (1H, d, J=2.4 Hz), 6.99 (1H, dd, J=8.8, 2.4 Hz), 7.85 (1H, d, J=8.8 Hz), 8.17 (1H, s)

Reference Example 284

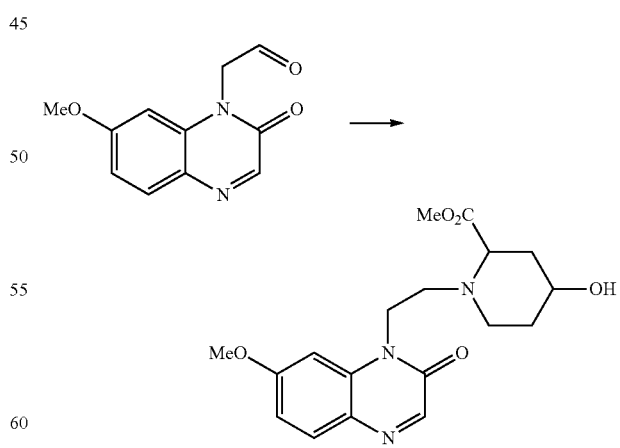

In the same method as in Example 24, methyl 4-hydroxy-1-(2-(7-methoxy-2-oxoquinoxalin-1(2H)-yl)ethyl)piperidine-2-carboxylate was obtained from (7-methoxy-2-oxoquinoxalin-1-(2H)-yl)acetaldehyde and methyl 4-hydroxypiperidine-2-carboxylate.

¹H-NMR (CDCl₃) δ:
1.58-1.68 (1H, m), 1.71-1.80 (2H, m), 1.86-1.95 (1H, m), 2.06-2.14 (1H, m), 2.40-2.49 (1H, m), 2.59-2.68 (1H, m), 2.82-2.91 (1H, m), 3.22-3.32 (2H, m), 3.68 (3H, s), 3.72-3.82 (1H, m), 3.98 (3H, s), 4.17-4.26 (1H, m), 4.49-4.59 (1H, m), 6.92 (1H, dd, J=9.0, 2.5 Hz), 6.95 (1H, d, J=2.5 Hz), 7.77 (1H, d, J=9.0 Hz), 8.11 (1H, s)

Reference Example 285

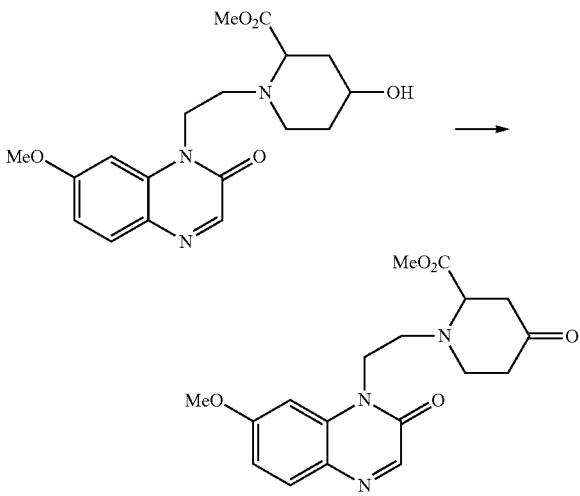

To 5 mL of a dichloromethane solution containing 0.2 g of methyl 4-hydroxy-1-(2-(7-methoxy-2-oxoquinoxalin-1(2H)-yl)ethyl)piperidine-2-carboxylate, 0.3 g of molecular sieves 3A was added at room temperature under a nitrogen atmosphere, thereto was further added 0.18 g of pyridinium chlorochromate under cooling with ice, and the mixture was stirred at room temperature for 4 hours. Thereto was further added 90 mg of pyridinium chlorochromate over 1 hour and 40 minutes, and the mixture was stirred at the same temperature for 1 hour and 30 minutes. The reaction mixture was added with water, chloroform and sodium chloride, and the organic layer was separated. The organic layer was dried over anhydrous magnesium sulfate, and the solvent was removed under reduced pressure to obtain 0.10 g of a brown oily substance, methyl 1-(2-(7-methoxy-2-oxoquinoxalin-1(2H)-yl)ethyl)-4-oxopiperidine-2-carboxylate.
¹H-NMR (CDCl₃) δ:
2.42-2.61 (4H, m), 2.92-3.24 (4H, m), 3.69 (3H, s), 3.83-3.86 (1H, m), 3.96 (3H, s), 4.38-4.46 (2H, m), 6.87-6.91 (1H, m), 6.94 (1H, dd, J=8.9, 1.6 Hz), 7.81 (1H, d, J=8.9 Hz), 8.14 (1H, s)

Reference Example 286

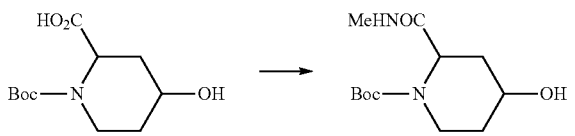

In the same method as in Reference Example 31, tert-butyl 4-hydroxy-2-((methylamino)carbonyl)piperidine-1-carboxylate was obtained from 1-(tert-butoxycarbonyl)-4-hydroxypiperidine-2-carboxylic acid and methylamine hydrochloride.
¹H-NMR (CDCl₃) δ:
1.48 (9H, s), 1.83-1.95 (2H, m), 1.99-2.10 (1H, m), 2.26-2.35 (1H, m), 2.80 (3H, s), 2.98-3.02 (1H, m), 3.14-3.28 (1H, m), 3.98-4.14 (1H, broad), 4.97 (1H, t, J=5.1 Hz)

Reference Example 287

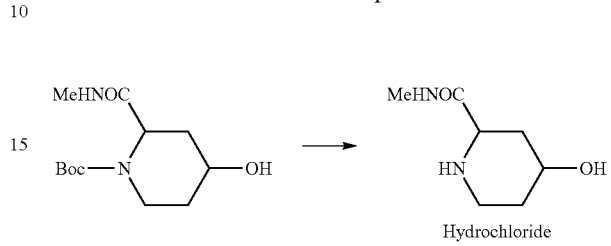

To 5 mL of an ethyl acetate solution containing 0.2 g of tert-butyl 4-hydroxy-2-((methylamino)carbonyl)piperidine-1-carboxylate, 1 mL of a 4 mol/L hydrogen chloride/ethyl acetate solution was added at room temperature, and the mixture was stirred for 2 hours and 45 minutes, and then left to stand overnight. Thereto was further added 0.3 mL of a 4 mol/L hydrogen chloride/ethyl acetate solution, and the mixture was stirred for 6 hours. A solid substance was collected by filtration to obtain 0.11 g of a white solid, 4-hydroxy-N-methylpiperidine-2-carboxamide hydrochloride.
¹H-NMR (D₂O) δ:
2.10-2.24 (2H, m), 2.27-2.36 (1H, m), 2.68-2.77 (1H, m), 3.33-3.43 (1H, m), 3.61-3.67 (1H, m), 4.30 (1H, d, J=4.9 Hz), 4.80 (3H, s), 5.27 (1H, t, J=5.5 Hz)

Reference Example 288

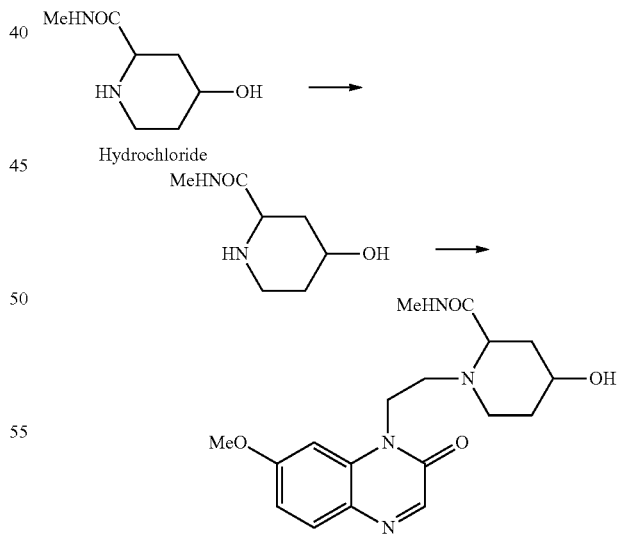

(1) To 3 mL of a methanol suspension containing 0.11 g of 4-hydroxy-N-methylpiperidine-2-carboxamide hydrochloride, 0.21 g of a 28% sodium methoxide/methanol solution was added at room temperature, and the mixture was stirred at the same temperature for 25 minutes. The solvent was removed under reduced pressure to obtain 0.10 g of a white foam, 4-hydroxy-N-methylpiperidine-2-carboxamide.

(2) In the same method as in Example 24, 4-hydroxy-1-(2-(7-methoxy-2-oxoquinoxalin-1(2H)-yl)ethyl)-N-methylpiperidine-2-carboxamide was obtained from (7-methoxy-2-oxoquinoxalin-1-(2H)-yl)acetaldehyde and 4-hydroxy-N-methylpiperidine-2-carboxamide.

$^1$H-NMR (CDCl$_3$) δ:

1.56-1.81 (2H, m), 1.86-1.95 (1H, m), 2.39-2.48 (1H, m), 2.59-2.69 (1H, m), 2.81-2.91 (1H, m), 3.22-3.32 (1H, m), 3.24 (1H, dd, J=9.3, 3.7 Hz), 3.68 (3H, s), 3.77 (2H, s), 3.98 (3H, s), 4.17-4.27 (1H, m), 4.49-4.59 (1H, m), 6.89-6.97 (2H, m), 7.77 (1H, d, J=8.8 Hz), 8.11 (1H, s)

Reference Example 289

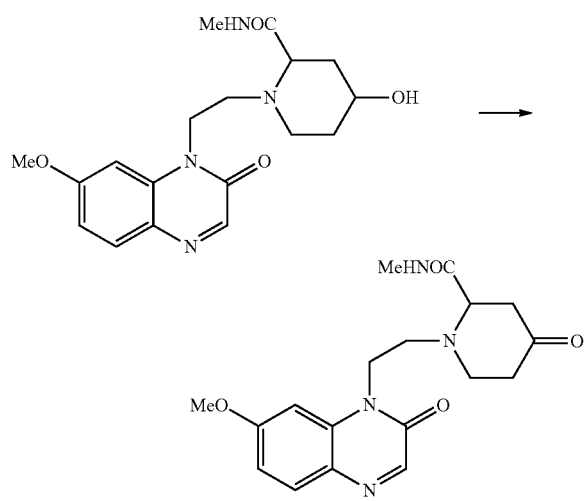

To 2 mL of a dichloromethane solution containing 11 mg of 4-hydroxy-1-(2-(7-methoxy-2-oxoquinoxalin-1(2H)-yl)ethyl)-N-methylpiperidine-2-carboxamide, 13 mg of Dess-Martin periodinane was added at room temperature, and the mixture was stirred at the same temperature for 1 hour. The reaction mixture was added with an aqueous saturated sodium hydrogen carbonate solution and chloroform. The organic layer was separated, washed with an aqueous saturated sodium chloride solution, and dried over anhydrous magnesium sulfate, and the solvent was removed under reduced pressure to obtain 12 mg of a yellow oily substance, 1-(2-(7-methoxy-2-oxoquinoxalin-1(2H)-yl)ethyl)-N-methyl-4-oxopiperidine-2-carboxamide.

$^1$H-NMR (CDCl$_3$) δ:

1.50-1.81 (3H, m), 1.86-1.95 (1H, m), 2.06-2.14 (1H, m), 2.39-2.48 (1H, m), 2.59-2.69 (1H, m), 2.81-2.91 (1H, m), 3.22-3.32 (2H, m), 3.68 (3H, s), 3.72-3.83 (1H, m), 3.98 (3H, s), 4.17-4.27 (1H, m), 4.49-4.59 (1H, m), 6.89-6.97 (2H, m), 7.77 (1H, d, J=8.8 Hz), 8.11 (1H, s)

Reference Example 290

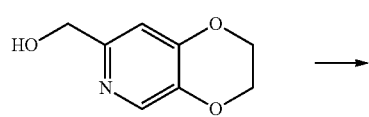 

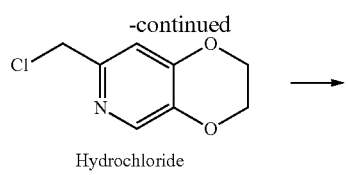

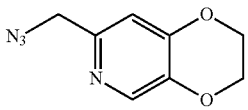

(1) To 30 mL of a tetrahydrofuran solution containing 0.60 g of 2,3-dihydro(1,4)dioxino(2,3-c)pyridin-7-ylmethanol, 0.40 mL of thionyl chloride was added under cooling with ice, the mixture was stirred at the same temperature for 20 minutes, and the solvent was removed under reduced pressure. The residue thus obtained was added with tetrahydrofuran, and a solid substance was collected by filtration to obtain 0.75 g of a white solid, 7-(chloromethyl)-2,3-dihydro(1,4)dioxino(2,3-c)pyridine hydrochloride.

(2) A solution of 5 mL of water containing 0.75 g of 7-(chloromethyl)-2,3-dihydro(1,4)dioxino(2,3-c)pyridine hydrochloride was adjusted to pH 7.8 with an aqueous saturated sodium hydrogen carbonate solution, thereto were added dichloromethane and sodium chloride, the organic layer was separated, and the solvent was removed under reduced pressure. The residue thus obtained was added with 30 mL of N,N-dimethylformamide, and then added with 0.26 g of sodium azide at room temperature, and the mixture was stirred at 40° C. for 2 hours. The reaction mixture was cooled to room temperature, and then water and ethyl acetate was added thereto, the organic layer was separated, and the aqueous layer was extracted with ethyl acetate. The organic layer and the extract were combined, and the resultant solution was washed with an aqueous saturated sodium chloride solution, and dried over anhydrous magnesium sulfate, and the solvent was removed under reduced pressure to obtain 0.53 g of a yellow oily substance, 7-(azidomethyl)-2,3-dihydro-(1,4)dioxino(2,3-c)pyridine.

$^1$H-NMR (CDCl$_3$) δ:

4.27-4.37 (6H, m), 6.85 (1H, s), 8.15 (1H, s)

Reference Example 291

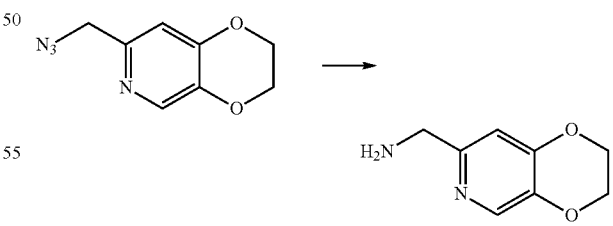

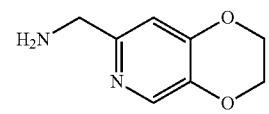

To 10 mL of an ethanol solution containing 0.53 g of 7-(azidomethyl)-2,3-dihydro-(1,4)dioxino(2,3-c)pyridine, 0.10 g of 5% palladium-carbon was added at room temperature, and the mixture was stirred for 1 hour and 45 minutes under a hydrogen atmosphere. The insoluble material filtered off, and the solvent was removed under reduced pressure to obtain 0.46 g of a brown oily substance, 1-(2,3-dihydro(1,4)dioxino(2,3-c)pyridin-7-yl)methaneamine.

¹H-NMR (CDCl₃) δ:
1.50-1.72 (2H, broad), 3.84 (2H, s), 4.24-4.36 (4H, m), 6.79 (1H, s), 8.11 (1H, s)

Reference Example 292

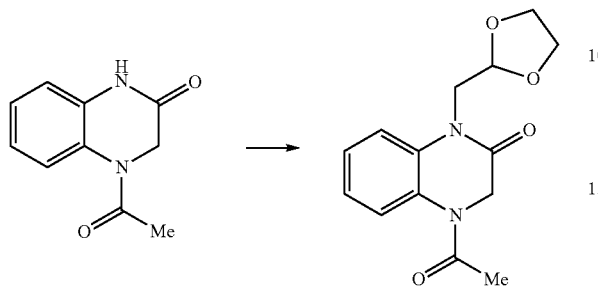

To 15 mL of an N,N-dimethylformamide solution containing 957 mg of 4-acetyl-3,4-dihydro-2-oxo-1H-quinoxaline, 668 mg of sodium hydride was added, and the mixture was stirred at room temperature for 1 hour. Thereto was added 2.6 mL of 2-bromomethyl-1,3-dioxolane, and the mixture was stirred at 90° C. for 6 hours. The reaction mixture was cooled to room temperature, and then ethyl acetate and 1 mol/L hydrochloric acid were added thereto. The organic layer was separated, washed sequentially with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform] to obtain 1.30 g of a brown oily substance, 4-acetyl-1-(1,3-dioxolan-2-ylmethyl)-2-oxo-3,4-dihydro-1H-quinoxaline.

¹H-NMR (CDCl₃) δ:
2.25 (3H, s), 3.86-3.92 (2H, m), 3.98-4.04 (2H, m), 4.14 (2H, d, J=4.1 Hz), 4.51-4.59 (2H, m), 5.18 (1H, t, J=4.4 Hz), 7.13 (1H, t, J=7.6 Hz), 7.24-7.30 (2H, m), 7.42 (1H, d, J=8.3 Hz)

Reference Example 293

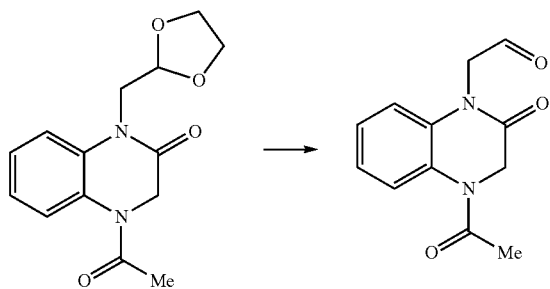 [SMILES: CC(=O)N1CC(=O)N(CC2OCCO2)c2ccccc21 ; CC(=O)N1CC(=O)N(CC=O)c2ccccc21]

Into 4 mL of a 90% aqueous trifluoroacetic acid solution, 800 mg of 4-acetyl-1-(1,3-dioxolan-2-ylmethyl)-2-oxo-3,4-dihydro-1H-quinoxaline was dissolved, and the mixture was stirred at room temperature overnight. The solvent was removed under reduced pressure, the reaction mixture was alkalified with an aqueous saturated sodium hydrogen carbonate solution, and then extracted with ethyl acetate. The organic layer was washed with water and an aqueous saturated sodium chloride solution and dried over anhydrous magnesium sulfate, and the solvent was removed under reduced pressure to obtain 561 mg of a pale yellow solid, (4-acetyl-2-oxo-3,4-dihydroquinoxalin-1(2H)-yl)acetaldehyde.

¹H-NMR (CDCl₃) δ:
2.27 (3H, s), 3.49 (2H, s), 4.74 (2H, s), 6.77 (1H, d, J=7.8 Hz), 7.16 (1H, t, J=7.8 Hz), 7.21-7.33 (2H, m), 9.71 (1H, s)

Reference Example 294

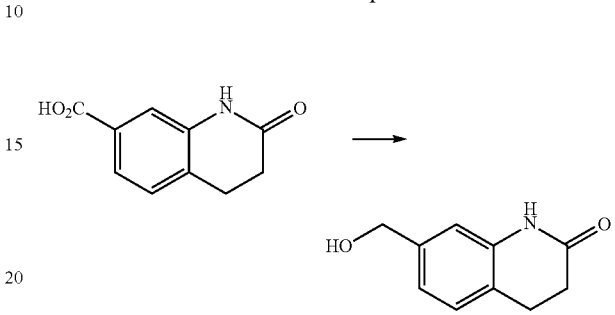

Into 50 mL of tetrahydrofuran, 774 mg of 2-oxo-1,2,3,4-tetrahydroquinoline-7-carboxylic acid was suspended, 0.68 mL of triethylamine was added to the suspension under cooling with ice, and thereto was added 0.63 mL of isobutyl chloroformate. The mixture was stirred for 1.5 hours, and then added with of 521 mg of sodium borohydride and 30 mL of water, and the mixture was stirred at room temperature for 1 hour. The reaction mixture was acidified with 1 mol/L hydrochloric acid, the solvent was removed under reduced pressure, and ethyl acetate was added thereto. The organic layer was separated, washed with an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform:methanol=20:1] to obtain 318 mg of a white solid, 7-hydroxymethyl-3,4-dihydro-1H-quinolin-2-one.

¹H-NMR (CDCl₃) δ:
2.58-2.68 (2H, m), 2.91-3.02 (2H, m), 4.66 (2H, s), 6.76-6.79 (1H, m), 6.94-7.01 (1H, m), 7.15 (1H, d, J=7.9 Hz)

Reference Example 295

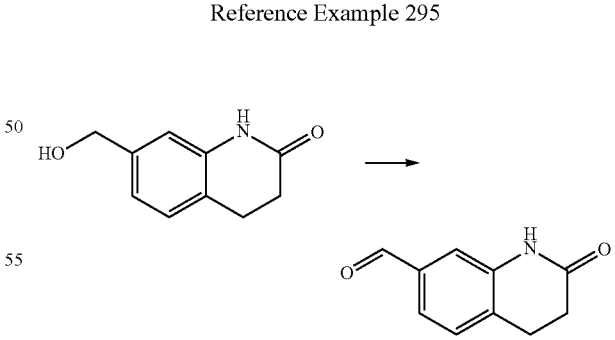

To 20 mL of tetrahydrofuran containing 310 mg of 7-hydroxymethyl-3,4-dihydro-1H-quinolin-2-one and 10 mL of a chloroform solution, 780 mg of manganese dioxide was added, and the mixture was stirred at room temperature overnight. The insoluble material filtered off, and the solvent was removed under reduced pressure. The residue thus obtained was purified by silica gel column chromatography [silica gel; Silica gel 60 manufactured by Kanto Chemical Co., Inc., eluent; chloroform:methanol=10:1] to obtain 107 mg of a white solid, 2-oxo-1,2,3,4-tetrahydroquinoline-7-carbaldehyde.

¹H-NMR (CDCl₃) δ:
2.63-2.73 (2H, m), 3.01-3.11 (2H, m), 7.24-7.26 (1H, m), 7.32-7.38 (1H, m), 7.48-7.54 (1H, m), 9.95 (1H, s)

Reference Example 296

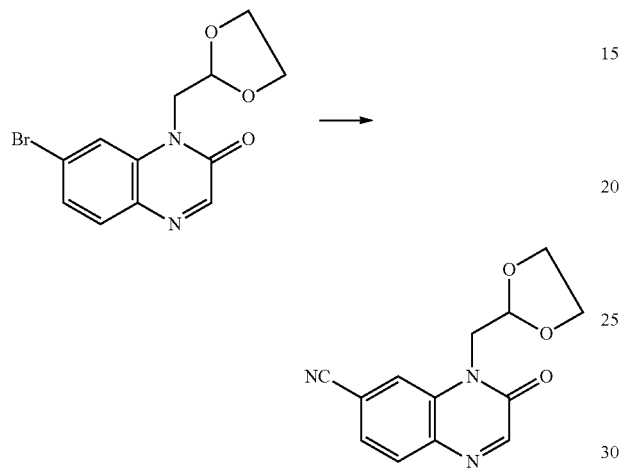

Into 10 mL of 1-methyl-2-pyrrolidinone, 447 mg of 7-bromo-1-(1,3-dioxolan-2-ylmethyl)quinoxalin-2(1H)-one and 210 mg of copper cyanide were suspended, and the suspension was refluxed by heating for 1 hour. The suspension was cooled to room temperature, and then added with ethyl acetate, the reaction mixture was washed sequentially with water and an aqueous saturated sodium chloride solution, dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane=1:1] to obtain 160 mg of a light brown solid, 7-cyano-1-(1,3-dioxolan-2-ylmethyl)quinoxalin-2(1H)-one.

¹H-NMR (CDCl₃) δ:
3.89-3.91 (2H, m), 3.99-4.03 (2H, m), 4.47 (2H, d, J=4.1 Hz), 5.22 (1H, t, J=4.1 Hz), 7.59 (1H, dd, J=8.0, 1.6 Hz), 7.91 (1H, d, J=1.6 Hz), 7.96 (1H, d, J=8.0 Hz), 8.40 (1H, s)

Reference Example 297

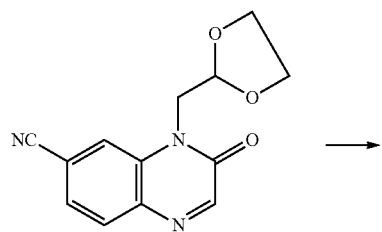

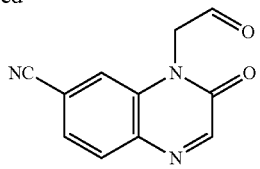

To 10 mL of a 90% aqueous trifluoroacetic acid solution, 452 mg of 7-cyano-1-(1,3-dioxolan-2-ylmethyl)quinoxalin-2(1H)-one was dissolved, and the mixture was stirred at room temperature for 2 days. After cooling the reaction mixture to room temperature, the solvent was removed under reduced pressure, and the resultant solution was alkalified with an aqueous saturated sodium hydrogen carbonate solution, and then the solvent was removed under reduced pressure. The residue thus obtained was purified by silica gel column chromatography [silica gel; Silica gel 60 manufactured by Kanto Chemical Co., Inc., eluent; ethyl acetate:hexane=1:1] to obtain 228 mg of a pale yellow solid, (7-cyano-2-oxoquinoxalin-1(2H)-yl)acetaldehyde.

¹H-NMR (CDCl₃) δ:
5.17 (2H, s), 7.25-7.26 (1H, m), 7.59-7.65 (1H, m), 8.03 (1H, d, J=8.4 Hz), 8.44 (1H, s), 9.82 (1H, s)

Reference Example 298

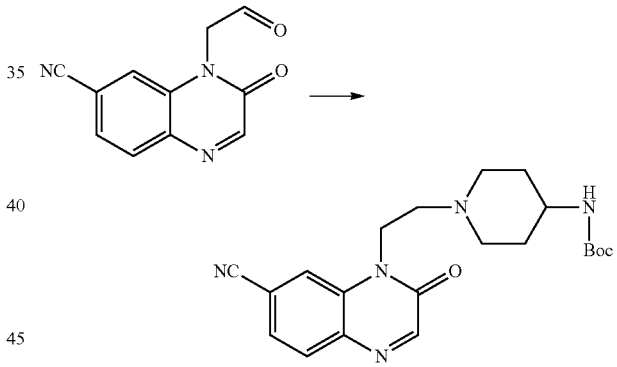

To 20 mL of a chloroform solution containing 219 mg of (7-cyano-2-oxoquinoxalin-1(2H)-yl)acetaldehyde and 209 mg of tert-butyl (piperidin-4-yl)carbamate, 59 µL of acetic acid was added, and the mixture was stirred at room temperature for 1 hour. The reaction mixture was added with 346 mg of sodium triacetoxyborohydride, and the mixture was stirred for 2 hours. Thereto was added an aqueous saturated sodium hydrogen carbonate solution, and the solvent was removed under reduced pressure. The residue thus obtained was purified by silica gel column chromatography [silica gel; Silica gel 60 manufactured by Kanto Chemical Co., Inc., eluent; ethyl acetate:hexane 2:1] to obtain 283 mg of a brown solid, tert-butyl (1-(2-(7-cyano-2-oxoquinoxalin-1(2H)-yl)ethyl)piperidin-4-yl)carbamate.

¹H-NMR (CDCl₃) δ:
1.34-1.41 (2H, m), 1.44 (9H, s), 1.91-1.97 (2H, m), 2.21-2.28 (2H, m), 2.64-2.71 (2H, m), 2.85-2.93 (2H, m), 3.44-3.52 (1H, m), 4.33 (2H, t, J=6.6 Hz), 7.59 (1H, dd, J=8.3, 1.4 Hz), 7.77-7.80 (1H, m), 7.97 (1H, d, J=8.3 Hz), 8.38 (1H, s)

Reference Example 299

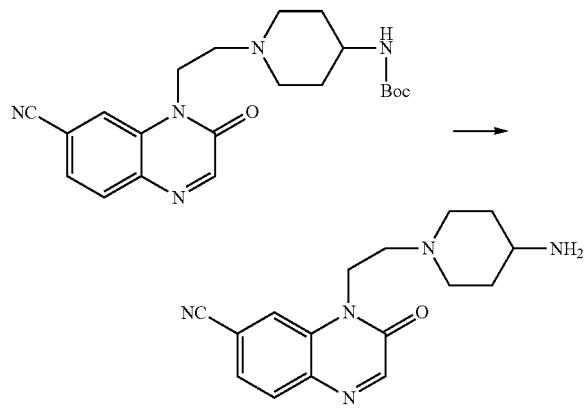

To 5 mL of a chloroform solution containing 277 mg of tert-butyl (1-(2-(7-cyano-2-oxoquinoxalin-1(2H)-yl)ethyl)piperidin-4-yl)carbamate, 5 mL of trifluoroacetic acid was added, and the mixture was stirred at room temperature for 3 hours. The solvent was removed under reduced pressure, the reaction mixture was alkalified with an aqueous saturated sodium hydrogen carbonate solution, and then the solvent was removed under reduced pressure. The residue thus obtained was purified by silica gel column chromatography [silica gel; Chromatorex-NH, manufactured by Fuji Silysia Chemical Ltd., eluent; chloroform:methanol=100:1] to obtain 61 mg of a light brown solid, 1-(2-(4-aminopiperidin-1-yl)ethyl)-7-cyanoquinoxalin-2(1H)-one.

$^1$H-NMR (CDCl$_3$) δ:
1.35-1.42 (2H, m), 1.81-1.86 (2H, m), 2.17-2.23 (2H, m), 2.66-2.73 (3H, m), 2.90-2.95 (2H, m), 4.29-4.36 (2H, m), 7.58-7.60 (1H, m), 7.78 (1H, d, J=1.4 Hz), 7.97 (1H, d, J=8.3 Hz), 8.38 (1H, s)

Reference Example 300

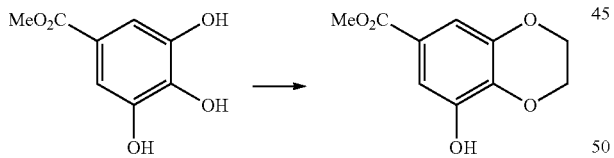

To 20 mL of an N,N-dimethylformamide solution containing 2.25 g of methyl gallate, 1.3 mL of 1,2-dibromoethane and 4.05 g of potassium carbonate were added, and the mixture was stirred at 100° C. overnight. The reaction mixture was cooled to room temperature, then fed into water, and the resultant solution was extracted with a mixed solvent of ethyl acetate:toluene of 5:1. The organic layer was washed with water and an aqueous saturated sodium chloride solution, and dried over anhydrous magnesium sulfate, and the solvent was removed under reduced pressure to obtain 1.66 g of a brown oily substance, methyl 8-hydroxy-2,3-dihydro-1,4-benzodioxin-6-carboxylate.

$^1$H-NMR (CDCl$_3$) δ:
3.86 (3H, s), 4.26-4.32 (2H, m), 4.34-4.40 (2H, m), 7.18-7.20 (1H, m), 7.23 (1H, d, J=2.2 Hz)

Reference Example 301

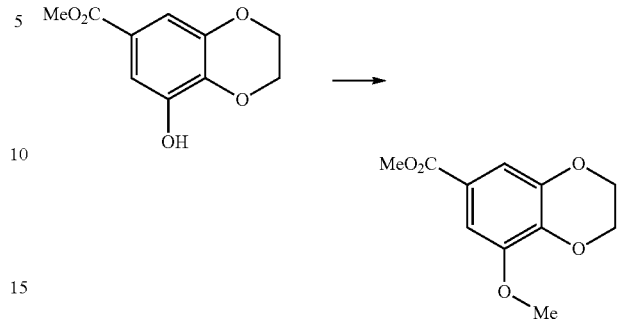

To 20 mL of an N,N-dimethylformamide solution containing 1.27 g of methyl 8-hydroxy-2,3-dihydro-1,4-benzodioxin-6-carboxylate, 1.16 g of potassium carbonate and 0.53 mL of methyl iodide were added, and the mixture was stirred at room temperature for 3 hours. The reaction mixture was fed into 5 mL of a 1 mol/L hydrochloric acid and 45 mL of water, and the resultant solution was extracted with a mixed solvent of ethyl acetate:toluene of 5:1. The organic layer was washed with water and an aqueous saturated sodium chloride solution and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane 1:2] to obtain 1.06 g of a white solid, methyl 8-methoxy-2,3-dihydro-1,4-benzodioxin-6-carboxylate.

$^1$H-NMR (CDCl$_3$) δ:
3.88 (3H, s), 3.93 (3H, s), 4.24-4.31 (2H, m), 4.34-4.40 (2H, m), 7.20 (1H, d, J=2.2 Hz), 7.27 (1H, t, J=2.2 Hz)

Reference Example 302

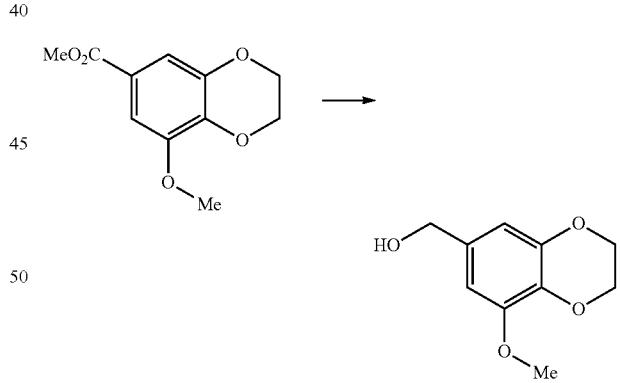

To 30 mL of a tetrahydrofuran solution containing 1.06 g of methyl 8-methoxy-2,3-dihydro-1,4-benzodioxin-6-carboxylate, 720 mg of lithium aluminum hydride was added under cooling with ice. The reaction mixture was stirred at room temperature for 1 hour, 5 mL of a 1 mol/L hydrochloric acid and 45 mL of water were added thereto, and the resultant solution was extracted with ethyl acetate. The organic layer was washed with an aqueous saturated sodium chloride solution and dried over anhydrous magnesium sulfate, and the solvent was removed under reduced pressure to obtain 940 mg of a brown oily substance, (8-methoxy-2,3-dihydro-1,4-benzodioxin-6-yl)methanol.

¹H-NMR (CDCl₃) δ:

3.89 (3H, s), 4.23-4.28 (2H, m), 4.29-4.35 (2H, m), 4.57 (2H, s), 6.52-6.56 (2H, m)

Reference Example 303

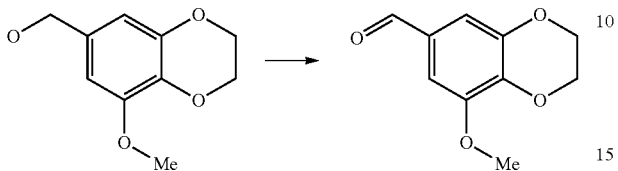

To 10 mL of chloroform and 10 mL of a tetrahydrofuran solution containing 921 mg of (8-methoxy-2,3-dihydro-1,4-benzodioxin-6-yl)methanol, 2.08 g of manganese dioxide was added, and the mixture was stirred at room temperature overnight. The insoluble material filtered off, and the solvent was removed under reduced pressure. The residue thus obtained was purified by silica gel column chromatography [silica gel; Silica gel 60 manufactured by Kanto Chemical Co., Inc., eluent; ethyl acetate:hexane 1:2] to obtain 749 mg of a white solid, 8-methoxy-2,3-dihydro-1,4-benzodioxin-6-carbaldehyde.

¹H-NMR (CDCl₃) δ:

3.95 (3H, s), 4.28-4.34 (4H, m), 4.38-4.44 (2H, m), 7.08 (1H, s)

Reference Example 304

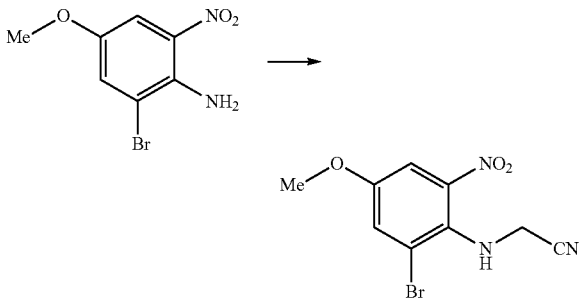

11.5 g of 2-bromo-4-methoxy-6-nitroaniline, 1.40 g of paraformaldehyde, 6.07 g of potassium cyanide, 6.07 g of zinc chloride, 64.5 g of acetic acid, and 175 mL of sulfuric acid were mixed, and the mixture was stirred at 50° C. for 15 hours. The reaction mixture was cooled to room temperature, and then fed into water, and ethyl acetate was added thereto. The organic layer was separated, washed with an aqueous saturated sodium chloride solution, an aqueous saturated sodium hydrogen carbonate solution and an aqueous saturated sodium chloride solution, and dried over anhydrous magnesium sulfate, and the solvent was removed under reduced pressure to obtain 4.71 g of an orange solid, (2-bromo-4-methoxy-6-nitrophenylamino)acetonitrile.

¹H-NMR (CDCl₃) δ:

3.86 (3H, s), 4.19-4.26 (2H, m), 7.47 (1H, d, J=3.1 Hz), 7.59 (1H, d, J=3.1 Hz)

Reference Example 305

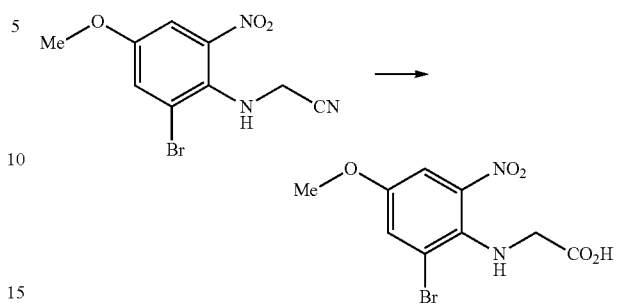

A mixture of 5.46 g of (2-bromo-4-methoxy-6-nitrophenylamino)acetonitrile, 100 mL of acetic acid and 250 mL of a 50% sulfuric acid was stirred with heating at 100° C. for 3 hours. The reaction mixture was cooled to room temperature, and then fed into water, and a solid substance was collected by filtration to obtain 5.50 g of an orange solid, (2-bromo-4-methoxy-6-nitrophenylamino) acetic acid.

¹H-NMR (DMSO-d₆) δ:

3.79 (3H, s), 3.91 (2H, s), 7.47 (1H, d, J=3.2 Hz), 7.59 (1H, d, J=3.2 Hz)

Reference Example 306

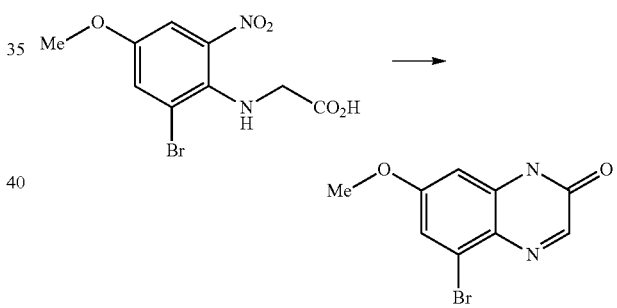

A mixture of 15.5 g of iron powder, 47 mL of acetic acid and 7 mL of water was heated to 70° C., and thereto was added a mixture of 7.54 g of (2-bromo-4-methoxy-6-nitrophenylamino) acetic acid, 64 mL of acetic acid and 74 mL of ethyl acetate, and the mixture was stirred at 70° C. for 4 hours. The reaction mixture was cooled to room temperature, then ethyl acetate and water were added thereto, and the organic layer was separated. The organic layer was washed with an aqueous saturated sodium chloride solution, an aqueous saturated sodium hydrogen carbonate solution and an aqueous saturated sodium chloride solution, and dried over anhydrous magnesium sulfate, and the solvent was removed under reduced pressure. The residue thus obtained was suspended into 140 mL of a 2 mol/L aqueous sodium hydroxide solution, and thereto was added 54 mL of a 30% aqueous hydrogen peroxide solution, and the mixture was stirred with heating at 100° C. for 2 hours. The reaction mixture was cooled with ice, and adjusted to pH about 5 with a concentrated hydrochloric acid, and a solid substance was collected by filtration to obtain 5.86 g of a brown solid, 5-bromo-7-methoxyquinoxalin-2(1H)-one.

$^1$H-NMR (DMSO-$d_6$) δ:

3.83 (3H, s), 6.72-6.92 (1H, m), 7.10-7.40 (1H, m), 8.02 (1H, s)

Reference Example 307

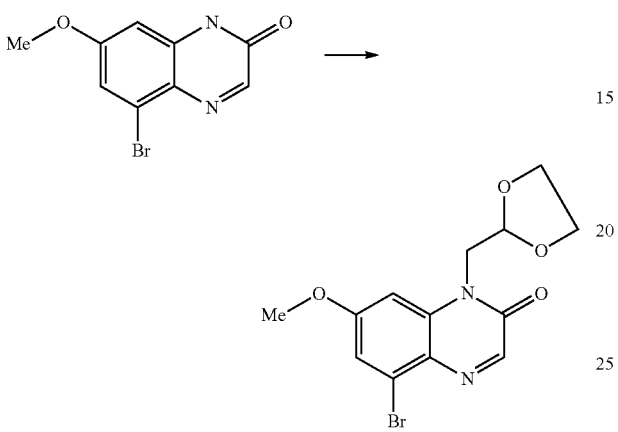

To 220 mL of an N,N-dimethylformamide solution containing 2.22 g of 5-bromo-7-methoxyquinoxalin-2(1H)-one, 0.69 g of 60% sodium hydride was added, and the mixture was stirred at room temperature for 1 hour. Thereto was added 7.60 g of 2-bromomethyl-1,3-dioxolane, and the mixture was stirred at 90° C. for 62 hours. The reaction mixture was cooled to room temperature, and then water and ethyl acetate were added thereto. The organic layer was separated, washed with an aqueous saturated sodium chloride solution, and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; ethyl acetate:hexane 2:1] to obtain 0.96 g of a yellow solid, 5-bromo-1-(1,3-dioxolan-2-ylmeythyl)-7-methoxyquinoxalin-2(1H)-one.

$^1$H-NMR (CDCl$_3$) δ:

3.79-4.08 (4H, m), 3.92 (3H, s), 4.45 (2H, d, J=4.4 Hz), 5.22 (1H, t, J=4.4 Hz), 7.02 (1H, d, J=2.2 Hz), 7.25 (1H, d, J=2.2 Hz), 8.23 (1H, s)

Reference Example 308

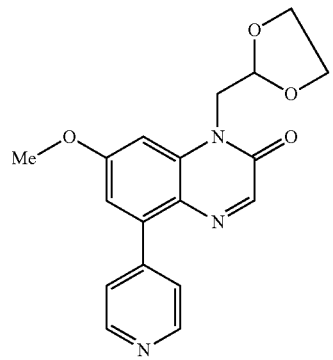

12 mL of a 1,2-dichloroethane suspension containing 469 mg of 5-bromo-1-(1,3-dioxolan-2-ylmeythyl)-7-methoxyquinoxalin-2(1H)-one and 160 mg of a 10 mol % tetrakis triphenylphosphine palladium was stirred at room temperature for 0.5 hour under a nitrogen atmosphere, 250 mg of 4-pyridineboronic acid and 2.1 mL of a 2 mol/L aqueous sodium carbonate solution were added thereto, and the mixture was stirred at 80° C. for 22 hours. After standing to cool, the insoluble material filtered off, and concentrated under reduced pressure. The residue thus obtained was purified by silica gel column chromatography [silica gel; Chromatorex-NH, manufactured by Fuji Silysia Chemical Ltd., eluent; ethyl acetate:methanol=20:1] to obtain 400 mg of a white solid, 1-(1,3-dioxolan-2-ylmeythyl)-7-methoxy-5-(pyridin-4-yl)quinoxalin-2(1H)-one.

$^1$H-NMR (CDCl$_3$) δ:

3.90-3.94 (2H, m), 3.97 (3H, s), 4.04-4.08 (2H, m), 4.51 (2H, d, J=4.1 Hz), 5.28 (1H, t, J=4.4 Hz), 6.94 (1H, d, J=2.8 Hz), 7.12 (1H, d, J=2.8 Hz), 7.52-7.57 (2H, m), 8.15 (1H, s), 8.69-8.73 (2H, m)

Reference Example 309

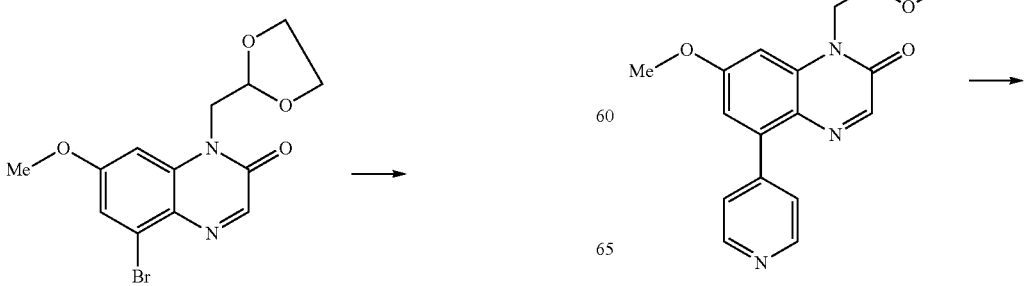

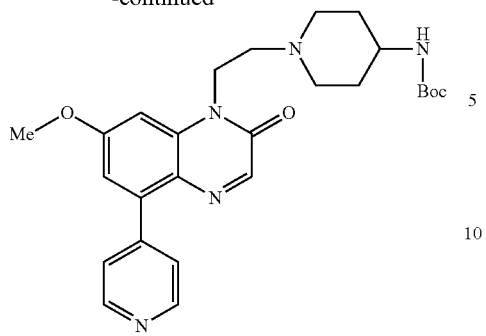

Into 15 mL of an 80% aqueous trifluoroacetic acid solution, 370 mg of 1-(1,3-dioxolan-2-ylmethyl)-7-methoxy-5-(pyridin-4-yl)quinoxalin-2(1H)-one was dissolved, and the mixture was stirred at room temperature for 3 days. The reaction mixture was added with chloroform and water, and the organic layer was separated. The aqueous layer was concentrated under reduced pressure, and thereto were added chloroform and an aqueous saturated sodium hydrogen carbonate solution, and the organic layer was separated. The organic layers were combined, washed with an aqueous saturated sodium chloride solution, and then dried over anhydrous magnesium sulfate, and the solvent was removed under reduced pressure to obtain 230 mg of a pale yellow foam residue.

To 5 mL of a chloroform solution containing 230 mg of the obtained residue and 156 mg of tert-butyl (piperidin-4-yl)carbamate, 0.09 mL of acetic acid was added, and the mixture was stirred at room temperature for 1 hour. The reaction mixture was added with 261 mg of sodium triacetoxyborohydride, and stirred for 14 hours. Thereto was added an aqueous saturated sodium hydrogen carbonate solution, and the organic layer was separated. The organic layer was washed with an aqueous saturated sodium chloride solution, and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform:methanol=10:1] to obtain 300 mg of a white foam, tert-butyl (1-(2-(7-methoxy-5-(pyridin-4-yl)-2-oxoquinoxalin-1(2H)-yl)ethyl)piperidin-4-yl)carbamate.

$^{1}$H-NMR (CDCl$_3$) δ:
1.45 (9H, s), 1.91-2.01 (2H, m), 2.23-2.33 (2H, m), 2.67-2.74 (2H, m), 2.91-3.02 (2H, m), 3.44-3.56 (1H, m), 3.97 (3H, s), 4.34-4.41 (2H, m), 4.42-4.50 (2H, m), 6.88-6.97 (2H, m), 7.43-7.49 (2H, m), 8.12 (1H, s), 8.68-8.74 (2H, m)

Reference Example 310

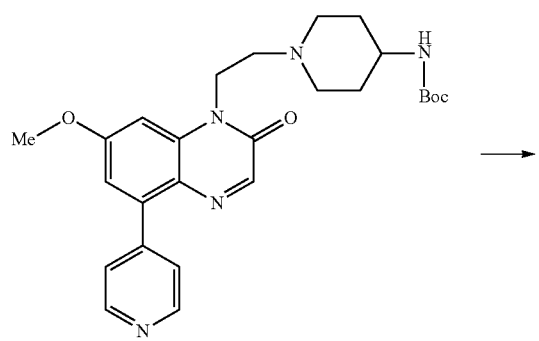

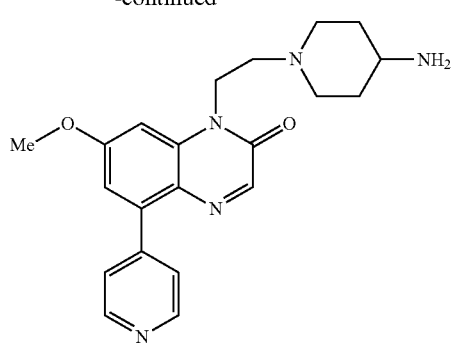

To 2 mL of a chloroform solution containing 280 mg of tert-butyl (1-(2-(7-methoxy-5-(pyridin-4-yl)-2-oxoquinoxalin-1(2H)-yl)ethyl)piperidin-4-yl)carbamate, 0.84 mL of trifluoroacetic acid was added, and the mixture was stirred at room temperature for 2 hours. The reaction mixture was concentrated under reduced pressure, chloroform and water were added thereto, the resultant solution was adjusted to pH about 12 with a 2 mol/L aqueous sodium hydroxide solution, and the organic layer was separated. The organic layer was washed with an aqueous saturated sodium chloride solution, and dried over anhydrous magnesium sulfate, and the solvent was removed under reduced pressure to obtain 230 mg of a yellow oily substance, 1-(2-(4-aminopiperidin-1-yl)ethyl)-7-methoxy-5-(pyridin-4-yl)quinoxalin-2(1H)-one.

$^{1}$H-NMR (CDCl$_3$) δ:
1.34-1.51 (2H, m), 1.79-1.89 (2H, m), 2.17-2.29 (2H, m), 2.65-2.76 (3H, m), 2.96-3.04 (2H, m), 3.97 (3H, s), 4.34-4.42 (2H, m), 6.87-6.99 (2H, m), 7.42-7.51 (2H, m), 8.13 (1H, s), 8.68-8.76 (2H, m)

Reference Example 311

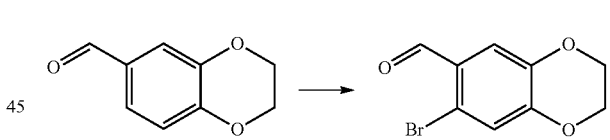

To 2 mL of an acetic acid solution containing 153 mg of 2,3-dihydro-1,4-benzodioxin-6-carbaldehyde, 206 mg of bromine per 1 mL of acetic acid was added, and the mixture was stirred at room temperature for 2.5 hours. The reaction mixture was alkalified with an aqueous saturated sodium hydrogen carbonate solution, the solvent was removed under reduced pressure, and thereto was added ethyl acetate. The resultant solution was washed with an aqueous saturated sodium chloride solution, and dried over anhydrous magnesium sulfate, and the solvent was removed under reduced pressure. The residue thus obtained was purified by silica gel column chromatography [silica gel; Silica gel 60 manufactured by Kanto Chemical Co., Inc., eluent; chloroform] to obtain 112 mg of a white solid, 7-bromo-2,3-dihydro-1,4-benzodioxin-6-carbaldehyde.

$^{1}$H-NMR (CDCl$_3$) δ:
4.25-4.29 (2H, m), 4.30-4.35 (2H, m), 7.13 (1H, s), 7.47 (1H, s), 10.16 (1H, s)

Reference Example 312

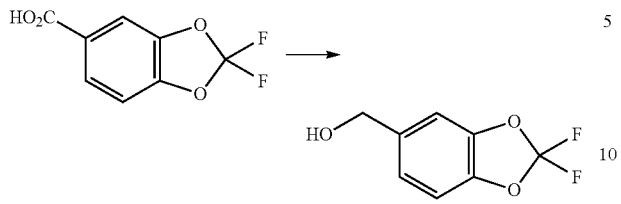

Into 50 mL of tetrahydrofuran, 962 mg of 2,2-difluorobenzo[1,3]dioxol-5-carboxylic acid was suspended, 0.8 mL of triethylamine was added to the suspension, and after cooling with ice, thereto was added 0.75 mL of isobutyl chloroformate. The mixture was stirred for 1 hour, and then 662 mg of sodium borohydride was added thereto, and the reaction mixture was stirred at room temperature for 2 hours. The reaction mixture was acidified with 1 mol/L hydrochloric acid, the solvent was removed under reduced pressure, and ethyl acetate was added thereto. The organic layer was separated, washed with an aqueous saturated sodium chloride solution, and dried over anhydrous magnesium sulfate, and the solvent was removed under reduced pressure to obtain 942 mg of a colorless oily substance, (2,2-difluorobenzo[1,3]dioxol-5-yl)methanol.

$^1$H-NMR (CDCl$_3$) δ:
4.68 (2H, s), 6.96-7.05 (2H, m), 7.10-7.14 (1H, m)

Reference Example 313

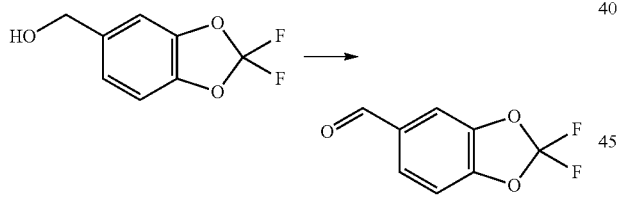

To 20 mL of chloroform containing 930 mg of (2,2-difluorobenzo[1,3]dioxol-5-yl)methanol and 20 mL of a tetrahydrofuran solution, 2.20 g of manganese dioxide was added, and the mixture was stirred at room temperature for 3 days. The insoluble material filtered off, and the solvent was removed under reduced pressure. The residue thus obtained was purified by silica gel column chromatography [silica gel; Silica gel 60 manufactured by Kanto Chemical Co., Inc., eluent; ethyl acetate:hexane 1:2] to obtain 687 mg of a yellow oily substance, 2,2-difluorobenzo[1,3]dioxol-5-carbaldehyde.

$^1$H-NMR (CDCl$_3$) δ:
7.23 (1H, d, J=7.9 Hz), 7.60-7.63 (1H, m), 7.64-7.71 (1H, m), 9.93 (1H, s)

Example 1

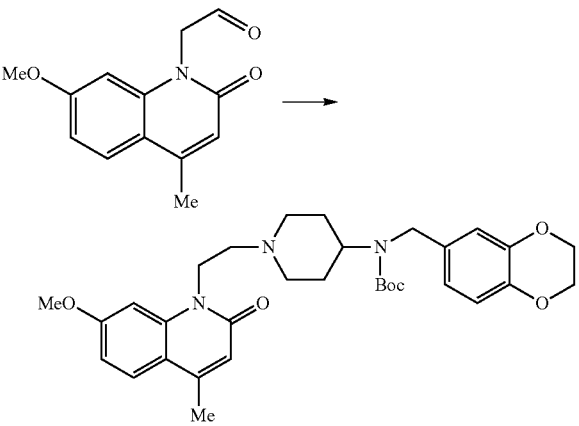

To 5 mL of a dichloromethane solution containing 64 mg of (7-methoxy-4-methyl-2-oxoquinolin-1(2H)-yl)acetaldehyde, 0.11 g of tert-butyl (2,3-dihydro-1,4-benzodioxin-6-ylmethyl)(piperidin-4-yl)carbamate and 16 µL of acetic acid were added and stirred for 1 hour. To the reaction mixture, 89 mg of sodium triacetoxyborohydride was added and stirred for 1 hour. Water and ethyl acetate were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform] to give 98 mg of tert-butyl (2,3-dihydro-1,4-benzodioxin-6-ylmethyl) (1-(2-(7-methoxy-4-methyl-2-oxoquinolin-1(2H)-yl)ethyl)piperidin-4-yl)carbamate as a yellow oil.

$^1$H-NMR (CDCl$_3$) δ:
1.30-1.55 (9H, m), 1.60-1.83 (4H, m), 2.10-2.30 (2H, m), 2.41 (3H, s), 2.60-2.70 (2H, m), 3.08-3.17 (2H, m), 3.90 (3H, s), 4.00-4.20 (1H, m), 4.24 (4H, s), 4.25-4.45 (4H, m), 6.42 (1H, s), 6.66-6.93 (5H, m), 7.60 (1H, d, J=8.8 Hz)

Example 2

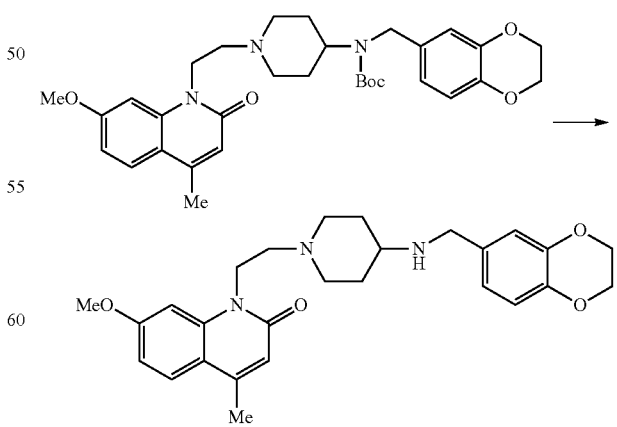

To 2 mL of a dichloromethane solution containing 95 mg of tert-butyl (2,3-dihydro-1,4-benzodioxin-6-ylmethyl) (1-(2-

(7-methoxy-4-methyl-2-oxoquinolin-1(2H)-yl)ethyl)piperidin-4-yl)carbamate, 2 mL of trifluoroacetic acid was added and stirred for 3 hours. The solvent was removed under reduced pressure, and aqueous saturated sodium hydrogen carbonate solution and ethyl acetate were added. The organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=9:1] to give 60 mg of 1-(2-(4-((2,3-dihydro-1,4-benzodioxin-6-ylmethyl)amino)piperidin-1-yl)ethyl)-7-methoxy-4-methylquinolin-2(1H)-one as a white solid.

$^1$H-NMR (DMSO-$d_6$) δ:
1.40-1.55 (2H, m), 1.90-2.10 (4H, m), 2.39 (3H, s), 2.50-2.60 (2H, m), 2.77-2.90 (1H, m), 3.00-3.10 (2H, m), 3.90 (3H, s), 3.91-3.98 (2H, m), 4.24 (4H, s), 4.30-4.38 (2H, m), 6.34 (1H, s), 6.85-7.05 (5H, m), 7.71 (1H, d, J=8.8 Hz)

Example 3

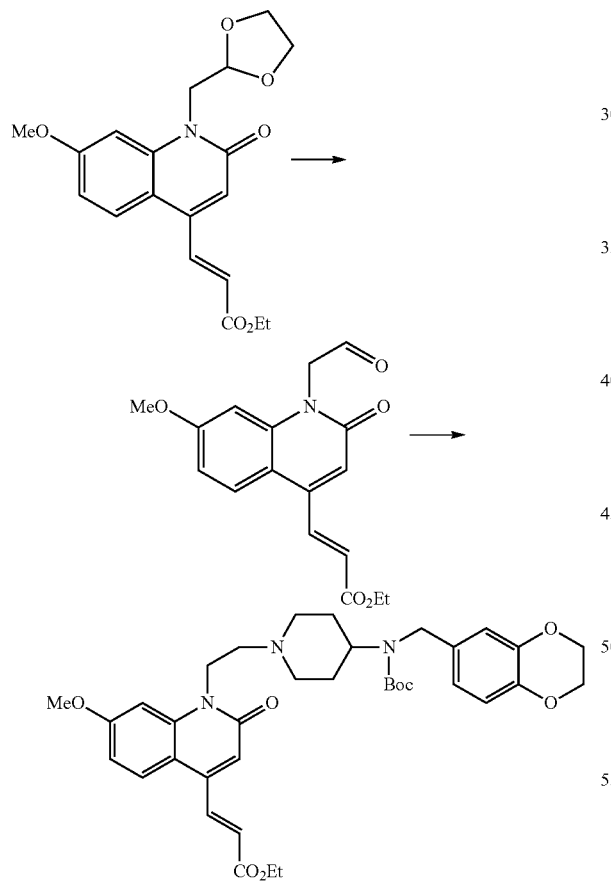

(1) To 0.16 g of ethyl (2E)-3-(1-(1,3-dioxolan-2-ylmethyl)-7-methoxy-2-oxo-1,2-dihydroquinolin-4-yl)acrylate, 2 mL of 90% aqueous trifluoroacetic acid solution was added and stirred for 2 hours. The solvent was removed under reduced pressure, and aqueous saturated sodium hydrogen carbonate solution and chloroform were added. The organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography (eluent; chloroform) to give 84 mg of ethyl (2E)-3-(7-methoxy-2-oxo-1-(2-oxoethyl)-1,2-dihydroquinolin-4-yl)acrylate as a yellow oil.

(2) To 3 mL of a dichloromethane solution containing 84 mg of ethyl (2E)-3-(7-methoxy-2-oxo-1-(2-oxoethyl)-1,2-dihydroquinolin-4-yl)acrylate, 98 mg of tert-butyl (2,3-dihydro-1,4-benzodioxin-6-ylmethyl)(piperidin-4-yl)carbamate and 14 μL of acetic acid were added and stirred for 1 hour. To the reaction mixture, 81 mg of sodium triacetoxyborohydride was added and stirred for 2 hours. Water, ethyl acetate and aqueous saturated sodium hydrogen carbonate solution were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=100:1] to give 0.11 g of ethyl (2E)-3-(1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinolin-4-yl)acrylate as a yellow oil.

$^1$H-NMR (CDCl$_3$) δ:
1.36 (3H, t, J=7.1 Hz), 1.34-1.55 (9H, m), 1.60-1.75 (4H, m), 2.10-2.25 (2H, m), 2.60-2.66 (2H, m), 3.03-3.10 (2H, m), 3.90 (3H, s), 3.95-4.15 (1H, m), 4.24 (4H, s), 4.20-4.40 (4H, m), 4.32 (2H, q, J=7.1 Hz), 6.46 (1H, d, J=15.8 Hz), 6.66 (1H, s), 6.68-6.80 (3H, m), 6.85 (1H, dd, J=9.0, 2.2 Hz), 6.91 (1H, d, J=2.2 Hz), 7.70 (1H, d, J=9.0 Hz), 8.02 (1H, d, J=15.8 Hz)

Example 4

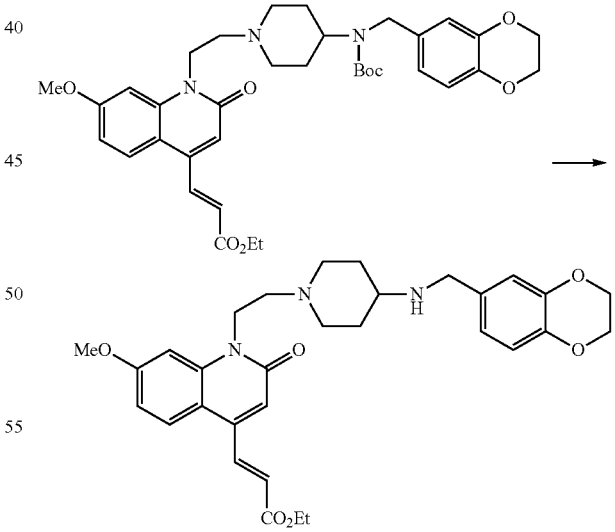

To 1 mL of a chloroform solution containing 0.10 g of ethyl (2E)-3-(1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinolin-4-yl)acrylate, 1 mL of trifluoroacetic acid was added and stirred for 2 hours. The solvent was removed under reduced pressure, and aqueous saturated sodium hydrogen carbonate solution and ethyl acetate were added. The organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=5:1] to give 68 mg of ethyl (2E)-3-(1-(2-(4-((2,3-dihydro-1,4-benzodioxin-6-ylmethyl)amino)piperidin-1-yl)ethyl)-7-methoxy-2-oxo-1,2-dihydroquinolin-4-yl)acrylate as a yellow oil.

$^1$H-NMR (CDCl$_3$) δ:

1.36 (3H, t, J=7.2 Hz), 1.40-1.52 (2H, m), 1.87-1.96 (2H, m), 2.15-2.25 (2H, m), 2.50-2.58 (1H, m), 2.62-2.70 (2H, m), 2.98-3.05 (2H, m), 3.71 (2H, s), 3.92 (3H, s), 4.24 (4H, s), 4.30 (2H, q, J=7.2 Hz), 4.36-4.44 (2H, m), 6.47 (1H, d, J=15.8 Hz), 6.67 (1H, s), 6.75-6.88 (4H, m), 6.97 (1H, d, J=2.2 Hz), 7.70 (1H, d, J=8.8 Hz), 8.03 (1H, d, J=15.8 Hz)

Example 5

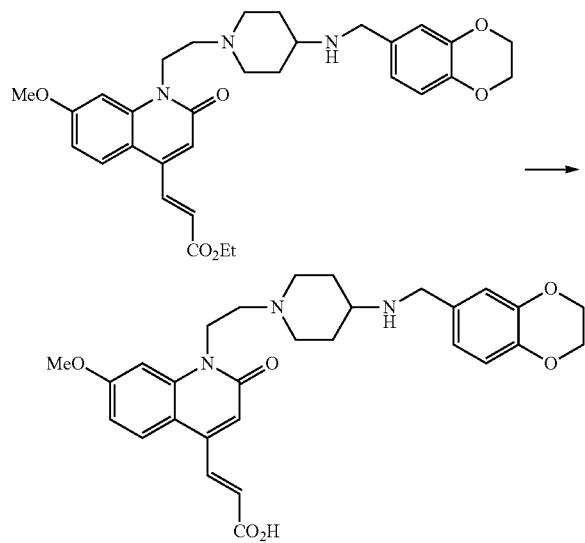

To 1 mL of an ethanol solution containing 65 mg of ethyl (2E)-3-(1-(2-(4-((2,3-dihydro-1,4-benzodioxin-6-ylmethyl)amino)piperidin-1-yl)ethyl)-7-methoxy-2-oxo-1,2-dihydroquinolin-4-yl)acrylate, 0.2 mL of water and 0.11 mL of 5 mol/L aqueous sodium hydroxide solution were added and stirred for 1 hour. 2 mL of water was added, removed ethanol under reduced pressure, adjusted to pH 6.0 with 1 mol/L hydrochloric acid, and the resulting solid was filtered to afford 48 mg of (2E)-3-(1-(2-(4-((2,3-dihydro-1,4-benzodioxin-6-ylmethyl)amino)piperidin-1-yl)ethyl)-7-methoxy-2-oxo-1,2-dihydroquinolin-4-yl)acrylic acid as a yellow solid.

$^1$H-NMR (DMSO-d$_6$, D$_2$O) δ:

1.60-1.78 (2H, m), 2.08-2.20 (2H, m), 2.52-3.50 (7H, m), 3.94 (3H, s), 4.06 (2H, s), 4.26 (4H, s), 4.43-4.53 (2H, m), 6.59 (1H, d, J=15.6 Hz), 6.72 (1H, s), 6.90-7.20 (5H, m), 7.83 (1H, d, J=9.0 Hz), 7.98 (1H, d, J=15.6 Hz)

Example 6

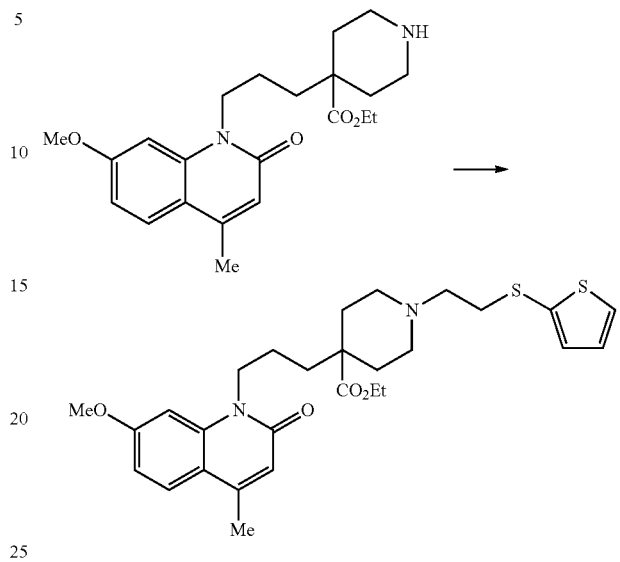

To 4 mL of an N,N-dimethylformamide solution containing 0.29 g of ethyl 4-(3-(7-methoxy-4-methyl-2-oxoquinolin-1(2H)-yl)propyl)piperidine-4-carboxylate, 0.25 g of potassium carbonate and 0.20 g of 2-(2-bromoethylthio)thiophene were added and stirred at 60-70° C. for 2 hours. Water and ethyl acetate were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=100:1] to give 0.27 g of ethyl 4-(3-(7-methoxy-4-methyl-2-oxoquinolin-1(2H)-yl)propyl)-1-(2-(2-thienylthio)ethyl)piperidine-4-carboxylate as a pale yellow oil.

$^1$H-NMR (CDCl$_3$) δ:

1.18 (3H, t, J=7.1 Hz), 1.41-1.49 (2H, m), 1.60-1.68 (4H, m), 2.00-2.15 (4H, m), 2.41 (3H, s), 2.53-2.58 (2H, m), 2.58-2.70 (2H, m), 2.85-2.90 (2H, m), 3.90 (3H, s), 4.08 (2H, q, J=7.1 Hz), 4.13-4.23 (2H, m), 6.41 (1H, s), 6.71 (1H, d, J=2.4 Hz), 6.82 (1H, dd, J=8.9, 2.4 Hz), 6.95 (1H, dd, J=5.4, 3.7 Hz), 7.10 (1H, dd, J=3.7, 1.2 Hz), 7.31 (1H, dd, J=5.4, 1.2 Hz), 7.61 (1H, d, J=8.9 Hz)

Example 7

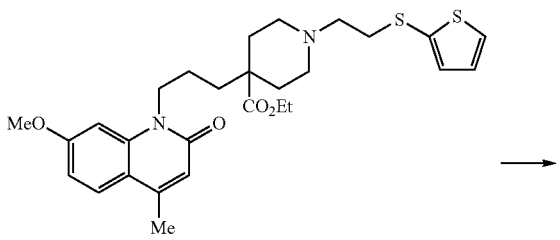

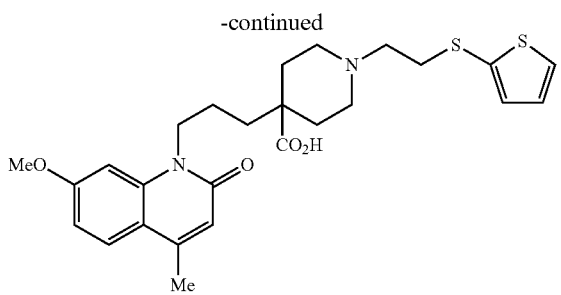

To 1 mL of an ethanol solution containing 0.25 g of ethyl 4-(3-(7-methoxy-4-methyl-2-oxoquinolin-1(2H)-yl)propyl)-1-(2-(2-thienylthio)ethyl)piperidine-4-carboxylate, 1 mL of 5 mol/L aqueous sodium hydroxide solution was added and stirred under reflux with heating for 5 hours. 2 mL of water was added, removed ethanol under reduced pressure, adjusted to pH 6.0 with 6 mol/L hydrochloric acid, and the resulting solid was filtered to afford 0.21 g of 4-(3-(7-methoxy-4-methyl-2-oxoquinolin-1(2H)-yl)propyl)-1-(2-(2-thienylthio)ethyl)piperidine-4-carboxylic acid as a pale yellow solid.

$^1$H-NMR (DMSO-$d_6$) δ:
1.33-1.43 (2H, m), 1.50-1.57 (4H, m), 1.97-2.06 (2H, m), 2.35-2.48 (5H, m), 2.70-3.10 (6H, m), 3.90 (3H, s), 4.03-4.25 (2H, m), 6.38 (1H, s), 6.90 (1H, s), 6.97 (1H, d, J=8.8 Hz), 7.04-7.12 (1H, m), 7.22 (1H, d, J=3.4 Hz), 7.59 (1H, d, J=5.1 Hz), 7.77 (1H, d, J=8.8 Hz)

Example 8

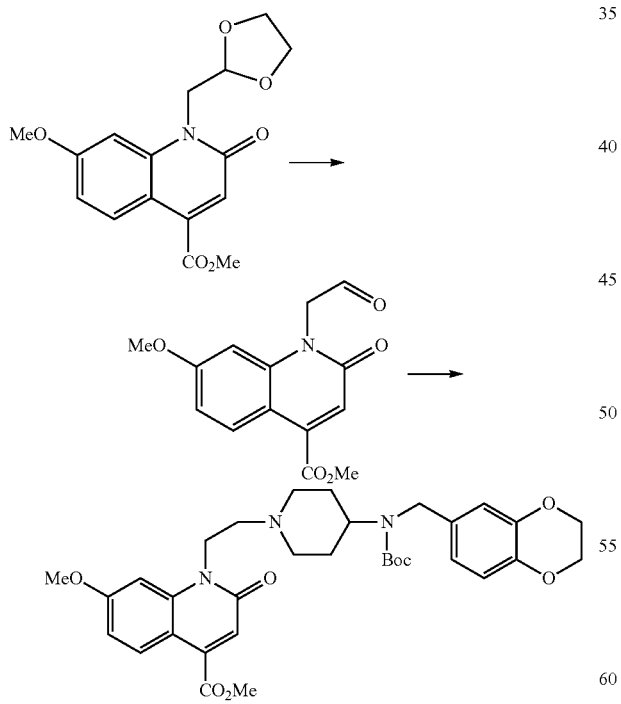

(1) To 0.19 g of methyl 1-(1,3-dioxolan-2-ylmethyl)-7-methoxy-2-oxo-1,2-dihydroquinoline-4-carboxylate, 2 mL of 90% aqueous trifluoroacetic acid solution was added and stirred for 14 hours. The solvent was removed under reduced pressure, and aqueous saturated sodium hydrogen carbonate solution and ethyl acetate were added. The organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure to give 0.19 g of methyl 7-methoxy-2-oxo-1-(2-oxoethyl)-1,2-dihydroquinoline-4-carboxylate.

(2) To 3 mL of a dichloromethane solution containing 0.17 g of methyl 7-methoxy-2-oxo-1-(2-oxoethyl)-1,2-dihydroquinoline-4-carboxylate, 0.24 g of tert-butyl (2,3-dihydro-1,4-benzodioxin-6-ylmethyl)(piperidin-4-yl)carbamate and 34 μL of acetic acid were added and stirred for 1 hour. To the reaction mixture, 0.19 g of sodium triacetoxyborohydride was added and stirred for 1 hour. Ethyl acetate and aqueous sodium hydrogen carbonate solution were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=100:1] to give 0.25 g of methyl 1-(2-(4-((tert-butoxycarbonyl) (2,3-dihydro-1,4-benzodioxin-6-ylmethyl)amino)piperidin-1-yl)ethyl)-7-methoxy-2-oxo-1,2-dihydroquinoline-4-carboxylate as a brown oil.

$^1$H-NMR (CDCl$_3$) δ:
1.32-1.55 (9H, m), 1.60-1.88 (4H, m), 2.05-2.25 (2H, m), 2.57-2.66 (2H, m), 3.00-3.08 (2H, m), 3.90 (3H, s), 3.97 (3H, s), 3.97-4.15 (1H, m), 4.20-4.40 (4H, m), 4.25 (4H, s), 6.65-6.72 (1H, m), 6.74 (1H, d, J=1.7 Hz), 6.78 (1H, d, J=8.3 Hz), 6.86 (1H, dd, J=9.1, 2.3 Hz), 6.90 (1H, d, J=2.3 Hz), 7.01 (1H, s), 8.27 (1H, d, J=9.1 Hz)

Example 9

To 2 mL of a chloroform solution containing 0.25 g of methyl 1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinoline-4-carboxylate, 2 mL of trifluoroacetic acid was added and stirred for 16 hours. The solvent was removed under reduced pressure, and aqueous saturated sodium hydrogen carbonate solution and chloroform were added. The organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=10:1] to give 0.12 g of methyl 1-(2-(4-((2,3-dihydro-1,4-benzodioxin-6-ylmethyl)amino)piperidin-1-yl)ethyl)-7-methoxy-2-oxo-1,2-dihydroquinoline-4-carboxylate as a white solid.

¹H-NMR (CDCl₃) δ:
1.38-1.52 (2H, m), 1.85-1.95 (2H, m), 2.13-2.23 (2H, m), 2.50-2.59 (1H, m), 2.62-2.69 (2H, m), 2.95-3.05 (2H, m), 3.71 (2H, s), 3.92 (3H, s), 3.97 (3H, s), 4.24 (4H, s), 4.37-4.45 (2H, m), 6.78 (1H, dd, J=8.1, 1.7 Hz), 6.81 (1H, d, J=8.1 Hz), 6.83 (1H, d, J=1.7 Hz), 6.86 (1H, dd, J=9.2, 2.4 Hz), 6.96 (1H, d, J=2.4 Hz), 7.01 (1H, s), 8.26 (1H, d, J=9.2 Hz)

Example 10

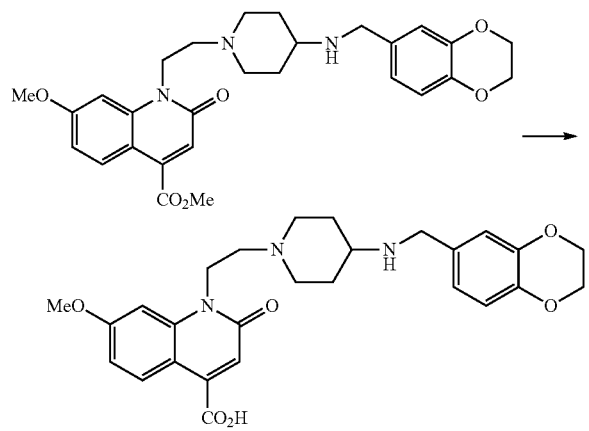

To 1 mL of an ethanol solution containing 0.12 g of methyl 1-(2-(4-((2,3-dihydro-1,4-benzodioxin-6-ylmethyl)amino)piperidin-1-yl)ethyl)-7-methoxy-2-oxo-1,2-dihydroquinoline-4-carboxylate, 0.5 mL of 5 mol/L aqueous sodium hydroxide solution was added and stirred for 1 hour. 2 mL of water was added, removed ethanol under reduced pressure, adjusted to pH 6.0 with 6 mol/L hydrochloric acid, and the resulting solid was filtered to afford 40 mg of 1-(2-(4-((2,3-dihydro-1,4-benzodioxin-6-ylmethyl)amino)piperidin-1-yl) ethyl)-7-methoxy-2-oxo-1,2-dihydroquinoline-4-carboxylic acid as a white solid.

¹H-NMR (DMSO-d₆, D₂O) δ:
1.75-1.90 (2H, m), 2.23-2.32 (2H, m), 2.80-2.95 (2H, m), 3.15-3.35 (3H, m), 3.60-3.70 (2H, m), 3.94 (3H, s), 4.08 (2H, s), 4.26 (4H, s), 4.55-4.65 (2H, m), 6.70 (1H, s), 6.92-7.08 (5H, m), 8.12 (1H, d, J=9.5 Hz)

Example 11

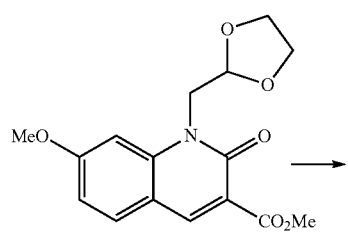

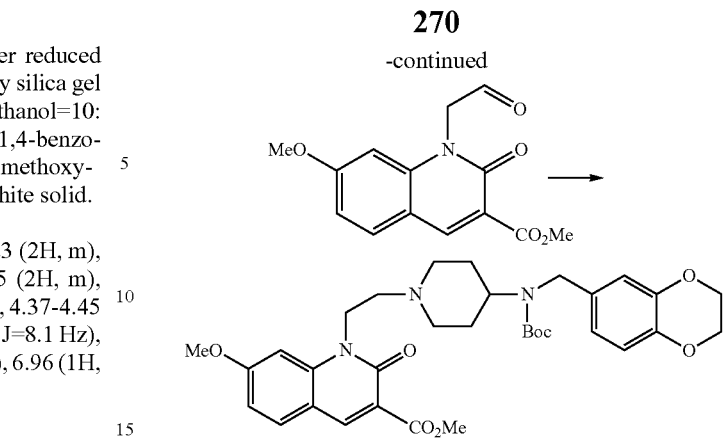

(1) To 0.37 g of methyl 1-(1,3-dioxolan-2-ylmethyl)-7-methoxy-2-oxo-1,2-dihydroquinoline-3-carboxylate, 2 mL of 90% aqueous trifluoroacetic acid solution was added and stirred for 4 hours. The solvent was removed under reduced pressure, and aqueous saturated sodium hydrogen carbonate solution and chloroform were added. The organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure to give 0.44 g of methyl 7-methoxy-2-oxo-1-(2-oxoethyl)-1,2-dihydroquinoline-3-carboxylate.

(2) To 5 mL of a dichloromethane solution containing 0.44 g of methyl 7-methoxy-2-oxo-1-(2-oxoethyl)-1,2-dihydroquinoline-3-carboxylate, 0.46 g of tert-butyl (2,3-dihydro-1,4-benzodioxin-6-ylmethyl)(piperidin-4-yl)carbamate and 60 μL of acetic acid were added and stirred for 1 hour. To the reaction mixture, 0.37 g of sodium triacetoxyborohydride was added and stirred for 2 hours. Chloroform and water were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure to give 0.31 g of methyl 1-(2-(4-((tert-butoxycarbonyl) (2,3-dihydro-1,4-benzodioxin-6-ylmethyl)amino)piperidin-1-yl)ethyl)-7-methoxy-2-oxo-1,2-dihydroquinoline-3-carboxylate as a yellow oil.

¹H-NMR (CDCl₃) δ:
1.30-1.55 (9H, m), 1.55-1.75 (4H, m), 2.05-2.28 (2H, m), 2.60-2.68 (2H, m), 3.02-3.10 (2H, m), 3.91 (3H, s), 3.93 (3H, s), 4.00-4.15 (1H, m), 4.16-4.45 (4H, m), 4.25 (4H, s), 6.65-6.90 (5H, m), 7.57 (1H, d, J=8.5 Hz), 8.43 (1H, s)

Example 12

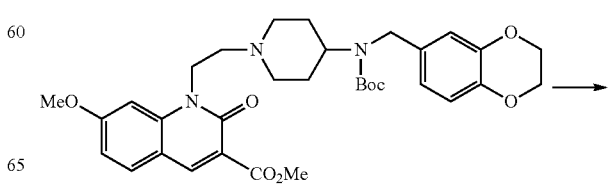

-continued

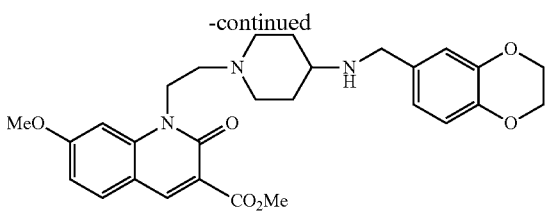

To 2 mL of a chloroform solution containing 0.31 g of methyl 1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinoline-3-carboxylate, 1 mL of trifluoroacetic acid was added and stirred for 3 hours. The solvent was removed under reduced pressure, and aqueous saturated sodium hydrogen carbonate solution and ethyl acetate were added. The organic layer was separated, and the aqueous layer was extracted twice with ethyl acetate. The organic layer and extracts were combined, washed with aqueous saturated sodium chloride solution, dried over anhydrous magnesium sulfate, and the solvent was removed under reduced pressure to give 0.22 g of methyl 1-(2-(4-((2,3-dihydro-1,4-benzodioxin-6-ylmethyl)amino)piperidin-1-yl)ethyl)-7-methoxy-2-oxo-1,2-dihydroquinoline-3-carboxylate as a colorless oil.

$^1$H-NMR (CDCl$_3$) δ:
1.57-1.70 (2H, m), 1.90-2.02 (2H, m), 2.10-2.40 (2H, m), 2.67-2.87 (3H, m), 3.05-3.20 (2H, m), 3.78 (2H, s), 3.94 (3H, s), 3.96 (3H, s), 4.21 (4H, s), 4.40-4.52 (2H, m), 6.78-6.95 (5H, m), 7.58 (1H, d, J=8.5 Hz), 8.47 (1H, s)

Example 13

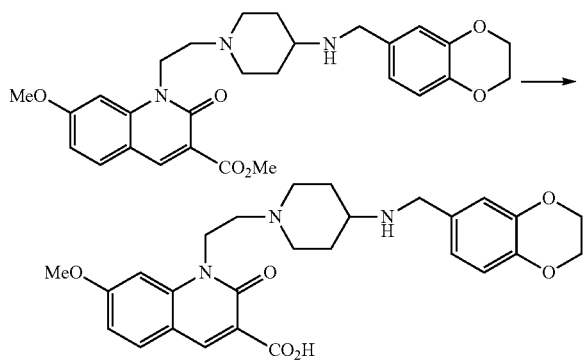

To 1 mL of a methanol solution containing 0.20 g of methyl 1-(2-(4-((2,3-dihydro-1,4-benzodioxin-6-ylmethyl)amino)piperidin-1-yl)ethyl)-7-methoxy-2-oxo-1,2-dihydroquinoline-3-carboxylate, 0.5 mL of 20% aqueous sodium hydroxide solution was added and stirred for 1 hour. 3 mL of water was added, removed methanol under reduced pressure, adjusted to pH 6.0 with 6 mol/L hydrochloric acid, and the resulting solid was filtered to afford 0.15 g of 1-(2-(4-((2,3-dihydro-1,4-benzodioxin-6-ylmethyl)amino)piperidin-1-yl)ethyl)-7-methoxy-2-oxo-1,2-dihydroquinoline-3-carboxylic acid as a white solid.

$^1$H-NMR (DMSO-d$_6$, D$_2$O) δ:
1.45-1.60 (2H, m), 1.95-2.10 (4H, m), 2.60-2.68 (2H, m), 2.80-2.90 (1H, m), 3.01-3.10 (2H, m), 3.96 (2H, s), 3.99 (3H, s), 4.24 (4H, s), 4.50-4.58 (2H, m), 6.87 (1H, d, J=8.2 Hz), 6.98 (1H, d, J=8.2 Hz), 7.09-7.16 (3H, m), 8.05 (1H, d, J=8.8 Hz), 8.90 (1H, s)

Example 14

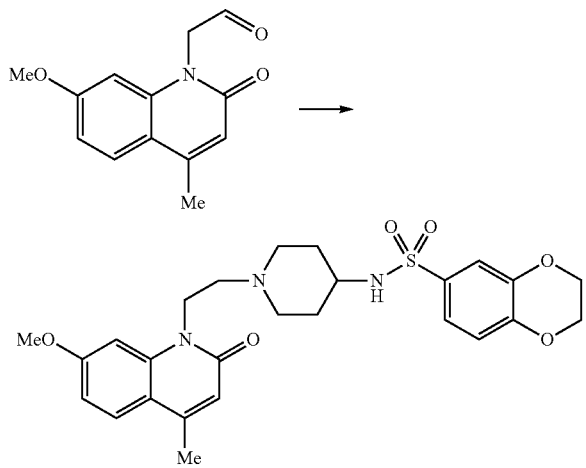

To 2 mL of dichloromethane solution containing 30 mg of (7-methoxy-4-methyl-2-oxoquinolin-1(2H)-yl)acetaldehyde, 39 mg of N-(piperidin-4-yl)-2,3-dihydro-1,4-benzodioxin-6-sulfonamide and 7.4 μl of acetic acid were added and stirred at room temperature for 2 hours. To the reaction mixture, 41 mg of sodium triacetoxyborohydride was added and stirred at the same temperature for 2 hours. Chloroform and water were added, and adjusted to pH 7.8 with aqueous saturated sodium hydrogen carbonate solution. The organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=10:1] to give 55 mg of N-(1-(2-(7-methoxy-4-methyl-2-oxoquinolin-1(2H)-yl)ethyl)piperidin-4-yl)-2,3-dihydro-1,4-benzodioxin-6-sulfonamide as a light brown foam.

$^1$H-NMR (CDCl$_3$) δ:
1.44-1.52 (2H, m), 1.75-1.85 (2H, m), 2.17-2.23 (2H, m), 2.41 (3H, s), 2.59-2.63 (2H, m), 2.86-2.92 (2H, m), 3.12-3.22 (1H, m), 3.90 (3H, s), 4.28-4.37 (6H, m), 4.50-4.55 (1H, m), 6.41 (1H, s), 6.80-6.90 (2H, m), 6.94 (1H, d, J=8.5 Hz), 7.34-7.41 (2H, m), 7.61 (1H, d, J=8.8 Hz)

Example 15

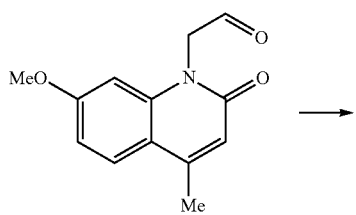

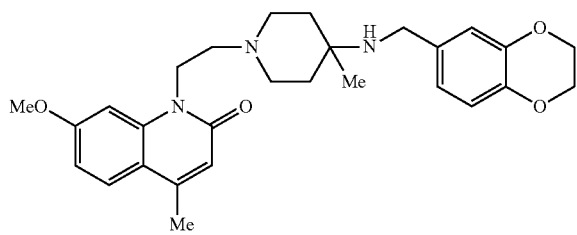

To 2 mL of dichloromethane solution containing 77 mg of N-(2,3-dihydro-1,4-benzodioxin-6-ylmethyl)-4-methylpiperidine-4-amine, 68 mg of (7-methoxy-4-methyl-2-oxoquinolin-1(2H)-yl)acetaldehyde and 17 μL of acetic acid were added and stirred at room temperature for 1 hour. To the reaction mixture, 93 mg of sodium triacetoxyborohydride was added and stirred at the same temperature for 30 min. Chloroform and aqueous saturated sodium hydrogen carbonate solution were added, the organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; chloroform:methanol=5:1] to give 0.13 g of 1-(2-(4-((2,3-dihydro-1,4-benzodioxin-6-ylmethyl)amino)-4-methylpiperidin-1-yl)ethyl)-7-methoxy-4-methylquinolin-2(1H)-one as a colorless oil.

$^1$H-NMR (CDCl$_3$) δ:

1.16 (3H, s), 1.60-1.73 (4H, m), 2.42 (3H, d, J=1.1 Hz), 2.60-2.72 (6H, m), 3.58 (2H, s), 3.92 (3H, s), 4.24 (4H, s), 4.39-4.45 (2H, m), 6.43 (1H, d, J=1.1 Hz), 6.80-6.81 (2H, m), 6.83 (1H, dd, J=8.9, 2.3 Hz), 6.88 (1H, s), 6.94 (1H, s), 7.61 (1H, d, J=8.9 Hz)

Example 16

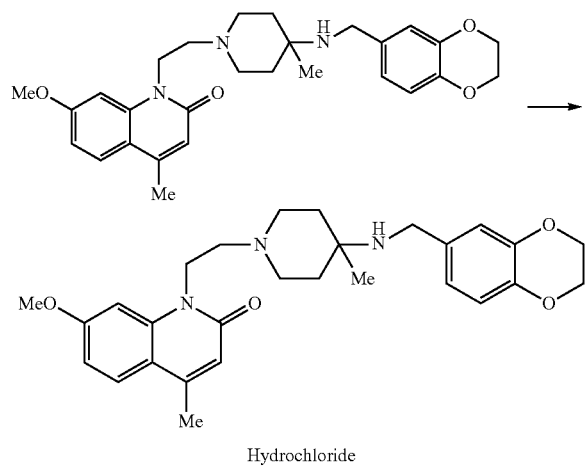

Hydrochloride

To 20 mL of an ethyl acetate solution containing 0.12 g of 1-(2-(4-((2,3-dihydro-1,4-benzodioxin-6-ylmethyl)amino)-4-methylpiperidin-1-yl)ethyl)-7-methoxy-4-methylquinolin-2(1H)-one, 5 mL of 4.0 mol/L hydrogen chloride/ethyl acetate was added at room temperature. The mixture was stirred at the same temperature for 10 min, and the solvent was removed under reduced pressure. To the residue thus obtained, ethyl acetate was added and the resulting solid was filtered to afford 0.13 g of 1-(2-(4-((2,3-dihydro-1,4-benzodioxin-6-ylmethyl)amino)-4-methylpiperidin-1-yl)ethyl)-7-methoxy-4-methylquinolin-2(1H)-one hydrochloride as a white solid.

$^1$H-NMR (DMSO-d$_6$) δ:

1.55 (3H, s), 2.04-2.34 (4H, m), 2.42 (3H, s), 3.10-3.56 (6H, m), 3.65-3.80 (2H, m), 3.97 (3H, s), 4.26 (4H, s), 4.64-4.74 (2H, m), 6.40 (1H, s), 6.92 (1H, d, J=8.3 Hz), 6.97 (1H, dd, J=8.8, 2.2 Hz), 7.00-7.20 (3H, m), 7.76 (1H, d, J=8.8 Hz), 9.31 (2H, s)

Example 17

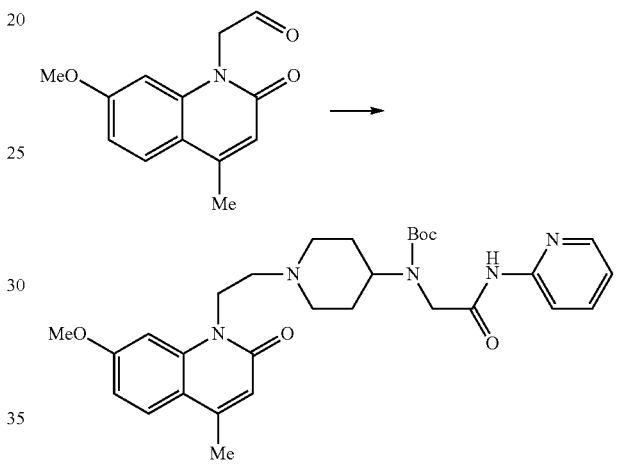

To 3 mL of dichloromethane solution containing 85 mg of (7-methoxy-4-methyl-2-oxoquinolin-1(2H)-yl)acetaldehyde, 0.12 g of tert-butyl (2-oxo-2-(pyridin-2-ylamino)ethyl)(piperidin-4-yl)carbamate and 21 μl of acetic acid were added and stirred at room temperature for 1 hour. To the reaction mixture, 0.12 g of sodium triacetoxyborohydride was added and stirred at the same temperature for 30 min. Chloroform and aqueous saturated sodium hydrogen carbonate solution were added, the organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; chloroform:methanol=9:1] to give 0.12 g of tert-butyl (1-(2-(7-methoxy-4-methyl-2-oxoquinolin-1(2H)-yl)ethyl)piperidin-4-yl)(2-oxo-2-(pyridin-2-ylamino)ethyl)carbamate as a white foam.

$^1$H-NMR (CDCl$_3$) δ:

1.46 (9H, s), 1.64-1.83 (4H, m), 2.15-2.30 (2H, m), 2.41 (3H, d, J=0.98 Hz), 2.62-2.68 (2H, m), 3.08-3.14 (2H, m), 3.90 (3H, s), 3.90-4.20 (3H, m), 4.33-4.40 (2H, m), 6.42 (1H, d, J=0.98 Hz), 6.83 (1H, dd, J=8.8, 2.4 Hz), 6.89 (1H, d, J=2.2 Hz), 7.02-7.07 (1H, m), 7.61 (1H, d, J=9.0 Hz), 7.68-7.73 (1H, m), 8.20 (1H, d, J=8.3 Hz), 8.27 (1H, ddd, J=4.9, 1.7, 0.85 Hz)

Example 18

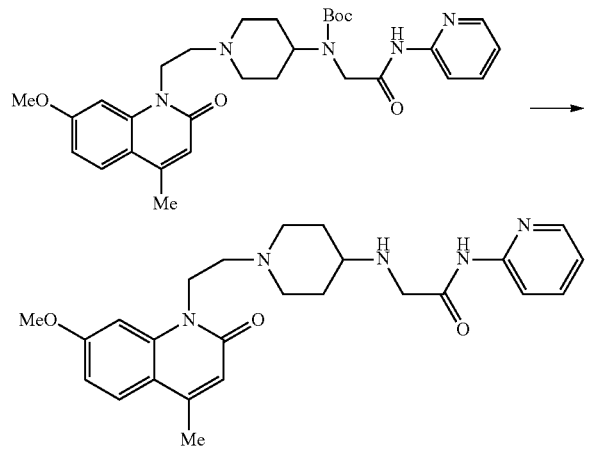

To 5 mL of a dichloromethane solution containing 0.11 g of tert-butyl (1-(2-(7-methoxy-4-methyl-2-oxoquinolin-1(2H)-yl)ethyl)piperidin-4-yl) (2-oxo-2-(pyridin-2-ylamino)ethyl)carbamate, 5 mL of trifluoroacetic acid was added and stirred at room temperature for 30 min. The solvent was removed under reduced pressure, chloroform and water were added, and adjusted to pH 13 with 20% aqueous sodium hydroxide solution under ice-cooling. The organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure to give 83 mg of N-(pyridin-2-yl)-$N^2$-(1-(2-(7-methoxy-4-methyl-2-oxoquinolin-1(2H)-yl)ethyl)piperidin-4-yl)glycinamide as a light brown foam.

$^1$H-NMR (CDCl$_3$) δ:
1.45-1.65 (2H, m), 1.90-2.00 (2H, m), 2.15-2.30 (2H, m), 2.42 (3H, s), 2.50-2.73 (3H, m), 3.00-3.13 (2H, m), 3.45 (2H, s), 3.92 (3H, s), 4.35-4.47 (2H, m), 6.42 (1H, s), 6.84 (1H, dd, J=8.8, 2.4 Hz), 6.92 (1H, s), 7.02-7.06 (1H, m), 7.61 (1H, d, J=8.8 Hz), 7.68-7.73 (1H, m), 8.25 (1H, d, J=8.3 Hz), 8.29-8.32 (1H, m), 9.75-9.85 (1H, broad)

Example 19

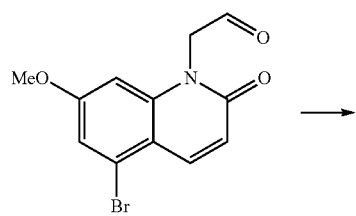

To 5 mL of dichloromethane solution containing 0.18 g of tert-butyl (2,3-dihydro-1,4-benzodioxin-6-ylmethyl)(piperidin-4-yl)carbamate, 0.15 g of (5-bromo-7-methoxy-2-oxoquinolin-1(2H)-yl)acetaldehyde and 29 μL of acetic acid were added and stirred at room temperature for 1 hour. To the reaction mixture, 0.16 g of sodium triacetoxyborohydride was added and stirred at the same temperature for 30 min. Chloroform and aqueous saturated sodium hydrogen carbonate solution were added, the organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; ethyl acetate] to give 0.17 g of tert-butyl (1-(2-(5-bromo-7-methoxy-2-oxoquinolin-1(2H)-yl)ethyl)piperidin-4-yl)(2,3-dihydro-1,4-benzodioxin-6-ylmethyl)carbamate as a light brown foam.

$^1$H-NMR (CDCl$_3$) δ:
1.42 (9H, s), 1.57-1.75 (4H, m), 2.08-2.25 (2H, m), 2.57-2.63 (2H, m), 2.99-3.06 (2H, m), 3.88 (3H, s), 3.95-4.15 (1H, m), 4.25 (4H, s), 4.25-4.35 (4H, m), 6.58 (1H, d, J=9.8 Hz), 6.67-6.74 (2H, m), 6.78 (1H, d, J=8.2 Hz), 6.86 (1H, d, J=2.2 Hz), 7.10 (1H, d, J=2.2 Hz), 8.00 (1H, d, J=9.8 Hz)

Example 20

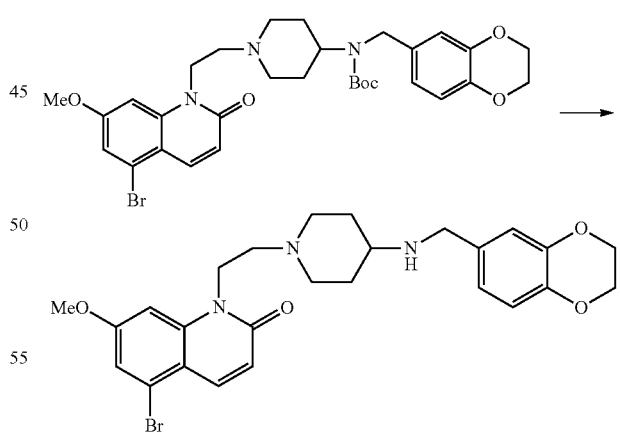

To 2 mL of a dichloromethane solution containing 20 mg of tert-butyl (1-(2-(5-bromo-7-methoxy-2-oxoquinolin-1(2H)-yl)ethyl)piperidin-4-yl) (2,3-dihydro-1,4-benzodioxin-6-ylmethyl)carbamate, 1 mL of trifluoroacetic acid was added and stirred at room temperature for 2 hours. The solvent was removed under reduced pressure, chloroform and water were added, and adjusted to pH 13 with 20% aqueous sodium hydroxide solution. The organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure to give 16 mg of 5-bromo-1-(2-(4-((2,3-dihydro-1,4-benzodioxin-6-ylmethyl)amino)piperidin-1-yl)ethyl-7-methoxyquinolin-2(1H)-one as a light brown oil.

$^1$H-NMR (CDCl$_3$) δ:
1.41-1.52 (2H, m), 1.88-1.96 (2H, m), 2.16-2.26 (2H, m), 2.51-2.67 (3H, m), 2.97-3.05 (2H, m), 3.71 (2H, s), 3.90 (3H, s), 4.24 (4H, s), 4.36-4.43 (2H, m), 6.58 (1H, d, J=9.9 Hz), 6.77-6.84 (3H, m), 6.92 (1H, d, J=2.1 Hz), 7.10 (1H, d, J=2.1 Hz), 8.01 (1H, d, J=9.9 Hz)

Example 21

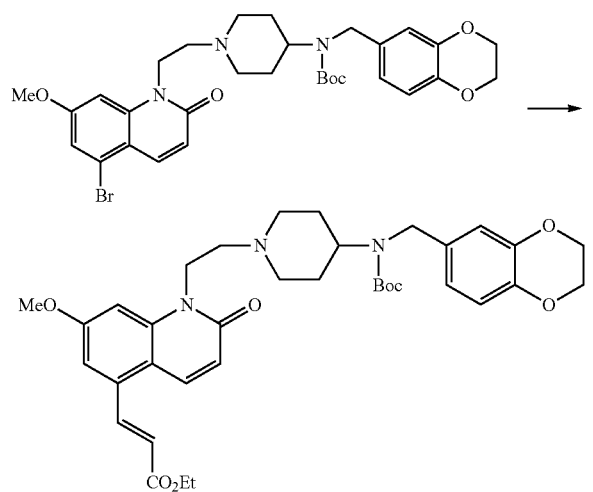

To 4.0 mL of an N,N-dimethylformamide solution containing 0.15 g of tert-butyl (1-(2-(5-bromo-7-methoxy-2-oxoquinolin-1(2H)-yl)ethyl)piperidin-4-yl)(2,3-dihydro-1,4-benzodioxin-6-ylmethyl)carbamate, 39 µl of ethyl acrylate, 50 µL of triethylamine and 6.1 mg of bis(tri-tert-butylphosphine)palladium(0) were added and heated under nitrogen atmosphere at 90° C. for 1.5 hours. The reaction mixture was cooled to the room temperature, and the solvent was removed under reduced pressure. The residue thus obtained was purified by silica gel column chromatography [eluent; chloroform:methanol=20:1] to give 0.15 g of ethyl (2E)-3-(1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinolin-5-yl)acrylate as a light brown foam.

$^1$H-NMR (CDCl$_3$) δ:
1.36 (3H, t, J=7.1 Hz), 1.42 (9H, s), 1.60-1.74 (4H, m), 2.10-2.25 (2H, m), 2.60-2.65 (2H, m), 3.01-3.08 (2H, m), 3.91 (3H, s), 3.95-4.15 (1H, m), 4.25 (4H, s), 4.30 (2H, q, J=7.1 Hz), 4.26-4.40 (4H, m), 6.44 (1H, d, J=15.7 Hz), 6.59 (1H, d, J=9.9 Hz), 6.67-6.71 (1H, m), 6.74 (1H, d, J=1.7 Hz), 6.78 (1H, d, J=8.4 Hz), 6.95 (1H, d, J=1.7 Hz), 7.00 (1H, d, J=2.2 Hz), 7.95 (1H, d, J=9.9 Hz), 8.18 (1H, d, J=15.7 Hz)

Example 22

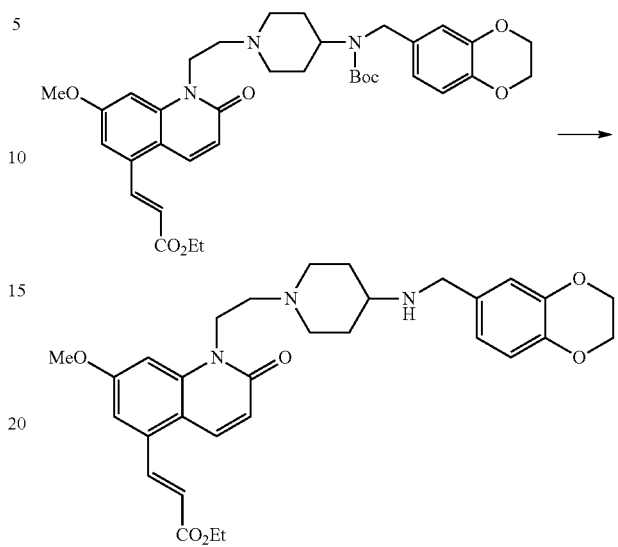

To 3 mL of a dichloromethane solution containing 0.15 g of ethyl (2E)-3-(1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinolin-5-yl)acrylate, 3 mL of trifluoroacetic acid was added and stirred at room temperature for 1 hour. The solvent was removed under reduced pressure, chloroform and water were added, and adjusted to pH 10 with 20% aqueous sodium hydroxide solution, under ice-cooling. The organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. To the residue thus obtained, hexane was added and the resulting solid was filtered to give 0.12 g of ethyl (2E)-3-(1-(2-(4-((2,3-dihydro-1,4-benzodioxin-6-ylmethyl)amino)piperidin-1-yl)ethyl)-7-methoxy-2-oxo-1,2-dihydroquinolin-5-yl)acrylate as a light brown solid.

$^1$H-NMR (CDCl$_3$) δ:
1.36 (3H, t, J=7.1 Hz), 1.42-1.63 (2H, m), 1.87-1.96 (2H, m), 2.15-2.25 (2H, m), 2.48-2.70 (3H, m), 2.97-3.05 (2H, m), 3.71 (2H, s), 3.93 (3H, s), 4.25 (4H, s), 4.30 (2H, q, J=7.1 Hz), 4.38-4.45 (2H, m), 6.44 (1H, d, J=15.7 Hz), 6.60 (1H, d, J=9.8 Hz), 6.76-6.84 (3H, m), 6.68-7.03 (2H, m), 7.96 (1H, d, J=9.8 Hz), 8.18 (1H, d, J=15.7 Hz)

Example 23

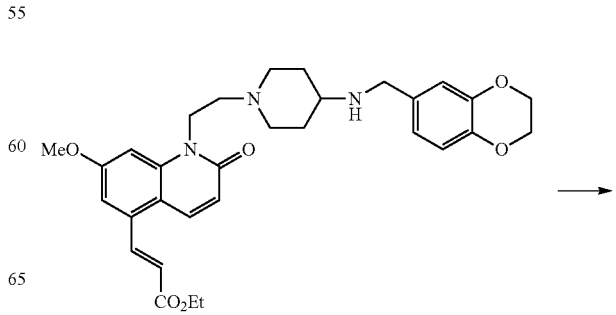

-continued

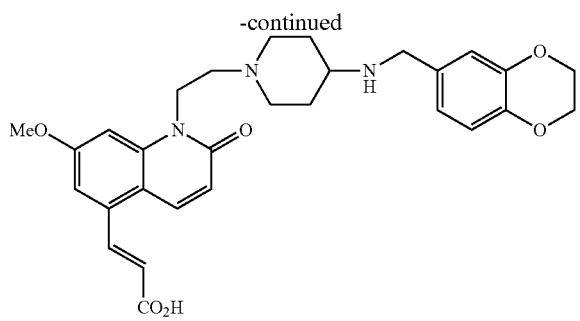

To 2 mL of an ethanol solution containing 0.10 g of ethyl (2E)-3-(1-(2-(4-((2,3-dihydro-1,4-benzodioxin-6-ylmethyl) amino)piperidin-1-yl)ethyl)-7-methoxy-2-oxo-1,2-dihydroquinolin-5-yl)acrylate, 0.22 mL of 20% aqueous sodium hydroxide solution was added and stirred at room temperature for 3 hours. Ethanol was removed under reduced pressure, water was added, and adjusted to pH 6.0 with 1 mol/L hydrochloric acid under ice-cooling. The resulting solid was filtered to afford 85 mg of (2E)-3-(1-(2-(4-((2,3-dihydro-1,4-benzodioxin-6-ylmethyl)amino)piperidin-1-yl)ethyl)-7-methoxy-2-oxo-1,2-dihydroquinolin-5-yl)acrylic acid as a light brown solid.

$^1$H-NMR (DMSO-$d_6$) δ:
1.50-1.64 (2H, m), 1.98-2.10 (4H, m), 2.52-2.62 (2H, m), 2.88-3.00 (1H, m), 3.04-3.14 (2H, m), 3.95 (3H, s), 4.01 (2H, s), 4.25 (4H, s), 4.36-4.42 (2H, m), 6.49 (1H, d, J=10.0 Hz), 6.63 (1H, d, J=15.6 Hz), 6.90 (1H, d, J=8.3 Hz), 6.98 (1H, dd, J=8.3, 2.0 Hz), 7.05 (1H, d, J=2.0 Hz), 7.09 (1H, d, J=2.0 Hz), 7.26 (1H, d, J=2.0 Hz), 8.11 (1H, d, J=10.0 Hz), 8.12 (1H, d, J=15.6 Hz)

Example 24

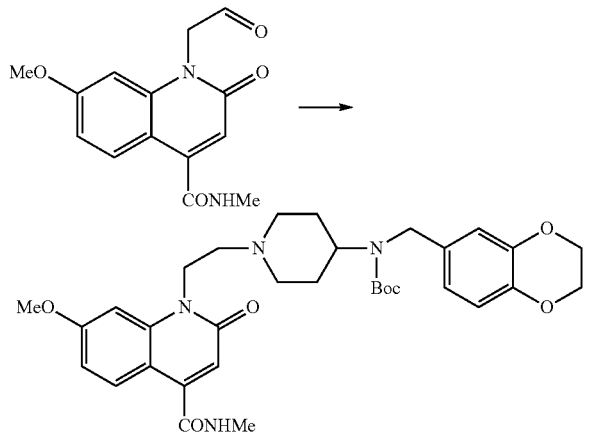

To 2 mL of dichloromethane suspension containing 77 mg of 7-methoxy-N-methyl-2-oxo-1-(2-oxoethyl)-1,2-dihydroquinoline-4-carboxamide, 2 mL of dichloromethane solution containing 98 mg of tert-butyl (2,3-dihydro-1,4-benzodioxin-6-ylmethyl)(piperidin-4-yl)carbamate and 16 µL of acetic acid were added and stirred at room temperature for 2 hours. To the reaction mixture, 89 mg of sodium triacetoxyborohydride was added and stirred at the same temperature for 30 min. Chloroform and aqueous saturated sodium hydrogen carbonate solution were added, the organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; chloroform:methanol=10:1] to give 0.16 g of tert-butyl (2,3-dihydro-1,4-benzodioxin-6-ylmethyl)(1-(2-(7-methoxy-4-((methylamino)carbonyl)-2-oxoquinolin-1(2H)-yl)ethyl)piperidin-4-yl)carbamate as a light brown foam.

$^1$H-NMR (CDCl$_3$) δ:
1.41 (9H, s), 1.58-1.72 (4H, m), 2.05-2.22 (2H, m), 2.52-2.60 (2H, m), 2.97-3.06 (2H, m), 3.05 (3H, d, J=4.9 Hz), 3.88 (3H, s), 3.90-4.20 (1H, m), 4.25 (4H, s), 4.24-4.34 (4H, m), 6.18-6.26 (1H, m), 6.55 (1H, s), 6.67-6.85 (5H, m), 7.87 (1H, d, J=8.5 Hz)

Example 25

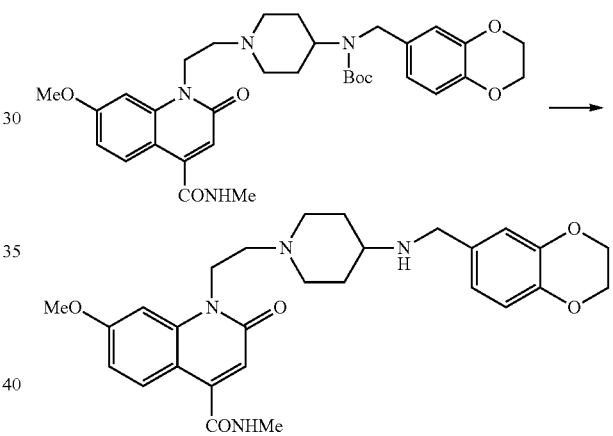

To 2 mL of a dichloromethane solution containing 0.15 g of tert-butyl (2,3-dihydro-1,4-benzodioxin-6-ylmethyl)(1-(2-(7-methoxy-4-((methylamino)carbonyl)-2-oxoquinolin-1 (2H)-yl)ethyl)piperidin-4-yl)carbamate, 2 mL of trifluoroacetic acid was added and stirred at room temperature for 30 min. The solvent was removed under reduced pressure, chloroform and water were added, and adjusted to pH 11 with 20% aqueous sodium hydroxide solution. The organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure to give 88 mg of 1-(2-(4-((2, 3-dihydro-1,4-benzodioxin-6-ylmethyl)amino)piperidin-1-yl)ethyl)-7-methoxy-N-methyl-2-oxo-1,2-dihydroquinoline-4-carboxamide as a pale yellow foam.

$^1$H-NMR (CDCl$_3$) δ:
1.38-1.50 (2H, m), 1.86-1.93 (2H, m), 2.09-2.19 (2H, m), 2.48-2.59 (3H, m), 2.91-2.99 (2H, m), 3.05 (3H, d, J=4.6 Hz), 3.71 (2H, s), 3.90 (3H, s), 4.24 (4H, s), 4.25-4.33 (2H, m), 6.46-6.53 (1H, m), 6.54 (1H, s), 6.76-6.89 (5H, m), 7.87 (1H, d, J=9.0 Hz)

Example 26

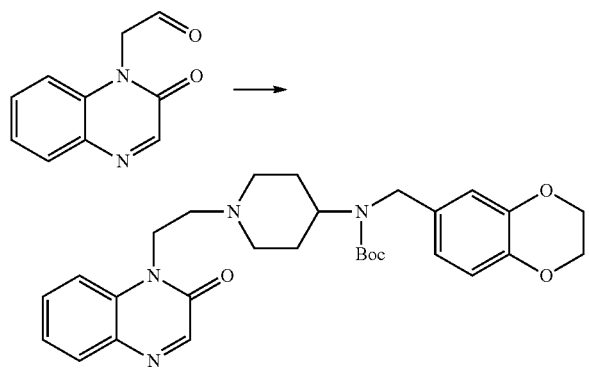

To 3 mL of dichloromethane solution containing 0.19 g of tert-butyl (2,3-dihydro-1,4-benzodioxin-6-ylmethyl)(piperidin-4-yl)carbamate, 0.10 g of (2-oxoquinoxalin-1(2H)-yl)acetaldehyde and 30 μL of acetic acid were added and stirred at room temperature for 2 hours. To the reaction mixture, 0.17 g of sodium triacetoxyborohydride was added and stirred at the same temperature for 30 min. Chloroform and aqueous saturated sodium hydrogen carbonate solution were added, the organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; ethyl acetate] to give 0.22 g of tert-butyl (2,3-dihydro-1,4-benzodioxin-6-ylmethyl)(1-(2-(2-oxoquinoxalin-1(2H)-yl)ethyl)piperidin-4-yl)carbamate as a light brown oil.

$^1$H-NMR (CDCl$_3$) δ:
1.42 (9H, s), 1.57-1.72 (4H, m), 2.08-2.23 (2H, m), 2.61-2.66 (2H, m), 2.97-3.05 (2H, m), 4.00-4.15 (1H, m), 4.25 (4H, s), 4.20-4.36 (4H, m), 6.66-6.70 (1H, m), 6.73 (1H, d, J=1.7 Hz), 6.78 (1H, d, J=8.3 Hz), 7.33-7.38 (2H, m), 7.54-7.60 (1H, m), 7.88 (1H, dd, J=7.8, 1.3 Hz), 8.29 (1H, s)

Example 27

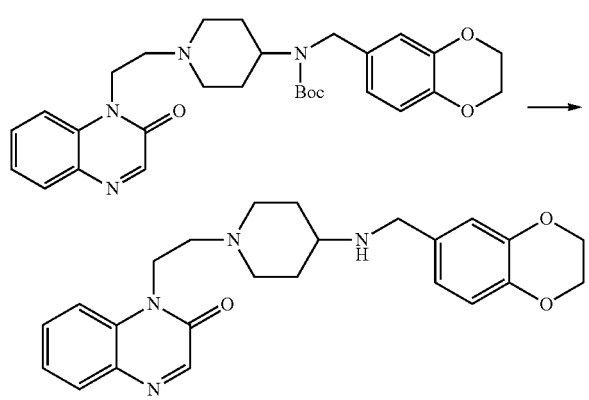

To 3 mL of a dichloromethane solution containing 0.21 g of tert-butyl (2,3-dihydro-1,4-benzodioxin-6-ylmethyl)(1-(2-(2-oxoquinoxalin-1(2H)-yl)ethyl)piperidin-4-yl)carbamate, 3 mL of trifluoroacetic acid was added and stirred at room temperature for 1 hour. The solvent was removed under reduced pressure, chloroform and water were added, and adjusted to pH 13 with 20% aqueous sodium hydroxide solution. The organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure to give 0.16 g of 1-(2-(4-((2,3-dihydro-1,4-benzodioxin-6-ylmethyl)amino)piperidin-1-yl)ethyl)quinoxalin-2(1H)-one as a light brown oil.

$^1$H-NMR (CDCl$_3$) δ:
1.36-1.47 (2H, m), 1.86-1.93 (2H, m), 2.16-2.22 (2H, m), 2.48-2.57 (1H, m), 2.67 (2H, t, J=7.3 Hz), 2.94-3.01 (2H, m), 3.70 (2H, s), 4.25 (4H, s), 4.38 (2H, t, J=7.3 Hz), 6.76-6.83 (3H, m), 7.33-7.37 (1H, m), 7.42 (1H, d, J=8.5 Hz), 7.56-7.61 (1H, m), 7.88 (1H, d, J=8.0 Hz), 8.29 (1H, s)

Example 28

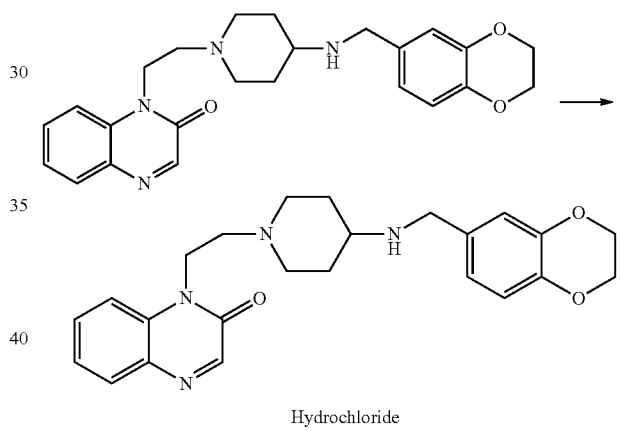

To 5 mL of an ethyl acetate solution containing 0.15 g of 1-(2-(4-((2,3-dihydro-1,4-benzodioxin-6-ylmethyl)amino)piperidin-1-yl)ethyl)quinoxalin-2(1H)-one, 5 mL of 4.0 mol/L hydrogen chloride/ethyl acetate was added at room temperature. The mixture was stirred at the same temperature for 10 min, and the solvent was removed under reduced pressure. To the residue thus obtained, ethyl acetate was added and the resulting solid was filtered to afford 0.16 g of 1-(2-(4-((2,3-dihydro-1,4-benzodioxin-6-ylmethyl)amino)piperidin-1-yl)ethyl)quinoxalin-2(1H)-one hydrochloride as a red-brown solid.

$^1$H-NMR (DMSO-d$_6$) δ:
2.00-2.13 (2H, m), 2.31-2.41 (2H, m), 3.05-3.50 (5H, m), 3.77-3.85 (2H, m), 4.03-4.12 (2H, m), 4.25 (4H, s), 4.63-4.69 (2H, m), 6.90 (1H, d, J=8.0 Hz), 7.03-7.07 (1H, m), 7.16-7.18 (1H, m), 7.44 (1H, t, J=7.6 Hz), 7.69 (1H, t, J=7.8 Hz), 7.83-7.90 (2H, m), 8.28 (1H, s), 9.56 (1H, s), 9.65 (1H, s), 10.83 (1H, s)

Example 29

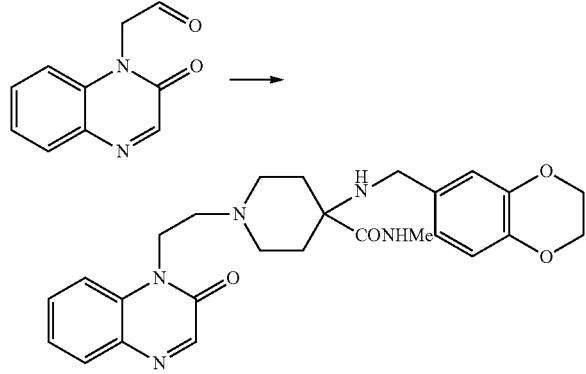

To 3 mL of dichloromethane solution containing 0.11 g of 4-((2,3-dihydro-1,4-benzodioxin-6-ylmethyl)amino)-N-methylpiperidine-4-carboxamide, 65 mg of (2-oxoquinoxalin-1 (2H)-yl)acetaldehyde and 20 μL of acetic acid were added and stirred at room temperature for 3 hours. To the reaction mixture, 0.11 g of sodium triacetoxyborohydride was added and stirred at the same temperature for 30 min. Chloroform and aqueous saturated sodium hydrogen carbonate solution were added, the organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; chloroform:methanol=10:1] to give 0.12 g of 4-((2,3-dihydro-1,4-benzodioxin-6-ylmethyl)amino)-N-methyl-1-(2-(2-oxoquinoxalin-1(2H)-yl)ethyl)piperidine-4-carboxamide as a yellow oil.

$^1$H-NMR (CDCl$_3$) δ:
1.63-1.72 (2H, m), 2.16-2.26 (2H, m), 2.32-2.39 (2H, m), 2.70 (2H, t, J=7.3 Hz), 2.82 (3H, d, J=4.9 Hz), 2.85-2.94 (2H, m), 3.46 (2H, s), 4.26 (4H, s), 4.39 (2H, t, J=7.3 Hz), 6.76 (1H, dd, J=8.0, 1.8 Hz), 6.82-6.86 (2H, m), 7.31-7.39 (2H, m), 7.43 (2H, d, J=8.5 Hz), 7.57-7.68 (1H, m), 7.89 (1H, dd, J=8.0, 1.5 Hz), 8.29 (1H, s)

Example 30

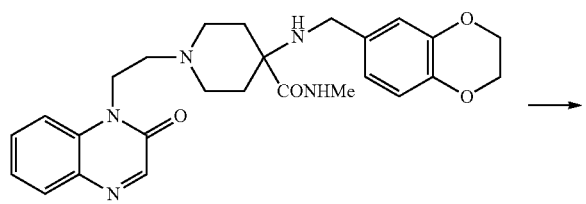

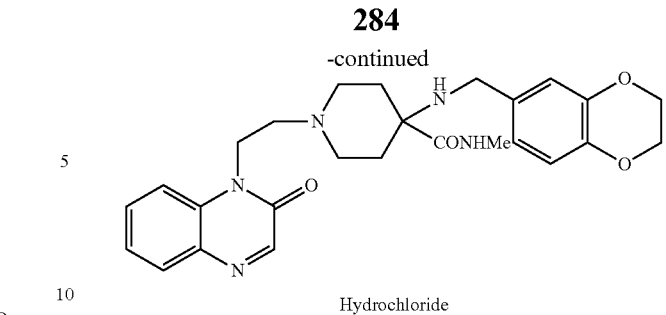

Hydrochloride

To 5 mL of an ethyl acetate solution containing 0.12 g of 4-((2,3-dihydro-1,4-benzodioxin-6-ylmethyl)amino)-N-methyl-1-(2-(2-oxoquinoxalin-1(2H)-yl)ethyl)piperidine-4-carboxamide, 5 mL of 4.0 mol/L hydrogen chloride/ethyl acetate was added at room temperature. The mixture was stirred at the same temperature for 10 min, and the solvent was removed under reduced pressure. To the residue thus obtained, ethyl acetate was added and the resulting solid was filtered to afford 0.11 g of 4-((2,3-dihydro-1,4-benzodioxin-6-ylmethyl)amino)-N-methyl-1-(2-(2-oxoquinoxalin-1 (2H)-yl)ethyl)piperidine-4-carboxamide hydrochloride as a yellow solid.

$^1$H-NMR (DMSO-d$_6$) δ:
2.20-3.15 (6H, m), 2.77 (3H, d, J=3.7 Hz), 3.35-4.00 (6H, m), 4.25 (4H, s), 4.60-4.72 (2H, m), 6.88 (1H, d, J=8.3 Hz), 6.96-7.01 (1H, m), 7.09 (1H, s), 7.41-7.48 (1H, m), 7.66-7.73 (1H, m), 7.83 (1H, d, J=8.5 Hz), 7.88 (1H, dd, J=8.0, 1.5 Hz), 8.27 (1H, s), 8.78-8.87 (1H, m)

Example 31

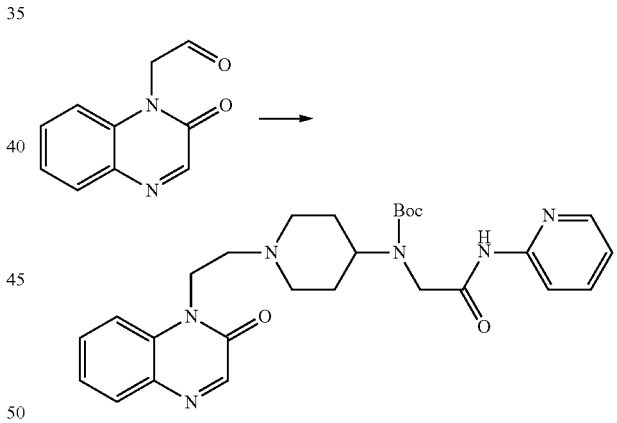

To 3 mL of dichloromethane solution containing 0.18 g of tert-butyl (2-oxo-2-(pyridin-2-ylamino)ethyl)(piperidin-4-yl)carbamate, 0.10 g of (2-oxoquinoxalin-1(2H)-yl)acetaldehyde and 30 μl of acetic acid were added and stirred at room temperature for 2 hours. To the reaction mixture, 0.17 g of sodium triacetoxyborohydride was added and stirred at the same temperature for 30 min. Chloroform and aqueous saturated sodium hydrogen carbonate solution were added, the organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; chloroform:methanol=10:1] to give 0.26 g of tert-butyl (2-oxo-2-(pyridin-2-ylamino)ethyl) (1-(2-(2-oxoquinoxalin-1(2H)-yl)ethyl)piperidin-4-yl)carbamate as a pale yellow foam.

$^1$H-NMR (CDCl$_3$) δ:
1.46 (9H, s), 1.52-1.84 (4H, m), 2.15-2.28 (2H, m), 2.67 (2H, t, J=7.3 Hz), 3.03-3.12 (2H, m), 3.91 (2H, s), 3.90-4.20 (1H, m), 4.36 (2H, t, J=7.2 Hz), 7.02-7.08 (1H, m), 7.33-7.39 (2H, m), 7.59 (1H, t, J=7.3 Hz), 7.71 (1H, t, J=7.2 Hz), 7.89 (1H, d, J=7.6 Hz), 8.20 (1H, d, J=8.3 Hz), 8.26-8.30 (2H, m)

Example 32

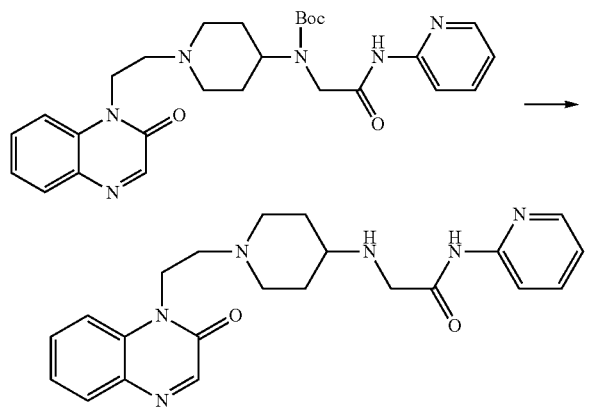

To 3 mL of a dichloromethane solution containing 0.26 g of tert-butyl (2-oxo-2-(pyridin-2-ylamino)ethyl)(1-(2-(2-oxoquinoxalin-1(2H)-yl)ethyl)piperidin-4-yl)carbamate, 3 mL of trifluoroacetic acid was added and stirred at room temperature for 1 hour. The solvent was removed under reduced pressure, chloroform and water were added, and adjusted to pH 11 with 20% aqueous sodium hydroxide solution. The organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure to give 0.20 g of N$^2$-(1-(2-(2-oxoquinoxalin-1(2H)-yl)ethyl)piperidin-4-yl)-N-(pyridin-2-yl)glycinamide as a light brown oil.

$^1$H-NMR (CDCl$_3$) δ:
1.40-1.52 (2H, m), 1.89-1.97 (2H, m), 2.14-2.22 (2H, m), 2.48-2.57 (1H, m), 2.68 (2H, t, J=7.3 Hz), 2.96-3.04 (2H, m), 3.44 (2H, s), 4.38 (2H, t, J=7.3 Hz), 7.04 (1H, ddd, J=7.3, 4.9, 1.0 Hz), 7.33-7.38 (1H, m), 7.40 (1H, d, J=8.5 Hz), 7.59 (1H, ddd, J=8.5, 7.2, 1.5 Hz), 7.68-7.73 (1H, m), 7.89 (1H, dd, J=8.0, 1.5 Hz), 8.23-8.26 (1H, m), 8.29-8.32 (2H, m), 9.80 (1H, s)

Example 33

To 5 mL of an ethyl acetate solution containing 0.19 g of N$^2$-(1-(2-(2-oxoquinoxalin-1(2H)-yl)ethyl)piperidin-4-yl)-N-(pyridin-2-yl)glycinamide, 5 mL of 4.0 mol/L hydrogen chloride/ethyl acetate was added at room temperature. The mixture was stirred at the same temperature for 10 min, and the solvent was removed under reduced pressure. To the residue thus obtained, ethyl acetate was added and the resulting solid was filtered to afford 0.19 g of N$^2$-(1-(2-(2-oxoquinoxalin-1(2H)-yl)ethyl)piperidin-4-yl)-N-(pyridin-2-yl)glycinamide hydrochloride as a yellow solid.

$^1$H-NMR (DMSO-d$_6$) δ:
2.10-2.40 (4H, m), 3.13-3.27 (2H, m), 3.34-3.52 (3H, m), 3.83-3.93 (2H, m), 4.00-4.40 (2H, m), 4.73 (2H, t, J=7.0 Hz), 7.25 (1H, dd, J=7.3, 5.1 Hz), 7.48-7.53 (1H, m), 7.72-7.78 (1H, m), 7.90-7.97 (3H, m), 8.08-8.16 (1H, m), 8.34 (1H, s), 8.42-8.45 (1H, m), 9.68-9.81 (2H, broad), 9.81-9.92 (1H, broad), 10.90-11.00 (1H, broad), 11.15 (1H, s)

Example 34

To 2 mL of an N,N-dimethylformamide solution containing 95 mg of ethyl 4-(3-(2-oxoquinoxalin-1(2H)-yl)propyl)piperidine-4-carboxylate, 69 mg of 2-(2-bromoethylthio)thiophene and 84 mg of potassium carbonate were added at room temperature, and stirred at 50-55° C. for 1 hour. Additional 35 mg of 2-(2-bromoethylthio)thiophene was added and stirred at 50-55° C. for 1 hour, then stirred at 60° C. for 1 hour. The mixture was cooled to the room temperature, ethyl acetate and water were added, the organic layer was separated, and the aqueous layer was extracted with ethyl acetate. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; chloroform:methanol=20:1] to give 98 mg of ethyl 4-(3-(2-oxoquinoxalin-1(2H)-yl)propyl)-1-(2-(2-thienylthio)ethyl)piperidine-4-carboxylate as a light brown oil.

$^1$H-NMR (CDCl$_3$) δ:
1.17 (3H, t, J=7.1 Hz), 1.40-1.50 (2H, m), 1.60-1.72 (4H, m), 2.00-2.15 (4H, m), 2.52-2.60 (2H, m), 2.64-2.72 (2H, m), 2.84-2.92 (2H, m), 4.08 (2H, q, J=7.1 Hz), 4.16-4.22 (2H, m), 6.95 (1H, dd, J=5.2, 3.5 Hz), 7.10 (1H, d, J=2.9 Hz), 7.24-7.38 (3H, m), 7.57 (1H, t, J=7.3 Hz), 7.89 (1H, d, J=7.3 Hz), 8.29 (1H, s)

Example 35

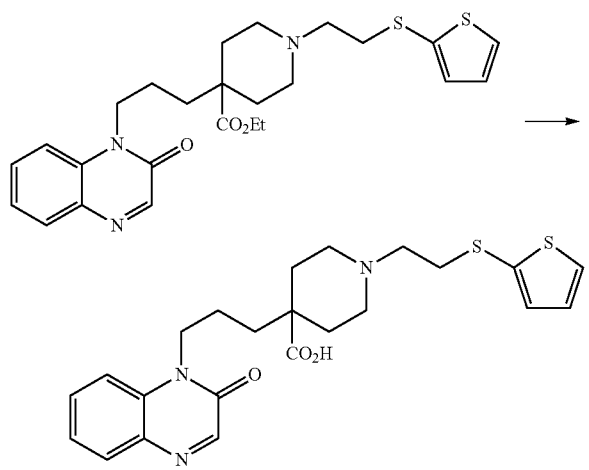

To 2 mL of an ethanol solution containing 90 mg of ethyl 4-(3-(2-oxoquinoxalin-1(2H)-yl)propyl)-1-(2-(2-thienylthio)ethyl)piperidine-4-carboxylate, 0.5 mL of 20% aqueous sodium hydroxide solution was added and stirred at 55-60° C. for 5 hours. 0.5 mL of 20% aqueous sodium hydroxide solution and 0.5 mL of water were added at the same temperature, and stirred at 55-60° C. for 1 hour. The mixture was cooled to the room temperature, and left to stand for 2 nights. The solvent was removed under reduced pressure, water was added, adjusted to pH 6.5 with 6.0 mol/L hydrochloric acid, acetonitrile was added, and the solvent was removed under reduced pressure. Water was added, and the resulting solid was filtered to afford 35 mg of 4-(3-(2-oxoquinoxaline-1(2H)-yl)propyl)-1-(2-(2-thienylthio)ethyl)piperidine-4-carboxylic acid as a brown solid.

$^1$H-NMR (DMSO-d$_6$) δ:
1.20-2.10 (8H, m), 2.40-2.70 (6H, m), 2.85-2.95 (2H, m), 4.10-4.25 (2H, m), 6.98-7.08 (1H, m), 7.12-7.23 (1H, m), 7.30-7.45 (1H, m), 7.52-7.72 (3H, m), 7.80-7.88 (1H, m), 8.22 (1H, s)

Example 36

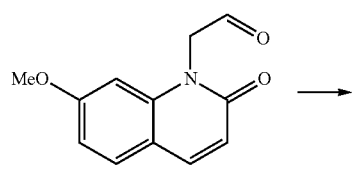

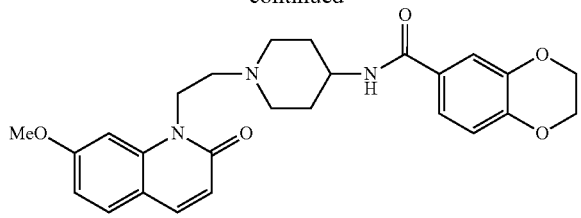

To 3 mL of dichloromethane suspension containing 70 mg of 7-methoxy-2-oxoquinolin-1(2H)-yl)acetaldehyde, 84 mg of N-(piperidin-4-yl)-2,3-dihydro-1,4-benzodioxin-6-carboxamide, 2 mL of dichloromethane and 18 μl of acetic acid were added and stirred at room temperature for 2 hours. To the reaction mixture, 0.10 g of sodium triacetoxyborohydride was added and stirred at the same temperature for 30 min. Chloroform and aqueous saturated sodium hydrogen carbonate solution were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=10:1] and to the residue thus obtained, diethyl ether and hexane were added, and the resulting solid was filtered to give 63 mg of N-(1-(2-(7-methoxy-2-oxoquinolin-1(2H)-yl)ethyl)piperidin-4-yl)-2,3-dihydro-1,4-benzodioxin-6-carboxamide as a white solid.

$^1$H-NMR (CDCl$_3$) δ:
1.50-1.62 (2H, m), 2.00-2.10 (2H, m), 2.32-2.42 (2H, m), 2.70 (2H, t, J=7.6 Hz), 2.98-3.06 (2H, m), 3.92 (3H, s), 3.94-4.06 (1H, m), 4.26-4.32 (4H, m), 4.41 (2H, t, J=7.6 Hz), 5.85 (1H, d, J=8.5 Hz), 6.53 (1H, d, J=9.4 Hz), 6.82 (1H, dd, J=8.5, 2.2 Hz), 6.89 (1H, d, J=8.3 Hz), 6.89 (1H, d, J=2.2 Hz), 7.22-7.28 (1H, m), 7.31 (1H, d, J=2.2 Hz), 7.47 (1H, d, J=8.5 Hz), 7.59 (1H, d, J=9.4 Hz)

Example 37

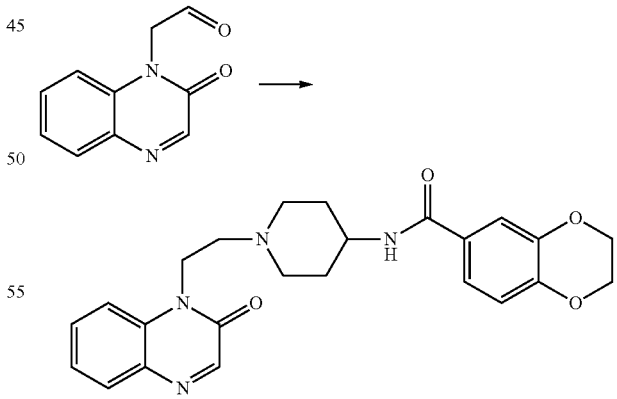

To 3 mL of dichloromethane solution containing 70 mg of (2-oxoquinoxalin-1(2H)-yl)acetaldehyde, 98 mg of N-(piperidin-4-yl)-2,3-dihydro-1,4-benzodioxin-6-carboxamide and 21 μl of acetic acid were added and stirred at room temperature for 2 hours. To the reaction mixture, 0.12 g of sodium triacetoxyborohydride was added and stirred at the same temperature for 30 min. Chloroform and aqueous saturated sodium hydrogen carbonate solution were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=20:1], and to the residue thus obtained, diethyl ether was added, and the resulting solid was filtered to give 0.12 g of N-(1-(2-(2-oxoquinoxalin-1 (2H)-yl)ethyl)piperidin-4-yl)-2,3-dihydro-1,4-benzodioxin-6-carboxamide as a light brown solid.

$^1$H-NMR (CDCl$_3$) δ:

1.46-1.60 (2H, m), 2.00-2.08 (2H, m), 2.28-2.38 (2H, m), 2.72 (2H, t, J=7.3 Hz), 2.94-3.02 (2H, m), 3.92-4.04 (1H, m), 4.24-4.32 (4H, m), 4.40 (2H, t, J=7.3 Hz), 5.83 (1H, d, J=7.8 Hz), 6.89 (1H, d, J=8.3 Hz), 7.24 (1H, dd, J=8.5, 2.0 Hz), 7.30 (1H, d, J=2.0 Hz), 7.34-7.38 (1H, m), 7.40 (1H, d, J=8.3 Hz), 7.60 (1H, ddd, J=8.5, 7.3, 1.5 Hz), 7.90 (1H, dd, J=8.0, 1.5 Hz), 8.30 (1H, s)

Example 38

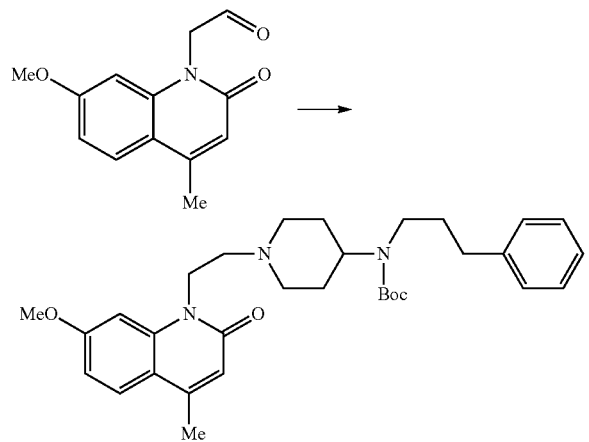

To 3 mL of dichloromethane solution containing 95 mg of (7-methoxy-4-methyl-2-oxoquinolin-1(2H)-yl)acetaldehyde, 81 mg of tert-butyl (3-phenylpropyl) (piperidin-4-yl) carbamate, 18 μl of acetic acid and 98 mg of sodium triacetoxyborohydride were added and stirred at room temperature for 1 hour. To the reaction mixture, water, ethyl acetate and aqueous saturated sodium hydrogen carbonate solution were added. The organic layer was separated, and washed with aqueous saturated sodium chloride solution, dried over anhydrous magnesium sulfate, and the solvent was removed under reduced pressure to give 0.16 g of tert-butyl (1-(2-(7-methoxy-4-methyl-2-oxoquinolin-1(2H)-yl)ethyl) piperidin-4-yl)(3-phenylpropyl)carbamate as a brown foam.

$^1$H-NMR (CDCl$_3$) δ:

1.44 (9H, s), 1.63-1.90 (6H, m), 2.14-2.26 (2H, m), 2.42 (3H, d, J=0.8 Hz), 2.59 (2H, t, J=7.8 Hz), 2.64 (2H, t, J=7.8 Hz), 3.05-3.18 (4H, m), 3.90 (3H, s), 3.92-4.05 (1H, m), 4.38 (2H, t, J=7.7 Hz), 6.42 (1H, d, J=0.8 Hz), 6.84 (1H, dd, J=8.8, 2.2 Hz), 6.89 (1H, d, J=2.2 Hz), 7.14-7.22 (3H, m), 7.24-7.33 (2H, m), 7.61 (1H, d, J=8.8 Hz)

Example 39

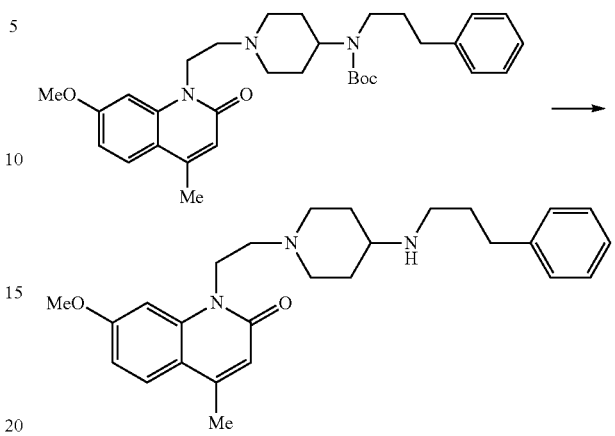

To 2 mL of a dichloromethane solution containing 0.16 g of tert-butyl (1-(2-(7-methoxy-4-methyl-2-oxoquinolin-1(2H)-yl)ethyl)piperidin-4-yl) (3-phenylpropyl)carbamate, 0.5 mL of trifluoroacetic acid was added under ice-cooling and stirred for 1.5 hours, thereafter the mixture was raised to the room temperature and left to stand for one night. The solvent was removed under reduced pressure, and to the residue thus obtained, ethyl acetate and water were added, and adjusted to pH 12.3 with 20% aqueous sodium hydroxide solution. The organic layer was separated, washed with aqueous saturated sodium chloride solution, dried over anhydrous magnesium sulfate, and the solvent was removed under reduced pressure to give 0.11 g of 7-methoxy-4-methyl-1-(2-(4-((3-phenylpropyl)amino)piperidin-1-yl)ethyl)quinolin-2(1H)-one as a yellow oil.

$^1$H-NMR (CDCl$_3$) δ:

1.34-1.46 (2H, m), 1.78-1.92 (4H, m), 2.14-2.24 (2H, m), 2.41 (3H, s), 2.42-2.50 (1H, m), 2.61-2.70 (6H, m), 2.98-3.06 (2H, m), 3.91 (3H, s), 4.39 (2H, t, J=7.6 Hz), 6.42 (1H, s), 6.83 (1H, dd, J=9.0, 2.3 Hz), 6.93 (1H, d, J=2.3 Hz), 7.15-7.22 (3H, m), 7.24-7.32 (2H, m), 7.61 (1H, d, J=9.0 Hz)

Example 40

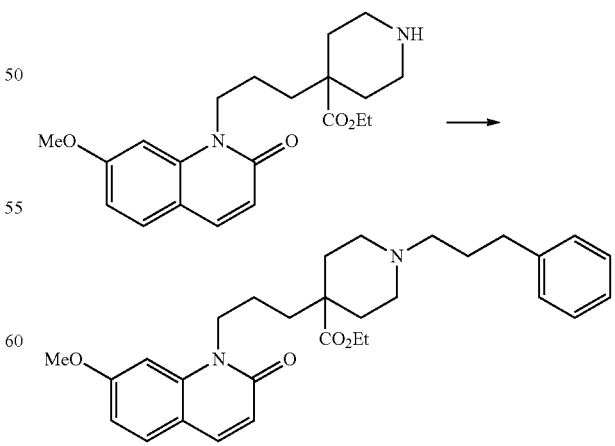

To 1.25 mL of an N,N-dimethylformamide solution containing 70 mg of ethyl 4-(3-(7-methoxy-2-oxoquinolin-1

(2H)-yl)propyl)piperidine-4-carboxylate, 57 mg of potassium carbonate and 0.25 mL of an N,N-dimethylformamide solution containing 31 μL of (3-bromopropyl)benzene were added at room temperature, and stirred at 60-75° C. for 1.5 hours. After the reaction mixture was cooled to the room temperature, ethyl acetate and water were added. The organic layer was separated, and the mixture was washed sequentially with water and aqueous saturated sodium chloride solution, dried over anhydrous magnesium sulfate, and the solvent was removed under reduced pressure to give 81 mg of ethyl 4-(3-(7-methoxy-2-oxoquinolin-1(2H)-yl)propyl)-1-(3-phenylpropyl)piperidine-4-carboxylate as a yellow oil.

¹H-NMR (CDCl₃) δ:
1.18 (3H, t, J=7.3 Hz), 1.44-1.50 (2H, m), 1.65-1.85 (4H, m), 1.95-2.07 (2H, m), 2.10-2.25 (4H, m), 2.25-2.35 (2H, m), 2.60 (2H, t, J=7.7 Hz), 2.65-2.75 (2H, m), 3.91 (3H, s), 4.09 (2H, q, J=7.3 Hz), 4.16-4.24 (2H, m), 6.52 (1H, d, J=9.5 Hz), 6.72 (1H, d, J=2.2 Hz), 6.80 (1H, dd, J=8.5, 2.2 Hz), 7.14-7.34 (5H, m), 7.46 (1H, d, J=8.5 Hz), 7.58 (1H, d, J=9.5 Hz)

Example 41

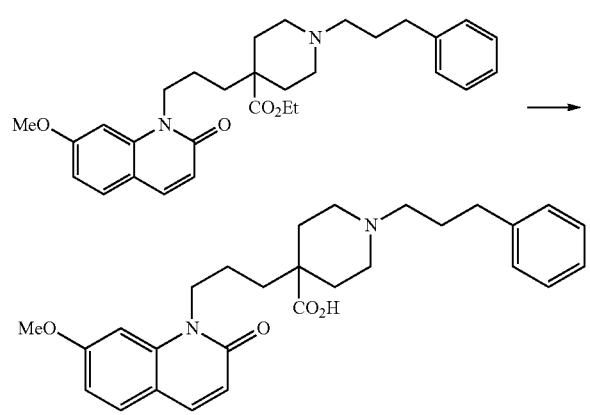

To 0.8 mL of an ethanol solution containing 80 mg of ethyl 4-(3-(7-methoxy-2-oxoquinolin-1(2H)-yl)propyl)-1-(3-phenylpropyl)piperidine-4-carboxylate, 0.2 mL of 20% aqueous sodium hydroxide solution was added and refluxed with heating for 5 hours. After the reaction mixture was cooled to the room temperature, the solvent was removed under reduced pressure, water was added, and adjusted to pH 6.8 with 6.0 mol/L hydrochloric acid. The solvent was removed under reduced pressure, and the residue thus obtained was purified by reversed-phase silica gel column chromatography [eluent; acetonitrile:water=3:7] to give 23 mg of 4-(3-(7-methoxy-2-oxoquinolin-1(2H)-yl)propyl)-1-(3-phenylpropyl)piperidine-4-carboxylic acid as a white solid.

¹H-NMR (CD₃OD) δ:
1.43-1.80 (6H, m), 1.90-2.02 (2H, m), 2.20-2.32 (2H, m), 2.56-2.70 (2H, m), 2.80-2.98 (4H, m), 3.22-3.36 (2H, m), 3.93 (3H, s), 4.20-4.32 (2H, m), 6.46 (1H, d, J=9.3 Hz), 6.90 (1H, dd, J=8.8, 2.2 Hz), 6.96-6.98 (1H, m), 7.11-7.30 (5H, m), 7.58 (1H, d, J=8.8 Hz), 7.79 (1H, d, J=9.3 Hz)

Example 42

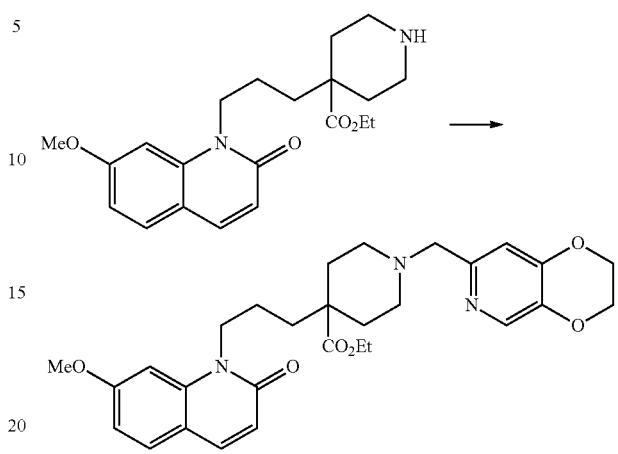

To 2 mL of dichloromethane solution containing 80 mg of ethyl 4-(3-(7-methoxy-2-oxoquinolin-1(2H)-yl)propyl)-piperidine-4-carboxylate, 41 mg of 2,3-dihydro(1,4)dioxino(2,3-c)pyridine-7-carbaldehyde and 14 μL of acetic acid were added at room temperature, 78 mg of sodium triacetoxyborohydride was added under ice-cooling, and stirred at room temperature for 1 hour. To the reaction mixture, water, chloroform and aqueous saturated sodium hydrogen carbonate solution were added. The organic layer was separated, washed with aqueous saturated sodium chloride solution, dried over anhydrous magnesium sulfate, and the solvent was removed under reduced pressure. The residue thus obtained was purified by silica gel column chromatography [eluent; chloroform:methanol=20:1], to give 65 mg of ethyl 1-(2,3-dihydro(1,4)dioxino(2,3-c)pyridin-7-ylmethyl)-4-(3-(7-methoxy-2-oxoquinolin-1(2H)-yl)propyl)piperidine-4-carboxylate as a yellow oil.

¹H-NMR (CDCl₃) δ:
1.18 (3H, t, J=7.2 Hz), 1.47-1.58 (2H, m), 1.64-1.70 (4H, m), 2.08-2.18 (4H, m), 2.66-2.74 (2H, m), 3.46 (2H, s), 3.91 (3H, s), 4.10 (2H, q, J=7.2 Hz), 4.16-4.22 (2H, m), 4.24-4.36 (4H, m), 6.52 (1H, d, J=9.5 Hz), 6.72 (1H, d, J=2.4 Hz), 6.81 (1H, dd, J=8.6, 2.4 Hz), 6.88 (1H, s), 7.46 (1H, d, J=8.6 Hz), 7.58 (1H, d, J=9.5 Hz), 8.10 (1H, d, J=9.5 Hz)

Example 43

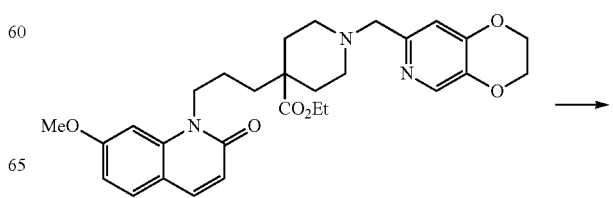

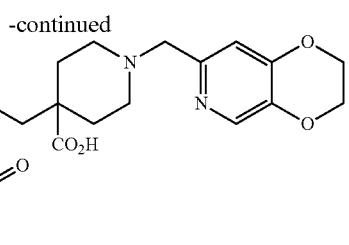

To 1 mL of an ethanol solution containing 80 mg of ethyl 1-(2,3-dihydro(1,4)dioxino(2,3-c)pyridin-7-ylmethyl)-4-(3-(7-methoxy-2-oxoquinolin-1(2H)-yl)propyl)piperidine-4-carboxylate, 0.25 mL of 20% aqueous sodium hydroxide solution was added and refluxed with heating for 7.5 hours. Further, 0.30 mL of 20% aqueous sodium hydroxide solution was added and left to stand at room temperature overnight. The solvent was removed under reduced pressure, water was added, and adjusted to pH 6.5 with 6.0 mol/L hydrochloric acid. The resulting solid was filtered to give 11 mg of 1-(2,3-dihydro(1,4)dioxino(2,3-c)pyridin-7-ylmethyl)-4-(3-(7-methoxy-2-oxoquinolin-1(2H)-yl)propyl)piperidine-4-carboxylic acid as a white solid. Also, the filtrate was removed under reduced pressure, and the residue thus obtained was purified by reversed-phase silica gel column chromatography [eluent; acetonitrile: water=2:8] to give 31 mg of 1-(2,3-dihydro(1,4)dioxino (2,3-c)pyridin-7-ylmethyl)-4-(3-(7-methoxy-2-oxoquinolin-1(2H)-yl) propyl)piperidine-4-carboxylic acid.

$^1$H-NMR (DMSO-$d_6$) δ:
1.40-1.66 (6H, m), 1.96-2.06 (2H, m), 2.27-2.40 (2H, m), 2.77-2.89 (2H, m), 3.62-3.74 (2H, m), 3.89 (3H, s), 4.15-4.25 (2H, m), 4.26-4.40 (4H, m), 6.44 (1H, d, J=9.6 Hz), 6.90-6.94 (2H, m), 6.98 (1H, s), 7.67 (1H, d, J=8.8 Hz), 7.85 (1H, d, J=9.6 Hz), 8.05 (1H, s)

Example 44

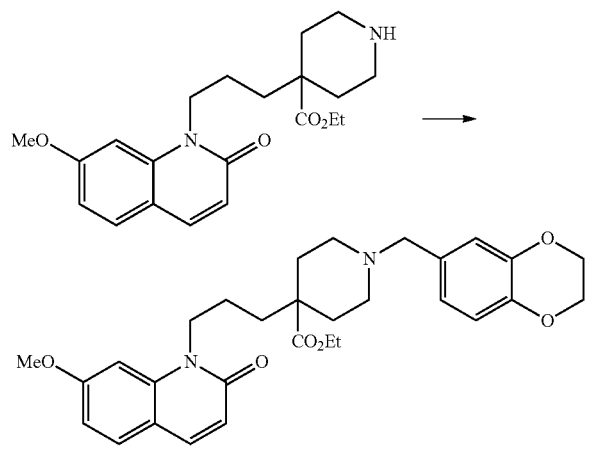

To 2 mL of dichloromethane solution containing 80 mg of ethyl 4-(3-(7-methoxy-2-oxoquinolin-1(2H)-yl)propyl)piperidine-4-carboxylate, 40 mg of 2,3-dihydrobenzo(b)(1,4)dioxin-6-carbaldehyde and 14 µL of acetic acid were added at room temperature, 78 mg of sodium triacetoxyborohydride was added under ice-cooling, and stirred at room temperature for 1 hour. To the reaction mixture, water, chloroform and aqueous saturated sodium hydrogen carbonate solution were added. The organic layer was separated, washed with aqueous saturated sodium chloride solution, dried over anhydrous magnesium sulfate, and the solvent was removed under reduced pressure. The residue thus obtained was purified by silica gel column chromatography [eluent; chloroform:methanol=15:1], to give 0.10 g of ethyl 1-(2,3-dihydro-1,4-benzodioxin-6-ylmethyl)-4-(3-(7-methoxy-2-oxoquinolin-1(2H)-yl)propyl)piperidine-4-carboxylate as a yellow oil.

$^1$H-NMR (CDCl$_3$) δ:
1.18 (3H, t, J=7.1 Hz), 1.45-1.55 (2H, m), 1.62-1.70 (4H, m), 1.98-2.16 (4H, m), 2.64-2.73 (2H, m), 3.34 (2H, s), 3.90 (3H, s), 4.10 (2H, q, J=7.1 Hz), 4.17-4.22 (2H, m), 4.24 (4H, s), 6.51 (1H, d, J=9.4 Hz), 6.71 (1H, d, J=2.2 Hz), 6.72-6.86 (4H, m), 7.45 (1H, d, J=8.6 Hz), 7.57 (1H, d, J=9.4 Hz)

Example 45

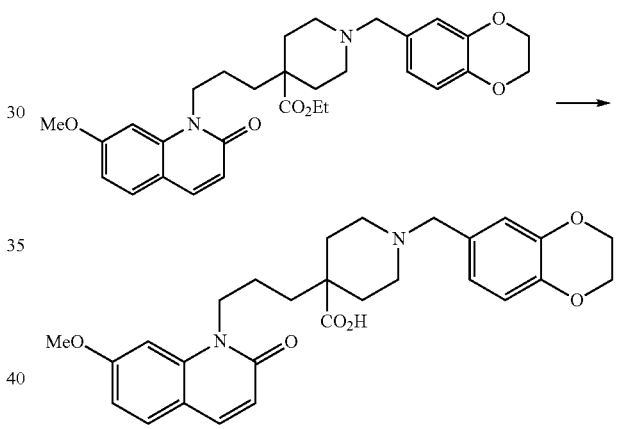

To 1 mL of an ethanol solution containing 0.10 g of ethyl 1-(2,3-dihydro-1,4-benzodioxin-6-ylmethyl)-4-(3-(7-methoxy-2-oxoquinolin-1(2H)-yl)propyl)piperidine-4-carboxylate, 0.15 mL of 20% aqueous sodium hydroxide solution was added and refluxed with heating for 2 hours. Then, more 0.10 mL of 20% aqueous sodium hydroxide solution was added and refluxed with heating for 5 hours. After left to stand at room temperature overnight, the solvent was removed under reduced pressure, water was added, and adjusted to pH 6.7 with 6.0 mol/L hydrochloric acid. The solvent was removed under reduced pressure, and the residue thus obtained was purified by reversed-phase silica gel column chromatography [eluent; acetonitrile: water=3: 7] to give 21 mg of 1-(2,3-dihydro-1,4-benzodioxin-6-ylmethyl)-4-(3-(7-methoxy-2-oxoquinolin-1(2H)-yl)propyl)piperidine-4-carboxylic acid as a white solid.

$^1$H-NMR (DMSO-$d_6$) δ:
1.32-1.44 (2H, m), 1.48-1.60 (4H, m), 1.94-2.06 (2H, m), 2.18-2.36 (2H, m), 2.70-2.85 (2H, m), 3.46-3.62 (2H, m), 3.89 (3H, s), 4.14-4.26 (6H, m), 6.44 (1H, d, J=9.2 Hz), 6.77-6.96 (5H, m), 7.66 (1H, d, J=8.3 Hz), 7.84 (1H, d, J=9.2 Hz)

Example 46

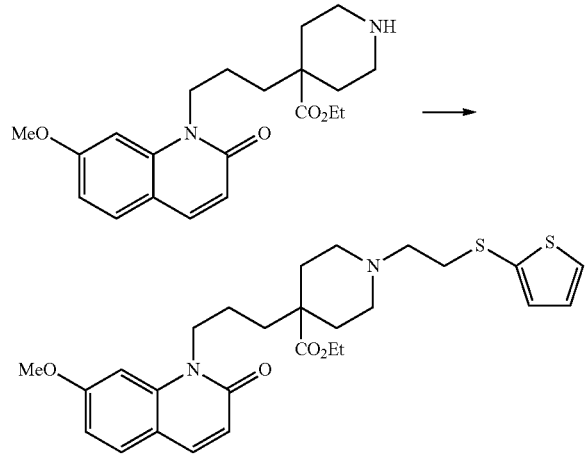

To 1.25 mL of an N,N-dimethylformamide solution containing 70 mg of ethyl 4-(3-(7-methoxy-2-oxoquinolin-1(2H)-yl)propyl)piperidine-4-carboxylate, 57 mg of potassium carbonate and 0.25 mL of N,N-dimethylformamide containing 47 mg of 2-(2-bromoethylthio)thiophene were added at room temperature, and stirred at 60° C. for 3 hours. To the reaction mixture, ethyl acetate and water were added. The organic layer was separated, washed sequentially with water and aqueous saturated sodium chloride solution, dried over anhydrous magnesium sulfate, and the solvent was removed under reduced pressure. The residue thus obtained was purified by silica gel column chromatography [eluent; chloroform: methanol=10:1], to give 91 mg of ethyl 4-(3-(7-methoxy-2-oxoquinolin-1(2H)-yl)propyl)-1-(2-(2-thienylthio)ethyl)piperidine-4-carboxylate as a yellow oil.

$^1$H-NMR (CDCl$_3$) δ:
1.18 (3H, t, J=7.1 Hz), 1.41-1.52 (2H, m), 1.59-1.74 (4H, m), 2.00-2.16 (4H, m), 2.52-2.60 (2H, m), 2.62-2.72 (2H, m), 2.85-2.90 (2H, m), 3.90 (3H, s), 4.09 (2H, q, J=7.1 Hz), 4.14-4.24 (2H, m), 6.51 (1H, d, J=9.4 Hz), 6.71 (1H, d, J=2.0 Hz), 6.80 (1H, dd, J=8.6, 2.0 Hz), 6.95 (1H, dd, J=5.4, 3.6 Hz), 7.10 (1H, dd, J=3.6, 0.5 Hz), 7.32 (1H, dd, J=5.4, 0.5 Hz), 7.46 (1H, d, J=8.6 Hz), 7.57 (1H, d, J=9.4 Hz)

Example 47

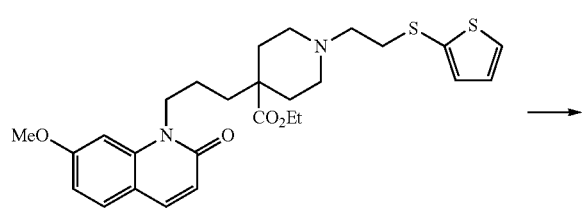

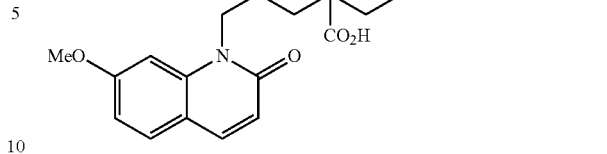

To 1 mL of an ethanol solution containing 90 mg of ethyl 4-(3-(7-methoxy-2-oxoquinolin-1(2H)-yl)propyl)-1-(2-(2-thienylthio)ethyl)piperidine-4-carboxylate, 0.3 mL of 20% aqueous sodium hydroxide solution was added and refluxed with heating for 1.5 hours. Then, more 0.3 mL of 20% aqueous sodium hydroxide solution was added and refluxed with heating for 3 hours. After the reaction mixture was cooled to room temperature, water was added, and the solvent was removed under reduced pressure. Water was added, and adjusted to pH 6.7 with 6.0 mol/L hydrochloric acid. The resulting solid was filtered to afford 57 mg of 4-(3-(7-methoxy-2-oxoquinolin-1(2H)-yl)propyl)-1-(2-(2-thienylthio)ethyl)piperidine-4-carboxylic acid as a white solid.

$^1$H-NMR (CDCl$_3$) δ:
1.48-1.58 (2H, m), 1.65-1.76 (4H, m), 2.13-2.21 (2H, m), 2.24-2.37 (2H, m), 2.65-2.74 (2H, m), 2.78-2.88 (2H, m), 2.88-2.97 (2H, m), 3.92 (3H, s), 4.17-4.25 (2H, m), 6.51 (1H, d, J=9.3 Hz), 6.80 (1H, d, J=1.7 Hz), 6.87 (1H, dd, J=8.5, 1.7 Hz), 6.96-6.99 (1H, m), 7.14 (1H, d, J=3.6 Hz), 7.32-7.42 (1H, m), 7.51 (1H, d, J=8.5 Hz), 7.67 (1H, d, J=9.3 Hz)

Example 48

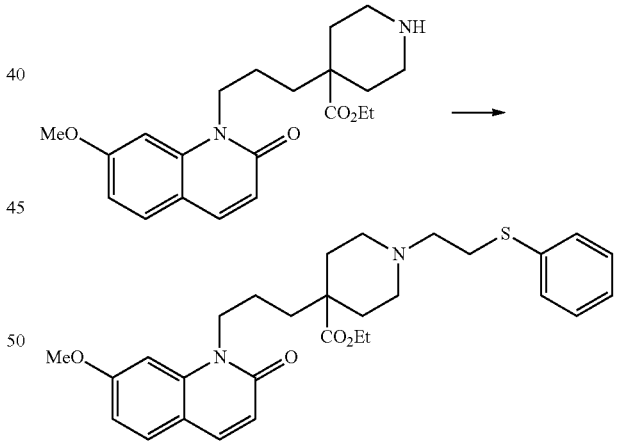

To 2.5 mL of an N,N-dimethylformamide solution containing 0.10 g of ethyl 4-(3-(7-methoxy-2-oxoquinolin-1(2H)-yl)propyl)piperidine-4-carboxylate, 74 mg of potassium carbonate and 64 mg of 1-phenylthio-2-bromoethane were added at room temperature, and stirred at 55-60° C. for 4.5 hours. After the reaction mixture was cooled to room temperature, ethyl acetate and water were added. The organic layer was separated, was washed with aqueous saturated sodium chloride solution, dried over anhydrous magnesium sulfate, and the solvent was removed under reduced pressure. The residue thus obtained was purified by silica gel column chromatography [eluent; chloroform:methanol=20:1], to give 93 mg of ethyl 4-(3-(7-methoxy-2-oxoquinolin-1(2H)-yl)propyl)-1-(2-(phenylthio)ethyl)piperidine-4-carboxylate as a yellow oil.

¹H-NMR (CDCl₃) δ:
1.18 (3H, t, J=7.1 Hz), 1.42-1.54 (2H, m), 1.58-1.72 (4H, m), 2.02-2.19 (4H, m), 2.53-2.62 (2H, m), 2.66-2.77 (2H, m), 2.98-3.06 (2H, m), 3.91 (3H, s), 4.09 (2H, q, J=7.1 Hz), 4.14-4.25 (2H, m), 6.52 (1H, d, J=9.4 Hz), 6.71 (1H, d, J=2.2 Hz), 6.81 (1H, dd, J=8.6, 2.2 Hz), 7.13-7.19 (1H, m), 7.22-7.35 (4H, m), 7.46 (1H, d, J=8.6 Hz), 7.58 (1H, d, J=9.4 Hz)

Example 49

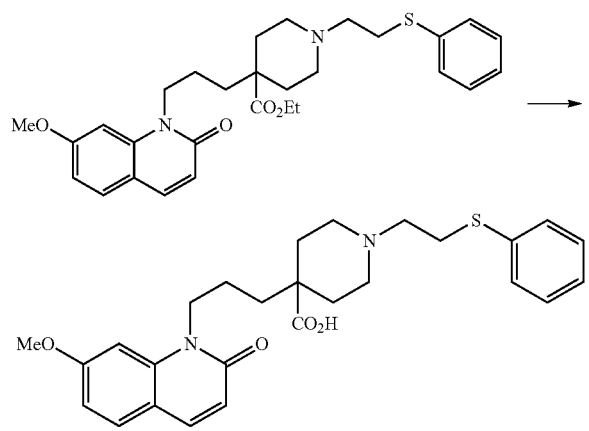

To 1.5 mL of an ethanol solution containing 90 mg of ethyl 4-(3-(7-methoxy-2-oxoquinolin-1(2H)-yl)propyl)-1-(2-(phenylthio)ethyl)piperidine-4-carboxylate, 0.5 mL of 20% aqueous sodium hydroxide solution was added and refluxed with heating for 3 hours and 10 min. After the reaction mixture was cooled to room temperature, the solvent was removed under reduced pressure, water was added, and adjusted to pH 6.5 with 6.0 mol/L hydrochloric acid. The resulting solid was filtered to give 25 mg of 4-(3-(7-methoxy-2-oxoquinolin-1(2H)-yl)propyl)-1-(2-(phenylthio)ethyl)piperidine-4-carboxylic acid as a pale yellow solid.

¹H-NMR (DMSO-d₆) δ:
1.30-1.70 (6H, m), 1.86-2.16 (4H, m), 2.40-2.75 (4H, m), 3.00-3.13 (2H, m), 3.89 (3H, s), 4.10-4.26 (2H, m), 6.35-6.50 (1H, m), 6.84-6.96 (2H, m), 7.12-7.22 (1H, m), 7.25-7.40 (4H, m), 7.60-7.72 (1H, m), 7.78-7.90 (1H, m)

Example 50

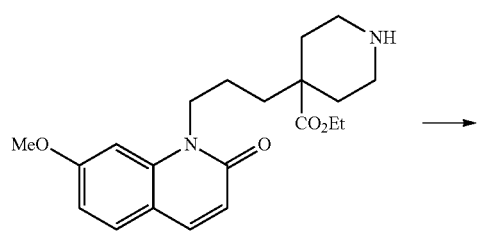

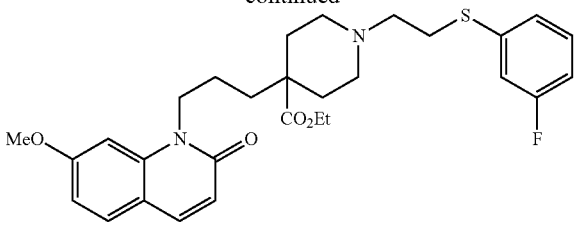

To 2.5 mL of an N,N-dimethylformamide solution containing 0.10 g of ethyl 4-(3-(7-methoxy-2-oxoquinolin-1(2H)-yl)propyl)piperidine-4-carboxylate, 74 mg of potassium carbonate and 69 mg of 1-(3-fluorophenyl)thio-2-bromoethane were added at room temperature, and stirred at 60° C. for 4 hours. After the reaction mixture was cooled to room temperature, ethyl acetate and water were added. The organic layer was separated, washed with aqueous saturated sodium chloride solution, dried over anhydrous magnesium sulfate, and the solvent was removed under reduced pressure. The residue thus obtained was purified by silica gel column chromatography [eluent; chloroform:methanol=10:1], to give 95 mg of ethyl 1-(2-((3-fluorophenyl)thio)ethyl)-4-(3-(7-methoxy-2-oxoquinolin-1(2H)-yl)propyl)piperidine-4-carboxylate as a yellow oil.

¹H-NMR (CDCl₃) δ:
1.19 (3H, t, J=7.1 Hz), 1.42-1.54 (2H, m), 1.64-1.70 (4H, m), 2.02-2.20 (4H, m), 2.54-2.62 (2H, m), 2.68-2.76 (2H, m), 3.00-3.06 (2H, m), 3.91 (3H, s), 4.10 (2H, q, J=7.1 Hz), 4.16-4.24 (2H, m), 6.52 (1H, d, J=9.3 Hz), 6.72 (1H, d, J=2.1 Hz), 6.81 (1H, dd, J=8.8, 2.1 Hz), 6.85 (1H, ddd, J=8.4, 2.4, 0.9 Hz), 7.01 (1H, dt, J=9.2, 2.1 Hz), 7.04-7.09 (1H, m), 7.22 (1H, td, J=8.2, 6.0 Hz), 7.46 (1H, d, J=8.8 Hz), 7.58 (1H, d, J=9.3 Hz)

Example 51

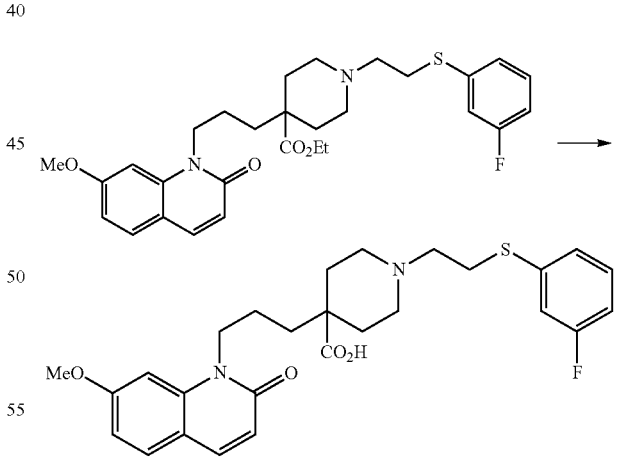

To 1.5 mL of an ethanol solution containing 90 mg of ethyl 1-(2-((3-fluorophenyl)thio)ethyl)-4-(3-(7-methoxy-2-oxoquinolin-1(2H)-yl)propyl)piperidine-4-carboxylate, 0.50 mL of 20% aqueous sodium hydroxide solution was added and refluxed with heating for 3.5 hours. After the reaction mixture was cooled to room temperature, the solvent was removed under reduced pressure, water was added, and adjusted to pH 6.5 with 6.0 mol/L hydrochloric acid. The resulting solid was filtered to give 64 mg of 1-(2-((3-fluorophenyl)thio)ethyl)-4-(3-(7-methoxy-2-oxoquinolin-1(2H)-yl)propyl)piperidine-4-carboxylic acid as a pale yellow solid.

$^1$H-NMR (DMSO-$d_6$) δ:

1.26-1.38 (2H, m), 1.46-1.62 (4H, m), 1.88-2.06 (4H, m), 2.42-2.57 (2H, m), 2.61-2.72 (2H, m), 3.10 (2H, t, J=7.2 Hz), 3.89 (3H, s), 4.12-4.22 (2H, m), 6.40 (1H, d, J=9.5 Hz), 6.89-6.92 (2H, m), 6.92-7.01 (1H, m), 7.09-7.20 (2H, m), 7.28-7.38 (1H, m), 7.64 (1H, d, J=9.0 Hz), 7.81 (1H, d, J=9.5 Hz)

Example 52

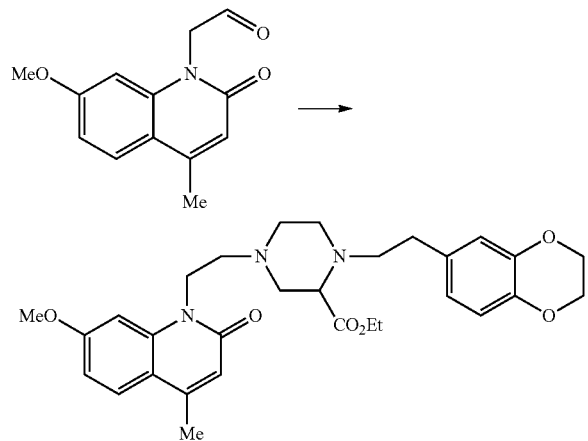

To 2.5 mL of dichloromethane solution containing 0.14 g of ethyl 1-(2-(2,3-dihydro-1,4-benzodioxin-6-yl)ethyl)piperazine-2-carboxylate and 0.10 g of (7-methoxy-4-methyl-2-oxoquinolin-1(2H)-yl)acetaldehyde, 25 µL of acetic acid were added and stirred at room temperature for 50 min. Then, 0.14 g of sodium triacetoxyborohydride was added, and stirred at room temperature for 1 hour. To the reaction mixture, chloroform and water were added, the organic layer was separated, and the aqueous layer was extracted with chloroform. The organic layer and extracts were combined, dried over anhydrous magnesium sulfate, and the solvent was removed under reduced pressure. The residue thus obtained was purified by silica gel column chromatography [eluent; chloroform: acetone=50:1], to give 0.15 g of ethyl 1-(2-(2,3-dihydro-1,4-benzodioxin-6-yl)ethyl)-4-(2-(7-methoxy-4-methyl-2-oxoquinolin-1(2H)-yl)ethyl)piperazine-2-carboxylate as a colorless foam.

$^1$H-NMR (CDCl$_3$) δ:

1.18-1.31 (3H, m), 2.42 (3H, s), 2.48-2.92 (11H, m), 3.10-3.41 (2H, m), 3.92 (3H, s), 4.12-4.26 (2H, m), 4.23 (4H, s), 4.29-4.45 (2H, m), 6.42 (1H, s), 6.65 (1H, d, J=8.2 Hz), 6.69 (1H, s), 6.77 (1H, d, J=8.2 Hz), 6.80-6.91 (1H, m), 6.84 (1H, d, J=8.8 Hz), 7.61 (1H, d, J=8.8 Hz)

Example 53

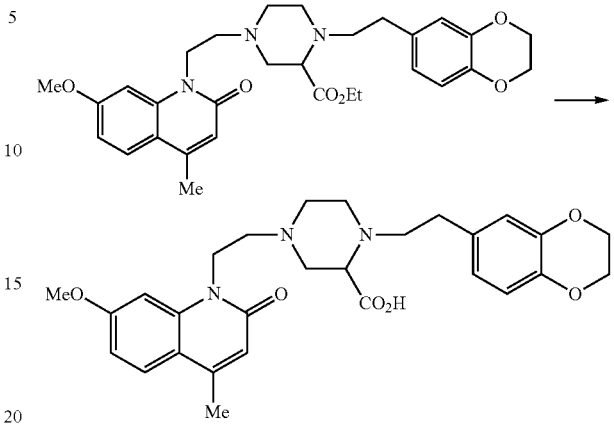

To 3.3 mL of a 90% aqueous methanol solution containing 58 mg of ethyl 1-(2-(2,3-dihydro-1,4-benzodioxin-6-yl)ethyl)-4-(2-(7-methoxy-4-methyl-2-oxoquinolin-1(2H)-yl)ethyl)piperazine-2-carboxylate, 22 mg of sodium hydroxide was added and stirred at room temperature for 30 min. Further, 66 mg of sodium hydroxide and 1.1 mL of a 90% aqueous methanol solution were added and stirred at room temperature for 6 hours. After the solvent was removed under reduced pressure, water was added, and adjusted to pH 1 with 6.0 mol/L hydrochloric acid, thereafter ethanol was added and adjusted to pH 6.5 with aqueous saturated sodium hydrogen carbonate solution and 1.0 mol/L hydrochloric acid. The resulting solid was filtered to give 35 mg of 1-(2-(2,3-dihydro-1,4-benzodioxin-6-yl)ethyl)-4-(2-(7-methoxy-4-methyl-2-oxoquinolin-1(2H)-yl)ethyl)piperazine-2-carboxylic acid as a white solid.

$^1$H-NMR (DMSO-$d_6$, $D_2O$) δ:

2.43 (3H, s), 2.70-3.26 (11H, m), 3.36-3.51 (2H, m), 3.92 (3H, s), 4.21 (4H, s), 4.40-4.53 (2H, m), 6.41 (1H, s), 6.71 (1H, d, J=8.4 Hz), 6.76 (1H, s), 6.81 (1H, d, J=8.4 Hz), 6.98 (1H, s), 7.00 (1H, d, J=9.0 Hz), 7.80 (1H, d, J=9.0 Hz)

Example 54

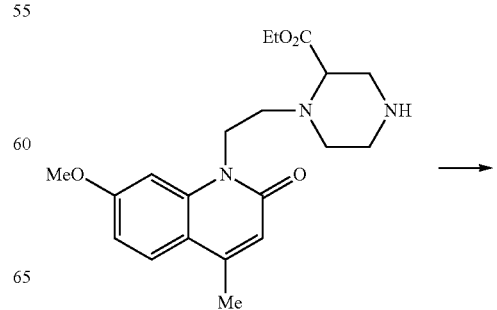

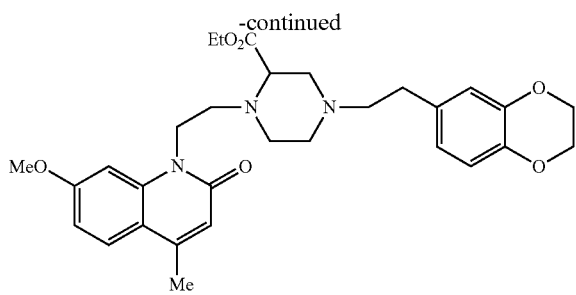

To 2.4 mL of dichloromethane solution containing 89 mg of ethyl 1-(2-(7-methoxy-4-methyl-2-oxoquinolin-1(2H)-yl)ethyl)piperazine-2-carboxylate and 94 mg of (2,3-dihydro-1,4-benzodioxin-6-yl)acetaldehyde, 24 μL of acetic acid was added and stirred at room temperature for 30 min. To the reaction mixture, 76 mg of sodium triacetoxyborohydride was added, and stirred at room temperature for 1 hour. To the reaction mixture, chloroform and water were added, and adjusted to pH 1 with 6 mol/L hydrochloric acid. The organic layer was separated, and adjusted to pH 13 by adding 5 mol/L aqueous sodium hydroxide solution to the aqueous layer, thereafter extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=50:1], to give 87 mg of ethyl 4-(2-(2,3-dihydro-1,4-benzodioxin-6-yl)ethyl)-1-(2-(7-methoxy-4-methyl-2-oxoquinolin-1(2H)-yl)ethyl)piperazine-2-carboxylate as a colorless oil.

$^1$H-NMR (CDCl$_3$) δ:
1.25 (3H, t, J=7.3 Hz), 2.37-2.82 (10H, m), 2.41 (3H, s), 2.89-3.00 (1H, m), 3.23-3.46 (2H, m), 3.96 (3H, s), 4.12-4.29 (1H, m), 4.23 (4H, s), 4.57-4.70 (1H, m), 6.41 (1H, s), 6.65 (1H, d, J=8.3 Hz), 6.70 (1H, s), 6.77 (1H, d, J=8.3 Hz), 6.79-6.85 (1H, m), 6.95-7.00 (1H, m), 7.59 (1H, dd, J=8.8, 1.7 Hz)

Example 55

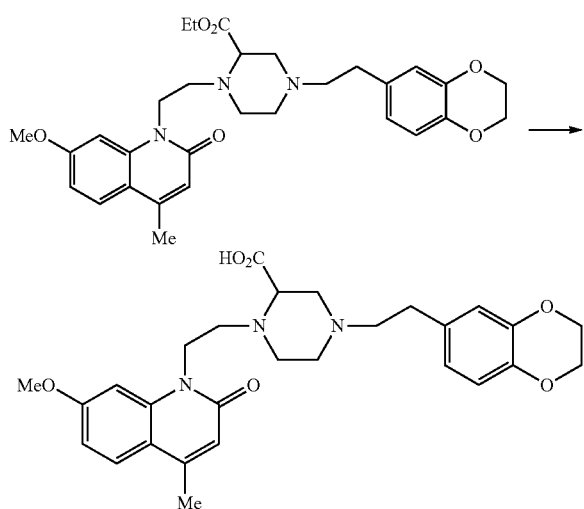

To 3.2 mL of a 90% aqueous methanol solution containing 85 mg of ethyl 4-(2-(2,3-dihydro-1,4-benzodioxin-6-yl)ethyl)-1-(2-(7-methoxy-4-methyl-2-oxoquinolin-1(2H)-yl)ethyl)piperazine-2-carboxylate, 95 mg of sodium hydroxide was added and stirred at 40-50° C. for 2 hours. The reaction mixture was adjusted to pH 6.7 with 6.0 mol/L hydrochloric acid, aqueous saturated sodium chloride solution and aqueous saturated ammonium chloride solution. The resulting solid was filtered to 60 mg of 4-(2-(2,3-dihydro-1,4-benzodioxin-6-yl)ethyl)-1-(2-(7-methoxy-4-methyl-2-oxoquinolin-1(2H)-yl)ethyl)piperazine-2-carboxylic acid as a white solid.

$^1$H-NMR (DMSO-d$_6$, D$_2$O) δ:
2.41 (3H, s), 2.42-2.97 (11H, m), 3.07-3.18 (1H, m), 3.31-3.40 (1H, m), 3.93 (3H, s), 4.20 (4H, s), 4.30-4.39 (1H, m), 4.42-4.49 (1H, m), 6.37 (1H, s), 6.67-6.80 (3H, m), 6.93 (1H, d, J=8.9, 2.2 Hz), 7.08 (1H, d, J=2.2 Hz), 7.74 (1H, d, J=8.9 Hz)

Example 56

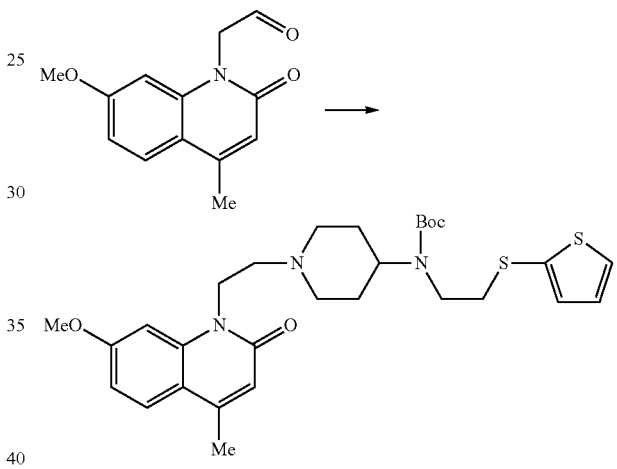

To 2.2 mL of dichloromethane solution containing 0.10 g of (7-methoxy-4-methyl-2-oxoquinolin-1(2H)-yl)acetaldehyde, 0.15 g of tert-butyl (piperidin-4-yl)(2-(2-thienylthio)ethyl)carbamate and 22 μL of acetic acid were added and stirred at room temperature for 10 min. Then, 0.14 g of sodium triacetoxyborohydride was added, and stirred at room temperature for 1.5 hours. To the reaction mixture, water and chloroform were added. The organic layer was separated, and the aqueous layer was extracted with chloroform. The organic layer and extracts were combined, washed with a mixed solvent of aqueous saturated sodium chloride solution and aqueous saturated sodium hydrogen carbonate solution, dried over anhydrous magnesium sulfate, and the solvent was removed under reduced pressure. The residue thus obtained was purified by silica gel column chromatography [eluent; chloroform], to give 0.15 g of tert-butyl 1-(2-(7-methoxy-4-methyl-2-oxoquinolin-1(2H)-yl)ethyl)piperidin-4-yl)(2-(2-thienylthio)ethyl)carbamate as a colorless oil.

$^1$H-NMR (CDCl$_3$) δ:
1.37 (9H, s), 1.57-1.67 (4H, m), 2.12-2.25 (2H, m), 2.42 (3H, s), 2.60-2.65 (2H, m), 2.77-2.90 (2H, m), 3.04-3.11 (2H, m), 3.26-3.36 (2H, m), 3.90-3.98 (1H, m), 3.92 (3H, s), 4.33-4.39 (2H, m), 6.43 (1H, s), 6.84 (1H, dd, J=8.8, 2.3 Hz), 6.89 (1H, d, J=2.3 Hz), 6.97 (1H, dd, J=5.2, 3.6 Hz), 7.15 (1H, dd, J=3.6, 1.3 Hz), 7.32-7.35 (1H, m), 7.62 (1H, d, J=8.8 Hz)

Example 57

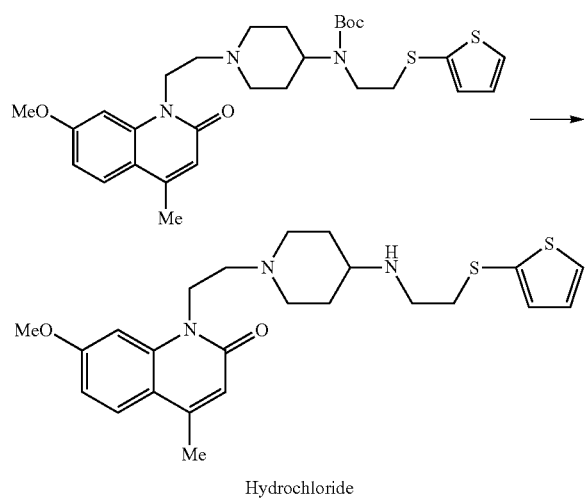

Hydrochloride

To 2.0 mL of a methanol solution containing 0.15 g of tert-butyl 1-(2-(7-methoxy-4-methyl-2-oxoquinolin-1(2H)-yl)ethyl)piperidin-4-yl)(2-(2-thienylthio)ethyl)carbamate, 1.0 mL of 10 mol/L hydrogen chloride/ethanol solution was added, stirred for 2 hours and the solvent was removed under reduced pressure, thereafter ethyl acetate was added to the residue obtained, and the resulting solid was filtered to afford 0.11 g of 7-methoxy-4-methyl-1-(2-(4-((2-(2-thienylthio)ethyl)amino)piperidin-1-yl)ethyl)quinolin-2(1H)one hydrochloride as a white solid.

$^1$H-NMR (DMSO-$d_6$) δ:
1.90-2.04 (2H, m), 2.21-2.35 (2H, m), 2.42 (3H, s), 3.00-3.50 (9H, m), 3.76-3.86 (2H, m), 3.96 (3H, s), 4.60-4.71 (2H, m), 6.40 (1H, s), 6.97 (1H, d, J=8.9 Hz), 7.10-7.16 (2H, m), 7.34 (1H, d, J=3.6 Hz), 7.72 (1H, d, J=5.1 Hz), 7.76 (1H, d, J=8.9 Hz), 9.33 (2H, s), 10.75 (1H, s)

Example 58

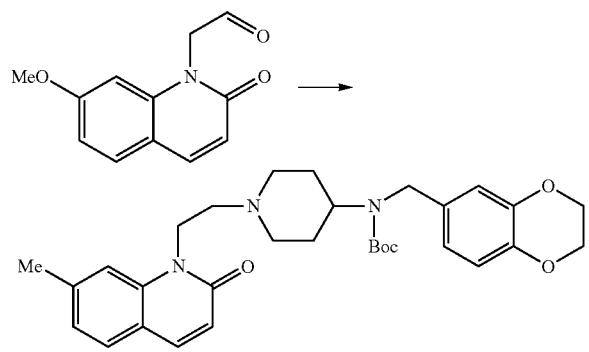

To 8.0 mL of dichloromethane solution containing 0.16 g of (7-methyl-2-oxoquinolin-1(2H)-yl)acetaldehyde, 0.28 g of tert-butyl (2,3-dihydro-1,4-benzodioxin-6-ylmethyl)(piperidin-4-yl)carbamate and 80 μL of acetic acid were added, stirred at room temperature for 15 min, then, 0.25 g of sodium triacetoxyborohydride was added, and stirred at room temperature for 1 hour. To the reaction mixture, aqueous saturated sodium hydrogen carbonate solution, water and chloroform were added. The organic layer was separated, and the aqueous layer was extracted with chloroform. The organic layer and extracts were combined, dried over anhydrous magnesium sulfate, and the solvent was removed under reduced pressure. The residue thus obtained was purified by silica gel column chromatography [eluent; hexane:ethyl acetate=1:3], to give 0.26 g of tert-butyl (2,3-dihydro-1,4-benzodioxin-6-ylmethyl)(1-(2-(7-methyl-2-oxoquinolin-1(2H)-yl)ethyl)piperidin-4-yl)carbamate as a brown oil.

$^1$H-NMR (CDCl$_3$) δ:
1.42 (9H, s), 1.62-1.73 (4H, m), 2.08-2.24 (2H, m), 2.48 (3H, s), 2.58-2.65 (2H, m), 3.02-3.11 (2H, m), 4.00-4.15 (1H, m), 4.20-4.43 (4H, m), 4.24 (4H, s), 6.60 (1H, d, J=9.5 Hz), 6.66-6.72 (1H, m), 6.72-6.75 (1H, m), 6.78 (1H, d, J=8.3 Hz), 7.03 (1H, d, J=8.3 Hz), 7.19 (1H, s), 7.43 (1H, d, J=7.8 Hz), 7.61 (1H, d, J=9.5 Hz)

Example 59

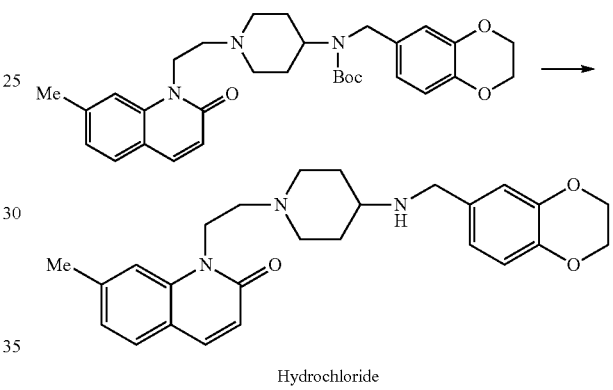

Hydrochloride

To 2.0 mL of a methanol solution containing 0.25 g of tert-butyl (2,3-dihydro-1,4-benzodioxin-6-ylmethyl)(1-(2-(7-methyl-2-oxoquinolin-1(2H)-yl)ethyl)piperidin-4-yl)carbamate, 2.0 mL of 4 mol/L hydrogen chloride/ethyl acetate solution was added and stirred for 30 min. Ethyl acetate was added, and the resulting solid was filtered to afford 0.18 g of 1-(2-(4-((2,3-dihydro-1,4-benzodioxin-6-ylmethyl)amino)piperidin-1-yl)ethyl)-7-methylquinolin-2(1H)-one hydrochloride as a white solid.

$^1$H-NMR (DMSO-$d_6$, D$_2$O) δ:
1.87-2.02 (2H, m), 2.34-2.46 (2H, m), 2.52 (3H, s), 3.06-3.29 (2H, m), 3.38-3.50 (3H, m), 3.78-3.96 (2H, m), 4.10 (2H, s), 4.26 (4H, s), 4.62-4.72 (2H, m), 6.65 (1H, d, J=9.4 Hz), 6.94-7.01 (2H, m), 7.06 (1H, d, J=2.0 Hz), 7.24 (1H, d, J=8.2 Hz), 7.45 (1H, s), 7.70 (1H, d, J=8.2 Hz), 8.00 (1H, d, J=9.4 Hz)

Example 60

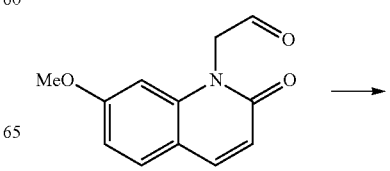

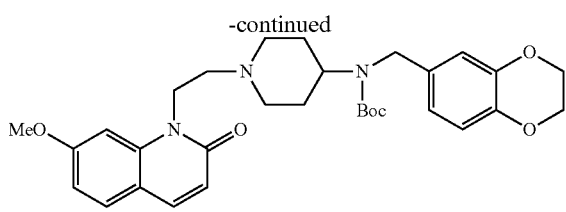

¹H-NMR (DMSO-d₆) δ:

2.00-2.20 (2H, m), 2.30-2.50 (2H, m), 3.00-3.55 (5H, m), 3.70-3.85 (2H, m), 3.98 (3H, s), 4.00-4.15 (2H, m), 4.25 (4H, s), 4.65-4.75 (2H, m), 6.46 (1H, d, J=9.4 Hz), 6.87-6.96 (2H, m), 7.04-7.09 (1H, m), 7.18-7.24 (2H, m), 7.69 (1H, d, J=8.3 Hz), 7.89 (1H, d, J=9.4 Hz)

Example 62

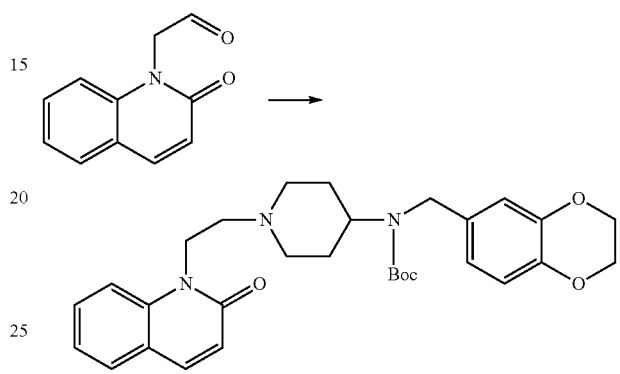

To 5 mL of dichloromethane solution containing 0.14 g of (7-methoxy-2-oxoquinolin-1(2H)-yl)acetaldehyde, 0.22 g of tert-butyl (2,3-dihydro-1,4-benzodioxin-6-ylmethyl)(piperidin-4-yl)carbamate and 36 μL of acetic acid were added, then, 0.20 g of sodium triacetoxyborohydride was added to the reaction mixture, and stirred for 3 hours. To the reaction mixture, water, ethyl acetate and aqueous saturated sodium hydrogen carbonate solution were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=100:1], to give 0.30 g of tert-butyl (2,3-dihydro-1,4-benzodioxin-6-ylmethyl) (1-(2-(7-methoxy-2-oxoquinolin-1(2H)-yl)ethyl)piperidin-4-yl)carbamate as a yellow oil.

¹H-NMR (CDCl₃) δ:

1.42 (9H, s), 1.61-1.76 (4H, m), 2.10-2.25 (2H, m), 2.60-2.66 (2H, m), 3.02-3.09 (2H, m), 3.89 (3H, s), 3.98-4.15 (1H, m), 4.24 (4H, s), 4.27-4.33 (2H, m), 4.36 (2H, t, J=7.6 Hz), 6.51 (1H, d, J=9.4 Hz), 6.66-6.72 (1H, m), 6.74 (1H, d, J=2.0 Hz), 6.78 (1H, d, J=8.3 Hz), 6.81 (1H, dd, J=8.6, 2.3 Hz), 6.85-6.90 (1H, m), 7.45 (1H, d, J=8.8 Hz), 7.58 (1H, d, J=9.4 Hz)

Example 61

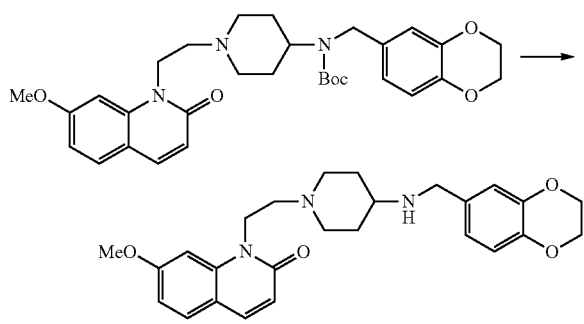

Hydrochloride 0.29 g of tert-butyl (2,3-dihydro-1,4-benzodioxin-6-ylmethyl)(1-(2-(7-methoxy-2-oxoquinolin-1(2H)-yl)ethyl)piperidin-4-yl)carbamate was added to 10 mL of 4 mol/L hydrogen chloride/ethyl acetate solution, and stirred at room temperature for 22 hours. The solvent was removed under reduced pressure, 2-propanol was added to the residue obtained and the resulting solid was filtered to afford 0.20 g of 1-(2-(4-(2,3-dihydro-1,4-benzodioxin-6-ylmethyl)amino) piperidin-1-yl)ethyl)-7-methoxyquinolin-2(1H)one hydrochloride as a pale yellowish white solid.

To 5 mL of dichloromethane solution containing 0.15 g of (2-oxoquinolin-1(2H)-yl)acetaldehyde, 0.27 g of tert-butyl (2,3-dihydro-1,4-benzodioxin-6-ylmethyl)(piperidin-4-yl) carbamate, 45 μL of acetic acid and 0.25 g of sodium triacetoxyborohydride were added and stirred for 4 hours. To the reaction mixture, water and ethyl acetate were added, neutralized with aqueous saturated sodium hydrogen carbonate solution, thereafter the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=100:1], to give 0.13 g of tert-butyl (2,3-dihydro-1,4-benzodioxin-6-ylmethyl) (1-(2-(2-oxoquinolin-1(2H)-yl)ethyl)piperidin-4-yl)carbamate as a yellow oil.

¹H-NMR (CDCl₃) δ:

1.42 (9H, s), 1.60-1.75 (4H, m), 2.10-2.25 (2H, m), 2.62 (2H, t, J=7.8 Hz), 3.02-3.09 (2H, m), 3.95-4.20 (1H, m), 4.20-4.38 (2H, m), 4.24 (4H, s), 4.40 (2H, t, J=7.7 Hz), 6.67 (1H, d, J=9.4 Hz), 6.67-6.71 (1H, m), 6.75 (1H, d, J=2.0 Hz), 6.78 (1H, d, J=8.0 Hz), 7.19-7.24 (1H, m), 7.40 (1H, d, J=8.8 Hz), 7.52-7.57 (2H, m), 7.66 (1H, d, J=9.4 Hz)

Example 63

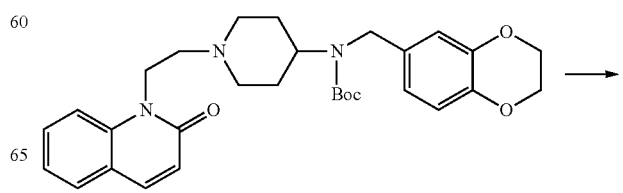

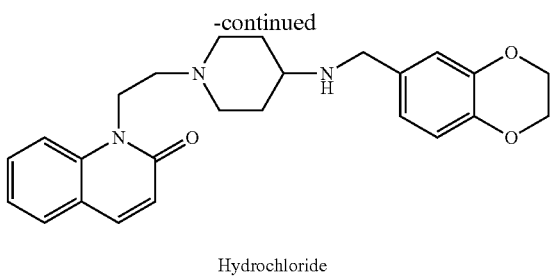

Hydrochloride

To 0.13 g of tert-butyl (2,3-dihydro-1,4-benzodioxin-6-ylmethyl)(1-(2-(2-oxoquinolin-1(2H)-yl)ethyl)piperidin-4-yl)carbamate, 10 mL of 4 mol/L hydrogen chloride/ethyl acetate solution was added, and left to stand at room temperature for 3 days. The solvent was removed under reduced pressure, 2-propanol was added to the residue obtained and the solvent was removed under reduced pressure. Ethyl acetate was added to the residue thus obtained and the resulting solid was filtered to afford 0.10 g of 1-(2-(4-(2,3-dihydro-1,4-benzodioxin-6-ylmethyl)amino)piperidin-1-yl)ethyl)-quinolin-2(1H)one hydrochloride as a yellow solid.

$^1$H-NMR (D$_2$O) δ:

1.98-2.12 (2H, m), 2.48-2.57 (2H, m), 3.20-3.32 (2H, m), 3.57-3.68 (3H, m), 3.90-4.10 (2H, m), 4.20-4.25 (2H, m), 4.34 (4H, s), 4.70-4.90 (2H, m), 6.77 (1H, d, J=9.4 Hz), 6.80-7.06 (3H, m), 7.46 (1H, t, J=7.6 Hz), 7.58 (1H, d, J=8.6 Hz), 7.77 (1H, t, J=7.9 Hz), 7.82 (1H, d, J=7.8 Hz), 8.05 (1H, d, J=9.4 Hz)

Example 64

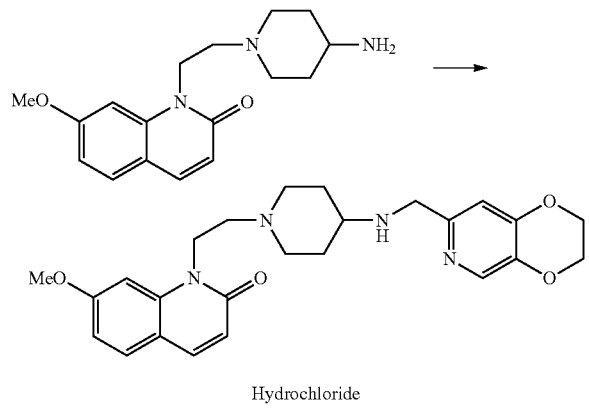

Hydrochloride

To 7 mL of dichloromethane solution containing 0.18 g of 1-(2-(4-aminopiperidin-1-yl)ethyl)-7-methoxyquinolin-2(1H)-one, 99 mg of 2,3-dihydro(1,4)dioxino(2,3-c)pyridine-7-carbaldehyde and 34 μL of acetic acid were added. After stirring for 5 min, 0.19 g of sodium triacetoxyborohydride was added and stirred at room temperature for 1 hour. To the reaction mixture, aqueous saturated sodium hydrogen carbonate solution and chloroform were added, the organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. After the residue thus obtained was dissolved in 6 mol/L hydrochloric acid, the solvent was removed under reduced pressure. To the residue thus obtained, a mixture of ethanol:methanol(5:1) was added and the resulting solid was filtered to give 0.16 g of 1-(2-(4-((2,3-dihydro(1,4)dioxino(2,3-c)pyridin-7-ylmethyl)amino)piperidin-1-yl)ethyl)-7-methoxyquinolin-2(1H)-one as a pale yellow solid.

$^1$H-NMR (D$_2$O) δ:

1.87-2.01 (2H, m), 2.38-2.47 (2H, m), 3.00-3.30 (2H, m), 3.30-3.70 (3H, m), 3.79 (3H, s), 3.75-3.95 (2H, m), 4.30-4.60 (8H, m), 6.39 (1H, d, J=9.4 Hz), 6.68 (1H, s), 6.87 (1H, d, J=8.5 Hz), 7.36 (1H, s), 7.51 (1H, d, J=8.5 Hz), 7.74 (1H, d, J=9.4 Hz), 8.24 (1H, s)

Example 65

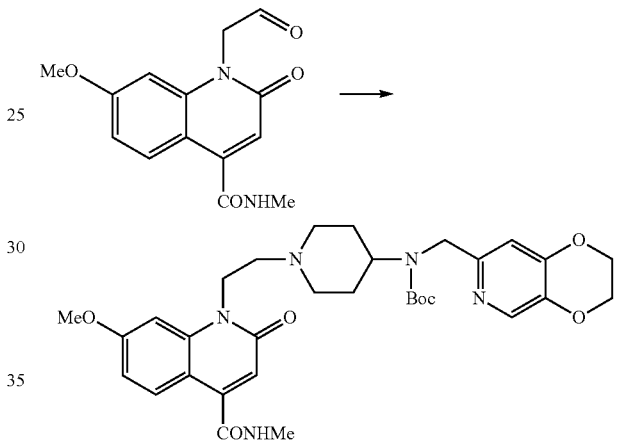

According to a procedure similar to Example 24, tert-butyl (2,3-dihydro(1,4)dioxino(2,3-c)pyridin-7-ylmethyl)(1-(2-(7-methoxy-4-((methylamino)carbonyl)-2-oxo-1,2-dihydroquinolin-1-yl)ethyl)piperidin-4-yl)carbamate was obtained from 7-methoxy-N-methyl-2-oxo-1-(2-oxoethyl)-1,2-dihydroquinoline-4-carboxamide and tert-butyl (2,3-dihydro(1,4)dioxino(2,3-c)pyridin-7-ylmethyl)piperidin-4-yl)carbamate.

$^1$H-NMR (CDCl$_3$) δ:

1.34-1.69 (13H, m), 2.06-2.22 (2H, m), 2.56-2.63 (2H, m), 2.95-3.05 (2H, m), 3.04 (3H, d, J=4.9 Hz), 3.89 (3H, s), 4.03-4.17 (1H, m), 4.25-4.46 (8H, m), 6.25-6.32 (1H, m), 6.56 (1H, s), 6.73 (1H, s), 6.83 (1H, dd, J=9.1, 2.1 Hz), 6.86 (1H, d, J=2.1 Hz), 7.89 (1H, d, J=9.1 Hz), 8.05 (1H, s)

Example 66

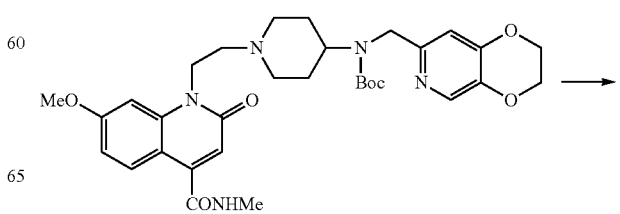

309

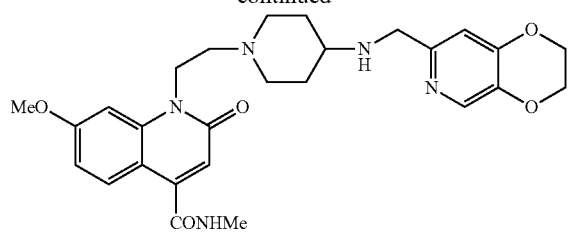

According to a procedure similar to Example 25, 1-(2-(4-((2,3-dihydro(1,4)dioxino(2,3-c)pyridin-7-ylmethyl)amino)piperidin-1-yl)ethyl)-7-methoxy-N-methyl-2-oxo-1,2-dihydroquinoline-4-carboxamide was obtained from tert-butyl (2,3-dihydro(1,4)dioxino(2,3-c)pyridin-7-ylmethyl)(1-(2-(7-methoxy-4-((methylamino)carbonyl)-2-oxo-1,2-dihydroquinolin-1-yl)ethyl)piperidin-4-yl)carbamate.

$^1$H-NMR (CDCl$_3$) δ:

1.40-1.52 (2H, m), 1.85-1.95 (2H, m), 2.10-2.20 (2H, m), 2.47-2.60 (3H, m), 2.93-3.00 (2H, m), 3.05 (3H, d, J=4.9 Hz), 3.79 (2H, s), 3.91 (3H, s), 4.25-4.35 (6H, m), 6.31-6.37 (1H, m), 6.55 (1H, s), 6.82 (1H, s), 6.83 (1H, dd, J=8.9, 2.3 Hz), 6.91 (1H, d, J=2.3 Hz), 7.87 (1H, d, J=8.9 Hz), 8.10 (1H, s)

Example 67

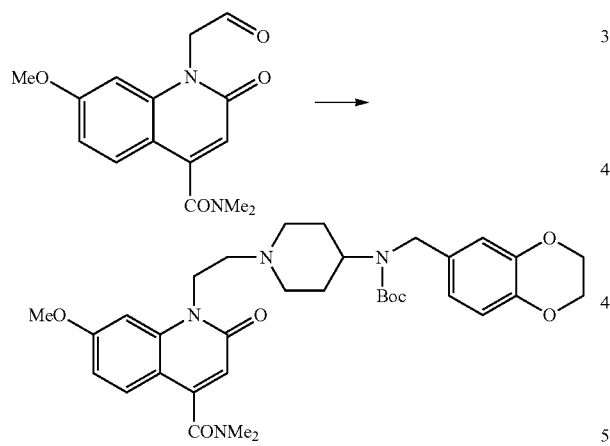

According to a procedure similar to Example 24, tert-butyl (2,3-dihydro(1,4)benzodioxin-6-ylmethyl)(1-(2-(4-((dimethylamino)carbonyl)-7-methoxy-2-oxo-1,2-dihydroquinolin-1-yl)ethyl)piperidin-4-yl)carbamate was obtained from 7-methoxy-N,N-dimethyl-2-oxo-1-(2-oxoethyl)-1,2-dihydroquinoline-4-carboxamide and tert-butyl (2,3-dihydro-1,4-benzodioxin-6-ylmethyl)(piperidin-4-yl)carbamate.

$^1$H-NMR (CDCl$_3$) δ:

1.42 (9H, s), 1.61-1.77 (2H, m), 1.85-1.99 (2H, m), 2.08-2.25 (2H, m), 2.58-2.66 (2H, m), 2.92 (3H, s), 3.00-3.09 (2H, m), 3.18 (3H, s), 3.89 (3H, s), 3.97-4.45 (9H, m), 6.43 (1H, s), 6.66-6.72 (1H, m), 6.72-6.76 (1H, m), 6.78 (1H, d, J=8.3 Hz), 6.82 (1H, dd, J=8.9, 2.4 Hz), 6.90 (1H, d, J=2.4 Hz), 7.38 (1H, d, J=8.9 Hz)

310

Example 68

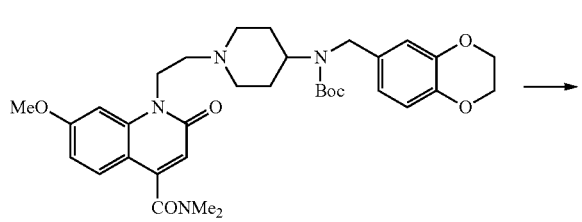

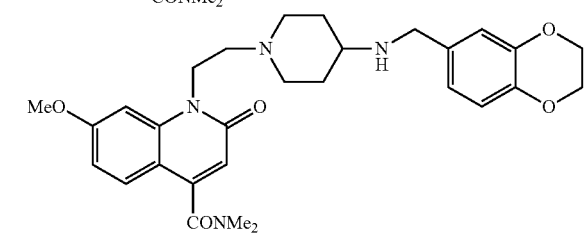

According to a procedure similar to Example 25, 1-(2-(4-((2,3-dihydro(1,4)benzodioxin-6-ylmethyl)amino)piperidin-1-yl)ethyl)-7-methoxy-N,N-dimethyl-2-oxo-1,2-dihydroquinoline-4-carboxamide was obtained from tert-butyl (2,3-dihydro(1,4)benzodioxin-6-ylmethyl)(1-(2-(4-((dimethylamino) carbonyl)-7-methoxy-2-oxo-1,2-dihydroquinolin-1-yl)ethyl)piperidin-4-yl) carbamate.

$^1$H-NMR (CDCl$_3$) δ:

1.39-1.51 (2H, m), 1.87-1.96 (2H, m), 2.15-2.25 (2H, m), 2.48-2.58 (1H, m), 2.61-2.69 (2H, m), 2.92 (3H, s), 2.97-3.05 (2H, m), 3.19 (3H, s), 3.71 (2H, s), 3.91 (3H, s), 4.25 (4H, s), 4.28-4.56 (2H, m), 6.44 (1H, s), 6.76-6.84 (4H, m), 6.96 (1H, d, J=2.2 Hz), 7.39 (1H, d, J=9.0 Hz)

Example 69

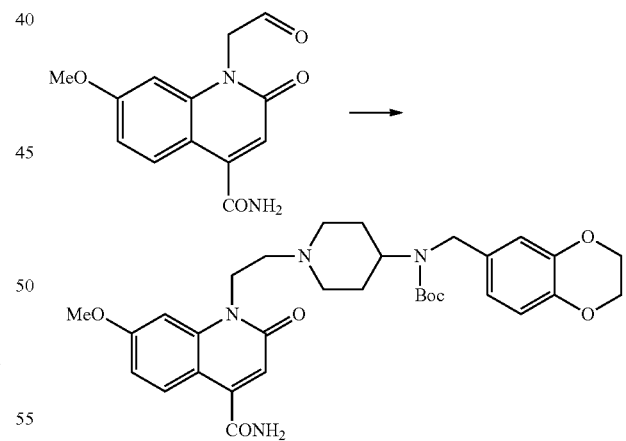

According to a procedure similar to Example 24, tert-butyl (1-(2-(4-(aminocarbonyl)-7-methoxy-2-oxoquinolin-1(2H)-yl)ethyl)piperidin-4-yl)(2,3-dihydro-1,4-benzodioxin-6-ylmethyl)carbamate was obtained from 7-methoxy-2-oxo-1-(2-oxoethyl)-1,2-dihydroquinoline-4-carboxamide and tert-butyl (2,3-dihydro-1,4-benzodioxin-6-ylmethyl)(piperidin-4-yl)carbamate.

$^1$H-NMR (CDCl$_3$) δ:

1.42 (9H, s), 1.58-1.85 (4H, m), 2.03-2.19 (2H, m), 2.47-2.57 (2H, m), 2.94-3.04 (2H, m), 3.89 (3H, s), 3.94-4.11 (1H, m), 4.17-4.36 (8H, m), 6.00 (1H, s), 6.58 (1H, s), 6.63 (1H, s), 6.66-6.71 (1H, m), 6.73 (1H, d, J=1.7 Hz), 6.78 (1H, d, J=8.3 Hz), 6.82-6.88 (2H, m), 7.94 (1H, d, J=8.9 Hz)

Example 70

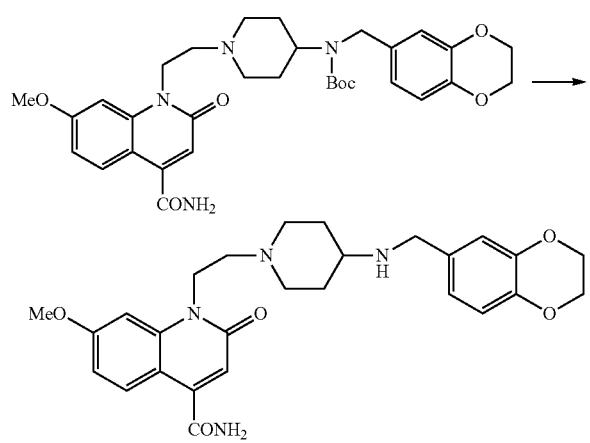

According to a procedure similar to Example 25, 1-(2-(4-((2,3-dihydro-1,4-benzodioxin-6-ylmethyl)amino)piperidin-1-yl)ethyl)-7-methoxy-2-oxo-1,2-dihydroquinoline-4-carboxamide was obtained from tert-butyl (1-(2-(4-(aminocarbonyl)-7-methoxy-2-oxo-1,2-dihydroquinolin-1-yl)ethyl)piperidin-4-yl) (2,3-dihydro-1,4-benzodioxin-6-ylmethyl)carbamate.

$^1$H-NMR (CDCl$_3$) δ:
1.39-1.51 (2H, m), 1.86-1.94 (2H, m), 2.12-2.21 (2H, m), 2.49-2.63 (3H, m), 2.94-3.01 (2H, m), 3.71 (2H, s), 3.91 (3H, s), 4.25 (4H, s), 4.32-4.38 (2H, m), 5.89 (1H, s), 6.37 (1H, s), 6.66 (1H, s), 6.78 (1H, dd, J=8.2, 1.9 Hz), 6.82 (1H, d, J=8.2 Hz), 6.84 (1H, d, J=1.9 Hz), 6.86 (1H, dd, J=9.0, 2.2 Hz), 6.92 (1H, d, J=2.2 Hz), 7.95 (1H, d, J=9.0 Hz)

Example 71

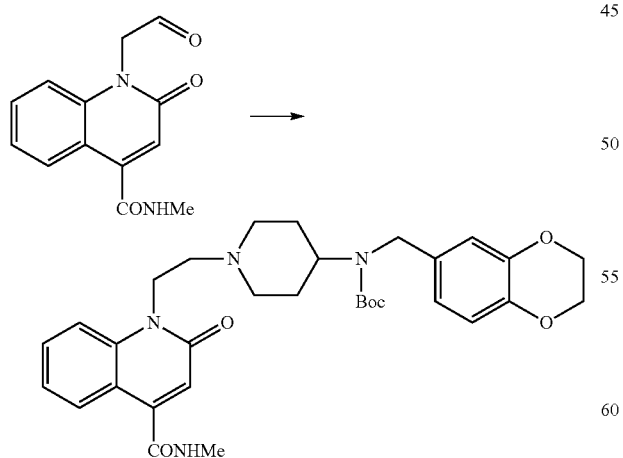

According to a procedure similar to Example 24, tert-butyl (2,3-dihydro-1,4-benzodioxin-6-ylmethyl)(1-(2-(4-((methylamino)carbonyl)-2-oxoquinolin-1(2H)-yl)ethyl)piperidin-4-yl)carbamate was obtained from N-methyl-2-oxo-1-(2-oxoethyl)-1,2-dihydroquinoline-4-carboxamide and tert-butyl (2,3-dihydro-1,4-benzodioxin-6-ylmethyl)piperidin-4-yl)carbamate.

$^1$H-NMR (CDCl$_3$) δ:
1.42 (9H, s), 1.61-1.73 (4H, m), 2.07-2.20 (2H, m), 2.53-2.60 (2H, m), 2.96-3.04 (2H, m), 3.06 (3H, d, J=5.2 Hz), 3.96-4.11 (1H, m), 4.21-4.38 (8H, m), 6.16-6.23 (1H, m), 6.65-6.71 (1H, m), 6.71 (1H, s), 6.74 (1H, d, J=2.0 Hz), 6.78 (1H, d, J=8.3 Hz), 7.22-7.28 (1H, m), 7.36-7.43 (1H, m), 7.55-7.60 (1H, m), 7.93 (1H, dd, J=8.0, 1.5 Hz)

Example 72

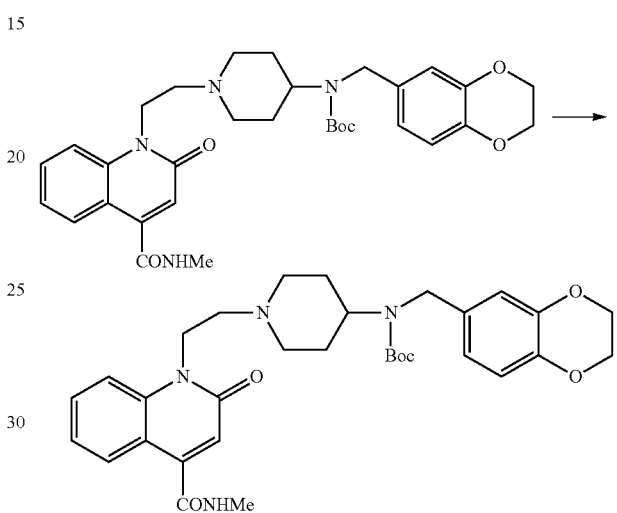

According to a procedure similar to Example 25, 1-(2-(4-((2,3-dihydro-1,4-benzodioxin-6-ylmethyl)amino)piperidin-1-yl)ethyl)-N-methyl-2-oxo-1,2-dihydroquinoline-4-carboxamide was obtained from tert-butyl (2,3-dihydro-1,4-benzodioxin-6-ylmethyl) (1-(2-(4-((methylamino) carbonyl)-2-oxoquinolin-1(2H)-yl)ethyl)piperidin-4-yl) carbamate.

$^1$H-NMR (CDCl$_3$) δ:
1.38-1.50 (2H, m), 1.85-1.93 (2H, m), 2.10-2.19 (2H, m), 2.49-2.60 (3H, m), 2.92-2.99 (2H, m), 3.06 (3H, d, J=4.9 Hz), 3.71 (2H, s), 4.24 (4H, s), 4.32-4.38 (2H, m), 6.42-6.49 (1H, m), 6.71 (1H, s), 6.78 (1H, dd, J=8.3, 1.9 Hz), 6.81 (1H, d, J=8.3 Hz), 6.84 (1H, d, J=1.9 Hz), 7.22-7.28 (1H, m), 7.43 (1H, d, J=8.5 Hz), 7.56-7.61 (1H, m), 7.94 (1H, dd, J=8.2, 1.3 Hz)

Example 73

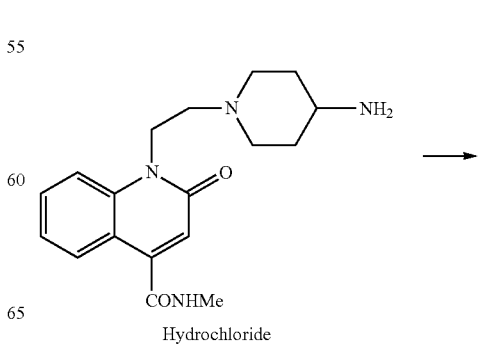

Hydrochloride

-continued

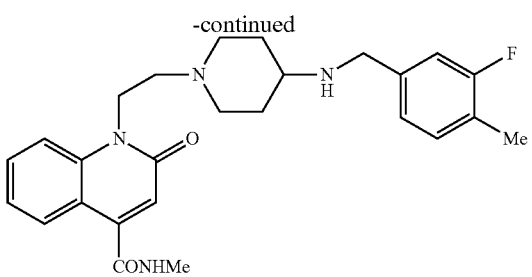

To 3.0 mL of methanol suspension containing 0.12 g of 1-(2-(4-aminopiperidin-1-yl)ethyl)-N-methyl-2-oxo-1,2-dihydroquinoline-4-carboxamide hydrochloride, 38 mg of sodium cyanoborohydride, 37 μL of 3-fluoro-4-methylbenzaldehyde and 69 μL of acetic acid were added at room temperature and stirred at the same temperature for 3 hours. Chloroform and aqueous saturated sodium hydrogen carbonate solution were added to be adjusted to pH 10, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by flash silica gel column chromatography [gradient elution of chloroform:methanol=100:0-70:30], to give 26 mg of 1-(2-(4-((3-fluoro-4-methylbenzyl)amino)piperidin-1-yl)ethyl)-N-methyl-2-oxo-1,2-dihydroquinoline-4-carboxamide as a white solid.

$^1$H-NMR (CDCl$_3$) δ:
1.33-1.67 (2H, m), 1.79-1.94 (2H, m), 2.06-2.26 (2H, m), 2.25 (3H, s), 2.42-2.63 (3H, m), 2.87-3.08 (2H, m), 3.07 (3H, d, J=4.9 Hz), 3.77 (2H, s), 4.27-4.42 (2H, m), 6.15-6.27 (1H, m), 6.72 (1H, s), 6.88-7.01 (2H, m), 7.05-7.14 (1H, m), 7.14-7.28 (1H, m), 7.45 (1H, d, J=8.5 Hz), 7.50-7.62 (1H, m), 7.90-7.95 (1H, m)

Example 74

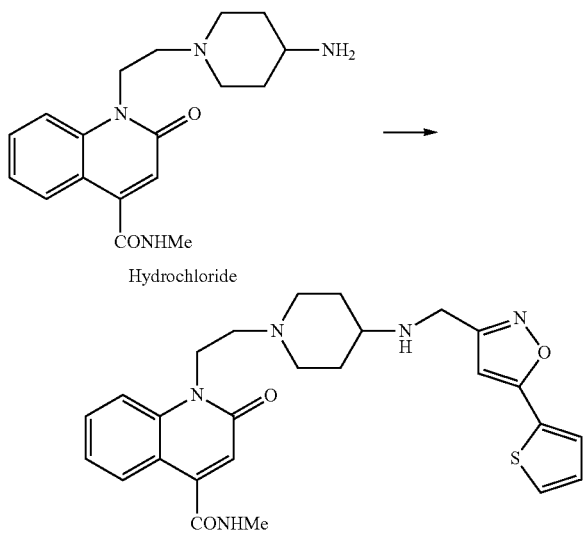

According to a procedure similar to Example 73, N-methyl-2-oxo-1-(2-(4-(((5-(2-thienyl)isooxazol-3-yl)methyl)amino)piperidin-1-yl)ethyl)-1,2-dihydroquinoline-4-carboxamide was obtained from 1-(2-(4-aminopiperidin-1-yl)ethyl)-N-methyl-2-oxo-1,2-dihydroquinoline-4-carboxamide hydrochloride and 5-(2-thienyl)-3-isoxazolcarbaldehyde.

$^1$H-NMR (CDCl$_3$) δ:
1.36-1.48 (2H, m), 1.81-1.98 (2H, m), 2.05-2.15 (2H, m), 2.43-2.59 (3H, m), 2.86-2.95 (2H, m), 3.06 (3H, d, J=4.9 Hz), 3.91 (2H, s), 4.17-4.25 (2H, m), 6.40 (1H, s), 6.67 (1H, s), 6.96-7.03 (1H, m), 7.12 (1H, dd, J=5.1, 3.7 Hz), 7.20-7.29 (1H, m), 7.36 (1H, d, J=8.6 Hz), 7.44 (1H, dd, J=5.1, 1.1 Hz), 7.49 (1H, dd, J=3.7, 1.1 Hz), 7.53-7.60 (1H, m), 7.92 (1H, dd, J=8.0, 1.4 Hz)

Example 75

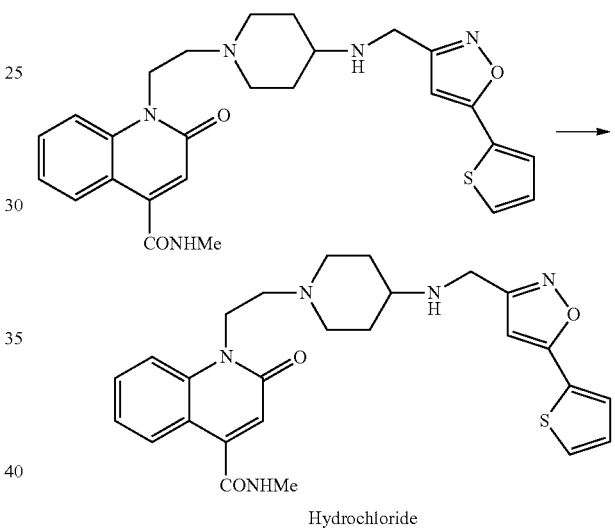

To 2.0 mL of ethyl acetate solution containing 25 mg of N-methyl-2-oxo-1-(2-(4-(((5-(2-thienyl)isooxazol-3-yl)methyl)amino)piperidin-1-yl)ethyl)-1,2-dihydroquinoline-4-carboxamide, 0.5 mL of 4.0 mol/L hydrogen chloride/ethyl acetate solution was added under ice-cooling. The mixture was stirred at the same temperature for 10 min, and the solvent was removed under reduced pressure. To the residue thus obtained, ethyl acetate was added, the resulting solid was filtered to give 23 mg of N-methyl-2-oxo-1-(2-(4-(((5-(2-thienyl)isooxazol-3-yl)methyl)amino)piperidin-1-yl)ethyl)-1,2-dihydroquinoline-4-carboxamide hydrochloride as a light brown solid.

$^1$H-NMR (D$_2$O) δ:
1.95-2.09 (2H, m), 2.47-2.55 (2H, m), 3.00 (3H, s), 3.16-3.28 (2H, m), 3.57-3.68 (3H, m), 3.90-4.00 (2H, m), 4.45 (2H, s), 4.75-4.86 (2H, m), 6.77 (1H, s), 6.85 (1H, s), 7.24 (1H, dd, J=5.0, 3.8 Hz), 7.47 (1H, t, J=7.5 Hz), 7.64 (1H, d, J=8.6 Hz), 7.68-7.72 (2H, m), 7.81 (1H, ddd, J=8.6, 7.5, 1.3 Hz), 7.86 (1H, dd, J=8.2, 1.3 Hz)

Example 76

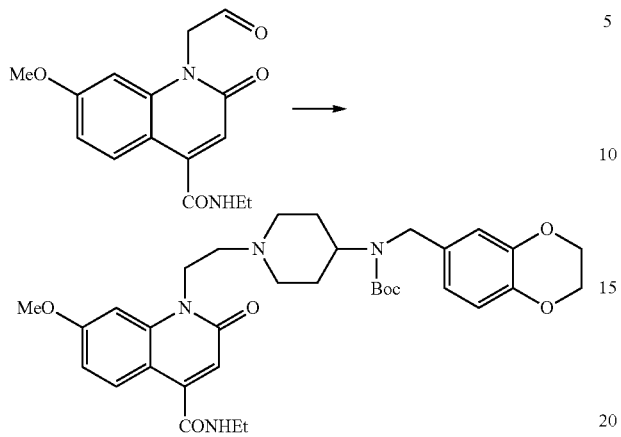

According to a procedure similar to Example 24, tert-butyl (2,3-dihydro-1,4-benzodioxin-6-ylmethyl)(1-(2-(4-((ethylamino)carbonyl)-7-methoxy-2-oxo-1,2-dihydroquinolin-1-yl)ethyl)piperidin-4-yl)carbamate was obtained from N-ethyl-7-methoxy-2-oxo-1-(2-oxoethyl)-1,2-dihydroquinoline-4-carboxamide and tert-butyl (2,3-dihydro-1,4-benzodioxin-6-ylmethyl)piperidin-4-yl)carbamate.

$^1$H-NMR (CDCl$_3$) δ:
1.27 (3H, t, J=7.3 Hz), 1.42 (9H, s), 1.57-1.75 (4H, m), 2.06-2.22 (2H, m), 2.54-2.60 (2H, m), 2.98-3.05 (2H, m), 3.48-3.57 (2H, m), 3.88 (3H, s), 3.98-4.14 (1H, m), 4.21-4.35 (4H, m), 4.25 (4H, s), 6.10-6.16 (1H, m), 6.55 (1H, s), 6.66-6.71 (1H, m), 6.74 (1H, d, J=2.0 Hz), 6.78 (1H, d, J=8.3 Hz), 6.82-6.88 (2H, m), 7.87 (1H, d, J=8.7 Hz)

Example 77

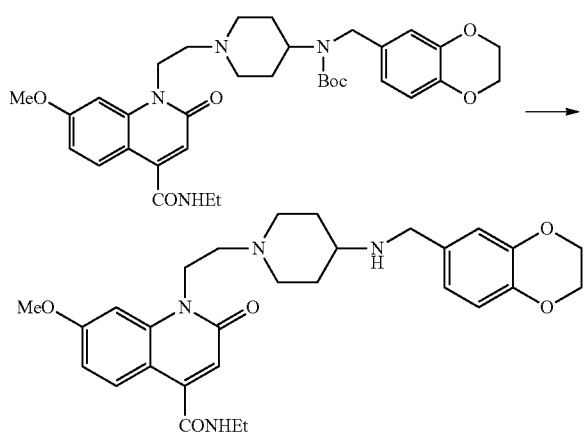

According to a procedure similar to Example 25, 1-(2-(4-((2,3-dihydro-1,4-benzodioxin-6-ylmethyl)amino)piperidin-1-yl)ethyl)N-ethyl-7-methoxy-2-oxo-1,2-dihydroquinoline-4-carboxamide was obtained from tert-butyl (2,3-dihydro-1,4-benzodioxin-6-ylmethyl)(1-(2-(4-((ethylamino)carbonyl)-7-methoxy-2-oxoquinolin-1(2H)-yl)ethyl)piperidine)-4-yl)carbamate.

$^1$H-NMR (CDCl$_3$) δ:
1.28 (3H, t, J=7.3 Hz), 1.38-1.50 (2H, m), 1.86-1.94 (2H, m), 2.13-2.23 (2H, m), 2.48-2.65 (3H, m), 2.95-3.02 (2H, m), 3.48-3.56 (2H, m), 3.71 (2H, s), 3.91 (3H, s), 4.25 (4H, s), 4.34-4.41 (2H, m), 6.09-6.14 (1H, m), 6.57 (1H, s), 6.78 (1H, dd, J=8.3, 1.7 Hz), 6.80-6.86 (3H, m), 6.92 (1H, d, J=2.0 Hz), 7.88 (1H, d, J=9.0 Hz)

Example 78

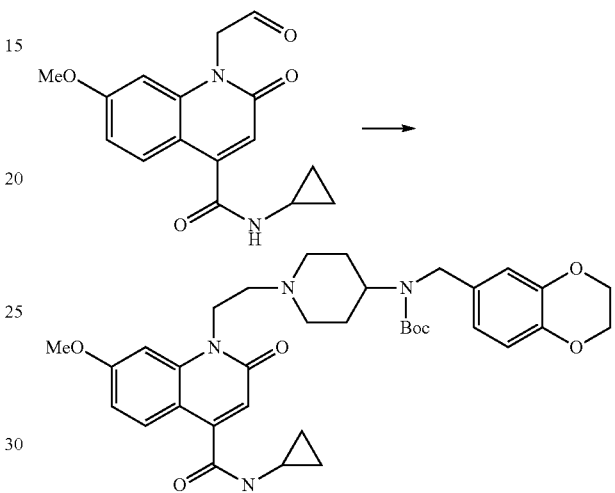

To 1.0 mL of methanol solution containing 0.13 g of N-cyclopropyl-7-methoxy-2-oxo-1-(2-oxoethyl)-1,2-dihydroquinoline-4-carboxamide, 0.16 g of tert-butyl (2,3-dihydro-1,4-benzodioxin-6-ylmethyl)(piperidin-4-yl)carbamate and 25 μL of acetic acid were added at room temperature and stirred at the same temperature for 1.5 hours. To the reaction mixture, 42 mg of sodium cyanoborohydride was added and stirred at the same temperature for 2 hours. Further, 42 mg of sodium cyanoborohydride was added and stirred at the same temperature for 2 hours and 15 min. 76 μL of acetic acid was added and stirred at the same temperature for 2 hours. To the mixture, aqueous saturated sodium hydrogen carbonate solution was added under ice-cooling to be adjusted to pH 8.7, 5.0 mL of methanol and 15 mL of chloroform were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by flash silica gel column chromatography [gradient elution of chloroform:methanol=100:0-70:30], to give 0.13 g of tert-butyl (1-(2-(4-((cyclopropylamino)carbonyl)-7-methoxy-2-oxoquinolin-1-(2H)-yl)ethyl)piperidin-4-yl)(2,3-dihydro-1,4-benzodioxin-6-ylmethyl)carbamate as a white foam.

$^1$H-NMR (CDCl$_3$) δ:
0.62-0.68 (2H, m), 0.89-0.95 (2H, m), 1.42 (9H, s), 1.50-1.73 (4H, m), 2.06-2.19 (2H, m), 2.52-2.58 (2H, m), 2.91-3.04 (3H, m), 3.88 (3H, s), 3.99-4.11 (1H, m), 4.24 (4H, s), 4.20-4.33 (4H, m), 6.25-6.30 (1H, m), 6.51 (1H, s), 6.66-6.71 (1H, m), 6.73 (1H, d, J=1.7 Hz), 6.78 (1H, d, J=8.3 Hz), 6.82-6.86 (2H, m), 7.88 (1H, d, J=9.5 Hz)

Example 79

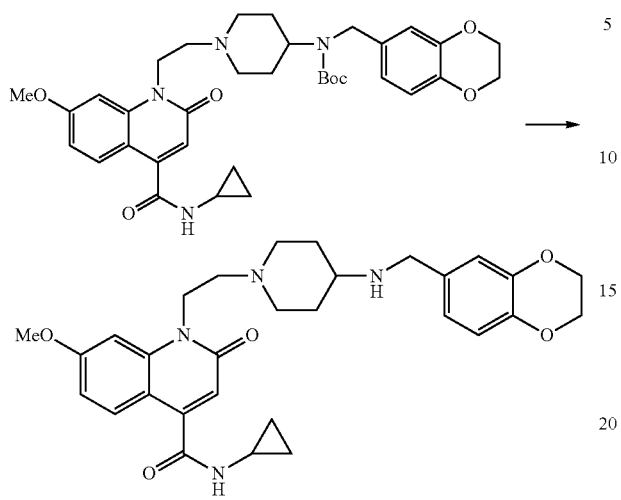

According to a procedure similar to Example 25, N-cyclopropyl-1-(2-(4-(((2,3-dihydro-1,4-benzodioxin-6-ylmethyl)amino)piperidin-1-yl)ethyl)-7-methoxy-2-oxo-1,2-dihydroquinoline-4-carboxamide was obtained from tert-butyl (1-(2-(4-(((cyclopropylamino)carbonyl)-7-methoxy-2-oxoquinolin-1-(2H)-yl)ethyl)piperidin-4-yl)(2,3-dihydro-1,4-benzodioxin-6-ylmethyl)carbamate.

$^{1}$H-NMR (CDCl$_{3}$) δ:
0.63-0.69 (2H, m), 0.88-0.96 (2H, m), 1.37-1.49 (2H, m), 1.85-1.94 (2H, m), 2.10-2.21 (2H, m), 2.47-2.62 (3H, m), 2.92-3.00 (3H, m), 3.70 (2H, s), 3.90 (3H, s), 4.25 (4H, s), 4.29-4.36 (2H, m), 6.33-6.37 (1H, m), 6.51 (1H, s), 6.78 (1H, dd, J=8.4, 2.0 Hz), 6.81 (1H, d, J=8.4 Hz), 6.82-6.86 (2H, m), 6.90 (1H, d, J=2.2 Hz), 7.88 (1H, d, J=9.0 Hz)

Example 80

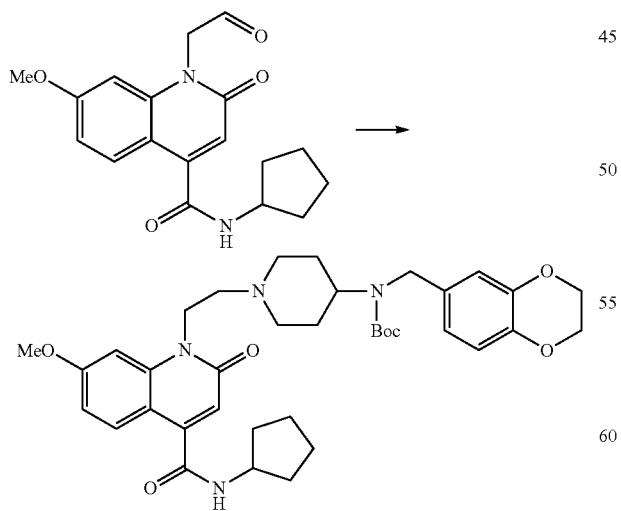

According to a procedure similar to Example 24, tert-butyl (1-(2-(4-(((cyclopentyl)carbonyl)-7-methoxy-2-oxoquinolin-1-(2H)-yl)ethyl)piperidin-4-yl) (2,3-dihydro-1,4-benzodioxin-6-ylmethyl)carbamate was obtained from N-cyclopentyl-7-methoxy-2-oxo-1-(2-oxoethyl-1,2-dihydroquinoline-4-carboxamide and tert-butyl (2,3-dihydro-1,4-benzodioxin-6-ylmethyl)(piperidin-4-yl)carbamate.

$^{1}$H-NMR (CDCl$_{3}$) δ:
1.42 (9H, s), 1.36-1.56 (2H, m), 1.57-1.78 (8H, m), 2.06-2.21 (4H, m), 2.52-2.58 (2H, m), 2.97-3.04 (2H, m), 3.88 (3H, s), 3.98-4.12 (1H, m), 4.24 (4H, s), 4.23-4.33 (4H, m), 4.38-4.48 (1H, m), 6.09-6.14 (1H, m), 6.53 (1H, s), 6.66-6.71 (1H, m), 6.74 (1H, d, J=1.7 Hz), 6.78 (1H, d, J=8.3 Hz), 6.82-6.86 (2H, m), 7.87 (1H, d, J=9.5 Hz)

Example 81

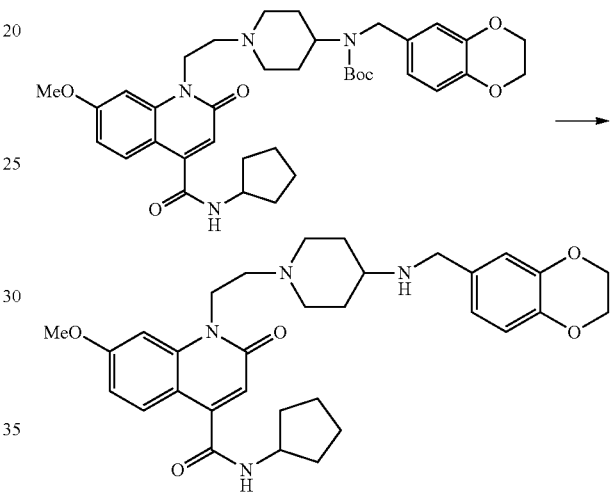

According to a procedure similar to Example 25, N-cyclopentyl-(1-(2-(4-((2,3-dihydro-1,4-benzodioxin-6-ylmethyl)amino)piperidin-1-yl)ethyl)-7-methoxy-2-oxo-1,2-dihydroquinoline-4-carboxamide was obtained from tert-butyl (1-(2-(((4-cyclopentylamino)carbonyl)-7-methoxy-2-oxoquinolin-1(2H)-yl)ethyl)piperidin-4-yl)(2,3-dihydro-1,4-benzodioxin-6-ylmethyl)carbamate $^{1}$H-NMR (CDCl$_{3}$) δ:
1.37-1.60 (4H, m), 1.63-1.77 (4H, m), 1.86-1.94 (2H, m), 2.06-2.22 (4H, m), 2.48-2.64 (3H, m), 2.94-3.02 (2H, m), 3.70 (2H, s), 3.91 (3H, s), 4.25 (4H, s), 4.33-4.40 (2H, m), 4.40-4.47 (1H, m), 6.01-6.06 (1H, m), 6.55 (1H, s), 6.75-6.86 (4H, m), 6.92 (1H, d, J=1.9 Hz), 7.88 (1H, d, J=8.9 Hz)

Example 82

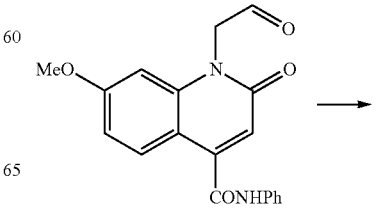

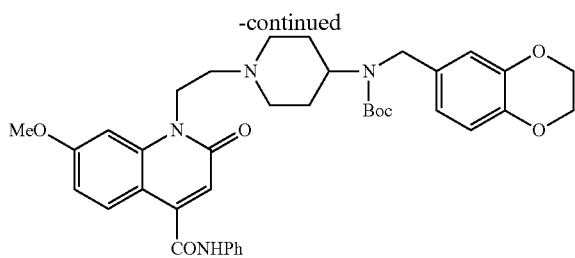

s), 4.17-4.23 (2H, m), 4.25 (4H, s), 6.70 (1H, s), 6.78 (1H, dd, J=8.2, 1.8 Hz), 6.80-6.87 (4H, m), 7.20 (1H, t, J=7.7 Hz), 7.41 (2H, t, J=7.7 Hz), 7.75 (2H, d, J=7.7 Hz), 7.94 (1H, d, J=9.8 Hz), 8.73 (1H, s)

According to a procedure similar to Example 24, tert-butyl (1-(2-(4-(anilinocarbonyl)-7-methoxy-2-oxoquinolin-1-(2H)-yl)ethyl)piperidin-4-yl)(2,3-dihydro-1,4-benzodioxin-6-ylmethyl)carbamate was obtained from 7-methoxy-2-oxo-1-(2-oxoethyl)-N-phenyl-1,2-dihydroquinoline-4-carboxamide and tert-butyl (2,3-dihydro-1,4-benzodioxin-6-ylmethyl)(piperidin-4-yl)carbamate.

¹H-NMR (CDCl₃) δ:
1.42 (9H, s), 1.56-1.68 (4H, m), 1.98-2.09 (2H, m), 2.38-2.45 (2H, m), 2.88-2.95 (2H, m), 3.88 (3H, s), 3.96-4.07 (1H, m), 4.12-4.18 (2H, m), 4.22-4.32 (2H, m), 4.24 (4H, s), 6.66-6.70 (1H, m), 6.69 (1H, s), 6.73 (1H, d, J=2.0 Hz), 6.78 (1H, d, J=8.3 Hz), 6.78 (1H, d, J=2.4 Hz), 6.86 (1H, dd, J=9.0, 2.4 Hz), 7.20 (1H, t, J=7.6 Hz), 7.40 (2H, t, J=7.6 Hz), 7.73 (2H, d, J=7.6 Hz), 7.93 (1H, d, J=9.0 Hz), 8.65 (1H, s)

Example 84

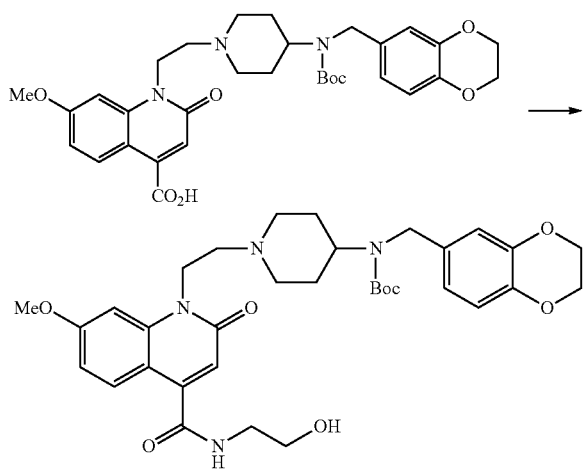

To 3.0 mL of tetrahydrofuran suspension containing 0.15 g of 1-(2-(4-(((tert-butoxycarbonyl)(2,3-dihydro-1,4-benzodioxin-6-ylmethyl)amino)piperidin-1-yl)ethyl)-7-methoxy-2-oxo-1,2-dihydroquinoline-4-carboxylic acid, 39 µL of triethylamine was added at room temperature, 25 µL of ethyl chlorocarbonate was added dropwise under ice-cooling, and the reaction mixture was stirred at the same temperature for 2 hours. Then, 15 µL of 2-aminoethanol was added dropwise. After stirred at the same temperature for 3 hours, 15 µL of 2-aminoethanol was added dropwise and stirred for 1.5 hours. Further, 15 µL of 2-aminoethanol was added dropwise and stirred at room temperature for 40 min. To the reaction mixture, ethyl acetate and water were added, the organic layer was separated, and the aqueous layer was extracted with ethyl acetate. The organic layer and extracts were combined, washed sequentially with water and aqueous saturated sodium chloride solution, dried over anhydrous magnesium sulfate, and the solvent was removed under reduced pressure. To the residue thus obtained, diethyl ether and diisopropyl ether were added, and the resulting solid was filtered to give 84 mg of tert-butyl (2,3-dihydro-1,4-benzodioxin-6-ylmethyl)(1-(2-(4-(((2-hydroxyethyl)amino)carbonyl)-7-methoxy-2-oxoquinolin-1(2H)-yl)ethyl)piperidin-4-yl)carbamate as a slight yellow solid.

¹H-NMR (CDCl₃) δ:
1.43 (9H, s), 1.56-1.84 (4H, m), 2.12-2.25 (2H, m), 2.54-2.64 (2H, m), 3.02-3.13 (2H, m), 3.61-3.69 (2H, m), 3.82-3.91 (2H, m), 3.87 (3H, s), 3.97-4.09 (1H, m), 4.24 (4H, s), 4.18-4.36 (4H, m), 6.59 (1H, s), 6.65-6.89 (5H, m), 6.89-6.98 (1H, m), 7.86 (1H, d, J=9.0 Hz)

Example 83

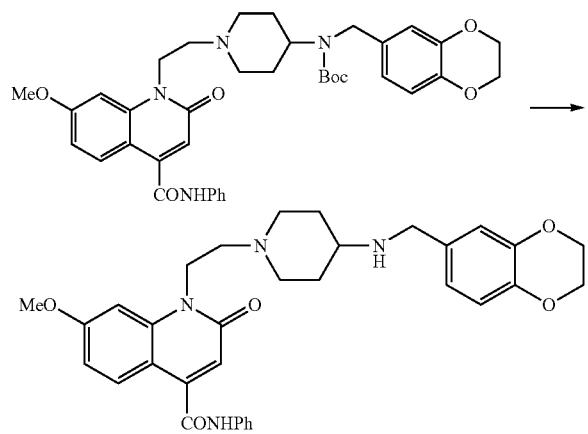

According to a procedure similar to Example 25, 1-(2-(4-((2,3-dihydro-1,4-benzodioxin-6-ylmethyl)amino)piperidin-1-yl)ethyl)-7-methoxy-2-oxo-N-phenyl-1,2-dihydroquinoline-4-carboxamide was obtained from tert-butyl (1-(2-(4-(anilinocarbonyl)-7-methoxy-2-oxoquinolin-1-(2H)-yl)ethyl)piperidin-4-yl)(2,3-dihydro-1,4-benzodioxin-6-ylmethyl)carbamate.

¹H-NMR (CDCl₃) δ:
1.34-1.46 (2H, m), 1.82-1.90 (2H, m), 2.01-2.11 (2H, m), 2.40-2.54 (3H, m), 2.85-2.92 (2H, m), 3.70 (2H, s), 3.89 (3H,

Example 85

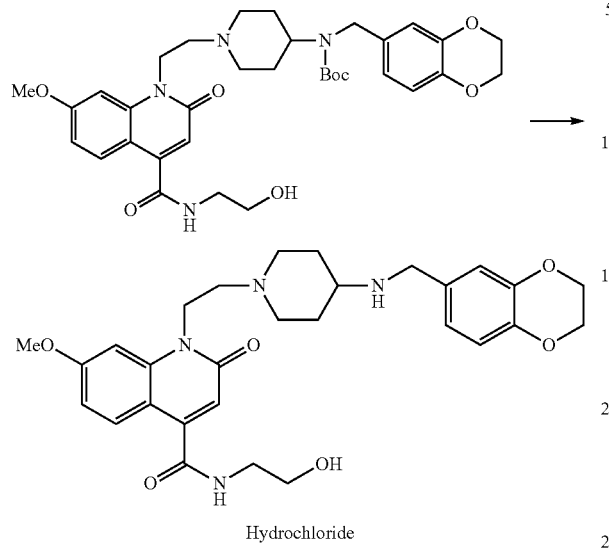

Hydrochloride

To 1.0 mL of ethanol suspension containing 77 mg of tert-butyl (2,3-dihydro-1,4-benzodioxin-6-ylmethyl)(1-(2-(4-(((2-hydroxyethyl)amino)carbonyl)-7-methoxy-2-oxo-quinolin-1(2H)-yl)ethyl)piperidin-4-yl)carbamate, 3.0 mL of 6.2 mol/L hydrogen chloride/ethanol solution was added at room temperature, stirred at the same temperature for 1 hour and 20 min. Further, 1.0 mL of ethanol and 3.0 mL of 6.2 mol/L hydrogen chloride/ethanol solution was added at the same temperature, and after stirred for 2.5 hours, the mixture was left to stand overnight. The solvent was removed under reduced pressure, diethyl ether was added to the residue obtained and the resulting solid was filtered to afford 56 mg of 1-(2-(4-((2,3-dihydro-1,4-benzodioxin-6-ylmethyl)amino)piperidin-1-yl)ethyl)-N-(2-hydroxyethyl)-7-methozy-2-oxo-1,2-dihydroquinoline-4-carboxamide hydrochloride as a pale yellow solid.

$^1$H-NMR (D$_2$O) δ:
1.95-2.08 (2H, m), 2.46-2.54 (2H, m), 3.17-3.27 (2H, m), 3.55-3.65 (5H, m), 3.81 (2H, t, J=5.4 Hz), 3.94-4.01 (2H, m), 3.98 (3H, s), 4.22 (2H, s), 4.33 (4H, s), 4.74-4.85 (2H, m), 6.72 (1H, s), 6.97-7.04 (4H, m), 7.12 (1H, dd, J=9.0, 2.2 Hz), 7.82 (1H, d, J=9.0 Hz)

Example 86

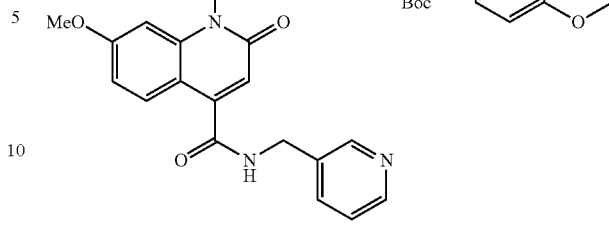

To 3.0 mL of tetrahydrofuran suspension containing 0.15 g of 1-(2-(4-(((tert-butoxycarbonyl)(2,3-dihydro-1,4-benzodioxin-6-ylmethyl)amino)piperidin-1-yl)ethyl)-7-methoxy-2-oxo-1,2-dihydroquinoline-4-carboxylic acid, 39 μL of triethylamine was added at room temperature, 36 μL of isobutyl chlorocarbonate was added dropwise under ice-cooling. After the reaction mixture was stirred at the same temperature for 2 hours, 26 μL of 3-(aminomethyl)pyridine was added, further 39 μL of triethylamine was added and stirred at the same temperature for 3 hours. To the reaction mixture, ethyl acetate and water were added, the organic layer was separated, and the aqueous layer was extracted with ethyl acetate. The organic layer and extracts were combined, washed sequentially with water and aqueous saturated sodium chloride solution, dried over anhydrous magnesium sulfate, and the solvent was removed under reduced pressure. The residue thus obtained was purified by flash silica gel column chromatography [gradient elution of chloroform:methanol=100:0-90:10], to give 0.12 g of tert-butyl (2,3-dihydro-1,4-benzodioxin-6-ylmethyl)(1-(2-(7-methoxy-2-oxo-4-(((pyridin-3-ylmethyl)amino)carbonyl)quinolin-1(2H)-yl)ethyl)piperidin-4-yl)carbamate as a white foam.

$^1$H-NMR (CDCl$_3$) δ:
1.42 (9H, s), 1.55-1.71 (4H, m), 2.03-2.16 (2H, m), 2.47-2.54 (2H, m), 2.92-3.00 (2H, m), 3.88 (3H, s), 3.95-4.10 (1H, m), 4.19-4.33 (8H, m), 4.69 (2H, d, J=5.9 Hz), 6.56 (1H, s), 6.65-6.71 (1H, m), 6.73 (1H, d, J=1.7 Hz), 6.75-6.88 (4H, m), 7.29-7.33 (1H, m), 7.71-7.76 (1H, m), 7.86 (1H, d, J=9.8 Hz), 8.57 (1H, dd, J=4.8, 1.6 Hz), 8.64 (1H, d, J=2.2 Hz)

Example 87

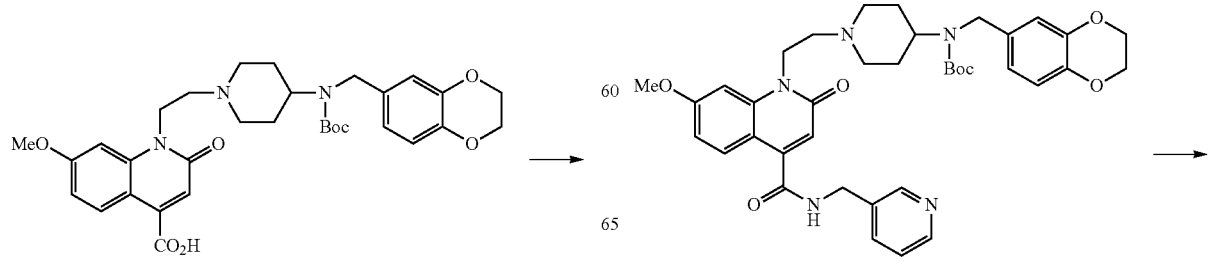

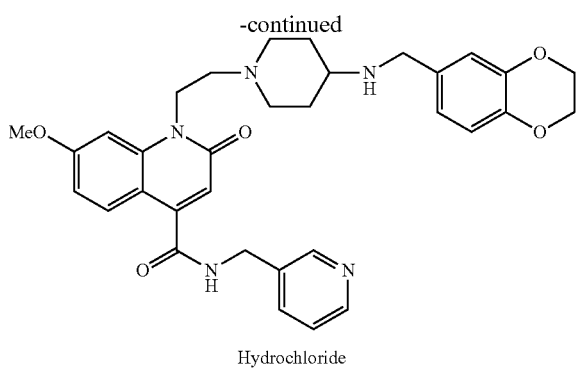

Hydrochloride

According to a procedure similar to Example 85, 1-(2-(4-((2,3-dihydro-1,4-benzodioxin-6-ylmethyl)amino)piperidin-1-yl)ethyl)-7-methoxy-2-oxo-N-(pyridin-3-ylmethyl)-1,2-dihydroquinoline-4-carboxamide hydrochloride was obtained from tert-butyl (2,3-dihydro-1,4-benzodioxin-6-ylmethyl)(1-(2-(7-methoxy-2-oxo-4-(((pyridin-3-ylmethyl)amino)carbonyl)quinolin-1-(2H)-yl)ethyl)piperidin-4-yl)carbamate.

$^1$H-NMR (D$_2$O) δ:
1.95-2.09 (2H, m), 2.47-2.56 (2H, m), 3.19-3.31 (2H, m), 3.55-3.66 (3H, m), 3.94-4.04 (2H, m), 3.98 (3H, s), 4.22 (2H, s), 4.33 (4H, s), 4.73-4.83 (2H, m), 4.87 (2H, s), 6.75 (1H, s), 6.98-7.00 (2H, m), 7.02-7.05 (2H, m), 7.11 (1H, dd, J=9.0, 2.2 Hz), 7.76 (1H, d, J=9.0 Hz), 8.13 (1H, dd, J=8.3, 5.9 Hz), 8.66-8.70 (1H, m), 8.78 (1H, d, J=5.9 Hz), 8.87-8.89 (1H, m)

Example 88

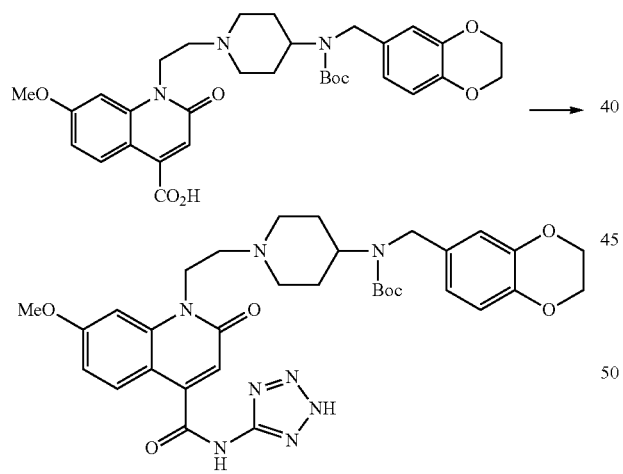

According to a procedure similar to Example 86, tert-butyl (2,3-dihydro-1,4-benzodioxin-6-ylmethyl)(1-(2-(7-methoxy-2-oxo-4-((2H-tetrazol-5-ylamino)carbonyl)quinolin-1-(2H)-yl)ethyl)piperidin-4-yl)carbamate was obtained from 1-(2-(4-(((tert-butoxycarbonyl)(2,3-dihydro-1,4-benzodioxin-6-ylmethyl)amino)piperidin-1-yl)ethyl)-7-methoxy-2-oxo-1,2-dihydroquinoline-4-carboxylic acid and 5-amino-1,2,3,4,-tetrazole.

$^1$H-NMR (DMSO-d$_6$) δ:
1.31-1.55 (2H, m), 1.38 (9H, s), 1.57-1.70 (2H, m), 2.03-2.17 (2H, m), 2.45-2.63 (2H, m), 3.01-3.12 (2H, m), 3.76-3.97 (1H, m), 3.90 (3H, s), 4.17-4.28 (6H, m), 4.32-4.44 (2H, m), 6.44 (1H, s), 6.60-6.74 (3H, m), 6.79 (1H, d, J=8.0 Hz), 6.92-7.04 (2H, m), 7.76 (1H, d, J=8.8 Hz)

Example 89

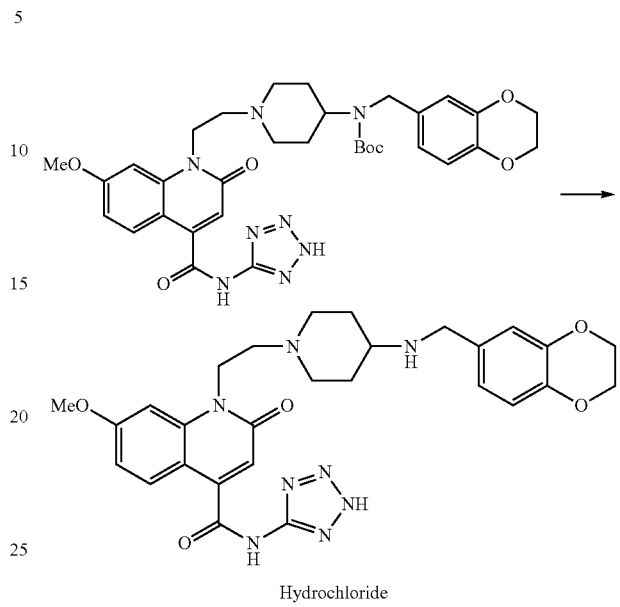

Hydrochloride

According to a procedure similar to Example 85, 1-(2-(4-((2,3-dihydro-1,4-benzodioxin-6-ylmethyl)amino)piperidin-1-yl)ethyl)-7-methoxy-2-oxo-N-(2H-tetrazol-5-yl)-1,2-dihydroquinoline-4-carboxamide hydrochloride was obtained from tert-butyl (2,3-dihydro-1,4-benzodioxin-6-ylmethyl)(1-(2-(7-methoxy-2-oxo-4-((2H-tetrazol-5-ylamino)carbonyl)quinolin-1-(2H)-yl)ethyl)piperidin-4-yl)carbamate.

$^1$H-NMR (D$_2$O) δ:
1.96-2.11 (2H, m), 2.47-2.56 (2H, m), 3.20-3.32 (2H, m), 3.55-3.69 (3H, m), 3.94-4.08 (2H, m), 3.98 (3H, s), 4.22 (2H, s), 4.33 (4H, s), 4.74-4.86 (2H, m), 6.89 (1H, s), 6.97-7.05 (4H, m), 7.13 (1H, dd, J=9.0, 2.1 Hz), 7.90 (1H, d, J=9.0 Hz)

Example 90

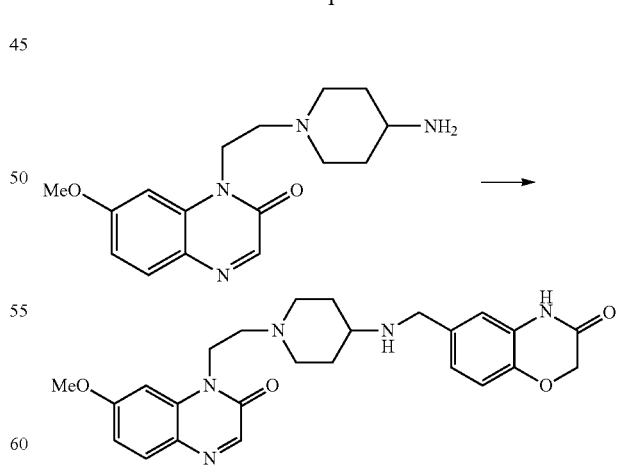

To 3.0 mL of a methanol solution containing 0.20 g of 1-(2-(4-aminopiperidin-1-yl)ethyl)-7-methoxyquinoxalin-2(1H)-one, 0.12 g of 3-oxo-3,4-dihydro-2H-1,4-benzooxazine-6-carbaldehyde, 38 μL of acetic acid and 83 mg of sodium cyanoborohydride were added at room temperature and stirred at the same temperature for 6.5 hours. To the reaction mixture, chloroform and aqueous saturated sodium hydrogen carbonate solution were added to be adjusted to pH 10.2, the organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; chloroform: methanol=5:1], diethyl ether was added to the foam thus obtained, and the resulting solid was filtered to afford a yellow solid. To this solid, ethyl acetate and chloroform were added, the mixture was cooled to the room temperature after heating, and the resulting solid was filtered to give 59 mg of 6-(((1-(2-(7-methoxy-2-oxoquinoxaline-1-(2H)-yl)ethyl)piperidin-4-yl)amino)methyl)-2H-1,4-benzooxazine-3(4H)-one a pale yellow solid.

$^1$H-NMR (CDCl$_3$) δ:
1.36-1.48 (2H, m), 1.86-1.94 (2H, m), 2.14-2.23 (2H, m), 2.47-2.56 (1H, m), 2.64-2.71 (2H, m), 2.96-3.03 (2H, m), 3.74 (2H, s), 3.93 (3H, s), 4.31-4.37 (2H, m), 4.60 (2H, s), 6.80 (1H, s), 6.85 (1H, d, J=2.4 Hz), 6.90-6.95 (3H, m), 7.64 (1H, s), 7.79 (1H, d, J=8.8 Hz), 8.12 (1H, s)

Example 91

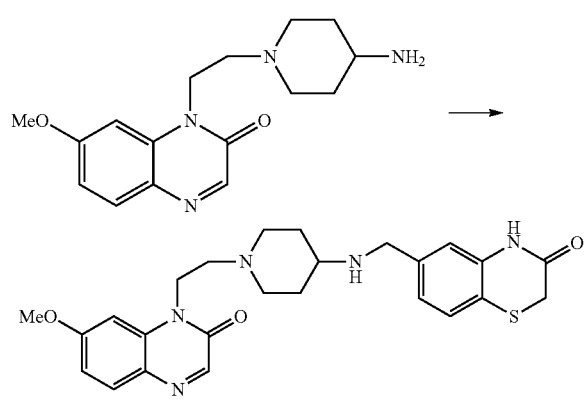

To 3.0 mL of methanol solution containing 0.20 g of 1-(2-(4-aminopiperidin-1-yl)ethyl)-7-methoxyquinoxalin-2(1H)-one, 0.13 g of 3-oxo-3,4-dihydro-2H-1,4-benzothiazine-6-carbaldehyde, 38 μL of acetic acid and 83 mg of sodium cyanoborohydride were added at room temperature and stirred at the same temperature for 4 hours. To the mixture, chloroform and aqueous saturated sodium hydrogen carbonate solution was added to be adjusted to pH 9.5, the organic layer was separated, and the aqueous layer was extracted with chloroform. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; chloroform:methanol=20:3], to give 60 mg of 6-(((1-(2-(7-methoxy-2-oxoquinoxaline-1-(2H)-yl)ethyl)piperidin-4-yl)amino)methyl)-2H-1,4-benzothiazine-3(4H)-one a pale yellow solid.

$^1$H-NMR (CDCl$_3$) δ:
1.36-1.47 (2H, m), 1.86-1.94 (2H, m), 2.14-2.23 (2H, m), 2.47-2.56 (1H, m), 2.64-2.70 (2H, m), 2.96-3.03 (2H, m), 3.42 (2H, s), 3.77 (2H, s), 3.92 (3H, s), 4.31-4.37 (2H, m), 6.82-6.87 (2H, m), 6.93 (1H, dd, J=8.8, 2.7 Hz), 6.97 (1H, dd, J=8.0, 1.0 Hz), 7.26 (1H, d, J=8.0 Hz), 7.67-7.71 (1H, m), 7.79 (1H, d, J=8.8 Hz), 8.12 (1H, s)

Example 92

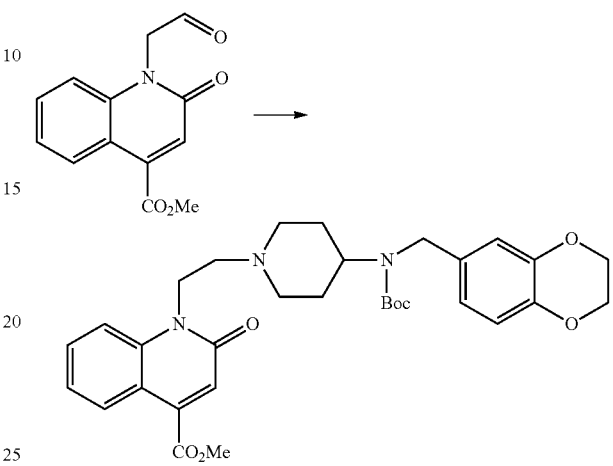

To 24 mL of dichloromethane suspension containing 0.8 g of methyl 2-oxo-1-(2-oxoethyl)-1,2-dihydroquinoline-4-carboxylate and 1.1 g of tert-butyl (2,3-dihydro-1,4-benzodioxin-6-ylmethyl)(piperidin-4-yl)carbamate, 0.24 mL of acetic acid was added, at room temperature and stirred at room temperature for 1 hour. To the reaction mixture, 1.0 g of sodium triacetoxyborohydride was added, and stirred at room temperature for 1 hour. Aqueous saturated sodium hydrogen carbonate solution was added, the organic layer was separated, and the aqueous layer was extracted with dichloromethane. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; ethyl acetate], to give 1.25 g of methyl 1-(2-(4-(((tert-butoxycarbonyl)(2,3-dihydro-1,4-benzodioxin-6-ylmethyl)amino)piperidin-1-yl)ethyl)-2-oxo-1,2-dihydroquinoline-4-carboxylate as a slight yellow oil.

$^1$H-NMR (CDCl$_3$) δ:
1.42 (9H, s), 1.58-1.72 (4H, m), 2.08-2.26 (2H, m), 2.58-2.66 (2H, m), 2.98-3.08 (2H, m), 3.99 (3H, s), 4.02-4.16 (1H, m), 4.18-4.36 (2H, m), 4.24 (4H, s), 4.38-4.46 (2H, m), 6.66-6.70 (1H, m), 6.74 (1H, d, J=1.7 Hz), 6.78 (1H, d, J=8.3 Hz), 7.16 (1H, s), 7.26-7.32 (1H, m), 7.42-7.45 (1H, m), 7.54-7.62 (1H, m), 8.32 (1H, dd, J=8.1, 1.5 Hz)

Example 93

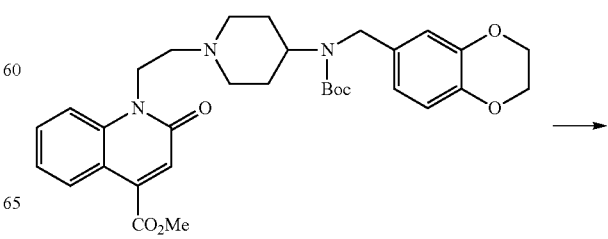

-continued

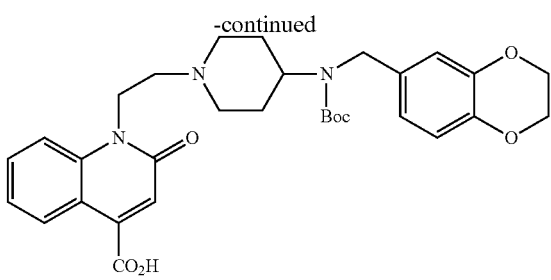

To 11 mL of acetone solution containing 1.1 g of methyl 1-(2-(4-(((tert-butoxycarbonyl)(2,3-dihydro-1,4-benzodioxin-6-ylmethyl)amino)piperidin-1-yl)ethyl)-2-oxo-1,2-dihydroquinoline-4-carboxylate, 2.2 mL of water solution containing 0.23 g of sodium hydroxide was added at room temperature, and stirred at 50° C. for 30 min. After cooled to the room temperature, the solvent was removed under reduced pressure, 40 mL of water was added, and adjusted to pH 4 with 2 mol/L hydrochloric acid. The resulting solid was filtered to afford 0.97 g of 1-(2-(4-(((tert-butoxycarbonyl)(2,3-dihydro-1,4-benzodioxin-6-ylmethyl)amino)piperidin-1-yl)ethyl)-2-oxo-1,2-dihydroquinoline-4-carboxylic acid as a white solid.

$^1$H-NMR (DMSO-$d_6$) δ:
1.38 (9H, s), 1.46-1.58 (2H, m), 1.60-1.78 (2H, m), 2.10-2.34 (2H, m), 2.60-2.74 (2H, m), 3.06-3.52 (2H, m), 4.16-4.28 (3H, m), 4.21 (4H, s), 4.32-4.44 (2H, m), 6.68 (1H, dd, J=8.2, 1.7 Hz), 6.70-6.72 (1H, m), 6.76 (1H, s), 6.78 (1H, d, J=8.2 Hz), 7.24-7.32 (1H, m), 7.57 (1H, d, J=8.6 Hz), 7.60-7.68 (1H, m), 8.16 (1H, d, J=8.5 Hz)

Example 94

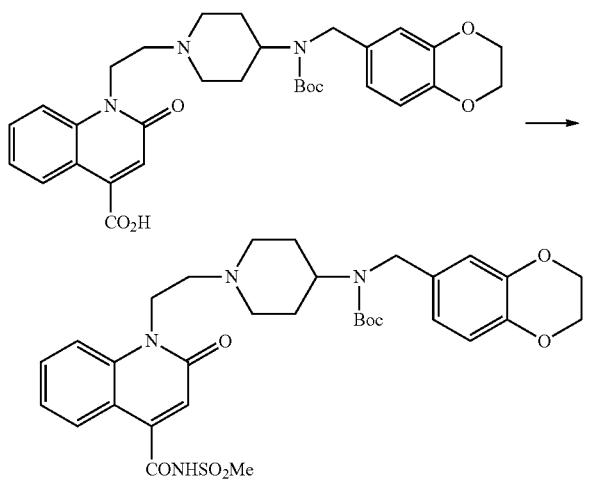

To 5 mL of tetrahydrofuran suspension containing 0.10 g of 1-(2-(4-(((tert-butoxycarbonyl)(2,3-dihydro-1,4-benzodioxin-6-ylmethyl)amino)piperidin-1-yl)ethyl)-2-oxo-1,2-dihydroquinoline-4-carboxylic acid, 58 mg of 1,1'-carbonyldiimidazole was added, and stirred at 50° C. for 1 hour. The reaction mixture was cooled to the room temperature, then 84 mg of methanesulfonamide and 0.13 mL of 1,8-diazabicylo[5.4.0]undec-7-ene were added, and stirred at room temperature for 2 hours. The solvent was removed under reduced pressure, water was added, and adjusted to pH 4 with 1 mol/L hydrochloric acid. The resulting solid was filtered to afford 0.10 g of tert-butyl (2,3-dihydro-1,4-benzodioxin-6-ylmethyl)(1-(2-(4-(((methylsulfonyl)amino)carbonyl)-2-oxo-quinolin-1(2H)-yl)ethyl)piperidin-4-yl)carbamate as a white solid.

$^1$H-NMR (DMSO-$d_6$) δ:
1.40 (9H, s), 1.58-2.02 (4H, m), 2.97 (3H, s), 3.08-4.06 (6H, m), 4.12-4.36 (3H, m), 4.21 (4H, s), 4.46-4.62 (2H, m), 6.54 (1H, s), 6.69 (1H, d, J=8.4 Hz), 6.72 (1H, s), 6.81 (1H, d, J=8.4 Hz), 7.24-7.34 (1H, m), 7.52-7.68 (2H, m), 8.10 (1H, d, J=7.3 Hz)

Example 95

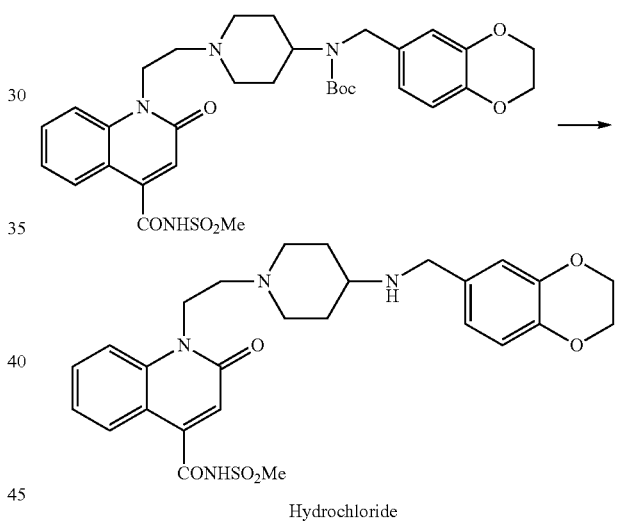

To 1.8 mL of methanol solution containing 90 mg of tert-butyl (2,3-dihydro-1,4-benzodioxin-6-ylmethyl)(1-(2-(4-(((methylsulfonyl)amino) carbonyl)-2-oxoquinolin-1(2H)-yl)ethyl)piperidin-4-yl)carbamate, 1.8 mL of 4 mol/L hydrogen chloride/ethyl acetate solution was added at room temperature, and stirred at room temperature for 3 hours. Ethyl acetate was added and the resulting solid was filtered to give 70 mg of (1-(2-(4-(2,3-dihydro-1,4-benzodioxin-6-ylmethyl)amino)piperidin-1-yl)ethyl)-N-(methylsulfonyl)-2-oxo-1,2-dihydroquinoline-4-carboxamide hydrochloride as a white solid.

$^1$H-NMR (DMSO-$d_6$) δ:
2.00-2.16 (2H, m), 2.30-2.44 (2H, m), 3.04-3.56 (5H, m), 3.48 (3H, s), 3.74-3.86 (2H, m), 4.02-4.14 (2H, m), 4.25 (4H, s), 4.66-4.80 (2H, m), 6.86-6.96 (2H, m), 7.05 (1H, d, J=8.3 Hz), 7.17 (1H, s), 7.38-7.46 (1H, m), 7.70-7.80 (2H, m), 7.94 (1H, d, J=9.0 Hz), 9.50-9.66 (2H, broad), 10.98-11.14 (1H, broad)

Example 96

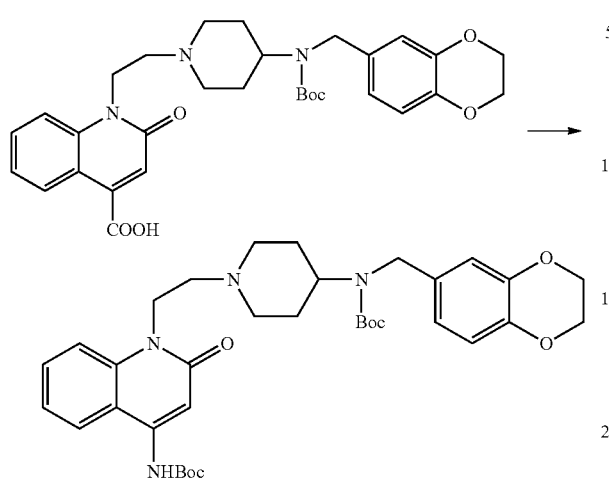

To 2.3 mL of tert-butanol suspension containing 0.23 g of 1-(2-(4-(((tert-butoxycarbonyl)(2,3-dihydro-1,4-benzodioxin-6-ylmethyl)amino)piperidin-1-yl)ethyl)-2-oxo-1,2-dihydroquinoline-4-carboxylic acid, 0.11 mL of diphenylphosphorylazide and 70 μL of triethylamine were added at the room temperature, and stirred under reflux with heating for 10 hours. After cooled to the room temperature, ethyl acetate and water were added, the organic layer was separated, and washed with aqueous saturated sodium chloride solution, dried over anhydrous sodium sulfate, and the solvent was removed under reduced pressure. The residue thus obtained was purified by silica gel column chromatography [eluent; ethyl acetate: toluene=2:1], to give 0.13 g of tert-butyl 1-(2-(4-(((tert-butoxycarbonyl)amino)-2-oxoquinolin-1(2H)-yl)ethyl)piperidin-4-yl)(2,3-dihydro-1,4-benzodioxin-6-ylmethyl)carbamate as a colorless oil.

$^1$H-NMR (CDCl$_3$) δ:
1.42 (9H, s), 1.50-1.78 (4H, m), 1.55 (9H, s), 1.96-2.28 (2H, m), 2.54-2.68 (2H, m), 2.98-3.12 (2H, m), 3.95-4.48 (5H, m), 4.24 (4H, s), 6.66-6.71 (1H, m), 6.74 (1H, d, J=1.7 Hz), 6.78 (1H, d, J=8.3 Hz), 7.01 (1H, s), 7.18-7.30 (1H, m), 7.36 (1H, s), 7.42 (1H, d, J=8.8 Hz), 7.50-7.66 (2H, m)

Example 97

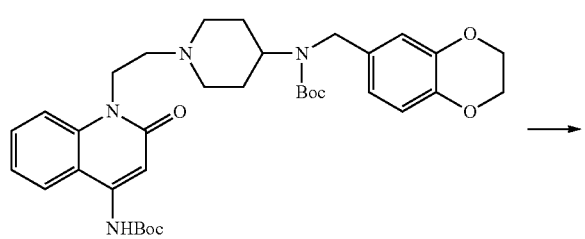

-continued

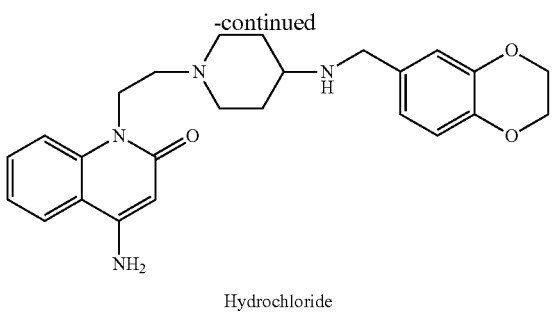

Hydrochloride

To 1 mL of methanol solution containing 100 mg of tert-butyl 1-(2-(4-(((tert-butoxycarbonyl)amino)-2-oxo-1,2-dihydroquinolin-1-yl)ethyl)piperidin-4-yl) (2,3-dihydro-1,4-benzodioxin-6-ylmethyl)carbamate, 1 mL of 4 mol/L hydrogen chloride/ethyl acetate solution was added, and stirred at room temperature for 5 hours. Ethyl acetate was added and the resulting solid was filtered to give 80 mg of 4-amino-1-(2-(4-(((2,3-dihydro-1,4-benzodioxin-6-ylmethyl)amino)piperidin-1-yl)ethyl)-quinolin-2(1H)-one hydrochloride as a white solid.

$^1$H-NMR (DMSO-d$_6$) δ:
1.98-2.14 (2H, m), 2.30-2.42 (2H, m), 3.00-3.16 (2H, m), 3.16-3.36 (3H, m), 3.36-3.88 (2H, m), 4.00-4.12 (2H, m), 4.25 (4H, s), 4.52-4.64 (2H, m), 5.67 (1H, s), 6.90 (1H, d, J=8.3 Hz), 7.06 (1H, dd, J=8.3, 1.7 Hz), 7.18 (1H, d, J=1.7 Hz), 7.24-7.30 (1H, m), 7.56-7.66 (1H, m), 7.72 (1H, d, J=8.3 Hz), 8.04 (1H, d, J=8.1 Hz), 9.52-9.72 (2H, broad), 10.75-10.90 (1H, broad)

Example 98

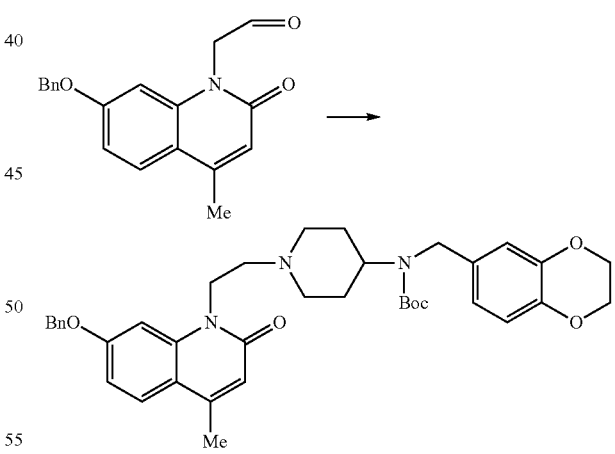

To 23 mL of dichloromethane suspension containing 2.3 g of (7-(benzyloxy)-4-methyl-2-oxoquinolin-1(2H)-yl)acetaldehyde, 23 mL of dichloromethane suspension containing 2.6 g of tert-butyl (2,3-dihydro-1,4-benzodioxin-6-ylmethyl)(piperidin-4-yl)carbamate and 0.43 mL of acetic acid were added, stirred at room temperature for 30 min, thereafter 2.4 g of sodium triacetoxyborohydride was added, and stirred at room temperature for 1 hour. Aqueous saturated sodium hydrogen carbonate solution and water were added, the organic layer was separated, washed sequentially with water and aqueous saturated sodium chloride solution, dried over anhydrous sodium sulfate, and the solvent was removed under reduced pressure. The residue thus obtained was purified by silica gel column chromatography [eluent; ethyl acetate:hexane=2:1], to give 3.1 g of tert-butyl 1-(2-(7-benzyloxy)-4-methyl-2-oxoquinolin-1(2H)-yl)ethyl)piperidin-4-yl) (2,3-dihydro-1,4-benzodioxin-6-ylmethyl)carbamate as a slight yellow foam.

$^1$H-NMR (CDCl$_3$) δ:

1.42 (9H, s), 1.56-1.84 (4H, m), 2.00-2.22 (2H, m), 2.40 (3H, s), 2.50-2.60 (2H, m), 2.94-3.08 (2H, m), 3.98-4.36 (5H, m), 4.23 (4H, s), 5.18 (2H, s), 6.41 (1H, s), 6.65-6.68 (1H, m), 6.73 (1H, d, J=1.2 Hz), 6.77 (1H, d, J=8.0 Hz), 6.89 (1H, dd, J=8.8, 2.2 Hz), 6.93 (1H, d, J=2.2 Hz), 7.30-7.48 (5H, m), 7.60 (1H, d, J=8.8 Hz)

Example 99

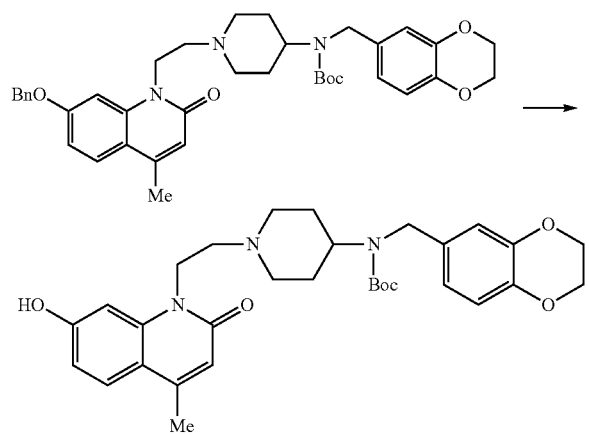

To 25 mL of ethanol solution containing 2.5 g of tert-butyl 1-(2-(7-benzyloxy)-4-methyl-2-oxoquinolin-1(2H)-yl)ethyl)piperidin-4-yl)(2,3-dihydro-1,4-benzodioxin-6-ylmethyl)carbamate, 0.50 g of 5% palladium on carbon was added at room temperature, and stirred under hydrogen atmosphere at room temperature for 1 hour. The insoluble material was filtered off, and the filter cake was washed with 25 mL of ethyl acetate. The filtrate and washings were combined, the solvent was removed under reduced pressure, diisopropyl ether was added and the resulting solid was filtered to give 2.0 g of tert-butyl (2,3-dihydro-1,4-benzodioxin-6-ylmethyl)(1-(2-(7-hydroxy)-4-methyl-2-oxo-1,2-dihydroquinolin-1-yl)ethyl)piperidin-4-yl)carbamate as a slight yellow solid.

$^1$H-NMR (CDCl$_3$) δ:

1.43 (9H, s), 1.56-1.66 (2H, m), 1.68-1.84 (2H, m), 2.08-2.20 (2H, m), 2.38 (3H, d, J=0.9 Hz), 2.58-2.68 (2H, m), 3.00-3.10 (2H, m), 3.86-4.02 (1H, m), 4.16-4.38 (4H, m), 4.22 (4H, s), 6.37 (1H, d, J=0.9 Hz), 6.62-6.67 (1H, m), 6.70 (1H, d, J=1.4 Hz), 6.75 (1H, d, J=8.3 Hz), 6.80 (1H, dd, J=8.7, 2.0 Hz), 7.00 (1H, d, J=2.0 Hz), 7.54 (1H, d, J=8.7 Hz)

Example 100

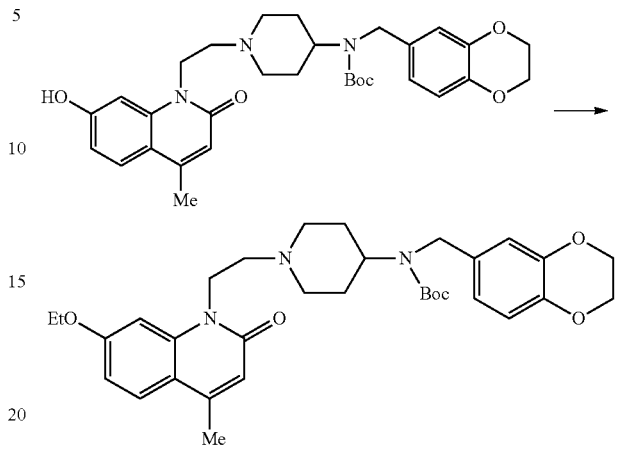

To 6 mL of an N,N-dimethylformamide solution containing 0.30 g of tert-butyl (2,3-dihydro-1,4-benzodioxin-6-ylmethyl) (1-(2-(7-hydroxy)-4-methyl-2-oxo-1,2-dihydroquinolin-1-yl)ethyl)piperidin-4-yl)carbamate, 0.11 g of potassium carbonate and 87 μL of iodoethane were added, and stirred at 50° C. for 3 hours. After cooled to the room temperature, ethyl acetate and water were added, the organic layer was separated, and the aqueous layer was extracted with ethyl acetate. The organic layer and extracts were combined, washed sequentially with water and aqueous saturated sodium chloride solution, dried over anhydrous sodium sulfate, and the solvent was removed under reduced pressure. The residue thus obtained was purified by silica gel column chromatography [eluent; ethyl acetate], to give 0.29 g of tert-butyl (2,3-dihydro-1,4-benzodioxin-6-ylmethyl)(1-(2-(7-ethoxy)-4-methyl-2-oxoquinolin-1(2H)-yl)ethyl)piperidin-4-yl) carbamate as a white foam.

$^1$H-NMR (CDCl$_3$) δ:

1.42 (9H, s), 1.46 (3H, t, J=6.9 Hz), 1.60-1.82 (4H, m), 2.08-2.26 (2H, m), 2.40 (3H, d, J=1.0 Hz), 2.56-2.66 (2H, m), 3.00-3.12 (2H, m), 3.96-4.20 (1H, m), 4.12 (2H, q, J=6.9 Hz), 4.20-4.40 (4H, m), 4.24 (4H, s), 6.40 (1H, d, J=1.0 Hz), 6.66-6.71 (1H, m), 6.74 (1H, d, J=1.9 Hz), 6.78 (1H, d, J=8.3 Hz), 6.81 (1H, dd, J=8.8, 2.2 Hz), 6.86 (1H, d, J=2.2 Hz), 7.59 (1H, d, J=8.8 Hz)

Example 101

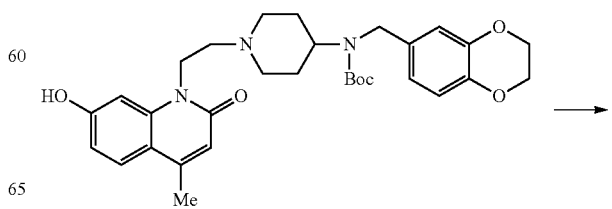

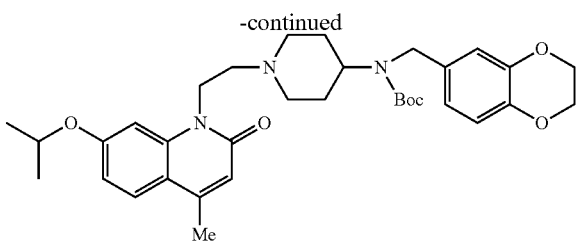

To 6 mL of an N,N-dimethylformamide solution containing 0.30 g of tert-butyl (2,3-dihydro-1,4-benzodioxin-6-ylmethyl) (1-(2-(7-hydroxy)-4-methyl-2-oxoquinolin-1(2H)-yl)ethyl)piperidin-4-yl)carbamate, 0.11 g of potassium carbonate and 0.10 mL of isopropyl bromide were added, and stirred at 80° C. for 3 hour. Further, 0.11 g of potassium carbonate and 0.10 mL of isopropyl bromide were added at 50° C., and stirred at 80° C. for 1 hour. After cooled to the room temperature, ethyl acetate and water were added, the organic layer was separated, and the aqueous layer was extracted with ethyl acetate. The organic layer and extracts were combined, washed sequentially with water and aqueous saturated sodium chloride solution, dried over anhydrous sodium sulfate, and the solvent was removed under reduced pressure. The residue thus obtained was purified by silica gel column chromatography [eluent; ethyl acetate], to give 0.29 g of tert-butyl (2,3-dihydro-1,4-benzodioxin-6-ylmethyl) (1-(2-(7-isopropoxy)-4-methyl-2-oxoquinolin-1(2H)-yl)ethyl)piperidin-4-yl)carbamate as a white foam.

$^1$H-NMR (CDCl$_3$) δ:
1.38 (6H, d, J=5.9 Hz), 1.41 (9H, s), 1.60-1.80 (4H, m), 2.08-2.26 (2H, m), 2.40 (3H, s), 2.56-2.64 (2H, m), 3.00-3.12 (2H, m), 3.98-4.40 (5H, m), 4.24 (4H, s), 4.60-4.72 (1H, m), 6.40 (1H, s), 6.67-6.71 (1H, m), 6.74 (1H, d, J=1.7 Hz), 6.76-6.82 (2H, m), 6.85 (1H, d, J=2.2 Hz), 7.58 (1H, d, J=8.8 Hz)

Example 102

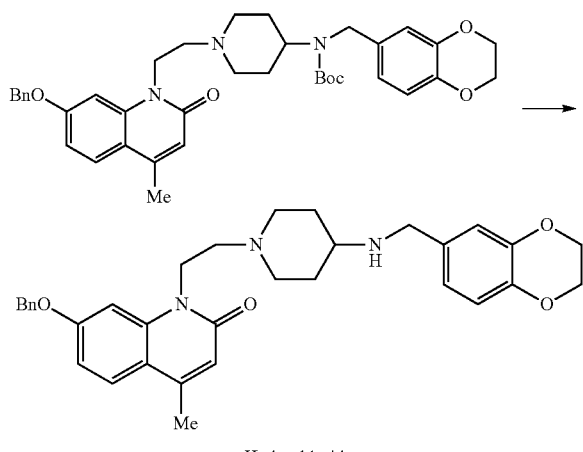

Hydrochloride

To 2.0 mL of methanol solution containing 0.20 g of tert-butyl 1-(2-(7-benzyloxy)-4-methyl-2-oxo-1,2-dihydroquinolin-1-yl)ethyl)piperidin-4-yl) (2,3-dihydro-1,4-benzodioxin-6-ylmethyl)carbamate, 2.0 mL of 4 mol/L hydrogen chloride/ethyl acetate solution was added at room temperature, and stirred at room temperature for 1.5 hours. The resulting solid was filtered to give 0.18 g of 7-(benzyloxy)-1-(2-(4-((2,3-dihydro-1,4-benzodioxin-6-ylmethyl)amino)piperidin-1-yl)ethyl)-4-methylquinolin-2(1H)-one hydrochloride as a slight yellow solid.

$^1$H-NMR (DMSO-d$_6$) δ:
2.00-2.14 (2H, m), 2.30-2.45 (5H, m), 3.00-3.15 (2H, m), 3.18-3.36 (3H, m), 3.74-3.84 (2H, m), 4.00-4.15 (2H, m), 4.25 (4H, s), 4.62-4.74 (2H, m), 5.37 (2H, s), 6.41 (1H, s), 6.90 (1H, d, J=8.3 Hz), 7.00-7.10 (2H, m), 7.15-7.18 (1H, m), 7.27-7.28 (1H, m), 7.32-7.56 (5H, m), 7.77 (1H, d, J=8.8 Hz), 9.46-9.70 (2H, broad), 10.90-11.10 (1H, broad)

Example 103

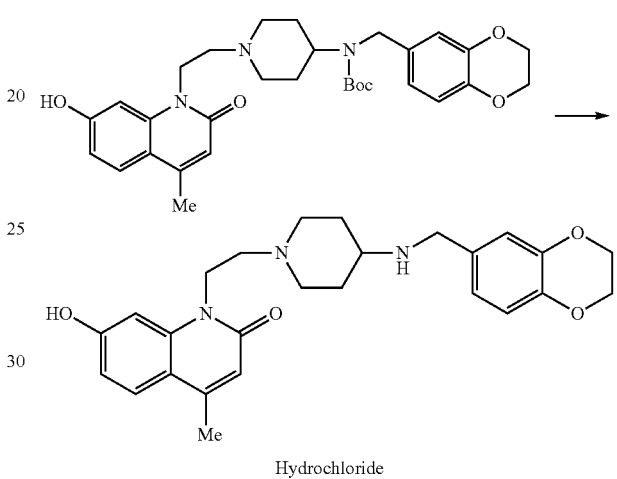

Hydrochloride

To 1.5 mL of methanol solution containing 0.15 g of tert-butyl (2,3-dihydro-1,4-benzodioxin-6-ylmethyl)(1-(2-(7-hydroxy)-4-methyl-2-oxo-1,2-dihydroquinolin-1-yl)ethyl)piperidin-4-yl)carbamate, 1.5 mL of 4 mol/L hydrogen chloride/ethyl acetate solution was added at room temperature, and stirred at room temperature for 1.5 hours. 4.5 mL of ethyl acetate was added, and the resulting solid was filtered to give 0.12 g of 1-(2-(4-((2,3-dihydro-1,4-benzodioxin-6-ylmethyl)amino)piperidin-1-yl)ethyl)-7-hydroxy-4-methylquinolin-2(1H)-one hydrochloride as a pale yellow solid.

$^1$H-NMR (DMSO-d$_6$) δ:
1.98-2.16 (2H, m), 2.30-2.44 (2H, m), 2.38 (3H, s), 3.04-3.38 (5H, m), 3.74-3.88 (2H, m), 4.00-4.12 (2H, m), 4.25 (4H, s), 4.50-4.62 (2H, m), 6.32 (1H, s), 6.85 (1H, dd, J=8.5, 2.1 Hz), 6.90 (1H, d, J=8.5 Hz), 7.02-7.03 (1H, m), 7.06 (1H, dd, J=8.5, 1.7 Hz), 7.19 (1H, d, J=1.7 Hz), 7.65 (1H, d, J=8.5 Hz), 9.60-9.86 (2H, broad), 10.28-10.98 (2H, broad)

Example 104

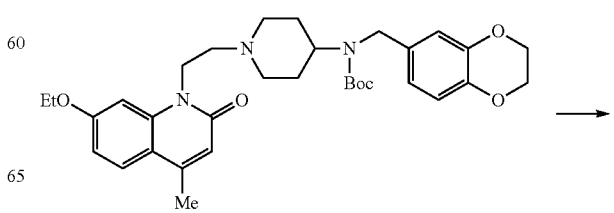

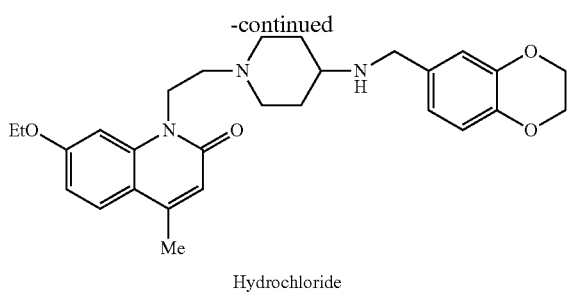

Hydrochloride

To 2.5 mL of methanol solution containing 0.25 g of tert-butyl (2,3-dihydro-1,4-benzodioxin-6-ylmethyl)(1-(2-(7-ethoxy)-4-methyl-2-oxo-1,2-dihydroquinolin-1-yl)ethyl)piperidin-4-yl)carbamate, 2.5 mL of 4 mol/L hydrogen chloride/ethyl acetate solution was added at room temperature, and stirred at room temperature for 2 hours. 10 mL of ethyl acetate was added, and the resulting solid was filtered to give 0.22 g of 1-(2-(4-((2,3-dihydro-1,4-benzodioxin-6-ylmethyl)amino)piperidin-1-yl)ethyl)-7-ethoxy-4-methylquinolin-2(1H)-one hydrochloride as a white solid.

$^1$H-NMR (DMSO-$d_6$) δ:
1.38 (3H, t, J=7.0 Hz), 2.02-2.16 (2H, m), 2.32-2.46 (5H, m), 3.02-3.16 (2H, m), 3.18-3.36 (3H, m), 3.74-3.84 (2H, m), 4.02-4.12 (2H, m), 4.20-4.34 (6H, m), 4.60-4.72 (2H, m), 6.39 (1H, s), 6.90 (1H, d, J=8.3 Hz), 6.93-6.96 (1H, m), 7.05-7.08 (1H, m), 7.13 (1H, s), 7.19 (1H, s), 7.74 (1H, d, J=9.0 Hz), 9.60-9.86 (2H, broad), 11.00-11.20 (1H, broad)

Example 105

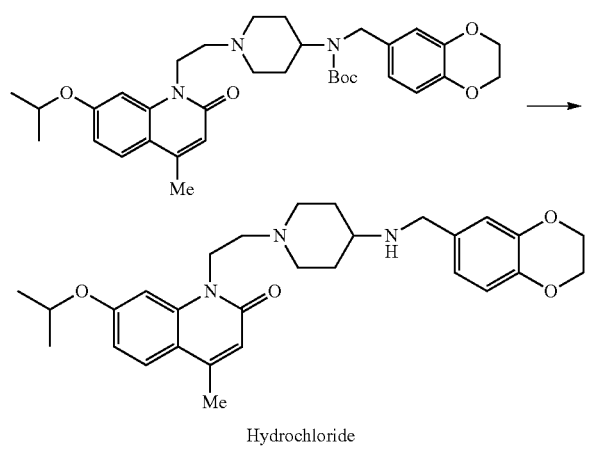

Hydrochloride

To 2.4 mL of methanol solution containing 0.24 g of tert-butyl (2,3-dihydro-1,4-benzodioxin-6-ylmethyl)(1-(2-(7-isopropoxy)-4-methyl-2-oxo-1,2-dihydroquinolin-1-yl)ethyl)piperidin-4-yl)carbamate, 2.4 mL of 4 mol/L hydrogen chloride/ethyl acetate solution was added at room temperature, and stirred at room temperature for 2 hours. 10 mL of ethyl acetate was added, and the resulting solid was filtered to give 0.21 g of 1-(2-(4-((2,3-dihydro-1,4-benzodioxin-6-ylmethyl)amino)piperidin-1-yl)ethyl)-7-isopropoxy-4-methylquinolin-2(1H)-one hydrochloride as a white solid.

$^1$H-NMR (DMSO-$d_6$) δ:
1.32 (6H, d, J=6.1 Hz), 2.00-2.16 (2H, m), 2.30-2.45 (5H, m), 3.04-3.16 (2H, m), 3.18-3.28 (3H, m), 3.74-3.82 (2H, m), 3.94-4.12 (2H, m), 4.25 (4H, s), 4.58-4.70 (2H, m), 4.98-5.12 (1H, m), 6.38 (1H, s), 6.90 (1H, d, J=8.3 Hz), 6.94 (1H, d, J=8.8 Hz), 7.07 (1H, d, J=8.3 Hz), 7.11 (1H, s), 7.19 (1H, s), 7.73 (1H, d, J=8.8 Hz), 9.58-9.84 (2H, broad), 10.95-11.10 (1H, broad)

Example 106

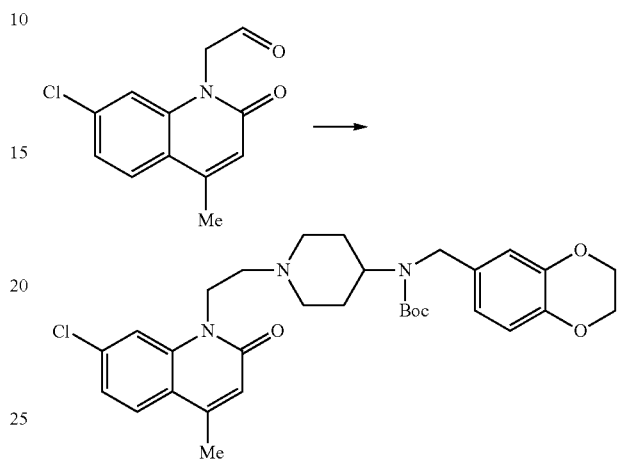

To 2 mL of dichloromethane solution containing 0.10 g of (7-chloro-4-methyl-2-oxo-1,2-dihydroquinolin-1-yl)acetaldehyde, 0.15 g of tert-butyl (2,3-dihydro-1,4-benzodioxin-6-ylmethyl)(piperidin-4-yl)carbamate and 0.020 mL of acetic acid were added, and stirred for 10 min. To the reaction mixture, 0.14 g of sodium triacetoxyborohydride was added, and stirred for 1 hour. Aqueous sodium hydrogen carbonate solution and chloroform were added, the organic layer was separated, and the aqueous layer was extracted with chloroform. The organic layer and extracts were combined, dried over anhydrous magnesium sulfate, and the solvent was removed under reduced pressure. The residue thus obtained was purified by silica gel column chromatography [eluent; hexane:ethyl acetate=1:1], to give 0.11 g of tert-butyl 1-(2-(7-chloro-4-methyl-2-oxo-1,2-dihydroquinolin-1-yl)ethyl) piperidin-4-yl) (2,3-dihydro-1,4-benzodioxin-6-ylmethyl) carbamate as a white oil.

$^1$H-NMR (CDCl$_3$) δ:
1.41 (9H, s), 1.56-1.73 (4H, m), 2.08-2.22 (2H, m), 2.43 (3H, d, J=1.0 Hz), 2.58-2.64 (2H, m), 2.98-3.06 (2H, m), 4.24 (4H, s), 4.24-4.36 (5H, m), 6.54 (1H, d, J=1.0 Hz), 6.66-6.80 (3H, m), 7.20 (1H, dd, J=8.6, 1.8 Hz), 7.47 (1H, d, J=1.8 Hz), 7.60 (1H, d, J=8.6 Hz)

Example 107

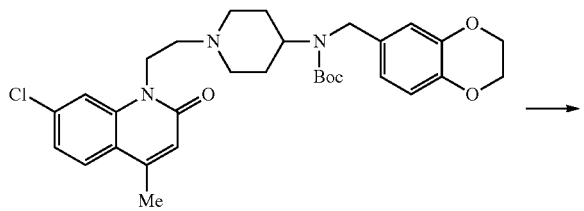

-continued

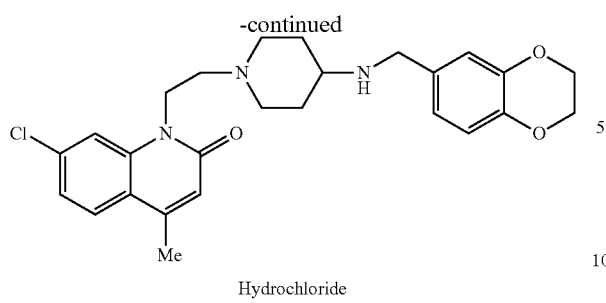

Hydrochloride

To 1 mL of methanol solution containing 0.11 g of tert-butyl 1-(2-(7-chloro-4-methyl-2-oxo-1,2-dihydroquinolin-1-yl)ethyl)piperidin-4-yl)(2,3-dihydro-1,4-benzodioxin-6-ylmethyl)carbamate, 1 mL of 4 mol/L hydrogen chloride/ethyl acetate solution was added, and stirred at room temperature for 4.5 hours. Ethyl acetate was added, and the resulting solid was filtered to give 0.080 g of 7-chloro-1-(2-(4-((2,3-dihydro-1,4-benzodioxin-6-ylmethyl)amino)piperidin-1-yl)ethyl)-4-methylquinolin-2(1H)-one hydrochloride as a white solid.

¹H-NMR (DMSO-$d_6$) δ:
1.85-1.98 (2H, m), 2.31-2.42 (2H, m), 2.47 (3H, d, J=1.0 Hz), 3.07-3.18 (2H, m), 3.32-3.43 (3H, m), 3.72-3.94 (2H, m), 4.09 (2H, s), 4.26 (4H, s), 4.57-4.64 (2H, m), 6.62 (1H, d, J=1.0 Hz), 6.94 (1H, d, J=8.3 Hz), 7.01 (1H, dd, J=8.3, 1.9 Hz), 7.10 (1H, d, J=1.9 Hz), 7.43 (1H, dd, J=8.6, 1.8 Hz), 7.76 (1H, d, J=1.8 Hz), 7.89 (1H, d, J=8.6 Hz)

Example 108

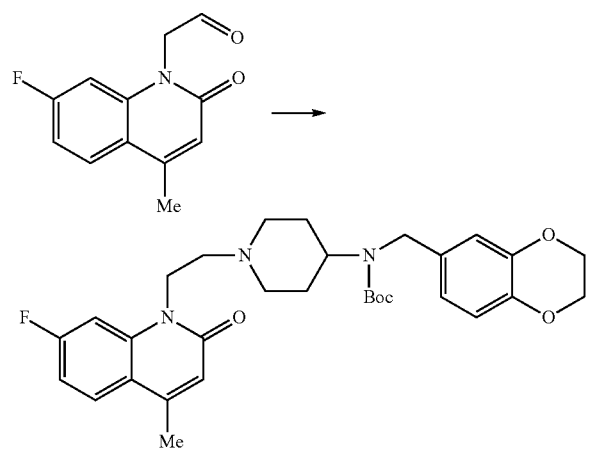

To 2.5 mL of dichloromethane solution containing 83 mg of (7-fluoro-4-methyl-2-oxo-1,2-dihydroquinolin-1-yl)acetaldehyde, 0.13 g of tert-butyl (2,3-dihydro-1,4-benzodioxin-6-ylmethyl)(piperidin-4-yl)carbamate and 25 μL of acetic acid were added, and stirred for 1 hour. To the reaction mixture, 0.12 g of sodium triacetoxyborohydride was added, and stirred for 50 min. Water and chloroform were added, and adjusted to pH 10.0 with aqueous saturated sodium hydrogen carbonate solution. The organic layer was separated, dried over anhydrous magnesium sulfate, and the solvent was removed under reduced pressure. The residue thus obtained was purified by silica gel column chromatography [eluent; hexane:ethyl acetate=1:3], to give 0.19 g of tert-butyl (2,3-dihydro-1,4-benzodioxin-6-ylmethyl)(1-(2-(7-fluoro-4-methyl-2-oxo-1,2-dihydroquinolin-1-yl)ethyl)piperidin-4-yl)carbamate as a colorless oil.

¹H-NMR (CDCl₃) δ:
1.33-1.78 (13H, m), 2.08-2.25 (2H, m), 2.43 (3H, s), 2.56-2.64 (2H, m), 2.98-3.11 (2H, m), 4.24 (4H, s), 4.24-4.35 (5H, m), 6.51 (1H, s), 6.73-6.80 (3H, m), 6.93-7.01 (1H, m), 7.09-7.18 (1H, m), 7.66 (1H, dd, J=6.2, 8.7 Hz)

Example 109

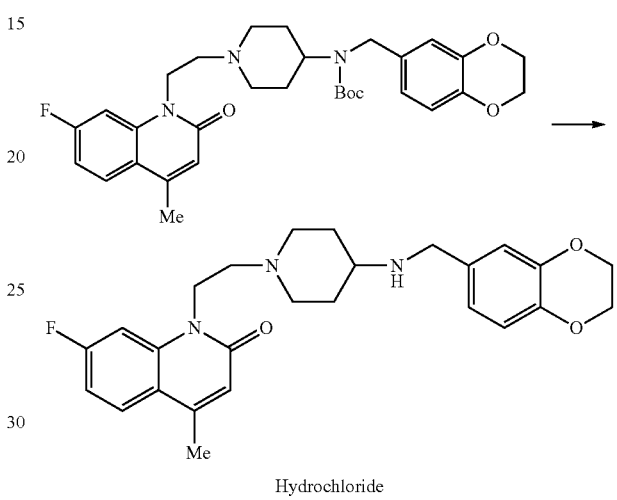

Hydrochloride

To 1.5 mL of methanol solution containing 0.17 g of tert-butyl (2,3-dihydro-1,4-benzodioxin-6-ylmethyl)(1-(2-(7-fluoro-4-methyl-2-oxoquinolin-1(2H)-yl)ethyl)piperidin-4-yl)carbamate, 1.5 mL of 4 mol/L hydrogen chloride/ethyl acetate solution was added, and stirred for 4 hours. Ethyl acetate was added, and the resulting solid was filtered to give 0.15 g of 1-(2-(4-((2,3-dihydro-1,4-benzodioxin-6-ylmethyl)amino)piperidin-1-yl)ethyl)-7-fluoro-4-methylquinolin-2(1H)-one hydrochloride as a white solid.

¹H-NMR (DMSO-$d_6$) δ:
1.73-1.91 (2H, m), 2.24-2.40 (2H, m), 2.48 (3H, s), 2.76-3.40 (5H, m), 3.65-3.84 (2H, m), 4.08 (2H, s), 4.26 (4H, s), 4.50-4.60 (2H, m), 6.57 (1H, s), 6.93-7.00 (2H, m), 7.06 (1H, s), 7.22-7.28 (1H, m), 7.46-7.52 (1H, m), 7.95 (1H, dd, J=8.8, 6.6 Hz)

Example 110

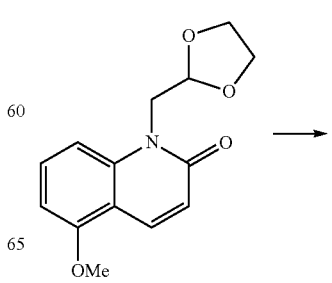

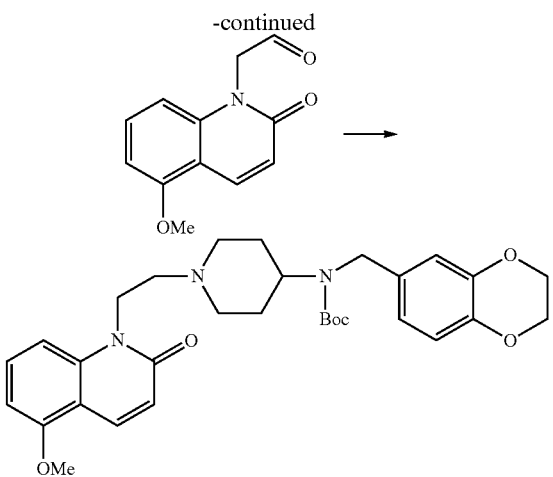

Example 111

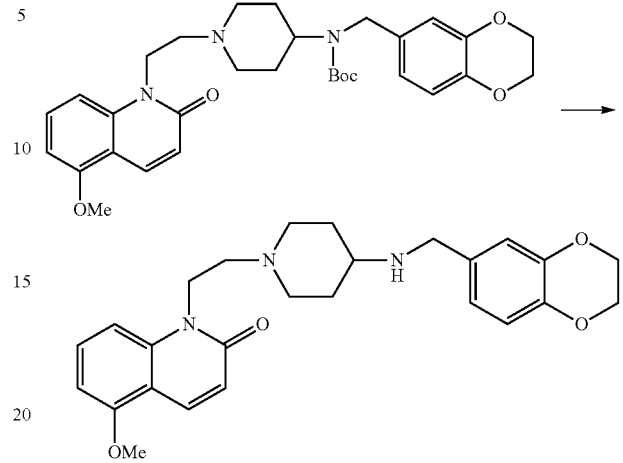

Hydrochloride (1) To 15 mL of 80% aqueous trifluoroacetic acid solution, 0.44 g of 1-(1,3-dioxolan-2-ylmethyl)-5-methoxyquinolin-2 (1H)-one was added, and stirred at room temperature for 5 hours. The solvent was removed under reduced pressure, ethyl acetate and water were added, the organic layer was separated, and sodium chloride was added to the aqueous layer, and extracted twice with ethyl acetate. The organic layer and extracts were combined, washed with aqueous saturated sodium chloride solution, dried over anhydrous magnesium sulfate, and the solvent was removed under reduced pressure to give (5-methoxy-2-oxoquinolin-1(2H)-yl)acetaldehyde as a pale brown solid.

$^1$H-NMR (CDCl$_3$) δ:

3.96 (3H, s), 5.13 (2H, s), 6.63 (1H, d, J=8.4 Hz), 6.70 (1H, d, J=9.8 Hz), 6.71 (1H, d, J=8.4 Hz), 7.45 (1H, t, J=8.4 Hz), 8.24 (1H, d, J=9.8 Hz), 9.66 (1H, s)

(2) To 2.4 mL of dichloromethane solution containing 0.10 g of (5-methoxy-2-oxoquinolin-1(2H)-yl)acetaldehyde, 0.16 g of tert-butyl (2,3-dihydro-1,4-benzodioxin-6-ylmethyl)(piperidin-4-yl)carbamate and 24 μL of acetic acid were added, and stirred for 20 min. To the reaction mixture, 0.15 g of sodium triacetoxyborohydride was added, and stirred for 50 min. Chloroform and aqueous saturated sodium hydrogen carbonate solution were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; hexane:ethyl acetate=1:3], to give 0.18 g of tert-butyl (2,3-dihydro-1,4-benzodioxin-6-ylmethyl)(1-(2-(5-methoxy-2-oxoquinolin-1 (2H)-yl)ethyl)piperidin-4-yl)carbamate as a pale yellow oil.

$^1$H-NMR (CDCl$_3$) δ:

1.30-1.75 (13H, m), 2.09-2.24 (2H, m), 2.56-2.65 (2H, m), 2.98-3.09 (2H, m), 3.94 (3H, s), 3.98-4.41 (9H, m), 6.61 (1H, d, J=9.8 Hz), 6.64-6.71 (2H, m), 6.74 (1H, s), 6.78 (1H, d, J=8.5 Hz), 6.98 (1H, d, J=8.5 Hz), 7.42-7.47 (1H, m), 8.12 (1H, d, J=9.8 Hz)

To 1.5 mL of methanol solution containing 0.182 g of tert-butyl (2,3-dihydro-1,4-benzodioxin-6-ylmethyl)(1-(2-(5-methoxy-2-oxoquinolin-1(2H)-yl)ethyl)piperidin-4-yl) carbamate, 1.5 mL of 4 mol/L hydrogen chloride/ethyl acetate solution was added, and stirred for 1.5 hours. Ethyl acetate was added, and the resulting solid was filtered to give 0.13 g of 1-(2-(4-((2,3-dihydro-1,4-benzodioxin-6-ylmethyl) amino)piperidin-1-yl)ethyl)-5-methoxyquinolin-2(1H)-one hydrochloride as a pale yellow solid.

$^1$H-NMR (DMSO-d$_6$) δ:

1.98-2.14 (2H, m), 2.30-2.40 (2H, m), 3.04-3.19 (2H, m), 3.19-3.30 (3H, m), 3.73-3.82 (2H, m), 3.94 (3H, s), 3.99-4.22 (2H, s), 4.25 (4H, s), 4.60-4.69 (2H, m), 6.59 (1H, d, J=9.8 Hz), 6.91 (1H, d, J=8.3 Hz), 6.92 (1H, d, J=8.0 Hz), 7.04 (1H, dd, J=2.1, 8.3 Hz), 7.16 (1H, d, J=2.1 Hz), 7.40 (1H, d, J=8.6 Hz), 7.56-7.63 (1H, m), 8.14 (1H, d, J=9.8 Hz), 9.52 (2H, s), 10.89 (1H, m)

Example 112

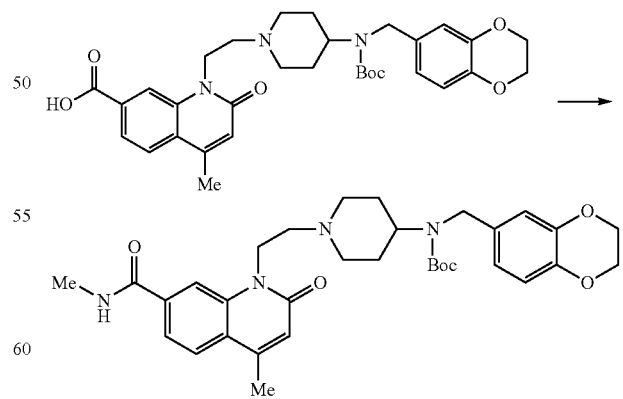

To 1.7 mL of dichloromethane solution containing 0.10 g of 1-(2-(4-((tert-butoxycarbonyl)(2,3-dihydro-1,4-benzodioxin-6-ylmethyl)amino)piperidin-1-yl)ethyl)-4-methyl-2-oxo-1,2-dihydroquinoline-7-carboxylic acid, 13 mg of methylamine hydrochloride, 0.12 g of O-(7-azabenzotriazol-1-yl)-1,1,3,3-tetramethyluronium hexafluorophosphate and 89 μL of triethylamine were added at room temperature, stirred for 30 min, and allowed to stand for 12 hours. Further, 13 mg of methylamine hydrochloride, 0.12 g of O-(7-azabenzotriazol-1-yl)-1,1,3,3-tetramethyluronium hexafluorophosphate, and 89 μL of triethylamine were added. Water and ethyl acetate were added, the insoluble material was filtered off, the organic layer was separated, washed with aqueous saturated sodium chloride solution, dried over anhydrous magnesium sulfate, and the solvent was removed under reduced pressure. The residue thus obtained was purified by basic silica gel column chromatography [eluent; chloroform: water=100:1], to give 58 mg of tert-butyl (2,3-dihydro-1,4-benzodioxin-6-ylmethyl) (1-(2-(4-methyl-7-((methylamino)carbonyl)-2-oxo-1,2-dihydroquinolin-1-yl)ethyl)piperidin-4-yl)carbamate as a brown oil.

$^1$H-NMR (CDCl$_3$) δ:
1.43 (9H, s), 1.60-1.84 (4H, m), 2.16-2.37 (2H, m), 2.48 (3H, s), 2.64-2.80 (2H, m), 2.97-3.16 (3H, m), 3.06 (3H, d, J=4.9 Hz), 3.85-4.33 (3H, m), 4.25 (4H, s), 4.42-4.50 (2H, m), 6.00-6.67 (1H, m), 6.62 (1H, s), 6.67-6.73 (1H, m), 6.75 (1H, d, J=2.0 Hz), 6.79 (1H, d, J=8.3 Hz), 7.58-7.64 (1H, m), 7.74 (1H, d, J=8.3 Hz), 7.95 (1H, s)

Example 113

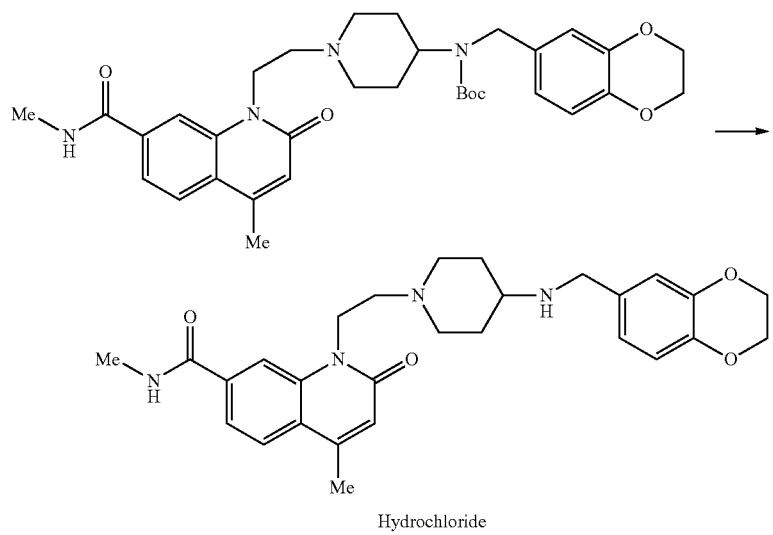

To 0.5 mL of methanol solution containing 58 mg of tert-butyl (2,3-dihydro-1,4-benzodioxin-6-ylmethyl)(1-(2-(4-methyl-7-((methylamino) carbonyl)-2-oxoquinolin-1(2H)-yl)ethyl)piperidin-4-yl)carbamate, 0.5 mL of 4 mol/L hydrogen chloride/ethyl acetate solution was added, and stirred for 5.5 hours. Ethyl acetate was added, and the resulting solid was filtered to give 0.032 g of 1-(2-(4-((2,3-dihydro-1,4-benzodioxin-6-ylmethyl)amino)piperidin-1-yl)ethyl)-N-methyl-4-methyl-2-oxo-1,2-dihydroquinoline-7-carboxamide hydrochloride as a white solid.

$^1$H-NMR (DMSO-d$_6$) δ:
1.84-1.99 (2H, m), 2.32-2.42 (2H, m), 2.50-2.51 (1H, m), 2.50 (3H, s), 2.86 (3H, s), 3.08-3.22 (2H, m), 3.25-3.46 (3H, m), 3.81-3.94 (2H, m), 4.10 (2H, s), 4.26 (4H, s), 4.66-4.73 (2H, m), 6.68 (1H, d, J=1.2 Hz), 6.94 (1H, d, J=8.4 Hz), 7.00 (1H, dd, J=8.3, 2.0 Hz), 7.09 (1H, d, J=2.0 Hz), 7.79 (1H, dd, J=8.4, 1.5 Hz), 7.96 (1H, d, J=8.4 Hz), 7.98-8.00 (1H, m)

Example 114

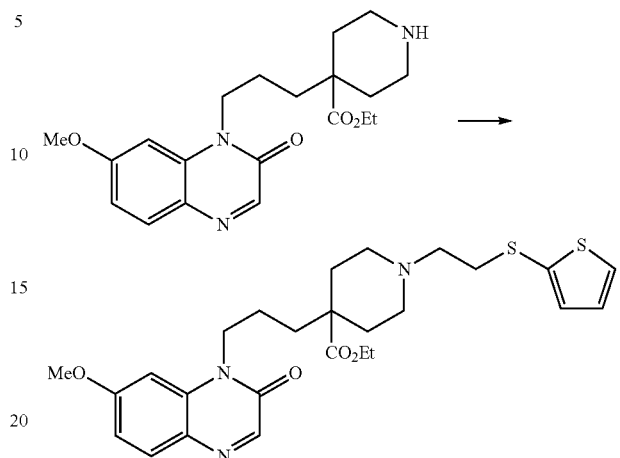

To 2 mL of an N,N-dimethylformamide solution containing 0.15 g of ethyl 4-(3-(7-methoxy-2-oxoquinoxalin-1(2H)-yl)propyl)piperidine-4-carboxylate, 0.25 mL of an N,N-dimethylformamide solution containing 0.10 g of 2-(2-bromoethylthio)thiophene and 0.12 g of potassium carbonate were added, and stirred at 55-60° C. for 4.5 hours. Water and ethyl acetate were added, the organic layer was separated, washed sequentially with water and aqueous saturated sodium chloride solution, dried over anhydrous sodium sulfate, and the solvent was removed under reduced pressure. The residue thus obtained was purified by silica gel column chromatography [eluent; chloroform:methanol=20:1], to give 0.23 g of ethyl 4-(3-(7-methoxy-2-oxoquinoxalin-1 (2H)-yl)propyl)-1-(2-(2-thienylthio-ethyl)piperidine-4-carboxylate as a yellow oil.

$^1$H-NMR (CDCl$_3$) δ:
1.18 (3H, t, J=7.1 Hz), 1.40-1.51 (2H, m), 1.56-1.72 (4H, m), 2.00-2.16 (4H, m), 2.52-2.60 (2H, m), 2.64-2.72 (2H, m), 2.86-2.91 (2H, m), 3.92 (3H, s), 4.06-4.20 (2H, m), 4.09 (2H, q, J=7.1 Hz), 6.68 (1H, d, J=2.5 Hz), 6.92 (1H, dd, J=8.9, 2.5

Hz), 6.95 (1H, dd, J=5.3, 3.5 Hz), 7.09-7.12 (1H, m), 7.30-7.34 (1H, m), 7.79 (1H, d, J=8.9 Hz), 8.11 (1H, s)

Example 115

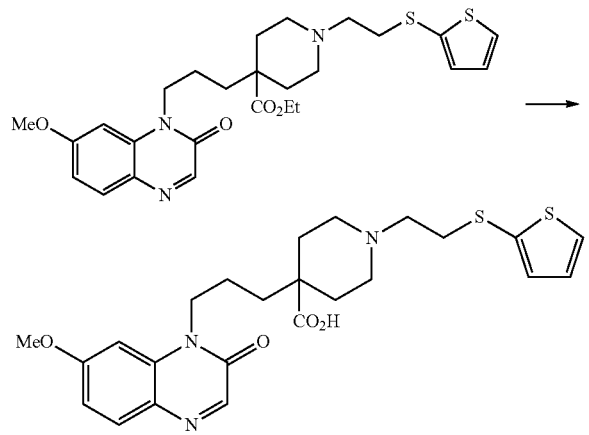

To 2 mL of an ethanol solution containing 0.23 g of ethyl 4-(3-(7-methoxy-2-oxoquinoxalin-1(2H)-yl)propyl)-1-(2-(2-thienylthio-ethyl)piperidine-4-carboxylate, 1 mL of 20% aqueous sodium hydroxide solution was added and stirred under reflux with heating for 2 hours. After ethanol was removed under reduced pressure, water was added, adjusted to pH 5.4 with 6.0 mol/L hydrochloric acid, and the solvent was removed under reduced pressure. The residue thus obtained was purified by silica gel column chromatography [eluent; chloroform:methanol=5:1], to give 40 mg of 4-(3-(7-methoxy-2-oxoquinoxalin-1(2H)-yl)propyl)-1-(2-(2-thienylthio)ethyl)piperidine-4-carboxylic acid as a pale yellow solid.

$^1$H-NMR (DMSO-$d_6$) δ:
1.27-1.36 (2H, m), 1.50-1.61 (4H, m), 1.88-2.00 (4H, m), 2.41-2.69 (4H, m), 2.87-2.94 (2H, m), 3.91 (3H, s), 4.13-4.20 (2H, m), 6.96 (1H, d, J=2.4 Hz), 7.00 (1H, dd, J=8.8, 2.4 Hz), 7.03 (1H, dd, J=5.4, 3.4 Hz), 7.16 (1H, dd, J=3.4, 1.3 Hz), 7.58 (1H, dd, J=5.4, 1.3 Hz), 7.75 (1H, d, J=8.8 Hz), 8.03 (1H, s)

Example 116

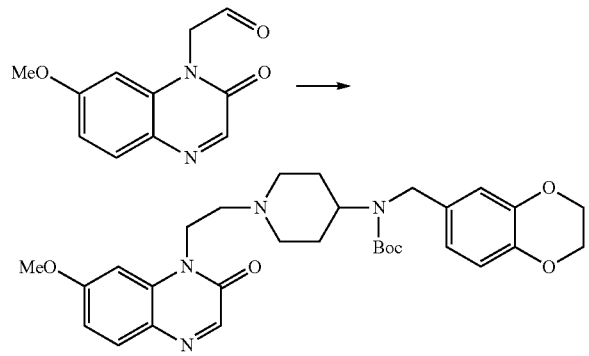

To 2.0 mL of dichloromethane solution containing 70 mg of (7-methoxy-2-oxoquinoxalin-1(2H)-yl)acetaldehyde, 0.11 g of tert-butyl (2,3-dihydro-1,4-benzodioxin-6-ylmethyl)(piperidin-4-yl)carbamate and 20 μL of acetic acid were added, and stirred at room temperature for 20 min. To the reaction mixture, 0.10 g of sodium triacetoxyborohydride was added, and stirred at the same temperature for 2 hours. Chloroform and water were added, and aqueous saturated sodium hydrogen carbonate solution was added to make the pH 8.0 or more. The organic layer was separated, dried over anhydrous magnesium sulfate, and the solvent was removed under reduced pressure. The residue thus obtained was purified by silica gel column chromatography [eluent; hexane:ethyl acetate=1:2], to give 83 mg of tert-butyl (2,3-dihydro-1,4-benzodioxin-6-ylmethyl)(1-(2-(7-methoxy-2-oxoquinoxalin-1(2H)-yl)ethyl)piperidin-4-yl)carbamate as a brown oil.

$^1$H-NMR (CDCl$_3$) δ:
1.43 (9H, s), 1.56-1.72 (4H, m), 2.07-2.27 (2H, m), 2.60-2.69 (2H, m), 2.94-3.08 (2H, m), 3.90 (3H, s), 4.25 (4H, s), 4.23-4.38 (5H, m), 6.66-6.83 (4H, m), 6.90-6.94 (1H, m), 7.78 (1H, d, J=9.0 Hz), 8.11 (1H, s)

Example 117

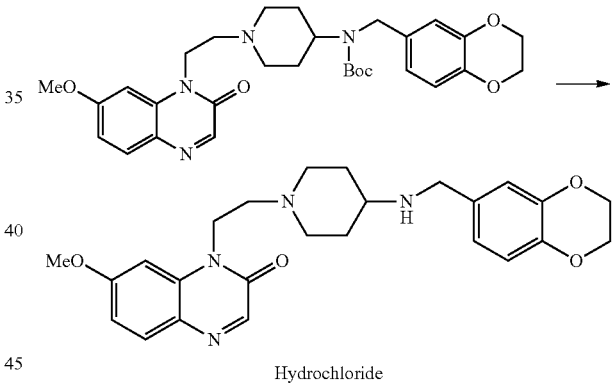

To 0.5 mL of methanol solution containing 83 mg of tert-butyl (2,3-dihydro-1,4-benzodioxin-6-ylmethyl)(1-(2-(7-methoxy-2-oxoquinoxalin-1(2H)-yl)ethyl)piperidin-4-yl)carbamate, 0.5 mL of 4 mol/L hydrogen chloride/ethyl acetate solution was added, stirred at room temperature for 2 hours, and allowed to stand at the same temperature for 14 hours. Ethyl acetate was added, and the resulting solid was filtered to give 68 mg of 1-(2-(4-((2,3-dihydro-1,4-benzodioxin-6-ylmethyl)amino)piperidin-1-yl)ethyl)-7-methoxyquinoxalin-2(1H)-one hydrochloride as a black solid.

$^1$H-NMR (DMSO-$d_6$) δ:
1.86-1.96 (2H, m), 2.30-2.42 (2H, m), 3.06-3.21 (2H, m), 3.28-3.48 (3H, m), 3.63-3.93 (2H, m), 3.96 (3H, s), 4.09 (2H, s), 4.26 (4H, s), 4.59-4.66 (2H, m), 6.91-7.02 (2H, m), 7.06-7.12 (3H, m), 7.84 (1H, d, J=8.5 Hz), 8.10 (1H, s)

Example 118

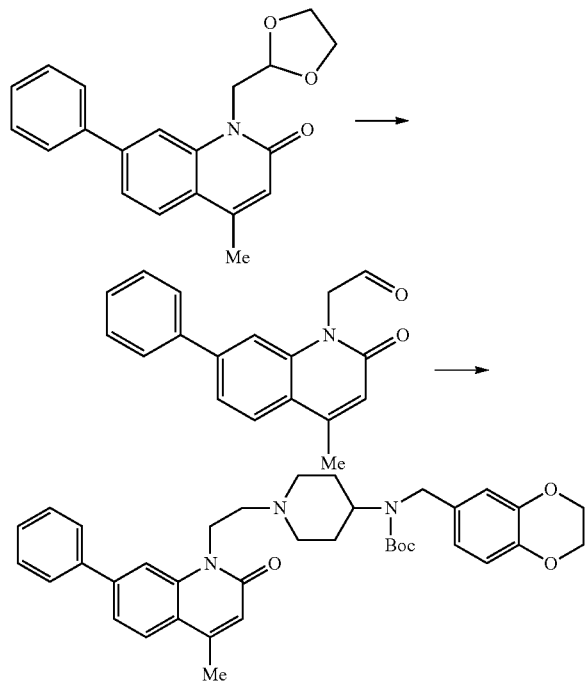

(1), To 94 mg of 1-(1,3-dioxolan-2-ylmethyl)-4-methyl-7-phenylquinolin-2(1H)-one, 3 mL of 80% aqueous trifluoroacetic acid solution was added, and stirred at room temperature for 5 and half hours, thereafter ethyl acetate and aqueous saturated sodium hydrogen carbonate solution were added, the organic layer was separated, and the aqueous layer was extracted with ethyl acetate. The organic layer and extracts were combined, washed sequentially with water and aqueous saturated sodium chloride solution, dried over anhydrous magnesium sulfate, and the solvent was removed under reduced pressure to give (4-methyl-2-oxo-7-phenyl-1,2-dihydroquinolin-1-yl)acetaldehyde as a pale brown oil.

$^1$H-NMR (CDCl$_3$) δ:
2.54 (3H, d, J=1.0 Hz), 5.22 (2H, s), 6.65-6.66 (1H, m), 7.18 (1H, d, J=1.7 Hz), 7.38-7.45 (1H, m), 7.46-7.53 (3H, m), 7.56-7.60 (2H, m), 7.82 (1H, d, J=8.3 Hz), 9.73 (1H, s)

(2) To 2 mL of dichloromethane solution containing the (4-methyl-2-oxo-7-phenyl-1,2-dihydroquinolin-1-yl)acetaldehyde obtained, 61 mg of tert-butyl (2,3-dihydro-1,4-benzodioxin-6-ylmethyl) (piperidin-4-yl)carbamate and 20 μL of acetic acid were added, and stirred for 20 min. To the reaction mixture, 55 mg of sodium triacetoxyborohydride was added, and stirred for 40 min. Water, chloroform and aqueous saturated sodium hydrogen carbonate solution were added, the organic layer was separated, dried over anhydrous magnesium sulfate, and the solvent was removed under reduced pressure. The residue thus obtained was purified by silica gel column chromatography [eluent; hexane:ethyl acetate=1:2], to give 47 mg of tert-butyl (2,3-dihydro-1,4-benzodioxin-6-ylmethyl) (1-(2-(4-methyl-2-oxo-7-phenyl-1,2-dihydroquinolin-1-yl)ethyl)piperidin-4-yl)carbamate as a colorless oil.

$^1$H-NMR (CDCl$_3$) δ:
1.35-1.70 (13H, m), 2.09-2.22 (2H, m), 2.48 (3H, s), 2.62-2.69 (2H, m), 3.02-3.10 (2H, m), 4.22-4.26 (7H, m), 4.42-4.49 (2H, m), 6.57 (1H, s), 6.63-6.80 (3H, m), 7.39-7.52 (4H, m), 7.58-7.66 (3H, m), 7.76 (1H, d, J=8.1 Hz)

Example 119

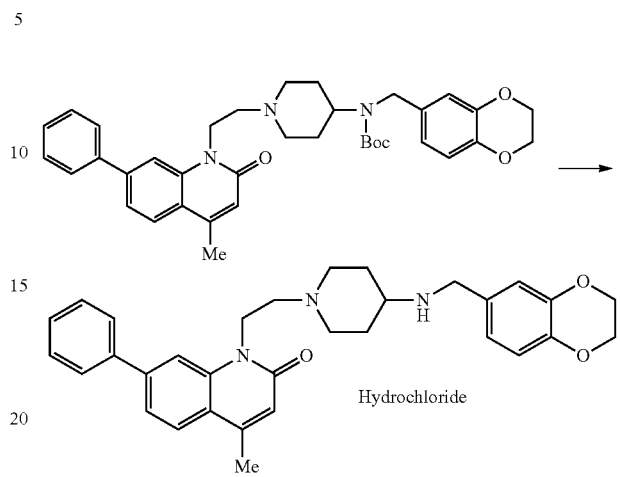

To 0.4 mL of methanol solution containing 47 mg of tert-butyl (2,3-dihydro-1,4-benzodioxin-6-ylmethyl)(1-(2-(4-methyl-2-oxo-7-phenylquinolin-1(2H)-yl)ethyl)piperidin-4-yl)carbamate, 0.4 mL of 4 mol/L hydrogen chloride/ethyl acetate solution was added, and stirred for 30 min. 0.8 mL of methanol and 0.8 mL of 4 mol/L hydrogen chloride/ethyl acetate solution were further added, stirred for 2 hours and allowed to stand at room temperature for 13 hours. Ethyl acetate was added, and the resulting solid was filtered to give 34 mg of 1-(2-(4-(((2,3-dihydro-1,4-benzodioxin-6-ylmethyl)amino)piperidin-1-yl)ethyl)-4-methyl-7-phenylquinolin-2 (1H)-one hydrochloride as a white solid.

$^1$H-NMR (DMSO-d$_6$) δ:
1.98-2.10 (2H, m), 2.32-2.40 (2H, m), 2.49-2.52 (3H, m), 3.05-3.16 (2H, m), 3.20-3.58 (3H, m), 3.80-3.88 (2H, m), 4.04-4.11 (2H, m), 4.25 (4H, s), 4.74-4.82 (2H, m), 6.61 (1H, d, J=1.0 Hz), 6.91 (1H, d, J=8.4 Hz), 7.04 (1H, dd, J=8.4, 2.0 Hz), 7.15 (1H, d, J=2.0 Hz), 7.43-7.48 (1H, m), 7.50-7.56 (2H, m), 7.66 (1H, dd, J=8.4, 1.2 Hz), 7.82-7.84 (1H, m), 7.91-7.96 (3H, m)

Example 120

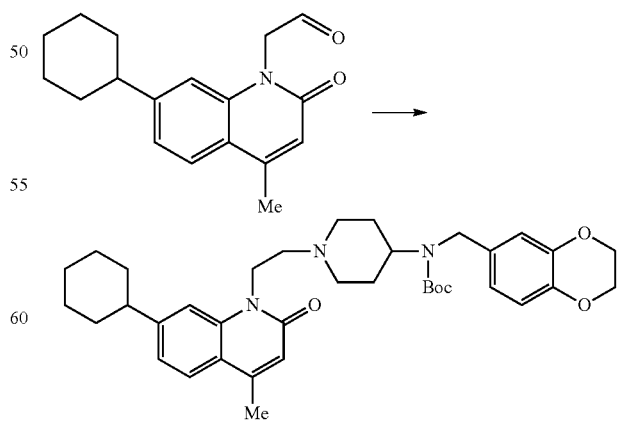

To 1.5 mL of dichloromethane solution containing 56 mg of (7-cyclohexyl-4-methyl-2-oxo-1,2-dihydroquinolin-1-yl)

acetaldehyde, 69 mg of tert-butyl (2,3-dihydro-1,4-benzo-dioxin-6-ylmethyl)(piperidin-4-yl)carbamate and 15 µL of acetic acid were added, and stirred for 5 min. To the reaction mixture, 63 mg of sodium triacetoxyborohydride was added, and stirred for 45 min. Water and chloroform were added, the organic layer was separated, washed sequentially with water and aqueous saturated sodium chloride solution, dried over anhydrous magnesium sulfate, and the solvent was removed under reduced pressure. The residue thus obtained was purified by silica gel column chromatography [eluent; hexane:ethyl acetate=1:2], to give 73 mg of tert-butyl (1-(2-(7-cyclohexyl-4-methyl-2-oxo-1,2-dihydroquinolin-1-yl)ethyl)piperidin-4-yl)(2,3-dihydro-1,4-benzodioxin-6-ylmethyl)carbamate as a colorless oil.

$^1$H-NMR (CDCl$_3$) δ:
1.22-1.82 (19H, m), 1.86-1.95 (4H, m), 2.10-2.25 (2H, m), 2.42 (3H, s), 2.57-2.66 (3H, m), 3.04-3.12 (2H, m), 4.00-4.34 (3H, m), 4.24 (4H, s), 4.37-4.43 (2H, m), 6.50 (1H, s), 6.66-6.70 (1H, m), 6.74 (1H, s), 6.78 (1H, d, J=8.3 Hz), 7.10 (1H, d, J=8.2 Hz), 7.22 (1H, s), 7.61 (1H, d, J=8.2 Hz)

Example 121

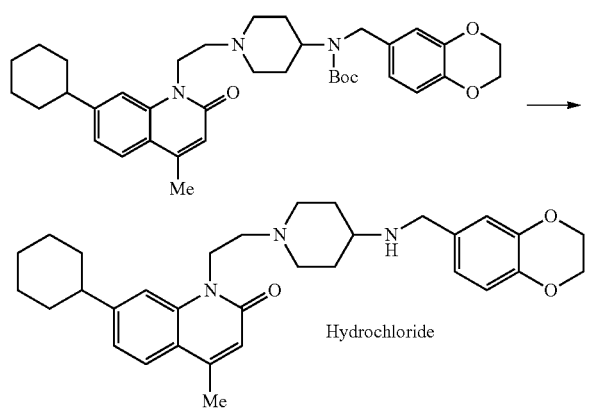

To 0.7 mL of methanol solution containing 73 mg of tert-butyl (1-(2-(7-cyclohexyl-4-methyl-2-oxo-1,2-dihydroquinolin-1-yl)ethyl)piperidin-4-yl) (2,3-dihydro-1,4-benzodioxin-6-ylmethyl)carbamate, 0.7 mL of 4 mol/L hydrogen chloride/ethyl acetate solution was added at room temperature, and stirred for 1.5 hours. Ethyl acetate was added, and the resulting solid was filtered to give 43 mg of 7-cyclohexyl-1-(2-(4-((2,3-dihydro-1,4-benzodioxin-6-ylmethyl)amino)piperidin-1-yl)ethyl)-4-methylquinolin-2(1H)-one hydrochloride as a white solid.

$^1$H-NMR (DMSO-d$_6$) δ:
1.29-1.46 (4H, m), 1.54-1.76 (2H, m), 1.79-1.87 (4H, m), 1.97-2.10 (2H, m), 2.31-2.39 (2H, m), 2.44 (3H, s), 2.66-2.79 (1H, m), 3.06-3.17 (2H, m), 3.21-3.53 (3H, m), 3.76-3.84 (2H, m), 4.05-4.12 (2H, m), 4.26 (4H, s), 4.63-4.70 (2H, m), 6.51 (1H, s), 6.92 (1H, d, J=8.3 Hz), 7.03 (1H, dd, J=8.3, 2.0 Hz), 7.14 (1H, d, J=2.0 Hz), 7.24 (1H, d, J=8.3 Hz), 7.55 (1H, s), 7.75 (1H, d, J=8.3 Hz)

Example 122

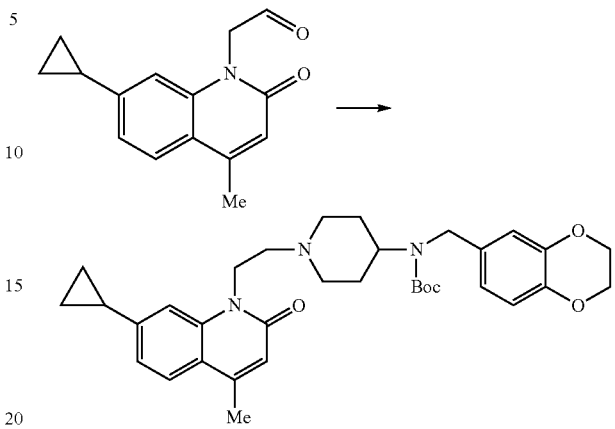

To 1.5 mL of dichloromethane solution containing 53 mg of (7-cyclopropyl-4-methyl-2-oxo-1,2-dihydroquinolin-1-yl)acetaldehyde, 77 mg of tert-butyl (2,3-dihydro-1,4-benzodioxin-6-ylmethyl)(piperidin-4-yl)carbamate and 15 µL of acetic acid were added, and stirred for 10 min. To the reaction mixture, 70 mg of sodium triacetoxyborohydride was added, and stirred for 30 min. Water, chloroform and aqueous saturated sodium hydrogen carbonate solution were added, the organic layer was separated, and the aqueous layer was neutralized with aqueous saturated sodium hydrogen carbonate solution, thereafter extracted with ethyl acetate. The organic layer and extracts were combined, washed sequentially with water and aqueous saturated sodium chloride solution, dried over anhydrous magnesium sulfate, and the solvent was removed under reduced pressure. The residue thus obtained was purified by silica gel column chromatography [eluent; hexane:ethyl acetate=1:2], to give 99 mg of tert-butyl (1-(2-(7-cyclopropyl-4-methyl-2-oxo-1,2-dihydroquinolin-1-yl)ethyl)piperidin-4-yl)(2,3-dihydro-1,4-benzodioxin-6-ylmethyl)carbamate as a colorless oil.

$^1$H-NMR (CDCl$_3$) δ:
0.76-0.81 (2H, m), 1.05-1.11 (2H, m), 1.36-1.76 (13H, m), 1.96-2.04 (1H, m), 2.11-2.26 (2H, m), 2.41 (3H, d, J=1.0 Hz), 2.56-2.64 (2H, m), 3.02-3.12 (2H, m), 4.02-4.41 (5H, m), 4.24 (4H, s), 6.47 (1H, d, J=1.0 Hz), 6.69 (1H, d, J=8.3 Hz), 6.74 (1H, s), 6.78 (1H, d, J=8.3 Hz), 6.89 (1H, dd, J=8.3, 1.5 Hz), 7.11-7.13 (1H, m), 7.56 (1H, d, J=8.3 Hz)

Example 123

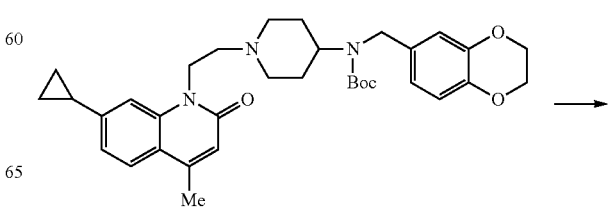

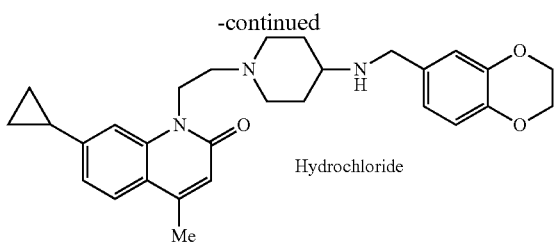

Hydrochloride

To 1 mL of methanol solution containing 95 mg of tert-butyl (1-(2-(7-cyclopropyl-4-methyl-2-oxoquinolin-1(2H)-yl)ethyl)piperidin-4-yl)(2,3-dihydro-1,4-benzodioxin-6-yl-methyl)carbamate, 1 mL of 4 mol/L hydrogen chloride/ethyl acetate solution was added at room temperature, and stirred for 1.5 hours. Ethyl acetate was added, and the resulting solid was filtered to give 45 mg of 7-cyclopropyl-1-(2-(4-((2,3-dihydro-1,4-benzodioxin-6-ylmethyl)amino)piperidin-1-yl)ethyl)-4-methylquinolin-2(1H)-one hydrochloride as a white solid.

$^1$H-NMR (DMSO-$d_6$) δ:
0.86-0.92 (2H, m), 1.07-1.14 (2H, m), 1.83-2.02 (2H, m), 2.12-2.20 (1H, m), 2.31-2.41 (2H, m), 2.45 (3H, s), 3.06-3.22 (2H, m), 3.31-3.42 (3H, m), 3.60-4.15 (4H, m), 4.26 (4H, s), 4.62-4.68 (2H, m), 6.51 (1H, s), 6.92-7.02 (3H, m), 7.08 (1H, s), 7.35 (1H, s), 7.75 (1H, d, J=8.0 Hz)

Example 124

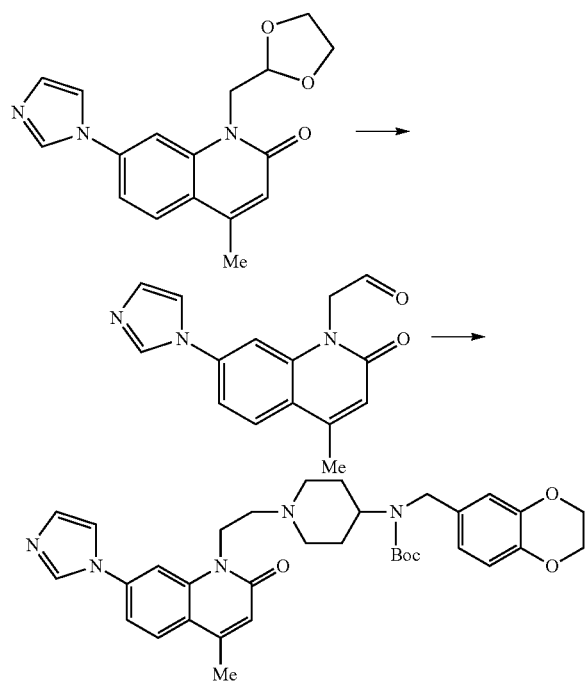

(1) To 70 mg of 1-(1,3-dioxolan-2-ylmethyl)-7-(1H-imidazol-1-yl)-4-methylquinolin-2(1H)-one, 2 mL of 80% aqueous trifluoroacetic acid solution, was added, and stirred at room temperature for 1 hour, thereafter allowed to stand at room temperature for 14 hours. Ethyl acetate was added, neutralized with aqueous saturated sodium hydrogen carbonate solution, ethyl acetate was added, the organic layer was separated, and the aqueous layer was extracted 3 times with ethyl acetate. The organic layer and extracts were combined, dried over anhydrous magnesium sulfate, and the solvent was removed under reduced pressure to give (7-(1H-imidazol-1-yl)-4-methyl-2-oxo-1,2-dihydroquinolin-1-yl)acetaldehyde as a white solid.

$^1$H-NMR (CDCl$_3$) δ:
2.46 (3H, s), 5.36 (2H, s), 6.07-6.11 (1H, m), 6.54-6.58 (1H, m), 7.15-7.18 (1H, m), 7.58-7.62 (1H, m), 7.86-7.95 (2H, m), 8.45 (1H, s), 9.70 (1H, s)

(2) To 4 mL of dichloromethane solution containing the (7-(1H-imidazol-1-yl)-4-methyl-2-oxo-1,2-dihydroquinolin-1-yl)acetaldehyde obtained, 78 mg of tert-butyl (2,3-dihydro-1,4-benzodioxin-6-ylmethyl)(piperidin-4-yl)carbamate and 40 μL of acetic acid were added, and stirred for 5 min. To the reaction mixture, 71 mg of sodium triacetoxyborohydride was added, and stirred for 1.5 hours. 0.4 mL of methanol was added and stirred for 1 hour. 7.2 mg of sodium cyanoborohydride was added, and stirred for 1 hour and 40 min. Chloroform and aqueous saturated sodium hydrogen carbonate solution were added, and the aqueous layer was extracted with chloroform. The organic layer and extracts were combined, dried over anhydrous magnesium sulfate, and the solvent was removed under reduced pressure. The residue thus obtained was purified by silica gel column chromatography [eluent; chloroform:methanol=50:1], to give 47 mg of tert-butyl (2,3-dihydro-1,4-benzodioxin-6-ylmethyl) (1-(2-(7-(1H-imidazol-1-yl)-4-methyl-2-oxoquinolin-1(2H)-yl)ethyl)piperidin-4-yl)carbamate as a pale brown oil.

$^1$H-NMR (CDCl$_3$) δ:
1.35-1.74 (13H, m), 2.08-2.24 (2H, m), 2.48 (3H, s), 2.60-2.70 (2H, m), 2.98-3.10 (2H, m), 4.00-4.47 (9H, m), 6.59 (1H, s), 6.66-6.82 (3H, m), 7.20-7.55 (4H, m), 7.79 (1H, d, J=8.8 Hz), 7.97 (1H, s)

Example 125

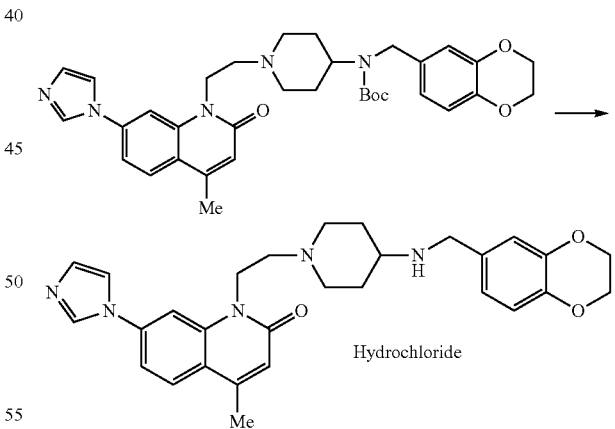

Hydrochloride

To 0.5 mL of methanol solution containing 45 mg of tert-butyl (2,3-dihydro-1,4-benzodioxin-6-ylmethyl)(1-(2-(7-(1H-imidazol-1-yl)-4-methyl-2-oxoquinolin-1(2H)-yl)ethyl)piperidin-4-yl)carbamate, 1 mL of 4 mol/L hydrogen chloride/ethyl acetate solution was added at room temperature, and stirred for 2 hours. Ethyl acetate was added, and the resulting solid was filtered to give 32 mg of 1-(2-(4-((2,3-dihydro-1,4-benzodioxin-6-ylmethyl)amino)piperidin-1-yl)ethyl)-7-(1H-imidazol-1-yl)-4-methylquinolin-2(1H)-one hydrochloride as a white solid.

¹H-NMR (DMSO-d₆) δ:
1.88-2.02 (2H, m), 2.32-2.42 (2H, m), 2.46-2.56 (3H, m), 3.09-3.20 (2H, m), 3.29-3.45 (3H, m), 3.80-3.89 (2H, m), 4.10 (2H, s), 4.26 (4H, s), 4.71-4.78 (2H, s), 6.70 (1H, d, J=1.2 Hz), 6.94 (1H, d, J=8.3 Hz), 7.00 (1H, dd, J=8.3, 2.0 Hz), 7.10 (1H, d, J=2.0 Hz), 7.76 (1H, dd, J=8.7, 1.8 Hz), 7.84 (1H, s), 8.03 (1H, J=1.8 Hz), 8.09 (1H, d, J=8.7 Hz), 8.43 (1H, s), 9.73 (1H, s)

Example 126

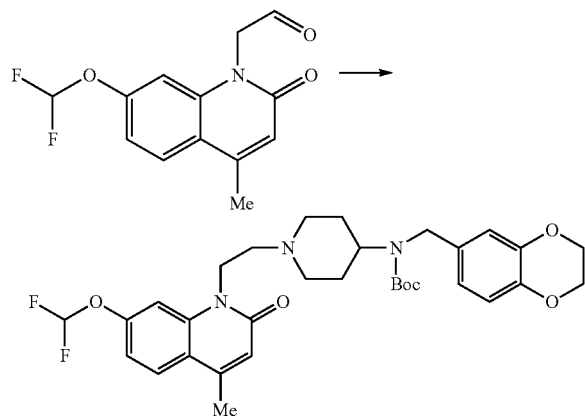

To 1.5 mL of dichloromethane solution containing 0.12 g of (7-(difluoromethoxy)-4-methyl-2-oxoquinolin-1(2H)-yl)acetaldehyde, 0.16 g of tert-butyl (2,3-dihydro-1,4-benzodioxin-6-ylmethyl)(piperidin-4-yl)carbamate and 15 μL of acetic acid were added, and stirred for 5 min. To the reaction mixture, 0.14 g of sodium triacetoxyborohydride was added, and stirred for 40 min. Water, chloroform and aqueous saturated sodium hydrogen carbonate solution were added, the organic layer was separated, washed sequentially with water and aqueous saturated sodium chloride solution, dried over anhydrous magnesium sulfate, and the solvent was removed under reduced pressure. The residue thus obtained was purified by silica gel column chromatography [eluent; hexane:ethyl acetate=2:3], to give 0.19 mg of tert-butyl (1-(2-(7-(difluoromethoxy)-4-methyl-2-oxo-1,2-dihydroquinolin-1-yl)ethyl)piperidin-4-yl)(2,3-dihydro-1,4-benzodioxin-6-ylmethyl)carbamate as a colorless oil.

¹H-NMR (CDCl₃) δ:
1.42 (9H, s), 1.60-1.72 (4H, m), 2.06-2.23 (2H, m), 2.44 (3H, d, J=1.0 Hz), 2.56-2.64 (2H, m), 2.98-3.06 (2H, m), 4.00-4.35 (9H, m), 6.53 (1H, d, J=1.0 Hz), 6.61 (1H, t, J=73.1 Hz), 6.66-6.72 (1H, m), 6.74 (1H, d, J=1.7 Hz), 6.78 (1H, d, J=8.5 Hz), 7.01 (1H, dd, J=8.6, 2.2 Hz), 7.19 (1H, d.=2.2 Hz), 7.68 (1H, d, J=8.6 Hz)

Example 127

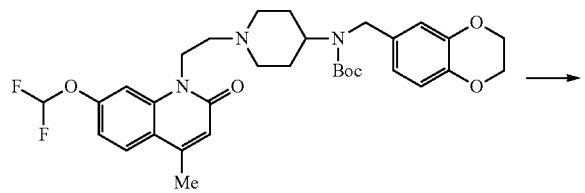

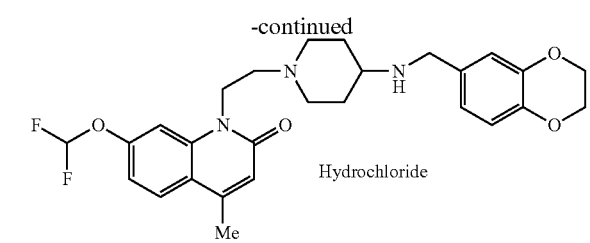

To 1 mL of methanol solution containing 0.16 g of tert-butyl (1-(2-(7-(difluoromethoxy)-4-methyl-2-oxo-1,2-dihydroquinolin-1-yl)ethyl)piperidin-4-yl)(2,3-dihydro-1,4-benzodioxin-6-ylmethyl)carbamate, 1 mL of 4 mol/L hydrogen chloride/ethyl acetate solution was added at room temperature, and stirred for 1 hour. Ethyl acetate was added, and the resulting solid was filtered to give 87 mg of 7-(difluoromethoxy)-1-(2-(4-((2,3-dihydro-1,4-benzodioxin-6-ylmethyl)amino)piperidin-1-yl)ethyl)-4-methylquinolin-2(1H)-one hydrochloride as a white solid.

¹H-NMR (DMSO-d₆) δ:
2.00-2.11 (2H, m), 2.32-2.42 (2H, m), 2.45 (3H, s), 3.06-3.40 (5H, m), 3.74-3.83 (2H, m), 4.03-4.12 (2H, m), 4.25 (4H, s), 4.60-4.68 (2H, m), 6.55 (1H, s), 6.88-6.92 (1H, m), 7.06 (1H, d, J=8.3 Hz), 7.14-7.20 (2H, m), 7.58 (1H, s), 7.70 (1H, t, J=74.4 Hz), 7.87-7.92 (1H, m), 9.53-9.71 (2H, m), 10.78-10.96 (1H, m)

Example 128

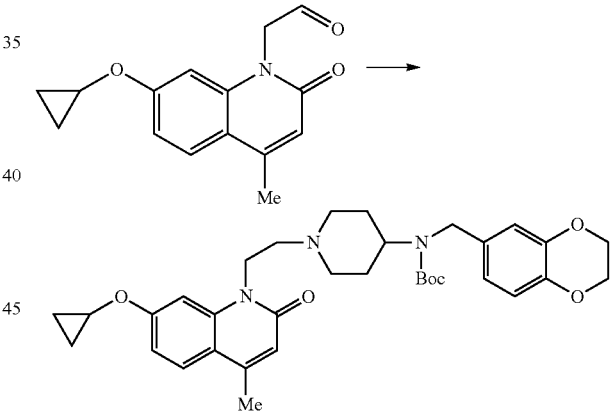

To 2 mL of dichloromethane solution containing 60 mg of (7-cyclopropoxy-4-methyl-2-oxo-1,2-dihydroquinolin-1-yl)acetaldehyde, 81 mg of tert-butyl (2,3-dihydro-1,4-benzodioxin-6-ylmethyl)(piperidin-4-yl)carbamate and 20 μL of acetic acid were added, and stirred for 15 min. To the reaction mixture, 74 mg of sodium triacetoxyborohydride was added, and stirred for 40 min. Chloroform and aqueous saturated sodium hydrogen carbonate solution were added, the organic layer was separated, washed sequentially with water and aqueous saturated sodium chloride solution, dried over anhydrous magnesium sulfate, and the solvent was removed under reduced pressure. The residue thus obtained was purified by silica gel column chromatography [eluent; hexane:ethyl acetate=1:4], to give 0.10 g of tert-butyl (1-(2-(7-cyclopropoxy-4-methyl-2-oxo-1,2-dihydroquinolin-1-yl)ethyl)piperidin-4-yl)(2,3-dihydro-1,4-benzodioxin-6-ylmethyl)carbamate as a colorless oil.

¹H-NMR (CDCl₃) δ:
0.82-0.86 (4H, m), 1.42 (9H, m), 1.50-1.74 (4H, m), 2.11-2.25 (2H, m), 2.41 (3H, d, J=1.0 Hz), 2.59-2.65 (2H, m), 3.02-3.10 (2H, m), 3.78-3.84 (1H, m), 3.94-4.38 (5H, m), 4.24 (4H, s), 6.42 (1H, d, J=1.0 Hz), 6.66-6.72 (1H, m), 6.74 (1H, d, J=2.2 Hz), 6.78 (1H, d, J=8.3 Hz), 6.95 (1H, dd, J=8.9, 2.1 Hz), 7.05 (1H, d, J=2.1 Hz), 7.60 (1H, d, J=8.9 Hz)

Example 129

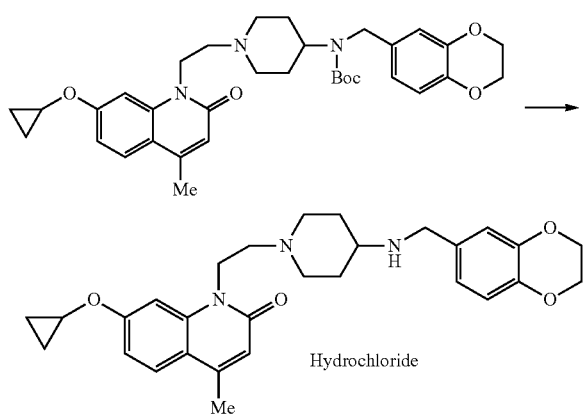

To 1 mL of methanol solution containing 85 mg of tert-butyl (1-(2-(7-cyclopropoxy-4-methyl-2-oxoquinolin-1(2H)-yl)ethyl)piperidin-4-yl)(2,3-dihydro-1,4-benzodioxin-6-ylmethyl)carbamate, 1 mL of 4 mol/L hydrogen chloride/ethyl acetate solution was added at room temperature, and stirred for 1.5 hours. 1 mL of 4 mol/L hydrogen chloride/ethyl acetate solution was added, and further stirred for 30 min. Ethyl acetate was added, and the resulting solid was filtered to give 60 mg of 7-cyclopropoxy-1-(2-(4-((2,3-dihydro-1,4-benzodioxin-6-ylmethyl)amino)piperidin-1-yl)ethyl)-4-methylquinolin-2(1H)-one hydrochloride as a white solid.

¹H-NMR (DMSO-d₆) δ:
0.68-0.74 (2H, m), 0.88-0.95 (2H, m), 2.00-2.14 (2H, m), 2.32-2.40 (2H, m), 2.42 (3H, s), 3.04-3.16 (2H, m), 3.20-3.36 (3H, m), 3.75-3.83 (2H, m), 4.04-4.10 (2H, m), 4.12-4.20 (1H, m), 4.25 (4H, s), 4.62-4.70 (2H, m), 6.41 (1H, d, J=1.0 Hz), 6.90 (1H, d, J=8.3 Hz), 7.02-7.10 (2H, m), 7.17 (1H, d, J=1.7 Hz), 7.26 (1H, d, J=1.7 Hz), 7.78 (1H, d, J=8.8 Hz), 9.52-9.72 (2H, m), 10.92-11.08 (1H, m)

Example 130

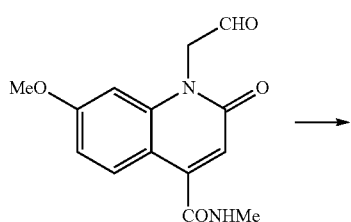

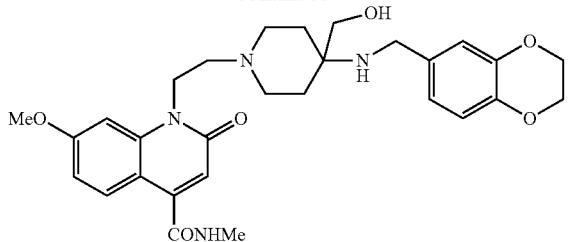

According to a procedure similar to Example 1, 1-(2-(4-((2,3-dihydro-1,4-benzodioxin-6-ylmethyl)amino)-4-(hydroxymethyl)piperidin-1-yl)ethyl)-7-methoxy-N-methyl-2-oxo-1,2-dihydroquinoline-4-carboxamide was obtained from 7-methoxy-N-methyl-2-oxo-1-(2-oxoethyl)-1,2-dihydroquinoline-4-carboxamide and (4-((2,3-dihydro-1,4-benzodioxin-6-ylmethyl)amino)piperidin-4-yl)methanol.

¹H-NMR (CDCl₃) δ:
1.50-1.90 (4H, m), 2.52-2.84 (6H, m), 3.05 (3H, d, J=4.9 Hz), 3.45 (2H, s), 3.55 (2H, s), 3.93 (3H, s), 4.24 (4H, s), 4.38-4.48 (2H, m), 6.24-6.32 (1H, m), 6.56 (1H, s), 6.80-6.89 (5H, m), 7.89 (1H, d, J=9.0 Hz)

Example 131

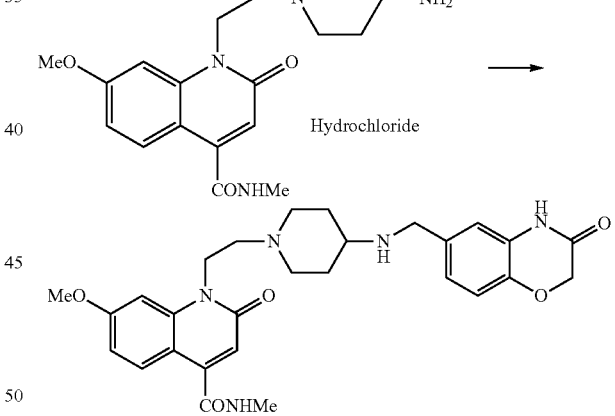

According to a procedure similar to Example 73, 7-methoxy-N-methyl-2-oxo-1-(2-(4-(((3-oxo-3,4-dihydro-2H-1,4-benzoxazin-6-yl)methyl)amino)piperidin-1-yl)ethyl)-1,2-dihydroquinoline-4-carboxamide was obtained from 1-(2-(4-aminopiperidin-1-yl)ethyl)-7-methoxy-N-methyl-2-oxo-1,2-dihydroquinoline-4-carboxamide hydrochloride and 3-oxo-3,4-dihydro-2H-1,4-benzoxazine-6-carbaldehyde.

¹H-NMR (DMSO-d₆) δ:
1.20-1.32 (2H, m), 1.74-1.84 (2H, m), 2.00-2.10 (2H, m), 2.30-2.40 (1H, m), 2.79 (3H, d, J=4.4 Hz), 2.88-2.98 (2H, m), 3.30-3.50 (2H, m), 3.61 (2H, s), 3.90 (3H, s), 4.32-4.40 (2H, m), 4.52 (2H, s), 6.41 (1H, s), 6.85-6.94 (4H, m), 6.99-7.02 (1H, m), 7.71 (1H, d, J=9.0 Hz), 8.62-8.68 (1H, m), 10.64 (1H, s)

Example 132

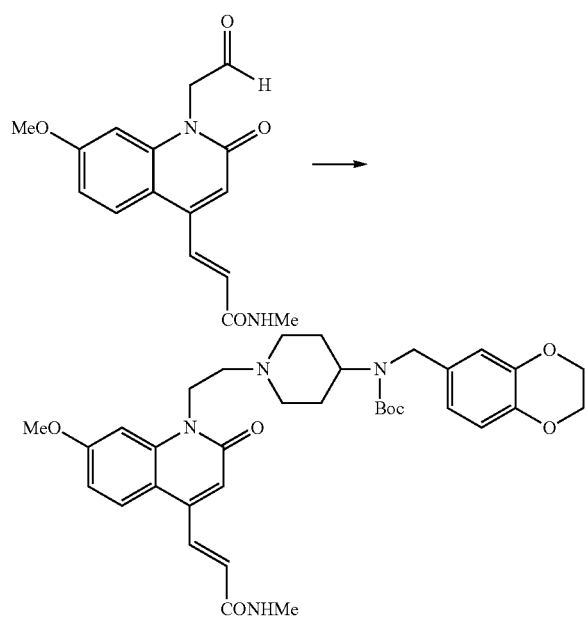

According to a procedure similar to Example 24, tert-butyl (2,3-dihydro-1,4-benzodioxin-6-ylmethyl)(1-(2-(7-methoxy-4-((1E)-3-(methylamino)-3-oxo-1-propenyl)-2-oxo-quinolin-1(2H)-yl)ethyl)piperidin-4-yl)carbamate was obtained from (2E)-(7-methoxy-2-oxo-1-(2-oxoethyl)-1,2-dihydroquinolin-4-yl)-N-methylacrylamide and tert-butyl (2,3-dihydro-1,4-benzodioxin-6-ylmethyl)(piperidin-4-yl)carbamate.

$^1$H-NMR (CDCl$_3$) δ:

1.42 (9H, s), 1.62-1.78 (4H, m), 2.10-2.24 (2H, m), 2.58-2.66 (2H, m), 2.97 (3H, d, J=4.9 Hz), 3.00-3.08 (2H, m), 3.89 (3H, s), 3.90-4.20 (1H, m), 4.24 (4H, s), 4.24-4.40 (4H, m), 6.26 (1H, d, J=4.9 Hz), 6.49 (1H, d, J=15.1 Hz), 6.63 (1H, s), 6.65-6.71 (1H, m), 6.73 (1H, d, J=2.0 Hz), 6.78 (1H, d, J=8.3 Hz), 6.84 (1H, dd, J=8.9, 2.4 Hz), 6.90 (1H, d, J=2.4 Hz), 7.76 (1H, d, J=8.9 Hz), 8.01 (1H, d, J=15.1 Hz)

Example 133

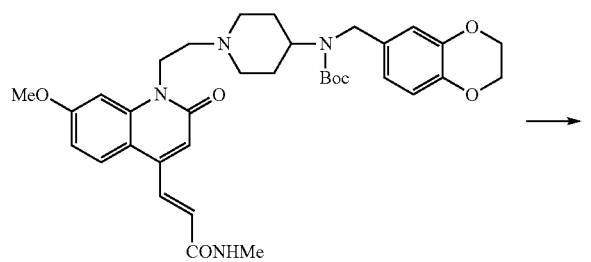

-continued

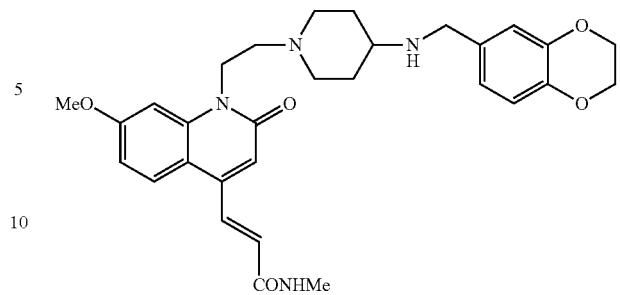

According to a procedure similar to Example 25, 2(E)-3-(1-(2-(4-(((2,3-dihydro-1,4-benzodioxin-6-ylmethyl)amino)piperidin-1-yl)ethyl-7-methoxy-2-oxo-1,2-dihydroquinolin-4-yl)-N-methylacrylamide was obtained from tert-butyl (2,3-dihydro-1,4-benzodioxin-6-ylmethyl)(1-(2-(7-methoxy-4-((1E)-3-(methylamino)-3-oxo-1-propenyl)-2-oxo-1,2-dihydroquinolin-1-yl)ethyl)piperidin-4-yl)carbamate.

$^1$H-NMR (CDCl$_3$) δ:

1.40-1.70 (2H, m), 1.88-1.96 (2H, m), 2.14-2.26 (2H, m), 2.50-2.60 (1H, m), 2.62-2.71 (2H, m), 2.96-3.06 (2H, m), 2.98 (3H, d, J=4.9 Hz), 3.71 (2H, s), 3.92 (3H, s), 4.24 (4H, s), 4.38-4.45 (2H, m), 5.82-5.90 (1H, m), 6.44 (1H, d, J=15.4 Hz), 6.63 (1H, s), 6.78-6.88 (4H, m), 6.96 (1H, d, J=2.2 Hz), 7.75 (1H, d, J=9.0 Hz), 8.01 (1H, d, J=15.4 Hz)

Example 134

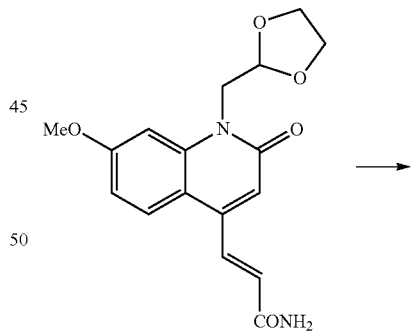

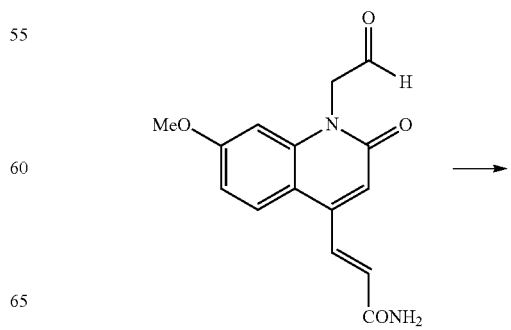

-continued

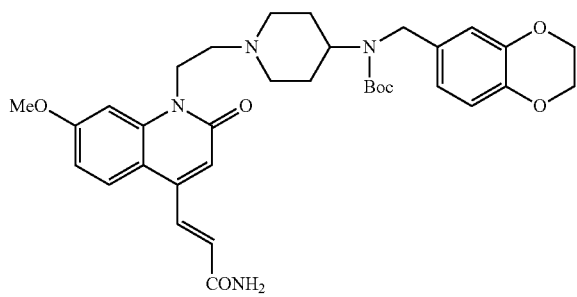

To 0.20 g of (2E)-3-(1-(1,3-dioxolan-2-ylmethyl)-7-methoxy-2-oxo-1,2-dihydroquinolin-4-yl)-acrylamide, 5 mL of 80% aqueous trifluoroacetic acid solution was added, and stirred at room temperature for 4 hours, thereafter allowed to stand at the same temperature overnight. After the solvent was removed under reduced pressure, water was added and adjusted to pH 7.8 with 1.0 mol/L aqueous sodium hydroxide solution. The resulting solid was filtered to give 98 mg of (2E)-3-(7-methoxy-2-oxo-1-(2-oxoethyl)-1,2-dihydroquinolin-4-yl)acrylamide as a light brown solid.

To 3 mL of methanol solution containing 0.11 g of tert-butyl (2,3-dihydro-1,4-benzodioxin-6-ylmethyl)(piperidin-4-yl)carbamate, 93 mg of (2E)-3-(7-methoxy-2-oxo-1-(2-oxoethyl)-1,2-dihydroquinolin-4-yl)acrylamide was added, and 3 mL of dichloromethane and 3 mL of tetrahydrofuran were added. 19 µL of acetic acid was added, and stirred at room temperature for 5 hours. To the reaction mixture, 31 mg of sodium cyanoborohydride was added, stirred at the same temperature for 1 hour and allowed to stand at room temperature overnight. Chloroform and aqueous saturated sodium hydrogen carbonate solution were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by flash silica gel column chromatography [gradient elution of chloroform:methanol=100:0-80:20], to give 14 mg of tert-butyl 1-(2-(4-((1E)-3-amino-3-oxo-1-propenyl)-7-methoxy-2-oxoquinolin-1(2H)-yl)ethyl)piperidin-4-yl)(2,3-dihydro-1,4-benzodioxin-6-ylmethyl)carbamate as a pale brown solid.

$^1$H-NMR (CDCl$_3$) δ:
1.42 (9H, s), 1.60-1.90 (4H, m), 2.08-2.24 (2H, m), 2.58-2.66 (2H, m), 3.00-3.08 (2H, m), 3.90 (3H, s), 3.98-4.14 (1H, m), 4.24 (4H, s), 4.22-4.40 (4H, m), 5.64-5.74 (1H, broad), 6.12-6.22 (1H, broad), 6.56 (1H, d, J=15.4 Hz), 6.66 (1H, s), 6.67-6.80 (3H, m), 6.85 (1H, dd, J=8.9, 2.3 Hz), 6.91 (1H, d, J=2.3 Hz), 7.74 (1H, d, J=8.9 Hz), 8.03 (1H, d, J=15.4 Hz)

Example 135

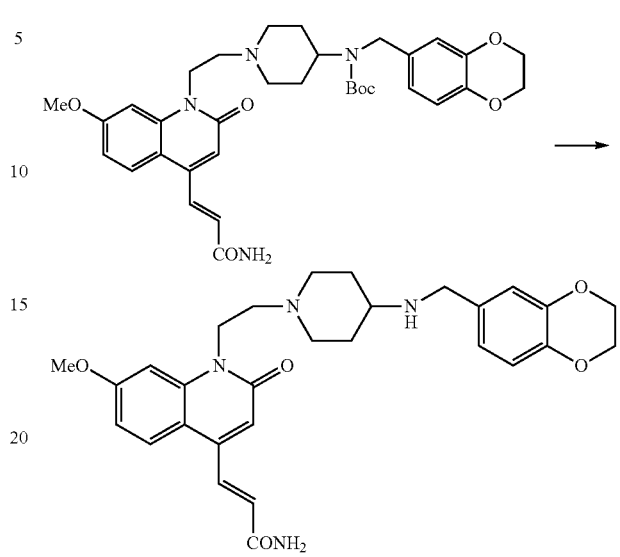

According to a procedure similar to Example 25, (2E)-3-(1-(2-(4-((2,3-dihydro-1,4-benzodioxin-6-ylmethyl)amino)piperidin-1-yl)ethyl)-7-methoxy-2-oxo-1,2-dihydroquinolin-4-yl)acrylamide was obtained from tert-butyl 1-(2-(4-((1E)-3-amino)-3-oxo-1-propenyl)-7-methoxy-2-oxoquinolin-1(2H)-yl)ethyl)piperidin-4-yl) (2,3-dihydro-1,4-benzodioxin-6-ylmethyl)carbamate.

$^1$H-NMR (CDCl$_3$) δ:
1.40-1.80 (2H, m), 1.90-2.00 (2H, m), 2.15-2.28 (2H, m), 2.54-2.78 (3H, m), 3.00-3.12 (2H, m), 3.74 (2H, s), 3.93 (3H, s), 4.23 (4H, s), 4.38-4.49 (2H, m), 5.52-5.64 (1H, broad), 5.84-5.96 (1H, broad), 6.55 (1H, d, J=15.2 Hz), 6.65 (1H, s), 6.78-6.88 (4H, m), 6.94-6.99 (1H, m), 7.75 (1H, d, J=9.0 Hz), 8.04 (1H, d, J=15.2 Hz)

Example 136

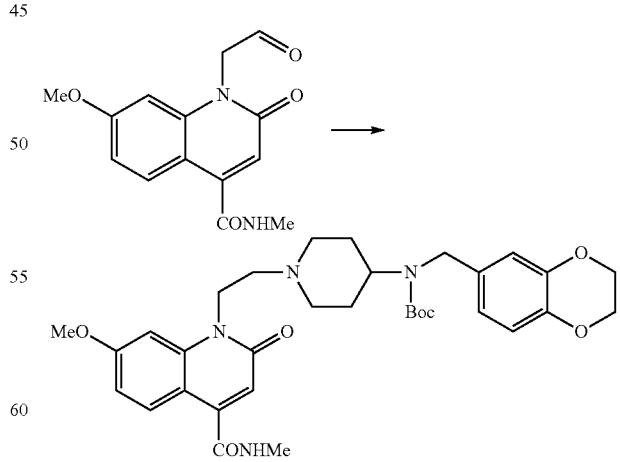

According to a procedure similar to Example 1, tert-butyl (2,3-dihydro-1,4-benzodioxin-6-ylmethyl)(1-(2-(7-methyl-4-((methylamino)carbonyl)-2-oxoquinolin-1(2H)-yl)ethyl)piperidin-4-yl)carbamate was obtained from N-methyl-7- methyl-2-oxo-1-(2-oxoethyl)-1,2-dihydroquinoline-4-carboxamide and tert-butyl (2,3-dihydro-1,4-benzodioxin-6-ylmethyl)(piperidin-4-yl)carbamate.

¹H-NMR (CDCl₃) δ:

1.42 (9H, s), 1.55-1.75 (4H, m), 2.06-2.20 (2H, m), 2.47 (3H, s), 2.50-2.56 (2H, m), 2.97-3.06 (2H, m), 3.05 (3H, d, J=4.9 Hz), 3.98-4.10 (1H, m), 4.22-4.34 (4H, m), 4.24 (4H, s), 6.30-6.38 (1H, m), 6.63 (1H, s), 6.66-6.71 (1H, m), 6.73 (1H, d, J=1.7 Hz), 6.78 (1H, d, J=8.3 Hz), 7.05-7.09 (1H, m), 7.17 (1H, s), 7.81 (1H, d, J=8.3 Hz)

Example 137

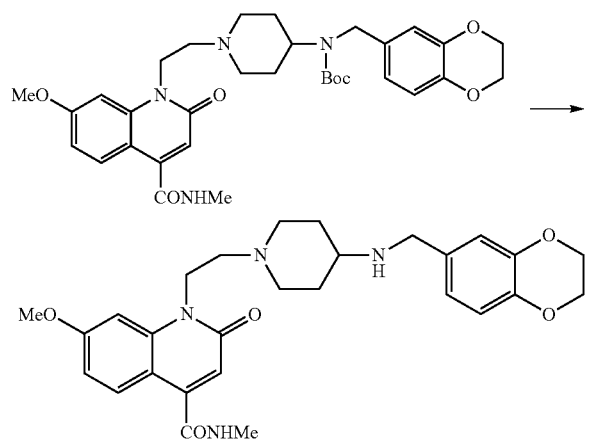

According to a procedure similar to Example 2,1-(2-(4-((2,3-dihydro-1,4-benzodioxin-6-ylmethyl)amino)piperidin-1-yl)ethyl)-N-methyl-7-methyl-2-oxo-1,2-dihydroquinoline-4-carboxamide was obtained from tert-butyl (2,3-dihydro-1,4-benzodioxin-6-ylmethyl)(1-(2-(7-methyl-4-((methylamino)carbonyl)-2-oxoquinolin-1(2H)-yl)ethyl)piperidin-4-yl)carbamate.

¹H-NMR (CDCl₃) δ:

1.40-1.52 (2H, m), 1.87-1.95 (2H, m), 2.12-2.24 (2H, m), 2.49 (3H, s), 2.50-2.64 (3H, m), 2.96-3.03 (2H, m), 3.05 (3H, d, J=5.1 Hz), 3.72 (2H, s), 4.24 (4H, s), 4.35-4.42 (2H, m), 6.24-6.32 (1H, m), 6.65 (1H, s), 6.76-6.80 (1H, m), 6.82 (1H, d, J=8.0 Hz), 6.84 (1H, d, J=1.7 Hz), 7.05-7.09 (1H, m), 7.25 (1H, s), 7.82 (1H, d, J=8.3 Hz)

Example 138

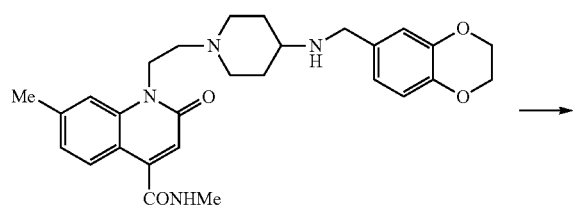

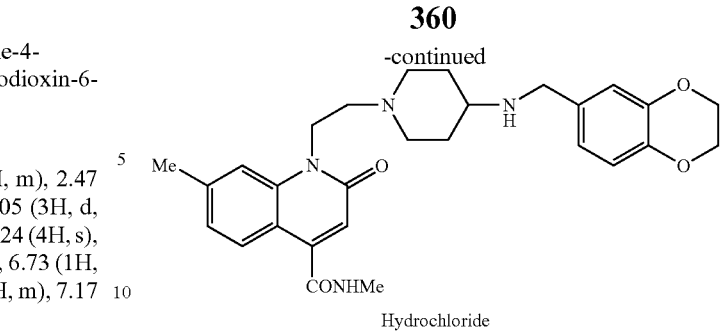

According to a procedure similar to Example 16, 1-(2-(4-((2,3-dihydro-1,4-benzodioxin-6-ylmethyl)amino)piperidin-1-yl)ethyl)-N-methyl-7-methyl-2-oxo-1,2-dihydroquinoline-4-carboxamide hydrochloride was obtained from 1-(2-(4-((2,3-dihydro-1,4-benzodioxin-6-ylmethyl)amino)piperidin-1-yl)ethyl)-N-methyl-7-methyl-2-oxo-1,2-dihydroquinoline-4-carboxamide.

¹H-NMR (DMSO-d₆) δ:

1.97-2.14 (2H, m), 2.30-2.42 (2H, m), 2.49 (3H, s), 2.81 (3H, d, J=4.6 Hz), 3.06-3.19 (2H, m), 3.19-3.60 (3H, m), 3.74-3.85 (2H, m), 4.04-4.13 (2H, m), 4.25 (4H, s), 4.63-4.72 (2H, m), 6.57 (1H, s), 6.91 (1H, d, J=8.3 Hz), 7.01-7.06 (1H, m), 7.13-7.20 (2H, m), 7.71 (1H, d, J=8.3 Hz), 7.76-7.83 (1H, m), 8.66-8.72 (1H, m), 9.38-9.54 (2H, broad), 11.02-11.14 (1H, broad)

Example 139

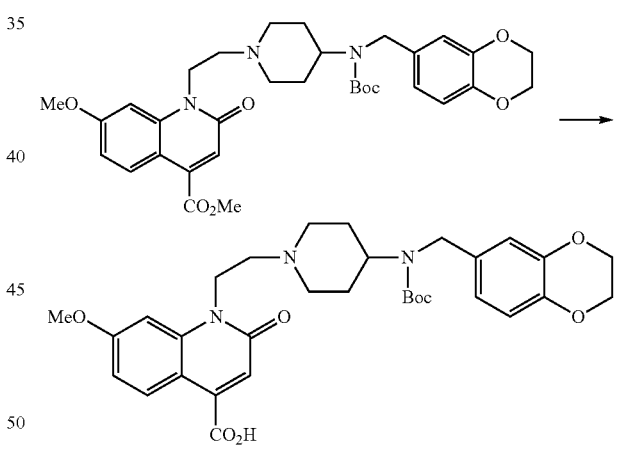

According to a procedure similar to Example 5,1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinoline-4-carboxylic acid was obtained from methyl 1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinoline-4-carboxylate.

¹H-NMR (DMSO-d₆) δ:

1.38 (9H, s), 1.54-1.63 (2H, m), 1.78-1.96 (2H, m), 2.43-2.63 (2H, m), 2.81-2.96 (2H, m), 3.29-3.43 (2H, m), 3.70-4.10 (1H, m), 3.89 (3H, s), 4.21 (4H, s), 4.25 (2H, s), 4.44-4.53 (2H, m), 6.58 (1H, s), 6.68 (1H, dd, J=8.2, 1.9 Hz), 6.71 (1H, d, J=1.9 Hz), 6.78 (1H, d, J=8.2 Hz), 6.91 (1H, dd, J=9.0, 2.1 Hz), 7.01 (1H, d, J=2.1 Hz), 8.11 (1H, d, J=9.0 Hz)

Example 140

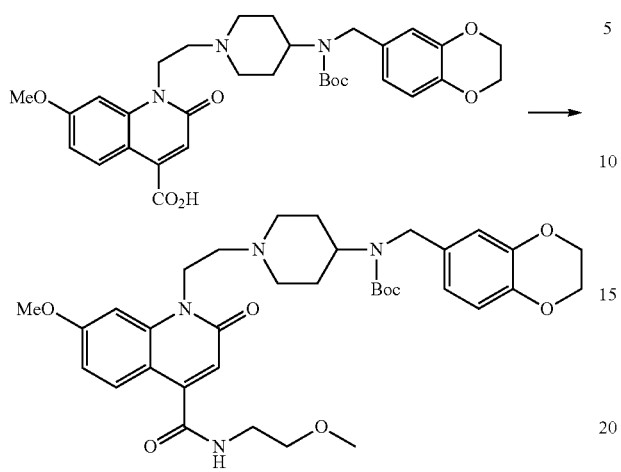

According to a procedure similar to Example 86, tert-butyl (2,3-dihydro-1,4-benzodioxin-6-ylmethyl)(1-(2-(7-methoxy-4-(((2-methoxyethyl)amino)carbonyl)-2-oxo-1,2-dihydroquinolin-1-yl)ethyl)piperidin-4-yl)carbamate was obtained from 1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinoline-4-carboxylic acid and 2-methoxyethylamine.

$^1$H-NMR (CDCl$_3$) δ:
1.42 (9H, s), 1.60-1.74 (4H, m), 2.08-2.22 (2H, m), 2.55-2.63 (2H, m), 2.98-3.07 (2H, m), 3.38 (3H, s), 3.55-3.58 (2H, m), 3.64-3.69 (2H, m), 3.89 (3H, s), 4.00-4.14 (1H, m), 4.22-4.37 (4H, m), 4.24 (4H, s), 6.41-6.45 (1H, m), 6.59 (1H, s), 6.66-6.71 (1H, m), 6.74 (1H, d, J=1.7 Hz), 6.78 (1H, d, J=8.3 Hz), 6.83 (1H, dd, J=9.0, 2.2 Hz), 6.87 (1H, d, J=2.2 Hz), 7.88 (1H, d, J=9.0 Hz)

Example 141

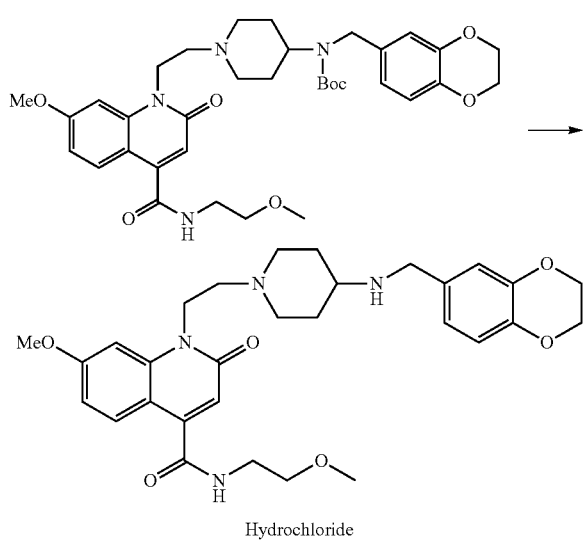

Hydrochloride

According to a procedure similar to Example 85, 1-(2-(4-((2,3-dihydro-1,4-benzodioxin-6-ylmethyl)amino)piperidin-1-yl)ethyl)-7-methoxy-N-(2-methoxyethyl)-2-oxo-1,2-dihydroquinoline-4-carboxamide hydrochloride was obtained from tert-butyl (2,3-dihydro-1,4-benzodioxin-6-ylmethyl)(1-(2-(7-methoxy-4-(((2-methoxyethyl)amino)carbonyl)-2-oxoquinolin-1(2H)-yl)ethyl)piperidin-4-yl)carbamate.

$^1$H-NMR (D$_2$O) δ:
1.95-2.09 (2H, m), 2.45-2.55 (2H, m), 3.16-3.27 (2H, m), 3.43 (3H, s), 3.54-3.74 (7H, m), 3.92-4.00 (2H, m), 3.98 (3H, s), 4.22 (2H, s), 4.33 (4H, s), 4.70-4.90 (2H, m), 6.69 (1H, s), 6.97-7.05 (4H, m), 7.13 (1H, dd, J=9.0, 2.0 Hz), 7.80 (1H, d, J=9.0 Hz)

Example 142

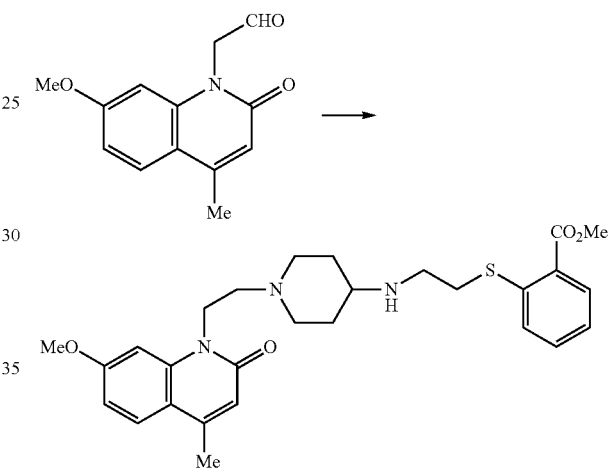

To 2 mL of dichloromethane solution containing 47 mg of (7-methoxy-4-methyl-2-oxo-1,2-dihydroquinolin-1-yl)acetaldehyde, 60 mg of methyl 2-((2-piperidin-4-ylamino)ethyl)thio)benzoate and 11.6 μL of acetic acid were added at room temperature, further 65 mg of sodium triacetoxyborohydride was added under ice-cooling, and stirred at room temperature for 5 hours. To the reaction mixture, water, ethyl acetate and aqueous saturated sodium hydrogen carbonate solution were added. The organic layer was separated, washed with aqueous saturated sodium chloride solution, dried over anhydrous magnesium sulfate, and the solvent was removed under reduced pressure. The residue thus obtained was purified by silica gel column chromatography [eluent; chloroform:methanol=10:1], to give 61 mg of methyl 2-((2-(1-(2-(7-methoxy-4-methyl-2-oxo-1,2-dihydroquinolin-1-yl)ethyl)piperidin-4-ylamino)ethyl)thio)benzoate as a yellow oil.

$^1$H-NMR (CDCl$_3$) δ:
1.36-1.48 (2H, m), 1.84-1.92 (2H, m), 2.14-2.24 (2H, m), 2.41 (3H, d, J=1.1 Hz), 2.46-2.70 (3H, m), 2.98 (2H, t, J=6.5 Hz), 2.98-3.06 (2H, m), 3.11 (2H, t, J=6.5 Hz), 3.91 (3H, s), 3.92 (3H, s), 4.36-4.42 (2H, m), 6.42 (1H, d, J=1.1 Hz), 6.83 (1H, dd, J=8.9, 2.3 Hz), 6.94 (1H, d, J=2.3 Hz), 7.15-7.20 (1H, m), 7.34-7.38 (1H, m), 7.42-7.48 (1H, m), 7.61 (1H, d, J=8.9 Hz), 7.95 (1H, dd, J=7.8, 1.4 Hz)

Example 143

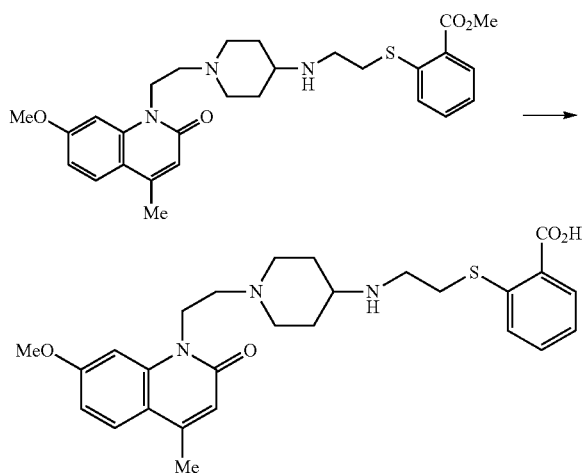

To 1 mL of an ethanol solution containing 60 mg of methyl 2-((2-(1-(2-(7-methoxy-4-methyl-2-oxoquinolin-1(2H)-yl)ethyl)piperidin-4-ylamino)ethyl)thio)benzoate, 0.1 mL of 20% aqueous sodium hydroxide solution was added at room temperature and stirred for 1 hour and 40 min. After the solvent was removed from the reaction mixture under reduced pressure, water was added, adjusted to pH 6.2 with 6.0 mol/L hydrochloric acid. The resulting solid was filtered, washed with water and diethylether to give 28 mg of 2-((2-(1-(2-(7-methoxy-4-methyl-2-oxoquinolin-1(2H)-yl)ethyl)piperidin-4-ylamino)ethyl)thio)benzoic acid as a white solid.

$^1$H-NMR (CDCl$_3$) δ:
1.80-2.15 (6H, m), 2.37 (3H, s), 2.56-2.66 (2H, m), 2.82-2.94 (1H, m), 3.02-3.16 (4H, m), 3.31-3.38 (2H, m), 3.84 (3H, s), 4.30-4.35 (2H, m), 6.36 (1H, s), 6.77 (1H, dd, J=8.8, 2.2 Hz), 6.84 (1H, d, J=2.3 Hz), 7.20-7.40 (2H, m), 7.50-7.60 (3H, m)

Example 144

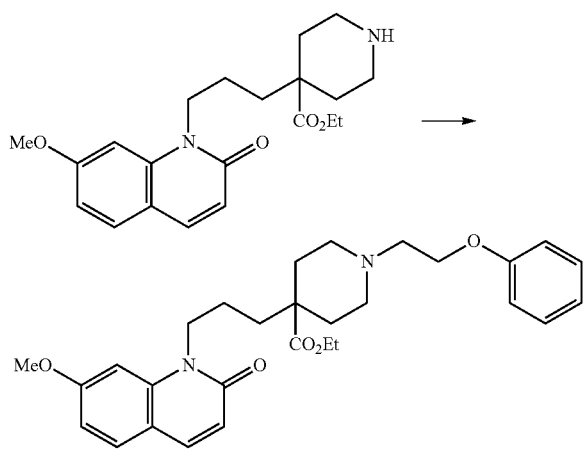

To 2 mL of an N,N-dimethylformamide solution containing 0.10 g of ethyl 4-(3-(7-methoxy-2-oxo-1,2-dihydroquinolin-1-yl)propyl)piperidine-4-carboxylate, 74 mg of potassium carbonate and 1 mL of an N,N-dimethylformamide solution containing 60 mg of (2-bromoethoxy)benzene were added at room temperature. After stirred at 50° C. for 30 min, it was allowed to stand overnight. To the reaction mixture, water and ethyl acetate were added. The organic layer was separated, washed with aqueous saturated sodium chloride solution, dried over anhydrous magnesium sulfate, and the solvent was removed under reduced pressure. The residue thus obtained was purified by silica gel column chromatography [eluent; chloroform:methanol=30:1], to give 0.12 g of ethyl 4-(3-(7-methoxy-2-oxo-1,2-dihydroquinolin-1-yl)propyl)-1-(2-phenoxyethyl)piperidine-4-carboxylate as a yellow oil.

$^1$H-NMR (CDCl$_3$) δ:
1.19 (3H, t, J=7.1 Hz), 1.46-1.58 (2H, m), 1.60-1.72 (4H, m), 2.10-2.25 (4H, m), 2.75 (2H, t, J=5.9 Hz), 2.75-2.85 (2H, m), 3.91 (3H, s), 4.07 (2H, t, J=5.9 Hz), 4.11 (2H, q, J=7.1 Hz), 4.17-4.23 (2H, m), 6.52 (1H, d, J=9.4 Hz), 6.72 (1H, d, J=2.3 Hz), 6.81 (1H, dd, J=8.6, 2.3 Hz), 6.86-6.97 (3H, m), 7.24-7.30 (2H, m), 7.46 (1H, d, J=8.6 Hz), 7.58 (1H, d, J=9.4 Hz)

Example 145

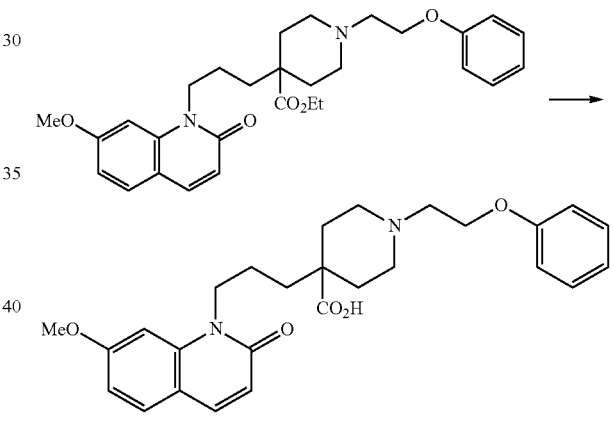

To 1.5 mL of an ethanol solution containing 0.12 g of ethyl 4-(3-(7-methoxy-2-oxo-1,2-dihydroquinolin-1-yl)propyl)-1-(2-phenoxyethyl)piperidine-4-carboxylate, 0.7 mL of 20% aqueous sodium hydroxide solution was added at room temperature and refluxed with heating for 4.5 hours. After the reaction mixture was cooled to the room temperature, the solvent was removed under reduced pressure, water was added, adjusted to pH 6.5 with 6.0 mol/L hydrochloric acid. The resulting solid was filtered to give 87 mg of 4-(3-(7-methoxy-2-oxo-1,2-dihydroquinolin-1-yl)propyl)-1-(2-phenoxyethyl)piperidine-4-carboxylic acid as a pale yellow solid.

$^1$H-NMR (DMSO-d$_6$) δ:
1.30-1.40 (2H, m), 1.45-1.63 (4H, m), 1.90-2.00 (2H, m), 2.02-2.12 (2H, m), 2.62 (2H, t, J=5.8 Hz), 2.66-2.75 (2H, m), 3.89 (3H, s), 4.02 (2H, t, J=5.8 Hz), 4.14-4.22 (2H, m), 6.40 (1H, d, J=9.3 Hz), 6.86-6.94 (5H, m), 7.24-7.30 (2H, m), 7.64 (1H, d, J=9.3 Hz), 7.81 (1H, d, J=9.3 Hz)

Example 146

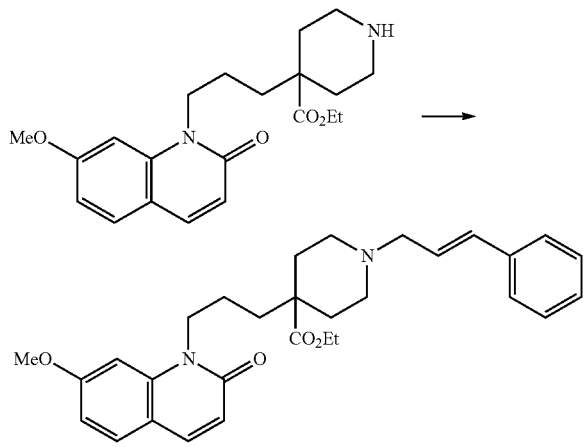

To 3 mL of an N,N-dimethylformamide solution containing 0.10 g of ethyl 4-(3-(7-methoxy-2-oxo-1,2-dihydroquinolin-1-yl)propyl)piperidine-4-carboxylate, 0.11 g of potassium carbonate, 41 μL of ((1E)-3-chloro-1-propenyl)benzene and 45 mg of potassium iodide were added at room temperature and stirred for 4.5 hours. To the reaction mixture, water and ethyl acetate were added. The organic layer was separated, washed with aqueous saturated sodium chloride solution, dried over anhydrous magnesium sulfate, and the solvent was removed under reduced pressure. The residue thus obtained was purified by silica gel column chromatography [eluent; chloroform:methanol=35:1], to give 0.11 g of ethyl 4-(3-(7-methoxy-2-oxoquinolin-1(2H)-yl)propyl)-1-((2E)-3-phenyl-2-propen-1-yl)piperidine-4-carboxylate as a yellow oil.

$^1$H-NMR (CDCl$_3$) δ:
1.19 (3H, t, J=7.2 Hz), 1.47-1.58 (2H, m), 1.64-1.72 (4H, m), 2.02-2.12 (2H, m), 2.12-2.20 (2H, m), 2.74-2.85 (2H, m), 3.11 (2H, d, J=6.7 Hz), 3.90 (3H, s), 4.11 (2H, q, J=7.2 Hz), 4.15-4.25 (2H, m), 6.26 (1H, dt, J=15.9, 6.7 Hz), 6.49 (1H, d, J=15.9 Hz), 6.52 (1H, d, J=9.3 Hz), 6.72 (1H, d, J=2.2 Hz), 6.81 (1H, dd, J=8.7, 2.2 Hz), 7.18-7.38 (5H, m), 7.46 (1H, d, J=8.7 Hz), 7.58 (1H, d, J=9.3 Hz)

Example 147

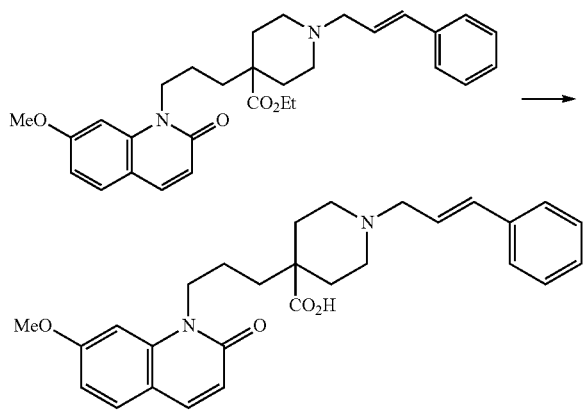

To 1.8 mL of an ethanol solution containing 0.11 g of ethyl 4-(3-(7-methoxy-2-oxoquinolin-1(2H)-yl)propyl)-1-((2E)-3-phenyl-2-propen-1-yl)piperidine-4-carboxylate, 0.6 mL of 20% aqueous sodium hydroxide solution was added at room temperature and refluxed with heating for 7 hours. After the reaction mixture was cooled to the room temperature, the solvent was removed under reduced pressure, water was added, adjusted to pH 6.6 with 6.0 mol/L hydrochloric acid. The resulting solid was filtered to give 82 mg of 4-(3-(7-methoxy-2-oxoquinolin-1(2H)-yl)propyl)-1-((2E)-3-phenyl-2-propen-1-yl)piperidine-4-carboxylic acid as a white solid.

$^1$H-NMR (DMSO-d$_6$) δ:
1.30-1.42 (2H, m), 1.46-1.62 (4H, m), 1.90-2.06 (4H, m), 2.60-2.70 (2H, m), 3.02 (2H, d, J=6.7 Hz), 3.89 (3H, s), 4.12-4.23 (2H, m), 6.26 (1H, dt, J=15.8, 6.5 Hz), 6.40 (1H, d, J=9.7 Hz), 6.49 (1H, d, J=15.8 Hz), 6.86-6.92 (2H, m), 7.22 (1H, t, J=7.3 Hz), 7.31 (2H, t, J=7.3 Hz), 7.42 (2H, d, J=7.3 Hz), 7.46 (1H, d, J=9.3 Hz), 7.81 (1H, d, J=9.7 Hz)

Example 148

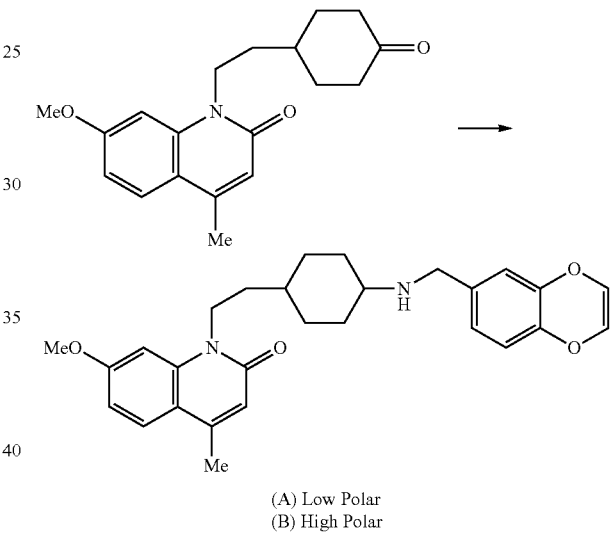

(A) Low Polar
(B) High Polar

To 2 mL of methanol solution containing 45 mg of 7-methoxy-4-methyl-1-(2-(4-oxocyclohexyl)ethyl)quinolin-2(1H)-one and 21 mg of (2,3-dihydrobenzo[b][1,4-]dioxin-6-yl)methylamine, 10 μL of acetic acid and 12 mg of sodium cyanoborohydride were added, and stirred at the same temperature for 30 min. To the reaction mixture, water, chloroform and aqueous saturated sodium hydrogen carbonate solution were added. The organic layer was separated, washed with aqueous saturated sodium chloride solution, dried over anhydrous magnesium sulfate, and the solvent was removed under reduced pressure. The residue thus obtained was purified by flash silica gel column chromatography [eluent; chloroform:methanol=20:1], to give (A) 5.4 mg of 1-(2-(4-((2,3-dihydro-1,4-benzodioxin-6-ylmethyl)amino)cyclohexyl)ethyl)-7-methoxy-4-methylquinolin-2(1H)-one as a yellow oil and (B) 17 mg of 1-(2-(4-((2,3-dihydro-1,4-benzodioxin-6-ylmethyl)amino)cyclohexyl)ethyl)-7-methoxy-4-methylquinolin-2(1H)-one as a pale yellow foam.

(A) $^1$H-NMR (CDCl$_3$) δ:
1.20-1.32 (2H, m), 1.55-1.74 (5H, m), 1.89-2.12 (4H, m), 2.41 (3H, d, J=1.0 Hz), 2.78-2.84 (1H, m), 3.72 (2H, s), 3.91 (3H, s), 4.20-4.30 (6H, m), 6.39-6.41 (1H, m), 6.78-6.88 (5H, m), 7.61 (1H, d, J=8.8 Hz)

(B) ¹H-NMR (CDCl₃) δ:
1.00-1.30 (4H, m), 1.40-1.50 (1H, m), 1.50-1.65 (2H, m), 1.88-2.06 (4H, m), 2.41 (3H, d, J=1.0 Hz), 2.45-2.54 (1H, m), 3.73 (2H, s), 3.91 (3H, s), 4.20-4.30 (6H, m), 6.41-6.43 (1H, m), 6.77-6.86 (5H, m), 7.61 (1H, d, J=8.8 Hz)

Example 149

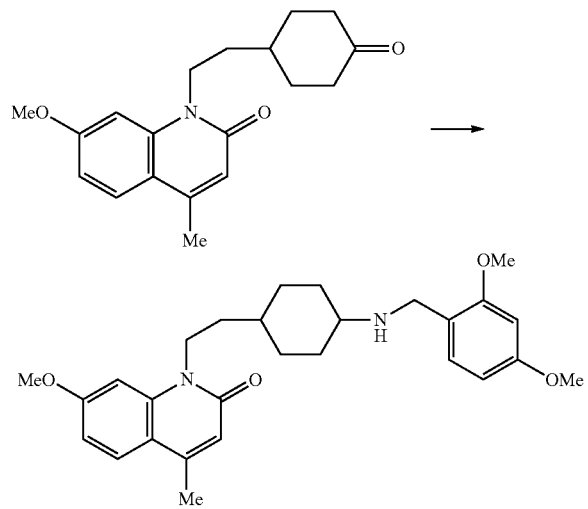

To 3 mL of methanol solution containing 30 mg of 7-methoxy-4-methyl-1-(2-(4-oxocyclohexyl)ethyl)quinolin-2(1H)-one, 16 mg of 3,5-dimethoxybenzylamine, 8 μL of acetic acid and 9 mg of sodium cyanoborohydride were added, and the mixture was allowed to stand overnight after stirred at room temperature for 1 hour. To the reaction mixture, chloroform and aqueous saturated sodium hydrogen carbonate solution were added, the organic layer was separated, washed with aqueous saturated sodium chloride solution, dried over anhydrous magnesium sulfate, and the solvent was removed under reduced pressure. The residue thus obtained was purified by flash silica gel column chromatography [gradient elution of chloroform:methanol=90:10-80:20], to give 22 mg of 1-(2-(4-((2,4-dimethoxybenzyl)amino)cyclohexyl)ethyl)-7-methoxy-4-methylquinolin-2(1H)-one as a yellow oil.
¹H-NMR (CDCl₃) δ:
1.00-1.80 (7H, m), 1.88-2.04 (2H, m), 2.20-2.75 (3H, m), 2.41 (3H, s), 3.78-3.83 (2H, m), 3.79 (6H, s), 3.91 (3H, s), 4.20-4.30 (2H, m), 6.42-6.45 (3H, m), 6.77-6.85 (2H, m), 7.14-7.18 (1H, m), 7.61 (1H, d, J=9.0 Hz)

Example 150

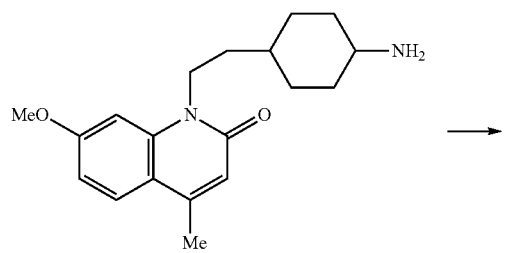

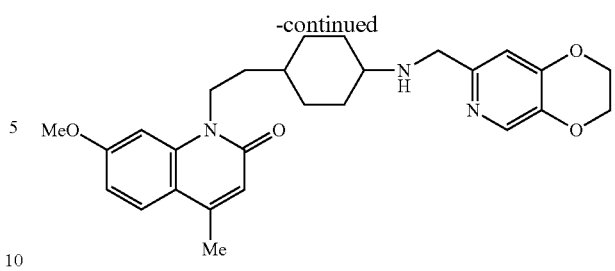

To 1.5 mL of dichloromethane solution containing 6.0 mg of 1-(2-(4-aminocyclohexyl)ethyl)-7-methoxy-4-methylquinolin-2(1H)-one, 10 mg of molecular sieves 3A, 3.4 mg of 2,3-dihydro(1,4)dioxino(2,3-c)pyridine-7-carbaldehyde and 1.6 μL of acetic acid were added at room temperature, and stirred at the same temperature for 1.5 hours. To the reaction mixture, 6.0 mg of sodium triacetoxyborohydride was added, and stirred at the same temperature for 1.5 hours. To the reaction mixture, aqueous saturated sodium hydrogen carbonate solution and chloroform were added. The organic layer was separated, washed with aqueous saturated sodium chloride solution, dried over anhydrous magnesium sulfate, and the solvent was removed under reduced pressure. The residue thus obtained was purified by silica gel column chromatography[eluent; chloroform: methanol=10:1], to give 5.5 mg of 1-(2-(4-((2,3-dihydro(1,4)dioxino(2,3-c)pyridin-7-yl-methyl)amino)cyclohexyl)ethyl)-7-methoxy-4-methylquinolin-2(1H)-one as a yellow oil.
¹H-NMR (CDCl₃) δ:
1.00-1.74 (7H, m), 1.80-2.10 (4H, m), 2.41 (3H, s), 2.46-2.81 (1H, m), 3.65 (2H, s), 3.91 (3H, s), 4.20-4.35 (6H, m), 6.43 (1H, s), 6.77-6.85 (3H, m), 7.62 (1H, d, J=8.8 Hz), 8.10 (1H, s)

Example 151

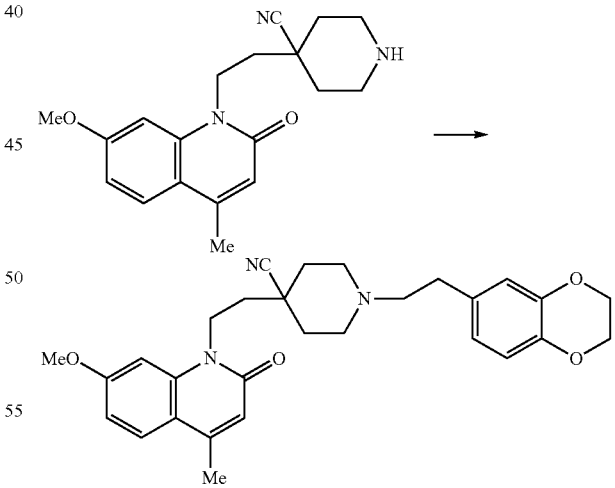

To 5 mL of methanol solution containing 0.20 g of 4-(2-(7-methoxy-4-methyl-2-oxo-1,2-dihydroquinolin-1-yl)ethyl)piperidine-4-carbonitrile, 1.5 mL of dichloromethane solution containing 0.33 g of (2,3-dihydrobenzo[b](1,4)dioxin-6-yl)acetaldehyde and 70 μL of acetic acid were added at room temperature, and stirred at the same temperature for 55 min. 77 mg of sodium cyanoborohydride was added at room temperature, and stirred 1 hour and 50 min, thereafter 0.5 mL of dichloromethane solution containing 0.10 g of (2,3-dihydrobenzo[b](1,4)dioxin-6-yl)acetaldehyde was further added and stirred for 1 hour. To the reaction mixture, water, chloroform and aqueous saturated sodium hydrogen carbonate solution were added, the organic layer was separated, and the aqueous layer was extracted with chloroform. The organic layer and extracts were combined, washed with aqueous saturated sodium chloride solution, thereafter dried over anhydrous magnesium sulfate, and the solvent was removed under reduced pressure. The residue thus obtained was purified by flash silica gel column chromatography[gradient elution of chloroform:methanol=99:1-97:3], to give 0.24 g of 1-(2-(2,3-dihydro-1,4-benzodioxin-6-yl)ethyl)-4-(2-(7-methoxy-4-methyl-2-oxo-1,2-dihydroquinolin-1-yl)ethyl)piperidine-4-carbonitrile as a white foam.

$^1$H-NMR (CDCl$_3$) δ:
1.50-1.80 (4H, m), 1.94-2.12 (4H, m), 2.43 (3H, s), 2.58-2.74 (4H, m), 2.94-3.04 (2H, m), 3.94 (3H, s), 4.24 (4H, s), 4.44-4.54 (2H, m), 6.43 (1H, s), 6.62-6.82 (3H, m), 6.86 (1H, dd, J=8.9, 2.2 Hz), 6.93 (1H, d, J=2.2 Hz), 7.63 (1H, d, J=8.9 Hz)

Example 152

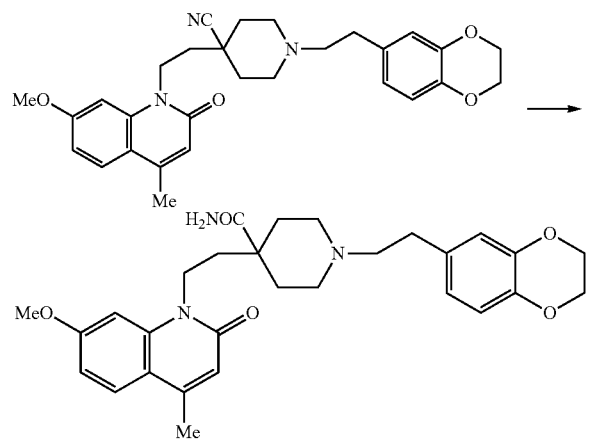

To 4 mL of an ethanol solution containing 0.10 g of 1-(2-(2,3-dihydro-1,4-benzodioxin-6-yl)ethyl)-4-(2-(7-methoxy-4-methyl-2-oxo-1,2-dihydroquinolin-1-yl)piperidine-4-carbonitrile, 1 mL of 20% aqueous potassium hydroxide solution was added at room temperature and refluxed with heating for 3 hours and 10 min. Further, 1 mL of 20% aqueous potassium hydroxide solution was added and refluxed with heating for 1 hour and 20 min, thereafter 1 mL of 20% aqueous potassium hydroxide solution was further added and refluxed with heating for 9.5 hours. After the reaction mixture was cooled to the room temperature, the solvent was removed under reduced pressure, adjusted to pH 12 with 2.0 mol/L hydrochloric acid and chloroform was added. The insoluble material was filtered off, the organic layer in the filtrate was separated, washed with aqueous saturated sodium chloride solution, dried over anhydrous magnesium sulfate, and the solvent was removed under reduced pressure. The residue thus obtained was purified by silica gel column chromatography[eluent; chloroform:methanol=15:1], to give 52 mg of 1-(2-(2,3-dihydro-1,4-benzodioxin-6-yl)ethyl)-4-(2-(7-methoxy-4-methyl-2-oxo-1(2H)-yl)ethyl)piperidine-4-carboxamide as a pale yellow solid.

$^1$H-NMR (CDCl$_3$) δ:
1.50-1.80 (4H, m), 1.90-2.20 (4H, m), 2.43 (3H, s), 2.48-2.75 (4H, m), 3.95 (3H, s), 4.16-4.34 (4H, m), 4.23 (4H, s), 6.41 (1H, s), 6.65 (1H, dd, J=8.2, 1.9 Hz), 6.70 (1H, d, J=1.9 Hz), 6.77 (1H, d, J=8.2 Hz), 6.85 (1H, dd, J=8.8, 2.0 Hz), 6.96 (1H, d, J=2.0 Hz), 7.62 (1H, d, J=8.8 Hz)

Example 153

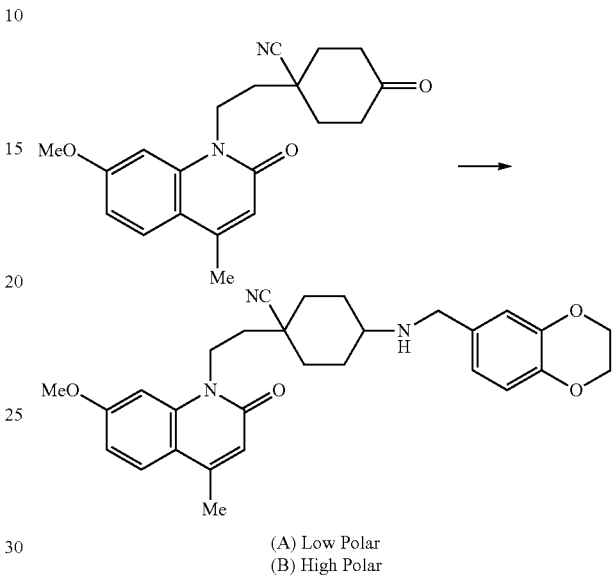

(A) Low Polar
(B) High Polar

To a mixture of 3 mL of ethanol and 3 mL of dichloromethane solution containing 0.18 g of 1-(2-(7-methoxy-4-methyl-2-oxoquinolin-1(2H)-yl)ethyl)-4-oxocyclohexanecarbonitrile, 1 mL of ethanol solution containing 0.13 g of (2,3-dihydrobenzo[b][1,4-]dioxin-6-yl)methylamine, 0.30 g of molecular sieves 3A, and 45 μL of acetic acid were added at room temperature. After stirred at 40° C. for 1.5 hours, the mixture was cooled to the room temperature, 36 mg of sodium cyanoborohydride was added, and stirred at the same temperature for 15 min. To the reaction mixture, aqueous saturated sodium hydrogen carbonate solution and chloroform were added, the organic layer was separated, washed with aqueous saturated sodium chloride solution, dried over anhydrous magnesium sulfate, and the solvent was removed under reduced pressure. The residue thus obtained was purified by flash silica gel column chromatography [hexane:ethyl acetate=4:1], to give (A) 36 mg of 4-((2,3-dihydro-1,4-benzodioxin-6-ylmethyl)amino)-1-(2-(7-methoxy-4-methyl-2-oxo-1,2-dihydroquinolin-1-yl)ethyl)cyclohexanecarbonitrile as a colorless oil and (B) 0.11 g of 4-((2,3-dihydro-1,4-benzodioxin-6-ylmethyl)amino)-1-(2-(7-methoxy-4-methyl-2-oxo-1,2-dihydroquinolin-1-yl)ethyl)cyclohexanecarbonitrile as a white foam.

(A) $^1$H-NMR (CDCl$_3$) δ:
1.65-1.75 (2H, m), 1.78-2.05 (8H, m), 2.43 (3H, s), 2.88-2.94 (1H, m), 3.63 (2H, s), 3.94 (3H, s), 4.25 (4H, s), 4.42-4.52 (2H, m), 6.43 (1H, s), 6.77 (1H, dd, J=8.3, 2.0 Hz), 6.80-6.83 (2H, m), 6.85 (1H, dd, J=8.9, 2.3 Hz), 6.94 (1H, d, J=2.3 Hz), 7.62 (1H, d, J=8.9 Hz)

(B) $^1$H-NMR (CDCl$_3$) δ:
1.40-1.60 (4H, m), 1.90-2.10 (4H, m), 2.12-2.20 (2H, m), 2.42 (3H, d, J=1.2 Hz), 2.46-2.54 (1H, m), 3.73 (2H, s), 3.94 (3H, s), 4.25 (4H, s), 4.42-4.52 (2H, m), 6.41-6.43 (1H, m), 6.75-6.88 (4H, m), 6.94 (1H, d, J=2.2 Hz), 7.62 (1H, d, J=8.8 Hz)

Example 154

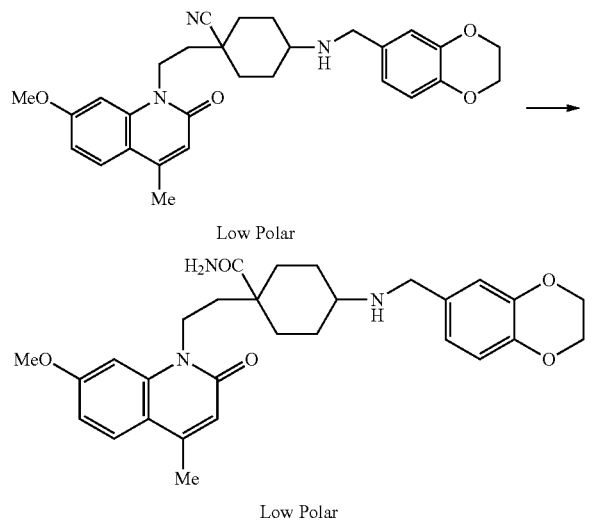

Low Polar

Low Polar

Example 155

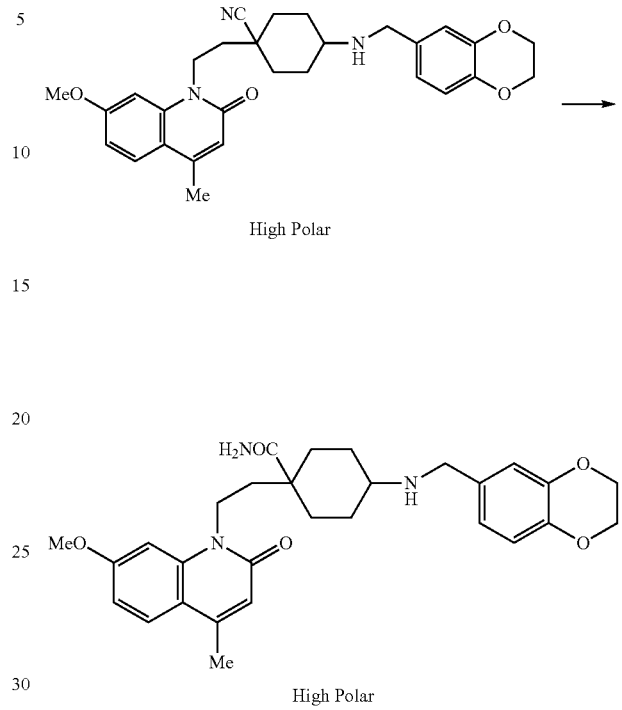

High Polar

High Polar

To 1 mL of a 1,4-dioxane solution containing 30 mg of 4-((2,3-dihydro-1,4-benzodioxin-6-ylmethyl)amino)-1-(2-(7-methoxy-4-methyl-2-oxoquinolin-1(2H)-yl)ethyl)cyclohexanecarbonitrile, 1 mL of 20% aqueous potassium hydroxide solution and 1 mL of ethanol were added at room temperature and refluxed with heating for 4 hours. Further, 1 mL of 20% aqueous potassium hydroxide solution was added and refluxed with heating for 4 hours, thereafter 1.5 mL of 20% aqueous potassium hydroxide solution was further added and refluxed with heating for 9.5 hours. After 1 mL of 20% aqueous potassium hydroxide solution and 0.5 mL of ethanol were added and refluxed with heating for 1 hour, further 1 mL of 20% aqueous potassium hydroxide solution was added and refluxed with heating for 8 hours. After 1 mL of 20% aqueous potassium hydroxide solution was added and refluxed with heating for 6 hours, the reaction mixture was cooled to the room temperature, the solvent was removed under reduced pressure. The residue was adjusted to pH 11 with 2.0 mol/L hydrochloric acid and chloroform was added. The organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. To the residue thus obtained, diethyl ether was added, and the resulting solid was filtered to give 21 mg of 4-((2,3-dihydro-1,4-benzodioxin-6-ylmethyl)amino)-1-(2-(7-methoxy-4-methyl-2-oxoquinolin-1(2H)-yl)ethyl)cyclohexanecarboxamide as a white solid.

$^1$H-NMR (CDCl$_3$, D$_2$O) δ:

1.40-1.54 (2H, m), 1.78-2.10 (8H, m), 2.44 (3H, s), 2.56-2.68 (1H, m), 3.70 (2H, s), 3.95 (3H, s), 4.18-4.27 (2H, m), 4.24 (4H, s), 6.42 (1H, s), 6.74-6.90 (4H, m), 6.98 (1H, s), 7.63 (1H, d, J=8.8 Hz)

To 1.5 mL of a 1,4-dioxane solution containing 90 mg of 4-((2,3-dihydro-1,4-benzodioxin-6-ylmethyl)amino)-1-(2-(7-methoxy-4-methyl-2-oxoquinolin-1(2H)-yl)ethyl)cyclohexanecarbonitrile, 1 mL of 20% aqueous potassium hydroxide solution and 1 mL of ethanol were added at room temperature and refluxed with heating for 4 hours. Further, 1 mL of 20% aqueous potassium hydroxide solution was added and refluxed with heating for 4 hours, 2 mL of the solution was added and for 9.5 hours, 1 mL of the solution was added and for 1 hour, 1 mL of the solution was added and for 8 hours, further 1 mL of the solution was added and refluxed with heating for 3 hours. The reaction mixture was cooled to the room temperature, and the solvent was removed under reduced pressure. The residue was adjusted to pH 11 with 2.0 mol/L hydrochloric acid and ethyl acetate was added. The organic layer was separated, and washed with aqueous saturated sodium chloride solution, dried over anhydrous magnesium sulfate, and the solvent was removed under reduced pressure. To the residue thus obtained, diethyl ether was added, and the resulting solid was filtered to give 53 mg of 4-((2,3-dihydro-1,4-benzodioxin-6-ylmethyl)amino)-1-(2-(7-methoxy-4-methyl-2-oxoquinolin-1(2H)-yl)ethyl)cyclohexanecarboxamide as a white solid.

$^1$H-NMR (CDCl$_3$, D$_2$O) δ:

1.34-1.48 (4H, m), 1.80-2.00 (4H, m), 2.20-2.32 (2H, m), 2.41 (3H, s), 2.54-2.64 (1H, m), 3.71 (2H, s), 3.93 (3H, s), 4.20-4.30 (2H, m), 4.23 (4H, s), 6.40 (1H, s), 6.74-6.92 (5H, m), 7.60 (1H, d, J=8.8 Hz)

Example 156

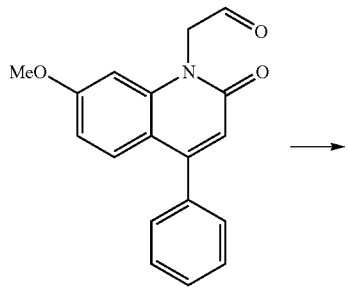

→

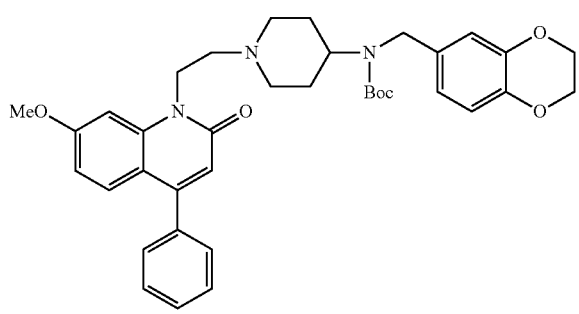

According to a procedure similar to Example 1, tert-butyl (2,3-dihydro-1,4-benzodioxin-6-ylmethyl)(1-(2-(7-methoxy-2-oxo-4-phenylquinolin-1(2H)-yl)ethyl)piperidin-4-yl)carbamate was obtained from (7-methoxy-2-oxo-4-phenylquinolin-1(2H)-yl)acetaldehyde and tert-butyl (2,3-dihydro-1,4-benzodioxin-6-ylmethyl)(piperidin-4-yl)carbamate.

$^1$H-NMR (CDCl$_3$) δ:
1.43 (9H, s), 1.60-1.80 (2H, m), 1.90-2.00 (2H, m), 2.10-2.30 (2H, m), 2.65-2.73 (2H, m), 3.05-3.15 (2H, m), 3.89 (3H, s), 3.95-4.20 (1H, m), 4.20-4.35 (2H, m), 4.25 (4H, s), 4.38-4.46 (2H, m), 6.49 (1H, s), 6.65-6.80 (3H, m), 6.95 (1H, d, J=2.2 Hz), 7.35-7.55 (7H, m)

Example 157

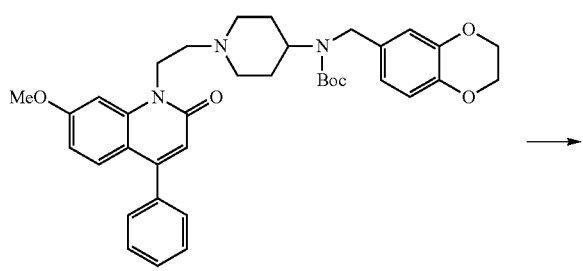

→

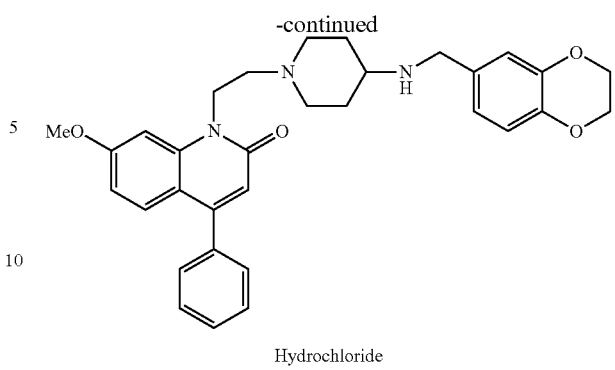

Hydrochloride

According to a procedure similar to Example 85, 1-(2-(4-((2,3-dihydro-1,4-benzodioxin-6-ylmethyl)amino)piperidin-1-yl)ethyl)-7-methoxy-4-phenylquinolin-2(1H)-one hydrochloride was obtained from tert-butyl (2,3-dihydro-1,4-benzodioxin-6-ylmethyl)(1-(2-(7-methoxy-2-oxo-4-phenylquinolin-1(2H)-yl)ethyl)piperidin-4-yl)carbamate.

$^1$H-NMR (DMSO-d$_6$) δ:
2.00-2.15 (2H, m), 2.30-2.45 (2H, m), 3.05-3.50 (5H, m), 3.75-3.90 (2H, m), 3.96 (3H, s), 4.00-4.15 (2H, m), 4.24 (4H, s), 4.65-4.85 (2H, m), 6.36 (1H, s), 6.85-6.90 (2H, m), 7.00-7.10 (1H, m), 7.15-7.60 (8H, m)

Example 158

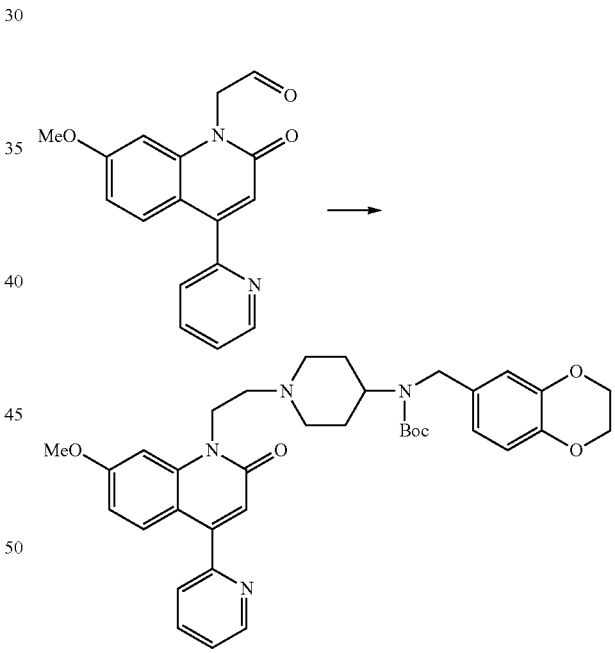

According to a procedure similar to Example 1, tert-butyl (2,3-dihydro-1,4-benzodioxin-6-ylmethyl)(1-(2-(7-methoxy-2-oxo-4-(pyridin-2-yl)quinolin-1(2H)-yl)ethyl)piperidin-4-yl)carbamate was obtained from (7-methoxy-2-oxo-4-(pyridin-2-yl)quinolin-1(2H)-yl)acetaldehyde and tert-butyl (2,3-dihydro-1,4-benzodioxin-6-ylmethyl)(piperidin-4-yl)carbamate.

$^1$H-NMR (CDCl$_3$) δ:
1.43 (9H, s), 1.60-1.75 (4H, m), 2.10-2.25 (2H, m), 2.64-2.72 (2H, m), 3.02-3.11 (2H, m), 3.89 (3H, s), 4.00-4.20 (1H, m), 4.24 (4H, s), 4.24-4.36 (2H, m), 4.40-4.46 (2H, m), 6.60 (1H, s), 6.66-6.82 (4H, m), 6.94 (1H, d, J=2.2 Hz), 7.36-7.41

(1H, m), 7.51 (1H, d, J=7.8 Hz), 7.66 (1H, d, J=9.0 Hz), 7.81-7.87 (1H, m), 8.74-8.77 (1H, m)

Example 159

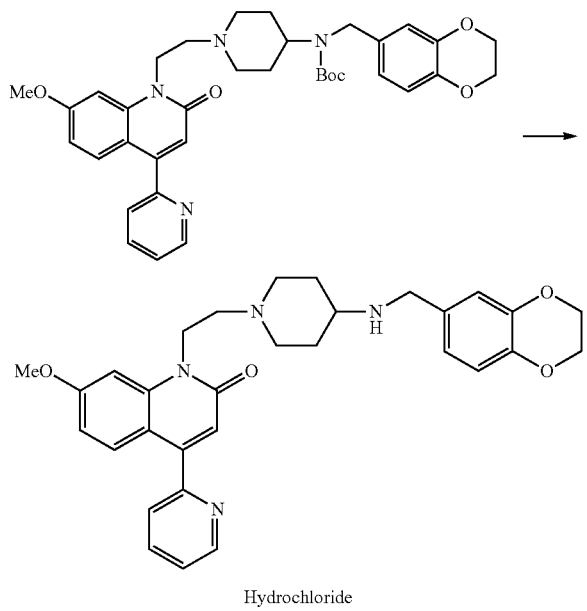

Hydrochloride

According to a procedure similar to Example 85, 1-(2-(4-((2,3-dihydro-1,4-benzodioxin-6-ylmethyl)amino)piperidin-1-yl)ethyl)-7-methoxy-4-(pyridin-2-yl)quinolin-2(1H)-one hydrochloride was obtained from tert-butyl (2,3-dihydro-1,4-benzodioxin-6-ylmethyl)(1-(2-(7-methoxy-2-oxo-4-(pyridin-2-yl)quinolin-1(2H)-yl)ethyl)piperidin-4-yl) carbamate.

$^1$H-NMR (DMSO-$d_6$) δ:

2.05-2.45 (4H, m), 3.05-3.50 (5H, m), 3.80-3.90 (2H, m), 3.90-4.20 (5H, m), 4.26 (4H, s), 4.75-4.90 (2H, m), 6.59 (1H, s), 6.85-6.95 (2H, m), 7.05-7.10 (1H, m), 7.20 (1H, d, J=2.0 Hz), 7.28 (1H, d, J=2.0 Hz), 7.58 (1H, d, J=9.0 Hz), 7.65-7.70 (1H, m), 7.76 (1H, d, J=7.8 Hz), 8.12-8.17 (1H, m), 8.82 (1H, d, J=4.9 Hz), 9.60-9.80 (2H, broad), 11.20-11.40 (1H, broad)

Example 160

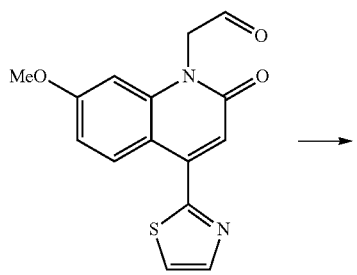

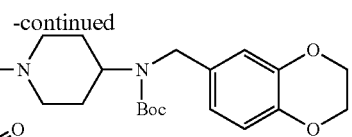

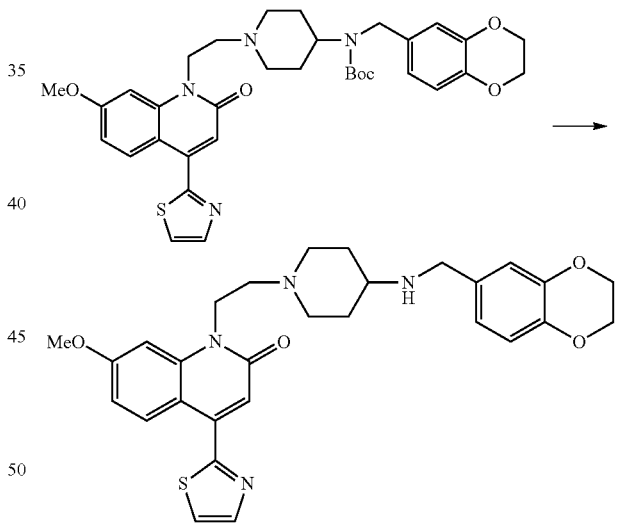

According to a procedure similar to Example 1, tert-butyl (2,3-dihydro-1,4-benzodioxin-6-ylmethyl)(1-(2-(7-methoxy-2-oxo-4-(1,3-thiazol-2-yl)quinolin-1(2H)-yl)ethyl)piperidin-4-yl)carbamate was obtained from (7-methoxy-2-oxo-4-(1,3-thiazol-2-yl)quinolin-1(2H)-yl)acetaldehyde and tert-butyl (2,3-dihydro-1,4-benzodioxin-6-ylmethyl)(piperidin-4-yl)carbamate.

$^1$H-NMR (CDCl$_3$) δ:

1.42 (9H, s), 1.62-1.74 (2H, m), 1.94-2.26 (4H, m), 2.62-2.70 (2H, m), 3.02-3.11 (2H, m), 3.90 (3H, s), 4.00-4.14 (1H, m), 4.24 (4H, s), 4.25-4.35 (2H, m), 4.35-4.44 (2H, m), 6.65-6.96 (6H, m), 7.51 (1H, d, J=3.3 Hz), 8.05 (1H, d, J=3.3 Hz), 8.48 (1H, d, d=9.0 Hz)

Example 161

According to a procedure similar to Example 2, 1-(2-(4-((2,3-dihydro-1,4-benzodioxin-6-ylmethyl)amino)piperidin-1-yl)ethyl)-7-methoxy-4-(1,3-thiazol-2-yl)quinolin-2(1H)-one was obtained from tert-butyl (2,3-dihydro-1,4-benzodioxin-6-ylmethyl) (1-(2-(7-methoxy-2-oxo-4-(1,3-thiazol-2-yl)quinolin-1(2H)-yl)ethyl)piperidin-4-yl) carbamate.

$^1$H-NMR (DMSO-$d_6$) δ:

1.45-1.60 (2H, m), 1.98-2.12 (4H, m), 2.60-2.66 (2H, m), 2.92-3.04 (1H, m), 3.04-3.16 (2H, m), 3.94 (3H, s), 4.02-4.07 (2H, m), 4.25 (4H, s), 4.40-4.48 (2H, m), 6.77 (1H, s), 6.88-7.10 (5H, m), 8.05 (1H, d, J=3.3 Hz), 8.16 (1H, d, J=3.3 Hz), 8.42 (1H, d, J=9.0 Hz)

Example 162

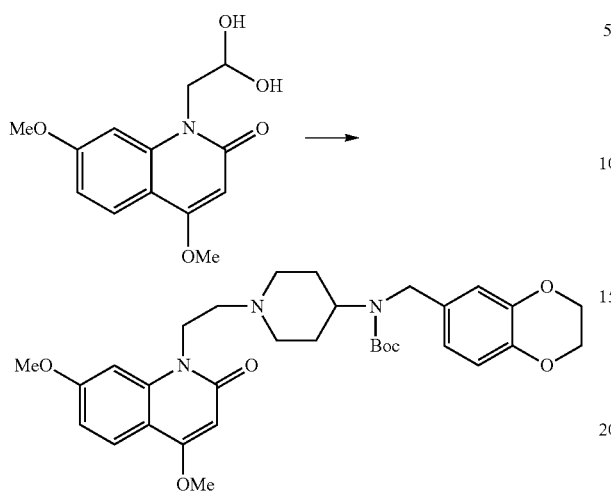

According to a procedure similar to Example 1, tert-butyl (2,3-dihydro-1,4-benzodioxin-6-ylmethyl)(1-(2-(4,7-dimethoxy-2-oxoquinolin-1(2H)-yl)ethyl)piperidin-4-yl)carbamate was obtained from 1-(2,2-dihydroxyethyl)-4,7-dimethoxyquinolin-2(1H)-one and tert-butyl (2,3-dihydro-1,4-benzodioxin-6-ylmethyl)(piperidin-4-yl)carbamate.

¹H-NMR (CDCl₃) δ:
1.42 (9H, s), 1.55-1.75 (4H, m), 2.05-2.25 (2H, m), 2.55-2.65 (2H, m), 2.95-3.15 (2H, m), 3.89 (3H, s), 3.91 (3H, s), 3.95-4.20 (1H, m), 4.24 (4H, s), 4.25-4.40 (4H, m), 5.87 (1H, s), 6.65-6.90 (5H, m), 7.86 (1H, d, J=8.8 Hz)

Example 163

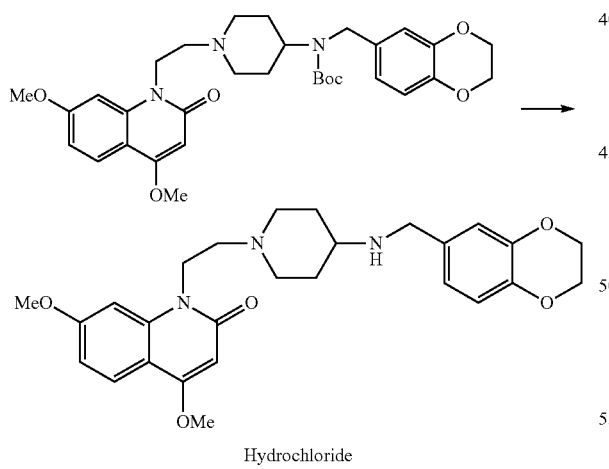

According to a procedure similar to Example 85, 1-(2-(4-((2,3-dihydro-1,4-benzodioxin-6-ylmethyl)amino)piperidin-1-yl)ethyl)-4,7-dimethoxyquinolin-2(1H)-one hydrochloride was obtained from tert-butyl (2,3-dihydro-1,4-benzodioxin-6-ylmethyl)(1-(2-(4,7-dimethoxy-2-oxoquinolin-1(2H)-yl)ethyl)piperidin-4-yl)carbamate.

¹H-NMR (DMSO-d₆) δ:
1.95-2.40 (4H, m), 3.02-3.15 (2H, m), 3.20-3.50 (3H, m), 3.75-3.85 (2H, m), 3.93 (3H, s), 3.96 (3H, s), 4.03-4.10 (2H, m), 4.25 (4H, s), 4.60-4.70 (2H, m), 5.94 (1H, s), 6.86-6.95 (2H, m), 7.00-7.06 (1H, m), 7.10-7.20 (2H, m), 7.84 (1H, d, J=8.8 Hz), 9.45-9.65 (2H, broad), 10.85-11.05 (1H, broad)

Example 164

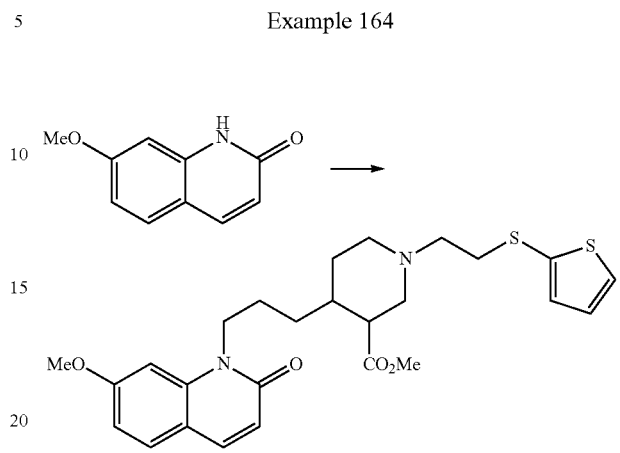

According to a procedure similar to Reference Example 47, methyl 4-(3-(7-methoxy-2-oxoquinolin-1(2H)-yl)propyl)-1-(2-(2-thienylthio)ethyl)piperidine-3-carboxylate was obtained from 7-methoxyquinolin-2(1H)-one and methyl 4-(3-((methylsulfonyl)oxy)propyl)-1-(2-(2-thienylthio)ethyl)piperidine-3-carboxylate.

¹H-NMR (CDCl₃) δ:
1.40-3.20 (16H, m), 3.66 (3H, s), 3.91 (3H, s), 4.10-4.30 (2H, m), 6.53 (1H, d, J=9.4 Hz), 6.75 (1H, s), 6.80-6.84 (1H, m), 6.94-7.02 (1H, m), 7.08-7.14 (1H, m), 7.30-7.36 (1H, m), 7.47 (1H, d, J=8.5 Hz), 7.58 (1H, d, J=9.4 Hz)

Example 165

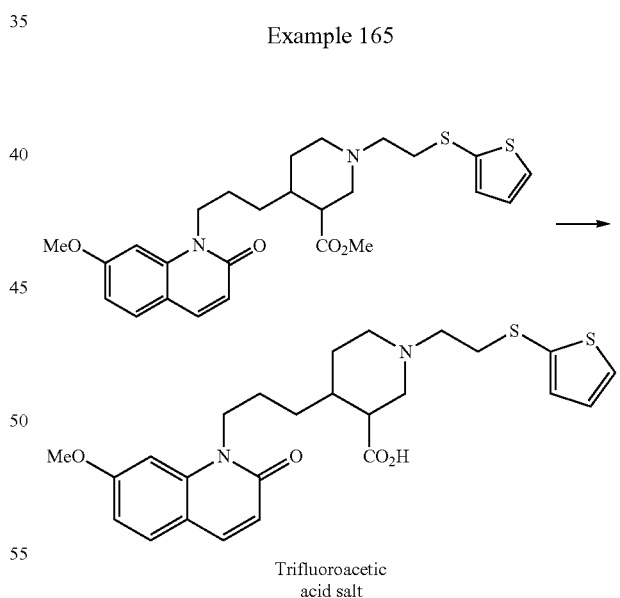

According to a procedure similar to Example 53, 4-(3-(7-methoxy-2-oxoquinolin-1(2H)-yl)propyl)-1-(2-(2-thienylthio)ethyl)piperidine-3-carboxylic acid trifluoroacetic acid salt was obtained from methyl 4-(3-(7-methoxy-2-oxoquinolin-1(2H)-yl)propyl)-1-(2-(2-thienylthio)ethyl)piperidine-3-carboxylate.

¹H-NMR (CD₃OD) δ:
1.40-2.20 (7H, m), 2.40-2.70 (1H, m), 2.90-3.80 (8H, m), 3.93 (3H, s), 4.16-4.50 (2H, m), 6.47-6.51 (1H, m), 6.92-7.02

(2H, m), 7.02-7.08 (1H, m), 7.26-7.32 (1H, m), 7.54-7.64 (2H, m), 7.83 (1H, d, J=9.5 Hz)

Example 166

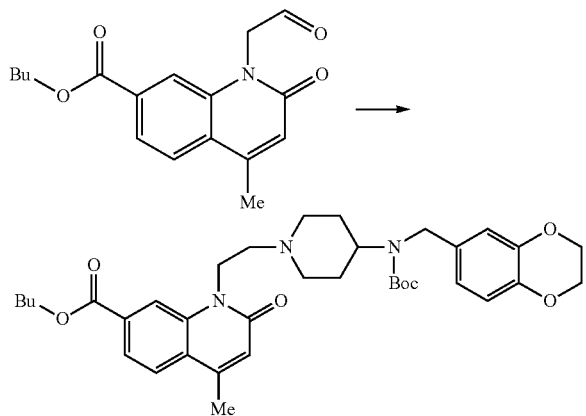

According to a procedure similar to Example 1, butyl 1-(2-(4-((tert-butoxycarbonyl)(2,3-dihydro-1,4-benzodioxin-6-ylmethyl)amino)piperidin-1-yl)ethyl)-4-methyl-2-oxo-1,2-dihydroquinoline-7-carboxylate was obtained from butyl 4-methyl-2-oxo-1-(2-oxoethyl)-1,2-dihydroquinoline-7-carboxylate and tert-butyl (2,3-dihydro-1,4-benzodioxin-6-ylmethyl)(piperidin-4-yl)carbamate.

$^1$H-NMR (CDCl$_3$) δ:

0.99 (3H, t, J=7.3 Hz), 1.36-1.80 (17H, m), 2.10-2.30 (2H, m), 2.48 (3H, d, J=1.0 Hz), 2.61-2.68 (2H, m), 3.03-3.10 (2H, m), 4.04-4.14 (1H, m), 4.20-4.32 (6H, m), 4.33-4.46 (4H, m), 6.63-6.79 (4H, m), 7.74 (1H, d, J=8.3 Hz), 7.87 (1H, dd, J=8.3, 1.2 Hz), 8.13 (1H, d, J=1.2 Hz)

Example 167

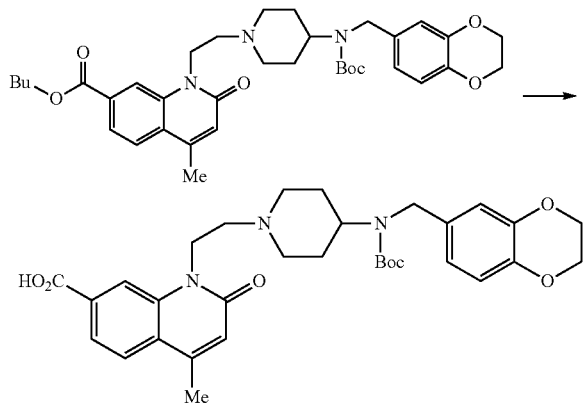

To 11 mL of a methanol solution containing 0.65 g of butyl 1-(2-(4-((tert-butoxycarbonyl) (2,3-dihydro-1,4-benzodioxin-6-ylmethyl)amino)piperidin-1-yl)ethyl)-4-methyl-2-oxo-1,2-dihydroquinoline-7-carboxylate, 55 mg of lithium hydroxide monohydrate was added and stirred for 30 min. Then, 55 mg of lithium hydroxide monohydrate and 1.1 mL of water were added and stirred for 2 hours. The methanol was removed under reduced pressure, water and chloroform were added, and adjusted to pH 5.0 with acetic acid. The organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure to give 0.60 g of 1-(2-(4-((tert-butoxycarbonyl)(2,3-dihydro-1,4-benzodioxin-6-ylmethyl)amino)piperidin-1-yl)ethyl)-4-methyl-2-oxo-1,2-dihydroquinoline-7-carboxylic acid as a white foam.

$^1$H-NMR (CDCl$_3$) δ:

1.46 (9H, s), 1.75-1.84 (2H, m), 2.20-2.40 (2H, m), 2.50 (3H, s), 2.65-2.80 (2H, m), 3.18-3.28 (2H, m), 3.75-3.85 (2H, m), 3.95-4.40 (3H, m), 4.21 (4H, s), 4.72-4.80 (2H, m), 6.61 (1H, s), 6.70-6.81 (3H, m), 7.75 (1H, d, J=8.2 Hz), 7.94 (1H, d, J=8.2 Hz), 8.60 (1H, s)

Example 168

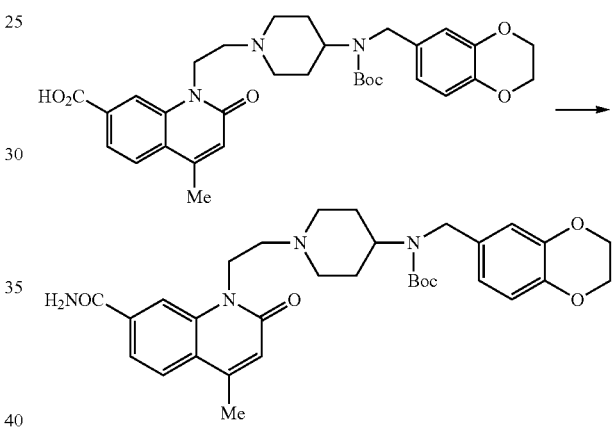

To 1.5 mL of a dioxane solution containing 0.12 g of 1-(2-(4-((tert-butoxycarbonyl)(2,3-dihydro-1,4-benzodioxin-6-ylmethyl)amino)piperidin-1-yl)ethyl)-4-methyl-2-oxo-1,2-dihydroquinoline-7-carboxylic acid, 50 μL of pyridine and 85 mg of ammonium carbonate were added, and stirred at room temperature for 13 hours. Water and ethyl acetate were added, and the organic layer was separated. The organic layer was washed with water and aqueous saturated sodium chloride solution, dried over anhydrous magnesium sulfate, and the solvent was removed under reduced pressure. To the residue thus obtained, diethyl ether was added, and resulting solid was filtered 86 mg of tert-butyl (1-(2-(7-(aminocarbonyl)-4-methyl-2-oxoquinolin-1(2H)-yl)ethyl)piperidin-4-yl)(2,3-dihydro-1,4-benzodioxin-6-ylmethyl)carbamate as a white solid.

$^1$H-NMR (CDCl$_3$) δ:

1.35-1.52 (9H, m), 1.60-1.80 (4H, m), 2.10-2.25 (2H, m), 2.48 (3H, d, J=1.0 Hz), 2.60-2.68 (2H, m), 3.00-3.10 (2H, m), 3.80-4.35 (3H, m), 4.25 (4H, s), 4.40-4.50 (2H, m), 6.63-6.65 (1H, m), 6.68-6.82 (3H, m), 7.64-7.72 (1H, m), 7.76 (1H, d, J=8.3 Hz), 8.05-8.10 (1H, m)

Example 169

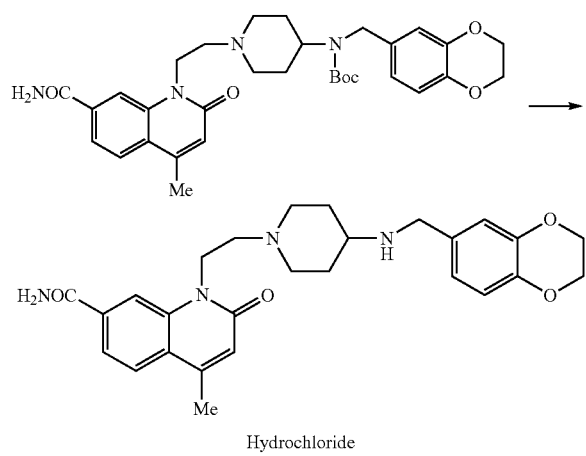

Hydrochloride

According to a procedure similar to Example 59, 1-(2-(4-((2,3-dihydro-1,4-benzodioxin-6-ylmethyl)amino)piperidin-1-yl)ethyl)-4-methyl-2-oxo-1,2-dihydroquinoline-7-carboxamide hydrochloride was obtained from tert-butyl (1-(2-(7-(aminocarbonyl)-4-methyl-2-oxoquinolin-1(2H)-yl)ethyl)piperidin-4-yl) (2,3-dihydro-1,4-benzodioxin-6-ylmethyl)carbamate.

$^1$H-NMR (DMSO-$d_6$) δ:
1.90-2.10 (2H, m), 2.30-2.45 (2H, m), 2.45-2.60 (3H, m), 3.00-3.60 (5H, m), 3.75-3.90 (2H, m), 4.05-4.15 (2H, m), 4.26 (4H, s), 4.65-4.80 (2H, m), 6.67 (1H, s), 6.91 (1H, d, J=8.2 Hz), 7.02-7.08 (1H, m), 7.15-7.19 (1H, m), 7.70 (1H, s), 7.85 (1H, d, J=8.3 Hz), 7.93 (1H, d, J=8.3 Hz), 8.12 (1H, s), 8.43 (1H, s), 9.40-9.55 (1H, broad), 10.40-10.60 (1H, broad)

Example 170

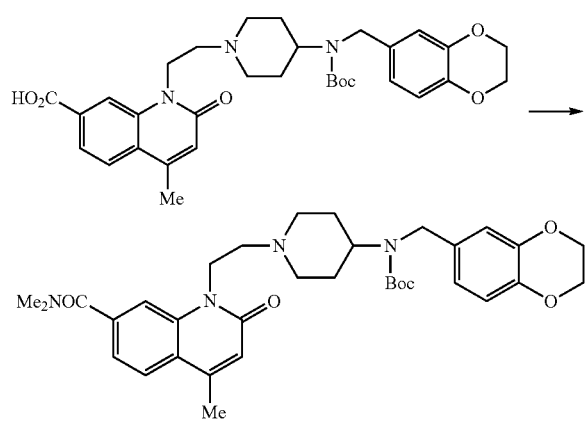

To 1.7 mL of a dichloromethane solution containing 0.10 g of 1-(2-(4-((tert-butoxycarbonyl)(2,3-dihydro-1,4-benzodioxin-6-ylmethyl)amino)piperidin-1-yl)ethyl)-4-methyl-2-oxo-1,2-dihydroquinoline-7-carboxylic acid, 89 μL of triethylamine, 51 mg of dimethylamine hydrochloride and 0.12 g of O-(7-azabenzotriazol-1-yl)-1,1,3,3-tetramethyluronium hexafluorophosphate were added at room temperature, and stirred at the same temperature for 1 hour. Water and ethyl acetate were added to the reaction mixture. The organic layer was separated, washed with aqueous saturated sodium chloride solution, dried over anhydrous magnesium sulfate, and the solvent was removed under reduced pressure. The residue thus obtained was purified by basic silica gel column chromatography [eluent; chloroform:methanol=100:1], to give 93 mg of tert-butyl (2,3-dihydro-1,4-benzodioxin-6-ylmethyl)(1-(2-(7-((dimethylamino)carbonyl)-4-methyl-2-oxoquinolin-1(2H)-yl)ethyl)piperidin-4-yl)carbamate as a white solid.

$^1$H-NMR (CDCl$_3$) δ:
1.42 (9H, s), 1.60-1.80 (4H, m), 2.15-2.30 (2H, m), 2.46-2.48 (3H, m), 2.65-2.72 (2H, m), 2.99 (3H, s), 3.05-3.20 (2H, m), 3.15 (3H, s), 4.00-4.20 (1H, m), 4.24 (4H, s), 4.24-4.34 (2H, m), 4.36-4.44 (2H, m), 6.61 (1H, d, J=1.2 Hz), 6.65-6.72 (1H, m), 6.74 (1H, d, J=2.0 Hz), 6.78 (1H, d, J=8.0 Hz), 7.10-7.30 (1H, m), 7.47 (1H, s), 7.73 (1H, d, J=8.0 Hz)

Example 171

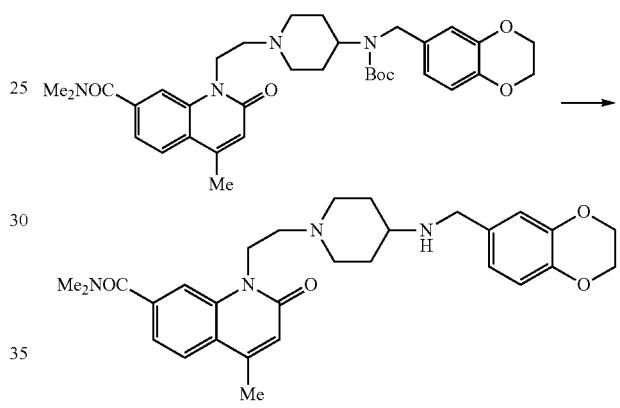

Hydrochloride

According to a procedure similar to Example 59, 1-(2-(4-((2,3-dihydro-1,4-benzodioxin-6-ylmethyl)amino)piperidin-1-yl)ethyl)-N,N-dimethyl-4-methyl-2-oxo-1,2-dihydroquinoline-7-carboxamide hydrochloride was obtained from tert-butyl (2,3-dihydro-1,4-benzodioxin-6-ylmethyl)(1-(2-(7-((dimethylamino)carbonyl)-4-methyl-2-oxoquinolin-1(2H)-yl)ethyl)piperidin-4-yl)carbamate.

$^1$H-NMR (DMSO-$d_6$) δ:
1.95-2.10 (2H, m), 2.30-2.40 (2H, m), 2.48 (3H, s), 2.90-3.50 (5H, m), 2.96 (3H, s), 3.04 (3H, s), 3.74-3.82 (1H, m), 4.05-4.10 (2H, m), 4.25 (4H, s), 4.62-4.68 (2H, m), 6.64 (1H, s), 6.91 (1H, d, J=8.2 Hz), 7.04 (1H, d, J=8.2 Hz), 7.16 (1H, s), 7.34 (1H, d, J=8.0 Hz), 7.72 (1H, s), 7.90 (1H, d, J=8.0 Hz)

Example 172

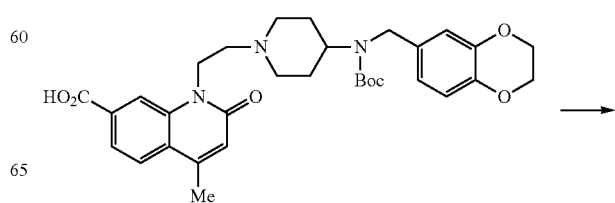

-continued

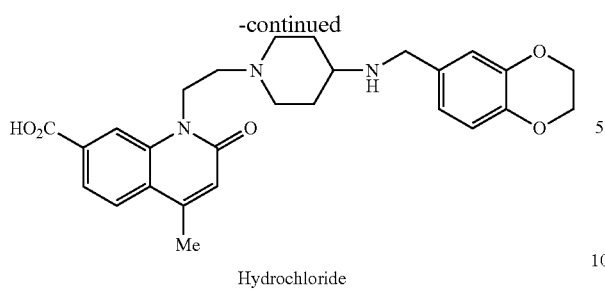

Hydrochloride

According to a procedure similar to Example 85, 1-(2-(4-((2,3-dihydro-1,4-benzodioxin-6-ylmethyl)amino)piperidin-1-yl)ethyl)-4-methyl-2-oxo-1,2-dihydroquinoline-7-carboxylic acid hydrochloride was obtained from 1-(2-(4-((tert-butoxycarbonyl)(2,3-dihydro-1,4-benzodioxin-6-ylmethyl)amino)piperidin-1-yl)ethyl)-4-methyl-2-oxo-1,2-dihydroquinoline-7-carboxylic acid.

$^1$H-NMR (DMSO-$d_6$) δ:
1.70-1.90 (2H, m), 2.25-2.45 (2H, m), 2.52 (3H, s), 2.90-3.95 (7H, m), 4.09 (2H, s), 4.26 (4H, s), 4.60-4.70 (2H, m), 6.73 (1H, s), 6.94 (1H, d, J=8.3 Hz), 6.99 (1H, dd, J=8.3, 2.0 Hz), 7.08 (1H, d, J=2.0 Hz), 7.89 (1H, d, J=8.2 Hz), 8.00 (1H, d, 8.2 Hz), 8.03 (1H, s)

Example 173

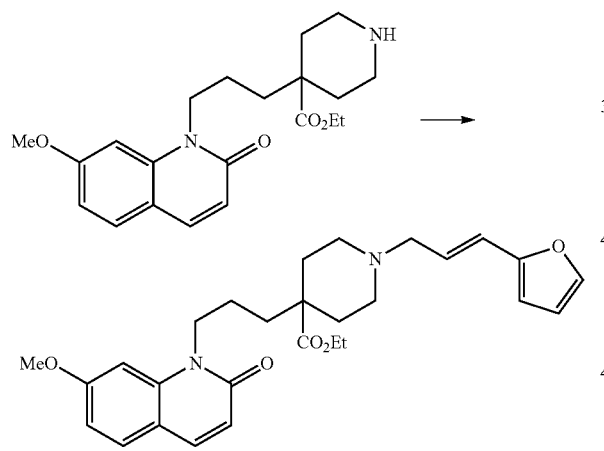

To 2 mL of a dichloromethane solution containing 50 mg of ethyl 4-(3-(7-methoxy-2-oxoquinolin-1(2H)-yl)propyl)piperidine-4-carboxylate, 18 mg of (2E)-3-(2-furyl)acrolein and 20 μL of acetic acid were added, and stirred for 40 min. To the reaction mixture, 43 mg of sodium triacetoxyborohydride was added, stirred for 30 min. Chloroform and aqueous saturated sodium hydrogen carbonate solution were added, the organic layer was separated, dried over anhydrous magnesium sulfate, and the solvent was removed under reduced pressure. The residue thus obtained was purified by silica gel column chromatography [eluent; chloroform:methanol=50:1], to give 60 mg of ethyl 1-((2E)-3-(2-furyl)-2-propen-1-yl)-4-(3-(7-methoxy-2-oxoquinolin-1(2H)-yl)propyl)piperidine-4-carboxylate as a brown solid.

$^1$H-NMR (CDCl$_3$) δ:
1.20 (3H, d, J=7.1 Hz), 1.23-1.29 (2H, m), 1.50-1.80 (6H, m), 2.15-2.25 (2H, m), 2.75-3.00 (2H, m), 3.10-3.30 (2H, m), 3.91 (3H, s), 4.12 (2H, q, J=7.1 Hz), 4.17-4.24 (2H, m), 6.10-6.30 (2H, m), 6.30-6.40 (2H, m), 6.52 (1H, d, J=9.4 Hz), 6.72 (1H, s), 6.78-6.84 (1H, m), 7.34 (1H, s), 7.46 (1H, d, J=8.6 Hz), 7.58 (1H, d, J=9.5 Hz)

Example 174

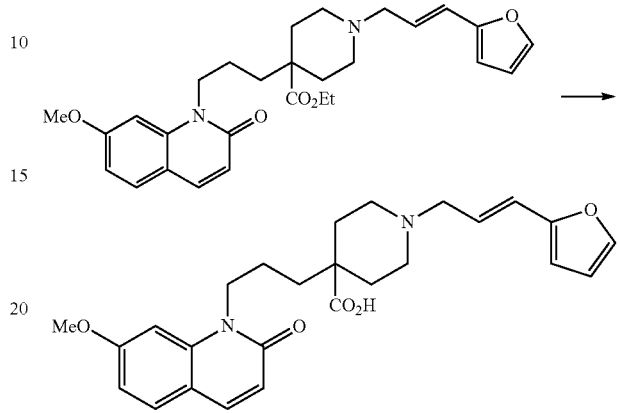

According to a procedure similar to Example 35, 1-((2E)-3-(2-furyl)-2-propen-1-yl)-4-(3-(7-methoxy-2-oxoquinolin-1(2H)-yl)propyl)piperidine-4-carboxylic acid was obtained from ethyl 1-((2E)-3-(2-furyl)-2-propen-1-yl)-4-(3-(7-methoxy-2-oxoquinolin-1(2H)-yl)propyl)piperidine-4-carboxylate.

$^1$H-NMR (CDCl$_3$) δ:
1.30-1.45 (2H, m), 1.46-1.60 (4H, m), 1.90-2.10 (4H, m), 2.60-2.70 (2H, m), 3.00-3.10 (2H, m), 3.89 (3H, s), 4.15-4.25 (2H, m), 5.98-6.08 (1H, m), 6.37-6.47 (4H, m), 6.87-6.93 (2H, m), 7.58 (1H, s), 7.65 (1H, d, 9.4 Hz), 7.82 (1H, d, J=9.4 Hz)

Example 175

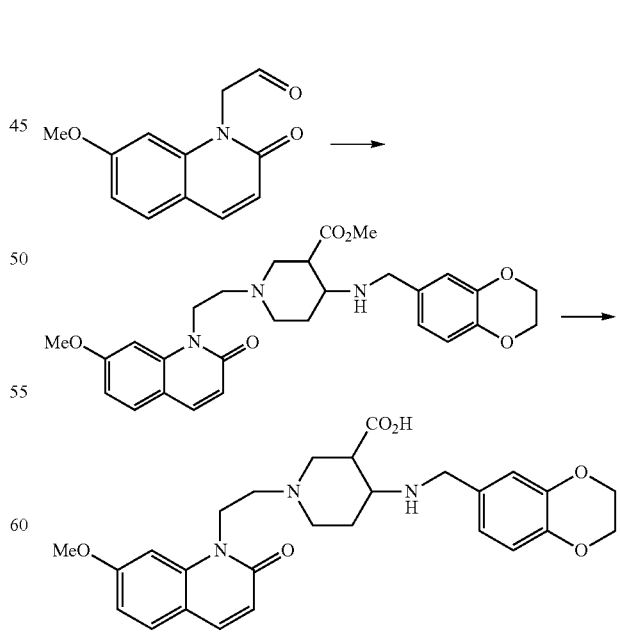

Hydrochloride

385

As similarly to Example 1, to 0.10 g of methyl 4-((2,3-dihydro-1,4-benzodioxin-6-ylmethyl)amino)-1-(2-(7-methoxy-2-oxoquinolin-1(2H)-yl)ethyl)piperidine-3-carboxylate obtained from (7-methoxy-2-oxoquinolin-1(2H)-yl)acetaldehyde and methyl 4-((2,3-dihydro-1,4-benzodioxin-6-ylmethyl)amino)piperidine-3-carboxylate hydrochloride, 1.0 mL of 6 mol/L hydrochloric acid and 1.0 mL of dioxane were added. The reaction mixture was stirred under reflux with heating for 3 hours. The solvent was removed, acetonitrile was added, and resulting solid was filtered to afford 54 mg of 4-((2,3-dihydro-1,4-benzodioxin-6-ylmethyl)amino)-1-(2-(7-methoxy-2-oxoquinolin-1(2H)-yl)ethyl)piperidine-3-carboxylic acid hydrochloride as a brown solid.

$^1$H-NMR (DMSO-$d_6$) δ:
2.00-2.40 (2H, m), 3.10-3.50 (3H, m), 3.50-4.00 (5H, m), 3.94 (3H, s), 4.03-4.30 (2H, m), 4.26 (4H, s), 4.50-4.75 (2H, m), 6.49 (1H, d, J=9.5 Hz), 6.90-7.05 (3H, m), 7.05-7.15 (2H, m), 7.69-7.75 (1H, m), 7.92 (1H, d, J=9.5 Hz)

Example 176

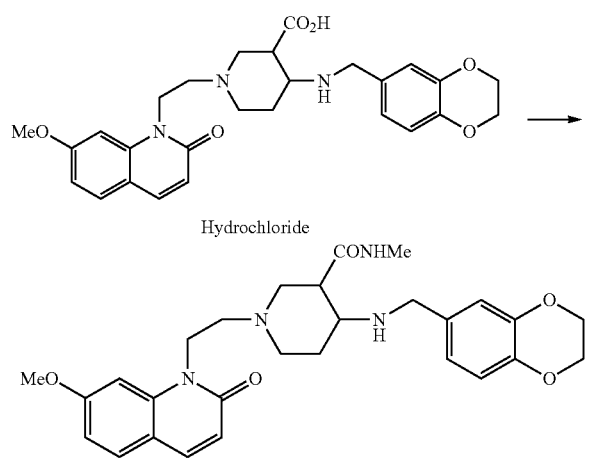

According to a procedure similar to Example 170, 4-((2,3-dihydro-1,4-benzodioxin-6-ylmethyl)amino)-1-(2-(7-methoxy-2-oxoquinolin-1(2H)-yl)ethyl)-N-methylpiperidine-3-carboxamide was obtained from 4-((2,3-dihydro-1,4-benzodioxin-6-ylmethyl)amino)-1-(2-(7-methoxy-2-oxoquinolin-1(2H)-yl)ethyl)piperidine-3-carboxylic acid hydrochloride and methylamine hydrochloride.

Isomer A $^1$H-NMR (CDCl$_3$) δ:
1.60-1.85 (2H, m), 2.10-2.35 (2H, m), 2.66 (3H, d, J=4.9 Hz), 2.65-2.80 (4H, m), 3.10-3.24 (2H, m), 3.62-3.95 (2H, m), 3.91 (3H, s), 4.24 (4H, s), 4.28-4.38 (1H, m), 4.45-4.53 (1H, m), 6.54 (1H, d, J=9.4 Hz), 6.77-6.87 (4H, m), 7.49 (1H, d, J=8.6 Hz), 7.62 (1H, d, J=9.4 Hz), 8.40-8.50 (1H, m)

Isomer B $^1$H-NMR (CDCl$_3$) δ:
1.40-1.55 (1H, m), 1.70-1.90 (2H, m), 2.05-2.15 (1H, m), 2.25-2.40 (3H, m), 2.73 (3H, d, J=4.9 Hz), 2.75-2.90 (1H, m), 2.90-3.00 (1H, m), 3.26-3.35 (1H, m), 3.64 (1H, d, J=12.8 Hz), 3.82 (1H, d, J=12.8 Hz), 3.92 (3H, s), 4.25 (4H, s), 4.25-4.35 (1H, m), 4.45-4.60 (1H, m), 6.52 (1H, d, J=9.4 Hz), 6.75-6.90 (5H, m), 7.47 (1H, d, J=8.6 Hz), 7.60 (1H, d, J=9.4 Hz), 8.00-8.10 (1H, m)

Example 177

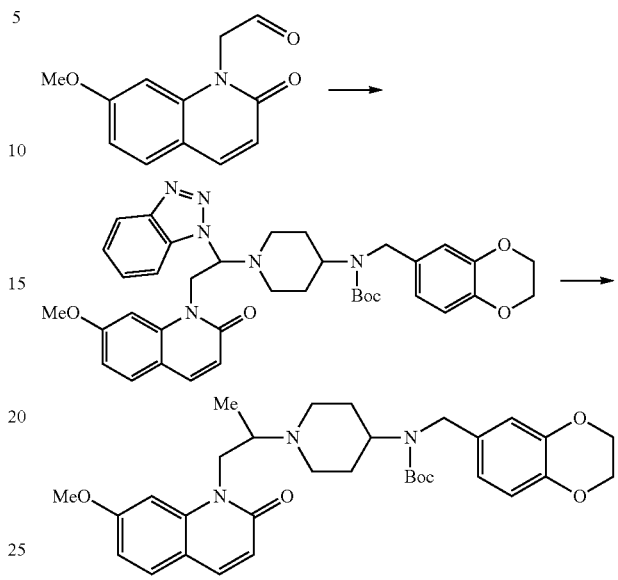

To 44 mL of a dichloromethane solution containing 0.22 g of (7-methoxy-2-oxoquinolin-1(2H)-yl)acetaldehyde, 0.40 mL of acetic acid, 0.35 g of tert-butyl (2,3-dihydro-1,4-benzodioxin-6-ylmethyl)(piperidin-4-yl)carbamate and 0.12 g of benzotriazole were added, and stirred for 1 day. The solvent was removed under reduced pressure to afford a pale yellow solid. To 4.0 mL of tetrahydrofuran containing this pale yellow solid, 1.0 mL of 3.0 mol/L methylmagnesium bromide/diethyl ether was added and stirred for 1 hour. The reaction solution was poured onto aqueous saturated ammonium chloride solution, and water and ethyl acetate were added. The organic layer was separated, washed with aqueous saturated sodium chloride solution, dried over anhydrous magnesium sulfate, and the solvent was removed under reduced pressure. The residue thus obtained was purified by silica gel column chromatography[eluent; hexane:ethyl acetate=7:3], to give 50 mg of tert-butyl (2,3-dihydro-1,4-benzodioxin-6-ylmethyl)(1-(2-(7-methoxy-2-oxoquinolin-1(2H)-yl)-1-methylethyl)piperidin-4-yl)carbamate as a colorless foam.

$^1$H-NMR (CDCl$_3$) δ:
0.99 (3H, d, J=6.8 Hz), 1.30-1.70 (15H, m), 2.35-2.50 (1H, m), 2.65-2.75 (1H, m), 2.95-3.20 (2H, m), 3.87 (3H, s), 3.96-4.10 (1H, m), 4.22-4.28 (6H, m), 4.45-4.65 (1H, m), 6.51 (1H, d, J=9.5 Hz), 6.65-6.90 (5H, m), 7.44 (1H, d, J=8.5 Hz), 7.57 (1H, d, J=9.5 Hz)

Example 178

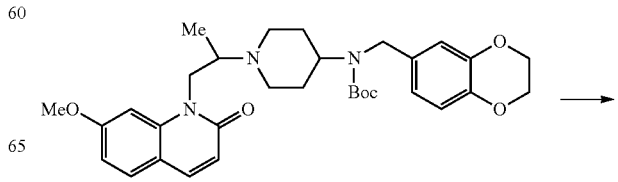

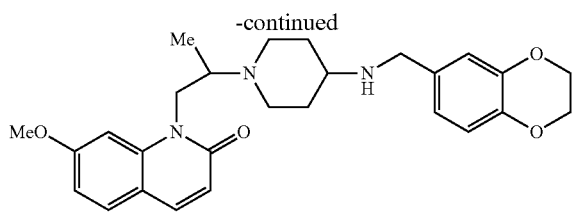

According to a procedure similar to Example 2, 1-(2-(4-(2,3-dihydro-1,4-benzodioxin-6-ylmethyl)amino)piperidin-1-yl)propyl)-7-methoxyquinolin-2(1H)-one was obtained from tert-butyl (2,3-dihydro-1,4-benzodioxin-6-ylmethyl)(1-(2-(7-methoxy-2-oxoquinolin-1(2H)-yl)-1-methylethyl)piperidin-4-yl)carbamate.

$^1$H-NMR (CDCl$_3$) δ:
1.02 (3H, d, J=6.6 Hz), 1.20-1.45 (3H, m), 1.80-2.00 (2H, m), 2.30-2.55 (3H, m), 2.65-2.75 (1H, m), 2.95-3.03 (1H, m), 3.10-3.20 (1H, m), 3.70 (2H, s), 3.90 (3H, s), 4.25 (4H, s), 4.55-4.66 (1H, m), 6.52 (1H, d, J=9.4 Hz), 6.75-6.85 (4H, m), 6.92 (1H, d, J=2.0 Hz), 7.44 (1H, d, J=8.5 Hz), 7.57 (1H, d, J=9.4 Hz)

Example 179

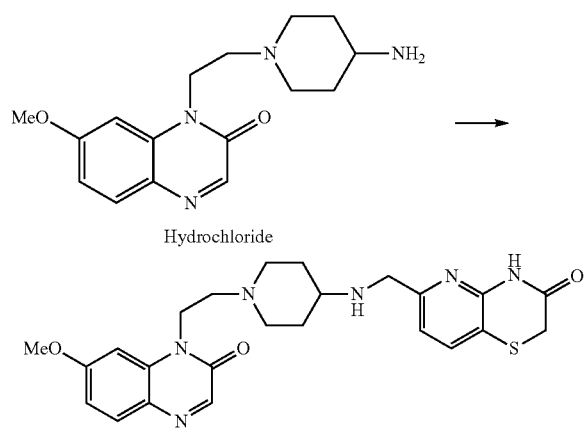

To 2 mL of an N,N-dimethylformamide solution containing 63 mg of 1-(2-(4-aminopiperidin-1-yl)ethyl)-7-methoxyquinoxalin-2(1H)-one hydrochloride, 36 mg of 3-oxo-3,4-dihydro-2H-pyrido(3,2-b)(1,4)thiazine-6-carbaldehyde, 0.14 mL of acetic acid and 0.12 mL of triethylamine were added, and stirred for 3 hours, thereafter 53 mg of sodium triacetoxyborohydride was added, and stirred at room temperature for 45 min. Aqueous saturated sodium hydrogen carbonate solution and ethyl acetate were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by basic silica gel column chromatography [eluent; chloroform:methanol=10:1], to give 25 mg of 6-(((1-(2-(7-methoxy-2-oxoquinoxalin-1(2H)-yl)ethyl)piperidin-4-yl)amino)methyl)-2H-pyrido(3,2-b)(1,4)thiazin-3(4H)-one as a white solid.

$^1$H-NMR (CDCl$_3$) δ:
1.40-1.64 (2H, m), 1.85-1.95 (2H, m), 2.15-2.25 (2H, m), 2.45-2.60 (1H, m), 2.62-2.72 (2H, m), 2.95-3.05 (2H, m), 3.48 (2H, s), 3.83 (2H, s), 3.92 (3H, s), 4.30-4.40 (2H, m), 6.86 (1H, d, J=2.4 Hz), 6.92 (1H, dd, J=8.8, 2.4 Hz), 6.98 (1H, d, J=7.8 Hz), 7.57 (1H, d, J=7.8 Hz), 7.79 (1H, d, J=8.8 Hz), 7.97 (1H, s), 8.12 (1H, s)

Example 180

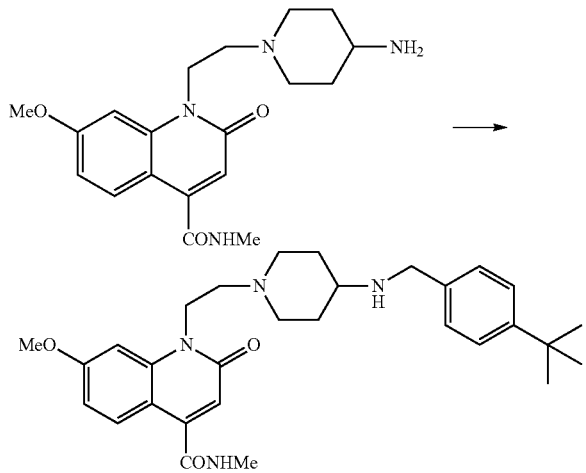

According to a procedure similar to Example 179, 7-methoxy-N-methyl-2-oxo-1-(2-(4-(((3-oxo-3,4-dihydro-2H-pyrido(3,2-b)(1,4)thiazin-6-yl)methyl)amino)piperidin-1-yl)ethyl)-1,2-dihydroquinoline-4-carboxamide was obtained from 1-(2-(4-aminopiperidin-1-yl)ethyl-7-methoxy-N-methyl-2-oxo-1,2-dihydroquinoline-4-carboxamide and 3-oxo-3,4-dihydro-2H-pyrido(3,2-b)(1,4)thiazine-6-carbaldehyde.

$^1$H-NMR (CDCl$_3$) δ:
1.50-2.40 (6H, m), 2.60-2.80 (3H, m), 3.00-3.20 (2H, m), 3.03 (3H, d, J=4.9 Hz), 3.40-3.52 (2H, m), 3.88 (2H, s), 3.93 (3H, s), 4.40-4.50 (2H, m), 6.42 (1H, s), 6.58 (1H, s), 6.84 (1H, d, J=9.2 Hz), 6.92-7.01 (2H, m), 7.25-7.27 (1H, m), 7.58 (1H, d, J=8.0 Hz), 7.90 (1H, d, J=9.0 Hz)

Example 181

According to a procedure similar to Example 179, 1-(2-(4-((4-tert-butylbenzyl)amino)piperidin-1-yl)ethyl)-7-methoxy-N-methyl-2-oxo-1,2-dihydroquinoline-4-carboxamide was obtained from 1-(2-(4-aminopiperidin-1-yl)ethyl-7-methoxy-N-methyl-2-oxo-1,2-dihydroquinoline-4-carboxamide and 4-tert-butylbenzaldehyde.

¹H-NMR (CDCl₃) δ:

1.31 (9H, s), 1.40-1.55 (2H, m), 1.85-1.95 (2H, m), 2.13-2.23 (2H, m), 2.50-2.63 (3H, m), 2.94-3.02 (2H, m), 3.05 (3H, d, J=4.9 Hz), 3.78 (2H, s), 3.91 (3H, s), 4.30-4.40 (2H, m), 6.17-6.27 (1H, m), 6.56 (1H, s), 6.84 (1H, dd, J=8.9, 2.4 Hz), 6.90-6.92 (1H, m), 7.22-7.27 (2H, m), 7.35 (2H, d, J=8.3 Hz), 7.88 (1H, d, J=8.9 Hz)

Example 182

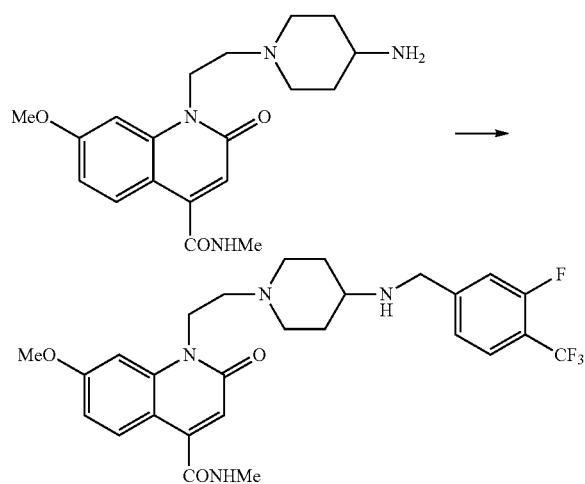

According to a procedure similar to Example 179, 1-(2-(4-((3-fluoro-4-(trifluoromethyl)benzyl)amino)piperidin-1-yl)ethyl)-7-methoxy-N-methyl-2-oxo-1,2-dihydroquinoline-4-carboxamide was obtained from 1-(2-(4-aminopiperidin-1-yl)ethyl)-7-methoxy-N-methyl-2-oxo-1,2-dihydroquinoline-4-carboxamide and 3-fluoro-4-(trifluoromethyl)benzaldehyde.

¹H-NMR (CDCl₃) δ:

1.35-1.50 (2H, m), 1.86-1.96 (2H, m), 2.12-2.22 (2H, m), 2.45-2.55 (1H, m), 2.55-2.65 (2H, m), 2.95-3.00 (2H, m), 3.05 (3H, d, J=4.9 Hz), 3.87 (2H, s), 3.91 (3H, s), 4.30-4.38 (2H, m), 6.22-6.28 (1H, m), 6.56 (1H, s), 6.84 (1H, dd, J=9.0, 2.1 Hz), 6.89 (1H, d, J=2.1 Hz), 7.18-7.28 (2H, m), 7.54 (1H, t, J=7.6 Hz), 7.88 (1H, d, J=9.0 Hz)

Example 183

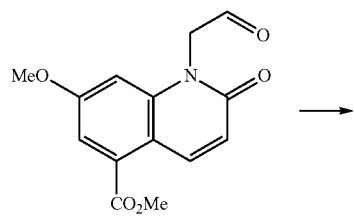

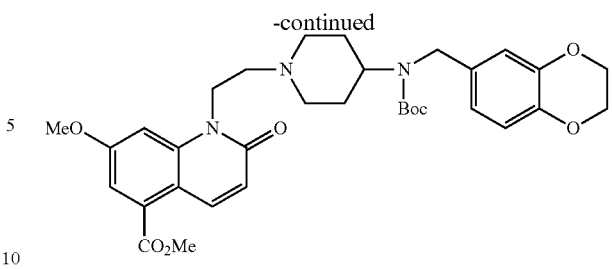

To 10 mL of a chloroform solution containing 472 mg of methyl 7-methoxy-2-oxo-1-(2-oxoethyl)-1,2-dihydroquinoline-5-carboxylate and 374 mg of tert-butyl (2,3-dihydro-1,4-benzodioxin-6-ylmethyl)(piperidin-4-yl)carbamate, 62 μL of acetic acid was added and stirred at room temperature for 1 hour. To the reaction mixture, 352 mg of sodium triacetoxyborohydride was added and stirred for 30 min. Aqueous saturated sodium hydrogen carbonate solution was added and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; ethyl acetate:hexane=2:1], to give 493 mg of methyl 1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinoline-5-carboxylate as a white solid.

¹H-NMR (CDCl₃) δ:

1.43 (9H, s), 1.58-1.76 (2H, m), 1.76-1.91 (2H, m), 2.09-2.28 (2H, m), 2.49-2.75 (3H, m), 2.91-3.20 (2H, m), 3.92 (3H, s), 3.97 (3H, s), 4.24 (4H, s), 4.27-4.46 (4H, m), 6.52-6.87 (4H, m), 7.08 (1H, d, J=1.8 Hz), 7.39 (1H, d, J=2.2 Hz), 8.60 (1H, d, J=10.1 Hz)

Example 184

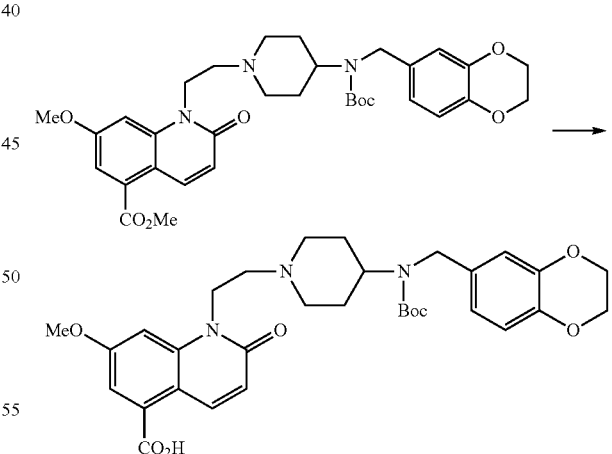

466 mg of methyl 1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinoline-5-carboxylate was dissolved in a mixture of 7 mL of methanol, 5 mL of tetrahydrofuran and 3 mL of water. To this mixture, 0.77 mL of 5 mol/L sodium hydroxide was added and stirred at room temperature for 1 hour. To the reaction mixture, hydrochloric acid was added to make acidic, the resulting solid was filtered and dissolved in chloroform. The chloroform solution was dried over anhydrous magnesium sulfate, and the solvent was removed under reduced pressure to give 553 mg of 1-(2-(4-((tert-butoxycarbonyl)(2,3-dihydro-1,4-benzodioxin-6-ylmethyl)amino)piperidin-1-yl)ethyl)-7-methoxy-2-oxo-1,2-dihydroquinoline-5-carboxylic acid.

$^1$H-NMR (CDCl$_3$) δ:
1.46 (9H, s), 1.81-1.94 (2H, m), 2.39-2.52 (2H, m), 2.81-2.97 (2H, m), 3.15-3.28 (3H, m), 3.64-3.78 (2H, m), 4.07 (3H, s), 4.23 (4H, s), 4.31-4.42 (2H, m), 4.84-5.01 (2H, m), 6.57 (1H, d, J=10.1 Hz), 6.71-6.79 (3H, m), 7.47-7.52 (1H, m), 7.53-7.61 (1H, m), 8.75 (1H, d, J=10.1 Hz)

Example 185

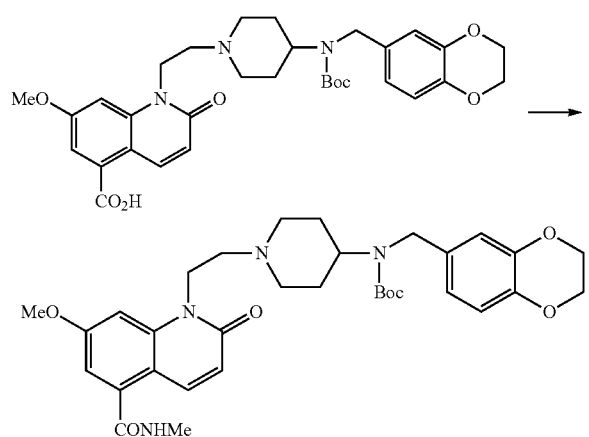

463 mg of 1-(2-(4-((tert-butoxycarbonyl) (2,3-dihydro-1,4-benzodioxin-6-ylmethyl)amino)piperidin-1-yl)ethyl)-7-methoxy-2-oxo-1,2-dihydroquinoline-5-carboxylic acid and 144 mg of methylamine hydrochloride were dissolved in 10 mL of N,N-dimethylformamide. To the mixture, 706 mg of (benzotriazol-1-yloxy)tripyrrolidinophosphonium hexafluorophosphate and 0.47 mL of N,N-diisopropylethylamine were added and stirred at room temperature overnight. The reaction mixture was poured into water, and extracted with a mixture of ethyl acetate: toluene=5:1. The organic layer was washed sequentially with water and aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=20:1], to give 401 mg of tert-butyl (2,3-dihydro-1,4-benzodioxin-6-ylmethyl)(1-(2-(7-methoxy-5-((methylamino)carbonyl)-2-oxoquinolin-1(2H)-yl)ethyl)piperidin-4-yl)carbamate as a pale brown foam.

$^1$H-NMR (CDCl$_3$) δ:
1.46 (9H, s), 1.76-1.93 (2H, m), 2.11-2.24 (2H, m), 2.72-2.94 (2H, m), 3.03 (3H, d, J=4.8 Hz), 3.27-3.42 (3H, m), 3.56-3.72 (2H, m), 3.87 (3H, s), 4.24 (4H, s), 4.26-4.33 (2H, m), 4.51-4.66 (2H, m), 6.41 (1H, d, J=9.7 Hz), 6.64-6.73 (2H, m), 6.74-6.81 (1H, m), 6.85-6.96 (2H, m), 8.04 (1H, d, J=9.7 Hz)

Example 186

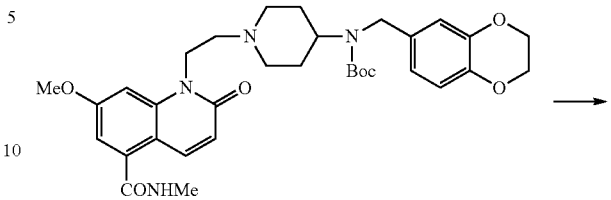

To 5 mL of an ethyl acetate solution containing 369 mg of tert-butyl (2,3-dihydro-1,4-benzodioxin-6-ylmethyl)(1-(2-(7-methoxy-5-((methylamino)carbonyl)-2-oxoquinolin-1(2H)-yl)ethyl)piperidin-4-yl)carbamate, 9 mL of 4 mol/L hydrogen chloride/ethyl acetate was added and stirred at room temperature for 2 hours. The solvent was removed under reduced pressure, ethyl acetate was added to the residue thus obtained, and the resulting solid was filtered to give 205 mg of 1-(2-(4-((2,3-dihydro-1,4-benzodioxin-6-ylmethyl)amino)piperidin-1-yl)ethyl)-7-methoxy-N-methyl-2-oxo-1,2-dihydroquinoline-5-carboxamide hydrochloride as a white solid.

$^1$H-NMR (DMSO-d$_6$) δ:
2.01-2.10 (2H, m), 2.30-2.40 (2H, m), 2.81 (3H, d, J=4.6 Hz), 3.04-3.14 (2H, m), 3.19-3.32 (3H, m), 3.74-3.84 (2H, m), 4.00 (3H, s), 4.05-4.11 (2H, m), 4.25 (4H, s), 4.66-4.73 (2H, m), 6.51 (1H, d, J=9.6 Hz), 6.91 (1H, d, J=8.3 Hz), 7.00 (1H, d, J=2.3 Hz), 7.03 (1H, d, J=8.3 Hz), 7.15 (1H, s), 7.24 (1H, s), 8.08 (1H, d, J=9.6 Hz), 9.38-9.47 (2H, broad), 10.89-11.28 (1H, broad)

Example 187

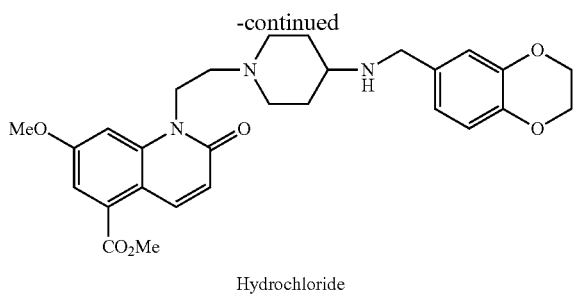

Hydrochloride

To 12 mL of an ethyl acetate solution containing 200 mg of tert-butyl (2,3-dihydro-1,4-benzodioxin-6-ylmethyl)(1-(2-(7-methoxy-5-methoxycarbonyl)-2-oxoquinolin-1(2H)-yl)ethyl)piperidin-4-yl)carbamate, 2 mL of 4 mol/L hydrogen chloride/ethyl acetate was added and stirred at room temperature. The resulting solid was filtered to give 140 mg of methyl 1-(2-(4-((2,3-dihydro-1,4-benzodioxin-6-ylmethyl)amino)piperidin-1-yl)ethyl)-7-methoxy-2-oxo-1,2-dihydroquinoline-5-carboxylate hydrochloride as a white solid.

$^1$H-NMR (DMSO-$d_6$, $D_2O$) δ:
2.02-2.12 (2H, m), 2.34-2.40 (2H, m), 3.07-3.16 (2H, m), 3.20-3.31 (3H, m), 3.73-3.82 (2H, m), 3.92 (3H, s), 4.02 (3H, s), 4.04-4.09 (2H, m), 4.25 (4H, s), 4.69-4.78 (2H, m), 6.59-6.65 (1H, m), 6.90 (1H, d, J=8.3 Hz), 7.04 (1H, dd, J=8.3, 1.8 Hz), 7.17 (1H, d, J=1.8 Hz), 7.35 (1H, d, J=2.3 Hz), 7.40 (1H, s), 8.45-8.51 (1H, m), 9.46-9.65 (2H, broad), 11.10-11.45 (1H, broad)

Example 188

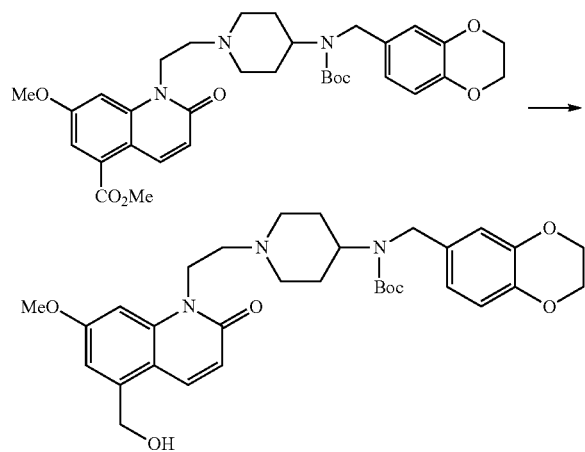

800 mg of tert-butyl (2,3-dihydro-1,4-benzodioxin-6-ylmethyl)(1-(2-(7-methoxy-5-methoxycarbonyl)-2-oxoquinolin-1(2H)-yl)ethyl)piperidin-4-yl)carbamate was dissolved in 8 mL of methanol, 250 mg of sodium borohydride was added under ice-water cooling, and stirred at room temperature for 4 hours. To the reaction mixture, water and chloroform were added. The organic layer was separated, washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 727 mg of tert-butyl (2,3-dihydro-1,4-benzodioxin-6-ylmethyl) (1-(2-(5-hydroxymethyl-7-methoxy-2-oxoquinolin-1(2H)-yl)ethyl)piperidin-4-yl) carbamate as a white foam.

$^1$H-NMR (CDCl$_3$) δ:
1.41 (9H, s), 1.60-1.72 (5H, m), 1.98-2.02 (1H, m), 2.11-2.23 (2H, m), 2.59-2.64 (2H, m), 3.01-3.06 (2H, m), 3.89 (3H, s), 4.22-4.40 (8H, m), 4.94 (2H, d, J=5.5 Hz), 6.55 (1H, d, J=10.1 Hz), 6.66-6.71 (1H, m), 6.73 (1H, d, J=1.8 Hz), 6.78 (1H, d, J=8.3 Hz), 6.84 (1H, s), 6.91 (1H, d, J=2.3 Hz), 7.90 (1H, d, J=10.1 Hz)

Example 189

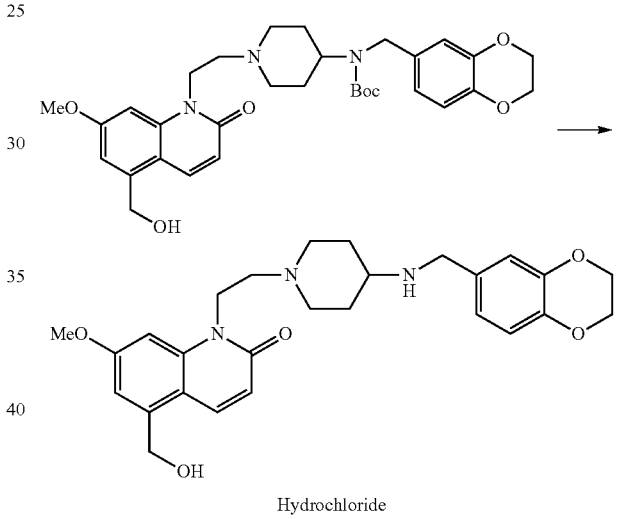

Hydrochloride

To 10 mL of an ethyl acetate solution containing 220 mg of tert-butyl (2,3-dihydro-1,4-benzodioxin-6-ylmethyl)(1-(2-(5-hydroxymethyl-7-methoxy-2-oxoquinolin-1(2H)-yl)ethyl)piperidin-4-yl)carbamate, 5 mL of 4 mol/L hydrogen chloride/ethyl acetate was added and stirred at room temperature. The resulting solid was filtered, 5 mL of 4 mol/L hydrochloric acid was added and stirred at room temperature. To the reaction mixture, methanol was added, and the solvent was removed under reduced pressure to give 118 mg of 1-(2-(4-((2,3-dihydro-1,4-benzodioxin-6-ylmethyl)amino)piperidin-1-yl)ethyl)-5-hydroxymethyl-7-methoxyquinolin-2(1H)-one hydrochloride as a pale yellow solid.

$^1$H-NMR (DMSO-$d_6$, $D_2O$) δ:
2.02-2.12 (2H, m), 2.34-2.39 (2H, m), 3.07-3.15 (2H, m), 3.23-3.29 (3H, m), 3.80 (2H, d, J=11.0 Hz), 3.97 (3H, s), 4.05-4.09 (2H, m), 4.25 (4H, s), 4.69-4.73 (2H, m), 4.77 (2H, s), 6.48 (1H, d, J=10.1 Hz), 6.90 (1H, d, J=8.3 Hz), 6.99 (1H, d, J=1.8 Hz), 7.04 (1H, dd, J=8.3, 2.3 Hz), 7.09 (1H, d, J=1.8 Hz), 7.16 (1H, d, J=2.3 Hz), 8.04 (1H, d, J=10.1 Hz), 9.48-9.61 (2H, broad), 11.12-11.48 (1H, broad)

Example 190

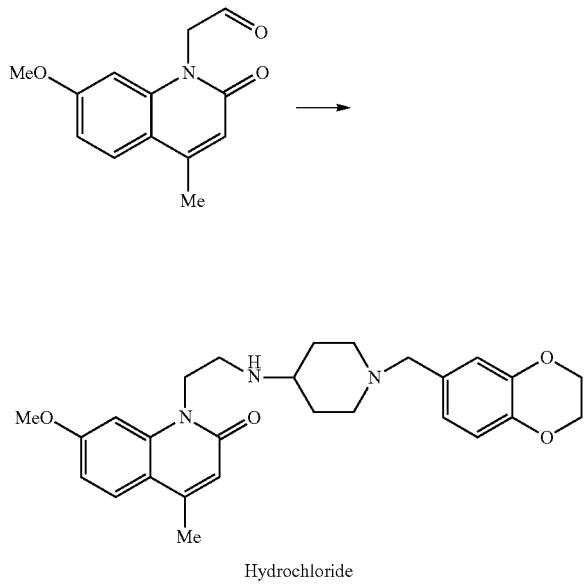

To 10 mL of a chloroform solution containing 120 mg of (7-methoxy-4-methyl-2-oxoquinolin-1(2H)-yl)acetaldehyde and 165 mg of 1-(2,3-dihydro-1,4-benzodioxin-6-ylmethyl)piperidin-4-ylamine, 30 µL of acetic acid was added and stirred at room temperature for 1 hour. To the reaction mixture, 176 mg of sodium triacetoxyborohydride was added and stirred overnight. Aqueous saturated sodium hydrogen carbonate solution was added and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=5:1], to give 150 mg of 1-(2-(1-(2,3-dihydro-1,4-benzodioxin-6-ylmethyl)piperidin-4-ylamino)ethyl)-7-methoxy-4-methylquinolin-2(1H)-one.

To 5 mL of an ethyl acetate solution containing 139 mg of 1-(2-(1-(2,3-dihydro-1,4-benzodioxin-6-ylmethyl)piperidin-4-ylamino)ethyl)-7-methoxy-4-methylquinolin-2(1H)-one, 0.3 mL of 4.0 mol/L hydrogen chloride/ethyl acetate was added, stirred at the same temperature for 10 min, and the resulting solid was filtered to give 117 mg of 1-(2-(1-(2,3-dihydro-1,4-benzodioxin-6-ylmethyl)piperidin-4-ylamino)ethyl)-7-methoxy-4-methylquinolin-2(1H)-one hydrochloride as a pale yellow solid.

$^1$H-NMR (DMSO-$d_6$) δ:
1.98-2.07 (2H, m), 2.20-2.26 (2H, m), 2.41 (3H, d, J=0.9 Hz), 2.85-2.92 (2H, m), 3.07-3.14 (3H, m), 3.38-3.43 (2H, m), 3.95 (3H, s), 4.11-4.15 (2H, m), 4.26 (4H, s), 4.55-4.60 (2H, m), 6.39 (1H, d, J=0.9 Hz), 6.91 (1H, d, J=8.3 Hz), 6.95 (1H, dd, J=9.2, 2.3 Hz), 7.01 (1H, dd, J=8.3, 1.8 Hz), 7.15 (1H, d, J=1.8 Hz), 7.18 (1H, d, J=2.3 Hz), 7.75 (1H, d, J=8.7 Hz), 9.63-9.69 (2H, broad), 10.79-10.86 (1H, broad)

Example 191

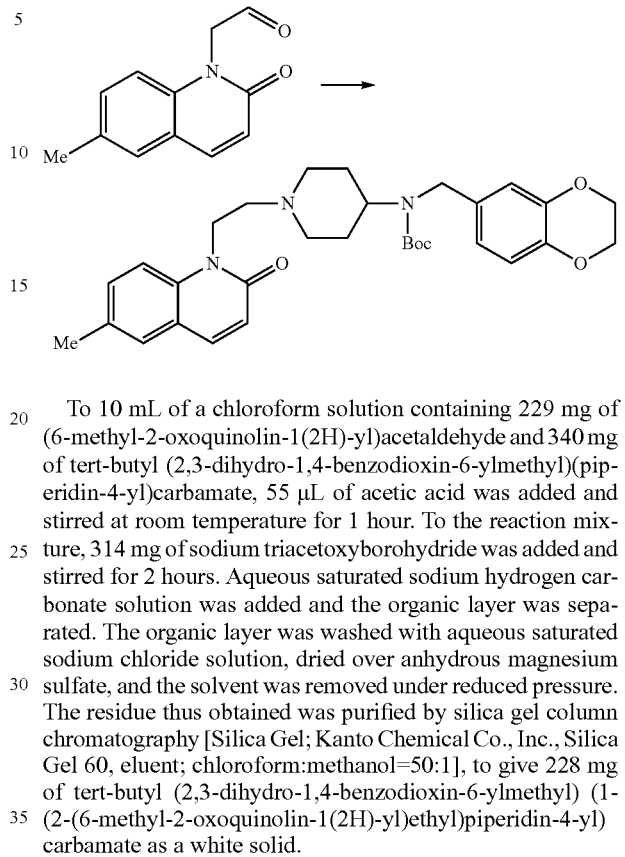

To 10 mL of a chloroform solution containing 229 mg of (6-methyl-2-oxoquinolin-1(2H)-yl)acetaldehyde and 340 mg of tert-butyl (2,3-dihydro-1,4-benzodioxin-6-ylmethyl)(piperidin-4-yl)carbamate, 55 µL of acetic acid was added and stirred at room temperature for 1 hour. To the reaction mixture, 314 mg of sodium triacetoxyborohydride was added and stirred for 2 hours. Aqueous saturated sodium hydrogen carbonate solution was added and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=50:1], to give 228 mg of tert-butyl (2,3-dihydro-1,4-benzodioxin-6-ylmethyl) (1-(2-(6-methyl-2-oxoquinolin-1(2H)-yl)ethyl)piperidin-4-yl)carbamate as a white solid.

$^1$H-NMR (CDCl$_3$) δ:
1.56 (9H, s), 1.63-1.72 (4H, m), 2.13-2.21 (2H, m), 2.41 (3H, s), 2.57-2.64 (2H, m), 3.02-3.08 (3H, m), 4.25 (4H, s), 4.26-4.32 (2H, m), 4.34-4.41 (2H, m), 6.65 (1H, d, J=9.2 Hz), 6.67-6.71 (1H, m), 6.75 (1H, s), 6.78 (1H, d, J=8.3 Hz), 7.27-7.31 (1H, m), 7.34 (1H, s), 7.35-7.39 (1H, m), 7.59 (1H, d, J=9.2 Hz)

Example 192

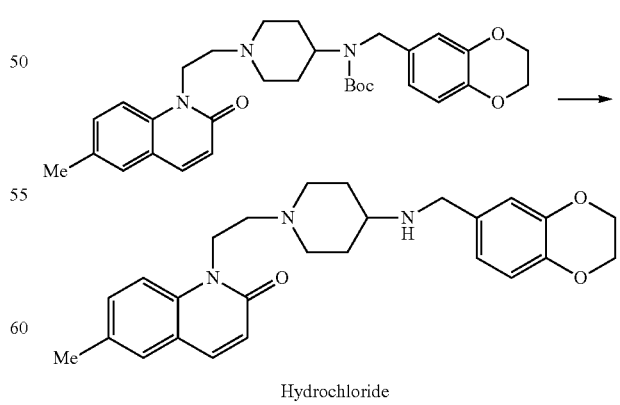

To 5 mL of a 1,4-dioxane solution containing 206 mg of tert-butyl (2,3-dihydro-1,4-benzodioxin-6-ylmethyl)(1-(2-(6-methyl-2-oxoquinolin-1(2H)-yl)ethyl)piperidin-4-yl)carbamate, 5 mL of 4 mol/L hydrogen chloride/1,4-dioxane was added, and stirred at room temperature for 4 hours. The solvent was removed under reduced pressure, 1,4-dioxane was added to the residue thus obtained, and the resulting solid was filtered to give 110 mg of 1-(2-(4-((2,3-dihydro-1,4-benzodioxin-6-ylmethyl)amino)piperidin-1-yl)ethyl)-6-methylquinolin-2(1H)-one hydrochloride as a white solid.

$^1$H-NMR (DMSO-$d_6$) δ:
2.01-2.15 (2H, m), 2.30-2.38 (2H, m), 2.39 (3H, s), 3.04-3.16 (2H, m), 3.18-3.29 (3H, m), 3.73-3.81 (2H, m), 4.04-4.10 (2H, m), 4.25 (4H, s), 4.52-4.71 (2H, m), 6.63 (1H, d, J=9.6 Hz), 6.90 (1H, d, J=8.3 Hz), 7.05 (1H, d, J=8.3 Hz), 7.17 (1H, s), 7.44-7.51 (1H, m), 7.57 (1H, s), 7.73 (1H, d, J=8.3 Hz), 7.91 (1H, d, J=9.6 Hz), 9.49-9.61 (2H, broad), 10.84-11.21 (1H, broad)

Example 193

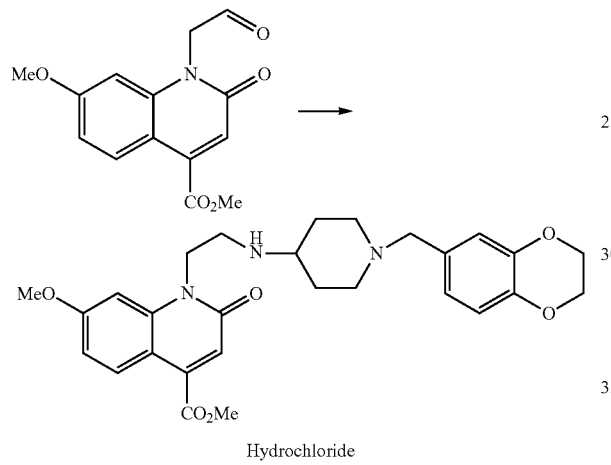

Hydrochloride

To 10 mL of a chloroform solution containing 111 mg of methyl 7-methoxy-2-oxo-1-(2-oxoethyl)-1,2-dihydroquinoline-4-carboxylate and 93 mg of 1-(2,3-dihydro-1,4-benzodioxin-6-ylmethyl)piperidin-4-ylamine, 23 μL of acetic acid was added and stirred at room temperature for 1 hour. To the reaction mixture, 132 mg of sodium triacetoxyborohydride was added and stirred for 0.5 hours. Aqueous saturated sodium hydrogen carbonate solution was added and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate:hexane=3:1], to give 134 mg of methyl 1-(2-(1-(2,3-dihydro-1,4-benzodioxin-6-ylmethyl)piperidin-4-ylamino)ethyl)-7-methoxy-2-oxo-1,2-dihydroquinoline-4-carboxylate.

To 2 mL of an ethyl acetate solution containing 95 mg of methyl 1-(2-(1-(2,3-dihydro-1,4-benzodioxin-6-ylmethyl)piperidin-4-ylamino)ethyl)-7-methoxy-2-oxo-1,2-dihydroquinoline-4-carboxylate, 0.2 mL of 4.0 mol/L hydrogen chloride/ethyl acetate was added at room temperature, stirred at the same temperature for 10 min, and the resulting solid was filtered to give 84 mg of methyl 1-(2-(1-(2,3-dihydro-1,4-benzodioxin-6-ylmethyl)piperidin-4-ylamino)ethyl)-7-methoxy-2-oxo-1,2-dihydroquinoline-4-carboxylate hydrochloride as a yellow solid.

$^1$H-NMR (DMSO-$d_6$) δ:
1.95-2.05 (2H, m), 2.20-2.26 (2H, m), 2.84-2.93 (2H, m), 3.15-3.25 (3H, m), 3.37-3.44 (2H, m), 3.93 (3H, s), 3.97 (3H, s), 4.13 (2H, d, J=5.0 Hz), 4.26 (4H, s), 4.62 (2H, t, J=7.1 Hz), 6.82 (1H, s), 6.92 (1H, d, J=8.3 Hz), 6.98-7.03 (2H, m), 7.14 (1H, d, J=2.3 Hz), 7.21 (1H, d, J=2.3 Hz), 8.04 (1H, d, J=9.2 Hz), 9.51-9.63 (2H, broad), 10.60-10.70 (1H, broad)

Example 194

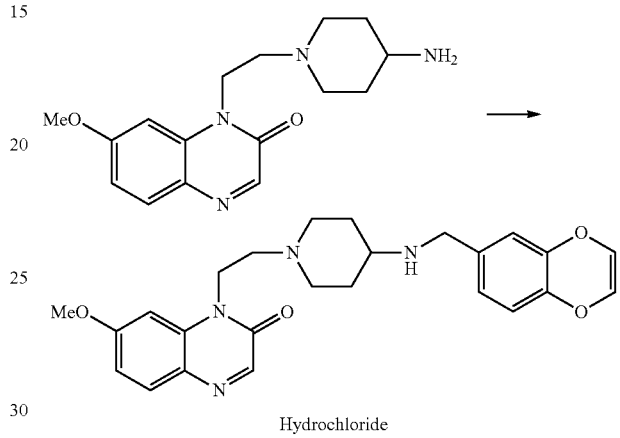

Hydrochloride

To 15 mL of a chloroform solution containing 141 mg of 1-(2-(4-aminopiperidin-1-yl)ethyl)-7-methoxyquinoxalin-2(1H)-one and 68 mg of 1,4-benzodioxine-6-carbaldehyde, 28 mg of acetic acid was added and stirred at room temperature for 4.5 hours. To the reaction mixture, 148 mg of sodium triacetoxyborohydride was added and stirred for 1 hour. Aqueous saturated sodium hydrogen carbonate solution was added and the organic layer was separated. The organic layer was dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=10:1], to give 20 mg of 1-(2-(4-((1,4-benzodioxin-6-ylmethyl)amino)piperidin-1-yl)ethyl)-7-methoxyquinoxalin-2(1H)-one as a brown oil.

To 3 mL of an ethyl acetate solution containing 20 mg of 1-(2-(4-((1,4-benzodioxin-6-ylmethyl)amino)piperidin-1-yl)ethyl)-7-methoxyquinoxalin-2(1H)-one, 1 mL of 4 mol/L hydrogen chloride/ethyl acetate was added, and stirred at room temperature. The resulting solid was filtered to give 23 mg of 1-(2-(4-((1,4-benzodioxin-6-ylmethyl)amino)piperidin-1-yl)ethyl)-7-methoxyquinoxalin-2(1H)-one hydrochloride as a brown solid.

$^1$H-NMR (DMSO-$d_6$) δ:
1.97-2.09 (2H, m), 2.30-2.38 (2H, m), 3.05-3.17 (2H, m), 3.19-3.42 (3H, m), 3.78-3.85 (2H, m), 3.98 (3H, s), 4.02-4.06 (2H, m), 4.63-4.70 (2H, m), 6.22-6.25 (2H, m), 6.78 (1H, d, J=7.8 Hz), 7.01-7.06 (2H, m), 7.09 (1H, dd, J=8.7, 2.8 Hz), 7.20 (1H, d, J=2.8 Hz), 7.79 (1H, d, J=8.7 Hz), 8.09 (1H, s), 9.41-9.63 (2H, broad), 10.76-10.97 (1H, broad)

Example 195

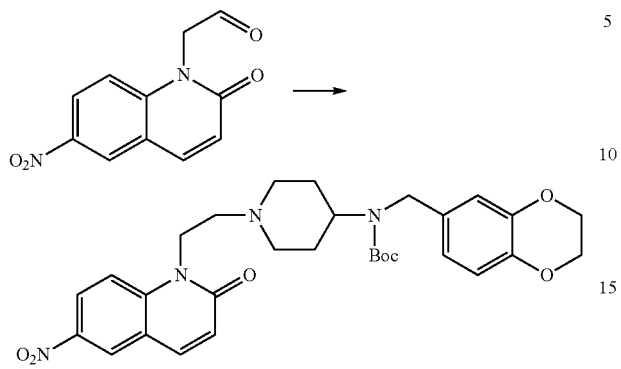

To 2 mL of a chloroform solution containing 0.32 g of tert-butyl (2,3-dihydro-1,4-benzodioxin-6-ylmethyl)(piperidin-4-yl)carbamate, 0.21 g of (6-nitro-2-oxoquinolin-1(2H)-yl)acetaldehyde and 20 μL of acetic acid were added, then, to the reaction mixture, 0.29 g of sodium triacetoxyborohydride was added and stirred at room temperature for 2 nights. Aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; ethyl acetate], to give 0.28 g of tert-butyl (2,3-dihydro-1,4-benzodioxin-6-ylmethyl)(1-(2-(6-nitro-2-oxoquinolin-1(2H)-yl)ethyl)piperidin-4-yl)carbamate as a pale yellow foam.

$^1$H-NMR (CDCl$_3$) δ:

1.42 (9H, s), 1.59-1.72 (4H, m), 2.07-2.23 (2H, m), 2.55-2.67 (2H, m), 2.95-3.04 (2H, m), 3.99-4.10 (1H, m), 4.22-4.31 (6H, m), 4.35-4.43 (2H, m), 6.65-6.70 (1H, m), 6.72 (1H, s), 6.76-6.81 (2H, m), 7.45-7.52 (1H, m), 7.74 (1H, d, J=9.6 Hz), 8.34-8.40 (1H, m), 8.46 (1H, d, J=2.8 Hz)

Example 196

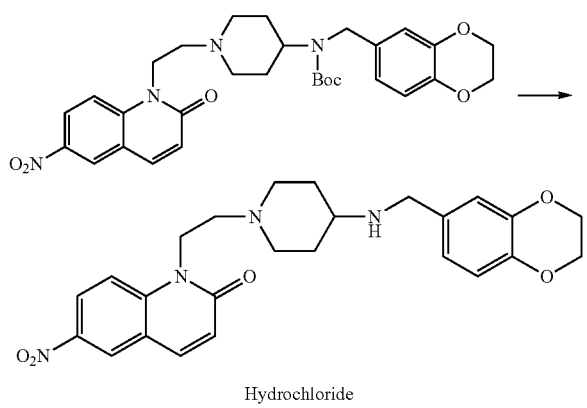

Hydrochloride

To 80 mg of tert-butyl (2,3-dihydro-1,4-benzodioxin-6-ylmethyl)(1-(2-(6-nitro-2-oxoquinolin-1(2H)-yl)ethyl)piperidin-4-yl)carbamate, 3 mL of 1,4-dioxane and 1 mL of 4.0 mol/L hydrogen chloride/1,4-dioxane were added, and stirred at room temperature overnight. The resulting solid was filtered to give 24 mg of 1-(2-(4-((2,3-dihydro-1,4-benzodioxin-6-ylmethyl)amino)piperidin-1-yl)ethyl)-6-nitroquinolin-2(1H)-one hydrochloride as a yellow solid.

$^1$H-NMR (DMSO-d$_6$) δ:

1.95-2.08 (2H, m), 2.31-2.41 (2H, m), 3.09-3.46 (5H, m), 3.76-3.84 (2H, m), 4.06-4.13 (2H, m), 4.26 (3H, s), 4.67-4.73 (2H, m), 6.86 (1H, d, J=9.6 Hz), 6.92 (1H, d, J=8.3 Hz), 7.02 (1H, d, J=8.3 Hz), 7.13 (1H, s), 7.97-8.03 (1H, m), 8.23 (1H, d, J=9.6 Hz), 8.40 (1H, d, J=9.6 Hz), 8.82 (1H, d, J=2.8 Hz), 9.26-9.44 (2H, broad), 10.45-10.60 (1H, broad)

Example 197

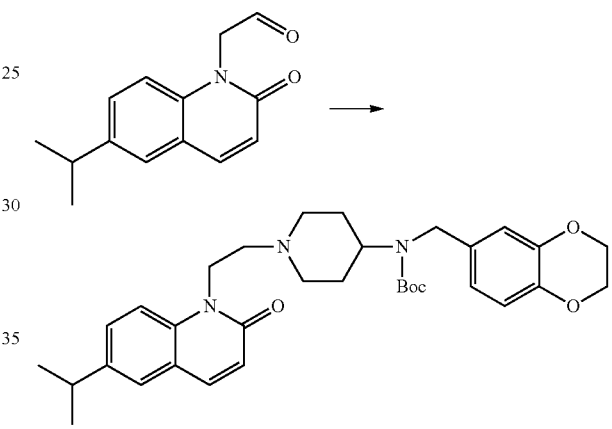

To 4 mL of a chloroform solution containing 0.62 g of tert-butyl (2,3-dihydro-1,4-benzodioxin-6-ylmethyl)(piperidin-4-yl)carbamate, 0.41 g of (6-isopropyl-2-oxoquinolin-1(2H)-yl)acetaldehyde and 40 μL of acetic acid were added, then, to the reaction mixture, 0.57 g of sodium triacetoxyborohydride was added and stirred at room temperature for 2 nights. Aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; ethyl acetate], to give 0.44 g of tert-butyl (2,3-dihydro-1,4-benzodioxin-6-ylmethyl)(1-(2-(6-isopropyl-2-oxoquinolin-1(2H)-yl)ethyl)piperidin-4-yl)carbamate as a white foam.

$^1$H-NMR (CDCl$_3$) δ:

1.29 (6H, d, J=7.3 Hz), 1.42 (9H, s), 1.61-1.75 (4H, m), 2.09-2.25 (2H, m), 2.59-2.66 (2H, m), 2.94-3.01 (1H, m), 3.02-3.10 (2H, m), 4.03-4.16 (1H, m), 4.21-4.34 (6H, m), 4.35-4.44 (2H, m), 6.66 (1H, d, J=9.6 Hz), 6.67-6.71 (1H, m), 6.73-6.75 (1H, m), 6.78 (1H, d, J=8.7 Hz), 7.31-7.35 (1H, m), 7.37 (1H, d, J=2.3 Hz), 7.43 (1H, dd, J=8.7, 2.3 Hz), 7.63 (1H, d, J=9.6 Hz)

Example 198

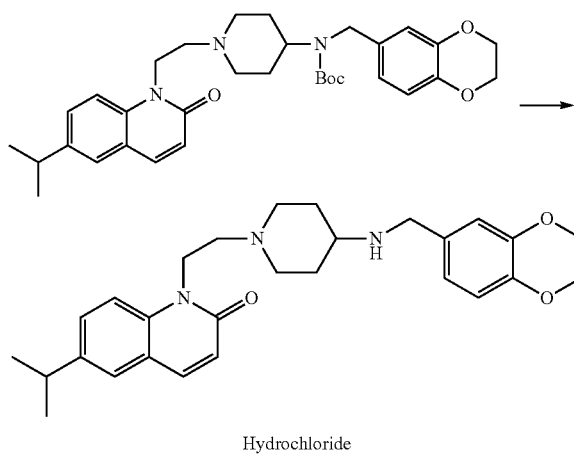

Hydrochloride

To 0.24 g of tert-butyl (2,3-dihydro-1,4-benzodioxin-6-ylmethyl)(1-(2-(6-isopropyl-2-oxoquinolin-1(2H)-yl)ethyl)piperidin-4-yl)carbamate, 6 mL of 1,4-dioxane and 2 mL of 4.0 mol/L hydrogen chloride/1,4-dioxane were added, and stirred at room temperature overnight. The solvent was removed under reduced pressure, and the resulting solid was recrystallized in methanol-ethyl acetate to give 91 mg of 1-(2-(4-((2,3-dihydro-1,4-benzodioxin-6-ylmethyl)amino)piperidin-1-yl)ethyl)-6-isopropylquinolin-2(1H)-one hydrochloride as a white solid.

$^1$H-NMR (DMSO-$d_6$) δ:
1.26 (6H, d, J=7.3 Hz), 2.02-2.11 (2H, m), 2.32-2.40 (2H, m), 2.97-3.03 (1H, m), 3.06-3.31 (5H, m), 3.75-3.82 (2H, m), 4.06-4.11 (2H, m), 4.25 (4H, s), 4.62-4.67 (2H, m), 6.63 (1H, d, J=9.2 Hz), 6.91 (1H, d, J=8.3 Hz), 7.04 (1H, d, J=8.3 Hz), 7.16 (1H, s), 7.55 (1H, dd, J=8.7, 1.8 Hz), 7.64 (1H, d, J=1.8 Hz), 7.72-7.79 (1H, m), 7.95 (1H, d, J=9.2 Hz), 9.42-9.62 (2H, broad), 10.81-11.09 (1H, broad)

Example 199

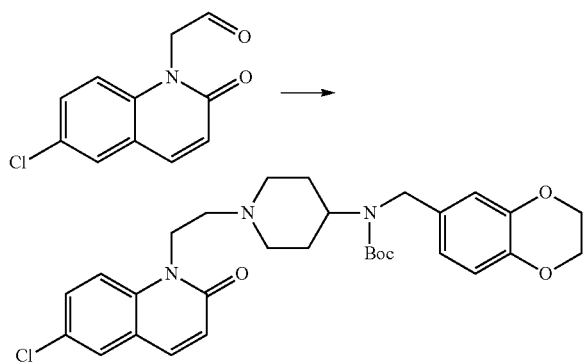

To 4 mL of a chloroform solution containing 0.68 g of tert-butyl (2,3-dihydro-1,4-benzodioxin-6-ylmethyl)(piperidin-4-yl)carbamate, 0.44 g of (6-chloro-2-oxoquinolin-1(2H)-yl)acetaldehyde and 40 μL of acetic acid were added, then, to the reaction mixture, 0.62 g of sodium triacetoxyborohydride was added and stirred at room temperature for 2 nights. Aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; ethyl acetate], to give 0.65 g of tert-butyl (2,3-dihydro-1,4-benzodioxin-6-ylmethyl)(1-(2-(6-chloro-2-oxoquinolin-1(2H)-yl)ethyl)piperidin-4-yl)carbamate as a white foam.

$^1$H-NMR (CDCl$_3$) δ:
1.42 (9H, s), 1.62-1.73 (4H, m), 2.09-2.23 (2H, m), 2.52-2.63 (2H, m), 2.98-3.05 (2H, m), 4.02-4.12 (1H, m), 4.21-4.39 (8H, m), 6.67-6.72 (2H, m), 6.74 (1H, s), 6.79 (1H, d, J=8.3 Hz), 7.32-7.37 (1H, m), 7.49 (1H, dd, J=9.2, 2.3 Hz), 7.53 (1H, d, J=2.3 Hz), 7.58 (1H, d, J=9.2 Hz)

Example 200

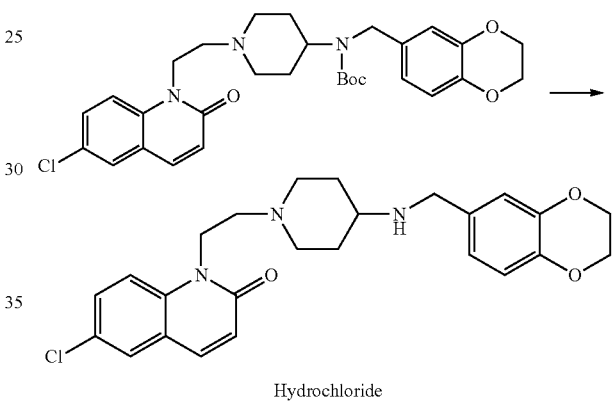

Hydrochloride

To 0.35 g of tert-butyl (2,3-dihydro-1,4-benzodioxin-6-ylmethyl)(1-(2-(6-chloro-2-oxoquinolin-1(2H)-yl)ethyl)piperidin-4-yl)carbamate, 6 mL of 1,4-dioxane and 2 mL of 4.0 mol/L hydrogen chloride/1,4-dioxane were added, and stirred at room temperature overnight. The resulting solid was filtered to give 0.11 g of 1-(2-(4-((2,3-dihydro-1,4-benzodioxin-6-ylmethyl)amino)piperidin-1-yl)ethyl)-6-chloroquinolin-2(1H)-one hydrochloride as a white solid.

$^1$H-NMR (DMSO-$d_6$) δ:
2.00-2.11 (2H, m), 2.32-2.39 (2H, m), 3.06-3.15 (2H, m), 3.22-3.80 (5H, m), 4.04-4.11 (2H, m), 4.25 (4H, s), 4.59-4.67 (2H, m), 6.73 (1H, d, J=9.2 Hz), 6.91 (1H, d, J=8.3 Hz), 7.04 (1H, d, J=8.3 Hz), 7.16 (1H, s), 7.66 (1H, dd, J=9.2, 2.3 Hz), 7.82-7.88 (1H, m), 7.94 (1H, d, J=2.3 Hz), 7.97 (1H, d, J=9.2 Hz), 9.45-9.66 (2H, broad), 10.75-11.07 (1H, broad)

Example 201

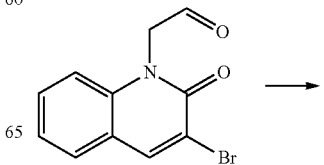

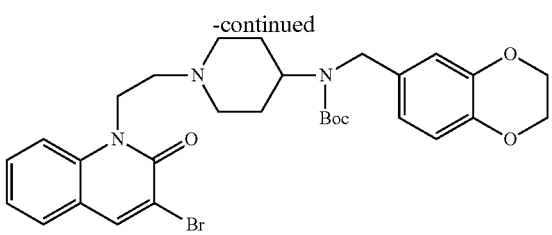

4.26 (4H, s), 4.70-4.77 (2H, m), 6.92 (1H, d, J=8.3 Hz), 7.03 (1H, d, J=8.3 Hz), 7.15 (1H, s), 7.37 (1H, t, J=7.3 Hz), 7.68-7.72 (1H, m), 7.78-7.85 (2H, m), 8.62 (1H, s), 9.37-9.55 (2H, broad), 10.68-10.95 (1H, broad)

Example 203

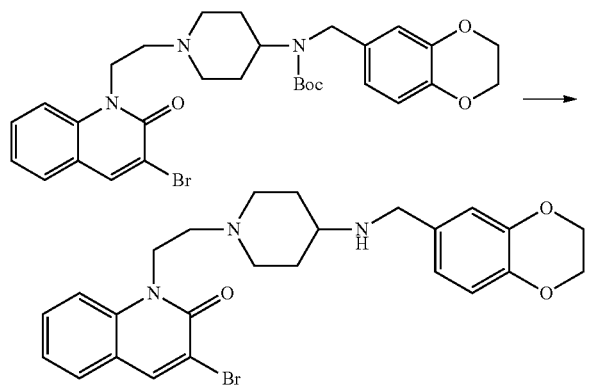

To 3 mL of a chloroform solution containing 0.47 g of tert-butyl (2,3-dihydro-1,4-benzodioxin-6-ylmethyl)(piperidin-4-yl)carbamate, 0.36 g of (3-bromo-2-oxoquinolin-1(2H)-yl)acetaldehyde, 30 μL of acetic acid and 0.43 g of sodium triacetoxyborohydride were added and stirred at room temperature for 2 nights. Aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; ethyl acetate], to give 0.54 g of tert-butyl (2,3-dihydro-1,4-benzodioxin-6-ylmethyl)(1-(2-(3-bromo-2-oxoquinolin-1(2H)-yl)ethyl)piperidin-4-yl)carbamate as a white foam.

$^1$H-NMR (CDCl$_3$) δ:

1.42 (9H, s), 1.62-1.73 (4H, m), 2.09-2.27 (2H, m), 2.60-2.69 (2H, m), 2.99-3.11 (2H, m), 4.04-4.15 (1H, m), 4.21-4.35 (6H, m), 4.39-4.50 (2H, m), 6.66-6.72 (1H, m), 6.74 (1H, s), 6.78 (1H, d, J=8.3 Hz), 7.23-7.27 (1H, m), 7.35-7.45 (1H, m), 7.52 (1H, d, J=8.3 Hz), 7.58 (1H, t, J=8.3 Hz), 8.12 (1H, s)

Example 202

To 0.30 g of tert-butyl (2,3-dihydro-1,4-benzodioxin-6-ylmethyl)(1-(2-(3-bromo-2-oxoquinolin-1(2H)-yl)ethyl)piperidin-4-yl)carbamate, 6 mL of 1,4-dioxane and 2 mL of 4.0 mol/L hydrogen chloride/1,4-dioxane were added, and stirred at room temperature overnight. The resulting solid was filtered to give 0.21 g of 1-(2-(4-((2,3-dihydro-1,4-benzodioxin-6-ylmethyl)amino)piperidin-1-yl)ethyl)-3-bromo-quinolin-2(1H)-one hydrochloride as a white solid.

$^1$H-NMR (DMSO-d$_6$) δ:

1.99-2.09 (2H, m), 2.32-2.40 (2H, m), 3.08-3.16 (2H, m), 3.22-3.43 (3H, m), 3.76-3.85 (2H, m), 4.04-4.13 (2H, m),

To 1 mL of a chloroform solution containing 0.20 g of tert-butyl (2,3-dihydro-1,4-benzodioxin-6-ylmethyl)(piperidin-4-yl)carbamate, 0.14 g of (5-nitro-2-oxoquinolin-1(2H)-yl)acetaldehyde, 10 μL of acetic acid and 0.18 g of sodium triacetoxyborohydride were added and stirred at room temperature for 2 nights. Aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography[Silica Gel; Kanto Chemical Co., Inc., Silica Gel 60, eluent; ethyl acetate], to give 0.24 g of tert-butyl (2,3-dihydro-1,4-benzodioxin-6-ylmethyl)(1-(2-(5-nitro-2-oxoquinolin-1(2H)-yl)ethyl)piperidin-4-yl)carbamate as a yellow foam.

$^1$H-NMR (CDCl$_3$) δ:

1.42 (9H, s), 1.63-1.71 (4H, m), 2.08-2.26 (2H, m), 2.57-2.68 (2H, m), 2.94-3.04 (2H, m), 3.99-4.14 (1H, m), 4.20-4.31 (6H, m), 4.36-4.49 (2H, m), 6.66-6.71 (1H, m), 6.73 (1H, s), 6.79 (1H, d, J=8.3 Hz), 6.86 (1H, d, J=10.1 Hz), 7.60-7.72 (2H, m), 7.80 (1H, d, J=8.3 Hz), 8.26 (1H, d, J=10.1 Hz)

Example 204

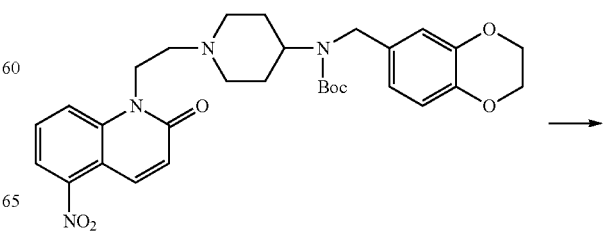

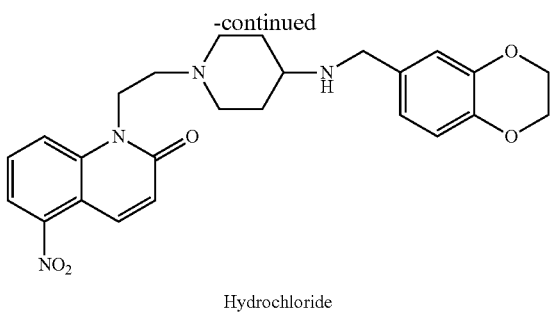

Hydrochloride

To 80 mg of tert-butyl (2,3-dihydro-1,4-benzodioxin-6-ylmethyl)(1-(2-(5-nitro-2-oxoquinolin-1(2H)-yl)ethyl)piperidin-4-yl)carbamate, 3 mL of 1,4-dioxane and 1 mL of 4.0 mol/L hydrogen chloride/1,4-dioxane were added, and stirred at room temperature overnight. The resulting solid was filtered to give 23 mg of 1-(2-(4-((2,3-dihydro-1,4-benzodioxin-6-ylmethyl)amino)piperidin-1-yl)ethyl)-5-nitroquinolin-2(1H)-one hydrochloride as a yellow solid.

$^1$H-NMR (DMSO-$d_6$) δ:
1.95-2.06 (2H, m), 2.31-2.40 (2H, m), 3.08-3.17 (2H, m), 3.22-3.54 (3H, m), 3.76-3.84 (2H, m), 4.05-4.13 (2H, m), 4.21-4.28 (4H, m), 4.67-4.76 (2H, m), 6.87-6.94 (2H, m), 7.02 (1H, d, J=8.3 Hz), 7.13 (1H, s), 7.85 (1H, t, J=8.3 Hz), 7.95 (1H, d, J=8.3 Hz), 8.14-8.24 (2H, m), 9.25-9.45 (2H, broad), 10.46-10.61 (1H, broad)

Example 205

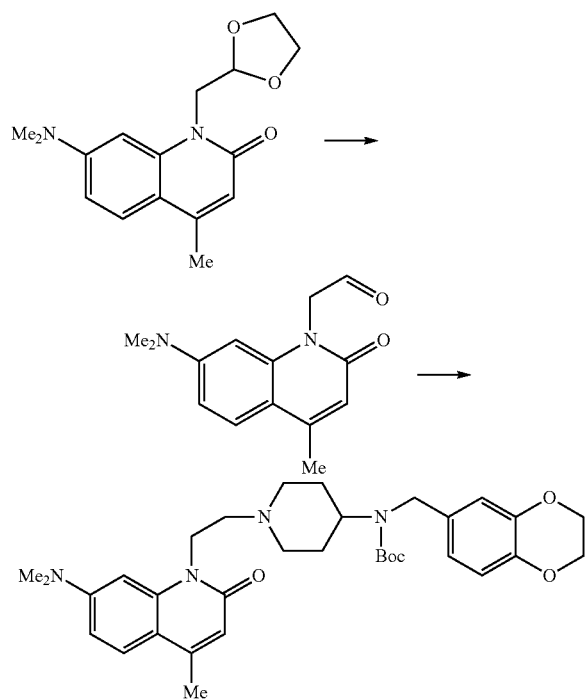

To 0.32 g of 1-(1,3-dioxolan-2-ylmethyl)-7-dimethylamino-4-methylquinolin-2(1H)-one, 3 mL of 90% aqueous trifluoroacetic acid solution was added, and stirred at room temperature for four days, the solvent was removed under reduced pressure, ethyl acetate and aqueous saturated sodium hydrogen carbonate solution were added, the organic layer was separated, and the aqueous layer was extracted with ethyl acetate. The organic layer and extracts were combined, dried over anhydrous magnesium sulfate, and the solvent was removed under reduced pressure to give 0.16 g of (7-dimethylamino-4-methyl-2-oxoquinolin-1(2H)-yl)acetaldehyde as a yellow foam.

To 2 mL of a chloroform solution containing 0.21 g of tert-butyl (2,3-dihydro-1,4-benzodioxin-6-ylmethyl)(piperidin-4-yl)carbamate, 0.15 g of (7-dimethylamino-4-methyl-2-oxoquinolin-1(2H)-yl)acetaldehyde, 10 µL of acetic acid and 0.20 g of sodium triacetoxyborohydride were added, and stirred at room temperature overnight. Aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; ethyl acetate: 8 mol/L ammonia/methanol=50:1], to give 0.14 g of tert-butyl (2,3-dihydro-1,4-benzodioxin-6-ylmethyl)(1-(2-(7-dimethylamino-4-methyl-2-oxoquinolin-1(2H)-yl)ethyl)piperidin-4-yl)carbamate as a pale yellow foam.

$^1$H-NMR (CDCl$_3$) δ:
1.42 (9H, s), 1.63-1.73 (4H, m), 2.15-2.23 (2H, m), 2.37 (3H, s), 2.61-2.67 (2H, m), 3.04-3.11 (8H, m), 4.03-4.15 (1H, m), 4.23-4.31 (6H, m), 4.33-4.40 (2H, m), 6.28 (1H, s), 6.50 (1H, s), 6.65 (1H, d, J=9.2 Hz), 6.67-6.71 (1H, m), 6.74 (1H, s), 6.78 (1H, d, J=8.3 Hz), 7.52 (1H, d, J=9.2 Hz)

Example 206

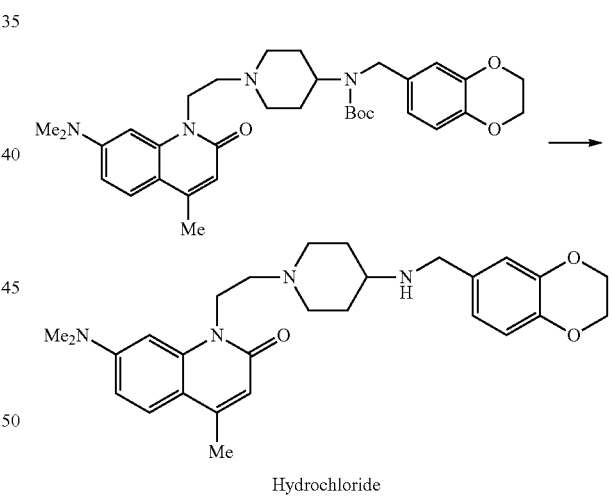

Hydrochloride

To 0.12 g of tert-butyl (2,3-dihydro-1,4-benzodioxin-6-ylmethyl)(1-(2-(7-dimethylamino-4-methyl-2-oxoquinolin-1(2H)-yl)ethyl)piperidin-4-yl)carbamate, 3 mL of 1,4-dioxane and 1 mL of 4.0 mol/L hydrogen chloride/1,4-dioxane were added, and stirred at room temperature overnight. The solvent was removed under reduced pressure, the resulting solid was recrystallized in methanol-ethyl acetate to give 44 mg of 1-(2-(4-((2,3-dihydro-1,4-benzodioxin-6-ylmethyl)amino)piperidin-1-yl)ethyl)-7-dimethylamino-4-methylquinolin-2(1H)-one hydrochloride as a brown solid.

$^1$H-NMR (DMSO-$d_6$) δ:
2.02-2.12 (2H, m), 2.31-2.41 (5H, m), 3.05-3.15 (8H, m), 3.20-3.70 (3H, m), 3.75-3.85 (2H, m), 4.03-4.11 (2H, m), 4.25 (4H, s), 4.65-4.71 (2H, m), 6.21 (1H, s), 6.61 (1H, s), 6.78 (1H, d, J=8.7 Hz), 6.91 (1H, d, J=8.3 Hz), 7.04 (1H, d, J=8.3 Hz), 7.16 (1H, s), 7.61 (1H, d, J=8.7 Hz), 9.43-9.64 (2H, broad), 11.10-11.43 (1H, broad)

Example 207

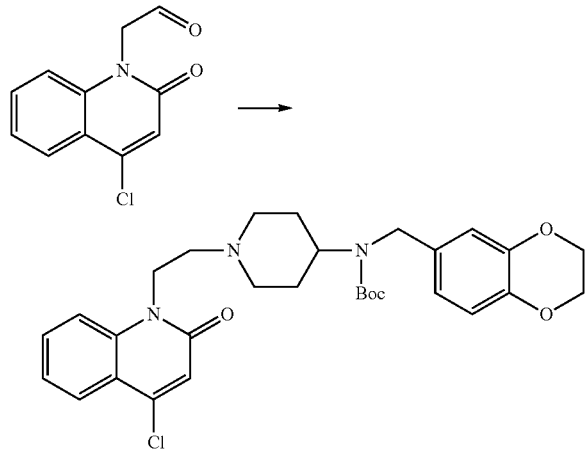

To 20 mL of a chloroform solution containing 179 mg of (4-chloro-2-oxoquinolin-1(2H)-yl)acetaldehyde and 286 mg of tert-butyl (2,3-dihydro-1,4-benzodioxin-6-ylmethyl)(piperidin-4-yl)carbamate, 47 μL of acetic acid was added, and stirred at room temperature for 1 hour. To the reaction mixture, 269 mg of sodium triacetoxyborohydride was added and stirred for 1 hour. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography[Silica Gel; Kanto Chemical Co., Inc., Silica Gel 60, eluent; chloroform:methanol=50:1], to give 177 mg of tert-butyl (2,3-dihydro-1,4-benzodioxin-6-ylmethyl)(1-(2-(4-chloro-2-oxoquinolin-1(2H)-yl)ethyl)piperidin-4-yl)carbamate as a white solid.

$^1$H-NMR (CDCl$_3$) δ:

1.57 (9H, s), 1.62-1.74 (4H, m), 2.09-2.23 (2H, m), 2.56-2.66 (2H, m), 2.96-3.11 (3H, m), 4.25 (4H, s), 4.27-4.33 (2H, m), 4.34-4.43 (2H, m), 6.66-6.71 (1H, m), 6.74 (1H, s), 6.78 (1H, d, J=8.3 Hz), 6.87 (1H, s), 7.28-7.33 (1H, m), 7.41-7.45 (1H, m), 7.59-7.68 (1H, m), 8.03 (1H, d, J=8.3 Hz)

Example 208

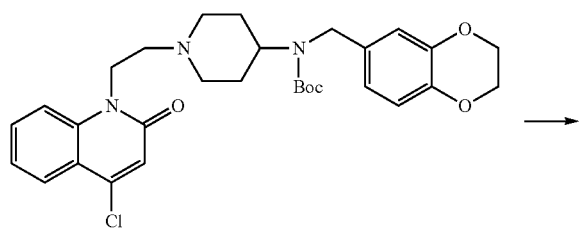

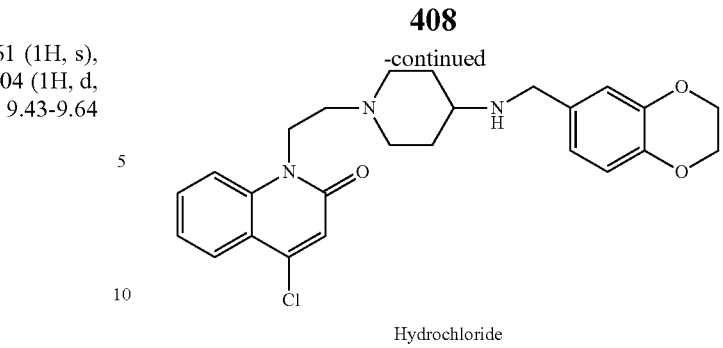

Hydrochloride

To 2 mL of a chloroform solution containing 149 mg of tert-butyl (2,3-dihydro-1,4-benzodioxin-6-ylmethyl)(1-(2-(4-chloro-2-oxoquinolin-1(2H)-yl)ethyl)piperidin-4-yl)carbamate, 2 mL of trifluoroacetic acid was added and stirred at room temperature for 3 hours. After the solvent was removed under reduced pressure and the residue was alkalized by aqueous saturated sodium hydrogen carbonate solution, it was extracted with ethyl acetate. The organic layer was washed sequentially with water and aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform], to give 71 mg of 1-(2-(4-(((2,3-dihydro-1,4-benzodioxin-6-ylmethyl)amino)piperidin-1-yl)ethyl)-4-chloroquinolin-2(1H)-one as a pale yellow solid.

To 2 mL of an ethyl acetate solution containing 68 mg of 1-(2-(4-(((2,3-dihydro-1,4-benzodioxin-6-ylmethyl)amino)piperidin-1-yl)ethyl)-4-chloroquinolin-2(1H)-one, 0.2 mL of 4 mol/L hydrogen chloride/ethyl acetate was added, and stirred at room temperature for 10 min. The resulting solid was filtered to give 47 mg of 1-(2-(4-(((2,3-dihydro-1,4-benzodioxin-6-ylmethyl)amino)piperidin-1-yl)ethyl)-4-chloroquinolin-2(1H)-one hydrochloride as a yellow solid.

$^1$H-NMR (DMSO-d$_6$) δ:

1.94-2.05 (2H, m), 2.31-2.37 (2H, m), 3.09-3.13 (3H, m), 3.76-3.85 (2H, m), 4.06-4.12 (4H, m), 4.26 (4H, s), 4.67 (2H, t, J=4.8 Hz), 6.92 (1H, d, J=8.3 Hz), 6.99-7.05 (2H, m), 7.13 (1H, s), 7.47 (1H, t, J=7.6 Hz), 7.77-7.81 (1H, m), 7.85-7.89 (1H, m), 8.04 (1H, d, J=7.8 Hz), 9.27-9.37 (1H, broad), 10.34-10.43 (2H, broad)

Example 209

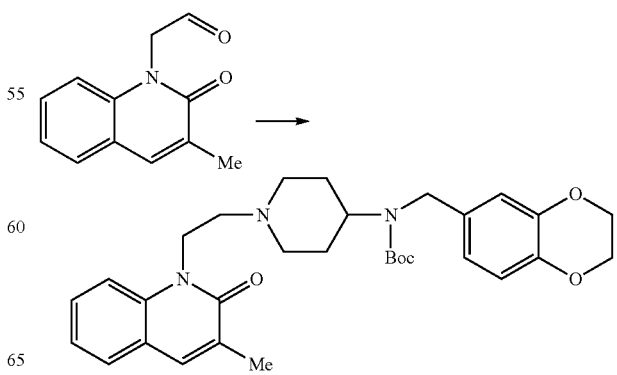

To 25 mL of a chloroform solution containing 341 mg of (3-methyl-2-oxoquinolin-1(2H)-yl)acetaldehyde and 498 mg of tert-butyl (2,3-dihydro-1,4-benzodioxin-6-ylmethyl)(piperidin-4-yl)carbamate, 80 µL of acetic acid was added, and stirred at room temperature for 1 hour. To the reaction mixture, 480 mg of sodium triacetoxyborohydride was added, and stirred for 1 hour. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=20:1], to give 126 mg of tert-butyl (2,3-dihydro-1,4-benzodioxin-6-ylmethyl) (1-(2-(3-methyl-2-oxoquinolin-1(2H)-yl)ethyl)piperidin-4-yl) carbamate as a white solid.

$^1$H-NMR (CDCl$_3$) δ:
1.59 (9H, s), 1.63-1.76 (4H, m), 2.14-2.22 (2H, m), 2.24 (3H, s), 2.59-2.67 (2H, m), 3.03-3.12 (3H, m), 4.25 (4H, s), 4.27-4.34 (2H, m), 4.38-4.46 (2H, m), 6.66-6.72 (1H, m), 6.74 (1H, s), 6.78 (1H, d, J=8.3 Hz), 7.20 (1H, t, J=7.3 Hz), 7.33-7.39 (1H, m), 7.45-7.51 (2H, m), 7.54 (1H, s)

Example 210

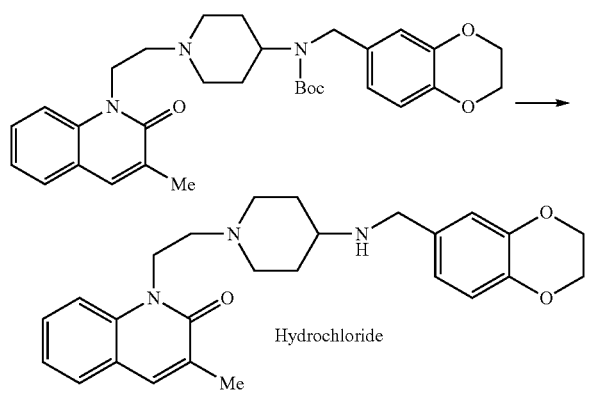

To 2 mL of a chloroform solution containing 97 mg of tert-butyl (2,3-dihydro-1,4-benzodioxin-6-ylmethyl)(1-(2-(3-methyl-2-oxoquinolin-1(2H)-yl)ethyl)piperidin-4-yl)carbamate, 2 mL of trifluoroacetic acid was added and stirred at room temperature for 4 hours. After the solvent was removed under reduced pressure and the residue was alkalized by aqueous saturated sodium hydrogen carbonate solution, it was extracted with ethyl acetate. The organic layer was washed sequentially with water and aqueous saturated sodium chloride solution, dried over anhydrous magnesium sulfate, and the solvent was removed under reduced pressure to give 78 mg of 1-(2-(4-((2,3-dihydro-1,4-benzodioxin-6-ylmethyl)amino)piperidin-1-yl)ethyl)-3-methylquinolin-2(1H)-one as a pale yellow solid.

To 5 mL of an ethyl acetate solution containing 75 mg of 1-(2-(4-((2,3-dihydro-1,4-benzodioxin-6-ylmethyl)amino)piperidin-1-yl)ethyl)-3-methylquinolin-2(1H)-one, 0.2 mL of 4 mol/L hydrogen chloride/ethyl acetate was added, and stirred at room temperature for 10 min. The resulting solid was filtered to give 29 mg of 1-(2-(4-((2,3-dihydro-1,4-benzodioxin-6-ylmethyl)amino)piperidin-1-yl)ethyl)-3-methylquinolin-2(1H)-one hydrochloride as a yellow solid.

$^1$H-NMR (DMSO-d$_6$) δ:
2.00-2.06 (2H, m), 2.12-2.14 (2H, m), 2.15 (3H, d, J=0.9 Hz), 2.33-2.37 (2H, m), 3.08-3.10 (3H, m), 3.79-3.85 (2H, m), 4.06-4.11 (2H, m), 4.26 (4H, s), 4.65-4.71 (2H, m), 6.92 (1H, d, J=8.3 Hz), 7.01-7.04 (1H, m), 7.13-7.15 (1H, m), 7.30 (1H, t, J=7.3 Hz), 7.57-7.61 (1H, m), 7.69-7.71 (1H, m), 7.74 (1H, d, J=7.8 Hz), 7.86-7.88 (1H, m), 9.29-9.48 (2H, broad), 10.52-10.83 (1H, broad)

Example 211

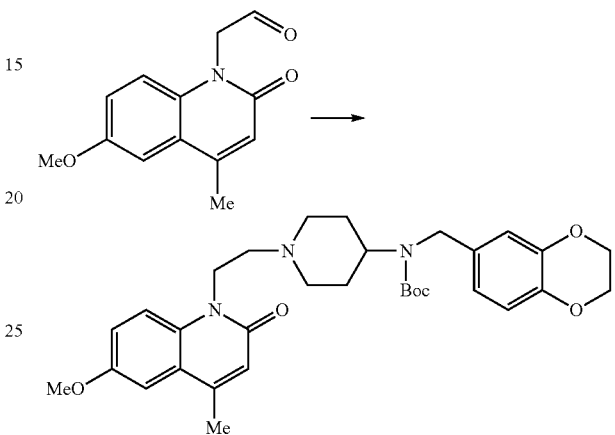

To 25 mL of a chloroform solution containing 71 mg of (4-methyl-6-methoxy-2-oxoquinolin-1(2H)-yl)acetaldehyde and 108 mg of tert-butyl (2,3-dihydro-1,4-benzodioxin-6-ylmethyl) (piperidin-4-yl)carbamate, 18 µL of acetic acid was added, and stirred at room temperature for 1 hour. To the reaction mixture, 121 mg of sodium triacetoxyborohydride was added, and stirred for 2 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=20:1], to give 140 mg of tert-butyl (2,3-dihydro-1,4-benzodioxin-6-ylmethyl)(1-(2-(4-methyl-6-methoxy-2-oxoquinolin-1(2H)-yl)ethyl)piperidin-4-yl)carbamate as a white solid.

$^1$H-NMR (CDCl$_3$) δ:
1.61 (9H, s), 1.63-1.75 (4H, m), 2.09-2.22 (2H, m), 2.43 (3H, s), 2.55-2.63 (3H, m), 2.99-3.08 (2H, m), 3.88 (3H, s), 4.24 (4H, s), 4.26-4.32 (2H, m), 4.33-4.42 (2H, m), 6.58 (1H, s), 6.67-6.71 (1H, m), 6.74 (1H, s), 6.78 (1H, d, J=8.3 Hz), 7.12 (1H, d, J=3.2 Hz), 7.14-7.19 (1H, m), 7.31-7.37 (1H, m)

Example 212

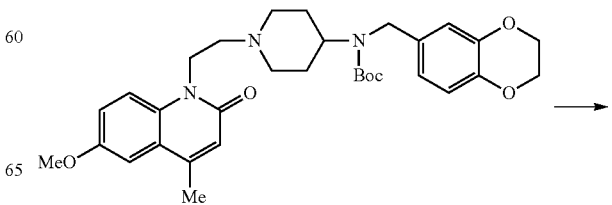

411

-continued

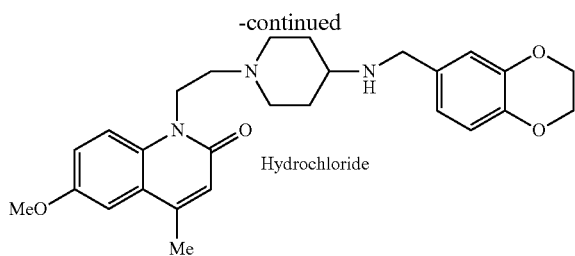

Hydrochloride

To 2 mL of a chloroform solution containing 109 mg of tert-butyl (2,3-dihydro-1,4-benzodioxin-6-ylmethyl)(1-(2-(4-methyl-6-methoxy-2-oxoquinolin-1(2H)-yl)ethyl)piperidin-4-yl)carbamate, 2 mL of trifluoroacetic acid was added and stirred at room temperature for 3 hours. After the solvent was removed under reduced pressure and the residue was alkalized by aqueous saturated sodium hydrogen carbonate solution, it was extracted with ethyl acetate. The organic layer was washed sequentially with water and aqueous saturated sodium chloride solution, dried over anhydrous magnesium sulfate, and the solvent was removed under reduced pressure to give 67 mg of 1-(2-(4-((2,3-dihydro-1,4-benzodioxin-6-ylmethyl)amino)piperidin-1-yl)ethyl)-4-methyl-6-methoxyquinolin-2(1H)-one as a pale yellow oil.

To 2 mL of an ethyl acetate solution containing 60 mg of 1-(2-(4-((2,3-dihydro-1,4-benzodioxin-6-ylmethyl)amino)piperidin-1-yl)ethyl)-4-methyl-6-methoxyquinolin-2(1H)-one, 0.2 mL of 4 mol/L hydrogen chloride/ethyl acetate was added, and stirred at room temperature for 10 min. The resulting solid was filtered to give 35 mg of 1-(2-(4-((2,3-dihydro-1,4-benzodioxin-6-ylmethyl)amino)piperidin-1-yl)ethyl)-4-methyl-6-methoxyquinolin-2(1H)-one hydrochloride as a pale yellow powder.

$^1$H-NMR (DMSO-$d_6$) δ:

1.95-2.06 (2H, m), 2.12-2.22 (2H, m), 2.30-2.37 (2H, m), 2.47 (3H, s), 3.06-3.12 (3H, m), 3.75-3.83 (2H, m), 3.86 (3H, s), 4.05-4.14 (2H, m), 4.25 (4H, s), 4.62 (2H, t, J=6.4 Hz), 6.59 (1H, s), 6.92 (1H, d, J=8.3 Hz), 7.02 (1H, dd, J=8.3, 1.4 Hz), 7.12-7.14 (1H, m), 7.25-7.29 (2H, m), 7.72 (1H, d, J=9.2 Hz), 9.34 (2H, broad), 10.39-10.50 (1H, broad)

Example 213

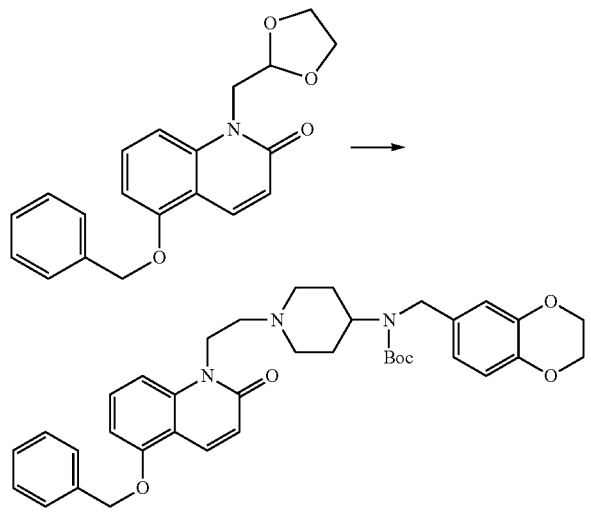

412

(1) 750 mg of 1-(1,3-dioxolan-2-ylmethyl)-5-benzyloxyquinolin-2(1H)-one was dissolved in 3 mL of 90% aqueous trifluoroacetic acid solution, and stirred at room temperature for 3 days. The solvent was removed under reduced pressure, and after it was alkalized by aqueous saturated sodium hydrogen carbonate solution, it was extracted with ethyl acetate. The organic layer was washed sequentially with water and aqueous saturated sodium chloride solution, dried over anhydrous magnesium sulfate, and the solvent was removed under reduced pressure to give (5-benzyloxy-2-oxoquinolin-1(2H)-yl)acetaldehyde as a pale yellow solid.

(2) To 25 mL of a chloroform solution containing (5-benzyloxy-2-oxoquinolin-1(2H)-yl)acetaldehyde and 877 mg of tert-butyl (2,3-dihydro-1,4-benzodioxin-6-ylmethyl)(piperidin-4-yl)carbamate, 144 µL of acetic acid was added, and stirred at room temperature for 1 hour. To the reaction mixture, 811 mg of sodium triacetoxyborohydride was added, and stirred for 1.5 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=100:1], to give 592 mg of tert-butyl (2,3-dihydro-1,4-benzodioxin-6-ylmethyl) (1-(2-(5-benzyloxy-2-oxoquinolin-1(2H)-yl)ethyl)piperidin-4-yl)carbamate as a pale brown foam.

$^1$H-NMR (CDCl$_3$) δ:

1.57 (9H, s), 1.62-1.74 (4H, m), 2.13-2.22 (2H, m), 2.56-2.65 (3H, m), 3.00-3.09 (2H, m), 4.24 (4H, s), 4.27-4.31 (2H, m), 4.35-4.42 (2H, m), 5.18 (2H, s), 6.61 (1H, d, J=9.6 Hz), 6.66-6.70 (1H, m), 6.71-6.76 (2H, m), 6.78 (1H, d, J=8.3 Hz), 6.94-7.03 (1H, m), 7.33-7.48 (6H, m), 8.20 (1H, d, J=9.6 Hz)

Example 214

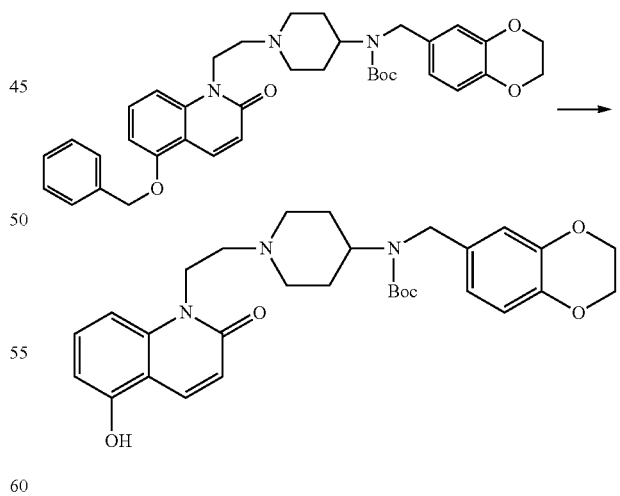

To 15 mL of a methanol solution containing 309 mg of tert-butyl (2,3-dihydro-1,4-benzodioxin-6-ylmethyl)(1-(2-(5-benzyloxy-2-oxoquinolin-1(2H)-yl)ethyl)piperidin-4-yl)carbamate, 31 mg of 5% palladium on carbon was added, and stirred at room temperature under hydrogen atmosphere overnight. The insoluble material was filtered off, and the solvent was removed under reduced pressure. The residue thus obtained was purified by silica gel column chromatography [Silica Gel; Kanto Chemical Co., Inc., Silica Gel 60, eluent; chloroform:methanol=20:1], to give 239 mg of tert-butyl (2,3-dihydro-1,4-benzodioxin-6-ylmethyl)(1-(2-(5-hydroxy-2-oxoquinolin-1(2H)-yl)ethyl)piperidin-4-yl)carbamate as a pale brown foam.

$^1$H-NMR (CDCl$_3$) δ:

1.43 (9H, s), 1.69-1.82 (4H, m), 2.39-2.61 (2H, m), 2.80-3.02 (3H, m), 3.25-3.48 (2H, m), 4.23 (4H, s), 4.28-4.36 (2H, m), 4.52-4.63 (2H, m), 6.53 (1H, d, J=9.6 Hz), 6.63-6.71 (2H, m), 6.72-6.79 (2H, m), 7.22-7.27 (2H, m), 8.08 (1H, d, J=9.6 Hz)

Example 215

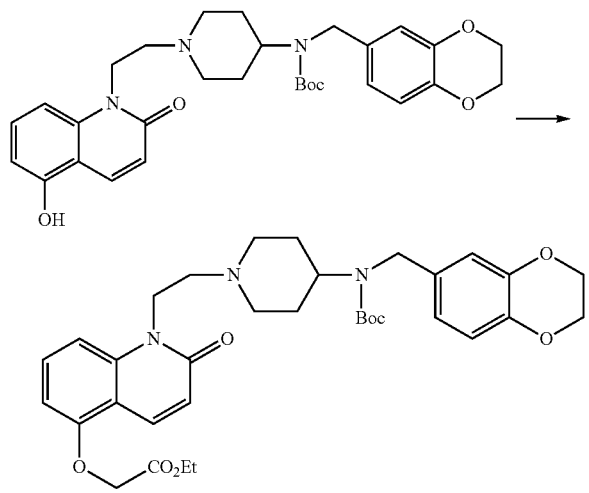

To 3 mL of an N,N-dimethylformamide solution containing 166 mg of tert-butyl (2,3-dihydro-1,4-benzodioxin-6-ylmethyl)(1-(2-(5-hydroxy-2-oxoquinolin-1(2H)-yl)ethyl)piperidin-4-yl)carbamate, 65 mg of potassium carbonate and 43 μL of ethyl bromoacetate were added, and stirred at room temperature for 2 hours. After water was added to the reaction mixture and acidified with hydrochloric acid, the mixture was extracted with a mixture of ethyl acetate: toluene=5:1. The extracts were washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=20:1], to give 196 mg of ethyl (1-(2-(4-((tert-butoxycarbonyl)(2,3-dihydro-1,4-benzodioxin-6-ylmethyl)amino)piperidin-1-yl)ethyl)-2-oxo-1,2-dihydroquinolin-5-yloxy)acetate as a pale brown oil.

$^1$H-NMR (CDCl$_3$) δ:

1.31 (3H, t, J=7.3 Hz), 1.44 (9H, s), 1.64-1.89 (4H, m), 2.76-2.86 (2H, m), 3.08-3.17 (3H, m), 3.58-3.69 (2H, m), 4.24 (4H, s), 4.28 (2H, q, J=7.3 Hz), 4.32-4.38 (2H, m), 4.75 (2H, s), 4.80-4.92 (2H, m), 6.56-6.64 (2H, m), 6.72-6.77 (1H, m), 6.77-6.81 (2H, m), 7.53-7.69 (2H, m), 8.29 (1H, d, J=9.6 Hz)

Example 216

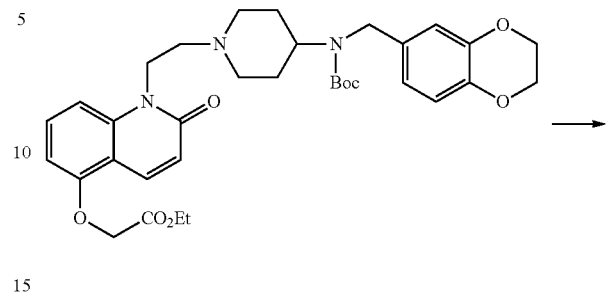

To 2 mL of a chloroform solution containing 83 mg of ethyl (1-(2-(4-((tert-butoxycarbonyl) (2,3-dihydro-1,4-benzodioxin-6-ylmethyl)amino)piperidin-1-yl)ethyl)-2-oxo-1,2-dihydroquinolin-5-yloxy)acetate, 2 mL of trifluoroacetic acid was added and stirred at room temperature for 6 hours. After the solvent was removed under reduced pressure and the residue was alkalized by aqueous saturated sodium hydrogen carbonate solution, it was extracted with ethyl acetate. The organic layer was washed sequentially with water and aqueous saturated sodium chloride solution, dried over anhydrous magnesium sulfate, and the solvent was removed under reduced pressure to give 48 mg of ethyl (1-(2-(4-((2,3-dihydro-1,4-benzodioxin-6-ylmethyl)amino)piperidin-1-yl) ethyl)-2-oxo-1,2-dihydroquinolin-5-yloxy)acetate as a white solid.

To 20 mL of an ethyl acetate solution containing 40 mg of ethyl (1-(2-(4-((2,3-dihydro-1,4-benzodioxin-6-ylmethyl)amino)piperidin-1-yl)ethyl)-2-oxo-1,2-dihydroquinolin-5-yloxy)acetate, 0.1 mL of 4 mol/L hydrogen chloride/ethyl acetate was added, and stirred at room temperature for 10 min. The resulting solid was filtered to give 19 mg of ethyl (1-(2-(4-((2,3-dihydro-1,4-benzodioxin-6-ylmethyl)amino) piperidin-1-yl)ethyl)-2-oxo-1,2-dihydroquinolin-5-yloxy) acetate hydrochloride as a pale yellow solid.

$^1$H-NMR (DMSO-d$_6$) δ:

1.22 (3H, t, J=7.3 Hz), 1.94-2.04 (2H, m), 2.14-2.21 (1H, m), 2.31-2.37 (2H, m), 3.07-3.15 (4H, m), 3.76-3.83 (2H, m), 4.05-4.10 (2H, m), 4.19 (2H, q, J=7.3 Hz), 4.26 (4H, s), 4.61-4.66 (2H, m), 4.99 (2H, s), 6.65 (1H, d, J=9.6 Hz), 6.86 (1H, d, J=8.3 Hz), 6.92 (1H, d, J=8.3 Hz), 7.00-7.03 (1H, m), 7.13 (1H, s), 7.34-7.38 (1H, m), 7.57 (1H, t, J=8.3 Hz), 8.20 (1H, d, J=9.2 Hz), 9.26-9.36 (2H, broad), 10.37-10.44 (1H, broad)

Example 217

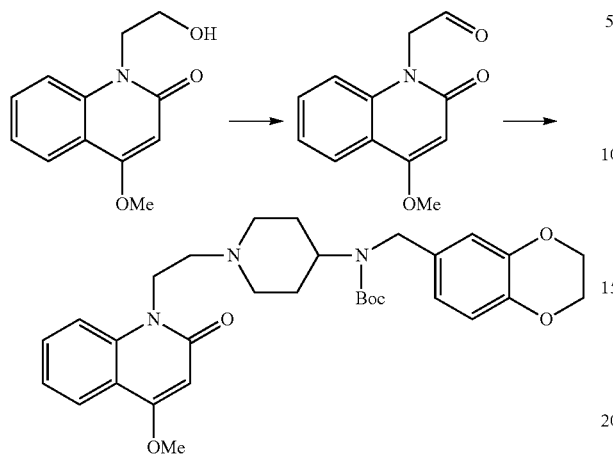

To 5 mL of a dichloromethane solution containing 0.11 mL of oxalyl chloride, 0.22 mL of dimethylsulfoxide was added dropwise under nitrogen atmosphere at −60° C., and stirred for 10 min. 20 mL of a dichloromethane solution containing 0.23 g of 1-(2-hydroxyethyl)-4-methoxyquinolin-2(1H)-one was added dropwise at the same temperature, and stirred for 10 min. After 0.58 mL of triethylamine was added at the same temperature, it was stirred at room temperature for 1.5 hours, and water was added. The organic layer was separated, and the aqueous layer was extracted with chloroform. The organic layer and extracts were combined, dried over anhydrous magnesium sulfate, and the solvent was removed under reduced pressure to give (4-methoxy-2-oxoquinolin-1(2H)-yl)acetaldehyde as a pale yellow solid.

To 8 mL of a dichloromethane solution containing (4-methoxy-2-oxoquinolin-1(2H)-yl)acetaldehyde, 0.44 g of tert-butyl (2,3-dihydro-1,4-benzodioxin-6-ylmethyl)(piperidin-4-yl)carbamate and 60 μL of acetic acid were added, and stirred at room temperature for 80 min. To the reaction mixture, 0.35 g of sodium triacetoxyborohydride was added, stirred at the same temperature for 80 min, aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; hexane:ethyl acetate=1:1], to give 0.48 g of tert-butyl 1-(2-(4-methoxy-2-oxoquinolin-1(2H)-yl)ethyl)piperidin-4-yl)(2,3-dihydro-1,4-benzodioxin-6-ylmethyl)carbamate as a white foam.

$^1$H-NMR (CDCl$_3$) δ:

1.34-1.52 (9H, s), 1.61-1.74 (5H, m), 2.08-2.24 (2H, m), 2.51-2.65 (2H, m), 2.97-3.10 (2H, m), 3.93 (3H, s), 4.24 (4H, s), 4.25-4.42 (4H, m), 5.99 (1H, s), 6.68 (1H, d, J=7.6 Hz), 6.73 (1H, s), 6.77 (1H, d, J=8.3 Hz), 7.20 (1H, t, J=7.6 Hz), 7.31-7.40 (1H, m), 7.49-7.59 (1H, m), 7.96 (1H, dd, J=8.3, 1.4 Hz)

Example 218

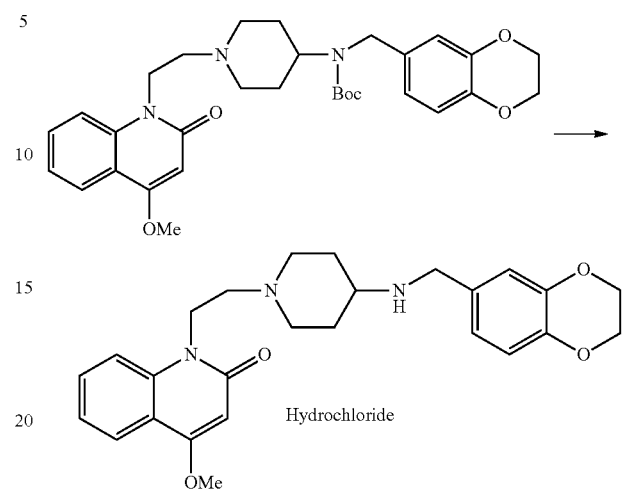

To 2 mL of a chloroform solution containing 0.30 g of tert-butyl 1-(2-(4-methoxy-2-oxoquinolin-1(2H)-yl)ethyl)piperidin-4-yl)(2,3-dihydro-1,4-benzodioxin-6-ylmethyl)carbamate, 2 mL of trifluoroacetic acid was added and stirred at room temperature for 3 hours, thereafter the solvent was removed under reduced pressure. To the residue thus obtained, chloroform and aqueous saturated sodium hydrogen carbonate solution were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. To the residue thus obtained, 3 mL of 4 mol/L hydrogen chloride/ethyl acetate was added, and the resulting solid was filtered to give 0.23 g of 1-(2-(4-((2,3-dihydro-1,4-benzodioxin-6-ylmethyl)amino)piperidin-1-yl)ethyl)-4-methoxyquinolin-2(1H)-one hydrochloride as a white solid.

$^1$H-NMR (DMSO-d$_6$) δ:

2.01-2.11 (2H, m), 2.31-2.39 (2H, m), 3.04-3.16 (2H, m), 3.20-3.30 (2H, m), 3.63-3.84 (3H, m), 3.97 (3H, s), 4.05-4.09 (2H, m), 4.25 (4H, s), 4.63 (2H, t, J=7.1 Hz), 6.10 (1H, s), 6.91 (1H, d, J=8.3 Hz), 7.04 (1H, d, J=8.3 Hz), 7.16 (1H, s), 7.32 (1H, t, J=7.6 Hz), 7.66-7.70 (1H, m), 7.77-7.83 (1H, m), 7.94 (1H, dd, J=8.0, 1.6 Hz), 9.46-9.70 (2H, broad), 10.71-11.05 (1H, broad)

Example 219

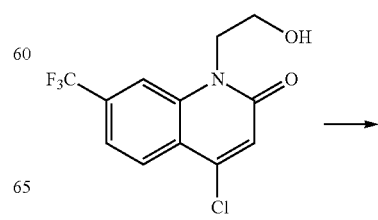

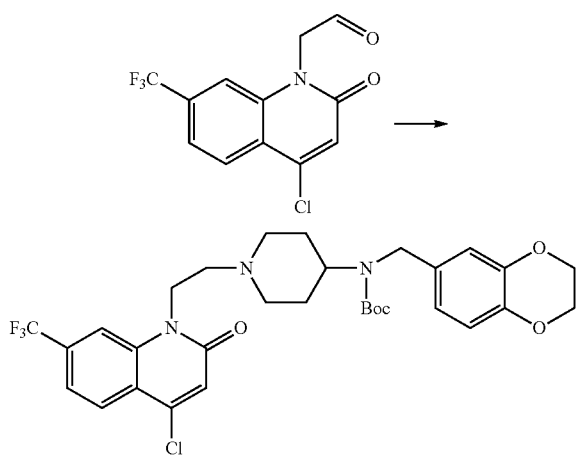

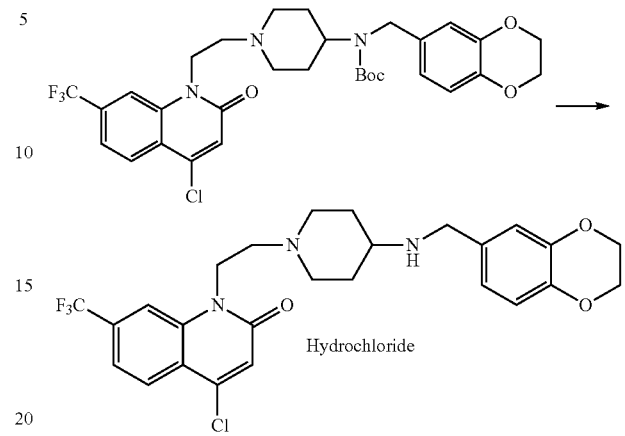

Example 220

To 2 mL of a dichloromethane solution containing 10 μL of oxalyl chloride, 20 μL of dimethylsulfoxide was added dropwise under nitrogen atmosphere at −60° C., and stirred for 10 min. 3 mL of a dichloromethane solution containing 31 mg of 4-chloro-1-(2-hydroxyethyl)-7-trifluoromethylquinolin-2 (1H)-one was added dropwise at the same temperature, and stirred for 10 min. 60 μL of triethylamine was added at the same temperature, the mixture was stirred for 1 hour while slowly raising the reaction mixture to room temperature, and water was added. The organic layer was separated, and the aqueous layer was extracted with chloroform. The organic layer and extracts were combined, dried over anhydrous magnesium sulfate, and the solvent was removed under reduced pressure to give (4-chloro-7-trifluoromethyl-2-oxoquinolin-1(2H)-yl)acetaldehyde as a brown oil.

To 3 mL of a dichloromethane solution containing the (4-chloro-7-trifluoromethyl-2-oxoquinolin-1(2H)-yl)acetaldehyde obtained, 44 mg of tert-butyl (2,3-dihydro-1,4-benzodioxin-6-ylmethyl)(piperidin-4-yl)carbamate and 20 μL of acetic acid were added, and stirred at room temperature for 80 min. To the reaction mixture, 35 mg of sodium triacetoxyborohydride was added, stirred at the same temperature for 80 min, aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; hexane:ethyl acetate=1:1], to give 27 mg of tert-butyl 1-(2-(4-chloro-2-oxo-7-trifluoromethylquinolin-1(2H)-yl)ethyl)piperidin-4-yl) (2,3-dihydro-1,4-benzodioxin-6-ylmethyl)carbamate as a white foam.

$^1$H-NMR (CDCl$_3$) δ:
1.40 (9H, s), 1.59-1.69 (5H, m), 2.09-2.23 (2H, m), 2.62 (2H, t, J=6.9 Hz), 2.97 (2H, m), 4.23 (4H, s), 4.24-4.27 (2H, m), 4.36 (2H, t, J=6.9 Hz), 6.64-6.69 (1H, m), 6.72 (1H, s), 6.76 (1H, d, J=8.3 Hz), 6.96 (1H, s), 7.52 (1H, d, J=8.3 Hz), 7.78 (1H, s), 8.13 (1H, d, J=8.3 Hz)

To 25 mg of tert-butyl 1-(2-(4-chloro-2-oxo-7-trifluoromethylquinolin-1(2H)-yl)ethyl)piperidin-4-yl) (2,3-dihydro-1,4-benzodioxin-6-ylmethyl)carbamate, 3 mL of 4 mol/L hydrogen chloride/ethyl acetate was added, and after stirred at room temperature for 24 hours, the resulting solid was filtered to give 11 mg of 4-chloro-1-(2-(4-((2,3-dihydro-1,4-benzodioxin-6-ylmethyl)amino)piperidin-1-yl)ethyl)-7-trifluoromethylquinolin-2(1H)-one hydrochloride as a pale yellow solid.

$^1$H-NMR (DMSO-d$_6$) δ:
1.99-2.07 (2H, m), 2.31-2.38 (2H, m), 3.12 (2H, m), 3.20-3.28 (1H, m), 3.35-3.39 (2H, m), 3.78-3.84 (2H, m), 4.06-4.09 (2H, m), 4.25 (4H, s), 4.74 (2H, m), 6.91 (1H, d, J=8.3 Hz), 7.03 (1H, d, J=8.3 Hz), 7.12-7.17 (1H, m), 7.21-7.25 (1H, m), 7.77 (1H, d, J=8.3 Hz), 8.05-8.11 (1H, m), 8.23 (1H, d, J=8.3 Hz), 9.34-9.61 (2H, broad), 10.51-10.70 (1H, broad)

Example 221

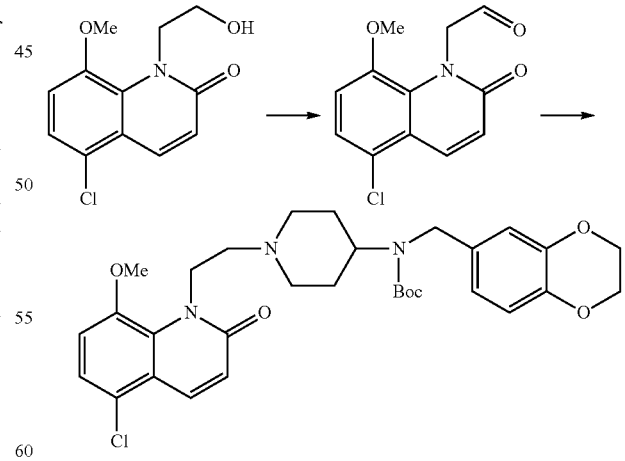

To 1.2 mL of a dichloromethane solution containing 21 μL of oxalyl chloride, 26 μL of dimethylsulfoxide was added dropwise under nitrogen atmosphere at −78° C., and stirred for 15 min. 1 mL of a dichloromethane solution containing 31 mg of 5-chloro-1-(2-hydroxyethyl)-8-methoxyquinolin-2 (1H)-one was added dropwise at the same temperature, and stirred for 30 min. 84 μL of triethylamine was added at the same temperature, the mixture was stirred for 1.5 hours while slowly raising the reaction mixture to room temperature, and 0.5 mL of water was added. The organic layer was separated, and the aqueous layer was extracted with chloroform. The organic layer and extracts were combined, dried over anhydrous magnesium sulfate, and the solvent was removed under reduced pressure to give (5-chloro-8-methoxy-2-oxoquinolin-1(2H)-yl)acetaldehyde as a yellow solid.

To 1 mL of a dichloromethane solution containing (5-chloro-8-methoxy-2-oxoquinolin-1(2H)-yl)acetaldehyde, 49 mg of tert-butyl (2,3-dihydro-1,4-benzodioxin-6-ylmethyl)(piperidin-4-yl)carbamate and 7 μL of acetic acid were added, and stirred at room temperature for 2 hours. To the reaction mixture, 41 mg of sodium triacetoxyborohydride was added, stirred at the same temperature for 12 hours, aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; hexane:ethyl acetate=1:2], to give 48 mg of tert-butyl 1-(2-(5-chloro-8-methoxy-2-oxoquinolin-1(2H)-yl)ethyl)piperidin-4-yl)(2,3-dihydro-1,4-benzodioxin-6-ylmethyl)carbamate as a pale yellow solid.

$^1$H-NMR (CDCl$_3$) δ:
1.34-1.53 (12H, m), 2.11-2.26 (2H, m), 2.71 (2H, s), 2.97-3.10 (2H, m), 3.49 (3H, s), 3.88-3.97 (2H, m), 4.24 (4H, s), 4.26-4.36 (2H, m), 4.61-4.76 (2H, m), 6.66-6.72 (1H, m), 6.73-6.76 (1H, m), 6.74 (1H, d, J=9.6 Hz), 6.78 (1H, d, J=8.3 Hz), 6.97 (1H, d, J=8.7 Hz), 7.22 (1H, d, J=8.7 Hz), 8.12 (1H, d, J=9.6 Hz)

Example 222

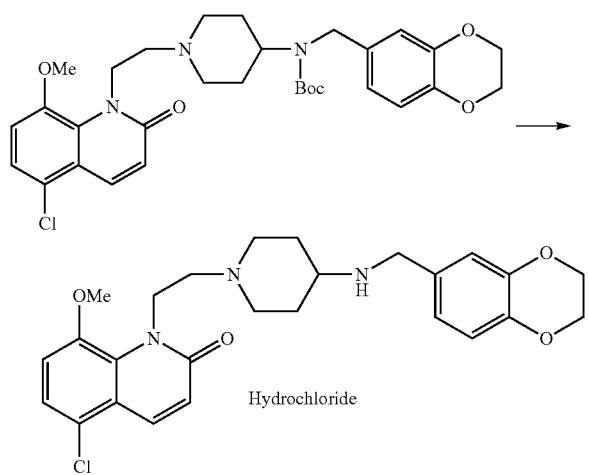

To 48 mg of tert-butyl 1-(2-(5-chloro-8-methoxy-2-oxoquinolin-1(2H)-yl)ethyl)piperidin-4-yl) (2,3-dihydro-1,4-benzodioxin-6-ylmethyl)carbamate, 1.5 mL of 4 mol/L hydrogen chloride/1,4-dioxane was added, and after stirred at room temperature for 24 hours, the resulting solid was filtered to give 19 mg of 5-chloro-1-(2-(4-((2,3-dihydro-1,4-benzodioxin-6-ylmethyl)amino)piperidin-1-yl)ethyl)-8-methoxyquinolin-2(1H)-one hydrochloride as a pale yellow solid.

$^1$H-NMR (DMSO-d$_6$) δ:
1.98-2.07 (2H, m), 2.34-2.40 (2H, m), 2.59-2.64 (1H, m), 3.07-3.16 (2H, m), 3.39-3.45 (2H, m), 3.74-3.80 (2H, m), 3.97 (3H, s), 4.06-4.10 (2H, m), 4.26 (4H, s), 4.72-4.76 (2H, m), 6.82 (1H, d, J=9.6 Hz), 6.92 (1H, d, J=8.3 Hz), 7.02-7.05 (1H, m), 7.14-7.17 (1H, m), 7.34 (1H, d, J=8.7 Hz), 7.45 (1H, d, J=8.7 Hz), 8.18 (1H, d, J=9.6 Hz), 9.41-9.56 (2H, broad), 10.03-10.11 (1H, broad)

Example 223

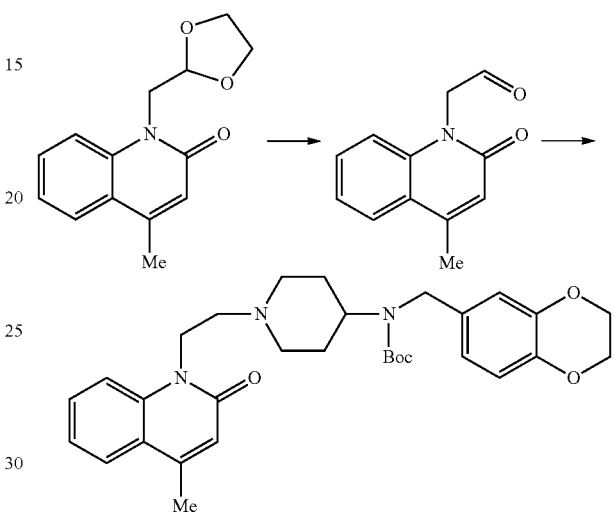

0.74 g of 1-(1,3-dioxolan-2-ylmethyl)-4-methylquinolin-2(1H)-one was dissolved in 6 mL of 67% aqueous trifluoroacetic acid solution, and stirred at room temperature for 15.5 hours, at 40° C. for 9.5 hours, further at room temperature for 15 hours. After the reaction mixture was alkalized by adding aqueous saturated sodium hydrogen carbonate solution, it was extracted with ethyl acetate. The organic layer was washed with aqueous saturated sodium chloride solution, dried over anhydrous magnesium sulfate, and the solvent was removed under reduced pressure to give (4-methyl-2-oxoquinolin-1(2H)-yl)acetaldehyde as a yellow oil.

To 30 mL of a chloroform solution containing (4-methyl-2-oxoquinolin-1(2H)-yl)acetaldehyde, 1.05 g of tert-butyl (2,3-dihydro-1,4-benzodioxin-6-ylmethyl)(piperidin-4-yl)carbamate and 0.18 g of acetic acid were added, and stirred at room temperature for 1 hour. To the reaction mixture, 0.77 g of sodium triacetoxyborohydride was added, and stirred for 1 hour. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; ethyl acetate], to give 1.23 g of tert-butyl 1-(2-(4-methyl-2-oxoquinolin-1(2H)-yl)ethyl)piperidin-4-yl) (2,3-dihydro-1,4-benzodioxin-6-ylmethyl)carbamate as a white foam.

$^1$H-NMR (CDCl$_3$) δ:
1.33-1.56 (9H, s), 1.61-1.78 (4H, m), 2.09-2.28 (2H, m), 2.45 (3H, d, J=0.9 Hz), 2.58-2.65 (2H, m), 3.01-3.11 (2H, m), 4.02-4.46 (9H, m), 6.57 (1H, d, J=0.9 Hz), 6.69 (1H, d, J=7.8 Hz), 6.74 (1H, d, J=1.4 Hz), 6.78 (1H, d, J=8.3 Hz), 7.21-7.26 (1H, m), 7.41 (1H, d, J=8.3 Hz), 7.52-7.57 (1H, m), 7.70 (1H, dd, J=7.8, 1.4 Hz)

Example 224

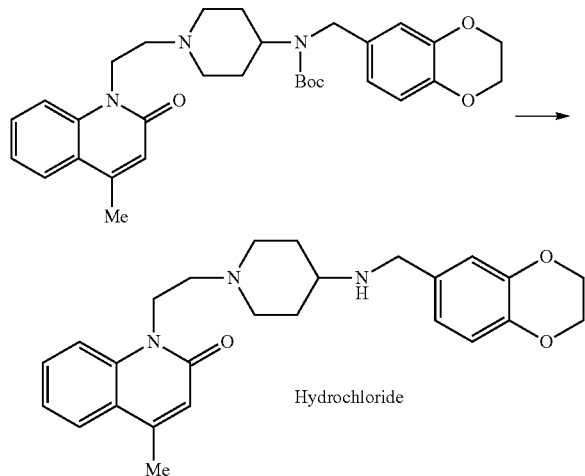

To 12 mL of an ethyl acetate solution containing 250 mg of tert-butyl 1-(2-(4-methyl-2-oxoquinolin-1(2H)-yl)ethyl)piperidin-4-yl)(2,3-dihydro-1,4-benzodioxin-6-ylmethyl)carbamate, 2 mL of 4 mol/L hydrogen chloride/ethyl acetate was added, and stirred at room temperature for 176 hours. The resulting solid was filtered to give 196 mg of 1-(2-(4-((2,3-dihydro-1,4-benzodioxin-6-ylmethyl)amino)piperidin-1-yl)ethyl)-4-methylquinolin-2(1H)-one hydrochloride as a white solid.

$^1$H-NMR (DMSO-$d_6$, $D_2O$) δ:
2.03-2.13 (2H, m), 2.34-2.40 (2H, m), 2.46-2.47 (3H, m), 3.07-3.15 (2H, m), 3.19-3.29 (3H, m), 3.78 (2H, d, J=11.9 Hz), 4.05-4.08 (2H, m), 4.25 (4H, s), 4.64-4.70 (2H, m), 6.59 (1H, d, J=1.4 Hz), 6.90 (1H, d, J=8.3 Hz), 7.05 (1H, dd, J=8.5, 2.1 Hz), 7.18 (1H, d, J=1.8 Hz), 7.35 (1H, t, J=7.6 Hz), 7.64-7.68 (1H, m), 7.82-7.86 (2H, m), 9.55-9.70 (2H, broad), 10.89-11.28 (1H, broad)

Example 225

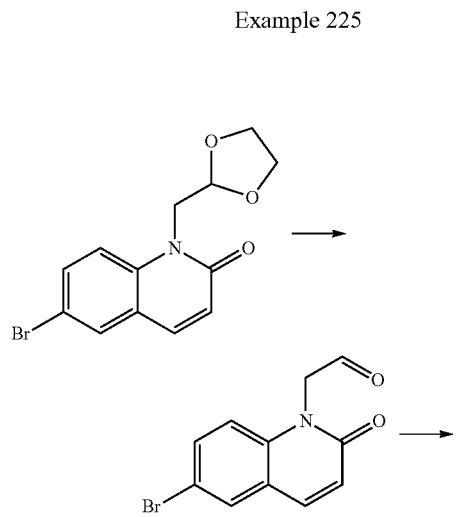

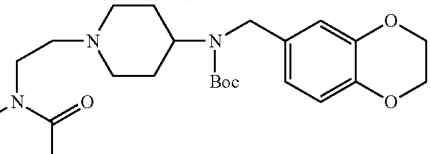

0.56 g of 1-(1,3-dioxolan-2-ylmethyl)-6-bromoquinolin-2(1H)-one was dissolved in 4.5 mL of 67% aqueous trifluoroacetic acid solution, and stirred at room temperature for 18.5 hours, at 40° C. for 7.5 hours, further at room temperature for 15 hours. After the reaction mixture was alkalized by adding aqueous saturated sodium hydrogen carbonate solution, it was extracted with ethyl acetate. The organic layer was washed with aqueous saturated sodium chloride solution, dried over anhydrous magnesium sulfate, and the solvent was removed under reduced pressure to give (6-bromo-2-oxoquinolin-1(2H)-yl)acetaldehyde as a pale yellow solid.

To 22 mL of a chloroform solution containing (6-bromo-2-oxoquinolin-1(2H)-yl)acetaldehyde, 0.63 g of tert-butyl (2,3-dihydro-1,4-benzodioxin-6-ylmethyl)(piperidin-4-yl)carbamate and 0.11 g of acetic acid were added, and stirred at room temperature for 1 hour. To the reaction mixture, 0.46 g of sodium triacetoxyborohydride was added, and stirred for 1 hour. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; ethyl acetate], to give 0.88 g of tert-butyl 1-(2-(6-bromol-2-oxoquinolin-1(2H)-yl)ethyl)piperidin-4-yl) (2,3-dihydro-1,4-benzodioxin-6-ylmethyl)carbamate as a white foam.

$^1$H-NMR (CDCl$_3$) δ:
1.41 (9H, s), 1.59-1.72 (5H, m), 2.08-2.24 (2H, m), 2.56-2.62 (2H, m) 2.98-3.05 (2H, m), 4.21-4.40 (8H, m), 6.66-6.71 (2H, m), 6.74 (1H, s), 6.79 (1H, d, J=8.3 Hz), 7.27-7.31 (1H, m), 7.57 (1H, d, J=9.2 Hz), 7.61 (1H, dd, J=9.2, 2.3 Hz), 7.68 (1H, d, J=2.3 Hz)

Example 226

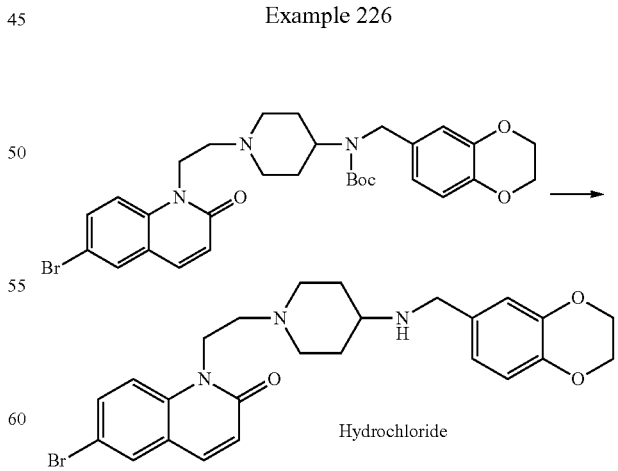

To 12 mL of an ethyl acetate solution containing 220 mg of tert-butyl 1-(2-(6-bromo-2-oxoquinolin-1(2H)-yl)ethyl)piperidin-4-yl)(2,3-dihydro-1,4-benzodioxin-6-ylmethyl)carbamate, 2 mL of 4 mol/L hydrogen chloride/ethyl acetate was added, and stirred at room temperature for 132 hours. The resulting solid was filtered to give 153 mg of 1-(2-(4-((2,3-dihydro-1,4-benzodioxin-6-ylmethyl)amino)piperidin-1-yl)ethyl)-6-bromoquinolin-2(1H)-one hydrochloride as a pale yellow solid.

$^1$H-NMR (DMSO-$d_6$) δ:
2.01-2.09 (2H, m), 2.33-2.38 (2H, m), 3.06-3.14 (2H, m), 3.19-3.31 (3H, m), 3.78 (2H, d, J=12.4 Hz), 4.05-4.09 (2H, m), 4.25 (4H, s), 4.62-4.66 (2H, m), 6.72 (1H, d, J=9.6 Hz), 6.91 (1H, d, J=8.3 Hz), 7.04 (1H, dd, J=8.3, 2.3 Hz), 7.16 (1H, d, J=2.3 Hz), 7.77-7.79 (2H, m), 7.96 (1H, d, J=9.6 Hz), 8.06 (1H, d, J=1.8 Hz), 9.44-9.52 (2H, broad), 10.66-10.76 (1H, broad)

Example 227

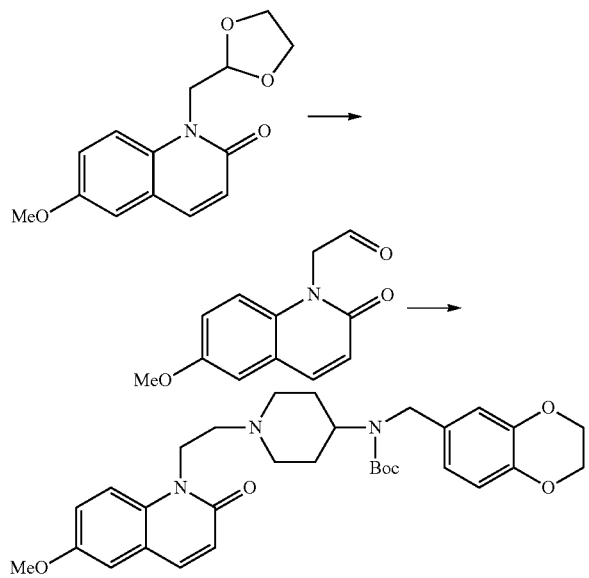

95 mg of 1-(1,3-dioxolan-2-ylmethyl)-6-methoxyquinolin-2(1H)-one was dissolved in 1.5 mL of 67% aqueous trifluoroacetic acid solution, and stirred at room temperature for 18 hours, at 40° C. for 6.5 hours, further at room temperature for 15 hours. After the reaction mixture was alkalized by adding aqueous saturated sodium hydrogen carbonate solution, it was extracted with ethyl acetate. The organic layer was washed with aqueous saturated sodium chloride solution, dried over anhydrous magnesium sulfate, and the solvent was removed under reduced pressure to give (6-methoxy-2-oxoquinolin-1(2H)-yl)acetaldehyde as a yellow oil.

To 4.5 mL of a chloroform solution containing (6-methoxy-2-oxoquinolin-1(2H)-yl)acetaldehyde, 127 mg of tert-butyl (2,3-dihydro-1,4-benzodioxin-6-ylmethyl)(piperidin-4-yl)carbamate and 22 mg of acetic acid were added, and stirred at room temperature for 1 hour. To the reaction mixture, 93 mg of sodium triacetoxyborohydride was added, and stirred for 1 hour. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; ethyl acetate], to give 146 mg of tert-butyl 1-(2-(6-methoxy-2-oxoquinolin-1(2H)-yl)ethyl)piperidin-4-yl)(2,3-dihydro-1,4-benzodioxin-6-ylmethyl)carbamate as a white foam.

$^1$H-NMR (CDCl$_3$) δ:
1.41 (9H, s), 1.59-1.74 (5H, m), 2.09-2.25 (2H, m), 2.58-2.65 (2H, m), 3.01-3.07 (2H, m), 3.86 (3H, s), 4.20-4.43 (8H, m), 6.66-6.72 (2H, m), 6.74 (1H, s), 6.78 (1H, d, J=8.3 Hz), 6.99 (1H, d, J=2.8 Hz), 7.15-7.19 (1H, m), 7.30-7.36 (1H, m), 7.59 (1H, d, J=9.6 Hz)

Example 228

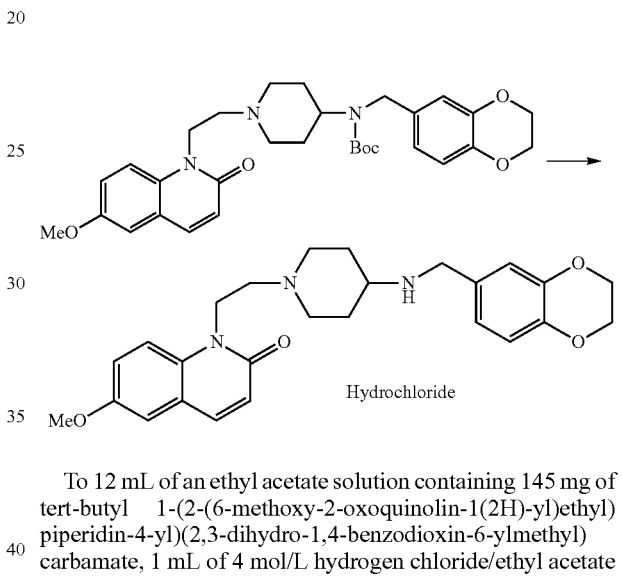

To 12 mL of an ethyl acetate solution containing 145 mg of tert-butyl 1-(2-(6-methoxy-2-oxoquinolin-1(2H)-yl)ethyl)piperidin-4-yl)(2,3-dihydro-1,4-benzodioxin-6-ylmethyl)carbamate, 1 mL of 4 mol/L hydrogen chloride/ethyl acetate was added, and stirred at room temperature for 132 hours. The resulting solid was filtered to give 88 mg of 1-(2-(4-((2,3-dihydro-1,4-benzodioxin-6-ylmethyl)amino)piperidin-1-yl)ethyl)-6-methoxyquinolin-2(1H)-one hydrochloride as a pale yellow solid.

$^1$H-NMR (DMSO-$d_6$) δ:
2.01-2.10 (2H, m), 2.33-2.38 (2H, m), 3.06-3.15 (2H, m), 3.21-3.30 (3H, m), 3.76-3.81 (2H, m), 3.83 (3H, s), 4.05-4.09 (2H, m), 4.25 (4H, s), 4.62-4.66 (2H, m), 6.66 (1H, d, J=9.2 Hz), 6.91 (1H, d, J=8.3 Hz), 7.04 (1H, dd, J=8.3, 1.8 Hz), 7.16 (1H, d, J=1.8 Hz), 7.26 (1H, dd, J=9.2, 3.2 Hz), 7.36 (1H, d, J=3.2 Hz), 7.76 (1H, d, J=9.2 Hz), 7.93 (1H, d, J=9.2 Hz), 9.43-9.52 (2H, broad), 10.73-10.82 (1H, broad)

Example 229

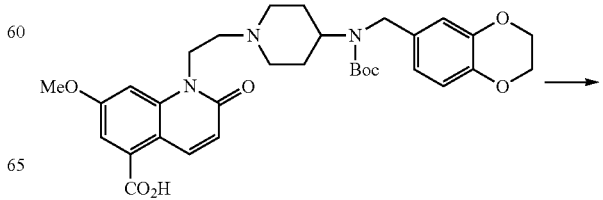

-continued

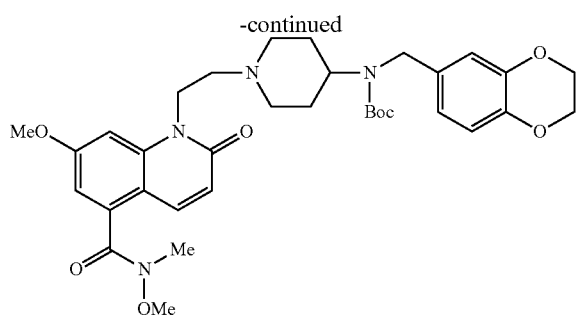

To 10 mL of a tetrahydrofuran solution containing 600 mg of tert-butyl (2,3-dihydro-1,4-benzodioxin-6-ylmethyl)(1-(2-(7-methoxy-5-carboxy-2-oxoquinolin-1(2H)-yl)ethyl)piperidin-4-yl)carbamate, 420 mg of 4-(4,6-dimethoxy-1,3,5-triazin-2-yl)-4-methylmorpholinium chloride, 108 mg of O,N-dimethylhydroxylamine hydrochloride and 112 mg of N-methylmorpholine were added, and stirred at room temperature for 22 hours. Hydrochloric acid was added to the reaction mixture to make acidic, the organic layer was separated, washed sequentially with water, aqueous saturated sodium hydrogen carbonate solution and aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate], to give 0.69 g of tert-butyl (2,3-dihydro-1,4-benzodioxin-6-ylmethyl)(1-(2-(7-methoxy-5-((methoxy)(methyl)carbamoyl)-2-oxoquinolin-1(2H)-yl)ethyl)piperidin-4-yl)carbamate as a colorless oil.

$^1$H-NMR (CDCl$_3$) δ:
1.40 (9H, s), 1.61-1.72 (5H, m), 2.10-2.22 (2H, m), 2.58-2.64 (2H, m), 3.00-3.06 (2H, m), 3.36-3.48 (6H, m), 3.88 (3H, s), 4.22-4.38 (8H, m), 6.54 (1H, d, J=9.6 Hz), 6.66-6.70 (1H, m), 6.73 (1H, s), 6.77 (1H, d, J=8.3 Hz), 6.81 (1H, s), 6.92 (1H, s), 7.59 (1H, d, J=9.6 Hz)

Example 230

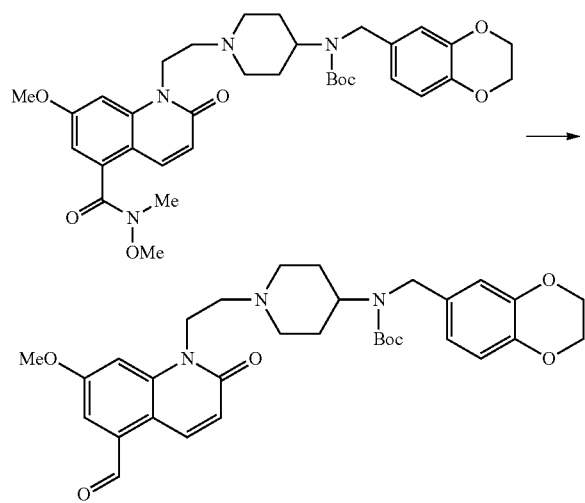

To 20 mL of a tetrahydrofuran solution containing 1.05 g of tert-butyl (2,3-dihydro-1,4-benzodioxin-6-ylmethyl)(1-(2-(7-methoxy-5-((methoxy)(methyl)carbamoyl)-2-oxoquinolin-1(2H)-yl)ethyl)piperidin-4-yl)carbamate, 4.95 mL of 1 mol/L diisobutyl aluminum hydride/toluene was added at −78° C. and stirred for 1 hour. To the reaction mixture, aqueous saturated ammonium chloride solution and ethyl acetate were added. The organic layer was separated, washed sequentially with aqueous saturated sodium hydrogen carbonate solution and aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 0.65 g of tert-butyl (2,3-dihydro-1,4-benzodioxin-6-ylmethyl) (1-(2-(5-formyl-7-methoxy-2-oxoquinolin-1(2H)-yl)ethyl)piperidin-4-yl) carbamate as a colorless oil.

$^1$H-NMR (CDCl$_3$) δ:
1.41 (9H, s), 1.62-1.70 (5H, m), 2.13-2.24 (2H, m), 2.60-2.65 (2H, m), 3.00-3.05 (2H, m), 3.96 (3H, s), 4.22-4.42 (8H, m), 6.66-6.71 (2H, m), 6.72-6.74 (1H, m), 6.78 (1H, d, J=8.3 Hz), 7.16 (1H, s), 7.28 (1H, d, J=2.3 Hz), 8.88 (1H, d, J=10.1 Hz), 10.26 (1H, s)

Example 231

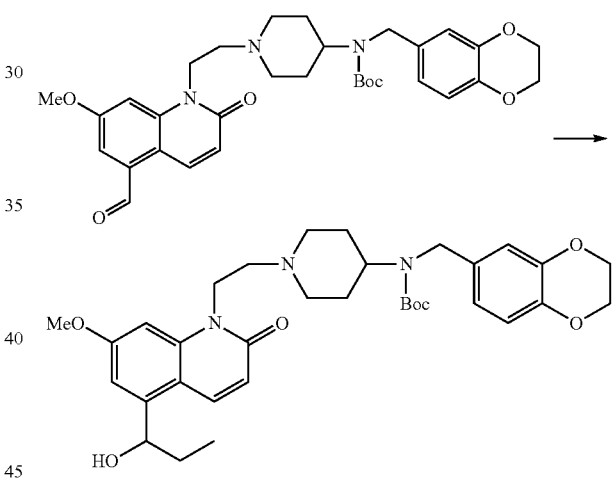

To 20 mL of a tetrahydrofuran solution containing 0.65 g of tert-butyl (2,3-dihydro-1,4-benzodioxin-6-ylmethyl)(1-(2-(5-formyl-7-methoxy-2-oxoquinolin-1(2H)-yl)ethyl)piperidin-4-yl)carbamate, 8.8 mL of 1 mol/L ethylmagnesium bromide/tetrahydrofuran was added at −78° C. and stirred for 1.5 hours. To the reaction mixture, aqueous saturated ammonium chloride solution, water and chloroform were added. The organic layer was separated, washed sequentially with aqueous saturated sodium hydrogen carbonate solution and aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=20:1], to give 200 mg of tert-butyl (2,3-dihydro-1,4-benzodioxin-6-ylmethyl) (1-(2-(5-(1-hydroxypropyl)-7-methoxy-2-oxoquinolin-1(2H)-yl)ethyl)piperidin-4-yl) carbamate as a yellow oil.

$^1$H-NMR (CDCl$_3$) δ:
1.01 (3H, t, J=7.6 Hz), 1.41 (9H, s), 1.60-1.73 (5H, m), 1.80-1.87 (2H, m), 2.12-2.25 (2H, m), 2.59-2.65 (2H, m),

427

3.02-3.08 (2H, m), 3.90 (3H, s), 4.22-4.40 (8H, m), 5.10-5.15 (1H, m), 6.52 (1H, d, J=9.6 Hz), 6.67-6.71 (1H, m), 6.74 (1H, s), 6.78 (1H, d, J=8.3 Hz), 6.82 (1H, s), 7.00 (1H, d, J=2.3 Hz), 7.92 (1H, d, J=9.6 Hz)

Example 232

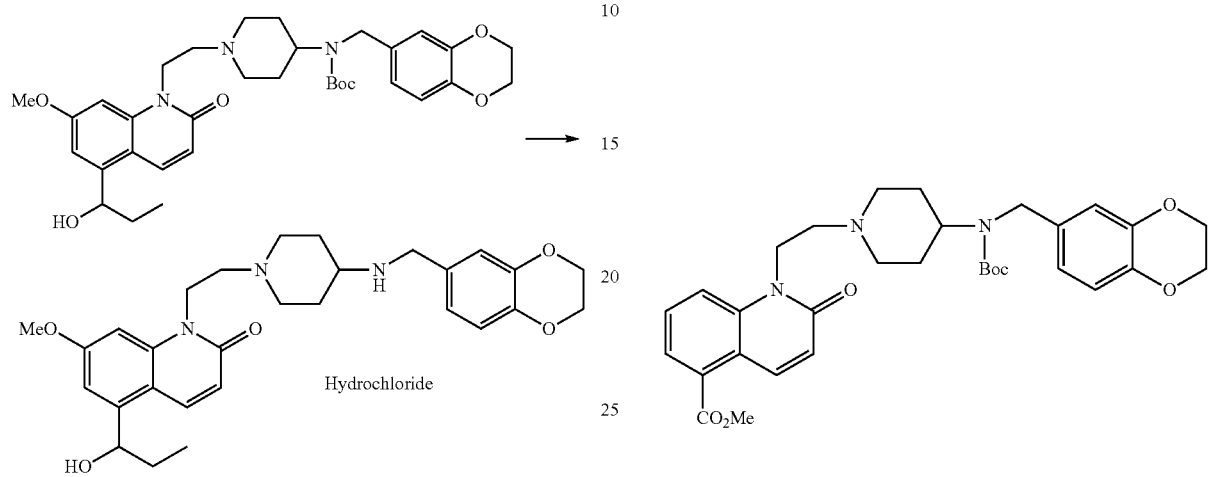

To 1 mL of a 1,4-dioxane solution containing 165 mg of tert-butyl (2,3-dihydro-1,4-benzodioxin-6-ylmethyl)(1-(2-(5-(1-hydroxypropyl)-7-methoxy-2-oxoquinolin-1(2H)-yl)ethyl)piperidin-4-yl)carbamate, 1 mL of 4 mol/L hydrogen chloride/1,4-dioxane were added, and stirred at room temperature. The solvent was removed under reduced pressure to give 24 mg of 1-(2-(4-((2,3-dihydro-1,4-benzodioxin-6-ylmethyl)amino)piperidin-1-yl)ethyl)-5-(1-hydroxypropyl)-7-methoxyquinolin-2(1H)-one hydrochloride as a brown solid.

¹H-NMR (DMSO-$d_6$) δ:

0.89 (3H, t, J=7.3 Hz), 1.57-1.70 (2H, m), 1.98-2.07 (2H, m), 2.32-2.38 (2H, m), 3.06-3.15 (2H, m), 3.20-3.30 (3H, m), 3.77-3.85 (2H, m), 3.96 (3H, s), 4.05-4.10 (2H, m), 4.26 (4H, s), 4.64-4.72 (2H, m), 4.98-5.03 (1H, m), 5.40-5.48 (1H, m), 6.46 (1H, d, J=10.1 Hz), 6.92 (1H, d, J=8.3 Hz), 6.99-7.05 (3H, m), 7.11-7.17 (1H, m), 8.18 (1H, d, J=9.6 Hz), 9.29-9.42 (2H, broad), 10.72-10.86 (1H, broad)

Example 233

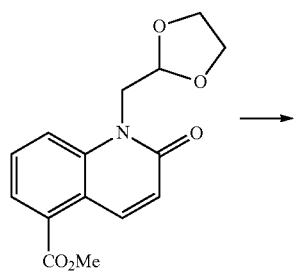

428

-continued

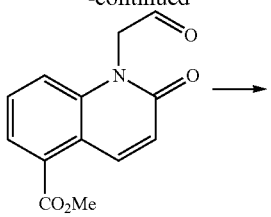

22 mg of methyl 1-(1,3-dioxolan-2-ylmethyl)-1,2-dihydro-2-oxoquinoline-5-carboxylate was dissolved in 2 mL of 50% aqueous trifluoroacetic acid solution, and stirred at room temperature for 11.5 hours. After the reaction mixture was alkalized by adding aqueous saturated sodium hydrogen carbonate solution, it was extracted with ethyl acetate. The organic layer was washed with aqueous saturated sodium chloride solution, dried over anhydrous magnesium sulfate, and the solvent was removed under reduced pressure to give methyl 2-oxo-1-(2-oxoethyl)-1,2-dihydroquinoline-5-carboxylate as a colorless oil.

To 1 mL of a chloroform solution containing methyl 2-oxo-1-(2-oxoethyl)-1,2-dihydroquinoline-5-carboxylate, 26.5 mg of tert-butyl (2,3-dihydro-1,4-benzodioxin-6-ylmethyl)(piperidin-4-yl)carbamate and 6.9 mg of acetic acid were added, and stirred at room temperature for 2 hours. To the reaction mixture, 24.2 mg of sodium triacetoxyborohydride was added, and stirred for 1.5 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; ethyl acetate], to give 9.3 mg of tert-butyl (2,3-dihydro-1,4-benzodioxin-6-ylmethyl)(1-(2-(5-methoxycarbonyl-2-oxoquinolin-1(2H)-yl)ethyl)piperidin-4-yl)carbamate as a colorless oil.

¹H-NMR (CDCl₃) δ:

1.38 (9H, s), 1.56-1.72 (4H, m), 2.05-2.21 (2H, m), 2.51-2.64 (2H, m), 2.95-3.08 (2H, m), 3.94 (3H, s), 4.02-4.46 (9H, m), 6.62-6.78 (4H, m), 7.50-7.61 (2H, m), 7.78 (1H, d, J=7.8 Hz), 8.72 (1H, d, J=9.6 Hz)

Example 234

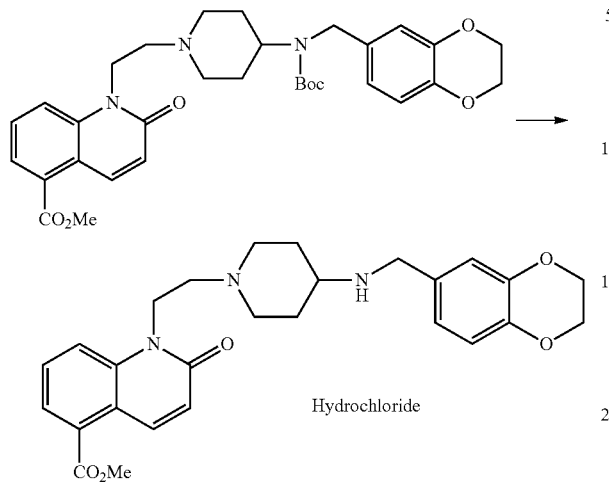

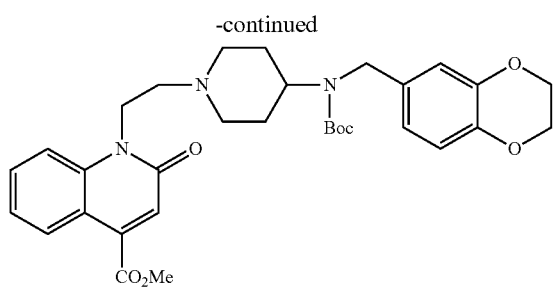

To 0.2 mL of an ethyl acetate solution containing 9.0 mg of tert-butyl (2,3-dihydro-1,4-benzodioxin-6-ylmethyl)(1-(2-(5-methoxycarbonyl-2-oxoquinolin-1(2H)-yl)ethyl)piperidin-4-yl)carbamate, 2 mL of 4 mol/L hydrogen chloride/ethyl acetate was added, and stirred at room temperature for 42 hours. The solvent was removed under reduced pressure to give 8.4 mg of methyl 1-(2-(4-((2,3-dihydro-1,4-benzodioxin-6-ylmethyl)amino)piperidin-1-yl)ethyl)-1,2-dihydro-2-oxoquinoline-5-carboxylate hydrochloride as a white solid.

¹H-NMR (DMSO-$d_6$) δ:
1.95-2.08 (2H, m), 2.31-2.37 (2H, m), 3.06-3.18 (2H, m), 3.21-3.44 (3H, m), 3.76-3.85 (2H, m), 3.93 (3H, s), 4.04-4.13 (2H, m), 4.26 (4H, s), 4.66-4.74 (2H, m), 6.81 (1H, d, J=10.1 Hz), 6.92 (1H, d, J=8.3 Hz), 7.02 (1H, d, J=8.3 Hz), 7.11-7.17 (1H, m), 7.73-7.84 (2H, m), 8.02-8.08 (1H, m), 8.56-8.66 (1H, m), 9.28-9.43 (2H, broad), 10.42-10.63 (1H, broad)

Example 235

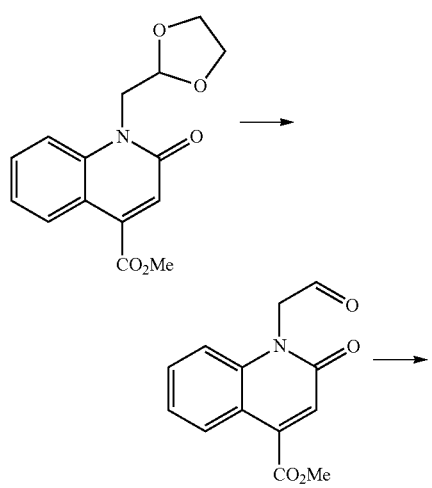

0.10 mg of methyl 1-(1,3-dioxolan-2-ylmethyl)-1,2-dihydro-2-oxoquinoline-4-carboxylate was dissolved in 3 mL of 67% aqueous trifluoroacetic acid solution, and stirred at room temperature for 11.5 hours. After the reaction mixture was alkalized by adding aqueous saturated sodium hydrogen carbonate solution, it was extracted with ethyl acetate. The organic layer was washed with aqueous saturated sodium chloride solution, dried over anhydrous magnesium sulfate, and the solvent was removed under reduced pressure to give methyl 2-oxo-1-(2-oxoethyl)-1,2-dihydroquinoline-4-carboxylate as a yellow oil.

To 4 mL of a chloroform solution containing methyl 2-oxo-1-(2-oxoethyl)-1,2-dihydroquinoline-4-carboxylate, 0.12 g of tert-butyl (2,3-dihydro-1,4-benzodioxin-6-ylmethyl)(piperidin-4-yl)carbamate and 0.03 g of acetic acid were added, and stirred at room temperature for 2 hours. To the reaction mixture, 0.11 g of sodium triacetoxyborohydride was added, and stirred for 1.5 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; ethyl acetate], to give 109 mg of tert-butyl (2,3-dihydro-1,4-benzodioxin-6-ylmethyl)(1-(2-(4-methoxycarbonyl-2-oxoquinolin-1(2H)-yl)ethyl)piperidin-4-yl)carbamate as a yellow oil.

¹H-NMR (CDCl₃) δ:
1.41 (9H, s), 1.57-1.74 (5H, m), 2.10-2.24 (2H, m), 2.58-2.67 (2H, m), 3.00-3.08 (2H, m), 3.99 (3H, s), 4.22-4.46 (8H, m), 6.65-6.72 (1H, m), 6.74 (1H, s), 6.78 (1H, d, J=8.3 Hz), 7.16 (1H, s), 7.26-7.30 (1H, m), 7.41-7.47 (1H, m), 7.56-7.61 (1H, m), 8.32 (1H, dd, J=8.0, 1.6 Hz)

Example 236

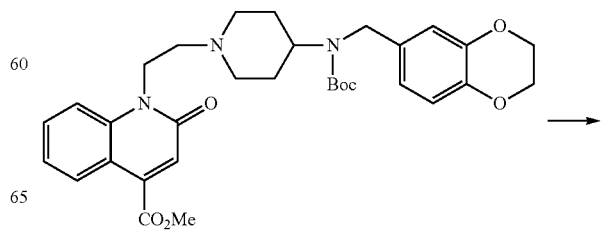

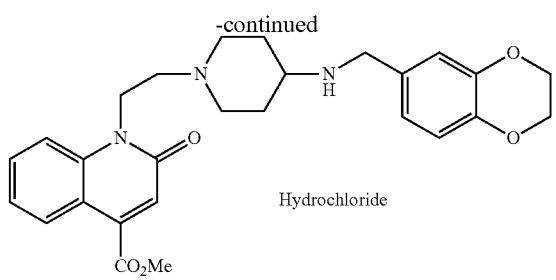

To 1 mL of an ethyl acetate solution containing 30 mg of tert-butyl (2,3-dihydro-1,4-benzodioxin-6-ylmethyl)(1-(2-(4-methoxycarbonyl-2-oxoquinolin-1(2H)-yl)ethyl)piperidin-4-yl)carbamate, 1 mL of 4 mol/L hydrogen chloride/ethyl acetate was added, and stirred at room temperature for 42 hours. The resulting solid was filtered to give 18 mg of methyl 1-(2-(4-((2,3-dihydro-1,4-benzodioxin-6-ylmethyl)amino)piperidin-1-yl)ethyl)-1,2-dihydro-2-oxoquinoline-4-carboxylate hydrochloride as a yellow solid.

$^1$H-NMR (DMSO-$d_6$) δ:

1.98-2.08 (2H, m), 2.33-2.38 (2H, m), 3.06-3.16 (2H, m), 3.20-3.35 (3H, m), 3.77-3.85 (2H, m), 3.95 (3H, s), 4.05-4.10 (2H, m), 4.25 (4H, s), 4.67-4.74 (2H, m), 6.91 (1H, d, J=8.3 Hz), 7.02 (1H, s), 7.03-7.05 (1H, m), 7.14-7.18 (1H, m), 7.38-7.42 (1H, m), 7.71-7.76 (1H, m), 7.87 (1H, d, J=8.7 Hz), 8.11 (1H, dd, J=8.3, 1.4 Hz), 9.38-9.53 (2H, broad), 10.53-10.77 (1H, broad)

Example 237

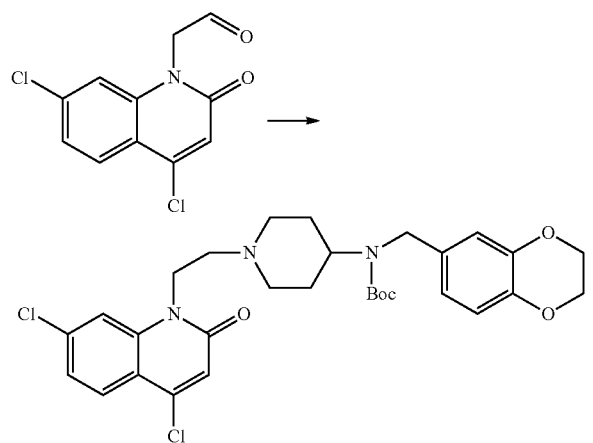

To 3 mL of a chloroform solution containing 69 mg of (4,7-dichloro-2-oxoquinolin-1(2H)-yl)acetaldehyde, 94 mg of tert-butyl (2,3-dihydro-1,4-benzodioxin-6-ylmethyl)(piperidin-4-yl)carbamate and 24 mg of acetic acid were added, and stirred at room temperature for 2 hours. To the reaction mixture, 86 mg of sodium triacetoxyborohydride was added, and stirred for 2.5 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; ethyl acetate], to give 109 mg of tert-butyl (2,3-dihydro-1,4-benzodioxin-6-ylmethyl)(1-(2-(4,7-dichloro-2-oxoquinolin-1(2H)-yl)ethyl)piperidin-4-yl)carbamate as a yellow oil.

$^1$H-NMR (CDCl$_3$) δ:

1.40 (9H, s), 1.57-1.70 (5H, m), 2.10-2.21 (2H, m), 2.57-2.62 (2H, m), 2.96-3.01 (2H, m), 4.21-4.33 (8H, m), 6.65-6.69 (1H, m), 6.72 (1H, s), 6.76 (1H, d, J=8.7 Hz), 6.83 (1H, s), 7.24-7.30 (1H, m), 7.51 (1H, s), 7.92 (1H, d, J=8.7 Hz)

Example 238

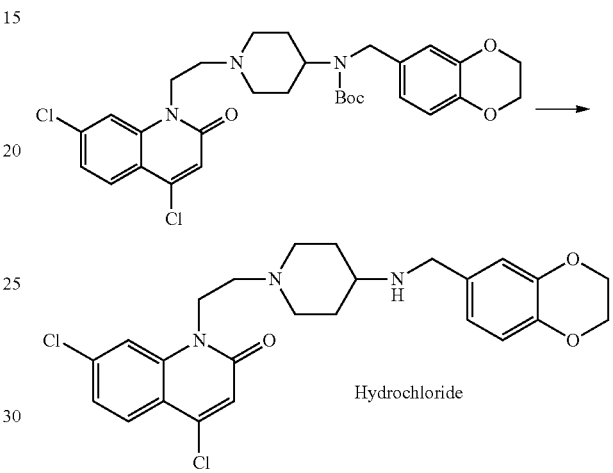

To 1 mL of an ethyl acetate solution containing 104 mg of tert-butyl (2,3-dihydro-1,4-benzodioxin-6-ylmethyl)(1-(2-(4,7-dichloro-2-oxoquinolin-1(2H)-yl)ethyl)piperidin-4-yl)carbamate, 2 mL of 4 mol/L hydrogen chloride/ethyl acetate was added, and stirred at room temperature. The resulting solid was filtered to give 62 mg of 1-(2-(4-((2,3-dihydro-1,4-benzodioxin-6-ylmethyl)amino)piperidin-1-yl)ethyl)-4,7-dichloroquinolin-2(1H)-one hydrochloride as a pale yellow solid.

$^1$H-NMR (DMSO-$d_6$, D$_2$O) δ:

1.87-1.98 (2H, m), 2.43 (2H, d, J=13.3 Hz), 3.16 (2H, t, J=11.7 Hz), 3.45-3.53 (3H, m), 3.90 (2H, d, J=11.0 Hz), 4.12 (2H, s), 4.28 (4H, s), 4.66 (2H, t, J=6.2 Hz), 6.98 (2H, s), 7.01-7.06 (2H, m), 7.55 (1H, dd, J=8.7, 1.8 Hz), 7.75 (1H, s), 8.14 (1H, d, J=8.7 Hz)

Example 239

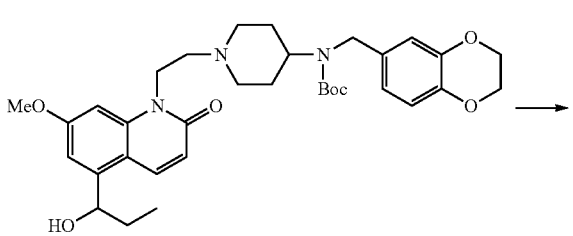

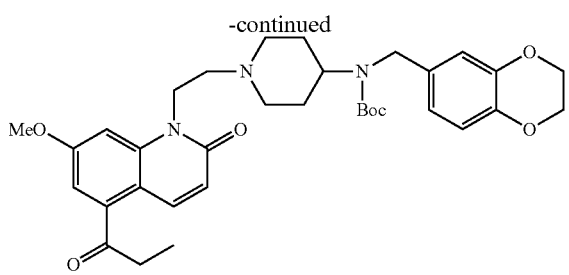

To 20 mL of a chloroform solution containing 165 mg of tert-butyl (2,3-dihydro-1,4-benzodioxin-6-ylmethyl)(1-(2-(5-(1-hydroxypropyl)-7-methoxy-2-oxoquinolin-1(2H)-yl)ethyl)piperidin-4-yl)carbamate, 115 mg of Dess-Martin Periodinane was added, and stirred at room temperature for 2 hours. To the reaction mixture, aqueous saturated sodium hydrogen carbonate solution was added. The organic layer was separated, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 115 mg of tert-butyl (2,3-dihydro-1,4-benzodioxin-6-ylmethyl)(1-(2-(7-methoxy-2-oxo-5-propionylquinolin-1(2H)-yl)ethyl)piperidin-4-yl)carbamate as a yellow oil.

$^1$H-NMR (CDCl$_3$) δ:
1.22-1.25 (3H, m), 1.41 (9H, s), 1.60-1.73 (5H, m), 2.09-2.24 (2H, m), 2.58-2.65 (2H, m), 2.92-2.99 (2H, m), 3.00-3.06 (2H, m), 3.92 (3H, s), 4.22-4.42 (8H, m), 6.57 (1H, d, J=9.6 Hz), 6.66-6.71 (1H, m), 6.74 (1H, s), 6.78 (1H, d, J=8.3 Hz), 7.01 (1H, s), 7.04 (1H, s), 8.10 (1H, d, J=9.6 Hz)

Example 240

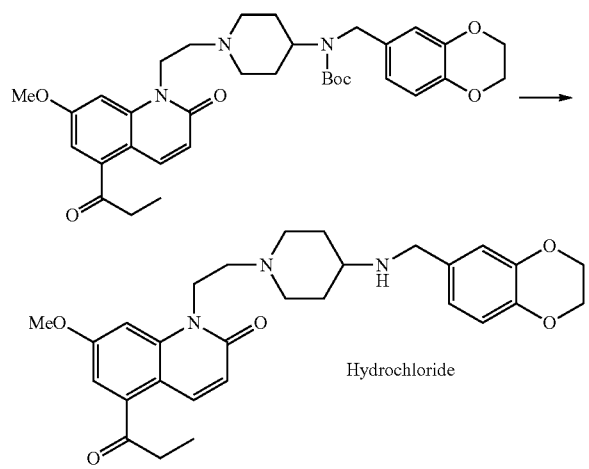

To 1 mL of an ethyl acetate solution containing 30 mg of tert-butyl (2,3-dihydro-1,4-benzodioxin-6-ylmethyl)(1-(2-(7-methoxy-2-oxo-5-propionylquinolin-1(2H)-yl)ethyl)piperidin-4-yl)carbamate, 1 mL of 4 mol/L hydrogen chloride/ethyl acetate was added, and stirred at room temperature. The resulting solid was filtered to give 18 mg of 1-(2-(4-((2,3-dihydro-1,4-benzodioxin-6-ylmethyl)amino)piperidin-1-yl)ethyl)-7-methoxy-5-propionyl-1,2-dihydro-2-oxoquinoline hydrochloride as a white solid.

$^1$H-NMR (DMSO-d$_6$) δ:
1.10 (3H, t, J=7.1 Hz), 1.96-2.07 (2H, m), 2.31-2.39 (2H, m), 3.02-3.16 (4H, m), 3.21-3.37 (3H, m), 3.81 (2H, d, J=11.5 Hz), 4.02 (3H, s), 4.05-4.11 (2H, m), 4.26 (4H, s), 4.66-4.76 (2H, m), 6.54 (1H, d, J=9.6 Hz), 6.92 (1H, d, J=8.3 Hz), 6.98-7.05 (1H, m), 7.09-7.17 (1H, m), 7.25-7.31 (1H, m), 7.34-7.38 (1H, m), 8.01 (1H, d, J=9.6 Hz), 9.25-9.43 (2H, broad), 10.65-10.92 (1H, broad)

Example 241

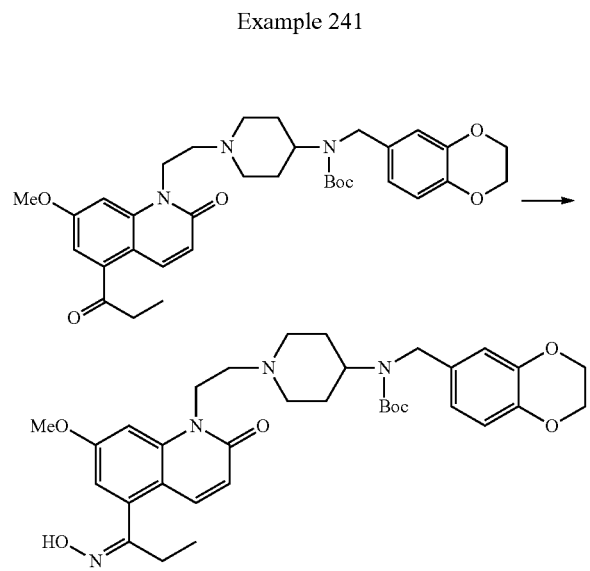

To 2 mL of a methanol solution containing 84 mg of tert-butyl (2,3-dihydro-1,4-benzodioxin-6-ylmethyl)(1-(2-(7-methoxy-2-oxo-5-propionylquinolin-1(2H)-yl)ethyl)piperidin-4-yl)carbamate, 40 mg of hydroxylammonium chloride was added, and stirred at room temperature for 9.5 hours. To the reaction mixture, aqueous saturated sodium hydrogen carbonate solution was added. The organic layer was separated, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=20:1], to give 84 mg of tert-butyl (2,3-dihydro-1,4-benzodioxin-6-ylmethyl)(1-(2-(5-(1-(hydroxyimino)propyl)-7-methoxy-2-oxoquinolin-1(2H)-yl)ethyl)piperidin-4-yl)carbamate as a colorless oil.

$^1$H-NMR (CDCl$_3$) δ:
1.03-1.12 (3H, m), 1.41 (9H, s), 1.54-1.74 (5H, m), 2.10-2.24 (2H, m), 2.49-2.84 (4H, m), 3.01-3.09 (2H, m), 3.84-3.92 (3H, m), 4.04-4.15 (1H, m), 4.22-4.42 (8H, m), 6.50-7.93 (7H, m)

Example 242

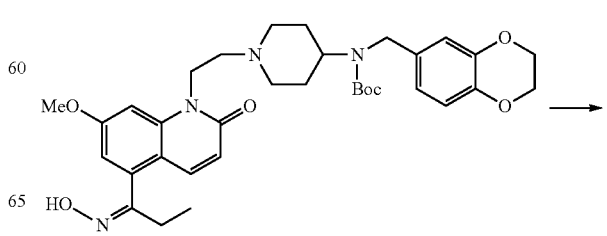

-continued

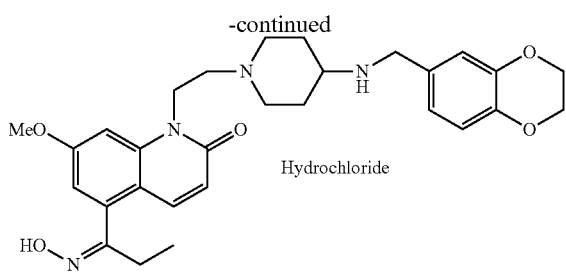

Hydrochloride

To 1 mL of an ethyl acetate solution containing 83 mg of tert-butyl (2,3-dihydro-1,4-benzodioxin-6-ylmethyl)(1-(2-(5-(1-(hydroxyimino)propyl)-7-methoxy-2-oxoquinolin-1(2H)-yl)ethyl)piperidin-4-yl)carbamate, 1 mL of 4 mol/L hydrogen chloride/ethyl acetate was added, and stirred at room temperature. The resulting solid was filtered to give 51 mg of 1-(2-(4-((2,3-dihydro-1,4-benzodioxin-6-ylmethyl)amino)piperidin-1-yl)ethyl)-7-methoxy-5-(1-(hydroxyimino)propyl)-1,2-dihydro-2-oxoquinoline hydrochloride as a green solid.

$^1$H-NMR (DMSO-$d_6$) δ:
0.89-1.03 (3H, m), 2.01-2.12 (2H, m), 2.32-2.41 (2H, m), 2.60-2.76 (2H, m), 3.06-3.16 (2H, m), 3.20-3.33 (3H, m), 3.77-3.85 (2H, m), 3.96-4.02 (3H, m), 4.05-4.11 (2H, m), 4.25 (4H, s), 4.65-4.75 (2H, m), 6.46-6.52 (1H, m), 6.74-7.92 (6H, m), 9.41-9.58 (2H, broad), 10.70-11.43 (2H, broad)

Example 243

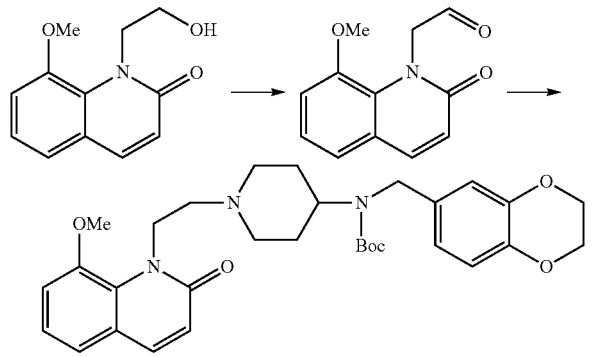

To 4 mL of a dichloromethane solution containing 0.07 mL of oxalyl chloride, 0.11 mL of dimethylsulfoxide was added dropwise under nitrogen atmosphere at −60° C., and stirred for 10 min. 10 mL of a dichloromethane solution containing 0.14 g of 1-(2-hydroxyethyl)-8-methoxyquinolin-2(1H)-one was added dropwise at the same temperature, and stirred for 12 min. After 0.36 mL of triethylamine was added at the same temperature, it was stirred at room temperature for 1.5 hours, and 20 mL of water was added. The organic layer was separated, and the aqueous layer was extracted with chloroform. The organic layer and extracts were combined, dried over anhydrous magnesium sulfate, and the solvent was removed under reduced pressure to give (8-methoxy-2-oxoquinolin-1(2H)-yl)acetaldehyde as a pale yellow solid.

To 2 mL of a dichloromethane solution containing (8-methoxy-2-oxoquinolin-1(2H)-yl)acetaldehyde, 4 mL of a dichloromethane solution containing 0.27 g of tert-butyl (2,3-dihydro-1,4-benzodioxin-6-ylmethyl)(piperidin-4-yl)carbamate and 40 μL of acetic acid were added, and stirred at room temperature for 90 min. To the reaction mixture, 0.22 g of sodium triacetoxyborohydride was added, stirred at the same temperature for 2 hours, aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; hexane:ethyl acetate=1:1], to give 0.28 g of tert-butyl 1-(2-(8-methoxy-2-oxoquinolin-1(2H)-yl)ethyl)piperidin-4-yl)(2,3-dihydro-1,4-benzodioxin-6-ylmethyl)carbamate as a yellow foam.

$^1$H-NMR (CDCl$_3$) δ:
1.42 (9H, s), 1.58-1.82 (5H, m), 2.20-2.28 (2H, m), 2.62-2.78 (2H, m), 2.99-3.12 (2H, m), 3.91 (3H, s), 4.24 (4H, s), 4.26-4.33 (2H, m), 4.64-4.75 (2H, m), 6.62-6.81 (4H, m), 7.01-7.18 (3H, m), 7.58 (1H, d, J=9.7 Hz)

Example 244

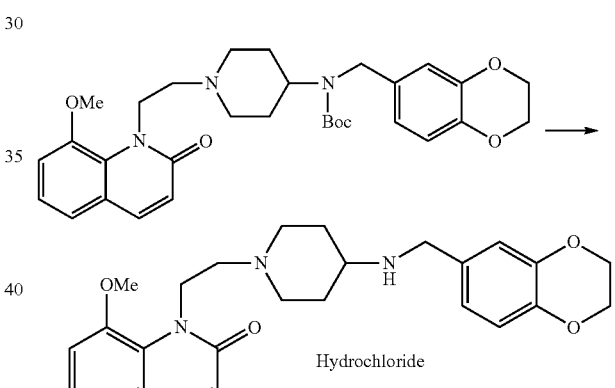

Hydrochloride

To 1 mL of an ethyl acetate solution containing 0.23 g of tert-butyl 1-(2-(8-methoxy-2-oxoquinolin-1(2H)-yl)ethyl)piperidin-4-yl)(2,3-dihydro-1,4-benzodioxin-6-ylmethyl)carbamate, 2 mL of 4 mol/L hydrogen chloride/ethyl acetate was added, and stirred at room temperature for 15 hours. The resulting solid was filtered to give 0.19 g of 1-(2-(4-((2,3-dihydro-1,4-benzodioxin-6-ylmethyl)amino)piperidin-1-yl)ethyl)-8-methoxyquinolin-2(1H)-one hydrochloride as a pale yellow solid.

$^1$H-NMR (DMSO-$d_6$) δ:
2.05-2.14 (2H, m), 2.35-2.40 (2H, m), 3.08-3.16 (2H, m), 3.23-3.30 (1H, m), 3.35-3.40 (2H, m), 3.73-3.79 (2H, m), 3.97 (3H, s), 4.05-4.08 (2H, m), 4.25 (4H, s), 4.75-4.80 (2H, m), 6.66 (1H, d, J=9.6 Hz), 6.90 (1H, d, J=8.3 Hz), 7.07 (1H, dd, J=8.3, 1.8 Hz), 7.19 (1H, d, J=1.8 Hz), 7.28 (1H, d, J=7.8 Hz), 7.32-7.36 (2H, m), 7.94 (1H, d, J=9.6 Hz), 9.59-9.74 (2H, broad), 10.31-10.79 (1H, broad)

Example 245

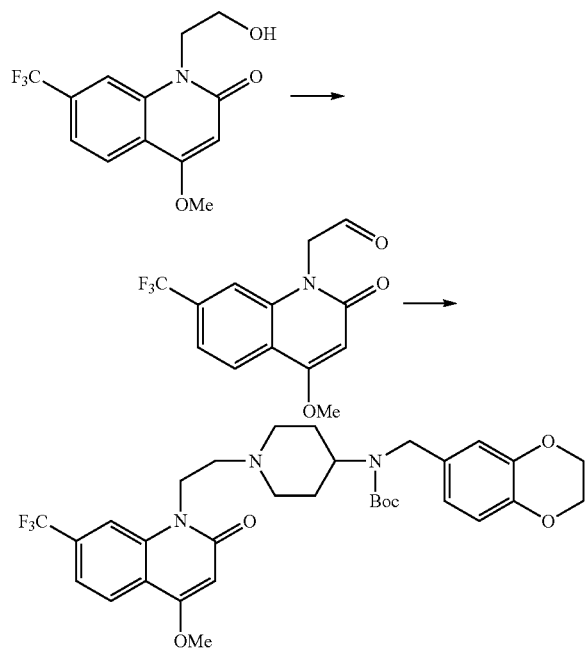

To 2 mL of a dichloromethane solution containing 30 μL of oxalyl chloride, 50 μL of dimethylsulfoxide was added dropwise under nitrogen atmosphere at −60° C., and stirred for 13 min. 6 mL of a dichloromethane solution containing 0.08 g of 1-(2-hydroxyethyl)-4-methoxy-7-trifluoromethylquinolin-2(1H)-one was added dropwise at the same temperature, and stirred for 10 min. After 0.16 mL of triethylamine was added at the same temperature, it was stirred at room temperature for 1 hour, and water was added. The organic layer was separated, and the aqueous layer was extracted with chloroform. The organic layer and extracts were combined, dried over anhydrous magnesium sulfate, and the solvent was removed under reduced pressure to give (4-methoxy-7-trifluoromethyl-2-oxoquinolin-1(2H)-yl)acetaldehyde as a pale yellow solid.

To 2 mL of a dichloromethane solution containing (4-methoxy-7-trifluoromethyl-2-oxoquinolin-1(2H)-yl)acetaldehyde, 2 mL of a dichloromethane solution containing 0.10 g of tert-butyl (2,3-dihydro-1,4-benzodioxin-6-ylmethyl) (piperidin-4-yl)carbamate and 20 μL of acetic acid were added, and stirred at room temperature for 90 min. To the reaction mixture, 0.08 g of sodium triacetoxyborohydride was added, stirred at the same temperature for 2 hours, 10 mL of aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; hexane:ethyl acetate=1:1], to give 0.14 g of tert-butyl 1-(2-(4-methoxy-2-oxo-7-trifluoromethylquinolin-1(2H)-yl)ethyl)piperidin-4-yl) (2,3-dihydro-1,4-benzodioxin-6-ylmethyl)carbamate as a yellow foam.

$^1$H-NMR (CDCl$_3$) δ:
1.43 (9H, s), 1.58-1.73 (5H, m), 2.19-2.24 (2H, m), 2.56-2.66 (2H, m), 2.94-3.08 (2H, m), 3.96 (3H, s), 4.24 (4H, s), 4.26-4.41 (4H, m), 6.07 (1H, s), 6.63-6.81 (3H, m), 7.40-7.46 (1H, m), 7.71 (1H, s), 8.07 (1H, d, J=7.9 Hz)

Example 246

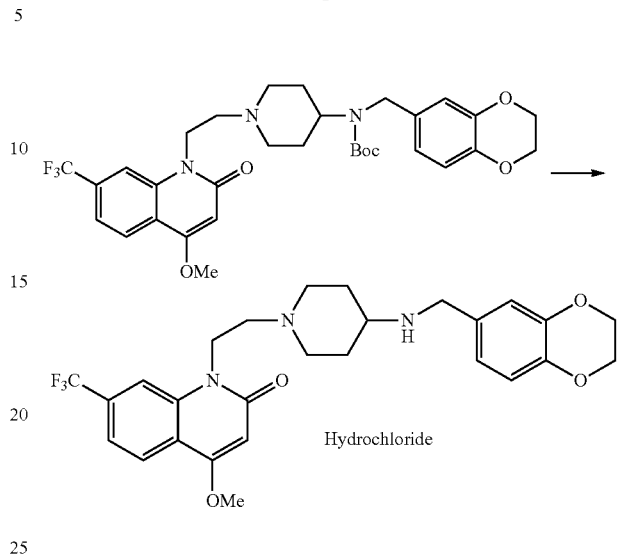

To 1 mL of an ethyl acetate solution containing 0.13 g of tert-butyl 1-(2-(4-methoxy-2-oxo-7-trifluoromethylquinolin-1(2H)-yl)ethyl)piperidin-4-yl) (2,3-dihydro-1,4-benzodioxin-6-ylmethyl)carbamate, 2 mL of 4 mol/L hydrogen chloride/ethyl acetate was added, and stirred at room temperature for 15 hours. The resulting solid was filtered to give 0.11 g of 1-(2-(4-(((2,3-dihydro-1,4-benzodioxin-6-ylmethyl)amino)piperidin-1-yl)ethyl)-4-methoxy-7-trifluoromethylquinolin-2(1H)-one hydrochloride as a pale yellow solid.

$^1$H-NMR (DMSO-d$_6$) δ:
2.02-2.11 (2H, m), 2.33-2.40 (2H, m), 3.06-3.14 (2H, m), 3.19-3.31 (3H, m), 3.77-3.82 (2H, m), 4.00 (3H, s), 4.05-4.09 (2H, m), 4.25 (4H, s), 4.69 (2H, t, J=7.3 Hz), 6.25 (1H, s), 6.91 (1H, d, J=8.3 Hz), 7.05 (1H, dd, J=8.3, 1.8 Hz), 7.17 (1H, d, J=1.8 Hz), 7.64 (1H, d, J=8.3 Hz), 8.01 (1H, s), 8.13 (1H, d, J=8.3 Hz), 9.55-9.63 (2H, m, broad), 10.73-11.03 (1H, broad)

Example 247

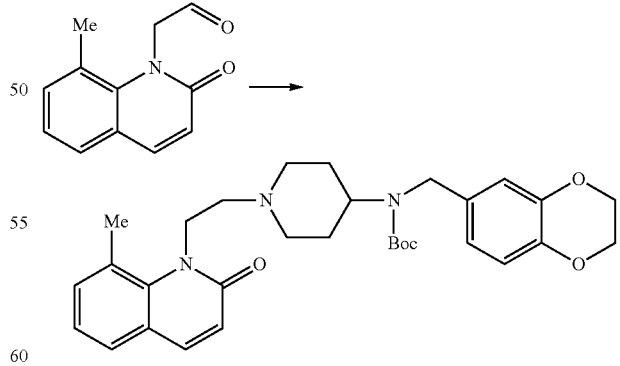

To 2 mL of a chloroform solution containing 0.24 g of tert-butyl (2,3-dihydro-1,4-benzodioxin-6-ylmethyl)(piperidin-4-yl)carbamate, 0.14 g of (8-methyl-2-oxoquinolin-1(2H)-yl)acetaldehyde, 20 μL of acetic acid and 0.22 g of sodium triacetoxyborohydride were added, and stirred at room temperature overnight. Aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; hexane: ethyl acetate=1:1], to give 0.13 g of tert-butyl (2,3-dihydro-1,4-benzodioxin-6-ylmethyl)(1-(2-(8-methyl-2-oxoquinolin-1(2H)-yl)ethyl)piperidin-4-yl)carbamate as a white foam.

$^1$H-NMR (CDCl$_3$) δ:

1.42 (9H, s), 1.62-1.75 (4H, m), 2.11-2.25 (2H, m), 2.67 (3H, s), 2.78-2.88 (2H, m), 3.01-3.13 (2H, m), 4.03-4.16 (1H, m), 4.19-4.35 (6H, m), 4.55-4.65 (2H, m), 6.64-6.69 (1H, m), 6.73 (1H, s), 6.76 (1H, d, J=8.3 Hz), 6.88 (1H, d, J=8.7 Hz), 7.24-7.29 (1H, m), 7.47 (1H, d, J=6.9 Hz), 7.55 (1H, d, J=8.7 Hz), 7.95 (1H, d, J=8.7 Hz)

Example 248

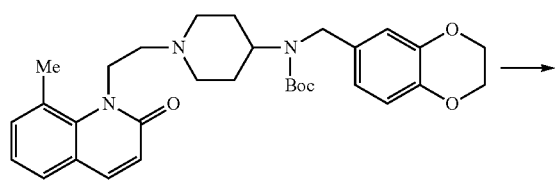

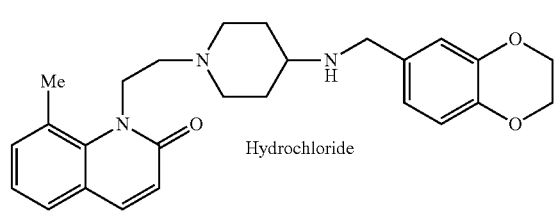

To 0.13 g of tert-butyl (2,3-dihydro-1,4-benzodioxin-6-ylmethyl)(1-(2-(8-methyl-2-oxoquinolin-1(2H)-yl)ethyl)piperidin-4-yl)carbamate, 3 mL of 1,4-dioxane and 1 mL of 4 mol/L hydrogen chloride/1,4-dioxane were added, and stirred at room temperature overnight. The resulting solid was filtered to give 0.10 g of 1-(2-(4-((2,3-dihydro-1,4-benzodioxin-6-ylmethyl)amino)piperidin-1-yl)ethyl)-8-methylquinolin-2(1H)-one hydrochloride as a white solid.

$^1$H-NMR (DMSO-d$_6$) δ:

2.07-2.16 (2H, m), 2.29-2.36 (2H, m), 2.65 (3H, s), 3.11-3.73 (7H, m), 4.01-4.07 (2H, m), 4.25 (4H, s), 4.85-4.88 (2H, m), 6.89 (1H, d, J=8.3 Hz), 7.05 (1H, d, J=8.3 Hz), 7.08 (1H, d, J=8.3 Hz), 7.17 (1H, s), 7.37 (1H, t, J=8.3 Hz), 7.58 (1H, d, J=8.3 Hz), 7.75 (1H, d, J=8.3 Hz), 8.28 (1H, d, J=8.3 Hz), 9.56-9.77 (2H, broad), 10.92-11.14 (1H, broad)

Example 249

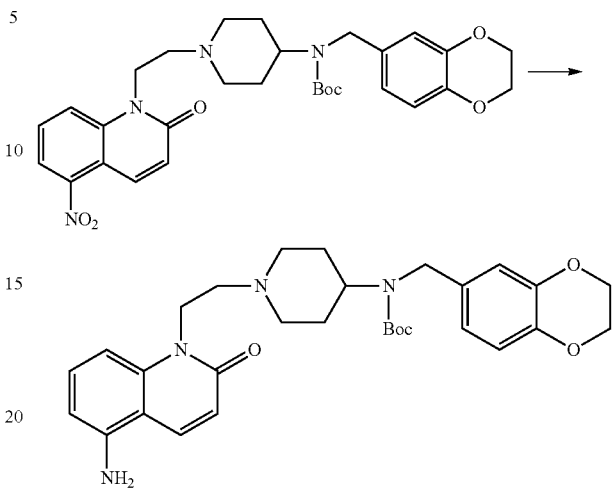

To 3 mL of a methanol solution containing 150 mg of tert-butyl (2,3-dihydro-1,4-benzodioxin-6-ylmethyl)(1-(2-(5-nitro-2-oxoquinolin-1(2H)-yl)ethyl)piperidin-4-yl)carbamate, 15 mg of 10% palladium on carbon was added under nitrogen atmosphere, then stirred under hydrogen atmosphere at room temperature for 2 hours. The insoluble material was filtered off, and the solvent was removed under reduced pressure to afford 140 mg of tert-butyl (2,3-dihydro-1,4-benzodioxin-6-ylmethyl)(1-(2-(5-amino-2-oxoquinolin-1(2H)-yl)ethyl)piperidin-4-yl)carbamate as a yellow oil.

$^1$H-NMR (CDCl$_3$) δ:

1.42 (9H, s), 1.65-1.89 (4H, m), 2.05-2.37 (2H, m), 2.51-2.82 (2H, m), 2.90-3.23 (2H, m), 4.08-4.15 (2H, m), 4.24 (4H, s), 4.29-4.46 (3H, m), 6.54 (1H, d, J=7.8 Hz), 6.59 (1H, d, J=9.6 Hz), 6.68-6.91 (4H, m), 7.32-7.40 (1H, m), 7.74 (1H, d, J=9.6 Hz)

Example 250

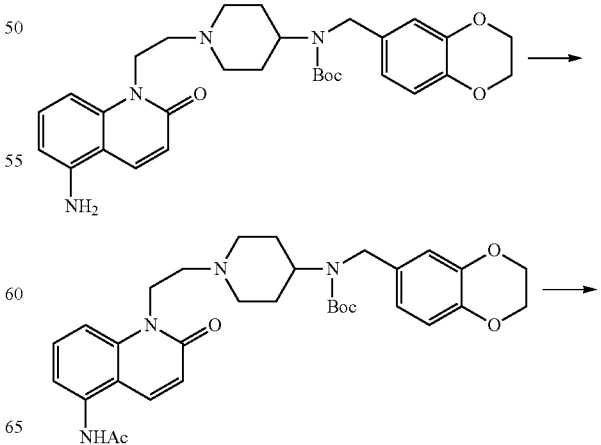

441

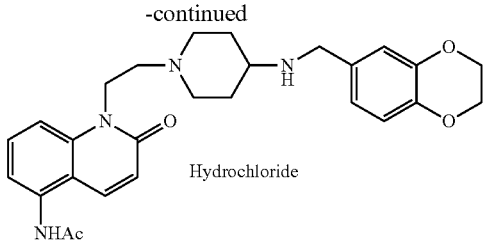

Hydrochloride

To 2 mL of a chloroform solution containing 60 mg of tert-butyl (2,3-dihydro-1,4-benzodioxin-6-ylmethyl)(1-(2-(5-amino-2-oxoquinolin-1(2H)-yl)ethyl)piperidin-4-yl)carbamate, 14 mg of triethylamine and 11 mg of acetyl chloride were added, and stirred at room temperature for 2 hours. Aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure to give 60 mg of tert-butyl (2,3-dihydro-1,4-benzodioxin-6-ylmethyl)(1-(2-(5-acetamino-2-oxoquinolin-1(2H)-yl)ethyl)piperidin-4-yl)carbamate as a yellow foam.

To 60 mg of tert-butyl (2,3-dihydro-1,4-benzodioxin-6-ylmethyl)(1-(2-(5-acetamino-2-oxoquinolin-1(2H)-yl)ethyl)piperidin-4-yl)carbamate, 3 mL of 1,4-dioxane and 1 mL of 4 mol/L hydrogen chloride/1,4-dioxane were added, and stirred at room temperature overnight. The solvent was removed under reduced pressure and the resulting solid was recrystallized in methanol-ethyl acetate to give 18 mg of 1-(2-(4-((2,3-dihydro-1,4-benzodioxin-6-ylmethyl)amino)piperidin-1-yl)ethyl)-5-acetaminoquinolin-2(1H)-one hydrochloride as a pale yellow solid.

$^1$H-NMR (DMSO-$d_6$) δ:
2.01-2.09 (2H, m), 2.14 (3H, s), 2.30-2.39 (2H, m), 3.02-3.17 (2H, m), 3.20-3.35 (3H, m), 3.76-3.85 (2H, m), 4.06-4.12 (2H, m), 4.26 (4H, s), 4.58-4.72 (2H, m), 6.66 (1H, d, J=9.6 Hz), 6.91 (1H, d, J=8.3 Hz), 7.04 (1H, d, J=8.3 Hz), 7.15 (1H, s), 7.37-7.43 (1H, m), 7.58-7.66 (2H, m), 8.06 (1H, d, J=9.6 Hz), 9.38-9.60 (2H, broad), 10.05 (1H, s), 10.62-10.90 (1H, broad)

Example 251

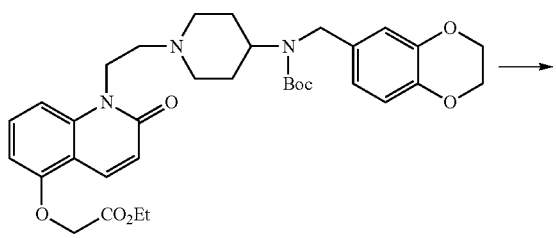

442

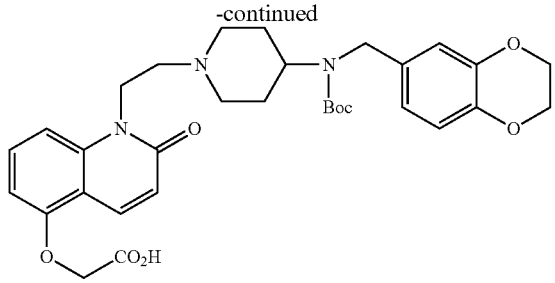

To a mixed solution of 5 mL methanol and 0.5 mL water containing 126 mg of ethyl (1-(2-(4-(((tert-butoxycarbonyl)(2,3-dihydro-1,4-benzodioxin-6-ylmethyl)amino)piperidin-1-yl)ethyl)-2-oxo-1,2-dihydroquinolin-5-yloxy)acetate, 0.2 mL of 5 mol/L aqueous sodium hydroxide solution was added and allowed to stand at room temperature for 2.5 hours. To the reaction mixture, water was added, and the solvent was removed under reduced pressure. After the residue thus obtained was acidified by adding 1 mol/L hydrochloric acid, it was extracted with chloroform. The extracts were washed with aqueous saturated sodium chloride solution, dried over anhydrous magnesium sulfate, and the solvent was removed under reduced pressure to give 90 mg of (1-(2-(4-((tert-butoxycarbonyl)(2,3-dihydro-1,4-benzodioxin-6-ylmethyl)amino)piperidin-1-yl)ethyl)-2-oxo-1,2-dihydroquinolin-5-yloxy)acetic acid as a white foam.

$^1$H-NMR (CDCl$_3$) δ:
1.44 (9H, s), 1.78-1.90 (2H, m), 2.34-2.52 (2H, m), 2.76-2.83 (2H, m), 3.09-3.19 (3H, m), 3.68-3.76 (2H, m), 4.25 (4H, s), 4.30-4.39 (2H, m), 4.78 (2H, s), 4.79-4.83 (2H, m), 6.50-6.57 (2H, m), 6.73-6.77 (1H, m), 6.77-6.83 (2H, m), 8.02 (2H, s), 8.23 (1H, d, J=10.1 Hz)

Example 252

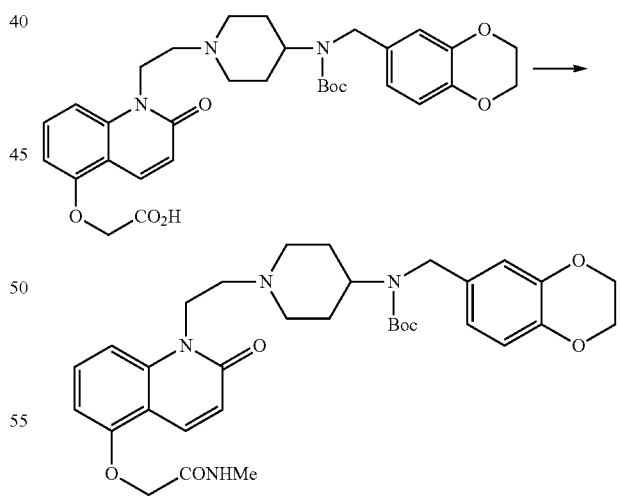

To 5 mL of an N,N-dimethylformamide solution containing 88 mg of (1-(2-(4-(((tert-butoxycarbonyl)(2,3-dihydro-1,4-benzodioxin-6-ylmethyl)amino)piperidin-1-yl)ethyl)-2-oxo-1,2-dihydroquinolin-5-yloxy)acetic acid and 41 mg of methylamine hydrochloride, 183 mg of (benzotriazol-1-yloxy)tripyrrolidinophosphonium hexafluorophosphate and 0.11 mL of N,N-diisopropylethylamine were added, and stirred at room temperature overnight. The reaction mixture was poured into water, and extracted with a mixture of ethyl acetate: toluene=5:1. The organic layer was washed sequentially with water and aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform: methanol=10:1], to give 89 mg of tert-butyl (2,3-dihydro-1,4-benzodioxin-6-ylmethyl)(1-(2-(5-((methylamino)carbonylmethyloxy)-2-oxoquinolin-1(2H)-yl)ethyl) piperidin-4-yl)carbamate as a pale yellow foam.

$^1$H-NMR (CDCl$_3$) δ:

1.46 (9H, s), 1.86-1.91 (4H, m), 2.27-2.33 (2H, m), 2.92 (3H, d, J=5.0 Hz), 3.36-3.41 (3H, m), 3.75-3.80 (2H, m), 4.24 (4H, s), 4.30-4.33 (2H, m), 4.46-4.50 (2H, m), 4.66-4.71 (2H, m), 6.63 (1H, d, J=8.3 Hz), 6.67-6.71 (2H, m), 6.73-6.75 (1H, m), 6.79 (1H, d, J=8.3 Hz), 7.38-7.45 (1H, m), 7.54 (1H, t, J=8.5 Hz), 8.21 (1H, d, J=9.6 Hz)

piperidin-1-yl)ethyl)-2-oxo-1,2-dihydroquinolin-5-yloxy)-N-methylacetamide, 0.2 mL of 4 mol/L hydrogen chloride/ethyl acetate was added, and stirred at room temperature for 10 min. The resulting solid was filtered to give 40 mg of (1-(2-(4-((2,3-dihydro-1,4-benzodioxin-6-ylmethyl)amino) piperidin-1-yl)ethyl)-2-oxo-1,2-dihydroquinolin-5-yloxy)-N-methylacetamide hydrochloride as a pale brown solid.

$^1$H-NMR (DMSO-d$_6$) δ:

2.00-2.07 (2H, m), 2.31-2.37 (2H, m), 2.70 (3H, d, J=4.6 Hz), 3.07-3.15 (2H, m), 3.26-3.30 (3H, m), 3.75-3.82 (2H, m), 4.05-4.10 (2H, m), 4.26 (4H, s), 4.62-4.66 (4H, m), 6.63 (1H, d, J=10.1 Hz), 6.85 (1H, d, J=7.8 Hz), 6.92 (1H, d, J=8.3 Hz), 7.00-7.05 (1H, m), 7.14 (1H, s), 7.58 (1H, t, J=8.5 Hz), 8.10-8.14 (1H, m), 8.44 (1H, d, J=9.6 Hz), 9.35-9.43 (2H, broad), 10.62-10.67 (1H, broad)

Example 253

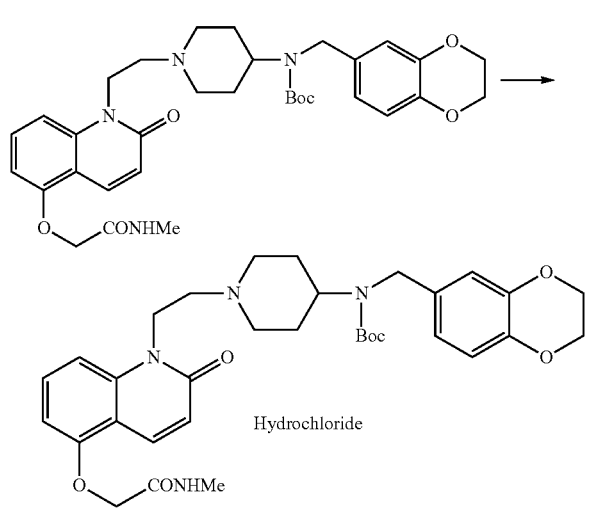

Example 254

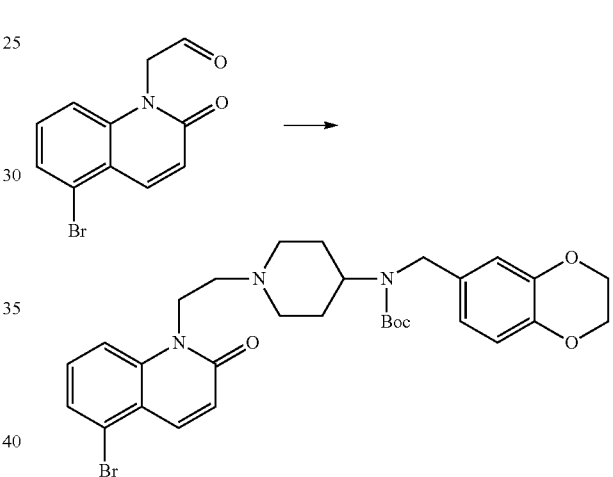

To 2 mL of a chloroform solution containing 87 mg of tert-butyl (2,3-dihydro-1,4-benzodioxin-6-ylmethyl)(1-(2-(5-((methylamino)carbonylmethyloxy)-2-oxoquinolin-1 (2H)-yl)ethyl)piperidin-4-yl)carbamate, 2 mL of trifluoroacetic acid was added and stirred at room temperature for 1 hour. After solvents of the reaction mixture were removed under reduced pressure and the residue was alkalized by aqueous saturated sodium hydrogen carbonate solution, it was extracted with ethyl acetate. The organic layer was washed sequentially with water and aqueous saturated sodium chloride solution, dried over anhydrous magnesium sulfate, and the solvent was removed under reduced pressure to give 49 mg of (1-(2-(4-((2,3-dihydro-1,4-benzodioxin-6-ylmethyl)amino)piperidin-1-yl)ethyl)-2-oxo-1,2-dihydroquinolin-5-yloxy)-N-methylacetamide as a pale yellow foam.

To 10 mL of an ethyl acetate solution containing 46 mg of (1-(2-(4-((2,3-dihydro-1,4-benzodioxin-6-ylmethyl)amino)

To 25 mL of a chloroform solution containing 520 mg of (5-bromo-2-oxoquinolin-1(2H)-yl)acetaldehyde and 705 mg of tert-butyl (2,3-dihydro-1,4-benzodioxin-6-ylmethyl)(piperidin-4-yl)carbamate, 112 μL of acetic acid was added, and stirred at room temperature for 1 hour. To the reaction mixture, 629 mg of sodium triacetoxyborohydride was added, and stirred for 1.5 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform], to give 890 mg of tert-butyl (2,3-dihydro-1,4-benzodioxin-6-ylmethyl)(1-(2-(5-bromo-2-oxoquinolin-1(2H)-yl)ethyl)piperidin-4-yl)carbamate as a pale yellow foam.

$^1$H-NMR (CDCl$_3$) δ:

1.41 (9H, s), 1.63-1.73 (4H, m), 2.13-2.22 (2H, m), 2.57-2.62 (3H, m), 2.99-3.05 (2H, m), 4.25 (4H, s), 4.26-4.30 (2H, m), 4.36-4.41 (2H, m), 6.72-6.75 (1H, m), 6.75-6.79 (2H, m), 7.26 (1H, s), 7.35-7.38 (2H, m), 7.46-7.49 (1H, m), 8.12 (1H, d, J=9.6 Hz)

Example 255

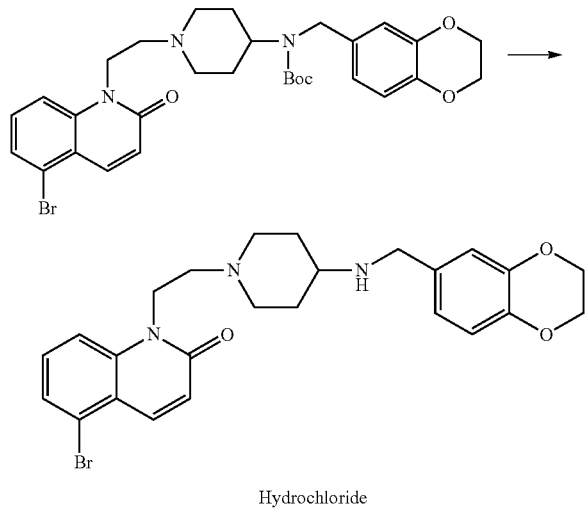

Hydrochloride

To 2 mL of a chloroform solution containing 244 mg of tert-butyl (2,3-dihydro-1,4-benzodioxin-6-ylmethyl)(1-(2-(5-bromo-2-oxoquinolin-1(2H)-yl)ethyl)piperidin-4-yl)carbamate, 2 mL of trifluoroacetic acid was added and stirred at room temperature for 3 hours. After solvents of the reaction mixture were removed under reduced pressure and the residue was alkalized by aqueous saturated sodium hydrogen carbonate solution, it was extracted with ethyl acetate. The organic layer was washed sequentially with water and aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform], to give 143 mg of (1-(2-(4-((2,3-dihydro-1,4-benzodioxin-6-ylmethyl)amino)piperidin-1-yl)ethyl)-5-bromoquinolin-2(1H)-one as a colorless oil.

To 20 mL of an ethyl acetate solution containing 122 mg of (1-(2-(4-((2,3-dihydro-1,4-benzodioxin-6-ylmethyl)amino)piperidin-1-yl)ethyl)-5-bromoquinolin-2(1H)-one, 0.2 mL of 4 mol/L hydrogen chloride/ethyl acetate was added, and stirred at room temperature for 10 min. The resulting solid was filtered to give 98 mg of (1-(2-(4-((2,3-dihydro-1,4-benzodioxin-6-ylmethyl)amino)piperidin-1-yl)ethyl)-5-bromoquinolin-2(1H)-one hydrochloride as a white solid.

Example 256

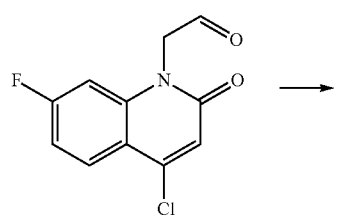

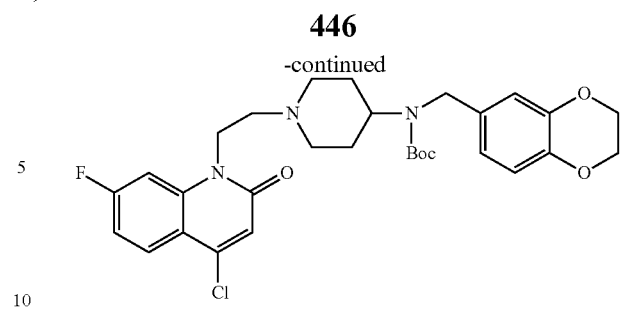

-continued

To 20 mL of a chloroform solution containing 0.71 g of (4-chloro-7-fluoro-2-oxoquinolin-1(2H)-yl)acetaldehyde, 1.03 g of tert-butyl (2,3-dihydro-1,4-benzodioxin-6-ylmethyl)(piperidin-4-yl)carbamate and 0.18 g of acetic acid were added, and stirred at room temperature for 1 hour. To the reaction mixture, 0.99 g of sodium triacetoxyborohydride was added, and stirred for 1 hour. Aqueous saturated sodium hydrogen carbonate solution was added, and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; ethyl acetate:hexane=4:1], to give 0.76 g of tert-butyl (2,3-dihydro-1,4-benzodioxin-6-ylmethyl)(1-(2-(4-chloro-7-fluoro-2-oxoquinolin-1(2H)-yl)ethyl)piperidin-4-yl)carbamate as a yellow oil.

$^1$H-NMR (CDCl$_3$) δ:
1.41 (9H, s), 1.59-1.73 (5H, m), 2.10-2.23 (2H, m), 2.58-2.63 (2H, m), 2.97-3.04 (2H, m), 4.23-4.35 (8H, m), 6.65-6.82 (4H, m), 7.00-7.06 (1H, m), 7.14-7.21 (1H, m), 7.97-8.03 (1H, m)

Example 257

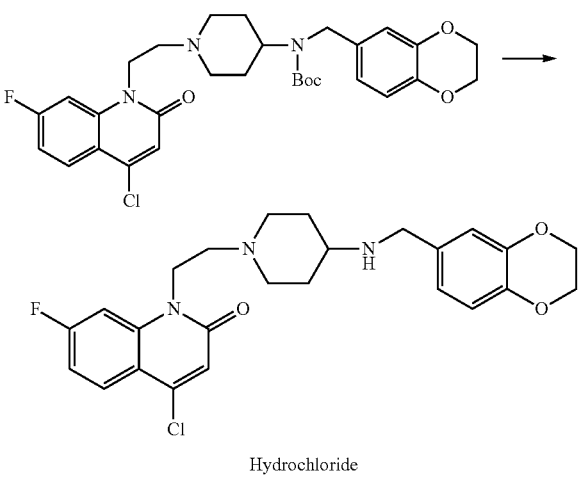

Hydrochloride

To 5 mL of an ethyl acetate solution containing 0.76 g of tert-butyl (2,3-dihydro-1,4-benzodioxin-6-ylmethyl)(1-(2-(4-chloro-7-fluoro-2-oxoquinolin-1(2H)-yl)ethyl)piperidin-4-yl)carbamate, 5 mL of 4 mol/L hydrogen chloride/ethyl acetate was added, and stirred at room temperature. The resulting solid was filtered to give 572 mg of (1-(2-(4-((2,3-dihydro-1,4-benzodioxin-6-ylmethyl)amino)piperidin-1-yl)ethyl)-4-chloro-7-fluoroquinolin-2(1H)-one hydrochloride as a brown solid.

¹H-NMR (DMSO-d₆, D₂O) δ:
1.79-1.94 (2H, m), 2.29-2.42 (2H, m), 3.03-3.19 (2H, m), 3.32-3.46 (3H, m), 3.75-3.90 (2H, m), 4.07-4.10 (2H, m), 4.26 (4H, s), 4.55-4.65 (2H, m), 6.94-6.97 (1H, m), 6.97-7.00 (2H, m), 7.06 (1H, d, J=2.3 Hz), 7.33-7.38 (1H, m), 7.61 (1H, dd, J=11.5, 2.3 Hz), 8.15 (1H, dd, J=9.2, 6.0 Hz)

Example 258

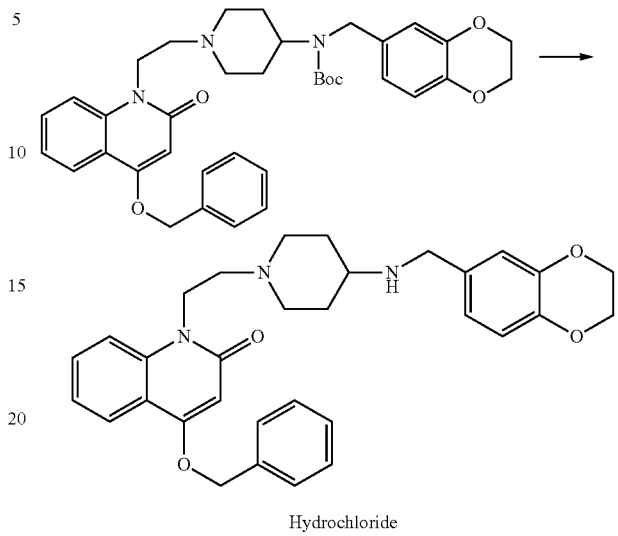

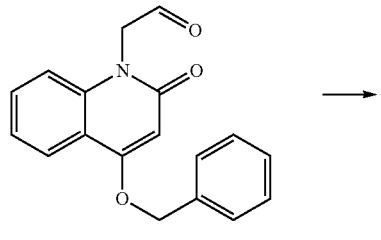

To 30 mL of a dichloromethane solution containing 1.20 g of (4-benzyloxy-2-oxoquinolin-1(2H)-yl)acetaldehyde, 40 mL of a dichloromethane solution containing 1.71 g of tert-butyl (2,3-dihydro-1,4-benzodioxin-6-ylmethyl)(piperidin-4-yl)carbamate and 0.25 g of acetic acid were added, and stirred at room temperature for 90 min. To the reaction mixture, 1.37 g of sodium triacetoxyborohydride was added, and stirred at the same temperature for 2.5 hours. Aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; hexane:ethyl acetate=1:1], to give 2.10 g of tert-butyl (1-(2-(4-benzyloxy-2-oxoquinolin-1(2H)-yl)ethyl)piperidin-4-yl)(2,3-dihydro-1,4-benzodioxin-6-ylmethyl)carbamate as a white solid.

¹H-NMR (CDCl₃) δ:
1.41 (9H, s), 1.56-1.74 (5H, m), 2.12-2.22 (2H, m), 2.57-2.64 (2H, m), 3.02-3.09 (2H, m), 4.24 (4H, s), 4.26-4.42 (4H, m), 5.16 (2H, s), 6.09 (1H, s), 6.67-6.72 (1H, m), 6.74 (1H, s), 6.78 (1H, d, J=8.3 Hz), 7.20 (1H, t, J=7.6 Hz), 7.34-7.48 (6H, m), 7.56 (1H, t, J=7.6 Hz), 8.04 (1H, dd, J=8.3, 1.4 Hz)

Example 259

To a mixed solution of 1 mL ethyl acetate and 3 mL chloroform containing 0.20 g of tert-butyl (1-(2-(4-benzyloxy-2-oxoquinolin-1(2H)-yl)ethyl)piperidin-4-yl) (2,3-dihydro-1,4-benzodioxin-6-ylmethyl)carbamate, 2 mL of 4 mol/L hydrogen chloride/ethyl acetate was added, and stirred at room temperature for 24 hours, thereafter the resulting solid was filtered to give 0.15 g of 4-benzyloxy-1-(2-(4-((2,3-dihydro-1,4-benzodioxin-6-ylmethyl)amino)piperidin-1-yl)ethyl)quinolin-2(1H)-one hydrochloride as a white solid.

¹H-NMR (DMSO-d₆) δ:
2.03-2.13 (2H, m), 2.33-2.40 (2H, m), 3.06-3.15 (2H, m), 3.19-3.28 (3H, m), 3.75-3.81 (2H, m), 4.04-4.08 (2H, m), 4.25 (4H, s), 4.61-4.66 (2H, m), 5.32 (2H, s), 6.21 (1H, s), 6.90 (1H, d, J=8.3 Hz), 7.06 (1H, dd, J=8.3, 2.3 Hz), 7.18 (1H, d, J=2.3 Hz), 7.33 (1H, t, J=7.6 Hz), 7.37-7.41 (1H, m), 7.45 (2H, t, J=7.3 Hz), 7.51-7.55 (2H, m), 7.66-7.71 (1H, m), 7.83 (1H, d, J=8.7 Hz), 7.98 (1H, dd, J=7.8, 1.4 Hz), 9.55-9.76 (2H, broad), 10.86-11.28 (1H, broad)

Example 260

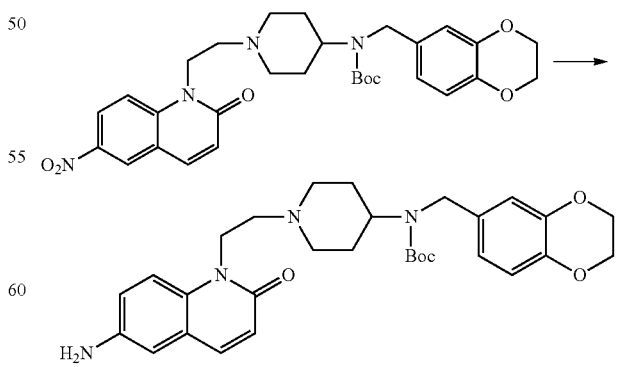

To 4 mL of a methanol solution containing 200 mg of tert-butyl (2,3-dihydro-1,4-benzodioxin-6-ylmethyl)(1-(2-(6-nitro-2-oxoquinolin-1(2H)-yl)ethyl)piperidin-4-yl)carbamate, 20 mg of 10% palladium on carbon was added under nitrogen atmosphere, then stirred under hydrogen atmosphere at room temperature for 2 hours. The insoluble material was filtered off, and the solvent was removed under reduced pressure to afford 180 mg of tert-butyl (2,3-dihydro-1,4-benzodioxin-6-ylmethyl)(1-(2-(6-amino-2-oxoquinolin-1(2H)-yl)ethyl)piperidin-4-yl)carbamate as a yellow foam.

$^1$H-NMR (CDCl$_3$) δ:

1.42 (9H, s), 1.61-1.75 (4H, m), 2.07-2.29 (2H, m), 2.55-2.68 (2H, m), 2.99-3.14 (2H, m), 3.64-3.75 (2H, m), 4.22-4.40 (7H, m), 6.63 (1H, d, J=9.2 Hz), 6.69-6.73 (1H, m), 6.75 (1H, s), 6.78 (1H, d, J=8.3 Hz), 6.81 (1H, d, J=2.8 Hz), 6.92-7.00 (1H, m), 7.19-7.25 (1H, m), 7.51 (1H, d, J=9.2 Hz)

Example 261

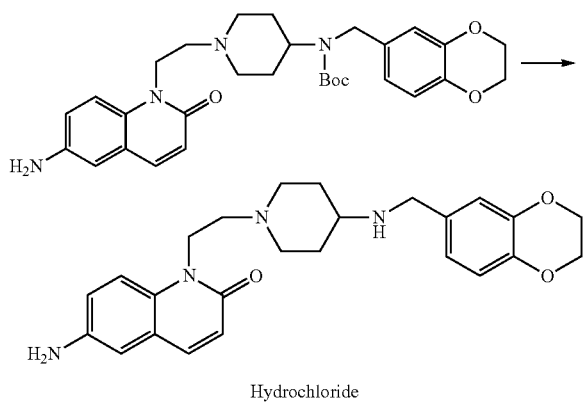

Hydrochloride

To 60 mg of tert-butyl (2,3-dihydro-1,4-benzodioxin-6-ylmethyl) (1-(2-(6-amino-2-oxoquinolin-1(2H)-yl)ethyl)piperidin-4-yl)carbamate, 3 mL of 1,4-dioxane and 1 mL of 4 mol/L hydrogen chloride/1,4-dioxane were added, and stirred at room temperature overnight. The solvent was removed under reduced pressure, and the resulting solid was recrystallized in methanol-ethyl acetate to give 40 mg of 1-(2-(4-((2,3-dihydro-1,4-benzodioxin-6-ylmethyl)amino)piperidin-1-yl)ethyl)-6-aminoquinolin-2(1H)-one hydrochloride as a brown solid.

$^1$H-NMR (DMSO-d$_6$) δ:

2.02-2.13 (2H, m), 2.32-2.40 (2H, m), 3.08-3.31 (4H, m), 3.47-3.81 (3H, m), 4.03-4.14 (2H, m), 4.25 (4H, s), 4.60-4.69 (2H, m), 6.66-6.72 (1H, m), 6.91 (1H, d, J=8.3 Hz), 7.04 (1H, d, J=8.3 Hz), 7.16 (1H, s), 7.43-7.65 (2H, m), 7.84-8.04 (2H, m), 9.42-9.64 (2H, broad), 10.90-11.07 (1H, broad)

Example 262

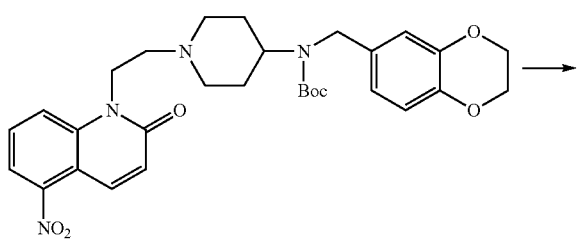

-continued

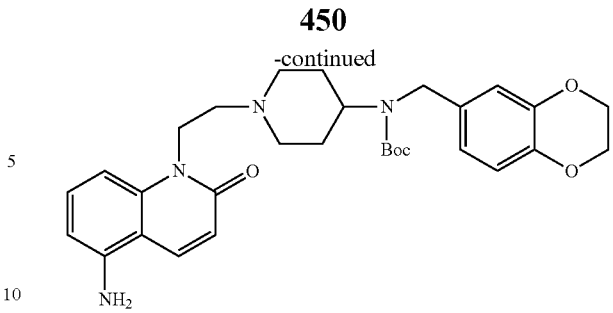

To 3 mL of a methanol solution containing 150 mg of tert-butyl (2,3-dihydro-1,4-benzodioxin-6-ylmethyl)(1-(2-(5-nitro-2-oxoquinolin-1(2H)-yl)ethyl)piperidin-4-yl)carbamate, 15 mg of 10% palladium on carbon was added under nitrogen atmosphere, then stirred under hydrogen atmosphere at room temperature for 2 hours. The insoluble material was filtered off, and the solvent was removed under reduced pressure to afford 140 mg of tert-butyl (2,3-dihydro-1,4-benzodioxin-6-ylmethyl)(1-(2-(5-amino-2-oxoquinolin-1(2H)-yl)ethyl)piperidin-4-yl)carbamate as a yellow oil.

$^1$H-NMR (CDCl$_3$) δ:

1.42 (9H, s), 1.65-1.89 (4H, m), 2.05-2.37 (2H, m), 2.51-2.82 (2H, m), 2.90-3.23 (2H, m), 4.08-4.15 (2H, m), 4.24 (4H, s), 4.29-4.46 (3H, m), 6.54 (1H, d, J=7.8 Hz), 6.59 (1H, d, J=9.6 Hz), 6.68-6.91 (4H, m), 7.32-7.40 (1H, m), 7.74 (1H, d, J=9.6 Hz)

Example 263

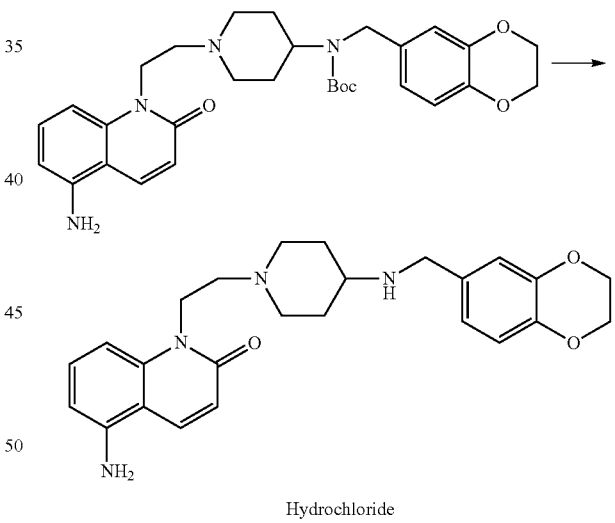

Hydrochloride

To 80 mg of tert-butyl (2,3-dihydro-1,4-benzodioxin-6-ylmethyl)(1-(2-(5-amino-2-oxoquinolin-1(2H)-yl)ethyl)piperidin-4-yl)carbamate, 3 mL of 1,4-dioxane and 1 mL of 4.0 mol/L hydrogen chloride/1,4-dioxane were added, and stirred at room temperature overnight. The solvent was removed under reduced pressure, and the resulting solid was recrystallized in methanol-ethyl acetate to give 45 mg of 1-(2-(4-((2,3-dihydro-1,4-benzodioxin-6-ylmethyl)amino)piperidin-1-yl)ethyl)-5-aminoquinolin-2(1H)-one hydrochloride as a brown solid.

$^1$H-NMR (DMSO-d$_6$) δ:

2.01-2.21 (2H, m), 2.30-2.41 (2H, m), 3.05-3.15 (2H, m), 3.19-3.33 (3H, m), 3.73-3.82 (2H, m), 4.04-4.11 (2H, m), 4.24 (4H, s), 4.55-4.64 (2H, m), 6.42-6.48 (1H, m), 6.53-6.62 (1H, m), 6.84-6.95 (2H, m), 7.04 (1H, d, J=8.7 Hz), 7.14-7.20 (1H, m), 7.26-7.33 (1H, m), 8.16 (1H, d, J=9.6 Hz), 9.41-9.67 (2H, broad), 10.57-10.87 (1H, broad)

Example 264

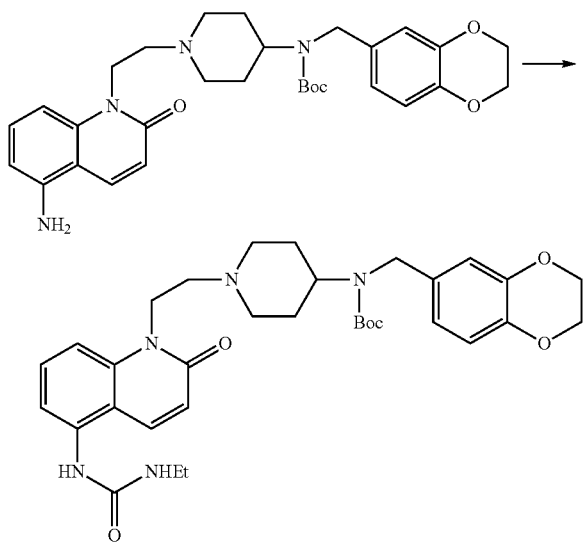

To 2 mL of a chloroform solution containing 80 mg of tert-butyl (2,3-dihydro-1,4-benzodioxin-6-ylmethyl)(1-(2-(5-amino-2-oxoquinolin-1(2H)-yl)ethyl)piperidin-4-yl)carbamate, 45 mg of triethylamine and 31 mg of ethyl isocyanate were added, and stirred at room temperature for 3 days. The reaction mixture was purified by silica gel column chromatography [Silica Gel; Fuji Silysia Chemical Ltd., Chromatorex-NH, eluent; ethyl acetate: methanol=10:1], to give 60 mg of tert-butyl (2,3-dihydro-1,4-benzodioxin-6-ylmethyl)(1-(2-(5-(3-ethylureido)-2-oxoquinolin-1(2H)-yl)ethyl)piperidin-4-yl)carbamate as a yellow oil.

$^1$H-NMR (CDCl$_3$) δ:
1.12 (3H, t, J=7.1 Hz), 1.42 (9H, s), 1.64-1.77 (4H, m), 2.11-2.21 (2H, m), 2.56-2.67 (2H, m), 3.01-3.09 (2H, m), 3.25-3.31 (2H, m), 4.00-4.10 (1H, m), 4.21-4.31 (6H, m), 4.35-4.42 (2H, m), 4.77 (1H, s), 6.52-6.61 (1H, m), 6.63-6.70 (2H, m), 6.73 (1H, s), 6.78 (1H, d, J=8.3 Hz), 7.26-7.29 (2H, m), 7.49-7.53 (1H, m), 7.91 (1H, d, J=10.1 Hz)

Example 265

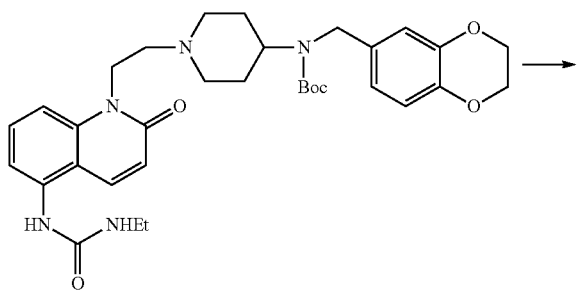

-continued

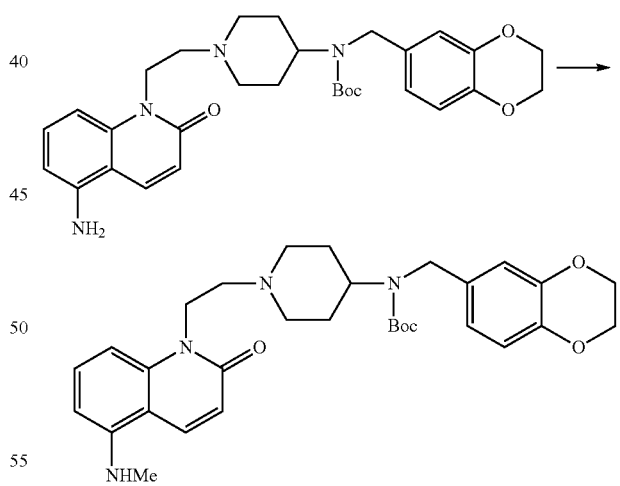

Hydrochloride

To 55 mg of tert-butyl (2,3-dihydro-1,4-benzodioxin-6-ylmethyl)(1-(2-(5-(3-ethylureido)-2-oxoquinolin-1(2H)-yl)ethyl)piperidin-4-yl)carbamate, 3 mL of 1,4-dioxane and 1 mL of 4 mol/L hydrogen chloride/1,4-dioxane were added, and stirred at room temperature for 3 hours. The resulting solid was filtered to give 26 mg of 1-ethyl-3-(1-(2-(4-((2,3-dihydro-1,4-benzodioxin-6-ylmethyl)amino)piperidin-1-yl)ethyl)quinolin-2(1H)-on-5-yl)urea hydrochloride as a yellow solid.

$^1$H-NMR (DMSO-d$_6$) δ:
1.08 (3H, t, J=7.3 Hz), 2.00-2.21 (2H, m), 2.31-2.40 (2H, m), 3.08-3.17 (4H, m), 3.19-3.38 (3H, m), 3.76-3.83 (2H, m), 4.04-4.11 (2H, m), 4.25 (4H, s), 4.60-4.90 (3H, m), 6.62 (1H, d, J=10.1 Hz), 6.91 (1H, d, J=8.3 Hz), 7.04 (1H, d, J=8.3 Hz), 7.16 (1H, s), 7.40 (1H, d, J=7.8 Hz), 7.52 (1H, t, J=8.3 Hz), 7.77 (1H, d, J=7.8 Hz), 8.29 (1H, d, J=10.1 Hz), 8.92 (1H, s), 9.42-9.63 (1H, broad), 10.64-11.06 (1H, broad)

Example 266

To 1.5 mL of a methanol solution containing 280 mg of tert-butyl (2,3-dihydro-1,4-benzodioxin-6-ylmethyl)(1-(2-(5-amino-2-oxoquinolin-1(2H)-yl)ethyl)piperidin-4-yl)carbamate, 0.5 mL of water, 83 mg of sodium carbonate and 99 mg of dimethyl sulfate were added, and stirred at room temperature for 3 days. The insoluble material was filtered off, and the solvent was removed under reduced pressure, and purified by silica gel column chromatography [Silica Gel; Fuji Silysia Chemical Ltd., Chromatorex-NH, eluent; ethyl acetate: methanol=10:1], to give 65 mg of tert-butyl (2,3- dihydro-1,4-benzodioxin-6-ylmethyl)(1-(2-(5-(N-methylamino)-2-oxoquinolin-1(2H)-yl)ethyl)piperidin-4-yl)carbamate as a yellow oil.

¹H-NMR (CDCl₃) δ:
1.49 (9H, s), 1.69-1.80 (4H, m), 2.67-2.85 (2H, m), 3.29 (3H, s), 3.51-3.70 (3H, m), 3.80-3.92 (2H, m), 4.25 (4H, s), 4.30-4.37 (2H, m), 4.68-4.75 (2H, m), 6.47 (1H, d, J=9.6 Hz), 6.56 (1H, d, J=8.0 Hz), 6.74-6.84 (3H, m), 7.00 (1H, d, J=8.0 Hz), 7.40 (1H, t, J=8.0 Hz), 7.81 (1H, d, J=9.6 Hz)

Example 267

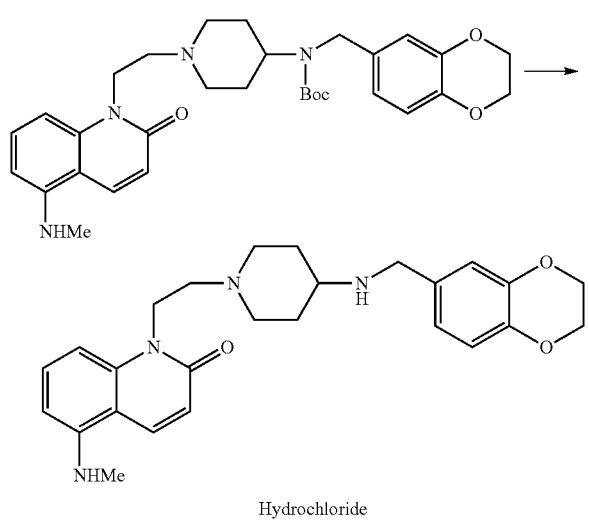

Hydrochloride

To 60 mg of tert-butyl (2,3-dihydro-1,4-benzodioxin-6-ylmethyl)(1-(2-(5-(N-methylamino)-2-oxoquinolin-1(2H)-yl)ethyl)piperidin-4-yl)carbamate, 3 mL of 1,4-dioxane and 1 mL of 4 mol/L hydrogen chloride/1,4-dioxane were added, and stirred at room temperature for 3 hours. The resulting solid was filtered to give 30 mg of 1-(2-(4-((2,3-dihydro-1,4-benzodioxin-6-ylmethyl)amino)piperidin-1-yl)ethyl)-5-(N-methylamino)quinolin-2(1H)-one hydrochloride as a yellow solid.

¹H-NMR (DMSO-d₆) δ:
2.24-2.43 (4H, m), 3.24-3.36 (5H, m), 3.51-3.61 (3H, m), 3.74-3.84 (2H, m), 4.07-4.12 (2H, m), 4.26 (4H, s), 4.61-4.69 (2H, m), 6.46 (1H, d, J=9.6 Hz), 6.55 (1H, d, J=8.3 Hz), 6.72 (1H, d, J=8.3 Hz), 6.92 (1H, d, J=8.3 Hz), 7.03-7.08 (1H, m), 7.17 (1H, s), 7.31 (1H, t, J=8.3 Hz), 8.19 (1H, d, J=9.6 Hz), 9.56-9.85 (2H, m)

Example 268

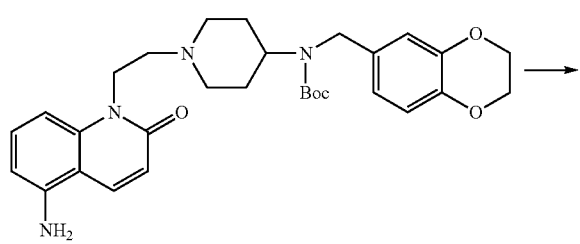

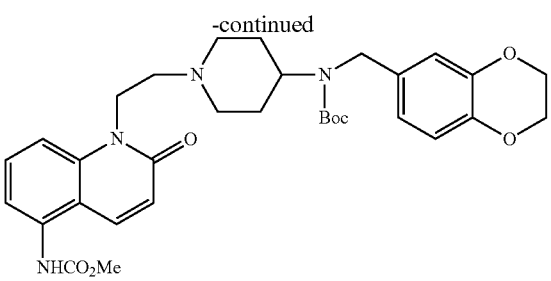

To 2 mL of a chloroform solution containing 80 mg of tert-butyl (2,3-dihydro-1,4-benzodioxin-6-ylmethyl)(1-(2-(5-amino-2-oxoquinolin-1(2H)-yl)ethyl)piperidin-4-yl)carbamate, 45 mg of triethylamine and 42 mg of methyl chloroformate were added, and stirred at room temperature for 3 days. To the reaction mixture, 225 mg of triethylamine and 210 mg of methyl chloroformate were added, and stirred at room temperature overnight. The reaction mixture was purified by silica gel column chromatography [Silica Gel; Fuji Silysia Chemical Ltd., Chromatorex-NH, eluent; hexane:ethyl acetate=1:4], to give 40 mg of N-(1-(2-(4-((tert-butoxycarbonyl) (2,3-dihydro-1,4-benzodioxin-6-ylmethyl)amino) piperidin-1-yl)ethyl)-2-oxo-1,2-dihydroquinolin-5-yl) carbamic acid methyl ester as a pale yellow oil.

¹H-NMR (CDCl₃) δ:
1.42 (9H, s), 1.62-1.73 (4H, m), 2.11-2.24 (2H, m), 2.56-2.66 (2H, m), 2.95-3.08 (2H, m), 3.81 (3H, s), 4.03-4.15 (1H, m), 4.21-4.32 (6H, m), 4.35-4.43 (2H, m), 6.66-6.72 (3H, m), 6.74 (1H, s), 6.78 (1H, d, J=8.3 Hz), 7.42-7.56 (2H, m), 7.79 (1H, d, J=10.1 Hz)

Example 269

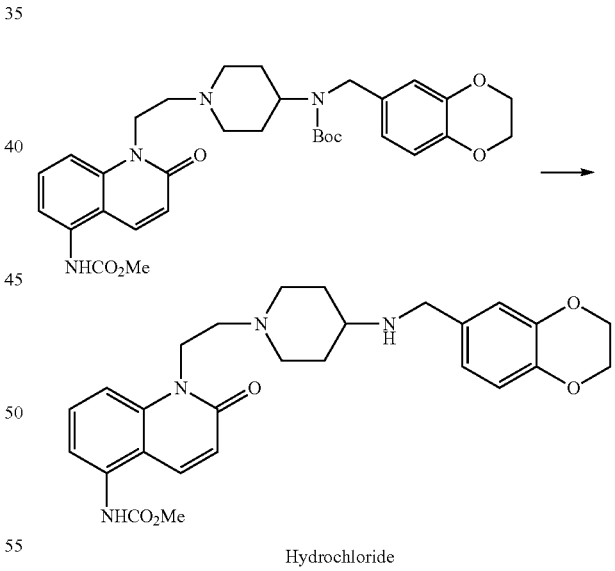

Hydrochloride

To 35 mg of N-(1-(2-(4-((tert-butoxycarbonyl)(2,3-dihydro-1,4-benzodioxin-6-ylmethyl)amino)piperidin-1-yl) ethyl)-2-oxo-1,2-dihydroquinolin-5-yl)carbamic acid methyl ester, 2 mL of 1,4-dioxane and 0.8 mL of 4 mol/L hydrogen chloride/1,4-dioxane were added, and stirred at room temperature for 3 hours. The resulting solid was filtered to give 23 mg of N-(1-(2-(4-((2,3-dihydro-1,4-benzodioxin-6-ylmethyl)amino)piperidin-1-yl)ethyl)-2-oxo-1,2-dihydroquinolin-5-yl)carbamic acid methyl ester hydrochloride as a yellow solid.

¹H-NMR (DMSO-d₆) δ:

1.98-2.10 (2H, m), 2.32-2.41 (2H, m), 3.07-3.16 (2H, m), 3.21-3.33 (3H, m), 3.69 (3H, s), 3.77-3.85 (2H, m), 4.06-4.12 (2H, m), 4.26 (4H, s), 4.61-4.71 (2H, m), 6.65 (1H, d, J=10.1 Hz), 6.91 (1H, d, J=8.3 Hz), 7.03 (1H, d, J=8.3 Hz), 7.14 (1H, s), 7.35-7.43 (1H, m), 7.55-7.65 (2H, m), 8.06 (1H, d, J=10.1 Hz), 9.37-9.55 (2H, broad), 9.69 (1H, s), 10.56-10.74 (1H, broad)

Example 270

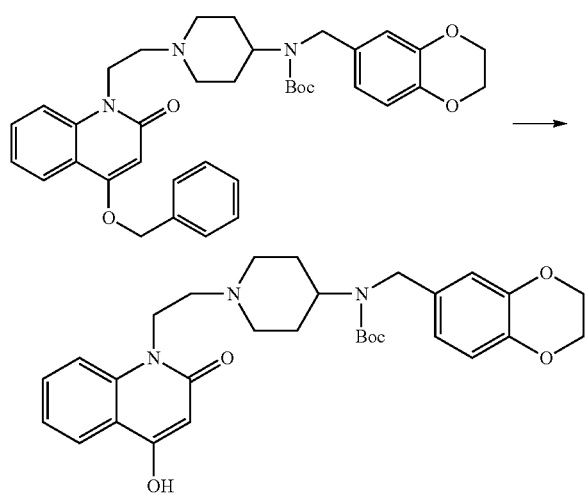

To a mixed solution of 130 mL methanol and 10 mL tetrahydrofuran containing 1.76 g of tert-butyl (1-(2-(4-benzyloxy-2-oxoquinolin-1(2H)-yl)ethyl)piperidin-4-yl)(2,3-dihydro-1,4-benzodioxin-6-ylmethyl)carbamate, 0.86 g of 5% palladium on carbon was added, and stirred under hydrogen atmosphere for 3.5 hours. The insoluble material was filtered off, and the solvent was removed under reduced pressure to afford 1.48 g of tert-butyl (2,3-dihydro-1,4-benzodioxin-6-ylmethyl)(1-(2-(4-hydroxy-2-oxoquinolin-1(2H)-yl)ethyl)piperidin-4-yl)carbamate as a white solid.

¹H-NMR (CDCl₃) δ:

1.41 (9H, s), 1.59-1.74 (5H, m), 2.12 (2H, m), 2.47-2.53 (2H, m), 2.96-3.03 (2H, m), 4.02-4.11 (2H, m), 4.23 (4H, s), 4.24-4.28 (2H, m), 6.06 (1H, s), 6.63-6.69 (1H, m), 6.71-6.74 (1H, m), 6.75 (1H, d, J=8.3 Hz), 7.11-7.16 (2H, m), 7.41-7.45 (1H, m), 7.97 (1H, dd, J=7.8, 0.9 Hz)

Example 271

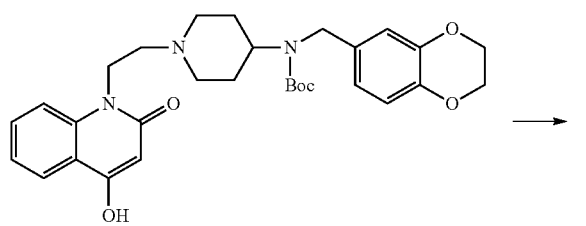

-continued

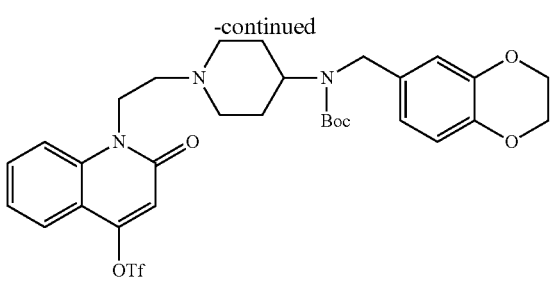

To 6 mL of a dichloromethane solution containing 0.32 g of tert-butyl (2,3-dihydro-1,4-benzodioxin-6-ylmethyl)(1-(2-(4-hydroxy-2-oxoquinolin-1(2H)-yl)ethyl)piperidin-4-yl)carbamate, 0.18 g of triethylamine and 0.19 g of trifluoromethanesulfonic acid anhydride were added, and stirred for 1 hour. To the reaction mixture, 8 mL of aqueous saturated ammonium chloride solution and 10 mL of chloroform were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=30:1], to give 0.16 g of tert-butyl (2,3-dihydro-1,4-benzodioxin-6-ylmethyl)(1-(2-(4-(trifluoromethanesulfonyl)oxy-2-oxoquinolin-1(2H)-yl)ethyl)piperidin-4-yl)carbamate as a pale yellow solid.

¹H-NMR (CDCl₃) δ:

1.41 (9H, s), 1.62-1.72 (5H, m), 2.11-2.22 (2H, m), 2.59-2.66 (2H, m), 2.99-3.05 (2H, m), 4.25 (4H, s), 4.26-4.32 (2H, m), 4.36-4.41 (2H, m), 6.67-6.70 (1H, m), 6.73 (1H, s), 6.73-6.74 (1H, m), 6.78 (1H, d, J=8.3 Hz), 7.35 (1H, t, J=7.8 Hz), 7.46-7.51 (1H, m), 7.65-7.70 (1H, m), 7.81 (1H, dd, J=7.8, 1.1 Hz)

Example 272

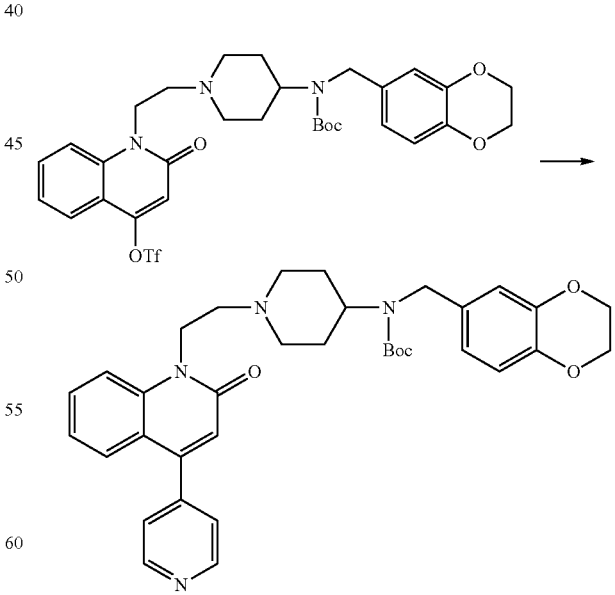

To 2 mL of an N,N-dimethylformamide solution containing 0.14 g of tert-butyl (2,3-dihydro-1,4-benzodioxin-6-ylmethyl)(1-(2-(4-(trifluoromethanesulfonyl)oxy-2-oxoquinolin-1(2H)-yl)ethyl)piperidin-4-yl)carbamate, 0.24 mL of 2.0 mol/L aqueous sodium carbonate solution, 12 mg of tetrakis triphenylphosphine palladium and 39 mg of 4-pyridineboronic acid were added, and stirred at 120° C. under nitrogen atmosphere for 80 min. The reaction mixture was cooled to the room temperature, ethyl acetate and water were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [eluent; chloroform:methanol=10:1], to give 42 mg of tert-butyl (2,3-dihydro-1,4-benzodioxin-6-ylmethyl)(1-(2-(2-oxo-4-(pyridin-4-yl)quinolin-1(2H)-yl)ethyl)piperidin-4-yl)carbamate as a pale yellow solid.

$^1$H-NMR (CDCl$_3$) δ:

1.42 (9H, s), 1.64-1.76 (5H, m), 2.15-2.25 (2H, m), 2.66-2.70 (2H, m), 3.06-3.11 (2H, m), 4.25 (4H, s), 4.28-4.32 (2H, m), 4.44-4.49 (2H, m), 6.64 (1H, s), 6.68-6.71 (1H, m), 6.75 (1H, d, J=1.8 Hz), 6.79 (1H, d, J=8.3 Hz), 7.17-7.20 (1H, m), 7.34-7.36 (2H, m), 7.43 (1H, dd, J=8.3, 1.4 Hz), 7.50 (1H, d, J=8.7 Hz), 7.58-7.62 (1H, m), 8.75-8.77 (2H, m)

Example 273

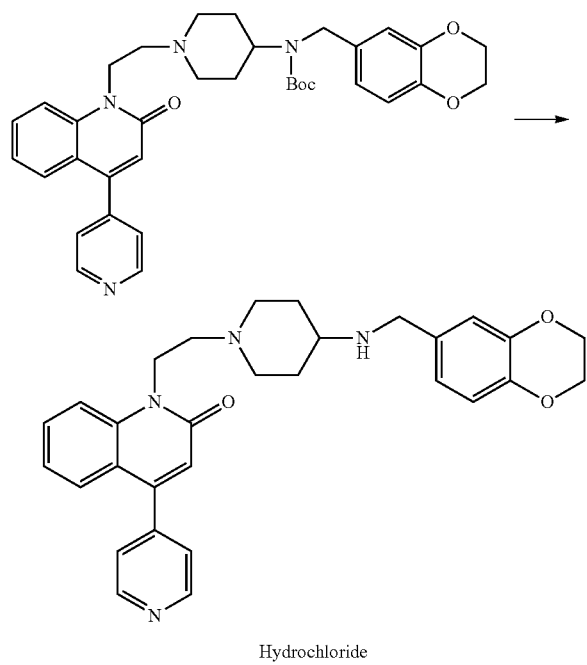

Hydrochloride

To 1 mL of a chloroform solution containing 42 mg of tert-butyl (2,3-dihydro-1,4-benzodioxin-6-ylmethyl)(1-(2-(2-oxo-4-(pyridin-4-yl)quinolin-1(2H)-yl)ethyl)piperidin-4-yl)carbamate, 1 mL of trifluoroacetic acid was added at room temperature and stirred for 3.5 hours, thereafter the solvent was removed under reduced pressure. To the residue thus obtained, chloroform and aqueous saturated sodium hydrogen carbonate solution were added, the organic layer was separated and the aqueous layer was extracted with chloroform. The organic layer and extracts were combined, washed with aqueous saturated sodium chloride solution, dried over anhydrous magnesium sulfate, and the solvent was removed under reduced pressure. To the residue thus obtained, 1 mL of 4 mol/L hydrogen chloride/ethyl acetate was added, the resulting solid was filtered to give 21 mg of (1-(2-(4-((2,3-dihydro-1,4-benzodioxin-6-ylmethyl)amino)piperidin-1-yl)ethyl)-4-(pyridin-4-yl)quinolin-2(1H)-one hydrochloride as a pale yellow solid.

$^1$H-NMR (DMSO-d$_6$) δ:

2.05-2.15 (2H, m), 2.35-2.41 (2H, m), 3.11-3.19 (2H, m), 3.22-3.29 (1H, m), 3.31-3.36 (2H, m), 3.80-3.85 (2H, m), 4.06-4.10 (2H, m), 4.26 (4H, s), 4.74-4.78 (2H, m), 6.72 (1H, s), 6.91 (1H, d, J=8.3 Hz), 7.05 (1H, dd, J=8.3, 2.3 Hz), 7.18 (1H, d, J=1.8 Hz), 7.32 (1H, t, J=7.8 Hz), 7.42 (1H, dd, J=8.3, 1.4 Hz), 7.71-7.75 (1H, m), 7.76-7.80 (2H, m), 7.99 (1H, d, J=8.7 Hz), 8.91 (2H, m), 9.51-9.66 (2H, broad), 11.00-11.09 (1H, broad)

Example 274

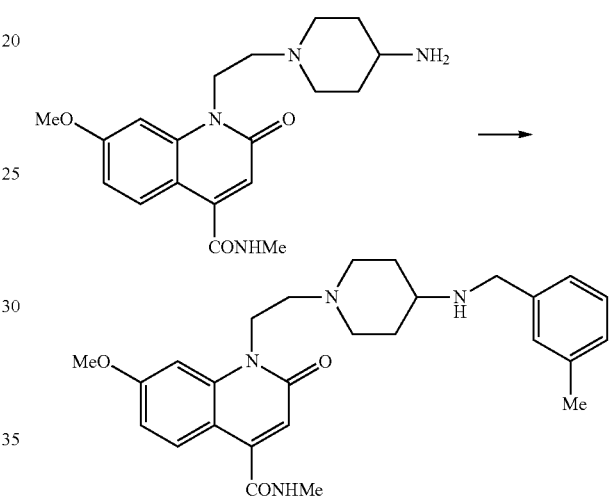

370 μL of a methanol solution containing 14 mg of 1-(2-(4-aminopiperidin-1-yl)ethyl)-7-methoxy-N-methyl-2-oxo-1,2-dihydroquinolin-4-carboxamide and 10 μL of acetic acid were added to 3.6 mg of 3-methylbenzaldehyde, and stirred at room temperature for 1 min. To the reaction mixture, 120 μL, of a methanol solution containing 3.8 mg of sodium cyanoborohydride was added, and stirred at the same temperature overnight. After the solvent was removed under reduced pressure, ethyl acetate and aqueous saturated sodium hydrogen carbonate solution were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate: methanol=20:1], to give 7.6 mg of (1-(2-(4-(3-methylbenzylamino)piperidin-1-yl)ethyl)-7-methoxy-N-methyl-2-oxo-1,2-dihydroquinolin-4-carboxamide as a pale yellow foam.

$^1$H-NMR (DMSO-d$_6$) δ:

1.23-1.31 (2H, m), 1.75-1.83 (2H, m), 2.00-2.08 (2H, m), 2.27 (3H, s), 2.33-2.55 (3H, m), 2.79 (3H, d, J=4.6 Hz), 2.89-2.97 (2H, m), 3.66 (2H, s), 3.90 (3H, s), 4.33-4.38 (2H, m), 6.41 (1H, s), 6.91 (1H, dd, J=9.2, 2.3 Hz), 6.98-7.03 (2H, m), 7.09-7.20 (3H, m), 7.71 (1H, d, J=9.2 Hz), 8.60-8.67 (1H, m)

Examples 275-335

According to a procedure similar to Example 123, the following compounds were obtained.

TABLE 10

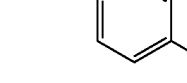

| Example No. | —X²—X³—R⁶ |
|---|---|
| 275 | 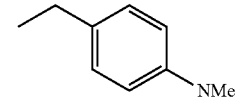 |
| 276 | 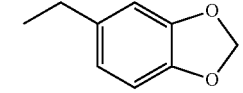 |
| 277 | 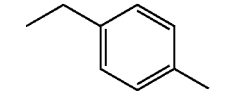 |
| 278 | 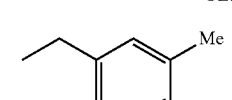 |
| 279 | 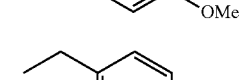 |
| 280 | 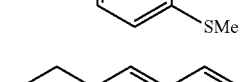 |
| 281 | 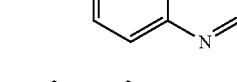 |
| 282 | 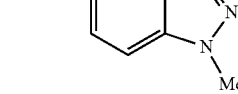 |
| 283 | 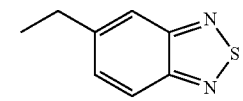 |
| 284 | 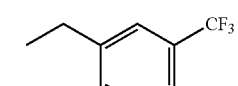 |

TABLE 10-continued

| Example No. | —X²—X³—R⁶ |
|---|---|
| 285 | 4-Ac-phenylethyl |
| 286 | 4-NMe₂-phenylethyl |
| 287 | benzodioxole-ethyl |
| 288 | 4-OEt-phenylethyl |
| 289 | 3-Me-4-OMe-phenylethyl |
| 290 | 4-SMe-phenylethyl |
| 291 | quinolinyl-ethyl |
| 292 | 1-Me-benzotriazolyl-ethyl |
| 293 | benzothiadiazolyl-ethyl |
| 294 | 3-CF₃-phenylethyl |
| 295 | 4-CF₃-phenylethyl |

TABLE 10-continued

| Example No. | —X²—X³—R⁶ |
|---|---|
| 296 | 6-ethyl-1-methyl-1,2,3,4-tetrahydroquinoline |
| 297 | 7-ethyl-4-methyl-3,4-dihydro-2H-benzo[b][1,4]oxazine |
| 298 | 7-ethyl-2,3,4,5-tetrahydrobenzo[b][1,4]dioxepine |
| 299 | 6-propyl-2,3-dihydro-1,4-benzodioxine |
| 300 | 4-ethyl-1-(trifluoromethoxy)benzene |
| 301 | 2-ethylbenzofuran |
| 302 | 2-ethylquinoline |
| 303 | 2-ethyl-1,8-naphthyridine |
| 304 | 2-ethyl-1-methyl-1H-indole |
| 305 | 3-ethyl-2H-chromene |

TABLE 10-continued

| Example No. | —X²—X³—R⁶ |
|---|---|
| 306 | 2-ethyl-8-hydroxyquinoline |
| 307 | 2-ethyl-3-methylbenzo[b]thiophene |
| 308 | 6-ethyl-4-methoxybenzo[d][1,3]dioxole |
| 309 | 3-ethyl-6-methoxy-2H-chromene |
| 310 | 1-chloro-2-ethyl-3,4-dihydronaphthalene |
| 311 | 2-ethyl-3,6-dimethylthieno[3,2-b]thiophene |
| 312 | 3-chloro-2-ethylbenzo[b]thiophene |
| 313 | 2-chloro-3-ethyl-6-methylquinoline |
| 314 | 2-chloro-3-ethyl-6-methoxyquinoline |

TABLE 10-continued

[Structure: 7-MeO, 4-CONHMe quinolin-2-one with N-CH2CH2-piperidin-4-yl-NH-X²-X³-R⁶]

| Example No. | —X²—X³—R⁶ |
|---|---|
| 315 | 3-ethyl-4-chloro-6-fluoro-2H-thiochromene |
| 316 | 5-ethyl-6-bromo-benzo[1,3]dioxole |
| 317 | 5-ethyl-3-(CF₃)-1-methyl-thieno[2,3-c]pyrazole |
| 318 | CH₂-CH=CH-CH=CH-Me (hexa-2,4-dienyl) |
| 319 | n-octyl (CH₂)₇Me |
| 320 | CH₂-CH=CH-(2-furyl) |
| 321 | CH₂-C≡C-(CH₂)₃-Me |
| 322 | CH₂-CH=CH-Ph (cinnamyl) |
| 323 | (CH₂)₃-Ph |
| 324 | CH₂-C(Me)=CH-(2-furyl) |
| 325 | CH₂-C(Me)=CH-Ph |

TABLE 10-continued

[Structure: 7-MeO, 4-CONHMe quinolin-2-one with N-CH2CH2-piperidin-4-yl-NH-X²-X³-R⁶]

| Example No. | —X²—X³—R⁶ |
|---|---|
| 326 | CH₂-CH(Et)-Ph with α-Me (1-methyl-1-phenylbutyl type) |
| 327 | CH₂-(1-naphthyl) |
| 328 | CH₂-CH=CH-(2-methoxyphenyl) |
| 329 | CH₂-(5-phenyl-2-furyl) |
| 330 | CH₂-(4-(pyrrolidin-1-yl)phenyl) |
| 331 | CH₂-(2-fluoro-5-trifluoromethylphenyl) |
| 332 | CH₂-(5-(thiophen-2-yl)thiophen-2-yl) |
| 333 | CH₂-(phenanthren-9-yl) |

TABLE 10-continued

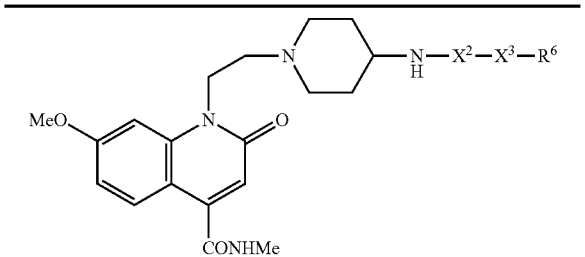

| Example No. | —X²—X³—R⁶ |
|---|---|
| 334 | 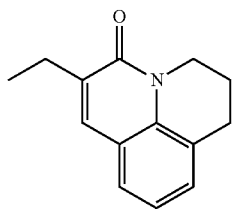 |
| 335 | 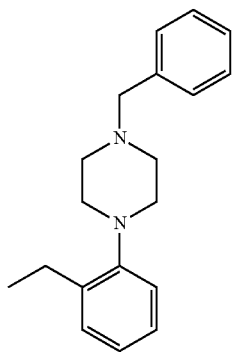 |

1-(2-(4-(4-methylbenzylamino)piperidin-1-yl)ethyl)-7-methoxy-N-methyl-2-oxo-1,2-dihydroquinolin-4-carboxamide ¹H-NMR (DMSO-d₆) δ:
1.16-1.25 (2H, m), 1.69-1.77 (2H, m), 1.94-2.02 (2H, m), 2.27 (3H, s), 2.27-2.50 (3H, m), 2.74 (3H, d, J=5.0 Hz), 2.83-2.91 (2H, m), 3.61 (2H, s), 3.85 (3H, s), 4.27-4.33 (2H, m), 6.36 (1H, s), 6.86 (1H, dd, J=9.2, 2.3 Hz), 6.95 (1H, d, J=2.3 Hz), 7.05 (2H, d, J=7.8 Hz), 7.15 (2H, d, J=7.8 Hz), 7.66 (1H, d, J=9.2 Hz), 8.57-8.61 (1H, m)

1-(2-(4-(3-vinylbenzylamino)piperidin-1-yl)ethyl)-7-methoxy-N-methyl-2-oxo-1,2-dihydroquinoline-4-carboxamide ¹H-NMR (DMSO-d₆) δ:
1.23-1.32 (2H, m), 1.76-1.84 (2H, m), 2.01-2.07 (2H, m), 2.35-2.55 (3H, m), 2.79 (3H, d, J=4.6 Hz), 2.89-2.97 (2H, m), 3.71 (2H, s), 3.90 (3H, s), 4.33-4.39 (2H, m), 5.24 (1H, d, J=10.5 Hz), 5.81 (1H, d, J=16.5 Hz), 6.41 (1H, s), 6.72 (1H, dd, J=16.5, 10.5 Hz), 6.91 (1H, dd, J=9.2, 2.3 Hz), 7.00 (1H, d, J=2.3 Hz), 7.21-7.34 (3H, m), 7.42 (1H, s), 7.71 (1H, d, J=9.2 Hz), 8.62-8.67 (1H, m)

1-(2-(4-(3,4-dimethylbenzylamino)piperidin-1-yl)ethyl)-7-methoxy-N-methyl-2-oxo-1,2-dihydroquinoline-4-carboxamide ¹H-NMR (DMSO-d₆) δ:
1.22-1.29 (2H, m), 1.74-1.82 (2H, m), 1.99-2.07 (2H, m), 2.18 (3H, s), 2.19 (3H, s), 2.33-2.54 (3H, m), 2.79 (3H, d, J=5.0 Hz), 2.88-2.96 (2H, m), 3.62 (2H, s), 3.90 (3H, s), 4.31-4.38 (2H, m), 6.41 (1H, s), 6.91 (1H, dd, J=8.7, 2.3 Hz), 6.98-7.09 (4H, m), 7.71 (1H, d, J=8.7 Hz), 8.62-8.67 (1H, m)

1-(2-(4-(3-methoxybenzylamino)piperidin-1-yl)ethyl)-7-methoxy-N-methyl-2-oxo-1,2-dihydroquinoline-4-carboxamide ¹H-NMR (DMSO-d₆) δ:
1.22-1.30 (2H, m), 1.75-1.83 (2H, m), 2.00-2.08 (2H, m), 2.34-2.54 (3H, m), 2.79 (3H, d, J=4.6 Hz), 2.88-2.96 (2H, m), 3.68 (2H, s), 3.73 (3H, s), 3.90 (3H, s), 4.33-4.38 (2H, m), 6.41 (1H, s), 6.76 (1H, dd, J=8.7, 2.3 Hz), 6.86-6.93 (3H, m), 7.00 (1H, d, J=2.3 Hz), 7.20 (1H, t, J=7.8 Hz), 7.71 (1H, d, J=8.7 Hz), 8.56-8.67 (1H, m)

1-(2-(4-(4-methoxybenzylamino)piperidin-1-yl)ethyl)-7-methoxy-N-methyl-2-oxo-1,2-dihydroquinoline-4-carboxamide ¹H-NMR (DMSO-d₆) δ:
1.22-1.29 (2H, m), 1.75-1.80 (2H, m), 1.99-2.07 (2H, m), 2.33-2.54 (3H, m), 2.79 (3H, d, J=5.0 Hz), 2.88-2.96 (2H, m), 3.63 (2H, s), 3.72 (3H, s), 3.90 (3H, s), 4.33-4.38 (2H, m), 6.41 (1H, s), 6.85 (2H, d, J=8.7 Hz), 6.91 (1H, dd, J=8.7, 2.3 Hz), 7.00 (1H, d, J=2.3 Hz), 7.23 (2H, d, J=8.7 Hz), 7.71 (1H, d, J=8.7 Hz), 8.60-8.67 (1H, m)

1-(2-(4-(3,4-difluorobenzylamino)piperidin-1-yl)ethyl)-7-methoxy-N-methyl-2-oxo-1,2-dihydroquinoline-4-carboxamide ¹H-NMR (DMSO-d₆) δ:
1.20-1.31 (2H, m), 1.74-1.81 (2H, m), 2.00-2.08 (2H, m), 2.31-2.54 (3H, m), 2.79 (3H, d, J=4.6 Hz), 2.88-2.96 (2H, m), 3.69 (2H, s), 3.90 (3H, s), 4.32-4.39 (2H, m), 6.41 (1H, s), 6.91 (1H, dd, J=8.9, 2.3 Hz), 7.00 (1H, d, J=2.3 Hz), 7.14-7.20 (1H, m), 7.29-7.42 (2H, m), 7.71 (1H, d, J=8.7 Hz), 8.61-8.67 (1H, m)

1-(2-(4-((1H-indol-6-yl)methylamino)piperidin-1-yl)ethyl)-7-methoxy-N-methyl-2-oxo-1,2-dihydroquinoline-4-carboxamide ¹H-NMR (DMSO-d₆) δ:
1.21-1.33 (2H, m), 1.78-1.85 (2H, m), 2.00-2.08 (2H, m), 2.38-2.54 (3H, m), 2.79 (3H, d, J=4.6 Hz), 2.89-2.97 (2H, m), 3.78 (2H, s), 3.90 (3H, s), 4.33-4.39 (2H, m), 6.35-6.37 (1H, m), 6.41 (1H, s), 6.91 (1H, dd, J=8.7, 2.3 Hz), 6.96 (1H, d, J=9.6 Hz), 7.00 (1H, d, J=2.3 Hz), 7.24-7.28 (1H, m), 7.34 (1H, s), 7.43 (1H, d, J=7.8 Hz), 7.71 (1H, d, J=8.7 Hz), 8.62-8.66 (1H, m)

1-(2-(4-((benzofuran-5-yl)methylamino)piperidin-1-yl)ethyl)-7-methoxy-N-methyl-2-oxo-1,2-dihydroquinoline-4-carboxamide ¹H-NMR (DMSO-d₆) δ:
1.24-1.33 (2H, m), 1.77-1.85 (2H, m), 2.00-2.08 (2H, m), 2.37-2.54 (3H, m), 2.79 (3H, d, J=4.6 Hz), 2.89-2.97 (2H, m), 3.79 (2H, s), 3.90 (3H, s), 4.32-4.39 (2H, m), 6.41 (1H, s), 6.89-6.93 (2H, m), 7.00 (1H, d, J=2.3 Hz), 7.26-7.30 (1H, m), 7.50 (1H, d, J=8.3 Hz), 7.59 (1H, s), 7.71 (1H, d, J=8.7 Hz), 7.94 (1H, d, J=2.3 Hz), 8.60-8.67 (1H, m)

1-(2-(4-((2,1,3-benzooxadiazol-5-yl)methylamino)
piperidin-1-yl)ethyl)-7-methoxy-N-methyl-2-oxo-1,
2-dihydroquinoline-4-carboxamide ¹H-NMR (DMSO-d₆) δ:
1.23-1.34 (2H, m), 1.78-1.86 (2H, m), 2.02-2.09 (2H, m), 2.37-2.54 (3H, m), 2.79 (3H, d, J=4.6 Hz), 2.90-2.98 (2H, m), 3.84 (2H, s), 3.90 (3H, s), 4.30-4.39 (2H, m), 6.41 (1H, s), 6.91 (1H, dd, J=8.7, 2.3 Hz), 7.00 (1H, d, J=2.3 Hz), 7.61 (1H, d, J=9.2 Hz), 7.71 (1H, d, J=8.7 Hz), 7.87 (1H, s), 7.97 (1H, d, J=9.2 Hz), 8.60-8.66 (1H, m)

1-(2-(4-((2,3-dihydrobenzo[b]furan-5-yl)methylamino)piperidin-1-yl)ethyl)-7-methoxy-N-methyl-2-oxo-1,2-dihydroquinoline-4-carboxamide ¹H-NMR (DMSO-d₆) δ:
1.21-1.29 (2H, m), 1.74-1.82 (2H, m), 2.00-2.08 (2H, m), 2.33-2.54 (3H, m), 2.79 (3H, d, J=4.6 Hz), 2.88-2.96 (2H, m), 3.13 (2H, t, J=8.7 Hz), 3.61 (2H, s), 3.90 (3H, s), 4.33-4.38 (2H, m), 4.48 (2H, t, J=8.7 Hz), 6.41 (1H, s), 6.65 (1H, d, J=8.3 Hz), 6.91 (1H, dd, J=8.7, 2.3 Hz), 6.98-7.02 (2H, m), 7.18 (1H, s), 7.71 (1H, d, J=8.7 Hz), 8.61-8.66 (1H, m)

1-(2-(4-(4-acetylbenzylamino)piperidin-1-yl)ethyl)-
7-methoxy-N-methyl-2-oxo-1,2-dihydroquinoline-4-
carboxamide ¹H-NMR (DMSO-d₆) δ:
1.22-1.32 (2H, m), 1.75-1.82 (2H, m), 1.99-2.07 (2H, m), 2.33-2.53 (3H, m), 2.56 (3H, s), 2.79 (3H, d, J=4.6 Hz), 2.90-2.96 (2H, m), 3.79 (2H, s), 3.90 (3H, s), 4.32-4.39 (2H, m), 6.41 (1H, s), 6.91 (1H, dd, J=8.7, 2.3 Hz), 7.00 (1H, d, J=2.3 Hz), 7.48 (2H, d, J=8.3 Hz), 7.71 (1H, d, J=8.7 Hz), 7.89 (2H, d, J=8.3 Hz), 8.61-8.67 (1H, m)

1-(2-(4-(4-(dimethylamino)benzylamino)piperidin-1-
yl)ethyl)-7-methoxy-N-methyl-2-oxo-1,2-dihydro-
quinoline-4-carboxamide ¹H-NMR (DMSO-d₆) δ:
1.20-1.29 (2H, m), 1.74-1.82 (2H, m), 1.99-2.07 (2H, m), 2.33-2.54 (3H, m), 2.79 (3H, d, J=5.0 Hz), 2.85 (6H, s), 2.88-2.96 (2H, m), 3.58 (2H, s), 3.90 (3H, s), 4.33-4.38 (2H, m), 6.41 (1H, s), 6.66 (2H, d, J=8.7 Hz), 6.91 (1H, dd, J=8.7, 2.3 Hz), 7.00 (1H, d, J=2.3 Hz), 7.12 (2H, d, J=8.7 Hz), 7.71 (1H, d, J=8.7 Hz), 8.62-8.68 (1H, m)

1-(2-(4-((benzo[1,3]dioxol-5-yl)methylamino)piperidin-1-yl)ethyl)-7-methoxy-N-methyl-2-oxo-1,2-dihydroquinoline-4-carboxamide ¹H-NMR (DMSO-d₆) δ:
1.21-1.29 (2H, m), 1.73-1.81 (2H, m), 1.99-2.07 (2H, m), 2.31-2.54 (3H, m), 2.79 (3H, d, J=4.6 Hz), 2.88-2.96 (2H, m), 3.61 (2H, s), 3.90 (3H, s), 4.33-4.38 (2H, m), 5.96 (2H, s), 6.41 (1H, s), 6.75-6.83 (2H, m), 6.89-6.93 (2H, m), 7.00 (1H, d, J=2.3 Hz), 7.71 (1H, d, J=8.7 Hz), 8.61-8.67 (1H, m)

1-(2-(4-(4-ethoxybenzylamino)piperidin-1-yl)ethyl)-
7-methoxy-N-methyl-2-oxo-1,2-dihydroquinoline-4-
carboxamide ¹H-NMR (DMSO-d₆) δ:
1.22-1.33 (5H, m), 1.74-1.82 (2H, m), 1.99-2.07 (2H, m), 2.32-2.54 (3H, m), 2.79 (3H, d, J=5.0 Hz), 2.88-2.96 (2H, m), 3.62 (2H, s), 3.90 (3H, s), 3.98 (2H, q, J=6.9 Hz), 4.33-4.38 (2H, m), 6.41 (1H, s), 6.83 (2H, d, J=8.3 Hz), 6.91 (1H, dd, J=8.7, 2.3 Hz), 7.00 (1H, d, J=2.3 Hz), 7.21 (2H, d, J=8.3 Hz), 7.71 (1H, d, J=8.7 Hz), 8.61-8.67 (1H, m)

1-(2-(4-(4-methoxy-3-methylbenzylamino)piperidin-
1-yl)ethyl)-7-methoxy-N-methyl-2-oxo-1,2-dihydro-
quinoline-4-carboxamide ¹H-NMR (DMSO-d₆) δ:
1.22-1.29 (2H, m), 1.74-1.82 (2H, m), 2.01-2.07 (2H, m), 2.12 (3H, s), 2.33-2.54 (3H, m), 2.79 (3H, d, J=4.6 Hz), 2.88-2.96 (2H, m), 3.60 (2H, s), 3.75 (3H, s), 3.90 (3H, s), 4.33-4.38 (2H, m), 6.41 (1H, s), 6.83 (1H, d, J=8.7 Hz), 6.91 (1H, dd, J=8.7, 2.3 Hz), 7.00 (1H, d, J=2.3 Hz), 7.07-7.11 (2H, m), 7.71 (1H, d, J=8.7 Hz), 8.60-8.67 (1H, m)

1-(2-(4-(4-(methylthio)benzylamino)piperidin-1-yl)
ethyl)-7-methoxy-N-methyl-2-oxo-1,2-dihydro-
quinoline-4-carboxamide ¹H-NMR (DMSO-d₆) δ:
1.21-1.29 (2H, m), 1.74-1.82 (2H, m), 1.99-2.07 (2H, m), 2.32-2.53 (6H, m), 2.79 (3H, d, J=5.0 Hz), 2.88-2.96 (2H, m), 3.66 (2H, s), 3.90 (3H, s), 4.33-4.38 (2H, m), 6.41 (1H, s), 6.91 (1H, dd, J=8.7, 2.3 Hz), 7.00 (1H, d, J=2.3 Hz), 7.19 (2H, d, J=8.3 Hz), 7.27 (2H, d, J=8.3 Hz), 7.71 (1H, d, J=8.7 Hz), 8.59-8.67 (1H, m)

1-(2-(4-((quinolin-6-yl)methylamino)piperidin-1-yl)
ethyl)-7-methoxy-N-methyl-2-oxo-1,2-dihydro-
quinoline-4-carboxamide ¹H-NMR (DMSO-d₆) δ:
1.28-1.34 (2H, m), 1.80-1.88 (2H, m), 2.00-2.08 (2H, m), 2.40-2.54 (3H, m), 2.79 (3H, d, J=5.0 Hz), 2.90-2.98 (2H, m), 3.88 (2H, s), 3.90 (3H, s), 4.33-4.39 (2H, m), 6.41 (1H, s), 6.91 (1H, dd, J=8.7, 2.3 Hz), 7.00 (1H, d, J=2.3 Hz), 7.43-7.54 (3H, m), 7.71 (1H, d, J=8.7 Hz), 7.80-7.89 (3H, m), 8.62-8.67 (1H, m)

1-(2-(4-((1-methyl-1H-1,2,3-benzotriazol-5-yl)methylamino)piperidin-1-yl)ethyl)-7-methoxy-N-methyl-2-oxo-1,2-dihydroquinoline-4-carboxamide ¹H-NMR (DMSO-d₆) δ:
1.25-1.33 (2H, m), 1.77-1.85 (2H, m), 1.99-2.07 (2H, m), 2.35-2.53 (3H, m), 2.79 (3H, d, J=5.0 Hz), 2.89-2.97 (2H, m), 3.87 (2H, s), 3.90 (3H, s), 4.28 (3H, s), 4.34-4.37 (2H, m), 6.41 (1H, s), 6.91 (1H, dd, J=8.7, 2.3 Hz), 7.00 (1H, d, J=2.3 Hz), 7.56 (1H, d, J=8.3 Hz), 7.71 (1H, d, J=8.7 Hz), 7.76 (1H, d, J=8.3 Hz), 7.92 (1H, s), 8.61-8.67 (1H, m)

1-(2-(4-((2,1,3-benzothiadiazol-5-yl)methylamino)
piperidin-1-yl)ethyl)-7-methoxy-N-methyl-2-oxo-1,
2-dihydroquinoline-4-carboxamide ¹H-NMR (DMSO-d₆) δ:
1.27-1.34 (2H, m), 1.79-1.87 (2H, m), 2.01-2.09 (2H, m), 2.39-2.53 (3H, m), 2.79 (3H, d, J=4.6 Hz), 2.90-2.98 (2H, m), 3.90 (3H, s), 3.92 (2H, s), 4.33-4.37 (2H, m), 6.41 (1H, s), 6.91 (1H, dd, J=8.7, 2.3 Hz), 7.00 (1H, d, J=2.3 Hz), 7.71 (1H, d, J=8.7 Hz), 7.74 (1H, d, J=9.2 Hz), 7.98 (1H, s), 8.02 (1H, d, J=9.2 Hz), 8.62-8.66 (1H, m)

1-(2-(4-(3-(trifluoromethyl)benzylamino)piperidin-1-yl)ethyl)-7-methoxy-N-methyl-2-oxo-1,2-dihydroquinoline-4-carboxamide $^1$H-NMR (DMSO-$d_6$) δ:
1.21-1.29 (2H, m), 1.73-1.81 (2H, m), 1.99-2.04 (2H, m), 2.31-2.51 (3H, m), 2.76 (3H, d, J=4.6 Hz), 2.86-2.94 (2H, m), 3.77 (2H, s), 3.87 (3H, s), 4.28-4.37 (2H, m), 6.38 (1H, s), 6.88 (1H, dd, J=8.7, 2.3 Hz), 6.97 (1H, d, J=2.3 Hz), 7.47-7.56 (2H, m), 7.61 (1H, d, J=7.3 Hz), 7.66-7.71 (2H, m), 8.58-8.64 (1H, m)

1-(2-(4-(4-(trifluoromethyl)benzylamino)piperidin-1-yl)ethyl)-7-methoxy-N-methyl-2-oxo-1,2-dihydroquinoline-4-carboxamide $^1$H-NMR (DMSO-$d_6$) δ:
1.23-1.32 (2H, m), 1.75-1.83 (2H, m), 2.00-2.08 (2H, m), 2.34-2.54 (3H, m), 2.79 (3H, d, J=4.6 Hz), 2.89-2.97 (2H, m), 3.80 (2H, s), 3.90 (3H, s), 4.32-4.38 (2H, m), 6.41 (1H, s), 6.91 (1H, dd, J=8.7, 2.3 Hz), 7.00 (1H, d, J=2.3 Hz), 7.57 (2H, d, J=8.3 Hz), 7.65 (2H, d, J=8.3 Hz), 7.71 (1H, d, J=8.7 Hz), 8.61-8.68 (1H, m)

1-(2-(4-((1-methyl-1,2,3,4-tetrahydroquinolin-6-yl)methylamino)piperidin-1-yl)ethyl)-7-methoxy-N-methyl-2-oxo-1,2-dihydroquinoline-4-carboxamide $^1$H-NMR (DMSO-$d_6$) δ:
1.19-1.28 (2H, m), 1.75-1.81 (2H, m), 1.84-1.90 (2H, m), 2.01-2.07 (2H, m), 2.34-2.54 (3H, m), 2.66 (2H, t, J=6.6 Hz), 2.77-2.80 (6H, m), 2.88-2.96 (2H, m), 3.10-3.15 (2H, m), 3.52 (2H, s), 3.90 (3H, s), 4.34-4.39 (2H, m), 6.41 (1H, s), 6.49 (1H, d, J=8.3 Hz), 6.83 (1H, s), 6.89-6.93 (2H, m), 7.00 (1H, d, J=2.3 Hz), 7.71 (1H, d, J=8.7 Hz), 8.61-8.67 (1H, m)

1-(2-(4-((4-methyl-3,4-dihydro-2H-benz[1,4]oxazin-7-yl)methylamino)piperidin-1-yl)ethyl)-7-methoxy-N-methyl-2-oxo-1,2-dihydroquinoline-4-carboxamide $^1$H-NMR (DMSO-$d_6$) δ:
1.20-1.28 (2H, m), 1.73-1.79 (2H, m), 1.99-2.07 (2H, m), 2.31-2.54 (3H, m), 2.77-2.80 (6H, m), 2.87-2.95 (2H, m), 3.15-3.19 (2H, m), 3.53 (2H, s), 3.90 (3H, s), 4.18-4.22 (2H, m), 4.33-4.38 (2H, m), 6.41 (1H, s), 6.60 (1H, d, J=8.3 Hz), 6.64 (1H, d, J=2.1 Hz), 6.70 (1H, dd, J=8.3, 2.1 Hz), 6.91 (1H, dd, J=8.7, 2.3 Hz), 7.00 (1H, d, J=2.3 Hz), 7.71 (1H, d, J=8.7 Hz), 8.62-8.67 (1H, m)

1-(2-(4-((3,4-dihydro-2H-benzo[b][1,5]dioxepin-7-yl)methylamino)piperidin-1-yl)ethyl)-7-methoxy-N-methyl-2-oxo-1,2-dihydroquinoline-4-carboxamide $^1$H-NMR (DMSO-$d_6$) δ:
1.22-1.30 (2H, m), 1.74-1.82 (2H, m), 2.01-2.10 (4H, m), 2.33-2.54 (3H, m), 2.79 (3H, d, J=4.6 Hz), 2.88-2.96 (2H, m), 3.60 (2H, s), 3.90 (3H, s), 4.05-4.12 (4H, m), 4.33-4.38 (2H, m), 6.41 (1H, s), 6.86-6.94 (4H, m), 7.00 (1H, d, J=2.3 Hz), 7.71 (1H, d, J=8.7 Hz), 8.61-8.67 (1H, m)

1-(2-(4-(2-(2,3-dihydrobenzo[b][1,4]dioxin-6-yl)ethylamino)piperidin-1-yl)ethyl)-7-methoxy-N-methyl-2-oxo-1,2-dihydroquinoline-4-carboxamide $^1$H-NMR (DMSO-$d_6$) δ:
1.15-1.26 (2H, m), 1.72-1.79 (2H, m), 2.02-2.09 (2H, m), 2.36-2.57 (5H, m), 2.68 (2H, t, J=7.3 Hz), 2.79 (3H, d, J=4.6 Hz), 2.88-2.94 (2H, m), 3.90 (3H, s), 4.16-4.24 (4H, m), 4.32-4.39 (2H, m), 6.41 (1H, s), 6.62-6.66 (1H, m), 6.69 (1H, d, J=2.3 Hz), 6.73 (1H, d, J=8.3 Hz), 6.91 (1H, dd, J=8.7, 2.3 Hz), 7.00 (1H, d, J=2.3 Hz), 7.71 (1H, d, J=8.7 Hz), 8.61-8.67 (1H, m)

1-(2-(4-(4-(trifluoromethoxy)benzylamino)piperidin-1-yl)ethyl)-7-methoxy-N-methyl-2-oxo-1,2-dihydroquinoline-4-carboxamide $^1$H-NMR (DMSO-$d_6$) δ:
1.23-1.31 (2H, m), 1.75-1.83 (2H, m), 2.02-2.07 (2H, m), 2.35-2.54 (3H, m), 2.79 (3H, d, J=4.6 Hz), 2.89-2.97 (2H, m), 3.73 (2H, s), 3.90 (3H, s), 4.31-4.38 (2H, m), 6.41 (1H, s), 6.91 (1H, dd, J=8.7, 2.3 Hz), 7.00 (1H, d, J=2.3 Hz), 7.28 (2H, d, J=8.3 Hz), 7.46 (2H, d, J=8.3 Hz), 7.71 (1H, d, J=8.7 Hz), 8.61-8.67 (1H, m)

1-(2-(4-((benzofuran-2-yl)methylamino)piperidin-1-yl)ethyl)-7-methoxy-N-methyl-2-oxo-1,2-dihydroquinoline-4-carboxamide $^1$H-NMR (DMSO-$d_6$) δ:
1.23-1.31 (2H, m), 1.77-1.84 (2H, m), 2.02-2.09 (2H, m), 2.41-2.55 (3H, m), 2.79 (3H, d, J=4.6 Hz), 2.91-2.96 (2H, m), 3.86 (2H, s), 3.90 (3H, s), 4.34-4.38 (2H, m), 6.41 (1H, s), 6.71 (1H, s), 6.91 (1H, dd, J=8.7, 2.3 Hz), 7.00 (1H, d, J=2.3 Hz), 7.17-7.26 (2H, m), 7.50 (1H, d, J=8.3 Hz), 7.56 (1H, d, J=8.3 Hz), 7.71 (1H, d, J=8.7 Hz), 8.62-8.66 (1H, m)

1-(2-(4-((quinolin-2-yl)methylamino)piperidin-1-yl)ethyl)-7-methoxy-N-methyl-2-oxo-1,2-dihydroquinoline-4-carboxamide $^1$H-NMR (DMSO-$d_6$) δ:
1.28-1.37 (2H, m), 1.79-1.87 (2H, m), 2.01-2.09 (2H, m), 2.43-2.55 (3H, m), 2.79 (3H, d, J=4.6 Hz), 2.90-2.98 (2H, m), 3.90 (3H, s), 4.00 (2H, s), 4.33-4.39 (2H, m), 6.41 (1H, s), 6.91 (1H, dd, J=8.7, 2.3 Hz), 7.00 (1H, d, J=2.3 Hz), 7.55 (1H, t, J=7.6 Hz), 7.64 (1H, d, J=8.7 Hz), 7.69-7.74 (2H, m), 7.91-7.98 (2H, m), 8.30 (1H, d, J=8.7 Hz), 8.62-8.67 (1H, m)

1-(2-(4-(([1,8]naphthylidin-2-yl)methylamino)piperidin-1-yl)ethyl)-7-methoxy-N-methyl-2-oxo-1,2-dihydroquinoline-4-carboxamide $^1$H-NMR (DMSO-$d_6$) δ:
1.22-1.34 (2H, m), 1.72-1.87 (2H, m), 2.02-2.10 (2H, m), 2.44-2.55 (3H, m), 2.79 (3H, d, J=4.6 Hz), 2.89-2.97 (2H, m), 3.89-3.91 (5H, m), 4.34-4.38 (2H, m), 6.41 (1H, s), 6.89-6.95 (1H, m), 7.00 (1H, d, J=2.3 Hz), 7.59 (1H, dd, J=8.3, 4.4 Hz), 7.71 (1H, d, J=8.7 Hz), 7.75 (1H, d, J=8.3 Hz), 8.39-8.46 (2H, m), 8.61-8.68 (1H, m), 9.04 (1H, dd, J=4.4, 2.1 Hz)

1-(2-(4-((1-methylindol-2-yl)methylamino)piperidin-1-yl)ethyl)-7-methoxy-N-methyl-2-oxo-1,2-dihydroquinoline-4-carboxamide $^1$H-NMR (DMSO-$d_6$) δ:
1.26-1.34 (2H, m), 1.80-1.88 (2H, m), 2.03-2.11 (2H, m), 2.43-2.54 (3H, m), 2.79 (3H, d, J=4.6 Hz), 2.90-2.98 (2H, m), 3.74 (3H, s), 3.89 (2H, s), 3.90 (3H, s), 4.34-4.38 (2H, m), 6.32 (1H, s), 6.41 (1H, s), 6.91 (1H, dd, J=8.7, 2.3 Hz), 6.97 (1H, t, J=7.8 Hz), 7.00 (1H, d, J=2.3 Hz), 7.08 (1H, t, J=7.8

Hz), 7.38 (1H, d, J=7.8 Hz), 7.45 (1H, d, J=7.8 Hz), 7.71 (1H, d, J=8.7 Hz), 8.61-8.67 (1H, m)

1-(2-(4-((2H-chromen-3-yl)methylamino)piperidin-1-yl)ethyl)-7-methoxy-N-methyl-2-oxo-1,2-dihydroquinoline-4-carboxamide ¹H-NMR (DMSO-d₆) δ:
1.20-1.30 (2H, m), 1.76-1.84 (2H, m), 2.02-2.10 (2H, m), 2.35-2.55 (3H, m), 2.79 (3H, d, J=4.6 Hz), 2.89-2.97 (2H, m), 3.25 (2H, s), 3.90 (3H, s), 4.33-4.39 (2H, m), 4.71 (2H, s), 6.36 (1H, s), 6.41 (1H, s), 6.73 (1H, d, J=7.8 Hz), 6.84 (1H, t, J=7.8 Hz), 6.91 (1H, dd, J=8.7, 2.3 Hz), 6.99-7.08 (3H, m), 7.71 (1H, d, J=8.7 Hz), 8.61-8.67 (1H, m)

1-(2-(4-((8-hydroxyquinolin-2-yl)methylamino)piperidin-1-yl)ethyl)-7-methoxy-N-methyl-2-oxo-1,2-dihydroquinoline-4-carboxamide ¹H-NMR (DMSO-d₆) δ:
1.31-1.39 (2H, m), 1.82-1.90 (2H, m), 2.02-2.10 (2H, m), 2.42-2.54 (3H, m), 2.79 (3H, d, J=4.6 Hz), 2.92-3.00 (2H, m), 3.90 (3H, s), 4.01 (2H, s), 4.33-4.39 (2H, m), 6.41 (1H, s), 6.91 (1H, dd, J=8.7, 2.3 Hz), 7.01 (1H, d, J=2.3 Hz), 7.07 (1H, d, J=7.8 Hz), 7.33-7.41 (2H, m), 7.56 (1H, d, J=7.8 Hz), 7.71 (1H, d, J=8.7 Hz), 8.23 (1H, d, J=8.7 Hz), 8.62-8.66 (1H, m)

1-(2-(4-((3-methylbenzo[b]thiophen-2-yl)methylamino)piperidin-1-yl)ethyl)-7-methoxy-N-methyl-2-oxo-1,2-dihydroquinoline-4-carboxamide ¹H-NMR (DMSO-d₆) δ:
1.27-1.34 (2H, m), 1.81-1.86 (2H, m), 2.02-2.10 (2H, m), 2.31 (3H, s), 2.43-2.54 (3H, m), 2.79 (3H, d, J=4.6 Hz), 2.90-2.98 (2H, m), 3.90 (3H, s), 3.98 (2H, s), 4.33-4.38 (2H, m), 6.41 (1H, s), 6.91 (1H, dd, J=8.7, 2.3 Hz), 7.00 (1H, d, J=2.3 Hz), 7.28 (1H, t, J=7.6 Hz), 7.35 (1H, t, J=7.6 Hz), 7.67 (1H, d, J=7.8 Hz), 7.71 (1H, d, J=8.7 Hz), 7.85 (1H, d, J=7.6 Hz), 8.61-8.66 (1H, m)

1-(2-(4-((4-methoxybenzo[1,3]dioxol-6-yl)methylamino)piperidin-1-yl)ethyl)-7-methoxy-N-methyl-2-oxo-1,2-dihydroquinoline-4-carboxamide ¹H-NMR (DMSO-d₆) δ:
1.17-1.26 (2H, m), 1.70-1.77 (2H, m), 1.96-2.04 (2H, m), 2.29-2.51 (3H, m), 2.75 (3H, d, J=4.6 Hz), 2.85-2.93 (2H, m), 3.57 (2H, s), 3.77 (3H, s), 3.87 (3H, s), 4.28-4.35 (2H, m), 5.90 (2H, s), 6.38 (1H, s), 6.55 (1H, s), 6.58 (1H, s), 6.88 (1H, dd, J=8.7, 2.3 Hz), 6.97 (1H, d, J=2.3 Hz), 7.68 (1H, d, J=8.7 Hz), 8.57-8.64 (1H, m)

1-(2-(4-((6-methoxy-2H-chromen-3-yl)methylamino)piperidin-1-yl)ethyl)-7-methoxy-N-methyl-2-oxo-1,2-dihydroquinoline-4-carboxamide ¹H-NMR (DMSO-d₆) δ:
1.20-1.29 (2H, m), 1.76-1.84 (2H, m), 2.02-2.10 (2H, m), 2.35-2.54 (3H, m), 2.79 (3H, d, J=4.6 Hz), 2.89-2.97 (2H, m), 3.25 (2H, s), 3.68 (3H, s), 3.90 (3H, s), 4.32-4.38 (2H, m), 4.63 (2H, s), 6.35 (1H, s), 6.41 (1H, s), 6.61-6.69 (3H, m), 6.91 (1H, dd, J=8.7, 2.3 Hz), 7.00 (1H, d, J=2.3 Hz), 7.71 (1H, d, J=8.7 Hz), 8.61-8.67 (1H, m)

1-(2-(4-((1-chloro-3,4-dihydronaphthalen-2-yl)methylamino)piperidin-1-yl)ethyl)-7-methoxy-N-methyl-2-oxo-1,2-dihydroquinoline-4-carboxamide ¹H-NMR (DMSO-d₆) δ:
1.22-1.32 (2H, m), 1.77-1.85 (2H, m), 2.02-2.10 (2H, m), 2.34-2.55 (5H, m), 2.75-2.80 (5H, m), 2.89-2.97 (2H, m), 3.54 (2H, s), 3.90 (3H, s), 4.31-4.39 (2H, m), 6.41 (1H, s), 6.91 (1H, dd, J=8.7, 2.3 Hz), 7.00 (1H, d, J=2.3 Hz), 7.17-7.30 (3H, m), 7.49 (1H, d, J=8.7 Hz), 7.71 (1H, d, J=8.7 Hz), 8.60-8.67 (1H, m)

1-(2-(4-((3,4-dimethylthieno[2,3-b]thiophen-2-yl)methylamino)piperidin-1-yl)ethyl)-7-methoxy-N-methyl-2-oxo-1,2-dihydroquinoline-4-carboxamide ¹H-NMR (DMSO-d₆) δ:
1.23-1.31 (2H, m), 1.78-1.85 (2H, m), 2.02-2.10 (2H, m), 2.35 (3H, s), 2.42-2.55 (6H, m), 2.79 (3H, d, J=4.6 Hz), 2.90-2.98 (2H, m), 3.87 (2H, s), 3.90 (3H, s), 4.32-4.38 (2H, m), 6.41 (1H, s), 6.91 (1H, dd, J=8.7, 2.3 Hz), 7.00 (1H, d, J=2.3 Hz), 7.07 (1H, s), 7.71 (1H, d, J=8.7 Hz), 8.62-8.66 (1H, m)

1-(2-(4-((3-chlorobenzo[b]thiophen-2-yl)methylamino)piperidin-1-yl)ethyl)-7-methoxy-N-methyl-2-oxo-1,2-dihydroquinoline-4-carboxamide ¹H-NMR (DMSO-d₆) δ:
1.27-1.34 (2H, m), 1.78-1.86 (2H, m), 2.02-2.10 (2H, m), 2.42-2.55 (3H, m), 2.79 (3H, d, J=4.6 Hz), 2.90-2.98 (2H, m), 3.90 (3H, s), 4.06 (2H, s), 4.34-4.38 (2H, m), 6.41 (1H, s), 6.91 (1H, dd, J=8.7, 2.3 Hz), 7.00 (1H, d, J=2.3 Hz), 7.40-7.44 (1H, m), 7.46-7.49 (1H, m), 7.71 (2H, d, J=8.7 Hz), 7.98 (1H, d, J=8.7 Hz), 8.61-8.66 (1H, m)

1-(2-(4-((2-chloro-6-methylquinolin-3-yl)methylamino)piperidin-1-yl)ethyl)-7-methoxy-N-methyl-2-oxo-1,2-dihydroquinoline-4-carboxamide ¹H-NMR (DMSO-d₆) δ:
1.27-1.36 (2H, m), 1.80-1.87 (2H, m), 2.01-2.09 (2H, m), 2.42-2.51 (6H, m), 2.76 (3H, d, J=4.6 Hz), 2.89-2.97 (2H, m), 3.87 (5H, s), 4.31-4.37 (2H, m), 6.38 (1H, s), 6.88 (1H, dd, J=8.7, 2.3 Hz), 6.97 (1H, d, J=2.3 Hz), 7.58 (1H, dd, J=8.7, 2.3 Hz), 7.68 (1H, d, J=8.7 Hz), 7.77 (1H, s), 7.80 (1H, d, J=8.7 Hz), 8.33 (1H, s), 8.55-8.64 (1H, m)

1-(2-(4-((2-chloro-6-methoxyquinolin-3-yl)methylamino)piperidin-1-yl)ethyl)-7-methoxy-N-methyl-2-oxo-1,2-dihydroquinoline-4-carboxamide ¹H-NMR (DMSO-d₆) δ:
1.31-1.39 (2H, m), 1.83-1.91 (2H, m), 2.05-2.13 (2H, m), 2.45-2.55 (3H, m), 2.79 (3H, d, J=4.6 Hz), 2.93-3.01 (2H, m), 3.88-3.92 (8H, m), 4.33-4.40 (2H, m), 6.42 (1H, s), 6.92 (1H, dd, J=8.7, 2.3 Hz), 7.01 (1H, d, J=2.3 Hz), 7.40 (1H, dd, J=9.2, 2.8 Hz), 7.46 (1H, d, J=2.8 Hz), 7.72 (1H, d, J=8.7 Hz), 7.84 (1H, d, J=9.2 Hz), 8.38 (1H, s), 8.62-8.67 (1H, m)

1-(2-(4-((4-chloro-6-fluoro-2H-thiochromen-3-yl)methylamino)piperidin-1-yl)ethyl)-7-methoxy-N-methyl-2-oxo-1,2-dihydroquinoline-4-carboxamide ¹H-NMR (DMSO-d₆) δ:
1.23-1.31 (2H, m), 1.76-1.84 (2H, m), 2.02-2.10 (2H, m), 2.38-2.54 (3H, m), 2.79 (3H, d, J=4.6 Hz), 2.89-2.97 (2H, m), 3.62 (2H, s), 3.65 (2H, s), 3.90 (3H, s), 4.32-4.38 (2H, m), 6.41 (1H, s), 6.91 (1H, dd, J=8.7, 2.3 Hz), 7.00 (1H, d, J=2.3 Hz), 7.10-7.15 (1H, m), 7.35-7.41 (2H, m), 7.71 (1H, d, J=8.7 Hz), 8.61-8.66 (1H, m)

1-(2-(4-((6-bromobenzo[1,3]dioxol-5-yl)methylamino)piperidin-1-yl)ethyl)-7-methoxy-N-methyl-2-oxo-1,2-dihydroquinoline-4-carboxamide $^1$H-NMR (DMSO-$d_6$) δ:
1.23-1.31 (2H, m), 1.75-1.83 (2H, m), 2.02-2.10 (2H, m), 2.33-2.54 (3H, m), 2.79 (3H, d, J=4.6 Hz), 2.89-2.97 (2H, m), 3.66 (2H, s), 3.90 (3H, s), 4.33-4.39 (2H, m), 6.04 (2H, s), 6.41 (1H, s), 6.91 (1H, dd, J=8.7, 2.3 Hz), 7.00 (1H, d, J=2.3 Hz), 7.12 (1H, s), 7.15 (1H, s), 7.71 (1H, d, J=8.7 Hz), 8.61-8.67 (1H, m)

1-(2-(4-((1-methyl-3-(trifluoromethyl)-1H-thieno[2,3-c]pyrazol-5-yl)methylamino)piperidin-1-yl)ethyl)-7-methoxy-N-methyl-2-oxo-1,2-dihydroquinoline-4-carboxamide $^1$H-NMR (DMSO-$d_6$) δ:
1.23-1.31 (2H, m), 1.77-1.85 (2H, m), 2.00-2.08 (2H, m), 2.40-2.54 (3H, m), 2.79 (3H, d, J=4.6 Hz), 2.89-2.97 (2H, m), 3.90 (3H, s), 3.93 (2H, s), 4.02 (3H, s), 4.33-4.38 (2H, m), 6.41 (1H, s), 6.91 (1H, dd, J=8.7, 2.3 Hz), 6.95 (1H, s), 7.00 (1H, d, J=2.3 Hz), 7.71 (1H, d, J=8.7 Hz), 8.61-8.66 (1H, m)

1-(2-(4-((E,E)-2,4-hexadienylamino)piperidin-1-yl)ethyl)-7-methoxy-N-methyl-2-oxo-1,2-dihydroquinoline-4-carboxamide $^1$H-NMR (DMSO-$d_6$) δ:
1.16-1.27 (2H, m), 1.67-1.79 (5H, m), 2.01-2.10 (2H, m), 2.33-2.56 (3H, m), 2.79 (3H, d, J=4.6 Hz), 2.88-2.96 (2H, m), 3.11-3.20 (2H, m), 3.90 (3H, s), 4.31-4.40 (2H, m), 5.53-5.66 (2H, m), 5.97-6.13 (2H, m), 6.41 (1H, s), 6.91 (1H, dd, J=8.7, 2.3 Hz), 7.00 (1H, d, J=2.3 Hz), 7.71 (1H, d, J=8.7 Hz), 8.59-8.68 (1H, m)

1-(2-(4-heptylaminopiperidin-1-yl)ethyl)-7-methoxy-N-methyl-2-oxo-1,2-dihydroquinoline-4-carboxamide $^1$H-NMR (DMSO-$d_6$) δ:
0.86 (3H, t, J=7.1 Hz), 1.15-1.40 (12H, m), 1.71-1.79 (2H, m), 2.02-2.10 (2H, m), 2.30-2.54 (5H, m), 2.79 (3H, d, J=4.6 Hz), 2.88-2.96 (2H, m), 3.90 (3H, s), 4.32-4.39 (2H, m), 6.41 (1H, s), 6.91 (1H, dd, J=8.7, 2.3 Hz), 7.00 (1H, d, J=2.3 Hz), 7.71 (1H, d, J=8.7 Hz), 8.62-8.67 (1H, m)

1-(2-(4-((E)-3-(2-furyl)allylamino)piperidin-1-yl)ethyl)-7-methoxy-N-methyl-2-oxo-1,2-dihydroquinoline-4-carboxamide $^1$H-NMR (DMSO-$d_6$) δ:
1.20-1.28 (2H, m), 1.74-1.82 (2H, m), 2.02-2.10 (2H, m), 2.38-2.54 (3H, m), 2.79 (3H, d, J=4.6 Hz), 2.89-2.97 (2H, m), 3.27-3.31 (2H, m), 3.90 (3H, s), 4.33-4.38 (2H, m), 6.08-6.15 (1H, m), 6.32-6.47 (4H, m), 6.91 (1H, dd, J=8.7, 2.3 Hz), 7.01 (1H, d, J=2.3 Hz), 7.57 (1H, s), 7.71 (1H, d, J=8.7 Hz), 8.61-8.67 (1H, m)

1-(2-(4-(octa-2-ynylamino)piperidin-1-yl)ethyl)-7-methoxy-N-methyl-2-oxo-1,2-dihydroquinoline-4-carboxamide $^1$H-NMR (DMSO-$d_6$) δ:
0.87 (3H, t, J=7.3 Hz), 1.17-1.46 (8H, m), 1.69-1.77 (2H, m), 2.02-2.10 (2H, m), 2.13-2.17 (2H, m), 2.47-2.59 (3H, m), 2.79 (3H, d, J=4.6 Hz), 2.88-2.96 (2H, m), 3.27-3.30 (2H, m), 3.90 (3H, s), 4.32-4.38 (2H, m), 6.41 (1H, s), 6.91 (1H, dd, J=8.7, 2.3 Hz), 7.01 (1H, d, J=2.3 Hz), 7.71 (1H, d, J=8.7 Hz), 8.61-8.67 (1H, m)

1-(2-(4-((E)-(3-phenyl)allylamino)piperidin-1-yl)ethyl)-7-methoxy-N-methyl-2-oxo-1,2-dihydroquinoline-4-carboxamide $^1$H-NMR (DMSO-$d_6$) δ:
1.19-1.30 (2H, m), 1.76-1.84 (2H, m), 2.03-2.11 (2H, m), 2.41-2.54 (3H, m), 2.79 (3H, d, J=4.6 Hz), 2.90-2.98 (2H, m), 3.34-3.37 (2H, m), 3.90 (3H, s), 4.32-4.39 (2H, m), 6.28-6.35 (1H, m), 6.42 (1H, s), 6.51 (1H, d, J=16.0 Hz), 6.91 (1H, dd, J=8.7, 2.3 Hz), 7.01 (1H, t, J=2.3 Hz), 7.21 (1H, t, J=7.6 Hz), 7.31 (2H, t, J=7.6 Hz), 7.40 (2H, d, J=7.6 Hz), 7.71 (1H, d, J=8.7 Hz), 8.61-8.67 (1H, m)

1-(2-(4-(3-phenylpropylamino)piperidin-1-yl)ethyl)-7-methoxy-N-methyl-2-oxo-1,2-dihydroquinoline-4-carboxamide $^1$H-NMR (DMSO-$d_6$) δ:
1.17-1.25 (2H, m), 1.63-1.70 (2H, m), 1.70-1.78 (2H, m), 2.01-2.09 (2H, m), 2.30-2.54 (5H, m), 2.57-2.63 (2H, m), 2.79 (3H, d, J=4.6 Hz), 2.88-2.96 (2H, m), 3.90 (3H, s), 4.31-4.39 (2H, m), 6.41 (1H, s), 6.91 (1H, dd, J=8.7, 2.3 Hz), 7.00 (1H, d, J=2.3 Hz), 7.13-7.21 (3H, m), 7.27 (2H, t, J=7.3 Hz), 7.71 (1H, d, J=8.7 Hz), 8.61-8.67 (1H, m)

1-(2-(4-((E)-2-methyl-3-(2-furyl)allylamino)piperidin-1-yl)ethyl)-7-methoxy-N-methyl-2-oxo-1,2-dihydroquinoline-4-carboxamide $^1$H-NMR (DMSO-$d_6$) δ:
1.21-1.29 (2H, m), 1.75-1.81 (2H, m), 1.92 (3H, s), 2.02-2.10 (2H, m), 2.33-2.54 (3H, m), 2.79 (3H, d, J=4.6 Hz), 2.90-2.95 (2H, m), 3.21 (2H, s), 3.90 (3H, s), 4.33-4.38 (2H, m), 6.28 (1H, s), 6.34 (1H, d, J=3.7 Hz), 6.41 (1H, s), 6.47-6.49 (1H, m), 6.91 (1H, dd, J=8.7, 2.3 Hz), 7.00 (1H, d, J=2.3 Hz), 7.59 (1H, s), 7.71 (1H, d, J=8.7 Hz), 8.61-8.67 (1H, m)

1-(2-(4-((E)-2-methyl-3-phenylallylamino)piperidin-1-yl)ethyl)-7-methoxy-N-methyl-2-oxo-1,2-dihydroquinoline-4-carboxamide $^1$H-NMR (DMSO-$d_6$) δ:
1.24-1.31 (2H, m), 1.79-1.84 (5H, m), 2.05-2.10 (2H, m), 2.38-2.54 (3H, m), 2.79 (3H, d, J=4.6 Hz), 2.92-2.96 (2H, m), 3.24 (2H, s), 3.90 (3H, s), 4.35-4.38 (2H, m), 6.41-6.43 (2H, m), 6.92 (1H, dd, J=8.7, 2.3 Hz), 7.01 (1H, d, J=2.3 Hz), 7.20 (1H, t, J=7.6 Hz), 7.26 (2H, d, J=7.6 Hz), 7.33 (2H, t, J=7.6 Hz), 7.71 (1H, d, J=8.7 Hz), 8.62-8.66 (1H, m)

1-(2-(4-(3-phenylbutylamino)piperidin-1-yl)ethyl)-7-methoxy-N-methyl-2-oxo-1,2-dihydroquinoline-4-carboxamide $^1$H-NMR (DMSO-$d_6$) δ:
1.13-1.19 (5H, m), 1.66 (4H, m), 1.98-2.06 (2H, m), 2.23-2.54 (5H, m), 2.75-2.80 (4H, m), 2.86-2.91 (2H, m), 3.90 (3H, s), 4.32-4.37 (2H, m), 6.41 (1H, s), 6.91 (1H, dd, J=8.7, 2.3 Hz), 6.99 (1H, d, J=2.3 Hz), 7.16 (1H, t, J=7.6 Hz), 7.20 (2H, d, J=7.6 Hz), 7.28 (2H, t, J=7.6 Hz), 7.71 (1H, d, J=8.7 Hz), 8.61-8.68 (1H, m)

7-methoxy-N-methyl-1-(2-(4-((naphthalen-1-ylmethyl)amino)piperidin-1-yl)ethyl)-2-oxo-1,2-dihydroquinoline-4-carboxamide $^1$H-NMR (DMSO-$d_6$) δ:
1.31-1.38 (2H, m), 1.86-1.94 (2H, m), 2.05-2.13 (2H, m), 2.47-2.55 (3H, m), 2.79 (3H, d, J=4.6 Hz), 2.92-3.00 (2H, m), 3.91 (3H, s), 4.16 (2H, s), 4.35-4.40 (2H, m), 6.43 (1H, s), 6.92 (1H, dd, J=8.7, 2.3 Hz), 7.01 (1H, d, J=2.3 Hz), 7.44 (1H, t, J=8.3 Hz), 7.48-7.55 (3H, m), 7.72 (1H, d, J=8.7 Hz), 7.80 (1H, d, J=8.7 Hz), 7.91 (1H, d, J=8.3 Hz), 8.18 (1H, d, J=8.3 Hz), 8.62-8.67 (1H, m)

1-(2-(4-((E)-(3-(2-methoxyphenyl)allylamino)piperidin-1-yl)ethyl)-7-methoxy-N-methyl-2-oxo-1,2-dihydroquinoline-4-carboxamide ¹H-NMR (DMSO-d₆) δ:
1.18-1.30 (2H, m), 1.76-1.84 (2H, m), 2.03-2.11 (2H, m), 2.41-2.54 (3H, m), 2.79 (3H, d, J=4.6 Hz), 2.90-2.97 (2H, m), 3.30-3.35 (2H, m), 3.79 (3H, s), 3.91 (3H, s), 4.34-4.39 (2H, m), 6.22-6.29 (1H, m), 6.42 (1H, s), 6.73 (1H, d, J=16.0 Hz), 6.87-7.02 (4H, m), 7.18-7.24 (1H, m), 7.44 (1H, dd, J=7.6, 1.6 Hz), 7.71 (1H, d, J=8.7 Hz), 8.61-8.67 (1H, m)

1-(2-(4-((5-phenylfuran-2-yl)methylamino)piperidin-1-yl)ethyl)-7-methoxy-N-methyl-2-oxo-1,2-dihydroquinoline-4-carboxamide ¹H-NMR (DMSO-d₆) δ:
1.23-1.31 (2H, m), 1.77-1.85 (2H, m), 2.02-2.10 (2H, m), 2.41-2.53 (3H, m), 2.79 (3H, d, J=4.6 Hz), 2.90-2.98 (2H, m), 3.76 (2H, s), 3.90 (3H, s), 4.34-4.38 (2H, m), 6.34 (1H, d, J=3.2 Hz), 6.41 (1H, s), 6.84 (1H, d, J=3.2 Hz), 6.91 (1H, dd, J=8.7, 2.3 Hz), 7.00 (1H, d, J=2.3 Hz), 7.26 (1H, t, J=7.8 Hz), 7.40 (2H, t, J=7.8 Hz), 7.66 (2H, d, J=7.8 Hz), 7.71 (1H, d, J=8.7 Hz), 8.62-8.67 (1H, m)

1-(2-(4-(4-(1-pyrrolidino)benzylamino)piperidin-1-yl)ethyl)-7-methoxy-N-methyl-2-oxo-1,2-dihydroquinoline-4-carboxamide ¹H-NMR (DMSO-d₆) δ:
1.20-1.30 (2H, m), 1.74-1.79 (2H, m), 1.92-1.95 (4H, m), 1.99-2.07 (2H, m), 2.32-2.54 (3H, m), 2.79 (3H, d, J=4.6 Hz), 2.88-2.96 (2H, m), 3.16-3.20 (4H, m), 3.57 (2H, s), 3.90 (3H, s), 4.32-4.38 (2H, m), 6.41 (1H, s), 6.46 (2H, d, J=8.3 Hz), 6.91 (1H, dd, J=8.7, 2.3 Hz), 7.00 (1H, d, J=2.3 Hz), 7.10 (2H, d, J=8.3 Hz), 7.71 (1H, d, J=8.7 Hz), 8.62-8.67 (1H, m)

1-(2-(4-(2-fluoro-5-(trifluoromethyl)benzylamino)piperidin-1-yl)ethyl)-7-methoxy-N-methyl-2-oxo-1,2-dihydroquinoline-4-carboxamide ¹H-NMR (DMSO-d₆) δ:
1.24-1.32 (2H, m), 1.77-1.83 (2H, m), 2.02-2.10 (2H, m), 2.36-2.54 (3H, m), 2.79 (3H, d, J=4.6 Hz), 2.90-2.98 (2H, m), 3.81 (2H, s), 3.90 (3H, s), 4.33-4.38 (2H, m), 6.41 (1H, s), 6.91 (1H, dd, J=8.7, 2.3 Hz), 7.00 (1H, d, J=2.3 Hz), 7.38 (1H, t, J=9.2 Hz), 7.65-7.69 (1H, m), 7.71 (1H, d, J=8.7 Hz), 7.88-7.91 (1H, m), 8.61-8.67 (1H, m)

1-(2-(4-((2,2'-bithiophen-5-yl)methylamino)piperidin-1-yl)ethyl)-7-methoxy-N-methyl-2-oxo-1,2-dihydroquinoline-4-carboxamide ¹H-NMR (DMSO-d₆) δ:
1.23-1.30 (2H, m), 1.76-1.84 (2H, m), 2.01-2.09 (2H, m), 2.41-2.54 (3H, m), 2.79 (3H, d, J=4.6 Hz), 2.90-2.98 (2H, m), 3.87-3.92 (5H, m), 4.33-4.38 (2H, m), 6.41 (1H, s), 6.88 (1H, d, J=3.7 Hz), 6.91 (1H, dd, J=8.7, 2.3 Hz), 7.00 (1H, d, J=2.3 Hz), 7.06 (1H, dd, J=5.3, 3.7 Hz), 7.10 (1H, d, J=3.7 Hz), 7.22 (1H, dd, J=3.7, 0.9 Hz), 7.45 (1H, dd, J=5.0, 0.9 Hz), 7.71 (1H, d, J=8.7 Hz), 8.62-8.67 (1H, m)

1-(2-(4-((phenanthren-9-yl)methylamino)piperidin-1-yl)ethyl)-7-methoxy-N-methyl-2-oxo-1,2-dihydroquinoline-4-carboxamide ¹H-NMR (DMSO-d₆) δ:
1.35-1.42 (2H, m), 1.90-1.98 (2H, m), 2.07-2.15 (2H, m), 2.46-2.60 (3H, m), 2.79 (3H, d, J=5.0 Hz), 2.94-3.02 (2H, m), 3.91 (3H, s), 4.22 (2H, s), 4.35-4.40 (2H, m), 6.42 (1H, s), 6.92 (1H, dd, J=8.7, 2.3 Hz), 7.02 (1H, d, J=2.3 Hz), 7.60-7.73 (5H, m), 7.85 (1H, s), 7.95 (1H, d, J=8.3 Hz), 8.27 (1H, d, J=8.3 Hz), 8.62-8.67 (1H, m), 8.79 (1H, d, J=8.3 Hz), 8.85 (1H, d, J=8.3 Hz)

1-(2-(4-((2,3-dihydro-5-oxo-(1H,5H)-benzo[IJ]quinolin-6-yl)methylamino)piperidin-1-yl)ethyl)-7-methoxy-N-methyl-2-oxo-1,2-dihydroquinoline-4-carboxamide ¹H-NMR (DMSO-d₆) δ:
1.26-1.34 (2H, m), 1.79-1.87 (2H, m), 1.99-2.04 (2H, m), 2.05-2.12 (2H, m), 2.40-2.54 (3H, m), 2.79 (3H, d, J=4.6 Hz), 2.90-2.97 (4H, m), 3.63 (2H, s), 3.90 (3H, s), 4.05-4.09 (2H, m), 4.32-4.39 (2H, m), 6.42 (1H, s), 6.91 (1H, dd, J=8.7, 2.3 Hz), 7.01 (1H, d, J=2.3 Hz), 7.14 (1H, t, J=7.8 Hz), 7.33 (1H, d, J=7.8 Hz), 7.53 (1H, d, J=7.8 Hz), 7.71 (1H, d, J=8.7 Hz), 7.85 (1H, s), 8.61-8.67 (1H, m)

1-(2-(4-(2-(4-benzylpiperazino)benzylamino)piperidin-1-yl)ethyl)-7-methoxy-N-methyl-2-oxo-1,2-dihydroquinoline-4-carboxamide ¹H-NMR (DMSO-d₆) δ:
1.21-1.31 (2H, m), 1.75-1.83 (2H, m), 2.02-2.10 (2H, m), 2.34-2.55 (7H, m), 2.79 (3H, d, J=4.6 Hz), 2.85-2.95 (6H, m), 3.53 (2H, s), 3.70 (2H, s), 3.90 (3H, s), 4.33-4.39 (2H, m), 6.42 (1H, s), 6.91 (1H, dd, J=8.7, 2.3 Hz), 6.99-7.03 (2H, m), 7.06 (1H, d, J=7.8 Hz), 7.18 (1H, t, J=7.8 Hz), 7.24-7.28 (1H, m), 7.31-7.38 (5H, m), 7.72 (1H, d, J=8.7 Hz), 8.62-8.67 (1H, m)

Example 336

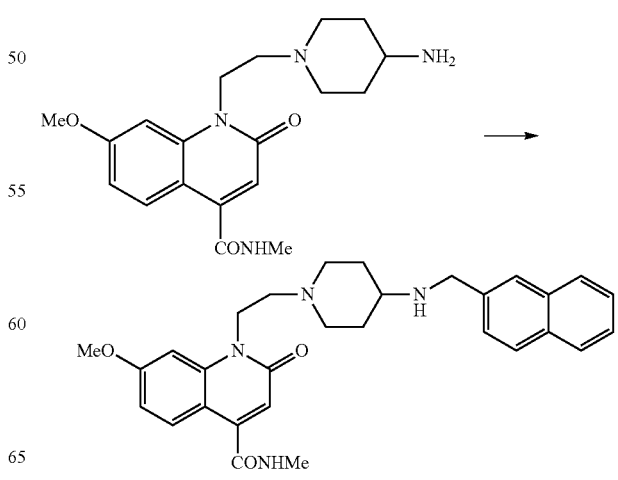

To 4 mL of a methanol solution containing 0.14 g of 1-(2-(4-aminopiperidin-1-yl)ethyl)-7-methoxy-N-methyl-2-oxo-1,2-dihydroquinoline-4-carboxamide, 55 mg of 2-naphthoaldehyde and 40 μL of acetic acid were added, and stirred at room temperature for 80 min. To the reaction mixture, 52 mg of sodium cyanoborohydride was added, and stirred at the same temperature for 75 min. After the solvent was removed under reduced pressure, chloroform and aqueous saturated sodium hydrogen carbonate solution were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform:methanol=30:1], to give 0.21 g of 7-methoxy-N-methyl-1-(2-(4-((naphthalen-2-ylmethyl)amino)piperidin-1-yl)ethyl)-2-oxo-1,2-dihydroquinoline-4-carboxamide as a yellow foam.

$^1$H-NMR (CDCl$_3$) δ:
1.37-1.70 (2H, m), 1.86-2.02 (2H, m), 2.06-2.22 (2H, m), 2.49-2.64 (3H, m), 2.89-3.02 (2H, m), 3.05 (3H, d, J=4.4 Hz), 3.89 (3H, s), 3.99 (2H, s), 4.22-4.36 (2H, m), 6.43 (1H, m), 6.54 (1H, s), 6.79-6.90 (2H, m), 7.42-7.52 (3H, m), 7.73-7.90 (5H, m)

Example 337

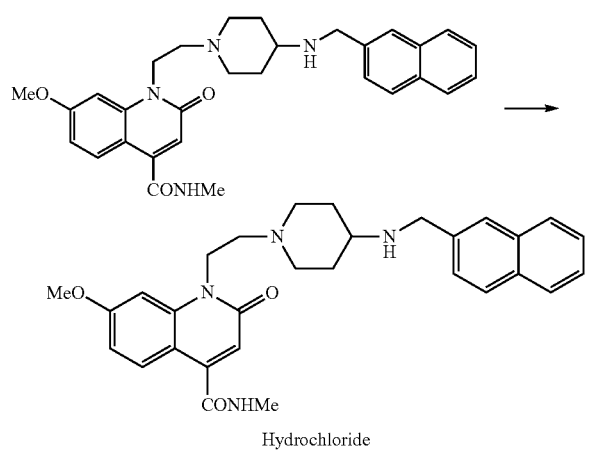

To a mixed solution of 1 mL ethyl acetate and 2 mL methanol containing 0.20 g of 7-methoxy-N-methyl-1-(2-(4-((naphthalen-2-ylmethyl)amino)piperidin-1-yl)ethyl)-2-oxo-1,2-dihydroquinoline-4-carboxamide, 1 mL of 4 mol/L hydrogen chloride/ethyl acetate was added at room temperature, and the solvent was removed under reduced pressure. Ethyl acetate was added to the residue thus obtained, and the resulting solid was filtered to give 0.16 g of 7-methoxy-N-methyl-1-(2-(4-((naphthalen-2-ylmethyl)amino)piperidin-1-yl)ethyl)-2-oxo-1,2-dihydroquinoline-4-carboxamide hydrochloride as a pale yellow solid.

$^1$H-NMR (DMSO-d$_6$) δ:
2.09-2.19 (2H, m), 2.41-2.47 (2H, m), 2.81 (3H, d, J=4.6 Hz), 3.09-3.17 (2H, m), 3.23-3.31 (3H, m), 3.80-3.86 (2H, m), 3.98 (3H, s), 4.37 (2H, t, J=5.5 Hz), 4.70-4.76 (2H, m), 6.47 (1H, s), 6.97 (1H, dd, J=8.7, 1.8 Hz), 7.21 (1H, d, J=1.8 Hz), 7.57-7.60 (2H, m), 7.75 (1H, d, J=8.7 Hz), 7.77 (1H, dd, J=8.7, 1.8 Hz), 7.92-7.98 (2H, m), 8.00 (1H, d, J=8.3 Hz), 8.14 (1H, s), 8.68 (1H, m), 9.70-9.91 (2H, broad), 11.18-11.58 (1H, broad)

Example 338

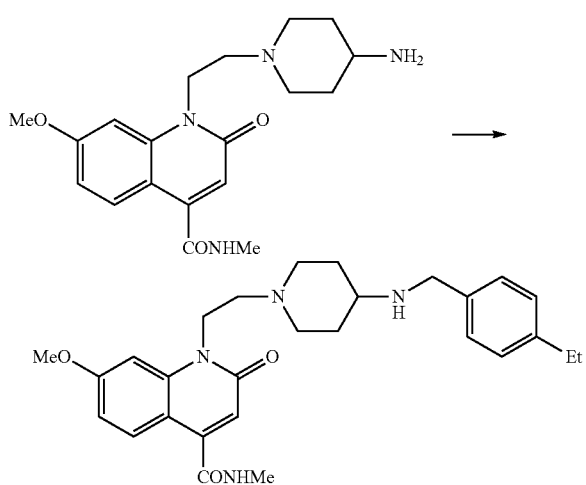

To 4 mL of a methanol solution containing 0.14 g of 1-(2-(4-aminopiperidin-1-yl)ethyl)-7-methoxy-N-methyl-2-oxo-1,2-dihydroquinoline-4-carboxamide, 48 mg of 4-ethylbenzaldehyde and 40 μL of acetic acid were added, and stirred at room temperature for 80 min. To the reaction mixture, 52 mg of sodium cyanoborohydride was added, and stirred at the same temperature for 75 min. After the solvent was removed under reduced pressure, chloroform and aqueous saturated sodium hydrogen carbonate solution were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform:methanol=30:1], to give 0.14 g of 1-(2-(4-(4-ethylbenzylamino)piperidin-1-yl)ethyl)-7-methoxy-N-methyl-2-oxo-1,2-dihydroquinoline-4-carboxamide as a pale yellow solid.

$^1$H-NMR (CDCl$_3$) δ:
1.14-1.30 (3H, t, J=7.9 Hz), 1.37-1.53 (2H, m), 1.84-1.98 (2H, m), 2.08-2.24 (2H, m), 2.45-2.70 (3H, m), 2.60 (2H, q, J=7.9 Hz), 2.91-3.02 (2H, m), 3.05 (3H, d, J=4.8 Hz), 3.79 (2H, s), 3.90 (3H, s), 4.27-4.38 (2H, m), 6.25-6.36 (1H, m), 6.55 (1H, s), 6.79-6.93 (2H, m), 7.08-7.25 (4H, m), 7.88 (1H, d, J=8.8 Hz)

Example 339

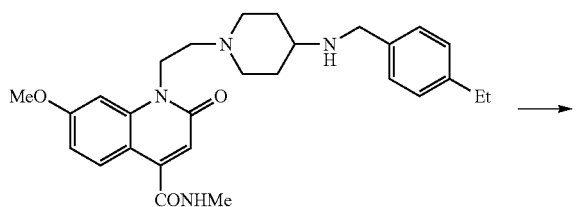

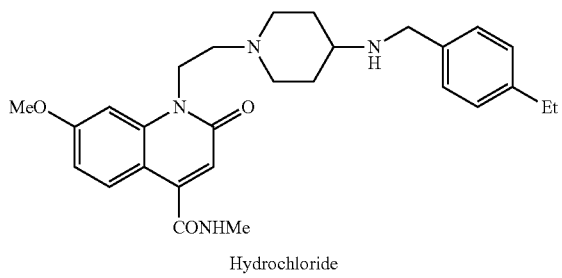
Hydrochloride

To 2 mL of a methanol solution containing 0.14 g of 1-(2-(4-(4-ethylbenzylamino)piperidin-1-yl)ethyl)-7-methoxy-N-methyl-2-oxo-1,2-dihydroquinoline-4-carboxamide, 1 mL of 4 mol/L hydrogen chloride/ethyl acetate was added at room temperature, and the solvent was removed under reduced pressure. Ethyl acetate was added to the residue thus obtained, and the resulting solid was filtered to give 0.15 g of 1-(2-(4-(4-ethylbenzylamino)piperidin-1-yl)ethyl)-7-methoxy-N-methyl-2-oxo-1,2-dihydroquinoline-4-carboxamide hydrochloride as a pale yellow solid.

$^1$H-NMR (DMSO-$d_6$) δ:
1.18 (3H, t, J=7.6 Hz), 2.03-2.13 (2H, m), 2.35-2.41 (2H, m), 2.63 (2H, q, J=7.6 Hz), 2.80 (3H, d, J=4.6 Hz), 3.06-3.17 (2H, m), 3.24-3.31 (3H, m), 3.78-3.86 (2H, m), 3.98 (3H, s), 4.12-4.19 (2H, m), 4.68-4.76 (2H, m), 6.47 (1H, s), 6.97 (1H, dd, J=8.7, 2.3 Hz), 7.20 (1H, s), 7.28 (2H, d, J=8.3 Hz), 7.51 (2H, d, J=8.3 Hz), 7.75 (1H, d, J=8.7 Hz), 8.67 (1H, m), 9.50-9.64 (2H, broad), 11.06-11.37 (1H, broad)

Example 340

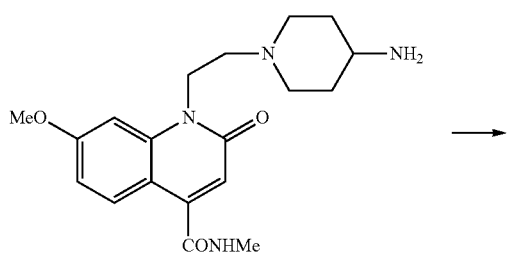

To 4 mL of a methanol solution containing 0.14 g of 1-(2-(4-aminopiperidin-1-yl)ethyl)-7-methoxy-N-methyl-2-oxo-1,2-dihydroquinoline-4-carboxamide, 50 mg of 3-fluoro-4-methylbenzaldehyde and 40 μL of acetic acid were added, and stirred at room temperature for 80 min. To the reaction mixture, 52 mg of sodium cyanoborohydride was added, and stirred at the same temperature for 75 min. After the solvent was removed under reduced pressure, chloroform and aqueous saturated sodium hydrogen carbonate solution were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform:methanol=30:1], to give 1-(2-(4-(3-fluoro-4-methylbenzylamino)piperidin-1-yl)ethyl)-7-methoxy-N-methyl-2-oxo-1,2-dihydroquinoline-4-carboxamide as a pale yellow solid.

To 2 mL of a methanol solution containing the 1-(2-(4-(3-fluoro-4-methylbenzylamino)piperidin-1-yl)ethyl)-7-methoxy-N-methyl-2-oxo-1,2-dihydroquinoline-4-carboxamide obtained, 1 mL of 4 mol/L hydrogen chloride/ethyl acetate was added at room temperature, and the solvent was removed under reduced pressure. Ethyl acetate was added to the residue thus obtained, and the resulting solid was filtered to give 0.15 g of 1-(2-(4-(3-fluoro-4-methylbenzylamino)piperidin-1-yl)ethyl)-7-methoxy-N-methyl-2-oxo-1,2-dihydroquinoline-4-carboxamide hydrochloride as a pale yellow solid.

$^1$H-NMR (DMSO-$d_6$) δ:
2.04-2.13 (2H, m), 2.25 (3H, d, J=1.4 Hz), 2.35-2.42 (2H, m), 2.80 (3H, d, J=4.6 Hz), 3.07-3.16 (2H, m), 3.23-3.30 (3H, m), 3.79-3.85 (2H, m), 3.98 (3H, s), 4.15-4.21 (2H, m), 4.69-4.75 (2H, m), 6.47 (1H, s), 6.97 (1H, dd, J=8.7, 2.3 Hz), 7.21 (1H, s), 7.34-7.37 (2H, m), 7.48 (1H, d, J=10.1 Hz), 7.75 (1H, d, J=8.7 Hz), 8.66-8.71 (1H, m), 9.69-9.85 (2H, broad), 11.15-11.50 (1H, broad)

Example 341

481

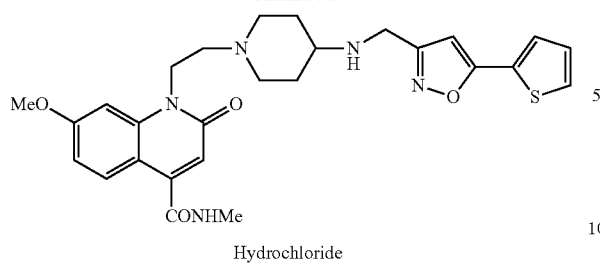

Hydrochloride

482

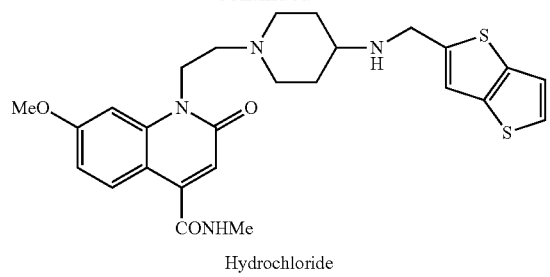

Hydrochloride 2 mL of a methanol solution containing 140 mg of 1-(2-(4-aminopiperidin-1-yl)ethyl)-7-methoxy-N-methyl-2-oxo-1,2-dihydroquinoline-4-carboxamide and 20 μL of acetic acid were added to 63 mg of 5-(thiophen-2-yl)isoxazole-3-carbaldehyde, and stirred at room temperature for 30 min. To the reaction mixture, 63 mg of sodium cyanoborohydride was added, and stirred at the same temperature overnight. After the solvent was removed under reduced pressure, ethyl acetate and aqueous saturated sodium hydrogen carbonate solution were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate: methanol=20:1]. To the purified product, 2 mL of 1,4-dioxane and 0.5 mL of 4 mol/L hydrogen chloride/1,4-dioxane were added, and the solvent was removed under reduced to give 73 mg of 7-methoxy-N-methyl-2-oxo-1-(2-(4-((5-(thiophen-2-yl)isoxazol-3-yl)methylamino)piperidin-1-yl)ethyl)-1,2-dihydroquinoline-4-carboxamide hydrochloride as a white solid.

$^1$H-NMR (DMSO-$d_6$) δ:

2.00-2.13 (2H, m), 2.34-2.42 (2H, m), 2.78-2.82 (3H, m), 3.10-3.45 (5H, m), 3.82-3.89 (2H, m), 3.97 (3H, s), 4.38-4.46 (2H, m), 4.68-4.73 (2H, m), 6.47 (1H, s), 6.98 (1H, dd, J=8.7, 2.1 Hz), 7.09 (1H, s), 7.18 (1H, s), 7.28 (1H, dd, J=5.0, 3.7 Hz), 7.74-7.78 (2H, m), 7.89 (1H, dd, J=5.0, 0.9 Hz), 8.62-8.70 (1H, m), 9.95-10.17 (2H, broad), 10.82-11.14 (1H, broad)

2 mL of a methanol solution containing 140 mg of 1-(2-(4-aminopiperidin-1-yl)ethyl)-7-methoxy-N-methyl-2-oxo-1,2-dihydroquinoline-4-carboxamide and 20 μL of acetic acid were added to 60 mg of thieno[3,2-b]thiophene-2-carbaldehyde, and stirred at room temperature for 30 min. To the reaction mixture, 49 mg of sodium cyanoborohydride was added, and stirred at the same temperature overnight. After the solvent was removed under reduced pressure, ethyl acetate and aqueous saturated sodium hydrogen carbonate solution were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate: methanol=20:1]. To the purified product, 2 mL of 1,4-dioxane and 0.5 mL of 4 mol/L hydrogen chloride/1,4-dioxane were added, and the solvent was removed under reduced to give 65 mg of 7-methoxy-N-methyl-2-oxo-1-(2-(4-((thieno[3,2-b]thiophen-2-yl)methylamino)piperidin-1-yl)ethyl)-1,2-dihydroquinoline-4-carboxamide hydrochloride as a white solid.

$^1$H-NMR (DMSO-$d_6$) δ:

2.01-2.12 (2H, m), 2.33-2.43 (2H, m), 2.80 (3H, d, J=4.6 Hz), 3.09-3.88 (5H, m), 3.79-3.86 (2H, m), 3.97 (3H, s), 4.50-4.57 (2H, m), 4.66-4.75 (2H, m), 6.47 (1H, s), 6.97 (1H, d, J=8.7 Hz), 7.18 (1H, s), 7.48 (1H, d, J=5.0 Hz), 7.70-7.78 (3H, m), 8.63-8.71 (1H, m), 9.65-9.88 (2H, broad), 10.82-11.07 (1H, broad)

Example 342

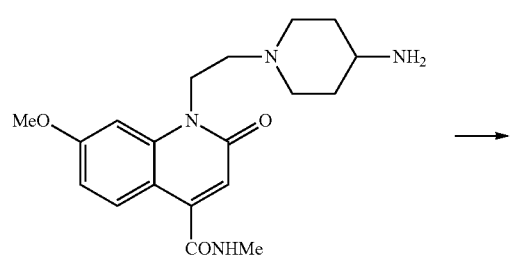

Example 343

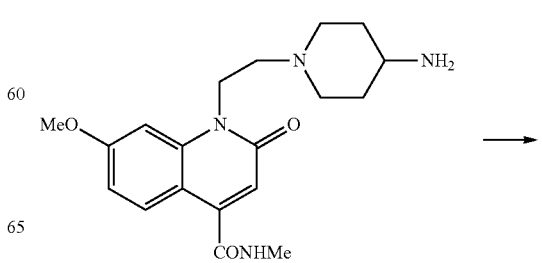

483

-continued

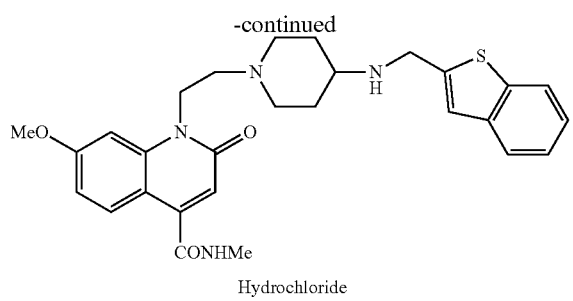

Hydrochloride 2 mL of a methanol solution containing 140 mg of 1-(2-(4-aminopiperidin-1-yl)ethyl)-7-methoxy-N-methyl-2-oxo-1,2-dihydroquinoline-4-carboxamide and 20 μL of acetic acid were added to 57 mg of benzo[b]thiophene-2-carbaldehyde, and stirred at room temperature for 30 min. To the reaction mixture, 49 mg of sodium cyanoborohydride was added, and stirred at the same temperature overnight. After the solvent was removed under reduced pressure, ethyl acetate and aqueous saturated sodium hydrogen carbonate solution were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate: methanol=20:1]. To the purified product, 2 mL of 1,4-dioxane and 0.5 mL of 4 mol/L hydrogen chloride/1,4-dioxane were added, and the solvent was removed under reduced to give 80 mg of 1-(2-(4-((benzo[b]thiophen-2-yl)methylamino)piperidin-1-yl)ethyl)-7-methoxy-N-methyl-2-oxo-1,2-dihydroquinoline-4-carboxamide hydrochloride as a white solid.

$^1$H-NMR (DMSO-d$_6$) δ:
1.94-2.09 (2H, m), 2.36-2.42 (2H, m), 2.80 (3H, d, J=4.6 Hz), 3.10-3.38 (5H, m), 3.82-3.88 (2H, m), 3.96 (3H, s), 4.57-4.71 (4H, m), 6.47 (1H, s), 6.99 (1H, d, J=8.7 Hz), 7.14 (1H, s), 7.39-7.45 (2H, m), 7.69 (1H, s), 7.77 (1H, d, J=8.7 Hz), 7.88-7.93 (1H, m), 8.01-8.05 (1H, m), 8.62-8.68 (1H, m), 9.53-9.78 (2H, broad), 10.34-10.56 (1H, broad)

Example 344

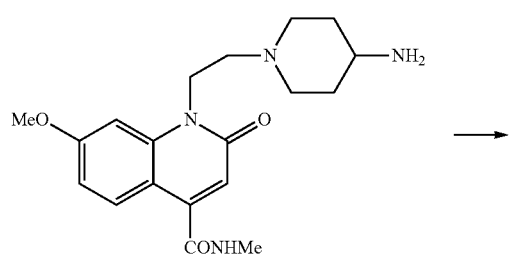

484

-continued

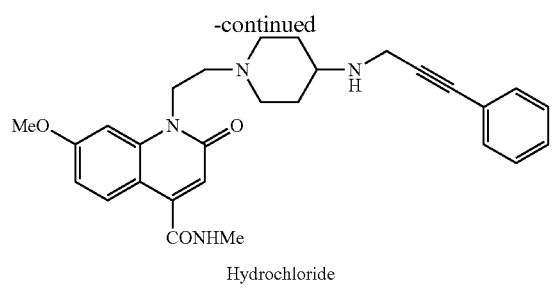

Hydrochloride 2 mL of a methanol solution containing 140 mg of 1-(2-(4-aminopiperidin-1-yl)ethyl)-7-methoxy-N-methyl-2-oxo-1,2-dihydroquinoline-4-carboxamide and 20 μL of acetic acid were added to 46 mg of phenylpropargylaldehyde, and stirred at room temperature for 30 min. To the reaction mixture, 49 mg of sodium cyanoborohydride was added, and stirred at the same temperature overnight. After the solvent was removed under reduced pressure, ethyl acetate and aqueous saturated sodium hydrogen carbonate solution were added, the organic layer was separated, and the aqueous layer was extracted with ethyl acetate. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate: methanol=20:1]. To the purified product, 2 mL of 1,4-dioxane and 0.5 mL of 4 mol/L hydrogen chloride/1,4-dioxane were added, and the solvent was removed under reduced to give 42 mg of 7-methoxy-N-methyl-2-oxo-1-(2-(4-(3-phenyl-2-propyn-1-ylamino)piperidin-1-yl)ethyl)-1,2-dihydroquinoline-4-carboxamide hydrochloride as a white solid.

$^1$H-NMR (DMSO-d$_6$) δ:
1.94-2.05 (2H, m), 2.28-2.38 (2H, m), 2.77-2.83 (3H, m), 3.14-3.50 (5H, m), 3.81-3.90 (2H, m), 3.97 (3H, s), 4.17-4.35 (2H, m), 4.64-4.75 (2H, m), 6.47 (1H, s), 6.98 (1H, d, J=8.7 Hz), 7.16 (1H, s), 7.41-7.57 (5H, m), 7.77 (1H, d, J=8.7 Hz), 8.61-8.72 (1H, m), 9.72-9.94 (2H, broad), 10.54-10.78 (1H, broad)

Example 345

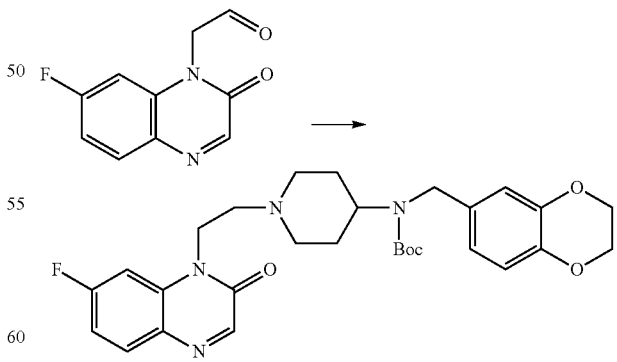

To 20 mL of a chloroform solution containing 355 mg of (7-fluoro-2-oxoquinoxalin-1(2H)-yl)acetaldehyde and 553 mg of tert-butyl (2,3-dihydro-1,4-benzodioxin-6-ylmethyl)(piperidin-4-yl)carbamate, 98 μL of acetic acid were added, and stirred at room temperature for 1 hour. To the reaction mixture, 549 mg of sodium triacetoxyborohydride was added, and stirred for 1 hour. Aqueous saturated sodium hydrogen carbonate solution were added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate:hexane=1:1] to give 655 mg of tert-butyl (2,3-dihydro-1,4-benzodioxin-6-ylmethyl) (1-(2-(7-fluoro-2-oxoquinoxalin-1(2H)-yl)ethyl)piperidin-4-yl)carbamate as a white solid.

$^1$H-NMR (CDCl$_3$) δ:

1.61 (9H, s), 1.62-1.67 (4H, m), 2.10-2.21 (2H, m), 2.60-2.65 (3H, m), 2.95-3.01 (2H, m), 4.24 (4H, s), 4.25-4.29 (4H, m), 6.65-6.70 (1H, m), 6.73 (1H, s), 6.78 (1H, d, J=8.3 Hz), 7.04-7.12 (2H, m), 7.85 (1H, dd, J=8.7, 6.0 Hz), 8.21 (1H, s)

Example 346

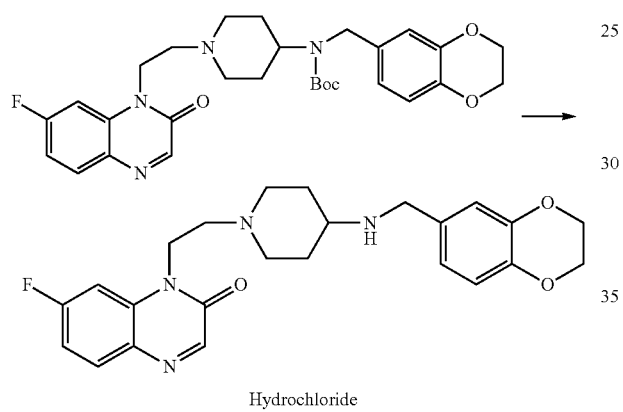

Hydrochloride

To 3 mL of a chloroform solution containing 631 mg of tert-butyl (2,3-dihydro-1,4-benzodioxin-6-ylmethyl)(1-(2-(7-fluoro-2-oxoquinoxalin-1(2H)-yl)ethyl)piperidin-4-yl) carbamate, 3 mL of trifluoroacetic acid was added and stirred at room temperature for 6 hours. After solvents of the reaction mixture were removed under reduced pressure and the residue was alkalized by aqueous saturated sodium hydrogen carbonate solution, it was extracted with ethyl acetate. The organic layer was washed sequentially with water and aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform:methanol=5:1], to give 400 mg of (1-(2-(4-((2,3-dihydro-1,4-benzodioxin-6-ylmethyl)amino)piperidin-1-yl)ethyl)-7-fluoroquinoxalin-2(1H)-one as a brown solid.

To 15 mL of an ethyl acetate solution containing 393 mg of 1-(2-(4-((2,3-dihydro-1,4-benzodioxin-6-ylmethyl)amino) piperidn-1-yl)ethyl)-7-fluoroquinoxalin-2(1H)-one, 1 mL of 4 mol/L hydrogen chloride/ethyl acetate was added, and stirred at room temperature for 10 min. The resulting solid was filtered to give 437 mg of (1-(2-(4-((2,3-dihydro-1,4-benzodioxin-6-ylmethyl)amino)piperidin-1-yl)ethyl)-7-fluoroquinoxalin-2(1H)-one hydrochloride as a light brown powder.

$^1$H-NMR (DMSO-d$_6$) δ:

1.89-2.05 (2H, m), 2.29-2.37 (2H, m), 3.04-3.15 (2H, m), 3.20-3.27 (3H, m), 3.79-3.85 (2H, m), 4.06-4.14 (2H, m), 4.26 (4H, s), 4.55-4.61 (2H, m), 6.92 (1H, d, J=7.8 Hz), 7.01 (1H, d, J=7.8 Hz), 7.12 (1H, s), 7.28-7.35 (1H, m), 7.69-7.76 (1H, m), 7.91-7.97 (1H, m), 8.24 (1H, s), 9.19-9.30 (2H, broad), 10.07-10.21 (1H, broad)

Example 347

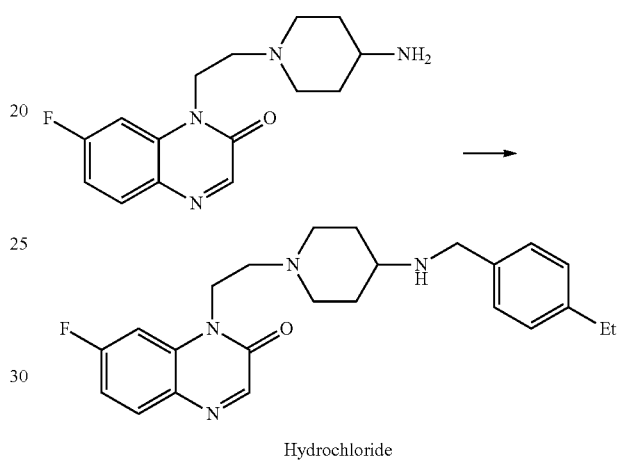

Hydrochloride

To 5 mL of a chloroform solution containing 301 mg of 1-(2-(4-aminopiperidin-1-yl)ethyl)-7-fluoroquinoxalin-2 (1H)-one and 143 mg of 4-ethylbenzaldehyde, 60 μL of acetic acid were added, and stirred at room temperature for 1 hour. To the reaction mixture, 352 mg of sodium triacetoxyborohydride was added, and stirred for 1.5 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate:hexane=1:1], to give 1-(2-(4-(4-ethylbenzylamino) piperidin-1-yl)ethyl)-7-fluoroquinoxalin-2(1H)-one as pale yellow solid.

To 10 mL of an ethyl acetate solution containing 1-(2-(4-(4-ethylbenzylamino)piperidin-1-yl)ethyl)-7-fluoroquinoxalin-2(1H)-one, 1 mL of 4 mol/L hydrogen chloride/ethyl acetate was added, and stirred at room temperature for 10 min. The resulting solid was filtered to give 292 mg of 1-(2-(4-(4-ethylbenzylamino)piperidin-1-yl)ethyl)-7-fluoroquinoxalin-2(1H)-one hydrochloride as a pale brown solid.

$^1$H-NMR (DMSO-d$_6$) δ:

1.18 (3H, t, J=7.6 Hz), 1.98-2.08 (2H, m), 2.32-2.40 (2H, m), 2.60-2.65 (2H, m), 3.07-3.16 (3H, m), 3.24-3.29 (2H, m), 3.78-3.85 (2H, m), 4.13-4.17 (2H, m), 4.60 (2H, t, J=6.6 Hz), 7.27-7.31 (3H, m), 7.49 (2H, d, J=7.8 Hz), 7.74-7.80 (1H, m), 7.93 (1H, dd, J=8.5, 6.2 Hz), 8.23 (1H, s), 9.44-9.52 (2H, broad), 10.48-10.57 (1H, broad)

Example 348

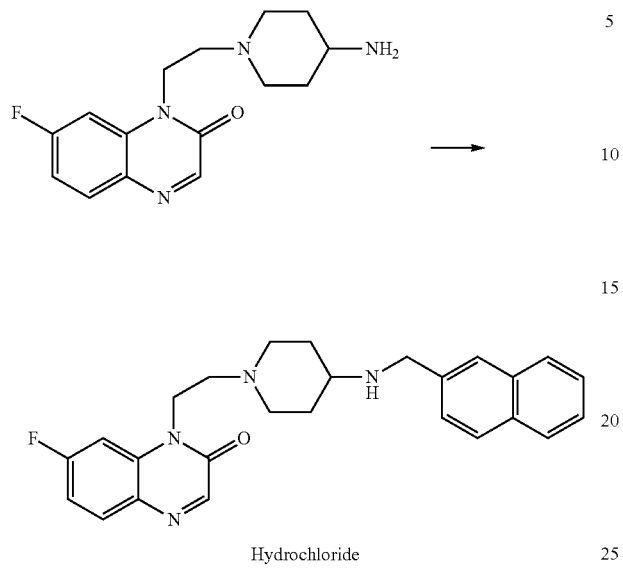

Hydrochloride

To 10 mL of a chloroform solution containing 252 mg of 1-(2-(4-aminopiperidin-1-yl)ethyl)-7-fluoroquinoxalin-2(1H)-one and 136 mg of 2-naphtoaldehyde, 50 μL of acetic acid were added, and stirred at room temperature for 1 hour. To the reaction mixture, 276 mg of sodium triacetoxyborohydride was added, and stirred overnight. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate:hexane=2:1], to give 279 mg of 7-fluoro-1-(2-(4-((naphthalen-2-yl)methylamino)piperidin-1-yl)ethyl)quinoxalin-2(1H)-one as pale yellow solid.

To a mixed solution of 20 mL chloroform and 10 mL ethyl acetate containing 255 mg of 7-fluoro-1-(2-(4-((naphthalen-2-yl)methylamino)piperidin-1-yl)ethyl)-quinoxalin-2(1H)-one, 1 mL of 4 mol/L hydrogen chloride/ethyl acetate was added, and stirred at room temperature for 10 min. The solvent was removed under reduced pressure, ethyl acetate was added, and the resulting solid was filtered to give 257 mg of 7-fluoro-1-(2-(4-((naphthalen-2-yl)methylamino)piperidin-1-yl)ethyl)quinoxalin-2(1H)-one hydrochloride as a pale brown solid.

$^1$H-NMR (DMSO-$d_6$) δ:
2.02-2.08 (2H, m), 2.38-2.44 (4H, m), 3.08-3.16 (3H, m), 3.82-3.87 (2H, m), 4.37-4.40 (2H, m), 4.60 (2H, t, J=6.6 Hz), 7.28-7.33 (1H, m), 7.58-7.61 (2H, m), 7.71-7.78 (2H, m), 7.92-7.96 (2H, m), 7.96-7.99 (1H, m), 8.02 (1H, d, J=8.7 Hz), 8.12 (1H, s), 8.24 (1H, s), 9.53-9.63 (2H, broad), 10.33-10.45 (1H, broad)

Example 349

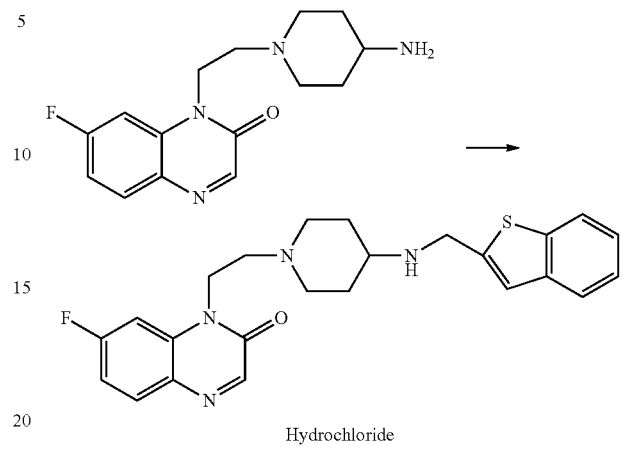

Hydrochloride

To 10 mL of a chloroform solution containing 310 mg of 1-(2-(4-aminopiperidin-1-yl)ethyl)-7-fluoroquinoxalin-2(1H)-one and 172 mg of 1-benzo[b]thiophene-2-carbaldehyde, 61 μL of acetic acid were added, and stirred at room temperature for 1 hour. To the reaction mixture, 354 mg of sodium triacetoxyborohydride was added, and stirred overnight. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate:hexane=2:1], to give 232 mg of 1-(2-(4-((benzo[b]thiophen-2-yl)methylamino)piperidin-1-yl)ethyl)-7-fluoroquinoxalin-2(1H)-one as pale yellow solid.

To 10 mL of a chloroform solution containing 228 mg of 1-(2-(4-((benzo[b]thiophen-2-yl)methylamino)piperidin-1-yl)ethyl)-7-fluoroquinoxalin-2(1H)-one, 1 mL of 4 mol/L hydrogen chloride/ethyl acetate was added, and stirred at room temperature for 10 min. The solvent was removed under reduced pressure, ethyl acetate was added, and the resulting solid was filtered to give 247 mg of 1-(2-(4-((benzo[b]thiophen-2-yl)methylamino)piperidin-1-yl)ethyl)-7-fluoroquinoxalin-2(1H)-one hydrochloride as a pale brown solid.

$^1$H-NMR (DMSO-$d_6$) δ:
2.01-2.11 (2H, m), 2.35-2.43 (2H, m), 2.46-2.49 (2H, m), 3.06-3.16 (3H, m), 3.79-3.88 (2H, m), 4.54-4.63 (4H, m), 7.27-7.33 (1H, m), 7.40-7.45 (2H, m), 7.70 (1H, s), 7.72-7.80 (1H, m), 7.89-7.96 (2H, m), 8.01-8.05 (1H, m), 8.23 (1H, s), 9.76-9.85 (2H, broad), 10.43-10.59 (1H, broad)

Example 350

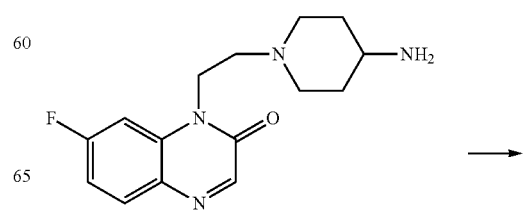

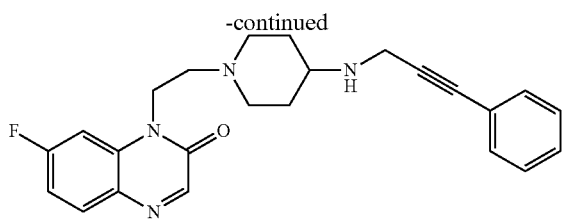

Hydrochloride

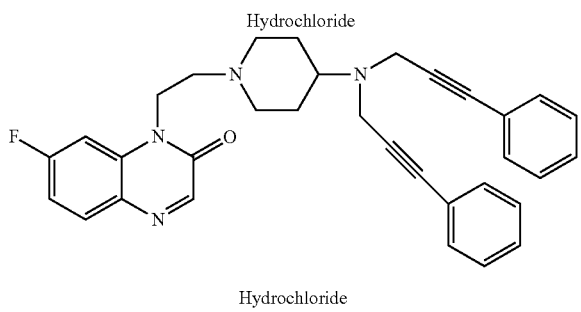

Hydrochloride

To 10 mL of a chloroform solution containing 404 mg of 1-(2-(4-aminopiperidin-1-yl)ethyl)-7-fluoroquinoxalin-2 (1H)-one and 180 mg of phenylpropargylaldehyde, 80 μL of acetic acid were added, and stirred at room temperature for 1 hour. To the reaction mixture, 474 mg of sodium triacetoxyborohydride was added, and stirred overnight. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate:hexane=2:1], to give 224 mg of 7-fluoro-1-(2-(4-(3-phenyl-2-propyn-1-ylamino)piperidin-1-yl)ethyl)quinoxalin-2(1H)-one as brown solid and 158 mg of 1-(2-(4-(bis(3-phenyl-2-propyn-1-yl)amino)piperidin-1-yl)ethyl)-7-fluoroquinoxalin-2(1H)-one as yellow oil.

To 10 mL of a chloroform solution containing 209 mg of 7-fluoro-1-(2-(4-(3-phenyl-2-propyn-1-ylamino)piperidin-1-yl)ethyl)quinoxalin-2(1H)-one, 1 mL of 4 mol/L hydrogen chloride/ethyl acetate was added, and stirred at room temperature for 10 min. The solvent was removed under reduced pressure, ethyl acetate was added, and the resulting solid was filtered to give 197 mg of 7-fluoro-1-(2-(4-(3-phenyl-2-propyn-1-ylamino)piperidin-1-yl)ethyl)quinoxalin-2(1H)-one hydrochloride as a pale brown solid.

$^1$H-NMR (DMSO-$d_6$) δ:

1.97-2.06 (2H, m), 2.31-2.37 (2H, m), 3.13-3.21 (2H, m), 3.42-3.50 (3H, m), 3.81-3.88 (2H, m), 4.23-4.27 (2H, m), 4.60 (2H, t, J=6.0 Hz), 7.30 (1H, dt, J=8.5, 2.3 Hz), 7.42-7.49 (3H, m), 7.51-7.54 (2H, m), 7.74-7.79 (1H, m), 7.93 (1H, dd, J=8.7, 6.0 Hz), 8.24 (1H, s), 9.87-9.96 (2H, broad), 10.52-10.61 (1H, broad)

To 5 mL of a chloroform solution containing 132 mg of 1-(2-(4-(bis(3-phenyl-2-propyn-1-yl)amino)piperidin-1-yl) ethyl)-7-fluoroquinoxalin-2(1H)-one, 0.5 mL of 4 mol/L hydrogen chloride/ethyl acetate was added, and stirred at room temperature for 10 min. The solvent was removed under reduced pressure, ethyl acetate was added, and the resulting solid was filtered to give 141 mg of 1-(2-(4-(bis(3-phenyl-2-propyn-1-yl)amino)piperidin-1-yl)ethyl)-7-fluoroquinoxalin-2(1H)-one hydrochloride as a pale brown solid.

$^1$H-NMR (DMSO-$d_6$) δ:

1.95-2.07 (2H, m), 2.22-2.28 (1H, m), 2.31-2.37 (2H, m), 3.13-3.23 (2H, m), 3.34-3.41 (2H, m), 3.84 (2H, d, J=11.0 Hz), 4.11-4.24 (4H, m), 4.61 (2H, t, J=6.9 Hz), 7.30 (1H, dt, J=8.6, 2.5 Hz), 7.33-7.44 (7H, m), 7.46-7.49 (3H, m), 7.77 (1H, dd, J=10.8, 2.1 Hz), 7.93 (1H, dd, J=8.9, 6.2 Hz), 8.23 (1H, s), 10.31-10.41 (1H, broad)

Example 351

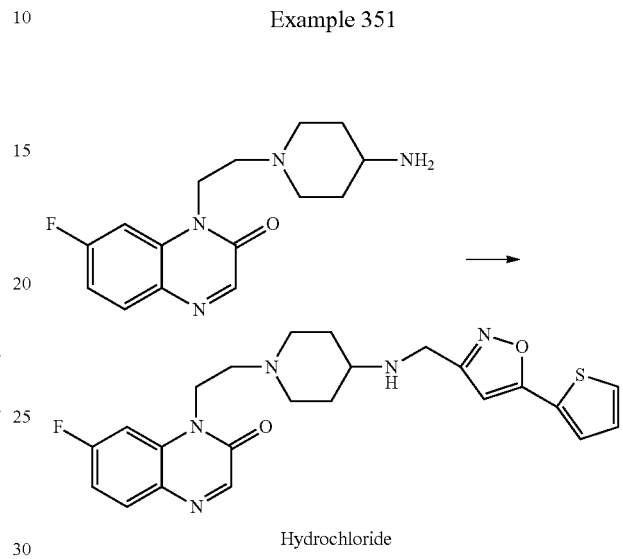

Hydrochloride

To 10 mL of a chloroform solution containing 407 mg of 1-(2-(4-aminopiperidin-1-yl)ethyl)-7-fluoroquinoxalin-2 (1H)-one and 275 mg of 5-(2-thienyl)-3-isoxazolecarbaldehyde, 80 μL of acetic acid were added, and stirred at room temperature for 1 hour. To the reaction mixture, 468 mg of sodium triacetoxyborohydride was added, and stirred overnight. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate:hexane=2:1], to give 232 mg of 7-fluoro-1-(2-(4-((5-(thiophen-2-yl)isoxazol-3-yl)methylamino)piperidin-1-yl)ethyl)quinoxalin-2(1H)-one as pale yellow solid.

To 10 mL of a chloroform solution containing 232 mg of 7-fluoro-1-(2-(4-((5-(thiophen-2-yl)isoxazol-3-yl)methylamino)piperidin-1-yl)ethyl)quinoxalin-2(1H)-one, 1 mL of 4 mol/L hydrogen chloride/ethyl acetate was added, and stirred at room temperature for 10 min. The solvent was removed under reduced pressure, ethyl acetate was added, and the resulting solid was filtered to give 247 mg of 7-fluoro-1-(2-(4-((5-(thiophen-2-yl)isoxazol-3-yl)methylamino)piperidin-1-yl)ethyl)quinoxalin-2(1H)-one hydrochloride as a pale brown solid.

$^1$H-NMR (DMSO-$d_6$) δ:

1.96-2.06 (2H, m), 2.34-2.41 (2H, m), 2.43-2.47 (2H, m), 3.08-3.17 (3H, m), 3.82-3.88 (2H, m), 4.39-4.47 (2H, m), 4.55-4.63 (2H, m), 7.07 (1H, s), 7.27-7.34 (2H, m), 7.71-7.77 (2H, m), 7.90 (1H, d, J=5.0 Hz), 7.94 (1H, dd, J=8.7, 6.4 Hz), 8.24 (1H, s), 9.89-9.98 (2H, broad), 10.19-10.29 (1H, broad)

Example 352

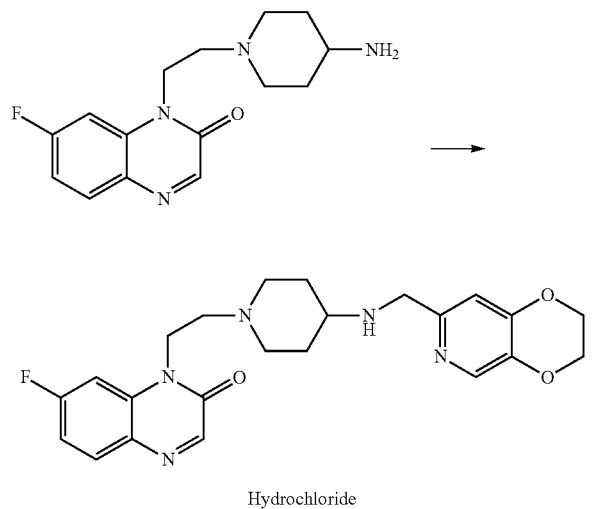

Hydrochloride

To 10 mL of a chloroform solution containing 327 mg of 1-(2-(4-aminopiperidin-1-yl)ethyl)-7-fluoroquinoxalin-2 (1H)-one and 230 mg of 2,3-dihydro-1,4-dioxino[2,3-c]pyridine-7-carbaldehyde, 65 μL of acetic acid were added, and stirred at room temperature for 1 hour. To the reaction mixture, 364 mg of sodium triacetoxyborohydride was added, and stirred overnight. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform], to give 311 mg of 1-(2-(4-((2,3-dihydro-1,4-dioxino[2,3-c]pyridin-7-yl)methylamino)piperidin-1-yl)ethyl)-7-fluoroquinoxalin-2(1H)-one as a pale yellow solid.

To 10 mL of a chloroform solution containing 281 mg of 1-(2-(4-((2,3-dihydro-1,4-dioxino[2,3-c]pyridin-7-yl)methylamino)piperidin-1-yl)ethyl)-7-fluoroquinoxalin-2(1H)-one, 1 mL of 4 mol/L hydrogen chloride/ethyl acetate was added, and stirred at room temperature for 10 min. The solvent was removed under reduced pressure, ethyl acetate was added, and the resulting solid was filtered to give 311 mg of 1-(2-(4-((2,3-dihydro-1,4-dioxino[2,3-c]pyridin-7-yl)methylamino)piperidin-1-yl)ethyl)-7-fluoroquinoxalin-2(1H)-one hydrochloride as a pale brown solid.

$^1$H-NMR (DMSO-$d_6$) δ:
2.01-2.09 (2H, m), 2.32-2.37 (2H, m), 3.06-3.14 (2H, m), 3.26-3.36 (3H, m), 3.78-3.84 (2H, m), 4.21-4.24 (2H, m), 4.34-4.37 (2H, m), 4.41 (2H, dd, J=5.5, 2.3 Hz), 4.60 (2H, t, J=6.9 Hz), 7.26 (1H, s), 7.30 (1H, dt, J=8.9, 2.3 Hz), 7.79 (1H, dd, J=11.0, 2.3 Hz), 7.92 (1H, dd, J=8.9, 6.2 Hz), 8.23 (1H, s), 8.23 (1H, s), 9.66-9.72 (2H, broad), 10.70-10.77 (1H, broad)

Example 353

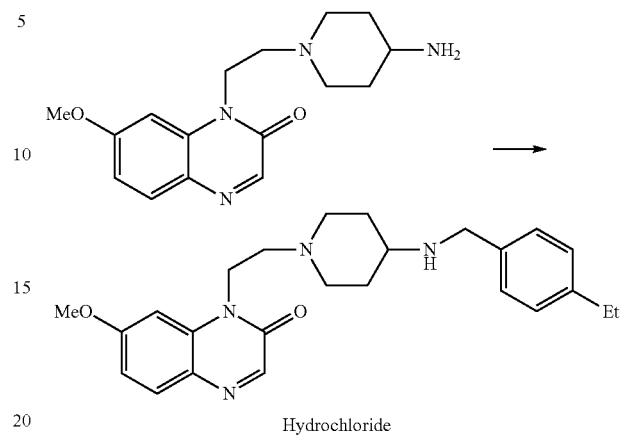

Hydrochloride

To 10 mL of a chloroform solution containing 500 mg of 1-(2-(4-aminopiperidin-1-yl)ethyl)-7-methoxyquinoxalin-2 (1H)-one and 200 mg of 4-ethylbenzaldehyde, 100 mg of acetic acid were added, and stirred at room temperature for 1 hour. To the reaction mixture, 526 mg of sodium triacetoxyborohydride was added, and stirred for 15 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 0.32 g of 1-(2-(4-(4-ethylbenzylamino)piperidin-1-yl)ethyl)-7-methoxyquinoxalin-2(1H)-one as a brown oil.

To 3 mL of an ethyl acetate solution containing 0.32 g of 1-(2-(4-(4-ethylbenzylamino)piperidin-1-yl)ethyl)-7-methoxyquinoxalin-2(1H)-one, 2 mL of 4 mol/L hydrogen chloride/ethyl acetate was added, and stirred at room temperature. The resulting solid was filtered to give 302 mg of 1-(2-(4-(4-ethylbenzylamino)piperidin-1-yl)ethyl)-7-methoxyquinoxalin-2(1H)-one hydrochloride as a brown solid.

$^1$H-NMR (DMSO-$d_6$, $D_2O$) δ:
1.18 (3H, t, J=7.6 Hz), 1.88-2.01 (2H, m), 2.33-2.45 (2H, m), 2.63 (2H, q, J=7.6 Hz), 3.05-3.19 (2H, m), 3.30-3.48 (3H, m), 3.81-3.92 (2H, m), 3.96 (3H, s), 4.17 (2H, s), 4.60-4.68 (2H, m), 7.07-7.14 (2H, m), 7.31 (2H, d, J=8.3 Hz), 7.46 (2H, d, J=8.3 Hz), 7.83 (1H, d, J=8.7 Hz), 8.10 (1H, s)

Example 354

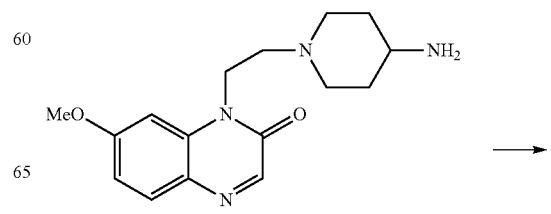

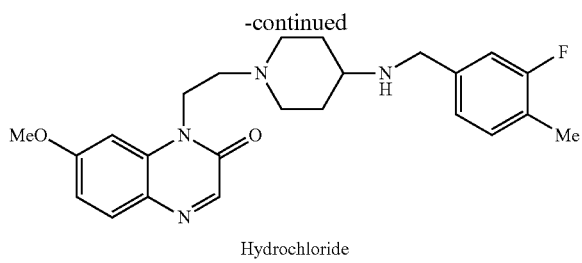

Hydrochloride

To 10 mL of a chloroform solution containing 500 mg of 1-(2-(4-aminopiperidin-1-yl)ethyl)-7-methoxyquinoxalin-2(1H)-one and 206 mg of 3-fluoro-4-methylbenzaldehyde, 100 mg of acetic acid were added, and stirred at room temperature for 1 hour. To the reaction mixture, 526 mg of sodium triacetoxyborohydride was added, and stirred for 15 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 0.44 g of 1-(2-(4-(3-fluoro-4-methylbenzylamino)piperidin-1-yl)ethyl)-7-methoxyquinoxalin-2(1H)-one as a brown oil.

To a mixed solution of 10 mL chloroform and 4 mL ethyl acetate containing 0.44 g of 1-(2-(4-(3-fluoro-4-methylbenzylamino)piperidin-1-yl)ethyl)-7-methoxyquinoxalin-2(1H)-one, 2 mL of 4 mol/L hydrogen chloride/ethyl acetate was added, and stirred at room temperature. The solvent was removed under reduced pressure, ethyl acetate was added, and the resulting solid was filtered to give 422 mg of 1-(2-(4-(3-fluoro-4-methylbenzylamino)piperidin-1-yl)ethyl)-7-methoxyquinoxalin-2(1H)-one hydrochloride as a brown solid.

$^1$H-NMR (DMSO-$d_6$, $D_2O$) δ:
1.91-2.04 (2H, m), 2.26 (3H, s), 2.31-2.43 (2H, m), 3.05-3.20 (2H, m), 3.26-3.44 (3H, m), 3.80-3.91 (2H, m), 3.97 (3H, s), 4.13-4.26 (2H, m), 4.59-4.69 (2H, m), 7.07 (1H, dd, J=8.9, 2.5 Hz), 7.13 (1H, d, J=2.8 Hz), 7.30 (1H, d, J=7.8 Hz), 7.33-7.46 (2H, m), 7.82 (1H, d, J=9.2 Hz), 8.10 (1H, s)

Example 355

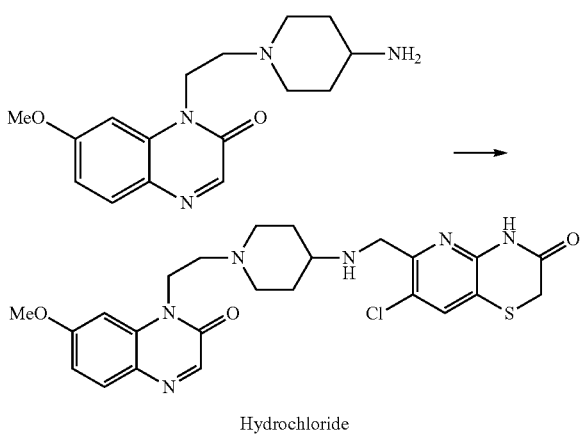

Hydrochloride

To 12 mL of a chloroform solution containing 609 mg of 1-(2-(4-aminopiperidin-1-yl)ethyl)-7-methoxyquinoxalin-2(1H)-one and 414 mg of 7-chloro-3-oxo-3,4-dihydro-2H-pyrido[3,2-b][1,4]thiazine-6-carbaldehyde, 121 mg of acetic acid was added, and stirred at room temperature for 3 hours. To the reaction mixture, 618 mg of sodium triacetoxyborohydride was added, and stirred for 10.5 hours. Aqueous saturated sodium hydrogen carbonate solution was added, and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 0.73 g of 1-(2-(4-((7-chloro-3-oxo-3,4-dihydro-2H-pyrido[3,2-b][1,4]thiazin-6-yl)methylamino)piperidin-1-yl)ethyl)-7-methoxyquinoxalin-2(1H)-one as a pale yellow foam. To 3 mL of an ethyl acetate solution containing 0.30 g of 1-(2-(4-((7-chloro-3-oxo-3,4-dihydro-2H-pyrido[3,2-b][1,4]thiazin-6-yl)methylamino)piperidin-1-yl)ethyl)-7-methoxyquinoxalin-2(1H)-one, 2 mL of 4 mol/L hydrogen chloride/ethyl acetate was added, and stirred at room temperature. The resulting solid was filtered to give 300 mg of 1-(2-(4-((7-chloro-3-oxo-3,4-dihydro-2H-pyrido[3,2-b][1,4]thiazin-6-yl)methylamino)piperidin-1-yl)ethyl)-7-methoxyquinoxalin-2(1H)-one hydrochloride as a pale yellow solid.

$^1$H-NMR (DMSO-$d_6$, $D_2O$) δ:
1.94-2.04 (2H, m), 2.41-2.49 (2H, m), 3.05-3.16 (2H, m), 3.38-3.45 (2H, m), 3.65 (2H, s), 3.84-3.92 (3H, m), 3.97 (3H, s), 4.35-4.42 (2H, m), 4.62-4.68 (2H, m), 7.08 (1H, dd, J=8.7, 2.3 Hz), 7.13 (1H, d, J=2.3 Hz), 7.82 (1H, d, J=8.7 Hz), 8.10 (1H, s), 8.14 (1H, s)

Example 356

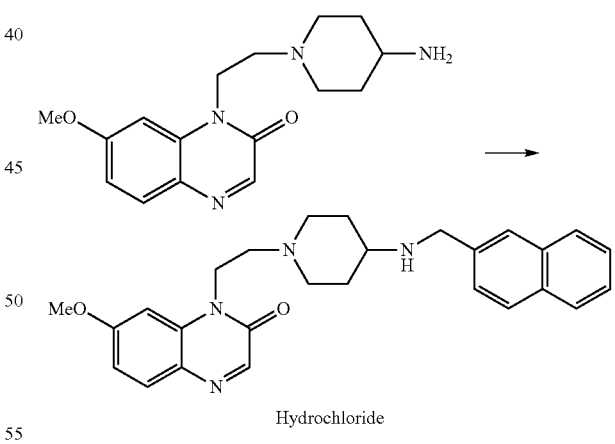

Hydrochloride

To 10 mL of a chloroform solution containing 500 mg of 1-(2-(4-aminopiperidin-1-yl)ethyl)-7-methoxyquinoxalin-2(1H)-one and 232 mg of 2-naphthoaldehyde, 100 mg of acetic acid was added, and stirred at room temperature for 2 hours. To the reaction mixture, 526 mg of sodium triacetoxyborohydride was added, and stirred for 14 hours. Aqueous saturated sodium hydrogen carbonate solution was added, and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 0.41 g of 7-methoxy-1-(2-(4-((naphthalen-2-yl)methylamino)piperidin-1-yl)ethyl)quinoxalin-2 (1H)-one as a brown oil.

To a mixed solution of 10 mL chloroform and 10 mL ethyl acetate containing 0.41 g of 7-methoxy-1-(2-(4-((naphthalen-2-yl)methylamino)piperidin-1-yl)ethyl)quinoxalin-2 (1H)-one, 3 mL of 4 mol/L hydrogen chloride/ethyl acetate was added, and stirred at room temperature. The solvent was removed under reduced pressure, ethyl acetate was added and the resulting solid was filtered to give 452 mg of 7-methoxy-1-(2-(4-((naphthalen-2-yl)methylamino)piperidin-1-yl)ethyl)quinoxalin-2(1H)-one hydrochloride as a pale brown solid.

$^1$H-NMR (DMSO-$d_6$, $D_2O$) δ:
1.96-2.07 (2H, m), 2.38-2.48 (2H, m), 3.08-3.21 (2H, m), 3.36-3.47 (3H, m), 3.84-3.93 (2H, m), 3.97 (3H, s), 4.37-4.42 (2H, m), 4.62-4.68 (2H, m), 7.08 (1H, dd, J=8.9, 2.5 Hz), 7.12 (1H, d, J=2.8 Hz), 7.59-7.62 (2H, m), 7.69 (1H, d, J=8.3 Hz), 7.82 (1H, d, J=8.7 Hz), 7.95-8.00 (2H, m), 8.03 (1H, d, J=8.3 Hz), 8.09-8.14 (2H, m)

Example 357

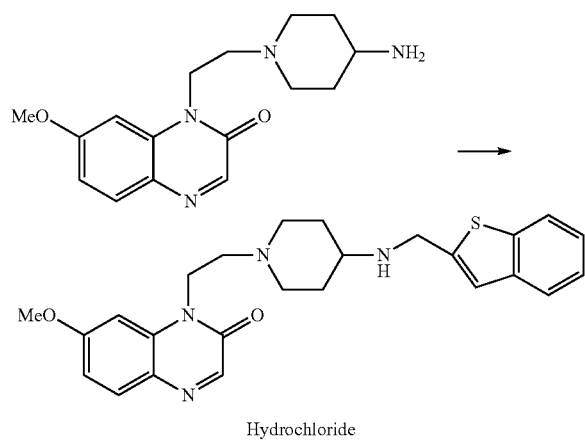

Hydrochloride

To 10 mL of a chloroform solution containing 500 mg of 1-(2-(4-aminopiperidin-1-yl)ethyl)-7-methoxyquinoxalin-2 (1H)-one and 241 mg of 1-benzo[b]thiophene-2-carbaldehyde, 100 mg of acetic acid was added, and stirred at room temperature for 2 hours. To the reaction mixture, 526 mg of sodium triacetoxyborohydride was added, and stirred for 14 hours. Aqueous saturated sodium hydrogen carbonate solution was added, and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 0.52 g of 1-(2-(4-((benzo[b]thiophen-2-yl)methylamino)piperidin-1-yl)ethyl)-7-methoxyquinoxalin-2(1H)-one as a pale brown solid.

To a mixed solution of 10 mL chloroform and 10 mL ethyl acetate containing 0.52 g of 1-(2-(4-((benzo[b]thiophen-2-yl)methylamino)piperidin-1-yl)ethyl)-7-methoxyquinoxalin-2 (1H)-one, 3 mL of 4 mol/L hydrogen chloride/ethyl acetate was added, and stirred at room temperature. The solvent was removed under reduced pressure, ethyl acetate was added and the resulting solid was filtered to give 526 mg of 1-(2-(4-((benzo[b]thiophen-2-yl)methylamino)piperidin-1-yl) ethyl)-7-methoxyquinoxalin-2(1H)-one hydrochloride as a yellow solid.

$^1$H-NMR (DMSO-$d_6$, $D_2O$) δ:
1.80-2.00 (2H, m), 2.29-2.45 (2H, m), 2.97-3.21 (2H, m), 3.28-3.49 (3H, m), 3.74-3.90 (2H, m), 3.96 (3H, s), 4.49-4.69 (4H, m), 7.04-7.13 (2H, m), 7.40-7.50 (2H, m), 7.62-7.71 (1H, m), 7.80-7.86 (1H, m), 7.89-7.96 (1H, m), 8.00-8.05 (1H, m), 8.08-8.14 (1H, m)

Example 358

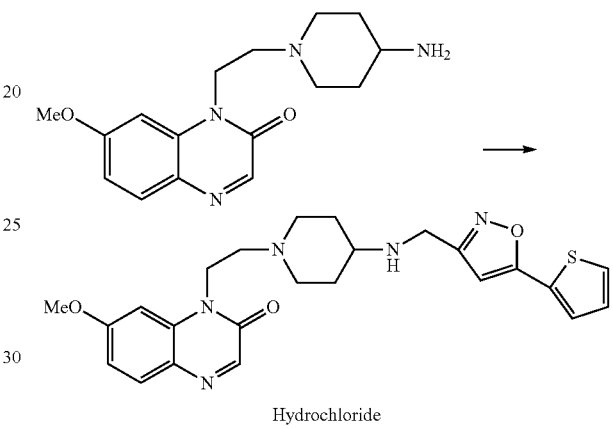

Hydrochloride

To 10 mL of a chloroform solution containing 500 mg of 1-(2-(4-aminopiperidin-1-yl)ethyl)-7-methoxyquinoxalin-2 (1H)-one and 267 mg of 5-(2-thienyl)-3-isoxazolecarbaldehyde, 100 mg of acetic acid was added, and stirred at room temperature for 2 hours. To the reaction mixture, 526 mg of sodium triacetoxyborohydride was added, and stirred for 18 hours. Aqueous saturated sodium hydrogen carbonate solution was added, and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 0.63 g of 7-methoxy-1-(2-(4-((5-(thiophen-2-yl)isoxazol-3-yl)methylamino)piperidin-1-yl)ethyl)quinoxalin-2(1H)-one as a brown oil.

To 20 mL of an ethyl acetate solution containing 0.63 g of 7-methoxy-1-(2-(4-((5-(thiophen-2-yl)isoxazol-3-yl)methylamino)piperidin-1-yl)ethyl)quinoxalin-2(1H)-one, 3 mL of 4 mol/L hydrogen chloride/ethyl acetate was added, and stirred at room temperature. The resulting solid was filtered to give 661 mg of 7-methoxy-1-(2-(4-((5-(thiophen-2-yl)isoxazol-3-yl)methylamino)piperidin-1-yl)ethyl)quinoxalin-2 (1H)-one hydrochloride as a green solid.

$^1$H-NMR (DMSO-$d_6$, $D_2O$) δ:
1.86-2.01 (2H, m), 2.32-2.43 (2H, m), 3.02-3.21 (2H, m), 3.32-3.53 (3H, m), 3.78-3.93 (2H, m), 3.96 (3H, s), 4.36-4.48 (2H, m), 4.57-4.69 (2H, m), 7.01 (1H, s), 7.06-7.13 (2H, m), 7.29 (1H, dd, J=5.0, 3.7 Hz), 7.75 (1H, d, J=3.7, 1.4 Hz), 7.83 (1H, d, J=8.7 Hz), 7.87 (1H, dd, J=5.0, 1.4 Hz), 8.10 (1H, s)

Example 359

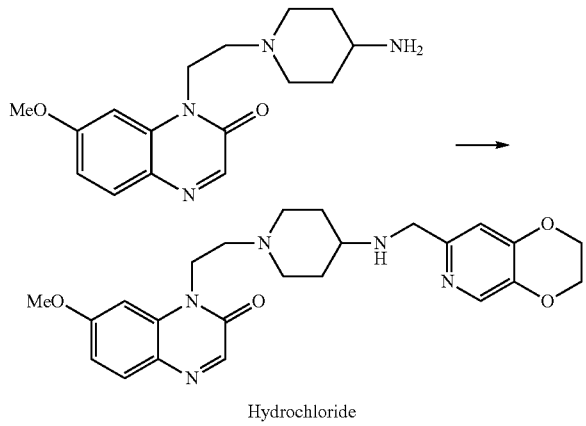

Hydrochloride

To 10 mL of a chloroform solution containing 500 mg of 1-(2-(4-aminopiperidin-1-yl)ethyl)-7-methoxyquinoxalin-2(1H)-one and 246 mg of 2,3-dihydro-1,4-dioxino[2,3-c]pyridine-7-carbaldehyde, 100 mg of acetic acid was added, and stirred at room temperature for 2 hours. To the reaction mixture, 526 mg of sodium triacetoxyborohydride was added, and stirred for 18 hours. Aqueous saturated sodium hydrogen carbonate solution was added, and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 540 mg of 1-(2-(4-((2,3-dihydro-1,4-dioxino[2,3-c]pyridin-7-yl)methylamino)piperidin-1-yl)ethyl)-7-methoxyquinoxalin-2(1H)-one as a brown oil.

To 5 mL of an ethyl acetate solution containing 540 mg of 1-(2-(4-((2,3-dihydro-1,4-dioxino[2,3-c]pyridin-7-yl)methylamino)piperidin-1-yl)ethyl)-7-methoxy-quinoxalin-2(1H)-one, 2 mL of 4 mol/L hydrogen chloride/ethyl acetate was added, and stirred at room temperature. The resulting solid was filtered to give 661 mg of 1-(2-(4-((2,3-dihydro-1,4-dioxino[2,3-c]pyridin-7-yl)methylamino)piperidin-1-yl)ethyl)-7-methoxy-quinoxalin-2(1H)-one hydrochloride as a pale green solid.

$^1$H-NMR (DMSO-$d_6$, $D_2O$) δ:
1.89-2.01 (2H, m), 2.30-2.42 (2H, m), 3.06-3.19 (2H, m), 3.33-3.45 (3H, m), 3.82-3.90 (2H, m), 3.96 (3H, s), 4.20-4.26 (2H, m), 4.32-4.44 (4H, m), 4.59-4.69 (2H, m), 7.06-7.09 (1H, m), 7.11 (1H, d, J=2.3 Hz), 7.19 (1H, s), 7.82 (1H, d, J=8.7 Hz), 8.10 (1H, s), 8.23 (1H, s)

Example 360

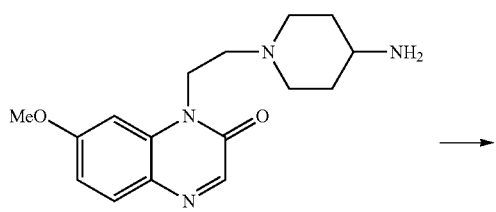

-continued

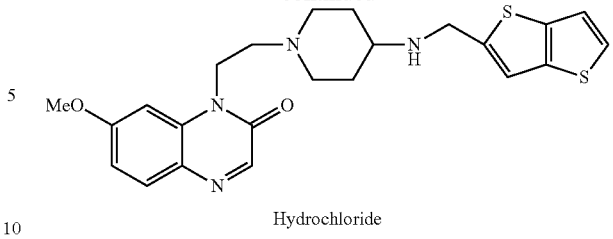

Hydrochloride

To 6 mL of a chloroform solution containing 270 mg of 1-(2-(4-aminopiperidin-1-yl)ethyl)-7-methoxyquinoxalin-2(1H)-one and 135 mg of thieno[3,2-b]thiophene-2-carbaldehyde, 54 mg of acetic acid were added, and stirred at room temperature for 2 hours. To the reaction mixture, 284 mg of sodium triacetoxyborohydride was added, and stirred for 18 hours. Aqueous saturated sodium hydrogen carbonate solution was added, and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 0.31 g of 1-(2-(4-(((thieno[3,2-b]thiophen-2-yl)methylamino)piperidin-1-yl)ethyl)-7-methoxyquinoxalin-2(1H)-one as a brown oil.

To a mixed solution of 20 mL chloroform and 5 mL ethyl acetate containing 0.31 g of 1-(2-(4-(((thieno[3,2-b]thiophen-2-yl)methylamino)piperidin-1-yl)ethyl)-7-methoxyquinoxalin-2(1H)-one, 3 mL of 4 mol/L hydrogen chloride/ethyl acetate was added, and stirred at room temperature. The solvent was removed under reduced pressure, ethyl acetate was added, and the resulting solid was filtered to give 313 mg of 1-(2-(4-(((thieno[3,2-b]thiophen-2-yl)methylamino)piperidin-1-yl)ethyl)-7-methoxyquinoxalin-2(1H)-one hydrochloride as a yellow solid.

$^1$H-NMR (DMSO-$d_6$, $D_2O$) δ:
1.93-2.05 (2H, m), 2.33-2.43 (2H, m), 3.06-3.20 (2H, m), 3.31-3.58 (3H, m), 3.80-3.91 (2H, m), 3.97 (3H, s), 4.48-4.59 (2H, m), 4.59-4.70 (2H, m), 7.04-7.09 (1H, m), 7.14 (1H, s), 7.48 (1H, d, J=6.0 Hz), 7.70 (1H, s), 7.75 (1H, d, J=5.5 Hz), 7.81 (1H, d, J=8.7 Hz), 8.09 (1H, s)

Example 361

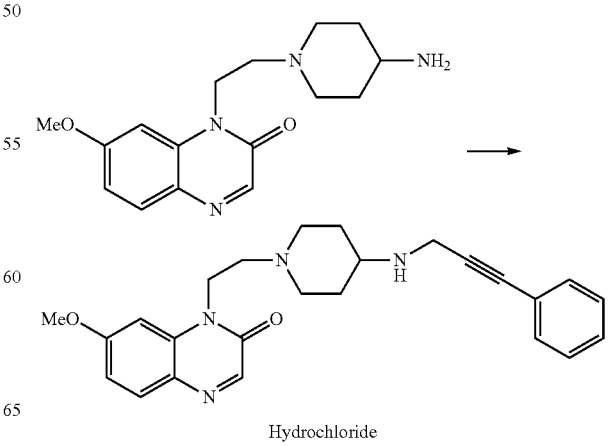

Hydrochloride

-continued

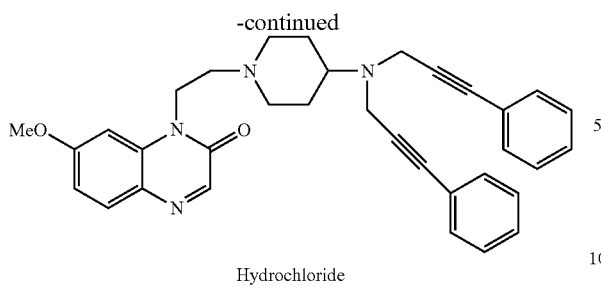

Hydrochloride

To 10 mL of a chloroform solution containing 500 mg of 1-(2-(4-aminopiperidin-1-yl)ethyl)-7-methoxyquinoxalin-2(1H)-one and 1940 mg of phenylpropargylaldehyde, 100 mg of acetic acid were added, and stirred at room temperature for 2 hours. To the reaction mixture, 526 mg of sodium triacetoxyborohydride was added, and stirred for 14 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 0.27 g of 7-methoxy-1-(2-(4-(3-phenyl-2-propyn-1-ylamino)piperidin-1-yl)ethyl)quinoxalin-2(1H)-one as a brown oil and 0.23 g of 1-(2-(4-(bis(3-phenyl-2-propyn-1-ylamino)piperidin-1-yl)ethyl)-7-methoxyquinoxalin-2(1H)-one as a brown oil.

To 10 mL of an ethyl acetate solution containing 0.23 g of 7-methoxy-1-(2-(4-(3-phenyl-2-propyn-1-ylamino)piperidin-1-yl)ethyl)quinoxalin-2(1H)-one, 2 mL of 4 mol/L hydrogen chloride/ethyl acetate was added, and stirred at room temperature. The resulting solid was filtered to give 155 mg of 7-methoxy-1-(2-(4-(3-phenyl-2-propyn-1-ylamino)piperidin-1-yl)ethyl)quinoxalin-2(1H)-one hydrochloride as a brown solid.

$^1$H-NMR (DMSO-$d_6$, $D_2O$) δ:

1.80-1.99 (2H, m), 2.26-2.40 (2H, m), 3.07-3.25 (2H, m), 3.30-3.53 (3H, m), 3.75-3.93 (2H, m), 3.96 (3H, s), 4.20-4.31 (2H, m), 4.55-4.69 (2H, m), 7.08 (1H, dd, J=8.7, 2.3 Hz), 7.11 (1H, d, J=1.4 Hz), 7.43-7.50 (3H, m), 7.51-7.55 (2H, m), 7.82 (1H, d, J=8.7 Hz), 8.10 (1H, s)

To 5 mL of an ethyl acetate solution containing 0.24 g of 1-(2-(4-(bis(3-phenyl-2-propyn-1-yl)amino)piperidin-1-yl)ethyl)-7-methoxyquinoxalin-2(1H)-one, 2 mL of 4 mol/L hydrogen chloride/ethyl acetate was added, and stirred at room temperature. The resulting solid was filtered to give 224 mg of 1-(2-(4-(bis(3-phenyl-2-propyn-1-yl)amino)piperidin-1-yl)ethyl)-7-methoxyquinoxalin-2(1H)-one hydrochloride as a brown solid.

$^1$H-NMR (DMSO-$d_6$, $D_2O$) δ:

1.86-1.93 (2H, m), 2.33-2.38 (2H, m), 3.15-3.22 (2H, m), 3.30 (1H, s), 3.39-3.47 (2H, m), 3.83-3.92 (2H, m), 3.96 (3H, s), 4.14 (4H, s), 4.59-4.67 (2H, m), 7.06-7.12 (2H, m), 7.32-7.54 (10H, m), 7.82 (1H, d, J=8.7 Hz), 8.10 (1H, s)

Example 362

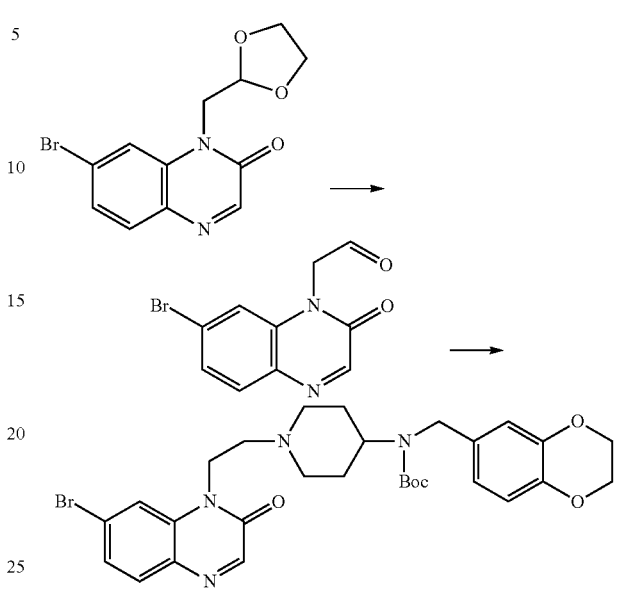

0.38 g of 7-bromo-1-(1,3-dioxolan-2-ylmethyl)quinoxalin-2(1H)-one was dissolved in 15 mL of 80% aqueous trifluoroacetic acid solution, and stirred at room temperature for 16 hours. After the solvent was removed under reduced pressure, and the reaction mixture was alkalized by adding aqueous saturated sodium hydrogen carbonate solution, it was extracted with ethyl acetate. The organic layer was washed with aqueous saturated sodium chloride solution, dried over anhydrous magnesium sulfate, and the solvent was removed under reduced pressure to give (7-bromo-2-oxoquinoxalin-1(2H)-yl)acetaldehyde.

To 200 mL of a chloroform solution containing (7-bromo-2-oxoquinoxalin-1(2H)-yl)acetaldehyde, 0.43 g of tert-butyl (2,3-dihydro-1,4-benzodioxin-6-ylmethyl)(piperidin-4-yl)carbamate and 73 mg of acetic acid were added, and stirred at room temperature for 30 min. To the reaction mixture, 0.39 g of sodium triacetoxyborohydride was added, and stirred for 2.5 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=30:1], to give 0.47 g of tert-butyl (2,3-dihydro-1,4-benzodioxin-6-ylmethyl)1-(2-(7-bromo-2-oxoquinoxalin-1(2H)-yl)ethyl)piperidin-4-yl)carbamate as a pale brown foam.

$^1$H-NMR (CDCl$_3$) δ:

1.41 (9H, s), 1.58-1.69 (5H, m), 2.06-2.23 (2H, m), 2.61-2.66 (2H, m), 2.94-3.00 (2H, m), 4.22-4.32 (8H, m), 6.65-6.71 (1H, m), 6.72-6.74 (1H, m), 6.77 (1H, d, J=8.3 Hz), 7.43-7.46 (1H, m), 7.62 (1H, s), 7.72 (1H, d, J=8.3 Hz), 8.26 (1H, s)

Example 363

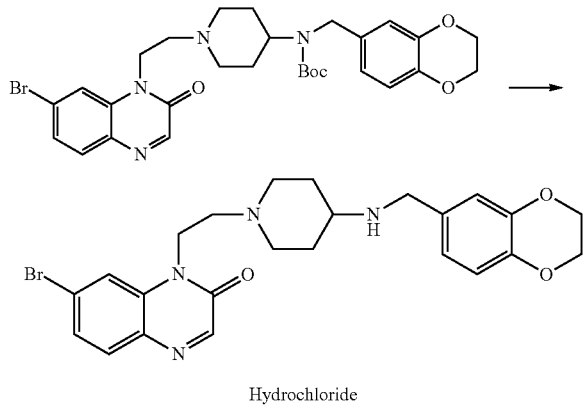

Hydrochloride

To 20 mL of a chloroform solution containing 0.47 g of tert-butyl (2,3-dihydro-1,4-benzodioxin-6-ylmethyl)(1-(2-(7-bromo-2-oxoquinoxalin-1(2H)-yl)ethyl)piperidin-4-yl) carbamate, 20 mL of trifluoroacetic acid was added and stirred at room temperature for 12 hours. After solvents of the reaction mixture were removed under reduced pressure and the residue was alkalized by aqueous saturated sodium hydrogen carbonate solution, it was extracted with chloroform. The organic layer was dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform: methanol=10:1], to give 280 mg of 1-(2-(4-((2,3-dihydro-1,4-benzodioxin-6-ylmethyl)amino)piperidin-1-yl)ethyl)-7-bromoquinoxalin-2(1H)-one as a pale brown foam.

To 5 mL of an ethyl acetate solution containing 280 mg of 1-(2-(4-((2,3-dihydro-1,4-benzodioxin-6-ylmethyl)amino)piperidin-1-yl)ethyl)-7-bromoquinoxalin-2(1H)-one, 2 mL of 4 mol/L hydrogen chloride/ethyl acetate was added, and stirred at room temperature. The resulting solid was filtered to give 285 mg of 1-(2-(4-((2,3-dihydro-1,4-benzodioxin-6-ylmethyl)amino)piperidin-1-yl)ethyl)-7-bromoquinoxalin-2(1H)-one hydrochloride as a brown solid.

$^1$H-NMR (DMSO-$d_6$, $D_2O$) δ:
1.83-2.01 (2H, m), 2.28-2.41 (2H, m), 3.01-3.20 (2H, m), 3.24-3.47 (3H, m), 3.78-3.92 (2H, m), 4.05-4.14 (2H, m), 4.26 (4H, s), 4.53-4.65 (2H, m), 6.91-6.95 (1H, m), 6.99-7.03 (1H, m), 7.09-7.13 (1H, m), 7.60-7.64 (1H, m), 7.80-7.83 (1H, m), 7.95-7.99 (1H, m), 8.28-8.31 (1H, m)

Example 364

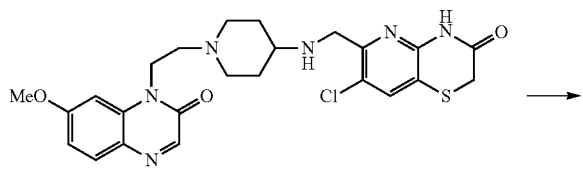

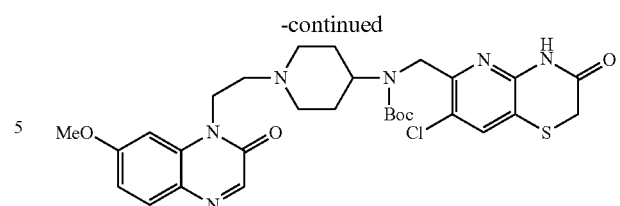

To 30 mL of a chloroform solution containing 0.43 g of 1-(2-(4-((7-chloro-3-oxo-3,4-dihydro-2H-pyrido[3,2-b][1,4]thiazin-6-yl)methylamino)piperidin-1-yl)ethyl)-7-methoxyquinoxalin-2(1H)-one, 0.55 g of di-tert-butyl dicarbonate and 0.05 g of triethylamine were added, and stirred at room temperature for 15 hours. The solvent was removed under reduced pressure, and the residue thus obtained was purified by silica gel column chromatography [Silica Gel; Kanto Chemical Co., Inc., Silica Gel 60N, eluent; chloroform: methanol=10:1] to give 0.57 g of tert-butyl (7-chloro-3-oxo-3,4-dihydro-2H-pyrido[3,2-b][1,4]thiazin-6-ylmethyl)(1-(2-(7-methoxy-2-oxoquinoxalin-1(2H)-yl)ethyl)piperidin-4-yl) carbamate as a brown oil.

$^1$H-NMR (CDCl$_3$) δ:
1.23-1.66 (12H, m), 1.72-1.82 (2H, m), 2.13-2.27 (2H, m), 2.63-2.69 (2H, m), 3.01-3.07 (2H, m), 3.45-3.53 (2H, m), 3.90 (3H, s), 4.28-4.33 (2H, m), 4.39-4.55 (2H, m), 6.80 (1H, s), 6.90-6.94 (1H, m), 7.54-7.59 (1H, m), 7.78 (1H, d, J=8.7 Hz), 7.86-7.98 (1H, m), 8.11 (1H, s)

Example 365

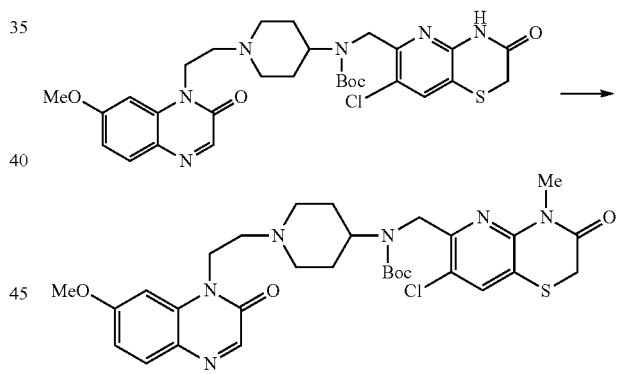

To 20 mL of an N,N-dimethylformamide solution containing 0.57 g of tert-butyl (7-chloro-3-oxo-3,4-dihydro-2H-pyrido[3,2-b][1,4]thiazin-6-ylmethyl)(1-(2-(7-methoxy-2-oxoquinoxalin-1(2H)-yl)ethyl)piperidin-4-yl)carbamate, 0.04 g of 60% sodium hydride was added, and stirred at room temperature for 1 hour. 0.24 g of methyl iodide was added, and stirred at room temperature for 2 hours. To the reaction mixture, water, ethyl acetate and toluene were added. The organic layer was separated, washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=30:1] to give 0.23 g of tert-butyl (7-chloro-4-methyl-3-oxo-3,4-dihydro-2H-pyrido[3,2-b][1,4]thiazin-6-ylmethyl)(1-(2-(7-methoxy-2-oxoquinoxalin-1(2H)-yl)ethyl)piperidin-4-yl)carbamate as a pale brown foam.

¹H-NMR (CDCl₃) δ:
1.23-1.51 (9H, m), 1.52-1.62 (3H, m), 1.72-1.84 (2H, m), 2.14-2.27 (2H, m), 2.63-2.68 (2H, m), 3.01-3.07 (2H, m), 3.45-3.51 (5H, m), 3.90 (3H, s), 4.27-4.33 (2H, m), 4.45-4.58 (2H, m), 6.79 (1H, s), 6.89-6.94 (1H, m), 7.55-7.61 (1H, m), 7.76-7.80 (1H, m), 8.11 (1H, s)

7.08 (1H, dd, J=8.7, 2.3 Hz), 7.13 (1H, d, J=2.3 Hz), 7.82 (1H, d, J=8.7 Hz), 8.10 (1H, s), 8.19 (1H, s)

Example 366

Example 367

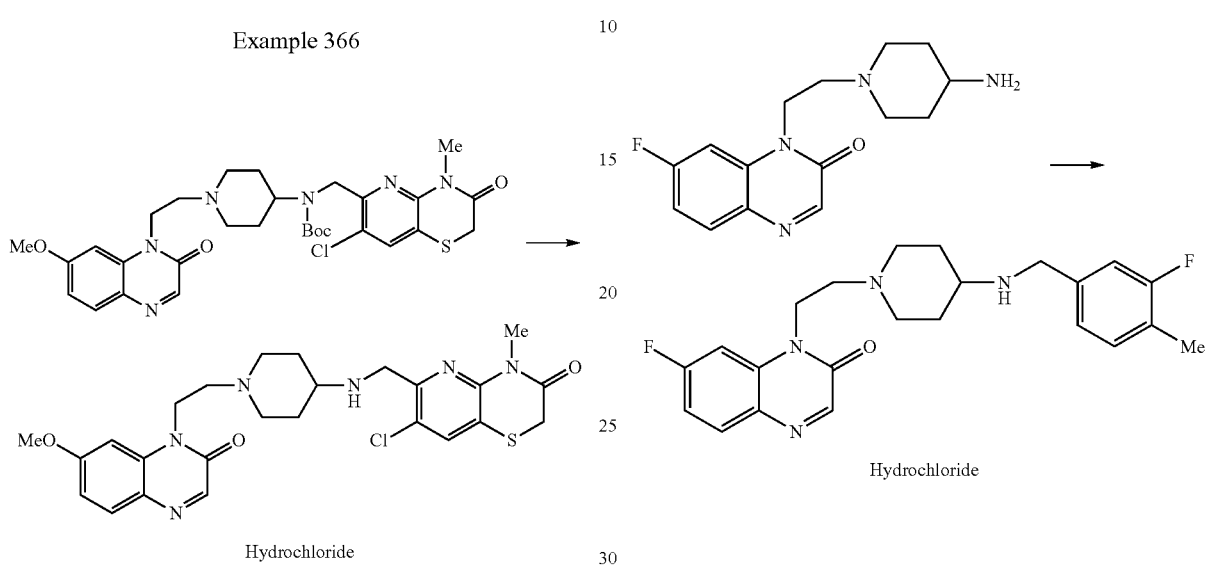

Hydrochloride

Hydrochloride

To 20 mL of a chloroform solution containing 0.23 g of tert-butyl (7-chloro-4-methyl-3-oxo-3,4-dihydro-2H-pyrido[3,2-b][1,4]thiazin-6-ylmethyl)(1-(2-(7-methoxy-2-oxoquinoxalin-1(2H)-yl)ethyl)piperidin-4-yl)carbamate, 20 mL of trifluoroacetic acid was added and stirred at room temperature for 12 hours. After solvents of the reaction mixture were removed under reduced pressure and the residue was alkalized by aqueous saturated sodium hydrogen carbonate solution, it was extracted with chloroform. The organic layer was dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform:methanol=10:1], to give 0.16 g of 1-(2-(4-((7-chloro-4-methyl-3-oxo-3,4-dihydro-2H-pyrido[3,2-b][1,4]thiazin-6-yl)methylamino)piperidin-1-yl)ethyl)-7-methoxyquinoxalin-2(1H)-one as a pale brown foam.

To 5 mL of an ethyl acetate solution containing 0.16 g of 1-(2-(4-((7-chloro-4-methyl-3-oxo-3,4-dihydro-2H-pyrido[3,2-b][1,4]thiazin-6-yl)methylamino)piperidin-1-yl)ethyl)-7-methoxyquinoxalin-2(1H)-one, 2 mL of 4 mol/L hydrogen chloride/ethyl acetate was added, and stirred at room temperature. The resulting solid was filtered to give 161 mg of 1-(2-(4-((7-chloro-4-methyl-3-oxo-3,4-dihydro-2H-pyrido[3,2-b][1,4]thiazin-6-yl)methylamino)piperidin-1-yl)ethyl)-7-methoxyquinoxalin-2(1H)-one hydrochloride as a yellow solid.

¹H-NMR (DMSO-d₆, D₂O) δ:
1.95-2.07 (2H, m), 2.36-2.46 (2H, m), 3.07-3.19 (2H, m), 3.36-3.59 (6H, m), 3.69-3.74 (2H, m), 3.84-3.93 (2H, m), 3.95-3.99 (3H, m), 4.44-4.52 (2H, m), 4.60-4.68 (2H, m),

To 10 mL of a chloroform solution containing 383 mg of 1-(2-(4-aminopiperidin-1-yl)ethyl)-7-fluoroquinoxalin-2(1H)-one and 160 mg of 3-fluoro-4-methylbenzaldehyde, 76 μL of acetic acid was added, and stirred at room temperature for 1 hour. To the reaction mixture, 437 mg of sodium triacetoxyborohydride was added, and stirred overnight. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; ethyl acetate:hexane=1:1] to give 429 mg of 1-(2-(4-((3-fluoro-4-methylbenzyl)amino)piperidin-1-yl)ethyl)-7-fluoroquinoxalin-2(1H)-one as a pale yellow solid.

To 10 mL of a chloroform solution containing 375 mg of 1-(2-(4-((3-fluoro-4-methylbenzyl)amino)piperidin-1-yl)ethyl)-7-fluoroquinoxalin-2(1H)-one, 1 mL of 4 mol/L hydrogen chloride/ethyl acetate was added, and stirred at room temperature for 10 min. The solvent was removed under reduced pressure, ethyl acetate was added, and the resulting solid was filtered to give 373 mg of 1-(2-(4-((3-fluoro-4-methylbenzyl)amino)piperidin-1-yl)ethyl)-7-fluoroquinoxalin-2(1H)-one hydrochloride as a pale brown solid.

¹H-NMR (DMSO-d₆) δ:
2.00-2.06 (2H, m), 2.26 (3H, s), 2.32-2.38 (2H, m), 3.07-3.14 (2H, m), 3.21-3.48 (3H, m), 3.80-3.85 (2H, m), 4.16-4.20 (2H, m), 4.57-4.61 (2H, m), 7.28-7.33 (2H, m), 7.37 (1H, t, J=8.0 Hz), 7.44 (1H, d, J=10.5 Hz), 7.76 (1H, d, J=9.6 Hz), 7.93 (1H, dd, J=8.0, 6.2 Hz), 8.23 (1H, s), 9.54-9.59 (2H, broad), 10.39-10.45 (1H, broad)

Example 368

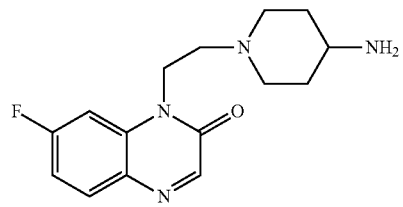

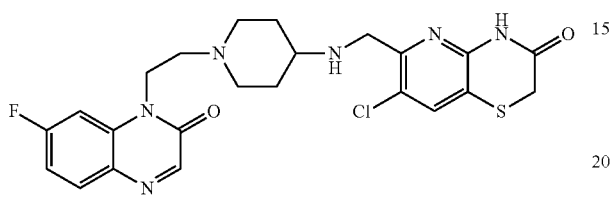

Hydrochloride

To 10 mL of a chloroform solution containing 325 mg of 1-(2-(4-aminopiperidin-1-yl)ethyl)-7-fluoroquinoxalin-2(1H)-one and 234 mg of 7-chloro-3-oxo-3,4-dihydro-2H-pyrido[3,2-b][1,4]thiazine-6-carbaldehyde, 64 μL of acetic acid was added, and stirred at room temperature for 1 hour. To the reaction mixture, 367 mg of sodium triacetoxyborohydride was added, and stirred overnight. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform:methanol=100:1] to give 478 mg of 1-(2-(4-((7-chloro-3-oxo-3,4-dihydro-2H-pyrido[3,2-b][1,4]thiazin-6-yl)methylamino)piperidin-1-yl)ethyl)-7-fluoroquinoxalin-2(1H)-one as a pale brown foam.

To 5 mL of a chloroform solution containing 452 mg of 1-(2-(4-((7-chloro-3-oxo-3,4-dihydro-2H-pyrido[3,2-b][1,4]thiazin-6-yl)methylamino)piperidin-1-yl)ethyl)-7-fluoroquinoxalin-2(1H)-one, 1 mL of 4 mol/L hydrogen chloride/ethyl acetate was added, and stirred at room temperature for 10 min. The solvent was removed under reduced pressure, ethyl acetate was added, and the resulting solid was filtered to give 311 mg of 1-(2-(4-((7-chloro-3-oxo-3,4-dihydro-2H-pyrido[3,2-b][1,4]thiazin-6-yl)methylamino)piperidin-1-yl)ethyl)-7-fluoroquinoxalin-2(1H)-one hydrochloride as a pale brown solid.

$^1$H-NMR (DMSO-$d_6$) δ:
2.00-2.11 (2H, m), 2.43-2.55 (2H, m), 3.03-3.14 (2H, m), 3.27-3.57 (3H, m), 3.65-3.67 (2H, m), 3.79-3.90 (2H, m), 4.31-4.40 (2H, m), 4.57-4.67 (2H, m), 7.28-7.33 (1H, m), 7.79 (1H, d, J=10.1 Hz), 7.93 (1H, dd, J=8.7, 6.0 Hz), 8.16 (1H, s), 8.24 (1H, s), 9.55-9.70 (2H, broad), 10.67-10.79 (1H, broad), 11.28 (1H, s)

Example 369

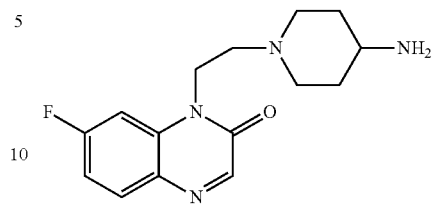

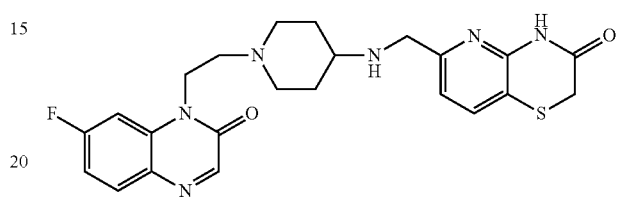

Hydrochloride

To 10 mL of a chloroform solution containing 183 mg of 1-(2-(4-aminopiperidin-1-yl)ethyl)-7-fluoroquinoxalin-2(1H)-one and 114 mg of 3-oxo-3,4-dihydro-2H-pyrido[3,2-b][1,4]thiazine-6-carbaldehyde, 36 μL of acetic acid was added, and stirred at room temperature for 1 hour. To the reaction mixture, 228 mg of sodium triacetoxyborohydride was added, and stirred overnight. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform:methanol=100:1] to give 135 mg of 7-fluoro-1-(2-(4-((3-oxo-3,4-dihydro-2H-pyrido[3,2-b][1,4]thiazin-6-yl)methylamino)piperidin-1-yl)ethyl)quinoxalin-2(1H)-one as a pale yellow solid.

To 5 mL of a chloroform solution containing 126 mg of 7-fluoro-1-(2-(4-((3-oxo-3,4-dihydro-2H-pyrido[3,2-b][1,4]thiazin-6-yl)methylamino)piperidin-1-yl)ethyl)quinoxalin-2(1H)-one, 0.5 mL of 4 mol/L hydrogen chloride/ethyl acetate was added, and stirred at room temperature for 10 min. The solvent was removed under reduced pressure, ethyl acetate was added, and the resulting solid was filtered to give 92 mg of 7-fluoro-1-(2-(4-((3-oxo-3,4-dihydro-2H-pyrido[3,2-b][1,4]thiazin-6-yl)methylamino)piperidin-1-yl)ethyl)quinoxalin-2(1H)-one hydrochloride as a pale brown solid.

$^1$H-NMR (DMSO-$d_6$) δ:
1.97-2.05 (2H, m), 2.17-2.23 (1H, m), 2.38-2.44 (2H, m), 3.06-3.15 (2H, m), 3.41-3.46 (2H, m), 3.61 (2H, s), 3.82-3.86 (2H, m), 4.23-4.28 (2H, m), 4.61 (2H, t, J=6.0 Hz), 7.23 (1H, d, J=7.8 Hz), 7.29-7.33 (1H, m), 7.67-7.73 (1H, m), 7.90-7.95 (2H, m), 8.24 (1H, s), 9.55-9.63 (2H, broad), 10.47-10.54 (1H, broad), 11.05 (1H, s)

Example 370

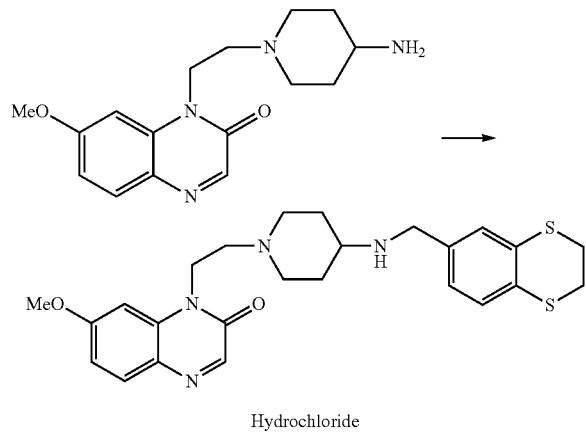

Hydrochloride

To 20 mL of a chloroform solution containing 205 mg of 1-(2-(4-aminopiperidin-1-yl)ethyl)-7-methoxyquinoxalin-2 (1H)-one and 120 mg of 2,3-dihydro-1,4-benzodithiin-6-carbaldehyde, 41 mg of acetic acid was added, and stirred at room temperature for 4.5 hours. To the reaction mixture, 216 mg of sodium triacetoxyborohydride was added, and stirred for 1 hour. Aqueous saturated sodium hydrogen carbonate solution was added, and the organic layer was separated. The organic layer was dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; chloroform: methanol=10:1] to give 195 mg of 1-(2-(4-((2,3-dihydro-1,4-benzodithiin-6-ylmethyl)amino) piperidin-1-yl)ethyl)-7-methoxyquinoxalin-2(1H)-one as a brown oil.

To 5 mL of an ethyl acetate solution containing 190 mg of 1-(2-(4-((2,3-dihydro-1,4-benzodithiin-6-ylmethyl)amino) piperidin-1-yl)ethyl)-7-methoxyquinoxalin-2(1H)-one, 2 mL of 4 mol/L hydrogen chloride/ethyl acetate was added, and stirred at room temperature. The resulting solid was filtered to give 192 mg of 1-(2-(4-((2,3-dihydro-1,4-benzodithiin-6-ylmethyl)amino)piperidin-1-yl)ethyl)-7-methoxyquinoxalin-2(1H)-one hydrochloride as a brown solid.

$^1$H-NMR (DMSO-$d_6$) δ:
1.98-2.07 (2H, m), 2.31-2.38 (2H, m), 3.06-3.15 (2H, m), 3.21-3.36 (7H, m), 3.78-3.85 (2H, m), 3.98 (3H, s), 4.06-4.14 (2H, m), 4.63-4.70 (2H, m), 7.03-7.06 (1H, m), 7.20 (1H, d, J=2.3 Hz), 7.22-7.23 (2H, m), 7.40-7.41 (1H, m), 7.79 (1H, d, J=9.2 Hz), 8.09 (1H, s), 9.40-9.54 (2H, broad), 10.80-10.96 (1H, broad)

Example 371

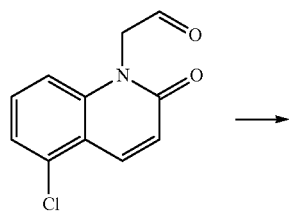

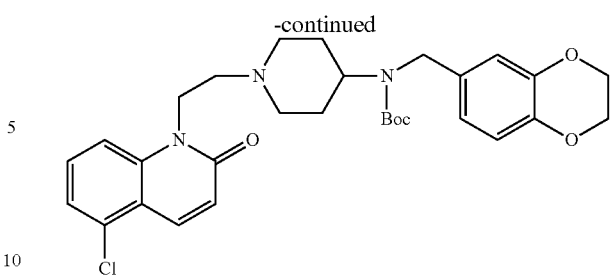

To 3 mL of a chloroform solution containing 0.58 g of tert-butyl (2,3-dihydro-1,4-benzodioxin-6-ylmethyl)(piperidin-4-yl)carbamate, 0.37 g of (5-chloro-2-oxoquinolin-1 (2H)-yl)acetaldehyde, 30 μL of acetic acid and 0.52 g of sodium triacetoxyborohydride were added, and stirred at room temperature for 2 nights. Aqueous saturated sodium hydrogen carbonate solution was added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60N, eluent; ethyl acetate] to give 0.48 g of tert-butyl 1-(2-(5-chloro-2-oxoquinolin-1(2H)-yl)ethyl)piperidin-4-yl)(2,3-dihydro-1,4-benzodioxin-6-ylmethyl)carbamate as a pale yellow foam.

$^1$H-NMR (CDCl$_3$) δ:
1.42 (9H, s), 1.64-1.71 (4H, m), 2.10-2.25 (2H, m), 2.57-2.65 (2H, m), 2.98-3.06 (2H, m), 4.03-4.15 (1H, m), 4.21-4.31 (6H, m), 4.34-4.43 (2H, m), 6.66-6.80 (4H, m), 7.26-7.34 (2H, m), 7.44 (1H, t, J=8.3 Hz), 8.14 (1H, d, J=10.1 Hz)

Example 372

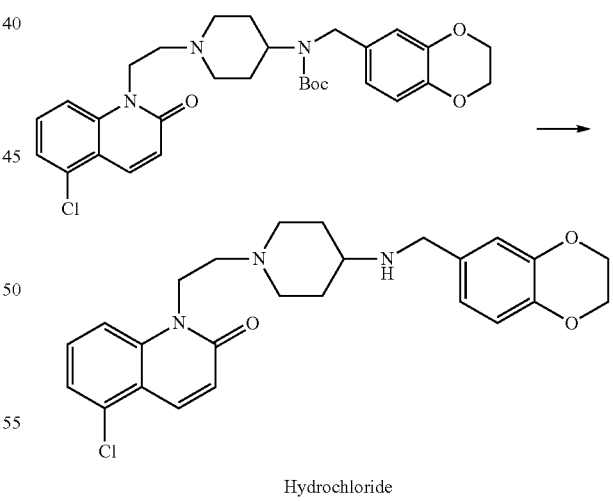

Hydrochloride

To 0.28 g of tert-butyl (1-(2-(5-chloro-2-oxoquinolin-1 (2H)-yl)ethyl)piperidin-4-yl)(2,3-dihydro-1,4-benzodioxin-6-ylmethyl)carbamate, 6 mL of 1,4-dioxane and 2 mL of 4 mol/L hydrogen chloride/1,4-dioxane were added, and stirred at room temperature overnight. The resulting solid was filtered to give 0.16 g of 5-chloro-1-(2-(4-((2,3-dihydro-1,4-benzodioxin-6-ylmethyl)amino)piperidin-1-yl)ethyl)quinolin-2(1H)-one hydrochloride as a white solid.

¹H-NMR (DMSO-d₆) δ:
1.98-2.11 (2H, m), 2.31-2.41 (2H, m), 3.07-3.17 (2H, m), 3.22-3.43 (3H, m), 3.75-3.83 (2H, m), 4.03-4.13 (2H, m), 4.26 (4H, s), 4.62-4.71 (2H, m), 6.81 (1H, d, J=9.6 Hz), 6.92 (1H, d, J=8.3 Hz), 7.00-7.07 (1H, m), 7.14 (1H, s), 7.48 (1H, d, J=8.3 Hz), 7.65 (1H, t, J=8.3 Hz), 7.78-7.86 (1H, m), 8.21 (1H, d, J=9.6 Hz), 9.33-9.55 (2H, broad), 10.63-10.79 (1H, broad)

Example 373

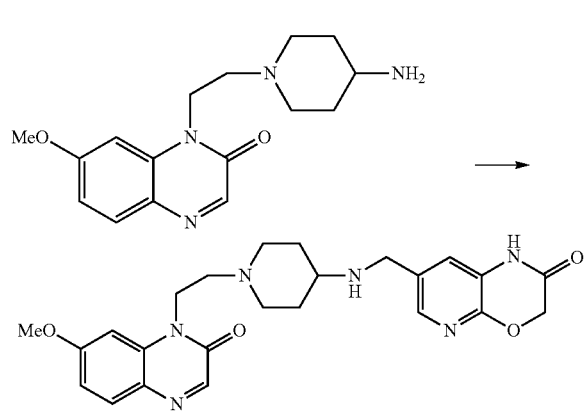

According to a procedure similar to Example 73, 7-(((1-(2-(7-methoxy-2-oxoquinoxalin-1(2H)-yl)ethyl)piperidin-4-yl)amino)methyl)-1H-pyrido(2,3-b)(1,4-)oxazin-2(3H)-one was obtained from 1-(2-(4-aminopyridin-1-yl)ethyl)-7-methoxyquinoxalin-2(1H)-one and 2-oxo-2,3-dihydro-1H-pyrido(2,3-b)(1,4)oxazine-7-carbaldehyde.

¹H-NMR (CDCl₃) δ:
1.35-1.47 (2H, m), 1.86-1.94 (2H, m), 2.14-2.23 (2H, m), 2.47-2.57 (1H, m), 2.65-2.72 (2H, m), 2.96-3.04 (2H, m), 3.76 (2H, s), 3.93 (3H, s), 4.31-4.38 (2H, m), 4.82 (2H, s), 6.84 (1H, d, J=2.4 Hz), 6.93 (1H, dd, J=8.9, 2.4 Hz), 7.22 (1H, d, J=1.7 Hz), 7.79 (1H, d, J=8.9 Hz), 7.84 (1H, d, J=1.7 Hz), 8.12 (1H, s)

Example 374

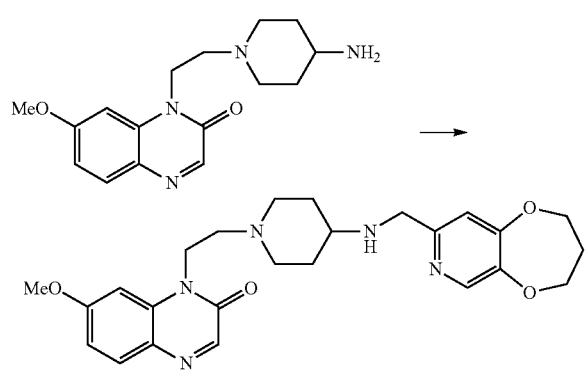

According to a procedure similar to Example 179, 1-(2-(4-((3,4-dihydro-2H-(1,4)dioxepino(2,3-c)pyridin-8-ylmethyl)amino)piperidin-1-yl)ethyl)-7-methoxyquinoxalin-2(1H)-one was obtained from 1-(2-(4-aminopyridin-1-yl)ethyl)-7-methoxyquinoxalin-2(1H)-one and 3,4-dihydro-2H-(1,4)dioxepino(2,3-c)pyridine-8-carbaldehyde.

¹H-NMR (CDCl₃) δ:
1.40-1.51 (2H, m), 1.87-1.96 (2H, m), 2.14-2.29 (4H, m), 2.47-2.58 (1H, m), 2.63-2.71 (2H, m), 2.95-3.03 (2H, m), 3.80 (2H, s), 3.92 (3H, s), 4.24 (2H, t, J=6.0 Hz), 4.30-4.38 (4H, m), 6.85-6.89 (1H, m), 6.87 (1H, s), 6.92 (1H, dd, J=8.9, 2.7 Hz), 7.78 (1H, d, J=8.9 Hz), 8.12 (1H, s), 8.18 (1H, s)

Example 375

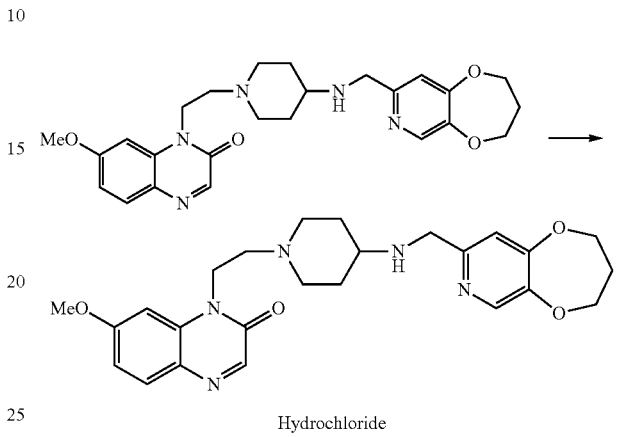

According to a procedure similar to Example 16, 1-(2-(4-((3,4-dihydro-2H-(1,4)dioxepino(2,3-c)pyridin-8-ylmethyl)amino)pyridin-1-yl)ethyl)-7-methoxyquinoxalin-2(1H)-one hydrochloride was obtained from 1-(2-(4-((3,4-dihydro-2H-(1,4)dioxepino(2,3-c)pyridin-8-ylmethyl)amino)piperidin-1-yl)ethyl)-7-methoxyquinoxalin-2(1H)-one.

¹H-NMR (D₂O) δ:
1.97-2.10 (2H, m), 2.32 (2H, q, J=5.7 Hz), 2.48-2.57 (2H, m), 3.20-3.31 (2H, m), 3.61-3.72 (3H, m), 3.95-4.04 (2H, m), 3.98 (3H, s), 4.33-4.40 (2H, m), 4.38 (2H, s), 4.48 (2H, t, J=5.6 Hz), 4.73-4.83 (2H, m), 7.00 (1H, d, J=2.2 Hz), 7.17-7.22 (1H, m), 7.21 (1H, s), 7.88 (1H, d, J=9.3 Hz), 8.13 (1H, s), 8.28 (1H, s)

Example 376

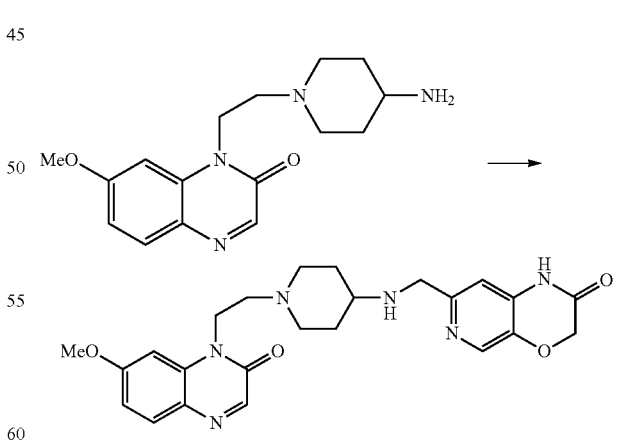

According to a procedure similar to Example 73, 7-(((1-(2-(7-methoxy-2-oxoquinoxalin-1(2H)-yl)ethyl)piperidin-4-yl)amino)methyl-1H-pyrido(3,4-b)(1,4)oxazin-2(3H)-one was obtained from 1-(2-(4-aminopiperidin-1-yl)ethyl)-7-methoxyquinoxalin-2(1H)-one and 2-oxo-2,3-dihydro-1H-pyrido(3,4-b)(1,4)oxazine-7-carbaldehyde.

¹H-NMR (DMSO-d₆) δ:
1.16-1.28 (2H, m), 1.72-1.81 (2H, m), 1.99-2.10 (2H, m), 2.32-2.58 (3H, m), 2.86-2.95 (2H, m), 3.69 (2H, s), 3.92 (3H, s), 4.28-4.36 (2H, m), 4.65 (2H, s), 6.96-7.03 (3H, m), 7.74 (1H, d, J=8.6 Hz), 8.03-8.06 (2H, m), 8.32 (1H, s)

Example 377

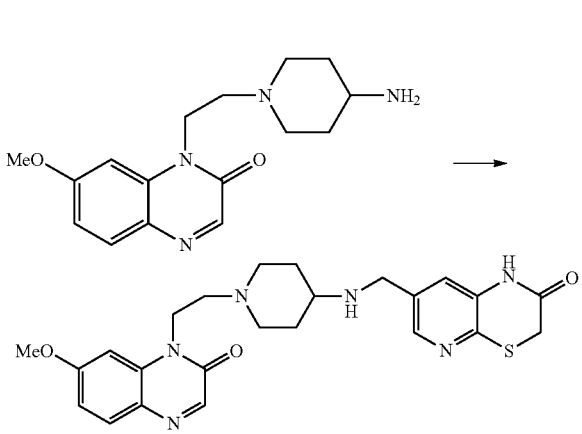

According to a procedure similar to Example 73, 7-(((1-(2-(7-methoxy-2-oxoquinoxalin-1(2H)-yl)ethyl)piperidin-4-yl)amino)methyl-1H-pyrido(2,3-b)(1,4)thiazin-2(3H)-one was obtained from 1-(2-(4-aminopiperidin-1-yl)ethyl)-7-methoxyquinoxalin-2(1H)-one and 2-oxo-2,3-dihydro-1H-pyrido(2,3-b)(1,4)thiazine-7-carbaldehyde.

¹H-NMR (DMSO-d₆) δ:
1.16-1.31 (2H, m), 1.73-1.81 (2H, m), 1.98-2.08 (2H, m), 2.29-2.38 (1H, m), 2.45-2.59 (2H, m), 2.87-2.94 (2H, m), 3.61 (2H, s), 3.66 (2H, s), 3.91 (3H, s), 4.28-4.36 (2H, m), 6.98-7.02 (2H, m), 7.25 (1H, d, J=1.7 Hz), 7.74 (1H, d, J=8.8 Hz), 8.02-8.04 (2H, m), 10.57 (1H, s)

Example 378

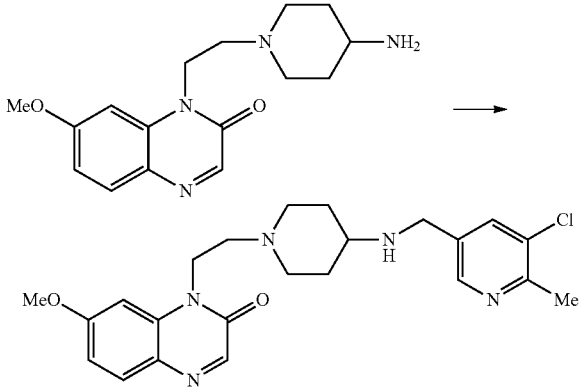

According to a procedure similar to Example 179, 1-(2-(4-(((5-chloro-6-methylpyridin-3-yl)methyl)amino)piperidin-1-yl)ethyl)-7-methoxyquinoxalin-2(1H)-one was obtained from 1-(2-(4-aminopiperidin-1-yl)ethyl)-7-methoxyquinoxalin-2(1H)-one and 5-chloro-6-methylnicotinealdehyde.

¹H-NMR (CDCl₃) δ:
1.37-1.48 (2H, m), 1.86-1.95 (2H, m), 2.15-2.24 (2H, m), 2.47-2.70 (3H, m), 2.61 (3H, s), 2.95-3.03 (2H, m), 3.79 (2H, s), 3.93 (3H, s), 4.30-4.37 (2H, m), 6.86 (1H, d, J=2.4 Hz), 6.93 (1H, dd, J=8.8, 2.4 Hz), 7.66 (1H, d, J=1.6 Hz), 7.79 (1H, d, J=8.8 Hz), 8.12 (1H, s), 8.31 (1H, d, J=1.6 Hz)

Example 379

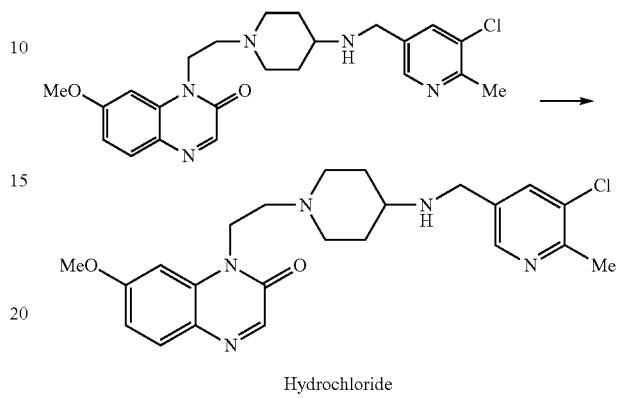

According to a procedure similar to Example 16, 1-(2-(4-(((5-chloro-6-methylpyridin-3-yl)methyl)amino)piperidin-1-yl)ethyl)-7-methoxyquinoxalin-2(1H)-one hydrochloride was obtained from 1-(2-(4-(((5-chloro-6-methylpyridin-3-yl)methyl)amino)piperidin-1-yl)ethyl)-7-methoxyquinoxalin-2(1H)-one.

¹H-NMR (DMSO-d₆, D₂O) δ:
1.95-2.10 (2H, m), 2.33-2.44 (2H, m), 2.59 (3H, s), 3.08-3.23 (2H, m), 3.34-3.47 (3H, m), 3.83-3.91 (2H, m), 3.97 (3H, s), 4.27 (2H, s), 4.63-4.70 (2H, m), 7.07 (1H, dd, J=8.9, 2.1 Hz), 7.15 (1H, d, J=2.1 Hz), 7.81 (1H, d, J=8.9 Hz), 8.10 (1H, s), 8.20 (1H, s), 8.60 (1H, s)

Example 380

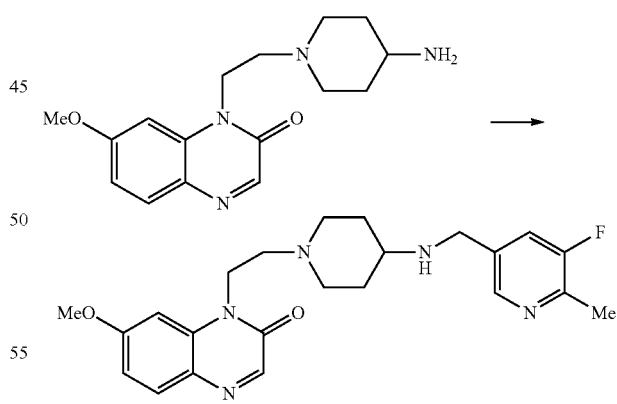

According to a procedure similar to Example 179, 1-(2-(4-(((5-fluoro-6-methylpyridin-3-yl)methyl)amino)piperidin-1-yl)ethyl)-7-methoxyquinoxalin-2(1H)-one was obtained from 1-(2-(4-aminopiperidin-1-yl)ethyl)-7-methoxyquinoxalin-2(1H)-one and 5-fluoro-6-methylnicotinealdehyde.

¹H-NMR (CDCl₃) δ:
1.36-1.48 (2H, m), 1.86-1.95 (2H, m), 2.14-2.23 (2H, m), 2.47-2.55 (1H, m), 2.51 (3H, d, J=2.7 Hz), 2.64-2.71 (2H, m), 2.95-3.03 (2H, m), 3.82 (2H, s), 3.93 (3H, s), 4.30-4.39 (2H, m), 6.85 (1H, d, J=2.4 Hz), 6.93 (1H, dd, J=8.9, 2.4 Hz), 7.37 (1H, d, J=10.3 Hz), 7.79 (1H, d, J=8.9 Hz), 8.12 (1H, s), 8.23 (1H, s)

Example 381

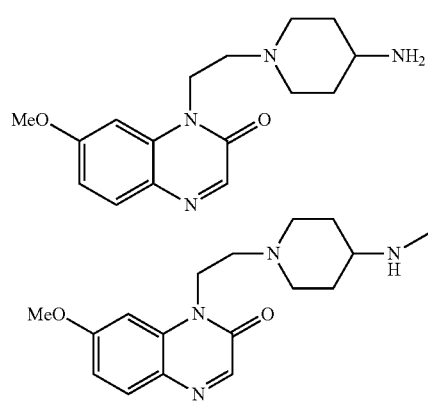

According to a procedure similar to Example 179, 7-methoxy-1-(2-(4-(((6-methylpyridin-3-yl)methyl)amino)piperidin-1-yl)ethyl)quinoxalin-2(1H)-one was obtained from 1-(2-(4-aminopiperidin-1-yl)ethyl)-7-methoxyquinoxalin-2(1H)-one and 6-methylnicotinealdehyde.

$^1$H-NMR (CDCl$_3$) δ:
1.36-1.49 (2H, m), 1.86-1.96 (2H, m), 2.14-2.23 (2H, m), 2.47-2.58 (1H, m), 2.54 (3H, s), 2.63-2.72 (2H, m), 2.95-3.03 (2H, m), 3.79 (2H, s), 3.92 (3H, s), 4.30-4.38 (2H, m), 6.86 (1H, d, J=2.5 Hz), 6.92 (1H, dd, J=8.9, 2.5 Hz), 7.12 (1H, d, J=7.9 Hz), 7.57 (1H, dd, J=7.9, 2.2 Hz), 7.78 (1H, d, J=8.9 Hz), 8.12 (1H, s), 8.42 (1H, d, J=2.2 Hz)

Example 382

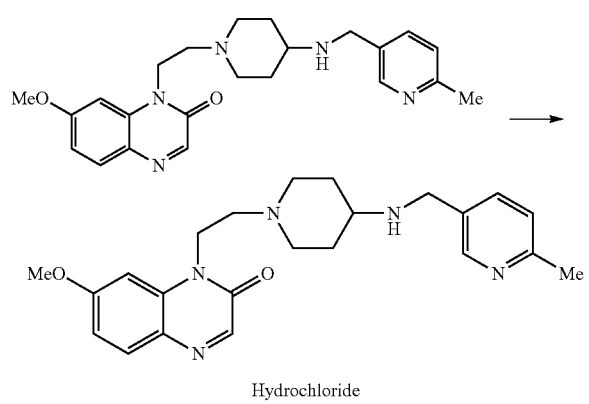

Hydrochloride

According to a procedure similar to Example 16, 7-methoxy-1-(2-(4-(((6-methylpyridin-3-yl)methyl)amino)piperidin-1-yl)ethyl)quinoxalin-2(1H)-one hydrochloride was obtained from 7-methoxy-1-(2-(4-(((6-methylpyridin-3-yl)methyl)amino)piperidin-1-yl)ethyl)quinoxalin-2(1H)-one.

$^1$H-NMR (D$_2$O) δ:
1.99-2.14 (2H, m), 2.53-2.62 (2H, m), 2.80 (3H, s), 3.23-3.35 (2H, m), 3.62-3.81 (3H, m), 3.96-4.07 (2H, m), 3.98 (3H, s), 4.54 (2H, s), 4.70-4.90 (2H, m), 7.00 (1H, d, J=2.4 Hz), 7.19 (1H, dd, J=9.0, 2.4 Hz), 7.88 (1H, d, J=9.0 Hz), 7.94 (1H, d, J=8.4 Hz), 8.13 (1H, s), 8.53 (1H, dd, J=8.4, 1.9 Hz), 8.78 (1H, d, J=1.9 Hz)

Example 383

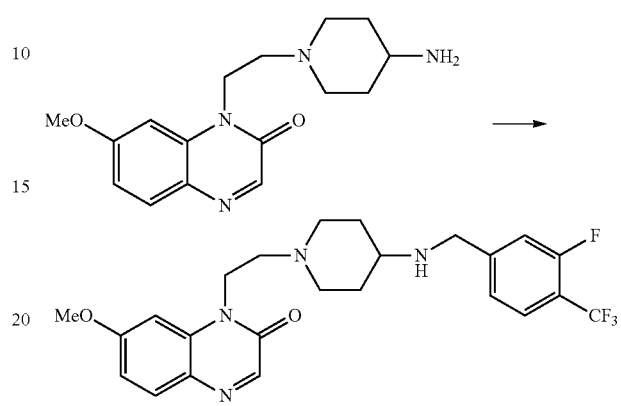

According to a procedure similar to Example 179, 1-(2-(4-((3-fluoro-4-(trifluoromethyl)benzyl)amino)piperidin-1-yl)ethyl)-7-methoxyquinoxalin-2(1H)-one was obtained from 1-(2-(4-aminopiperidin-1-yl)ethyl)-7-methoxyquinoxalin-2(1H)-one and 3-fluoro-4-(trifluoromethyl)benzaldehyde.

$^1$H-NMR (CDCl$_3$) δ:
1.36-1.48 (2H, m), 1.86-1.95 (2H, m), 2.14-2.24 (2H, m), 2.46-2.56 (1H, m), 2.64-2.71 (2H, m), 2.95-3.03 (2H, m), 3.87 (2H, s), 3.93 (3H, s), 4.31-4.37 (2H, m), 6.85 (1H, d, J=2.5 Hz), 6.93 (1H, dd, J=8.9, 2.5 Hz), 7.18-7.26 (2H, m), 7.54 (1H, t, J=7.6 Hz), 7.79 (1H, d, J=8.9 Hz), 8.12 (1H, s)

Example 384

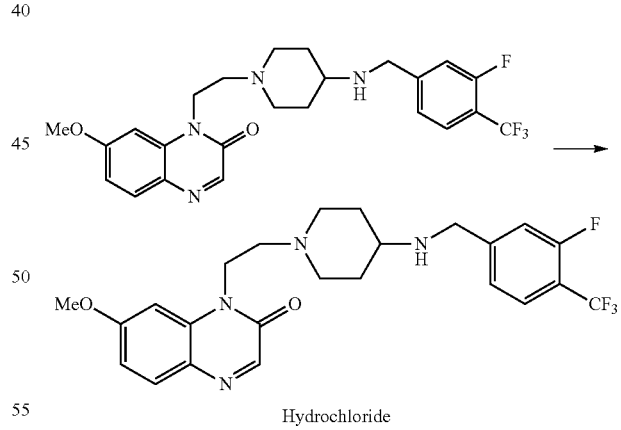

Hydrochloride

According to a procedure similar to Example 16, 1-(2-(4-((3-fluoro-4-(trifluoromethyl)benzyl)amino)piperidin-1-yl)ethyl)-7-methoxyquinoxalin-2(1H)-one hydrochloride was obtained from 1-(2-(4-((3-fluoro-4-(trifluoromethyl)benzyl)amino)piperidin-1-yl)ethyl)-7-methoxyquinoxalin-2(1H)-one.

$^1$H-NMR (D$_2$O) δ:
1.98-2.12 (2H, m), 2.51-2.60 (2H, m), 3.21-3.33 (2H, m), 3.61-3.74 (3H, m), 3.96-4.06 (2H, m), 3.98 (3H, s), 4.42 (2H, s), 4.71-4.80 (2H, m), 6.97 (1H, d, J=2.4 Hz), 7.18 (1H, dd,

J=9.0, 2.4 Hz), 7.44-7.50 (2H, m), 7.82 (1H, t, J=7.9 Hz), 7.86 (1H, d, J=9.0 Hz), 8.11 (1H, s)

Example 385

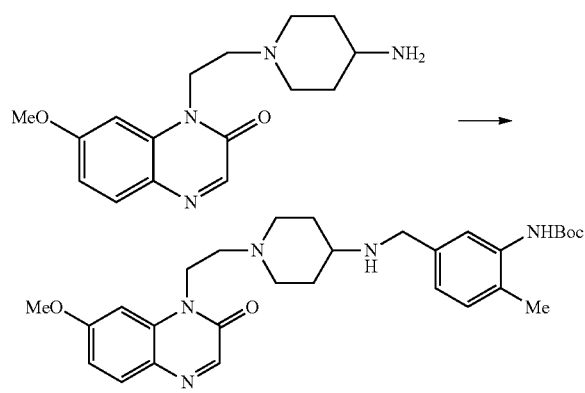

To 10 mL of a methylene chloride solution containing 0.20 g of 1-(2-(4-aminopiperidin-1-yl)ethyl)-7-methoxyquinoxalin-2(1H)-one, 0.19 g of tert-butyl (5-formyl-2-methylphenyl)carbamate and 45 µL of acetic acid were added, and stirred for 30 min. To the reaction mixture, 0.21 g of sodium triacetoxyborohydride was added, and stirred for 10 hours. After allowed to stand overnight, 45 µl of acetic acid was added and stirred for 40 min, then 0.17 g of sodium triacetoxyborohydride was added, and stirred at room temperature for 2 hours and 40 min. 90 µL of acetic acid was further added and stirred for 40 min, then 0.34 g of sodium triacetoxyborohydride was added, and stirred at room temperature for 2 hours. To the reaction mixture, aqueous saturated sodium hydrogen carbonate solution and chloroform were added, the organic layer was separated, and the aqueous layer was extracted with chloroform. The organic layer and extracts were combined, dried over anhydrous magnesium sulfate, and the solvent was removed under reduced pressure. The residue thus obtained was purified by silica gel column chromatography [eluent; chloroform:methanol=5:1], to give 0.28 g of tert-butyl (5-(((1-(2-(7-methoxy-2-oxoquinoxalin-1 (2H)-yl)ethyl)piperidin-4-yl)amino)methyl)-2-methylphenyl)carbamate as a pale yellow oil.

$^1$H-NMR (CDCl$_3$) δ:
1.42-1.56 (2H, m), 1.52 (9H, s), 1.89-1.98 (2H, m), 2.16-2.24 (5H, m), 2.52-2.71 (3H, m), 2.97-3.06 (2H, m), 3.79 (2H, s), 3.93 (3H, s), 4.31-4.39 (2H, m), 6.41 (1H, s), 6.88-7.01 (3H, m), 7.10 (1H, d, J=7.8 Hz), 7.72-7.81 (2H, m), 8.10 (1H, s)

Example 386

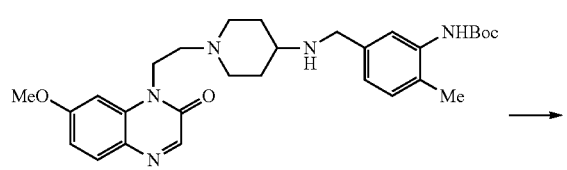

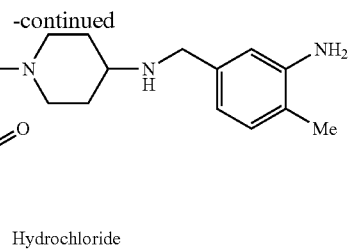

Hydrochloride

To 0.28 g of tert-butyl (5-(((1-(2-(7-methoxy-2-oxoquinoxalin-1(2H)-yl)ethyl)piperidin-4-yl)amino)methyl)-2-methylphenyl)carbamate, 30 mL of 4 mol/L hydrogen chloride/ethyl acetate solution was added, and stirred at room temperature for 41 hours. The solvent was removed under reduced pressure, ethyl acetate was added and the resulting solid was filtered to give 0.26 g of (1-(2-(4-((3-amino-4-methylbenzyl)amino)piperidin-1-yl)ethyl)-7-methoxyquinoxalin-2(1H)-one hydrochloride as a yellow solid.

$^1$H-NMR (D$_2$O) δ:
2.01-2.12 (2H, m), 2.38 (3H, s), 2.51-2.59 (2H, m), 3.21-3.33 (2H, m), 3.61-3.72 (3H, m), 3.96-4.06 (5H, m), 4.34 (2H, s), 4.71-4.78 (2H, m), 6.96 (1H, d, J=2.4 Hz), 7.17 (1H, dd, J=9.0, 2.4 Hz), 7.42-7.50 (3H, m), 7.85 (1H, d, J=9.0 Hz), 8.11 (1H, s)

Example 387

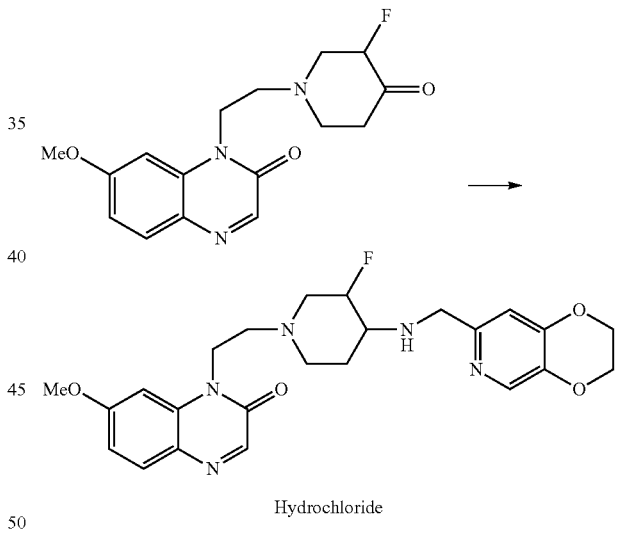

Hydrochloride

To 2 mL of a dichloromethane solution containing 48 mg of 1-(2-(3-fluoro-4-oxopiperidin-1-yl)ethyl)-7-methoxyquinoxalin-2(1H)-one and 30 mg of 1-(2,3-dihydro(1,4)dioxino (2,3-c)pyridin-7-yl)methaneamine, 26 µL of acetic acid was added, and stirred at room temperature for 1.5 hours. To the reaction mixture, 48 mg of sodium triacetoxyborohydride was added, and stirred for 1.5 hours. To the reaction mixture, aqueous saturated sodium hydrogen carbonate solution and chloroform were added, the organic layer was separated, dried over anhydrous magnesium sulfate, and the solvent was removed under reduced pressure. The residue thus obtained was purified by basic silica gel column chromatography [eluent; chloroform:methanol=50:1], to give 31 mg of 1-(2-(4-((2,3-dihydro(1,4)dioxino(2,3-c)pyridin-7-ylmethyl) amino)-3-fluoropiperidin-1-yl)ethyl)-7-methoxyquinoxalin-2(1H)-one as a brown oil.

To 2 mL of an ethyl acetate solution containing 31 mg of 1-(2-(4-((2,3-dihydro(1,4)dioxino(2,3-c)pyridin-7-ylmethyl)amino)-3-fluoropiperidin-1-yl)ethyl)-7-methoxyquinoxalin-2(1H)-one, 0.20 mL of 4 mol/L hydrogen chloride/ethyl acetate solution was added at room temperature, and the solvent was removed under reduced pressure, diethyl ether was added and the resulting solid was filtered to give 25 mg of 1-(2-(4-((2,3-dihydro(1,4)dioxino(2,3-c)pyridin-7-ylmethyl)amino)-3-fluoropiperidin-1-yl)ethyl)-7-methoxyquinoxalin-2(1H)-one hydrochloride as a pale brown solid.

$^1$H-NMR (D$_2$O) δ:

2.18-2.44 (2H, m), 3.26-3.82 (5H, m), 3.98 (3H, s), 4.22-4.34 (3H, m), 4.41-4.51 (4H, m), 4.51-4.66 (3H, m), 5.40-5.52 (1H, m), 7.00 (1H, d, J=2.5 Hz), 7.19 (1H, dd, J=9.0, 2.5 Hz), 7.23-7.30 (1H, m), 7.88 (1H, d, J=9.0 Hz), 8.12 (1H, s), 8.22-8.27 (1H, m)

Example 388

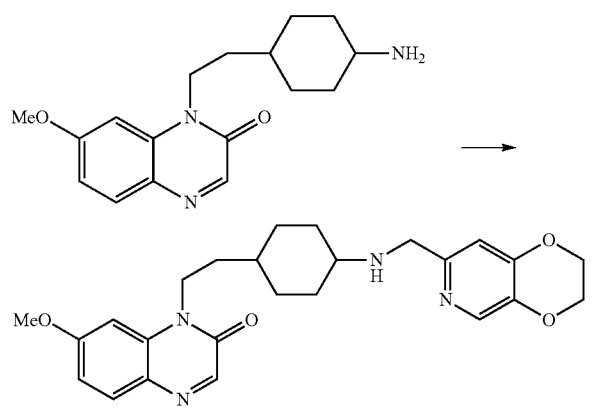

According to a procedure similar to Example 179, 1-(2-(4-((2,3-dihydro(1,4)dioxino(2,3-c)pyridin-7-ylmethyl)amino)cyclohexyl)ethyl)-7-methoxyquinoxalin-2(1H)-one was obtained from 1-(2-(4-aminocyclohexyl)ethyl)-7-methoxyquinoxalin-2(1H)-one and 2,3-dihydro-1,4-dioxino(2,3-c)pyridine-7-carbaldehyde.

$^1$H-NMR (DMSO-d$_6$, D$_2$O) δ:

0.96-2.16 (11H, m), 2.92-3.14 (1H, m), 3.92 (3H, s), 4.14-4.28 (4H, m), 4.30-4.44 (4H, m), 6.90-7.08 (2H, m), 7.15 (1H, s), 7.73-7.82 (1H, m), 8.05 (1H, s), 8.20 (1H, s)

Example 389

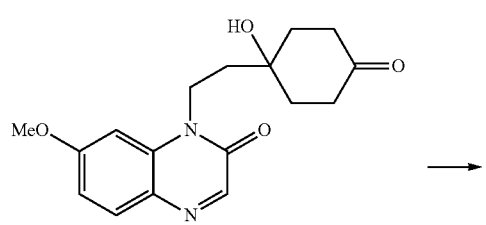

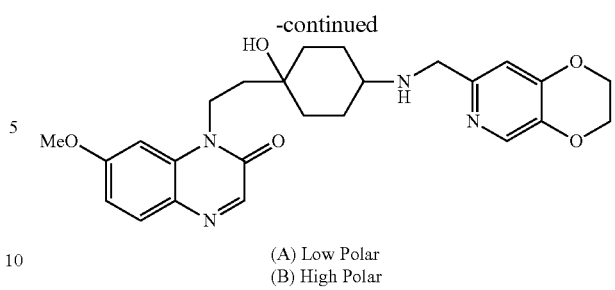

(A) Low Polar
(B) High Polar

To 4 mL of a dichloromethane solution containing 90 mg of 1-(2-(1-hydroxy-4-oxocyclohexyl)ethyl)-7-methoxyquinoxalin-2(1H)-one, 2 mL of a dichloromethane solution containing 57 mg of 1-(2,3-dihydro(1,4)dioxino(2,3-c)pyridin-7-yl)methaneamine and 24 µL of acetic acid were added at room temperature, and stirred at the same temperature for 1.5 hours. To the reaction mixture, 59 mg of sodium triacetoxyborohydride was added, and stirred at room temperature for 1.5 hours. To the reaction mixture, aqueous saturated sodium hydrogen carbonate solution and chloroform were added. The organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure. The residue thus obtained was purified by basic silica gel column chromatography [eluent; chloroform:methanol=50:1], to give (A) 29 mg as a light red oil and (B)$_{24}$ mg as a light red oil. To the purified products A and B, a mixture of diethyl ether and hexane was added, respectively, and each resulting solid was filtered to give (A) 28 mg of 1-(2-(4-((2,3-dihydro(1,4)dioxino(2,3-c)pyridin-7-ylmethyl)amino)-1-hydroxycyclohexyl)ethyl)-7-methoxyquinoxalin-2(1H)-one as a light red solid and (B) 21 mg of 1-(2-(4-((2,3-dihydro(1,4)dioxino(2,3-c)pyridin-7-ylmethyl)amino)-1-hydroxycyclohexyl)ethyl)-7-methoxyquinoxalin-2(1H)-one as a light red solid.

(A) $^1$H-NMR (CDCl$_3$, D$_2$O) δ:

1.37-1.56 (4H, m), 1.82-2.00 (6H, m), 2.63-2.72 (1H, m), 3.75 (2H, s), 3.92 (3H, s), 4.24-4.40 (6H, m), 6.80 (1H, s), 6.91-6.97 (2H, m), 7.79 (1H, d, J=9.3 Hz), 8.10 (1H, s), 8.13 (1H, s)

(B) $^1$H-NMR (CDCl$_3$, D$_2$O) δ:

1.42-1.59 (4H, m), 1.76-1.91 (6H, m), 2.44-2.57 (1H, m), 3.80 (2H, s), 3.92 (3H, s), 4.24-4.43 (6H, m), 6.81 (1H, s), 6.93 (1H, dd, J=8.9, 2.1 Hz), 6.99 (1H, d, J=2.1 Hz), 7.79 (1H, d, J=8.9 Hz), 8.10 (1H, s), 8.12 (1H, s)

Example 390

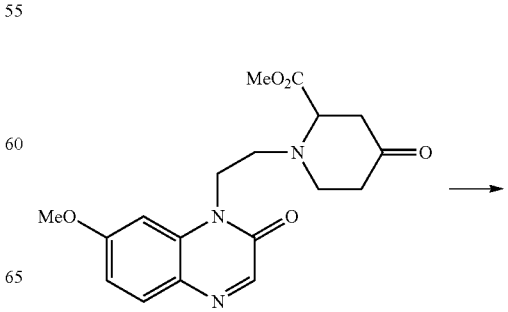

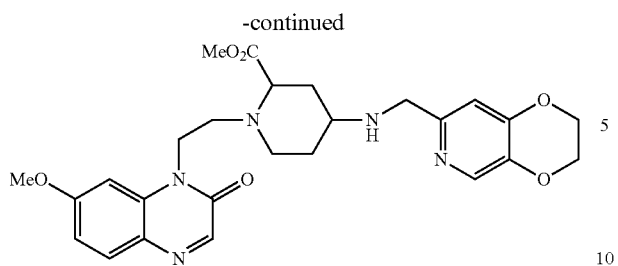

To 10 mL of a dichloromethane solution containing 0.10 g of methyl 1-(2-(7-methoxy-2-oxoquinoxalin-1(2H)-yl)ethyl)-4-oxopiperidine-2-carboxylate, 2 mL of a dichloromethane solution containing 55 mg of 1-(2,3-dihydro(1,4)dioxino(2,3-c)pyridin-7-yl)methaneamine and 32 μL of acetic acid were added at room temperature, and stirred at the same temperature for 1 hour, thereafter, 8 μL of acetic acid was further added, and stirred for 2.5 hours. To the reaction mixture, 59 mg of sodium triacetoxyborohydride was added, and stirred for 1 hour. To the reaction mixture, aqueous saturated sodium hydrogen carbonate solution and chloroform were added. The organic layer was separated, washed with aqueous saturated sodium chloride solution, dried over anhydrous magnesium sulfate, and the solvent was removed under reduced pressure. The residue thus obtained was purified by basic silica gel column chromatography [eluent; chloroform:methanol=50:1], to give 64 mg of methyl 4-((2,3-dihydro(1,4)dioxino(2,3-c)pyridin-7-ylmethyl)amino)-1-(2-(7-methoxy-2-oxoquinoxalin-1(2H)-yl)ethyl)piperidine-2-carboxylate as a white foam.

$^1$H-NMR (CDCl$_3$, D$_2$O) δ:

1.41-1.70 (3H, m), 1.83-1.95 (1H, m), 2.04-2.20 (1H, m), 2.29-2.38 (1H, m), 2.48-3.02 (3H, m), 3.02-3.31 (1H, m), 3.63-3.68 (3H, m), 3.72-3.80 (2H, m), 3.94 (0.9H, s), 3.99 (2.1H, s), 4.01-4.11 (0.3H, m), 4.12-4.24 (0.7H, m), 4.25-4.45 (4.3H, m), 4.56-4.66 (0.7H, m), 6.77-6.82 (1H, m), 6.85-6.94 (1.3H, m), 7.01 (0.7H, d, J=2.4 Hz), 7.73-7.79 (1H, m), 8.09 (1H, s), 8.11 (1H, s)

Example 391

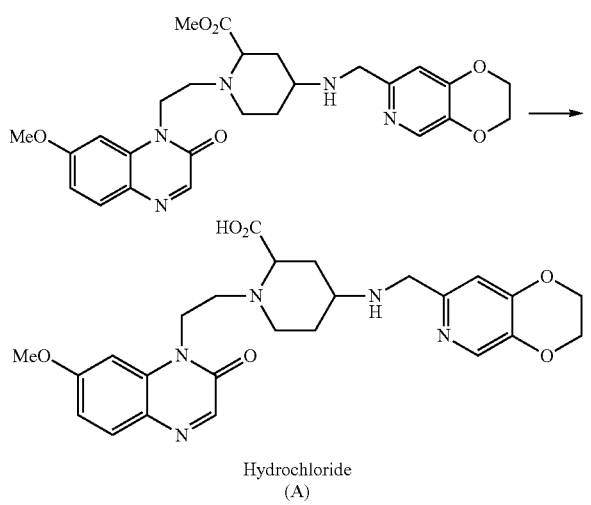

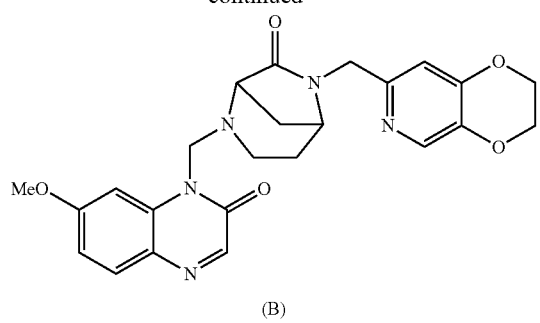

To 5 mL of a methanol solution containing 60 mg of methyl 4-((2,3-dihydro(1,4)dioxino(2,3-c)pyridin-7-ylmethyl)amino)-1-(2-(7-methoxy-2-oxoquinoxalin-1(2H)-yl)ethyl)piperidine-2-carboxylate, 0.2 mL of 20% aqueous sodium hydroxide solution was added at room temperature, and stirred for 1 hour and 10 min. Further, 0.5 mL of 20% aqueous sodium hydroxide solution was added at room temperature, and stirred at the sane temperature for 1 hour and 50 min. The reaction mixture was adjusted to pH 6.2 with 2 mol/L hydrochloric acid under water-cooling, the solvent was removed under reduced pressure, water, ethyl acetate and diethyl ether were added, and the resulting solid (A') was filtered. Also, the solvent of the filtrate (B') was removed under reduced pressure. To the residue thus obtained, water, ethyl acetate and diethyl ether were added, the organic layer was separated, and the solvent was removed under reduced pressure. To the residue thus obtained, hexane and diethyl ether were added, and the resulting solid (B) was filtered to give 9 mg of 1-(2-(6-(2,3-dihydro(1,4)dioxino(2,3-c)pyridin-7-ylmethyl)-7-oxo-2,6-diazabicyclo(3.2.1)oct-2-yl)ethyl)-7-methoxyquinoxalin-2(1H)-one as a pale yellow solid.

To ethyl acetate-ethanol suspension of the solid (A'), 1 mL of 4 mol/L hydrogen chloride/ethanol solution was added, and the solvent was removed under reduced pressure. To the residue thus obtained, water and conc. hydrochloric acid were added, and stirred at 30° C. for 1.5 hours. The solvent was removed under reduced pressure, ethyl acetate was added and the resulting solid was filtered to give (A) 24 mg of 4-((2,3-dihydro(1,4)dioxino(2,3-c)pyridin-7-ylmethyl)amino)-1-(2-(7-methoxy-2-oxoquinoxalin-1(2H)-yl)ethyl)piperidine-2-carboxylic acid hydrochloride as a yellow solid.

(A) $^1$H-NMR (D$_2$O) δ:

1.96-2.85 (5H, m), 3.20-3.94 (5H, m), 3.98 (3H, s), 4.10-4.28 (1H, m), 4.49 (2H, s), 4.52-4.66 (4H, m), 5.10-5.19 (1H, m), 6.94-7.02 (1H, m), 7.12-7.22 (1H, m), 7.36-7.54 (1H, m), 7.82-7.90 (1H, m), 8.08-8.16 (1H, m), 8.28-8.42 (1H, m)

(B) $^1$H-NMR (CDCl$_3$) δ:

1.68-1.82 (2H, m), 2.02-2.14 (1H, m), 2.28-2.42 (1H, m), 2.66-2.78 (1H, m), 3.00-3.22 (2H, m), 3.30-3.38 (1H, m), 3.62-3.74 (1H, m), 3.96 (3H, s), 4.07-4.16 (1H, m), 4.22-4.36 (6H, m), 4.42-4.54 (1H, m), 4.76-4.84 (1H, m), 6.82 (1H, s), 6.86-6.95 (2H, m), 7.74-7.80 (1H, m), 8.07 (1H, s), 8.11 (1H, s)

Example 392

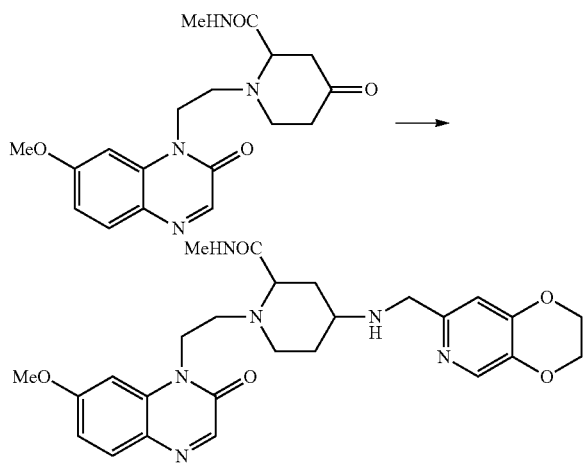

According to a procedure similar to Example 389, 4-((2,3-dihydro(1,4)dioxino(2,3-c)pyridin-7-ylmethyl)amino)-1-(2-(7-methoxy-2-oxoquinoxalin-1(2H)-yl)ethyl)-N-methylpiperidine-2-carboxamide was obtained from 1-(2-(7-methoxy-2-oxoquinoxalin-1(2H)-yl)ethyl)-N-methyl-4-oxopiperidine-2-carboxamide and 1-(2,3-dihydro(1,4)dioxino(2,3-c)pyridin-7-yl)methaneamine.

$^1$H-NMR (CDCl$_3$) δ:
1.44-1.70 (2H, m), 1.82-2.38 (3H, m), 2.50-3.30 (5H, m), 3.74-3.78 (2H, m), 3.84 (3H, s), 3.91 (3H, s), 4.02-4.66 (6H, m), 6.76-7.02 (3H, m), 7.74-7.80 (1H, m), 8.06-8.16 (2H, m)

Example 393

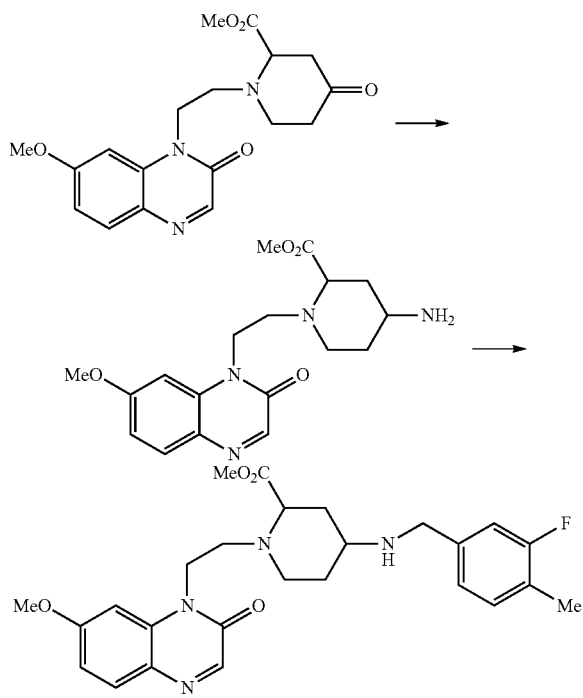

(1) To 5 mL of an ethanol suspension containing 0.15 g of methyl 1-(2-(7-methoxy-2-oxoquinoxalin-1(2H)-yl)ethyl)-4-oxopiperidine-2-carboxylate, 0.16 g of ammonium acetate and 0.20 g of molecular sieves 3A were added at room temperature. After the mixture was stirred for 2 hours and 55 min at room temperature, 21 mg of sodium cyanoborohydride was added, and stirred for 1 hour and 40 min. To the reaction mixture, aqueous saturated sodium hydrogen carbonate solution and chloroform were added, the organic layer was separated, and the aqueous layer was extracted with chloroform. The organic layer and extracts were combined, washed with aqueous saturated sodium chloride solution, dried over anhydrous magnesium sulfate, and the solvent was removed under reduced pressure to give 0.11 g of methyl 4-amino-1-(2-(7-methoxy-2-oxoquinoxalin-1(2H)-yl)ethyl)piperidine-2-carboxylate as a brown foam.

(2) According to a procedure similar to Example 179, methyl 4-((3-fluoro-4-methylbenzyl)amino)-1-(2-(7-methoxy-2-oxoquinoxalin-1(2H)-yl)ethyl)piperidine-2-carboxylate was obtained from methyl 4-amino-1-(2-(7-methoxy-2-oxoquinoxalin-1(2H)-yl)ethyl)piperidine-2-carboxylate.

$^1$H-NMR (CDCl$_3$) δ:
1.35-2.20 (4H, m), 2.25 (3H, s), 2.30-3.35 (4H, m), 3.64-3.80 (5H, m), 3.92-4.00 (5H, m), 4.10-4.65 (2H, m), 6.86-7.16 (5H, m), 7.74-7.80 (1H, m), 8.10-8.13 (1H, m)

Example 394

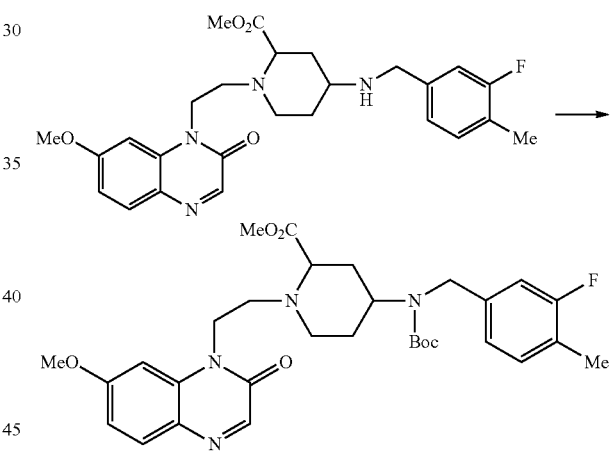

To 6 mL of a dichloromethane solution containing 60 mg of methyl 4-((3-fluoro-4-methybenzyl)amino)-1-(2-(7-methoxy-2-oxoquinoxalin-1(2H)-yl)ethyl)piperidine-2-carboxylate, 59 mg of di-tert-butyl dicarbonate was added in portions at room temperature, and stirred for 2 days. To the reaction mixture, water and chloroform were added, the organic layer was separated, washed with aqueous saturated sodium chloride solution, dried over anhydrous magnesium sulfate, and the solvent was removed under reduced pressure. The residue thus obtained was purified by flash silica gel column chromatography [gradient elution of chloroform:methanol=100:0-98:2] to give 80 mg of methyl 4-((tert-butoxycarbonyl)(3-fluoro-4-methybenzyl)amino)-1-(2-(7-methoxy-2-oxoquinoxalin-1(2H)-yl)ethyl)piperidine-2-carboxylate as a yellow oil.

$^1$H-NMR (CDCl$_3$) δ:
1.53 (9H, s), 1.88-2.08 (2H, m), 2.25 (3H, s), 2.30-2.54 (2H, m), 2.68-3.00 (4H, m), 3.06-3.42 (2H, m), 3.65 (3H, s), 3.99 (3H, s), 4.10-4.65 (4H, m), 6.77-6.98 (4H, m), 7.09 (1H, t, J=7.7 Hz), 7.73-7.80 (1H, m), 8.08-8.11 (1H, m)

Example 395

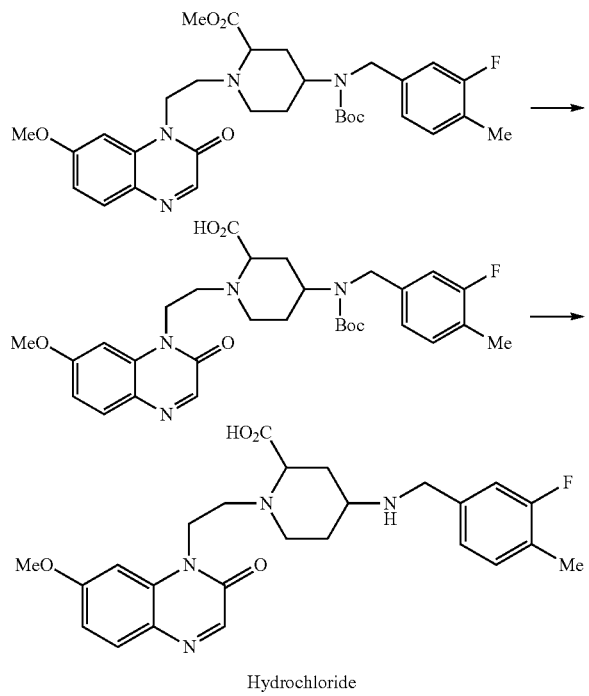

Hydrochloride (1) To 5 mL of a methanol solution containing 80 mg of methyl 4-((tert-butoxycarbonyl) (3-fluoro-4-methybenzyl)amino)-1-(2-(7-methoxy-2-oxoquinoxalin-1(2H)-yl)ethyl)piperidine-2-carboxylate, 0.2 mL of 2 mol/L aqueous sodium hydroxide solution was added at room temperature, and stirred for 2.5 hours. Further, 0.2 mL of 2 mol/L aqueous sodium hydroxide solution and 0.5 mL of water were added, stirred at the sane temperature for 4 hour and 40 min, and allowed to stand overnight. The solvent was removed under reduced pressure, and the reaction mixture was adjusted to pH 7.0 with 2 mol/L hydrochloric acid. To the mixture, water and ethyl acetate were added, the organic layer was separated, washed with aqueous saturated sodium chloride solution, dried over anhydrous magnesium sulfate, and the solvent was removed under reduced pressure to give 31 mg of 4-((tert-butoxycarbonyl) (3-fluoro-4-methybenzyl)amino)-1-(2-(7-methoxy-2-oxoquinoxalin-1(2H)-yl)ethyl)piperidine-2-carboxylic acid as a yellow solid.

(2) To 5 mL of an ethyl acetate solution containing 31 mg of 4-((tert-butoxycarbonyl)(3-fluoro-4-methybenzyl)amino)-1-(2-(7-methoxy-2-oxoquinoxalin-1(2H)-yl)ethyl)piperidine-2-carboxylic acid, 0.1 mL of 4 mol/L hydrogen chloride/ethyl acetate solution was added at room temperature, and stirred for 6 hours and 40 min, further, 0.1 mL of 4 mol/L hydrogen chloride/ethyl acetate solution was added, and stirred for 3.5 hours. The resulting solid was filtered to give 30 mg of 4-((3-fluoro-4-methybenzyl)amino)-1-(2-(7-methoxy-2-oxoquinoxalin-1(2H)-yl)ethyl)piperidine-2-carboxylic acid hydrochloride as a yellow solid.

$^1$H-NMR (D$_2$O) δ:
1.93-2.29 (2H, m), 2.28 (3H, s), 2.34-2.45 (0.4H, m), 2.52-2.63 (0.6H, m), 2.70-2.84 (1H, m), 3.32-3.93 (4.6H, m), 3.97-4.00 (3H, m), 4.19-4.26 (0.4H, m), 4.28-4.32 (2H, m), 4.49-4.54 (1H, m), 4.72-4.88 (2H, m), 6.95-7.01 (1H, m), 7.13-7.20 (3H, m), 7.36 (1H, t, J=7.8 Hz), 7.82-7.88 (1H, m), 8.11-8.14 (1H, m)

Example 396

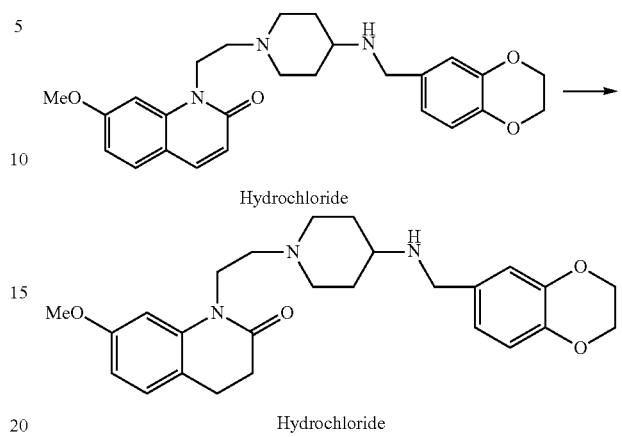

Hydrochloride

To 15 mL of a methanol solution containing 0.11 g of 1-(2-(4-((2,3-dihydro-1,4-benzodioxin-6-ylmethyl)amino)piperidin-1-yl)ethyl)-7-methoxyquinolin-2(1H)-one hydrochloride, 50 mg of 10% palladium on carbon was added, and stirred under hydrogen atmosphere at 45-50° C. for 8.5 hours. The insoluble material was filtered off, the solvent was removed under reduced pressure to afford 0.15 g of 1-(2-(4-((2,3-dihydro-1,4-benzodioxin-6-ylmethyl)amino)piperidin-1-yl)ethyl)-7-methoxy-3,4-dihydroquinolin-2(1H)-one hydrochloride as a yellow foam.

$^1$H-NMR (D$_2$O) δ:
1.89-2.16 (2H, m), 2.39-2.60 (2H, m), 2.60-2.77 (2H, m), 2.80-2.97 (2H, m), 3.08-3.36 (2H, m), 3.44-3.55 (2H, m), 3.55-3.68 (1H, m), 3.80-4.04 (5H, m), 4.17-4.27 (2H, m), 4.27-4.44 (6H, m), 6.65-6.72 (1H, m), 6.78 (1H, d, J=7.3 Hz), 6.94-7.07 (3H, m), 7.25 (1H, d, J=7.8 Hz)

Example 397

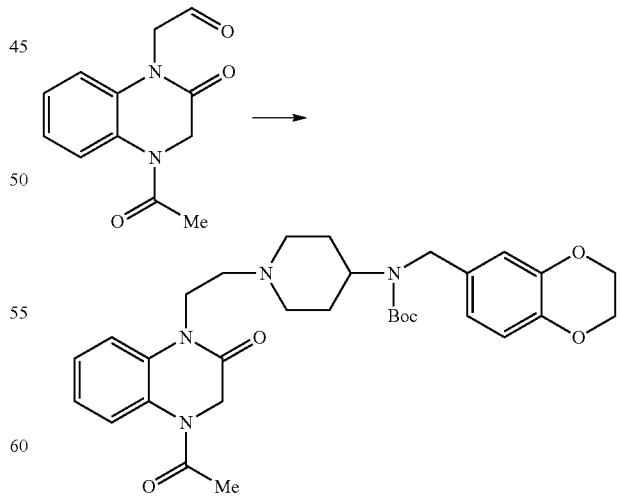

To 15 mL of a chloroform solution containing 337 mg of (4-acetyl-2-oxo-3,4-dihydroquinoxalin-1(2H)-yl)acetaldehyde and 504 mg of tert-butyl (2,3-dihydro-1,4-benzodioxin-6-ylmethyl) (piperidin-4-yl)carbamate, 83 µL of acetic acid was added, and stirred at room temperature for 1 hour. To the reaction mixture, 477 mg of sodium triacetoxyborohydride was added, and stirred for 1.5 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=20:1] to give 691 mg of tert-butyl (2,3-dihydro-1,4-benzodioxin-6-ylmethyl)(1-(2-(4-acetyl-2-oxo-3,4-dihydroquinoxalin-1(2H)-yl)ethyl)piperidin-4-yl)carbamate as a pale yellow foam.

$^1$H-NMR (CDCl$_3$) δ:
1.60 (9H, s), 1.61-1.65 (2H, m), 2.06-2.14 (2H, m), 2.19-2.25 (3H, m), 2.52-2.58 (2H, m), 2.89-2.95 (3H, m), 3.99-4.07 (2H, m), 4.24 (4H, s), 4.25-4.35 (4H, m), 4.46-4.53 (2H, m), 6.67-6.70 (1H, m), 6.74 (1H, d, J=1.8 Hz), 6.78 (1H, d, J=8.7 Hz), 7.11 (1H, t, J=7.6 Hz), 7.15-7.20 (1H, m), 7.23-7.26 (1H, m), 7.26 (1H, s)

To 5 mL of an ethyl acetate solution containing 415 mg of 4-acetyl-1-(2-(4-(2,3-dihydro-1,4-benzodioxin-6-ylmethyl)amino)piperidin-1-yl)ethyl-3,4-dihydro-2-oxo-1H-quinoxaline, 1 mL of 4 mol/L hydrogen chloride/ethyl acetate was added, and stirred at room temperature for 10 min. The resulting solid was filtered to give 377 mg of 4-acetyl-1-(2-(4-(2,3-dihydro-1,4-benzodioxin-6-ylmethyl)amino)piperidin-1-yl)ethyl-3,4-dihydro-2-oxo-1H-quinoxaline hydrochloride as a light violet powder.

$^1$H-NMR (DMSO-d$_6$) δ:
2.02-2.11 (2H, m), 2.16 (3H, s), 2.29-2.36 (2H, m), 3.02-3.12 (3H, m), 3.19-3.27 (2H, m), 3.67-3.74 (2H, m), 4.04-4.10 (2H, m), 4.25 (4H, s), 4.30-4.36 (2H, m), 4.42-4.48 (2H, m), 6.91 (1H, d, J=8.3 Hz), 7.03 (1H, dd, J=8.3, 1.8 Hz), 7.14-7.16 (1H, m), 7.18 (1H, t, J=7.6 Hz), 7.29-7.36 (1H, m), 7.48-7.59 (2H, m), 9.41-9.50 (2H, m), 10.95-11.02 (1H, m)

Example 399

Example 398

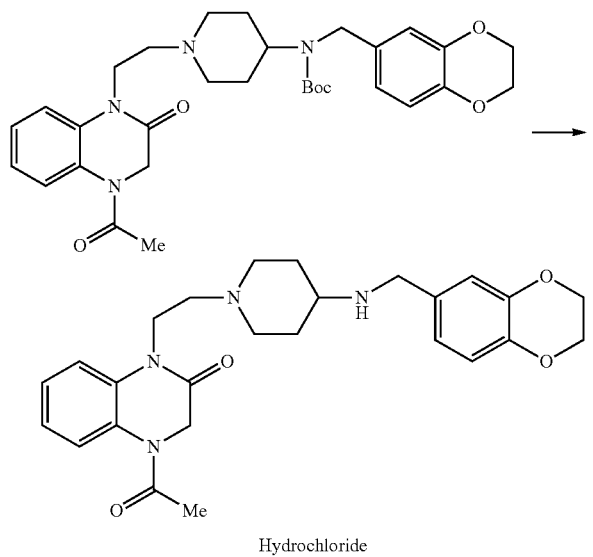

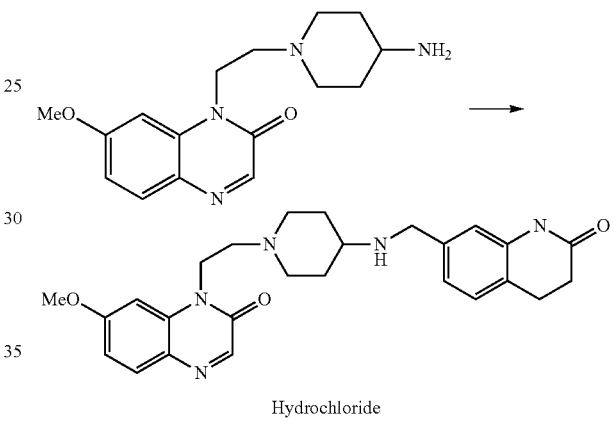

Hydrochloride

Hydrochloride

To 5 mL of a chloroform solution containing 653 mg of tert-butyl (2,3-dihydro-1,4-benzodioxin-6-ylmethyl)(1-(2-(4-acetyl-2-oxo-3,4-dihydroquinoxalin-1(2H)-yl)ethyl)piperidin-4-yl)carbamate, 2 mL of trifluoroacetic acid was added and stirred at room temperature for 1.5 hours. After solvents of the reaction mixture were removed under reduced pressure and the residue was alkalized by aqueous saturated sodium hydrogen carbonate solution, it was extracted with ethyl acetate. The organic layer was washed with water and aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=10:1] to give 424 mg of 4-acetyl-1-(2-(4-(2,3-dihydro-1,4-benzodioxin-6-ylmethyl)amino)piperidin-1-yl)ethyl-3,4-dihydro-2-oxo-1H-quinoxaline as a pale brown foam.

To 20 mL of a chloroform solution containing 176 mg of 1-(2-(4-aminopiperidin-1-yl)ethyl)-7-methoxyquinoxalin-2(1H)-one and 102 mg of 2-oxo-1,2,3,4-tetrahydroquinoline-7-carbaldehyde, 34 µL of acetic acid was added, and stirred at room temperature for 1 hour. To the reaction mixture, 200 mg of sodium triacetoxyborohydride was added, and stirred for 2.5 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=100:1] to give 178 mg of 7-methoxy-1-(2-(4-(((2-oxo-1,2,3,4-tetrahydroquinolin-7-ylmethyl)amino)piperidin-1-yl)ethyl)quinoxalin-2(1H)-one as a pale brown foam.

To 5 mL of a chloroform solution containing 169 mg of 7-methoxy-1-(2-(4-(((2-oxo-1,2,3,4-tetrahydroquinolin-7-ylmethyl)amino)piperidin-1-yl)ethyl)quinoxalin-2(1H)-one, 1 mL of 4 mol/L hydrogen chloride/ethyl acetate and 5 mL of chloroform were added, and stirred at room temperature. The solvent was removed under reduced pressure, ethyl acetate was added, and the resulting solid was filtered to give 166 mg of 7-methoxy-1-(2-(4-(((2-oxo-1,2,3,4-tetrahydroquinolin-7-ylmethyl)amino)piperidin-1-yl)ethyl)quinoxalin-2(1H)-one hydrochloride as a pale brown powder.

¹H-NMR (DMSO-d₆) δ:
2.00-2.07 (2H, m), 2.32-2.38 (2H, m), 2.43-2.47 (2H, m), 2.86-2.91 (2H, m), 3.06-3.14 (3H, m), 3.25-3.31 (2H, m), 3.81-3.86 (2H, m), 3.98 (3H, s), 4.09-4.13 (2H, m), 4.67 (2H, t, J=6.9 Hz), 6.95 (1H, s), 7.05 (1H, dd, J=9.2, 2.3 Hz), 7.14 (1H, d, J=7.8 Hz), 7.19-7.22 (1H, m), 7.25 (1H, d, J=7.8 Hz), 7.79 (1H, d, J=8.7 Hz), 8.09 (1H, s), 9.35-9.46 (2H, m), 10.31 (1H, s)

Example 400

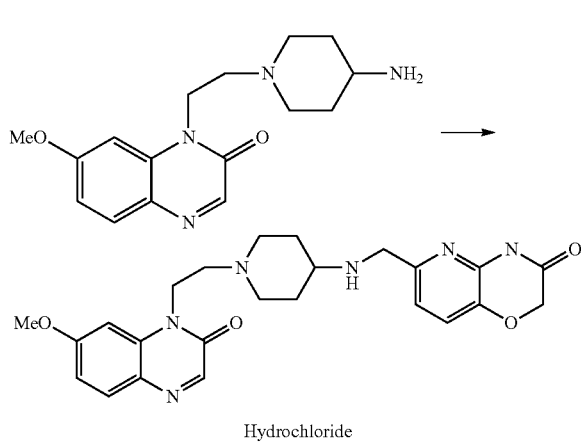

Hydrochloride

To 10 mL of a methylene chloride solution containing 280 mg of 1-(2-(4-aminopiperidin-1-yl)ethyl)-7-methoxyquinoxalin-2(1H)-one and 150 mg of 3-oxo-3,4-dihydro-2H-pyrido[3,2-b][1,4]oxazine-6-carbaldehyde, 0.05 mL of acetic acid was added, and stirred at room temperature for 1.5 hours. To the reaction mixture, 280 mg of sodium triacetoxyborohydride was added, and stirred for 1.5 hours. Aqueous saturated sodium hydrogen carbonate solution was added, the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=5:1] to give 233 mg of 7-methoxy-1-(2-(4-((3-oxo-3,4-dihydro-2H-pyrido[3,2-b][1,4]oxazin-6-yl)methylamino)piperidin-1-yl)ethyl)quinoxalin-2(1H)-one as a pale yellow solid.

To 3 mL of a methanol solution containing 202 mg of 7-methoxy-1-(2-(4-((3-oxo-3,4-dihydro-2H-pyrido[3,2-b][1,4]oxazin-6-yl)methylamino)piperidin-1-yl)ethyl)quinoxalin-2(1H)-one, 1 mL of 4 mol/L hydrogen chloride/ethyl acetate was added, and the solvent was removed under reduced pressure, ethyl acetate was added, and the resulting solid was filtered to give 209 mg of 7-methoxy-1-(2-(4-((3-oxo-3,4-dihydro-2H-pyrido[3,2-b][1,4]oxazin-6-yl)methylamino)piperidin-1-yl)ethyl)quinoxalin-2(1H)-one hydrochloride as a pale yellow powder.

¹H-NMR (DMSO-d₆) δ:
2.02-2.12 (2H, m), 2.37-2.44 (2H, m), 3.07-3.16 (3H, m), 3.30-3.36 (2H, m), 3.79-3.85 (2H, m), 3.97 (3H, s), 4.15-4.22 (2H, m), 4.65-4.72 (4H, m), 7.04 (1H, dd, J=8.9, 2.5 Hz), 7.22-7.24 (1H, m), 7.25 (1H, d, J=8.3 Hz), 7.45 (1H, d, J=7.8 Hz), 7.79 (1H, d, J=8.9 Hz), 8.09 (1H, s), 9.63-9.71 (2H, m), 11.07-11.17 (1H, m)

Example 401

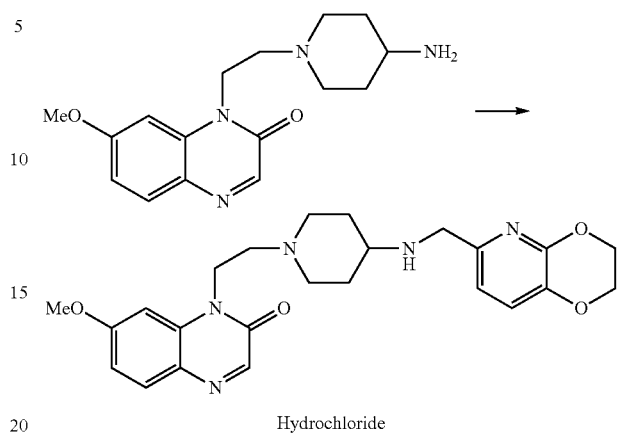

Hydrochloride

To 5 mL of an N,N-dimethylformamide solution containing 170 mg of 1-(2-(4-aminopiperidin-1-yl)ethyl)-7-methoxyquinoxalin-2(1H)-one and 130 mg of 6-bromomethyl-2,3-dihydro-1,4-dioxino[2,3-b]pyridine, 230 mg of potassium carbonate was added, and stirred at room temperature for 3 days. The solvent was removed under reduced pressure, and the residue thus obtained was purified by silica gel column chromatography [Silica Gel; Kanto Chemical Co., Inc., Silica Gel N, eluent; chloroform:methanol=5:1] to give 95.1 mg of 1-(2-(4-((2,3-dihydro-1,4-dioxino[2,3-b]pyridin-6-yl)methylamino)piperidin-1-yl)ethyl)-7-methoxyquinoxalin-2 (1H)-one as a yellow oil.

To 2 mL of an ethyl acetate solution containing 95.0 mg of 1-(2-(4-((2,3-dihydro-1,4-dioxino[2,3-b]pyridin-6-yl)methylamino)piperidin-1-yl)ethyl)-7-methoxyquinoxalin-2 (1H)-one, 1 mL of 4 mol/L hydrogen chloride/ethyl acetate was added, and stirred at room temperature. The resulting solid was filtered to give 104 mg of 1-(2-(4-((2,3-dihydro-1,4-dioxino[2,3-b]pyridin-6-yl)methylamino)piperidin-1-yl)ethyl)-7-methoxyquinoxalin-2(1H)-one hydrochloride as a yellow powder.

¹H-NMR (DMSO-d₆) δ:
1.98-2.07 (2H, m), 2.31-2.37 (2H, m), 3.06-3.14 (2H, m), 3.27-3.36 (3H, m), 3.79-3.85 (2H, m), 3.98 (3H, s), 4.15-4.19 (2H, m), 4.28-4.31 (2H, m), 4.43-4.47 (2H, m), 4.64-4.69 (2H, m), 7.05 (1H, dd, J=8.9, 2.5 Hz), 7.14 (1H, d, J=7.8 Hz), 7.21 (1H, d, J=2.5 Hz), 7.40 (1H, d, J=7.8 Hz), 7.79 (1H, d, J=8.9 Hz), 8.09 (1H, s), 9.45-9.51 (2H, m), 10.77-10.85 (1H, m)

Example 402

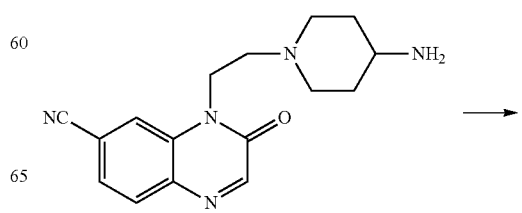

-continued

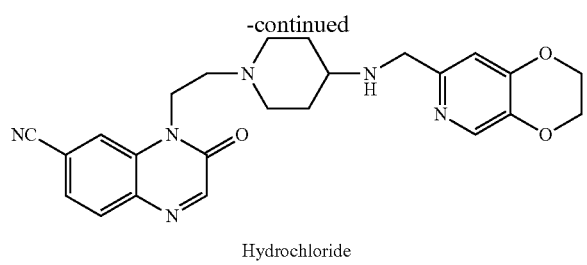

Hydrochloride

To 10 mL of a chloroform solution containing 58 mg of 1-(2-(4-aminopiperidin-1-yl)ethyl)-7-cyanoquinoxalin-2(1H)-one and 35 mg of 2,3-dihydro-1,4-dioxino[2,3-c]pyridine-7-carbaldehyde, 11 μL of acetic acid was added, and stirred at room temperature for 1 hour. To the reaction mixture, 67 mg of sodium triacetoxyborohydride was added, and stirred for 2 hours. Aqueous saturated sodium hydrogen carbonate solution was added, and the solvent was removed under reduced pressure. The residue thus obtained was purified by silica gel column chromatography [Silica Gel; Kanto Chemical Co., Inc., Silica Gel 60, eluent; chloroform:methanol=5:1] to give 43 mg of 1-(2-(4-((2,3-dihydro-1,4-dioxino[2,3-c]pyridin-7-yl)methylamino)piperidin-1-yl)ethyl)-7-cyanoquinoxalin-2(1H)-one as a pale yellow solid.

To 5 mL of a chloroform solution containing 40 mg of 1-(2-(4-((2,3-dihydro-1,4-dioxino[2,3-c]pyridin-7-yl)methylamino)piperidin-1-yl)ethyl)-7-cyanoquinoxalin-2(1H)-one, 0.5 mL of 4 mol/L hydrogen chloride/ethyl acetate and 5 mL of chloroform were added, and stirred at room temperature for 10 min. The solvent was removed under reduced pressure, ethyl acetate was added, and the resulting solid was filtered to give 33 mg of 1-(2-(4-((2,3-dihydro-1,4-dioxino[2,3-c]pyridin-7-yl)methylamino)piperidin-1-yl)ethyl)-7-cyanoquinoxalin-2(1H)-one hydrochloride as a dark brown powder.

$^1$H-NMR (DMSO-$d_6$) δ:
2.00-2.08 (2H, m), 2.31-2.37 (2H, m), 3.06-3.14 (3H, m), 3.35-3.39 (2H, m), 3.80-3.85 (2H, m), 4.20-4.24 (2H, m), 4.33-4.37 (2H, m), 4.40-4.43 (2H, m), 4.59-4.66 (2H, m), 7.26 (1H, s), 7.84 (1H, dd, J=8.3, 1.4 Hz), 8.02 (1H, d, J=8.3 Hz), 8.23-8.24 (1H, m), 8.34-8.36 (1H, m), 8.40 (1H, s), 9.65-9.71 (2H, m), 10.59-10.65 (1H, m)

Example 403

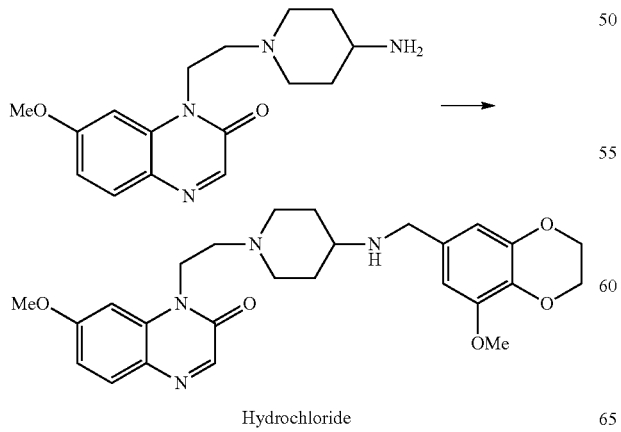

Hydrochloride

To 10 mL of a chloroform solution containing 598 mg of 1-(2-(4-aminopiperidin-1-yl)ethyl)-7-methoxyquinoxalin-2(1H)-one and 384 mg of 8-methoxy-2,3-dihydro-1,4-benzodioxin-6-carbaldehyde, 113 μL of acetic acid was added, and stirred at room temperature for 1 hour. To the reaction mixture, 639 mg of sodium triacetoxyborohydride was added, and stirred for 2 hours. To the reaction mixture, aqueous saturated sodium hydrogen carbonate solution was added, and the solvent was removed under reduced pressure. The residue thus obtained was purified by silica gel column chromatography [Silica Gel; Kanto Chemical Co., Inc., Silica Gel 60, eluent; chloroform:methanol=5:1] to give 492 mg of 7-methoxy-1-(2-(4-((8-methoxy-2,3-dihydro-1,4-benzodioxin-6-yl)methylamino)piperidin-1-yl)ethyl)quinoxalin-2(1H)-one as a pale yellow solid.

To 10 mL of a chloroform solution containing 478 mg of 7-methoxy-1-(2-(4-((8-methoxy-2,3-dihydro-1,4-benzodioxin-6-yl)methylamino)piperidin-1-yl)ethyl)quinoxalin-2(1H)-one, 1 mL of 4 mol/L hydrogen chloride/ethyl acetate and 5 mL of chloroform were added, and stirred at room temperature for 10 min. The solvent was removed under reduced pressure, ethyl acetate was added, and the resulting solid was filtered to give 429 mg of 7-methoxy-1-(2-(4-((8-methoxy-2,3-dihydro-1,4-benzodioxin-6-yl)methylamino)piperidin-1-yl)ethyl)quinoxalin-2(1H)-one hydrochloride as a dark brown powder.

$^1$H-NMR (DMSO-$d_6$) δ:
2.01-2.09 (2H, m), 2.35-2.40 (2H, m), 3.07-3.15 (2H, m), 3.19-3.25 (1H, m), 3.30-3.35 (2H, m), 3.48-3.54 (2H, m), 3.78 (3H, s), 3.79-3.83 (2H, m), 3.98 (3H, s), 4.23 (4H, s), 4.67 (2H, t, J=7.1 Hz), 6.96-6.98 (2H, m), 7.04 (1H, dd, J=8.7, 2.3 Hz), 7.22 (1H, d, J=2.3 Hz), 7.78 (1H, d, J=8.7 Hz), 8.08 (1H, s), 9.59-9.64 (2H, m), 10.96-10.99 (1H, m)

Example 404

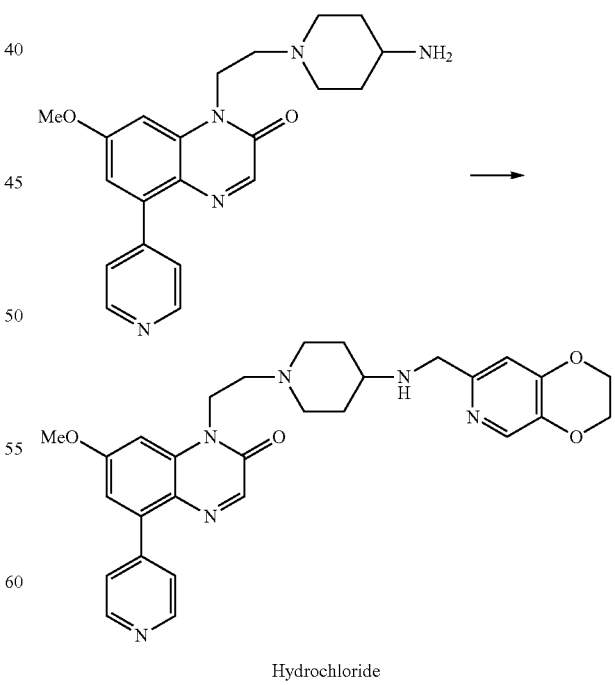

Hydrochloride

To 3 mL of a chloroform solution containing 160 mg of 1-(2-(4-aminopiperidin-1-yl)ethyl)-7-methoxy-5-(pyridin- 4-yl)quinoxalin-2(1H)-one and 63 mg of 2,3-dihydro-1,4-dioxino[2,3-c]pyridine-7-carbaldehyde, 0.04 mL of acetic acid was added, and stirred at room temperature for 4 hours. To the reaction mixture, 140 mg of sodium triacetoxyborohydride was added, and stirred for 13 hours. To the reaction mixture, aqueous saturated sodium hydrogen carbonate solution was added, and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel 60, eluent; chloroform:methanol=4:1] to give 139 mg of 1-(2-(4-((2,3-dihydro-1,4-dioxino[2,3-c]pyridin-7-yl)methylamino)piperidin-1-yl)ethyl)-7-methoxy-5-(pyridin-4-yl)quinoxalin-2(1H)-one as a white foam.

To 2 mL of an ethyl acetate solution containing 134 mg of 1-(2-(4-((2,3-dihydro-1,4-dioxino[2,3-c]pyridin-7-yl)methylamino)piperidin-1-yl)ethyl)-7-methoxy-5-(pyridin-4-yl)quinoxalin-2(1H)-one, 1.5 mL of 4 mol/L hydrogen chloride/ethyl acetate was added at room temperature, and the resulting solid was filtered to give 150 mg of 1-(2-(4-((2,3-dihydro-1,4-dioxino[2,3-c]pyridin-7-yl)methylamino)piperidin-1-yl)ethyl)-7-methoxy-5-(pyridin-4-yl)quinoxalin-2(1H)-one hydrochloride as a pale yellow solid.

$^1$H-NMR (DMSO-$d_6$) δ:
2.04-2.13 (2H, m), 2.32-2.38 (2H, m), 3.08-3.17 (2H, m), 3.27-3.38 (3H, m), 3.80-3.85 (2H, m), 4.07 (3H, s), 4.21-4.26 (2H, m), 4.33-4.37 (2H, m), 4.40-4.44 (2H, m), 4.72-4.78 (2H, m), 7.24-7.29 (2H, m), 7.41-7.44 (1H, m), 8.08-8.13 (3H, m), 8.24 (1H, s), 8.97 (2H, d, J=6.4 Hz), 9.65-9.72 (2H, m), 11.23-11.29 (1H, m)

Example 405

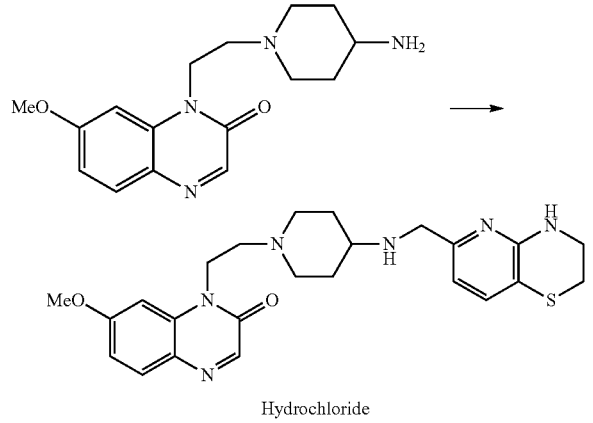

Hydrochloride

To 5 mL of a chloroform solution containing 280 mg of 1-(2-(4-aminopiperidin-1-yl)ethyl)-7-methoxy-5-(pyridin-4-yl)quinoxalin-2(1H)-one and 130 mg of 3,4-dihydro-2H-pyrido[3,2-b]-1,4-thiazine-6-carbaldehyde, 0.08 mL of acetic acid was added, and stirred at room temperature for 2.5 hours. To the reaction mixture, 260 mg of sodium triacetoxyborohydride was added, and stirred for 13 hours. To the reaction mixture, aqueous saturated sodium hydrogen carbonate solution was added, and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Fuji Silysia Chemical Ltd., Chromatorex-NH, eluent; chloroform:methanol=20:1] to give 140 mg of 1-(2-(4-((2,3-dihydro-2(1H)-pyrido[3,2-b][1,4]thiazin-6-ylmethyl)amino)piperidin-1-yl)ethyl)-7-methoxyquinoxalin-2(1H)-one as a pale yellow foam.

To 2 mL of an ethyl acetate solution containing 131 mg of 1-(2-(4-((2,3-dihydro-2(1H)-pyrido[3,2-b]-1,4-thiazin-6-ylmethyl)amino)piperidin-1-yl)ethyl)-7-methoxyquinoxalin-2(1H)-one, 1.5 mL of 4 mol/L hydrogen chloride/ethyl acetate and 5 mL of ethyl acetate were added, and the resulting solid was filtered to give 141 mg of 1-(2-(4-((2,3-dihydro-2(1H)-pyrido[3,2-b][1,4]thiazin-6-ylmethyl)amino)piperidin-1-yl)ethyl)-7-methoxyquinoxalin-2(1H)-one hydrochloride as a yellow solid.

$^1$H-NMR (DMSO-$d_6$) δ:
2.01-2.10 (2H, m), 2.33-2.40 (2H, m), 2.97-3.02 (2H, m), 3.08-3.17 (2H, m), 3.30-3.38 (3H, m), 3.64-3.69 (2H, m), 3.78-3.85 (2H, m), 3.98 (3H, s), 4.06-4.12 (2H, m), 4.68 (2H, t, J=7.1 Hz), 6.73 (1H, d, J=7.8 Hz), 7.04 (1H, dd, J=8.7, 2.3 Hz), 7.22 (1H, d, J=2.3 Hz), 7.41 (1H, d, J=7.8 Hz), 7.79 (1H, d, J=8.7 Hz), 8.09 (1H, s), 9.50-9.58 (2H, m), 10.98-11.06 (1H, m)

Example 406

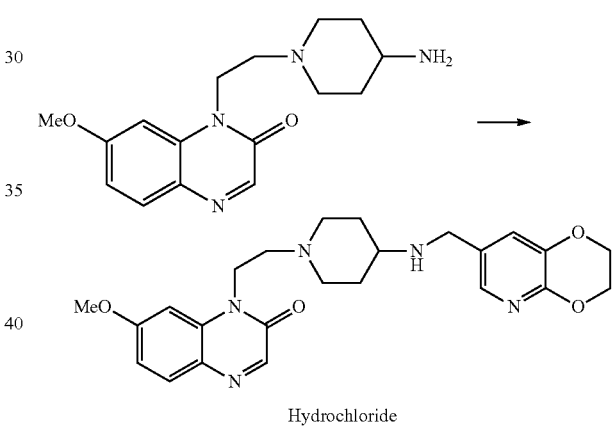

Hydrochloride

To 10 mL of a chloroform solution containing 139 mg of 1-(2-(4-aminopiperidin-1-yl)ethyl)-7-methoxyquinoxalin-2(1H)-one and 69 mg of 2,3-dihydro-1,4-dioxino[2,3-b]pyridine-7-carbaldehyde, 28 mg of acetic acid was added, and stirred at room temperature for 1 hour. To the reaction mixture, 133 mg of sodium triacetoxyborohydride was added, and stirred overnight. To the reaction mixture, aqueous saturated sodium hydrogen carbonate solution was added, and the organic layer was separated. The organic layer was washed with aqueous saturated sodium chloride solution, dried over anhydrous magnesium sulfate, and the solvent was removed under reduced pressure. The residue thus obtained was purified by silica gel column chromatography [Silica Gel; Kanto Chemical Co., Inc., Silica Gel N, eluent; chloroform:methanol=10:1] to give 162 mg of 1-(2-(4-((2,3-dihydro-1,4-dioxino[2,3-b]pyridin-7-yl)methylamino)piperidin-1-yl)ethyl)-7-methoxyquinoxalin-2(1H)-one as a white solid.

To 4 mL of an ethyl acetate solution containing 160 mg of 1-(2-(4-((2,3-dihydro-1,4-dioxino[2,3-b]pyridin-7-yl)methylamino)piperidin-1-yl)ethyl)-7-methoxyquinoxalin-2(1H)-one, 2 mL of 4 mol/L hydrogen chloride/ethyl acetate was added, and stirred at room temperature. The resulting solid was filtered to give 166 mg of 1-(2-(4-((2,3-dihydro-1,4-dioxino[2,3-b]pyridin-7-yl)methylamino)piperidin-1-yl)ethyl)-7-methoxyquinoxalin-2(1H)-one hydrochloride as a white powder.

$^1$H-NMR (DMSO-$d_6$) δ:
2.00-2.09 (2H, m), 2.34-2.40 (2H, m), 3.06-3.15 (2H, m), 3.22-3.30 (1H, m), 3.29-3.38 (2H, m), 3.77-3.86 (2H, m), 3.98 (3H, s), 4.11-4.17 (2H, m), 4.24-4.31 (2H, m), 4.40-4.46 (2H, m), 4.64-4.71 (2H, m), 7.04 (1H, dd, J=8.7, 2.3 Hz), 7.20 (1H, d, J=2.8 Hz), 7.63 (1H, d, J=2.3 Hz), 7.79 (1H, d, J=8.7 Hz), 7.92 (1H, d, J=2.3 Hz), 8.09 (1H, s), 9.54-9.65 (2H, m), 10.79-10.93 (1H, m)

Example 407

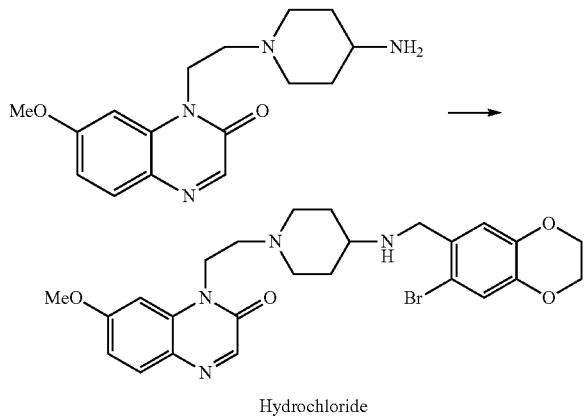

Hydrochloride

To 10 mL of a chloroform solution containing 130 mg of 1-(2-(4-aminopiperidin-1-yl)ethyl)-7-methoxyquinoxalin-2(1H)-one and 109 mg of 7-bromo-2,3-dihydro-1,4-benzodioxin-6-carbaldehyde, 25 μL of acetic acid was added, and stirred at room temperature for 1 hour. To the reaction mixture, 140 mg of sodium triacetoxyborohydride was added, and stirred for 1.5 hours. To the reaction mixture, aqueous saturated sodium hydrogen carbonate solution was added, and the solvent was removed under reduced pressure. The residue thus obtained was purified by silica gel column chromatography [Silica Gel; Kanto Chemical Co., Inc., Silica Gel 60, eluent; chloroform:methanol=10:1] to give 113 mg of 1-(2-(4-((7-bromo-2,3-dihydro-1,4-benzodioxin-6-yl)methylamino)piperidin-1-yl)ethyl)-7-methoxyquinoxalin-2(1H)-one as a pale yellow solid.

101 mg of 1-(2-(4-((7-bromo-2,3-dihydro-1,4-benzodioxin-6-yl)methylamino)piperidin-1-yl)ethyl)-7-methoxyquinoxalin-2(1H)-one was dissolved in 3 mL of chloroform, 0.5 mL of 4 mol/L hydrogen chloride/ethyl acetate and 3 mL of chloroform were added, and stirred at room temperature for 10 min. The solvent was removed under reduced pressure, ethyl acetate was added and the resulting solid was filtered to give 92 mg of 1-(2-(4-((7-bromo-2,3-dihydro-1,4-benzodioxin-6-yl)methylamino)piperidin-1-yl)ethyl)-7-methoxyquinoxalin-2(1H)-one hydrochloride as a dark brown powder.

$^1$H-NMR (DMSO-$d_6$) δ:
2.00-2.08 (2H, m), 2.37-2.42 (2H, m), 3.08-3.16 (3H, m), 3.82-3.87 (2H, m), 3.98 (3H, s), 4.16-4.21 (2H, m), 4.29 (4H, s), 4.36-4.39 (2H, m), 4.64-4.69 (2H, m), 7.05 (1H, dd, J=8.7, 2.3 Hz), 7.17-7.21 (1H, m), 7.25 (1H, s), 7.35 (1H, s), 7.80 (1H, d, J=8.7 Hz), 8.09 (1H, s), 9.40-9.47 (2H, m), 10.71-10.77 (1H, m)

Example 408

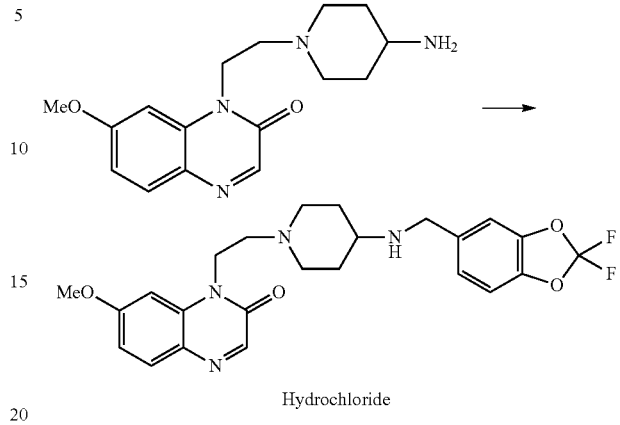

Hydrochloride

To 10 mL of a chloroform solution containing 226 mg of 1-(2-(4-aminopiperidin-1-yl)ethyl)-7-methoxyquinoxalin-2(1H)-one and 150 mg of 2,2-difluorobenzo[1,3]dioxol-5-carbaldehyde, 43 μL of acetic acid was added, and stirred at room temperature for 1 hour. To the reaction mixture, 257 mg of sodium triacetoxyborohydride was added, and stirred for 2.5 hours. To the reaction mixture, aqueous saturated sodium hydrogen carbonate solution was added, and the solvent was removed under reduced pressure. The residue thus obtained was purified by silica gel column chromatography [Silica Gel; Kanto Chemical Co., Inc., Silica Gel 60, eluent; chloroform:methanol=10:1] to give 188 mg of 1-(2-(4-((2,2-difluorobenzo[1,3]dioxol-5-yl)methylamino)piperidin-1-yl)ethyl)-7-methoxyquinoxalin-2(1H)-one as a pale yellow solid.

To 3 mL of a chloroform solution containing 171 mg of 1-(2-(4-((2,2-difluorobenzo[1,3]dioxol-5-yl)methylamino)piperidin-1-yl)ethyl)-7-methoxyquinoxalin-2(1H)-one, 0.5 mL of 4 mol/L hydrogen chloride/ethyl acetate and 3 mL of chloroform were added, and stirred at room temperature for 10 min. The solvent was removed under reduced pressure, ethyl acetate was added and the resulting solid was filtered to give 150 mg of 1-(2-(4-((2,2-difluoro-benzo[1,3]dioxol-5-yl)methylamino)piperidin-1-yl)ethyl)-7-methoxyquinoxalin-2(1H)-one hydrochloride as a pale brown powder.

$^1$H-NMR (DMSO-$d_6$) δ:
2.00-2.07 (2H, m), 2.32-2.40 (2H, m), 3.05-3.15 (3H, m), 3.21-3.30 (2H, m), 3.80-3.87 (2H, m), 3.97 (3H, s), 4.20-4.26 (2H, m), 4.66 (2H, t, J=6.6 Hz), 7.05 (1H, dd, J=8.7, 2.3 Hz), 7.17-7.20 (1H, m), 7.46 (1H, d, J=8.7 Hz), 7.50-7.54 (1H, m), 7.73 (1H, s), 7.80 (1H, d, J=8.7 Hz), 8.09 (1H, s), 9.58-9.66 (2H, m), 10.61-10.69 (1H, m)

INDUSTRIAL APPLICABILITY

The nitrogen-containing heterocyclic compounds or salts thereof of the present invention are useful as excellent antibacterial agents since they have strong antibacterial activities and sufficient safety.

What we claim is:

1. A compound represented by formula (I):

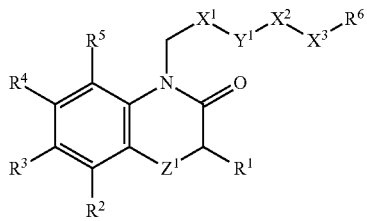

wherein:

a dashed line represents a double bond;

$R^1$, $R^2$, $R^3$, $R^4$ and $R^5$ are the same or different and represent a hydrogen atom, a halogen atom, a hydroxy group, a nitro group, a formyl group, an amino group which may be protected or substituted, a lower alkyl, cycloalkyl, aryl, lower alkoxy, cycloalkyloxy, aralkyloxy, alkanoyl, ureido or monocyclic heterocyclic group which may be substituted, -$Q^1$-CONR$^7$R$^8$, -$Q^1$-CO$_2$R$^9$, or -$Q^1$-CN, wherein $R^7$ and $R^8$ are the same or different and represent a hydrogen atom, a lower alkyl, cycloalkyl, aralkyl, aryl, lower alkoxy, alkanesulfonyl or monocyclic heterocyclic group which may be substituted, or $R^7$ and $R^8$, together with the nitrogen atom to which they are attached, represent a cyclic amino group which may be substituted;

$R^9$ represents a hydrogen atom or a carboxy protective group; and $Q^1$ represents a lower alkylene or lower alkenylene group which may be substituted, a lower oxyalkylene group which is attached to the ring via a terminal oxygen atom and which may be substituted or a bond;

$R^6$ represents a lower alkyl, aryl, monocyclic heterocyclic, bicyclic heterocyclic or tricyclic heterocyclic group which may be substituted;

$X^1$ represents a lower alkylene group which may be substituted with one or more groups selected from a hydroxy and a carboxy groups which may be protected, a lower alkyl group, a lower alkenyl group, a lower alkynyl group, a lower alkoxy group and an aryl group;

$X^2$ represents a lower alkylene, lower alkenylene or lower alkynylene group which may be substituted;

$X^3$ represents an oxygen atom, a sulfur atom, a sulfinyl group, a sulfonyl group, NR$^{10}$, wherein R$^{10}$ represents a hydrogen atom, a lower alkyl or lower alkynyl group which may be substituted or an imino protective group or a bond;

$Y^1$ represents formula

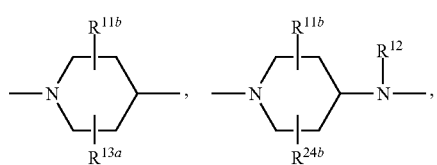

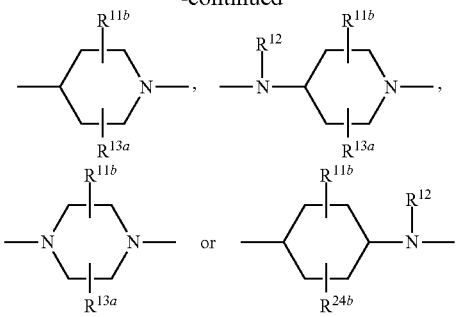

wherein:

$R^{11b}$ and $R^{24b}$ are the same or different and represent a hydrogen atom, a halogen atom, a hydroxy group, an amino, lower alkyl or lower alkoxy group which may be substituted, -$Q^2$-CONR$^{14}$R$^{15}$, -$Q^2$-CO$_2$R$^{16}$, -$Q^2$-CN, wherein $R^{14}$ and $R^{15}$ are the same or different and represent a hydrogen atom, a lower alkyl, cycloalkyl, aralkyl, aryl, lower alkoxy, alkanesulfonyl or monocyclic heterocyclic group which may be substituted, or $R^{14}$ and $R^{15}$, together with the nitrogen atom to which they are attached, represent a cyclic amino group which may be substituted;

$R^{16}$ represents a hydrogen atom or a carboxy protective group; and $Q^2$ represents a lower alkylene or lower alkenylene group which may be substituted, a lower oxyalkylene group which is attached to the ring via a terminal oxygen atom and which may be substituted or a bond; and $R^{12}$ represents a hydrogen atom, a lower alkyl or lower alkynyl group which may be substituted or an imino protective group;

$R^{13a}$ represents -$Q^{3a}$-CONR$^{17a}$R$^{18a}$ or -$Q^{3a}$-CO$_2$R$^{19}$, wherein $R^{17a}$ and $R^{18a}$ are the same or different and represent a hydrogen atom, a lower alkyl, cycloalkyl, aralkyl or aryl group which may be substituted, or $R^{17a}$ and $R^{18a}$, together with the nitrogen atom to which they are attached, represent a cyclic amino group which may be substituted;

$R^{19}$ represents a hydrogen atom or a carboxy protective group; and $Q^{3a}$ represents a lower alkylene or lower alkenylene group which may be substituted or a bond;

$Z^1$ represents CR$^{20}$, wherein $R^{20}$ represents -$Q^4$-CONR$^{21}$R$^{22}$, wherein $R^{21}$ and $R^{22}$ are the same or different and represent a hydrogen atom, a lower alkyl, cycloalkyl, aralkyl, aryl, lower alkoxy, alkanesulfonyl or monocyclic heterocyclic group which may be substituted, or $R^{21}$ and $R^{22}$, together with the nitrogen atom to which they are attached, represent a cyclic amino group which may be substituted;

and $Q^4$ represents a lower alkylene or lower alkenylene group which may be substituted, a lower oxyalkylene group which is attached to the ring via a terminal oxygen atom and which may be substituted or a bond, or a pharmaceutically acceptable salt thereof;

wherein the substituent group for a lower alkyl, cycloalkyl, aryl, lower alkoxy, cycloalkyloxy, aralkyloxy, alkanoyl, ureido and monocyclic heterocyclic group in $R^1$, $R^2$, $R^3$, $R^4$, $R^5$ and $R^{20}$ is one or more groups selected from a halogen atom,
a hydroxy and carboxy group which may be protected,
a lower alkyl, lower alkenyl, lower alkynyl and lower alkoxy group which may be substituted with a halogen atom,
a hydroxyimino group,
a lower alkyl, lower alkenyl and lower alkynyl group which may be substituted with an aryl group,
an aryl group, and
a monocyclic heterocyclic group;
the substituent group for an amino group in $R^1$, $R^2$, $R^3$, $R^4$, $R^5$, and $R^{20}$, is one or more groups selected from
a lower alkyl, lower alkenyl, lower alkynyl, acyl, alkyloxycarbonyl, aryl and monocyclic heterocyclic group which may be substituted with a halogen atom;
the substituent group for a lower alkyl group, an aryl group, a monocyclic heterocyclic group, a bicyclic heterocyclic group and a tricyclic heterocyclic group in $R^6$ is one or more groups selected from
a halogen atom,
a hydroxy and carboxy group which may be protected,
a lower alkyl, lower alkenyl, lower alkynyl and lower alkoxy group which may be substituted with a halogen atom,
an alkylthio group,
an amino group,
a lower alkylamino group,
an acyl group,
an aryl group,
a monocyclic heterocyclic group,
and an oxo group;
the substituent group for a lower alkyl, cycloalkyl, aralkyl, aryl, lower alkoxy, alkanesulfonyl and monocyclic heterocyclic group in $R^7$, $R^8$, $R^{14}$, $R^{15}$, $R^{21}$ and $R^{22}$ is one or more groups selected from
a halogen atom,
a hydroxy and carboxy group which may be protected,
lower alkyl, lower alkenyl, lower alkynyl and lower alkoxy group which may be substituted with a halogen atom,
an aryl group, and
a monocyclic heterocyclic group;
the substituent group for a cyclic amino group which is formed by $R^7$ and $R^8$, $R^{14}$ and $R^{15}$, as well as $R^{21}$ and $R^{22}$, together with the nitrogen atom to which they are attached, is one or more groups selected from
a halogen atom,
a hydroxy and carboxy group which may be protected,
a lower alkyl, lower alkenyl, lower alkynyl and lower alkoxy group which may be substituted with a halogen atom,
an acyl group,
an amino group,
a lower alkylamino group,
an alkylthio group,
an aryl group,
a monocyclic heterocyclic group, and
an oxo group;
the substituent group for a lower alkyl group and a lower alkynyl group in $R^{10}$ and $R^{12}$ is one or more groups selected from
a halogen atom,
a hydroxy and carboxy group which may be protected,
a lower alkyl, lower alkenyl, lower alkynyl and lower alkoxy group which may be substituted with a halogen atom,
an aryl group,
a monocyclic heterocyclic group, and
an oxo group;
the substituent group for a lower alkylene group, a lower alkenylene group, and a lower oxyalkylene group which is attached to the ring via a terminal oxygen atom in $Q^1$, $Q^2$, and $Q^4$ is one or more groups selected from
an oxo group,
a hydroxy and carboxy group which may be protected,
a lower alkyl group,
a lower alkenyl group,
a lower alkynyl group,
a lower alkoxy group, and
an aryl group;
the substituent group for a lower alkylene group, a lower alkenylene group and a lower alkynylene group in $X^2$ is one or more groups selected from
a hydroxy and a carboxy groups which may be protected,
a lower alkyl, lower alkenyl, lower alkynyl and lower alkoxy group which may be substituted with a halogen atom,
an aryl group, and
an oxo group;
the substituent group for an amino group in $R^{11b}$ and $R^{24b}$ is one or more groups selected from
a lower alkyl, lower alkenyl, lower alkynyl, acyl, alkyloxycarbonyl, aryl and monocyclic heterocyclic group which may be substituted with a halogen atom;
the substituent group for a lower alkyl, cycloalkyl, aralkyl and aryl group in $R^{17a}$ and $R^{18a}$ is one or more groups selected from
a halogen atom,
a hydroxy and carboxy group which may be protected,
lower alkyl, lower alkenyl, lower alkynyl and lower alkoxy group which may be substituted with a halogen atom,
an aryl group, and
a monocyclic heterocyclic group;
the substituent group for a cyclic amino group which is formed by $R^{17a}$ and $R^{18a}$, together with the nitrogen atom to which they are attached, is one or more groups selected from
a halogen atom,
a hydroxy and carboxy group which may be protected,
a lower alkyl, lower alkenyl, lower alkynyl and lower alkoxy group which may be substituted with a halogen atom,
an acyl group,
an amino group,
a lower alkylamino group,
an alkylthio group,
an aryl group,
a monocyclic heterocyclic group, and
an oxo group;
the substituent group for a lower alkyl group and a lower alkoxy group in $R^{11b}$ and $R^{24b}$ is one or more groups selected from
a halogen atom,
a hydroxy and carboxy group which may be protected,
a lower alkoxy group which may be substituted with a halogen atom,
an aryl group, and
a monocyclic heterocyclic group;
the substituent group for a lower alkylene group and a lower alkenylene group in $Q^{3a}$ is one or more groups selected from an oxo group,
a hydroxy and carboxy group which may be protected,
a lower alkyl group,
a lower alkenyl group, a lower alkynyl group,
a lower alkoxy group, and
an aryl group.

2. The compound or a pharmaceutically acceptable salt thereof according to claim 1, wherein:

$R^1$, $R^2$, $R^3$, $R^4$ and $R^5$ are the same or different and represent a hydrogen atom, a halogen atom, a hydroxy group, a cyano group, an amino, lower alkyl or lower alkoxy group which may be substituted, $-Q^{1a}\text{-CONR}^{7a}R^{8a}$ or $-Q^{1a}\text{-CO}_2R^9$, wherein $R^{7a}$ and $R^{8a}$ are the same or different and represent a hydrogen atom, a lower alkyl, cycloalkyl, aralkyl or aryl group which may be substituted, or $R^{7a}$ and $R^{8a}$, together with the nitrogen atom to which they are attached, represent a cyclic amino group which may be substituted;

$R^9$ represents a hydrogen atom or a carboxy protective group; and $Q^{1a}$ represents a lower alkylene or lower alkenylene group which may be substituted or a bond;

$R^6$ represents an aryl, monocyclic heterocyclic or bicyclic heterocyclic group which may be substituted;

$X^2$ represents a lower alkylene group which may be substituted;

$X^3$ represents an oxygen atom, a sulfur atom, a sulfinyl group, a sulfonyl group, or formula $NR^{10a}$, wherein $R^{10a}$ represents a hydrogen atom, a lower alkyl group which may be substituted or an imino protective group or a bond; and $Y^1$ represents formula VII

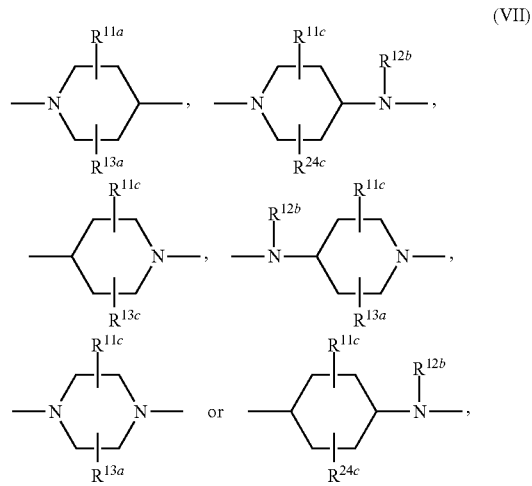

(VII)

wherein:

$R^{11c}$ and $R^{24c}$ are the same or different and represent a hydrogen atom, a halogen atom, a hydroxy group, a cyano group, an amino, lower alkyl or lower alkoxy group which may be substituted, $-Q^{2a}\text{-CONR}^{14a}R^{15a}$ or $-Q^{2a}\text{-CO}_2R^{16}$, wherein $R^{14a}$ and $R^{15a}$ are the same or different and represent a hydrogen atom, a lower alkyl, cycloalkyl, aralkyl or aryl group which may be substituted, or $R^{14a}$ and $R^{15a}$, together with the nitrogen atom to which they are attached, represent a cyclic amino group which may be substituted;

$R^{16}$ represents a hydrogen atom or a carboxy protective group; and $Q^{2a}$ represents a lower alkylene or lower alkenylene group which may be substituted or a bond;

$R^{12b}$ represents a hydrogen atom, a lower alkyl group which may be substituted or an imino protective group;

$R^{13a}$ represents $-Q^{3a}\text{-CONR}^{17a}R^{18a}$ or $-Q^{3a}\text{-CO}_2R^{19}$, wherein $R^{17a}$ and $R^{18a}$ are the same or different and represent a hydrogen atom, a lower alkyl, cycloalkyl, aralkyl or aryl group which may be substituted, or $R^{17a}$ and $R^{18a}$, together with the nitrogen atom to which they are attached, represent a cyclic amino group which may be substituted;

$R^{19}$ represents a hydrogen atom or a carboxy protective group; and $Q^{3a}$ represents a lower alkylene or lower alkenylene group which may be substituted or a bond; and $Z^1$ represents $CR^{20a}$, wherein $R^{20a}$ represents $-Q^{4a}\text{-CONR}^{21a}R^{22a}$ or $-Q^{4a}\text{-CO}_2R^{23}$, wherein $R^{21a}$ and $R^{22a}$ are the same or different and represent a hydrogen atom, a lower alkyl, cycloalkyl, aralkyl or aryl group which may be substituted, or $R^{21a}$ and $R^{22a}$, together with the nitrogen atom to which they are attached, represent a cyclic amino group which may be substituted;

and $Q^{4a}$ represents a lower alkylene or lower alkenylene group which may be substituted or a bond;

wherein the substituent group for a lower alkyl and lower alkoxy group in $R^{20a}$ is one or more groups selected from
a halogen atom,
a hydroxy and carboxy group which may be protected,
a lower alkyl, lower alkenyl, lower alkynyl and lower alkoxy group which may be substituted with a halogen atom,
a hydroxyimino group,
a lower alkyl, lower alkenyl and lower alkynyl group which may be substituted with an aryl group,
an aryl group, and
a monocyclic heterocyclic group;

the substituent group for an amino group in $R^{11c}$, $R^{20a}$ and $R^{24c}$ is one or more groups selected from
a lower alkyl, lower alkenyl, lower alkynyl, acyl, alkyloxycarbonyl, aryl and monocyclic heterocyclic group which may be substituted with a halogen atom;

the substituent group for a lower alkyl, cycloalkyl, aralkyl and aryl group in $R^{7a}$, $R^{8a}$, $R^{14a}$, $R^{15a}$, $R^{21a}$ and $R^{22a}$ is one or more groups selected from
a halogen atom,
a hydroxy and carboxy group which may be protected,
lower alkyl, lower alkenyl, lower alkynyl and lower alkoxy group which may be substituted with a halogen atom,
an aryl group, and
a monocyclic heterocyclic group;

the substituent group for a cyclic amino group which is formed by $R^{7a}$ and $R^{8a}$, $R^{14a}$ and $R^{15a}$ as well as $R^{21a}$ and $R^{22a}$, together with the nitrogen atom to which they are attached, is one or more groups selected from
a halogen atom, a hydroxy and carboxy group which may be protected,
a lower alkyl, lower alkenyl, lower alkynyl and lower alkoxy group which may be substituted with a halogen atom,
an acyl group,
an amino group,
a lower alkylamino group,
an alkylthio group,
an aryl group,
a monocyclic heterocyclic group, and
an oxo group;
the substituent group for a lower alkyl group in $R^{10a}$ and $R^{12b}$ is one or more groups selected from
a halogen atom,
a hydroxy and carboxy group which may be protected,
a lower alkyl, lower alkenyl, lower alkynyl and lower alkoxy group which may be substituted with a halogen atom,
an aryl group,
a monocyclic heterocyclic group, and
an oxo group;
the substituent group for a lower alkyl group and a lower alkoxy group in $R^{11c}$ and $R^{24c}$ is one or more groups selected from
a halogen atom,
a hydroxy and carboxy group which may be protected,
a lower alkoxy group which may be substituted with a halogen atom,
an aryl group, and
a monocyclic heterocyclic group;
the substituent group for a lower alkylene group and a lower alkenylene group in $Q^{1a}$, $Q^{2a}$ and $Q^{4a}$ is one or more groups selected from
an oxo group,
a hydroxy and carboxy group which may be protected,
a lower alkyl group,
a lower alkenyl group,
a lower alkynyl group,
a lower alkoxy group, and
an aryl group;
the substituent group for an amino group, a lower alkyl group, and lower alkoxy group in $R^1$, $R^2$, $R^3$, $R^4$, and $R^5$ is defined as claim 1;
the substituent group for an aryl group, a monocyclic heterocyclic group and a bicyclic heterocyclic group in $R^6$ is defined as claim 1;
the substituent group for a lower alkylene group in $X^2$ is defined as claim 1;
the substituent group for a lower alkyl, cycloalkyl, aralkyl and aryl group in $R^{17a}$ and $R^{18a}$ one or more groups is defined in claim 1;
the substituent group for a cyclic amino group which is formed by $R^{17a}$ and $R^{18a}$, together with the nitrogen atom to which they are attached, is defined in claim 1; and
the substituent group for a lower alkylene group and a lower alkenylene group in $Q^{3a}$ is defined in claim 1.

3. The compound or pharmaceutically acceptable salt thereof according to claim 1, wherein:
$X^1$ represents a methylene group, an ethylene group, or a propylene group; and
$X^2$ represents a methylene, ethylene or propylene group which may be substituted;

wherein the substituent group for a methylene, ethylene and propylene group in $X^2$ is one or more groups selected from
a hydroxy and a carboxy groups which may be protected,
a lower alkyl, lower alkenyl, lower alkynyl and lower alkoxy group which may be substituted with a halogen atom,
an aryl group, and
an oxo group.

4. The compound or a pharmaceutically acceptable salt thereof according to claim 1, wherein $R^1$, $R^2$, $R^3$, $R^4$ and $R^5$ are the same or different and represent a hydrogen atom, a halogen atom, a lower alkyl or lower alkoxy group which may be substituted or $-Q^{1a}-CONR^{7a}R^{8a}$,
wherein $R^{7a}$ and $R^{8a}$ are the same or different and represent a hydrogen atom, a lower alkyl, cycloalkyl, aralkyl or aryl group which may be substituted, or $R^{7a}$ and $R^{8a}$, together with the nitrogen atom to which they are attached, represent a cyclic amino group which may be substituted; and
$Q^{1a}$ represents a lower alkylene or lower alkenylene group which may be substituted or a bond;
wherein the substituent group for a lower alkyl and lower alkoxy group in $R^1$, $R^2$, $R^3$, $R^4$ and $R^5$ is defined as claim 1;
the substituent group for a lower alkyl, cycloalkyl, aralkyl and aryl group in $R^{7a}$ and $R^{8a}$ is one or more groups selected from
a halogen atom,
a hydroxy and carboxy group which may be protected,
lower alkyl, lower alkenyl, lower alkynyl and lower alkoxy group which may be substituted with a halogen atom,
an aryl group, and
a monocyclic heterocyclic group;
the substituent group for a cyclic amino group which is formed by $R^{7a}$ and $R^{8a}$, together with the nitrogen atom to which they are attached, is one or more groups selected from
a halogen atom,
a hydroxy and carboxy group which may be protected,
a lower alkyl, lower alkenyl, lower alkynyl and lower alkoxy group which may be substituted with a halogen atom,
an acyl group,
an amino group,
a lower alkylamino group,
an alkylthio group, an aryl group,
a monocyclic heterocyclic group, and
an oxo group; and
the substituent group for a lower alkylene group and a lower alkenylene group in $Q^{1a}$ is one or more groups selected from
an oxo group,
a hydroxy and carboxy group which may be protected,
a lower alkyl group,
a lower alkenyl group,
a lower alkynyl group,
a lower alkoxy group, and
an aryl group.

5. The compound or a pharmaceutically acceptable salt thereof according to claim 1, wherein $R^1$ represents a hydrogen atom or a lower alkyl group.

6. The compound or a pharmaceutically acceptable salt thereof according to claim 1, wherein $R^2$, $R^3$, $R^4$ and $R^5$ are the same or different and represent a hydrogen atom, a halogen atom or a lower alkoxy group which may be substituted; wherein the substituent group for a lower alkoxy group in $R^1$, $R^2$, $R^3$, $R^4$ and $R^5$ is defined as claim 1.

7. The compound or a pharmaceutically acceptable salt thereof according to claim 1, wherein $Y^1$ represents formula (VIII):

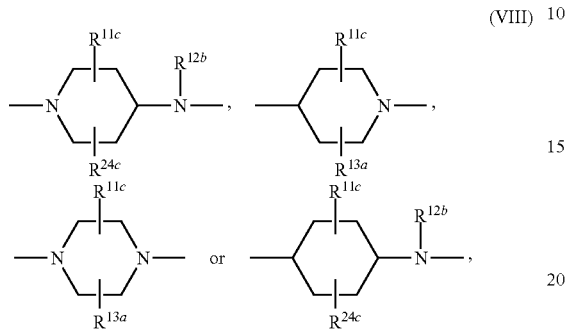

wherein:
$R^{11c}$ and $R^{24c}$ are the same or different and represent a hydrogen atom, a halogen atom, a hydroxy group, a cyano group, an amino, lower alkyl or lower alkoxy group which may be substituted, $-Q^{2a}\text{-CONR}^{14a}R^{15a}$ or $-Q^{2a}\text{-CO}_2R^{16}$,
wherein $R^{14a}$ and $R^{15a}$ are the same or different and represent a hydrogen atom, a lower alkyl, cycloalkyl, aralkyl or aryl group which may be substituted, or $R^{14a}$ and $R^{15a}$, together with the nitrogen atom to which they are attached, represent a cyclic amino group which may be substituted;
$R^{16}$ represents a hydrogen atom or a carboxy protective group; and
$Q^{2a}$ represents a lower alkylene or lower alkenylene group which may be substituted or a bond;
$R^{12b}$ represents a hydrogen atom, a lower alkyl group which may be substituted or an imino protective group;
$R^{13a}$ represents $-Q^{3a}\text{-CONR}^{17a}R^{18a}$ or $-Q^{3a}\text{-CO}_2R^{19}$,
wherein $R^{17a}$ and $R^{18a}$ are the same or different and represent a hydrogen atom, a lower alkyl, cycloalkyl, aralkyl or aryl group which may be substituted, or $R^{17a}$ and $R^{18a}$, together with the nitrogen atom to which they are attached, represent a cyclic amino group which may be substituted;
$R^{19}$ represents a hydrogen atom or a carboxy protective group; and
$Q^{3a}$ represents a lower alkylene or lower alkenylene group which may be substituted or a bond;
wherein the substituent group for a lower alkyl, cycloalkyl, aralkyl and aryl group in $R^{17a}$ and $R^{18a}$ is one or more groups selected from
a halogen atom,
a hydroxy and carboxy group which may be protected,
lower alkyl, lower alkenyl, lower alkynyl and lower alkoxy group which may be substituted with a halogen atom,
an aryl group, and
a monocyclic heterocyclic group;
the substituent group for a cyclic amino group which is formed by $R^{17a}$ and $R^{18a}$, together with the nitrogen atom to which they are attached, is one or more groups selected from
a halogen atom,
a hydroxy and carboxy group which may be protected,
a lower alkyl, lower alkenyl, lower alkynyl and lower alkoxy group which may be substituted with a halogen atom,
an acyl group,
an amino group,
a lower alkylamino group,
an alkylthio group,
an aryl group,
a monocyclic heterocyclic group, and
an oxo group;
the substituent group for a lower alkylene group and a lower alkenylene group in $Q^{3a}$ is one or more groups selected from
an oxo group,
a hydroxy and carboxy group which may be protected,
a lower alkyl group,
a lower alkenyl group,
a lower alkynyl group,
a lower alkoxy group, and
an aryl group;
the substituent group for a lower alkyl, cycloalkyl, aralkyl and aryl group in $R^{14a}$ and $R^{15a}$ is one or more groups selected from
a halogen atom,
a hydroxy and carboxy group which may be protected,
lower alkyl, lower alkenyl, lower alkynyl and lower alkoxy group which may be substituted with a halogen atom,
an aryl group, and
a monocyclic heterocyclic group;
the substituent group for a cyclic amino group which is formed by $R^{14a}$ and $R^{15a}$, together with the nitrogen atom to which they are attached, is one or more groups selected from
a halogen atom,
a hydroxy and carboxy group which may be protected,
a lower alkyl, lower alkenyl, lower alkynyl and lower alkoxy group which may be substituted with a halogen atom,
an acyl group,
an amino group,
a lower alkylamino group,
an alkylthio group,
an aryl group,
a monocyclic heterocyclic group, and
an oxo group;
the substituent group for a lower alkyl group in $R^{12b}$ is one or more groups selected from
a halogen atom,
a hydroxy and carboxy group which may be protected,
a lower alkyl, lower alkenyl, lower alkynyl and lower alkoxy group which may be substituted with a halogen atom,
an aryl group,
a monocyclic heterocyclic group, and
an oxo group;
the substituent group for an amino group, a lower alkyl group and a lower alkoxy group in $R^{11c}$ and $R^{24c}$ is one or more groups selected from a halogen atom,
a hydroxy and carboxy group which may be protected,
a lower alkoxy group which may be substituted with a halogen atom,
an aryl group, and
a monocyclic heterocyclic group; and
the substituent group for a lower alkylene group and a lower alkenylene group in $Q^{2a}$ is one or more groups selected from
an oxo group,
a hydroxy and carboxy group which may be protected,
a lower alkyl group,
a lower alkenyl group,
a lower alkynyl group,
a lower alkoxy group, and
an aryl group.

8. The compound or a pharmaceutically acceptable salt thereof according to claim 1, wherein $Y^1$ represents formula (IX)

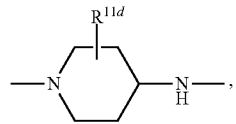

wherein:

$R^{11d}$ represents a hydrogen atom, a halogen atom, —CONR$^{14b}$R$^{15b}$ or —CO$_2$R$^{16}$, wherein R$^{14b}$ and R$^{15b}$ are the same or different and represent a hydrogen atom or a lower alkyl group; and R$^{16}$
represents a hydrogen atom or a carboxy protective group.

9. An antibacterial composition comprising the compound or a pharmaceutically acceptable salt thereof according to claim 1, and at least one additive selected from the group consisting of an excipient, a carrier and a dilution agent.

* * * * *